US012501900B2

(12) United States Patent
Chen et al.

(10) Patent No.: US 12,501,900 B2
(45) Date of Patent: Dec. 23, 2025

(54) HETEROCYCLYL PYRIDAZINE AS FUNGICIDAL COMPOUNDS

(71) Applicant: Bayer Aktiengesellschaft, Leverkusen (DE)

(72) Inventors: Victor Chen, Lyons (FR); Pierre Cristau, Lyons (FR); Mazen Es-Sayed, Langenfeld (DE); Julie Geist, Lyons (FR); Mathieu Gourgues, Lyons (FR); Dominique Loque, Vernier (CH); Anthony Millet, Tignieu-Jameyzieu (FR); Anne-Sophie Rebstock, Champagne au Mont d'or (FR); Alexander Sudau, Langenfeld (DE); Vincent Pierre Andre Thomas, Aurillac (FR); Valérie Toquin, Saint-Romain-au-Mont d'Or (FR); Tomoki Tsuchiya, Lyons (FR)

(73) Assignee: Bayer Aktiengesellschaft, Leverkusen (DE)

( * ) Notice: Subject to any disclaimer, the term of this patent is extended or adjusted under 35 U.S.C. 154(b) by 1221 days.

(21) Appl. No.: 17/309,764

(22) PCT Filed: Dec. 19, 2019

(86) PCT No.: PCT/EP2019/086373
§ 371 (c)(1),
(2) Date: Jun. 17, 2021

(87) PCT Pub. No.: WO2020/127780
PCT Pub. Date: Jun. 25, 2020

(65) Prior Publication Data

US 2023/0064576 A1 Mar. 2, 2023

(30) Foreign Application Priority Data

Dec. 20, 2018 (EP) .................................... 18214866

(51) Int. Cl.

| | |
|---|---|
| ***A01N 43/88*** | (2006.01) |
| ***A01N 43/58*** | (2006.01) |
| ***A01N 43/707*** | (2006.01) |
| ***A01P 3/00*** | (2006.01) |
| ***C07D 403/04*** | (2006.01) |
| ***C07D 413/04*** | (2006.01) |
| ***C07D 417/04*** | (2006.01) |

(52) U.S. Cl.
CPC ............. *A01N 43/88* (2013.01); *A01N 43/58* (2013.01); *A01N 43/707* (2013.01); *A01P 3/00* (2021.08); *C07D 403/04* (2013.01); *C07D 413/04* (2013.01); *C07D 417/04* (2013.01)

(58) Field of Classification Search
CPC ...... A01N 43/58; A01N 43/707; A01N 43/88; A01P 3/00; C07D 237/12; C07D 237/14; C07D 403/04; C07D 403/12; C07D 413/04; C07D 413/14; C07D 417/04; C07D 417/14; C07D 471/04
See application file for complete search history.

(56) References Cited

U.S. PATENT DOCUMENTS

| | | | |
|---|---|---|---|
| 6,251,899 B1 | 6/2001 | Gerdes | |
| 2006/0252755 A1 | 11/2006 | Shaber | |
| 2023/0354812 A1* | 11/2023 | Geist | C07D 403/12 |
| 2024/0016152 A1* | 1/2024 | Klüken | A01N 43/88 |

FOREIGN PATENT DOCUMENTS

| | | |
|---|---|---|
| WO | 2007031213 A1 | 3/2007 |
| WO | 2008009406 A1 | 1/2008 |
| WO | 2008049585 A1 | 5/2008 |
| WO | 2008089934 A1 | 7/2008 |
| WO | 2008135413 A1 | 11/2008 |
| WO | 2016201168 A1 | 12/2016 |
| WO | 2020109391 A1 | 6/2020 |

OTHER PUBLICATIONS

European Search Report dated Mar. 14, 2019, for European Application No. 18214866.8, filed on Dec. 20, 2018. 8 pages.
International Search Report mailed on Apr. 21, 2020, for PCT Patent Application No. PCT/EP2019/086373, filed on Dec. 19, 2019. 4 pages.

* cited by examiner

*Primary Examiner* — Kara R. Mcmillian
(74) *Attorney, Agent, or Firm* — MORRISON & FOERSTER LLP

(57) ABSTRACT

The present disclosure relates to heterocyclyl pyridazine compounds, processes and intermediates for their preparation as well as the uses thereof for controlling phytopathogenic microorganisms, such as phytopathogenic fungi.

12 Claims, No Drawings

HETEROCYCLYL PYRIDAZINE AS FUNGICIDAL COMPOUNDS

CROSS REFERENCE TO RELATED APPLICATIONS

This application is a national stage application under 35 U.S.C. § 371 of International Application No. PCT/EP2019/086373, filed internationally on Dec. 19, 2019, which claims benefit of European Application No. 18214866.8, filed Dec. 20, 2018.

TECHNICAL FIELD

The present invention relates to heterocyclyl pyridazine compounds and the uses thereof for controlling phytopathogenic microorganisms such as phytopathogenic fungi. It also relates to processes and intermediates for preparing these compounds.

BACKGROUND

Numerous crop protection agents to combat or prevent microorganisms' infestations have been developed until now. However, the need remains for the development of new compounds as such, so as to provide compounds being effective against a broad spectrum of phytopathogenic microorganisms, such as fungi, having low toxicity, high selectivity or that can be used at low application rate whilst still allowing effective pest control. It may also be desired to have new compounds to prevent the emergence of resistances.

The present invention provides new compounds for controlling phytopathogenic microorganisms such as fungi which have advantages over known compounds and compositions in at least some of these aspects.

SUMMARY

The present invention relates compounds of the formula (I):

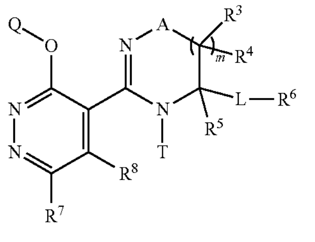

(I)

Wherein A, T, m, $R^3$, $R^4$, $R^5$, $R^6$, $R^7$ $R^8$, L and Q are as recited herein as well as their salts, N-oxides and solvates.

The present invention relates to a composition comprising at least one compound of formula (I) as defined herein and at least one agriculturally suitable auxiliary.

The present invention also relates to the use of a compound of formula (I) as defined herein or a composition as defined herein for controlling phytopathogenic fungi.

The present invention relates to a method for controlling phytopathogenic fungi which comprises the step of applying at least one compound of formula (I) as defined herein or a composition as defined herein to the plants, plant parts, seeds, fruits or to the soil in which the plants grow.

The present invention also relates to processes and intermediates for preparing compounds of formula (I) as disclosed herein.

Definitions

The term "halogen" as used herein refers to fluorine, chlorine, bromine or iodine atom.

The term "methylidene" as used herein refers to a $CH_2$ group connected to a carbon atom via a double bond.

The term "halomethylidene" as used herein refers to a $CX_2$ group connected to a carbon atom via a double bond, wherein X is halogen.

The term "oxo" as used herein refers to an oxygen atom which is bound to a carbon atom or sulfur atom via a double bound.

The term "formyl" as used herein refers to —CH(═O).

The term "$C_1$-$C_6$-alkyl" as used herein refers to a saturated, branched or straight hydrocarbon chain having 1, 2, 3, 4, 5 or 6 carbon atoms. Examples of $C_1$-$C_6$-alkyl include but are not limited to methyl, ethyl, propyl (n-propyl), 1-methylethyl (iso-propyl), butyl (n-butyl), 1-methylpropyl (sec-butyl), 2-methylpropyl (iso-butyl), 1,1-dimethylethyl (tert-butyl), pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Particularly, said hydrocarbon chain has 1, 2, 3 or 4 carbon atoms ("$C_1$-$C_4$-alkyl"), e.g. methyl, ethyl, propyl, iso-propyl, butyl, sec-butyl, iso-butyl or tert-butyl.

The term "$C_1$-$C_6$-alkylene" as used herein refers to a divalent $C_1$-$C_6$-alkyl group as defined herein. Examples of $C_1$-$C_6$-alkylene include but are not limited to $—CH_2—$, $—CH_2—CH_2—$, $—CH_2—CH_2—CH_2—$, $—CH_2—C(CH_3)—CH_2—$, $—CH_2—CH_2—CH_2—CH_2—$, $—CH_2—C(CH_3)—CH_2—CH_2—$, $—CH_2—CH_2—CH_2—CH_2—CH_2—$ and $—CH_2—CH_2—CH_2—CH_2—CH_2—CH_2—$.

The term "$C_2$-$C_6$-alkenyl" or "alkanediyl" as used herein refers to an unsaturated, branched or straight hydrocarbon chain having 2, 3, 4, 5 or 6 carbon atoms and comprising at least one double bond.

Examples of $C_2$-$C_6$-alkenyl include but are not limited to ethenyl (or "vinyl"), prop-2-en-1-yl (or "allyl"), prop-1-en-1-yl, but-3-enyl, but-2-enyl, but-1-enyl, pent-4-enyl, pent-3-enyl, pent-2-enyl, pent-1-enyl, hex-5-enyl, hex-4-enyl, hex-3-enyl, hex-2-enyl, hex-1-enyl, prop-1-en-2-yl (or "iso-propenyl"), 2-methylprop-2-enyl, 1-methylprop-2-enyl, 2-methylprop-1-enyl, 1-methylprop-1-enyl, 3-methylbut-3-enyl, 2-methylbut-3-enyl, 1-methylbut-3-enyl, 3-methylbut-2-enyl, 2-methylbut-2-enyl, 1-methylbut-2-enyl, 3-methyl-but-1-enyl, 2-methylbut-1-enyl, 1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methyl-pent-3-enyl, 3-methylpent-3-enyl, 2-methylpent-3-enyl, 1-methylpent-3-enyl, 4-methylpent-2-enyl, 3-methylpent-2-enyl, 2-methylpent-2-enyl, 1-methylpent-2-enyl, 4-methyl-pent-1-enyl, 3-methylpent-1-enyl, 2-methylpent-1-enyl, 1-methylpent-1-enyl, 3-ethylbut-3-enyl, 2-ethyl-but-3-enyl, 1-ethylbut-3-enyl, 3-ethylbut-2-enyl, 2-ethylbut-2-enyl, 1-ethylbut-2-enyl, 3-ethylbut-1-enyl, 2-ethylbut-1-enyl, 1-ethylbut-1-enyl, 2-propylprop-2-enyl, 1-propylprop-2-enyl, 2-isopropylprop-2-enyl, 1-isopropylprop-2-enyl, 2-propylprop-1-enyl, 1-propylprop-1-enyl, 2-isopropylprop-1-enyl, 1-isopropyl-prop-1-enyl, 3,3-dimethylprop-1-enyl, 1-(1,1-dimethylethyl)ethenyl, buta-1,3-dienyl, penta-1,4-dienyl, hexa-1,5-dienyl or methylhexadienyl group.

The term "$C_2$-$C_6$-alkenylene" as used herein refers to a divalent $C_2$-$C_6$-alkenyl group as defined herein. Examples of $C_2$-$C_6$-alkenylene include but are not limited to ethenylene, propenylene, butenylene, pentenylene, hexenylene, heptenylene, octenylene, nonenylene, decenylene, undecenylene, dodecenylene, and the like.

The term "$C_2$-$C_6$-alkynyl" as used herein refers to a branched or straight hydrocarbon chain having 2, 3, 4, 5 or 6 carbon atoms and comprising at least one triple bond. Examples of $C_2$-$C_6$-alkynyl include but are not limited to ethynyl, prop-1-ynyl, prop-2-ynyl (or "propargyl"), but-1-ynyl, but-2-ynyl, but-3-ynyl, pent-1-ynyl, pent-2-ynyl, pent-3-ynyl, pent-4-ynyl, hex-1-ynyl, hex-2-ynyl, hex-3-ynyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methyl-pent-4-ynyl, 2-methylpent-3-ynyl, 1-methylpent-3-ynyl, 4-methylpent-2-ynyl, 1-methyl-pent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-ynyl, 1,1-dimethylbut-3-ynyl, 1,1-dimethylbut-2-ynyl or 3,3-dimethylbut-1-ynyl group.

The term "$C_2$-$C_6$-alkynylene" as used herein refers to a divalent $C_2$-$C_6$-alkynyl group as defined herein.

The term "$C_1$-$C_6$-haloalkyl" as used herein refers to a $C_1$-$C_6$-alkyl group as defined above in which one or more hydrogen atoms are replaced with one or more halogen atoms that may be the same or different.

The term "$C_2$-$C_6$-haloalkenyl" as used herein refers to a $C_2$-$C_6$-alkenyl group as defined above in which one or more hydrogen atoms are replaced with one or more halogen atoms that may be the same or different.

The term "$C_2$-$C_6$-haloalkynyl" as used herein refers to a $C_2$-$C_6$-alkynyl group as defined above in which one or more hydrogen atoms are replaced with one or more halogen atoms that may be the same or different.

The term "$C_1$-$C_6$-alkoxy" as used herein refers to a group of formula ($C_1$-$C_6$-alkyl)-O—, in which the term "$C_1$-$C_6$-alkyl" is as defined herein. Examples of $C_1$-$C_6$-alkoxy include but are not limited to methoxy, ethoxy, n-propoxy, 1-methylethoxy, n-butoxy, 1-methylpropoxy, 2-methylpropoxy, 1,1-dimethylethoxy, n-pentoxy, 1-methylbutoxy, 2-methylbutoxy, 3-methylbutoxy, 2,2-dimethylpropoxy, 1-ethylpropoxy, 1,1-dimethylpropoxy, 1,2-dimethylpropoxy, n-hexyloxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy.

The term "$C_1$-$C_6$-haloalkoxy" as used herein refers to a $C_1$-$C_6$-alkoxy group as defined above in which one or more hydrogen atoms are replaced with one or more halogen atoms that may be the same or different. Examples of $C_1$-$C_6$-haloalkoxy include but are not limited to chloromethoxy, bromomethoxy, dichloromethoxy, trichloromethoxy, fluoromethoxy, difluoromethoxy, trifluoromethoxy, chlorofluoro-methoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 1,1,1-trifluoroprop-2-oxy.

The term "$C_1$-$C_6$-haloalkoxy" as used herein refers to a $C_1$-$C_6$-alkoxy group as defined above in which one or more hydrogen atoms are replaced with one or more halogen atoms that may be the same or different.

The term "$C_1$-$C_6$-hydroxyalkyl" as used herein refers to a $C_1$-$C_6$-alkyl group as defined above in which at least one hydrogen atom is replaced with a hydroxyl group. Examples of $C_1$-$C_6$-hydroxyalkyl include but are not limited to hydroxymethyl, 1-hydroxyethyl, 2-hydroxyethyl,1,2-dihydroxyethyl, 3-hydroxy-propyl, 2-hydroxypropyl, 1-hydroxypropyl, 1-hydroxypropan-2-yl, 2-hydroxypropan-2-yl, 2, 3-dihydroxy-propyl and 1,3-dihydroxypropan-2-yl.

The term "$C_1$-$C_6$-alkylsulfanyl" as used herein refers to a saturated, linear or branched group of formula ($C_1$-$C_6$-alkyl)-S—, in which the term "$C_1$-$C_6$-alkyl" is as defined herein. Examples of $C_1$-$C_6$-alkylsulfanyl include but are not limited to methylsulfanyl, ethylsulfanyl, propylsulfanyl, isopropyl-sulfanyl, butylsulfanyl, sec-butylsulfanyl, isobutylsulfanyl, tert-butylsulfanyl, pentylsulfanyl, isopentyl-sulfanyl, hexylsulfanyl group.

The term "$C_1$-$C_6$-haloalkylsulfanyl" as used herein refers to a $C_1$-$C_6$-alkylsulfanyl as defined above in which one or more hydrogen atoms are replaced with one or more halogen atoms that may be the same or different.

The term "$C_1$-$C_6$-alkylsulfinyl" s used herein refers to a saturated, linear or branched group of formula ($C_1$-$C_6$-alkyl)-S(═O)—, in which the term "$C_1$-$C_6$-alkyl" is as defined herein. Examples of $C_1$-$C_6$-alkylsulfinyl include but are not limited to saturated, straight-chain or branched alkylsulfinyl radicals having 1 to 8, preferably 1 to 6 and more preferably 1 to 4 carbon atoms, for example (but not limited to) $C_1$-$C_6$-alkylsulfinyl such as methylsulfinyl, ethylsulfinyl, propylsulfinyl, 1-methylethylsulfinyl, butyl-sulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethyl-propylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl.

The term "$C_1$-$C_6$-haloalkylsulfinyl" as used herein refers to a $C_1$-$C_6$-alkylsulfinyl as defined above in which one or more hydrogen atoms are replaced with one or more halogen atoms that may be the same or different.

The term "$C_1$-$C_6$-alkylsulfonyl" s used herein refers to a saturated, linear or branched group of formula ($C_1$-$C_6$-alkyl)-S(═O)$_2$—, in which the term "$C_1$-$C_6$-alkyl" is as defined herein. Examples of $C_1$-$C_6$-alkylsulfonyl include but are not limited to methylsulfonyl, ethylsulfonyl, propylsulfonyl, 1-methyl-ethylsulfonyl, butylsulfonyl, 1-methylpropylsulfonyl, 2-methylpropylsulfonyl, 1,1-dimethylethylsulfonyl, pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, 1,1-dimethylpropylsulfonyl, 1,2-dimethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl.

The term "$C_1$-$C_6$-haloalkylsulfonyl" as used herein refers to a $C_1$-$C_6$-alkylsulfonyl as defined above in which one or more hydrogen atoms are replaced with one or more halogen atoms that may be the same or different.

The term "$C_1$-$C_6$-alkylcarbonyl" as used herein refers to a saturated, linear or branched group of formula ($C_1$-$C_6$-alkyl)-C(═O)—, in which the term "$C_1$-$C_6$-alkyl" is as defined herein.

The term "$C_1$-$C_6$-haloalkylcarbonyl" as used herein refers to a $C_1$-$C_6$-alkylcarbonyl as defined above in which one or more hydrogen atoms are replaced with one or more halogen atoms that may be the same or different.

The term "$C_1$-$C_6$-alkoxycarbonyl" as used herein refers to a saturated, linear or branched group of formula ($C_1$-$C_6$-alkoxy)-C(═O)—, in which the term "$C_1$-$C_6$-alkoxy" is as defined herein.

The term "$C_1$-$C_6$-haloalkoxycarbonyl" as used herein refers to a $C_1$-$C_6$-alkoxycarbonyl as defined above in which one or more hydrogen atoms are replaced with one or more halogen atoms that may be the same or different.

The term "$C_1$-$C_6$-dialkylamino" as used herein refers to an amino radical having two independently selected $C_1$-$C_6$-alkyl groups as defined herein. Examples of $C_1$-$C_6$-dialkylamino include but are not limited to N,N-dimethylamino, N,N-diethylamino, N,N-diisopropylamino, N-ethyl-N-methylamino, N-methyl-N-n-propylamino, N-isopropyl-N-n-propylamino and N-tert-butyl-N-methylamino.

The term "non-aromatic $C_3$-$C_{12}$-carbocycle" as used herein refers to a non-aromatic, saturated or unsaturated, hydrocarbon ring system in which all of the ring members, which vary from 3 to 12, are carbon atoms. The ring system may be monocyclic or polycyclic (fused, spiro or bridged). Non-aromatic $C_3$-$C_{12}$-carbocycles include but are not limited to $C_3$-$C_{12}$-cycloalkyl (mono or bicyclic), $C_3$-$C_{12}$-cycloalkenyl (mono or bicyclic), bicylic system comprising an aryl (e.g. phenyl) fused to a monocyclic $C_3$-$C_8$-cycloalkyl (e.g. tetrahydronaphthalenyl, indanyl), bicylic system comprising an aryl (e.g. phenyl) fused to a monocyclic $C_3$-$C_8$-cycloalkenyl (e.g. indenyl, dihydronaphthalenyl) and tricyclic system comprising a cyclopropyl connected through one carbon atom to a bicylic system comprising an aryl (e.g. phenyl) fused to a monocyclic $C_3$-$C_8$-cycloalkyl or to a monocyclic $C_3$-$C_8$-cycloalkenyl. The non-aromatic $C_3$-$C_{12}$-carbocycle can be attached to the parent molecular moiety through any carbon atom.

The term "$C_3$-$C_{12}$-cycloalkyl" as used herein refers to a saturated, monovalent, mono- or bicylic hydrocarbon ring which contains 3, 4, 5, 6, 7, 8, 9, 10, 11 or 12 carbon atoms. Examples of monocyclic $C_3$-$C_8$-cycloalkyls include but are not limited to cyclopropyl, cyclobutyl, cyclopentyl, cyclohexyl, cycloheptyl, or cyclooctyl. Examples of bicyclic $C_6$-$C_{12}$-cycloalkyls include but are not limited to bicyclo[3.1.1]heptane, bicyclo[2.2.1]heptane, bicyclo[2.2.2]octane, bicyclo[3.2.2]nonane, bicyclo[3.3.1]nonane, bicyclo[4.2.0]octyl, octahydropentalenyl and bicyclo[4.2.1]nonane.

The term "$C_3$-$C_{12}$-cycloalkylene" as used herein refers to a divalent $C_3$-$C_{12}$-cycloalkyl group as defined herein, such as cyclopropylene, cyclobutylene, cyclopentylene, cyclohexylene, cycloheptylene and bicyclo[2.2.1]hept-2-ylene.

The term "$C_3$-$C_{12}$-cycloalkenyl" as used herein refers to an unsaturated, monovalent, mono- or bicylic hydrocarbon ring which contains 3, 4, 5, 6, 7, 8, 9, 10, 11 or 12 carbon atoms. Examples of monocyclic $C_3$-$C_8$-cycloalkenyl group include but are not limited to cyclobutenyl, cyclopentenyl, cyclohexenyl, cycloheptenyl and cyclooctenyl group. Examples of bicyclic $C_6$-$C_{12}$-cycloalkenyl group include but are not limited to bicyclo[2.2.1]hept-2-enyl or bicyclo[2.2.2]oct-2-enyl.

The term "$C_3$-$C_{12}$-cycloalkenylene" as used herein refers to a divalent $C_3$-$C_{12}$-cycloalkenyl as disclosed herein.

The term "aromatic $C_6$-$C_{14}$-carbocycle" or "aryl" as used herein refers to an aromatic hydrocarbon ring system in which all of the ring members, which vary from 6 to 14, preferably from 6 to 10, are carbon atoms. The ring system may be monocyclic or fused polycyclic (e.g. bicyclic or tricyclic). Examples of aryl include but are not limited to phenyl, azulenyl and naphthyl. The aryl can be attached to the parent molecular moiety through any carbon atom. It is further understood that when said aryl group is substituted with one or more substituents, said substituent(s) may be at any positions on said aryl ring(s). Particularly, in the case of aryl being a phenyl group, said substituent(s) may occupy one or both ortho positions, one or both meta positions, or the para position, or any combination of these positions.

The term "non-aromatic 3- to 14-membered heterocycle" as used herein refers to a saturated or unsaturated non-aromatic ring system comprising 1 to 4 heteroatoms independently selected from the group consisting of oxygen, nitrogen and sulfur. If the ring system contains more than one oxygen atoms, they are not directly adjacent. Non aromatic heterocycles include but are not limited to 3- to 7-membered monocyclic non-aromatic heterocycles and 6- to 14-membered polycyclic (e.g. bicyclic or tricyclic) non-aromatic heterocycles. The non-aromatic 3- to 14-membered heterocycle can be connected to the parent molecular moiety through any carbon atom or nitrogen atom contained within the heterocycle.

The term "non-aromatic 3- to 7-membered monocyclic heterocycle" as used herein refers to a 3-, 4-, 5-, 6- or 7-membered monocyclic ring system containing 1, 2 or 3 heteroatoms independently selected from the group consisting of oxygen, nitrogen and sulfur where the ring system is saturated or unsaturated but not aromatic. For instance, the heterocycle may comprise one to three nitrogen atoms, or one or two oxygen atoms, or one or two sulfur atoms, or one to three nitrogen atoms and one oxygen atom, or one to three nitrogen atoms and a sulfur atom or one sulfur atom and one oxygen atom. Examples of saturated non-aromatic heterocycles include but are not limited to 3-membered ring such as oxiranyl, aziridinyl, 4-membered ring such as azetidinyl, oxetanyl, thietanyl, 5-membered ring such as tetrahydrofuranyl, 1,3-dioxolanyl, tetrahydrothienyl, pyrrolidinyl, pyrazolidinyl, imidazolidinyl, triazolidinyl, isoxazolidinyl, oxazolidinyl, oxadiazolidinyl, thiazolidinyl, isothiazolidinyl, thiadiazolidinyl, 6-membered ring such as piperidinyl, hexahydropyridazinyl, hexahydropyrimidinyl, piperazinyl, triazinanyl, hexahydrotriazinyl, tetrahydropyranyl, dioxanyl, tetrahydrothiopyranyl, dithianyl, morpholinyl, 1,2-oxazinanyl, oxathianyl, thiomorpholinyl or 7-membered ring such as oxepanyl, azepanyl, 1,4-diazepanyl and 1,4-oxazepanyl. Examples of unsaturated non-aromatic hererocyles include but are not limited to 5-membered ring such as dihydrofuranyl, 1,3-dioxolyl, dihydrothienyl, pyrrolinyl, dihydroimidazolyl, dihydropyrazolyl, isoxazolinyl, dihydrooxazolyl, dihydrothiazolyl or 6-membered ring such as pyranyl, thiopyranyl, thiazinyl and thiadiazinyl.

The term "non-aromatic 6- to 14-membered polycyclic heterocycle" as used herein refers to a 6-, 7-, 8-, 9-, 10-, 11-, 12-, 13- or 14-membered polycyclic (e.g. bicyclic or tricyclic) ring system containing 1, 2 or 3 heteroatoms independently selected from the group consisting of oxygen, nitrogen and sulfur where the ring system is saturated or unsaturated but not aromatic. Non-aromatic bicyclic heterocycles may consist of a monocyclic heteroaryl as defined herein fused to a monocyclic $C_3$-$C_8$-cycloalkyl, a monocyclic $C_3$-$C_8$-cycloalkenyl or a monocyclic non-aromatic heterocycle or may consist of a monocyclic non-aromatic heterocycle fused either to an aryl (e.g. phenyl), a monocyclic $C_3$-$C_8$-cycloalkyl, a monocyclic $C_3$-$C_8$-cycloalkenyl or a monocyclic non-aromatic heterocycle. When two monocyclic heterocycles (aromatic or non-aromatic) comprising nitrogen atoms are fused, nitrogen atom may be at the bridgehead (e.g. 4,5,6,7-tetrahydropyrazolo[1,5-a]pyridinyl, 5,6,7,8-tetrahydro-[1,2,4]triazolo[1,5-a]pyridinyl, 5,6,7,8-tetrahydroimidazo[1,2-a]pyridinyl). Non-aromatic tricyclic heterocycles may consist of a monocyclic cycloalkyl connected through one common atom to a non-aromatic bicyclic heterocycle.

The term "non-aromatic 3- to 7-membered monocyclic heterocyclylene" as used herein refers to a divalent non-aromatic 3- to 7-membered monocyclic heterocycle as disclosed herein.

The term "aromatic 5- to 14-membered heterocycle" or "heteroaryl" as used herein refers to an aromatic ring system comprising 1 to 4 heteroatoms independently selected from the group consisting of oxygen, nitrogen and sulfur. If the ring system contains more than one oxygen atom, they are not directly adjacent. Aromatic heterocycles include aromatic 5- or 6-membered monocyclic heterocycles and 6- to 14-membered polycyclic (e.g. bicyclic or tricyclic) aromatic heterocycles. The 5- to 14-membered aromatic heterocycle can be connected to the parent molecular moiety through any carbon atom or nitrogen atom contained within the heterocycle.

The term "aromatic 5- or 6-membered monocyclic heterocycle" or "monocyclic heteroaryl" as used herein refers to a 5- or 6-membered monocyclic ring system containing 1, 2, 3 or 4 heteroatoms independently selected from the group consisting of oxygen, nitrogen and sulfur. Examples of 5-membered monocyclic heteroaryl include but are not limited to furyl (furanyl), thienyl, pyrrolyl, pyrazolyl, imidazolyl, triazolyl, tetrazolyl, isoxazolyl, oxazolyl, oxadiazolyl, oxatriazolyl, isothiazolyl, thiazolyl, thiadiazolyl and thiatriazolyl. Examples of 6-membered monocyclic heteroaryl include but are not limited to pyridinyl, pyridazinyl, pyrimidinyl, pyrazinyl, triazinyl, tetrazinyl.

The term "6- to 14-membered polycyclic aromatic heterocycle" or "polycyclic heteroaryl" as used herein refers to a 6-, 7-, 8-, 9-, 10-, 11-,12-, 13- or 14-membered polycyclic (e.g. bicyclic or tricyclic) ring system containing 1, 2 or 3 heteroatoms independently selected from the group consisting of oxygen, nitrogen and sulfur. Aromatic bicyclic heterocycles may consist of a monocyclic heteroaryl as defined herein fused to an aryl (e.g. phenyl) or to a monocyclic heteroaryl. Examples of bicyclic aromatic heterocycle include but are not limited to 9-membered ring such as indolyl, indolizinyl, isoindolyl, benzimadozolyl, imidazopyridinyl, indazolyl, benzotriazolyl, purinyl, benzofuranyl, benzothiophenyl, benzothiazolyl, benzoxazolyl and benzisoxazolyl or 10-membered ring such as quinolinyl, isoquinolinyl, cinnolinyl, quinazolinyl, quinoxalinyl, phthalazinyl, naphthyridinyl, pteridinal and benzodioxinyl. In 9- or 10-membered aromatic bicyclic heterocycles comprising two fused 5- or 6-membered monocyclic aromatic heterocycles, nitrogen atom may be at the bridgehead (e.g. imidazo[1,2-a]pyridinyl, [1,2,4]triazolo[4,3-a]pyridinyl, imidazo[1,2-a]pyridinyl, imidazo[2,1-b]oxazolyl, furo[2,3-d]isoxazolyl). Examples of tricyclic aromatic heterocyle include but are not limited to carbazolyl, acridinyl and phenazinyl.

The terms "non-aromatic $C_3$-$C_{12}$-carbocyclyloxy", "$C_3$-$C_8$-cycloalkyloxy", "aromatic $C_6$-$C_{14}$-carbocyclyloxy", "aromatic 5- to 14-membered heterocyclyloxy", "non-aromatic 5- to 14-membered heterocyclyloxy" as used herein designate a group of formula —O—R wherein R is respectively a non-aromatic $C_3$-$C_{12}$-carbocyclyl, a $C_3$-$C_8$-cycloalkyl, an aromatic $C_6$-$C_{14}$-carbocyclyl, an aromatic 5- to 14-membered heterocyclyl or a non-aromatic 5- to 14-membered heterocyclyl group as defined herein.

As used herein, when a group is said to be "substituted", the group may be substituted with one or more substituents. The expression "one or more substituents" refers to a number of substituents that ranges from one to the maximum number of substituents possible based on the number of available bonding sites, provided that the conditions of stability and chemical feasibility are met.

The term "leaving group" as used herein is to be understood as meaning a group which is displaced from a compound in a substitution or an elimination reaction, for example a halogen atom, a trifluoromethanesulphonate ("triflate") group, alkoxy, methanesulphonate, p-toluenesulphonate, etc.

The terms "as described herein" when referring to a variable A, Q, L, m, T, $R^1$, $R^2$, $R^3$, $R^4$, $R^5$, $R^6$, $R^7$, $R^8$ incorporates by reference the broad definition of the variable as well as preferred, more preferred and even more preferred definitions, if any.

DETAILED DESCRIPTION

Compounds of Formula (I)

The present invention relates to compounds of the formula (I)

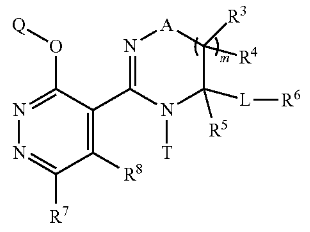

(I)

wherein

A is selected from the group consisting of O, S, C(=O), S(=O), $S(=O)_2$, $NR^1$ and $CR^1R^2$, with $R^1$ and $R^2$ being independently selected from the group consisting of hydrogen, $C_1$-$C_6$-alkyl and $C_3$-$C_8$-cycloalkyl, or $R^1$ and $R^2$ form, together with the carbon atom to which they are attached, a $C_3$-$C_8$-cycloalkyl or a non-aromatic 3- to 7-membered monocyclic heterocycle;

m is 0, 1 or 2;

T is selected from the group consisting of hydrogen, hydroxyl, $C_1$-$C_6$-alkyl, —C(=O)$R^{a1}$, —C(=O)(O$R^{a1}$), —C(=O)N$(R^{a2})_2$, —S(=O)$R^{a1}$, —$S(=O)_2R^{a1}$ and $S(=O)_2N(R^{a2})_2$, with $R^{a1}$ being selected from the group consisting of $C_1$-$C_6$-alkyl, $C_1$-$C_6$-haloalkyl, $C_3$-$C_8$-cycloalkyl and $C_2$-$C_6$-alkenyl, with $R^{a2}$ being independently selected from the group consisting of hydrogen, $C_1$-$C_6$-alkyl, $C_1$-$C_6$-haloalkyl, $C_3$-$C_8$-cycloalkyl and $C_2$-$C_6$-alkenyl;

$R^3$ and $R^4$ are independently selected from the group consisting of hydrogen, halogen, cyano, hydroxyl, formyl, carboxyl, $C_1$-$C_6$-alkyl, $C_1$-$C_6$-alkoxy, $C_1$-$C_6$-alkylcarbonyl, $C_1$-$C_6$-alkoxycarbonyl, $C_2$-$C_6$-alkenyl, $C_2$-$C_6$-alkynyl, $C_3$-$C_8$-cycloalkyl, aromatic $C_6$-$C_{14}$-carbocycle, aromatic 5- to 14-membered heterocycle, non-aromatic 3- to 14-membered heterocycle and —O—Si($C_1$-$C_6$-alkyl)$_3$, or $R^3$ and $R^4$ form, together with the carbon atom to which they are attached to, a carbonyl, a methylidene, a $C_3$-$C_8$-cycloalkyl or a non-aromatic 3- to 7-membered monocyclic heterocycle;

$R^5$ is selected from the group consisting of hydrogen, hydroxyl, $C_1$-$C_6$-alkyl, $C_1$-$C_6$-alkoxy, $C_1$-$C_6$-alkylcarbonyloxy, $C_1$-$C_6$-alkylsulfanyl, $C_1$-$C_6$-alkylsulfinyl, $C_1$-$C_6$-alkylsulfonyl, $C_3$-$C_8$-cycloalkyl and —O—Si($C_1$-$C_6$-alkyl)$_3$;

wherein aliphatic $R^1$, $R^2$, $R^3$, $R^4$ and $R^5$ substituents may be substituted with one or more substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and non-aromatic 3- to 7-membered monocyclic heterocycle;

wherein cyclic $R^1$, $R^2$, $R^3$, $R^4$ and $R^5$ substituents may be substituted with one or more substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and non-aromatic 3- to 7-membered monocyclic heterocycle;

$R^3$ or $R^4$, and $R^5$ may form, together with the carbon atom to which they are attached to, a $C_3$-$C_8$-cycloalkyl;

L represents a direct bond or L is selected from the group consisting of carbonyl, $C_1$-$C_6$-alkylene, $C_1$-$C_6$-alkylene substituted on a same carbon atom by two substituents forming together with the carbon atom to which they are attached to a $C_3$-$C_8$-cycloalkyl, $C_1$-$C_6$-alkylene substituted on a same carbon atom by two substituents forming together with the carbon atom to which they are attached to a non-aromatic 3- to 7-membered monocyclic heterocycle, $C_2$-$C_6$-alkenylene, $C_2$-$C_6$-alkynylene, $C_3$-$C_8$-cycloalkylene, $C_1$-$C_6$-alkylene-$C_3$-$C_8$-cycloalkylene, $C_3$-$C_8$-cycloalkylene-$C_1$-$C_6$-alkylene, $C_1$-$C_6$-alkylene-$C_3$-$C_8$-cycloalkylene-$C_1$-$C_6$-alkylene, $C_1$-$C_6$-alkylene-(C═O), C(═O)—$C_1$-$C_6$-alkylene, $C_3$-$C_8$-cycloalkenylene, $C_1$-$C_6$-alkylene-$C_3$-$C_8$-cycloalkenylene, $C_3$-$C_8$-cycloalkenylene-$C_1$-$C_6$-alkylene, $C_1$-$C_6$-alkylene-$C_3$-$C_8$-cycloalkenylene-$C_1$-$C_6$-alkylene, non-aromatic 3- to 7-membered monocyclic heterocyclylene, —$NR^{aL1}$—, —$NR^{aL1}$(C═O)—, —C(═O)$NR^{aL1}$—, —$NR^{aL1}$S(═O)$_2$—, —S(═O)$_2NR^{aL1}$—, —C(═$NOR^{aL2}$)—, —C(═N—N($R^{aL2}$)$_2$) and —C(═$NR^{aL2}$)—;

with $R^{aL1}$ being selected from the group consisting of hydrogen and $C_1$-$C_6$-alkyl, with $R^{aL2}$ being independently selected from the group consisting of hydrogen, $C_1$-$C_6$-alkyl, $C_1$-$C_6$-haloalkyl, $C_3$-$C_8$-cycloalkyl and $C_2$-$C_6$-alkylenyl, wherein aliphatic L substituents may be substituted with one or more $L^{Sa}$ substituents that may be the same or different wherein cyclic or cyclic moiety of L substituents may be substituted with one or more $L^{Sc}$ substituents that may be the same or different, $L^{sa}$ is selected from the group consisting of halogen, cyano, hydroxyl, carboxyl, methylidene, halomethylidene, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$ and non-aromatic 3- to 7-membered monocyclic heterocycle, $L^{Sc}$ is selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and non-aromatic 3- to 7-membered monocyclic heterocycle, and/or two $L^{Sc}$ substituents form, together with the carbon atom to which they are attached to, a $C_3$-$C_8$-cycloalkyl;

$R^6$ is selected from the group consisting of non-aromatic $C_3$-$C_{12}$-carbocycle, aromatic $C_6$-$C_{14}$-carbocycle, non-aromatic 3- to 14-membered heterocycle, aromatic 5- to 14-membered heterocycle, non-aromatic $C_3$-$C_{12}$-carbocyclyloxy, aromatic $C_6$-$C_{14}$-carbocyclyloxy, aromatic 5- to 14-membered heterocyclyloxy, non-aromatic 5- to 14-membered heterocyclyloxy, non-aromatic $C_3$-$C_{12}$-carbocyclylsulfanyl, aromatic $C_6$-$C_{14}$-carbocyclylsulfanyl, aromatic 5- to 14-membered heterocyclylsulfanyl, non-aromatic 5- to 14-membered heterocyclylsulfanyl, non-aromatic $C_3$-$C_{12}$-carbocyclylsulfinyl, aromatic $C_6$-$C_{14}$-carbocyclylsulfinyl, aromatic 5- to 14-membered heterocyclylsulfinyl, non-aromatic 5- to 14-membered heterocyclylsulfinyl, non-aromatic $C_3$-$C_{12}$-carbocyclylsulfonyl, aromatic $C_6$-$C_{14}$-carbocyclylsulfonyl, aromatic 5- to 14-membered heterocyclylsulfonyl, non-aromatic 5- to 14-membered heterocyclylsulfonyl, $C_1$-$C_3$-alkoxy substituted by a non-aromatic $C_3$-$C_{12}$-carbocycle, $C_1$-$C_3$-alkoxy substituted by an aromatic $C_6$-$C_{14}$-carbocycle, $C_1$-$C_3$-alkoxy substituted by a non-aromatic 3- to 14-membered heterocycle, $C_1$-$C_3$-alkoxy substituted by an aromatic 5- to 14-membered heterocycle, $C_1$-$C_3$-haloalkoxy substituted by a non-aromatic $C_3$-$C_{12}$-carbocycle, $C_1$-$C_3$-haloalkoxy substituted by an aromatic $C_6$-$C_{14}$-carbocycle, $C_1$-$C_3$-haloalkoxy substituted by a non-aromatic 3- to 14-membered heterocycle, $C_1$-$C_3$-haloalkoxy substituted by an aromatic 5- to 14-membered heterocycle, $C_1$-$C_3$-sulfanyl substituted by a non-aromatic $C_3$-$C_{12}$-carbocycle, $C_1$-$C_3$-sulfanyl substituted by an aromatic $C_6$-$C_{14}$-carbocycle, $C_1$-$C_3$-sulfanyl substituted by a non-aromatic 3- to 14-membered heterocycle and $C_1$-$C_3$-sulfanyl substituted by an aromatic 5- to 14-membered heterocycle, $C_1$-$C_3$-sulfinyl substituted by a non-aromatic $C_3$-$C_{12}$-carbocycle, $C_1$-$C_3$-sulfinyl substituted by an aromatic $C_6$-$C_{14}$-carbocycle, $C_1$-$C_3$-sulfinyl substituted by a non-aromatic 3- to 14-membered heterocycle and $C_1$-$C_3$-sulfinyl substituted by an aromatic 5- to 14-membered heterocycle, $C_1$-$C_3$-sulfonyl substituted by a non-aromatic $C_3$-$C_{12}$-carbocycle, $C_1$-$C_3$-sulfonyl substituted by an aromatic $C_6$-$C_{14}$-carbocycle, $C_1$-$C_3$-sulfonyl substituted by a non-aromatic 3- to 14-membered heterocycle and $C_1$-$C_3$-sulfonyl substituted by an aromatic 5- to 14-membered heterocycle;

wherein cyclic, or cyclic moiety of, $R^6$ substituents may be substituted with one or more $R^{6S}$ substituents that may be the same or different, $R^{6S}$ is selected from the group consisting of halogen, cyano, isocyano, nitro, hydroxyl, mercapto, pentafluorosulfanyl, oxo, methylidene, halomethylidene, formyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_3$-$C_8$-cycloalkylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, aromatic $C_6$-$C_{14}$-carbocycle, aromatic 5- or 6-membered monocyclic heterocycle, non-aromatic 3- to 7-membered monocyclic heterocycle, $—N(R^c)_2$, $—O—(C{=}O)R^d$, $—C({=}O)R^d$, $—C({=}O)(OR^d)$, $—C({=}O)N(R^d)_2$, $—S({=}O)_2N(R^d)_2$, $—O—Si(C_1$-$C_6$-alkyl$)_3$ and $—Si(C_1$-$C_6$-alkyl$)_3$, or two $R^{6S}$ substituents may form, together with the carbon atom to which they are attached to, a $C_3$-$C_8$-cycloalkyl, with $R^c$ being independently selected from the group consisting of hydrogen, $C_1$-$C_6$-alkyl and $C_3$-$C_8$-cycloalkyl, with $R^d$ being independently selected from the group consisting of hydrogen, $C_1$-$C_6$-alkyl and $C_1$-$C_6$-haloalkyl, wherein aliphatic $R^{6S}$, $R^c$ and $R^d$ substituents may be substituted with one or more substituents independently selected from the group consisting of cyano, halogen, hydroxyl, $C_1$-$C_6$-alkoxy, $C_1$-$C_6$-haloalkoxy, $—O—Si(C_1$-$C_6$-alkyl$)_3$, $—Si(C_1$-$C_6$-alkyl$)_3$, $C_3$-$C_8$-cycloalkyl, $C_3$-$C_8$-halocycloalkyl and non-aromatic 3- to 7-membered monocyclic heterocycle, wherein cyclic or cyclic moiety of $R^{6S}$ and cyclic $R^c$ substituents may be substituted with one or more substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, and/or cyclic or cyclic moiety of $R^{6S}$ substituents may be substituted with two substituents forming, together with the carbon atom to which they are attached to, a $C_3$-$C_8$-cycloalkyl;

$R^7$ is selected from the group consisting of hydrogen, halogen, cyano, isocyano, hydroxyl, mercapto, nitro, amino, formyl, $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_3$-$C_8$-cycloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_6$-cycloalkenyl, aromatic $C_6$-$C_{14}$-carbocycle, aromatic 5- or 6-membered monocyclic heterocycle, non-aromatic 3- to 7-membered monocyclic heterocycle, $C_3$-$C_8$-cycloalkyloxy, aromatic $C_6$-$C_{14}$-carbocyclyloxy, aromatic 5- or 6-membered monocyclic heterocyclyloxy, non-aromatic 3- to 7-membered monocyclic heterocyclyloxy, $—O—Si(C_1$-$C_6$-alkyl$)_3$, $—Si(C_1$-$C_6$-alkyl$)_3$, $—N(R^e)_2$, $—C({=}NR^f)R^f$, $NR^gC({=}O)R^g$, $—C({=}O)(OR^g)$, $—C({=}O)N(R^g)_2$, $—S({=}O)_2N(R^g)_2$ and $—S({=}O)({=}NR^g)R^g$, with $R^e$ being independently selected from the group consisting of hydrogen, $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, aromatic $C_6$-$C_{14}$-carbocycle, aromatic 5- or 6-membered monocyclic heterocycle and non-aromatic 3- to 7-membered monocyclic heterocycle, with $R^f$ being independently selected from the group consisting of hydroxyl, amino, cyano, $C_1$-$C_6$-alkyl, $C_1$-$C_6$-haloalkyl, $C_1$-$C_6$-alkoxy, $C_1$-$C_6$-alkylamino and di($C_1$-$C_6$-alkyl)amino, with $R^g$ being independently selected from the group consisting of hydrogen, $C_1$-$C_6$-alkyl, $C_1$-$C_6$-haloalkyl and $C_3$-$C_8$-cycloalkyl, wherein aliphatic $R^7$, $R^e$, $R^f$ and $R^g$ substituents may be substituted with one or more $R^{7Sa}$ substituents that may be the same or different, wherein cyclic or cyclic moiety of $R^7$, cyclic $R^e$ and cyclic $R^g$ substituents may be substituted with one or more $R^{7Sc}$ substituents that may be the same or different, $R^{7Sa}$ is selected from the group consisting of cyano, hydroxyl, carboxyl, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, $—O—Si(C_1$-$C_6$-alkyl$)_3$, $—Si(C_1$-$C_6$-alkyl$)_3$, aromatic $C_6$-$C_{14}$-carbocycle and non-aromatic 3- to 7-membered monocyclic heterocycle, $R^{7Sc}$ is selected from the group consisting of halogen, cyano, nitro, hydroxyl, formyl, oxo, methylidene, halomethylidene, $C_1$-$C_6$-alkyl, $C_1$-$C_6$-haloalkyl $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, $—O—Si(C_1$-$C_6$-alkyl$)_3$ and non-aromatic 3- to 7-membered monocyclic heterocycle, or two $R^{7Sc}$ substituents form, together with the carbon atom to which they are attached to, a $C_3$-$C_8$-cycloalkyl;

$R^8$ is selected from the group consisting of hydrogen, halogen, cyano, isocyano, amino, nitro, hydroxyl, mercapto, carboxyl, $C_1$-$C_6$-alkoxycarbonyl, $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_3$-$C_8$-cycloalkyl, $C_3$-$C_6$-cycloalkenyl, aromatic $C_6$-$C_{14}$-carbocycle, non-aromatic 3- to 14-membered heterocycle, aromatic 5- to 14-membered heterocycle, $C_3$-$C_8$-cycloalkyloxy, aromatic $C_6$-$C_{14}$-carbocyclyloxy, non-aromatic 3- to 14-membered heterocyclyloxy, aromatic 5- to 14-membered heterocyclyloxy, $—O—Si(C_1$-$C_6$-alkyl$)_3$, $—Si(C_1$-$C_6$-alkyl$)_3$, $—N(R^h)_2$, $—SR^i$, $—S({=}O)R^i$ and $—S({=}O)_2R^i$, with $R^h$ being independently selected from the group consisting of hydrogen, $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, aromatic $C_6$-$C_{14}$-carbocycle, aromatic 5- to 14-membered heterocycle and non-aromatic 3- to 7-membered monocyclic heterocycle, with $R^i$ being selected from the group consisting of $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, aromatic $C_6$-$C_{14}$-carbocycle, aromatic 5- to 14-membered heterocycle and non-aromatic 3- to 7-membered monocyclic heterocycle, wherein aliphatic $R^8$, $R^h$ and $R^i$ substituents may be substituted with one or more $R^{8Sa}$ substituents that may be the same or different, wherein cyclic or cyclic moiety of $R^8$, cyclic $R^h$ and cyclic $R^i$ substituents may be substituted with one or more $R^{8Sc}$ substituents that may be the same or different, $R^{8Sa}$ is selected from the group consisting of cyano, amino, nitro, hydroxyl, formyl, carboxyl, $C_1$-$C_6$-alkoxy, $C_1$-$C_6$-haloalkoxy, $C_1$-$C_6$-alkoxy-$C_1$-$C_6$-alkoxy, $C_1$-$C_6$-alkoxycarbonyl, $C_1$-$C_6$-haloalkoxycarbonyl, $C_1$-$C_6$-alkylcarbonyl, $C_1$-$C_6$-haloalkylcarbonyl, $C_3$-$C_8$-cycloalkyl, $C_3$-$C_8$-halocycloalkyl, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$, —Si($C_1$-$C_6$-alkyl)$_3$, non-aromatic 3- to 7-membered monocyclic heterocycle and —N($R^{a'}$)$_2$ with $R^{a'}$ being independently selected from the group consisting of hydrogen, formyl, $C_1$-$C_6$-alkyl, $C_1$-$C_6$-haloalkyl, $C_3$-$C_8$-cycloalkyl and $C_1$-$C_6$-alkylcarbonyl, wherein said non-aromatic 3- to 7-membered monocyclic heterocycle $R^{8Sa}$ may be substituted with one or more $C_1$-$C_6$-alkyl substituents that may be the same or different, $R^{8Sc}$ is selected from the group consisting of halogen, cyano, amino, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_1$-$C_6$-alkylsulfanyl, $C_1$-$C_6$-alkylsulfinyl, $C_1$-$C_6$-alkylsulfonyl, $C_3$-$C_8$-cycloalkyl, $C_3$-$C_8$-halocycloalkyl, —O—Si($C_1$-$C_6$-alkyl)$_3$ and non-aromatic 3- to 7-membered monocyclic heterocycle that may be substituted with one or more $C_1$-$C_6$-alkyl substituents that may be the same or different, or two $R^{8Sc}$ substituents form, together with the carbon atom to which they are attached to, a $C_3$-$C_8$-cycloalkyl or a non-aromatic 3- to 7-membered monocyclic heterocycle, wherein said non-aromatic 3- to 7-membered monocyclic heterocycle may be substituted with one or more $C_1$-$C_6$-alkyl substituents that may be the same or different;

Q is selected from the group consisting of aromatic $C_6$-$C_{14}$-carbocycle, non-aromatic $C_3$-$C_{12}$-carbocycle, non-aromatic 3- to 14-membered heterocycle and aromatic 5- to 14-membered heterocycle, wherein any of said carbocycle or heterocycle groups may be substituted with one or more $Q^S$ substituents that may be the same or different, $Q^S$ is selected from the group consisting of halogen, cyano, isocyano, nitro, hydroxyl, mercapto, formyl, carboxyl, $C_1$-$C_6$-alkyl, $C_1$-$C_6$-haloalkyl, $C_1$-$C_6$-alkylcarbonyl, $C_1$-$C_6$-haloalkylcarbonyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyloxy, $C_3$-$C_6$-cycloalkenyl, non-aromatic 3- to 7-membered monocyclic heterocycle, aromatic $C_6$-$C_{14}$-carbocycle, aromatic 5- to 14-membered heterocycle, —O—Si($C_1$-$C_6$-alkyl)$_3$, —Si($C_1$-$C_6$-alkyl)$_3$, —O—C(=O)$R^j$, —N$R^j$C(=O)$R^j$, —C(=O)N($R^j$)$_2$, —C(=S)$R^j$, —C(=S)N($R^j$)$_2$, —C(=N$R^j$)$R^j$ and —C(=NO$R^j$)$R^j$ and —N($R^k$)$_2$ with $R^j$ being independently selected from the group consisting of hydrogen, $C_1$-$C_6$-alkyl, $C_1$-$C_6$-haloalkyl and $C_1$-$C_6$-alkoxy, with $R^k$ being independently selected from the group consisting of hydrogen, hydroxyl, $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl and $C_3$-$C_8$-cycloalkyl, wherein aliphatic $Q^S$, $R^j$ and $R^k$ substituents may be substituted with one or more substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —Si($C_1$-$C_6$-alkyl)$_3$ and non-aromatic 3- to 7-membered monocyclic heterocycle, wherein cyclic or cyclic moiety of $Q^S$ and cyclic $R^k$ substituents may be substituted with one or more $R^{Qs}$ substituents independently selected from the group consisting of halogen, cyano, amino, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, $C_2$-$C_6$-alkenyl and non-aromatic 3- to 7-membered monocyclic heterocycle, wherein cyclic $R^{Qs}$ substituents may be substituted with two substituents forming, together with the carbon atom to which they are attached to, a $C_3$-$C_8$-cycloalkyl.

The embodiment disclosed above is referred herein as "embodiment 1".

Not encompassed herein are compounds resulting from combinations which are against natural laws and which the person skilled in the art would therefore exclude based on his/her expert knowledge. For instance, ring structures having three or more adjacent oxygen atoms are excluded.

The compound of formula (I) can suitably be in its free form, salt form, N-oxides form or solvate form (e.g. hydrate).

Depending on the nature of the substituents, the compound of formula (I) may be present in the form of different stereoisomers. These stereoisomers are, for example, enantiomers, diastereomers, atropisomers or geometric isomers. Accordingly, the invention encompasses both pure stereoisomers and any mixture of these isomers. Where a compound can be present in two or more tautomer forms in equilibrium, reference to the compound by means of one tautomeric description is to be considered to include all tautomer forms.

Any of the compounds of the present invention can also exist in one or more geometric isomer forms depending on the number of double bonds in the compound. Geometric isomers by nature of substituents about a double bond or a ring may be present in cis (=Z-) or trans (=E-) form. The invention thus relates equally to all geometric isomers and to all possible mixtures, in all proportions.

Depending on the nature of the substituents, the compound of formula (I) may be present in the form of the free compound and/or a salt thereof, such as an agrochemically active salt.

Agrochemically active salts include acid addition salts of inorganic and organic acids well as salts of customary bases. Examples of inorganic acids are hydrohalic acids, such as hydrogen fluoride, hydrogen chloride, hydrogen bromide and hydrogen iodide, sulfuric acid, phosphoric acid and nitric acid, and acidic salts, such as sodium bisulfate and potassium bisulfate. Useful organic acids include, for example, formic acid, carbonic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, saturated or mono- or diunsaturated fatty acids having 6 to 20 carbon atoms, alkylsulphuric monoesters, alkylsulphonic acids (sulphonic acids having straight-chain or branched alkyl radicals having 1 to 20 carbon atoms), arylsulphonic acids or aryldisulphonic acids (aromatic radicals, such as phenyl and naphthyl, which bear one or two sulphonic acid groups), alkylphosphonic acids (phosphonic acids having straight-chain or branched alkyl radicals having 1 to 20 carbon atoms), arylphosphonic acids or aryldiphosphonic acids (aromatic radicals, such as phenyl and naphthyl, which bear one or two phosphonic acid radicals), where the alkyl and aryl radicals may bear further substituents, for example p-toluenesulphonic acid, salicylic acid, p-aminosalicylic acid, 2-phenoxybenzoic acid, 2-acetoxybenzoic acid, etc.

Solvates of the compounds of the invention or their salts are stoichiometric compositions of the compounds with solvents.

The compounds of the invention may exist in multiple crystalline and/or amorphous forms. Crystalline forms include unsolvated crystalline forms, solvates and hydrates.

Aliphatic $R^1$ and $R^2$ substituents as used herein in the expression "aliphatic $R^1$, $R^2$, $R^3$, $R^4$ and $R^5$ substituents may be substituted with one or more substituents" designates $C_1$-$C_6$-alkyl.

Aliphatic $R^3$ and $R^4$ substituents as used herein in the expression "aliphatic $R^1$, $R^2$, $R^3$, $R^4$ and $R^5$ substituents may be substituted with one or more substituents" designates $C_1$-$C_6$-alkyl, $C_1$-$C_6$-alkoxy, $C_1$-$C_6$-alkoxycarbonyl and the $C_1$-$C_6$-alkyl moiety of —Si($C_1$-$C_6$-alkyl)$_3$.

Aliphatic $R^5$ substituents as used herein in the expression "aliphatic $R^1$, $R^2$, $R^3$, $R^4$ and $R^5$ substituents may be substituted with one or more substituents" designates $C_1$-$C_6$-alkyl, $C_1$-$C_6$-alkoxy, $C_1$-$C_6$-alkylsulfanyl, $C_1$-$C_6$-alkylsulfinyl, $C_1$-$C_6$-alkylsulfonyl and the $C_1$-$C_6$-alkyl moiety of —O—Si($C_1$-$C_6$-alkyl)$_3$.

Aliphatic L substituents as used herein in the expression "aliphatic L substituents may be substituted with one or more $L^{Sa}$ substituents" designates $C_1$-$C_6$-alkylene, $C_2$-$C_6$-alkenylene, $C_2$-$C_6$-alkynylene and the $C_1$-$C_6$-alkylene moiety of $C_1$-$C_6$-alkylene-$C_3$-$C_8$-cycloalkylene, $C_3$-$C_8$-cycloalkylene-$C_1$-$C_6$-alkylene, $C_1$-$C_6$-alkylene-$C_3$-$C_8$-cycloalkylene-$C_1$-$C_6$-alkylene, $C_1$-$C_6$-alkylene-(C=O)—, $C_1$-$C_6$-alkylene-$C_3$-$C_8$-cycloalkenylene, $C_3$-$C_8$-cycloalkenylene-$C_1$-$C_6$-alkylene, $C_1$-$C_6$-alkylene-$C_3$-$C_8$-cycloalkenylene-$C_1$-$C_6$-alkylene.

Aliphatic $R^{6S}$ substituents as used herein in the expression "aliphatic $R^{6S}$, $R^c$ and $R^d$ substituents may be substituted with one or more substituents" designates $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl and the $C_1$-$C_6$-alkyl moiety of —Si($C_1$-$C_6$-alkyl)$_3$ and —O—Si($C_1$-$C_6$-alkyl)$_3$.

Aliphatic $R^c$ substituents as used herein in the expression "aliphatic $R^{6S}$, $R^c$ and $R^d$ substituents may be substituted with one or more substituents" designates $C_1$-$C_6$-alkyl.

Aliphatic $R^d$ substituents as used herein in the expression "aliphatic $R^{6S}$, $R^c$ and $R^d$ substituents may be substituted with one or more substituents" designates $C_1$-$C_6$-alkyl and $C_1$-$C_6$-haloalkyl.

Aliphatic $R^7$ substituents as used herein in the expression "aliphatic $R^7$, $R^e$, $R^f$ and $R^g$ substituents may be substituted with one or more $R^{7Sa}$ substituents" designates $C_1$-$C_6$-alkyl, $C_1$-$C_6$-haloalkyl, $C_1$-$C_6$-hydroxyalkyl, $C_1$-$C_6$-alkylcarbonyl, $C_1$-$C_6$-haloalkylcarbonyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl and the $C_1$-$C_6$-alkyl moiety of —Si($C_1$-$C_6$-alkyl)$_3$ and —O—Si($C_1$-$C_6$-alkyl)$_3$.

Aliphatic $R^e$ substituents as used herein in the expression "aliphatic $R^7$, $R^e$, $R^f$ and $R^g$ substituents may be substituted with one or more $R^{7Sa}$ substituents" designates $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl and $C_2$-$C_6$-haloalkynyl.

Aliphatic $R^f$ substituents as used herein in the expression "aliphatic $R^7$, $R^e$, $R^f$ and $R^g$ substituents may be substituted with one or more $R^{7Sa}$ substituents" designates $C_1$-$C_6$-alkyl, $C_1$-$C_6$-haloalkyl, $C_1$-$C_6$-alkoxy and the $C_1$-$C_6$-alkyl moiety of $C_1$-$C_6$-alkylamino and di($C_1$-$C_6$-alkyl)amino.

Aliphatic $R^g$ substituents as used herein in the expression "aliphatic $R^7$, $R^e$, $R^f$ and $R^g$ substituents may be substituted with one or more $R^{7Sa}$ substituents" designates $C_1$-$C_6$-alkyl and $C_1$-$C_6$-haloalkyl.

Aliphatic $R^8$ substituents as used herein in the expression "aliphatic $R^8$, $R^h$ and $R^i$ substituents may be substituted with one or more $R^{8Sa}$ substituents" designates $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl and the $C_1$-$C_6$-alkyl moiety of —Si($C_1$-$C_6$-alkyl)$_3$ and —O—Si($C_1$-$C_6$-alkyl)$_3$.

Aliphatic $R^h$ substituents as used herein in the expression "aliphatic $R^8$, $R^h$ and $R^k$ substituents may be substituted with one or more $R^{8a}$ substituents" designates $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl and $C_2$-$C_6$-haloalkynyl.

Aliphatic $R^j$ substituents as used herein in the expression "aliphatic $R^8$, $R^h$ and $R^i$ substituents may be substituted with one or more $R^{8Sa}$ substituents" designates $C_2$-$C_6$-alkenyl, $C_2$-$C_6$-haloalkenyl, $C_2$-$C_6$-alkynyl and $C_2$-$C_6$-haloalkynyl.

Aliphatic $Q^S$ substituents as used herein in the expression "aliphatic $Q^S$, $R^j$ and $R^i$ substituents may be substituted with one or more substituents" designates $C_1$-$C_6$-alkyl, $C_1$-$C_6$-haloalkyl, $C_1$-$C_6$-alkylcarbonyl, $C_1$-$C_6$-haloalkylcarbonyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl and the $C_1$-$C_6$-alkyl moiety of —Si($C_1$-$C_6$-alkyl)$_3$ and —O—Si($C_1$-$C_6$-alkyl)$_3$.

Aliphatic $R^j$ substituents as used herein in the expression "aliphatic $Q^S$, $R^j$ and $R^k$ substituents may be substituted with one or more substituents" designates $C_1$-$C_6$-alkyl, $C_1$-$C_6$-haloalkyl and $C_1$-$C_6$-alkoxy.

Aliphatic $R^k$ substituents as used herein in the expression "aliphatic $Q^S$, $R^j$ and $R^k$ substituents may be substituted with one or more substituents" designates $C_1$-$C_6$-alkyl, $C_1$-$C_6$-haloalkyl, $C_1$-$C_6$-alkoxy, $C_2$-$C_6$-alkenyl and $C_2$-$C_6$-haloalkenyl.

Cyclic $R^1$, $R^2$ and $R^5$ substituents as used herein in the expression "cyclic $R^1$, $R^2$, $R^3$, $R^4$ and $R^5$ substituents may be substituted with one or more substituents" designates $C_3$-$C_8$-cycloalkyl.

Cyclic $R^3$ and $R^4$ substituents as used herein in the expression "cyclic $R^1$, $R^2$, $R^3$, $R^4$ and $R^5$ substituents may be substituted with one or more substituents" designates $C_3$-$C_8$-cycloalkyl, aromatic $C_6$-$C_{14}$-carbocycle, non-aromatic 3- to 14-membered heterocycle and aromatic 5- to 14-membered heterocycle.

Cyclic L substituents as used herein in the expression "cyclic or cyclic moiety of L substituents may be substituted with one or more $L^{Sc}$ substituents" designates $C_3$-$C_8$-cycloalkylene, $C_3$-$C_8$-cycloalkenylene and non-aromatic 3- to 7-membered monocyclic heterocyclylene.

Cyclic L substituents as used herein in the expression "cyclic or cyclic moiety of L substituents may be substituted with one or more $L^{Sc}$ substituents" designates $C_3$-$C_8$-cycloalkylene moiety of $C_1$-$C_6$-alkylene-$C_3$-$C_8$-cycloalkylene, $C_3$-$C_8$-cycloalkylene-$C_1$-$C_6$-alkylene, $C_1$-$C_6$-alkylene-$C_3$-$C_8$-cyclo-alkylene-$C_1$-$C_6$-alkylene and the $C_3$-$C_8$-cycloalkenylene moiety of $C_1$-$C_6$-alkylene-$C_3$-$C_8$-cycloalkenylene, $C_3$-$C_8$-cycloalkenylene-$C_1$-$C_6$-alkylene and $C_1$-$C_6$-alkylene-$C_3$-$C_8$-cycloalkenylene-$C_1$-$C_6$-alkylene.

Cyclic $R^6$ substituents as used herein in the expression "cyclic, or cyclic moiety of, $R^6$ substituents may be substituted with one or more $R^{6S}$ substituents" designate non-aromatic $C_3$-$C_{12}$-carbocycle, aromatic $C_6$-$C_{14}$-carbocycle, non-aromatic 3- to 14-membered heterocycle and aromatic 5- to 14-membered heterocycle.

Cyclic moiety of $R^6$ substituents as used herein in the expression "cyclic, or cyclic moiety of, $R^6$ substituents may be substituted with one or more $R^{6S}$ substituents" designate the non-aromatic $C_3$-$C_{12}$-carbocycle of non-aromatic $C_3$-$C_{12}$-carbocyclyloxy, the aromatic $C_6$-$C_{14}$-carbocyclyle of aromatic $C_6$-$C_{14}$-carbocyclyloxy, the aromatic 5- to 14-membered heterocycle of aromatic 5- to 14-membered heterocyclyloxy, the non-aromatic 5- to 14-membered heterocycle of non-aromatic 5- to 14-membered heterocyclyloxy, the non-aromatic $C_3$-$C_{12}$-carbocycle of $C_1$-$C_3$-alkoxy substituted by a non-aromatic $C_3$-$C_{12}$-carbocycle, the aromatic $C_6$-$C_{14}$-carbocycle of $C_1$-$C_3$-alkoxy substituted by an aromatic $C_6$-$C_{14}$-carbocycle, the non-aromatic 3- to 14-membered heterocycle of $C_1$-$C_3$-alkoxy substituted by a non-aromatic 3- to 14-membered heterocycle, the aromatic 5- to 14-membered heterocycle of $C_1$-$C_3$-alkoxy substituted by an aromatic 5- to 14-membered heterocycle, the non-aromatic $C_3$-$C_{12}$-carbocycle of $C_1$-$C_3$-haloalkoxy substituted by a non-aromatic $C_3$-$C_{12}$-carbocycle, the aromatic $C_6$-$C_{14}$-carbocycle of $C_1$-$C_3$-haloalkoxy substituted by an aromatic $C_6$-$C_{14}$-carbocycle, the non-aromatic 3- to 14-membered heterocycle of $C_1$-$C_3$-haloalkoxy substituted by a non-aromatic 3- to 14-membered heterocycle and the aromatic 5- to 14-membered heterocycle of $C_1$-$C_3$-haloalkoxy substituted by an aromatic 5- to 14-membered heterocycle.

Cyclic $R^{6S}$ substituents as used herein in the expression "cyclic $R^{6S}$ and $R^c$ substituents may be substituted with one or more substituents" designates $C_3$-$C_8$-cycloalkyl, $C_3$-$C_8$-cycloalkenyl, aromatic $C_6$-$C_{14}$-carbocycle, aromatic 5- or 6-membered monocyclic heterocycle and non-aromatic 3- to 7-membered monocyclic heterocycle.

Cyclic moiety of $R^{6S}$ substituents as used herein in the expression "cyclic or cyclic moiety of $R^{6S}$ and cyclic $R^c$ substituents may be substituted with one or more substituents" designates the $C_3$-$C_8$-cycloalkyl of $C_3$-$C_8$-cycloalkyloxy.

Cyclic $R^c$ substituents as used herein in the expression "cyclic or cyclic moiety of $R^{6S}$ and cyclic $R^c$ substituents may be substituted with one or more substituents" designates $C_3$-$C_8$-cycloalkyl.

Cyclic $R^7$ substituents as used herein in the expression "cyclic $R^7$, $R^e$ and $R^g$ substituents may be substituted with one or more $R^{7Sc}$ substituents" designates $C_3$-$C_8$-cycloalkyl, $C_3$-$C_6$-cycloalkenyl, aromatic $C_6$-$C_{14}$-carbocycle, aromatic 5- or 6-membered monocyclic heterocycle and non-aromatic 3- to 7-membered monocyclic heterocycle.

Cyclic moiety of $R^7$ substituents as used herein in the expression "cyclic or cyclic moiety of $R^7$, cyclic $R^e$ and cyclic $R^g$ substituents may be substituted with one or more $R^{7Sc}$ substituents" designates the $C_3$-$C_8$-cycloalkyl of $C_3$-$C_8$-cycloalkyloxy, the aromatic $C_6$-$C_{14}$-carbocycle of aromatic $C_6$-$C_{14}$-carbocyclyloxy, the aromatic 5- or 6-membered monocyclic heterocycle of aromatic 5- or 6-membered monocyclic heterocyclyloxy and the non-aromatic 3- to 7-membered monocyclic heterocycle of non-aromatic 3- to 7-membered monocyclic heterocyclyloxy.

Cyclic $R^e$ substituents as used herein in the expression "cyclic $R^7$, $R^e$ and $R^g$ substituents may be substituted with one or more $R^{7Sc}$ substituents" designates $C_3$-$C_8$-cycloalkyl, $C_3$-$C_8$-halocycloalkyl, aromatic $C_6$-$C_{14}$-carbocycle, aromatic 5- or 6-membered monocyclic heterocycle and non-aromatic 3- to 7-membered monocyclic heterocycle.

Cyclic $R^g$ substituents" as used herein in the expression "cyclic $R^7$, $R^e$ and $R^g$ substituents may be substituted with one or more $R^{7Sc}$ substituents" designates $C_3$-$C_8$-cycloalkyl.

Cyclic $R^8$ substituents as used herein in the expression "wherein cyclic $R^8$, $R^h$ and $R^i$ substituents may be substituted with one or more $R^{7Sc}$ substituents" designates $C_3$-$C_8$-cycloalkyl, $C_3$-$C_6$-cycloalkenyl, aromatic $C_6$-$C_{14}$-carbocycle, non-aromatic 3- to 14-membered heterocycle and aromatic 5- to 14-membered heterocycle.

Cyclic moiety of $R^8$ substituents as used herein in the expression "wherein cyclic or cyclic moiety of $R^8$, cyclic $R^h$ and cyclic $R^i$ substituents may be substituted with one or more $R^{8Sc}$ substituents" designates the $C_3$-$C_8$-cycloalkyl of $C_3$-$C_8$-cycloalkyloxy, the aromatic $C_6$-$C_{14}$-carbocycle of aromatic $C_6$-$C_{14}$-carbocyclyloxy, the non-aromatic 3- to 14-membered heterocycle of non-aromatic 3- to 14-membered heterocyclyloxy and the aromatic 5- to 14-membered heterocycle of aromatic 5- to 14-membered heterocyclyloxy.

Cyclic $R^h$ substituents as used herein in the expression "wherein cyclic or cyclic moiety of $R^8$, cyclic $R^h$ and cyclic $R^i$ substituents may be substituted with one or more $R^{8Sc}$ substituents" designates $C_3$-$C_8$-cycloalkyl, $C_3$-$C_8$-halocycloalkyl, aromatic $C_6$-$C_{14}$-carbocycle, aromatic 5- to 14-membered heterocycle and non-aromatic 3- to 7-membered monocyclic heterocycle.

Cyclic $R^i$ substituents as used herein in the expression "wherein cyclic $R^8$, $R^h$ and $R^i$ substituents may be substituted with one or more $R^{8Sc}$ substituents" designates $C_3$-$C_8$-cycloalkyl, $C_3$-$C_8$-halocycloalkyl, aromatic $C_6$-$C_{14}$-carbocycle, aromatic 5- to 14-membered heterocycle and non-aromatic 3- to 7-membered monocyclic heterocycle.

Cyclic $Q^S$ substituents as used herein in the expression "cyclic or cyclic moiety of $Q^S$ and cyclic $R^k$ substituents may be substituted with one or more $R^{Qs}$ substituents" designates $C_3$-$C_8$-cycloalkyl, $C_3$-$C_6$-cycloalkenyl, non-aromatic 3- to 7-membered monocyclic heterocycle and aromatic 5- to 14-membered heterocycle.

Cyclic moiety of $Q^S$ substituents as used herein in the expression "cyclic or cyclic moiety of $Q^S$ and cyclic $R^k$ substituents may be substituted with one or more $R^{Qs}$ substituents" designates the $C_3$-$C_8$-cycloalkyl of $C_3$-$C_8$-cycloalkyloxy.

Cyclic $R^k$ substituents as used herein in the expression "cyclic $Q^S$ and $R^k$ substituents may be substituted with one or more $R^{Qs}$ substituents" designates $C_3$-$C_8$-cycloalkyl.

In the above formula (I), A is preferably selected from the group consisting of O, C(=O), $S(=O)_2$, $NR^1$ and $CR^1R^2$ with $R^1$ and $R^2$ being as described herein above, preferably with $R^1$ being hydrogen or $C_1$-$C_4$-alkyl (e.g. methyl, ethyl) and $R^2$ being a hydrogen atom.

In the above formula (I), A is more preferably selected from the group consisting of O, C(=O), $NR^1$ and $CR^1R^2$ with $R^1$ and $R^2$ being hydrogen.

In the above formula (I), A is even more preferably selected from the group consisting of O, C(=O), $NR^1$ and $CR^1R^2$ with $R^1$ and $R^2$ being hydrogen.

In some embodiments, when m is 0, A is preferably $CR^1R^2$ with $R^1$ and $R^2$ being as described herein above, preferably with $R^1$ and $R^2$ being a hydrogen atom, or A is 0.

In some embodiments, when m is 0, A is more preferably $CR^1R^2$ with $R^1$ and $R^2$ being hydrogen.

In some embodiments, when m is 1, A is preferably O, C(=O), $S(=O)_2$, $NR^1$ and $CR^1R^2$ with $R^1$ and $R^2$ being as described herein above, preferably with $R^1$ and $R^2$ being a hydrogen atom.

In some embodiments, when m is 2, A is preferably O, C(=O) and $CR^1R^2$ with $R^1$ and $R^2$ being as described herein above, preferably with $R^1$ being hydrogen or $C_1$-$C_6$-alkyl (e.g. methyl, ethyl) and $R^2$ being a hydrogen atom.

In a more preferred embodiment, T is selected from the group consisting of hydrogen and $C_1$-$C_4$-alkyl, $R^3$ and $R^4$ are independently selected from the group consisting of hydrogen, fluorine, chlorine, $C_1$-$C_4$-alkyl, $C_2$-$C_4$-alkenyl, $C_2$-$C_4$-alkynyl and $C_3$-$C_6$-cycloalkyl, and $R^5$ is selected from the group consisting of hydrogen, hydroxyl, $C_1$-$C_4$-alkyl and $C_1$-$C_4$-alkoxy.

In the above formula (I), m is more preferably is 1.

In the above formula (I), T is preferably hydrogen or —C(=O)($OR^{a1}$) with $R^{a1}$ being as described herein above, more preferably $R^{a1}$ is $C_1$-$C_6$-alkyl, even more preferably T is hydrogen.

In the above formula (I), $R^3$ and $R^4$, when present, are preferably selected from the group consisting of hydrogen, halogen, $C_1$-$C_6$-alkyl, $C_3$-$C_8$-cycloalkyl and aromatic $C_6$-$C_{14}$-carbocycle (e.g. phenyl), or $R^3$ and $R^4$ form together with the carbon atom to which they are attached to a $C_3$-$C_8$-cycloalkyl (e.g. cyclopropyl), more preferably $R^3$ and $R^4$ are hydrogen, fluorine, methyl or ethyl, even more preferably $R^3$ and $R^4$ are hydrogen and fluorine.

In the above formula (I), $R^5$ is preferably selected from the group consisting of hydrogen, hydroxyl and $C_1$-$C_6$-alkoxy, more preferably $R^5$ is hydrogen.

In the above formula (I), when L is a $C_1$-$C_6$-alkylene substituted on a same carbon atom by two substituents, forming together with the carbon atom to which they are attached to, a $C_3$-$C_8$-cycloalkyl, L is preferably:

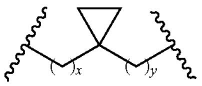
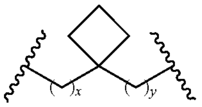
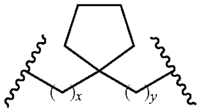

with x is 0 or 1 and y is 0 or 1, preferably x and y are 0.

In the above formula (I), when L is a $C_1$-$C_6$-alkylene substituted on a same carbon atom by two substituents, forming together with the carbon atom to which they are attached to, a non-aromatic 3- to 7-membered monocyclic heterocycle, L is preferably:

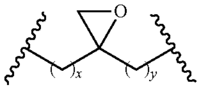
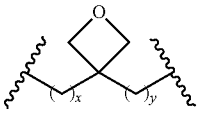
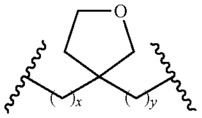

with x is 0 or 1 and y is 0 or 1, preferably x and y are 0.

In the above formula (I), when L is a $C_3$-$C_8$-cycloalkylene or comprises a $C_3$-$C_8$-cycloalkylene ($C_1$-$C_6$-alkylene-$C_3$-$C_8$-cycloalkylene, $C_3$-$C_8$-cycloalkylene-$C_1$-$C_6$-alkylene and $C_1$-$C_6$-alkylene-$C_3$-$C_8$-cyclo-alkylene-$C_1$-$C_6$-alkylene), L is more preferably $C_3$-$C_8$-cycloalkylene (x=0, y=0, $C_3$-cycloalkylene.

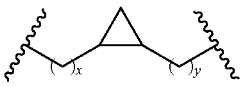
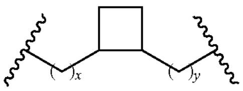

with x is 0 or 1 and y is 0 or 1, preferably x and y are 0.

In the above formula (I), when L is a $C_3$-$C_8$-cycloalkenylene or comprises a $C_3$-$C_8$-cycloalkenylene ($C_1$-$C_6$-alkylene-$C_3$-$C_8$-cycloalkenylene, $C_3$-$C_8$-cycloalkenylene-$C_1$-$C_6$-alkylene and $C_1$-$C_6$-alkylene-$C_3$-$C_8$-cycloalkenylene-$C_1$-$C_6$-alkylene), L is preferably:

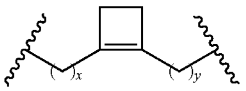

with x is 0 or 1 and y is 0 or 1, preferably x and y are 0.

In a preferred embodiment L represents a direct bond or L is selected from the group consisting of $C_1$-$C_6$-alkylene, $C_1$-$C_6$-alkylene substituted on a same carbon atom by two substituents forming together with the carbon atom to which they are attached to a $C_3$-$C_6$-cycloalkyl, $C_1$-$C_6$-alkylene substituted on a same carbon atom by two substituents forming together with the carbon atom to which they are attached to a non-aromatic 3- to 7-membered monocyclic heterocycle, wherein aliphatic L substituents may be substituted with one to three $L^{Sa}$ substituents independently selected from the group consisting of fluorine, chlorine, hydroxyl, $C_1$-$C_4$-alkoxy, $C_1$-$C_4$-haloalkoxy, $C_3$-$C_6$-cycloalkyl and $C_3$-$C_6$-halocycloalkyl, wherein cyclic or cyclic moiety of L substituents may be substituted with one to three $L^{Sc}$ substituents independently selected from the group consisting of fluorine, chlorine, hydroxyl, oxo, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_3$-$C_6$-cycloalkyl and $C_3$-$C_6$-halocycloalkyl.

In a more preferred embodiment L represents a direct bond or L is selected from the group consisting of $C_1$-$C_6$-alkylene, wherein aliphatic L substituents may be substituted with one to three $L^{Sa}$ substituents independently selected from the group consisting of fluorine, chlorine, hydroxyl, $C_1$-$C_4$-alkoxy, $C_1$-$C_4$-haloalkoxy and $C_3$-$C_6$-cycloalkyl, wherein cyclic or cyclic moiety of L substituents may be substituted with one to three $L^{Sc}$ substituents independently selected from the group consisting of fluorine, chlorine, hydroxyl, oxo, $C_1$-$C_4$-alkyl, $C_1$-$C_4$-haloalkyl, $C_1$-$C_4$-alkoxy, $C_1$-$C_4$-haloalkoxy and $C_3$-$C_6$-cycloalkyl.

In the above formula (I), L is preferably a direct bond or a $C_1$-$C_6$-alkylene that may be substituted as described herein, even more preferably L is a direct bond, $-CH_2-$ or $-CF_2$-.

When L is a "direct bond", it means that the $R^6$ group is directly attached to the carbon atom to which the $R^5$ group is attached, thus forming a "$-CR^5R^6$-" moiety.

In the above formula (I), $R^6$ is preferably selected from the group consisting of non-aromatic $C_3$-$C_{12}$-carbocycle, aromatic $C_6$-$C_{14}$-carbocycle, non-aromatic 3- to 14-membered heterocycle, aromatic 5- to 14-membered heterocycle, aromatic $C_6$-$C_{14}$-carbocyclyloxy, $C_1$-$C_3$-alkoxy substituted by an aromatic $C_6$-$C_{14}$-carbocycle and aromatic $C_6$-$C_{14}$-carbocyclylsulfanyl.

When $R^6$ is a non-aromatic $C_3$-$C_{12}$-carbocycle, $R^6$ is preferably a $C_7$-$C_{12}$ bicyclic system comprising an aryl fused to a $C_3$-$C_8$-cycloalkyl, a $C_7$-$C_{12}$ bicyclic system comprising an aryl fused to a $C_3$-$C_8$-cycloalkenyl or a $C_9$-$C_{12}$ tricyclic system comprising a cyclopropyl connected through one common atom to a bicyclic system comprising an aryl fused to either a $C_3$-$C_8$-cycloalkyl or a $C_3$-$C_8$-cycloalkenyl.

Preferred $C_7$-$C_{12}$ bicyclic systems comprising an aryl fused to a $C_3$-$C_8$-cycloalkyl include indanyl, 1,2,3,4-tetrahydronaphthalenyl, bicyclo[4.2.0]octa-1,3,5-trienyl and bicyclo[4.2.0]octa-1(6),2,4-trienyl.

Preferred $C_7$-$C_{12}$ bicyclic systems comprising an aryl fused to a $C_3$-$C_8$-cycloalkenyl include indenyl and 1,2-dihydronaphthalenyl.

Preferred $C_9$-$C_{12}$ tricyclic system comprising a cyclopropyl connected through one common atom to a bicyclic system which comprises an aryl fused to either a $C_3$-$C_8$-cycloalkyl or a $C_3$-$C_8$-cycloalkenyl include spiro[cyclopropane-2,1'-indane]-1-yl and spiro[cyclopropane-2,1'-tetralin]-1-yl.

When $R^6$ is a non-aromatic $C_3$-$C_{12}$-carbocycle, $R^6$ is more preferably an indanyl or a 1,2,3,4-tetrahydronaphthalenyl, even more preferably $R^6$ is indan-5-yl.

When $R^6$ is an aromatic $C_6$-$C_{14}$-carbocycle, $R^6$ is preferably phenyl or naphthyl, more preferably phenyl or naphth-2-yl.

When $R^6$ is a non-aromatic 3- to 14-membered heterocycle, $R^6$ is typically a non-aromatic 6- to 14-membered polycyclic heterocycle, $R^6$ is preferably a non-aromatic bicyclic heterocycle comprising a 4- to 6-membered monocyclic non-aromatic heterocycle fused to an aryl, a non-aromatic bicyclic heterocycle comprising a 5- or 6-membered monocyclic heteroaryl fused to a monocyclic $C_3$-$C_8$-cycloalkyl, a non-aromatic bicyclic heterocycle comprising a 5- or 6-membered monocyclic heteroaryl fused to a 3- to 7-membered monocyclic non-aromatic heterocycle, a non-aromatic tricyclic heterocycle comprising a cyclopropyl connected through one common atom to a non-aromatic bicyclic heterocycle, said heterocycle comprising a 4- to 6-membered monocyclic non-aromatic heterocycle fused to an aryl (e.g. phenyl), or a non-aromatic tricyclic heterocycle comprising a cyclopropyl connected through one common atom to a non-aromatic bicyclic heterocycle comprising a 5- or 6-membered monocyclic heteroaryl fused to a monocyclic $C_3$-$C_8$-cycloalkyl.

Preferred non-aromatic bicyclic heterocycles comprising a 4- to 6-membered monocyclic non-aromatic heterocycle fused to an aryl include 2,3-dihydrobenzofuranyl, 2,3-dihydro-benzothiophenyl, indolinyl, 1,3-benzodioxolyl, 1,2,3,4-tetrahydroquinolinyl, chromanyl, isochromanyl, thiochromanyl and 2,3-dihydro-1,4-benzodioxinyl.

Preferred non-aromatic bicyclic heterocycles comprising a 5- or 6-membered monocyclic heteroaryl fused to a monocyclic $C_3$-$C_8$-cycloalkyl include 6,7-dihydro-5H-cyclopenta[b]pyridinyl, 5,6,7,8-tetrahydroquinolinyl, 4,5,6,7-tetrahydrobenzothiophenyl, 4,5,6,7-tetrahydrobenzofuranyl, 4,5,6,7-tetrahydro-1,3-benzoxazolyl, 4,5,6,7-tetrahydro-1,3-benzothiazolyl, 4,5,6,7-tetrahydro-1H-benzimidazolyl, 4,5,6,7-tetrahydro-1H-indazolyl, 4,5,6,7-tetrahydro-2H-isoindolyl, 4,5,6,7-tetrahydro-2-benzothiophenyl, 5,6-dihydro-4H-cyclopenta[b]thiophenyl and 5,6-dihydro-4H-cyclopenta[d]thiazolyl.

Preferred non-aromatic bicyclic heterocycles comprising a 5- or 6-membered monocyclic heteroaryl fused to a 3- to 7-membered monocyclic non-aromatic heterocycle include 4,5,6,7-tetrahydropyrazolo[1,5-a]pyridinyl, 5,6,7,8-tetrahydro-[1,2,4]triazolo[1,5-a]pyridinyl, 5,6,7,8-tetrahydroimidazo[1,2-a]pyridinyl and 6,7-dihydro-5H-thieno[3,2-b]pyranyl.

Preferred non-aromatic tricyclic heterocycles comprising a cyclopropyl connected through one common atom to a non-aromatic bicyclic heterocycle comprising a 4- to 6-membered monocyclic non-aromatic heterocycle fused to an aryl include spiro[chromane-3,1'-cyclopropane]-yl.

Preferred non-aromatic tricyclic heterocycles comprising a cyclopropyl connected through one common atom to a non-aromatic bicyclic heterocycle comprising a 5- or 6-membered monocyclic heteroaryl fused to a monocyclic $C_3$-$C_8$-cycloalkyl include include spiro[7,8-dihydro-5H-quinoline-6,1'-cyclopropane]-yl.

When $R^6$ is a non-aromatic 3- to 14-membered heterocycle, $R^6$ is more preferably a 4- to 6-membered monocyclic non-aromatic hererocycle fused to a phenyl (preferably selected from the group consisting of 2,3-dihydrobenzofuranyl, indolinyl, 1,3-benzodioxolyl, chromanyl, isochromanyl, thiochromanyl and 2,3-dihydro-1,4-benzodioxinyl) or a 5- or 6-membered monocyclic heteroaryl fused to a monocyclic $C_3$-$C_8$-cycloalkyl (preferably 5,6,7,8-tetrahydroquinolinyl or 4,5,6,7-tetrahydrobenzothiophenyl).

When $R^6$ is a non-aromatic 3- to 14-membered heterocycle, $R^6$ is even more preferably, 2,3-dihydrobenzofuran-5-yl, 2,3-dihydrobenzofuran-7-yl, indolin-5-yl, 1,3-benzodioxol-5-yl, chroman-6-yl, chroman-7-yl, isochroman-6-yl, isochroman-7-yl thiochroman-6-yl, thiochroman-7-yl, 2,3-dihydro-1,4-benzodioxin-5-yl, 2,3-dihydro-1,4-benzodioxin-6-yl, 5,6,7,8-tetrahydroquinolin-2-yl, 5,6,7,8-tetrahydroquinolin-3-yl or 4,5,6,7-tetrahydrobenzothiophen-3-yl, more specifically 2,3-dihydrobenzofuran-5-yl or 2,3-dihydro-1,4-benzodioxin-6-yl.

When $R^6$ is an aromatic 5- to 14-membered heterocycle, $R^6$ is preferably an aromatic 5- or 6-membered monocyclic heterocycle, a 9- or 10-membered aromatic bicyclic heterocycle comprising a 5- or 6-membered monocyclic aromatic heterocycle fused to an aryl or a 9- or 10-membered aromatic bicyclic heterocycle comprising two fused 5- or 6-membered monocyclic aromatic heterocycles.

Preferred aromatic 5- or 6-membered monocyclic heterocycles include furanyl, thienyl, pyrazolyl, imidazolyl, triazolyl, oxazolyl, oxadiazolyl, thiazolyl, thiadiazolyl, pyridinyl, pyridazinyl and pyrimidinyl.

Preferred 9- or 10-membered aromatic bicyclic heterocycles comprising an aromatic 5- or 6-membered monocyclic heterocycle fused to an aryl (phenyl) include indolyl, benzimadazolyl, indazolyl, benzofuranyl, benzothiophenyl, benzothiazolyl (e.g. 1,3-benzothiazolyl, 2,1-benzothiazolyl, 1,2-benzothiazolyl), benzoxazolyl (e.g. 1,3-benzoxazolyl, 2,1-benzoxazolyl, 1,2-benzoxazolyl), quinolinyl, isoquinolinyl and quinoxalinyl.

Preferred 9- or 10-membered aromatic bicyclic heterocycles comprising two fused 5- or 6-membered monocyclic aromatic heterocycles include pyrrolo[2,3-b]pyridin-3-yl, imidazo[1,2-a]pyridinyl, [1,2,4]triazolo[4,3-a]pyridinyl, thieno[3,2-b]pyrrol-6-yl, thieno[3,2-b]thiophenyl, imidazo[2,1-b]oxazolyl, furo[2,3-d]isoxazolyl and thieno[2,3-d]isothiazolyl.

When $R^6$ is an aromatic 5- to 14-membered heterocycle, $R^6$ is more preferably an aromatic 5- or 6-membered monocyclic heterocycle selected from the group consisting of furanyl, thienyl, and pyridinyl, a 9- or 10-membered aromatic bicyclic heterocycle comprising a 5- or 6-membered monocyclic aromatic heterocycle fused to an aryl selected from the group consisting of indolyl, benzofuranyl, benzothiophenyl or pyrrolo[2,3-b]pyridin-3-yl.

When $R^6$ is an aromatic 5- to 14-membered heterocycle, $R^6$ is even more preferably furan-2-yl, furan-3-yl, thien-2-yl, thien-3-yl, pyridin-2-yl, indol-3-yl, indol-5-yl, benzofuran-2-yl, benzothio-phen-3-yl, or pyrrolo[2,3-b]pyridin-3-yl, more specifically $R^6$ is pyridin-2-yl, furan-2-yl, furan-3-yl, thien-2-yl, thien-3-yl, benzofuran-2-yl, benzothiophen-3-yl, or indol-3-yl.

When $R^6$ is an aromatic $C_6$-$C_{14}$-carbocyclyloxy, $R^6$ is preferably phenoxy.

When $R^6$ is a $C_1$-$C_3$-alkoxy substituted by an aromatic $C_6$-$C_{14}$-carbocycle, $R^6$ is preferably a $C_1$-$C_3$-alkoxy substituted by a phenyl, more preferably benzyloxy.

When $R^6$ is a $C_1$-$C_3$-haloalkoxy substituted by an aromatic $C_6$-$C_{14}$-carbocycle, $R^6$ is preferably a $C_1$-$C_3$-haloalkoxy substituted by phenyl, more preferably—$OCF_2$-phenyl.

When $R^6$ is an aromatic $C_6$-$C_{14}$-carbocyclylsulfanyl, $R^6$ is preferably phenylsulfanyl In some embodiments, $R^6$ is selected from the group consisting of indanyl, 1,2,3,4-tetrahydronaphthalenyl, spiro[cyclopropane-1,2'-indane]-1-yl, phenyl, naphthyl, 2,3-dihydrobenzofuranyl, indolinyl, 1,3-benzodioxolyl, chromanyl, isochromanyl, thiochromanyl, 2,3-dihydro-1,4-benzodioxinyl, 5,6,7,8-tetrahydroquinolinyl, 4,5,6,7-tetrahydrobenzothiophenyl, furanyl, thienyl, pyridinyl, pyrimidinyl, indolyl, benzofuranyl, benzothiophenyl, benzoxazolyl, quinolinyl, isoquinolinyl, pyrrolo[2,3-b]pyridin-3-yl, phenoxy, benzyloxy and phenylsulfanyl.

In the above formula (I), $R^6$ is more preferably selected from the group consisting of non-aromatic $C_3$-$C_{12}$-carbocycle (e.g. indan-5-yl) aromatic $C_6$-$C_{14}$-carbocycle (e.g. phenyl or 2-naphthyl) and aromatic 5- to 14-membered heterocycle (e.g. 2-furyl, 2-thienyl, indol-3-yl).

In some embodiments, $R^6$ is selected from the group consisting of indanyl, phenyl, naphthyl, furanyl, thienyl and indolyl.

Preferably $R^6$ is selected from the group consisting of non-aromatic $C_5$-$C_{10}$-carbocycle, phenyl, naphthyl, non-aromatic 5- to 10-membered heterocycle, aromatic 5- to 10-membered heterocycle, non-aromatic $C_5$-$C_{10}$-carbocyclyloxy, phenoxy, naphthyloxy, aromatic 5- to 10-membered heterocyclyloxy, non-aromatic 5- to 10-membered heterocyclyloxy and phenylsulfanyl.

More preferably $R^6$ is selected from the group consisting of indanyl, phenyl, naphthyl, 2,3-dihydrobenzofuranyl, 1,3-benzodioxolyl, furanyl, thienyl, pyridinyl, indolyl, benzofuranyl, benzothiophenyl, pyrrolo[2,3-b]pyridin-3-yl, phenoxy, benzyloxy and phenylsulfanyl.

Even more preferably $R^6$ is selected from the group consisting of indanyl, 1,2,3,4-tetrahydronaphthalenyl, phenyl, naphthyl, 2,3-dihydrobenzofuranyl, 2,3-dihydro-1,4-benzodioxinyl, thienyl, pyridinyl, indolyl, benzofuranyl, benzothiophenyl and phenoxy, In some embodiments, $R^6$ is

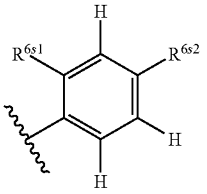

or

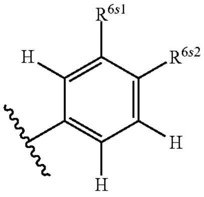

wherein $R^{6s1}$ is hydrogen or $R^{6s}$, $R^{6s2}$ is hydrogen or $R^{6s}$, $R^{6s}$ being as described herein (above or below), preferably at least one of $R^{6s1}$ and $R^{6s2}$ is different from hydrogen.

$R^6$ groups as disclosed herein may be substituted with one or more $R^{6S}$ substituents as disclosed herein above or as disclosed herein below.

$R^6$ groups as disclosed herein may be substituted preferably with one to three $R^{6S}$ substituents as disclosed herein above or as disclosed herein below that may be the same or different.

$R^6$ groups as disclosed herein may be substituted more preferably with one to three $R^{6S}$ substituents as disclosed herein above or as disclosed herein below that may be the same or different.

$R^6$ groups as disclosed herein may be substituted even more preferably with one or two $R^{6S}$ substituents as disclosed herein above or as disclosed herein below that may be the same or different.

In some embodiments, $R^6$ is substituted with one or more $R^{6S}$ substituents as disclosed herein above or as disclosed herein below that may be the same or different.

$R^{6S}$ substituents are preferably selected from the group consisting of halogen, nitro, cyano, hydroxyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-alkynyl, $C_1$-$C_6$-haloalkylsulfanyl, $C_3$-$C_8$-cycloalkyl (e.g. cyclopropyl, cyclobutyl, cyclopentyl, cyclohexyl), aromatic $C_6$-$C_{14}$-carbocycle (e.g. phenyl), aromatic 5- or 6-membered monocyclic heterocycle (e.g. pyridinyl, pyrimidinyl, thienyl, furanyl, imidazolyl, triazolyl, pyrazolyl, oxazolyl, thiazolyl, preferably pyridinyl, pyrazolyl, imidazolyl, triazolyl) and non-aromatic 3- to 7-membered monocyclic heterocycle (e.g. oxetanyl, tetrahydrofuranyl, tetrahydropyranyl (oxanyl), pyrrolidinyl, azetidinyl, morpholinyl, preferably oxetanyl, tetrahydrofuranyl, tetrahydropyranyl (oxanyl)), wherein cyclic $R^{6S}$ substituents may be substituted with one or more substituents independently selected from the group consisting of halogen, $C_1$-$C_6$-alkyl, $C_1$-$C_6$-haloalkyl and $C_1$-$C_6$-alkoxycarbonyl.

$R^{6S}$ substituents are more preferably selected from the group consisting of halogen (e.g. chlorine, bromine, fluorine), nitro, hydroxyl, $C_1$-$C_6$-alkyl (e.g. methyl, isopropyl), $C_1$-$C_6$-haloalkyl (e.g. $CF_3$, $CHF_2$), $C_1$-$C_6$-alkoxy (e.g. methoxy), $C_1$-$C_6$-haloalkoxy (e.g. difluoromethoxy, trifluoromethoxy), $C_2$-$C_6$-alkenyl (e.g. prop-1-en-2-yl), $C_2$-$C_6$-alkynyl (e.g. ethynyl), $C_1$-$C_6$-haloalkylsulfanyl (e.g. —$SCF_3$), cyclopropyl, cyclobutyl, cyclopentyl, pyridin-3-yl, oxetan-3-yl, and tetrahydrofuran-3-yl, wherein cyclic $R^{6S}$ substituents may be substituted with one or more substituents independently selected from the group consisting of halogen (e.g. chlorine), $C_1$-$C_6$-alkyl (e.g. methyl), $C_1$-$C_6$-haloalkyl (e.g. $CF_3$) and $C_1$-$C_6$-alkoxycarbonyl (e.g. methoxycarbonyl).

$R^{6S}$ substituents are likewise more preferably selected from the group consisting of halogen, nitro, hydroxyl, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-alkynyl, $C_1$-$C_4$-haloalkylsulfanyl, cyclopropyl, cyclobutyl, cyclopentyl, pyridinyl, oxetanyl and tetrahydrofuranyl, wherein cyclic $R^{6S}$ substituents may be substituted with one or two substituents independently selected from the group consisting of halogen, $C_1$-$C_4$-alkyl, $C_1$-$C_4$-haloalkyl and $C_1$-$C_4$-alkoxycarbonyl. $R^{6S}$ substituents are even more preferably selected from the group consisting of chlorine, bromine, nitro, hydroxyl, $C_1$-$C_4$-alkyl, $C_1$-$C_4$-haloalkyl, $C_1$-$C_4$-alkoxy, difluoromethoxy, trifluoromethoxy, $C_2$-$C_4$-alkenyl, $C_2$-$C_4$-alkynyl, difluoromethylsulfanyl, trifluoromethylsulfanyl, cyclopropyl, cyclobutyl, cyclopentyl, pyridinyl, oxetanyl and tetrahydrofuranyl.

Non-limiting examples of suitable -L-$R^6$ groups include any of the -L-$R^6$ groups disclosed in column "-L-$R^6$" of Table 1.

In the above formula (I), when L represents a direct bond, $R^6$ is preferably selected from the group consisting of non-aromatic $C_3$-$C_{12}$-carbocycle, aromatic $C_6$-$C_{14}$-carbocycle and aromatic 5- to 14-membered heterocycle, more preferably $R^6$ is selected from the group consisting of indanyl, phenyl, naphtyl, furanyl, thienyl, pyridyl, dihydrobenzofuranyl, benzofuranyl, benzothiophenyl, chromanyl, isochromanyl, quinolinyl, isoquinolinyl and indolyl.

In the above formula (I), when L represents a direct bond, $R^6$ is even more preferably selected from the group consisting of indan-5-yl, phenyl, naphtyl, furan-2-yl, furan-3-yl, pyridin-2-yl, thien-2-yl, thien-3-yl, benzofuran-2-yl, benzothiophen-3-yl, and indol-3-yl.

In the above formula (I), when L represents a $C_1$-$C_6$-alkylene, $R^6$ is preferably selected from the group consisting of an aromatic $C_6$-$C_{14}$-carbocycle (e.g. phenyl) and aromatic 5- to 14-membered heterocycle (pyridine, thienyl).

In the above formula (I), when L represents a $C_1$-$C_4$-alkylene, $R^6$ is more preferably selected from the consisting of phenyl, thienyl, furanyl, pyrazolyl, pyridinyl and pyrimidinyl.

In the above formula (I), $R^7$ is preferably selected from the group consisting of halogen, cyano, $C_1$-$C_6$-alkyl, $C_1$-$C_6$-haloalkyl, $C_1$-$C_6$-hydroxyalkyl, $C_1$-$C_6$-alkylcarbonyl, $C_1$-$C_6$-alkoxy, $C_2$-$C_6$-alkenyl, $C_2$-$C_6$-alkynyl, $C_1$-$C_6$-alkylsulfanyl, $C_1$-$C_6$-alkylsulfonyl, $C_3$-$C_8$-cycloalkyl, aromatic 5- or 6-membered monocyclic heterocycle, non-aromatic 3- to 7-membered monocyclic heterocycle, —$N(R^e)_2$, —$C(=NR^f)R^f$ and —$C(=O)N(R^g)_2$, with $R^e$ being as disclosed above, preferably $R^e$ is independently selected from the group consisting of hydrogen, $C_1$-$C_6$-alkyl and $C_3$-$C_8$-cycloalkyl (e.g. cyclopropyl), with $R^f$ being as disclosed above, preferably $R^f$ is independently selected from the group consisting of $C_1$-$C_6$-alkyl and $C_1$-$C_6$-alkoxy, with $R^g$ being as disclosed above, preferably $R^g$ is independently selected from the group consisting of hydrogen, $C_1$-$C_6$-alkyl and $C_3$-$C_8$-cycloalkyl.

When $R^7$ is a $C_3$-$C_8$-cycloalkyl, $R^7$ is preferably a cyclopropyl.

When $R^7$ is an aromatic 5- or 6-membered monocyclic heterocycle, $R^7$ is preferably selected from the group consisting of pyridinyl, pyrimidinyl, thienyl, furanyl, imidazolyl, triazolyl, pyrazolyl, oxazolyl and thiazolyl, more preferably pyridinyl (e.g. pyridin-4-yl), thiazolyl (e.g. thiazol-5-yl), imidazolyl (e.g. imidazol-1-yl) and pyrazolyl (e.g. pyrazol-1-yl).

When $R^7$ is a non-aromatic 3- to 7-membered monocyclic heterocycle, $R^7$ is preferably selected from the group consisting of oxiranyl, oxetanyl, tetrahydrofuranyl, tetrahydropyranyl, pyrrolidinyl, azetidinyl, aziridinyl, morpholinyl and 2-oxa-6-azaspiro[3.3]heptanyl, more preferably oxetanyl (e.g. oxetan-3-yl), tetrahydrofuranyl (e.g. tetrahydrofuran-3-yl), tetrahydropyranyl (e.g. tetrahydropyran-4-yl), pyrrolidinyl (e.g. pyrrolidin-1-yl) and azetidinyl (e.g. azetidin-1-yl).

When $R^7$ is a non-aromatic 3- to 7-membered monocyclic heterocycle, $R^7$ is more preferably selected from the group consisting of oxetanyl, tetrahydrofuranyl and pyrrolidinyl.

When $R^7$ is —$N(R^e)_2$, $R^7$ is preferably methylamino or cyclopropylamino.

When $R^7$ is —$C(=NR^f)R^f$, $R^7$ is preferably 1-(methoxyimino)ethyl.

When $R^7$ is —$C(=O)N(R^g)_2$, $R^g$ is preferably independently selected from the group consisting of hydrogen, and cyclopropyl.

$R^7$ is more preferably selected from the group consisting of hydrogen, halogen, cyano, $C_1$-$C_4$-alkyl, $C_1$-$C_4$-haloalkyl, $C_1$-$C_4$-hydroxyalkyl, $C_1$-$C_4$-alkylcarbonyl, $C_1$-$C_4$-alkoxy, $C_2$-$C_4$-alkenyl, $C_2$-$C_4$-alkynyl, $C_1$-$C_4$-alkylsulfanyl, $C_1$-$C_4$- alkenylsulfanyl, $C_1$-$C_4$-alkylsulfonyl, $C_3$-$C_6$-cycloalkyl, pyridinyl, imidazolyl, pyrazolyl, thiazolyl, oxetanyl, tetrahydrofuranyl, pyrrolidinyl, —N($R^e$)$_2$, —C(═N$R^f$)$R^f$ and —C(═O)N($R^g$)$_2$, with $R^e$ being independently selected from the group consisting of hydrogen, $C_1$-$C_4$-alkyl and $C_3$-$C_6$-cycloalkyl, with $R^f$ being independently selected from the group consisting of $C_1$-$C_4$-alkyl and $C_1$-$C_4$-alkoxy, with $R^g$ being independently selected from the group consisting of hydrogen, $C_1$-$C_4$-alkyl and $C_3$-$C_6$-cycloalkyl.

More preferred aliphatic $R^7$, $R^e$ and $R^g$ substituents as disclosed herein may be substituted with one to three $R^{7Sa}$ substituents independently selected from the group consisting of hydroxyl, $C_1$-$C_4$-alkoxy and $C_3$-$C_6$-cycloalkyl.

More preferred cyclic $R^7$, $R^e$ and $R^g$ substituents as disclosed herein may be substituted with one to three $R^{7Sc}$ substituents independently selected from the group consisting of halogen, hydroxyl, $C_1$-$C_4$-alkyl and $C_1$-$C_4$-alkoxy.

$R^7$ is even more preferably selected from the group consisting of halogen, cyano, $C_1$-$C_4$-alkyl, $C_1$-$C_4$-haloalkyl, $C_1$-$C_4$-hydroxyalkyl, $C_1$-$C_4$-alkylcarbonyl, $C_1$-$C_4$-alkoxy, $C_3$-$C_6$-cycloalkyl, pyridinyl, imidazolyl, pyrazolyl and thiazolyl, Even more preferred aliphatic $R^7$ substituents as disclosed herein may be substituted with one or two $R^{7Sa}$ substituents independently selected from the group consisting of cyano, $C_1$-$C_4$-alkoxy, $C_3$-$C_6$-cycloalkyl and —Si($C_1$-$C_6$-alkyl)$_3$.

More preferred cyclic $R^7$ substituents as disclosed herein may be substituted with one or two $R^{7Sc}$ substituents independently selected from the group consisting of fluorine, chlorine, hydroxyl, $C_1$-$C_4$-alkyl and $C_1$-$C_4$-alkoxy.

Preferred aliphatic $R^7$, $R^e$ substituents as disclosed herein may be substituted with one or more $R^{7Sa}$ substituents that may be the same or different as disclosed herein above or as disclosed herein below. $R^{7Sa}$ substituents are preferably selected from the group consisting of hydroxyl, $C_1$-$C_6$-alkoxy (e.g. methoxy, ethoxy), $C_3$-$C_8$-cycloalkyl (e.g. cyclobutyl), $C_1$-$C_6$-alkoxycarbonyl (e.g. ethoxycarbonyl) and aromatic $C_6$-$C_{14}$-carbocycle (e.g. phenyl), more preferably $C_1$-$C_6$-alkoxy.

Most preferably $R^{7Sa}$ substituents are $C_1$-$C_4$-alkoxy.

In some embodiments, $R^7$ is an unsubstituted $C_1$-$C_6$-alkenyl or a $C_1$-$C_6$-alkenyl substituted by a $C_1$-$C_6$-alkoxy.

Preferred cyclic $R^7$ and $R^e$ substituents as disclosed herein may be substituted with one or more $R^{7Sc}$ substituents that may be the same or different as disclosed herein above or as disclosed herein below. Preferred cyclic $R^7$ and $R^e$ substituents as disclosed herein may be substituted with one or more $R^{7Sc}$ substituents that may be the same or different as disclosed herein above or as disclosed herein below. $R^{7Sc}$ substituents are preferably selected from the group consisting of halogen (e.g. fluorine, chlorine), hydroxyl, $C_1$-$C_6$-alkyl (e.g. methyl) and $C_1$-$C_6$-alkoxy (e.g. methoxy), more preferably chlorine.

In some embodiments, $R^7$ is an unsubstituted pyridinyl (e.g. pyridin-4-yl) or a pyridinyl substituted by a halogen atom (e.g. chlorine).

Non-limiting examples of suitable $R^7$ include any of the $R^7$ groups listed in column "$R^7$" of Table 1.

In the above formula (I), $R^8$ is preferably selected from the group consisting of hydrogen, halogen, hydroxyl, $C_1$-$C_6$-alkyl, $C_1$-$C_6$-haloalkyl, $C_1$-$C_6$-alkoxy, $C_2$-$C_6$-alkenyl, $C_1$-$C_6$-alkylsulfanyl, $C_1$-$C_6$-haloalkylsulfanyl, $C_1$-$C_6$-alkylsulfinyl, $C_1$-$C_6$-alkylsulfonyl, $C_3$-$C_8$-cycloalkyl, aromatic $C_6$-$C_{14}$-carbocycle, non-aromatic 3- to 14-membered heterocycle, aromatic 5- to 14-membered heterocycle, $C_3$-$C_8$-cycloalkyloxy, non-aromatic 3- to 14-membered heterocyclyloxy and —N($R^h$)$_2$, with $R^h$ being as disclosed above, preferably $R^h$ is independently selected from the group consisting of hydrogen, $C_1$-$C_6$-alkyl, $C_1$-$C_6$-haloalkyl, $C_2$-$C_6$-alkenyl, $C_3$-$C_8$-cycloalkyl (e.g. cyclopropyl, cyclohexyl), aromatic $C_6$-$C_{14}$-carbocycle (e.g. phenyl) and non-aromatic 3- to 7-membered monocyclic heterocycle (e.g. oxetanyl).

Preferred aliphatic $R^8$ and $R^h$ substituents as disclosed herein may be substituted with one to three $R^{8Sa}$ substituents preferably independently selected from the group consisting of hydroxyl, carboxyl, $C_1$-$C_4$-alkoxy, $C_1$-$C_4$-alkoxycarbonyl, $C_3$-$C_6$-cycloalkyl, $C_1$-$C_4$-alkylsulfanyl and non-aromatic 3- to 7-membered monocyclic heterocycle.

Preferred cyclic $R^8$ and $R^h$ substituents may be substituted with one to three $R^{8Sc}$ substituents preferably independently selected from the group consisting of oxo, halogen, cyano, hydroxyl, $C_1$-$C_4$-alkyl, $C_1$-$C_4$-haloalkyl, $C_1$-$C_4$-alkoxy, $C_1$-$C_4$-alkoxycarbonyl, $C_3$-$C_6$-cycloalkyl and non-aromatic 3- to 7-membered monocyclic heterocycle or two $R^{8Sc}$ substituents form together with the carbon atom to which they are attached to a non-aromatic 3- to 7-membered monocyclic heterocycle.

When $R^8$ is a $C_3$-$C_8$-cycloalkyl, $R^8$ is preferably a cyclopropyl or cyclopentyl.

When $R^8$ is an aromatic $C_6$-$C_{14}$-carbocycle, $R^8$ is preferably phenyl.

When $R^8$ is a non-aromatic 3- to 14-membered heterocycle, $R^8$ is preferably a non-aromatic 3- to 7-membered monocyclic heterocycle.

Preferred non-aromatic 3- to 7-membered monocyclic heterocycles include oxiranyl, aziridinyl, oxetanyl, azetidinyl, tetrahydrofuranyl, pyrrolidinyl, tetrahydropyranyl (oxanyl) and morpholinyl.

When $R^8$ is a non-aromatic 3- to 14-membered heterocycle, $R^8$ is more preferably selected from the group consisting of oxetanyl, azetidinyl, pyrrolidinyl, tetrahydropyranyl and morpholinyl.

When $R^8$ is a non-aromatic 3- to 14-membered heterocycle, $R^8$ is even more preferably selected from the group consisting of oxetanyl, azetidinyl and pyrrolidinyl.

When $R^8$ is a non-aromatic 3- to 14-membered heterocycle, $R^8$ is most preferably selected from the group consisting of oxetan-3-yl, azetidin-1-yl and pyrrolidin-1-yl.

When $R^8$ is an aromatic 5- to 14-membered heterocycle, $R^8$ is preferably a 5- or 6-membered aromatic monocyclic heterocycle.

Preferred 5- or 6-membered aromatic monocyclic heterocycles include furanyl, thienyl, pyrazolyl, imidazolyl, triazolyl, oxazolyl, thiazolyl, pyridinyl and pyrimidinyl.

When $R^8$ is an aromatic 5- to 14-membered heterocycle, $R^8$ is more preferably selected from the group consisting of pyrazolyl, imidazolyl, thiazolyl and pyridinyl.

When $R^8$ is an aromatic 5- to 14-membered heterocycle, $R^8$ is even more preferably selected from the group consisting of pyrazolyl, thiazolyl and pyridinyl.

When $R^8$ is an aromatic 5- to 14-membered heterocycle, $R^8$ is most preferably selected from the group consisting of pyrazol-1-yl, thiazol-4-yl and pyridin-4-yl.

When $R^8$ is a $C_3$-$C_8$-cycloalkyloxy, $R^8$ is preferably a cyclopropyloxy.

When $R^8$ is a non-aromatic 3- to 14-membered heterocyclyloxy, $R^8$ is preferably a non-aromatic 3- to 7-membered monocyclic heterocyclyloxy.

Preferred non-aromatic 3- to 7-membered monocyclic heterocyclyloxy include oxetanyloxy and azetidinyloxy.

When $R^8$ is a non-aromatic 3- to 14-membered heterocyclyloxy, $R^8$ is more preferably oxetan-3-yloxy or azetidin-3-yloxy.

When $R^8$ is $N(R^h)_2$, $R^h$ is preferably independently selected from the group consisting of hydrogen, $C_1$-$C_6$-alkyl (e.g. methyl, ethyl, propyl, isobutyl), $C_1$-$C_6$-haloalkyl (e.g trifluoropropyl), $C_2$-$C_6$-alkenyl (e.g. buten-3-en-2-yl), $C_3$-$C_8$-cycloalkyl (e.g. cyclopropyl, cyclohexyl), aromatic $C_6$-$C_{14}$-carbocycle (e.g. phenyl) and non-aromatic 3- to 7-membered monocyclic heterocycle (e.g. oxetanyl).

When $R^8$ is $N(R^h)_2$, $R^h$ is more preferably independently selected from the group consisting of hydrogen, $C_1$-$C_4$-alkyl, $C_1$-$C_4$-haloalkyl, $C_2$-$C_4$-alkenyl, $C_3$-$C_6$-cycloalkyl and non-aromatic 3- to 7-membered monocyclic heterocycle.

In the above formula (I), $R^8$ is more preferably selected from the group consisting of hydrogen, halogen, hydroxyl, $C_1$-$C_4$-alkyl, $C_1$-$C_4$-haloalkyl, $C_1$-$C_4$-alkoxy, $C_2$-$C_4$-alkenyl, $C_1$-$C_4$-alkylsulfanyl, $C_1$-$C_4$-haloalkylsulfanyl, $C_1$-$C_4$-alkylsulfinyl, $C_1$-$C_4$-alkylsulfonyl, $C_3$-$C_6$-cycloalkyl, phenyl, naphthyl, oxetanyl, azetidinyl, tetrahydrofuranyl, pyrrolidinyl, tetrahydropyranyl, piperidinyl, piperazinyl, morpholinyl, furanyl, thienyl, pyrrolyl, pyrazolyl, thiazolyl, imidazolyl, oxazolyl, isoxazolyl, pyridinyl, pyrimidinyl, $C_3$-$C_6$-cycloalkyloxy and —$N(R^h)_2$, with $R^h$ being independently selected from the group consisting of hydrogen, $C_1$-$C_4$-alkyl, $C_1$-$C_4$-haloalkyl, $C_2$-$C_4$-alkenyl, $C_3$-$C_6$-cycloalkyl, phenyl, oxetanyl, azetidinyl, pyrrolidinyl and tetrahydrofuranyl.

More preferred aliphatic $R^8$ and $R^h$ substituents as disclosed herein may be substituted with one or two $R^8$ substituents independently selected from the group consisting of hydroxyl, $C_1$-$C_4$-alkoxy, $C_1$-$C_4$-alkoxycarbonyl, $C_3$-$C_6$-cycloalkyl, $C_1$-$C_4$-alkylsulfanyl oxetanyl, azetidinyl, pyrrolidinyl and tetrahydrofuranyl.

More preferred cyclic $R^8$ and $R^h$ substituents may be substituted with one or two $R^{8Sc}$ substituents independently selected from the group consisting of oxo, fluorine, chlorine, hydroxyl, $C_1$-$C_4$-alkyl, $C_1$-$C_4$-haloalkyl, $C_1$-$C_4$-alkoxy, $C_3$-$C_6$-cycloalkyl, oxetanyl, azetidinyl, pyrrolidinyl and tetrahydrofuranyl In the above formula (I), $R^8$ is even more preferably selected from the group consisting of hydrogen, halogen, $C_1$-$C_4$-alkyl, $C_1$-$C_4$-alkoxy, $C_1$-$C_4$-alkylsulfanyl, $C_3$-$C_6$-cycloalkyl, oxetanyl, azetidinyl, pyrrolidinyl, pyrazolyl, thiazolyl, pyridinyl and —$N(R^h)_2$, with $R^h$ being independently selected from the group consisting of hydrogen, $C_1$-$C_4$-alkyl, $C_1$-$C_4$-haloalkyl, $C_2$-$C_4$-alkenyl, $C_3$-$C_6$-cycloalkyl, oxetanyl, azetidinyl, pyrrolidinyl and tetrahydrofuranyl In the above formula (I), $R^8$ is most preferably selected from the group consisting of hydrogen, halogen, $C_1$-$C_4$-alkyl, $C_1$-$C_4$-haloalkyl, $C_1$-$C_4$-alkoxy, $C_3$-$C_6$-cycloalkyloxy and —$N(R^h)_2$, with $R^h$ being independently selected from the group consisting of hydrogen, $C_1$-$C_4$-alkyl, $C_1$-$C_4$-haloalkyl, $C_2$-$C_4$-alkenyl, and $C_3$-$C_6$-cycloalkyl.

Most preferred aliphatic $R^8$ and $R^h$ substituents may be substituted with one or two $R^{8Sa}$ substituents independently selected from the group consisting of hydroxyl, methoxy and ethoxy.

Most preferred cyclic or cyclic moiety of $R^8$ and cyclic $R^h$ substituents may be substituted with one or two $R^{8Sc}$ substituents independently selected from the group consisting of fluorine, methyl, ethyl and cyclopropyl.

In some embodiments, $R^8$ is selected from the group consisting of hydrogen, halogen, hydroxyl, $C_1$-$C_6$-alkyl, $C_1$-$C_6$-haloalkyl, $C_1$-$C_6$-alkoxy, $C_2$-$C_6$-alkenyl, $C_1$-$C_6$-alkylsulfanyl, $C_1$-$C_6$-haloalkylsulfanyl, $C_1$-$C_6$-alkylsulfinyl, $C_1$-$C_6$-alkylsulfonyl, cyclopropyl, cyclobutyl, cyclopentyl, phenyl, oxetanyl, azetidinyl, pyrrolidinyl, tetrahydropyranyl, morpholinyl, pyrazolyl, imidazolyl, thiazolyl, pyridinyl, cyclopropyloxy, oxetanyloxy, azetidinyloxy and —$N(R^h)_2$ with $R^h$ being preferably independently selected from the group consisting of hydrogen, $C_1$-$C_6$-alkyl, $C_2$-$C_6$-alkenyl, $C_3$-$C_8$-cycloalkyl (e.g. cyclopropyl, cyclohexyl), aromatic $C_6$-$C_{14}$-carbocycle (e.g. phenyl) and non-aromatic 3- to 7-membered monocyclic heterocycle (e.g. oxetanyl), In the above formula (I), $R^8$ is more preferably selected from the group consisting of hydrogen, halogen, $C_1$-$C_6$-alkyl, $C_1$-$C_6$-alkoxy and —$N(R^h)_2$ with $R^h$ being independently selected from the group consisting of hydrogen, $C_1$-$C_6$-alkyl and $C_3$-$C_8$-cycloalkyl.

Preferred aliphatic $R^8$ and $R^h$ substituents as disclosed herein may be substituted with one or more $R^{8Sa}$ substituents as disclosed herein above or as disclosed herein below.

$R^{8Sa}$ substituents are preferably selected from the group consisting of hydroxyl, carboxyl, $C_1$-$C_6$-alkoxy (e.g. methoxy), $C_1$-$C_6$-alkoxycarbonyl (e.g. methoxycarbonyl), $C_3$-$C_8$-cycloalkyl (e.g. cyclopropyl), $C_1$-$C_6$-alkylsulfanyl (e.g. methylsulfanyl, non-aromatic 3- to 7-membered monocyclic heterocycle (e.g. 1,3-dioxolanyl)

Preferred cyclic $R^8$ and $R^h$ substituents may be substituted with one or more $R^{8Sc}$ substituents that may be the same or different as disclosed herein above or below.

$R^{8Sc}$ substituents are preferably selected from the group consisting of oxo, halogen (e.g. chlorine), cyano, hydroxyl, $C_1$-$C_6$-alkyl (e.g. methyl), $C_1$-$C_6$-haloalkyl (e.g. difluoromethyl), $C_1$-$C_6$-alkoxy (e.g. methoxy), $C_1$-$C_6$-alkoxycarbonyl (e.g. ethoxycarbonyl, propyloxycarbonyl), $C_3$-$C_8$-cycloalkyl (e.g. cyclopropyl) and non-aromatic 3- to 7-membered monocyclic heterocycle (e.g. oxolanyl, oxetanyl, tetrahydrofuranyl) or two $R^{8Sc}$ substituents form together with the carbon atom to which they are attached to a non-aromatic 3- to 7-membered monocyclic heterocycle (e.g. oxetanyl).

$R^{8Sc}$ substituents are more preferably selected from the group consisting of oxo, $C_1$-$C_4$-alkyl, $C_1$-$C_4$-haloalkyl, $C_1$-$C_4$-alkoxy, $C_3$-$C_6$-cycloalkyl and non-aromatic 4- to 7-membered monocyclic heterocycle or two $R^{8Sc}$ substituents form together with the carbon atom to which they are attached to a non-aromatic 4- to 7-membered monocyclic heterocycle.

Non-limiting examples of suitable $R^8$ include any of the $R^8$ groups listed in column "$R^8$" of Table 1.

In the above formula (I), when Q is an aromatic $C_6$-$C_{14}$-carbocycle, Q is preferably phenyl or naphthyl, more preferably phenyl.

In the above formula (I), when Q is a non-aromatic $C_3$-$C_{12}$-carbocycle, Q is preferably a $C_7$-$C_{12}$ bicyclic system comprising an aryl fused to a $C_3$-$C_8$-cycloalkyl or a $C_7$-$C_{12}$ bicyclic system comprising an aryl fused to a $C_3$-$C_8$-cycloalkenyl.

Preferred $C_7$-$C_{12}$ bicyclic systems comprising an aryl fused to a $C_3$-$C_8$-cycloalkyl include bicyclo[4.2.0]octa-1,3,5-trienyl, indanyl and 1,2,3,4-tetrahydronaphthalenyl.

Preferred $C_7$-$C_{12}$ bicyclic systems comprising an aryl fused to a $C_3$-$C_8$-cycloalkenyl include indenyl and dihydronaphthalenyl.

When Q is a non-aromatic $C_3$-$C_{12}$-carbocycle, Q is more preferably a $C_7$-$C_{12}$ bicyclic system comprising an aryl (e.g. phenyl) fused to a $C_3$-$C_8$-cycloalkyl, even more preferably a bicyclo[4.2.0]octa-1,3,5-trienyl, more specifically 3-bicyclo[4.2.0]octa-1,3,5-trienyl, indan-4-yl and indan-5-yl.

In the above formula (I), when Q is a non-aromatic 3- to 14-membered heterocycle, Q is typically a non-aromatic 6- to 14-membered bicyclic heterocycle, preferably Q is a non-aromatic bicyclic heterocycle comprising a 4- to 6-membered monocyclic non-aromatic hererocycle fused to an aryl or a non-aromatic bicyclic heterocycle comprising a 5- or 6-membered monocyclic heteroaryl fused to a monocyclic $C_3$-$C_8$-cycloalkyl.

Preferred non-aromatic bicyclic heterocycles comprising a 4- to 6-membered monocyclic non-aromatic hererocycle fused to an aryl include 2,3-dihydrobenzofuranyl, 1,3-dihydroisobenzofuranyl, indolinyl, 1,3-benzodioxolyl, chromanyl, 2,3-dihydro-1,4-benzodioxinyl and [1,3]dioxolo[4,5-b]pyridinyl.

Preferred non-aromatic bicyclic heterocycles comprising a 5- or 6-membered monocyclic heteroaryl fused to a monocyclic $C_3$-$C_8$-cycloalkyl include 5,6,7,8-tetrahydroquinolinyl and 6,7-dihydro-5H-cyclopenta[b]pyridinyl.

When Q is a non-aromatic 3- to 14-membered heterocycle, Q is more preferably a non-aromatic bicyclic heterocycle comprising a 4- to 6-membered monocyclic non-aromatic hererocycle fused to an aryl, even more preferably Q is 1,3-benzodioxolyl or 2,3-dihydrobenzofuranyl, more specifically Q is 1,3-benzodioxol-5-yl or 2,3-dihydrobenzofuran-5-yl.

In the above formula (I), when Q is an aromatic 5- to 14-membered heterocycle, Q is preferably an aromatic 5- or 6-membered monocyclic heterocycle, an aromatic 9- or 10-membered bicyclic heterocycle comprising an aromatic 5- or 6-membered monocyclic heterocycle fused to an aryl (phenyl) or a 9- or 10-membered aromatic bicyclic heterocycle comprising two fused aromatic 5- or 6-membered monocyclic heterocycles.

Preferred aromatic 5- or 6-membered monocyclic heterocycles include pyrrolyl, pyrazolyl, furanyl, thienyl, imidazolyl, triazolyl, oxazolyl, thiazolyl, pyridinyl, pyridazinyl and pyrimidinyl.

Preferred aromatic 9- or 10-membered bicyclic heterocycles comprising an aromatic 5- or 6-membered monocyclic heterocycle fused to an aryl (phenyl) include indolyl, benzimadozolyl, indazolyl, benzofuranyl, benzothiophenyl, benzothiazolyl (e.g. 1,2-benzothiazolyl, 1,3-benzothiazolyl), benzoxazolyl (e.g. 1,2-benzoxazolyl, 1,3-benzoxazolyl) and quinolinyl.

Preferred aromatic 9- or 10-membered bicyclic heterocycles comprising two fused 5- or 6-membered monocyclic aromatic heterocycles include furo[3,2-b]pyridinyl, thieno[3,2-b]thiophenyl and thieno[2,3-d]thiazolyl.

When Q is an aromatic 5- to 14-membered heterocycle, Q is more preferably an aromatic 5- or 6-membered monocyclic heterocycle quinolinyl, benzothiophenyl or indolyl), even more preferably Q is pyrazolyl, thiazolyl, thienyl, pyridinyl or indolyl, more specifically Q is pyrazol-4-yl, thiazol-4-yl, pyridin-2-yl, pyridin-3-yl, thien-3-yl or indol-5-yl.

Preferably, Q is selected from the group consisting of phenyl, naphthyl, bicyclo[4.2.0]octa-1,3,5-trienyl, benzodioxolyl, 2,3-dihydrobenzofuranyl, indolinyl, benzofuranyl, benzothienyl, quinolinyl, pyridinyl, pyrazolyl, thiazolyl, thienyl and indolyl.

Preferred Q groups may be substituted with one to three $Q^S$ substituents independently selected from the group consisting of halogen, cyano, nitro, formyl, $C_1$-$C_4$-alkyl, $C_1$-$C_4$-haloalkyl, $C_1$-$C_4$-alkylcarbonyl, $C_1$-$C_4$-alkoxycarbonyl, $C_1$-$C_4$-alkoxy, $C_1$-$C_4$-haloalkoxy, $C_2$-$C_4$-alkenyl, $C_2$-$C_4$-alkynyl, $C_1$-$C_4$-alkylsulfanyl, $C_1$-$C_4$-haloalkylsulfanyl, $C_1$-$C_4$-alkylsulfonyl, $C_3$-$C_6$-cycloalkyl, non-aromatic 3- to 7-membered monocyclic heterocycle, phenyl, aromatic 5- or 6-membered heterocycle and —$N(R^k)_2$ with $R^k$ being independently selected from the group consisting of hydrogen, $C_1$-$C_4$-alkyl, $C_1$-$C_4$-haloalkyl and $C_3$-$C_6$-cycloalkyl.

Said preferred aliphatic $Q^S$ substituents may be substituted with one or two substituents independently selected from the group consisting of hydroxyl, $C_1$-$C_4$-alkoxy, $C_1$-$C_4$-haloalkoxy, $C_1$-$C_4$-alkoxycarbonyl, $C_1$-$C_4$-haloalkoxycarbonyl and $C_3$-$C_6$-cycloalkyl.

More preferably Q is selected from the group consisting of phenyl, 1,3-benzodioxol-5-yl, 2,3-dihydrobenzofuranyl, pyridinyl, thienyl and indol-5-yl.

More preferred Q groups may be substituted with one or two $Q^S$ substituents independently selected from the group consisting of halogen, cyano, nitro, formyl, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-alkynyl, $C_1$-$C_4$-alkylsulfanyl, $C_3$-$C_6$-cycloalkyl and non-aromatic 3- to 7-membered monocyclic heterocycle.

Said more preferred aliphatic $Q^S$ substituents may be substituted with one or two substituents independently selected from the group consisting of hydroxyl, $C_1$-$C_4$-alkoxy, $C_1$-$C_4$-haloalkoxy, $C_1$-$C_4$-alkoxycarbonyl, $C_1$-$C_4$-haloalkoxycarbonyl and $C_3$-$C_6$-cycloalkyl.

Even more preferably Q is selected from the group consisting of phenyl, pyridinyl and thien-yl.

Even more preferred Q groups may be substituted with one or two $Q^S$ substituents independently selected from the group consisting of halogen, cyano, nitro, formyl, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-alkynyl, $C_1$-$C_4$-alkylsulfanyl, $C_3$-$C_8$-cycloalkyl, oxiranyl and oxetanyl.

Said even more preferred aliphatic $Q^S$ substituents may be substituted with one or two substituents independently selected from the group consisting of hydroxyl, methoxy, ethoxy, difluoromethoxy and trifluoromethoxy.

Q groups as disclosed herein may be substituted with one or more $Q^S$ substituents that may be the same or different as disclosed herein above or as disclosed herein below.

In some embodiments, Q is substituted with one or more $Q^S$ substituents as disclosed herein above or as disclosed herein below that may be the same or different.

$Q^S$ substituents are preferably selected from the group consisting of halogen (e.g. fluorine, chlorine, bromine, iodine), cyano, nitro, formyl, $C_1$-$C_6$-alkyl (e.g. methyl, ethyl, propyl, isopropyl), $C_1$-$C_6$-haloalkyl (e.g. trifluoromethyl, difluoromethyl), $C_1$-$C_6$-alkylcarbonyl (e.g. methylcarbonyl), $C_1$-$C_6$-alkoxycarbonyl (e.g. methoxycarbonyl), $C_1$-$C_6$-alkoxy (e.g. methoxy, ethoxy), $C_1$-$C_6$-haloalkoxy (e.g. difluoromethoxy, trifluoromethoxy), $C_2$-$C_6$-alkenyl (e.g. vinyl), $C_2$-$C_6$-alkynyl (e.g. ethynyl), $C_1$-$C_6$-alkylsulfanyl (e.g. methylsulfanyl), $C_1$-$C_6$-haloalkylsulfanyl (e.g. trifluoromethylsulfanyl), $C_1$-$C_6$-alkylsulfonyl (e.g. methylsulfonyl), $C_3$-$C_8$-cycloalkyl (e.g. cyclopropyl, cyclobutyl), non-aromatic 3- to 7-membered monocyclic heterocycle (e.g. oxiranyl, oxetanyl), aromatic $C_6$-$C_{14}$-carbocycle (e.g.

phenyl), aromatic 5- to 14-membered heterocycle (e.g. pyrazole) and —$N(R^k)_2$ with $R^k$ being methyl.

Said aliphatic $Q^S$ substituents may be substituted with one or two substituents independently selected from the group consisting of hydroxyl, $C_1$-$C_4$-alkoxy, $C_1$-$C_4$-haloalkoxy, $C_1$-$C_4$-alkoxycarbonyl, $C_1$-$C_4$-haloalkoxycarbonyl and $C_3$-$C_6$-cycloalkyl.

Said cyclic $Q^S$ substituents may be substituted as disclosed herein or preferably with one or more halogen atom (e.g. fluorine).

$Q^S$ substituents are more preferably selected from the group consisting of halogen (e.g. chlorine, bromine, iodine, fluorine), $C_1$-$C_4$-alkyl (e.g. methyl, ethyl), $C_1$-$C_4$-haloalkyl (e.g. trifluoromethyl, difluoro-methyl), $C_1$-$C_4$-alkoxy (e.g. methoxy, ethoxy), $C_1$-$C_4$-haloalkoxy (e.g. difluoromethoxy, trifluoromethoxy), $C_2$-$C_4$-alkenyl (e.g. vinyl), $C_2$-$C_4$-alkynyl (e.g. ethynyl), $C_1$-$C_4$-alkylsulfanyl (e.g. methylsulfanyl) and $C_3$-$C_6$-cycloalkyl (e.g. cyclopropyl).

Said aliphatic $Q^S$ substituents may be substituted with one or two substituents independently selected from the group consisting of hydroxyl, methoxy, ethoxy, difluoromethoxy and trifluoromethoxy.

Said cyclic $Q^S$ substituents may be substituted as disclosed herein or preferably with one or more halogen atoms (e.g. fluorine).

Non-limiting examples of suitable Q include any of the Q groups listed in column "Q" of Table 1.

In some embodiments, Q is an unsubstituted phenyl or a phenyl substituted by one or more $Q^S$ substituents as described herein.

In some embodiments, Q is

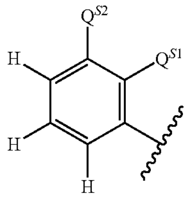

or

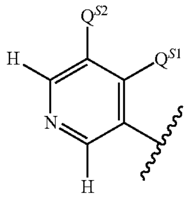

or

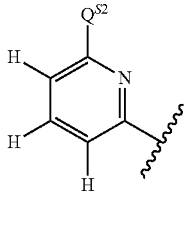

wherein $Q^{s1}$ is hydrogen or halogen (preferably fluorine).

$Q^{s2}$ is hydrogen or $Q^S$, wherein $Q^S$ is as described herein above, preferably $Q^{s2}$ is selected from the group consisting of hydrogen, halogen (e.g. fluorine, chlorine, bromine, iodine), cyano, nitro, hydroxyl, amino, $C_1$-$C_6$-alkyl (e.g. methyl, ethyl), $C_1$-$C_6$-haloalkyl (e.g. trifluoromethyl, difluoromethyl), $C_1$-$C_6$-alkylcarbonyl (e.g. methoxycarbonyl), $C_1$-$C_6$-alkoxy (e.g. methoxy), $C_1$-$C_6$-haloalkoxy (e.g. trifluoromethoxy), $C_2$-$C_6$-alkenyl (e.g. vinyl), $C_2$-$C_6$-alkynyl (e.g. ethynyl), $C_1$-$C_6$-alkylsulfanyl (e.g. methylsulfanyl), $C_1$-$C_6$-haloalkylsulfanyl (e.g. trifluoromethylsulfanyl), $C_3$-$C_8$-cycloalkyl (e.g. cyclopropyl, cyclobutyl) that may be substituted with one or more halogen atoms and non-aromatic 3- to 7-membered monocyclic heterocycle (e.g. oxetanyl) that may be substituted with one or more halogen atoms, more preferably $Q^{s2}$ is selected from the group consisting of fluorine, chlorine, bromine, iodine, cyano, nitro, hydroxyl, amino, methyl, trifluoromethyl, difluoromethyl, methoxy, trifluoromethoxy, vinyl, ethynyl, methylsulfanyl, trifluoromethylsulfanyl, cyclopropyl that may be substituted with one or more halogen atoms and oxetanyl that may be substituted with one or more halogen atoms, preferably at least one of $Q^{s1}$ and $Q^{s2}$ is different from hydrogen.

The above specified definitions of $R^1$, $R^2$, $R^3$, $R^4$, $R^5$, $R^6$, $R^7$, $R^8$, L, m and Q (broad definition as well as preferred, more preferred, even more preferred definitions) can be combined in various manners. These combinations of definitions thus provide sub-classes of compounds according to the invention, such as for instance the ones disclosed below.

Preferably the present invention relates to compounds of the formula (I), wherein A is selected from the group consisting of O, S, C(═O), S(═O), $S(═O)_2$, $NR^1$ and $CR^1R^2$, with $R^1$ and $R^2$ being independently selected from the group consisting of hydrogen, $C_1$-$C_4$-alkyl and $C_3$-$C_6$-cycloalkyl, m is 0, 1 or 2;

T is selected from the group consisting of hydrogen and $C_1$-$C_4$-alkyl, $R^3$ and $R^4$ are independently selected from the group consisting of hydrogen, fluorine, chlorine, $C_1$-$C_4$-alkyl, $C_2$-$C_4$-alkenyl, $C_2$-$C_4$-alkynyl, $C_3$-$C_6$-cycloalkyl, $R^5$ is selected from the group consisting of hydrogen, hydroxyl, $C_1$-$C_4$-alkyl, $C_1$-$C_4$-alkoxy, $C_1$-$C_4$-alkylsulfanyl, wherein aliphatic $R^1$, $R^2$, $R^3$, $R^4$ and $R^5$ substituents may be substituted with one to three substituents independently selected from the group consisting of fluorine, chlorine, $C_1$-$C_4$-alkoxy, $C_1$-$C_4$-haloalkoxy, $C_3$-$C_6$-cycloalkyl, $C_3$-$C_6$-halocycloalkyl, wherein cyclic $R^1$, $R^2$, $R^3$, $R^4$ and $R^5$ substituents may be substituted with one to three substituents independently selected from the group consisting of fluorine, chlorine oxo, methylidene, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_3$-$C_6$-cycloalkyl, $C_3$-$C_6$-halocycloalkyl, $R^3$ or $R^4$, and $R^5$ may form, together with the carbon atom to which they are attached to, a $C_3$-$C_6$-cycloalkyl;

L represents a direct bond or L is selected from the group consisting of $C_1$-$C_6$-alkylene, $C_1$-$C_6$-alkylene substituted on a same carbon atom by two substituents forming together with the carbon atom to which they are attached to a $C_3$-$C_6$-cycloalkyl, $C_1$-$C_6$-alkylene substituted on a same carbon atom by two substituents forming together with the carbon atom to which they are attached to a non-aromatic 3- to 7-membered monocyclic heterocycle, wherein aliphatic L substituents may be substituted with one to three $L^{Sa}$ substituents independently selected from the group consisting of fluorine, chlorine, hydroxyl, $C_1$-$C_4$-alkoxy, $C_1$-$C_4$-haloalkoxy, $C_3$-$C_6$-cycloalkyl and $C_3$-$C_6$-halocycloalkyl, wherein cyclic or cyclic moiety of L substituents may be substituted with one to three $L^{Sc}$ substituents independently selected from the group consisting of fluorine, chlorine, hydroxyl, oxo, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_3$-$C_6$-cycloalkyl and $C_3$-$C_6$-halocycloalkyl, $R^6$ is selected from the group consisting of non-aromatic $C_3$-$C_{12}$-carbocycle, aromatic $C_6$-$C_{14}$-carbocycle, non-aromatic 3- to 14-membered heterocycle, aromatic 5- to 14-membered heterocycle, non-aromatic $C_3$-$C_{12}$-carbocyclyloxy, aromatic $C_6$-$C_{14}$-carbocyclyloxy, aromatic 5- to 14-membered heterocyclyloxy, non-aromatic 5- to 14-membered heterocyclyloxy, non-aromatic $C_3$-$C_{12}$-carbocyclylsulfanyl, aromatic $C_6$-$C_{14}$-carbocyclylsulfanyl, aromatic 5- to 14-membered heterocyclylsulfanyl and non-aromatic 5- to 14-membered heterocyclylsulfanyl, wherein cyclic, or cyclic moiety of, $R^6$ substituents may be substituted with one to three $R^{6S}$ substituents that may be the same or different, $R^{6S}$ is selected from the group consisting of halogen, cyano, nitro, hydroxyl, mercapto, pentafluorosulfanyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylsulfanyl, $C_1$-$C_6$-haloalkylsulfanyl, $C_3$-$C_6$-cycloalkylsulfanyl, $C_3$-$C_6$-cycloalkyl, $C_3$-$C_6$-cycloalkyloxy, phenyl, naphthyl aromatic 5- or 6-membered monocyclic heterocycle, non-aromatic 3- to 7-membered monocyclic heterocycle, —C(═O)($OR^d$) and —C(═O)N($R^d$)$_2$, with $R^d$ being independently selected from the group consisting of hydrogen, $C_1$-$C_4$-alkyl and $C_1$-$C_4$-haloalkyl, wherein aliphatic $R^{6S}$, $R^c$ and $R^d$ substituents may be substituted with one to three substituents independently selected from the group consisting of fluorine, chlorine hydroxyl, $C_1$-$C_4$-alkoxy, $C_1$-$C_4$-haloalkoxy, $C_3$-$C_6$-cycloalkyl and $C_3$-$C_6$-halocycloalkyl, wherein cyclic or cyclic moiety of $R^{6S}$ and cyclic $R^c$ substituents may be substituted with one to three substituents independently selected from the group consisting of fluorine, chlorine $C_1$-$C_4$-alkyl, $C_1$-$C_4$-haloalkyl, $C_1$-$C_4$-alkoxy and $C_1$-$C_4$-haloalkoxy, $R^7$ is selected from the group consisting of hydrogen, halogen, cyano, hydroxyl, mercapto, $C_1$-$C_4$-alkyl, $C_1$-$C_4$-haloalkyl, $C_1$-$C_4$-hydroxyalkyl, $C_1$-$C_4$-alkoxy, $C_1$-$C_4$-haloalkoxy, $C_1$-$C_4$-alkylcarbonyl, $C_1$-$C_4$-haloalkylcarbonyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylsulfanyl, $C_1$-$C_4$-haloalkylsulfanyl, $C_3$-$C_6$-cycloalkylsulfanyl, $C_1$-$C_4$-alkylsulfinyl, $C_1$-$C_4$-haloalkylsulfinyl, $C_3$-$C_6$-cycloalkylsulfinyl, $C_1$-$C_4$-alkylsulfonyl, $C_1$-$C_4$-haloalkylsulfonyl, $C_3$-$C_6$-cycloalkylsulfonyl, $C_3$-$C_6$-cycloalkyl, $C_3$-$C_6$-cycloalkenyl, phenyl, naphthyl, aromatic 5- or 6-membered monocyclic heterocycle, non-aromatic 3- to 7-membered monocyclic heterocycle, $C_3$-$C_8$-cycloalkyloxy, aromatic $C_6$-$C_{14}$-carbocyclyloxy, aromatic 5- or 6-membered monocyclic heterocyclyloxy, non-aromatic 3- to 7-membered monocyclic heterocyclyloxy, —N($R^e$)$_2$, —C(═$NR^f$)$R^f$, $NR^g$C(═O)$R^g$, —C(═O)($OR^g$), —C(═O)N($R^g$)$_2$, —S(═O)$_2$N($R^g$)$_2$ and —S(═O)(═$NR^g$)$R^g$, with $R^e$ being independently selected from the group consisting of hydrogen, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, with $R^f$ being independently selected from the group consisting of hydroxyl, $C_1$-$C_4$-alkyl, $C_1$-$C_4$-haloalkyl, $C_1$-$C_4$-alkoxy, with $R^g$ being independently selected from the group consisting of hydrogen, $C_1$-$C_4$-alkyl, $C_1$-$C_4$-haloalkyl and $C_3$-$C_6$-cycloalkyl, wherein aliphatic $R^7$, $R^e$, $R^f$ and $R^g$ substituents may be substituted with one to three $R^{7Sa}$ substituents that may be the same or different, wherein cyclic or cyclic moiety of $R^7$, cyclic $R^e$ and cyclic $R^g$ substituents may be substituted with one to three $R^{7Sc}$ substituents that may be the same or different, $R^{7Sa}$ is selected from the group consisting of hydroxyl, $C_1$-$C_4$-alkoxy, $C_1$-$C_4$-haloalkoxy, $C_3$-$C_6$-cycloalkyl, $R^{7Sc}$ is selected from the group consisting of fluorine, chlorine hydroxyl, oxo, $C_1$-$C_4$-alkyl, $C_1$-$C_4$-haloalkyl $C_1$-$C_4$-alkoxy, $C_1$-$C_4$-haloalkoxy, $C_3$-$C_6$-cycloalkyl, $R^8$ is selected from the group consisting of hydrogen, halogen, amino, hydroxyl, mercapto, $C_1$-$C_4$-alkyl, $C_1$-$C_4$-haloalkyl, $C_1$-$C_4$-hydroxyalkyl, $C_1$-$C_4$-alkoxy, $C_1$-$C_4$-haloalkoxy, $C_2$-$C_4$-alkenyl, $C_2$-$C_4$-haloalkenyl, $C_2$-$C_4$-alkynyl, $C_2$-$C_4$-haloalkynyl, $C_2$-$C_4$-alkenyloxy, $C_2$-$C_4$-haloalkenyloxy, $C_2$-$C_4$-alkynyloxy, $C_2$-$C_4$-haloalkynyloxy, $C_3$-$C_6$-cycloalkyl, $C_3$-$C_6$-cycloalkenyl, phenyl, naphthyl, non-aromatic 3- to 7-membered heterocycle, aromatic 5- or 6-membered heterocycle, $C_3$-$C_6$-cycloalkyloxy, phenyloxy, naphthyloxy, non-aromatic 3- to 7-membered heterocyclyloxy, aromatic 5- or 6-membered heterocyclyloxy, —N($R^h$)$_2$,—$SR^i$, —S(═O)$R^i$ and —S(═O)$_2R^i$, with $R^h$ being independently selected from the group consisting of hydrogen, $C_1$-$C_4$-alkyl, $C_1$-$C_4$-haloalkyl, $C_2$-$C_4$-alkenyl, $C_2$-$C_4$-haloalkenyl, $C_3$-$C_6$-cycloalkyl, $C_3$-$C_6$-halocycloalkyl, phenyl, naphthyl aromatic 5- or 6-membered heterocycle and non-aromatic 3- to 7-membered monocyclic heterocycle, with $R^i$ being selected from the group consisting of $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, phenyl, naphthyl, aromatic 5- or 6-membered heterocycle and non-aromatic 3- to 7-membered monocyclic heterocycle, wherein aliphatic $R^8$, $R^h$ and $R^i$ substituents may be substituted with one to three $R^{8Sa}$ substituents that may be the same or different, wherein cyclic or cyclic moiety of $R^8$, cyclic $R^h$ and cyclic $R^i$ substituents may be substituted with one to three $R^{8Sc}$ substituents that may be the same or different, $R^{8Sa}$ is selected from the group consisting of hydroxyl, carboxyl, $C_1$-$C_4$-alkoxy, $C_1$-$C_4$-haloalkoxy, $C_1$-$C_4$-alkoxycarbonyl, $C_1$-$C_4$-haloalkoxycarbonyl, $C_3$-$C_6$-cycloalkyl, $C_3$-$C_6$-halocycloalkyl, $C_1$-$C_4$-alkylsulfanyl, $C_1$-$C_4$-haloalkylsulfanyl, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, - and non-aromatic 3- to 7-membered monocyclic heterocycle, wherein said non-aromatic 3- to 7-membered monocyclic heterocycle $R^{8Sa}$ may be substituted with one or two $C_1$-$C_4$-alkyl substituents that may be the same or different, $R^{8Sc}$ is selected from the group consisting of halogen, oxo, $C_1$-$C_4$-alkyl, $C_1$-$C_4$-haloalkyl, $C_1$-$C_4$-alkoxy, $C_1$-$C_4$-haloalkoxy and $C_3$-$C_6$-cycloalkyl, Q is selected from the group consisting of phenyl, naphthyl, non-aromatic $C_5$-$C_{10}$-carbocycle, non-aromatic 5- to 10-membered heterocycle and aromatic 5- to 10-membered heterocycle, wherein any of said carbocycle or heterocycle groups may be substituted with one to three $Q^S$ substituents that may be the same or different, $Q^S$ is selected from the group consisting of halogen, cyano, nitro, formyl, carboxyl, $C_1$-$C_4$-alkyl, $C_1$-$C_4$-haloalkyl, $C_1$-$C_4$-alkylcarbonyl, $C_1$-$C_4$-haloalkylcarbonyl, $C_1$-$C_4$-alkoxy, $C_1$-$C_4$-haloalkoxy, $C_1$-$C_4$-alkoxycarbonyl, $C_1$-$C_4$-haloalkoxycarbonyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylsulfanyl, $C_1$-$C_4$-haloalkylsulfanyl, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, non-aromatic 3- to 7-membered monocyclic heterocycle, phenyl, naphthyl and aromatic 5- to 10-membered heterocycle, wherein aliphatic $Q^S$, $R^j$ and $R^k$ substituents may be substituted with one to three substituents independently selected from the group consisting of hydroxyl, $C_1$-$C_4$-alkoxy, $C_1$-$C_4$-haloalkoxy, $C_3$-$C_6$-cycloalkyl and $C_3$-$C_6$-halocycloalkyl, wherein cyclic or cyclic moiety of $Q^S$ and cyclic $R^k$ substituents may be substituted with one to three $R^{Qs}$ substituents independently selected from the group consisting of fluorine, chlorine, $C_1$-$C_4$-alkyl, $C_1$-$C_4$-haloalkyl, $C_1$-$C_4$-alkoxy, $C_1$-$C_4$-haloalkoxy and $C_3$-$C_6$-cycloalkyl.

More preferably the present invention relates to compounds of the formula (I), wherein A is selected from the group consisting of O, $S(=O)_2$, $NR^1$ and $CR^1R^2$, with $R^1$ and $R^2$ being independently selected from the group consisting of hydrogen, $C_1$-$C_4$-alkyl and $C_3$-$C_6$-cycloalkyl, m is 0, 1 or 2;

T is selected from the group consisting of hydrogen and $C_1$-$C_4$-alkyl, $R^3$ and $R^4$ are independently selected from the group consisting of hydrogen, fluorine, chlorine, $C_1$-$C_4$-alkyl, $C_2$-$C_4$-alkenyl, $C_2$-$C_4$-alkynyl and $C_3$-$C_6$-cycloalkyl, $R^5$ is selected from the group consisting of hydrogen, hydroxyl, $C_1$-$C_4$-alkyl and $C_1$-$C_4$-alkoxy, L represents a direct bond or L is selected from the group consisting of $C_1$-$C_6$-alkylene, wherein aliphatic L substituents may be substituted with one to three $L^{Sa}$ substituents independently selected from the group consisting of fluorine, chlorine, hydroxyl, $C_1$-$C_4$-alkoxy, $C_1$-$C_4$-haloalkoxy and $C_3$-$C_6$-cycloalkyl, wherein cyclic or cyclic moiety of L substituents may be substituted with one to three $L^{Sc}$ substituents independently selected from the group consisting of fluorine, chlorine, hydroxyl, oxo, $C_1$-$C_4$-alkyl, $C_1$-$C_4$-haloalkyl, $C_1$-$C_4$-alkoxy, $C_1$-$C_4$-haloalkoxy and $C_3$-$C_6$-cycloalkyl, $R^6$ is selected from the group consisting of non-aromatic $C_5$-$C_{10}$-carbocycle, phenyl, naphthyl, non-aromatic 5- to 10-membered heterocycle, aromatic 5- to 10-membered heterocycle, non-aromatic $C_5$-$C_{10}$-carbocyclyloxy, phenoxy, naphthyloxy, aromatic 5- to 10-membered heterocyclyloxy, non-aromatic 5- to 10-membered heterocyclyloxy and phenylsulfanyl, wherein cyclic, or cyclic moiety of $R^6$ substituents may be substituted with one to three $R^{6S}$ substituents independently selected from the group consisting of halogen, nitro, hydroxyl, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-alkynyl, $C_1$-$C_4$-haloalkylsulfanyl, cyclopropyl, cyclobutyl, cyclopentyl, pyridinyl, oxetanyl and tetrahydrofuranyl, wherein cyclic $R^{6S}$ substituents may be substituted with one or two substituents independently selected from the group consisting of halogen, $C_1$-$C_4$-alkyl, $C_1$-$C_4$-haloalkyl and $C_1$-$C_4$-alkoxycarbonyl, $R^7$ is selected from the group consisting of hydrogen, halogen, cyano, $C_1$-$C_4$-alkyl, $C_1$-$C_4$-haloalkyl, $C_1$-$C_4$-hydroxyalkyl, $C_1$-$C_4$-alkylcarbonyl, $C_1$-$C_4$-alkoxy, $C_2$-$C_4$-alkenyl, $C_2$-$C_4$-alkynyl, $C_1$-$C_4$-alkylsulfanyl, $C_1$-$C_4$-alkenylsulfanyl, $C_1$-$C_4$-alkylsulfonyl, $C_3$-$C_6$-cycloalkyl, pyridinyl, imidazolyl, pyrazolyl, thiazolyl, oxetanyl, tetrahydrofuranyl, pyrrolidinyl, $-N(R^e)_2$, $-C(=NR^f)R^f$ and $-C(=O)N(R^g)_2$, with $R^e$ being independently selected from the group consisting of hydrogen, $C_1$-$C_4$-alkyl and $C_3$-$C_6$-cycloalkyl, with $R^f$ being independently selected from the group consisting of $C_1$-$C_4$-alkyl and $C_1$-$C_4$-alkoxy, with $R^g$ being independently selected from the group consisting of hydrogen, $C_1$-$C_4$-alkyl and $C_3$-$C_6$-cycloalkyl, wherein said aliphatic $R^7$, $R^e$ and $R^g$ substituents may be substituted with one to three $R^{7Sa}$ substituents independently selected from the group consisting of hydroxyl, $C_1$-$C_4$-alkoxy and $C_3$-$C_6$-cycloalkyl, wherein said cyclic $R^7$, $R^e$ and $R^g$ substituents may be substituted with one to three $R^{7Sc}$ substituents independently selected from the group consisting of halogen, hydroxyl, $C_1$-$C_4$-alkyl and $C_1$-$C_4$-alkoxy, $R^8$ is selected from the group consisting of hydrogen, halogen, hydroxyl, $C_1$-$C_4$-alkyl, $C_1$-$C_4$-haloalkyl, $C_1$-$C_4$-alkoxy, $C_2$-$C_4$-alkenyl, $C_1$-$C_4$-alkylsulfanyl, $C_1$-$C_4$-haloalkylsulfanyl, $C_1$-$C_4$-alkylsulfinyl, $C_1$-$C_4$-alkylsulfonyl, $C_3$-$C_6$-cycloalkyl, phenyl, naphthyl, oxetanyl, azetidinyl, tetrahydrofuranyl, pyrrolidinyl, tetrahydropyranyl, piperidinyl, piperazinyl, morpholinyl, furanyl, thienyl, pyrrolyl, pyrazolyl, thiazolyl, imidazolyl, oxazolyl, isoxazolyl, pyridinyl, pyrimidinyl, $C_3$-$C_6$-cycloalkyloxy and $-N(R^h)_2$, with $R^h$ being independently selected from the group consisting of hydrogen, $C_1$-$C_4$-alkyl, $C_1$-$C_4$-haloalkyl, $C_2$-$C_4$-alkenyl, $C_3$-$C_6$-cycloalkyl, phenyl, oxetanyl, azetidinyl, pyrrolidinyl and tetrahydrofuranyl, wherein aliphatic $R^8$ and $R^h$ substituents as disclosed herein may be substituted with one or two $R^{8Sa}$ substituents independently selected from the group consisting of hydroxyl, $C_1$-$C_4$-alkoxy, $C_1$-$C_4$-alkoxycarbonyl, $C_3$-$C_6$-cycloalkyl, $C_1$-$C_4$-alkylsulfanyl oxetanyl, azetidinyl, pyrrolidinyl and tetrahydrofuranyl, wherein cyclic $R^8$ and $R^h$ substituents as disclosed herein may be substituted with one or two $R^{8Sc}$ substituents independently selected from the group consisting of oxo, fluorine, chlorine, hydroxyl, $C_1$-$C_4$-alkyl, $C_1$-$C_4$-haloalkyl, $C_1$-$C_4$-alkoxy, $C_3$-$C_6$-cycloalkyl, oxetanyl, azetidinyl, pyrrolidinyl and tetrahydrofuranyl Q is selected from the group consisting of phenyl, 1,3-benzodioxol-5-yl, 2,3-dihydrobenzofuranyl, pyridinyl, thien-yl and indol-5-yl, wherein more preferred Q groups as disclosed herein may be substituted with one or two $Q^S$ substituents independently selected from the group consisting of halogen, cyano, nitro, formyl, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-alkynyl, $C_1$-$C_4$-alkylsulfanyl, $C_3$-$C_6$-cycloalkyl and non-aromatic 3- to 7-membered monocyclic heterocycle, wherein said more preferred aliphatic $Q^S$ substituents may be substituted with one or two substituents independently selected from the group consisting of hydroxyl, $C_1$-$C_4$-alkoxy, $C_1$-$C_4$-haloalkoxy, $C_1$-$C_4$-alkoxycarbonyl, $C_1$-$C_4$-haloalkoxycarbonyl and $C_3$-$C_6$-cycloalkyl.

Most preferably the present invention relates to compounds of the formula (1), wherein A is selected from the group consisting of O, $NR^1$ and $CR^1R^2$, with $R^1$ and $R^2$ being independently selected from the group consisting of hydrogen, methyl or ethyl, m is 1;

T is hydrogen, $R^3$ and $R^4$ are independently selected from the group consisting of hydrogen or fluorine, $R^5$ is hydrogen, L represents a direct bond or L is methylene, $R^6$ is indanyl, 1,2,3,4-tetrahydronaphthalenyl, phenyl, naphthyl, 2,3-dihydrobenzofuranyl, 2,3-dihydro-1,4-benzodioxinyl, thienyl, pyridinyl, indolyl, benzofuranyl, benzothiophenyl or phenoxy, wherein cyclic, or cyclic moiety of $R^6$ substituents may be substituted with one or two $R^{6S}$ substituents that may be the same or different, $R^{6S}$ is selected from the group consisting of halogen, cyano, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-alkynyl, $C_1$-$C_4$-haloalkylsulfanyl, $C_3$-$C_8$-cycloalkyl pyridinyl, oxetanyl and tetrahydrofuranyl $R^7$ is selected from the group consisting of halogen, cyano, $C_1$-$C_4$-alkyl, $C_1$-$C_4$-haloalkyl, $C_1$-$C_4$-hydroxyalkyl, $C_1$-$C_4$-alkoxy, $C_1$-$C_4$-alkylcarbonyl, $C_3$-$C_6$-cycloalkyl, imidazolyl, pyrazolyl, thiazolyl and pyridinyl, wherein aliphatic $R^7$, substituents may be substituted with one or two $R^{7Sa}$ substituents independently selected from the group consisting of hydroxyl, methoxy, ethoxy and cyclopropyl, wherein cyclic or cyclic moiety of $R^7$ substituents may be substituted with one or two $R^{7Sc}$ substituents independently selected from the group consisting of fluorine, methyl, ethyl and cyclopropyl, $R^8$ is selected from the group consisting of hydrogen, halogen, $C_1$-$C_4$-alkyl, $C_1$-$C_4$-haloalkyl, $C_1$-$C_4$-alkoxy, $C_3$-$C_6$-cycloalkyloxy and —$N(R^h)_2$, with $R^h$ being independently selected from the group consisting of hydrogen, $C_1$-$C_4$-alkyl, $C_1$-$C_4$-haloalkyl, $C_2$-$C_4$-alkenyl, and $C_3$-$C_6$-cycloalkyl, wherein aliphatic $R^8$ and $R^h$ substituents may be substituted with one or two $R^{8Sa}$ substituents independently selected from the group consisting of hydroxyl, methoxy and ethoxy, wherein cyclic or cyclic moiety of $R^8$ and cyclic $R^h$ substituents may be substituted with one or two $R^{8Sc}$ substituents independently selected from the group consisting of fluorine, methyl, ethyl and cyclopropyl, Q is selected from the group consisting of phenyl, 3-bicyclo[4.2.0]octa-1,3,5-trienyl, pyrazolyl, thiazolyl, thienyl and pyridinyl, wherein any of said carbocycle or heterocycle groups may be substituted with one to three $Q^S$ substituents that may be the same or different, $Q^S$ is selected from the group consisting of halogen, cyano, nitro, formyl, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-alkynyl, $C_1$-$C_4$-alkylsulfanyl $C_3$-$C_8$-cycloalkyl, oxiranyl and oxetanyl.

In some embodiments (referred herein as embodiment 2), compounds according to the present invention are compounds of the formula (I):

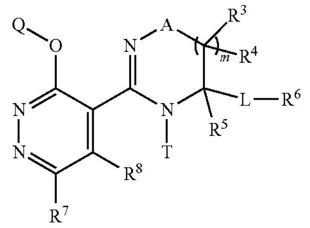

(I)

wherein

A is selected from the group consisting of O, C(═O) and $CR^1R^2$ with $R^1$ and $R^2$ being independently selected from the group consisting of hydrogen, $C_1$-$C_6$-alkyl and $C_3$-$C_8$-cycloalkyl, or $R^1$ and $R^2$ form, together with the carbon atom to which they are attached to, a $C_3$-$C_8$-cycloalkyl or a non-aromatic 3- to 7-membered monocyclic heterocycle, preferably $R^1$ and $R^2$ are hydrogen;

m is 0, 1 or 2;

T is hydrogen or —C(═O)($OR^{a1}$) with $R^{a1}$ being selected from the group consisting of $C_1$-$C_6$-alkyl, $C_1$-$C_6$-haloalkyl and $C_2$-$C_6$-alkylenyl, preferably T is hydrogen;

$R^3$ and $R^4$ are independently selected from the group consisting of hydrogen, halogen, cyano, hydroxyl, formyl, carboxyl, $C_1$-$C_6$-alkyl, $C_1$-$C_6$-alkoxy, $C_1$-$C_6$-alkoxycarbonyl, $C_3$-$C_8$-cycloalkyl, aromatic $C_6$-$C_{14}$-carbocycle, non-aromatic 3- to 14-membered heterocycle, —O—Si($C_1$-$C_6$-alkyl$)_3$ and aromatic 5- to 14-membered heterocycle, or $R^3$ and $R^4$ form, together with the carbon atom to which they are attached to, a carbonyl, a methylidene, a $C_3$-$C_8$-cycloalkyl or a non-aromatic 3- to 7-membered monocyclic heterocycle, preferably $R^3$ and $R^4$ are hydrogen;

$R^5$ is hydrogen, hydroxyl and $C_1$-$C_6$-alkoxy, preferably hydrogen;

wherein aliphatic $R^1$, $R^2$, $R^3$, $R^4$ and $R^5$ substituents may be substituted with one or more substituents as disclosed herein;

wherein cyclic $R^1$, $R^2$, $R^3$ and $R^4$ substituents may be substituted with one or more substituents as disclosed herein;

L represents a direct bond or L is selected from the group consisting of carbonyl, $C_1$-$C_6$-alkylene, $C_1$-$C_6$-alkylene substituted on a same carbon atom by two substituents forming together with the carbon atom to which they are attached to a $C_3$-$C_8$-cycloalkyl, $C_1$-$C_6$-alkylene substituted on a same carbon atom by two substituents forming together with the carbon atom to which they are attached to a non-aromatic 3- to 7-membered monocyclic heterocycle, $C_2$-$C_6$-alkenylene, $C_2$-$C_6$-alkynylene, $C_3$-$C_8$-cycloalkylene, $C_1$-$C_6$-alkylene-$C_3$-$C_8$-cycloalkylene, $C_3$-$C_8$-cycloalkylene-$C_1$-$C_6$-alkylene, $C_1$-$C_6$-alkylene-$C_3$-$C_8$-cycloalkylene-$C_1$-$C_6$-alkylene $C_1$-$C_6$-alkylene-(C═O), $C_3$-$C_8$-cycloalkenylene, $C_1$-$C_6$-alkylene-$C_3$-$C_8$-cycloalkenylene, $C_3$-$C_8$-cycloalkenylene-$C_1$-$C_6$-alkylene, $C_1$-$C_6$-alkylene-$C_3$-$C_8$-cycloalkenylene-$C_1$-$C_6$-alkylene, non-aromatic 3- to 7-membered monocyclic heterocyclylene;

wherein aliphatic L substituents may be substituted with one or more $L^{Sa}$ substituents that may be the same or different, as disclosed herein, wherein cyclic or cyclic moiety of L substituents may be substituted with one or more $L^{Sc}$ substituents that may be the same or different, as disclosed herein, $R^6$ is selected from the group consisting of non-aromatic $C_3$-$C_{12}$-carbocycle, aromatic $C_6$-$C_{14}$-carbocycle, non-aromatic 3- to 14-membered heterocycle, aromatic 5- to 14-membered heterocycle, aromatic $C_6$-$C_{14}$-carbocyclyloxy, $C_1$-$C_3$-alkoxy substituted by an aromatic $C_6$-$C_{14}$-carbocycle and $C_1$-$C_3$-haloalkoxy substituted by an aromatic $C_6$-$C_{14}$-carbocycle, preferably $R^6$ is selected from the group consisting of non-aromatic $C_3$-$C_{12}$-carbocycle, aromatic $C_6$-$C_{14}$-carbocycle and aromatic 5- to 14-membered heterocycle, wherein said cyclic, or cyclic moiety of, $R^6$ substituents may be substituted with one or more $R^{6S}$ substituents as disclosed herein (including preferred and more preferred $R^{6S}$ substituents);

$R^7$ is selected from the group consisting of hydrogen, halogen, cyano, $C_1$-$C_6$-alkyl, $C_1$-$C_6$-haloalkyl, $C_1$-$C_6$-hydroxyalkyl, $C_1$-$C_6$-alkylcarbonyl, $C_1$-$C_6$-alkoxy, $C_2$-$C_6$-alkenyl, $C_2$-$C_6$-alkynyl, $C_1$-$C_6$-alkylsulfanyl, $C_1$-$C_6$-alkylsulfinyl, $C_3$-$C_8$-cycloalkyl, aromatic 5- or 6-membered monocyclic heterocycle, non-aromatic 3- to 7-membered monocyclic heterocycle, —$N(R^e)_2$, —$C(=NR^f)R^f$ and —$C(=O)N(R^g)_2$, with $R^e$ being as disclosed above, preferably $R^e$ being independently selected from the group consisting of hydrogen, $C_1$-$C_6$-alkyl and $C_3$-$C_8$-cycloalkyl (e.g. cyclopropyl), with $R^f$ being as disclosed above, preferably $R^f$ being independently selected from the group consisting of hydroxyl, amino, $C_1$-$C_6$-alkyl and $C_1$-$C_6$-alkoxy, with $R^g$ being as disclosed above, preferably $R^g$ being independently selected from the group consisting of hydrogen, $C_1$-$C_6$-alkyl and $C_3$-$C_8$-cycloalkyl, preferably $R^7$ is selected from the group consisting of halogen, $C_1$-$C_6$-alkyl, $C_1$-$C_6$-alkylcarbonyl, $C_2$-$C_6$-alkenyl, $C_3$-$C_8$-cycloalkyl, aromatic 5- or 6-membered monocyclic heterocycle and —$N(R^e)_2$ with $R^e$ being independently selected from the group consisting of hydrogen, $C_1$-$C_6$-alkyl and $C_3$-$C_8$-cycloalkyl, wherein aliphatic $R^7$, $R^e$, $R^f$ and $R^g$ substituents may be substituted with one or more $R^{7Sa}$ substituents that may be the same or different, $R^{7Sa}$ being as disclosed herein (including preferred $R^{7Sa}$) wherein cyclic or cyclic moiety of $R^7$, cyclic $R^e$ and cyclic $R^g$ substituents may be substituted with one or more $R^{7Sc}$ substituents that may be the same or different, $R^{7Sc}$ being as disclosed herein (including preferred $R^{7Sc}$);

$R^8$ is selected from the group consisting of hydrogen, halogen, hydroxyl, $C_1$-$C_6$-alkyl, $C_1$-$C_6$-haloalkyl, $C_1$-$C_6$-alkoxy, $C_2$-$C_6$-alkenyl, $C_1$-$C_6$-alkylsulfanyl, $C_1$-$C_6$-haloalkylsulfanyl, $C_1$-$C_6$-alkylsulfinyl, $C_1$-$C_6$-alkylsulfonyl, $C_3$-$C_8$-cycloalkyl, aromatic $C_6$-$C_{14}$-carbocycle, non-aromatic 3- to 14-membered heterocycle (preferably non-aromatic 3- to 7-membered monocyclic heterocycle), aromatic 5- to 14-membered heterocycle (preferably 5- or 6-membered aromatic monocyclic heterocycle), $C_3$-$C_8$-cycloalkyloxy, non-aromatic 3- to 14-membered heterocyclyloxy (preferably non-aromatic 3- to 7-membered monocyclic heterocyclyloxy) and —$N(R^h)_2$, with $R^h$ being as disclosed above, preferably $R^h$ being independently selected from the group consisting of hydrogen, $C_1$-$C_6$-alkyl, $C_2$-$C_6$-alkenyl, $C_3$-$C_8$-cycloalkyl (e.g. cyclopropyl, cyclohexyl), aromatic $C_6$-$C_{14}$-carbocycle (e.g. phenyl) and non-aromatic 3- to 7-membered monocyclic heterocycle (e.g. oxetanyl), preferably $R^8$ is selected from the group consisting of hydrogen, halogen, $C_1$-$C_6$-alkyl, $C_1$-$C_6$-alkoxy and —$N(R^h)_2$ with $R^h$ being independently selected from the group consisting of hydrogen, $C_1$-$C_6$-alkyl and $C_3$-$C_8$-cycloalkyl, wherein aliphatic $R^8$ and $R^h$ substituents may be substituted with one or more $R^{8Sa}$ substituents that may be the same or different, $R^{8Sa}$ being as disclosed herein (including preferred $R^{8Sa}$)

wherein cyclic or cyclic moiety of $R^8$ and cyclic $R^h$ substituents may be substituted with one or more $R^{8Sc}$ substituents that may be the same or different, $R^{8Sc}$ being as disclosed herein (including preferred $R^{8Sc}$);

Q is selected from the group consisting of aromatic $C_6$-$C_{14}$-carbocycle, non-aromatic $C_3$-$C_{12}$-carbocycle, non-aromatic 3- to 14-membered heterocycle and aromatic 5- to 14-membered heterocycle, wherein each of said carbocycle or heterocycle group may be substituted with one or more $Q^S$ substituents that may be the same or different, $Q^S$ being as described herein (including preferred $Q^S$)

In some embodiments (referred herein as embodiment 3), compounds according to the present invention are compounds of the formula (I):

(I)

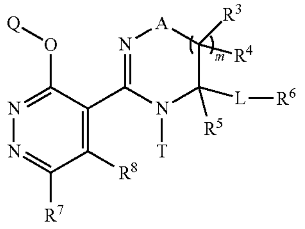

wherein

A is selected from the group consisting of O, C(=O) and $CR^1R^2$ with $R^1$ and $R^2$ being independently selected from the group consisting of hydrogen, $C_1$-$C_6$-alkyl and $C_3$-$C_8$-cycloalkyl, or $R^1$ and $R^2$ form, together with the carbon atom to which they are attached to, a $C_3$-$C_8$-cycloalkyl or a non-aromatic 3- to 7-membered monocyclic heterocycle, preferably $R^1$ and $R^2$ are hydrogen;

m is 0, 1 or 2;

T is hydrogen or —$C(=O)(OR^{a1})$ with $R^{a1}$ being selected from the group consisting of $C_1$-$C_6$-alkyl, $C_1$-$C_6$-haloalkyl and $C_2$-$C_6$-alkylenyl, preferably T is hydrogen;

$R^3$ and $R^4$ are independently selected from the group consisting of hydrogen, halogen, cyano, hydroxyl, formyl, carboxyl, $C_1$-$C_6$-alkyl, $C_1$-$C_6$-alkoxy, $C_1$-$C_6$-alkoxycarbonyl, $C_3$-$C_8$-cycloalkyl, aromatic $C_6$-$C_{14}$-carbocycle, non-aromatic 3- to 14-membered heterocycle, —O—Si($C_1$-$C_6$-alkyl)$_3$ and aromatic 5- to 14-membered heterocycle, or $R^3$ and $R^4$ form, together with the carbon atom to which they are attached to, a carbonyl, a methylidene, a $C_3$-$C_8$-cycloalkyl or a non-aromatic 3- to 7-membered monocyclic heterocycle, preferably $R^3$ and $R^4$ are hydrogen;

$R^5$ is hydrogen, hydroxyl and $C_1$-$C_6$-alkoxy, preferably hydrogen;

wherein aliphatic $R^1$, $R^2$, $R^3$, $R^4$ and $R^5$ substituents may be substituted with one or more substituents as disclosed herein;

wherein cyclic $R^1$, $R^2$, $R^3$ and $R^4$ substituents may be substituted with one or more substituents as disclosed herein;

L represents a direct bond or L is selected from the group consisting of carbonyl, $C_1$-$C_6$-alkylene, $C_1$-$C_6$-alkylene substituted on a same carbon atom by two substituents forming together with the carbon atom to which they are attached to a $C_3$-$C_8$-cycloalkyl, $C_1$-$C_6$-alkylene substituted on a same carbon atom by two substituents forming together with the carbon atom to which they are attached to a non-aromatic 3- to 7-membered monocyclic heterocycle, $C_2$-$C_6$-alkenylene, $C_2$-$C_6$-alkynylene, $C_3$-$C_8$-cycloalkylene, $C_1$-$C_6$-alkylene-$C_3$-$C_8$-cycloalkylene, $C_3$-$C_8$-cycloalkylene-$C_1$-$C_6$-alkylene, $C_1$-$C_6$-alkylene-$C_3$-$C_8$-cycloalkylene-$C_1$-$C_6$-alkylene $C_1$-$C_6$-alkylene-(C═O), $C_3$-$C_8$-cycloalkenylene, $C_1$-$C_6$-alkylene-$C_3$-$C_8$-cycloalkenylene, $C_3$-$C_8$-cycloalkenylene-$C_1$-$C_6$-alkylene, $C_1$-$C_6$-alkylene-$C_3$-$C_8$-cycloalkenylene-$C_1$-$C_6$-alkylene, non-aromatic 3- to 7-membered monocyclic heterocyclylene;

wherein aliphatic L substituents may be substituted with one or more $L^{Sa}$ substituents that may be the same or different, as disclosed herein, wherein cyclic or cyclic moiety of L substituents may be substituted with one or more $L^{Sc}$ substituents that may be the same or different, as disclosed herein, $R^6$ is selected from the group consisting of non-aromatic $C_3$-$C_{12}$-carbocycle, aromatic $C_6$-$C_{14}$-carbocycle, non-aromatic 3- to 14-membered heterocycle, aromatic 5- to 14-membered heterocycle, aromatic $C_6$-$C_{14}$-carbocyclyloxy, $C_1$-$C_3$-alkoxy substituted by an aromatic $C_6$-$C_{14}$-carbocycle and $C_1$-$C_3$-haloalkoxy substituted by an aromatic $C_6$-$C_{14}$-carbocycle, preferably $R^6$ is selected from the group consisting of non-aromatic $C_3$-$C_{12}$-carbocycle, aromatic $C_6$-$C_{14}$-carbocycle and aromatic 5- to 14-membered heterocycle, wherein said cyclic, or cyclic moiety of, $R^6$ substituents may be substituted with one or more $R^{6S}$ substituents as disclosed herein (including preferred and more preferred $R^{6S}$ substituents);

$R^7$ is selected from the group consisting of hydrogen, halogen, cyano, $C_1$-$C_6$-alkyl, $C_1$-$C_6$-haloalkyl, $C_1$-$C_6$-hydroxyalkyl, $C_1$-$C_6$-alkylcarbonyl, $C_1$-$C_6$-alkoxy, $C_2$-$C_6$-alkenyl, $C_2$-$C_6$-alkynyl, $C_1$-$C_6$-alkylsulfanyl, $C_1$-$C_6$-alkylsulfinyl, $C_3$-$C_8$-cycloalkyl, aromatic 5- or 6-membered monocyclic heterocycle, non-aromatic 3- to 7-membered monocyclic heterocycle, —N($R^e$)$_2$, —C(═N$R^f$)$R^f$ and —C(═O)N($R^g$)$_2$, with $R^e$ being as disclosed above, preferably $R^e$ being independently selected from the group consisting of hydrogen, $C_1$-$C_6$-alkyl and $C_3$-$C_8$-cycloalkyl (e.g. cyclopropyl), with $R^f$ being as disclosed above, preferably $R^f$ being independently selected from the group consisting of hydroxyl, amino, $C_1$-$C_6$-alkyl and $C_1$-$C_6$-alkoxy, with $R^g$ being as disclosed above, preferably $R^g$ being independently selected from the group consisting of hydrogen, $C_1$-$C_6$-alkyl and $C_3$-$C_8$-cycloalkyl, preferably $R^7$ is selected from the group consisting of halogen, $C_1$-$C_6$-alkyl, $C_1$-$C_6$-alkylcarbonyl, $C_2$-$C_6$-alkenyl, $C_3$-$C_8$-cycloalkyl, aromatic 5- or 6-membered monocyclic heterocycle and —N($R^e$)$_2$ with $R^e$ being independently selected from the group consisting of hydrogen, $C_1$-$C_6$-alkyl and $C_3$-$C_8$-cycloalkyl, wherein aliphatic $R^7$, $R^e$, $R^f$ and $R^g$ substituents may be substituted with one or more $R^{7Sa}$ substituents that may be the same or different, $R^{7Sa}$ being as disclosed herein (including preferred $R^{7Sa}$), wherein cyclic or cyclic moiety of $R^7$, cyclic $R^e$ and cyclic $R^g$ substituents may be substituted with one or more $R^{7Sc}$ substituents that may be the same or different, $R^{7Sc}$ being as disclosed herein (including preferred $R^{7Sc}$);

$R^8$ is selected from the group consisting of hydrogen, halogen, hydroxyl, $C_1$-$C_6$-alkyl, $C_1$-$C_6$-haloalkyl, $C_1$-$C_6$-alkoxy, $C_2$-$C_6$-alkenyl, $C_1$-$C_6$-alkylsulfanyl, $C_1$-$C_6$-haloalkylsulfanyl, $C_1$-$C_6$-alkylsulfinyl, $C_1$-$C_6$-alkylsulfonyl, $C_3$-$C_8$-cycloalkyl, aromatic $C_6$-$C_{14}$-carbocycle, non-aromatic 3- to 14-membered heterocycle (preferably non-aromatic 3- to 7-membered monocyclic heterocycle), aromatic 5- to 14-membered heterocycle (preferably 5- or 6-membered aromatic monocyclic heterocycle), $C_3$-$C_8$-cycloalkyloxy, non-aromatic 3- to 14-membered heterocyclyloxy (preferably non-aromatic 3- to 7-membered monocyclic heterocyclyloxy) and —N($R^h$)$_2$, with $R^h$ being as disclosed above, preferably $R^h$ being independently selected from the group consisting of hydrogen, $C_1$-$C_6$-alkyl, $C_2$-$C_6$-alkenyl, $C_3$-$C_8$-cycloalkyl (e.g. cyclopropyl, cyclohexyl), aromatic $C_6$-$C_{14}$-carbocycle (e.g. phenyl) and non-aromatic 3- to 7-membered monocyclic heterocycle (e.g. oxetanyl), preferably $R^8$ is selected from the group consisting of hydrogen, halogen, $C_1$-$C_6$-alkyl, $C_1$-$C_6$-alkoxy and —N($R^h$)$_2$ with $R^h$ being independently selected from the group consisting of hydrogen, $C_1$-$C_6$-alkyl and $C_3$-$C_8$-cycloalkyl, wherein aliphatic $R^8$ and $R^h$ substituents may be substituted with one or more $R^{8Sa}$ substituents that may be the same or different, $R^{8Sa}$ being as disclosed herein (including preferred $R^{8Sa}$), wherein cyclic or cyclic moiety of $R^8$ and cyclic $R^h$ substituents may be substituted with one or more $R^{8Sc}$ substituents that may be the same or different, $R^{8Sc}$ being as disclosed herein (including preferred $R^{8Sc}$);

Q is an aromatic $C_6$-$C_{14}$-carbocycle that may be substituted with one or more $Q^S$ substituents that may be the same or different, $Q^S$ being as described herein (including preferred $Q^S$).

In some embodiments (referred herein as embodiment 4), compounds according to the present invention are compounds of the formula (I):

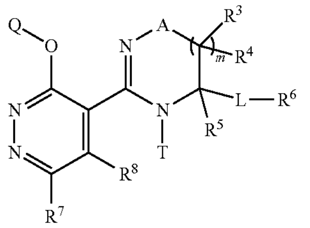

(I)

wherein

A is selected from the group consisting of O, C(═O) and $CR^1R^2$ with $R^1$ and $R^2$ being independently selected from the group consisting of hydrogen, $C_1$-$C_6$-alkyl and $C_3$-$C_8$-cycloalkyl, or $R^1$ and $R^2$ form, together with the carbon atom to which they are attached to, a $C_3$-$C_8$-cycloalkyl or a non-aromatic 3- to 7-membered monocyclic heterocycle, preferably $R^1$ and $R^2$ are hydrogen;

m is 0, 1 or 2;

T is hydrogen or —C(═O)($OR^{a1}$) with $R^{a1}$ being selected from the group consisting of $C_1$-$C_6$-alkyl, $C_1$-$C_6$-haloalkyl and $C_2$-$C_6$-alkylenyl, preferably T is hydrogen;

$R^3$ and $R^4$ are independently selected from the group consisting of hydrogen, halogen, cyano, hydroxyl, formyl, carboxyl, $C_1$-$C_6$-alkyl, $C_1$-$C_6$-alkoxy, $C_1$-$C_6$-alkoxycarbonyl, $C_3$-$C_8$-cycloalkyl, aromatic $C_6$-$C_{14}$-carbocycle, non-aromatic 3- to 14-membered heterocycle, —O—Si($C_1$-$C_6$-alkyl)$_3$ and aromatic 5- to 14-membered heterocycle, or $R^3$ and $R^4$ form, together with the carbon atom to which they are attached to, a carbonyl, a methylidene, a $C_3$-$C_8$-cycloalkyl or a non-aromatic 3- to 7-membered monocyclic heterocycle, preferably $R^3$ and $R^4$ are hydrogen;

$R^5$ is hydrogen, hydroxyl and $C_1$-$C_6$-alkoxy, preferably hydrogen;

wherein aliphatic $R^1$, $R^2$, $R^3$, $R^4$ and $R^5$ substituents may be substituted with one or more substituents as disclosed herein;

wherein cyclic $R^1$, $R^2$, $R^3$ and $R^4$ substituents may be substituted with one or more substituents as disclosed herein;

L represents a direct bond or L is selected from the group consisting of carbonyl, $C_1$-$C_6$-alkylene, $C_1$-$C_6$-alkylene substituted on a same carbon atom by two substituents forming together with the carbon atom to which they are attached to a $C_3$-$C_8$-cycloalkyl, $C_1$-$C_6$-alkylene substituted on a same carbon atom by two substituents forming together with the carbon atom to which they are attached to a non-aromatic 3- to 7-membered monocyclic heterocycle, $C_2$-$C_6$-alkenylene, $C_2$-$C_6$-alkynylene, $C_3$-$C_8$-cycloalkylene, $C_1$-$C_6$-alkylene-$C_3$-$C_8$-cycloalkylene, $C_3$-$C_8$-cycloalkylene-$C_1$-$C_6$-alkylene, $C_1$-$C_6$-alkylene-$C_3$-$C_8$-cycloalkylene-$C_1$-$C_6$-alkylene $C_1$-$C_6$-alkylene-(C═O), $C_3$-$C_8$-cycloalkenylene, $C_1$-$C_6$-alkylene-$C_3$-$C_8$-cycloalkenylene, $C_3$-$C_8$-cycloalkenylene-$C_1$-$C_6$-alkylene, $C_1$-$C_6$-alkylene-$C_3$-$C_8$-cycloalkenylene-$C_1$-$C_6$-alkylene, non-aromatic 3- to 7-membered monocyclic heterocyclylene;

wherein aliphatic L substituents may be substituted with one or more $L^{Sa}$ substituents that may be the same or different, as disclosed herein, wherein cyclic or cyclic moiety of L substituents may be substituted with one or more $L^{Sc}$ substituents that may be the same or different, as disclosed herein, $R^6$ is selected from the group consisting of non-aromatic $C_3$-$C_{12}$-carbocycle, aromatic $C_6$-$C_{14}$-carbocycle, non-aromatic 3- to 14-membered heterocycle, aromatic 5- to 14-membered heterocycle, aromatic $C_6$-$C_{14}$-carbocyclyloxy, $C_1$-$C_3$-alkoxy substituted by an aromatic $C_6$-$C_{14}$-carbocycle and $C_1$-$C_3$-haloalkoxy substituted by an aromatic $C_6$-$C_{14}$-carbocycle, preferably $R^6$ is selected from the group consisting of non-aromatic $C_3$-$C_{12}$-carbocycle, aromatic $C_6$-$C_{14}$-carbocycle and aromatic 5- to 14-membered heterocycle, wherein said cyclic, or cyclic moiety of, $R^6$ substituents may be substituted with one or more $R^{6S}$ substituents as disclosed herein (including preferred and more preferred $R^{6S}$ substituents);

$R^7$ is selected from the group consisting of hydrogen, halogen, cyano, $C_1$-$C_6$-alkyl, $C_1$-$C_6$-haloalkyl, $C_1$-$C_6$-hydroxyalkyl, $C_1$-$C_6$-alkylcarbonyl, $C_1$-$C_6$-alkoxy, $C_2$-$C_6$-alkenyl, $C_2$-$C_6$-alkynyl, $C_1$-$C_6$-alkylsulfanyl, $C_1$-$C_6$-alkylsulfinyl, $C_3$-$C_8$-cycloalkyl, aromatic 5- or 6-membered monocyclic heterocycle, non-aromatic 3- to 7-membered monocyclic heterocycle, —N($R^e$)$_2$, —C(═$NR^f$)$R^f$ and —C(═O)N($R^g$)$_2$, with $R^e$ being as disclosed above, preferably $R^e$ being independently selected from the group consisting of hydrogen, $C_1$-$C_6$-alkyl and $C_3$-$C_8$-cycloalkyl (e.g. cyclopropyl), with $R^f$ being as disclosed above, preferably $R^f$ being independently selected from the group consisting of hydroxyl, amino, $C_1$-$C_6$-alkyl and $C_1$-$C_6$-alkoxy, with $R^g$ being as disclosed above, preferably $R^g$ being independently selected from the group consisting of hydrogen, $C_1$-$C_6$-alkyl and $C_3$-$C_8$-cycloalkyl, preferably $R^7$ is selected from the group consisting of halogen, $C_1$-$C_6$-alkyl, $C_1$-$C_6$-alkylcarbonyl, $C_2$-$C_6$-alkenyl, $C_3$-$C_8$-cycloalkyl, aromatic 5- or 6-membered monocyclic heterocycle and —N($R^e$)$_2$ with $R^e$ being independently selected from the group consisting of hydrogen, $C_1$-$C_6$-alkyl and $C_3$-$C_8$-cycloalkyl, wherein aliphatic $R^7$, $R^e$, $R^f$ and $R^g$ substituents may be substituted with one or more $R^{7Sa}$ substituents that may be the same or different, $R^{7Sa}$ being as disclosed herein (including preferred $R^{7Sa}$), wherein cyclic or cyclic moiety of $R^7$, cyclic $R^e$ and cyclic $R^g$ substituents may be substituted with one or more $R^{7Sc}$ substituents that may be the same or different, $R^{7Sc}$ being as disclosed herein (including preferred $R^{7Sc}$);

$R^8$ is selected from the group consisting of hydrogen, halogen, hydroxyl, $C_1$-$C_6$-alkyl, $C_1$-$C_6$-haloalkyl, $C_1$-$C_6$-alkoxy, $C_2$-$C_6$-alkenyl, $C_1$-$C_6$-alkylsulfanyl, $C_1$-$C_6$-haloalkylsulfanyl, $C_1$-$C_6$-alkylsulfinyl, $C_1$-$C_6$-alkylsulfonyl, $C_3$-$C_8$-cycloalkyl, aromatic $C_6$-$C_{14}$-carbocycle, non-aromatic 3- to 14-membered heterocycle (preferably non-aromatic 3- to 7-membered monocyclic heterocycle), aromatic 5- to 14-membered heterocycle (preferably 5- or 6-membered aromatic monocyclic heterocycle), $C_3$-$C_8$-cycloalkyloxy, non-aromatic 3- to 14-membered heterocyclyloxy (preferably non-aromatic 3- to 7-membered monocyclic heterocyclyloxy) and —N($R^h$)$_2$, with $R^h$ being as disclosed above, preferably $R^h$ being independently selected from the group consisting of hydrogen, $C_1$-$C_6$-alkyl, $C_2$-$C_6$-alkenyl, $C_3$-$C_8$-cycloalkyl (e.g. cyclopropyl, cyclohexyl), aromatic $C_6$-$C_{14}$-carbocycle (e.g. phenyl) and non-aromatic 3- to 7-membered monocyclic heterocycle (e.g. oxetanyl), preferably $R^8$ is selected from the group consisting of hydrogen, halogen, $C_1$-$C_6$-alkyl, $C_1$-$C_6$-alkoxy and —N($R^h$)$_2$ with $R^h$ being independently selected from the group consisting of hydrogen, $C_1$-$C_6$-alkyl and $C_3$-$C_8$-cycloalkyl, wherein aliphatic $R^8$ and $R^h$ substituents may be substituted with one or more $R^{8Sa}$ substituents that may be the same or different, $R^{8Sa}$ being as disclosed herein (including preferred $R^{8Sa}$), wherein cyclic or cyclic moiety of $R^8$ and cyclic $R^h$ substituents may be substituted with one or more $R^{8Sc}$ substituents that may be the same or different, $R^{8Sc}$ being as disclosed herein (including preferred $R^{8Sc}$);

Q is

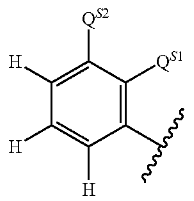
or
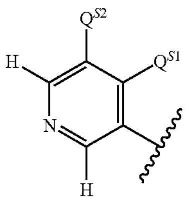
or
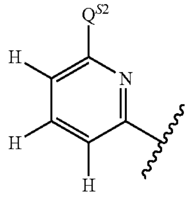

wherein $Q^{s1}$ is hydrogen or halogen (preferably fluorine), $Q^{s1}$ is hydrogen or $Q^s$, wherein $Q^s$ is as described herein above, preferably $Q^{S2}$ is selected from the group consisting of hydrogen, halogen (e.g. fluorine, chlorine, bromine, iodine), cyano, nitro, hydroxyl, amino, $C_1$-$C_6$-alkyl (e.g. methyl, ethyl), $C_1$-$C_6$-haloalkyl (e.g. trifluoromethyl, difluoromethyl), $C_1$-$C_6$-alkylcarbonyl (e.g. methoxycarbonyl), $C_1$-$C_6$-alkoxy (e.g. methoxy), $C_1$-$C_6$-haloalkoxy (e.g. trifluoromethoxy), $C_2$-$C_6$-alkenyl (e.g. vinyl), $C_2$-$C_6$-alkynyl (e.g. ethynyl), $C_1$-$C_6$-alkylsulfanyl (e.g. methylsulfanyl), $C_1$-$C_6$-haloalkylsulfanyl (e.g. trifluoromethylsulfanyl), $C_3$-$C_8$-cycloalkyl (e.g. cyclopropyl, cyclobutyl) that may be substituted with one or more halogen atoms and non-aromatic 3- to 7-membered monocyclic heterocycle (e.g. oxetanyl) that may be substituted with one or more halogen atoms, more preferably $Q^{s2}$ is selected from the group consisting of fluorine, chlorine, bromine, iodine, cyano, nitro, hydroxyl, amino, methyl, trifluoromethyl, difluoromethyl, methoxy, trifluoromethoxy, vinyl, ethynyl, methylsulfanyl, trifluoromethylsulfanyl, cyclopropyl that may be substituted with one or more halogen atoms and oxetanyl that may be substituted with one or more halogen atoms, preferably at least one of $Q^{s1}$ and $Q^{s2}$ is different from hydrogen.

In some embodiments (referred herein as embodiment 5), compounds according to the present invention are compounds of the formula (I):

(I)

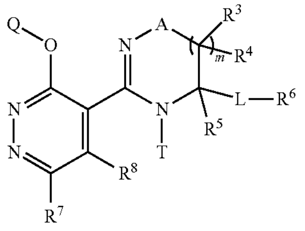

wherein

A is selected from the group consisting of O, C(═O) and $CR^1R^2$ with $R^1$ and $R^2$ being independently selected from the group consisting of hydrogen, $C_1$-$C_6$-alkyl and $C_3$-$C_8$-cycloalkyl, or $R^1$ and $R^2$ form, together with the carbon atom to which they are attached to, a $C_3$-$C_8$-cycloalkyl or a non-aromatic 3- to 7-membered monocyclic heterocycle, preferably $R^1$ and $R^2$ are hydrogen;

m is 0, 1 or 2;

T is hydrogen or —C(═O)(OR$^{a1}$) with $R^{a1}$ being selected from the group consisting of $C_1$-$C_6$-alkyl, $C_1$-$C_6$-haloalkyl and $C_2$-$C_6$-alkylenyl, preferably T is hydrogen;

$R^3$ and $R^4$ are independently selected from the group consisting of hydrogen, halogen, cyano, hydroxyl, formyl, carboxyl, $C_1$-$C_6$-alkyl, $C_1$-$C_6$-alkoxy, $C_1$-$C_6$-alkoxycarbonyl, $C_3$-$C_8$-cycloalkyl, aromatic $C_6$-$C_{14}$-carbocycle, non-aromatic 3- to 14-membered heterocycle, —O—Si($C_1$-$C_6$-alkyl)$_3$ and aromatic 5- to 14-membered heterocycle, or $R^3$ and $R^4$ form, together with the carbon atom to which they are attached to, a carbonyl, a methylidene, a $C_3$-$C_8$-cycloalkyl or a non-aromatic 3- to 7-membered monocyclic heterocycle, preferably $R^3$ and $R^4$ are hydrogen;

$R^5$ is hydrogen, hydroxyl and $C_1$-$C_6$-alkoxy, preferably hydrogen;

wherein aliphatic $R^1$, $R^2$, $R^3$, $R^4$ and $R^5$ substituents may be substituted with one or more substituents as disclosed herein;

wherein cyclic $R^1$, $R^2$, $R^3$ and $R^4$ substituents may be substituted with one or more substituents as disclosed herein;

L represents a direct bond or L is selected from the group consisting of carbonyl, $C_1$-$C_6$-alkylene, $C_1$-$C_6$-alkylene substituted on a same carbon atom by two substituents forming together with the carbon atom to which they are attached to a $C_3$-$C_8$-cycloalkyl, $C_1$-$C_6$-alkylene substituted on a same carbon atom by two substituents forming together with the carbon atom to which they are attached to a non-aromatic 3- to 7-membered monocyclic heterocycle, $C_2$-$C_6$-alkenylene, $C_2$-$C_6$-alkynylene, $C_3$-$C_8$-cycloalkylene, $C_1$-$C_6$-alkylene-$C_3$-$C_8$-cycloalkylene, $C_3$-$C_8$-cycloalkylene-$C_1$-$C_6$-alkylene, $C_1$-$C_6$-alkylene-$C_3$-$C_8$-cycloalkylene-$C_1$-$C_6$-alkylene $C_1$-$C_6$-alkylene-(C═O), $C_3$-$C_8$-cycloalkenylene, $C_1$-$C_6$-alkylene-$C_3$-$C_8$-cycloalkenylene, $C_3$-$C_8$-cycloalkenylene-$C_1$-$C_6$-alkylene, $C_1$-$C_6$-alkylene- $C_3$-$C_8$-cycloalkenylene-$C_1$-$C_6$-alkylene, non-aromatic 3- to 7-membered monocyclic heterocyclylene;

wherein aliphatic L substituents may be substituted with one or more $L^{Sa}$ substituents that may be the same or different, as disclosed herein, wherein cyclic or cyclic moiety of L substituents may be substituted with one or more $L^{Sc}$ substituents that may be the same or different, as disclosed herein, $R^6$ is

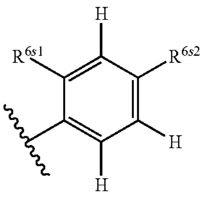
or
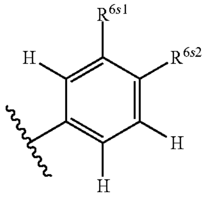

wherein $R^{6s1}$ is hydrogen or $R^{6s}$, $R^{6s2}$ is hydrogen or $R^{6s}$, $R^{6s}$ being as described herein (including preferred and more preferred $R^{6s}$), preferably at least one of $R^{6s1}$ and $R^{6s2}$ is different from hydrogen;

$R^7$ is selected from the group consisting of hydrogen, halogen, cyano, $C_1$-$C_6$-alkyl, $C_1$-$C_6$-haloalkyl, $C_1$-$C_6$-hydroxyalkyl, $C_1$-$C_6$-alkylcarbonyl, $C_1$-$C_6$-alkoxy, $C_2$-$C_6$-alkenyl, $C_2$-$C_6$-alkynyl, $C_1$-$C_6$-alkylsulfanyl, $C_1$-$C_6$-alkylsulfinyl, $C_3$-$C_8$-cycloalkyl, aromatic 5- or 6-membered monocyclic heterocycle, non-aromatic 3- to 7-membered monocyclic heterocycle, —$N(R^e)_2$, —$C(=NR^f)R^f$ and —$C(=O)N(R^g)_2$, with $R^e$ being as disclosed above, preferably $R^e$ being independently selected from the group consisting of hydrogen, $C_1$-$C_6$-alkyl and $C_3$-$C_8$-cycloalkyl (e.g. cyclopropyl), with $R^f$ being as disclosed above, preferably $R^f$ being independently selected from the group consisting of hydroxyl, amino, $C_1$-$C_6$-alkyl and $C_1$-$C_6$-alkoxy, with $R^g$ being as disclosed above, preferably $R^g$ being independently selected from the group consisting of hydrogen, $C_1$-$C_6$-alkyl and $C_3$-$C_8$-cycloalkyl, preferably $R^7$ is selected from the group consisting of halogen, $C_1$-$C_6$-alkyl, $C_1$-$C_6$-alkylcarbonyl, $C_2$-$C_6$-alkenyl, $C_3$-$C_8$-cycloalkyl, aromatic 5- or 6-membered monocyclic heterocycle and —$N(R^e)_2$ with $R^e$ being independently selected from the group consisting of hydrogen, $C_1$-$C_6$-alkyl and $C_3$-$C_8$-cycloalkyl, wherein aliphatic $R^7$, $R^e$, $R^f$ and $R^g$ substituents may be substituted with one or more $R^{7Sa}$ substituents that may be the same or different, $R^{7Sa}$ being as disclosed herein (including preferred $R^{7Sa}$)

wherein cyclic or cyclic moiety of $R^7$, cyclic $R^e$ and cyclic $R^g$ substituents may be substituted with one or more $R^{7Sc}$ substituents that may be the same or different, $R^{7Sc}$ being as disclosed herein (including preferred $R^{7Sc}$);

$R^8$ is selected from the group consisting of hydrogen, halogen, hydroxyl, $C_1$-$C_6$-alkyl, $C_1$-$C_6$-haloalkyl, $C_1$-$C_6$-alkoxy, $C_2$-$C_6$-alkenyl, $C_1$-$C_6$-alkylsulfanyl, $C_1$-$C_6$-haloalkylsulfanyl, $C_1$-$C_6$-alkylsulfinyl, $C_1$-$C_6$-alkylsulfonyl, $C_3$-$C_8$-cycloalkyl, aromatic $C_6$-$C_{14}$-carbocycle, non-aromatic 3- to 14-membered heterocycle (preferably non-aromatic 3- to 7-membered monocyclic heterocycle), aromatic 5- to 14-membered heterocycle (preferably 5- or 6-membered aromatic monocyclic heterocycle), $C_3$-$C_8$-cycloalkyloxy, non-aromatic 3- to 14-membered heterocyclyloxy (preferably non-aromatic 3- to 7-membered monocyclic heterocyclyloxy) and —$N(R^h)_2$, with $R^h$ being as disclosed above, preferably $R^h$ being independently selected from the group consisting of hydrogen, $C_1$-$C_6$-alkyl, $C_2$-$C_6$-alkenyl, $C_3$-$C_8$-cycloalkyl (e.g. cyclopropyl, cyclohexyl), aromatic $C_6$-$C_{14}$-carbocycle (e.g. phenyl) and non-aromatic 3- to 7-membered monocyclic heterocycle (e.g. oxetanyl), preferably $R^8$ is selected from the group consisting of hydrogen, halogen, $C_1$-$C_6$-alkyl, $C_1$-$C_6$-alkoxy and —$N(R^h)_2$ with $R^h$ being independently selected from the group consisting of hydrogen, $C_1$-$C_6$-alkyl and $C_3$-$C_8$-cycloalkyl, wherein aliphatic $R^8$ and $R^h$ substituents may be substituted with one or more $R^{8Sa}$ substituents that may be the same or different, $R^{8Sa}$ being as disclosed herein (including preferred $R^{8Sa}$), wherein cyclic or cyclic moiety of $R^8$ and cyclic $R^h$ substituents may be substituted with one or more $R^{8Sc}$ substituents that may be the same or different, $R^{8Sc}$ being as disclosed herein (including preferred $R^{8Sc}$);

Q is

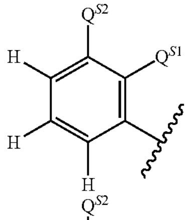
or
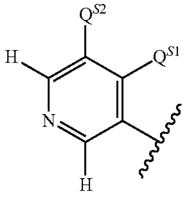
or
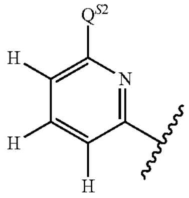

wherein $Q^{s1}$ is hydrogen or halogen (preferably fluorine), $Q^{s2}$ is hydrogen or $Q^s$, wherein $Q^s$ is as described herein above, preferably $Q^{s2}$ is selected from the group consisting of hydrogen, halogen (e.g. fluorine, chlorine, bromine, iodine), cyano, nitro, hydroxyl, amino, $C_1$-$C_6$-alkyl (e.g. methyl, ethyl), $C_1$-$C_6$-haloalkyl (e.g. trifluoromethyl, difluoromethyl), $C_1$-$C_6$-alkylcarbonyl (e.g. methoxycarbonyl), $C_1$-$C_6$-alkoxy (e.g. methoxy), $C_1$-$C_6$-haloalkoxy (e.g. trifluoromethoxy), $C_2$-$C_6$-alkenyl (e.g. vinyl), $C_2$-$C_6$-alkynyl (e.g. ethynyl), $C_1$-$C_6$-alkylsulfanyl (e.g. methylsulfanyl), $C_1$-$C_6$-haloalkylsulfanyl (e.g. trifluoromethylsulfanyl), $C_3$-$C_8$-cycloalkyl (e.g. cyclopropyl, cyclobutyl) that may be substituted with one or more halogen atoms and non-aromatic 3- to 7-membered monocyclic heterocycle (e.g. oxetanyl) that may be substituted with one or more halogen atoms, more preferably $Q^{s2}$ is selected from the group consisting of fluorine, chlorine, bromine, iodine, cyano, nitro, hydroxyl, amino, methyl, trifluoromethyl, difluoromethyl, methoxy, trifluoromethoxy, vinyl, ethynyl, methylsulfanyl, trifluoromethylsulfanyl, cyclopropyl that may be substituted with one or more halogen atoms and oxetanyl that may be substituted with one or more halogen atoms, preferably at least one of $Q^{s1}$ and $Q^{s2}$ is different from hydrogen.

In some embodiments, compounds according to the invention are compounds of formula (I) in accordance with embodiments 1, 2, 3, 4 or 5 wherein m is 0 and A is $CR^1R^2$ with $R^1$ and $R^2$ being as described herein above, preferably with $R^1$ and $R^2$ being a hydrogen atom, or A is O.

In some embodiments, compounds according to the invention are compounds of formula (I) in accordance with embodiments 1, 2, 3, 4 or 5 wherein m is 1 and A is O, C(═O) or $CR^1R^2$ with $R^1$ and $R^2$ being as described herein above, preferably with $R^1$ and $R^2$ being a hydrogen atom.

In some embodiments, compounds according to the invention are compounds of formula (I) in accordance with embodiments 1, 2, 3, 4 or 5 wherein m is 2 and A is O, C(═O) or $CR^1R^2$ with $R^1$ and $R^2$ being as described herein above, preferably with $R^1$ and $R^2$ being a hydrogen atom.

In some embodiments, compounds according to the invention are compounds of formula (I) in accordance with embodiments 1, 2, 3, 4 or 5 wherein L is a direct bond or $C_1$-$C_6$-alkylene (e.g. —$CH_2$-).

In some embodiments, compounds according to the invention are compounds of formula (I) in accordance with embodiments 1, 2, 3, 4 or 5 wherein L is

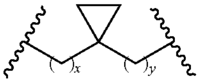

or

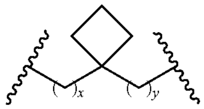

or

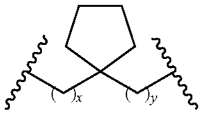

with x is 0 or 1 and y is 0 or 1, preferably x and y are 0.

In some embodiments, compounds according to the invention are compounds of formula (I) in accordance with embodiments 1, 2, 3, 4 or 5 wherein L is

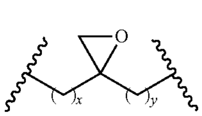

or

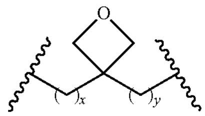

or

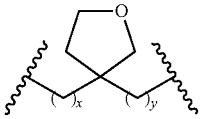

with x is 0 or 1 and y is 0 or 1, preferably x and y are 0.

In some embodiments, compounds according to the invention are compounds of formula (I) in accordance with embodiments 1, 2, 3, 4 or 5 wherein L is

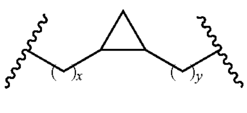

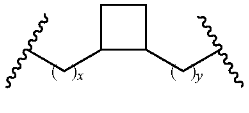

with x is 0 or 1 and y is 0 or 1, preferably x and y are 0.

In some embodiments, compounds according to the invention are compounds of formula (I) in accordance with embodiments 1, 2, 3, 4 or 5 wherein L is

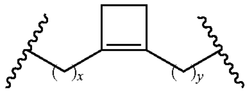

with x is 0 or 1 and y is 0 or 1, preferably x and y are 0.

In some embodiments, compounds according to the invention are compounds of formula (I) in accordance with embodiments 1, 2, 3, 4 or 5 wherein L represents a direct bond and $R^6$ is selected from the group consisting of non-aromatic $C_3$-$C_{12}$-carbocycle, aromatic $C_6$-$C_{14}$-carbocycle and aromatic 5- to 14-membered heterocycle, preferably $R^6$ is selected from the group consisting of indan-5-yl, phenyl, naphtyl, furan-2-yl and indol-3-yl.

In some embodiments, compounds according to the invention are compounds of formula (I) in accordance with embodiments 1, 2, 3, 4 or 5 wherein L represents a $C_1$-$C_6$-alkylene and $R^6$ is an aromatic $C_6$-$C_{14}$-carbocycle (e.g. phenyl).

In a more preferred embodiment, L represents a direct bond or L is selected from the group consisting of $C_1$-$C_6$-alkylene,

- wherein aliphatic L substituents may be substituted with one to three $L^{Sa}$ substituents independently selected from the group consisting of fluorine, chlorine, hydroxyl, $C_1$-$C_4$-alkoxy, $C_1$-$C_4$-haloalkoxy and $C_3$-$C_6$-cycloalkyl,
- wherein cyclic or cyclic moiety of L substituents may be substituted with one to three $L^{Sc}$ substituents independently selected from the group consisting of fluorine, chlorine, hydroxyl, oxo, $C_1$-$C_4$-alkyl, $C_1$-$C_4$-haloalkyl, $C_1$-$C_4$-alkoxy, $C_1$-$C_4$-haloalkoxy and $C_3$-$C_6$-cycloalkyl.

The present invention also relates to any compounds of formula (I) disclosed in Table 1.

The compounds of formula (I) may be used as fungicides (for controlling phytopathogenic fungi), in particular in methods for controlling phytopathogenic fungi which comprises the step of applying one or more compounds of formula (I) to the plants, plant parts, seeds, fruits or to the soil in which the plants grow.

Processes for the Preparation of Compounds of Formula (I) and Intermediates

The present invention relates to processes for the preparation of compounds of formula (I) and their intermediates. Unless indicated otherwise, the radicals A, Q, T, L, $R^1$, $R^2$, $R^3$, $R^4$, $R^5$, $R^6$, $R^7$, $R^8$, m have the meanings given above for the compounds of formula (I). These definitions apply not only to the end products of formula (I) but also to all intermediates.

Compounds of formula (I-a)-(I-f) are various subsets of formula (I). Compounds of formula (I-a-1)-(I-a-7) are various subsets of formula (I-a). All substituents for formula (I-a)-(I-f) and (I-a-1)-(I-a-7) are as defined above for formula (I) unless otherwise noted.

The compounds of formula (I) can be prepared by various routes in analogy to known processes (see e.g. and references therein). Non-limiting examples of suitable processes are herein described.

A compound of formula (I) may be directly obtained by performing process A to I or may be obtained by conversion or derivatization of another compound of formula (I) prepared in accordance with the processes described herein. For instance, a compound of formula (I) can be converted into another compound of formula (I) by replacing one or more substituents of the starting compound of formula (I) by other substituents. Non-limiting examples of such conversion or derivatization are described below (processes J to L).

The processes described herein may be suitably performed using one or more inert organic solvents which is/are customary for the considered reaction. Suitable inert organic solvents can be chosen from the following: aliphatic, alicyclic or aromatic hydrocarbons (e.g. petroleum ether, pentane, hexane, heptane, cyclohexane, methylcyclohexane, ligroin, benzene, toluene, xylene or decalin), halogenated aliphatic, alicyclic or aromatic hydrocarbons (e.g. chlorobenzene, dichlorobenzene, dichloromethane, chloroform, carbon tetrachloride, 1,2-dichloroethane or trichloroethane), ethers (e.g. diethyl ether, diisopropyl ether, methyl t-butyl ether, methyl t-amyl ether, dioxane, tetrahydrofuran, 2-methyltetrahydrofuran, 1,2-dimethoxyethane, 1,2-diethoxyethane or anisole), ketones (e.g. acetone, methyl ethyl ketone, methyl isopropyl ketone and methyl isobutyl ketone), esters (e.g. methyl acetate, ethyl acetate or butyl acetate), alcohols (e.g. methanol, ethanol, propanol, isopropanol, butanol, tert-butanol), nitriles (e.g. acetonitrile, propionitrile, n- or i-butyronitrile or benzonitrile), amides (e.g. N,N-dimethylformamide, N,N-dimethylacetamide, N-methylformanilide, N-methylpyrrolidone or hexamethylphosphoric triamide), sulfoxides (e.g. dimethyl sulfoxide) or sulfones (e.g. sulfolane), ureas (e.g. 1,3-dimethyl-3,4,5,6-tetrahydro-2(1H)-pyrimidinone) or any mixture thereof.

Some processes described herein may require or be optionally performed using one or more inorganic or organic bases which are customary for such reactions. Examples of suitable inorganic and organic bases include, but are not limited to, alkaline earth metal or alkali metal carbonates (e.g. sodium carbonate, potassium carbonate, potassium bicarbonate, sodium bicarbonate or cesium carbonate), alkali metal hydrides (e.g. sodium hydride), alkaline earth metal or alkali metal hydroxides (e.g. sodium hydroxide, calcium hydroxide, potassium hydroxide or other ammonium hydroxide derivatives), alkaline earth metal, alkali metal or ammonium fluorides (e.g. potassium fluoride, cesium fluoride or tetrabutylammonium fluoride), alkali metal or alkaline earth metal acetates (e.g. sodium acetate, lithium acetate, potassium acetate or calcium acetate), alkali metal alcoholates (e.g. potassium tert-butoxide or sodium tert-butoxide), alkali metal phosphates (e.g. tri-potassium phosphate), tertiary amines (e.g. trimethylamine, triethylamine, tributylamine, N,N-dimethylaniline, N,N-dicyclohexylmethyl-amine, N,N-diisopropylethylamine, N-methylpiperidine, N,N-dimethylaminopyridine, diazabicyclo-octane (DABCO), diazabicyclononene (DBN), diazabicycloundecene (DBU), quinuclidine, 3-acetoxy-quinuclidine, guanidines or aromatic bases (e.g. pyridines, picolines, lutidines or collidines).

Some of the processes described herein may be optionally performed in the presence of a transition metal catalyst, such as a metal (e.g. copper or palladium) salt or complex, if appropriate in the presence of a ligand.

Suitable copper salts or complexes and their hydrates include, but are not limited to, copper metal, copper(I) iodide, copper(I) chloride, copper(I) bromide, copper(II) chloride, copper(II) bromide, copper(II) oxide, copper(I) oxide, copper(II) acetate, copper(I) acetate, copper(I) thiophene-2-carboxylate, copper(I) cyanide, copper(II) sulfate, copper(II) bis(2,2,6,6-tetramethyl-3,5-heptane-dionate), copper(II) trifluoromethanesulfonate, tetrakis(acetonitrile) copper(I) hexafluorophosphate, tetrakis(acetonitrile)-copper (I) tetrafluoroborate.

It is also possible to generate in situ a suitable copper complex in the reaction mixture by separate addition to the reaction of a copper salt and a ligand or salt, such as ethylenediamine, N,N-dimethylethylenediamine, N,N'-dimethylethylenediamine, rac-trans-1,2-diaminocyclohexane, rac-trans-N,N'-dimethylcyclohexane-1,2-diamine, 1,1'-binaphthyl-2,2'-diamine, N,N,N',N'-tetramethylethylenediamine, proline, N,N-dimethylglycine, quinolin-8-ol, pyridine, 2-aminopyridine, 4-(dimethyl-amino)pyridine, 2,2'-bipyridyl, 2,6-di(2-pyridyl)pyridine, 2-picolinic acid, 2-(dimethylaminomethyl)-3-hydroxypyridine, 1,10-phenanthroline, 3,4,7,8-tetramethyl-1,10-phenanthroline, 2,9-dimethyl-1,10-phenanthroline, 4,7-dimethoxy-1,10-phenanthroline, N,N'-bis[(E)-pyridin-2-ylmethylidene]cyclohexane-1,2-diamine, N-[(E)-phenylmethylidene], N-[(E)-phenylmethylidene]-cyclohexanamine, 1,1,1-tris (hydroxymethyl)ethane, n-butylimidazol, ethylene glycol, 2,2,6,6-tetramethylheptane-3,5-dione, 2-(2,2-dimethylpropanoyl)cyclohexanone, acetylacetone, dibenzoylmethane, 2-(2-methyl-propanoyl)cyclohexanone, biphenyl-2-yl(di-tert-butyl)phosphane, ethylenebis-(diphenylphosphine), N,N-diethylsalicylamide, 2-hydroxybenzaldehyde oxime, oxo[(2,4,6-trimethylphenyl)amino]acetic acid or 1H-pyrrole-2-carboxylic acid.

Suitable palladium salts or complexes include, but are not limited to, palladium chloride, palladium acetate, tetrakis (triphenylphosphine)palladium(0), bis(dibenzylideneacetone)palladium(0), tris(dibenzylideneacetone)dipalladium (0), bis(triphenylphosphine)palladium(II) dichloride, [1,1'-bis(diphenylphosphino)ferrocene]dichloropalladium(II), bis (cinnamyl)dichlorodipalladium(II), bis(allyl)-dichlorodipalladium(II) or [1,1'-Bis(di-tert-butylphosphino) ferrocene]dichloropalladium(II).

It is also possible to generate a palladium complex in the reaction mixture by separate addition to the reaction of a palladium salt and a ligand or salt, such as triethylphosphine, tri-tert-butylphosphine, tri-tert-butylphosphonium tetrafluoroborate, tricyclohexylphosphine, 2-(dicyclohexylphosphino)biphenyl, 2-(di-tert-butylphosphino)biphenyl, 2-(dicyclohexylphosphino)-2'-(N,N-dimethylamino)biphenyl, 2-(tert-butylphosphino)-2'-(N,N-dimethylamino)biphenyl, 2-di-tert-butylphosphino-2',4',6'-triisopropylbiphenyl, 2-dicyclohexylphosphino-2',4',6'-triisopropylbiphenyl, 2-dicyclohexylphosphino-2,6'-dimethoxybiphenyl, 2-dicyclohexylphosphino-2',6'-diisopropoxybiphenyl, triphenylphosphine, tris-(o-tolyl)phosphine, sodium 3-(diphenylphosphino)benzenesulfonate, tris-(2-methoxyphenyl)phosphine, 2,2'-bis(diphenyl-phosphino)-1,1'-binaphthyl, 1,4-bis(diphenylphosphino)butane, 1,2-bis(diphenylphosphino) ethane, 1,4-bis(dicyclohexylphosphino) butane, 1,2-bis(dicyclohexylphosphino)-ethane, 2-(dicyclohexyl-phosphino)-2'-(N,N-dimethylamino)-biphenyl, 1,1'-bis(diphenylphosphino)-ferrocene, (R)-(−)-1-[(S)-2-diphenylphosphino)ferrocenyl]ethyldicyclohexylphosphine, tris-(2,4-tert-butyl-phenyl)phosphite, di(1-adamantyl)-2-morpholinophenylphosphine or 1,3-bis(2,4,6-trimethylphenyl)imidazolium chloride.

The appropriate catalyst and/or ligand may be chosen from commercial catalogues such as “Metal Catalysts for Organic Synthesis” by Strem Chemicals or from reviews (Chemical Society Reviews (2014), 43, 3525, Coordination Chemistry Reviews (2004), 248, 2337 and references therein).

Some of the processes described herein may be performed by metallo-photoredox catalysis according to methods reported in the literature (Nature chemistry review, (2017) 0052 and references therein; Science (2016) 352, 6291, 1304; Org. Lett. 2016, 18, 4012, J. Org. Chem 2016, 81, 6898; J. Am. Chem. Soc. 2016, 138, 12715, J. Am. Chem. Soc. 2016, 138, 13862; J. Am. Chem. Soc. 2016, 138, 8034; J. Org. Chem. 2016, 81, 12525, J. Org. Chem. 2015, 80, 7642). The process is then performed in the presence a photosensitizer, such as Ir and Ru complexes or organic dyes, and a metal catalyst such as Ni complexes. The reaction can be performed in the presence of a ligand and if appropriate in the presence of a base under irradiation with blue or white light.

Suitable photosensitizers include, but are not limited to, Ir(III) photocatalyst such as $[Ir(dFCF_3ppy)_2(bpy)]PF_6$ ($dFCF_3ppy$=2-(2,4-difluorophenyl)-5-trifluoromethylpyridine, bpy=2,2'-bipyridine), $[Ir(dFCF_3ppy)_2(dtbbpy)]PF_6$ (dtbbpy=4,4'-di-tert-butyl-2,2'-bipyridine), $Ir(ppy)_2(dtbbpy)PF_6$ (ppy=2-phenylpyridine), $Ir(ppy)_2(bpy)PF_6$, $Ir(dFppy)_3PF_6$ ($dFCF_3ppy$=2-(2,4-difluorophenyl)pyridine), fac-$Ir(ppy)_3$, $(Ir[diF(5-Me)ppy]2(tetraMePhen)PF_6$ (diF(5-Me)ppy=2-(2,4-difluorophenyl)-5-methy-pyridine, tetraMePhen=3,4,7,8-tetramethyl-1,10-phenanthroline), Ru(II) photocatalyst such as $Ru(bpy)_3Cl_2$ or $Ru(bpy)_3(PF_6)_2$ or organic dyes like 9-mesityl-10-acridinium perchlorate or tetrafluoroborate, or 2,4,5,6-tetra-9H-carbazol-9-yl-1,3-benzenedicarbonitrile, 9-fluorenone and 9,10-phenanthrenequinone.

Suitable nickel catalysts include, but are not limited to, bis(1,5-cyclooctadiene)nickel (0), nickel(II) choride, nickel (II) bromide, nickel(II) iodide under their anhydrous or hydrate forms or as dimethoxyethane complexes, nickel(II) acetylacetonate, nickel(II) nitrate hexahydrate. These nickel catalysts can be used in combination with bipyridine ligand such as 2,2'-bipyridine, 4,4'-di-tert-butyl-2,2'-bipyridine, 4,4'-dimethoxy-2,2'-bipyridine, 4,4'-dimethyl-2,2'-bipyridine or phenantroline such as 1,10-phenanthroline, 4,7-dimethyl-1,10-phenantroline, 4,7-dimethoxy-1,10-phenantroline or diamines such as N,N,N',N'-tetramethylethylenediamine or dione such as tetramethylheptanedione.

The processes described herein may be performed at temperature ranging from −105° C. to 250° C., preferably from −78° C. to 185° C.

The reaction time varies as a function of the scale of the reaction and of the reaction temperature, but is generally between a few minutes and 48 hours.

The processes described herein are generally performed under standard pressure. However, it is also possible to work under elevated or reduced pressure.

The processes described herein may optionally be performed under microwave irradiation under standard or elevated pressure.

In the processes described herein, the starting materials are generally used in approximately equimolar amounts. However, it is also possible to use one of the starting materials in a relatively large excess.

Processes for the Preparation of Compounds of Formula (I)

Process A

A compound of formula (I-a-1) (i.e. compound of formula (I) wherein A is 0, T is hydrogen and m is 1 or 2) can be prepared by a process, as shown in scheme 1, comprising the steps of:

- when W is hydrogen, treating the compound of formula (4) with a dehydrating agent, optionally in the presence of a base to obtain directly the compound of formula (I-a-1);
- when W is an aminoprotecting group, treating the compound of formula (4) with a dehydrating agent, optionally in the presence of a base, and then performing a deprotection step to obtain the compound of formula (I-a-1).

Scheme 1: Process A-Synthesis of compounds of formula (I-a-1)

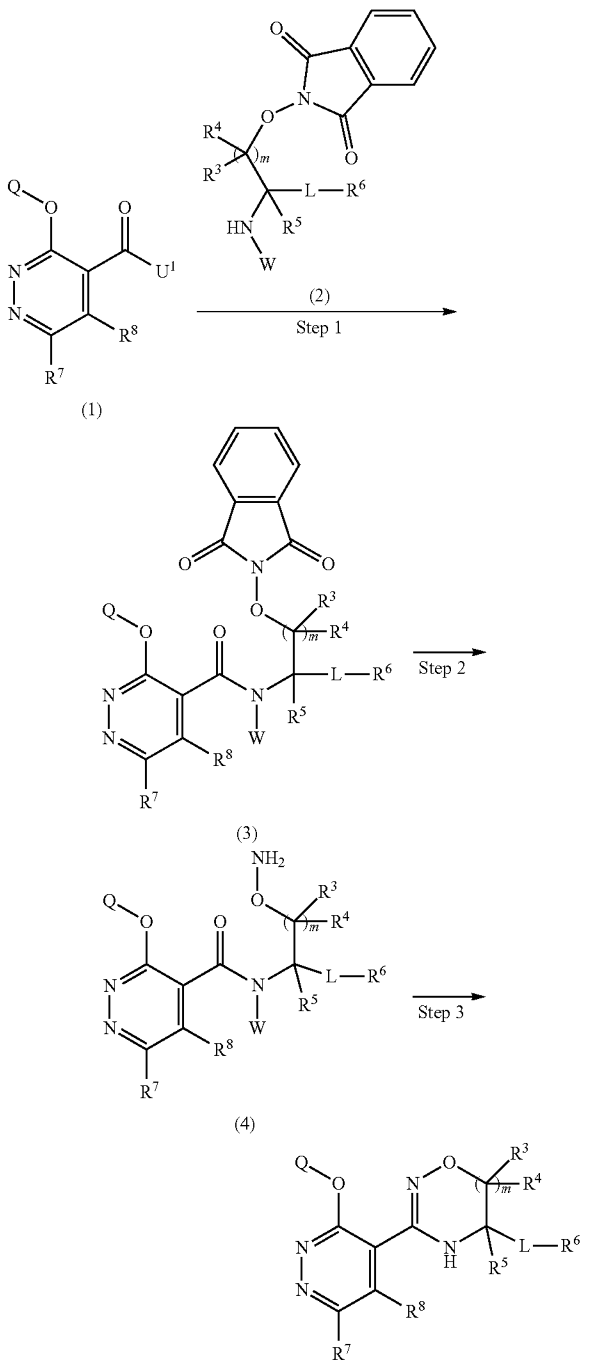

(1)

(3)

(4)

(I-a-1)

$U^1$ = hydroxyl, halogen, $C_1$-$C_6$-alkoxy

W = hydrogen, tert-butoxycarbonyl, benzyl, allyl or (4-methoxyphenyl)methyl m = 1 or 2

The compound of formula (I-a-1) can be obtained by treating a compound of formula (4) with a dehydrating agent such as $POCl_3$, $P_2O_5$ or triflic anhydride, optionally in the presence of a base. Such methods to form oxadiazine rings are known and have been described in the literature (J. Med. Chem. 2017, 60, 2383-2400). The reaction may be performed in any customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichlorethane or trichlorethane; ethers, such as diisopropyl ether, methyl t-butyl ether, methyl t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; alcohols, such as ethanol or isopropanol.

When W represents an amino protecting group, step 3 is followed by an additional deprotection step using reaction conditions described in the literature (Greene's Protective Groups in organic Synthesis; Peter G. M. Wuts; Wiley; Fifth Edition; 2014; 895-1194). For example a tert-butoxycarbonyl group can be removed in acidic medium such as hydrochloric acid or trifluoroacetic acid.

Compound of formula (4) can be obtained by:

reacting a compound of formula (1) with an amine of formula (2) or one of its salt to provide a compound of formula (3);

removing the phtalimide group of compound (3) to provide a compound of formula (4). Reaction conditions to remove a phtalimide group are well known and have been reported in the literature (Greene's Protective Groups in organic Synthesis; Peter G. M. Wuts; Wiley; Fifth Edition; 2014; 1012-1014).

Compounds of formula (1) can be prepared by one or more processes described herein (see processes N, O and P)

Amines of formula (2) can be prepared by process S described herein.

Compounds of formula (1) wherein $U^1$ is a hydroxyl group can be reacted with an amine of formula (2) in the presence of a condensing reagent by means of methods described in the literature (e.g. Tetrahedron 2005, 61, 10827-10852). Examples of suitable condensing reagents include, but are not limited to, halogenating reagents (e.g. phosgene, phosphorous tribromide, phosphorous trichloride, phosphorous pentachloride, phosphorous trichloride oxide, oxalyl chloride or thionyl chloride), dehydrating reagents (e.g. ethyl chloroformate, methyl chloroformate, isopropyl chloroformate, isobutyl chloroformate or methanesulfonyl chloride), carbodiimides (e.g. N,N'-dicyclohexylcarbodiimide (DCC)) or other customary condensing (or peptide coupling) reagents (e.g. phosphorous pentoxide, polyphosphoric acid, bis(2-oxo-3-oxazolidinyl)phosphinic chloride, 1-[Bis(dimethylamino)methylene]-1H-1,2,3-triazolo[4,5-b]pyridinium 3-oxid hexafluorophosphate (HATU), N,N'-carbonyl-diimidazole, 2-ethoxy-N-ethoxycarbonyl-1,2-dihydroquinoline (EEDQ), triphenylphosphine/tetrachloro-methane, 4-(4,6-dimethoxy[1.3.5]-triazin-2-yl)-4-methylmorpholinium chloride hydrate, bromo-tripyrrolidinophos-phoniumhexafluorophosphate or propanephosphonic anhydride (T3P).

Compounds of formula (1) wherein $U^1$ is a halogen atom can be reacted with an amine of formula (2) in the presence of an acid scavenger by means of well-known methods. Suitable acid scavengers include any inorganic and organic bases, as described herein, which are customary for such reactions. Preference is given to alkali metal carbonates, alkaline earth metal acetates, tertiary amines or aromatic bases.

Compounds of formula (1) wherein $U^1$ is a $C_1$-$C_6$-alkoxy group can be reacted with an excess of amine of formula (2), optionally in the presence of a Lewis acid such as trimethylaluminium.

Process B

A compound of formula (I-a-1) (i.e. compound of formula (I) wherein A is 0, T is hydrogen and m is 1 or 2) can be prepared by a process comprising the steps of reacting a compound of formula (7) with a compound of formula (8) in the presence of a base (e.g. organic or inorganic base) and optionally in the presence of a suitable copper salt or complex as shown in scheme 2.

Scheme 2: Process B-Synthesis of compounds of formula (I-a-1)

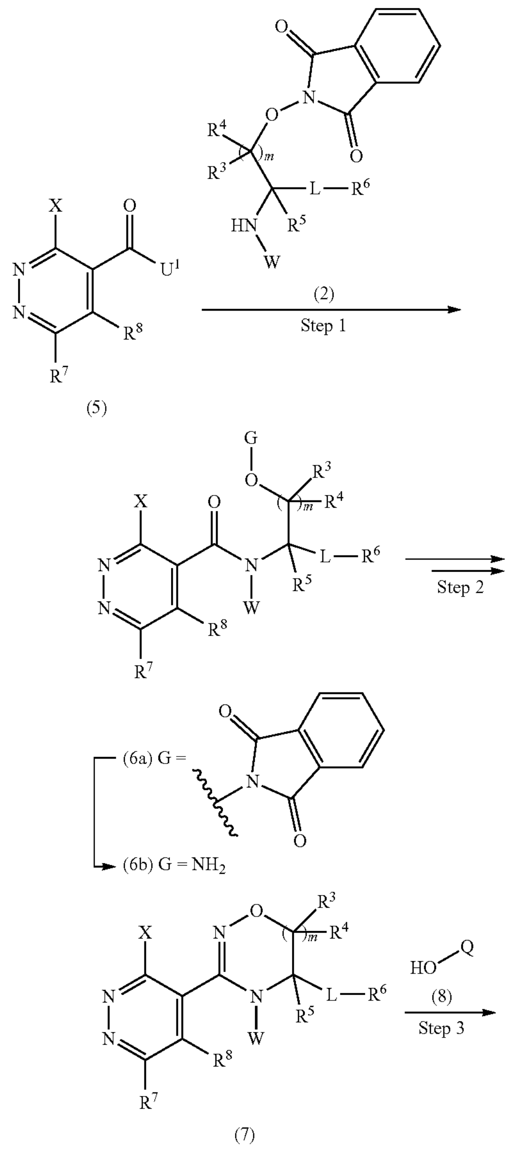

-continued

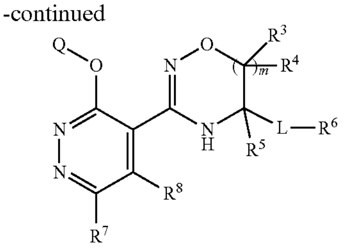

(I-a-1)

$U^1$ = hydroxyl, halogen, $C_1$-$C_6$-alkoxy
X = halogen, preferably chlorine
W = hydrogen, tert-butoxycarbonyl, benzyl, allyl or (4-methoxyphenyl)methyl
m = 1 or 2

Compounds of formula (7) can be prepared by:

reacting a compound of formula (5) with an amine of formula (2) or one of its salt to obtain a compound of formula (6a);

removing the phtalimide group of compound (6a) to obtain a compound of formula (6b);

when W is hydrogen, treating the compound of formula (6b) with a dehydrating agent, optionally in the presence of a base to obtain directly the compound of formula (7);

when W is an aminoprotecting group, treating the compound of formula (6b) with a dehydrating agent, optionally in the presence of a base and then performing a deprotection step to obtain the compound of formula (7), in the same conditions as described herein for process A.

The reaction of compound of formula (7) with a compound of formula (8) may be performed in the presence of a transition metal catalyst such as a copper salt or complex, and if appropriate in the presence of a ligand as described herein.

Compounds of formula (5) are commercially available or may be prepared by process Q described herein.

Compounds of formula (8) are commercially available or may be obtained by conversion or derivatization of another compound of formula (8) in accordance to well-known methods.

Process C

A compound of formula (I-a-1) (i.e. compound of formula (I) wherein A is 0, T is hydrogen and m is 1 or 2) can be prepared by a process, as shown in scheme 3, comprising the step of adding a reducing agent to the compound of formula (12) under acidic conditions to provide a compound of formula (I-a-1).

Scheme 3: Process C-Synthesis of compounds of formula (I-a-1)

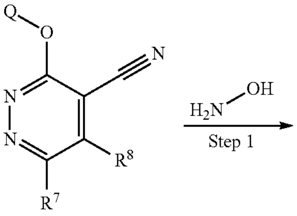

(9)

-continued

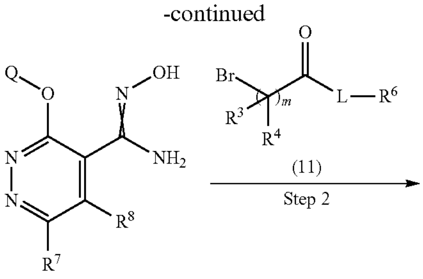

(10)

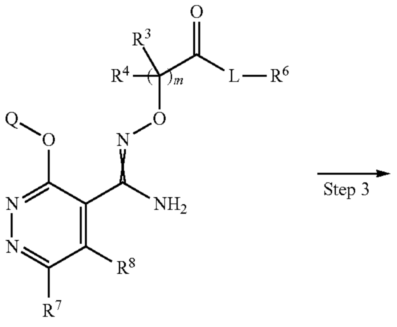

(12)

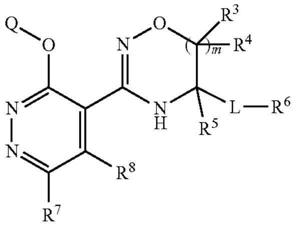

(I-a-1)

$R^5$ = hydrogen, hydroxyl, $C_1$-$C_6$-alkoxy
m = 1 or 2

Compound of formula (12) can be cyclized under acidic conditions in the presence of a reducing agent such as sodium cyanoborohydride to provide a compound of formula (I-a-1). Reaction conditions to form oxadiazine rings with this methodology are known and have been described in the literature (Heterocycles 2016, 92, 2166-2200).

Compound of formula (12) can be obtained by reacting a compound of formula (10) with a compound of formula (11) in the presence of a base. Suitable bases can be alkali metal hydrides such as sodium hydride, alkali metal carbonates such as potassium carbonate, alkali metal hydroxides such as potassium hydroxide, or phosphazene bases such as BEMP as described in the literature (Heterocycles 2016, 92, 2166-2200).

Compound of formula (10) can be obtained by reacting a compound of formula (9) with hydroxylamine or one of its salt. Reaction conditions to perform such transformations are known and have been reported in the literature (WO2010138600).

Compounds of formula (9) may be prepared by process R described herein.

Compounds of formula (11) are either commercially available or can be prepared by processes described in the literature (Eur. J. Med. Chem. 2014, 84, 302, Eur. J. Med. Chem. 2015, 100, 18-23, WO2017031325).

Process D

A compound of formula (I-a-1) (i.e. compound of formula (I) wherein A is 0, T is hydrogen, L is a direct bond and m is 1 or 2) can be prepared by a process comprising the steps of:

- placing a compound of formula (13) under oxidative condition to provide compound (14);
- when $R^6$—H (15) is an aromatic $C_6$-$C_{14}$-carbocycle, a non-aromatic $C_7$-$C_{14}$-carbocycle, a non-aromatic 7- to 14-membered heterocycle, or an aromatic 5- to 14-membered heterocycle, treating a compound of formula (14) with a compound of formula (15) under acidic conditions to form a compound of formula (I-a-1).
- when $R^6$—H (15) is an alcohol ($R^{6'}$—O)—H or a thiol ($R^{6'}$—S)—H derivative, treating a compound of formula (14) with an halogenating reagent such as $SOCl_2$ and a compound of formula (15) to form compounds of formula (I-a-1) in which $R^6$ represents an oxy, an alkoxy, or a thiol group.

as shown in scheme 4.

Scheme 4: Process D-Synthesis of compounds of formula (I-a-1)

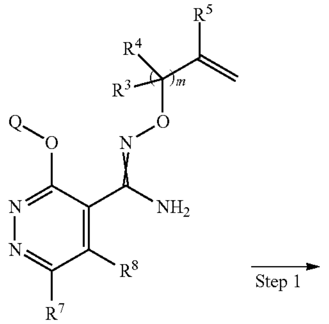

(13)

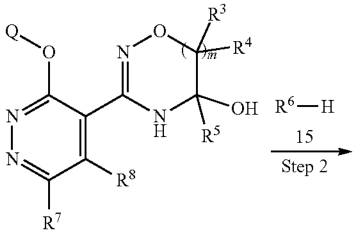

(14)

-continued

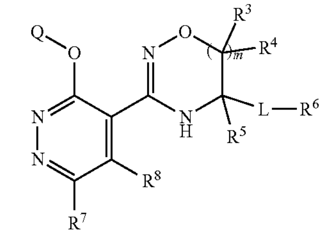

(I-a-1)

L = direct bond $R^6$ = aromatic $C_6$-$C_{14}$-carbocycle, non-aromatic $C_7$-$C_{14}$-carbocyle, non-aromatic 7- to 14-membered heterocycle, aromatic 5- to 14-membered heterocycle, aromatic $C_6$-$C_{14}$-carbocycloxy, non-aromatic $C_6$-$C_{14}$-carbocycloxy, non-aromatic 3- to 14-membered heterocycloxy, aromatic 5- to 14-membered heterocycloxy, non-aromatic $C_3$-$C_{12}$-carbocyclylsulfinyl, aromatic $C_6$-$C_{14}$-carbocyclylsulfinyl, aromatic 5- to 14-membered heterocyclylsulfinyl, non-aromatic 5- to 14-membered heterocyclylsulfinyl, non-aromatic $C_3$-$C_{12}$-carbocyclylsulfonyl, aromatic $C_6$-$C_{14}$-carbocyclylsulfonyl, aromatic 5- to 14-membered heterocyclylsulfonyl, non-aromatic 5- to 14-membered heterocyclylsulfonyl, $C_1$-$C_3$-alkoxy substituted by a non-aromatic $C_3$-$C_{12}$-carbocycle, $C_1$-$C_3$-alkoxy substituted by an aromatic $C_6$-$C_{14}$-carbocycle, $C_1$-$C_3$ alkoxy substituted by a non-aromatic 3- to 14-membered heterocycle, $C_1$-$C_3$-alkoxy substituted by an aromatic 5- to 14-membered heterocycle, $C_1$-$C_3$-haloalkoxy substituted by a non-aromatic $C_3$-$C_{12}$-carbocycle, $C_1$-$C_3$-haloalkoxy substituted by an aromatic $C_6$-$C_{14}$-carbocycle, $C_1$-$C_3$-haloalkoxy substituted by a non-aromatic 3- to 14-membered heterocycle, $C_1$-$C_3$-haloalkoxy substituted by an aromatic 5- to 14-membered heterocycle, $C_1$-$C_3$-sulfanyl substituted by a non-aromatic $C_3$-$C_{12}$-carbocycle, $C_1$-$C_3$-sulfanyl substituted by an aromatic $C_6$-$C_{14}$-carbocycle, $C_1$-$C_3$-sulfanyl substituted by a non-aromatic 3- to 14-membered heterocycle and $C_1$-$C_3$-sulfanyl substituted by an aromatic 5- to 14-membered heterocycle, m = 1 or 2

The compound of formula (14) can be reacted with an aromatic $C_6$-$C_{14}$-carbocycle, a non-aromatic $C_7$-$C_{14}$-carbocycle, a non-aromatic 7- to 14-membered heterocycle, or an aromatic 5- to 14-membered heterocycle ($R^6$—H) under acidic conditions to provide a compound of formula (I-a-1). Reaction conditions to form oxadiazine rings with this methodology are known and have been described in the literature (WO2017031325).

Compounds of formula (14) can be obtained from a compound of formula (13) under oxidative conditions, for example in the presence of osmium trioxide and sodium periodate.

Compounds of formula (13) may be prepared by process R described herein.

Process E

A compound of formula (I-a-1) (i.e. compound of formula (I) wherein A is 0, T is hydrogen and m is 1 or 2) can be prepared by a process comprising the steps of:

- reacting a compound of formula (18) with a compound of formula (19) or one of its salt to provide a compound of formula (20),
- when $E^1$ is hydroxyl, converting the compound of formula (20) into compound of formula (I-a-1) using Mitsunobu reaction conditions,
- when $E^1$ is halogen, converting the compound of formula (20) into compound of formula (I-a-1) in the presence of a base, as shown in scheme 5.

Scheme 5: Process E-Synthesis of compounds of formula (I-a-1)

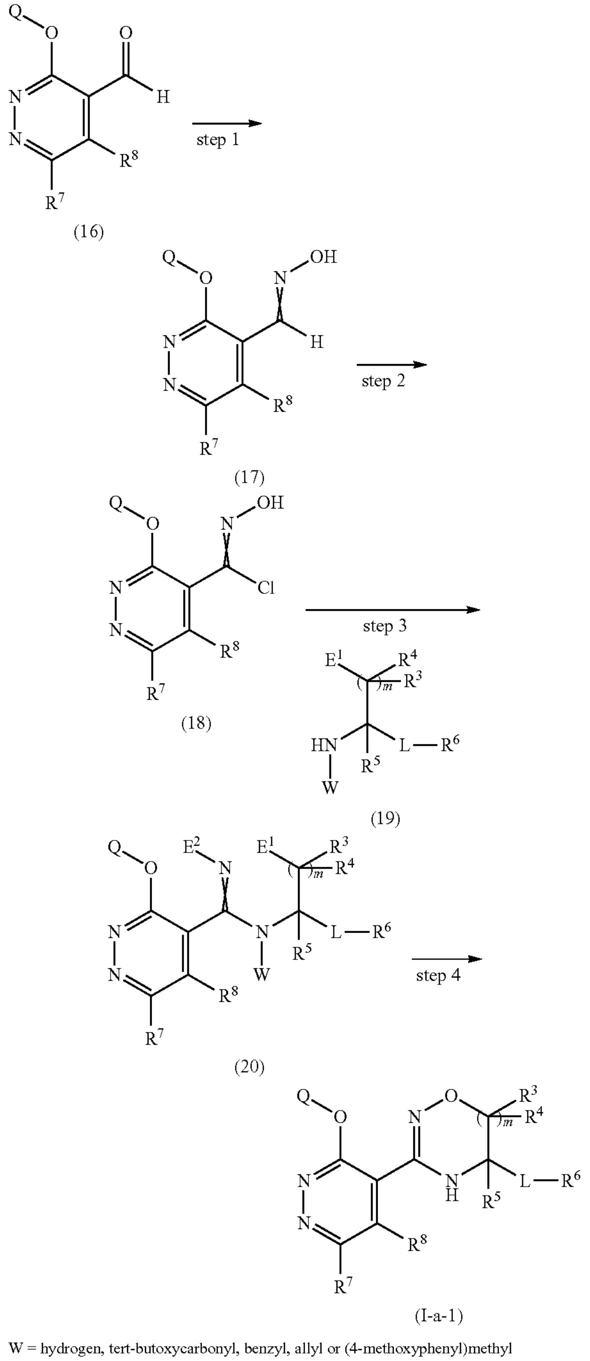

W = hydrogen, tert-butoxycarbonyl, benzyl, allyl or (4-methoxyphenyl)methyl
$E^1$ = hydroxyl or halogen
$E^2$ = hydroxyl
m = 1 or 2

Aminoalcohols of formula (19-a, $E^1$=hydroxyl) are commercially available or may be producible by methods described in the literature (Molecules, 9 (6), 405-426; 2004; WO2017203474). Compounds of formula (19-b, $E^1$=halogen) or one of its salts can be obtained from the corresponding aminoalcohol by well-known methods.

When $E^1$ is hydroxyl, the compound of formula (20) can be converted by Step 4 of the process into a compound of formula (I-a-1) using classical Mitsunobu reaction conditions known by the skilled person of the art (Strategic Applications of Named Reactions in Organic Synthesis; Laszlo Kürti, Barbara Czako; Elsevier; 2005; 294-295 and reference herein).

When $E^1$ is halogen, the compound of formula (20) can be converted by Step 4 of the process into a compound of formula (I-a-1) in the presence of a base as referred herein.

When W represents an amino protecting group, Step 4 is followed by an additional deprotection step using reaction conditions described in the literature (Greene's Protective Groups in organic Synthesis; Peter G. M. Wuts; Wiley; Fifth Edition; 2014; 895-1194) to provide a compound of formula (I-a-1). Compound of formula (18) can be treated with a compound of formula (19) or one of its salt in the presence of a base such as triethylamine to form a compound of formula (20).

Compound of formula (18) can be obtained by Step 2 of the process by treating an oxime of formula (17) with a halogenating reagent such as NCS. Reaction conditions to perform such transformations have been reported in the literature (WO2013173672; RSC Advances 2015, 5, 58587-58594).

An oxime of formula (17) can be obtained by Step 1 from an aldehyde of formula (16) in the presence of hydroxylamine or one of its salt, optionally in the presence of a base. Such transformations are known and have been reported in the literature (Tetrahedron 2000, 56, 1057-1064; ChemMedChem 2013, 8, 1210-1223).

Aldehydes of formula (16) can be prepared according to well-known methods for the one skilled in the art; for example either by treating the weinreb amide precursor with DIBAL-H (WO2016045591) or by converting the ester precursor into the primary alcohol followed by oxidation of the alcohol into the corresponding aldehyde (WO199850031). The ester precursors to access such aldehydes can be prepared according to Process N, O, P described herein.

Process F

A compound of formula (I-a-1) (i.e. compound of formula (I) wherein A is 0, T is hydrogen and m is 1 or 2) or (I-a-2) (i.e. compound of formula (I) wherein A is NH, T is hydrogen and m is 1 or 2) can be prepared by a process comprising the steps of:

- reacting a compound of formula (1) with an amine of formula (19) or one of its salt to provide a compound of formula (21) under similar conditions as described in process A,
- treating a compound of formula (21) with a dehydrating agent followed by hydroxylamine or hydrazine to form a compound of formula (20)
- when $E^1$ and $E^2$ is hydroxyl, converting the compound of formula (20) into compound of formula (I-a-1) using Mitsunobu reaction conditions,
- when $E^1$ is halogen and $E^2$ is hydroxyl or —$NH_2$, converting the compound of formula (20) into compound of formula (I-a-1) or (I-a-2) in the presence of a base, as shown in scheme 6.

Scheme 6: Process F-Synthesis of compounds of formuula (I-a-1) and (I-a-2)

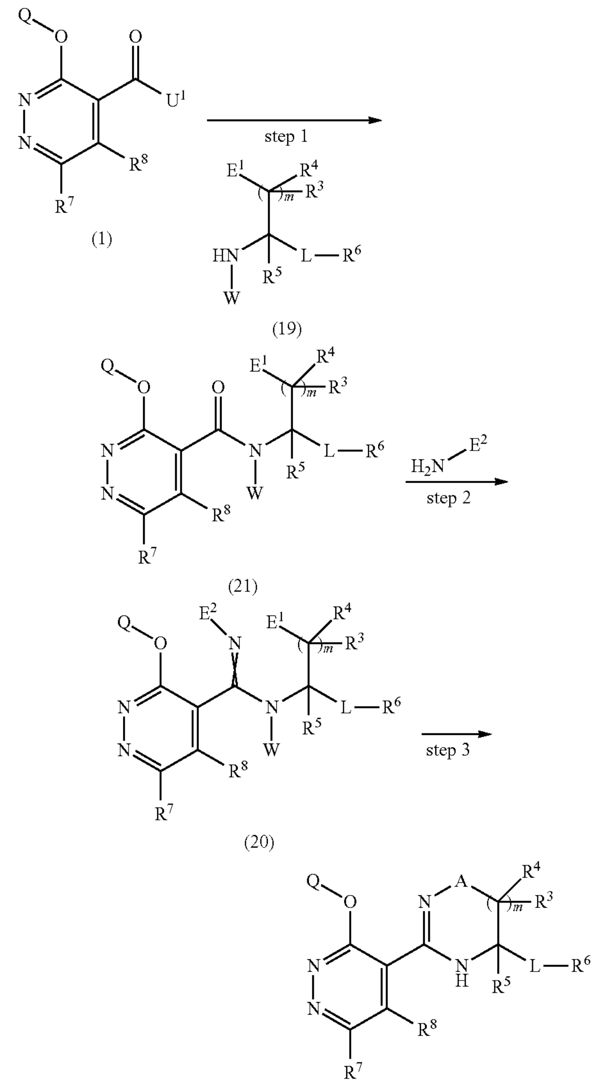

(I-a-1) A = —O—
(I-a-2) A = —NH—

$U^1$ = hydroxy, halogen, $C_1$-$C_6$-alkoxy
$E^1$ = hydroxyl or halogen
$E^2$ = hydroxyl or —$NH_2$
W = hydrogen, tert-butoxycarbonyl, benzyl, allyl or (4-methoxyphenyl)methyl
m = 1 or 2

Step 2 and step 3 of process F can be performed using similar reaction conditions as described in process E.

Aminoalcohols of formula (19-a, $E^1$=hydroxyl) are commercially available or may be producible by methods described in the literature (Molecules, 9 (6), 405-426; 2004; WO2017203474). Compounds of formula (19-b, $E^1$=halogen) or one of its salt can be obtained from the corresponding aminoalcohol by well-known methods.

Process G

A compound of formula (I-a-1) (i.e. compound of formula (I) wherein A is 0, T is hydrogen and m is 1 or 2) or (I-a-2) (i.e. compound of formula (I) wherein A is NH, T is hydrogen and m is 1 or 2) can be prepared by a process comprising the steps of:

reacting a compound of formula (5) with an amine of formula (19) to provide a compound of formula (22) under similar conditions as described in process A, treating a compound of formula (22) with a dehydrating agent followed by hydroxylamine or hydrazine to form a compound of formula (23)

when $E^1$ and $E^2$ is hydroxyl, converting the compound of formula (23) into compound of formula (7) using Mitsunobu reaction conditions, when $E^1$ is halogen and $E^2$ is hydroxyl or —$NH_2$, converting the compound of formula (23) into compound of formula (7) or (24) in the presence of a base, reacting a compound of formula (7) or (24) with a compound of formula (8) in the presence of a base (e.g. organic or inorganic base) and optionally in the presence of a suitable copper salt or complex to provide a compound of formula (I-a-1) or (I-a-2)

as shown in scheme 7.

Scheme 7: Process G-Synthesis of compounds of formuula (I-a-1) and (I-a-2)

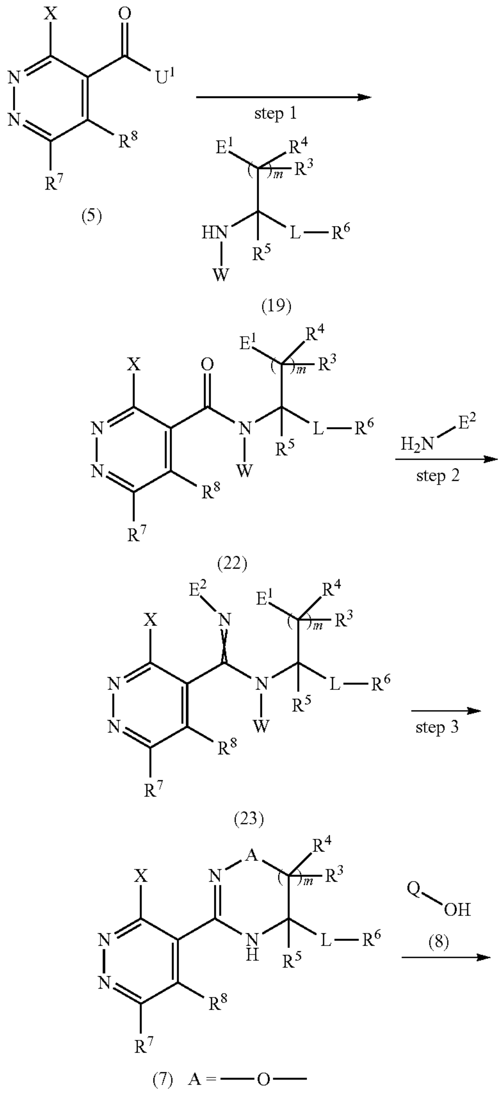

(7) A = —O—
(24) A = —NH—

-continued

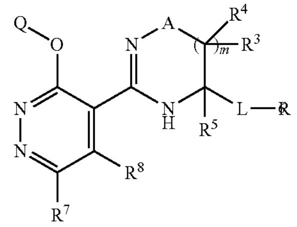

(I-a-1) A = —O—
(I-a-2) A = —NH—

$U^1$ = hydroxy, halogen, $C_1$-$C_6$-alkoxy
X = halogen preferably chlorine
$E^1$ = hydroxyl or halogen
$E^2$ = hydroxyl or —$NH_2$
W = hydrogen, tert-butoxycarbonyl, benzyl, allyl or (4-methoxyphenyl)methyl
m = 1 or 2

Process H

A compound of formula (I-a-1) (i.e. compound of formula (I) wherein A is 0, T is hydrogen and m is 1 or 2), (I-a-3) (i.e. compound of formula (I) wherein A is $CR^1R^2$, T is hydrogen and m is 1 or 2), (I-a-4) (i.e. compound of formula (I) wherein A is C(═O), T is hydrogen and m is 1 or 2) or (I-a-5) (i.e. compound of formula (I) wherein A is $S(═O)_2$, T is hydrogen and m is 1 or 2) can be prepared by a process comprising the steps of:

treating a compound of formula (9) with an alkoxide to provide compound of formula (25), reacting the compound of formula (25) with respectively an amine of formula (26a-1), (26a-2), (26a-3) or (26a-4), as shown in scheme 8.

Scheme 8: Process H-Synthesis of compounds of formula (I-a-1), (I-a-3), (I-a-4) or (I-a-5)

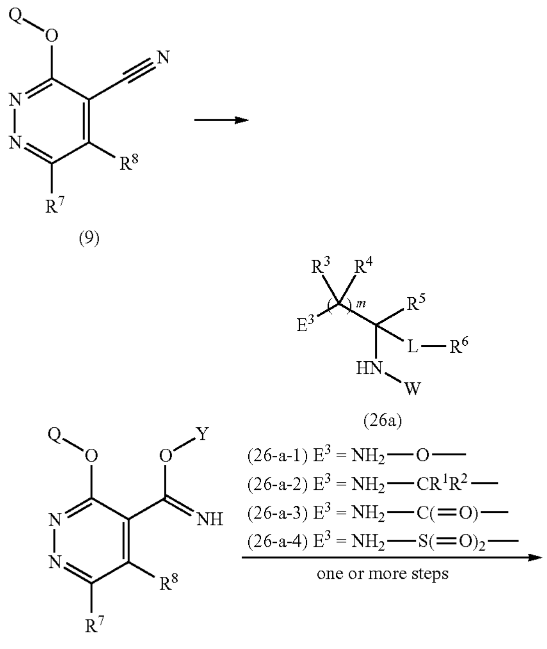

(9)
(26a)
(25)

-continued

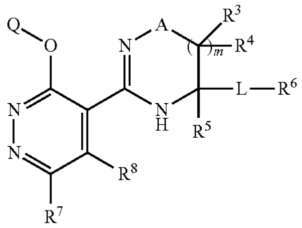

(I-a-1) A = —O—
(I-a-3) A = —$CR^1R^2$—
(I-a-4) A = —C(═O)—
(I-a-5) A = —$S(═O)_2$—

W = hydrogen, tert-butoxycarbonyl, benzyl, allyl or (4-methoxyphenyl)methyl
Y = $C_1$-$C_6$-alkyl
m = 1 or 2

Alternatively, a compound of formula (I-a-5) may be prepared by treating a pyridazine 4-carboxamidine compound with a trans-styrylsulfonyl chloride in analogy to methods described in the literature (J. Org. Chem. 1974, 39, 3080)

The compound of formula (25) can be obtained by treating a compound of formula (9) with an alkoxide such as sodium methanolate or sodium ethanolate according to methods described in the literature (Heterocycles, 34, 1992, 929-935).

The compound of formula (25) is treated with a compound of formula (26-a-1), (26-a-2), (26-a-3) or (26-a-4) and cyclized under acidic conditions to form respectively a compound of formula (I-a-1), (I-a-3), (I-a-4) or (I-a-5). Reaction conditions to perform such transformations based on this methodology have been described in the literature (Heterocycles 2016, 92, 2166-2200).

Amines of formula (26-a-1), (26-a-2), (26-a-3) or (26-a-4) are either commercially available, or may be prepared by methods described in the literature (Molecules, 9 (6), 405-426; 2004, WO2017203474; J. Med. Chem 1985, 28, 694-698; J. Med. Chem 2006, 49, 4333-4343) and by Process S of this invention.

Process I

A compound of formula (I-a-6) (i.e. compound of formula (I) wherein A is 0, T is hydrogen and m is 2), can be prepared by a process comprising the steps of:

treating a compound of formula (9) with an hydroxylamine derivative (27) in the presence of a suitable base as described herein to provide compound of formula (28), reacting the compound of formula (28) with a reagent of formula (29) in the presence of a metal catalyst and a suitable ligand to provide a compound of formula (30)

treating a compound of formula (30) with iodine and phenylsilane to form a compound of formula (I-a-6), as shown in scheme 9.

Scheme 9: Process I-Synthesis of compounds of formula (I-a-6)

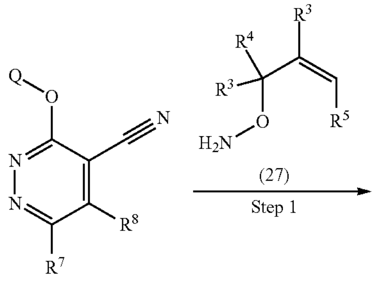

(9)

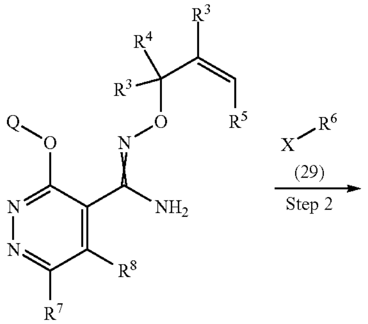

(28)

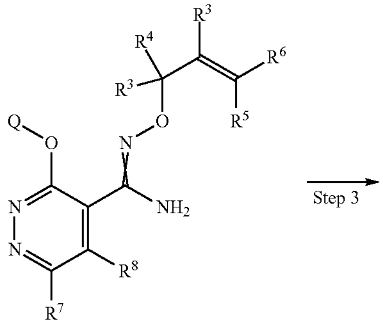

(30)

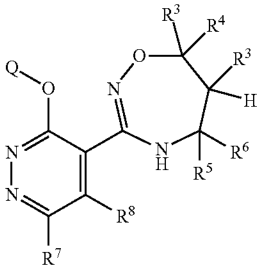

(I-a-6)

X = halogen $R^6$ = aromatic $C_6$-$C_{14}$-carbocycle, 5- or 6-membered monocyclic aromatic heterocycle, non-aromatic $C_3$-$C_{12}$-carbocycle, non-aromatic 3- 14-membered heterocycle Reagents of formula (27) are either commercially available or producible by processes described in the literature (WO2010099279).

Reagents of formula (29) are commercially available or can be prepared by known processes.

Process J

A compound of formula (I-a-7) (i.e. compound of formula (I) wherein A is $CR^1R^2$, T is hydrogen and m is 0) can be prepared by a process comprising the step of reacting a compound of formula (1) with a diamine of formula (31) as shown in scheme 10.

Scheme 10: Process J-Synthesis of imidazolines of formula (I-a-7)

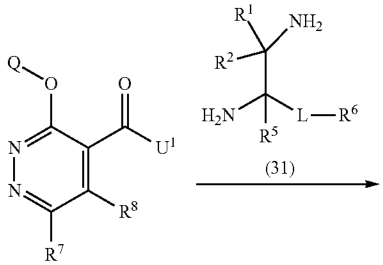

(1)

$U^1$ = hydroxyl, halogen

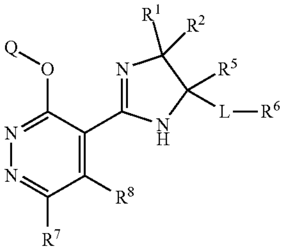

(I-a-7)

Process J can be performed in the presence of a dehydrating agent such as $POCl_3$.

Diamines of formula (31) are commercially available or can be prepared by methods described in the literature (Eur. J. Med. Chem 1990, 25(1), 35-44; J. Org. Chem 2012, 77(9), 4375-4384; WO2009003867).

Process K

A compound of formula (I-a) can be converted by means of methods described in the literature to the corresponding compounds (I-b) or (I-c) in one or more steps as shown in scheme 11.

Scheme 11: Process K-Synthesis of compounds of formula (I-b) and (I-c)

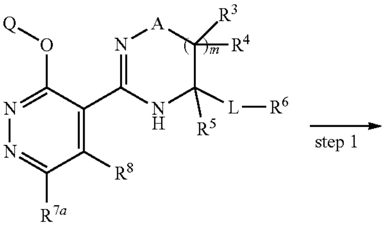

(I-a)

-continued

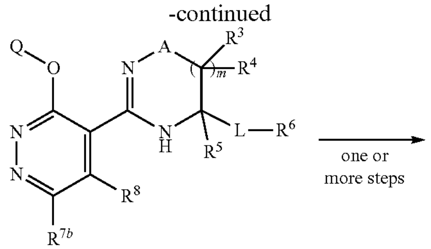

(I-b)

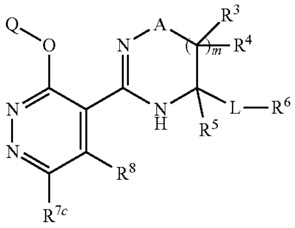

(I-c)

$R^{7a}$ = hydrogen or halogen (preferably chlorine)

$R^{7b}$ = hydrogen, halogen, cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylsulfanyl, $C_1$-$C_6$-haloalkylsulfanyl, $C_3$-$C_8$-cycloalkylsulfanyl, $C_3$-$C_8$-cycloalkyl, $C_3$-$C_6$-cycloalkenyl, aromatic $C_6$-$C_{14}$-carbocycle, aromatic 5- or 6-membered monocyclic heterocycle, non-aromatic 3- to 7-membered monocyclic heterocyle, —$N(R^e)_2$, —$C(=O)(OR^g)$ $R^{7c}$ = nitro, formyl, $C_1$-$C_6$-alkylcarbonyl, $C_1$-$C_6$-haloalkylcarbonyl, $C_1$-$C_6$-hydroxyalkyl, $C_1$-$C_6$-fluoroalkyl, $C_1$-$C_6$-alkylsulinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, —$C(=NR^f)R^f$, —$C(=O)N(R^g)_2$, —$S(=O)(=NR^g)R^g$, —$S(=O)_2N(R^g)_2$ In scheme 11, $R^e$, $R^f$, $R^g$ are as disclosed herein and the aliphatic and cyclic substituents $R^{7b}$, $R^{7c}$, $R^e$, $R^f$, $R^g$ may be substituted as disclosed herein.

Non-limiting examples of conversions performed in accordance with scheme 11 are provided below.

A compound of formula (I-a) wherein $R^{7a}$ is a chlorine atom can be converted into a compound of formula (I-b) wherein $R^{7b}$ is a bromine or an iodine atom by means of methods described in the literature (e.g. WO2016185342, WO2007022937).

A compound of formula (I-a) wherein $R^{7a}$ is a halogen atom can be converted into a compound of formula (I-b) wherein $R^{7b}$ is a hydrogen atom in the presence of a palladium catalyst as reported in the literature (Journal of Molecular Catalysis A: Chemical, 2014, 393, 191-209).

A compound of formula (I-a) wherein $R^{7a}$ is a hydrogen atom or a halogen atom can be converted into a compound of formula (I-b) wherein $R^{7b}$ is cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylsulfanyl, $C_1$-$C_6$-haloalkylsulfanyl, $C_3$-$C_8$-cycloalkyl, $C_3$-$C_6$-cycloalkenyl, aromatic $C_6$-$C_{14}$-carbocycle, aromatic 5- or 6-membered monocyclic heterocycle, non-aromatic 3- to 7-membered monocyclic heterocycle, —$N(R^e)_2$ or —$C(=O)(OR^g)$ by transition metal catalyzed or metallo-photoredox catalyzed processes as described herein.

A compound of formula (I-b) wherein $R^{7b}$ is a $C_2$-$C_6$-alkenyl group substituted by a $C_1$-$C_3$-alkoxy can be converted into a compound of formula (I-c) wherein $R^{7c}$ is a $C_1$-$C_6$-alkylcarbonyl group by means of methods described in the literature (e.g. J. Org. Chem. 1993, 55, 3114).

The compound of formula (I-c) wherein $R^{7c}$ is a $C_1$-$C_6$-alkylcarbonyl group can be further converted in a compound of formula (I-c) wherein $R^{7c}$ is —$C(=NR^f)$—$C_1$-$C_6$-alkyl group by methods described in the literature (e.g. Greene's Protective Groups in organic Synthesis; Peter G. M. Wuts; Wiley; Fifth Edition; 2014; 655, 661, 667).

A compound of formula (I-c) wherein $R^{7c}$ is a $C_1$-$C_6$-alkylcarbonyl group can be further converted in a compound of formula (I-c) wherein $R^{7c}$ is $C_1$-$C_6$-hydroxyalkyl group by classical functional group interconversion such as reductions of ketones to alcohols in the presence of $NaBH_4$ in MeOH.

A compound of formula (I-c) wherein $R^{7c}$ is $C_1$-$C_6$-hydroxyalkyl group can be further converted into a compound (I-c) wherein $R^{7c}$ is $C_1$-$C_6$-fluoroalkyl in the presence of a fluorinating agent. Non-limitative examples of fluorinating agents include sulfur fluorides such as sulfur tetrafluoride, diethylaminosulfurtrifluoride, morpholinosulfur trifluoride, bis(2-methoxyethyl)aminosulfur trifluoride, 2,2-difluoro-1,3-dimethylimidazolidine or 4-tert-butyl-2,6-dimethylphenylsulfur trifluoride.

A compound of formula (I-a) can be prepared by one or more of the processes herein described.

Process L

A compound of formula (I-a) can be converted by means of methods described in the literature to the corresponding compound of formula (I-d) or compound of formula (I-e) in one or more steps as shown in scheme 12.

Scheme 12: Process L-Synthesis of compounds of formula (I-d) and (I-e)

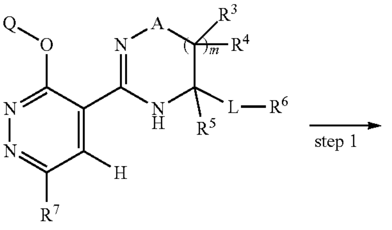

(I-a)

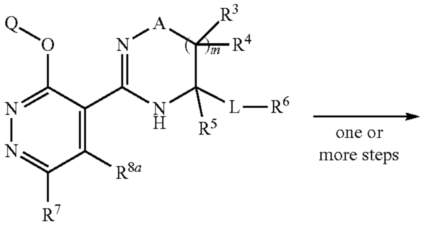

(I-d)

-continued

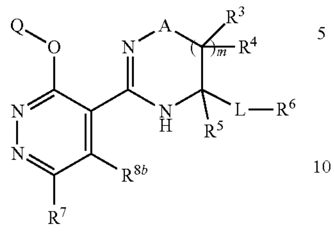

(I-e)

$R^7$ = halogen
$R^{8a}$ = halogen, $C_1$-$C_6$-alkyl, $C_1$-$C_6$-haloalkyl, $C_1$-$C_6$-hydroxyalkyl, $C_3$-$C_8$-cycloalkyl, $C_3$-$C_8$-halocycloalkyl, $C_3$-$C_6$-cycloalkenyl, aromatic $C_6$-$C_{14}$-carbocycle, 5- to 14-membered aromatic heterocylcle, 3- to 14-membered non-aromatic heterocycle;
$R^{8b}$ = halogen, cyano, nitro, amino, mercapto, hydroxyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_3$-$C_8$-cycloalkyl, $C_3$-$C_6$-cycloalkenyl, aromatic 5- to 14-membered heterocycle, $C_3$-$C_8$-cycloalkyloxy, aromatic $C_6$-$C_{14}$-carbocyclyloxy, non-armoatic 3- to 14-membered hetercyclyloxy, aromatic 5- to 14-membered heterocyclyloxy, —$N(R^h)_2$, $SR^i$, —$S(=O)R^i$ and —$S(=O)_2R^i$;
$R^h$ and $R^i$ are as disclosed herein and the aliphatic and cyclic substituents $R^{8a}$ and $R^{8b}$ may be substituted as disclosed herein.

Non-limiting examples of conversions performed in accordance with scheme 12 are provided below.

A compound of formula (I-a) can be converted into a compound of formula (I-d) wherein $R^{8a}$ is a halogen atom in the presence of a base and an electrophile such as NCS, NBS, NIS, hexachloroethane, bromine or iodine by means of methods described in the literature (e.g. Org. Lett. 2009, 11, 1837). Suitable bases for carrying out the process can be selected from lithium-diisopropylamide, lithium 2,2,6,6-tetramethylpiperidide, n-butyl lithium, methyl lithium, TMPZnCl·LiCl, $TMP_2Zn·2MgCl_2·2LiCl$ (see e.g. Dissertation Albrecht Metzer 2010, University Munich).

A compound of formula (I-a) can be converted into a compound of formula (I-d) wherein $R^{8a}$ is a $C_1$-$C_6$-alkyl, $C_1$-$C_6$-haloalkyl, $C_1$-$C_6$-hydroxyalkyl, $C_3$-$C_8$-cycloalkyl, $C_3$-$C_8$-halocycloalkyl, $C_3$-$C_6$-cycloalkenyl, aromatic $C_6$-$C_{14}$-carbocycle, 5- to 14-membered aromatic heterocycle or a 3- to 14-membered non-aromatic heterocycle, optionally in the presence of a base, and when appropriate in the presence of a transition metal catalyst such as a metal salt or complex and a ligand as described herein or by methods described in the literature (Heterocycles 1976, 4(8), 1331).

A compound of formula (I-d) wherein $R^{8a}$ is a halogen atom can be converted in a compound of formula (I-e) wherein $R^{8b}$ represents cyano, nitro, amino, mercapto, hydroxyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_2$-$C_6$-alkenyloxy, $C_2$-$C_6$-haloalkenyloxy, $C_3$-$C_8$-cycloalkyl, $C_3$-$C_6$-cycloalkenyl, aromatic 5- to 14-membered heterocycle, $C_3$-$C_8$-cycloalkyloxy, aromatic $C_6$-$C_{14}$-carbocyclyloxy, non-aromatic 3- to 14-membered heterocyclyloxy, aromatic 5- to 14-membered heterocyclyloxy, —$N(Rb)_2$ or —$SR^i$ in the presence of a base and optionally in the presence of a transition metal catalyst such as a metal salt or complex, and if appropriate in the presence of a ligand.

A compound of formula (I-e) wherein $R^{8b}$ is a $C_2$-$C_6$-alkenyl group can be further converted in a compound of formula (I-e) wherein $R^{8b}$ is $C_1$-$C_6$-alkyl substituted by $C_1$-$C_6$-alkoxy, $C_1$-$C_6$-haloalkoxy, $C_1$-$C_6$-alkoxy-$C_1$-$C_6$-alkoxy, $C_1$-$C_6$-alkylsulfanyl, $C_1$-$C_6$-haloalkylsulfanyl, non-aromatic 3- to 7-membered monocyclic heterocycle and —$N(R^{a'})_2$ with $R^{a'}$ being independently selected from the group consisting of hydrogen, $C_1$-$C_6$-alkyl, $C_1$-$C_6$-haloalkyl and $C_3$-$C_8$-cycloalkyl, by treating the reacting compound of formula (I-e) with an oxygen, a sulfur or an amino based nucleophile.

A compound of formula (I-e) wherein $R^{8b}$ is a $SR^i$ group can be further converted in a compound of formula (I-a-8) wherein $R^{8b}$ is a —$S(=O)R^i$ or a —$S(=O)_2R^i$ group by reacting the starting compound of formula (I-a-8) with an oxidant such as hydrogen peroxide.

A compound of formula (I-a) can be prepared by one or more of the processes herein described.

Process M

A compound of formula (I-f) (i.e. formula (I) wherein T is —$C(=O)R^{a1}$, —$C(=O)(OR^{a1})$, —$C(=O)N(R^{a2})_2$, —$S(=O)R^{a1}$, —$S(=O)_2R^{a1}$ and —$S(=O)_2N(R^{a2})_2$ with $R^{a1}$ and $R^{a2}$ being as described herein) can be prepared by a process comprising the step of reacting a compound of formula (I-a) formula with a compound of formula (32) as shown in scheme 13.

Scheme 13: Process M-Synthesis of compounds of formula (I-f)

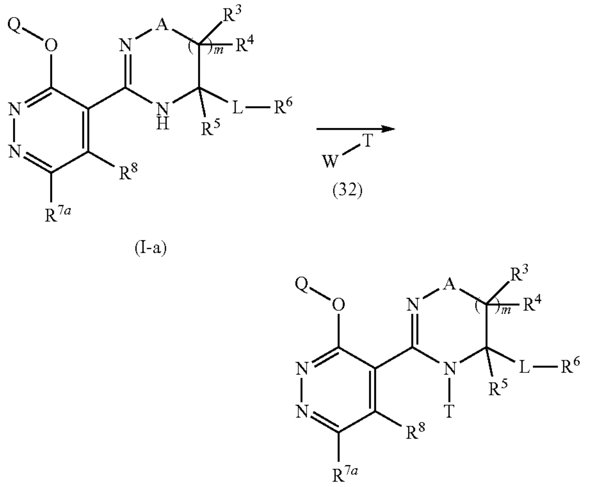

(I-a) (32) (I-f)

W = halogen, —O—$C(=O)(OR^{a1})$, —O—$C(=O)R^{a1}$ or —O—$S(=O)_2R^{a1}$ with $R^{a1}$ being selected from the group consisting of $C_1$-$C_6$-alkyl and $C_1$-$C_6$-haloalkyl
T = —$C(=O)R^{a1}$, —$C(=O)(OR^{a1})$, —$C(=O)N(R^{a2})_2$, —$S(=O)R^{a1}$, —$S(=O)_2R^{a1}$ and —$S(=O)N(R^{a2})_2$ with $R^{a1}$ and $R^{a2}$ as described herein.

Process M can be performed by means of methods described in the literature (e.g. Tetrahedron Lett. 1995, 36, 8949; Greene's Protective Groups in organic Synthesis; Peter G. M. Wuts; Wiley; Fifth Edition; 2014; 1174-1175).

Compounds of formula (32) are commercially available.

Compounds of formula (I-a) can be prepared by one or more of the processes herein described.

Processes for the Preparation of a Compound of Formula (1)

A compound of formula (1) as described herein may be directly obtained by performing process N described below or may be obtained by conversion or derivatization of another compound of formula (1) prepared in accordance with the processes described herein. Compounds of formula (1-a)-(1-e) are various subsets of formula (1).

Process N

A compound of formula (1-a) (i.e. formula (1) wherein $R^7$ and $R^8$ are as defined in scheme 14) can be prepared by a process comprising the step of reacting a compound of formula (5) with a reagent of formula (8) as shown in scheme 14 in the presence of a base.

Scheme 14: Process N-Preparation of compounds (1-a) and (1-b)

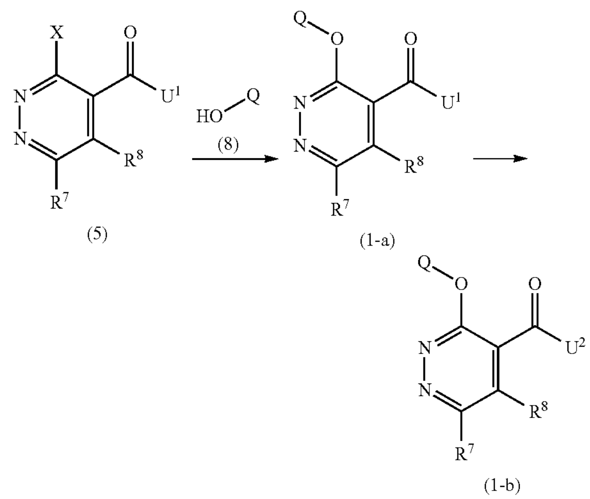

(5) (1-a) (1-b)

$U^1$ = $C_1$-$C_6$-alkoxy
$U^2$ = hydroxyl, halogen, —$N(CH_3)OCH_3$
X = halogen
$R^8$ = hydrogen, $C_1$-$C_6$-alkyl
$R^7$ = hydrogen, halogen, hydroxyl, mercapto, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_3$-$C_8$-cycloalkylsulfanyl, $C_3$-$C_8$-cycloalkyl, $C_3$-$C_6$-cycloalkenyl, $C_3$-$C_8$-cycloalkyloxy, aromatic $C_6$-$C_{14}$-carbocyclyloxy, aromatic 5- or 6-membered monocylic heterocyclyloxy, non-aromatic 3- to 7-membered monocyclic heterocyclyloxy, —$N(R^e)_2$ In scheme 14, $R^e$ is as disclosed herein and $R^7$, $R^8$ and $R^e$ may be substituted as disclosed herein.

Process N may be performed in the presence of suitable transition metal catalyst salts or complexes, if appropriate in the presence of a ligand.

The obtained compound of formula (1-a) can then be converted into a compound of formula (1-b) in one or more steps.

Non-limiting examples of such conversion are described below.

Compounds of formula (1-a) wherein $U^1$ is a $C_1$-$C_6$-alkoxy can be converted to compounds of formula (1-b) wherein $U^2$ is a hydroxyl group by well-known functional group interconversion methods, for example by hydrolysis of an ester group with LiOH in THE/water.

Compounds of formula (1-b) wherein $U^2$ is a hydroxyl can be converted to compounds of formula (1-b) wherein $U^2$ is a halogen in the presence of halogenating agents by well-known methods. Suitable halogenating reagents include, but are not limited to, phosphorous tribromide, phosphorous trichloride, phosphorous pentachloride, phosphorous trichloride oxide, oxalyl chloride or thionyl chloride.

Compounds of formula (1-b) wherein $U^2$ is a hydroxyl or halogen can be converted to compounds of formula (1-b) wherein $U^2$ is —$N(CH_3)OCH_3$ by well-known methods.

Compounds of formula (5) are commercially available or may be prepared by process Q described herein.

Compounds of formula (8) are commercially available or may be obtained by conversion or derivatization of another compound of formula (8) in accordance to well-known methods.

Process O

A compound of formula (1-c) (i.e. formula (1) wherein $R^7$ is $R^{7a}$ as defined in scheme 15) can be converted by means of known methods to the corresponding compounds of formula (1-d) (i.e. formula (1) wherein $R^7$ is $R^{7b}$ as defined in scheme 15) or (1-e) (i.e. formula (1) wherein $R^7$ is $R^{7c}$ as defined in scheme 15) in one or more steps as shown in scheme 15.

Scheme 15: Process O-Preparation of compounds (1-d) and (1-e)

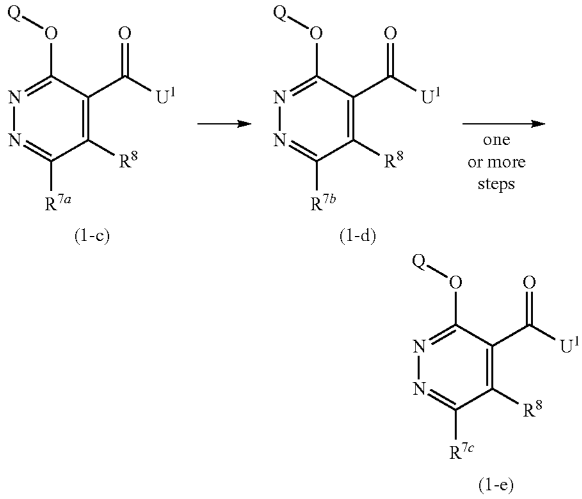

(1-c) (1-d) (1-e)

$U^1$ = $C_1$-$C_6$-alkoxy
$R^{7a}$ = hydrogen or halogen (preferably chlorine)
$R^{7b}$ = hydrogen, halogen, cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylsulfanyl, $C_1$-$C_6$-haloalkylsulfanyl, $C_3$-$C_8$-cycloalkylsulfanyl, $C_3$-$C_8$-cycloalkyl, $C_3$-$C_6$-cycloalkenyl, aromatic $C_6$-$C_{14}$-carbocycle, aromatic 5- or 6-membered monocyclic heterocycle, non-aromatic 3- to 7-membered monocyclic heterocyle, —$N(R^e)_2$, —$C(=O)(OR^g)$
$R^{7c}$ = nitro, formyl, $C_1$-$C_6$-alkylcarbonyl, $C_1$-$C_6$-haloalkylcarbonyl, $C_1$-$C_6$-hydroxyalkyl, $C_1$-$C_6$-fluoroalkyl, $C_1$-$C_6$-alkylsulinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, —$C(=NR^f)R^f$, —$C(=O)N(R^g)_2$, —$S(=O)(=NR^g)R^g$, —$S(=O)_2N(R^g)_2$ In scheme 15, $R^e$, $R^f$, $R^g$ are as disclosed herein and the aliphatic and cyclic substituents $R^{7b}$, $R^{7c}$, $R^e$, $R^f$, $R^g$ may be substituted as disclosed herein.

Non-limiting examples of conversion may be performed in accordance to the description provided in process K.

The obtained compound of formula (1-d) and (1-e) can then be converted into compound of formula (1-d) and (1-e) wherein $U^f$ ($C_1$-$C_6$-alkoxy) is replaced with hydroxyl or halogen.

Examples of such conversion are described below.

Compounds of formula (1-c), (1-d), (1-e) wherein $U^f$ is a $C_1$-$C_6$-alkoxy can be converted to compounds of formula (1-b), (1-c), (1-d) wherein $U^f$ is replaced with a hydroxyl group by well-known functional group interconversion methods, for example by hydrolysis of an ester group with LiOH in THE/water.

Compounds of formula (1-c), (1-d), (1-e) wherein $U^1$ has been replaced with a hydroxyl can then be further converted to compounds of formula (1-b), (1-c), (1-d) wherein the hydroxyl is replaced with a halogen in the presence of halogenating agents by well-known methods. Suitable halogenating reagents include, but are not limited to, phosphorous tribromide, phosphorous trichloride, phosphorous pentachloride, phosphorous trichloride oxide, oxalyl chloride or thionyl chloride.

Compounds of formula (1-c), (1-d), (1-e) wherein $U^1$ is a hydroxyl or halogen can be converted to compounds of formula (1-c), (1-d), (1-e) wherein $U^1$ is —$N(CH_3)OCH_3$ by well-known methods.

Compounds of formula (1-c) can be prepared by one or more of the processes described herein.

Process P

A compound of formula (1-f) (i.e. formula (1) wherein $R^8$ is H) can be converted by means of methods described in the literature to the corresponding compound of formula (1-g) (i.e. formula (1) wherein $R^8$ is $R^{8a}$ as defined in scheme 16) or compound of formula (1-h) (i.e. formula (1) wherein $R^8$ is $R^{8b}$ as defined in scheme 16) in one or more steps as shown in scheme 16.

Scheme 16: Process P-Preparation of compounds (1-g) and (1-h)

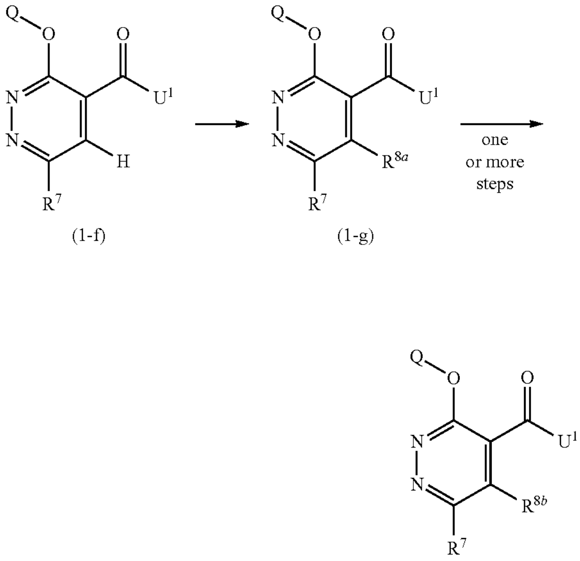

(1-f) (1-g) (1-h)

$U^1$ = $C_1$-$C_6$-alkoxy $R^{8a}$ = halogen, $C_1$-$C_6$-alkyl, $C_1$-$C_6$-haloalkyl, $C_1$-$C_6$-hydroxyalkyl, $C_3$-$C_8$-cycloalkyl, $C_3$-$C_8$-halocycloalkyl, $C_3$-$C_6$-cycloalkenyl, aromatic $C_6$-$C_{14}$-carbocycle, 5- to 14-membered aromatic heterocylcle, 3- to 14-membered non-aromatic heterocycle;

$R^{8b}$ = halogen, cyano, nitro, amino, mercapto, hydroxyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_3$-$C_8$-cycloalkyl, $C_3$-$C_6$-cycloalkenyl, aromatic 5- to 14-membered heterocycle, $C_3$-$C_8$-cycloalkyloxy, aromatic $C_6$-$C_{14}$-carbocyclyloxy, non-armoatic 3- to 14-membered hetercyclyloxy, aromatic 5- to 14-membered heterocyclyloxy, —$N(R^h)_2$, $SR^i$, —$S(=O)R^i$ and —$S(=O)_2R^i$ In scheme 16, $R^h$ and $R^i$ are as disclosed herein and the aliphatic and cyclic substituents $R^{8a}$ and $R^{8b}$ may be substituted as disclosed herein.

Non-limiting examples of conversion may be performed in accordance to the description provided in process L.

The obtained compound of formula (1-f) and (1-g) can then be converted into compound of formula (1-f) and (1-g) wherein $U^1$ ($C_1$-$C_6$-alkoxy) is replaced with hydroxyl or halogen.

Compounds of formula (1-f), (1-g), (1-h) wherein $U^1$ is a $C_1$-$C_6$-alkoxy can be converted to compounds of formula (1-f), (1-g), (1-h) wherein $U^1$ is replaced with a hydroxyl group by well-known functional group interconversion methods, for example by hydrolysis of an ester group with LiOH in THF/water.

Compounds of formula (1-f), (1-g), (1-h) wherein $U^1$ has been replaced with a hydroxyl can then be further converted to compounds of formula (1-f), (1-g), (1-h) wherein the hydroxyl is replaced with a halogen in the presence of halogenating agents by well-known methods. Suitable halogenating reagents include, but are not limited to, phosphorous tribromide, phosphorous trichloride, phosphorous pentachloride, phosphorous trichloride oxide, oxalyl chloride or thionyl chloride.

Compounds of formula (1-f), (1-g), (1-h) wherein $U^1$ is a hydroxyl or halogen can be converted to compounds of formula (1-f), (1-g), (1-h) wherein $U^1$ is —$N(CH_3)OCH_3$ by well-known methods.

Compounds (1-f) can be prepared by one or more of the processes described herein.

Process for the Preparation of Compound of Formula (5)

A compound of formula (5) as described herein may be commercially available or directly obtained by performing process Q described below. Compounds of formula (5-a) and (5-b) are various subsets of formula (5).

Process Q

A compound of formula (5-a) (i.e. compound of formula 5 wherein $R^7$ is halogen) can be converted by means of known methods (WO2000044755) into a compound of formula (5-b) (i.e. compound of formula 5 wherein $R^7$ is as shown in scheme 17) in the presence of either an oxygen (ethanol), a sulfur (thioethyl) or an amino (methylamine) based nucleophile, optionally in the presence of base as shown in scheme 17.

Scheme 17: Process Q-Preparation of compounds (5-b)

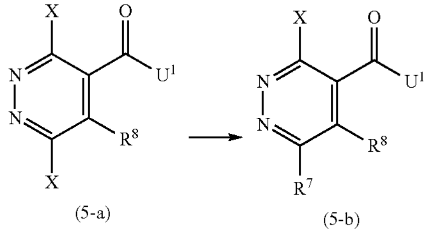

(5-a) (5-b)

$U^1$ = $C_1$-$C_6$-alkoxy

X = halogen $R^8$ = hydrogen, $C_1$-$C_6$-alkyl $R^7$ = halogen, hydroxyl, mercapto, $C_1$-$C_6$-alkoxy, $C_1$-$C_6$-haloalkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_3$-$C_8$-cycloalkylsulfanyl, $C_3$-$C_8$-cycloalkyloxy, aromatic $C_6$-$C_{14}$-carbocyclyloxy, aromatic 5- or 6-membered monocyclic heterocyclyloxy, non-aromatic 3- to 7-membered moncyclic heterocyclyloxy, —$N(R^e)_2$; wherein $R^e$ as disclosed herein and wherein $R^7$ and $R^e$ may be substituted as disclosed herein.

The compounds of formula (5-a) and (5-b) can be converted into compound of formula (5-a) and (5-b) wherein $U^1$ ($C_1$-$C_6$-alkoxy) is replaced with hydroxyl or halogen using the same conditions as described in process N.

Starting materials of formula (5-a) are commercially available.

Process for the Preparation of Compound of Formula (9) and (13)

A compound of formula (9) may be obtained by performing process R described below or may be obtained by conversion or derivatization of another compound of formula (9-a) prepared in accordance with the processes described herein. Compounds of formula (9-a) and (9-b) are various subsets of formula (9).

Process R

A compound of formula (9-a) can be converted by means of methods described in the literature to the corresponding compounds (13) in one or more steps as shown in scheme 18.

Scheme 18: Process R-Preparation of compounds (9-a), (9-b) and (13)

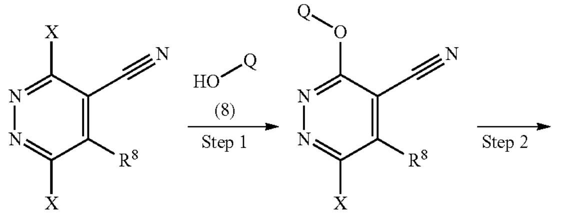

(33) (9-a)

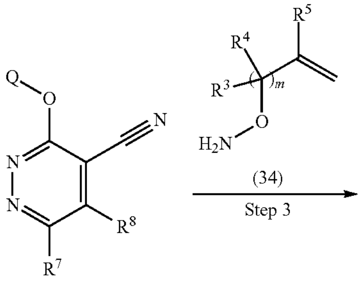

(9-b)

-continued

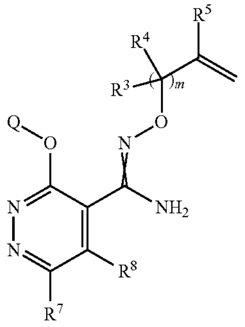

(13)

X = halogen
$R^8$ = hydrogen, $C_1$-$C_6$-alkyl
$R^7$ = halogen, hydroxyl, mercapto, $C_1$-$C_6$-alkoxy, $C_1$-$C_6$-haloalkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_3$-$C_8$-cycloalkylsulfanyl, $C_3$-$C_6$-cycloalkyloxy, aromatic $C_6$-$C_{14}$-carbocyclyloxy, aromatic 5- or 6-membered monocyclic heterocyclyloxy, non-aromatic 3- to 7-membered monocyclic heterocyclyloxy, —$N(R^e)_2$; wherein $R^e$ as disclosed herein and wherein $R^7$ and $R^e$ may be substituted as disclosed herein.

Compounds of formula (33) are commercially available or producible by processes described in the literature (Chemical & Pharmaceutical Bulletin 1977, 25(8), 1856-61).

A compound of formula (33) can be converted according to Step 1 of Process R into a compound of formula (9-a) in the presence of a reagent of formula (8) and a base (e.g organic or inorganic base) as described herein.

Non-limiting examples of conversion of (9-a) to (9-b) may be performed in accordance to scheme 18.

For example, a compound of formula (9-a) can be further converted in a compound of formula (9-b) wherein $R^7$ is hydroxyl, mercapto, $C_1$-$C_6$-alkoxy, $C_1$-$C_6$-haloalkoxy, $C_2$-$C_6$-alkenyloxy, $C_2$-$C_6$-haloalkenyloxy, $C_1$-$C_6$-alkylsulfanyl, $C_1$-$C_6$-haloalkylsulfanyl, $C_3$-$C_8$-cycloalkyloxy, aromatic $C_6$-$C_{14}$-carbocyclyloxy, aromatic 5- or 6-membered monocyclic heterocyclyloxy, non-aromatic 3- to 7-membered monocyclic heterocyclyloxy, —$N(R^e)_2$ by treating the reacting compound of formula (9-a) with an oxygen, a sulfur or an amino based nucleophile.

A compound of formula (9-a) can be converted into a compound of formula (9-b) wherein $R^7$ is cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_6$-cycloalkenyl, aromatic $C_6$-$C_{14}$-carbocycle, aromatic 5- or 6-membered monocyclic heterocycle, non-aromatic 3- to 7-membered monocyclic heterocycle by transition metal catalyzed or metallo-photoredox catalyzed processes as described herein.

An intermediate of formula (13) can be obtained according to Step 3 of Process R by treating a compound of formula (9) with a compound of formula (34) optionally in the presence of a base using well-known methods.

Compounds of formula (8) are commercially available or may be obtained by conversion or derivatization of another compound of formula (8) in accordance to well-known methods.

Process for the Preparation of Compounds of Formula (2), (19), (26-a-1)

Process S

A compound of formula (35) can be converted by means of methods described in the literature to the corresponding compounds (2), (19-a), (19-b) and (26-a-1) in one or more steps as shown in scheme 19.

Scheme 19: Process S-Preparation of compounds (2), (19-a), (19-b), (26-a-1).

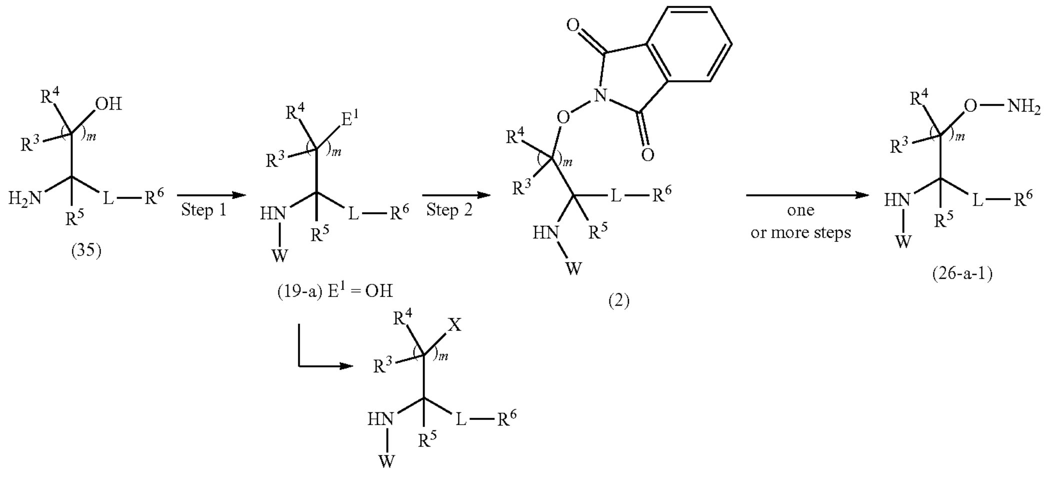

(35) (19-a) $E^1$ = OH (2) (26-a-1)

(19-b) $E^1$ = halogen

W = hydrogen, tert-butoxycarbonyl, benzyl, allyl or (4-methoxyphenyl)methyl

Aminoalcohols of formula (35) are commercially available or may be producible by methods described in the literature (Molecules, 9 (6), 405-426; 2004, WO2017203474).

The amino function of compound 35 is protected in accordance with known methods to provide compound of formula (19-a).

Subsequently, the compound of formula (19-a) can be converted by Step 2 of Process S into a compound of formula (2) using classical Mitsunobu reaction conditions known by the skilled person of the art (Strategic Applications of Named Reactions in Organic Synthesis; Laszlo Kürti, Barbara Czako; Elsevier; 2005; 294-295 and reference herein).

Compounds of formula (2) can be converted into compounds of formula (26-a-1) by well-known methods.

Intermediates

The present invention also relates to intermediates for the preparation of compounds of formula (I).

Thus, the present invention relates to compounds of formula (1):

(1)

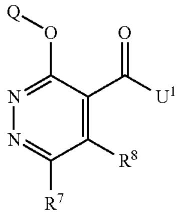

wherein

Q, $R^7$ and $R^8$ are as described herein, $U^1$ is hydroxyl, halogen, $C_1$-$C_6$-alkoxy or —$N(CH_3)OCH_3$, $R^7$, $R^8$ are as described herein and do not represent simultaneously hydrogen and methyl, provided that the compound of formula (1) is not:

| | |
|---|---|
| 5,6-diethyl-3-[(1-methyl-1H-1,2,4-triazol-3-yl)oxy]pyridazine-4-carboxylic acid | 1975960-40-7 |
| 5,6-diethyl-3-[(1-ethyl-1H-pyrazol-4-yl)oxy]pyridazine-4-carboxylic acid | 1771907-90-4 |
| 5,6-diethyl-3-[(1-methyl-1H-pyrazol-4-yl)oxy]pyridazine-4-carboxylic acid | 1714727-92-0 |
| 5,6-diethyl-3-(3-fluorophenoxy)pyridazine-4-carboxylic acid | 1541024-41-2 |
| 5,6-diethyl-3-(2-methylphenoxy)pyridazine-4-carboxylic acid | 1539896-16-6 |
| 3-[(1,3-dimethyl-1H-pyrazol-5-yl)oxy]-5,6-diethylpyridazine-4-carboxylic acid | 1539851-33-6 |
| 5,6-diethyl-3-[(6-methylpyridin-3-yl)oxy]pyridazine-4-carboxylic acid | 1538366-68-5 |
| 5,6-diethyl-3-(3-iodophenoxy)pyridazine-4-carboxylic acid | 1534170-61-0 |
| 3-(3-bromophenoxy)-5,6-diethylpyridazine-4-carboxylic acid | 1526727-36-5 |
| 5,6-diethyl-3-(3-methylphenoxy)pyridazine-4-carboxylic acid | 1526395-43-6 |
| 3-(2-bromophenoxy)-5,6-diethylpyridazine-4-carboxylic acid | 1522340-04-0 |
| 5,6-diethyl-3-(2-iodophenoxy)pyridazine-4-carboxylic acid | 1519917-68-0 |
| 3-(4-bromophenoxy)-5,6-diethylpyridazine-4-carboxylic acid | 1519366-71-2 |

-continued

| | |
|---|---|
| 5,6-diethyl-3-(2-fluorophenoxy)pyridazine-4-carboxylic acid | 1517176-58-7 |
| 3-(2-chlorophenoxy)-5,6-diethylpyridazine-4-carboxylic acid | 1516003-31-8 |
| 5,6-diethyl-3-(4-fluorophenoxy)pyridazine-4-carboxylic acid | 1514568-80-9 |
| 5,6-diethyl-3-phenoxypyridazine-4-carboxylic acid | 1514250-33-9 |
| 3-(4-chlorophenoxy)-5,6-diethylpyridazine-4-carboxylic acid | 1512553-56-8 |
| 5,6-diethyl-3-(pyridin-3-yloxy)pyridazine-4-carboxylic acid | 1506647-60-4 |
| 5,6-diethyl-3-(4-iodophenoxy)pyridazine-4-carboxylic acid | 1505870-09-6 |
| 5,6-diethyl-3-(4-methylphenoxy)pyridazine-4-carboxylic acid | 1503036-22-3 |
| 5,6-diethyl-3-[(2-methylpyridin-3-yl)oxy]pyridazine-4-carboxylic acid | 1501866-59-6 |
| 3-(3-chlorophenoxy)-5,6-diethylpyridazine-4-carboxylic acid | 1501136-89-5 |

The present invention also relates to compounds of formula (2):

(2)

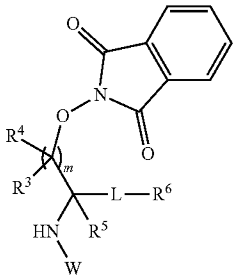

wherein

L, $R^5$, $R^6$ are as defined herein, $R^3$, $R^4$ represents hydrogen, halogen, or $C_1$-$C_6$-alkyl or $R^3$ and $R^4$ form, together with the carbon atom to which they are attached to a $C_3$-$C_8$-cycloalkyl, m is 1 and

W represents hydrogen, tert-butoxycarbonyl, benzyl, allyl or (4-methoxyphenyl)methyl, provided that the compound of formula (2) is not:

| | |
|---|---|
| 2-(2-amino-2-phenylethoxy)-1H-isoindole-1,3(2H)-dione | 1640226-54-5 |
| 2-{[rac-(1R,2R)-1-amino-1-(4-chlorophenyl)propan-2-yl]oxy}-1H-isoindole-1,3(2H)-dione | 2085782-61-0 |
| 2-{[rac-(1S,2S)-1-amino-1-(4-chlorophenyl)propan-2-yl]oxy}-1H-isoindole-1,3(2H)-dione hydrochloride (1:1) | 2085782-62-1 |
| 2-{[1-amino-1-(4-fluorophenyl)-2-methylpropan-2-yl]oxy}-1H-isoindole-1,3(2H)-dione | 1227082-96-3 |
| tert-butyl {(1RS)-2-[(1,3-dioxo-1,3-dihydro-2H-isoindol-2-yl)oxy]-1-phenylethyl}carbamate | 2102206-02-8 |
| tert-butyl {1-[(1,3-dioxo-1,3-dihydro-2H-isoindol-2-yl)oxy]-3-phenylpropan-2-yl}carbamate | 937641-57-1 |
| tert-butyl {rac-(1R,2R)-1-(4-chlorophenyl)-2-[(1,3-dioxo-1,3-dihydro-2H-isoindol-2-yl)oxy]propyl}carbamate | 2085782-59-6 |
| tert-butyl {2-[(1,3-dioxo-1,3-dihydro-2H-isoindol-2-yl)oxy]-1-(4-fluorophenyl)-2-methylpropyl}carbamate | 1227082-95-2 |

The present invention also relates to compounds of formula (3):

(3)

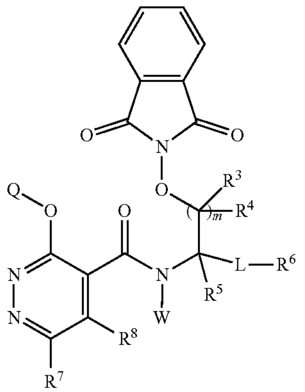

wherein

Q, L, $R^3$, $R^4$, $R^5$, $R^6$, $R^7$ and $R^8$ are defined as herein, m is 1 or 2, and W represents hydrogen, tert-butoxycarbonyl, benzyl, allyl or (4-methoxyphenyl)methyl.

The present invention also relates to compounds of formula (4):

(4)

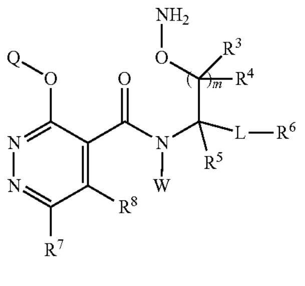

wherein

Q, L, $R^3$, $R^4$, $R^5$, $R^6$, $R^7$ and $R^8$ are defined as herein, m is 1 or 2, and W represents hydrogen, tert-butoxycarbonyl, benzyl, allyl or (4-methoxyphenyl)methyl.

The present invention also relates to compounds of formula (6a) and (6b):

(6a)

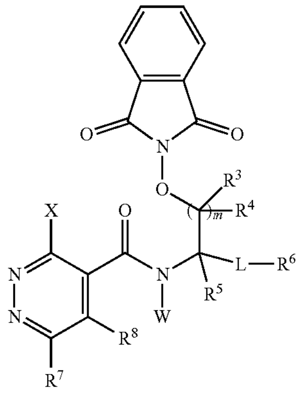

(6b)

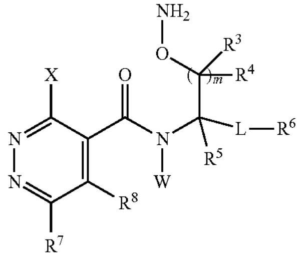

wherein

Q, L, $R^3$, $R^4$, $R^5$, $R^6$, $R^7$ and $R^8$ are defined as herein, m is 1 or 2, W represents hydrogen, tert-butoxycarbonyl, benzyl, allyl or (4-methoxyphenyl)methyl, and X represents halogen.

The present invention also relates to compounds of formula (7):

(7)

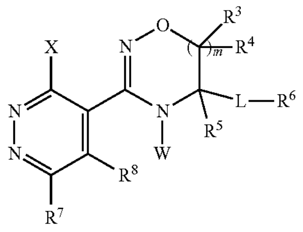

wherein

Q, L, $R^3$, $R^4$, $R^5$, $R^6$, $R^7$ and $R^8$ are defined as herein, m is 1 or 2, W represents hydrogen, tert-butoxycarbonyl, benzyl or (4-methoxyphenyl)methyl, and X represents halogen.

The present invention also relates to compounds of formula (9):

(9)

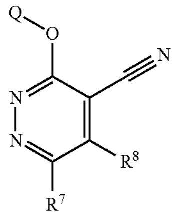

wherein

Q, $R^7$ and $R^8$ are as described herein, provided that $R^7$ and $R^8$ are not both simultaneously hydrogen, methyl or ethyl and the compound of formula (9) is not:

| | |
|---|---|
| 3-(4-methylphenoxy)-6-phenylpyridazine-4-carbonitrile | 338752-71-9 |
| 6-phenyl-3-[3-(trifluoromethyl)phenoxy]pyridazine-4-carbonitrile | 338751-76-1 |
| 3-(2-chlorophenoxy)-6-phenylpyridazine-4-carbonitrile | 338751-75-0 |
| 3-(4-fluorophenoxy)-6-phenylpyridazine-4-carbonitrile | 338751-73-8 |
| 3-phenoxy-6-phenylpyridazine-4-carbonitrile | 338751-72-7 |
| 3-(4-methoxyphenoxy)-6-phenylpyridazine-4-carbonitrile | 338751-62-5 |
| 3-(4-chlorophenoxy)-6-phenylpyridazine-4-carbonitrile | 338751-61-4 |

The present invention also relates to compounds of formula (10):

(10)

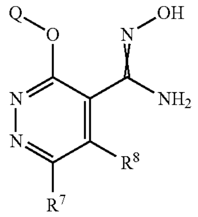

wherein

Q, $R^7$ and $R^8$ are as described herein, provided that $R^7$ and $R^8$ are not both simultaneously hydrogen or methyl and that the compound of formula (10) is not:

| | |
|---|---|
| 5,6-diethyl-N-hydroxy-3-[(1-methyl-1H-1,2,4-triazol-3-yl)oxy]pyridazine-4-carboximidamide | 1982384-84-8 |
| 5,6-diethyl-N-hydroxy-3-[(1-methyl-1H-pyrazol-4-yl)oxy]pyridazine-4-carboximidamide | 1922236-54-1 |
| 5,6-diethyl-N-hydroxy-3-(pyridin-3-yloxy)pyridazine-4-carboximidamide | 1563496-43-4 |

The present invention also relates to compounds of formula (12):

(12)

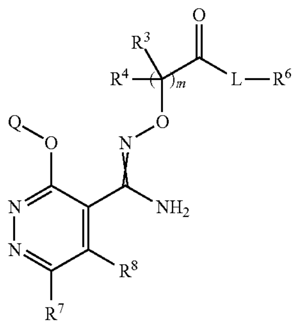

wherein Q, L, $R^3$, $R^4$, $R^6$, $R^7$ and $R^8$ are defined as herein and m is 1 or 2.

The present invention also relates to compounds of formula (13):

(13)

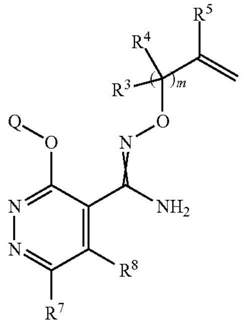

wherein Q, $R^3$, $R^4$, $R^5$, $R^7$ and $R^8$ are defined as herein and m is 1 or 2.

The present invention also relates to compounds of formula (14):

(14)

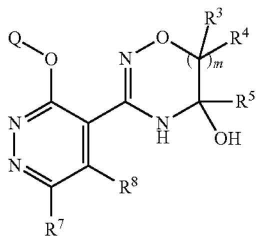

wherein Q, $R^3$, $R^4$, $R^5$, $R^7$, $R^8$ are defined as herein and m is 1 or 2.

The present invention also relates to compounds of formula (16):

(16)

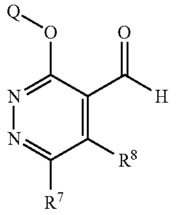

wherein Q, $R^7$ and $R^8$ are defined as herein.

The present invention also relates to compounds of formula (11):

(17)

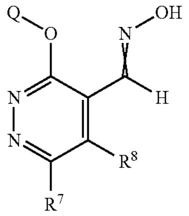

wherein Q, $R^7$ and $R^8$ are defined as herein.

The present invention also relates to compounds of formula (18):

(18)

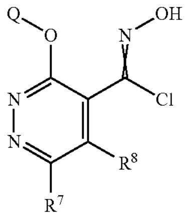

wherein Q, $R^7$ and $R^8$ are defined as herein.

The present invention also relates to compounds of formula (19)

(19)

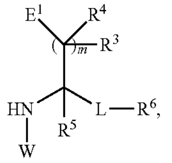

wherein m is 1,

L represents $—CH_2—$ or $—CF_2—$, $R^3$ and $R^4$ represent hydrogen, $E^1$ represents chlorine, bromine or iodine, W represents hydrogen, tert-butoxycarbonyl, benzyl or (4-methoxyphenyl)methyl and salts, solvates or salts of the solvates thereof.

The present invention also relates to compounds of formula (20):

(20)

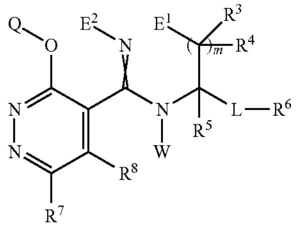

wherein

Q, L, $R^3$, $R^4$, $R^5$, $R^6$, $R^7$ and $R^8$ are defined as herein, m is 1 or 2, $E^1$ represents hydroxyl or halogen, $E^2$ represents hydroxyl or amino, and W represents hydrogen, tert-butoxycarbonyl, benzyl or (4-methoxyphenyl)methyl.

The present invention also relates to compounds of formula (21):

(21)

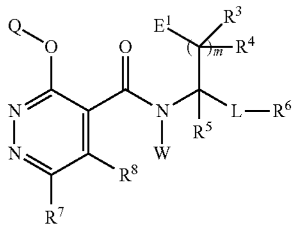

wherein

Q, L, $R^3$, $R^4$, $R^5$, $R^6$, $R^7$, $R^8$ and m are defined as herein, $E^1$ represents hydroxyl or halogen, and W represents hydrogen, tert-butoxycarbonyl, benzyl or (4-methoxyphenyl)methyl.

The present invention also relates to compounds of formula (21):

(21)

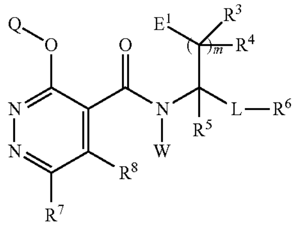

wherein

Q, $R^6$, $R^7$, $R^8$ and m are defined as herein, m is 1,

L is $CH_2$, CHF or $CF_2$, $R^3$, $R^4$ and $R^5$ represent hydrogen, $E^1$ represents hydroxyl or halogen, and W represents hydrogen, tert-butoxycarbonyl, benzyl or (4-methoxyphenyl)methyl.

The present invention also relates to compounds of formula (22):

(22)

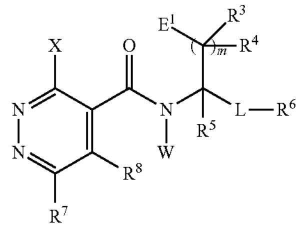

wherein

L, $R^3$, $R^4$, $R^5$, $R^6$, $R^7$, $R^8$ are defined as herein, m is 1 or 2,

X represents halogen, $E^1$ represents hydroxyl or halogen,

W represents hydrogen, tert-butoxycarbonyl, benzyl or (4-methoxyphenyl)methyl, provided the compound of formula (22) is not:

| | |
|---|---|
| 3,6-dichloro-N-(1-hydroxy-2-phenylpropan-2-yl)pyridazine-4-carboxamide | 1980402-62-7 |
| 3,6-dichloro-N-[(1RS)-2-hydroxy-1-phenylethyl]pyridazine-4-carboxamide | 1939959-83-7 |
| 3,6-dichloro-N-[(1RS)-2-hydroxy-1-phenylethyl]pyridazine-4-carboxamide | 1927369-37-6 |
| 3,6-dichloro-N-(2-hydroxy-1-phenylethyl)pyridazine-4-carboxamide | 1490216-99-3 |
| 3,6-dichloro-N-[(2RS)-1-hydroxy-3-phenylpropan-2-yl]pyridazine-4-carboxamide | 1961457-84-0 |
| 3,6-dichloro-N-[(2RS)-1-hydroxy-3-phenylpropan-2-yl]pyridazine-4-carboxamide | 1942775-34-9 |
| 3,6-dichloro-N-(1-hydroxy-3-phenylpropan-2-yl)pyridazine-4-carboxamide | 1409556-04-2 |

The present invention also relates to compounds of formula (23):

(23)

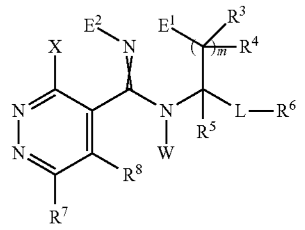

wherein

L, $R^3$, $R^4$, $R^5$, $R^6$, $R^7$, $R^8$ are defined as herein, m is 1 or 2,

X represents halogen, $E^1$ represents hydroxyl or halogen, $E^2$ represents hydroxyl or amino, and W represents hydrogen, tert-butoxycarbonyl, benzyl or (4-methoxyphenyl)methyl.

(24)

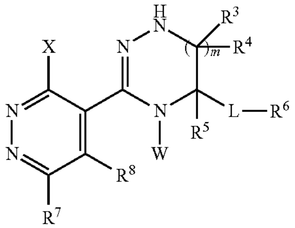

wherein

L, $R^3$, $R^4$, $R^5$, $R^6$, $R^7$, $R^8$ are defined as herein, m is 1 or 2,

X represents halogen,

W represents hydrogen, tert-butoxycarbonyl, benzyl or (4-methoxyphenyl)methyl.

The present invention also relates to compounds of formula (25):

(25)

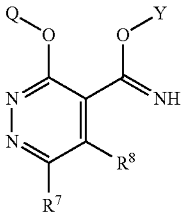

wherein Q, Y, $R^7$ and $R^8$ are defined as herein.

The present invention also relates to compounds of formula (28):

(28)

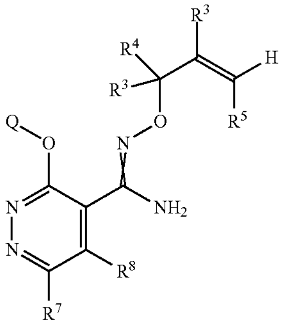

wherein Q, $R^3$, $R^4$, $R^5$, $R^7$ and $R^8$ are defined as herein.

The present invention also relates to compounds of formula (30):

(30)

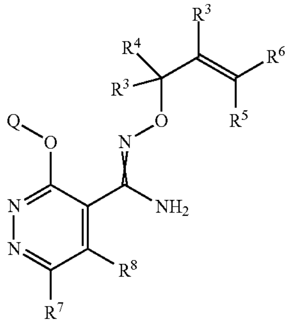

wherein Q, $R^3$, $R^4$, $R^5$, $R^6$, $R^7$ and $R^8$ are defined as herein.

The present invention also relates to intermediates of formula (8):

Q-OH (8)

wherein Q is

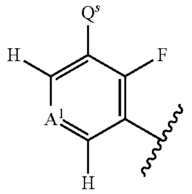

wherein $A^1$ is C or N, $Q^S$ is selected from the group consisting of $C_3$-$C_4$-cycloalkyl, $C_3$-$C_8$-halocycloalkyl, $C_2$-$C_6$-alkenyl, $C_2$-$C_6$-haloalkenyl and $C_2$-$C_6$-alkynyl, provided that the compound of formula (8) does not represent:

| | |
|---|---|
| 2-fluoro-3-(3,3,3-trifluoroprop-1-en-2-yl)phenol | 2168012-00-6 |
| 3-(1-ethoxyvinyl)-2-fluorophenol | 2137960-04-2 |
| 1-(2-fluoro-3-hydroxyphenyl)cyclopropanecarbonitrile | 1881320-49-5 |
| 3-(1-aminocyclopropyl)-2-fluorophenol | 1785193-75-0 |
| 1-(2-fluoro-3-hydroxyphenyl)cyclopropanecarboxylic acid | 1507131-96-5 |
| 2-fluoro-3-(prop-1-en-2-yl)phenol | 1375066-38-8 |

Compositions and Formulations

The present invention further relates to a composition, in particular a composition for controlling unwanted phytopathogenic microorganisms. The compositions may be applied to the microorganisms and/or in their habitat.

The composition typically comprises at least one compound of formula (I) and at least one agriculturally suitable auxiliary, e.g. carrier(s) and/or surfactant(s).

A carrier is a solid or liquid, natural or synthetic, organic or inorganic substance that is generally inert. The carrier generally improves the application of the compounds, for instance, to plants, plants parts or seeds. Examples of suitable solid carriers include, but are not limited to, ammonium salts, natural rock flours, such as kaolins, clays, talc, chalk, quartz, attapulgite, montmorillonite and diatomaceous earth, and synthetic rock flours, such as finely divided silica, alumina and silicates. Examples of typically useful solid carriers for preparing granules include, but are not limited to crushed and fractionated natural rocks such as calcite, marble, pumice, sepiolite and dolomite, synthetic granules of inorganic and organic flours and granules of organic material such as paper, sawdust, coconut shells, maize cobs and tobacco stalks. Examples of suitable liquid carriers include, but are not limited to, water, organic solvents and combinations thereof. Examples of suitable solvents include polar and nonpolar organic chemical liquids, for example from the classes of aromatic and nonaromatic hydrocarbons (such as cyclohexane, paraffins, alkylbenzenes, xylene, toluene alkylnaphthalenes, chlorinated aromatics or chlorinated aliphatic hydrocarbons such as chlorobenzenes, chloroethylenes or methylene chloride), alcohols and polyols (which may optionally also be substituted, etherified and/or esterified, such as butanol or glycol), ketones (such as acetone, methyl ethyl ketone, methyl isobutyl ketone or cyclohexanone), esters (including fats and oils) and (poly)ethers, unsubstituted and substituted amines, amides (such as dimethylformamide), lactams (such as N-alkylpyrrolidones) and lactones, sulfones and sulfoxides (such as dimethyl sulfoxide). The carrier may also be a liquefied gaseous extender, i.e. liquid which is gaseous at standard temperature and under standard pressure, for example aerosol propellants such as halohydrocarbons, butane, propane, nitrogen and carbon dioxide. The amount of carrier typically ranges from 1 to 99.99%, preferably from 5 to 99.9%, more preferably from 10 to 99.5%, and most preferably from 20 to 99% by weight of the composition.

The surfactant can be an ionic (cationic or anionic) or non-ionic surfactant, such as ionic or non-ionic emulsifier(s), foam former(s), dispersant(s), wetting agent(s) and any mixtures thereof. Examples of suitable surfactants include, but are not limited to, salts of polyacrylic acid, salts of lignosulfonic acid, salts of phenolsulfonic acid or naphthalenesulfonic acid, polycondensates of ethylene and/or propylene oxide with fatty alcohols, fatty acids or fatty amines (polyoxyethylene fatty acid esters, polyoxyethylene fatty alcohol ethers, for example alkylaryl polyglycol ethers), substituted phenols (preferably alkylphenols or arylphenols), salts of sulfosuccinic esters, taurine derivatives (preferably alkyl taurates), phosphoric esters of polyethoxylated alcohols or phenols, fatty esters of polyols and derivatives of compounds containing sulfates, sulfonates, phosphates (for example, alkylsulfonates, alkyl sulfates, arylsulfonates) and protein hydrolysates, lignosulfite waste liquors and methylcellulose. A surfactant is typically used when the compound of formula (I) and/or the carrier is insoluble in water and the application is made with water. Then, the amount of surfactants typically ranges from 5 to 40% by weight of the composition.

Further examples of suitable auxiliaries include water repellents, siccatives, binders (adhesive, tackifier, fixing agent, such as carboxymethylcellulose, natural and synthetic polymers in the form of powders, granules or latices, such as gum arabic, polyvinyl alcohol and polyvinyl acetate, natural phospholipids such as cephalins and lecithins and synthetic phospholipids, polyvinylpyrrolidone and tylose), thickeners, stabilizers (e.g. cold stabilizers, preservatives, antioxidants, light stabilizers, or other agents which improve chemical and/or physical stability), dyes or pigments (such as inorganic pigments, e.g. iron oxide, titanium oxide and Prussian Blue, organic dyes, e.g. alizarin, azo and metal phthalocyanine dyes), antifoams (e.g. silicone antifoams and magnesium stearate), preservatives (e.g. dichlorophene and benzyl alcohol hemiformal), secondary thickeners (cellulose derivatives, acrylic acid derivatives, xanthan, modified clays and finely divided silica), stickers, gibberellins and processing auxiliaries, mineral and vegetable oils, perfumes, waxes, nutrients (including trace nutrients, such as salts of iron, manganese, boron, copper, cobalt, molybdenum and zinc), protective colloids, thixotropic substances, penetrants, sequestering agents and complex formers.

The choice of the auxiliaries is related to the intended mode of application of the compound of formula (I) and/or on the physical properties. Furthermore, the auxiliaries may be chosen to impart particular properties (technical, physical and/or biological properties) to the compositions or use forms prepared therefrom. The choice of auxiliaries may allow customizing the compositions to specific needs.

The composition may be in any customary form, such as solutions (e.g aqueous solutions), emulsions, wettable powders, water- and oil-based suspensions, powders, dusts, pastes, soluble powders, soluble granules, granules for broadcasting, suspoemulsion concentrates, natural or synthetic products impregnated with the compound of formula (I), fertilizers and also microencapsulations in polymeric substances. The compound of formula (I) may be present in a suspended, emulsified or dissolved form.

The composition may be provided to the end user as ready-for-use formulation, i.e. the compositions may be directly applied to the plants or seeds by a suitable device, such as a spraying or dusting device.

Alternatively, the compositions may be provided to the end user in the form of concentrates which have to be diluted, preferably with water, prior to use.

The composition can be prepared in conventional manners, for example by mixing the compound of formula (I) with one or more suitable auxiliaries, such as disclosed herein above.

The composition contains generally from 0.01 to 99% by weight, from 0.05 to 98% by weight, preferably from 0.1 to 95% by weight, more preferably from 0.5 to 90% by weight, most preferably from 1 to 80% by weight of the compound of formula (I). It is possible that a composition comprises two or more compounds formula (I). In such case the outlined ranges refer to the total amount of compounds of the present invention.

Mixtures/Combinations

The compound of formula (I) and composition comprising thereof can be mixed with other active ingredients like fungicides, bactericides, acaricides, nematicides, insecticides, herbicides, fertilizers, growth regulators, safeners or semiochemicals. This may allow to broaden the activity spectrum or to prevent development of resistance. Examples of known fungicides, insecticides, acaricides, nematicides and bactericides are disclosed in the Pesticide Manual, 17th Edition.

Examples of especially preferred fungicides which could be mixed with the compound of formula (I) and the composition are:

1) Inhibitors of the ergosterol biosynthesis, for example (1.001) cyproconazole, (1.002) difenoconazole, (1.003) epoxiconazole, (1.004) fenhexamid, (1.005) fenpropidin, (1.006) fenpropimorph, (1.007) fenpyrazamine, (1.008) fluquinconazole, (1.009) flutriafol, (1.010) imazalil, (1.011) imazalil sulfate, (1.012) ipconazole, (1.013) metconazole, (1.014) myclobutanil, (1.015) paclobutrazol, (1.016) prochloraz, (1.017) propiconazole, (1.018) prothioconazole, (1.019) Pyrisoxazole, (1.020) spiroxamine, (1.021) tebuconazole, (1.022) tetraconazole, (1.023) triadimenol, (1.024) tridemorph, (1.025) triticonazole, (1.026) (1R,2S,5S)-5-(4-chlorobenzyl)-2-(chloromethyl)-2-methyl-1-(1H-1,2,4-triazol-1-ylmethyl)cyclopentanol, (1.027) (1S,2R,5R)-5-

(4-chlorobenzyl)-2-(chloromethyl)-2-methyl-1-(1H-1,2,4-triazol-1-ylmethyl)cyclopentanol, (1.028) (2R)-2-(1-chlorocyclopropyl)-4-[(1R)-2,2-dichlorocyclopropyl]-1-(1H-1,2,4-triazol-1-yl)butan-2-ol, (1.029) (2R)-2-(1-chlorocyclopropyl)-4-[(1S)-2,2-dichlorocyclopropyl]-1-(1H-1,2,4-triazol-1-yl)butan-2-ol, (1.030) (2R)-2-[4-(4-chlorophenoxy)-2-(trifluoro-methyl)phenyl]-1-(1H-1,2,4-triazol-1-yl)propan-2-ol, (1.031) (2S)-2-(1-chlorocyclopropyl)-4-[(1R)-2,2-dichlorocyclopropyl]-1-(1H-1,2,4-triazol-1-yl)butan-2-ol, (1.032) (2S)-2-(1-chlorocyclopropyl)-4-[(1S)-2,2-dichlorocyclopropyl]-1-(1H-1,2,4-triazol-1-yl)butan-2-ol, (1.033) (2S)-2-[4-(4-chlorophenoxy)-2-(trifluoromethyl)phenyl]-1-(1H-1,2,4-triazol-1-yl)propan-2-ol, (1.034) (R)-[3-(4-chloro-2-fluorophenyl)-5-(2,4-difluorophenyl)-1,2-oxazol-4-yl](pyridin-3-yl)methanol, (1.035) (S)-[3-(4-chloro-2-fluorophenyl)-5-(2,4-difluorophenyl)-1,2-oxazol-4-yl](pyridin-3-yl)methanol, (1.036) [3-(4-chloro-2-fluorophenyl)-5-(2,4-difluorophenyl)-1,2-oxazol-4-yl](pyridin-3-yl)methanol, (1.037) 1-({(2R,4S)-2-[2-chloro-4-(4-chloro-phenoxy)phenyl]-4-methyl-1,3-dioxolan-2-yl}methyl)-1H-1,2,4-triazole, (1.038) 1-({(2S,4S)-2-[2-chloro-4-(4-chlorophenoxy)phenyl]-4-methyl-1,3-dioxolan-2-yl}methyl)-1H-1,2,4-triazole, (1.039) 1-{[3-(2-chlorophenyl)-2-(2,4-difluorophenyl)oxiran-2-yl]methyl}-1H-1,2,4-triazol-5-yl thiocyanate, (1.040) 1-{[rel(2R,3R)-3-(2-chlorophenyl)-2-(2,4-difluorophenyl)oxiran-2-yl]methyl}-1H-1,2,4-triazol-5-yl thiocyanate, (1.041) 1-{[rel(2R,3S)-3-(2-chlorophenyl)-2-(2,4-difluorophenyl)oxiran-2-yl]methyl}-1H-1,2,4-triazol-5-yl thiocyanate, (1.042) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.043) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.044) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.045) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.046) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.047) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.048) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.049) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.050) 2-[1-(2,4-dichlorophenyl)-5-hydroxy-2,6,6-trimethylheptan-4-yl]-2,4-dihydro-3H-1,2,4-triazole-3-thione, (1.051) 2-[2-chloro-4-(2,4-dichlorophenoxy)phenyl]-1-(1H-1,2,4-triazol-1-yl)propan-2-ol, (1.052) 2-[2-chloro-4-(4-chlorophenoxy)phenyl]-1-(1H-1,2,4-triazol-1-yl)butan-2-ol, (1.053) 2-[4-(4-chlorophenoxy)-2-(trifluoromethyl)phenyl]-1-(1H-1,2,4-triazol-1-yl)butan-2-ol, (1.054) 2-[4-(4-chlorophenoxy)-2-(trifluoromethyl)phenyl]-1-(1H-1,2,4-triazol-1-yl)pentan-2-ol, (1.055) Mefentrifluconazole, (1.056) 2-{[3-(2-chlorophenyl)-2-(2,4-difluorophenyl)oxiran-2-yl]methyl}-2,4-dihydro-3H-1,2,4-triazole-3-thione, (1.057) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.058) 2-{[rel(2R,3S)-3-(2-chlorophenyl)-2-(2,4-difluorophenyl)oxiran-2-yl]methyl}-2,4-dihydro-3H-1,2,4-triazole-3-thione, (1.059) 5-(4-chlorobenzyl)-2-(chloromethyl)-2-methyl-1-(1H-1,2,4-triazol-1-ylmethyl)cyclopentanol, (1.060) 5-(allylsulfanyl)-1-{[3-(2-chlorophenyl)-2-(2,4-difluorophenyl)oxiran-2-yl]methyl}-1H-1,2,4-triazole, (1.061) 5-(allylsulfanyl)-1-{[rel(2R,3R)-3-(2-chlorophenyl)-2-(2,4-difluorophenyl)oxiran-2-yl]methyl}-1H-1,2,4-triazole, (1.062) 5-(allylsulfanyl)-1-{[rel(2R,3S)-3-(2-chlorophenyl)-2-(2,4-difluorophenyl)oxiran-2-yl]methyl}-1H-1,2,4-triazole, (1.063) N'-(2,5-dimethyl-4-{[3-(1,1,2,2-tetrafluoroethoxy)phenyl]sulfanyl}phenyl)-N-ethyl-N-methylimidoformamide, (1.064) N'-(2,5-dimethyl-4-{[3-(2,2,2-trifluoroethoxy)phenyl]sulfanyl}phenyl)-N-ethyl-N-methylimidoformamide, (1.065) N'-(2,5-dimethyl-4-{[3-(2,2,3,3-tetrafluoro-propoxy)phenyl]sulfanyl}phenyl)-N-ethyl-N-methylimidoformamide, (1.066) N'-(2,5-dimethyl-4-{[3-(pentafluoroethoxy)phenyl]sulfanyl}phenyl)-N-ethyl-N-methylimidoformamide, (1.067) N'-(2,5-dimethyl-4-{3-[(1,1,2,2-tetrafluoroethyl)sulfanyl]phenoxy}phenyl)-N-ethyl-N-methylimidoformamide, (1.068) N'-(2,5-dimethyl-4-{3-[(2,2,2-trifluoroethyl)sulfanyl]phenoxy}phenyl)-N-ethyl-N-methylimidoformamide, (1.069) N'-(2,5-dimethyl-4-{3-[(2,2,3,3-tetrafluoropropyl)sulfanyl]phenoxy}phenyl)-N-ethyl-N-methylimidoformamide, (1.070) N'-(2,5-dimethyl-4-{3-[(pentafluoroethyl)sulfanyl]phenoxy}phenyl)-N-ethyl-N-methylimidoformamide, (1.071) N'-(2,5-dimethyl-4-phenoxyphenyl)-N-ethyl-N-methylimidoformamide, (1.072) N'-(4-{[3-(difluoromethoxy)phenyl]sulfanyl}-2,5-dimethylphenyl)-N-ethyl-N-methylimidoformamide, (1.073) N'-(4-{3-[(difluoromethyl)sulfanyl]phenoxy}-2,5-dimethylphenyl)-N-ethyl-N-methylimidoformamide, (1.074) N'-[5-bromo-6-(2,3-dihydro-1H-inden-2-yloxy)-2-methylpyridin-3-yl]-N-ethyl-N-methylimidoformamide, (1.075) N'-{4-[(4,5-dichloro-1,3-thiazol-2-yl)oxy]-2,5-dimethylphenyl}-N-ethyl-N-methylimidoformamide, (1.076) N'-{5-bromo-6-[(1R)-1-(3,5-difluorophenyl)ethoxy]-2-methylpyridin-3-yl}-N-ethyl-N-methylimidoformamide, (1.077) N'-{5-bromo-6-[(1S)-1-(3,5-difluorophenyl)ethoxy]-2-methylpyridin-3-yl}-N-ethyl-N-methylimidoformamide, (1.078) N'-{5-bromo-6-[(cis-4-isopropylcyclohexyl)oxy]-2-methylpyridin-3-yl}-N-ethyl-N-methylimidoformamide, (1.079) N'-{5-bromo-6-[(trans-4-isopropylcyclohexyl)oxy]-2-methylpyridin-3-yl}-N-ethyl-N-methylimidoformamide, (1.080) N'-{5-bromo-6-[1-(3,5-difluorophenyl)ethoxy]-2-methylpyridin-3-yl}-N-ethyl-N-methylimidoformamide, (1.081) Ipfentrifluconazole.

2) Inhibitors of the respiratory chain at complex I or II, for example (2.001) benzovindiflupyr, (2.002) bixafen, (2.003) boscalid, (2.004) carboxin, (2.005) fluopyram, (2.006) flutolanil, (2.007) fluxapyroxad, (2.008) furametpyr, (2.009) Isofetamid, (2.010) isopyrazam (anti-epimeric enantiomer 1R,4S,9S), (2.011) isopyrazam (anti-epimeric enantiomer 1S,4R,9R), (2.012) isopyrazam (anti-epimeric racemate 1RS,4SR,9SR), (2.013) isopyrazam (mixture of syn-epimeric racemate 1RS,4SR,9RS and anti-epimeric racemate 1RS,4SR,9SR), (2.014) isopyrazam (syn-epimeric enantiomer 1R,4S,9R), (2.015) isopyrazam (syn-epimeric enantiomer 1S,4R,9S), (2.016) isopyrazam (syn-epimeric racemate 1 RS,4SR,9RS), (2.017) penflufen, (2.018) penthiopyrad, (2.019) pydiflumetofen, (2.020) Pyraziflumid, (2.021) sedaxane, (2.022) 1,3-dimethyl-N-(1,1,3-trimethyl-2,3-dihydro-1H-inden-4-yl)-1H-pyrazole-4-carboxamide, (2.023) 1,3-dimethyl-N-[(3R)-1,1,3-trimethyl-2,3-dihydro-1H-inden-4-yl]-1H-pyrazole-4-carboxamide, (2.024) 1,3-dimethyl-N-[(3S)-1,1,3-trimethyl-2,3-dihydro-1H-inden-4-yl]-1H-pyrazole-4-carboxamide, (2.025) 1-methyl-3-(trifluoromethyl)-N-[2'-(trifluoromethyl)biphenyl-2-yl]-1H-pyrazole-4-carboxamide, (2.026) 2-fluoro-6-(trifluoromethyl)-N-(1,1,3-trimethyl-2,3-dihydro-1H-inden-4-yl) benzamide, (2.027) 3-(difluoromethyl)-1-methyl-N-(1,1,3-trimethyl-2,3-dihydro-1H-inden-4-yl)-1H-pyrazole-4-carboxamide, (2.028) 3-(difluoromethyl)-1-methyl-N-[(3R)-1,1,3-trimethyl-2,3-dihydro-1H-inden-4-yl]-1H-pyrazole-4-carboxamide, (2.029) 3-(difluoromethyl)-1-methyl-N-[(3S)-1,1,3-trimethyl-2,3-dihydro-1H-inden-4-yl]-1H-pyrazole-4-carboxamide, (2.030) Fluindapyr, (2.031) 3-(difluoromethyl)-N-[(3R)-7-fluoro-1,1,3-trimethyl-2,3-dihydro-1H-inden-4-yl]-1-methyl-1H-pyrazole-4-carboxamide, (2.032) 3-(difluoromethyl)-N-[(3S)-7-fluoro-1,1,3-trimethyl-2,3-dihydro-1H-inden-4-yl]-1-methyl-1H-pyrazole-4-carboxamide, (2.033) 5,8-difluoro-N-[2-(2-fluoro-4-{[4-(trifluoromethyl)pyridin-2-yl]oxy}-phenyl)ethyl] quinazolin-4-amine, (2.034)N-(2-cyclopentyl-5-fluorobenzyl)-N-cyclopropyl-3-(difluoro-methyl)-5-fluoro-1-methyl-1H-pyrazole-4-carboxamide, (2.035) N-(2-tert-butyl-5-methylbenzyl)-N-cyclopropyl-3-(difluoromethyl)-5-fluoro-1-methyl-1H-pyrazole-4-carboxamide, (2.036)N-(2-tert-butylbenzyl)-N-cyclopropyl-3-(difluoromethyl)-5-fluoro-1-methyl-1H-pyrazole-4-carboxamide, (2.037) N-(5-chloro-2-ethylbenzyl)-N-cyclopropyl-3-(difluoromethyl)-5-fluoro-1-methyl-1H-pyrazole-4-carboxamide, (2.038) isoflucypram, (2.039)N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.040)N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.041)N-[1-(2,4-dichlorophenyl)-1-methoxypropan-2-yl]-3-(difluoromethyl)-1-methyl-1H-pyrazole-4-carboxamide, (2.042)N-[2-chloro-6-(trifluoromethyl)benzyl]-N-cyclopropyl-3-(difluoromethyl)-5-fluoro-1-methyl-1H-pyrazole-4-carboxamide, (2.043)N-[3-chloro-2-fluoro-6-(trifluoro-methyl)benzyl]-N-cyclopropyl-3-(difluoromethyl)-5-fluoro-1-methyl-1H-pyrazole-4-carboxamide, (2.044) N-[5-chloro-2-(trifluoromethyl) benzyl]-N-cyclopropyl-3-(difluoromethyl)-5-fluoro-1-methyl-1H-pyrazole-4-carboxamide, (2.045)N-cyclopropyl-3-(difluoromethyl)-5-fluoro-1-methyl-N-[5-methyl-2-(trifluoro-methyl)benzyl]-1H-pyrazole-4-carboxamide, (2.046)N-cyclopropyl-3-(difluoromethyl)-5-fluoro-N-(2-fluoro-6-isopropylbenzyl)-1-methyl-1H-pyrazole-4-carboxamide, (2.047)N-cyclopropyl-3-(difluoro-methyl)-5-fluoro-N-(2-isopropyl-5-methylbenzyl)-1-methyl-1H-pyrazole-4-carboxamide, (2.048)N-cyclopropyl-3-(difluoromethyl)-5-fluoro-N-(2-isopropylbenzyl)-1-methyl-1H-pyrazole-4-carbothioamide, (2.049)N-cyclopropyl-3-(difluoromethyl)-5-fluoro-N-(2-isopropylbenzyl)-1-methyl-1H-pyrazole-4-carboxamide, (2.050)N-cyclopropyl-3-(difluoromethyl)-5-fluoro-N-(5-fluoro-2-isopropylbenzyl)-1-methyl-1H-pyrazole-4-carboxamide, (2.051)N-cyclopropyl-3-(difluoromethyl)-N-(2-ethyl-4,5-dimethyl-benzyl)-5-fluoro-1-methyl-1H-pyrazole-4-carboxamide, (2.052) N-cyclopropyl-3-(difluoromethyl)-N-(2-ethyl-5-fluorobenzyl)-5-fluoro-1-methyl-1H-pyrazole-4-carboxamide, (2.053)N-cyclopropyl-3-(difluoro-methyl)-N-(2-ethyl-5-methylbenzyl)-5-fluoro-1-methyl-1H-pyrazole-4-carboxamide, (2.054)N-cyclopropyl-N-(2-cyclopropyl-5-fluorobenzyl)-3-(difluoromethyl)-5-fluoro-1-methyl-1H-pyrazole-4-carboxamide, (2.055)N-cyclopropyl-N-(2-cyclopropyl-5-methylbenzyl)-3-(difluoromethyl)-5-fluoro-1-methyl-1 H-pyrazole-4-carboxamide, (2.056) N-cyclopropyl-N-(2-cyclopropylbenzyl)-3-(difluoromethyl)-5-fluoro-1-methyl-1H-pyrazole-4-carboxamide, (2.057) pyrapropoyne.

3) Inhibitors of the respiratory chain at complex III, for example (3.001) ametoctradin, (3.002) amisulbrom, (3.003) azoxystrobin, (3.004) coumethoxystrobin, (3.005) coumoxystrobin, (3.006) cyazofamid, (3.007) dimoxystrobin, (3.008) enoxastrobin, (3.009) famoxadone, (3.010) fenamidone, (3.011) flufenoxystrobin, (3.012) fluoxastrobin, (3.013) kresoxim-methyl, (3.014) metominostrobin, (3.015) orysastrobin, (3.016) picoxystrobin, (3.017) pyraclostrobin, (3.018) pyrametostrobin, (3.019) pyraoxystrobin, (3.020) trifloxystrobin, (3.021) (2E)-2-{2-[({[(1E)-1-(3-{[(E)-1-fluoro-2-phenyl-vinyl]oxy}phenyl)ethylidene] amino}oxy)methyl]phenyl}-2-(methoxyimino)-N-methylacetamide, (3.022) (2E,3Z)-5-{[1-(4-chlorophenyl)-1H-pyrazol-3-yl]oxy}-2-(methoxyimino)-N,3-dimethylpent-3-enamide, (3.023) (2R)-2-{2-[(2,5-dimethylphenoxy)methyl]phenyl}-2-methoxy-N-methylacetamide, (3.024) (2S)-2-{2-[(2,5-dimethylphenoxy)methyl]phenyl}-2-methoxy-N-methylacetamide, (3.025) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (3.026) mandestrobin, (3.027)N-(3-ethyl-3,5,5-trimethylcyclohexyl)-3-formamido-2-hydroxybenzamide, (3.028) (2E,3Z)-5-{[1-(4-chloro-2-fluoro-phenyl)-1H-pyrazol-3-yl]oxy}-2-(methoxyimino)-N,3-dimethylpent-3-enamide, (3.029) methyl {5-[3-(2,4-dimethylphenyl)-1H-pyrazol-1-yl]-2-methylbenzyl}carbamate, (3.030) metyltetraprole, (3.031) florylpicoxamid.

4) Inhibitors of the mitosis and cell division, for example (4.001) carbendazim, (4.002) diethofencarb, (4.003) ethaboxam, (4.004) fluopicolide, (4.005) pencycuron, (4.006) thiabendazole, (4.007) thiophanate-methyl, (4.008) zoxamide, (4.009) 3-chloro-4-(2,6-difluorophenyl)-6-methyl-5-phenylpyridazine, (4.010) 3-chloro-5-(4-chlorophenyl)-4-(2,6-difluorophenyl)-6-methylpyridazine, (4.011) 3-chloro-5-(6-chloropyridin-3-yl)-6-methyl-4-(2,4,6-trifluorophenyl) pyridazine, (4.012) 4-(2-bromo-4-fluorophenyl)-N-(2,6-difluorophenyl)-1,3-dimethyl-1H-pyrazol-5-amine, (4.013) 4-(2-bromo-4-fluorophenyl)-N-(2-bromo-6-fluorophenyl)-1,3-dimethyl-1H-pyrazol-5-amine, (4.014) 4-(2-bromo-4-fluorophenyl)-N-(2-bromophenyl)-1,3-dimethyl-1H-pyrazol-5-amine, (4.015) 4-(2-bromo-4-fluoro-phenyl)-N-(2-chloro-6-fluorophenyl)-1,3-dimethyl-1H-pyrazol-5-amine, (4.016) 4-(2-bromo-4-fluoro-phenyl)-N-(2-chlorophenyl)-1,3-dimethyl-1H-pyrazol-5-amine, (4.017) 4-(2-bromo-4-fluorophenyl)-N-(2-fluorophenyl)-1,3-dimethyl-1H-pyrazol-5-amine, (4.018) 4-(2-chloro-4-fluorophenyl)-N-(2,6-difluoro-phenyl)-1,3-dimethyl-1H-pyrazol-5-amine, (4.019) 4-(2-chloro-4-fluorophenyl)-N-(2-chloro-6-fluoro-phenyl)-1,3-dimethyl-1H-pyrazol-5-amine, (4.020) 4-(2-chloro-4-fluorophenyl)-N-(2-chlorophenyl)-1,3-dimethyl-1H-pyrazol-5-amine, (4.021) 4-(2-chloro-4-fluorophenyl)-N-(2-fluorophenyl)-1,3-dimethyl-1H-pyrazol-5-amine, (4.022) 4-(4-chlorophenyl)-5-(2,6-difluorophenyl)-3,6-dimethylpyridazine, (4.023)N-(2-bromo-6-fluorophenyl)-4-(2-chloro-4-fluorophenyl)-1,3-dimethyl-1H-pyrazol-5-amine, (4.024)N-(2-bromophenyl)-4-(2-chloro-4-fluorophenyl)-1,3-dimethyl-1H-pyrazol-5-amine, (4.025)N-(4-chloro-2,6-difluorophenyl)-4-(2-chloro-4-fluorophenyl)-1,3-dimethyl-1H-pyrazol-5-amine.

5) Compounds capable to have a multisite action, for example (5.001) bordeaux mixture, (5.002) captafol, (5.003) captan, (5.004) chlorothalonil, (5.005) copper hydroxide, (5.006) copper naphthenate, (5.007) copper oxide, (5.008) copper oxychloride, (5.009) copper(2+) sulfate, (5.010) dithianon, (5.011) dodine, (5.012) folpet, (5.013) mancozeb, (5.014) maneb, (5.015) metiram, (5.016) metiram zinc, (5.017) oxine-copper, (5.018) propineb, (5.019) sulfur and sulfur preparations including calcium polysulfide, (5.020) thiram, (5.021) zineb, (5.022) ziram, (5.023) 6-ethyl-5,7-dioxo-6,7-dihydro-5H-pyrrolo[3',4':5,6][1,4]dithiino[2,3-c][1,2]thiazole-3-carbonitrile.

6) Compounds capable to induce a host defence, for example (6.001) acibenzolar-S-methyl, (6.002) isotianil, (6.003) probenazole, (6.004) tiadinil.

7) Inhibitors of the amino acid and/or protein biosynthesis, for example (7.001) cyprodinil, (7.002) kasugamycin, (7.003) kasugamycin hydrochloride hydrate, (7.004) oxytetracycline, (7.005) pyrimethanil, (7.006) 3-(5-fluoro-3,3,4,4-tetramethyl-3,4-dihydroisoquinolin-1-yl)quinoline.

8) Inhibitors of the ATP production, for example (8.001) silthiofam.

9) Inhibitors of the cell wall synthesis, for example (9.001) benthiavalicarb, (9.002) dimethomorph, (9.003) flumorph, (9.004) iprovalicarb, (9.005) mandipropamid, (9.006) pyrimorph, (9.007) valifenalate, (9.008) (2E)-3-(4-tert-butylphenyl)-3-(2-chloropyridin-4-yl)-1-(morpholin-4-yl)prop-2-en-1-one, (9.009) (2Z)-3-(4-tert-butylphenyl)-3-(2-chloropyridin-4-yl)-1-(morpholin-4-yl)prop-2-en-1-one.

10) Inhibitors of the lipid and membrane synthesis, for example (10.001) propamocarb, (10.002) propamocarb hydrochloride, (10.003) tolclofos-methyl.

11) Inhibitors of the melanin biosynthesis, for example (11.001) tricyclazole, (11.002) 2,2,2-trifluoroethyl {3-methyl-1-[(4-methylbenzoyl)amino]butan-2-yl}carbamate.

12) Inhibitors of the nucleic acid synthesis, for example (12.001) benalaxyl, (12.002) benalaxyl-M (kiralaxyl), (12.003) metalaxyl, (12.004) metalaxyl-M (mefenoxam).

13) Inhibitors of the signal transduction, for example (13.001) fludioxonil, (13.002) iprodione, (13.003) procymidone, (13.004) proquinazid, (13.005) quinoxyfen, (13.006) vinclozolin.

14) Compounds capable to act as an uncoupler, for example (14.001) fluazinam, (14.002) meptyldinocap.

15) Further compounds, for example (15.001) Abscisic acid, (15.002) benthiazole, (15.003) bethoxazin, (15.004) capsimycin, (15.005) carvone, (15.006) chinomethionat, (15.007) cufraneb, (15.008) cyflufenamid, (15.009) cymoxanil, (15.010) cyprosulfamide, (15.011) flutianil, (15.012) fosetyl-aluminium, (15.013) fosetyl-calcium, (15.014) fosetyl-sodium, (15.015) methyl isothiocyanate, (15.016) metrafenone, (15.017) mildiomycin, (15.018) natamycin, (15.019) nickel dimethyldithio-carbamate, (15.020) nitrothal-isopropyl, (15.021) oxamocarb, (15.022) oxathiapiprolin, (15.023) oxyfenthiin, (15.024) pentachlorophenol and salts, (15.025) phosphorous acid and its salts, (15.026) propamocarb-fosetylate, (15.027) pyriofenone (chlazafenone), (15.028) tebufloquin, (15.029) tecloftalam, (15.030) tolnifanide, (15.031) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.032) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.033) 2-(6-benzylpyridin-2-yl)quinazoline, (15.034) dipymetitrone, (15.035) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.036) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.037) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.038) 2-[6-(3-fluoro-4-methoxyphenyl)-5-methylpyridin-2-yl]quinazoline, (15.039) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.040) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.041) Ipflufenoquin, (15.042) 2-{2-fluoro-6-[(8-fluoro-2-methylquinolin-3-yl)oxy]phenyl}propan-2-ol, (15.043) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.044) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.045) 2-phenylphenol and salts, (15.046) 3-(4,4,5-trifluoro-3,3-dimethyl-3,4-dihydroisoquinolin-1-yl)quinoline, (15.047) quinofumelin, (15.048) 4-amino-5-fluoropyrimidin-2-ol (tautomeric form: 4-amino-5-fluoropyrimidin-2(1H)-one), (15.049) 4-oxo-4-[(2-phenylethyl)amino]butanoic acid, (15.050) 5-amino-1,3,4-thiadiazole-2-thiol, (15.051) 5-chloro-N'-phenyl-N'-(prop-2-yn-1-yl)thiophene-2-sulfonohydrazide, (15.052) 5-fluoro-2-[(4-fluoro-benzyl)oxy]pyrimidin-4-amine, (15.053) 5-fluoro-2-[(4-methylbenzyl)oxy]pyrimidin-4-amine, (15.054) 9-fluoro-2,2-dimethyl-5-(quinolin-3-yl)-2,3-dihydro-1,4-benzoxazepine, (15.055) but-3-yn-1-yl {6-[({[(Z)-(1-methyl-1H-tetrazol-5-yl)(phenyl)methylene]amino}oxy)methyl]pyridin-2-yl}carbamate, (15.056) ethyl (2Z)-3-amino-2-cyano-3-phenylacrylate, (15.057) phenazine-1-carboxylic acid, (15.058) propyl 3,4,5-trihydroxybenzoate, (15.059) quinolin-8-ol, (15.060) quinolin-8-ol sulfate (2:1), (15.061) tert-butyl {6-[({[(1-methyl-1H-tetrazol-5-yl)(phenyl)methylene]amino}oxy)methyl]pyridin-2-yl}carbamate, (15.062) 5-fluoro-4-imino-3-methyl-1-[(4-methylphenyl)sulfonyl]-3,4-dihydropyrimidin-2(1H)-one, (15.063) amino-pyrifen.

All named mixing partners of the classes (1) to (15) as described here above can be present in the form of the free compound and/or, if their functional groups enable this, an agriculturally acceptable salt thereof.

The compound of formula (I) and the composition may also be combined with one or more biological control agents.

Examples of biological control agents which may be combined with the compound of formula (I) and composition comprising thereof are:

(A) Antibacterial agents selected from the group of:

(A1) bacteria, such as (A1.1) *Bacillus subtilis*, in particular strain QST713/AQ713 (available as SERENADE OPTI or SERENADE ASO from Bayer CropScience LP, US, having NRRL Accession No. B21661 and described in U.S. Pat. No. 6,060,051); (A1.2) *Bacillus amyloliquefaciens*, in particular strain D747 (available as Double Nickel™ from Certis, US, having accession number FERM BP-8234 and disclosed in U.S. Pat. No. 7,094,592); (A1.3) *Bacillus pumilus*, in particular strain BU F-33 (having NRRL Accession No. 50185); (A1.4) *Bacillus subtilis* var. *amyloliquefaciens* strain FZB24 (available as Taegro® from Novozymes, US); (A1.5) a *Paenibacillus* sp. strain having Accession No. NRRL B-50972 or Accession No. NRRL B-67129 and described in International Patent Publication No. WO 2016/154297; and (A2) fungi, such as (A2.1) *Aureobasidium pullulans*, in particular blastospores of strain DSM14940; (A2.2) *Aureobasidium pullulans* blastospores of strain DSM 14941; (A2.3) *Aureobasidium pullulans*, in particular mixtures of blastospores of strains DSM14940 and DSM14941;

(B) Fungicides selected from the group of:

(B1) bacteria, for example (B1.1) *Bacillus subtilis*, in particular strain QST713/AQ713 (available as SERENADE OPTI or SERENADE ASO from Bayer CropScience LP, US, having NRRL Accession No. B21661 and described in U.S. Pat. No. 6,060,051); (B1.2) *Bacillus pumilus*, in particular strain QST2808 (available as SONATA® from Bayer CropScience LP, US, having Accession No. NRRL B-30087 and described in U.S. Pat. No. 6,245,551); (B1.3) *Bacillus pumilus*, in particular strain GB34 (available as Yield Shield® from Bayer AG, DE); (B11.4) *Bacillus pumilus*, in particular strain BU F-33 (having NRRL Accession No. 50185); (B11.5) *Bacillus amyloliquefaciens*, in particular strain D747 (available as Double Nickel™ from Certis, US, having accession number FERM BP-8234 and disclosed in U.S. Pat. No. 7,094,592); (B11.6) *Bacillus subtilis* Y1336 (available as BIOBAC® WP from Bion-Tech, Taiwan, registered as a biological fungicide in Taiwan under Registration Nos. 4764, 5454, 5096 and 5277); (B11.7) *Bacillus amyloliquefaciens* strain MBI 600 (available as SUBTILEX from BASF SE); (B11.8) *Bacillus subtilis* strain GB03 (available as Kodiak® from Bayer AG, DE); (B11.9) *Bacillus subtilis* var. *amyloliquefaciens* strain FZB24 (available from Novozymes Biologicals Inc., Salem, Virginia or Syngenta Crop Protection, LLC, Greensboro, North Carolina as the fungicide TAEGRO® or TAEGRO® ECO (EPA Registration No. 70127-5); (B1.10) *Bacillus mycoides*, isolate J (available as BmJ TGAI or WG from Certis USA); (B11.11) *Bacillus licheniformis*, in particular strain SB3086 (available as EcoGuard™ Biofungicide and Green Releaf from Novozymes); (B1.12) a *Paenibacillus* sp. strain having Accession No. NRRL B-50972 or Accession No. NRRL B-67129 and described in International Patent Publication No. WO 2016/154297.

In some embodiments, the biological control agent is a *Bacillus subtilis* or *Bacillus amyloliquefaciens* strain that produces a fengycin or plipastatin-type compound, an iturin-type compound, and/or a surfactin-type compound. For background, see the following review article: Ongena, M., et al., "*Bacillus* Lipopeptides: Versatile Weapons for Plant Disease Biocontrol," Trends in Microbiology, Vol 16, No. 3, March 2008, pp. 115-125. *Bacillus* strains capable of producing lipopeptides include *Bacillus subtilis* QST713 (available as SERENADE OPTI or SERENADE ASO from Bayer CropScience LP, US, having NRRL Accession No. B21661 and described in U.S. Pat. No. 6,060,051), *Bacillus amyloliquefaciens* strain D747 (available as Double Nickel™ from Certis, US, having accession number FERM BP-8234 and disclosed in U.S. Pat. No. 7,094,592); *Bacillus subtilis* MB1600 (available as SUBTILEX® from Becker Underwood, US EPA Reg. No. 71840-8); *Bacillus subtilis* Y1336 (available as BIOBAC® WP from Bion-Tech, Taiwan, registered as a biological fungicide in Taiwan under Registration Nos. 4764, 5454, 5096 and 5277); *Bacillus amyloliquefaciens*, in particular strain FZB42 (available as RHIZOVITAL® from ABiTEP, DE); and *Bacillus subtilis* var. *amyloliquefaciens* FZB24 (available from Novozymes Biologicals Inc., Salem, Virginia or Syngenta Crop Protection, LLC, Greensboro, North Carolina as the fungicide TAEGRO® or TAEGRO® ECO (EPA Registration No. 70127-5); and (B2) fungi, for example: (B2.1) *Coniothyrium minitans*, in particular strain CON/M/91-8 (Accession No. DSM-9660; e.g. Contans® from Bayer); (B2.2) *Metschnikowia fructicola*, in particular strain NRRL Y-30752 (e.g. Shemer®); (B2.3) *Microsphaeropsis ochracea* (e.g. Microx® from Prophyta); (B2.5) *Trichoderma* spp., including *Trichoderma atroviride*, strain SC1 described in International Application No. PCT/IT2008/000196); (B2.6) *Trichoderma harzianum* rifai strain KRL-AG2 (also known as strain T-22, /ATCC 208479, e.g. PLANTSHIELD T-22G, Rootshield®, and TurfShield from BioWorks, US); (B2.14) *Gliocladium roseum*, strain 321U from W.F. Stoneman Company LLC; (B2.35) *Talaromyces flavus*, strain V117b; (B2.36) *Trichoderma* asperellum, strain ICC 012 from Isagro; (B2.37) *Trichoderma* asperellum, strain SKT-1 (e.g. ECO-HOPE® from Kumiai Chemical Industry); (B2.38) *Trichoderma atroviride*, strain CNCM I-1237 (e.g. Esquive® WP from Agrauxine, FR); (B2.39) *Trichoderma atroviride*, strain no. V08/002387; (B2.40) *Trichoderma atroviride*, strain NMI no. V08/002388; (B2.41) *Trichoderma atroviride*, strain NMI no. V08/002389; (B2.42) *Trichoderma atroviride*, strain NMI no. V08/002390; (B2.43) *Trichoderma atroviride*, strain LC52 (e.g. Tenet by Agrimm Technologies Limited); (B2.44) *Trichoderma atroviride*, strain ATCC 20476 (IMI 206040); (B2.45) *Trichoderma atroviride*, strain T11 (IM1352941/CECT20498); (B2.46) *Trichoderma harmatum*; (B2.47) *Trichoderma harzianum*; (B2.48) *Trichoderma harzianum* rifai T39 (e.g. Trichodex® from Makhteshim, US); (B2.49) *Trichoderma harzianum*, in particular, strain KD (e.g. Trichoplus from Biological Control Products, SA (acquired by Becker Underwood)); (B2.50) *Trichoderma harzianum*, strain ITEM 908 (e.g. Trianum-P from Koppert); (B2.51) *Trichoderma harzianum*, strain TH35 (e.g. Root-Pro by Mycontrol); (B2.52) *Trichoderma virens* (also known as *Gliocladium virens*), in particular strain GL-21 (e.g. SoilGard 12G by Certis, US); (B2.53) *Trichoderma viride*, strain TV1 (e.g. Trianum-P by Koppert); (B2.54) *Ampelomyces quisqualis*, in particular strain AQ 10 (e.g. AQ 10® by IntrachemBio Italia); (B2.56) *Aureobasidium pullulans*, in particular blastospores of strain DSM14940; (B2.57) *Aureobasidium pullulans*, in particular blastospores of strain DSM 14941; (B2.58) *Aureobasidium pullulans*, in particular mixtures of blastospores of strains DSM14940 and DSM 14941 (e.g. Botector® by bio-ferm, CH); (B2.64) *Cladosporium cladosporioides*, strain H39 (by Stichting Dienst Landbouwkundig Onderzoek); (B2.69) *Gliocladium catenulatum* (Synonym: *Clonostachys rosea* f. *catenulate*) strain J1446 (e.g. Prestop® by AgBio Inc. and also e.g. Primastop® by Kemira Agro Oy); (B2.70) *Lecanicillium lecanii* (formerly known as *Verticillium lecanii*) conidia of strain KV01 (e.g. Vertalec® by Koppert/Arysta); (B2.71) *Penicillium vermiculatum*; (B2.72) *Pichia anomala*, strain WRL-076 (NRRL Y-30842); (B2.75) *Trichoderma atroviride*, strain SKT-1 (FERM P-16510); (B2.76) *Trichoderma atroviride*, strain SKT-2 (FERM P-16511); (B2.77) *Trichoderma atroviride*, strain SKT-3 (FERM P-17021); (B2.78) *Trichoderma gamsii* (formerly *T. viride*), strain ICC080 (IMI CC 392151 CABI, e.g. BioDerma by AGROBIOSOL DE MEXICO, S.A. DE C.V.); (B2.79) *Trichoderma harzianum*, strain DB 103 (e.g., T-Gro 7456 by Dagutat Biolab); (B2.80) *Trichoderma polysporum*, strain IMI 206039 (e.g. Binab TF WP by BINAB Bio-Innovation AB, Sweden); (B2.81) *Trichoderma stromaticum* (e.g. Tricovab by Ceplac, Brazil); (B2.83) *Ulocladium oudemansii*, in particular strain HRU3 (e.g. Botry-Zen® by Botry-Zen Ltd, NZ); (B2.84) *Verticillium albo-atrum* (formerly *V. dahliae*), strain WCS850 (CBS 276.92; e.g. Dutch Trig by Tree Care Innovations); (B2.86) *Verticillium chlamydosporium*; (B2.87) mixtures of *Trichoderma* asperellum strain ICC 012 and *Trichoderma gamsii* strain ICC 080 (product known as e.g. BIO-TAM™ from Bayer CropScience LP, US).

Further examples of biological control agents which may be combined with the compound of formula (I) and composition comprising thereof are:

bacteria selected from the group consisting of *Bacillus cereus*, in particular *B. cereus* strain CNCM I-1562 and *Bacillus firmus*, strain I-1582 (Accession number CNCM I-1582), *Bacillus subtilis* strain OST 30002 (Accession No. NRRL B-50421), *Bacillus thuringiensis*, in particular *B. thuringiensis* subspecies *israelensis* (serotype H-14), strain AM65-52 (Accession No. ATCC 1276), *B. thuringiensis* subsp. *aizawai*, in particular strain ABTS-1857 (SD-1372), *B. thuringiensis* subsp. kurstaki strain HD-1, *B. thuringiensis* subsp. *tenebrionis* strain NB 176 (SD-5428), *Pasteuria penetrans, Pasteuria* spp. (*Rotylenchulus reniformis* nematode)-PR3 (Accession Number ATCC SD-5834), *Streptomyces microflavus* strain AQ6121 (=QRD 31.013, NRRL B-50550), and *Streptomyces galbus* strain AQ 6047 (Acession Number NRRL 30232);

fungi and yeasts selected from the group consisting of *Beauveria bassiana*, in particular strain ATCC 74040, *Lecanicillium* spp., in particular strain HRO LEC 12, *Metarhizium anisopliae*, in particular strain F52 (DSM3884 or ATCC 90448), *Paecilomyces fumosoroseus* (now: *Isaria fumosorosea*), in particular strain IFPC 200613, or strain Apopka 97 (Accession No. ATCC 20874), and *Paecilomyces lilacinus*, in particular *P. lilacinus* strain 251 (AGAL 89/030550);

viruses selected from the group consisting of *Adoxophyes orana* (summer fruit tortrix) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, and *Spodoptera littoralis* (African cotton leafworm) NPV.

bacteria and fungi which can be added as 'inoculant' to plants or plant parts or plant organs and which, by virtue of their particular properties, promote plant growth and plant health. Examples are: *Agrobacterium* spp., *Azorhizobium caulinodans, Azospirillum* spp., *Azotobacter* spp., *Bradyrhizobium* spp., *Burkholderia* spp., in particular *Burkholderia cepacia* (formerly known as *Pseudomonas cepacia*), *Gigaspora* spp., or *Gigaspora monosporum, Glomus* spp., *Laccaria* spp., *Lactobacillus buchneri, Paraglomus* spp., *Pisolithus tinctorus, Pseudomonas* spp., *Rhizobium* spp., in particular *Rhizobium trifolii, Rhizopogon* spp., *Scleroderma* spp., *Suillus* spp., and *Streptomyces* spp.

plant extracts and products formed by microorganisms including proteins and secondary metabolites which can be used as biological control agents, such as *Allium sativum, Artemisia absinthium*, azadirachtin, Biokeeper WP, *Cassia nigricans, Celastrus angulatus, Chenopodium anthelminticum*, chitin, Armour-Zen, *Dryopteris filix-mas, Equisetum arvense*, Fortune Aza, Fungastop, Heads Up (*Chenopodium quinoa* saponin extract), *Pyrethrum/Pyrethrins, Quassia amara, Quercus, Quillaja*, Regalia, "Requiem™ Insecticide", rotenone, ryania/ryanodine, *Symphytum officinale, Tanacetum vulgare*, thymol, Triact 70, TriCon, *Tropaeulum majus, Urtica dioica*, Veratrin, *Viscum album*, Brassicaceae extract, in particular oilseed rape powder or mustard powder.

Examples of insecticides, acaricides and nematicides, respectively, which could be mixed with the compound of formula (I) and composition comprising thereof are:

(1) Acetylcholinesterase (AChE) inhibitors, such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel blockers, such as, for example, cyclodiene-organochlorines, for example chlordane and endosulfan or phenylpyrazoles (fiproles), for example ethiprole and fipronil.

(3) Sodium channel modulators, such as, for example, pyrethroids, e.g. acrinathrin, allethrin, d-cis-trans allethrin, d-trans allethrin, bifenthrin, bioallethrin, bioallethrin s-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomer], deltamethrin, empenthrin [(EZ)-(1R)-isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans-isomer], prallethrin, pyrethrins (pyrethrum), resmethrin, silafluofen, tefluthrin, tetramethrin, tetramethrin [(1R)-isomer)], tralomethrin and transfluthrin or DDT or methoxychlor.

(4) Nicotinic acetylcholine receptor (nAChR) competitive modulators, such as, for example, neonicotinoids, e.g. acetamiprid, clothianidin, dinotefuran, imidacloprid, nitenpyram, thiacloprid and thiamethoxam or nicotine or sulfoxaflor or flupyradifurone.

(5) Nicotinic acetylcholine receptor (nAChR) allosteric modulators, such as, for example, spinosyns, e.g. spinetoram and spinosad.

(6) Glutamate-gated chloride channel (GluCl) allosteric modulators, such as, for example, avermectins/milbemycins, for example abamectin, emamectin benzoate, lepimectin and milbemectin.

(7) Juvenile hormone mimics, such as, for example, juvenile hormone analogues, e.g. hydroprene, kinoprene and methoprene or fenoxycarb or pyriproxyfen.

(8) Miscellaneous non-specific (multi-site) inhibitors, such as, for example, alkyl halides, e.g. methyl bromide and other alkyl halides; or chloropicrine or sulphuryl fluoride or borax or tartar emetic or methyl isocyanate generators, e.g. diazomet and metam.

(9) Modulators of Chordotonal Organs, such as, for example pymetrozine or flonicamid.

(10) Mite growth inhibitors, such as, for example clofentezine, hexythiazox and diflovidazin or etoxazole.

(11) Microbial disruptors of the insect gut membrane, such as, for example *Bacillus thuringiensis* subspecies *israelensis, Bacillus sphaericus, Bacillus thuringiensis* subspecies *aizawai, Bacillus thuringiensis* subspecies kurstaki, *Bacillus thuringiensis* subspecies *tenebrionis*, and B.t. plant proteins: Cry1Ab, Cry1Ac, Cry1Fa, Cry1A.105, Cry2Ab, Vip3A, mCry3A, Cry3Ab, Cry3Bb, Cry34Ab1/35Ab1.

(12) Inhibitors of mitochondrial ATP synthase, such as, ATP disruptors such as, for example, diafenthiuron or organotin compounds, for example azocyclotin, cyhexatin and fenbutatin oxide or propargite or tetradifon.

(13) Uncouplers of oxidative phosphorylation via disruption of the proton gradient, such as, for example, chlorfenapyr, DNOC and sulfluramid.

(14) Nicotinic acetylcholine receptor channel blockers, such as, for example, bensultap, cartap hydrochloride, thiocylam, and thiosultap-sodium.

(15) Inhibitors of chitin biosynthesis, type 0, such as, for example, bistrifluron, chlorfluazuron, diflubenzuron, flucycloxuron, flufenoxuron, hexaflumuron, lufenuron, novaluron, noviflumuron, teflubenzuron and triflumuron.

(16) Inhibitors of chitin biosynthesis, type 1, for example buprofezin.

(17) Moulting disruptor (in particular for Diptera, i.e. dipterans), such as, for example, cyromazine.

(18) Ecdysone receptor agonists, such as, for example, chromafenozide, halofenozide, methoxyfenozide and tebufenozide.

(19) Octopamine receptor agonists, such as, for example, amitraz.

(20) Mitochondrial complex III electron transport inhibitors, such as, for example, hydramethylnone or acequinocyl or fluacrypyrim.

(21) Mitochondrial complex I electron transport inhibitors, such as, for example from the group of the METI acaricides, e.g. fenazaquin, fenpyroximate, pyrimidifen, pyridaben, tebufenpyrad and tolfenpyrad or rotenone (Derris).

(22) Voltage-dependent sodium channel blockers, such as, for example indoxacarb or metaflumizone.

(23) Inhibitors of acetyl CoA carboxylase, such as, for example, tetronic and tetramic acid derivatives, e.g. spirodiclofen, spiromesifen and spirotetramat.

(24) Mitochondrial complex IV electron transport inhibitors, such as, for example, phosphines, e.g. aluminium phosphide, calcium phosphide, phosphine and zinc phosphide or cyanides, e.g. calcium cyanide, potassium cyanide and sodium cyanide.

(25) Mitochondrial complex II electron transport inhibitors, such as, for example, beta-ketonitrile derivatives, e.g. cyenopyrafen and cyflumetofen and carboxanilides, such as, for example, pyflubumide.

(28) Ryanodine receptor modulators, such as, for example, diamides, e.g. chlorantraniliprole, cyantraniliprole and flubendiamide, further active compounds such as, for example, Afidopyropen, Afoxolaner, Azadirachtin, Benclothiaz, Benzoximate, Bifenazate, Broflanilide, Bromopropylate, Chinomethionat, Chloroprallethrin, Cryolite, Cyclaniliprole, Cycloxaprid, Cyhalodiamide, Dicloromezotiaz, Dicofol, epsilon-Metofluthrin, epsilon-Momfluthrin, Flometoquin, Fluazaindolizine, Fluensulfone, Flufenerim, Flufenoxystrobin, Flufiprole, Fluhexafon, Fluopyram, Fluralaner, Fluxametamide, Fufenozide, Guadipyr, Heptafluthrin, Imidaclothiz, Iprodione, kappa-Bifenthrin, kappa-Tefluthrin, Lotilaner, Meperfluthrin, Paichongding, Pyridalyl, Pyrifluquinazon, Pyriminostrobin, Spirobudiclofen, Tetramethylfluthrin, Tetraniliprole, Tetrachlorantraniliprole, Tigolaner, Tioxazafen, Thiofluoximate, Triflumezopyrim and iodomethane; furthermore preparations based on *Bacillus firmus* (1-1582, BioNeem, Votivo), and also the following compounds: 1-{2-fluoro-4-methyl-5-[(2,2,2-trifluoroethyl)sulphinyl]phenyl}-3-(trifluoromethyl)-1H-1,2,4-triazole-5-amine (known from WO2006/043635) (CAS 885026-50-6), {1'-[(2E)-3-(4-chlorophenyl)prop-2-en-1-yl]-5-fluorospiro[indol-3,4'-piperidin]-1(2H)-yl}(2-chloropyridin-4-yl)methanone (known from WO2003/106457) (CAS 637360-23-7), 2-chloro-N-[2-{1-[(2E)-3-(4-chlorophenyl)prop-2-en-1-yl]piperidin-4-yl}-4-(trifluoromethyl)phenyl]isonicotinamide (known from WO2006/003494) (CAS 872999-66-1), 3-(4-chloro-2, 6-dimethylphenyl)-4-hydroxy-8-methoxy-1,8-diazaspiro[4.5]dec-3-en-2-one (known from WO 2010052161) (CAS 1225292-17-0), 3-(4-chloro-2,6-dimethylphenyl)-8-methoxy-2-oxo-1,8-diazaspiro[4.5]dec-3-en-4-yl ethyl carbonate (known from EP2647626) (CAS 1440516-42-6), 4-(but-2-yn-1-yloxy)-6-(3,5-dimethylpiperidin-1-yl)-5-fluoropyrimidine (known from WO2004/099160) (CAS 792914-58-0), PF1364 (known from JP2010/018586) (CAS 1204776-60-2), N-[(2E)-1-[(6-chloropyridin-3-yl)methyl]pyridin-2(1H)-ylidene]-2,2,2-trifluoroacetamide (known from WO2012/029672) (CAS 1363400-41-2), (3E)-3-[1-[(6-chloro-3-pyridyl)methyl]-2-pyridylidene]-1,1,1-trifluoro-propan-2-one (known from WO2013/144213) (CAS 1461743-15-6), N-[3-(benzylcarbamoyl)-4-chlorophenyl]-1-methyl-3-(pentafluoroethyl)-4-(trifluoromethyl)-1H-pyrazole-5-carboxamide (known from WO2010/051926) (CAS 1226889-14-0), 5-bromo-4-chloro-N-[4-chloro-2-methyl-6-(methylcarbamoyl)phenyl]-2-(3-chloro-2-pyridyl)pyrazole-3-carboxamide (known from CN103232431) (CAS 1449220-44-3), 4-[5-(3,5-dichlorophenyl)-4,5-dihydro-5-(trifluoromethyl)-3-isoxazolyl]-2-methyl-N-(cis-1-oxido-3-thietanyl)-benzamide, 4-[5-(3,5-dichlorophenyl)-4,5-dihydro-5-(trifluoromethyl)-3-isoxazolyl]-2-methyl-N-(trans-1-oxido-3-thietanyl)-benzamide and 4-[(5S)-5-(3,5-dichlorophenyl)-4,5-dihydro-5-(trifluoromethyl)-3-isoxazolyl]-2-methyl-N-(cis-1-oxido-3-thietanyl) benzamide (known from WO 2013/050317 A1) (CAS 1332628-83-7), N-[3-chloro-1-(3-pyridinyl)-1H-pyrazol-4-yl]-N-ethyl-3-[(3, 3,3-trifluoropropyl)sulfinyl]-propanamide, (+)-N-[3-chloro-1-(3-pyridinyl)-1H-pyrazol-4-yl]-N-ethyl-3-[(3, 3,3-trifluoropropyl) sulfinyl]-propanamide and (−)-N-[3-chloro-1-(3-pyridinyl)-1H-pyrazol-4-yl]-N-ethyl-3-[(3,3,3-trifluoropropyl)sulfinyl]-propanamide (known from WO 2013/162715 A2, WO 2013/162716 A2, US 2014/0213448 A1) (CAS 1477923-37-7), 5-[[(2E)-3-chloro-2-propen-1-yl]amino]-1-[2,6-dichloro-4-(trifluoromethyl)phenyl]-4-[(trifluoromethyl)sulfinyl]-1H-pyrazole-3-carbonitrile (known from CN 101337937 A) (CAS 1105672-77-2), 3-bromo-N-[4-chloro-2-methyl-6-[(methylamino)thioxomethyl]phenyl]-1-(3-chloro-2-pyridinyl)-1H-pyrazole-5-carboxamide, (Liudaibenjiaxuanan, known from CN 103109816 A) (CAS 1232543-85-9); N-[4-chloro-2-[[(1,1-dimethylethyl) amino]carbonyl]-6-methylphenyl]-1-(3-chloro-2-pyridinyl)-3-(fluoromethoxy)-1H-Pyrazole-5-carboxamide (known from WO 2012/034403 A1) (CAS 1268277-22-0), N-[2-(5-amino-1,3,4-thiadiazol-2-yl)-4-chloro-6-methylphenyl]-3-bromo-1-(3-chloro-2-pyridinyl)-1H-pyrazole-5-carboxamide (known from WO 2011/085575 A1) (CAS 1233882-22-8), 4-[3-[2,6-dichloro-4-[(3,3-dichloro-2-propen-1-yl)oxy]phenoxy]propoxy]-2-methoxy-6-(trifluoromethyl)-pyrimidine (known from CN 101337940 A) (CAS 1108184-52-6); (2E)- and 2(Z)-2-[2-(4-cyanophenyl)-1-[3-(trifluoromethyl)phenyl]ethylidene]-N-[4-(difluoromethoxy)phenyl]-hydrazinecarboxamide (known from CN 101715774 A) (CAS 1232543-85-9); 3-(2,2-dichloroethenyl)-2,2-dimethyl-4-(1H-benzimidazol-2-yl)phenyl-cyclopropanecarboxylic acid ester (known from CN 103524422 A) (CAS 1542271-46-4); (4aS)-7-chloro-2,5-dihydro-2-[[(methoxycarbonyl)[4-[(trifluoromethyl)thio]phenyl]amino]carbonyl]-indeno[1,2-e][1,3,4]oxadiazine-4a(3H)-carboxylic acid methyl ester (known from CN 102391261 A) (CAS 1370358-69-2); 6-deoxy-3-O-ethyl-2,4-di-O-methyl-, 1-[N-[4-[1-[4-(1,1,2,2,2-pentafluoroethoxy)phenyl]-1H-1,2,4-triazol-3-yl]phenyl]carbamate]-α-L-mannopyranose (known from US 2014/0275503 A1) (CAS 1181213-14-8); 8-(2-cyclopropylmethoxy-4-trifluoromethyl-phenoxy)-3-(6-trifluoromethyl-pyridazin-3-yl)-3-aza-bicyclo[3.2.1]octane (CAS 1253850-56-4), (8-anti)-8-(2-cyclopropylmethoxy-4-trifluoromethyl-phenoxy)-3-(6-trifluoromethyl-pyridazin-3-yl)-3-aza-bicyclo[3.2.1]octane (CAS 933798-27-7), (8-syn)-8-(2-cyclopropylmethoxy-4-trifluoromethyl-phenoxy)-3-(6-trifluoromethyl-pyridazin-3-yl)-3-aza-bicyclo[3.2.1]octane (known from WO 2007040280 A1, WO 2007040282 A1) (CAS 934001-66-8), N-[3-chloro-1-(3-pyridinyl)-1H-pyrazol-4-yl]-N-ethyl-3-[(3,3,3-trifluoropropyl)thio]-propanamide (known from WO 2015/058021 A1, WO 2015/058028 A1) (CAS 1477919-27-9) and N-[4-(aminothioxomethyl)-2-methyl-6-[(methylamino)carbonyl]phenyl]-3-bromo-1-(3-chloro-2-pyridinyl)-1H-pyrazole-5-carboxamide (known from CN 103265527 A) (CAS 1452877-50-7), 5-(1,3-dioxan-2-yl)-4-[[4-(trifluoromethyl)phenyl]methoxy]-pyrimidine (known from WO 2013/115391 A1) (CAS 1449021-97-9), 3-(4-chloro-2,6-dimethylphenyl)-4-hydroxy-8-methoxy-1-methyl-1,8-diazaspiro[4.5]dec-3-en-2-one (known from WO 2010/066780 A1, WO 2011/151146 A1) (CAS 1229023-34-0), 3-(4-chloro-2,6-dimethylphenyl)-8-methoxy-1-methyl-1,8-diazaspiro[4.5]decane-2,4-dione (known from WO 2014/187846 A1) (CAS 1638765-58-8), 3-(4-chloro-2,6-dimethylphenyl)-8-methoxy-1-methyl-2-oxo-1, 8-diazaspiro[4.5]dec-3-en-4-yl-carbonic acid ethyl ester (known from WO 2010/066780 A1, WO 2011151146 A1) (CAS 1229023-00-0), N-[1-[(6-chloro-3-pyridinyl)methyl]-2(1H)-pyridinylidene]-2,2,2-trifluoro-acetamide (known from DE 3639877 A1, WO 2012029672 A1) (CAS 1363400-41-2), [N(E)]-N-[1-[(6-chloro-3-pyridinyl)methyl]-2(1H)-pyridinylidene]-2,2,2-trifluoro-acetamide, (known from WO 2016005276 A1) (CAS 1689566-03-7), [N(Z)]-N-[1-[(6-chloro-3-pyridinyl)methyl]-2(1H)-pyridinylidene]-2,2,2-trifluoro-acetamide, (CAS 1702305-40-5), 3-endo-3-[2-propoxy-4-(trifluoromethyl)phenoxy]-9-[[5-(trifluoromethyl)-2-pyridinyl]oxy]-9-azabicyclo[3.3.1]nonane (known from WO 2011/105506 A1, WO 2016/133011 A1) (CAS 1332838-17-1).

Examples of safeners which could be mixed with the compound of formula (I) and composition comprising thereof are, for example, benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}-sulphonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Examples of herbicides which could be mixed with the compound of formula (I) and composition comprising thereof are:

Acetochlor, acifluorfen, acifluorfen-sodium, aclonifen, alachlor, allidochlor, alloxydim, alloxydim-sodium, ametryn, amicarbazone, amidochlor, amidosulfuron, 4-amino-3-chloro-6-(4-chloro-2-fluoro-3-methylphenyl)-5-fluoropyridine-2-carboxylic acid, aminocyclopyrachlor, aminocyclopyrachlor-potassium, aminocyclopyrachlor-methyl, aminopyralid, amitrole, ammoniumsulfamate, anilofos, asulam, atrazine, azafenidin, azimsulfuron, beflubutamid, benazolin, benazolin-ethyl, benfluralin, benfuresate, bensulfuron, bensulfuron-methyl, bensulide, bentazone, benzobicyclon, benzofenap, bicyclopyron, bifenox, bilanafos, bilanafos-sodium, bispyribac, bispyribac-sodium, bromacil, bromobutide, bromofenoxim, bromoxynil, bromoxynil-butyrate, -potassium, -heptanoate, and -octanoate, busoxinone, butachlor, butafenacil, butamifos, butenachlor, butralin, butroxydim, butylate, cafenstrole, carbetamide, carfentrazone, carfentrazone-ethyl, chloramben, chlorbromuron, chlorfenac, chlorfenac-sodium, chlorfenprop, chlorflurenol, chlorflurenol-methyl, chloridazon, chlorimuron, chlorimuron-ethyl, chlorophthalim, chlorotoluron, chlorthal-dimethyl, chlorsulfuron, cinidon, cinidon-ethyl, cinmethylin, cinosulfuron, clacyfos, clethodim, clodinafop, clodinafop-propargyl, clomazone, clomeprop, clopyralid, cloransulam, cloransulam-methyl, cumyluron, cyanamide, cyanazine, cycloate, cyclopyrimorate, cyclosulfamuron, cycloxydim, cyhalofop, cyhalofop-butyl, cyprazine, 2,4-D, 2,4-D-butotyl, -butyl, -dimethylammonium, -diolamin, -ethyl, -2-ethylhexyl, -isobutyl, -isooctyl, -isopropylammonium, -potassium, -triisopropanolammonium, and -trolamine, 2,4-DB, 2,4-DB-butyl, -dimethylammonium, -isooctyl, -potassium, and -sodium, daimuron (dymron), dalapon, dazomet, n-decanol, desmedipham, detosyl-pyrazolate (DTP), dicamba, dichlobenil, 2-(2,4-dichlorobenzyl)-4,4-dimethyl-1,2-oxazolidin-3-one, 2-(2,5-dichlorobenzyl)-4,4-dimethyl-1,2-oxazolidin-3-one, dichlorprop, dichlorprop-P, diclofop, diclofop-methyl, diclofop-P-methyl, diclosulam, difenzoquat, diflufenican, diflufenzopyr, diflufenzopyr-sodium, dimefuron, dimepiperate, dimethachlor, dimethametryn, dimethenamid, dimethenamid-P, dimetrasulfuron, dinitramine, dinoterb, diphenamid, diquat, diquat-dibromid, dithiopyr, diuron, DNOC, endothal, EPTC, esprocarb, ethalfluralin, ethametsulfuron, etha-metsulfuron-methyl, ethiozin, ethofumesate, ethoxyfen, ethoxyfen-ethyl, ethoxysulfuron, etobenzanid, F-9600, F-5231, i.e. N-{2-chloro-4-fluoro-5-[4-(3-fluoropropyl)-5-oxo-4,5-dihydro-1H-tetrazol-1-yl]phenyl}ethanesulfonamide, F-7967, i. e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoxaprop, fenoxaprop-P, fenoxaprop-ethyl, fenoxaprop-P-ethyl, fenoxasulfone, fenquinotrione, fentrazamide, flamprop, flamprop-M-isopropyl, flamprop-M-methyl, flazasulfuron, florasulam, fluazifop, fluazifop-P, fluazifop-butyl, fluazifop-P-butyl, flucarbazone, flucarbazone-sodium, flucetosulfuron, fluchloralin, flufenacet, flufenpyr, flufenpyr-ethyl, flumetsulam, flumiclorac, flumiclorac-pentyl, flumioxazin, fluometuron, flurenol, flurenol-butyl, -dimethylammonium and -methyl, fluoroglycofen, fluoroglycofen-ethyl, flupropanate, flupyrsulfuron, flupyrsulfuron-methyl-sodium, fluridone, flurochloridone, fluroxypyr, fluroxypyr-meptyl, flurtamone, fluthiacet, fluthiacet-methyl, fomesafen, fomesafen-sodium, foramsulfuron, fosamine, glufosinate, glufosinate-ammonium, glufosinate-P-sodium, glufosinate-P-ammonium, glufosinate-P-sodium, glyphosate, glyphosate-ammonium, -isopropylammonium, -diammonium, -dimethylammonium, -potassium, -sodium, and -trimesium, H-9201, i.e. 0-(2,4-dimethyl-6-nitrophenyl) O-ethyl isopropylphosphoramidothioate, halauxifen, halauxifen-methyl, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl) ethyl-(2,4-dichlorophenoxy)acetate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazethapyr, imazethapyr-immonium, imazosulfuron, indanofan, indaziflam, iodosulfuron, iodosulfuron-methyl-sodium, ioxynil, ioxynil-octanoate, -potassium and -sodium, ipfencarbazone, isoproturon, isouron, isoxaben, isoxaflutole, karbutilate, KUH-043, i.e. 3-({[5-(difluoromethyl)-1-methyl-3-(trifluoromethyl)-1H-pyrazol-4-yl] methyl}sulfonyl)-5,5-dimethyl-4,5-dihydro-1,2-oxazole, ketospiradox, lactofen, lenacil, linuron, MCPA, MCPA-butotyl, -dimethylammonium, -2-ethylhexyl, -isopropylammonium, -potassium, and -sodium, MCPB, MCPB-methyl, -ethy,l and -sodium, mecoprop, mecoprop-sodium, and -butotyl, mecoprop-P, mecoprop-P-butotyl, -dimethylammonium, -2-ethylhexyl, and -potassium, mefenacet, mefluidide, mesosulfuron, mesosulfuron-methyl, mesotrione, methabenzthiazuron, metam, metamifop, metamitron, metazachlor, metazosulfuron, methabenzthiazuron, methiopyrsulfuron, methiozolin, methyl isothiocyanate, metobromuron, metolachlor, S-metolachlor, metosulam, metoxuron, metribuzin, metsulfuron, metsulfuron-methyl, molinat, monolinuron, monosulfuron, monosulfuron-ester, MT-5950, i.e. N-(3-chloro-4-isopropylphenyl)-2-methyl-pentan amide, NGGC-011, napropamide, NC-310, i.e. [5-(benzyloxy)-1-methyl-1H-pyrazol-4-yl](2,4-dichlorophenyl)methanone, neburon, nicosulfuron, nonanoic acid (pelargonic acid), norflurazon, oleic acid (fatty acids), orbencarb, orthosulfamuron, oryzalin, oxadiargyl, oxadiazon, oxasulfuron, oxaziclo-mefon, oxyfluorfen, paraquat, paraquat dichloride, pebulate, pendimethalin, penoxsulam, pentachlor-phenol, pentoxazone, pethoxamid, petroleum oils, phenmedipham, picloram, picolinafen, pinoxaden, piperophos, pretilachlor, primisulfuron, primisulfuron-methyl, prodiamine, profoxydim, prometon, prometryn, propachlor, propanil, propaquizafop, propazine, propham, propisochlor, propoxycarbazone, propoxycarbazone-sodium, propyrisulfuron, propyzamide, prosulfocarb, prosulfuron, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyri-buticarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, sethoxydim, siduron, simazine, simetryn, SL-261, sulcotrion, sulfentrazone, sulfometuron, sulfo-meturon-methyl, sulfosulfuron, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, 2,3,6-TBA, TCA (trichloroacetic acid), TCA-sodium, tebuthiuron, tefuryltrione, tembotrione, tepraloxydim, terbacil, terbucarb, terbumeton, terbuthylazin, terbutryn, thenylchlor, thiazopyr, thiencarbazone, thien-carbazone-methyl, thifensulfuron, thifensulfuron-methyl, thiobencarb, tiafenacil, tolpyralate, topra-mezone, tralkoxydim, triafamone, tri-allate, triasulfuron, triaziflam, tribenuron, tribenuron-methyl, triclopyr, trietazine, trifloxysulfuron, trifloxysulfuron-sodium, trifludimoxazin, trifluralin, triflusulfuron, triflusulfuron-methyl, tritosulfuron, urea sulfate, vernolate, XDE-848, ZJ-0862, i.e. 3,4-dichloro-N-{2-[(4,6-dimethoxypyrimidin-2-yl)oxy]benzyl}aniline, and the following compounds:

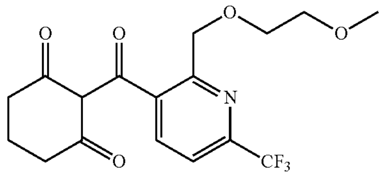

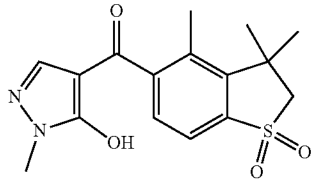

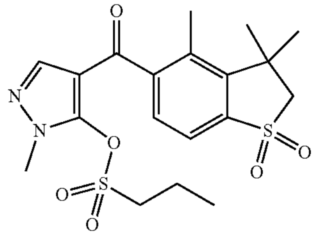

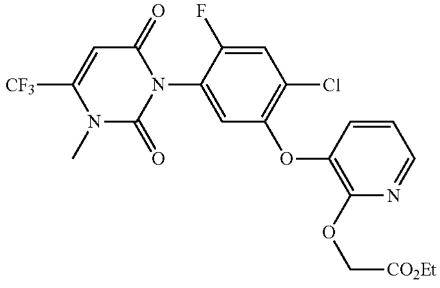

Examples for plant growth regulators are:

Acibenzolar, acibenzolar-S-methyl, 5-aminolevulinic acid, ancymidol, 6-benzylaminopurine, Brassinolid, catechine, chlormequat chloride, cloprop, cyclanilide, 3-(cycloprop-1-enyl) propionic acid, daminozide, dazomet, n-decanol, dikegulac, dikegulac-sodium, endothal, endothal-dipotassium, -disodium, and -mono (N,N-dimethylalkylammonium), ethephon, flumetralin, flurenol, flurenol-butyl, flurprimidol, forchlorfenuron, gibberellic acid, inabenfide, indol-3-acetic acid (IAA), 4-indol-3-ylbutyric acid, isoprothiolane, probenazole, jasmonic acid, maleic hydrazide, mepiquat chloride, 1-methyl-cyclopropene, methyl jasmonate, 2-(1-naphthyl)acetamide, 1-naphthylacetic acid, 2-naphthyloxy-acetic acid, nitrophenolate-mixture, paclobutrazol, N-(2-phenylethyl)-beta-alanine, N-phenylphthalamic acid, prohexadione, prohexadione-calcium, prohydrojasmone, salicylic acid, strigolactone, tecnazene, thidiazuron, triacontanol, trinexapac, trinexapac-ethyl, tsitodef, uniconazole, uniconazole-P.

Methods and Uses

The compound of formula (I) and composition comprising thereof comprising thereof have potent microbicidal activity and/or plant defense modulating potential. They can be used for controlling unwanted microorganisms, such as unwanted fungi and bacteria. They can be particularly useful in crop protection (they control microorganisms that cause plants diseases) or for protecting materials (e.g. industrial materials, timber, storage goods) as described in more details herein below. More specifically, the compound of formula (I) and composition comprising thereof can be used to protect seeds, germinating seeds, emerged seedlings, plants, plant parts, fruits, harvest goods and/or the soil in which the plants grow from unwanted microorganisms.

Control or controlling as used herein encompasses protective, curative and eradicative treatment of unwanted microorganisms. Unwanted microorganisms may be pathogenic bacteria, pathogenic virus, pathogenic oomycetes or pathogenic fungi, more specifically phytopathogenic bacteria, phytopathogenic virus, phytopathogenic oomycetes or phytopathogenic fungi. As detailed herein below, these phytopathogenic microorganims are the causal agents of a broad spectrum of plants diseases.

More specifically, the compound of formula (I) and composition comprising thereof can be used as fungicides. For the purpose of the specification, the term "fungicide" refers to a compound or composition that can be used in crop protection for the control of unwanted fungi, such as Plasmodiophoromycetes, Chytridiomycetes, Zygomycetes, Ascomycetes, Basidiomycetes and Deuteromycetes and/or for the control of Oomycetes.

The compound of formula (I) and composition comprising thereof may also be used as antibacterial agent. In particular, they may be used in crop protection, for example for the control of unwanted bacteria, such as Pseudomonadaceae, Rhizobiaceae, Xanthomonadaceae, Enterobacteriaceae, Corynebacteriaceae and Streptomycetaceae.

The compound of formula (I) and composition comprising thereof may also be used as antiviral agent in crop protection. For example the compound of formula (I) and composition comprising thereof may have effects on diseases from plant viruses, such as the tobacco mosaic virus (TMV), tobacco rattle virus, tobacco stunt virus (TStuV), tobacco leaf curl virus (VLCV), tobacco nervilia mosaic virus (TVBMV), tobacco necrotic dwarf virus (TNDV), tobacco streak virus (TSV), potato virus X (PVX), potato viruses Y, S, M, and A, potato acuba mosaic virus (PAMV), potato mop-top virus (PMTV), potato leaf-roll virus (PLRV), alfalfa mosaic virus (AMV), cucumber mosaic virus (CMV), cucumber green mottlemosaic virus (CGMMV), cucumber yellows virus (CuYV), watermelon mosaic virus (WMV), tomato spotted wilt virus (TSWV), tomato ringspot virus (TomRSV), sugarcane mosaic virus (SCMV), rice drawf virus, rice stripe virus, rice black-streaked drawf virus, strawberry mottle virus (SMoV), strawberry vein banding virus (SVBV), strawberry mild yellow edge virus (SMYEV), strawberry crinkle virus (SCrV), broad beanwilt virus (BBWV), and melon necrotic spot virus (MNSV).

The present invention also relates to a method for controlling unwanted microorganisms, such as unwanted fungi, oomycetes and bacteria, comprising the step of applying at least one compound of formula (I) or at least one composition to the microorganisms and/or their habitat (to the plants, plant parts, seeds, fruits or to the soil in which the plants grow).

Typically, when the compound of formula (I) and composition comprising thereof are used in curative or protective methods for controlling phytopathogenic fungi and/or phytopathogenic oomycetes, an effective and plant-compatible amount thereof is applied to the plants, plant parts, fruits, seeds or to the soil or substrates in which the plants grow. Suitable substrates that may be used for cultivating plants include inorganic based substrates, such as mineral wool, in particular stone wool, perlite, sand or gravel; organic substrates, such as peat, pine bark or sawdust; and petroleum based substrates such as polymeric foams or plastic beads. Effective and plant-compatible amount means an amount that is sufficient to control or destroy the fungi present or liable to appear on the cropland and that does not entail any appreciable symptom of phytotoxicity for said crops. Such an amount can vary within a wide range depending on the fungus to be controlled, the type of crop, the crop growth stage, the climatic conditions and the respective compound of formula (I) or composition used. This amount can be determined by systematic field trials that are within the capabilities of a person skilled in the art.

Plants and Plant Parts

The compound of formula (I) and composition comprising thereof may be applied to any plants or plant parts.

Plants mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the genetically modified plants (GMO or transgenic plants) and the plant cultivars which are protectable and non-protectable by plant breeders' rights.

Genetically Modified Plants (GMO)

Genetically modified plants (GMO or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome. This gene gives the transformed plant new or improved agronomic or other properties by expressing a protein or polypeptide of interest or by downregulating or silencing other gene(s) which are present in the plant (using for example, antisense technology, cosuppression technology, RNA interference—RNAi—technology or microRNA—miRNA—technology). A heterologous gene that is located in the genome is also called a transgene. A transgene that is defined by its particular location in the plant genome is called a transformation or transgenic event.

Plant cultivars are understood to mean plants which have new properties ("traits") and have been obtained by conventional breeding, by mutagenesis or by recombinant DNA techniques. They can be cultivars, varieties, bio- or genotypes.

Plant parts are understood to mean all parts and organs of plants above and below the ground, such as shoots, leaves, needles, stalks, stems, flowers, fruit bodies, fruits, seeds, roots, tubers and rhizomes. The plant parts also include harvested material and vegetative and generative propagation material, for example cuttings, tubers, rhizomes, slips and seeds.

Plants which may be treated in accordance with the methods described herein include the following: cotton, flax, grapevine, fruit, vegetables, such as *Rosaceae* sp. (for example pome fruits such as apples and pears, but also stone fruits such as apricots, cherries, almonds and peaches, and soft fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for example banana trees and plantations), *Rubiaceae* sp. (for example coffee), *Theaceae* sp., *Sterculiceae* sp., *Rutaceae* sp. (for example lemons, oranges and grapefruit); *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumber), *Alliaceae* sp. (for example leek, onion), *Papilionaceae* sp. (for example peas); major crop plants, such as *Gramineae* sp. (for example maize, turf, cereals such as wheat, rye, rice, barley, oats, millet and triticale), *Asteraceae* sp. (for example sunflower), *Brassicaceae* sp. (for example white cabbage, red cabbage, broccoli, cauliflower, Brussels sprouts, pak choi, kohlrabi, radishes, and oilseed rape, mustard, horseradish and cress), *Fabacae* sp. (for example bean, peanuts), *Papilionaceae* sp. (for example soya bean), *Solanaceae* sp. (for example potatoes), *Chenopodiaceae* sp. (for example sugar beet, fodder beet, swiss chard, beetroot); useful plants and ornamental plants for gardens and wooded areas; and genetically modified varieties of each of these plants.

Plants and plant cultivars which may be treated by the above disclosed methods include plants and plant cultivars which are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may be treated by the above disclosed methods include those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may be treated by the above disclosed methods include those plants characterized by enhanced yield characteristics. Increased yield in said plants may be the result of, for example, improved plant physiology, growth and development, such as water use efficiency, water retention efficiency, improved nitrogen use, enhanced carbon assimilation, improved photosynthesis, increased germination efficiency and accelerated maturation. Yield may furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance.

Further yield traits include seed composition, such as carbohydrate content and composition for example cotton or starch, protein content, oil content and composition, nutritional value, reduction in anti-nutritional compounds, improved processability and better storage stability.

Plants and plant cultivars which may be treated by the above disclosed methods include plants and plant cultivars which are hybrid plants that already express the characteristic of heterosis or hybrid vigor which results in generally higher yield, vigor, health and resistance towards biotic and abiotic stresses.

Plants and plant cultivars (obtained by plant biotechnology methods such as genetic engineering) which may be treated by the above disclosed methods include plants and plant cultivars which are herbicide-tolerant plants, i.e. plants made tolerant to one or more given herbicides. Such plants can be obtained either by genetic transformation, or by selection of plants containing a mutation imparting such herbicide tolerance.

Plants and plant cultivars (obtained by plant biotechnology methods such as genetic engineering) which may be treated by the above disclosed methods include plants and plant cultivars which are insect-resistant transgenic plants, i.e. plants made resistant to attack by certain target insects.

Such plants can be obtained by genetic transformation, or by selection of plants containing a mutation imparting such insect resistance.

Plants and plant cultivars (obtained by plant biotechnology methods such as genetic engineering) which may be treated by the above disclosed methods include plants and plant cultivars which are disease-resistant transgenic plants, i.e. plants made resistant to attack by certain target insects. Such plants can be obtained by genetic transformation, or by selection of plants containing a mutation imparting such insect resistance.

Plants and plant cultivars (obtained by plant biotechnology methods such as genetic engineering) which may be treated by the above disclosed methods include plants and plant cultivars which are tolerant to abiotic stresses. Such plants can be obtained by genetic transformation, or by selection of plants containing a mutation imparting such stress resistance.

Plants and plant cultivars (obtained by plant biotechnology methods such as genetic engineering) which may be treated by the above disclosed methods include plants and plant cultivars which show altered quantity, quality and/or storage-stability of the harvested product and/or altered properties of specific ingredients of the harvested product.

Plants and plant cultivars (obtained by plant biotechnology methods such as genetic engineering) which may be treated by the above disclosed methods include plants and plant cultivars, such as cotton plants, with altered fiber characteristics. Such plants can be obtained by genetic transformation, or by selection of plants contain a mutation imparting such altered fiber characteristics.

Plants and plant cultivars (obtained by plant biotechnology methods such as genetic engineering) which may be treated by the above disclosed methods include plants and plant cultivars, such as oilseed rape or related *Brassica* plants, with altered oil profile characteristics. Such plants can be obtained by genetic transformation, or by selection of plants contain a mutation imparting such altered oil profile characteristics.

Plants and plant cultivars (obtained by plant biotechnology methods such as genetic engineering) which may be treated by the above disclosed methods include plants and plant cultivars, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering.

Plants and plant cultivars (obtained by plant biotechnology methods such as genetic engineering) which may be treated by the above disclosed methods include plants and plant cultivars, such as Tobacco plants, with altered post-translational protein modification patterns.

Pathogens

Non-limiting examples of pathogens of fungal diseases which may be treated in accordance with the invention include:

- diseases caused by powdery mildew pathogens, for example *Blumeria* species, for example *Blumeria graminis; Podosphaera* species, for example *Podosphaera leucotricha; Sphaerotheca* species, for example *Sphaerotheca fuliginea; Uncinula* species, for example *Uncinula necator;*
- diseases caused by rust disease pathogens, for example *Gymnosporangium* species, for example *Gymnosporangium sabinae; Hemileia* species, for example *Hemileia vastatrix; Phakopsora* species, for example *Phakopsora pachyrhizi* or *Phakopsora meibomiae; Puccinia* species, for example *Puccinia recondita, Puccinia graminis* oder *Puccinia striiformis; Uromyces* species, for example *Uromyces appendiculatus;*
- diseases caused by pathogens from the group of the Oomycetes, for example *Albugo* species, for example *Albugo candida; Bremia* species, for example *Bremia lactucae; Peronospora* species, for example *Peronospora pisi* or *P. brassicae; Phytophthora* species, for example *Phytophthora infestans; Plasmopara* species, for example *Plasmopara viticola; Pseudoperonospora* species, for example *Pseudoperonospora humuli* or *Pseudoperonospora cubensis; Pythium* species, for example *Pythium ultimum;*
- leaf blotch diseases and leaf wilt diseases caused, for example, by *Alternaria* species, for example *Alternaria solani; Cercospora* species, for example *Cercospora beticola; Cladiosporium* species, for example *Cladiosporium cucumerinum; Cochliobolus* species, for example *Cochliobolus sativus* (conidial form: *Drechslera*, syn: *Helminthosporium*) or *Cochliobolus miyabeanus; Colletotrichum* species, for example *Colletotrichum lindemuthanium; Corynespora* species, for example *Corynespora cassiicola; Cycloconium* species, for example *Cycloconium oleaginum; Diaporthe* species, for example *Diaporthe citri; Elsinoe* species, for example *Elsinoe fawcettii; Gloeosporium* species, for example *Gloeosporium laeticolor; Glomerella* species, for example *Glomerella cingulata; Guignardia* species, for example *Guignardia bidwelli; Leptosphaeria* species, for example *Leptosphaeria maculans; Magnaporthe* species, for example *Magnaporthe grisea; Microdochium* species, for example *Microdochium nivale; Mycosphaerella* species, for example *Mycosphaerella graminicola, Mycosphaerella arachidicola* or *Mycosphaerella fijiensis; Phaeosphaeria* species, for example *Phaeosphaeria nodorum; Pyrenophora* species, for example *Pyrenophora teres* or *Pyrenophora tritici repentis; Ramularia* species, for example *Ramularia collo-cygni* or *Ramularia areola; Rhynchosporium* species, for example *Rhynchosporium secalis; Septoria* species, for example *Septoria apii* or *Septoria lycopersici; Stagonospora* species, for example *Stagonospora nodorum; Typhula* species, for example *Typhula incarnata; Venturia* species, for example *Venturia inaequalis;*
- root and stem diseases caused, for example, by *Corticium* species, for example *Corticium graminearum; Fusarium* species, for example *Fusarium oxysporum; Gaeumannomyces* species, for example *Gaeumannomyces graminis; Plasmodiophora* species, for example *Plasmodiophora brassicae; Rhizoctonia* species, for example *Rhizoctonia solani; Sarocladium* species, for example *Sarocladium oryzae; Sclerotium* species, for example *Sclerotium oryzae; Tapesia* species, for example *Tapesia acuformis; Thielaviopsis* species, for example *Thielaviopsis basicola;*
- ear and panicle diseases (including corn cobs) caused, for example, by *Alternaria* species, for example *Alternaria* spp.; *Aspergillus* species, for example *Aspergillus flavus; Cladosporium* species, for example *Cladosporium cladosporioides; Claviceps* species, for example *Claviceps purpurea; Fusarium* species, for example *Fusarium culmorum; Gibberella* species, for example *Gibberella zeae; Monographella* species, for example *Monographella nivalis; Stagnospora* species, for example *Stagnospora nodorum;* diseases caused by smut fungi, for example *Sphacelotheca* species, for example *Sphacelotheca reiliana; Tilletia* species, for example *Tilletia caries* or *Tilletia controversa; Urocystis* species, for example *Urocystis occulta; Ustilago* species, for example *Ustilago nuda;* fruit rot caused, for example, by *Aspergillus* species, for example *Aspergillus flavus; Botrytis* species, for example *Botrytis cinerea; Monilinia* species, for example *Monilinia laxa; Penicillium* species, for example *Penicillium expansum* or *Penicillium purpurogenum; Rhizopus* species, for example *Rhizopus stolonifer; Sclerotinia* species, for example *Sclerotinia sclerotiorum; Verticilium* species, for example *Verticilium alboatrum;* seed- and soil-borne rot and wilt diseases, and also diseases of seedlings, caused, for example, by *Alternaria* species, for example *Alternaria brassicicola; Aphanomyces* species, for example *Aphanomyces euteiches; Ascochyta* species, for example *Ascochyta lentis; Aspergillus* species, for example *Aspergillus flavus; Cladosporium* species, for example *Cladosporium herbarum; Cochliobolus* species, for example *Cochliobolus sativus* (conidial form: *Drechslera, Bipolaris* Syn: *Helminthosporium*); *Colletotrichum* species, for example *Colletotrichum coccodes; Fusarium* species, for example *Fusarium culmorum; Gibberella* species, for example *Gibberella zeae; Macrophomina* species, for example *Macrophomina phaseolina; Microdochium* species, for example *Microdochium nivale; Monographella* species, for example *Monographella nivalis; Penicillium* species, for example *Penicillium expansum; Phoma* species, for example *Phoma lingam; Phomopsis* species, for example *Phomopsis sojae; Phytophthora* species, for example *Phytophthora cactorum; Pyrenophora* species, for example *Pyrenophora graminea; Pyricularia* species, for example *Pyricularia oryzae; Pythium* species, for example *Pythium ultimum; Rhizoctonia* species, for example *Rhizoctonia solani; Rhizopus* species, for example *Rhizopus oryzae; Sclerotium* species, for example *Sclerotium rolfsii; Septoria* species, for example *Septoria nodorum; Typhula* species, for example *Typhula incarnata; Verticillium* species, for example *Verticillium dahliae;* cancers, galls and witches' broom caused, for example, by *Nectria* species, for example *Nectria galligena;* wilt diseases caused, for example, by *Verticillium* species, for example *Verticillium longisporum; Fusarium* species, for example *Fusarium oxysporum;* deformations of leaves, flowers and fruits caused, for example, by *Exobasidium* species, for example *Exobasidium vexans; Taphrina* species, for example *Taphrina deformans;* degenerative diseases in woody plants, caused, for example, by Esca species, for example *Phaeomoniella chlamydospora, Phaeoacremonium aleophilum* or *Fomitiporia mediterranea; Ganoderma* species, for example *Ganoderma boninense;* diseases of plant tubers caused, for example, by *Rhizoctonia* species, for example *Rhizoctonia solani; Helminthosporium* species, for example *Helminthosporium solani;* diseases caused by bacterial pathogens, for example *Xanthomonas* species, for example *Xanthomonas campestris* pv. *oryzae; Pseudomonas* species, for example *Pseudomonas syringae* pv. *lachrymans; Erwinia* species, for example *Erwinia amylovora; Liberibacter* species, for example *Liberibacter asiaticus; Xyella* species, for example *Xylella fastidiosa; Ralstonia* species, for example *Ralstonia solanacearum; Dickeya* species, for example *Dickeya solani; Clavibacter* species, for example *Clavibacter michiganensis; Streptomyces* species, for example *Streptomyces scabies.* diseases of soya beans:

Fungal diseases on leaves, stems, pods and seeds caused, for example, by *Alternaria* leaf spot (*Alternaria* spec. *atrans tenuissima*), Anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma* glycines), stemphylium leaf blight (*Stemphylium botryosum*), sudden death syndrome (*Fusarium virguliforme*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

Mycotoxins

In addition, the compound of formula (I) and composition comprising thereof may reduce the mycotoxin content in the harvested material and the foods and feeds prepared therefrom. Mycotoxins include particularly, but not exclusively, the following: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins which can be produced, for example, by the following fungi: *Fusarium* spec., such as *F. acuminatum, F. asiaticum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides* etc., and also by *Aspergillus* spec., such as *A. flavus, A. parasiticus, A. nomius, A. ochraceus, A. clavatus, A. terreus, A. versicolor, Penicillium* spec., such as *P. verrucosum, P. viridicatum, P. citrinum, P. expansum, P. clavi-*

*forme, P. roqueforti, Claviceps* spec., such as *C. purpurea, C. fusiformis, C. paspali, C. africana, Stachybotrys* spec. and others.

Material Protection

The compound of formula (I) and composition comprising thereof may also be used in the protection of materials, especially for the protection of industrial materials against attack and destruction by phytopathogenic fungi.

In addition, the compound of formula (I) and composition comprising thereof may be used as antifouling compositions, alone or in combinations with other active ingredients.

Industrial materials in the present context are understood to mean inanimate materials which have been prepared for use in industry. For example, industrial materials which are to be protected from microbial alteration or destruction may be adhesives, glues, paper, wallpaper and board/cardboard, textiles, carpets, leather, wood, fibers and tissues, paints and plastic articles, cooling lubricants and other materials which can be infected with or destroyed by microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials within the scope of the present invention preferably include adhesives, sizes, paper and card, leather, wood, paints, cooling lubricants and heat transfer fluids, more preferably wood.

The compound of formula (I) and composition comprising thereof may prevent adverse effects, such as rotting, decay, discoloration, decoloration or formation of mould.

In the case of treatment of wood the compound of formula (I) and composition comprising thereof may also be used against fungal diseases liable to grow on or inside timber.

Timber means all types of species of wood, and all types of working of this wood intended for construction, for example solid wood, high-density wood, laminated wood, and plywood. In addition, the compound of formula (I) and composition comprising thereof may be used to protect objects which come into contact with saltwater or brackish water, especially hulls, screens, nets, buildings, moorings and signalling systems, from fouling.

The compound of formula (I) and composition comprising thereof may also be employed for protecting storage goods. Storage goods are understood to mean natural substances of vegetable or animal origin or processed products thereof which are of natural origin, and for which long-term protection is desired.

Storage goods of vegetable origin, for example plants or plant parts, such as stems, leaves, tubers, seeds, fruits, grains, may be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture.

Storage goods of animal origin are, for example, hides, leather, furs and hairs. The compound of formula (I) and composition comprising thereof may prevent adverse effects, such as rotting, decay, discoloration, decoloration or formation of mould.

Microorganisms capable of degrading or altering industrial materials include, for example, bacteria, fungi, yeasts, algae and slime organisms. The compound of formula (I) and composition comprising thereof preferably act against fungi, especially moulds, wood-discoloring and wood-destroying fungi (Ascomycetes, Basidiomycetes, Deuteromycetes and Zygomycetes), and against slime organisms and algae. Examples include microorganisms of the following genera: *Alternaria*, such as *Alternaria tenuis; Aspergillus*, such as *Aspergillus niger; Chaetomium*, such as *Chaetomium globosum; Coniophora*, such as *Coniophora puetana; Lentinus*, such as *Lentinus tigrinus; Penicillium*, such as *Penicillium glaucum; Polyporus*, such as *Polyporus versicolor; Aureobasidium*, such as *Aureobasidium pullulans; Sclerophoma*, such as *Sclerophoma pityophila; Trichoderma*, such as *Trichoderma viride; Ophiostoma* spp., *Ceratocystis* spp., *Humicola* spp., *Petriella* spp., *Trichurus* spp., *Coriolus* spp., *Gloeophyllum* spp., *Pleurotus* spp., *Poria* spp., *Serpula* spp. and *Tyromyces* spp., *Cladosporium* spp., *Paecilomyces* spp. *Mucor* spp., *Escherichia*, such as *Escherichia coli; Pseudomonas*, such as *Pseudomonas aeruginosa; Staphylococcus*, such as *Staphylococcus aureus, Candida* spp. and *Saccharomyces* spp., such as *Saccharomyces cerevisae.*

Seed Treatment

The compound of formula (I) and composition comprising thereof may also be used to protect seeds from unwanted microorganisms, such as phytopathogenic microorganisms, for instance phytopathogenic fungi or phytopathogenic oomycetes. The term seed(s) as used herein include dormant seeds, primed seeds, pregerminated seeds and seeds with emerged roots and leaves.

Thus, the present invention also relates to a method for protecting seeds from unwanted microorganisms which comprises the step of treating the seeds with the compound of formula (I) or the composition.

The treatment of seeds with the compound of formula (I) or the composition protects the seeds from phytopathogenic microorganisms, but also protects the germinating seeds, the emerging seedlings and the plants after emergence from the treated seeds. Therefore, the present invention also relates to a method for protecting seeds, germinating seeds and emerging seedlings.

The seeds treatment may be performed prior to sowing, at the time of sowing or shortly thereafter.

When the seeds treatment is performed prior to sowing (e.g. so-called on-seed applications), the seeds treatment may be performed as follows: the seeds may be placed into a mixer with a desired amount of the compound of formula (I) or the composition, the seeds and the compound of formula (I) or the composition are mixed until an homogeneous distribution on seeds is achieved. If appropriate, the seeds may then be dried.

The invention also relates to seeds coated with the compound of formula (I) or composition comprising thereof.

Preferably, the seeds are treated in a state in which it is sufficiently stable for no damage to occur in the course of treatment. In general, seeds can be treated at any time between harvest and shortly after sowing. It is customary to use seeds which have been separated from the plant and freed from cobs, shells, stalks, coats, hairs or the flesh of the fruits. For example, it is possible to use seeds which have been harvested, cleaned and dried down to a moisture content of less than 15% by weight. Alternatively, it is also possible to use seeds which, after drying, for example, have been treated with water and then dried again, or seeds just after priming, or seeds stored in primed conditions or pre-germinated seeds, or seeds sown on nursery trays, tapes or paper.

The amount of the compound of formula (I) or composition comprising thereof applied to the seeds is typically such that the germination of the seed is not impaired, or that the resulting plant is not damaged. This must be ensured particularly in case the the compound of formula (I) would exhibit phytotoxic effects at certain application rates. The intrinsic phenotypes of transgenic plants should also be taken into consideration when determining the amount of the compound of formula (I) to be applied to the seed in order to achieve optimum seed and germinating plant protection with a minimum amount of compound being employed.

The compound of formula (I) can be applied as such, directly to the seeds, i.e. without the use of any other components and without having been diluted. Also the composition comprising thereof can be applied to the seeds.

The compound of formula (I) and composition comprising thereof are suitable for protecting seeds of any plant variety. Preferred seeds are that of cereals (such as wheat, barley, rye, millet, triticale, and oats), oilseed rape, maize, cotton, soybean, rice, potatoes, sunflower, beans, coffee, peas, beet (e.g. sugar beet and fodder beet), peanut, vegetables (such as tomato, cucumber, onions and lettuce), lawns and ornamental plants. More preferred are seeds of wheat, soybean, oilseed rape, maize and rice.

The compound of formula (I) and composition comprising thereof may be used for treating transgenic seeds, in particular seeds of plants capable of expressing a polypeptide or protein which acts against pests, herbicidal damage or abiotic stress, thereby increasing the protective effect. Seeds of plants capable of expressing a polypeptide or protein which acts against pests, herbicidal damage or abiotic stress may contain at least one heterologous gene which allows the expression of said polypeptide or protein. These heterologous genes in transgenic seeds may originate, for example, from microorganisms of the species *Bacillus, Rhizobium, Pseudomonas, Serratia, Trichoderma, Clavibacter, Glomus* or *Gliocladium*. These heterologous genes preferably originate from *Bacillus* sp., in which case the gene product is effective against the European corn borer and/or the Western corn rootworm. Particularly preferably, the heterologous genes originate from *Bacillus thuringiensis*.

Application

The compound of formula (I) can be applied as such, or for example in the form of as ready-to-use solutions, emulsions, water- or oil-based suspensions, powders, wettable powders, pastes, soluble powders, dusts, soluble granules, granules for broadcasting, suspoemulsion concentrates, natural products impregnated with the compound of formula (I), synthetic substances impregnated with the compound of formula (I), fertilizers or microencapsulations in polymeric substances.

Application is accomplished in a customary manner, for example by watering, spraying, atomizing, broadcasting, dusting, foaming, spreading-on and the like. It is also possible to deploy the compound of formula (I) by the ultra-low volume method, via a drip irrigation system or drench application, to apply it in-furrow or to inject it into the soil stem or trunk. It is further possible to apply the compound of formula (I) by means of a wound seal, paint or other wound dressing.

The effective and plant-compatible amount of the compound of formula (I) which is applied to the plants, plant parts, fruits, seeds or soil will depend on various factors, such as the compound/composition employed, the subject of the treatment (plant, plant part, fruit, seed or soil), the type of treatment (dusting, spraying, seed dressing), the purpose of the treatment (curative and protective), the type of microorganisms, the development stage of the microorganisms, the sensitivity of the microorganisms, the crop growth stage and the environmental conditions.

When the compound of formula (I) is used as a fungicide, the application rates can vary within a relatively wide range, depending on the kind of application. For the treatment of plant parts, such as leaves, the application rate may range from 0.1 to 10 000 g/ha, preferably from 10 to 1000 g/ha, more preferably from 50 to 300 g/ha (in the case of application by watering or dripping, it is even possible to reduce the application rate, especially when inert substrates such as rockwool or perlite are used). For the treatment of seeds, the application rate may range from 0.1 to 200 g per 100 kg of seeds, preferably from 1 to 150 g per 100 kg of seeds, more preferably from 2.5 to 25 g per 100 kg of seeds, even more preferably from 2.5 to 12.5 g per 100 kg of seeds. For the treatment of soil, the application rate may range from 0.1 to 10 000 g/ha, preferably from 1 to 5000 g/ha.

These application rates are merely examples and are not intended to limit the scope of the present invention.

Aspects of the present teaching may be further understood in light of the following examples, which should not be construed as limiting the scope of the present teaching in any way.

EXAMPLES

Generality

Measurement of Log P Values

Measurement of Log P values as provided herein was performed according to EEC directive 79/831 Annex V.A8 by HPLC (High Performance Liquid Chromatography) on reversed phase columns with the following methods:

[a] Log P value is determined by measurement of LC-UV, in an acidic range, with 0.1% formic acid in water and acetonitrile as eluent (linear gradient from 10% acetonitrile to 95% acetonitrile).

[b] Log P value is determined by measurement of LC-UV, in a neutral range, with 0.001 molar ammonium acetate solution in water and acetonitrile as eluent (linear gradient from 10% acetonitrile to 95% acetonitrile).

[c] Log P value is determined by measurement of LC-UV, in an acidic range, with 0.1% phosphoric acid and acetonitrile as eluent (linear gradient from 10% acetonitrile to 95% acetonitrile).

If more than one Log P value is available within the same method, all the values are given and separated by "+".

Calibration was done with straight-chain alkan2-ones (with 3 to 16 carbon atoms) with known Log P values (measurement of Log P values using retention times with linear interpolation between successive alkanones). Lambda-max-values were determined using UV-spectra from 200 nm to 400 nm and the peak values of the chromatographic signals 1H-NMR Data 1H-NMR data of selected examples as provided herein are written in form of 1H-NMR-peak lists. To each signal peak are listed the δ-value in ppm and the signal intensity in round brackets. Between the δ-value—signal intensity pairs are semicolons as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for 1H spectra, we use tetramethylsilane and/or the chemical shift of the solvent used, especially in the case of spectra measured in DMSO. Therefore in NMR peak lists, tetramethylsilane peak can occur but not necessarily.

The 1H-NMR peak lists are similar to classical 1H-NMR prints and contains therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical 1H-NMR interpretation.

Further details of NMR-data description with peak lists you find in the publication "Citation of NMR Peaklist Data within Patent Applications" of the Research Disclosure Database Number 564025.

Separation of Enantiomers

Enantiomeric separations of racemates are performed by preparative supercritical fluid chromatography using supercritical carbon dioxide as mobile phase and lower alcohols as modifier, more preferably methanol, ethanol or isopropanol in a ratio comprised between 15 and 30% by volume. Total flow rates are in a range 70-100 ml/min and chromatographic separations are done at a temperature in a range of between 30° C. and 50° C. and a back pressure in a range of between 70 bar to 130 bar on one of the thermostated chiral stationary phases, commercially available and known as follows:

- ChiralPak® IA, 250×20 mm from Daicel Chemical Industries, Ltd.
- Lux® Amylose-1, 250×21.2 mm 5 μm, Axia packed from Phenomenex Inc.
- Lux® Cellulose-1, 250×21.2 mm 5 μm, Axia packed from Phenomenex Inc.
- Lux® i-Cellulose-5, 250×21.2 mm 5 μm, Axia packed from Phenomenex Inc.

The separations on preparative scale were performed on apparatus SFC-PICLAB Hybrid 10-150 from Pic Solution with UV-detection in a range of between 210 nm and 280 nm, preferably 220 and 254 nm.

The following examples illustrate in a non-limiting manner the preparation and biological activity of the compounds of formula (I) according to the invention.

Synthesis of Compounds of Formula (1) and Intermediates

Synthesis of Compounds of Formula (1)

Preparation of Example 1: preparation of rac-3-[6-chloro-3-[3-(trifluoromethyl)phenoxy]pyridazin-4-yl]-5-[(2,4-dimethylphenyl)methyl]-5,6-dihydro-4H-1,2,4-oxadiazine (compound 1.059)

Step 1: preparation of ethyl 6-chloro-3-[3-(trifluoromethyl)phenoxy]pyridazine-4-carboxylate Under argon, sodium hydride (2.8 g, 70 mmol) was added to a solution of 3-(trifluoromethyl)phenol (9.7 g, 60 mmol) in DMF (30 mL). The reaction mixture was stirred 1 h at room temperature, then ethyl 3,6-dichloropyridazine-4-carboxylate (13.8 g, 50 mmol) was added portionwise to the solution. The reaction mixture was stirred for 18 h at room temperature, then diluted with water and extracted with ether (3×200 mL). The organic extracts were washed with water and brine, dried over magnesium sulfate, filtered and concentrated under reduced pressure. Purification of the residue by column chromatography on silica gel (gradient heptane/EtOAc) afforded, after evaporation of the solvents, 20 g (90% purity, 100% yield) of ethyl 6-chloro-3-[3-(trifluoromethyl)phenoxy]pyridazine-4-carboxylate as an oil.

Step 2: preparation of 6-chloro-3-[3-(trifluoromethyl)phenoxy]pyridazine-4-carboxylic acid To a solution of ethyl 6-chloro-3-[3-(trifluoromethyl)phenoxy]pyridazine-4-carboxylate (15 g, 35 mmol) in dioxane/water 2:1 (75 mL) was added lithium hydroxide (2.5 g, 105 mmol). The reaction was stirred for 4 h at room temperature then diluted with water. The aqueous phase was acidified with 1M aqueous HCl solution and extracted with ethyl acetate (3×200 mL). The organic extracts were dried over magnesium sulfate, filtered and concentrated under reduced pressure. Evaporation of the solvents afforded 9.7 g (98% purity, 85% yield) of 6-chloro-3-[3-(trifluoromethyl)phenoxy]pyridazine-4-carboxylic acid as a solid.

Step 3: preparation of 6-chloro-N-[rac-1-[(2,4-dimethylphenyl)methyl]-2-(1,3-dioxoisoindolin-2-yl)oxy-ethyl]-3-[3-(trifluoromethyl)phenoxy]pyridazine-4-carboxamide (compound 3-16)

Under argon, to a solution of 6-chloro-3-[3-(trifluoromethyl)phenoxy]pyridazine-4-carboxylic acid (5.0 g, 15.7 mmol) and HATU (6.56 g, 17.26 mmol) in DMF (100 mL) were successively added at 0° C., 2-[rac-2-amino-3-(2,4-dimethylphenyl)propoxy]isoindoline-1,3-dione;2,2,2-trifluoroacetic acid (7.57 g, 17.26 mmol) and N,N-Diisopropylethylamine (8.2 mL, 47.07 mmol). After 15 min at 0° C., the reaction mixture was stirred for 3 h at room temperature. It was then diluted with water and extracted with ethyl acetate (2×200 mL). The organic extracts were dried over magnesium sulfate, filtered and concentrated under reduced pressure. Purification of the residue by column chromatography on silica gel (gradient heptane/EtOAc) afforded, after evaporation of the solvents, 7.95 g (100% purity, 81% yield) of 6-chloro-N-[rac-1-[(2,4-dimethylphenyl)methyl]-2-(1,3-dioxoisoindolin-2-yl)oxy-ethyl]-3-[3-(trifluoromethyl)phenoxy]pyridazine-4-carboxamide as a white solid.

Step 4: preparation of 6-chloro-N-[rac-1-(aminooxymethyl)-2-(2,4-dimethylphenyl)ethyl]-3-[3-(trifluoro-methyl)phenoxy]pyridazine-4-carboxamide (compound 4-17)

Under argon, hydrazine monohydrate (2.31 mL, 37.92 mmol) was added to a solution of 6-chloro-N-[rac-1-[(2,4-dimethylphenyl)methyl]-2-(1,3-dioxoisoindolin-2-yl)oxy-ethyl]-3-[3-(trifluoro-methyl)phenoxy]pyridazine-4-carboxamide (7.9 g, 12.64 mmol) in DCM/MeOH (110 mL, 1:1). The reaction mixture was stirred for 4 h at room temperature and concentrated. It was then diluted with water and extracted with ethyl acetate (2×200 mL). The organic extracts were dried over magnesium sulfate, filtered and concentrated under reduced pressure. Evaporation of the solvents afforded 6.35 g (97% purity, 98% yield) of 6-chloro-N-[rac-1-(aminooxymethyl)-2-(2,4-dimethylphenyl)ethyl]-3-[3-(trifluoromethyl)phenoxy]pyridazine-4-carboxamide as a yellow oil.

Step 5: preparation of rac-3-[6-chloro-3-[3-(trifluoromethyl)phenoxy]pyridazin-4-yl]-5-[(2,4-dimethylphenyl)methyl]-5,6-dihydro-4H-1,2,4-oxadiazine Under argon, $POCl_3$ (3.56 mL, 38.19 mmol) was added at 80° C. to a solution 6-chloro-N-[rac-1-(aminooxymethyl)-2-(2,4-dimethylphenyl)ethyl]-3-[3-(trifluoromethyl)phenoxy]pyridazine-4-carboxamide (6.3 g, 12.73 mmol) in AcCN (114 mL). The reaction mixture was stirred for 18 h at 80° C. After cooling to room temperature, the mixture was poured into a saturated sodium bicarbonate solution, then extracted with ethyl acetate (2×200 mL). The organic extracts were dried over magnesium sulfate, filtered and concentrated under reduced pressure. Purification of the residue by column chromatography on silica gel (gradient heptane/EtOAc) afforded, after evaporation of the solvents, 2.52 g (98% purity, 41% yield) of rac-3-[6-chloro-3-[3-(trifluoromethyl)phenoxy]pyridazin-4-yl]-5-[(2,4-dimethylphenyl)methyl]-5,6-dihydro-4H-1,2,4-oxadiazine as a yellow solid.

Preparation of Example 2: preparation of rac-3-[6-chloro-3-[3-(trifluoromethyl)phenoxy]pyridazin-4-yl]-5-[(2,4-dimethylphenyl)methyl]-5,6-dihydro-4H-1,2,4-oxadiazine (compound 1.059)

Step 1: preparation of 6-chloro-N-[1-(chloromethyl)-2-(2,4-dimethylphenyl)ethyl]-3-[3-(trifluoromethyl)phenoxy]pyridazine-4-carboxamide (compound 21-01)

To a solution of 6-chloro-3-[3-(trifluoromethyl)phenoxy]pyridazine-4-carboxylic acid (100 mg, 0.31 mmol) in dichloromethane (2 mL) was added at room temperature oxalyl chloride (119 mg, 0.94 mmol) and a drop of dimethylformamide. After 30 min, the reaction was concentrated under reduced pressure. The residue was dissolved in dichloromethane (2 mL) and added at 0° C. to a suspension of 1-chloro-3-(2,4-dimethylphenyl)propan-2-amine; hydrochloride (73 mg, 0.31 mmol) in dichloromethane (1 mL), followed by addition of N,N-diisopropylethylamine (0.16 mL, 0.94 mmol). The reaction mixture was stirred at room temperature for 1 h, then concentrated under reduced pressure. Purification of the residue by column chromatography on silica gel (gradient heptane/EtOAc) afforded, after evaporation of the solvents, 142 mg (87% purity, 79% yield) of 6-chloro-N-[1-(chloromethyl)-2-(2,4-dimethylphenyl)ethyl]-3-[3-(trifluoromethyl)phenoxy]pyridazine-4-carboxamide as a colourless oil.

Step 2: preparation of 6-chloro-N-[1-(chloromethyl)-2-(2,4-dimethylphenyl)ethyl]-N'-hydroxy-3-[3-(trifluoromethyl)phenoxy]pyridazine-4-carboxamidine (compound 20-01)

To a solution of 6-chloro-N-[1-(chloromethyl)-2-(2,4-dimethylphenyl)ethyl]-3-[3-(trifluoro-methyl)phenoxy]pyridazine-4-carboxamide (130 mg, 0.23 mmol) in AcCN (2 mL) was added phosphorous pentachloride (205 mg, 0.99 mmol). The reaction mixture was stirred at room temperature for 18 h, then concentrated under reduced pressure. The residue was dissolved in AcCN (5 mL) and a solution of hydroxylamine in water (300 mg, 4.53 mmol, 50% in water) was added to the reaction mixture. After stirring at room temperature for 1 h the reaction mixture was diluted with water and toluene, and extracted with ethyl acetate (3×50 mL). The organic extracts were washed with water and brine, dried over sodium sulfate, filtered and concentrated under reduced pressure. Evaporation of the solvents, afforded 150 mg (65% purity, 83% yield) of 6-chloro-N-[1-(chloromethyl)-2-(2,4-dimethylphenyl)ethyl]-N'-hydroxy-3-[3-(trifluoromethyl)phenoxy]pyridazine-4-carboxamidine as a yellow oil.

Step 3: preparation of rac-3-[6-chloro-3-[3-(trifluoromethyl)phenoxy]pyridazin-4-yl]-5-[(2,4-dimethylphenyl)methyl]-5,6-dihydro-4H-1,2,4-oxadiazine To a solution of 6-chloro-N-[1-(chloromethyl)-2-(2,4-dimethylphenyl)ethyl]-N'-hydroxy-3-[3-(trifluoro-methyl)phenoxy]pyridazine-4-carboxamidine (150 mg, 0.23 mmol) in AcCN (2 mL) was added potassium tert-butoxide (47.3 mg, 0.42 mmol). The reaction mixture was stirred at room temperature for 1 h30, then diluted with a saturated ammonium chloride solution and extracted with dichloromethane (2×50 mL). The organic extracts were dried over sodium sulfate, filtered and concentrated under reduced pressure. Purification of the residue by column chromatography on silica gel (gradient heptane/EtOAc) afforded, after evaporation of the solvents, 56 mg (87% purity, 43% yield) of rac-3-[6-chloro-3-[3-(trifluoromethyl)phenoxy]pyridazin-4-yl]-5-[(2,4-dimethylphenyl)methyl]-5,6-dihydro-4H-1,2,4-oxadiazine as a yellow solid.

Preparation of Example 3: preparation of rac-5-(4-chlorophenyl)-3-[6-methyl-3-[3-(trifluoro-methyl)phenoxy]pyridazin-4-yl]-5,6-dihydro-4H-1,2,4-oxadiazine (compound 1.040)

Step 1: preparation of 6-chloro-3-[3-(trifluoromethyl)phenoxy]pyridazine-4-carbonitrile (compound 9-03)

Under argon, sodium hydride (1.30 g, 32 mmol) was added at 0° C. to a solution of 3-(trifluoro-methyl)phenol (4.6 g, 28 mmol) in THE (100 mL). After 30 min, 3,6-dichloropyridazine-4-carbonitrile (5.0 g, 28.7 mmol) was added portionwise to the solution. The reaction mixture was stirred for 3 h at room temperature, then diluted with saturated ammonium chloride solution and extracted with EtOAc (3×200 mL). The organic extracts were washed with water and brine, dried over magnesium sulfate, filtered and concentrated under reduced pressure. Purification of the residue by column chromatography on silica gel (gradient heptane/EtOAc) afforded, after evaporation of the solvents, 6.1 g (95% purity, 67% yield) of 6-chloro-3-[3-(trifluoromethyl)phenoxy]pyridazine-4-carbonitrile as an oil.

Step 2: preparation of 6-methyl-3-[3-(trifluoromethyl)phenoxy]pyridazine-4-carbonitrile (compound 9-02)

Under argon, 2,4,6-trimethyl-1,3,5,2,4,6-trioxatriborinane (12.57 g, 50.0 mmol) was added to a stirred solution of 6-chloro-3-[3-(trifluoromethyl)phenoxy]pyridazine-4-carbonitrile (3.0 g, 10.0 mmol), [1,1'-Bis(diphenylphosphino)ferrocene]dichloropalladium(II) complex with dichloromethane (64 mg, 0.10 mmol) and cesium carbonate (4.89 g, 15.0 mmol) in dioxane (30 mL). The reaction mixture was stirred at 100° C. for 4 h, then diluted with water and extracted with ethyl acetate (2×200 mL). The organic extracts were dried over magnesium sulfate, filtered and concentrated under reduced pressure. Purification of the residue by column chromatography on silica gel (gradient heptane/EtOAc) afforded, after evaporation of the solvents, 1.82 g (100% purity, 65% yield) of 6-methyl-3-[3-(trifluoromethyl)phenoxy]pyridazine-4-carbonitrile as a solid.

Step 3: preparation of N'-hydroxy-6-methyl-3-[3-(trifluoromethyl)phenoxy]pyridazine-4-carboxamidine (compound 10-02)

To a solution of 6-methyl-3-[3-(trifluoromethyl)phenoxy]pyridazine-4-carbonitrile (1.82 g, 6.52 mmol) in EtOH (32 mL) was added hydroxylamine hydrochloride (1.13 g, 16.29 mmol) and potassium carbonate (2.25 g, 16.29 mmol). The reaction mixture was stirred at 60° C. for 2 h. The precipitate was filtered off. The filtrate was concentrated, diluted with water and extracted with EtOAc (2×100 mL). The organic extracts were dried over magnesium sulfate, filtered and concentrated under reduced pressure. Purification of the residue by column chromatography on silica gel (gradient heptane/EtOAc) afforded, after evaporation of the solvents, 1.38 g (91% purity, 62% yield) of N'-hydroxy-6-methyl-3-[3-(trifluoromethyl)phenoxy]pyridazine-4-carboxamidine as a yellow solid.

Step 4: preparation of N'-[2-(4-chlorophenyl)-2-oxo-ethoxy]-6-methyl-3-[3-(trifluoro-methyl)phenoxy]pyridazine-4-carboxamidine (compound 12-03)

Under argon, 2-tert-butylimino-N,N-diethyl-1,3-dimethyl-1,3,2lambda5-diazaphosphinan-2-amine (BEMP) (210.9 mg, 0.77 mmol) was added at room temperature to a solution of N'-hydroxy-6-methyl-3-[3-(trifluoromethyl)phenoxy]pyridazine-4-carboxamidine (200 mg, 0.64 mmol) in AcCN (2.7 mL). After 15 min, 2-bromo-1-(4-chlorophenyl)ethanone (224 mg, 0.96 mmol) was added, the reaction was stirred further for 3 h, then concentrated under reduced pressure. Purification of the residue by column chromatography on silica gel (gradient heptane/EtOAc) afforded, after evaporation of the solvents, 65.6 mg (91% purity, 20% yield) of N'-[2-(4-chlorophenyl)-2-oxo-ethoxy]-6-methyl-3-[3-(trifluoro-methyl)phenoxy]pyridazine-4-carboxamidine as an oil.

Step 5: preparation of rac-5-(4-chlorophenyl)-3-[6-methyl-3-[3-(trifluoromethyl)phenoxy]pyridazin-4-yl]-5,6-dihydro-4H-1,2,4-oxadiazine Under argon, N'-[2-(4-chlorophenyl)-2-oxo-ethoxy]-6-methyl-3-[3-(trifluoromethyl)phenoxy]pyridazine-4-carboxamidine (69.2 mg, 0.13 mmol) was dissolved in MeOH (0.94 mL) and acetic acid (0.21 mL) and heated to 60° C. After 1 h, sodium cyanoborohydride (9.3 mg, 0.15 mmol) was added and the reaction was stirred further for 2 h. After cooling to room temperature, the mixture was poured into a 1 M NaOH solution and extracted with ethyl acetate (2×20 mL). The organic extracts were dried over magnesium sulfate, filtered and concentrated under reduced pressure. Purification of the residue by PREP-HPLC afforded, after evaporation of the solvents, 29 mg (100% purity, 47% yield) of rac-5-(4-chlorophenyl)-3-[6-methyl-3-[3-(trifluoromethyl)phenoxy]pyridazin-4-yl]-5,6-dihydro-4H-1,2,4-oxadiazine as a solid.

Preparation of Example 4: preparation of rac-5-(1-methylindol-3-yl)-3-[6-methyl-3-[3-(trifluoromethyl)phenoxy]pyridazin-4-yl]-5,6-dihydro-4H-1,2,4-oxadiazine (compound 1.011)

Step 1: preparation of N'-allyloxy-6-methyl-3-[3-(trifluoromethyl)phenoxy]pyridazine-4-carboxamidine (compound 13-01)

Under argon, O-allylhydroxylamine hydrochloride (658 mg, 5.4 mmol) was added at room temperature to a stirred solution of 6-methyl-3-[3-(trifluoromethyl)phenoxy]pyridazine-4-carbonitrile (500 mg, 1.79 mol) and $NaHCO_3$ (752.1 mg, 8.95 mmol) in MeOH. The resulting mixture was stirred at 60° C. for 36 h, cooled to room temperature and concentrated under vacuum. The resulting mixture was extracted with dichloromethane (3×200 mL). The organic extracts were washed with brine, dried over sodium sulfate, filtered and concentrated under reduced pressure. Purification of the residue by column chromatography on silica gel (gradient PE/EtOAc) afforded, after evaporation of the solvents, 400 mg (98% purity, 63% yield) of N'-allyloxy-6-methyl-3-[3-(trifluoromethyl)phenoxy]pyridazine-4-carboxamidine as a brown oil.

Step 2: preparation of rac-3-[6-methyl-3-[3-(trifluoromethyl)phenoxy]pyridazin-4-yl]-5,6-dihydro-4H-1,2,4-oxadiazin-5-ol (compound 14-01)

In a 50 mL round bottom flask $OSO_4$ (902 mg, 0.14 mmol, 4% wt in water) and $NaIO_4$ (759 mg, 3.55 mmol) were added at room temperature to a solution of N'-allyloxy-6-methyl-3-[3-(trifluoro-methyl)phenoxy]pyridazine-4-carboxamidine (500 mg, 1.42 mmol) in THE (20 mL) and water (5 mL). The reaction mixture was stirred for 2 h at room temperature, then diluted with a saturated ammonium chloride solution and extracted with ethyl acetate (2×100 mL). The organic extracts were dried over magnesium sulfate, filtered and concentrated under reduced pressure. Purification of the residue by column chromatography on silica gel (gradient heptane/EtOAc) afforded, after evaporation of the solvents, 260 mg (100% purity, 51% yield) of rac-3-[6-methyl-3-[3-(trifluoromethyl)phenoxy]pyridazin-4-yl]-5,6-dihydro-4H-1,2,4-oxadiazin-5-ol as a white solid.

Step 3: preparation of rac-5-(1-methylindol-3-yl)-3-[6-methyl-3-[3-(trifluoromethyl)phenoxy]pyridazin-4-yl]-5,6-dihydro-4H-1,2,4-oxadiazine In a 50 mL round bottom flask, 1-methylindole (37 mg, 0.28 mmol) was added to a solution of rac-3-[6-methyl-3-[3-(trifluoromethyl)phenoxy]pyridazin-4-yl]-5,6-dihydro-4H-1,2,4-oxadiazin-5-ol (50 mg, 0.14 mmol) in formic acid (2 mL). The reaction mixture was stirred for 45 min at 50° C. then cooled to room temperature and stirred further for 3 h. The solvent was removed under reduced pressure. Purification of the residue by column chromatography on silica gel (gradient heptane/EtOAc) afforded, after evaporation of the solvents, 59 mg (100% purity, 89% yield) of rac-5-(1-methylindol-3-yl)-3-[6-methyl-3-[3-(trifluoromethyl)phenoxy]pyridazin-4-yl]-5,6-dihydro-4H-1,2,4-oxadiazine as a pink solid.

Preparation of Example 5: preparation of rac-5-[(4-bromo-2-chloro-phenyl)methyl]-3-[6-chloro-3-[3-(trifluoromethyl)phenoxy]pyridazin-4-yl]-5,6-dihydro-4H-1,2,4-oxadiazine (compound 1.016)

Step 1: preparation of methyl 6-chloro-3-[3-(trifluoromethyl)phenoxy]pyridazine-4-carboximidate (compound 25-02)

Under argon, sodium methanolate (32 mg, 0.59 mmol) was added at 0° C. to a solution of 6-chloro-3-[3-(trifluoromethyl)phenoxy]pyridazine-4-carbonitrile (160 mg, 0.33 mmol) in MeOH (1.5 mL). The reaction mixture was stirred at 0° C. for 30 min. The crude solution contained 53% of methyl 6-chloro-3-[3-(trifluoromethyl)phenoxy]pyridazine-4-carboximidate and was used without further purification in the next step.

Step 2: preparation of rac-5-[(4-bromo-2-chloro-phenyl)methy]-3-[6-chloro-3-[3-(trifluoro-methyl)phenoxy]pyridazin-4-yl]-5,6-dihydro-4H-1,2,4-oxadiazine To the previous solution was added O-[rac-2-amino-3-(4-bromo-2-chloro-phenyl)propyl]hydroxylamine (157 mg, 0.51 mmol) dissolved in MeOH/acetic acid (1 mL, 1:1). The reaction mixture was stirred at room temperature for 3 h then heated at 100° C. for 7 h. After cooling to room temperature, the mixture was poured into a saturated sodium bicarbonate solution and extracted with ethyl acetate (2×50 mL). The organic extracts were washed with brine, dried over sodium sulfate, filtered and concentrated under reduced pressure. Purification of the residue by preparative HPLC afforded, after evaporation of the solvents, 5 mg (93% purity, 2% yield) of rac-5-[(4-bromo-2-chloro-phenyl)methyl]-3-[6-chloro-3-[3-(trifluoromethyl)phenoxy]pyridazin-4-yl]-5,6-dihydro-4H-1,2,4-oxadiazine as an oil.

Preparation of Example 6: preparation of rac-3-[6-chloro-3-(2-fluoro-3-methoxy-phenoxy)pyridazin-4-yl]-5-[(2,4-dimethylphenyl)methyl]-5,6-dihydro-4H-1,2,4-oxadiazine (compound 1.005)

Step 1: preparation of 3,6-dichloro-N-[rac-1-[(2,4-dimethylphenyl)methyl]-2-(1,3-dioxoisoindolin-2-yl)oxy-ethyl]pyridazine-4-carboxamide (compound 6-01)

Under argon, to a solution of 3,6-dichloropyridazine-4-carboxylic acid (700 mg, 3.62 mmol) and HATU (1.52 g, 3.99 mmol) in DMF (25 mL) were successively added at 0° C., 2-[rac-2-amino-3-(2,4-dimethylphenyl)propoxy]isoindoline-1,3-dione;2,2,2-trifluoroacetic acid (1.75 g, 4.0 mmol) and N,N-Diisopropylethylamine (1.89 mL, 10.88 mmol). After 15 min at 0° C., the reaction mixture was stirred for 18 h at room temperature. It was then diluted with water and extracted with ethyl acetate (2×200 mL). The organic extracts were dried over magnesium sulfate, filtered and concentrated under reduced pressure. Purification of the residue by column chromatography on silica gel (gradient heptane/EtOAc) afforded, after evaporation of the solvents, 1.15 g (87% purity, 55% yield) of 3,6-dichloro-N-[rac-1-[(2,4-dimethylphenyl)methyl]-2-(1,3-dioxoisoindolin-2-yl)oxy-ethyl]pyridazine-4-carboxamide as a white solid.

Step 2: preparation of 3,6-dichloro-N-[rac-1-(aminooxymethyl)-2-(2,4-dimethylphenyl)ethyl]pyridazine-4-carboxamide (compound 6-02)

Under argon, hydrazine monohydrate (0.42 mL, 6.91 mmol) was added to a solution of 3,6-dichloro-N-[rac-1-[(2,4-dimethylphenyl)methyl]-2-(1,3-dioxoisoindolin-2-yl)oxy-ethyl]pyridazine-4-carboxamide (1.15 g, 2.3 mmol) in DCM/MeOH (15 mL, 1:1). The reaction mixture was stirred for 3 h at room temperature and concentrated. It was then diluted with water and extracted with ethyl acetate (2×200 mL). The organic extracts were dried over magnesium sulfate, filtered and concentrated under reduced pressure. Evaporation of the solvents afforded 900 mg (74% purity, 78% yield) of 3,6-dichloro-N-[rac-1-(aminooxymethyl)-2-(2,4-dimethylphenyl)ethyl]pyridazine-4-carboxamide as a yellow solid.

Step 3: preparation of rac-3-(3,6-dichloropyridazin-4-yl)-5-[(2,4-dimethylphenyl)methyl]-5,6-dihydro-4H-1,2,4-oxadiazine (compound 7-01)

Under argon, $POCl_3$ (0.56 mL, 6.0 mmol) was added at 80° C. to a solution of 3,6-dichloro-N-[rac-1-(aminooxymethyl)-2-(2,4-dimethylphenyl)ethyl]pyridazine-4-carboxamide (738 mg, 2.0 mmol) in AcCN (15 mL). The reaction mixture was stirred for 18 h at 80° C. After cooling to room temperature, the mixture was poured into a saturated sodium bicarbonate solution, then extracted with ethyl acetate (2×200 mL). The organic extracts were dried over magnesium sulfate, filtered and concentrated under reduced pressure. Purification of the residue by PREP-HPLC afforded, after evaporation of the solvents, 90 mg (92% purity, 17% yield) of rac-3-(3,6-dichloropyridazin-4-yl)-5-[(2,4-dimethylphenyl)methyl]-5,6-dihydro-4H-1,2,4-oxadiazine as a yellow solid.

Step 4: preparation of rac-3-[6-chloro-3-(2-fluoro-3-methoxy-phenoxy)pyridazin-4-yl]-5-[(2,4-dimethylphenyl)methyl]-5,6-dihydro-4H-1,2,4-oxadiazine To a solution of rac-3-(3,6-dichloropyridazin-4-yl)-5-[(2,4-dimethylphenyl)methyl]-5,6-dihydro-4H-1,2,4-oxadiazine (60 mg, 0.17 mmol) in AcCN (1 mL) were added 2-fluoro-3-methoxy-phenol (27 mg, 0.19 mmol) and potassium carbonate (47 mg, 0.34 mmol). The reaction mixture was stirred at 50° C. for 5 h, then concentrated under reduced pressure. Purification of the residue by column chromatography on silica gel (gradient heptane/EtOAc) afforded, after evaporation of the solvents, 74 mg (97% purity, 90% yield) of rac-3-[6-chloro-3-(2-fluoro-3-methoxy-phenoxy)pyridazin-4-yl]-5-[(2,4-dimethyl-phenyl)methyl]-5,6-dihydro-4H-1,2,4-oxadiazine as a yellow oil.

Preparation of Example 7: preparation of 1-[5-[rac-5-[(2,4-dimethylphenyl)methyl]-5,6-dihydro-4H-1,2,4-oxadiazin-3-yl]-6-[3-(trifluoromethyl)phenoxy]pyridazin-3-yl]ethanone (compound 1.042)

Step 1: preparation of rac-5-[(2,4-dimethylphenyl)methyl]-3-[6-(1-ethoxyvinyl)-3-[3-(trifluoro-methyl)phenoxy]pyridazin-4-yl]-5,6-dihydro-4H-1,2,4-oxadiazine (compound 1.009)

In a microwave vial, rac-3-[6-chloro-3-[3-(trifluoromethyl)phenoxy]pyridazin-4-yl]-5-[(2,4-dimethyl-phenyl)methyl]-5,6-dihydro-4H-1,2,4-oxadiazine (500 mg, 1.05 mmol), tributyl(1-ethoxyvinyl)stannane (473 mg, 1.31 mmol) and bis(triphenylphosphine)palladium dichloride (73 mg, 0.103 mmol) were dissolved under argon in DMF (0.5 mL). The tube was sealed and the reaction mixture was heated in the microwave at 120° C. for 20 min. The reaction mixture was diluted with water and extracted with ethyl acetate (2×50 mL). The organic extracts were washed with water and brine, dried over magnesium sulfate, filtered and concentrated under reduced pressure. Purification of the residue by column chromatography on silica gel (gradient heptane/EtOAc) afforded, after evaporation of the solvents, 435 mg (100% purity, 80% yield) of rac-5-[(2,4-dimethylphenyl)methyl]-3-[6-(1-ethoxyvinyl)-3-[3-(trifluoromethyl)phenoxy]pyridazin-4-yl]-5,6-dihydro-4H-1,2,4-oxadiazine as an oil.

Step 2: preparation of 1-[5-[rac-5-[(2,4-dimethylphenyl)methyl]-5,6-dihydro-4H-1,2,4-oxadiazin-3-yl]-6-[3-(trifluoromethyl)phenoxy]pyridazin-3-yl]ethanone To a solution of rac-5-[(2,4-dimethylphenyl)methyl]-3-[6-(1-ethoxyvinyl)-3-[3-(trifluoro-methyl)phenoxy]pyridazin-4-yl]-5,6-dihydro-4H-1,2,4-oxadiazine (100 mg, 0.19 mmol) in THF (1 mL) was added at room temperature a 2M aqueous HCl solution (0.15 mL, 0.30 mmol). The reaction was stirred for 30 min then diluted with water and extracted with ethyl acetate (2×50 mL). The organic extracts were washed with water and brine, dried over magnesium sulfate, filtered and concentrated under reduced pressure. Purification of the residue by column chromatography on silica gel (gradient heptane/EtOAc) afforded, after evaporation of the solvents, 35 mg (100% purity, 37% yield) of 1-[5-[rac-5-[(2,4-dimethylphenyl)methyl]-5,6-dihydro-4H-1,2,4-oxadiazin-3-yl]-6-[3-(trifluoromethyl)phenoxy]pyridazin-3-yl]ethanone as a oil.

Preparation of Example 8: preparation of 3-chloro-N-cyclopropyl-5-[rac-5-[(2,4-dimethylphenyl)methyl]-5,6-dihydro-4H-1,2,4-oxadiazin-3-yl]-6-[3-(trifluoromethyl)phenoxy]pyridazin-4-amine (compound 1.041)

Step 1: preparation of rac-3-[6-chloro-5-iodo-3-[3-(trifluoromethyl)phenoxy]pyridazin-4-yl]-5-[(2,4-dimethylphenyl)methyl]-5,6-dihydro-4H-1,2,4-oxadiazine (compound 1.065)

Under argon, a solution of TMPZnCl·LiCl (2.77 mmol, 5.1 mL, 17% in THF, CAS number 109-99-9) was added to rac-3-[6-chloro-3-[3-(trifluoromethyl)phenoxy]pyridazin-4-yl]-5-[(2,4-dimethyl-phenyl)methyl]-5,6-dihydro-4H-1,2,4-oxadiazine (600 mg, 1.26 mmol) in THF (60 mL). After stirring 1 h at room temperature, NIS (566 mg, 2.52 mmol) was added portionwise. The reaction mixture was stirred 2 h at room temperature, then it was diluted with a saturated sodium thiosulfate solution and saturated sodium bicarbonate solution, and extracted with ethyl acetate (2×250 mL). The organic extracts were washed with brine, dried over magnesium sulfate, filtered and concentrated under reduced pressure. Purification of the residue by PREP-HPLC afforded, after evaporation of the solvents, 178 mg (70% purity, 16% yield) of rac-3-[6-chloro-5-iodo-3-[3-(trifluoromethyl)phenoxy]pyridazin-4-yl]-5-[(2,4-dimethylphenyl)methyl]-5,6-dihydro-4H-1,2,4-oxadiazine as a yellow solid.

Step 2: preparation of 3-chloro-N-cyclopropyl-5-[rac-5-[(2,4-dimethylphenyl)methyl]-5,6-dihydro-4H-1,2,4-oxadiazin-3-yl]-6-[3-(trifluoromethyl)phenoxy]pyridazin-4-amine Under argon, cyclopropylamine (6 mg, 0.10 mmol) and N,N-diisopropylethylamine (0.017 mL, 0.10 mmol) were added at room temperature to a solution of rac-3-[6-chloro-5-iodo-3-[3-(trifluoro-methyl)phenoxy]pyridazin-4-yl]-5-[(2,4-dimethylphenyl)methyl]-5,6-dihydro-4H-1,2,4-oxadiazine (50 mg, 0.08 mmol) in AcCN (0.7 mL). The reaction mixture was stirred at 50° C. for 18 h, then it was diluted with water and extracted with ethyl acetate (2×50 mL). The organic extracts were washed with brine, dried over magnesium sulfate, filtered and concentrated under reduced pressure. Evaporation of the solvent afforded 42 mg (98% purity, 93% yield) of 3-chloro-N-cyclopropyl-5-[rac-5-[(2,4-dimethylphenyl)methyl]-5,6-dihydro-4H-1,2,4-oxadiazin-3-yl]-6-[3-(trifluoromethyl)phenoxy]pyridazin-4-amine as an oil.

Preparation of Example 9: preparation of 6-chloro-4-[rac-5-[(2,4-dichlorophenyl)methyl]-4,5-dihydro-1H-imidazol-2-yl]-3-[3-(trifluoromethyl)phenoxy]pyridazine (compound 1.007)

A solution of $POCl_3$ (1.05 mL, 11.3 mmol) was added at room temperature to a mixture of 6-chloro-3-[3-(trifluoromethyl)phenoxy]pyridazine-4-carboxylic acid (400 mg, 1.25 mmol) and 3-(2,4-dichlorophenyl)propane-1,2-diamine (550 mg, 2.51 mmol) in 1,4-dioxane (10 mL). The reaction was heated to reflux and stirred for 36 h. After cooling, the reaction mixture was poured into a saturated sodium bicarbonate solution at 0° C., then extracted with ethyl acetate (2×100 mL). The organic extracts were washed with brine, dried over magnesium sulfate, filtered and concentrated under reduced pressure. Purification of the residue by PREP-HPLC afforded, after evaporation of the solvents, 90 mg (98% purity, 14% yield) of 6-chloro-4-[rac-5-[(2,4-dichlorophenyl)methyl]-4,5-dihydro-1H-imidazol-2-yl]-3-[3-(trifluoromethyl)phenoxy]pyridazine as a yellow oil.

Preparation of Example 10: preparation of (5S)-5-benzyl-3-[6-chloro-3-[3-(trifluoro-methyl)phenoxy]pyridazin-4-yl]-5,6-dihydro-4H-1,2,4-oxadiazine (compound 1-070)

Step 1: preparation of 6-chloro-N-methoxy-N-methyl-3-[3-(trifluoromethyl)phenoxy]pyridazine-4-carboxamide (compound 1.03)

To a suspension of 6-chloro-3-[3-(trifluoromethyl)phenoxy]pyridazine-4-carboxylic acid (5.0 g, 16.7 mmol) in dichloromethane (75 mL) was added oxalyl chloride (3.19 g, 25.14 mmol) followed by two drops of DMF. The reaction mixture was stirred at room temperature for 1 h. To the pre-formed acyl chloride was added N-methoxymethanamine; hydrochloride (2.12 g, 21.79 mmol) and triethylamine (8.17 mL, 58.68 mmol). The reaction mixture was stirred at room temperature for 2 h, then it was diluted with water and extracted with dichloromethane (2×200 mL). The organic extracts were washed with water and brine, dried over magnesium sulfate, filtered and concentrated under reduced pressure. The residue was diluted in dichloromethane and filtered over silica gel. Evaporation of the solvent afforded 3.38 g (95% purity, 56% yield) of 6-chloro-N-methoxy-N-methyl-3-[3-(trifluoro-methyl)phenoxy]pyridazine-4-carboxamide as a oil.

Step 2: preparation of 6-chloro-3-[3-(trifluoromethyl)phenoxy]pyridazine-4-carbaldehyde (compound 16-01)

Under argon, a solution of DIBAL-H (0.88 mL, 0.88 mmol, 1M in hexan) was added at −50° C. to a solution of 6-chloro-N-methoxy-N-methyl-3-[3-(trifluoromethyl)phenoxy]pyridazine-4-carboxamide (100 mg, 0.29 mmol) in THE (1.8 mL). After 4 h at −30° C., the reaction was stopped by addition of saturated ammonium chloride solution then the mixture was extracted with ethyl acetate (2×50 mL). The organic extracts were dried over magnesium sulfate, filtered and concentrated under reduced pressure. Purification of the residue by column chromatography on silica gel (gradient heptane/EtOAc) afforded, after evaporation of the solvents, 43.6 mg (90% purity, 47% yield) of 6-chloro-3-[3-(trifluoromethyl)phenoxy]pyridazine-4-carbaldehyde as an oil.

Step 3: preparation of 6-chloro-3-[3-(trifluoromethyl)phenoxy]pyridazine-4-carbaldehyde oxime (compound 17-01)

Under argon, hydroxylamine; hydrochloride (156 mg, 2.24 mmol) and potassium acetate (415 mg, 4.23 mmol) were added to 6-chloro-3-[3-(trifluoromethyl)phenoxy]pyridazine-4-carbaldehyde (400 mg, 1.32 mmol) in EtOH (40 mL). The reaction mixture was stirred at reflux for 2 h, diluted in water and extracted with ethyl acetate (2×50 mL). The organic extracts were dried over magnesium sulfate, filtered and concentrated under reduced pressure. Evaporation of the solvents afforded 215 mg (90% purity, 47% yield) of 6-chloro-3-[3-(trifluoromethyl)phenoxy]pyridazine-4-carbaldehyde oxime as a solid.

Step 4: preparation of (5S)-5-benzyl-3-[6-chloro-3-[3-(trifluoromethyl)phenoxy]pyridazin-4-yl]-5,6-dihydro-4H-1,2,4-oxadiazine To a solution of 6-chloro-3-[3-(trifluoromethyl)phenoxy]pyridazine-4-carbaldehyde oxime (10 mg, 0.031 mmol) in AcCN (0.2 mL) was added NCS (5.4 mg, 0.04 mmol) at room temperature. The reaction mixture was stirred for 1 h, then a solution of (2S)-1-bromo-3-phenyl-propan-2-amine; 2,2,2-trifluoroacetic acid (15.4 mg, 0.047 mmol) in AcCN/water (0.3 mL, 2:1) was added. The reaction was stirred at room temperature for 5 h then 1,2-bis(dimethylamino)ethane (18.3 mg, 0.16 mmol) was added to the reaction mixture. After 30 min, a solution of sodium carbonate (34 mg, 0.31 mmol, 1 M in water) was added and the reaction was further stirred for 1 h at room temperature. The reaction mixture was diluted with water and dichloromethane and the aqueous phase was extracted with dichloromethane (2×50 mL). The organic layer was dried over sodium sulfate, filtered and concentrated under reduced pressure. Purification of the residue by preparative HPLC afforded, after evaporation of the solvents, 10.9 mg (85% purity, 65% yield) of (5S)-5-benzyl-3-[6-chloro-3-[3-(trifluoromethyl)phenoxy]pyridazin-4-yl]-5,6-dihydro-4H-1,2,4-oxadiazine as a yellow solid.

Preparation of Example 11: preparation of rac-3-[6-chloro-5-(2-methoxyethoxy)-3-[3-(trifluoro-methyl)phenoxy]pyridazin-4-yl]-5-[(2,4-dimethylphenyl)methyl]-5,6-dihydro-4H-1,2,4-oxadiazine (compound 1.072)

Under argon, 2-methoxyethanol (0.15 mL, 0.30 mmol) and sodium hydride (11 mg, 0.27 mmol) were added at room temperature to a solution of rac-3-[6-chloro-5-iodo-3-[3-(trifluoro-methyl)phenoxy]pyridazin-4-yl]-5-[(2,4-dimethylphenyl)methyl]-5,6-dihydro-4H-1,2,4-oxadiazine (150 mg, 0.25 mmol) in AcCN (2 mL). The reaction mixture was stirred at room temperature for 1 h, then it was diluted with water and extracted with ethyl acetate (2×50 mL). The organic extracts were washed with brine, dried over magnesium sulfate, filtered and concentrated under reduced pressure. Purification of the residue by column chromatography on silica gel (gradient heptane/EtOAc) afforded, after evaporation of the solvents, 30 mg (90% purity, 19% yield) of rac-3-[6-chloro-5-(2-methoxyethoxy)-3-[3-(trifluoromethyl)phenoxy]pyridazin-4-yl]-5-[(2,4-dimethylphenyl)methyl]-5,6-dihydro-4H-1,2,4-oxadiazine as a colorless oil.

Preparation of Example 12: preparation of rac-3-[6-chloro-5-(4-pyridyl)-3-[3-(trifluoro-methyl)phenoxy]pyridazin-4-yl]-5-[(2,4-dimethylphenyl)methyl]-5,6-dihydro-4H-1,2,4-oxadiazine (compound 1.088)

Under argon, a solution of TMPZnCl·LiCl (0.22 mmol, 0.40 mL, 17% in THF, CAS number 109-99-9) was added to rac-3-[6-chloro-3-[3-(trifluoromethyl)phenoxy]pyridazin-4-yl]-5-[(2,4-dimethyl-phenyl)methyl]-5,6-dihydro-4H-1,2,4-oxadiazine (50 mg, 0.10 mmol) in THE (3 mL), followed by addition of 4-bromopyridine (20 mg, 0.12 mmol), $Pd(dba)_2$ (18 mg, 0.031 mmol) and trifurylphosphine (15 m, 0.063 mmol). The reaction mixture was stirred 4 h at 60° C., then diluted with saturated ammonium chloride solution and saturated sodium bicarbonate solution, and extracted with ethyl acetate (2×100 mL). The organic extracts were washed with brine, dried over magnesium sulfate, filtered and concentrated under reduced pressure. Purification of the residue by PREP-HPLC afforded, after evaporation of the solvents, 32 mg (86% purity, 47% yield) of rac-3-[6-chloro-5-(4-pyridyl)-3-[3-(trifluoromethyl)phenoxy]pyridazin-4-yl]-5-[(2,4-dimethylphenyl)methyl]-5,6-dihydro-4H-1,2,4-oxadiazine as an oil.

Preparation of Example 13: preparation of rac-5-[(2,4-dimethylphenyl)methyl]-3-[6-(2-methoxyethylsulfanyl)-5-methyl-3-[3-(trifluoromethyl)phenoxy]pyridazin-4-yl]-5,6-dihydro-4H-1,2,4-oxadiazine (compound 1.187)

Under argon, 2-methoxyethanethiol (20 mg, 0.22 mmol) and sodium hydride (8 mg, 0.22 mmol) were added at 0° C. to a solution of rac-3-[6-chloro-5-methyl-3-[3-(trifluoromethyl)phenoxy]pyridazin-4-yl]-5-[(2,4-dimethylphenyl)methyl]-5,6-dihydro-4H-1,2,4-oxadiazine (100 mg, 0.20 mmol) in THE (2 mL). The reaction mixture was stirred at 0° C. for 2 h, then it was diluted with water and extracted with ethyl acetate (2×50 mL). The organic extracts were washed with brine, dried over magnesium sulfate, filtered and concentrated under reduced pressure. Purification of the residue by column chromatography on silica gel (gradient heptane/EtOAc) afforded, after evaporation of the solvents, 21 mg (96% purity, 18% yield) of rac-5-[(2,4-dimethylphenyl)methyl]-3-[6-(2-methoxyethylsulfanyl)-5-methyl-3-[3-(trifluoromethyl)phenoxy]pyridazin-4-yl]-5,6-dihydro-4H-1,2,4-oxadiazine as a colorless oil.

Preparation of Example 14: preparation of rac-2-[6-chloro-3-(3-cyclopropylphenoxy)pyridazin-4-yl]-6-[(2,4-dimethylphenyl)methyl]-5,6-dihydro-1H-pyrimidin-4-one (compound 1.078)

Step 1: preparation of methyl 6-chloro-3-(3-cyclopropylphenoxy)pyridazine-4-carboximidate (compound 25-01)

Under argon, sodium methanolate (43 mg, 0.81 mmol) was added at 0° C. to a solution of 6-chloro-3-(3-cyclopropylphenoxy)pyridazine-4-carbonitrile (200 mg, 0.74 mmol) in MeOH (2 mL). The reaction mixture was stirred at 0° C. for 30 min. The crude solution contained 48% of methyl 6-chloro-3-(3-cyclopropylphenoxy)pyridazine-4-carboximidate and was used without further purification in the next step.

Step 2: preparation of rac-2-[6-chloro-3-(3-cyclopropylphenoxy)pyridazin-4-yl]-6-[(2,4-dimethylphenyl)methyl]-5,6-dihydro-1H-pyrimidin-4-one To the previous solution was added rac-3-amino-4-(2,4-dimethylphenyl)butanamide (93 mg, 0.45 mmol) dissolved in MeOH (0.5 mL) and acetic acid (17 μL). The reaction mixture was stirred at room temperature for 15 min then heated at 60° C. for 18 h. After cooling to room temperature, the mixture was poured into a saturated sodium bicarbonate solution and extracted with ethyl acetate (2×50 mL). The organic extracts were washed with brine, dried over sodium sulfate, filtered and concentrated under reduced pressure. Purification of the residue by preparative HPLC afforded, after evaporation of the solvents, 40.7 mg (100% purity, 29% yield) of rac-2-[6-chloro-3-(3-cyclopropylphenoxy)pyridazin-4-yl]-6-[(2,4-dimethylphenyl)methyl]-5,6-dihydro-1H-pyrimidin-4-one as an oil.

Preparation of Example 15: preparation of rac-5-[(2,4-dimethylphenoxy)methyl]-3-[6-methyl-3-[3-(trifluoromethyl)phenoxy]pyridazin-4-yl]-5,6-dihydro-4H-1,2,4-oxadiazine (compound 1.144)

Step 1: preparation of tert-butyl rac-4-[(2,4-dimethylphenoxy)methyl]-2,2-dimethyl-oxazolidine-3-carboxylate Under argon, diisopropyl azodicarboxylate (1.92 g, 9.51 mmol) was added to a solution of tert-butyl rac-4-(hydroxymethyl)-2,2-dimethyl-oxazolidine-3-carboxylate (2.0 g, 8.64 mmol), 2,4-dimethylphenol (1.16 g, 9.51 mmol) and triphenylphosphine (2.49 g, 9.51 mmol) in 2-methyltetrahydrofuran (30 mL). The reaction mixture was heated at 80° C. for 3 h, cooled to room temperature and extracted with ethyl acetate (2×200 mL). The organic layer was washed with 1 M aqueous NaOH solution and brine, dried over magnesium sulfate, filtered and concentrated under reduced pressure. Purification of the residue by column chromatography on silica gel (gradient heptane/EtOAc) afforded, after evaporation of the solvents, 1.82 g (95% purity, 59% yield) of tert-butyl rac-4-[(2,4-dimethylphenoxy)methyl]-2,2-dimethyl-oxazolidine-3-carboxylate as a colorless oil.

Step 2: preparation of rac-2-amino-3-(2,4-dimethylphenoxy)propan-1-ol

A solution of tert-butyl rac-4-[(2,4-dimethylphenoxy)methyl]-2,2-dimethyl-oxazolidine-3-carboxylate (1.8 g, 5.37 mmol) was dissolved in MeOH (25 mL) and aqueous 1M HCl solution (15 mL). The reaction mixture was stirred at 50° C. for 2 h. After cooling to room temperature, the solvents were evaporated and the residue was poured into a saturated sodium bicarbonate solution and extracted with ethyl acetate (2×200 mL). The organic extracts were dried over magnesium sulfate, filtered and concentrated under reduced pressure. Evaporation of the solvents afforded 833 mg (87% purity, 69% yield) of rac-2-amino-3-(2,4-dimethylphenoxy)propan-1-ol as a yellow oil.

Step 3: preparation of tert-butyl N-[rac-1-[(2,4-dimethylphenoxy)methyl]-2-hydroxy-ethyl]carbamate Di-tert-butyl dicarbonate (1.02 mL, 4.46 mmol) and N,N-Diisopropylethylamine (1.55 mL, 8.93 mmol) were successively added to a solution of rac-2-amino-3-(2,4-dimethylphenoxy)propan-1-ol (830 mg, 4.25 mmol) in 2-methyltetrahydrofuran (5.5 mL). The reaction mixture was stirred at room temperature for 1 h30, then it was diluted with brine and extracted with ethyl acetate (2×200 mL). The organic extracts were dried over magnesium sulfate, filtered and concentrated under reduced pressure. Purification of the residue by column chromatography on silica gel (gradient heptane/EtOAc) afforded, after evaporation of the solvents, 909 mg (97% purity, 70% yield) of tert-butyl N-[rac-1-[(2,4-dimethylphenoxy)methyl]-2-hydroxy-ethyl]carbamate as a colorless oil.

Step 4: preparation of tert-butyl N-[rac-1-[(2,4-dimethylphenoxy)methyl]-2-(1,3-dioxoisoindolin-2-yl)oxy-ethyl]carbamate (compound 2-13)

Under argon, diisopropyl azodicarboxylate (684 mg, 3.38 mmol) was added to a solution of tert-butyl N-[rac-1-[(2,4-dimethylphenoxy)methyl]-2-hydroxy-ethyl]carbamate (909 mg, 3.0 mmol), N-hydroxyphthalimide (552.2 mg, 3.38 mmol) and triphenylphosphine (888 mg, 3.38 mmol) in 2-methyltetrahydrofuran (10 mL). The reaction mixture was stirred at room temperature for 2 h, then extracted with ethylacetate (2×200 mL). The organic layer was washed with 1M aqueous NaOH solution and brine, dried over magnesium sulfate, filtered and concentrated under reduced pressure. Purification of the residue by column chromatography on silica gel (gradient heptane/EtOAc) afforded, after evaporation of the solvents, 1.16 g (92% purity, 79% yield) of tert-butyl N-[rac-1-[(2,4-dimethylphenoxy)methyl]-2-(1,3-dioxoisoindolin-2-yl)oxy-ethyl]carbamate as a colorless oil.

Step 5: preparation of 2-[rac-2-amino-3-(2,4-dimethylphenoxy)propoxy]isoindoline-1,3-dione 2,2,2-trifluoroacetate (compound 2-12)

To a solution of tert-butyl N-[rac-1-[(2,4-dimethylphenoxy)methyl]-2-(1,3-dioxoisoindolin-2-yl)oxy-ethyl]carbamate (1.16 g, 2.63 mmol) in 1,2-dichloroethane (15 mL) was added trifluoroacetic acid (1.014 mL, 13.17 mmol). The reaction mixture was stirred at room temperature for 4 h. Evaporation of the solvents afforded 1.4 g (79% purity, 93% yield) of 2-[rac-2-amino-3-(2,4-dimethyl-phenoxy) propoxy]isoindoline-1,3-dione;2,2,2-trifluoroacetic acid as a yellow oil.

Step 6: preparation of 6-methyl-N-[rac-1-[(2,4-dimethylphenoxy)methyl]-2-(1,3-dioxoisoindolin-2-yl) oxy-ethyl]-3-[3-(trifluoromethyl)phenoxy] pyridazine-4-carboxamide (compound 3-33)

Under argon, to a solution of 6-methyl-3-[3-(trifluoromethyl)phenoxy]pyridazine-4-carboxylic acid (405 mg, 1.36 mmol) and HATU (542 mg, 1.42 mmol) in DMF (10 mL) were successively added 2-[rac-2-amino-3-(2,4-dimethylphenoxy)propoxy]isoindoline-1,3-dione;2,2,2-trifluoroacetic acid (647 mg, 1.42 mmol) and N,N-Diisopropylethylamine (0.71 mL, 4.07 mmol). The reaction mixture was stirred for 1 h at room temperature. It was then diluted with water and extracted with ethyl acetate (2×200 mL). The organic extracts were dried over magnesium sulfate, filtered and concentrated under reduced pressure. Purification of the residue by column chromatography on silica gel (gradient heptane/EtOAc) afforded, after evaporation of the solvents, 550 mg (93% purity, 60% yield) of 6-methyl-N-[rac-1-[(2,4-dimethylphenoxy)methyl]-2-(1,3-dioxoisoindolin-2-yl) oxy-ethyl]-3-[3-(trifluoromethyl)phenoxy]pyridazine-4-carboxamide as a colorless oil.

Step 7: preparation of 6-methyl-N-[rac-1-(aminooxymethyl)-2-(2,4-dimethylphenoxy)ethyl]-3-[3-(trifluoromethyl)phenoxy]pyridazine-4-carboxamide (compound 4-33)

Under argon, hydrazine monohydrate (0.16 mL, 2.66 mmol) was added to a solution of 6-methyl-N-[rac-1-[(2,4-dimethylphenoxy)methyl]-2-(1,3-dioxoisoindolin-2-yl)oxy-ethyl]-3-[3-(trifluoro-methyl)phenoxy]pyridazine-4-carboxamide (550 mg, 0.89 mmol) in DCM/MeOH (16 mL, 1:1). The reaction mixture was stirred for 2 h at room temperature then concentrated. The residue was diluted with water and extracted with dichloromethane (2×200 mL). The organic extracts were dried over magnesium sulfate, filtered and concentrated under reduced pressure. Evaporation of the solvents afforded 490 mg (75% purity, 84% yield) of 6-methyl-N-[rac-1-(aminooxymethyl)-2-(2,4-dimethylphenoxy)ethyl]-3-[3-(trifluoromethyl)phenoxy]pyridazine-4-carboxamide as a white oil.

Step 8: preparation of rac-5-[(2,4-dimethylphenoxy) methyl]-3-[6-methyl-3-[3-(trifluoro-methyl)phenoxy]pyridazin-4-yl]-5,6-dihydro-4H-1,2,4-oxadiazine Under argon, $POCl_3$ (0.22 mL, 2.39 mmol) was added at 80° C. to a solution of 6-methyl-N-[rac-1-(aminooxymethyl)-2-(2,4-dimethylphenoxy)ethyl]-3-[3-(trifluoromethyl)phenoxy]pyridazine-4-carboxamide (490 mg, 0.80 mmol) in AcCN (10 mL). The reaction mixture was stirred for 4 h at 80° C. After cooling to room temperature, the mixture was poured into a saturated sodium bicarbonate solution, then extracted with ethyl acetate (2×200 mL). The organic extracts were dried over magnesium sulfate, filtered and concentrated under reduced pressure. Purification of the residue by column chromatography on silica gel (gradient heptane/EtOAc) afforded, after evaporation of the solvents, 89 mg (95% purity, 22% yield) of rac-5-[(2,4-dimethylphenoxy)methyl]-3-[6-methyl-3-[3-(trifluoro-methyl)phenoxy] pyridazin-4-yl]-5,6-dihydro-4H-1,2,4-oxadiazine as a brown oil.

Preparation of Example 16: preparation of rac-5-(1-methylindol-5-yl)-3-[6-methyl-3-[3-(trifluoromethyl)phenoxy]pyridazin-4-yl]-4,5,6,7-tetrahydro-1,2,4-oxadiazepine (compound 1.062)

Step 1: preparation of N'-allyloxy-6-methyl-3-[3-(trifluoromethyl)phenoxy]pyridazine-4-carboxamidine In analogy to step 1 of example 4.

Step 2: preparation of 6-methyl-N'-[3-(1-methylindol-5-yl)allyloxy]-3-[3-(trifluoromethyl)phenoxy] pyridazine-4-carboxamidine (compound 30-01)

Under argon, a mixture of N'-allyloxy-6-methyl-3-[3-(trifluoromethyl)phenoxy]pyridazine-4-carboxamidine (500 mg, 1.42 mmol), 5-bromo-1-methyl-indole (596 mg, 2.83 mmol), triethylamine (0.40 mL, 2.84 mmol), palladium(II) acetate (32 mg, 0.14 mmol) and tri-2tolylphosphine (86 mg, 0.28 mmol) in AcCN (5 mL) was stirred at reflux for 18 h. After cooling to room temperature, the reaction mixture was diluted with a saturated ammonium chloride solution and extracted with ethyl acetate (3×30 mL). Purification of the residue by column chromatography on silica gel (gradient heptane/EtOAc) afforded, after evaporation of the solvents, 203 mg (93% purity, 27% yield) of 6-methyl-N'-[3-(1-methylindol-5-yl)allyloxy]-3-[3-(trifluoromethyl)phenoxy] pyridazine-4-carboxamidine as an oil.

Step 3: preparation of rac-5-(1-methylindol-5-yl)-3-[6-methyl-3-[3-(trifluoromethyl)phenoxy]pyridazin-4-yl]-4,5,6,7-tetrahydro-1,2,4-oxadiazepine A solution of iodine (13.2 mg, 0.052 mmol) and phenylsilane (11.2 mg, 0.104 mmol) in dichloromethane (5 mL) was stirred at room temperature for 30 min, then 6-methyl-N'-[3-(1-methylindol-5-yl)allyloxy]-3-[3-(trifluoromethyl) phenoxy]pyridazine-4-carboxamidine (25.0 mg, 0.052 mmol) was added. The reaction mixture was stirred for 1 h, then diluted with a saturated sodium thiosulfate solution and extracted with ethyl acetate (2×50 mL). The organic extracts were dried over magnesium sulfate, filtered and concentrated under reduced pressure. Purification of the residue by PREP-HPLC afforded, after evaporation of the solvents, 8 mg (88% purity, 28% yield) of rac-5-(1-methylindol-5-yl)-3-[6-methyl-3-[3-(trifluoromethyl)phenoxy]pyridazin-4-yl]-4,5,6,7-tetrahydro-1,2,4-oxadiazepine as an oil.

Preparation of Example 17: preparation of rac-3-[6-chloro-3-[3-(trifluoromethyl)phenoxy]pyridazin-4-yl]-5-[(2,4-dimethylphenyl)methyl]-1,4,5,6-tetrahydro-1,2,4-triazine (compound 1.173)

Step 1: preparation of 6-chloro-N-[1-(chloromethyl)-2-(2,4-dimethylphenyl)ethyl]-3-[3-(trifluoromethyl)phenoxy]pyridazine-4-carboxamide See step 1 of example 2.

Step 2: preparation of rac-3-[6-chloro-3-[3-(trifluoromethyl)phenoxy]pyridazin-4-yl]-5-[(2,4-dimethylphenyl)methyl]-1,4,5,6-tetrahydro-1,2,4-triazine To a solution of 6-chloro-N-[1-(chloromethyl)-2-(2,4-dimethylphenyl)ethyl]-3-[3-(trifluoro-methyl)phenoxy] pyridazine-4-carboxamide (339 mg, 0.68 mmol) in toluene (6 mL) was added phosphorous pentachloride (425 mg, 2.04 mmol). The reaction mixture was stirred at 75° C. for 1 h30, then concentrated under reduced pressure. The residue was dissolved in AcCN (4 mL) and a solution of hydrazine hydrate (170.27 mg, 3.40 mmol) was added at room temperature to the reaction mixture. After stirring at room temperature for 1 h the reaction mixture was diluted with water and extracted with ethyl acetate (2×100 mL). The organic extracts were washed with water and brine, dried over sodium sulfate, filtered and concentrated under reduced pressure. Purification of the residue by column chromatography on silica gel (gradient heptane/EtOAc) afforded, after evaporation of the solvents, 197 mg (100% purity, 60% yield) of rac-3-[6-chloro-3-[3-(trifluoromethyl)phenoxy] pyridazin-4-yl]-5-[(2,4-dimethylphenyl)methyl]-1,4,5,6-tetrahydro-1,2,4-triazine.

Preparation of Example 18: preparation of 6-chloro-4-[rac-6-[(2,4-dimethylphenyl)methyl]-1,4,5,6-tetrahydropyrimidin-2-yl]-3-[3-(trifluoromethyl)phenoxy]pyridazine (compound 1.117)

Step 1: preparation of tert-butyl N-[rac-1-[(2,4-dimethylphenyl)methyl]-3-hydroxy-propyl]carbamate Di-tert-butyl dicarbonate (2.13 g, 9.79 mmol) and triethylamine (2.73 mL, 19.6 mmol) were successively added at 0° C. to a suspension of rac-3-amino-4-(2,4-dimethylphenyl)butan-1-ol hydrochloride (1.5 g, 6.52 mmol) in tetrahydrofuran (10 mL). The reaction mixture was stirred at room temperature for 18 h, then concentrated under reduced pressure. Purification of the residue by column chromatography on silica gel (gradient heptane/EtOAc) afforded, after evaporation of the solvents, 1.8 g (97% purity, 91% yield) of tert-butyl N-[rac-1-[(2,4-dimethylphenyl)methyl]-3-hydroxy-propyl]carbamate as a white solid.

Step 2: preparation of tert-butyl N-[rac-1-[(2,4-dimethylphenyl)methyl]-3-(1,3-dioxoisoindolin-2-yl)propyl]carbamate Under argon, diethyl azodicarboxylate (6.87 g, 15.3 mmol) was added at 0° C. to a solution of tert-butyl N-[rac-1-[(2,4-dimethylphenyl)methyl]-3-hydroxy-propyl] carbamate (1.8 g, 6.13 mmol), phthalimide (5.41 g, 36.8 mmol) and triphenylphosphine (9.65 g, 36.8 mmol) in tetrahydrofuran (200 mL). The reaction mixture was stirred at room temperature for 24 h, diluted with water and extracted with ethylacetate (3×200 mL). The organic layer was washed with brine, dried over magnesium sulfate, filtered and concentrated under reduced pressure. Purification of the residue by column chromatography on silica gel (gradient heptane/EtOAc) afforded, after evaporation of the solvents, 2.0 g (84% purity, 60% yield) of tert-butyl N-[rac-1-[(2,4-dimethylphenyl)methyl]-3-(1,3-dioxoisoindolin-2-yl)propyl]carbamate as a colorless oil.

Step 3: preparation of 2-[rac-3-amino-4-(2,4-dimethylphenyl)butyl]isoindoline-1,3-dione;2,2,2-trifluoroacetate To a solution of tert-butyl N-[rac-1-[(2,4-dimethylphenyl) methyl]-3-(1,3-dioxoisoindolin-2-yl)propyl]carbamate (1.2 g, 2.84 mmol) in dichloromethane (20 mL) was added trifluoroacetic acid (0.65 mL, 8.52 mmol). The reaction mixture was stirred at room temperature for 3 days. Evaporation of the solvents afforded 1.2 g (54% purity, 52% yield) of 2-[rac-3-amino-4-(2,4-dimethylphenyl)butyl]iso-indoline-1,3-dione;2,2,2-trifluoroacetic acid as a solid.

Step 4: preparation of rac-4-(2,4-dimethylphenyl)butane-1,3-diamine

Under argon, hydrazine monohydrate (3.73 mL, 41.24 mmol) was added to a solution of 2-[rac-3-amino-4-(2,4-dimethylphenyl)butyl]isoindoline-1,3-dione;2,2,2-trifluoroacetic acid (1.2 g, 2.75 mmol) in EtOH (5 mL). The reaction mixture was stirred for 3 days at room temperature then concentrated. It was then diluted with water and extracted with dichloromethane (2×200 mL). The organic extracts were dried over magnesium sulfate, filtered and concentrated under reduced pressure. The residue was stirred in MTBE and the white solid that formed was filtered off. Concentration of the filtrate afforded 520 mg (95% purity, 93% yield) of rac-4-(2,4-dimethylphenyl)butane-1,3-diamine as a white solid.

Step 5: preparation of methyl 6-chloro-3-[3-(trifluoromethyl)phenoxy]pyridazine-4-carboximidate See step 1 of example 5 starting from 6-chloro-3-[3-(trifluoromethyl)phenoxy]pyridazine-4-carbonitrile (100 mg, 0.33 mmol)

Step 6: preparation of 6-chloro-4-[rac-6-[(2,4-dimethylphenyl)methyl]-1,4,5,6-tetrahydropyrimidin-2-yl]-3-[3-(trifluoromethyl)phenoxy]pyridazine To the previous solution of methyl 6-chloro-3-[3-(trifluoromethyl)phenoxy]pyridazine-4-carboximidate was added at 0° C. rac-4-(2,4-dimethylphenyl)butane-1,3-diamine (124 mg, 0.45 mmol) dissolved in MeOH (0.5 mL) and acetic acid (9 μL). The reaction mixture was stirred at room temperature for 5 h, then the mixture was poured into a saturated sodium bicarbonate solution and extracted with ethyl acetate (2×50 mL). The organic extracts were washed with brine, dried over sodium sulfate, filtered and concentrated under reduced pressure. Purification of the residue by column chromatography on silica gel (gradient heptane/EtOAc) afforded, after evaporation of the solvents, 26 mg (90% purity, 16% yield) of 6-chloro-4-[rac-6-[(2,4-dimethylphenyl)methyl]-1,4,5,6-tetrahydropyrimidin-2-yl]-3-[3-(trifluoromethyl)phenoxy]pyridazine as a yellow oil.

Preparation of Example 19: preparation of rac-6,6-difluoro-5-(4-methoxyphenyl)-3-[6-methyl-3-[3-(trifluoromethyl)phenoxy]pyridazin-4-yl]-4,5-dihydro-1,2,4-oxadiazine (compound 1.154)

Step 1: preparation of N'-hydroxy-6-methyl-3-[3-(trifluoromethyl)phenoxy]pyridazine-4-carboxamidine (compound 10-02)

See step 3 of example 3

Step 2: preparation of N'-[1,1-difluoro-2-(4-methoxyphenyl)-2-oxo-ethoxy]-6-methyl-3-[3-(trifluoro-methyl)phenoxy]pyridazine-4-carboxamidine (compound 12-14)

Under argon, 2-tert-butylimino-N,N-diethyl-1,3-dimethyl-1,3,2lambda5-diazaphosphinan-2-amine (BEMP) (105 mg, 0.38 mmol) was added at room temperature to a solution of N'-hydroxy-6-methyl-3-[3-(trifluoromethyl)phenoxy]pyridazine-4-carboxamidine (100 mg, 0.32 mmol) in AcCN (1.5 mL). After 15 min, 2-bromo-2,2-difluoro-1-(4-methoxyphenyl)ethanone (127 mg, 0.48 mmol) was added and the reaction was stirred further for 15 min. The reaction mixture was diluted with a saturated ammonium chloride solution and extracted with ethyl acetate (2×50 mL). The organic extracts were dried over magnesium sulfate, filtered and concentrated under reduced pressure. Evaporation of the solvents afforded 222 mg (27% purity, 80% yield) of N'-[1,1-difluoro-2-(4-methoxyphenyl)-2-oxo-ethoxy]-6-methyl-3-[3-(trifluoromethyl)phenoxy]pyridazine-4-carboxamidine as an oil.

Step 3: preparation of rac-6,6-difluoro-5-(4-methoxyphenyl)-3-[6-methyl-3-[3-(trifluoro-methyl)phenoxy]pyridazine-4-yl]-4,5-dihydro-1,2,4-oxadiazine Under argon, N'-[1,1-difluoro-2-(4-methoxyphenyl)-2-oxo-ethoxy]-6-methyl-3-[3-(trifluoro-methyl)phenoxy]pyridazine-4-carboxamidine (222 mg, 0.25 mmol) was dissolved in tert-butanol (6.4 mL) and acetic acid (1.6 mL) and heated to 80° C. After 30 min, sodium cyanoborohydride (21 mg, 0.34 mmol) was added and the reaction was stirred further for 2 h. After cooling to room temperature, the mixture was poured into a 1M aqueous NaOH solution and extracted with ethyl acetate (2×20 mL). The organic extracts were dried over magnesium sulfate, filtered and concentrated under reduced pressure. Purification of the residue by PREP-HPLC afforded, after evaporation of the solvents, 4 mg (96% purity, 3% yield) of rac-6,6-difluoro-5-(4-methoxyphenyl)-3-[6-methyl-3-[3-(trifluoro-methyl)phenoxy]pyridazin-4-yl]-4,5-dihydro-1,2,4-oxadiazine as a yellow solid.

Preparation of Example 20: preparation of rac-3-[6-chloro-3-(3-cyclopropyl-2-fluoro-phenoxy)-5-methyl-pyridazin-4-yl]-5-[(2,4-dimethylphenyl)methyl]-5,6-dihydro-4H-1,2,4-oxadiazine (compound 1.058)

Step 1: preparation of isopropyl 6-chloro-3-(3-cyclopropyl-2-fluoro-phenoxy)-5-methyl-pyridazine-4-carboxylate (compound 1-24)

To a solution of isopropyl 6-chloro-3-(3-cyclopropyl-2-fluoro-phenoxy)pyridazine-4-carboxylate (800 mg, 2.28 mmol) in dimethyl sulfoxide (2.5 mL) was added nitromethane (0.62 mL, 11.40 mmol). The reaction was stirred at room temperature for 30 min, then triethylamine (0.48 mL, 3.42 mmol) was added. The reaction was stirred at room temperature for 24 h, then it was diluted with water and extracted with ethyl acetate (2×100 mL). The organic extracts were dried over magnesium sulfate, filtered and concentrated under reduced pressure. Evaporation of the solvents afforded 917 mg (76% purity, 84% yield) of isopropyl 6-chloro-3-(3-cyclopropyl-2-fluoro-phenoxy)-5-methyl-pyridazine-4-carboxylate as an orange oil.

Step 2: preparation of 6-chloro-3-(3-cyclopropyl-2-fluoro-phenoxy)-5-methyl-pyridazine-4-carboxylic acid (compound 1-02)

To a solution of isopropyl 6-chloro-3-(3-cyclopropyl-2-fluoro-phenoxy)-5-methyl-pyridazine-4-carboxylate (927 mg, 2.5 mmol) in tetrahydrofuran (4 mL) was added a 2M aqueous solution of lithium hydroxide (182 mg, 7.62 mmol). The reaction was stirred for 4 days at room temperature then it was diluted with water. The aqueous phase was acidified with 1 M aqueous HCl solution and extracted with ethyl acetate (3×200 mL). The organic extracts were dried over magnesium sulfate, filtered and concentrated under reduced pressure. Evaporation of the solvents afforded 617 mg (81% purity, 60% yield) of 6-chloro-3-(3-cyclopropyl-2-fluoro-phenoxy)-5-methyl-pyridazine-4-carboxylic acid as a solid.

Step 3: preparation of 6-chloro-3-(3-cyclopropyl-2-fluoro-phenoxy)-5-methyl-N-[rac-1-[(2,4-dimethyl-phenyl)methyl]-2-(1,3-dioxoisoindolin-2-yl)oxy-ethyl]pyridazine-4-carboxamide Under argon, to a solution of 6-chloro-3-(3-cyclopropyl-2-fluoro-phenoxy)-5-methyl-pyridazine-4-carboxylic acid (500 mg, 1.55 mmol) and HATU (648 mg, 1.70 mmol) in DMF (10 mL) were successively added at 0° C., 2-[rac-2-amino-3-(2,4-dimethylphenyl)propoxy]isoindoline-1,3-dione 2,2,2-trifluoroacetate (747 mg, 1.70 mmol) and N,N-Diisopropylethylamine (0.80 mL, 4.64 mmol). After 15 min at 0° C., the reaction mixture was stirred for 18 h at room temperature. It was then diluted with water and extracted with ethyl acetate (2×200 mL). The organic extracts were dried over magnesium sulfate, filtered and concentrated under reduced pressure. Purification of the residue by column chromatography on silica gel (gradient heptane/EtOAc) afforded, after evaporation of the solvents, 639.5 g (100% purity, 65% yield) of 6-chloro-3-(3-cyclopropyl-2-fluoro-phenoxy)-5-methyl-N-[rac-1-[(2,4-dimethylphenyl)methyl]-2-(1,3-dioxoisoindolin-2-yl)oxy-ethyl]pyridazine-4-carboxamide as a solid.

Step 4: preparation of 6-chloro-3-(3-cyclopropyl-2-fluoro-phenoxy)-5-methyl-N-[rac-1-(aminooxy-methyl)-2-(2,4-dimethylphenyl)ethyl]pyridazine-4-carboxamide Under argon, hydrazine monohydrate (0.18 mL, 3.0 mmol) was added to a solution of 6-chloro-3-(3-cyclopropyl-2-fluoro-phenoxy)-5-methyl-N-[rac-1-[(2,4-dimethylphenyl)methyl]-2-(1,3-dioxoisoindolin-2-yl)oxy-ethyl]pyridazine-4-carboxamide (639 mg, 1.0 mmol) in DCM/MeOH (12 mL, 1:1). The reaction mixture was stirred for 18 h at room temperature and concentrated. It was then diluted with water and extracted with dichloromethane (2×200 mL). The organic extracts were dried over magnesium sulfate, filtered and concentrated under reduced pressure. Evaporation of the solvents afforded 453 mg (100% purity, 89% yield) of 6-chloro-3-(3-cyclopropyl-2-fluoro-phenoxy)-5-methyl-N-[rac-1-(aminooxymethyl)-2-(2,4-dimethylphenyl)ethyl]pyridazine-4-carboxamide as a white oil.

Step 5: preparation of rac-3-[6-chloro-3-(3-cyclopropyl-2-fluoro-phenoxy)-5-methyl-pyridazin-4-yl]-5-[(2,4-dimethylphenyl)methyl]-5,6-dihydro-4H-1,2,4-oxadiazine Under argon, $POCl_3$ (0.25 mL, 2.72 mmol) was added at 80° C. to a solution 6-chloro-3-(3-cyclopropyl-2-fluoro-phenoxy)-5-methyl-N-[rac-1-(aminooxymethyl)-2-(2,4-dimethylphenyl)ethyl]pyridazine-4-carboxamide (453 mg, 0.90 mmol) in AcCN (5 mL). The reaction mixture was stirred for 18 h at 80° C. After cooling to room temperature, the mixture was poured into a saturated sodium bicarbonate solution, then extracted with ethyl acetate (2×200 mL). The organic extracts were dried over magnesium sulfate, filtered and concentrated under reduced pressure. Purification of the residue by column chromatography on silica gel (gradient heptane/EtOAc) afforded, after evaporation of the solvents, 196 mg (100% purity, 44% yield) of rac-3-[6-chloro-3-(3-cyclopropyl-2-fluoro-phenoxy)-5-methyl-pyridazin-4-yl]-5-[(2,4-dimethylphenyl)methyl]-5,6-dihydro-4H-1,2,4-oxadiazine as a yellow solid.

The compounds as shown in table 1 below were prepared in analogy with the examples provided above or following methods described herein. $^1$H-NMR data of these compounds is shown in table 2.

TABLE 1

Compounds according to formula (I)

(I)

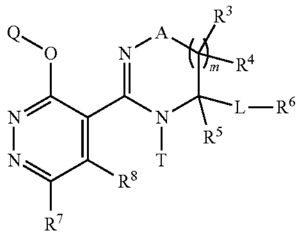

wherein 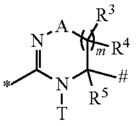 in table 1 has the following meanings:

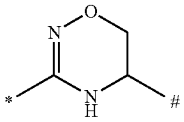

Ring 1

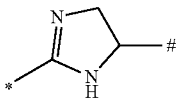

Ring 2

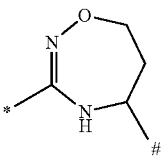

Ring 3

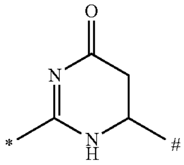

Ring 4

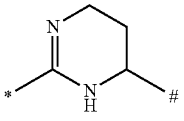

Ring 5

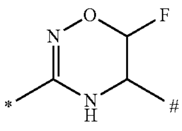

Ring 6

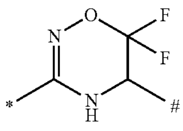

Ring 7

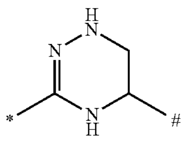

Ring 8

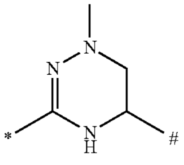

Ring 9

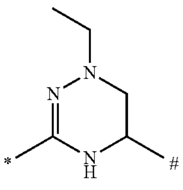

Ring 10

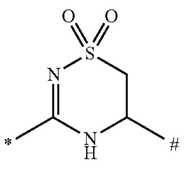

Ring 11

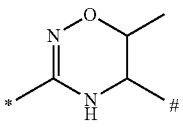

Ring 12

TABLE 1-continued

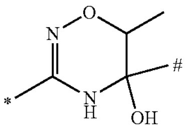

Ring 13

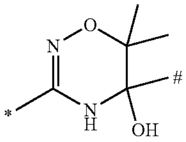

Ring 14

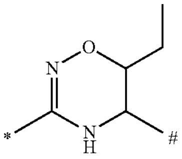

Ring 15

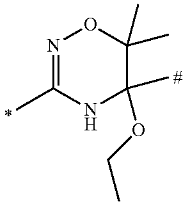

Ring 17

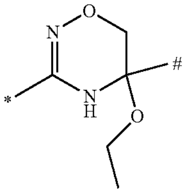

Ring 17

In table 1, "#" denotes the point of attachment to the L—$R^6$ group and "*" denotes the point of attachment to the pyridazin-4-yl group.

| Ex No | $R^7$ | $R^8$ | Q | 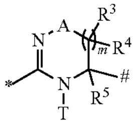 | L—$R^6$ | Log P |
|---|---|---|---|---|---|---|
| I-001 | chloro | H | 3-cyclopropyl-2-fluorophenyl | Ring 1 | (2,4-dimethylphenyl)methyl | 4.61[a] |
| I-002 | methylamino | H | 3-(trifluoromethyl)phenyl | Ring 1 | (2,4-dimethylphenyl)methyl | 2.84[a] |
| I-003 | chloro | H | 3-(trifluoromethyl)phenyl | Ring 1 | (4-chlorophenyl)methyl | 3.99[a]; 3.96[b] |
| I-004 | methyl | H | 2-fluoro-3-(trifluoromethyl) phenyl | Ring 1 | (2,4-dimethylphenyl)methyl | 3.99[a] |
| I-005 | chloro | H | 2-fluoro-3-methoxyphenyl | Ring 1 | (2,4-dimethylphenyl)methyl | 3.91[a] |
| I-006 | methyl | methoxy | 3-chlorophenyl | Ring 1 | (2,4-dimethylphenyl)methyl | 3.50[a] |
| I-007 | chloro | H | 3-(trifluoromethyl)phenyl | Ring 2 | (2,4-dichlorophenyl)methyl | 2.39[a] |
| I-008 | cyclopropylamino | H | 3-(trifluoromethyl)phenyl | Ring 1 | (2,4-dimethylphenyl)methyl | 3.17[a] |
| I-009 | 1-ethoxyethen-1-yl | H | 3-(trifluoromethyl)phenyl | Ring 1 | (2,4-dimethylphenyl)methyl | 4.98[a] |
| I-010 | methyl | H | 3-(trifluoromethyl)phenyl | Ring 1 | 2,4-dichlorophenyl | 3.85[a]; 3.80[b] |
| I-011 (*) | methyl | H | 3-(trifluoromethyl)phenyl | Ring 1 | 1-methyl-1H-indol-3-yl | 3.23[a] |
| I-012 | ethyl | H | 3-(trifluoromethyl)phenyl | Ring 1 | (2,4-dimethylphenyl)methyl | 4.20[a] |
| I-013 (*) | methyl | H | 3-(difluoromethyl)phenyl | Ring 1 | (2,4-dimethylphenyl)methyl | 3.29[a] |
| I-014 | vinyl | H | 3-(trifluoromethyl)phenyl | Ring 1 | (2,4-dimethylphenyl)methyl | 4.25[a] |
| I-015 | methyl | H | 3-(trifluoromethyl)phenyl | Ring 1 | naphthalen-2-yl | 3.48[a] |
| I-016 (*) | chloro | H | 3-(trifluoromethyl)phenyl | Ring 1 | (4-bromo-2-chlorophenyl)methyl | 4.61[a] |
| I-017 (*) | chloro | H | 3-(trifluoromethyl)phenyl | Ring 1 | (4-bromo-2-methylphenyl)methyl | 4.49[a] |
| I-018 | methyl | H | 3-(trifluoromethyl)phenyl | Ring 1 | 3,4-dimethylphenyl | 3.58[a] |
| I-019 | chloro | H | 3-(trifluoromethyl)phenyl | Ring 1 | (4-cyclopropyl-2-methylphenyl)methyl | 4.67[a] |
| I-020 | chloro | H | 3-(trifluoromethyl)phenyl | Ring 1 | (2-chloro-4-cyclopropylphenyl)methyl | 4.74[a] |
| I-021 | chloro | H | 3-(trifluoromethyl)phenyl | Ring 1 | (2-chloro-4-isopropylphenyl)methyl | 5.11[a] |
| I-022 | chloro | H | 3-(trifluoromethyl)phenyl | Ring 1 | (3,4-dimethylphenyl)methyl | 4.41[a] |
| I-023 | chloro | H | 3-(trifluoromethyl)phenyl | Ring 1 | (4-isopropyl-2-methylphenyl)methyl | 5.03[a] |
| I-024 | chloro | H | 3-(difluoromethyl)-2-fluorophenyl | Ring 1 | (2,4-dimethylphenyl)methyl | 4.08[a] |
| I-025 (*) | chloro | H | 3-(trifluoromethyl)phenyl | Ring 1 | (2,4-dichlorophenyl)methyl | 4.51[a] |
| I-026 | methyl | H | 3-(trifluoromethyl)phenyl | Ring 3 | 3-methylphenyl | 3.30[a] |
| I-027 (*) | methyl | H | 3-cyclopropyl-2-fluorophenyl | Ring 1 | (4-bromo-2-chlorophenyl)methyl | 4.28[a] |
| I-028 | methyl | H | 3-(difluoromethyl)phenyl | Ring 1 | (2,4-dichlorophenyl)methyl | 3.50[a] |
| I-029 | methyl | H | 3-(trifluoromethyl)phenyl | Ring 1 | furan-2-yl | 2.62[a] |
| I-030 (*) | methyl | H | 3-cyclopropyl-2-fluorophenyl | Ring 1 | (2,4-dichlorophenyl)methyl | 4.23[a] |
| I-031 | methyl | H | 3-(trifluoromethyl)phenyl | Ring 1 | phenyl | 2.94[a] |
| I-032 | methyl | H | 3-(trifluoromethyl)phenyl | Ring 1 | (2-chloro-4-isopropylphenyl)methyl | 4.56[a] |
| I-033 | chloro | H | 3-(2,2-difluorocyclopropyl) phenyl | Ring 1 | (4-bromo-2-chlorophenyl)methyl | 4.42[a] |
| I-034 | chloro | methyl | 3-(trifluoromethyl)phenyl | Ring 1 | (2,4-dimethylphenyl)methyl | 4.12[a] |
| I-035 | methyl | H | 3-(trifluoromethyl)phenyl | Ring 1 | (4-isopropyl-2-methylphenyl)methyl | 4.49[a] |
| I-036 | methyl | H | 2-fluoro-3-(trifluoromethyl) phenyl | Ring 1 | (2,4-dichlorophenyl)methyl | 4.03[a] |
| I-037 | chloro | methylamino | 3-(trifluoromethyl)phenyl | Ring 1 | (2,4-dimethylphenyl)methyl | 3.69[a] |
| I-038 | methyl | H | 3-(trifluoromethyl)phenyl | Ring 1 | (2-chloro-4-cyclopropylphenyl)methyl | 4.18[a] |

TABLE 1-continued

| | | | | | | |
|---|---|---|---|---|---|---|
| I-039 | chloro | H | 3-(1-fluorocyclopropyl) phenyl | Ring 1 | (2,4-dimethylphenyl)methyl | 4.34[a] |
| I-040 | methyl | H | 3-(trifluoromethyl)phenyl | Ring 1 | 4-chlorophenyl | 3.29[a] |
| I-041 | chloro | cyclopropylamino | 3-(trifluoromethyl)phenyl | Ring 1 | (2,4-dimethylphenyl)methyl | 4.03[a] |
| I-042 | acetyl | H | 3-(trifluoromethyl)phenyl | Ring 1 | (2,4-dimethylphenyl)methyl | 4.27[a] |
| I-043 | methyl | chloro | 3-chlorophenyl | Ring 1 | (2,4-dimethylphenyl)methyl | 3.83[a] |
| I-044 | chloro | H | 3-(2,2-difluorocyclopropyl) phenyl | Ring 1 | (2,4-dimethylphenyl)methyl | 4.24[a] |
| I-045 | methyl | H | 3-cyclopropyl-2-fluorophenyl | Ring 1 | (3,4-dimethylphenyl)methyl | 4.01[a] |
| I-046 | pyridin-4-yl | H | 3-(trifluoromethyl)phenyl | Ring 1 | (2,4-dimethylphenyl)methyl | 3.37[a] |
| I-047 | chloro | H | 2-fluoro-3-methylsulfanylphenyl | Ring 1 | (2,4-dimethylphenyl)methyl | 4.33[a] |
| I-048 | chloro | H | 2-fluoro-3-(trifluoromethoxy)phenyl | Ring 1 | (2,4-dimethylphenyl)methyl | 4.61[a] |
| I-049 | chloro | H | 3-(trifluoromethyl)phenyl | Ring 1 | 2,4-dichlorophenyl | 4.30[a]; 4.23[b] |
| I-050 | methyl | H | 3-cyclopropylphenyl | Ring 1 | (2,4-dimethylphenyl)methyl | 3.90[a] |
| I-051 (*) | chloro | H | 3-(trifluoromethyl)phenyl | Ring 1 | (2,4-dimethylphenyl)methyl | 4.39[a] |
| I-052 (*) | methyl | H | 3-cyclopropyl-2-fluorophenyl | Ring 1 | (2,4-dimethylphenyl)methyl | 4.01[a] |
| I-053 (*) | chloro | H | 3-(trifluoromethyl)phenyl | Ring 1 | (2,4-dimethylphenyl)methyl | 4.39[a] |
| I-054 | methyl | H | 3-(trifluoromethyl)phenyl | Ring 1 | indan-5-yl | 3.67[a] |
| I-055 (*) | methyl | methyl | 3-(trifluoromethyl)phenyl | Ring 1 | (2,4-dimethylphenyl)methyl | 3.63[a] |
| I-056 (*) | methyl | H | 3-cyclopropyl-2-fluorophenyl | Ring 1 | (4-bromo-2-methylphenyl)methyl | 4.12[a] |
| I-057 | methyl | H | 3-cyclopropyl-2-fluorophenyl | Ring 1 | (4-cyclopropyl-2-methylphenyl)methyl | 4.28[a] |
| I-058 | chloro | methyl | 3-cyclopropyl-2-fluorophenyl | Ring 1 | (2,4-dimethylphenyl)methyl | 4.30[a] |
| I-059 (*) | chloro | H | 3-(trifluoromethyl)phenyl | Ring 1 | (2,4-dimethylphenyl)methyl | 4.39[a] |
| I-060 | 3-chloropyridin-4-yl | H | 3-(trifluoromethyl)phenyl | Ring 1 | (2,4-dimethylphenyl)methyl | 4.37[a] |
| I-061 | methyl | H | 3-(trifluoromethyl)phenyl | Ring 1 | 4-methoxyphenyl | 2.90[a] |
| I-062 | methyl | H | 3-(trifluoromethyl)phenyl | Ring 3 | 1-methyl-1H-indol-5-yl | 1.92[a] |
| I-063 | (1Z)-1-(methoxyimino) ethyl | H | 3-(trifluoromethyl)phenyl | Ring 1 | (2,4-dimethylphenyl)methyl | 4.53[a] |
| I-064 | (1E)-1-(methoxyimino) ethyl | H | 3-(trifluoromethyl)phenyl | Ring 1 | (2,4-dimethylphenyl)methyl | 4.96[a] |
| I-065 | chloro | iodo | 3-(trifluoromethyl)phenyl | Ring 1 | (2,4-dimethylphenyl)methyl | 4.37[a] |
| I-066 | 1-hydroxyethyl | H | 3-(trifluoromethyl)phenyl | Ring 1 | (2,4-dimethylphenyl)methyl | 3.55[a] |
| I-067 | 1-fluoroethyl | H | 3-(trifluoromethyl)phenyl | Ring 1 | (2,4-dimethylphenyl)methyl | 4.30[a] |
| I-068 | cyclopropyl | H | 3-(trifluoromethyl)phenyl | Ring 1 | (2,4-dimethylphenyl)methyl | 4.47[a] |
| I-069 | 2-trimethylsilylethyn-1-yl | H | 3-(trifluoromethyl)phenyl | Ring 1 | (2,4-dimethylphenyl)methyl | 5.54[a] |
| I-070 (*) | chloro | H | 3-(trifluoromethyl)phenyl | Ring 1 | benzyl | 3.81[a] |
| I-071 | ethynyl | H | 3-(trifluoromethyl)phenyl | Ring 1 | (2,4-dimethylphenyl)methyl | 3.59[a] |
| I-072 | chloro | 2-methoxyethoxy | 3-(trifluoromethyl)phenyl | Ring 1 | (2,4-dimethylphenyl)methyl | 4.18[a] |
| I-073 | 1H-imidazol-1-yl | H | 3-(trifluoromethyl)phenyl | Ring 1 | (2,4-dimethylphenyl)methyl | 3.11[a] |
| I-074 | methyl | H | 3-(trifluoromethyl)phenyl | Ring 1 | 2-hydroxy-3,5-dimethylphenyl | 3.01[a] |
| I-075 | methyl | H | 3-cyclopropyl-2-fluorophenyl | Ring 1 | (2-chloro-4-cyclopropylphenyl)methyl | 4.39[a] |
| I-076 | chloro | methyl | 3-cyclopropyl-2-fluorophenyl | Ring 1 | (2,4-dichlorophenyl)methyl | 4.51[a] |
| I-077 | chloro | H | 3-cyclopropylphenyl | Ring 4 | 2,4-dimethylphenyl | 4.11[a] |
| I-078 | chloro | H | 3-cyclopropylphenyl | Ring 4 | (2,4-dimethylphenyl)methyl | 4.31[a] |
| I-079 | methyl | H | 3-(trifluoromethyl)phenyl | Ring 3 | (2,4-dichlorophenyl)methyl | 3.97[a] |
| I-080 | methyl | H | 3-(trifluoromethyl)phenyl | Ring 13 | 4-chlorophenyl | 3.35[a] |
| I-081 | methyl | H | 3-(trifluoromethyl)phenyl | Ring 12 | 4-chlorophenyl | 3.45[a] |
| I-082 | chloro | H | 5-bromopyridin-3-yl | Ring 1 | (2,4-dimethylphenyl)methyl | 3.67[a] |
| I-083 | chloro | H | 6-chloro-5-(trifluoromethyl) pyridin-3-yl | Ring 1 | (2,4-dimethylphenyl)methyl | 4.41[a] |
| I-084 | chloro | methyl | 3-cyclopropyl-2-fluorophenyl | Ring 1 | (4-bromo-2-chlorophenyl)methyl | 4.61[a] |
| I-085 | chloro | methyl | 3-cyclopropyl-2-fluorophenyl | Ring 1 | (2-chloro-4-cyclopropylphenyl)methyl | 4.69[a] |
| I-086 | chloro | H | 3-cyclopropylphenyl | Ring 1 | (2,4-dimethylphenyl)methyl | 4.53[a] |
| I-087 | methyl | H | 3-(trifluoromethyl)phenyl | Ring 1 | 2,3-dihydro-1-benzofuran-5-yl | 2.88[a] |
| I-088 | chloro | pyridin-4-yl | 3-(trifluoromethyl)phenyl | Ring 1 | (2,4-dimethylphenyl)methyl | 3.76[a] |
| I-089 | vinyl | H | 3-cyclopropyl-2-fluorophenyl | Ring 1 | (2,4-dimethylphenyl)methyl | 4.46[a] |
| I-090 | methyl | H | 3-(trifluoromethyl)phenyl | Ring 1 | 2,5-dimethyl-3-thienyl | 3.44[a] |
| I-091 | methyl | H | 3-(trifluoromethyl)phenyl | Ring 1 | 5-methyl-2-thienyl | 3.11[a] |
| I-092 | methyl | H | 3-(trifluoromethyl)phenyl | Ring 1 | 1-methyl-1H-pyrrolo[2,3-b]pyridin-3-yl | 2.25[a] |
| I-093 | methyl | H | 3-(trifluoromethyl)phenyl | Ring 1 | 2-(4-chloro-2,6-difluorophenypethyl | 3.96[a] |
| I-094 | methyl | H | 3-(trifluoromethyl)phenyl | Ring 1 | (4-methylphenyl)methyl | 3.58[a] |

TABLE 1-continued

| | | | | | | |
|---|---|---|---|---|---|---|
| I-095 | methyl | H | 3-(trifluoromethyl)phenyl | Ring 14 | 2,4-difluorophenyl | 3.13[a] |
| I-096 | methyl | H | 3-(trifluoromethyl)phenyl | Ring 15 | 2,4-dichlorophenyl | 4.56[a] |
| I-097 | chloro | H | 5-(difluoromethyl) pyridin-3-yl | Ring 1 | (2,4-dimethylphenyl)methyl | 3.42[a] |
| I-098 | 1-ethoxyethen-1-yl | H | 3-cyclopropylphenyl | Ring 1 | (2,4-dimethylphenyl)methyl | 5.11[a] |
| I-099 | methyl | H | 3-(trifluoromethyl)phenyl | Ring 1 | 5-chloro-2-thienyl | 3.25[a] |
| I-100 | methyl | H | 3-(trifluoromethyl)phenyl | Ring 1 | 5-methyl-2-furyl | 2.92[a] |
| I-101 | methyl | H | 3-(trifluoromethyl)phenyl | Ring 1 | 2,5-dimethyl-3-furyl | 3.13[a] |
| I-102 | methyl | H | 3-(trifluoromethyl)phenyl | Ring 1 | 4,5-dimethyl-2-furyl | 3.21[a] |
| I-103 | methyl | H | 3-(trifluoromethyl)phenyl | Ring 1 | 5-chloro-2-methyl-3-thienyl | 3.57[a] |
| I-104 | methyl | H | 3-(trifluoromethyl)phenyl | Ring 1 | 6-chloro-1-methyl-1H-indol-3-yl | 3.57[a] |
| I-105 | methyl | H | 3-(trifluoromethyl)phenyl | Ring 1 | thiophen-2-yl | 2.80[a] |
| I-106 | methyl | H | 3-(trifluoromethyl)phenyl | Ring 1 | 1-benzothiophen-3-yl | 3.44[a] |
| I-107 | methyl | H | 3-(trifluoromethyl)phenyl | Ring 1 | 5-chloro-4-methyl-2-thienyl | 3.62[a] |
| I-108 | pyrrolidin-1-yl | H | 3-(trifluoromethyl)phenyl | Ring 1 | (2,4-dimethylphenyl)methyl | 3.37[a] |
| I-109 | vinyl | H | 3-cyclopropylphenyl | Ring 1 | (2,4-dimethylphenyl)methyl | 4.36[a] |
| I-110 | ethyl | H | 3-cyclopropyl-2-fluorophenyl | Ring 1 | (2,4-dimethylphenyl)methyl | 4.44[a] |
| I-111 | ethyl | H | 3-cyclopropylphenyl | Ring 1 | (2,4-dimethylphenyl)methyl | 4.29[a] |
| I-112 | 1-ethoxyethen-1-yl | H | 3-cyclopropyl-2-fluorophenyl | Ring 1 | (2,4-dimethylphenyl)methyl | 5.27[a] |
| I-113 | chloro | H | 2-fluoro-3-vinylphenyl | Ring 1 | (2,4-dimethylphenyl)methyl | 4.46[a] |
| I-114 | methyl | H | 3-(trifluoromethyl)phenyl | Ring 1 | 1-benzofuran-2-yl | 3.31[a] |
| I-115 | methyl | H | 3-(trifluoromethyl)phenyl | Ring 1 | 3-methyl-2-thienyl | 3.11[a] |
| I-116 | methyl | H | 3-(trifluoromethyl)phenyl | Ring 1 | 4-methyl-2-thienyl | 3.15[a] |
| I-117 | chloro | H | 3-(trifluoromethyl)phenyl | Ring 5 | (2,4-dimethylphenyl)methyl | 2.56[a] |
| I-118 | chloro | H | 3-cyclopropylphenyl | Ring 5 | (2,4-dimethylphenyl)methyl | 2.41[a] |
| I-119 (*) | methyl | H | 3-cyclopropyl-2-fluorophenyl | Ring 1 | (2,4-dimethylphenyl)methyl | 4.12[a] |
| I-120 | acetyl | H | 3-cyclopropyl-2-fluorophenyl | Ring 1 | (2,4-dimethylphenyl)methyl | 4.49[a] |
| I-121 | acetyl | H | 3-cyclopropylphenyl | Ring 1 | (2,4-dimethylphenyl)methyl | 4.37[a] |
| I-122 | 1-hydroxyethyl | H | 3-cyclopropyl-2-fluorophenyl | Ring 1 | (2,4-dimethylphenyl)methyl | 3.70[a] |
| I-123 | chloro | H | 3-cyclopropylphenyl | Ring 1 | (2,4-dichlorophenyl)methyl | 4.67[a] |
| I-124 | 1-fluoroethyl | H | 3-cyclopropyl-2-fluorophenyl | Ring 1 | (2,4-dimethylphenyl)methyl | 4.59[a] |
| I-125 | 1-fluoroethyl | H | 3-cyclopropylphenyl | Ring 1 | (2,4-dimethylphenyl)methyl | 4.46[a] |
| I-126 | methyl | H | 3-(trifluoromethyl)phenyl | Ring 1 | (2,4-dimethylphenyl)methoxy | 3.55[a] |
| I-127 | vinyl | H | 3-cyclopropylphenyl | Ring 1 | (2,4-dichlorophenyl)methyl | 4.44[a] |
| I-128 | chloro | methyl | 5-(difluoromethyl) pyridin-3-yl | Ring 1 | (2,4-dimethylphenyl)methyl | 3.21[a] |
| I-129 | ethyl | H | 3-cyclopropylphenyl | Ring 1 | (2,4-dichlorophenyl)methyl | 4.37[a] |
| I-130 (*) | methyl | H | 3-cyclopropyl-2-fluorophenyl | Ring 1 | (2,4-dimethylphenyl)methyl | 4.12[a] |
| I-131 | methyl | H | 3-(trifluoromethyl)phenyl | Ring 1 | (2,4-dimethylphenyl)thio | 3.92[a] |
| I-132 | methyl | H | 3-(trifluoromethyl)phenyl | Ring 1 | 2-(2,4-dichlorophenyl)propan-2-yl | 4.49[a] |
| I-133 | methyl | H | 3-(trifluoromethyl)phenyl | Ring 1 | 2-(4-chlorophenyl)ethyl | 3.72[a] |
| I-134 | methyl | H | 3-(trifluoromethyl)phenyl | Ring 16 | 3,4-dichlorophenyl | 4.80[a] |
| I-135 | methyl | H | 3-(trifluoromethyl)phenyl | Ring 17 | (4-chlorophenoxy)methyl | 3.89[a] |
| I-136 | acetyl | H | 3-cyclopropylphenyl | Ring 1 | (2,4-dichlorophenyl)methyl | 4.49[a] |
| I-137 | 1-hydroxyethyl | H | 3-cyclopropylphenyl | Ring 1 | (2,4-dichlorophenyl)methyl | 3.71[a] |
| I-138 | methyl | H | 3-cyclopropyl-2-fluorophenyl | Ring 1 | (2-methyl-4-vinylphenyl)methyl | 4.08[a] |
| I-139 | methyl | H | 3-(trifluoromethyl)phenyl | Ring 1 | (4-chlorophenoxy)methyl | 3.64[a] |
| I-140 | methyl | H | 3-cyclopropyl-2-fluorophenyl | Ring 1 | (2-methyl-4-pyridin-3-ylphenyl)methyl | 2.28[a] |
| I-141 | 1-fluoroethyl | H | 3-cyclopropylphenyl | Ring 1 | (2,4-dichlorophenyl)methyl | 4.56[a] |
| I-142 | methyl | H | 3-cyclopropyl-2-fluorophenyl | Ring 1 | (4-ethynyl-2-methylphenyl)methyl | 3.67[a] |
| I-143 | methyl | H | 3-(trifluoromethyl)phenyl | Ring 6 | 4-chlorophenyl | 3.50[a] |
| I-144 | methyl | H | 3-(trifluoromethyl)phenyl | Ring 1 | (2,4-dimethylphenoxy)methyl | 3.98[a] |
| I-145 (*) | methyl | methyl | 3-(trifluoromethyl)phenyl | Ring 1 | (2,4-dimethylphenyl)methyl | 3.71[a] |
| I-146 (*) | methyl | methyl | 3-(trifluoromethyl)phenyl | Ring 1 | (2,4-dimethylphenyl)methyl | 3.71[a] |
| I-147 | chloro | H | 3-cyclopropyl-2-fluorophenyl | Ring 1 | (2,4-dichlorophenyl)methyl | 4.81[a] |
| I-148 | 3-methylpyridin-4-yl | H | 3-(trifluoromethyl)phenyl | Ring 1 | (2,4-dimethylphenyl)methyl | 3.37[a] |
| I-149 | 3-methoxypyridin-4-yl | H | 3-(trifluoromethyl)phenyl | Ring 1 | (2,4-dimethylphenyl)methyl | 3.72[a] |
| I-150 | pyridin-4-yl | methyl | 3-cyclopropyl-2-fluorophenyl | Ring 1 | (2,4-dimethylphenyl)methyl | 3.29[a] |
| I-151 (*) | chloro | H | 3-(trifluoromethyl)phenyl | Ring 1 | (2,4-dichlorophenyl)methyl | 4.59[a] |
| I-152 (*) | chloro | H | 3-(trifluoromethyl)phenyl | Ring 1 | (2,4-dichlorophenyl)methyl | 4.59[a] |
| I-153 | chloro | H | 2-fluoro-3-[rac-2,2-difluorocyclopropyl]phenyl | Ring 1 | (2,4-dimethylphenyl)methyl | 4.37[a] |
| I-154 | methyl | H | 3-(trifluoromethyl)phenyl | Ring 7 | 4-methoxyphenyl | 3.60[a] |
| I-155 | methyl | H | 2-fluoro-3-[rac-2,2-difluorocyclopropyl]phenyl | Ring 1 | (2,4-dimethylphenyl)methyl | 3.81[a] |
| I-156 | chloro | H | 3-(trifluoromethyl)phenyl | Ring 8 | benzyl | 2.72[a] |

TABLE 1-continued

| | | | | | | |
|---|---|---|---|---|---|---|
| I-157 | iodo | methyl | 3-(trifluoromethyl)phenyl | Ring 1 | (2,4-dimethylphenyl)methyl | 4.37[a] |
| I-158 | 1,3-thiazol-5-yl | H | 3-(trifluoromethyl)phenyl | Ring 1 | (2,4-dimethylphenyl)methyl | 4.18[a] |
| I-159 | cyano | H | 3-(trifluoromethyl)phenyl | Ring 1 | (2,4-dimethylphenyl)methyl | 4.30[a] |
| I-160 (*) | methyl | H | 3-(difluoromethyl)phenyl | Ring 1 | (2,4-dimethylphenyl)methyl | 3.47[a] |
| I-161 (*) | methyl | H | 3-(difluoromethyl)phenyl | Ring 1 | (2,4-dimethylphenyl)methyl | 3.47[a] |
| I-162 (*) | chloro | H | 3-(trifluoromethyl)phenyl | Ring 1 | (4-bromo-2-chlorophenyl)methyl | 4.70[a] |
| I-163 (*) | chloro | H | 3-(trifluoromethyl)phenyl | Ring 1 | (4-bromo-2-chlorophenyl)methyl | 4.70[a] |
| I-164 (*) | chloro | H | 3-(trifluoromethyl)phenyl | Ring 1 | (4-bromo-2-methylphenyl)methyl | 4.59[a] |
| I-165 (*) | chloro | H | 3-(trifluoromethyl)phenyl | Ring 1 | (4-bromo-2-methylphenyl)methyl | 4.59[a] |
| I-166 (*) | methyl | H | 3-(trifluoromethyl)phenyl | Ring 1 | 1-methyl-1H-indol-3-yl | 3.31[a] |
| I-167 (*) | methyl | H | 3-(trifluoromethyl)phenyl | Ring 1 | 1-methyl-1H-indol-3-yl | 3.31[a] |
| I-168 | methyl | H | 3-(trifluoromethyl)phenyl | Ring 1 | 3,5-dichloropyridin-2-yl | 3.54[a] |
| I-169 | (cyclopropylamino) carbonyl | methyl | 3-(trifluoromethyl)phenyl | Ring 1 | (2,4-dimethylphenyl)methyl | 3.84[a] |
| I-170 | vinyl | H | 3-cyclopropyl-2-fluorophenyl | Ring 1 | (2,4-dichlorophenyl)methyl | 4.66[a] |
| I-171 | acetyl | H | 3-cyclopropyl-2-fluorophenyl | Ring 1 | (2,4-dichlorophenyl)methyl | 4.66[a] |
| I-172 | ethyl | H | 3-cyclopropyl-2-fluorophenyl | Ring 1 | (2,4-dichlorophenyl)methyl | 4.59[a] |
| I-173 | chloro | H | 3-(trifluoromethyl)phenyl | Ring 8 | (2,4-dimethylphenyl)methyl | 3.31[a] |
| I-174 | chloro | methyl | 2-fluoro-3-[rac-2,2-difluorocyclopropyl]phenyl | Ring 1 | (2,4-dimethylphenyl)methyl | 4.15[a] |
| I-175 | chloro | H | 3-(trifluoromethyl)phenyl | Ring 1 | [4-(trifluoromethyl)phenyl]methyl | 4.23[a] |
| I-176 | methylsulfanyl | methyl | 3-(trifluoromethyl)phenyl | Ring 1 | (2,4-dimethylphenyl)methyl | 4.51[a] |
| I-177 | 4-methyl-1H-pyrazol-1-yl | H | 3-(trifluoromethyl)phenyl | Ring 1 | (2,4-dimethylphenyl)methyl | 4.55[a] |
| I-178 | allylthio | methyl | 3-(trifluoromethyl)phenyl | Ring 1 | (2,4-dimethylphenyl)methyl | 5.00[a] |
| I-179 | chloro | H | 3-(trifluoromethyl)phenyl | Ring 1 | [(2,4-dimethylphenyl)thio]methyl | 4.78[a] |
| I-180 | methylsulfonyl | methyl | 3-(trifluoromethyl)phenyl | Ring 1 | (2,4-dimethylphenyl)methyl | 4.01[a] |
| I-181 | chloro | H | 3-(trifluoromethyl)phenyl | Ring 9 | (2,4-dimethylphenyl)methyl | 5.00[a] |
| I-182 | chloro | H | 3-(trifluoromethyl)phenyl | Ring 10 | (2,4-dimethylphenyl)methyl | 5.61[a] |
| I-183 | chloro | H | 3-(trifluoromethyl)phenyl | Ring 1 | [4-(trifluoromethoxy)phenyl]methyl | 4.40[a] |
| I-184 | chloro | H | 3-(trifluoromethyl)phenyl | Ring 11 | 2,4-dichlorophenyl | 3.88[a] |
| I-185 | chloro | H | 3-(trifluoromethyl)phenyl | Ring 4 | 4-chlorophenyl | 4.13[a] |
| I-186 | chloro | H | 3-chloro-2-fluorophenyl | Ring 1 | (2,4-dimethylphenyl)methyl | 4.40[a] |
| I-187 | 2-methoxyethylthio | methyl | 3-(trifluoromethyl)phenyl | Ring 1 | (2,4-dimethylphenyl)methyl | 4.51[a] |
| I-188 | chloro | H | 3-(trifluoromethyl)phenyl | Ring 1 | [4-(difluoromethoxy)phenyl]methyl | 3.88[a] |
| I-189 | vinyl | H | 3-chloro-2-fluorophenyl | Ring 1 | (2,4-dimethylphenyl)methyl | 4.19[a] |
| I-190 | methyl | H | 3-chloro-2-fluorophenyl | Ring 1 | (2,4-dimethylphenyl)methyl | 3.81[a] |
| I-191 | methoxy | methyl | 3-(trifluoromethyl)phenyl | Ring 1 | (2,4-dimethylphenyl)methyl | 3.56[a] |
| I-192 | methyl | H | 3-cyclopropyl-2-fluorophenyl | Ring 1 | (4-cyclopentyl-2-methylphenyl)methyl | 5.28[a] |
| I-193 | methyl | H | 3-cyclopropyl-2-fluorophenyl | Ring 1 | (4-cyclobutyl-2-methylphenyl)methyl | 4.97[a] |
| I-194 | chloro | H | 3-(trifluoromethyl)phenyl | Ring 4 | 2,4-dichlorophenyl | 4.77[a] |
| I-195 | chloro | H | 3-(trifluoromethyl)phenyl | Ring 11 | 4-chlorophenyl | 3.56[a] |
| I-196 | chloro | H | 5-(trifluoromethyl)-3-thienyl | Ring 1 | (2,4-dimethylphenyl)methyl | 4.59[a] |
| I-197 | chloro | H | 5-chloro-4-fluoropyridin-3-yl | Ring 1 | (2,4-dimethylphenyl)methyl | 3.84[a] |
| I-198 | chloro | H | 5-cyclopropylpyridin-3-yl | Ring 1 | (2,4-dimethylphenyl)methyl | 3.34[a] |
| I-199 | chloro | H | phenyl | Ring 1 | (2,4-dimethylphenyl)methyl | 3.91[a] |
| I-200 | chloro | H | 3-methylphenyl | Ring 1 | (2,4-dimethylphenyl)methyl | 4.26[a] |
| I-201 | chloro | H | 3-ethynylphenyl | Ring 1 | (2,4-dimethylphenyl)methyl | 4.05[a] |
| I-202 | chloro | H | 3-formylphenyl | Ring 1 | (2,4-dimethylphenyl)methyl | 3.47[a] |
| I-203 | chloro | H | 3-ethylphenyl | Ring 1 | (2,4-dimethylphenyl)methyl | 4.59[a] |
| I-204 | chloro | H | 3-methoxphenyl | Ring 1 | (2,4-dimethylphenyl)methyl | 3.91[a] |
| I-205 | chloro | H | 2-fluoro-3-methylphenyl | Ring 1 | (2,4-dimethylphenyl)methyl | 4.33[a] |
| I-206 | chloro | H | 1-isopropyl-1H-pyrazol-4-yl | Ring 1 | (2,4-dimethylphenyl)methyl | 3.40[a] |
| I-207 | chloro | H | 2,3-difluorophenyl | Ring 1 | (2,4-dimethylphenyl)methyl | 4.08[a] |
| I-208 | chloro | H | 1H-indol-5-yl | Ring 1 | (2,4-dimethylphenyl)methyl | 3.57[a] |
| I-209 | chloro | H | indan-4-yl | Ring 1 | (2,4-dimethylphenyl)methyl | 4.74[a] |
| I-210 | chloro | H | indan-5-yl | Ring 1 | (2,4-dimethylphenyl)methyl | 4.78[a] |
| I-211 | chloro | H | 6,7-dihydro-5H-cyclopenta[b]pyridin-3-yl | Ring 1 | (2,4-dimethylphenyl)methyl | 3.14[a] |
| I-212 | chloro | H | 2,3-dihydro-1-benzofuran-5-yl | Ring 1 | (2,4-dimethylphenyl)methyl | 3.81[a] |
| I-213 | chloro | H | 3-acetylphenyl | Ring 1 | (2,4-dimethylphenyl)methyl | 3.54[a] |
| I-214 | chloro | H | 3-propylphenyl | Ring 1 | (2,4-dimethylphenyl)methyl | 5.00[a] |
| I-215 | chloro | H | 3-(dimethylamino)phenyl | Ring 1 | (2,4-dimethylphenyl)methyl | 4.12[a] |
| I-216 | chloro | H | 3-ethoxyphenyl | Ring 1 | (2,4-dimethylphenyl)methyl | 4.26[a] |
| I-217 | chloro | H | 3-(methoxymethyl)phenyl | Ring 1 | (2,4-dimethylphenyl)methyl | 3.87[a] |
| I-218 | chloro | H | 3-nitrophenyl | Ring 1 | (2,4-dimethylphenyl)methyl | 3.84[a] |
| I-219 | chloro | H | 2-fluoro-3-formylphenyl | Ring 1 | (2,4-dimethylphenyl)methyl | 3.64[a] |
| I-220 | chloro | H | 3-ethyl-2-fluorophenyl | Ring 1 | (2,4-dimethylphenyl)methyl | 4.70[a] |
| I-221 | chloro | H | 3-methylsulfanylphenyl | Ring 1 | (2,4-dimethylphenyl)methyl | 4.26[a] |
| I-222 | chloro | H | 3-chloro-4-methylphenyl | Ring 1 | (2,4-dimethylphenyl)methyl | 4.70[a] |
| I-223 | chloro | H | naphthalen-2-yl | Ring 1 | (2,4-dimethylphenyl)methyl | 4.51[a] |
| I-224 | chloro | H | quinolin-3-yl | Ring 1 | (2,4-dimethylphenyl)methyl | 3.57[a] |
| I-225 | chloro | H | 3-chloro-5-fluorophenyl | Ring 1 | (2,4-dimethylphenyl)methyl | 4.47[a] |
| I-226 | chloro | H | 3-chloro-4-fluorophenyl | Ring 1 | (2,4-dimethylphenyl)methyl | 4.37[a] |

TABLE 1-continued

| | | | | | | |
|---|---|---|---|---|---|---|
| I-227 | chloro | H | 2,4,5-trifluorophenyl | Ring 1 | (2,4-dimethylphenyl)methyl | 4.19[a] |
| I-228 | chloro | H | 3-cyclobutylphenyl | Ring 1 | (2,4-dimethylphenyl)methyl | 5.12[a] |
| I-229 | chloro | H | 3-(oxetan-3-yl)phenyl | Ring 1 | (2,4-dimethylphenyl)methyl | 3.47[a] |
| I-230 | chloro | H | 1-benzothiophen-6-yl | Ring 1 | (2,4-dimethylphenyl)methyl | 4.33[a] |
| I-231 | chloro | H | 3-(methoxycarbonyl)phenyl | Ring 1 | (2,4-dimethylphenyl)methyl | 3.84[a] |
| I-232 | chloro | H | 3-(2-fluorocyclopropyl) phenyl | Ring 1 | (2,4-dimethylphenyl)methyl | 4.15 & 4.26[a] |
| I-233 | chloro | H | 4-(trifluoromethyl)phenyl | Ring 1 | (2,4-dimethylphenyl)methyl | 4.44[a] |
| I-234 | chloro | H | 3,4-dichlorophenyl | Ring 1 | (2,4-dimethylphenyl)methyl | 4.74[a] |
| I-235 | chloro | H | 3-phenylphenyl | Ring 1 | (2,4-dimethylphenyl)methyl | 4.89[a] |
| I-236 | chloro | H | 3-bromophenyl | Ring 1 | (2,4-dimethylphenyl)methyl | 4.40[a] |
| I-237 | chloro | H | 3-(trifluoromethoxy)phenyl | Ring 1 | (2,4-dimethylphenyl)methyl | 4.59[a] |
| I-238 | chloro | H | 4-(trifluoromethoxy)phenyl | Ring 1 | (2,4-dimethylphenyl)methyl | 4.59[a] |
| I-239 (*) | chloro | H | 3-bromo-2-fluorophenyl | Ring 1 | (2,4-dimethylphenyl)methyl | 4.47[a] |
| I-240 | chloro | H | 3-(trifluoromethylthio) | Ring 1 | (2,4-dimethylphenyl)methyl | 4.85[a] |
| I-241 | chloro | H | phenyl3-iodophenyl | Ring 1 | (2,4-dimethylphenyl)methyl | 4.55[a] |
| I-242 | chloro | H | 3-[3-(trifluoromethyl)-1H-pyrazol-1-yl]phenyl | Ring 1 | (2,4-dimethylphenyl)methyl | 4.66[a] |
| I-243 | chloro | H | 3-methylsulfonylphenyl | Ring 1 | (2,4-dimethylphenyl)methyl | 3.13[a] |
| I-244 | chloro | H | 5-methyl-2-(trifluoromethyl)-1,3-thiazol-4-yl | Ring 1 | (2,4-dimethylphenyl)methyl | 4.40[a] |
| I-245 (*) | methyl | H | 3-cyclopropyl-2-fluorophenyl | Ring 1 | (2,4-dichlorophenyl)methyl | 4.19[a] |
| I-246 (*) | methyl | H | 3-cyclopropyl-2-fluorophenyl | Ring 1 | (4-bromo-2-chlorophenyl)methyl | 4.30[a] |
| I-247 (*) | methyl | H | 3-cyclopropyl-2-fluorophenyl | Ring 1 | (4-bromo-2-chlorophenyl)methyl | 4.30[a] |
| I-248 | methyl | H | 3-cyclopropyl-2-fluorophenyl | Ring 1 | [2-methyl-4-(oxetan-3-yl)phenyl]methyl | 3.13[a] |
| I-249 | methyl | H | 3-cyclopropyl-2-fluorophenyl | Ring 1 | [2-methyl-4-(oxolan-3-yl)phenyl]methyl | 3.97[a] |
| I-250 (*) | methyl | H | 3-cyclopropyl-2-fluorophenyl | Ring 1 | (2,4-dichlorophenyl)methyl | 4.19[a] |
| I-251 | 2-methoxyethyl | methyl | 3-(trifluoromethyl)phenyl | Ring 1 | (2,4-dimethylphenyl)methyl | 3.85[a] |
| I-252 | ethyl | H | 3-chloro-2-fluorophenyl | Ring 1 | (2,4-dimethylphenyl)methyl | 4.15[a] |
| I-253 | oxetan-3-yl | H | 3-(trifluoromethyl)phenyl | Ring 1 | (2,4-dimethylphenyl)methyl | 3.77[a] |
| I-254 | 2-methoxyethyl | H | 3-(trifluoromethyl)phenyl | Ring 1 | (2,4-dimethylphenyl)methyl | 4.05[a] |
| I-255 | oxolan-3-yl | H | 3-(trifluoromethyl)phenyl | Ring 1 | (2,4-dimethylphenyl)methyl | 4.01[a] |
| I-256 | 2-cyanoethyl | H | 3-(trifluoromethyl)phenyl | Ring 1 | (2,4-dimethylphenyl)methyl | 4.01[a] |
| I-257 | cyclobutylmethyl | H | 3-(trifluoromethyl)phenyl | Ring 1 | (2,4-dimethylphenyl)methyl | 5.08[a] |
| I-258 | chloro | H | 3-cyano-2-fluorophenyl | Ring 1 | (2,4-dimethylphenyl)methyl | 3.77[a] |
| I-259 | methyl | H | 3-cyclopropyl-2-fluorophenyl | Ring 1 | (2-bromo-4-methylphenyl)methyl | 4.26[a] |
| I-260 | chloro | H | 5-(trifluoromethyl)-3-thienyl | Ring 1 | (2,4-dichlorophenyl)methyl | 4.66[a] |
| I-261 | chloro | H | 5-(trifluoromethyl)-3-thienyl | Ring 1 | (4-bromo-2-chlorophenyl)methyl | 4.74[a] |
| I-262 | chloro | H | 2-fluoro-3-(1-fluorocyclopropyl)phenyl | Ring 1 | (2,4-dimethylphenyl)methyl | 4.44[a] |
| I-263 | chloro | methyl | 2-fluoro-3-(1-fluorocyclopropyl)phenyl | Ring 1 | (2,4-dimethylphenyl)methyl | 4.19[a] |
| I-264 | chloro | 2-methoxyethyl | 3-(trifluoromethyl)phenyl | Ring 1 | (2,4-dimethylphenyl)methyl | 4.47[a] |
| I-265 | chloro | cyclopentyl | 3-(trifluoromethyl)phenyl | Ring 1 | (2,4-dimethylphenyl)methyl | 5.20[a] |
| I-266 | chloro | (4-methoxy-4-oxobutyl)amino | 3-(trifluoromethyl)phenyl | Ring 1 | (2,4-dimethylphenyl)methyl | 4.05[a] |
| I-267 | chloro | (2-hydroxy-2-methyl-propyl)amino | 3-(trifluoromethyl)phenyl | Ring 1 | (2,4-dimethylphenyl)methyl | 3.88[a] |
| I-268 | chloro | 5-(trifluoromethyl)-1H-pyrazol-1-yl | 3-(trifluoromethyl)phenyl | Ring 1 | (2,4-dimethylphenyl)methyl | 5.04[a] |
| I-269 | chloro | 3-carboxy-propylamino | 3-(trifluoromethyl)phenyl | Ring 1 | (2,4-dimethylphenyl)methyl | 3.40[a] |
| I-270 | chloro | H | 3-(trifluoromethyl)phenyl | Ring 1 | [4-(difluoromethyl)phenyl]methyl | 3.48[a] |
| I-271 | chloro | H | 3-(difluoromethoxy)phenyl | Ring 1 | (2,4-dimethylphenyl)methyl | 4.08[a] |
| I-272 | chloro | H | 2,2-difluoro-1,3-benzodioxol-5-yl | Ring 1 | (2,4-dimethylphenyl)methyl | 4.55[a] |
| I-273 | methyl | H | 3-cyclopropyl-2-fluorophenyl | Ring 1 | [2-chloro-4-(trifluoromethyl)phenyl]methyl | 4.26[a] |
| I-274 | chloro | H | 3-(trifluoromethyl)phenyl | Ring 1 | (1-methyl-1H-indol-3-yl)methyl | 4.12[a] |
| I-275 | chloro | H | 3-bicyclo[4.2.0]octa-1,3,5-trienyl | Ring 1 | (2,4-dimethylphenyl)methyl | 4.44[a] |
| I-276 | chloro | H | 3-(difluoromethoxy)-2-fluorophenyl | Ring 1 | (2,4-dimethylphenyl)methyl | 4.12[a] |
| I-277 | 2-cyclopropyl-cyclopropyl | H | 3-(trifluoromethyl)phenyl | Ring 1 | (2,4-dimethylphenyl)methyl | 5.20[a] |
| I-278 | chloro | 2-cyclopropyl-cyclopropyl | 3-(trifluoromethyl)phenyl | Ring 1 | (2,4-dimethylphenyl)methyl | 5.16[a] |

TABLE 1-continued

| | | | | | | |
|---|---|---|---|---|---|---|
| I-279 | chloro | allyloxy | 3-(trifluoromethyl)phenyl | Ring 1 | (2,4-dimethylphenyl)methyl | 4.67[a] |
| I-280 | chloro | (2-methyl-1,3-dioxolan-4-yl)methylamino | 3-(trifluoromethyl)phenyl | Ring 1 | (2,4-dimethylphenyl)methyl | 4.19[a] |
| I-281 | chloro | 2-oxopyrrolidin-1-yl | 3-(trifluoromethyl)phenyl | Ring 1 | (2,4-dimethylphenyl)methyl | 4.12[a] |
| I-282 | chloro | 2-oxa-6-aza-spiro[3.3]heptan-6-yl | 3-(trifluoromethyl)phenyl | Ring 1 | (2,4-dimethylphenyl)methyl | 3.71[a] |
| I-283 | chloro | (1-methylcyclo-propyl)amino | 3-(trifluoromethyl)phenyl | Ring 1 | (2,4-dimethylphenyl)methyl | 4.44[a] |
| I-284 | chloro | 2-cyclopropyl-ethylamino | 3-(trifluoromethyl)phenyl | Ring 1 | (2,4-dimethylphenyl)methyl | 4.74[a] |
| I-285 | chloro | but-3-en-2-yl-amino | 3-(trifluoromethyl)phenyl | Ring 1 | (2,4-dimethylphenyl)methyl | 4.55[a] |
| I-286 | chloro | oxetan-3-ylamino | 3-(trifluoromethyl)phenyl | Ring 1 | (2,4-dimethylphenyl)methyl | 3.71[a] |
| I-287 | chloro | 3,3,3-trifluoro-propylamino | 3-(trifluoromethyl)phenyl | Ring 1 | (2,4-dimethylphenyl)methyl | 4.51[a] |
| I-288 | chloro | (2-cyclopropyl-cyclopropyl)amino | 3-(trifluoromethyl)phenyl | Ring 1 | (2,4-dimethylphenyl)methyl | 4.78[a] |
| I-289 | chloro | 2-methylsulfanyl-ethylamino | 3-(trifluoromethyl)phenyl | Ring 1 | (2,4-dimethylphenyl)methyl | 4.40[a] |
| I-290 | methyl | H | 3-cyclopropyl-2-fluorophenyl | Ring 1 | (2-chloro-4-methylphenyl)methyl | 4.12[a] |
| I-291 | chloro | 3-(oxolan-2-yl)-1H-pyrazol-1-yl | 3-(trifluoromethyl)phenyl | Ring 1 | (2,4-dimethylphenyl)methyl | 4.55[a] |
| I-292 | chloro | methylsulfanyl | 3-(trifluoromethyl)phenyl | Ring 1 | (2,4-dimethylphenyl)methyl | 4.51[a] |
| I-293 | 4-methoxy-1H-pyrazol-1-yl | 4-methoxy-1H-pyrazol-1-yl | 3-(trifluoromethyl)phenyl | Ring 1 | (2,4-dimethylphenyl)methyl | 4.40[a] |
| I-294 | chloro | 1,3-thiazol-4-yl | 3-(trifluoromethyl)phenyl | Ring 1 | (2,4-dimethylphenyl)methyl | 4.17[a] |
| I-295 | methyl | H | 3-cyclopropyl-2-fluorophenyl | Ring 1 | (3,4-dichlorophenyl)methyl | 4.08[a] |
| I-296 | chloro | H | 3-(trifluoromethyl)phenyl | Ring 1 | (4-nitrophenyl)methyl | 3.54[a] |
| I-297 | chloro | H | 3-(trifluoromethyl)phenyl | Ring 1 | [4-(trifluoromethylthio)phenyl]methyl | 4.67[a] |
| I-298 | methyl | H | 3-chloro-2-fluorophenyl | Ring 1 | (2-chloro-4-cyclopropylphenyl)methyl | 4.14[a] |
| I-299 | methyl | H | 3-chloro-2-fluorophenyl | Ring 1 | (4-cyclopropyl-2-methylphenyl)methyl | 4.12[a] |
| I-300 (*) | methyl | H | 3-chloro-2-fluorophenyl | Ring 1 | (4-bromo-2-methylphenyl)methyl | 3.94[a] |
| I-301 | methyl | H | 3-cyclopropyl-2-fluorophenyl | Ring 1 | (2-chloro-4-methoxyphenyl)methyl | 3.73[a] |
| I-302 (*) | methyl | H | 3-chloro-2-fluorophenyl | Ring 1 | (2-chloro-4-methylphenyl)methyl | 3.94[a] |
| I-303 | methyl | H | 3-chloro-2-fluorophenyl | Ring 1 | (3,4-dimethylphenyl)methyl | 3.87[a] |
| I-304 | chloro | H | 3-(trifluoromethyl)phenyl | Ring 5 | 2,4-dichlorophenyl | 2.76[a] |
| I-305 | methyl | H | 3-(difluoromethyl)phenyl | Ring 1 | (3,4-dimethylphenyl)methyl | 3.46[a] |
| I-306 | methyl | H | 3-(difluoromethyl)phenyl | Ring 1 | (4-cyclopropyl-2-methylphenyl)methyl | 3.72[a] |
| I-307 | chloro | H | 3-(trifluoromethyl)phenyl | Ring 1 | (5-chloropyridin-2-yl)methyl | 3.43[a] |
| I-308 | chloro | H | 3-ethynyl-2-fluorophenyl | Ring 1 | (2,4-dichlorophenyl)methyl | 4.16[a] |
| I-309 | methyl | H | 3-cyclopropyl-2-fluorophenyl | Ring 1 | (3-bromo-5-methylphenyl)methyl | 4.26[a] |
| I-310 | chloro | H | 3-(trifluoromethyl)phenyl | Ring 1 | (4,5-dimethyl-3-thienyl)methyl | 4.36[a] |
| I-311 | methyl | H | 3-(trifluoromethyl)phenyl | Ring 1 | 2-phenylcyclopropyl | 3.57[a] |
| I-312 (*) | chloro | H | 3-bromo-2-fluorophenyl | Ring 1 | (2,4-dimethylphenyl)methyl | 4.51[a] |
| I-313 (*) | chloro | H | 3-bromo-2-fluorophenyl | Ring 1 | (2,4-dimethylphenyl)methyl | 4.51[a] |
| I-314 | methyl | H | 3-cyclopropyl-2-fluorophenyl | Ring 1 | [4-methyl-2-(2-trimethylsilylethyn-1-yl)phenyl]methyl | 5.79[a] |
| I-315 | methyl | H | 3-cyclopropyl-2-fluorophenyl | Ring 1 | (2-ethynyl-4-methylphenyl)methyl | 3.88[a] |
| I-316 | methyl | H | 3-(difluoromethyl)-2-fluorophenyl | Ring 1 | (2,4-dimethylphenyl)methyl | 3.59[a] |
| I-317 | methyl | H | 3-(difluoromethyl)-2-fluorophenyl | Ring 1 | (3,4-dimethylphenyl)methyl | 3.62[a] |
| I-318 | methyl | H | 3-(trifluoromethyl)phenyl | Ring 1 | 2,3-dihydro-1,4-benzodioxin-6-yl | 2.89[a] |
| I-319 | chloro | H | 3-[rac-oxiran-2-yl]phenyl | Ring 1 | (2,4-dichlorophenyl)methyl | 3.84[a] |
| I-320 | chloro | 2-methoxy-ethylthio | 3-(trifluoromethyl)phenyl | Ring 1 | (2,4-dimethylphenyl)methyl | 4.52[a] |
| I-321 | chloro | H | 3-ethynyl-2-fluorophenyl | Ring 1 | (2,4-dimethylphenyl)methyl | 4.17[a] |
| I-322 (*) | methyl | H | 3-cyclopropyl-2-fluorophenyl | Ring 1 | (4-bromo-2-methylphenyl)methyl | 4.23[a] |
| I-323 (*) | methyl | H | 3-cyclopropyl-2-fluorophenyl | Ring 1 | (4-bromo-2-methylphenyl)methyl | 4.23[a] |
| I-324 | methyl | H | 3-(difluoromethyl)-2-fluorophenyl | Ring 1 | (4-cyclopropyl-2-methylphenyl)methyl | 3.88[a] |
| I-325 | methyl | H | 2-fluoro-3-vinylphenyl | Ring 1 | (2,4-dimethylphenyl)methyl | 3.88[a] |
| I-326 | methyl | H | 2-fluoro-3-methylphenyl | Ring 1 | (2,4-dimethylphenyl)methyl | 3.70[a] |
| I-327 | methyl | H | 3-cyclopropylphenyl | Ring 1 | (2-chloro-4-cyclopropylphenyl)methyl | 4.36[a] |
| I-328 | methyl | H | 3-cyclopropylphenyl | Ring 1 | (4-cyclopropyl-2-methylphenyl)methyl | 4.19[a] |
| I-329 | methyl | H | 3-cyclopropylphenyl | Ring 1 | (4-bromo-2-methylphenyl)methyl | 4.03[a] |
| I-330 | methyl | H | 3-cyclopropylphenyl | Ring 1 | (3,4-dimethylphenyl)methyl | 3.93[a] |
| I-331 | methyl | H | 3-cyclopropyl-2-fluorophenyl | Ring 1 | [2-chloro-4-(difluoro-methyl)phenyl]methyl | 3.73[a] |

TABLE 1-continued

| | | | | | | |
|---|---|---|---|---|---|---|
| I-332 | methyl | H | 3-cyclopropyl-2-fluorophenyl | Ring 1 | [2-chloro-4-(difluoro-methoxy)phenyl]methyl | 3.81[a] |
| I-333 | methyl | H | 3-(difluoromethyl)phenyl | Ring 1 | (2-chloro-4-methylphenyl)methyl | 3.49[a] |
| I-334 | methyl | H | 3-cyclopropyl-2-fluorophenyl | Ring 1 | [2-chloro-4-(trifluoro-methoxy)phenyl]methyl | 4.41[a] |
| I-335 | methyl | H | 3-cyclopropyl-2-fluorophenyl | Ring 1 | (2-cyclopropyl-4-methylphenyl)methyl | 4.51[a] |
| I-336 (*) | methyl | H | 3-chloro-2-fluorophenyl | Ring 1 | (4-bromo-2-methylphenyl)methyl | 3.94[a] |
| I-337 (*) | methyl | H | 3-chloro-2-fluorophenyl | Ring 1 | (4-bromo-2-methylphenyl)methyl | 3.94[a] |
| I-338 (*) | methyl | H | 3-chloro-2-fluorophenyl | Ring 1 | (2-chloro-4-methylphenyl)methyl | 3.87[a] |
| I-339 (*) | methyl | H | 3-chloro-2-fluorophenyl | Ring 1 | (2-chloro-4-methylphenyl)methyl | 3.87[a] |
| I-340 | chloro | H | 6-chloropyridin-2-yl | Ring 1 | (2,4-dichlorophenyl)methyl | 3.77[a] |
| I-341 | chloro | H | 3-vinylphenyl | Ring 1 | (2,4-dichlorophenyl)methyl | 4.44[a] |
| I-342 | chloro | 4-methoxy-1H-pyrazol-1-yl | 3-(trifluoromethyl)phenyl | Ring 1 | (2,4-dimethylphenyl)methyl | 4.35[a] |
| I-343 | chloro | cyclopropyl | 3-(trifluoromethyl)phenyl | Ring 1 | (2,4-dimethylphenyl)methyl | 4.46[a] |
| I-344 | methyl | H | 3-(difluoromethyl)-2-fluorophenyl | Ring 1 | (2-chloro-4-methylphenyl)methyl | 3.63[a] |
| I-345 | methyl | H | 2-fluoro-3-formylphenyl | Ring 1 | (2,4-dimethylphenyl)methyl | 3.09[a] |
| I-346 | methyl | H | 3-cyclopropylphenyl | Ring 1 | (2-chloro-4-methylphenyl)methyl | 3.96[a] |
| I-347 | chloro | H | 3-(trifluoromethyl)phenyl | Ring 1 | (E)-2-phenylethen-1-yl | 3.91[a] |
| I-348 | methyl | H | 3-ethynyl-2-fluorophenyl | Ring 1 | (2,4-dimethylphenyl)methyl | 3.52[a] |

(*) Ex I-051 and I-053 are the two enantiomers of Ex I-059
Ex I-051: Optical rotation: +92.7° (c = 0.95, DCM, 25° C.); concentration c is expressed in g/100 mL.
Ex I-053: Optical rotation: −86.6° (c = 1.04, DCM, 25° C.); concentration c is expressed in g/100 mL.
(*) Ex I-119 and I-130 are the 2 enantiomers of Ex I-052
Ex I-119: Optical rotation: +95.3° (c = 1.05, CDCl3, 20° C.); concentration c is expressed in g/100 mL.
Ex I-130: Optical rotation: −93.3° (c = 1.20, CDCl3, 20° C.); concentration c is expressed in g/100 mL.
(*) Ex I-145 and I-146 are the 2 enantiomers of Ex I-055
Ex I-145: Optical rotation: +86.3° (c = 1.62, CDCl3, 20° C.); concentration c is expressed in g/100 mL.
Ex I-146: Optical rotation: −90° (c = 1.60, CDCl3, 20° C.); concentration c is expressed in g/100 mL.
(*) Ex I-151 and I-152 are the 2 enantiomers of Ex I-025
Ex I-151: Optical rotation: +54.8° (c = 1.1, CDCl3, 25° C.); concentration c is expressed in g/100 mL.
Ex I-152: Optical rotation: −51.4° (c = 1.09, CDCl3, 25° C.); concentration c is expressed in g/100 mL.
(*) Ex I-160 and I-161 are the 2 enantiomers of Ex I-013
Ex I-160: Optical rotation: +85.6° (c = 2.15, CDCl3, 25° C.); concentration c is expressed in g/100 mL.
Ex I-161: Optical rotation: −78.1° (c = 2.15, CDCl3, 25° C.); concentration c is expressed in g/100 mL.
(*) Ex I-162 and I-163 are the 2 enantiomers of Ex I-016
Ex I-162: Optical rotation: +52.2° (c = 1.15, CDCl3, 25° C.); concentration c is expressed in g/100 mL.
Ex I-163: Optical rotation: −72° (c = 1.0, CDCl3, 25° C.); concentration c is expressed in g/100 mL.
(*) Ex I-164 and I-165 are the 2 enantiomers of Ex I-017
Ex I-164: Optical rotation: +78.3° (c = 1.15, CDCl3, 25° C.); concentration c is expressed in g/100 mL.
Ex I-165: Optical rotation: −85.5° (c = 1.1, CDCl3, 25° C.); concentration c is expressed in g/100 mL.
(*) Ex I-166 and I-167 are the 2 enantiomers of Ex I-011
Ex I-166: Optical rotation: 0° (c = 0.95, CDCl3, 25° C.); concentration c is expressed in g/100 mL.
Ex I-167: Optical rotation: −7.3° (c = 1.1, CDCl3, 25° C.); concentration c is expressed in g/100 mL.
(*) Ex I-245 and I-250 are the 2 enantiomers of Ex I-030
Ex I-245: Optical rotation: +57.1° (c = 0.67, CDCl3, 25° C.); concentration c is expressed in g/100 mL.
Ex I-250: Optical rotation: −63.8° (c = 0.69, CDCl3, 25° C.); concentration c is expressed in g/100 mL.
(*) Ex I-246 and I-247 are the 2 enantiomers of Ex I-027
Ex I-246: Optical rotation: +60° (c = 0.6, CDCl3, 25° C.); concentration c is expressed in g/100 mL.
Ex I-247: Optical rotation: −55° (c = 0.8, CDCl3, 25° C.); concentration c is expressed in g/100 mL.
(*) Ex I-312 and I-313 are the 2 enantiomers of Ex I-239
Ex I-312: Optical rotation: −88.6° (c = 3.50, DCM, 20° C.); concentration c is expressed in g/100 mL.
Ex I-313: Optical rotation: +73.2° (c = 2.95, DCM, 20° C.); concentration c is expressed in g/100 mL.
(*) Ex I-322 and I-323 are the 2 enantiomers of Ex I-056
(*) Ex I-336 and I-337 are the 2 enantiomers of Ex I-300
Ex I-336: Optical rotation: +71.6° (c = 1.01, CDCl3, 25° C.); concentration c is expressed in g/100 mL.
Ex I-337: Optical rotation: −72.5° (c = 1.02, CDCl3, 25° C.); concentration c is expressed in g/100 mL.
(*) Ex I-338 and I-339 are the 2 enantiomers of Ex I-302
Ex I-338: Optical rotation: +71.5° (c = 1.04, CDCl3, 25° C.); concentration c is expressed in g/100 mL.
Ex I-339: Optical rotation: −75.2° (c = 1.01, CDCl3, 25° C.); concentration c is expressed in g/100 mL.
(*) Ex I-070 is Single Stereoisomer
Ex I-070: Optical rotation: −78.1° (c = 2.51, CDCl3, 25° C.); concentration c is expressed in g/100 mL.

TABLE 2

I-001: $^1$H-NMR(300.2 MHz, CDCl3):
δ = 8.1367 (6.2); 7.2983 (14.2); 7.1511 (0.6); 7.1469 (0.6); 7.1244 (1.4); 7.1206 (1.4); 7.0979 (1.0); 7.0941 (1.0); 7.0120 (2.6); 6.9870 (3.2); 6.9609 (0.6); 6.9557 (0.6); 6.9061 (2.1); 6.8920 (0.9); 6.8868 (0.8); 6.8649 (1.3); 6.8434 (0.6); 6.8386 (0.6); 6.6980 (1.2); 6.6728 (1.0); 6.2039 (1.4); 5.3372 (8.7); 4.3108 (0.7); 4.3024 (1.0); 4.2776 (1.1); 4.2677 (0.9); 3.9014 (0.6); 3.8854 (0.6); 3.8792 (0.5); 3.8620 (2.1); 3.8417 (0.6); 3.8275 (1.4); 3.8068 (0.8); 3.0515 (0.7); 3.0359 (0.7); 3.0069 (1.0); 2.9905 (1.0); 2.7798 (0.9); 2.7488 (0.9); 2.7346 (0.8); 2.7033 (0.7); 2.3087 (11.5); 2.1735 (10.9); 2.1492 (0.6); 2.1373 (0.6); 2.1204 (1.0); 2.1032 (0.6); 2.0921 (0.6); 2.0830 (1.5); 1.5870 (16.0); 1.3455 (0.4); 1.3211 (1.0); 1.3053 (2.5); 1.2976 (2.7); 1.2736 (0.5); 1.1084 (0.7); 1.0953 (1.4); 1.0884 (1.8); 1.0831 (1.1); 1.0802 (1.1); 1.0753 (1.1); 1.0665 (1.4); 1.0601 (1.7); 1.0472 (0.9); 0.9420 (0.8); 0.9203 (2.6); 0.8972 (1.1); 0.8445 (0.8); 0.8369 (0.9); 0.8279 (1.9); 0.8203 (1.6); 0.8124

TABLE 2-continued (2.0); 0.8052 (1.2); 0.7949 (0.7); 0.1077 (3.9); 0.0489 (0.4); 0.0381 (12.7); 0.0272 (0.6)
I-002: $^1$H-NMR(499.9 MHz, CDCl3):
δ = 7.5046 (0.5); 7.4888 (2.4); 7.4771 (5.7); 7.4754 (5.5); 7.3398 (6.4); 7.2616 (4.9); 7.2520 (3.1); 7.1885 (1.0); 7.1827 (1.7); 7.1783 (1.6); 7.1702 (1.5); 7.1659 (1.0); 6.9515 (2.6); 6.9363 (3.0); 6.8897 (3.3); 6.7050 (1.8); 6.6901 (1.6); 6.1002 (2.2); 4.7630 (1.1); 4.7533 (1.2); 4.2173 (1.3); 4.2108 (1.5); 4.1958 (1.5); 4.1893 (1.6); 3.8515 (0.7); 3.8475 (0.7); 3.8417 (0.9); 3.8381 (0.9); 3.8319 (1.0); 3.8285 (0.9); 3.8249 (0.8); 3.8227 (0.8); 3.8122 (0.4); 3.7817 (2.0); 3.7692 (1.4); 3.7602 (1.8); 3.7476 (1.4); 2.9828 (8.6); 2.9727 (9.1); 2.9600 (1.6); 2.9503 (1.4); 2.9323 (1.5); 2.9228 (1.4); 2.7000 (1.5); 2.6804 (1.5); 2.6727 (1.4); 2.6529 (1.2); 2.6119 (12.8); 2.2491 (16.0); 2.1702 (15.0); 1.2548 (0.8); 0.8463 (0.4); 0.0712 (1.2); −0.0002 (5.3)
I-003: $^1$H-NMR(400.0 MHz, $d_6$-DMSO):
δ = 8.0691 (16.0); 7.7706 (1.0); 7.7504 (3.4); 7.7303 (3.6); 7.7152 (4.4); 7.7016 (5.9); 7.6184 (2.8); 7.5984 (2.1); 7.4089 (3.5); 7.4013 (3.3); 7.2721 (7.1); 7.2511 (10.1); 7.1570 (11.0); 7.1361 (7.7); 5.7549 (6.2); 4.0558 (0.5); 4.0380 (1.6); 4.0202 (1.7); 4.0024 (0.6); 3.8298 (1.1); 3.8230 (2.0); 3.7994 (4.4); 3.7725 (2.0); 3.7605 (3.2); 3.7534 (1.9); 3.7365 (1.8); 3.7284 (0.8); 3.3217 (129.8); 2.8669 (0.5); 2.8538 (0.6); 2.8337 (2.9); 2.8215 (4.4); 2.8054 (2.6); 2.7907 (0.6); 2.7712 (0.5); 2.6753 (0.8); 2.6709 (1.0); 2.6663 (0.8); 2.6619 (0.4); 2.5240 (3.1); 2.5106 (63.6); 2.5063 (131.0); 2.5018 (174.2); 2.4973 (124.7); 2.4929 (59.8); 2.3331 (0.7); 2.3285 (1.0); 2.3241 (0.7); 2.0739 (3.3); 1.9886 (7.0); 1.3358 (0.4); 1.2983 (0.7); 1.2587 (1.1); 1.2346 (2.6); 1.1928 (2.2); 1.1750 (4.2); 1.1572 (2.1); 0.9404 (0.4); 0.9235 (0.4); 0.8534 (0.4); 0.0077 (0.6); −0.0003 (17.2); −0.0084 (0.6)
I-004: $^1$H-NMR(499.9 MHz, CDCl3):
δ = 7.9364 (5.2); 7.5605 (0.6); 7.5473 (1.0); 7.5342 (0.6); 7.4162 (0.5); 7.4138 (0.5); 7.3999 (1.1); 7.3861 (0.7); 7.3837 (0.6); 7.3215 (0.9); 7.3054 (1.3); 7.2893 (0.5); 7.2598 (4.4); 6.9781 (1.8); 6.9628 (2.0); 6.8688 (2.0); 6.6891 (1.1); 6.6741 (1.0); 6.0251 (1.2); 4.2657 (0.9); 4.2592 (1.0); 4.2442 (1.0); 4.2377 (1.0); 3.8922 (0.4); 3.8876 (0.4); 3.8818 (0.6); 3.8780 (0.5); 3.8721 (0.6); 3.8684 (0.5); 3.8655 (0.4); 3.8623 (0.4); 3.8302 (1.6); 3.8179 (1.0); 3.8087 (1.4); 3.7963 (1.0); 2.9979 (0.8); 2.9881 (0.8); 2.9706 (1.0); 2.9607 (0.9); 2.7425 (1.1); 2.7230 (1.1); 2.7152 (0.9); 2.6956 (0.9); 2.6411 (16.0); 2.2708 (11.4); 2.1118 (10.6); −0.0002 (5.4)
I-005: $^1$H-NMR(400.2 MHz, $d_6$-DMSO):
δ = 8.0849 (8.6); 7.9524 (1.3); 7.4247 (1.5); 7.4167 (1.5); 7.2527 (0.5); 7.2484 (0.5); 7.2317 (1.4); 7.2276 (1.4); 7.2108 (1.1); 7.2070 (1.2); 7.1790 (0.9); 7.1751 (1.0); 7.1570 (1.4); 7.1390 (0.6); 7.1354 (0.5); 7.0574 (2.0); 7.0382 (2.4); 6.9707 (0.8); 6.9667 (0.9); 6.9537 (1.0); 6.9504 (1.5); 6.9466 (1.0); 6.9334 (3.1); 6.8353 (1.3); 6.8165 (1.1); 3.9038 (16.0); 3.7795 (0.3); 3.7611 (1.5); 3.7519 (3.0); 3.7482 (2.9); 3.7361 (0.7); 3.7264 (1.1); 3.7208 (0.9); 3.7084 (0.6); 3.6996 (0.4); 3.3316 (26.0); 2.8906 (9.7); 2.8112 (1.2); 2.7965 (2.0); 2.7804 (1.3); 2.7316 (8.4); 2.5249 (0.6); 2.5201 (0.8); 2.5114 (9.7); 2.5070 (19.6); 2.5025 (25.9); 2.4979 (19.2); 2.4934 (9.5); 2.2409 (11.6); 2.1940 (10.6); −0.0002 (5.1)
I-006: $^1$H-NMR(300.2 MHz, CDCl3):
δ = 7.3681 (1.0); 7.3416 (2.4); 7.3147 (1.8); 7.2998 (5.3); 7.2987 (5.2); 7.2380 (1.8); 7.2349 (1.8); 7.2048 (2.2); 7.1972 (2.7); 7.1910 (1.4); 7.1157 (1.3); 7.1113 (1.2); 7.0883 (1.0); 7.0847 (1.0); 7.0424 (2.7); 7.0212 (0.8); 6.9957 (3.7); 6.9854 (2.6); 6.9592 (0.6); 5.3371 (2.7); 5.3360 (2.6); 4.9524 (1.6); 4.2431 (16.0); 4.1684 (0.4); 4.1582 (0.9); 4.1461 (1.2); 4.1217 (1.2); 4.1102 (1.2); 3.9416 (0.5); 3.9328 (0.6); 3.9224 (0.7); 3.9135 (0.8); 3.9037 (0.7); 3.8945 (0.5); 3.8849 (0.4); 3.8417 (1.5); 3.8229 (1.0); 3.8052 (1.1); 3.7864 (0.9); 3.0132 (0.7); 2.9936 (0.7); 2.9671 (1.2); 2.9475 (1.1); 2.8402 (1.2); 2.8118 (1.1); 2.7942 (0.8); 2.7657 (0.7); 2.6456 (0.4); 2.5162 (15.1); 2.3298 (12.2); 2.3104 (13.5); 2.1655 (0.8); 2.0810 (1.2); 2.0433 (5.2); 2.0422 (5.1); 1.6617 (1.1); 1.3203 (0.4); 1.2952 (1.2); 1.2731 (0.6); 0.8981 (0.5); 0.8766 (0.6); 0.1081 (0.7); 0.0380 (5.1); 0.0368 (5.0)
I-007: $^1$H-NMR(499.9 MHz, $d_6$-DMSO):
δ = 8.1831 (16.0); 8.1727 (0.4); 8.1431 (8.2); 7.7474 (6.8); 7.7330 (4.5); 7.7171 (3.9); 7.6924 (4.7); 7.6769 (2.4); 7.6446 (3.4); 7.6284 (2.5); 7.5820 (6.9); 7.5777 (7.3); 7.4682 (3.6); 7.4517 (4.4); 7.3128 (2.7); 7.3093 (2.8); 7.2965 (2.3); 7.2930 (2.3); 4.3091 (1.2); 3.7162 (1.2); 3.5268 (0.9); 3.3395 (6.1); 3.0209 (2.1); 3.0071 (2.1); 2.9934 (2.9); 2.9797 (2.8); 2.8882 (2.8); 2.8746 (2.9); 2.8608 (2.1); 2.8471 (2.0); 2.6402 (0.7); 2.6366 (0.9); 2.6330 (0.8); 2.5231 (2.8); 2.5195 (3.6); 2.5053 (81.5); 2.5017 (113.2); 2.4982 (87.2); 2.3664 (0.6); 2.3628 (0.8); 2.3593 (0.6)
I-008: $^1$H-NMR(300.2 MHz, CDCl3):
δ = 7.6575 (6.0); 7.5545 (0.4); 7.5258 (2.8); 7.5083 (5.3); 7.2989 (10.6); 7.2789 (2.8); 7.2264 (0.3); 7.2119 (1.0); 7.1998 (1.4); 7.1931 (1.4); 7.1819 (1.1); 7.1740 (0.8); 6.9976 (2.5); 6.9722 (3.0); 6.9358 (3.2); 6.7594 (1.8); 6.7339 (1.5); 6.1087 (2.1); 5.3656 (2.2); 5.3375 (0.6); 4.2843 (1.2); 4.2745 (1.4); 4.2495 (1.5); 4.2400 (1.4); 3.8933 (0.8); 3.8766 (0.9); 3.8683 (0.7); 3.8608 (0.8); 3.8446 (2.6); 3.8238 (0.9); 3.8099 (1.8); 3.7889 (1.1); 3.0177 (1.0); 3.0031 (1.0); 2.9725 (1.4); 2.9571 (1.3); 2.7530 (1.4); 2.7214 (1.3); 2.7080 (1.1); 2.6757 (1.0); 2.6232 (0.9); 2.6111 (1.2); 2.6036 (0.9); 2.3343 (0.5); 2.3261 (0.4); 2.2904 (16.0); 2.2529 (0.5); 2.2179 (15.0); 1.7901 (0.8); 1.2916 (0.8); 0.9108 (0.6); 0.8898 (3.1); 0.8734 (3.2); 0.8683 (2.8); 0.8527 (0.9); 0.6339 (0.9); 0.6189 (2.8); 0.6109 (3.2); 0.6009 (2.6); 0.5845 (0.8); 0.1074 (1.3); 0.0373 (11.6)
I-009: $^1$H-NMR(300.2 MHz, CDCl3):
δ = 8.4299 (6.8); 7.6093 (4.4); 7.5923 (4.4); 7.5654 (0.3); 7.3649 (2.6); 7.3138 (1.1); 7.2989 (10.8); 7.2760 (0.7); 7.0123 (2.5); 6.9868 (2.9); 6.9249 (3.1); 6.7230 (1.7); 6.6994 (1.4); 6.0943 (2.1); 5.5674 (3.4); 5.5594 (3.5); 5.3373 (0.8); 4.4552 (3.1); 4.4472 (3.2); 4.3387 (1.1); 4.3290 (1.4); 4.3041 (1.5); 4.2949 (1.4); 4.0408 (1.4); 4.0176 (4.4); 3.9943 (4.5); 3.9709 (1.6); 3.9480 (0.6); 3.9313 (0.8); 3.9151 (0.8); 3.9065 (0.7); 3.8992 (0.8); 3.8865 (2.7); 3.8659 (0.8); 3.8522 (1.8); 3.8312 (1.1); 3.0565 (1.0); 3.0426 (1.0); 3.0115 (1.4); 2.9963 (1.3); 2.7774 (1.3); 2.7456 (1.3); 2.7323 (1.1); 2.6998 (1.0); 2.3049 (16.0); 2.2389 (0.4); 2.1940 (14.9); 1.5999 (14.5); 1.4943 (4.7); 1.4710 (9.8); 1.4478 (4.6); 1.4067 (0.4); 1.3835 (0.4); 1.3610 (0.6); 1.3333 (0.5); 1.3069 (1.1); 0.9852 (0.6); 0.9610 (1.2); 0.9369 (0.7); 0.9201 (0.8); 0.8968 (0.4); 0.1087 (1.2); 0.0485 (0.4); 0.0382 (10.6)
I-010: $^1$H-NMR(400.2 MHz, $d_6$-DMSO):
δ = 8.3149 (0.5); 8.0160 (1.7); 8.0061 (1.7); 7.8968 (6.8); 7.7408 (0.6); 7.7215 (1.8); 7.7004 (3.4); 7.6683 (3.9); 7.6630 (5.1); 7.6385 (2.1); 7.6175 (0.9); 7.6131 (0.9); 7.5242 (2.5); 7.5031 (3.3); 7.3900 (2.0); 7.3847 (1.9); 7.3690 (1.5); 7.3637 (1.4); 5.7548 (8.8); 5.0826 (0.6); 5.0741 (1.5); 5.0647 (1.5); 5.0558 (0.6); 4.0399 (0.9); 4.0314 (1.0); 4.0119 (1.5); 4.0035 (1.3); 3.9015 (1.2); 3.8933 (1.2); 3.8734 (0.9); 3.8650 (1.0); 3.3216 (143.7); 2.6751 (1.2); 2.6705 (1.7); 2.6660 (1.2); 2.6615 (0.6); 2.6263 (16.0); 2.5241 (5.2); 2.5192 (8.1); 2.5106 (99.3); 2.5061 (195.0); 2.5016 (253.0); 2.4970 (184.0); 2.4925 (90.1); 2.3375 (0.6); 2.3330 (1.2); 2.3284 (1.6); 2.3239 (1.2); 2.3195 (0.6); 2.0737 (0.3); 1.2352 (0.5); 0.8761 (0.4); 0.1460 (1.4); 0.1168 (3.2); 0.0899 (2.2); 0.0610 (2.0); 0.0080 (11.2); −0.0001 (308.4); −0.0084 (12.5); −0.1496 (1.4)
I-011: $^1$H-NMR(499.9 MHz, CDCl3):

TABLE 2-continued

δ = 7.9822 (5.1); 7.6532 (2.2); 7.6372 (2.1); 7.5021 (0.5); 7.4859 (2.9); 7.4759 (4.8); 7.3538 (2.8); 7.3316 (2.4); 7.3159 (3.8); 7.2585 (9.4); 7.2423 (1.9); 7.2272 (1.0); 7.0797 (4.9); 7.0568 (1.4); 7.0411 (2.1); 7.0267 (1.1); 6.1856 (2.1); 5.0888 (1.1); 5.0808 (1.2); 5.0732 (1.2); 5.0649 (1.0); 4.4325 (1.2); 4.4242 (1.2); 4.4105 (1.3); 4.4022 (1.2); 4.0366 (1.5); 4.0202 (1.6); 4.0147 (1.4); 3.9983 (1.2); 3.7438 (16.0); 2.6947 (15.5); 2.0428 (1.2); 1.5564 (2.7); 1.2723 (0.5); 1.2579 (0.9); 1.2437 (0.3); 0.0701 (0.6); −0.0002 (10.2)

I-012: $^{1}$H-NMR(300.2 MHz, CDCl3):

δ = 8.0009 (6.4); 7.5966 (4.6); 7.5798 (4.1); 7.5534 (0.3); 7.3519 (2.7); 7.2997 (14.2); 7.2981 (13.5); 7.2789 (1.4); 7.2726 (1.2); 7.2657 (1.0); 7.2574 (0.7); 7.0046 (2.5); 6.9790 (2.9); 6.9209 (3.1); 6.7152 (1.7); 6.6901 (1.4); 6.1644 (2.0); 4.3314 (1.2); 4.3213 (1.4); 4.2964 (1.5); 4.2863 (1.5); 4.1721 (0.9); 4.1483 (0.9); 4.1242 (0.4); 3.9181 (0.8); 3.9058 (0.9); 3.8987 (0.7); 3.8890 (0.7); 3.8818 (0.6); 3.8661 (2.3); 3.8450 (1.0); 3.8313 (1.8); 3.8101 (1.1); 3.0521 (1.1); 3.0377 (1.2); 3.0246 (1.6); 2.9992 (5.2); 2.9739 (4.9); 2.9485 (1.7); 2.7618 (1.4); 2.7295 (1.4); 2.7167 (1.2); 2.6837 (1.1); 2.3006 (16.0); 2.1898 (14.9); 2.0843 (4.1); 1.6221 (0.7); 1.3974 (5.0); 1.3725 (10.0); 1.3715 (9.9); 1.3470 (4.9); 1.3222 (1.2); 1.2967 (3.0); 1.2745 (1.2); 0.1082 (0.7); 0.0479 (0.6); 0.0386 (16.4); 0.0370 (15.8)

I-013: $^{1}$H-NMR(499.9 MHz, CDCl3):

δ = 7.9380 (5.2); 7.5220 (0.8); 7.5063 (1.8); 7.4904 (1.2); 7.4267 (1.6); 7.4113 (1.1); 7.2610 (11.8); 7.2063 (2.1); 7.1461 (1.1); 7.1439 (1.1); 7.1299 (1.1); 7.1276 (1.0); 6.9597 (2.0); 6.9444 (2.2); 6.8873 (2.4); 6.7791 (1.1); 6.6850 (1.3); 6.6665 (3.0); 6.5535 (1.1); 6.1534 (1.5); 5.2986 (7.8); 4.2586 (1.0); 4.2522 (1.1); 4.2371 (1.1); 4.2307 (1.2); 3.8749 (0.4); 3.8709 (0.5); 3.8654 (0.6); 3.8614 (0.6); 3.8552 (0.7); 3.8481 (0.5); 3.8455 (0.5); 3.8071 (1.6); 3.7945 (1.1); 3.7855 (1.4); 3.7729 (1.1); 2.9894 (0.8); 2.9800 (0.9); 2.9620 (1.0); 2.9526 (1.0); 2.7114 (1.1); 2.6916 (1.1); 2.6840 (1.0); 2.6642 (0.9); 2.6367 (16.0); 2.2594 (12.2); 2.1649 (11.5); 2.0445 (1.3); 1.5820 (9.2); 1.2586 (0.9); 1.2555 (0.9); 1.2446 (0.3); 0.9357 (0.4); 0.0062 (0.4); −0.0002 (11.4)

I-014: $^{1}$H-NMR(300.2 MHz, CDCl3):

δ = 8.2582 (3.2); 7.6116 (2.1); 7.5949 (1.7); 7.3622 (1.2); 7.2987 (8.5); 7.2881 (0.8); 7.2814 (0.6); 7.2679 (0.3); 7.0348 (0.7); 7.0072 (1.2); 6.9982 (0.9); 6.9815 (1.4); 6.9387 (0.9); 6.9231 (1.5); 6.7145 (0.8); 6.6896 (0.7); 6.2641 (1.5); 6.2049 (1.3); 6.1586 (1.0); 5.6878 (1.4); 5.6509 (1.4); 4.3449 (0.5); 4.3347 (0.6); 4.3096 (0.7); 4.2995 (0.7); 3.9299 (0.4); 3.9146 (0.4); 3.8985 (0.3); 3.8914 (0.3); 3.8778 (1.1); 3.8570 (0.4); 3.8430 (0.8); 3.8219 (0.5); 3.0604 (0.5); 3.0462 (0.5); 3.0154 (0.6); 2.9999 (0.6); 2.7673 (0.6); 2.7349 (0.6); 2.7221 (0.6); 2.6891 (0.5); 2.3039 (7.3); 2.1892 (6.9); 2.0834 (0.5); 1.6029 (16.0); 1.2973 (0.9); 0.9193 (0.6); 0.1070 (0.8); 0.0480 (0.3); 0.0372 (7.7)

I-015: $^{1}$H-NMR(300.2 MHz, CDCl3):

δ = 8.0398 (5.2); 7.9135 (1.8); 7.8942 (1.1); 7.8851 (2.7); 7.8628 (3.4); 7.7663 (0.9); 7.7483 (0.9); 7.7351 (1.1); 7.5838 (1.5); 7.5693 (2.0); 7.5644 (4.1); 7.5611 (4.1); 7.5538 (2.2); 7.5501 (2.4); 7.5356 (3.4); 7.5260 (3.2); 7.5030 (1.7); 7.4971 (1.5); 7.4744 (1.4); 7.4686 (1.4); 7.4634 (1.0); 7.4522 (1.2); 7.4448 (1.0); 7.4320 (0.8); 7.4238 (0.4); 7.2989 (15.3); 6.3678 (1.4); 4.9973 (0.6); 4.9882 (0.7); 4.9818 (0.8); 4.9732 (0.7); 4.9646 (0.6); 4.4812 (0.8); 4.4697 (0.8); 4.4441 (1.0); 4.4328 (0.9); 4.1707 (0.4); 4.1473 (0.4); 4.1240 (0.4); 4.1022 (0.6); 3.9204 (1.4); 3.8962 (1.4); 3.8834 (1.3); 3.8591 (1.2); 2.7518 (16.0); 2.0828 (3.6); 1.6711 (0.4); 1.6490 (0.5); 1.6402 (0.5); 1.6011 (1.3); 1.3444 (0.3); 1.3208 (0.8); 1.2940 (2.8); 1.2732 (0.7); 0.9980 (0.5); 0.9736 (1.0); 0.9492 (0.4); 0.9191 (0.4); 0.1089 (1.0); 0.0495 (0.6); 0.0387 (18.3); 0.0278 (0.8)

I-016: $^{1}$H-NMR(300.2 MHz, CDCl3):

δ = 8.1593 (8.5); 7.6555 (4.0); 7.6382 (5.0); 7.4904 (3.5); 7.4847 (3.6); 7.4149 (2.3); 7.3157 (0.9); 7.2987 (17.1); 7.2855 (1.1); 7.2769 (0.8); 7.1496 (1.0); 7.1436 (0.9); 7.1225 (3.4); 7.1164 (3.6); 7.1015 (5.3); 7.0744 (1.4); 6.0646 (1.5); 5.3375 (2.2); 4.2023 (1.2); 4.1925 (1.5); 4.1666 (1.8); 4.1565 (2.0); 4.0578 (0.6); 4.0472 (0.8); 4.0306 (0.9); 4.0184 (1.0); 4.0087 (0.6); 4.0012 (0.6); 3.9914 (0.4); 3.9757 (2.2); 3.9600 (1.3); 3.9398 (1.5); 3.9242 (1.1); 3.1762 (1.1); 3.1589 (1.1); 3.1311 (1.9); 3.1136 (1.8); 3.0183 (1.9); 2.9887 (1.8); 2.9734 (1.2); 2.9435 (1.1); 2.0823 (1.1); 1.5867 (16.0); 1.2968 (0.7); 0.1076 (3.9); 0.0488 (0.7); 0.0379 (19.0); 0.0269 (0.7)

I-017: $^{1}$H-NMR(300.2 MHz, CDCl3):

δ = 8.1640 (8.3); 7.6566 (3.3); 7.6519 (2.1); 7.6393 (4.9); 7.3917 (2.2); 7.2985 (14.8); 7.2564 (3.3); 7.2501 (3.5); 7.2432 (1.7); 7.2366 (1.3); 7.2270 (1.0); 7.2187 (0.7); 7.0563 (0.9); 7.0500 (0.8); 7.0293 (2.1); 7.0228 (2.2); 6.9936 (4.2); 6.9666 (1.6); 6.0785 (1.6); 5.3374 (2.7); 4.2585 (1.4); 4.2329 (1.7); 4.2136 (0.4); 3.9344 (0.5); 3.9249 (0.6); 3.9160 (0.9); 3.9019 (2.1); 3.8870 (0.9); 3.8724 (2.1); 3.8541 (0.8); 3.0382 (0.9); 3.0230 (0.9); 2.9926 (1.4); 2.9768 (1.3); 2.8220 (1.2); 2.7909 (1.2); 2.7766 (0.9); 2.7448 (0.8); 2.3204 (16.0); 2.0827 (1.2); 1.5830 (9.2); 1.2971 (0.5); 0.1078 (0.6); 0.0487 (0.7); 0.0381 (19.4); 0.0270 (0.6)

I-018: $^{1}$H-NMR(300.2 MHz, CDCl3):

δ = 8.0009 (5.2); 7.6148 (0.5); 7.5891 (1.7); 7.5671 (4.8); 7.5460 (0.5); 7.4934 (2.6); 7.4568 (1.0); 7.4492 (1.6); 7.4425 (1.1); 7.4265 (1.1); 7.3003 (11.0); 7.1857 (1.3); 7.1596 (3.3); 7.1476 (3.3); 7.1277 (2.2); 7.0992 (0.9); 6.1870 (1.9); 5.3393 (5.2); 4.7514 (0.9); 4.7380 (1.0); 4.7269 (1.0); 4.7124 (1.0); 4.3916 (1.2); 4.3777 (1.1); 4.3549 (1.3); 4.3409 (1.2); 3.7520 (1.5); 3.7260 (1.4); 3.7152 (1.4); 3.6893 (1.3); 2.7564 (0.4); 2.7335 (16.0); 2.3486 (0.4); 2.3228 (0.4); 2.2834 (13.3); 2.2222 (13.1); 2.1877 (0.3); 2.0844 (1.4); 1.6154 (4.2); 1.3223 (0.5); 1.2985 (1.0); 1.2748 (0.4); 0.1092 (3.2); 0.0392 (14.1)

I-019: $^{1}$H-NMR(300.2 MHz, CDCl3):

δ = 8.1622 (8.7); 7.6504 (0.4); 7.6394 (4.7); 7.6362 (4.7); 7.6288 (2.0); 7.6243 (2.1); 7.6182 (2.5); 7.5917 (0.4); 7.3989 (2.3); 7.2987 (14.6); 7.2847 (1.0); 7.2761 (1.2); 7.2641 (1.3); 7.2574 (1.2); 7.2460 (0.7); 6.9900 (2.6); 6.9641 (3.0); 6.8192 (2.8); 6.5891 (1.6); 6.5835 (1.6); 6.5634 (1.4); 6.5577 (1.4); 6.1172 (1.9); 4.3289 (1.0); 4.3202 (1.3); 4.2942 (1.4); 4.2857 (1.2); 3.9179 (0.5); 3.9019 (0.7); 3.8915 (0.6); 3.8851 (0.8); 3.8760 (0.6); 3.8689 (0.8); 3.8596 (2.7); 3.8390 (0.8); 3.8252 (1.9); 3.8043 (1.1); 3.0504 (1.0); 3.0364 (1.0); 3.0053 (1.4); 2.9902 (1.3); 2.7430 (1.2); 2.7108 (1.2); 2.6978 (1.2); 2.6650 (1.0); 2.2999 (16.0); 1.7742 (0.3); 1.7572 (0.7); 1.7459 (0.8); 1.7292 (1.5); 1.7123 (0.9); 1.7011 (0.9); 1.6841 (0.6); 1.6521 (5.5); 0.9521 (0.5); 0.9359 (2.4); 0.9295 (2.7); 0.9135 (1.2); 0.9077 (2.5); 0.9014 (2.4); 0.8857 (0.6); 0.5647 (1.0); 0.5576 (1.3); 0.5485 (2.0); 0.5417 (2.6); 0.5349 (2.2); 0.5251 (1.5); 0.5185 (1.1); 0.1077 (1.3); 0.0485 (0.5); 0.0377 (16.0); 0.0268 (0.6)

I-020: $^{1}$H-NMR(300.2 MHz, CDCl3):

δ = 8.2759 (0.5); 8.1614 (16.0); 7.6511 (0.9); 7.6402 (8.7); 7.6374 (8.0); 7.6284 (4.0); 7.6230 (5.9); 7.5938 (0.6); 7.4169 (4.4); 7.3341 (1.8); 7.3250 (2.1); 7.3151 (2.8); 7.3088 (2.4); 7.2986 (16.3); 7.0801 (5.7); 7.0540 (6.4); 7.0100 (6.5); 7.0041 (6.8); 6.9887 (0.3); 6.6804 (3.7); 6.6744 (3.7); 6.6543 (3.2); 6.6483 (3.2); 6.1040 (3.1); 4.2671 (2.3); 4.2564 (2.6); 4.2310 (2.9); 4.2203 (3.1); 4.0577 (0.4); 4.0473 (0.6); 4.0396 (1.0); 4.0305 (1.3); 4.0233 (1.3); 4.0153 (1.4); 4.0083 (1.4); 3.9999 (1.4); 3.9921 (1.1); 3.9833 (0.9); 3.9733 (0.5); 3.9182 (3.8); 3.8998 (2.7); 3.8820 (3.1); 3.8636 (2.4); 3.1723 (2.1); 3.1564 (2.1); 3.1272 (3.1); 3.1113 (2.9); 2.9287 (3.1); 2.8975 (3.0); 2.8837 (2.3); 2.8524 (2.1); 2.0819 (1.0); 2.0438 (0.9); 1.7885 (0.7); 1.7717 (1.3); 1.7605

TABLE 2-continued (1.4); 1.7437 (2.8); 1.7269 (1.6); 1.7158 (1.5); 1.6988 (0.8); 1.5983 (12.6); 1.2964 (0.5); 0.9968 (0.9); 0.9792 (4.5); 0.9733 (5.2); 0.9700 (4.3); 0.9512 (4.7); 0.9453 (4.5); 0.9283 (1.0); 0.9101 (0.3); 0.6107 (0.5); 0.6020 (0.4); 0.5935 (0.6); 0.5795 (2.9); 0.5757 (2.4); 0.5703 (2.3); 0.5632 (4.7); 0.5578 (4.4); 0.5543 (4.2); 0.5474 (2.3); 0.5399 (2.6); 0.5267 (0.5); 0.5224 (0.5); 0.5160 (0.4); 0.5056 (0.4); 0.0477 (0.6); 0.0371 (19.6); 0.0261 (0.7)
I-021: $^{1}$H-NMR(300.2 MHz, CDCl3):
δ = 8.1713 (12.5); 7.6375 (6.4); 7.6343 (6.6); 7.6261 (3.0); 7.6208 (3.8); 7.6172 (4.1); 7.5906 (0.6); 7.4428 (3.3); 7.3555 (1.3); 7.3470 (1.7); 7.3364 (2.0); 7.3298 (1.7); 7.3257 (1.3); 7.3169 (1.0); 7.2989 (19.2); 7.1958 (4.5); 7.1902 (4.8); 7.1358 (4.1); 7.1098 (4.8); 6.8484 (2.6); 6.8428 (2.6); 6.8224 (2.2); 6.8168 (2.2); 6.1296 (2.4); 5.3379 (0.4); 4.2733 (1.7); 4.2626 (2.0); 4.2372 (2.2); 4.2265 (2.4); 4.0481 (0.7); 4.0327 (1.0); 4.0244 (1.1); 4.0174 (1.0); 4.0086 (1.1); 4.0012 (0.8); 3.9929 (0.7); 3.9823 (0.4); 3.9344 (2.9); 3.9160 (2.0); 3.8983 (2.3); 3.8798 (1.7); 3.1899 (1.6); 3.1744 (1.6); 3.1450 (2.3); 3.1293 (2.2); 2.9467 (2.4); 2.9156 (2.2); 2.9019 (1.8); 2.8705 (1.6); 2.8134 (0.6); 2.7907 (1.5); 2.7678 (2.1); 2.7448 (1.6); 2.7216 (0.7); 1.6106 (4.4); 1.2911 (0.4); 1.2434 (0.5); 1.2203 (0.6); 1.1628 (15.5); 1.1543 (16.0); 1.1397 (15.5); 1.1313 (15.5); 0.9294 (0.4); 0.9052 (0.7); 0.1074 (1.8); 0.0482 (0.7); 0.0374 (21.2); 0.0265 (0.8)
I-022: $^{1}$H-NMR(300.2 MHz, CDCl3):
δ = 8.1556 (4.2); 7.6218 (2.2); 7.6188 (2.6); 7.6093 (0.9); 7.5989 (1.2); 7.3483 (1.2); 7.2987 (8.7); 7.2672 (0.5); 7.2595 (0.7); 7.2454 (0.6); 7.2380 (0.7); 7.2287 (0.4); 6.9673 (1.6); 6.8960 (1.8); 6.8897 (3.2); 6.1298 (0.9); 5.3372 (1.8); 4.3501 (0.6); 4.3400 (0.6); 4.3143 (0.7); 4.3038 (0.7); 4.1714 (1.0); 4.1476 (1.0); 4.1239 (0.4); 3.9270 (0.4); 3.9223 (0.4); 3.9164 (0.4); 3.9108 (0.3); 3.9054 (0.4); 3.8250 (1.2); 3.8029 (0.7); 3.7891 (1.0); 3.7670 (0.7); 3.0294 (0.5); 3.0140 (0.5); 2.9845 (0.7); 2.9690 (0.6); 2.6547 (0.8); 2.6217 (0.8); 2.6098 (0.7); 2.5765 (0.6); 2.1286 (7.9); 2.1021 (8.1); 2.0826 (5.0); 2.0440 (1.3); 1.5959 (16.0); 1.3208 (1.2); 1.2970 (2.4); 1.2732 (1.1); 0.1076 (1.9); 0.0378 (9.7); 0.0269 (0.4)
I-023: $^{1}$H-NMR(300.2 MHz, CDCl3):
δ = 8.1706 (8.2); 7.6486 (0.3); 7.6360 (4.0); 7.6328 (4.6); 7.6272 (1.9); 7.6226 (1.8); 7.6134 (2.2); 7.5870 (0.4); 7.4230 (2.1); 7.3165 (0.9); 7.3089 (1.3); 7.2987 (12.3); 7.2883 (1.4); 7.2784 (0.7); 7.0377 (2.3); 7.0119 (2.8); 6.9867 (2.7); 6.7625 (1.5); 6.7569 (1.5); 6.7367 (1.3); 6.7312 (1.3); 6.1531 (1.7); 4.3309 (0.9); 4.3222 (1.2); 4.2963 (1.3); 4.2876 (1.1); 4.1947 (0.9); 4.1708 (2.7); 4.1470 (2.8); 4.1233 (1.0); 3.9274 (0.5); 3.9144 (0.6); 3.9064 (0.6); 3.8952 (0.7); 3.8854 (0.6); 3.8716 (2.5); 3.8511 (0.6); 3.8373 (1.8); 3.8164 (1.0); 3.0636 (0.9); 3.0500 (0.9); 3.0183 (1.4); 3.0038 (1.3); 2.7925 (0.4); 2.7691 (1.1); 2.7576 (1.3); 2.7462 (1.5); 2.7243 (2.0); 2.7121 (1.2); 2.7007 (0.5); 2.6795 (1.0); 2.3677 (0.5); 2.3298 (14.7); 2.0830 (12.3); 1.6012 (16.0); 1.3210 (3.2); 1.2972 (6.5); 1.2839 (0.4); 1.2734 (3.2); 1.2609 (0.3); 1.2227 (0.6); 1.1997 (0.6); 1.1621 (10.2); 1.1526 (10.5); 1.1391 (10.2); 1.1296 (10.2); 0.1077 (1.1); 0.0484 (0.4); 0.0376 (12.9); 0.0266 (0.5)
I-024: $^{1}$H-NMR(499.9 MHz, CDCl3):
δ = 8.1176 (8.0); 7.5773 (0.7); 7.5655 (1.3); 7.5518 (0.8); 7.3426 (0.8); 7.3266 (2.1); 7.3108 (1.9); 7.3032 (1.1); 7.2999 (1.2); 7.2874 (1.4); 7.2716 (0.6); 7.2601 (7.6); 6.9914 (1.4); 6.9602 (2.5); 6.9449 (2.7); 6.8819 (2.9); 6.8645 (2.8); 6.7724 (1.4); 6.6673 (1.5); 6.6523 (1.3); 6.0266 (1.7); 4.2866 (1.3); 4.2802 (1.3); 4.2651 (1.4); 4.2585 (1.4); 3.8865 (0.6); 3.8824 (0.6); 3.8788 (0.8); 3.8765 (0.8); 3.8727 (0.7); 3.8665 (0.8); 3.8629 (0.6); 3.8597 (0.6); 3.8567 (0.6); 3.8530 (0.4); 3.8226 (2.1); 3.8101 (1.3); 3.8011 (1.8); 3.7886 (1.3); 3.0078 (1.1); 2.9981 (1.1); 2.9805 (1.3); 2.9708 (1.2); 2.7181 (1.4); 2.6983 (1.4); 2.6908 (1.2); 2.6710 (1.1); 2.2663 (15.0); 2.1374 (0.3); 2.1112 (14.0); 2.0035 (16.0); 1.5659 (3.3); 0.0062 (0.5); −0.0002 (7.6)
I-025: $^{1}$H-NMR(300.2 MHz, CDCl3):
δ = 8.1610 (3.5); 7.6500 (1.9); 7.6327 (1.8); 7.4041 (1.0); 7.3372 (1.5); 7.3302 (1.6); 7.3194 (0.4); 7.3107 (0.5); 7.2987 (8.3); 7.2807 (0.3); 7.1690 (1.2); 7.1417 (1.6); 6.9965 (1.0); 6.9894 (1.0); 6.9693 (0.7); 6.9622 (0.7); 6.0661 (0.6); 5.3373 (2.4); 4.2068 (0.5); 4.1966 (0.6); 4.1707 (0.8); 4.1608 (0.8); 4.0501 (0.3); 4.0331 (0.4); 4.0217 (0.4); 3.9754 (0.9); 3.9597 (0.6); 3.9396 (0.6); 3.9238 (0.5); 3.1899 (0.4); 3.1726 (0.4); 3.1448 (0.8); 3.1274 (0.7); 3.0286 (0.8); 2.9989 (0.7); 2.9836 (0.5); 2.9536 (0.4); 2.0820 (0.5); 1.5923 (16.0); 1.3452 (0.4); 1.3202 (0.8); 1.3045 (2.3); 1.2974 (2.1); 0.9414 (0.8); 0.9197 (2.5); 0.8964 (1.0); 0.1073 (2.3); 0.0376 (9.0); 0.0267 (0.3)
I-026: $^{1}$H-NMR(300.1 MHz, CDCl3):
δ = 7.6924 (5.4); 7.5036 (0.4); 7.4781 (2.0); 7.4678 (2.2); 7.4585 (4.7); 7.3058 (3.2); 7.2842 (1.6); 7.2645 (1.1); 7.1899 (3.9); 7.1099 (6.2); 7.0966 (6.2); 7.0421 (1.3); 7.0293 (1.4); 7.0105 (0.7); 5.2336 (1.4); 5.1971 (1.4); 5.1334 (1.9); 4.3992 (0.5); 4.3898 (0.6); 4.3753 (0.7); 4.3654 (0.8); 4.3586 (0.9); 4.3489 (0.9); 4.3345 (0.9); 4.3250 (0.8); 4.1797 (0.6); 4.1558 (0.9); 4.1503 (0.9); 4.1390 (0.6); 4.1263 (0.8); 4.1149 (0.7); 4.1093 (0.7); 4.0853 (0.5); 2.7381 (0.4); 2.7328 (0.4); 2.7270 (0.4); 2.7144 (0.5); 2.7088 (0.5); 2.7021 (0.5); 2.6907 (0.6); 2.6852 (0.6); 2.6786 (0.6); 2.6726 (0.5); 2.6604 (0.5); 2.6543 (0.5); 2.6492 (0.5); 2.6242 (0.4); 2.5767 (16.0); 2.1486 (0.7); 2.1251 (0.8); 2.1163 (0.8); 2.0887 (14.0); 1.9181 (0.4); 1.7135 (0.4); −0.0008 (1.9); −0.0762 (1.4)
I-027: $^{1}$H-NMR(499.9 MHz, CDCl3):
δ = 7.8980 (5.4); 7.4723 (3.2); 7.4687 (3.1); 7.2638 (1.8); 7.1046 (1.0); 7.0886 (2.3); 7.0828 (2.2); 7.0723 (1.9); 7.0665 (3.8); 7.0414 (2.5); 7.0378 (2.4); 7.0249 (2.1); 7.0101 (1.6); 6.9962 (0.8); 6.9936 (0.7); 6.8242 (1.0); 6.8220 (1.0); 6.8089 (1.6); 6.7954 (0.8); 6.1646 (1.7); 4.1371 (1.3); 4.1308 (1.4); 4.1153 (1.6); 4.1090 (1.5); 4.0015 (0.4); 3.9921 (0.7); 3.9856 (1.0); 3.9767 (1.0); 3.9682 (1.0); 3.9586 (0.6); 3.9207 (1.6); 3.9115 (1.2); 3.8989 (1.3); 3.8897 (1.0); 3.1377 (1.1); 3.1277 (1.1); 3.1108 (1.4); 3.1007 (1.3); 2.9453 (1.4); 2.9270 (1.4); 2.9184 (1.1); 2.9000 (1.0); 2.6365 (16.0); 2.1019 (0.4); 2.0915 (0.7); 2.0848 (0.8); 2.0747 (1.2); 2.0645 (0.8); 2.0579 (0.7); 1.6411 (1.0); 1.0409 (0.7); 1.0316 (2.3); 1.0282 (2.4); 1.0256 (2.0); 1.0147 (2.3); 1.0113 (2.2); 1.0022 (0.5); 0.8031 (0.4); 0.7996 (0.4); 0.7862 (1.7); 0.7804 (1.6); 0.7763 (2.4); 0.7732 (2.4); 0.7711 (2.4); 0.7609 (1.4); −0.0002 (2.4)
I-028: $^{1}$H-NMR(300.2 MHz, CDCl3):
δ = 7.9768 (4.5); 7.5997 (0.6); 7.5735 (1.4); 7.5470 (1.0); 7.4838 (1.2); 7.4579 (0.7); 7.3462 (2.3); 7.3392 (2.4); 7.2989 (10.5); 7.2770 (1.5); 7.2251 (0.8); 7.2218 (0.9); 7.2178 (0.8); 7.1950 (0.8); 7.1910 (0.7); 7.1625 (1.9); 7.1352 (2.4); 6.9665 (1.5); 6.9594 (1.5); 6.9393 (1.2); 6.9322 (1.1); 6.9082 (1.0); 6.7205 (1.9); 6.5327 (1.0); 6.1544 (0.9); 5.3374 (9.2); 4.1905 (0.8); 4.1803 (0.9); 4.1703 (0.4); 4.1546 (1.1); 4.1447 (1.4); 4.0373 (0.5); 4.0212 (0.5); 4.0082 (0.6); 3.9985 (0.4); 3.9912 (0.4); 3.9599 (1.4); 3.9442 (0.8); 3.9241 (0.9); 3.9083 (0.7); 3.1856 (0.7); 3.1684 (0.7); 3.1406 (1.1); 3.1233 (1.0); 3.0109 (1.1); 2.9810 (1.1); 2.9658 (0.7); 2.9358 (0.7); 2.6888 (14.2); 2.0824 (1.4); 1.6051 (16.0); 1.3203 (0.4); 1.2965 (0.8); 1.2727 (0.3); 0.1066 (1.8); 0.0478 (0.4); 0.0369 (11.6); 0.0258 (0.4)
I-029: $^{1}$H-NMR(499.9 MHz, CDCl3):
δ = 7.9706 (2.5); 7.8850 (4.3); 7.5588 (0.4); 7.5433 (1.4); 7.5274 (1.9); 7.5215 (2.1); 7.5062 (0.6); 7.4720 (1.9); 7.4249 (1.2); 7.4098 (0.9); 7.3756 (2.3); 7.2823 (0.9); 6.4695 (1.2); 6.3671 (1.0); 6.3607 (1.8); 6.3572

TABLE 2-continued (1.8); 6.3387 (2.3); 6.3322 (1.6); 4.8737 (0.5); 4.8668 (0.8); 4.8613 (1.2); 4.8555 (0.9); 4.8490 (0.6); 4.3114 (0.9); 4.3036 (1.0); 4.2894 (1.1); 4.2816 (1.1); 4.0395 (1.2); 4.0269 (1.2); 4.0176 (1.1); 4.0050 (1.0); 2.9393 (16.0); 2.8554 (14.8); 2.6614 (13.0); 1.9093 (0.6); −0.0002 (1.0)

I-030: $^1$H-NMR(400.1 MHz, $d_6$-DMSO):
δ = 7.7353 (16.0); 7.5384 (10.0); 7.4019 (7.4); 7.3811 (9.6); 7.3707 (6.9); 7.3622 (6.5); 7.1722 (6.9); 7.1555 (9.0); 7.1377 (9.8); 7.1163 (5.2); 7.0971 (1.8); 6.9317 (2.9); 6.9171 (5.2); 6.8983 (2.7); 5.7597 (1.1); 3.8638 (5.8); 3.8416 (9.8); 3.7722 (3.6); 3.7641 (5.0); 3.7435 (3.5); 3.3131 (22.3); 3.0449 (1.4); 3.0255 (1.6); 3.0111 (5.0); 2.9910 (7.5); 2.9735 (4.7); 2.9544 (1.6); 2.9395 (1.3); 2.5789 (43.3); 2.5101 (13.6); 2.1043 (1.0); 2.0910 (2.1); 2.0826 (2.6); 2.0706 (3.9); 2.0586 (2.6); 2.0505 (2.2); 2.0369 (1.0); 1.0606 (0.4); 1.0464 (2.4); 1.0323 (8.3); 1.0119 (8.0); 1.0008 (2.7); 0.8415 (0.4); 0.8282 (0.4); 0.8031 (3.1); 0.7909 (10.3); 0.7789 (9.7); 0.7661 (2.4)

I-031: $^1$H-NMR(300.2 MHz, CDCl3):
δ = 8.0083 (5.3); 7.5863 (1.3); 7.5644 (4.0); 7.5427 (0.4); 7.4936 (1.9); 7.4536 (0.9); 7.4451 (1.5); 7.4379 (1.1); 7.4211 (2.4); 7.4066 (13.7); 7.3887 (0.8); 7.3803 (0.7); 7.2986 (8.3); 6.2693 (1.2); 4.8288 (0.6); 4.8235 (0.6); 4.8155 (0.7); 4.8096 (0.8); 4.8053 (0.8); 4.7993 (0.7); 4.7913 (0.7); 4.7859 (0.7); 4.4019 (0.9); 4.3907 (0.8); 4.3672 (1.0); 4.3650 (1.0); 4.3537 (0.9); 3.8252 (1.5); 3.8010 (1.4); 3.7883 (1.4); 3.7641 (1.3); 2.7339 (16.0); 1.6570 (0.4); 1.2937 (0.6); 0.1086 (0.8); 0.0381 (7.9)

I-032: $^1$H-NMR(300.2 MHz, CDCl3):
δ = 7.9905 (5.3); 7.6025 (3.3); 7.5856 (3.9); 7.4362 (2.1); 7.3449 (0.8); 7.3371 (0.9); 7.3295 (1.2); 7.3237 (1.1); 7.3146 (0.9); 7.2999 (9.6); 7.2028 (2.7); 7.1979 (2.8); 7.1412 (2.3); 7.1152 (2.6); 6.8417 (1.5); 6.8364 (1.5); 6.8158 (1.3); 6.8106 (1.3); 6.1569 (1.5); 4.2561 (1.0); 4.2453 (1.1); 4.2201 (1.3); 4.2093 (1.4); 4.0222 (0.7); 4.0153 (0.7); 4.0077 (0.7); 3.9283 (1.6); 3.9100 (1.1); 3.8922 (1.2); 3.8738 (1.0); 3.1875 (0.9); 3.1718 (0.9); 3.1423 (1.3); 3.1267 (1.2); 2.9446 (1.3); 2.9135 (1.3); 2.8996 (1.0); 2.8685 (0.9); 2.8195 (0.4); 2.8102 (0.5); 2.7968 (0.9); 2.7739 (1.4); 2.7507 (1.0); 2.7277 (0.4); 2.6854 (16.0); 1.6057 (9.2); 1.3031 (1.3); 1.2613 (0.5); 1.1696 (8.4); 1.1618 (8.8); 1.1466 (8.4); 1.1388 (8.4); 0.9344 (0.6); 0.9198 (1.1); 0.9100 (0.6); 0.8965 (0.5); 0.0383 (11.8)

I-033: $^1$H-NMR(499.9 MHz, CDCl3):
δ = 8.0987 (3.8); 7.4527 (1.0); 7.4487 (1.3); 7.4444 (0.9); 7.4400 (0.7); 7.4233 (1.2); 7.4074 (0.9); 7.2604 (4.6); 7.2091 (0.5); 7.1955 (0.7); 7.1819 (0.5); 7.0428 (0.4); 7.0265 (1.5); 7.0212 (2.2); 7.0172 (1.4); 7.0011 (0.3); 6.9678 (0.7); 6.9635 (1.0); 6.9564 (0.8); 6.9512 (0.7); 6.9463 (1.0); 6.1527 (0.7); 5.2965 (16.0); 4.1433 (0.4); 4.1396 (0.4); 4.1372 (0.4); 4.1335 (0.4); 4.1215 (0.4); 4.1176 (0.6); 4.1154 (0.6); 4.1117 (0.5); 3.9788 (0.4); 3.9693 (0.4); 3.9611 (0.4); 3.9066 (0.6); 3.8971 (0.5); 3.8850 (0.5); 3.8755 (0.4); 3.1203 (0.5); 3.1100 (0.5); 3.0932 (0.7); 3.0829 (0.7); 2.9325 (0.5); 2.9297 (0.5); 2.9143 (0.5); 2.9114 (0.5); 2.9055 (0.4); 2.9026 (0.4); 2.8872 (0.4); 2.8843 (0.4); 2.8017 (0.4); 2.7858 (0.5); 2.7769 (0.4); 2.7609 (0.4); 2.2960 (0.4); 1.8918 (0.4); 1.8768 (0.4); 1.8673 (0.5); 1.6558 (0.3); 1.6476 (0.4); 1.6439 (0.4); 1.6388 (0.4); 1.6350 (0.4); 1.6305 (0.5); 1.6266 (0.4); 1.6224 (0.4); 1.6186 (0.4); 1.6142 (0.4); 1.6103 (0.3); 1.6063 (0.4); 1.6024 (0.4); 1.5862 (0.5); 1.2919 (0.3); 1.2555 (1.3); 1.2396 (0.4); 0.8810 (0.3); 0.8453 (0.4); 0.8382 (0.4); 0.8331 (0.4); −0.0002 (5.4)

I-034: $^1$H-NMR(300.2 MHz, $d_6$-DMSO):
δ = 7.7819 (0.6); 7.7562 (1.8); 7.7302 (2.1); 7.7118 (2.6); 7.6863 (1.1); 7.6251 (3.1); 7.5836 (1.4); 7.4295 (2.1); 7.0467 (1.9); 7.0212 (2.4); 6.9600 (3.0); 6.8484 (1.8); 6.8237 (1.4); 3.8068 (5.6); 3.7715 (1.2); 3.3540 (16.0); 2.8234 (2.8); 2.8043 (2.7); 2.5226 (2.7); 2.4553 (12.2); 2.2395 (12.4); 2.2208 (12.0); 2.0099 (0.8); 1.2521 (0.4); 1.1954 (0.4)

I-035: $^1$H-NMR(300.2 MHz, CDCl3):
δ = 7.9894 (5.2); 7.5999 (3.6); 7.5970 (3.2); 7.5827 (2.9); 7.4150 (1.9); 7.2993 (10.4); 7.2869 (1.3); 7.2807 (1.2); 7.2666 (0.6); 7.0522 (2.0); 7.0264 (2.4); 6.9910 (2.4); 6.7809 (1.3); 6.7757 (1.4); 6.7555 (1.1); 6.7505 (1.1); 6.1794 (1.6); 4.3094 (0.8); 4.3001 (1.1); 4.2745 (1.1); 4.2659 (1.0); 3.9279 (0.5); 3.9096 (0.7); 3.8957 (0.7); 3.8691 (2.2); 3.8488 (0.7); 3.8348 (1.5); 3.8140 (0.9); 3.0513 (0.8); 3.0373 (0.8); 3.0060 (1.2); 2.9912 (1.1); 2.8045 (0.4); 2.7814 (1.1); 2.7722 (1.3); 2.7585 (1.4); 2.7378 (1.6); 2.7271 (1.2); 2.7121 (0.7); 2.6932 (1.5); 2.6814 (16.0); 2.3301 (12.1); 1.6054 (4.2); 1.3710 (0.3); 1.3460 (0.6); 1.3047 (2.8); 1.2619 (0.5); 1.1729 (8.7); 1.1643 (9.0); 1.1498 (8.7); 1.1413 (8.6); 0.9419 (1.0); 0.9205 (2.8); 0.8971 (1.1); 0.0492 (0.6); 0.0385 (12.4); 0.0278 (0.7)

I-036: $^1$H-NMR(300.2 MHz, CDCl3):
δ = 8.0518 (2.5); 7.9605 (2.4); 7.6169 (0.4); 7.5937 (0.7); 7.5687 (0.4); 7.5290 (0.3); 7.5025 (0.7); 7.4794 (0.4); 7.3953 (0.6); 7.3675 (0.8); 7.3535 (1.4); 7.3467 (1.5); 7.2989 (10.8); 7.1995 (1.0); 7.1720 (1.4); 7.0196 (0.8); 7.0131 (0.8); 6.9924 (0.6); 6.9857 (0.6); 6.0153 (0.7); 5.3368 (0.4); 4.1899 (0.5); 4.1803 (0.6); 4.1544 (0.7); 4.1445 (0.8); 4.0605 (0.4); 4.0448 (0.4); 4.0333 (0.4); 3.9898 (0.8); 3.9746 (0.5); 3.9538 (0.6); 3.9386 (0.4); 3.2016 (0.4); 3.1843 (0.4); 3.1568 (0.7); 3.1393 (0.7); 3.0406 (0.8); 3.0105 (1.1); 2.9931 (16.0); 2.9670 (0.6); 2.9195 (14.7); 2.6942 (7.4); 1.6281 (0.4); 1.2897 (0.4); 0.1046 (1.3); 0.0352 (11.7)

I-037: $^1$H-NMR(300.2 MHz, CDCl3):
δ = 7.5712 (0.6); 7.5456 (2.0); 7.5210 (5.3); 7.4961 (0.7); 7.4253 (2.8); 7.3852 (1.2); 7.3784 (1.8); 7.3714 (1.2); 7.3554 (1.2); 7.2992 (11.9); 7.0362 (3.3); 7.0171 (1.6); 6.9915 (3.9); 6.9666 (2.6); 6.9409 (0.9); 5.7875 (0.8); 5.7693 (0.8); 4.9664 (1.9); 4.1941 (0.9); 4.1703 (3.2); 4.1465 (2.9); 4.1393 (1.5); 4.1234 (1.7); 3.9538 (0.6); 3.9445 (0.8); 3.9346 (0.9); 3.9245 (1.0); 3.9149 (0.9); 3.9051 (0.7); 3.8308 (1.5); 3.8111 (1.1); 3.7941 (1.3); 3.7746 (0.9); 3.3482 (0.3); 3.3304 (0.4); 3.2743 (9.2); 3.2562 (9.2); 3.0161 (0.9); 2.9972 (0.9); 2.9699 (1.4); 2.9511 (1.4); 2.8211 (1.4); 2.7921 (1.4); 2.7751 (1.0); 2.7457 (0.8); 2.3202 (15.4); 2.3054 (16.0); 2.0826 (11.0); 1.6119 (12.6); 1.3209 (3.1); 1.2970 (6.8); 1.2733 (3.1); 0.0378 (13.7)

I-038: $^1$H-NMR(499.9 MHz, CDCl3):
δ = 7.9415 (5.3); 7.5621 (3.4); 7.5520 (4.7); 7.3731 (2.5); 7.2786 (0.9); 7.2700 (1.5); 7.2613 (6.6); 7.0422 (2.4); 7.0265 (2.7); 6.9821 (3.0); 6.9790 (3.3); 6.6343 (1.6); 6.6312 (1.7); 6.6187 (1.6); 6.6156 (1.7); 6.0883 (1.8); 5.2981 (3.5); 4.1991 (1.1); 4.1926 (1.3); 4.1773 (1.4); 4.1708 (1.5); 3.9875 (0.6); 3.9732 (0.9); 3.9694 (0.9); 3.9645 (0.9); 3.9592 (0.7); 3.8646 (1.5); 3.8536 (1.3); 3.8428 (1.4); 3.8317 (1.2); 3.1161 (1.0); 3.1065 (1.1); 3.0890 (1.4); 3.0794 (1.4); 2.8777 (1.3); 2.8589 (1.3); 2.8507 (1.2); 2.8318 (1.0); 2.6456 (16.0); 1.7310 (0.7); 1.7241 (0.8); 1.7143 (1.4); 1.7044 (0.9); 1.6976 (0.8); 1.6875 (0.4); 1.5834 (8.5); 1.2547 (0.4); 0.9329 (2.8); 0.9303 (3.1); 0.9162 (3.0); 0.9136 (3.1); 0.8994 (0.5); 0.8911 (0.4); 0.5625 (0.3); 0.5597 (0.4); 0.5523 (0.4); 0.5433 (1.6); 0.5330 (1.7); 0.5299 (1.8); 0.5255 (1.9); 0.5154 (1.7); 0.5002 (0.5); 0.4967 (0.5); −0.0002 (6.7)

I-039: $^1$H-NMR(400.1 MHz, CDCl3):
δ = 8.1051 (5.7); 7.4339 (1.4); 7.4140 (2.8); 7.3942 (1.6); 7.2586 (39.1); 7.1119 (2.3); 7.0923 (2.0); 7.0155 (3.4); 6.9954 (0.5); 6.9506 (4.4); 6.9312 (4.5); 6.8850 (3.7); 6.6719 (2.0); 6.6530 (1.8); 6.1858 (2.4); 4.2683

TABLE 2-continued (1.4); 4.2612 (1.5); 4.2420 (1.6); 4.2348 (1.6); 3.8524 (1.0); 3.8406 (1.1); 3.8288 (0.9); 3.8057 (2.1); 3.7898 (1.1); 3.7792 (1.8); 3.7635 (1.1); 3.0013 (1.2); 2.9900 (1.2); 2.9673 (1.5); 2.9556 (1.4); 2.7062 (1.4); 2.6820 (1.4); 2.6724 (1.3); 2.6480 (1.1); 2.3027 (0.5); 2.2879 (0.4); 2.2618 (16.0); 2.2313 (0.4); 2.2192 (0.3); 2.1654 (15.0); 2.1436 (0.8); 1.5791 (1.9); 1.5599 (4.7); 1.5324 (10.1); 1.5173 (6.4); 1.4972 (2.5); 1.4326 (0.6); 1.3673 (0.4); 1.3331 (0.5); 1.2558 (4.3); 1.2172 (0.8); 1.2002 (0.7); 1.1534 (0.4); 1.1259 (0.9); 1.1081 (3.1); 1.0889 (3.2); 1.0705 (0.9); 0.8804 (0.7); 0.8600 (2.3); 0.8445 (2.8); −0.0002 (46.5)

I-040: $^{1}$H-NMR(300.2 MHz, CDCl3):
δ = 8.0064 (5.0); 7.5969 (1.4); 7.5759 (4.0); 7.4850 (1.8); 7.4396 (0.8); 7.4299 (1.3); 7.4227 (0.9); 7.4080 (2.9); 7.4010 (1.3); 7.3865 (1.4); 7.3792 (5.7); 7.3729 (1.1); 7.3446 (5.4); 7.3375 (1.3); 7.3224 (0.9); 7.3161 (2.1); 7.2984 (12.1); 6.2825 (1.2); 5.3368 (1.8); 4.8171 (0.6); 4.8101 (0.6); 4.8042 (0.7); 4.7964 (1.1); 4.7885 (0.7); 4.7826 (0.7); 4.7757 (0.6); 4.3523 (0.9); 4.3393 (0.9); 4.3154 (1.0); 4.3023 (1.0); 4.1933 (0.3); 4.1696 (1.0); 4.1457 (1.1); 4.1223 (0.5); 4.1009 (0.4); 3.8470 (1.4); 3.8250 (1.4); 3.8100 (1.3); 3.7881 (1.2); 2.7339 (16.0); 2.0810 (6.1); 1.6215 (0.4); 1.5974 (1.2); 1.3198 (1.4); 1.2960 (3.0); 1.2722 (1.3); 0.9972 (0.3); 0.9727 (0.7); 0.0483 (0.5); 0.0375 (13.5); 0.0266 (0.5)

I-041: $^{1}$H-NMR(300.2 MHz, CDCl3):
δ = 7.5778 (0.7); 7.5519 (2.1); 7.5283 (5.4); 7.5050 (0.7); 7.4129 (2.8); 7.3759 (1.4); 7.3686 (2.0); 7.3614 (1.3); 7.3461 (1.4); 7.2989 (14.2); 7.0299 (3.2); 7.0117 (1.8); 6.9861 (3.8); 6.9541 (2.3); 6.9266 (1.0); 6.0253 (1.5); 4.9370 (2.0); 4.1977 (1.1); 4.1858 (1.2); 4.1698 (0.7); 4.1615 (1.3); 4.1495 (1.4); 3.9180 (0.8); 3.9079 (0.9); 3.8991 (1.0); 3.8905 (0.9); 3.8794 (0.8); 3.8601 (0.4); 3.8009 (1.8); 3.7793 (1.3); 3.7645 (1.5); 3.7430 (1.2); 3.2025 (0.5); 3.1918 (0.8); 3.1796 (1.2); 3.1702 (1.2); 3.1577 (0.9); 3.1480 (0.6); 3.1352 (0.3); 2.9992 (0.9); 2.9803 (0.9); 2.9528 (1.4); 2.9336 (1.3); 2.7913 (1.5); 2.7620 (1.4); 2.7451 (1.2); 2.7160 (1.0); 2.3508 (0.7); 2.3151 (14.6); 2.2969 (16.0); 2.2303 (0.6); 2.2023 (0.3); 2.1853 (0.5); 2.1787 (0.4); 2.0824 (2.2); 1.9749 (1.0); 1.6375 (1.4); 1.3205 (0.6); 1.2966 (1.4); 1.2729 (0.6); 0.9955 (0.4); 0.9725 (0.8); 0.9613 (0.8); 0.9486 (1.1); 0.9384 (1.1); 0.9297 (1.2); 0.9253 (1.2); 0.9182 (1.5); 0.9055 (1.6); 0.8942 (1.2); 0.8868 (1.3); 0.8781 (1.3); 0.8646 (1.2); 0.8532 (0.9); 0.8464 (0.8); 0.8313 (0.7); 0.8123 (0.6); 0.7938 (0.5); 0.7648 (0.6); 0.7503 (0.8); 0.7300 (1.0); 0.7162 (1.4); 0.6991 (1.5); 0.6865 (0.9); 0.6681 (0.8); 0.6560 (1.4); 0.6439 (1.1); 0.6371 (1.4); 0.6236 (1.1); 0.6107 (0.7); 0.6034 (0.7); 0.5900 (0.5); 0.5697 (0.4); 0.5530 (0.4); 0.5352 (0.5); 0.5165 (0.4); 0.5002 (0.3); 0.1077 (8.2); 0.0481 (0.6); 0.0373 (17.4); 0.0266 (1.5)

I-042: $^{1}$H-NMR(300.2 MHz, CDCl3):
δ = 8.7320 (5.6); 7.6696 (3.1); 7.6666 (2.8); 7.6577 (1.4); 7.6524 (2.1); 7.3995 (1.6); 7.3541 (0.7); 7.3452 (0.7); 7.3354 (1.0); 7.3291 (0.8); 7.3240 (0.6); 7.3157 (0.5); 7.2989 (8.7); 7.0075 (1.6); 6.9819 (1.9); 6.9263 (1.9); 6.7168 (1.0); 6.6912 (0.8); 5.9713 (1.2); 4.3525 (0.7); 4.3430 (0.8); 4.3174 (0.9); 4.3084 (0.9); 3.9512 (0.3); 3.9366 (0.5); 3.9297 (0.4); 3.9183 (0.5); 3.9084 (0.4); 3.9021 (0.5); 3.8876 (1.8); 3.8669 (0.6); 3.8529 (1.3); 3.8320 (0.8); 3.0708 (0.6); 3.0567 (0.6); 3.0258 (0.9); 3.0106 (0.8); 2.8013 (16.0); 2.7738 (1.0); 2.7414 (0.9); 2.7286 (0.8); 2.6955 (0.7); 2.3075 (10.5); 2.1886 (9.7); 1.6012 (15.3); 1.3601 (0.3); 1.3432 (0.6); 1.3038 (3.7); 0.9409 (1.3); 0.9192 (4.2); 0.8959 (1.6); 0.1075 (1.1); 0.0372 (9.7); 0.0264 (0.4)

I-043: $^{1}$H-NMR(499.9 MHz, $d_6$-DMSO):
δ = 7.8070 (0.5); 7.5225 (1.4); 7.5062 (3.2); 7.4899 (2.0); 7.4263 (1.8); 7.4210 (1.7); 7.3783 (1.5); 7.3769 (1.6); 7.3746 (1.7); 7.3732 (1.5); 7.3622 (1.2); 7.3607 (1.2); 7.3585 (1.4); 7.3572 (1.2); 7.3255 (2.1); 7.3213 (3.3); 7.3171 (1.7); 7.2362 (1.5); 7.2348 (1.6); 7.2318 (1.4); 7.2198 (1.4); 7.2184 (1.3); 7.2154 (1.3); 7.0407 (2.1); 7.0254 (2.4); 6.9556 (2.7); 6.8623 (1.5); 6.8472 (1.3); 4.0573 (0.4); 4.0430 (1.1); 4.0288 (1.1); 4.0146 (0.4); 3.7869 (1.0); 3.7700 (2.6); 3.7635 (2.8); 3.7603 (2.8); 3.7351 (0.8); 3.3236 (16.8); 2.8005 (1.5); 2.7877 (2.2); 2.7778 (1.2); 2.7621 (0.3); 2.6728 (16.0); 2.5136 (1.3); 2.5103 (2.3); 2.5068 (2.9); 2.5032 (2.1); 2.4608 (0.6); 2.3486 (0.5); 2.2639 (0.5); 2.2354 (12.6); 2.2198 (11.8); 2.1545 (0.3); 1.9945 (4.7); 1.1954 (1.3); 1.1812 (2.5); 1.1670 (1.2)

I-044: $^{1}$H-NMR(600.1 MHz, $d_6$-DMSO):
δ = 8.0423 (0.4); 8.0383 (0.5); 5.7559 (0.9); 3.3179 (16.0); 2.5188 (0.4); 2.5157 (0.4); 2.5069 (7.0); 2.5039 (15.0); 2.5008 (20.9); 2.4978 (15.5); 2.4948 (7.4); 2.2309 (0.8); 2.2267 (0.8); 2.1867 (0.7); 2.1834 (0.7); −0.0001 (1.0)

I-045: $^{1}$H-NMR(300.2 MHz, CDCl3):
δ = 7.9417 (5.1); 7.2986 (13.9); 7.1243 (0.6); 7.1204 (0.6); 7.0977 (1.4); 7.0940 (1.4); 7.0713 (1.0); 7.0676 (1.1); 7.0088 (0.9); 7.0031 (1.1); 6.9812 (3.3); 6.9529 (1.2); 6.9282 (1.8); 6.9232 (1.8); 6.9069 (2.7); 6.8815 (0.8); 6.8479 (0.7); 6.8424 (0.7); 6.8212 (1.2); 6.7996 (0.6); 6.7946 (0.6); 6.2640 (1.3); 5.3372 (10.4); 4.2937 (0.8); 4.2838 (0.9); 4.2583 (1.0); 4.2478 (1.0); 3.9239 (0.4); 3.9075 (0.6); 3.8959 (0.5); 3.8756 (0.4); 3.8698 (0.3); 3.8274 (1.7); 3.8058 (1.0); 3.7917 (1.3); 3.7703 (0.9); 2.9967 (0.7); 2.9797 (0.7); 2.9517 (1.0); 2.9352 (0.9); 2.7207 (1.2); 2.6896 (1.1); 2.6757 (1.1); 2.6617 (16.0); 2.6449 (0.9); 2.1415 (11.0); 2.1161 (11.1); 2.0928 (0.7); 2.0830 (1.4); 1.5960 (12.1); 1.3213 (0.4); 1.3057 (0.4); 1.2975 (0.8); 1.0859 (0.6); 1.0722 (1.6); 1.0653 (1.8); 1.0519 (1.0); 1.0435 (1.7); 1.0369 (1.7); 1.0237 (0.8); 0.8264 (0.9); 0.8127 (1.7); 0.8092 (2.0); 0.8047 (1.6); 0.7955 (1.9); 0.7927 (1.8); 0.7877 (1.4); 0.7755 (0.6); 0.1080 (6.3); 0.0491 (0.6); 0.0384 (16.0); 0.0274 (0.6)

I-046: $^{1}$H-NMR(499.9 MHz, CDCl3):
δ = 8.7600 (4.2); 8.7483 (4.1); 8.7364 (0.5); 8.7241 (0.3); 8.5985 (7.4); 8.5708 (0.4); 7.9420 (5.2); 7.9326 (3.7); 7.9298 (4.8); 7.6179 (5.3); 7.6171 (5.3); 7.6087 (3.1); 7.6067 (3.1); 7.5902 (0.4); 7.3692 (3.0); 7.3125 (1.2); 7.3077 (1.5); 7.3010 (1.6); 7.2970 (1.4); 7.2900 (0.9); 7.2612 (8.2); 6.9781 (2.7); 6.9629 (2.9); 6.8904 (3.4); 6.6719 (1.9); 6.6570 (1.7); 6.2023 (2.5); 4.3392 (1.4); 4.3328 (1.5); 4.3177 (1.6); 4.3113 (1.5); 4.1279 (0.9); 4.1136 (0.9); 3.9296 (0.7); 3.9216 (1.0); 3.9100 (1.0); 3.9026 (0.8); 3.8585 (2.0); 3.8456 (1.4); 3.8369 (1.8); 3.8241 (1.3); 3.0390 (1.2); 3.0300 (1.2); 3.0117 (1.4); 3.0026 (1.3); 2.7316 (1.4); 2.7113 (1.5); 2.7043 (1.3); 2.6840 (1.2); 2.3245 (1.0); 2.3041 (1.1); 2.2803 (16.0); 2.1499 (15.2); 2.0432 (4.2); 1.6182 (7.0); 1.2726 (1.0); 1.2583 (2.1); 1.2440 (1.0); −0.0002 (9.6)

I-047: $^{1}$H-NMR(400.2 MHz, $d_6$-DMSO):
δ = 8.3164 (0.4); 8.0962 (9.8); 7.9525 (1.7); 7.4134 (2.1); 7.4052 (2.1); 7.3427 (0.5); 7.3280 (1.7); 7.3218 (3.4); 7.3189 (3.8); 7.3082 (2.1); 7.3038 (4.3); 7.2837 (1.0); 7.2330 (1.2); 7.2274 (1.3); 7.2146 (1.8); 7.2087 (1.0); 7.2049 (1.1); 7.2009 (0.9); 7.1906 (0.7); 7.0533 (2.7); 7.0342 (3.2); 6.9293 (3.3); 6.8264 (1.8); 6.8072 (1.5); 3.7543 (5.3); 3.7401 (1.0); 3.7307 (1.4); 3.7213 (1.1); 3.7127 (0.8); 3.7038 (0.5); 3.3314 (34.7); 2.8908 (11.4); 2.8461 (0.3); 2.8282 (0.4); 2.8112 (1.8); 2.8005 (2.3); 2.7955 (2.2); 2.7838 (1.9); 2.7664 (0.4); 2.7320 (10.0); 2.5455 (24.0); 2.5250 (0.7); 2.5201 (1.0); 2.5114 (12.8); 2.5071 (26.0); 2.5026 (34.4); 2.4981 (25.7); 2.4938 (13.0); 2.2401 (16.0); 2.1912 (14.7); −0.0002 (6.2)

I-048: $^{1}$H-NMR(300.2 MHz, CDCl3):
δ = 8.1592 (8.0); 7.3738 (0.5); 7.3466 (1.2); 7.3250 (1.1); 7.2987 (11.0); 7.2745 (2.0); 7.2690 (2.1); 7.2466 (0.9); 7.2412 (1.1); 7.2000 (1.3); 7.1941 (1.3); 7.1785 (1.3); 7.1724 (1.9); 7.1669 (0.8); 7.1516 (0.8); 7.1454

TABLE 2-continued (0.8); 7.0113 (2.5); 6.9858 (2.9); 6.9083 (2.9); 6.7238 (1.6); 6.6993 (1.4); 6.0356 (1.9); 4.3301 (1.1); 4.3210 (1.4); 4.2955 (1.5); 4.2864 (1.4); 3.9198 (0.8); 3.9096 (0.7); 3.9039 (0.8); 3.8972 (0.6); 3.8881 (0.7); 3.8756 (2.8); 3.8554 (0.8); 3.8411 (1.9); 3.8205 (1.2); 3.0596 (1.0); 3.0446 (1.0); 3.0146 (1.4); 2.9986 (1.3); 2.7801 (1.4); 2.7486 (1.3); 2.7350 (1.2); 2.7029 (1.1); 2.3073 (16.0); 2.1635 (15.1); 1.6012 (0.8); 1.3716 (0.4); 1.2931 (7.9); 1.0386 (0.4); 1.0162 (0.4); 0.9186 (0.7); 0.8946 (0.8); 0.8806 (0.7); 0.0492 (0.3); 0.0382 (11.7); 0.0275 (0.5)

I-049: $^{1}$H-NMR(400.2 MHz, $d_6$-DMSO):
δ = 8.3142 (1.5); 8.2404 (15.3); 8.0564 (3.1); 8.0466 (3.1); 7.7721 (4.3); 7.7680 (3.5); 7.7464 (2.7); 7.7267 (3.6); 7.6950 (5.1); 7.6896 (3.0); 7.6742 (8.2); 7.6689 (8.0); 7.5448 (4.7); 7.5238 (6.3); 7.4038 (3.6); 7.3985 (3.4); 7.3828 (2.7); 7.3774 (2.6); 5.7544 (16.0); 5.1088 (1.0); 5.1010 (2.8); 5.0919 (2.8); 5.0833 (1.0); 4.0629 (1.7); 4.0544 (1.9); 4.0349 (2.8); 4.0265 (2.4); 3.9250 (2.3); 3.9167 (2.3); 3.8969 (1.7); 3.8888 (1.6); 3.3172 (234.5); 2.6932 (0.7); 2.6791 (1.7); 2.6747 (3.6); 2.6702 (5.0); 2.6656 (3.7); 2.6610 (1.7); 2.5237 (14.7); 2.5189 (21.5); 2.5102 (297.3); 2.5058 (611.1); 2.5012 (807.2); 2.4966 (578.2); 2.4921 (277.7); 2.3372 (1.6); 2.3326 (3.6); 2.3280 (5.0); 2.3235 (3.7); 2.3189 (1.7); 2.0734 (1.7); 1.9882 (1.2); 1.2346 (1.0); 1.1927 (0.5); 1.1749 (0.8); 1.1570 (0.4); 0.1548 (0.5); 0.1458 (1.2); 0.1224 (3.6); 0.0879 (3.0); 0.0814 (0.5); 0.0656 (0.3); 0.0573 (2.4); 0.0080 (8.2); −0.0002 (284.6); −0.0085 (9.3); −0.1497 (1.1)

I-050: $^{1}$H-NMR(300.2 MHz, CDCl3):
δ = 7.9516 (5.1); 7.3391 (1.3); 7.3128 (2.8); 7.2984 (13.2); 7.2866 (1.9); 7.0024 (2.6); 6.9768 (2.9); 6.9335 (2.4); 6.8479 (1.2); 6.8450 (1.2); 6.8402 (1.4); 6.8213 (1.0); 6.8182 (1.0); 6.8134 (1.4); 6.7890 (1.9); 6.7831 (2.4); 6.7198 (1.4); 6.6947 (1.1); 6.3121 (1.5); 5.3370 (7.4); 4.2646 (0.8); 4.2561 (1.2); 4.2307 (1.2); 4.2216 (1.0); 4.1953 (0.4); 4.1715 (1.1); 4.1477 (1.1); 4.1241 (0.5); 3.8750 (0.7); 3.8651 (0.7); 3.8596 (0.7); 3.8526 (0.7); 3.8374 (2.3); 3.8176 (0.6); 3.8035 (1.5); 3.7827 (0.9); 3.0246 (0.7); 3.0101 (0.8); 2.9803 (1.1); 2.9642 (1.1); 2.7638 (1.1); 2.7330 (1.1); 2.7181 (1.1); 2.6871 (1.0); 2.6649 (16.0); 2.2984 (12.2); 2.2308 (11.6); 2.0831 (5.5); 2.0442 (1.5); 1.9841 (0.4); 1.9673 (0.6); 1.9558 (0.7); 1.9394 (1.2); 1.9226 (0.8); 1.9116 (0.7); 1.8944 (0.4); 1.6054 (14.1); 1.3210 (1.5); 1.2971 (2.9); 1.2733 (1.4); 1.0531 (0.8); 1.0383 (2.1); 1.0313 (2.3); 1.0165 (1.3); 1.0098 (2.2); 1.0033 (2.1); 0.9886 (1.1); 0.9733 (0.5); 0.7682 (1.0); 0.7532 (2.6); 0.7481 (2.3); 0.7366 (2.3); 0.7313 (2.6); 0.7148 (0.9); 0.1073 (0.9); 0.0483 (0.6); 0.0376 (13.3); 0.0268 (0.9)

I-051: $^{1}$H-NMR(499.9 MHz, CDCl3):
δ = 8.1253 (7.9); 7.6006 (0.5); 7.5856 (5.1); 7.5709 (2.1); 7.5552 (0.6); 7.3128 (2.5); 7.2593 (9.1); 7.2432 (1.0); 7.2391 (1.4); 7.2292 (1.0); 7.2250 (1.6); 7.2206 (0.7); 6.9450 (2.5); 6.9298 (2.8); 6.8791 (2.9); 6.6589 (1.5); 6.6438 (1.4); 6.0731 (1.8); 5.2975 (6.2); 4.2956 (1.3); 4.2890 (1.4); 4.2740 (1.4); 4.2674 (1.4); 3.8848 (0.5); 3.8809 (0.5); 3.8770 (0.7); 3.8715 (0.6); 3.8682 (0.6); 3.8647 (0.8); 3.8609 (0.6); 3.8574 (0.6); 3.8550 (0.5); 3.8136 (2.1); 3.8008 (1.4); 3.7919 (1.8); 3.7792 (1.4); 3.0080 (1.1); 2.9988 (1.1); 2.9806 (1.3); 2.9714 (1.2); 2.6946 (1.4); 2.6744 (1.4); 2.6672 (1.3); 2.6469 (1.2); 2.2591 (16.0); 2.1419 (14.8); 1.5511 (4.3); −0.0002 (8.6)

I-052: $^{1}$H-NMR(499.9 MHz, CDCl3):
δ = 7.9145 (5.3); 7.2597 (11.3); 7.0779 (0.7); 7.0620 (1.6); 7.0461 (1.0); 6.9827 (1.9); 6.9752 (0.9); 6.9720 (1.1); 6.9674 (2.3); 6.9581 (1.4); 6.9448 (0.6); 6.9418 (0.6); 6.8703 (2.2); 6.8100 (0.7); 6.8073 (0.7); 6.7943 (1.3); 6.7811 (0.6); 6.7785 (0.6); 6.6683 (1.2); 6.6534 (1.1); 6.2105 (1.4); 5.2980 (0.9); 4.2377 (0.9); 4.2312 (1.0); 4.2163 (1.1); 4.2098 (1.1); 3.8698 (0.4); 3.8628 (0.5); 3.8590 (0.6); 3.8553 (0.5); 3.8518 (0.6); 3.8483 (0.6); 3.8401 (0.5); 3.8358 (0.3); 3.8132 (1.6); 3.8009 (0.9); 3.7918 (1.4); 3.7795 (1.0); 2.9882 (0.8); 2.9781 (0.8); 2.9610 (1.0); 2.9507 (1.0); 2.7468 (1.1); 2.7279 (1.1); 2.7197 (0.9); 2.7007 (0.8); 2.6274 (16.0); 2.2715 (11.9); 2.1441 (11.3); 2.0931 (0.5); 2.0865 (0.6); 2.0762 (1.0); 2.0660 (0.6); 2.0593 (0.6); 2.0044 (0.4); 1.5590 (15.4); 1.0340 (0.6); 1.0313 (0.8); 1.0272 (1.3); 1.0243 (1.7); 1.0182 (1.4); 1.0146 (1.0); 1.0106 (1.4); 1.0073 (1.7); 1.0031 (0.9); 0.7832 (1.1); 0.7794 (0.9); 0.7753 (1.6); 0.7721 (1.7); 0.7685 (1.8); 0.7658 (1.7); 0.7610 (0.9); 0.7579 (1.1); 0.0063 (0.4); −0.0002 (13.0); −0.0066 (0.7)

I-053: $^{1}$H-NMR(499.9 MHz, CDCl3):
δ = 8.1251 (7.5); 7.6004 (0.7); 7.5977 (0.7); 7.5855 (5.2); 7.5708 (2.1); 7.5552 (0.6); 7.3128 (2.6); 7.2592 (8.6); 7.2432 (1.2); 7.2391 (1.5); 7.2291 (1.1); 7.2250 (1.6); 7.2206 (0.8); 6.9450 (2.6); 6.9297 (2.8); 6.8793 (3.0); 6.6591 (1.7); 6.6441 (1.4); 6.0734 (1.9); 5.2974 (6.3); 4.2954 (1.4); 4.2887 (1.4); 4.2738 (1.5); 4.2671 (1.4); 3.8846 (0.6); 3.8808 (0.7); 3.8768 (0.8); 3.8680 (0.7); 3.8647 (0.9); 3.8609 (0.6); 3.8573 (0.6); 3.8448 (0.3); 3.8135 (2.1); 3.8007 (1.4); 3.7918 (1.8); 3.7791 (1.4); 3.0079 (1.2); 2.9987 (1.2); 2.9805 (1.4); 2.9713 (1.3); 2.6946 (1.5); 2.6744 (1.5); 2.6672 (1.3); 2.6469 (1.2); 2.3031 (0.4); 2.2590 (16.0); 2.1419 (14.9); 1.5522 (3.8); 0.0059 (0.5); −0.0002 (7.9); −0.0066 (0.3)

I-054: $^{1}$H-NMR(300.2 MHz, CDCl3):
δ = 8.0002 (5.3); 7.6152 (0.4); 7.5885 (1.5); 7.5663 (4.4); 7.5442 (0.4); 7.4950 (2.2); 7.4560 (0.9); 7.4480 (1.4); 7.4405 (0.9); 7.4256 (0.9); 7.2991 (7.1); 7.2649 (3.1); 7.2424 (2.2); 7.1598 (1.7); 7.1334 (1.1); 6.2020 (1.7); 5.3382 (0.9); 4.7865 (0.7); 4.7718 (0.9); 4.7627 (0.9); 4.7479 (0.8); 4.3983 (1.0); 4.3845 (1.0); 4.3614 (1.1); 4.3477 (1.0); 3.7639 (1.4); 3.7383 (1.4); 3.7272 (1.3); 3.7015 (1.2); 2.9523 (1.9); 2.9277 (3.7); 2.9025 (2.7); 2.8750 (1.6); 2.8450 (1.6); 2.8187 (0.8); 2.7904 (0.4); 2.7326 (16.0); 2.1522 (0.7); 2.1274 (2.3); 2.1026 (3.2); 2.0779 (2.0); 2.0530 (0.5); 1.6084 (2.7); 1.2937 (0.4); 0.0489 (0.4); 0.0383 (9.1)

I-055: $^{1}$H-NMR(300.2 MHz, CDCl3):
δ = 7.5891 (0.4); 7.5632 (1.3); 7.5376 (3.5); 7.5133 (0.4); 7.4448 (1.9); 7.4118 (0.8); 7.4048 (1.3); 7.3976 (0.7); 7.3871 (0.5); 7.3813 (0.8); 7.3745 (0.5); 7.2990 (7.3); 7.0373 (1.7); 7.0261 (2.1); 7.0126 (2.5); 6.9469 (1.3); 6.9205 (0.8); 4.7215 (1.3); 4.1991 (1.0); 4.1734 (1.2); 3.9658 (0.3); 3.9562 (0.5); 3.9327 (1.7); 3.9277 (1.4); 3.9192 (0.7); 3.9099 (0.6); 3.9018 (1.3); 3.8847 (0.6); 3.0322 (0.5); 3.0162 (0.5); 2.9866 (1.0); 2.9699 (0.9); 2.9049 (0.9); 2.8753 (0.8); 2.8593 (0.5); 2.8291 (0.4); 2.6255 (14.3); 2.4371 (14.2); 2.3169 (16.0); 1.6242 (3.6); 0.0376 (7.7)

I-056: $^{1}$H-NMR(499.9 MHz, CDCl3):
δ = 7.9093 (3.3); 7.2606 (12.8); 7.2105 (3.5); 7.1071 (1.0); 7.0912 (2.3); 7.0754 (1.5); 7.0278 (0.3); 7.0200 (0.4); 7.0044 (0.9); 6.9857 (4.1); 6.9770 (5.6); 6.9604 (1.8); 6.8265 (1.1); 6.8130 (1.9); 6.7994 (1.0); 6.1910 (2.0); 4.1948 (0.5); 4.1842 (1.6); 4.1690 (1.7); 4.1582 (0.6); 3.8500 (2.8); 3.8347 (2.7); 3.8240 (1.0); 2.9674 (1.1); 2.9582 (1.1); 2.9401 (1.4); 2.9306 (1.4); 2.8002 (1.2); 2.7825 (1.2); 2.7734 (1.0); 2.7626 (0.4); 2.7547 (0.9); 2.7252 (0.6); 2.6347 (14.4); 2.3286 (0.8); 2.3216 (0.4); 2.3131 (0.5); 2.2860 (16.0); 2.1092 (0.4); 2.0988 (0.8); 2.0921 (0.9); 2.0819 (1.5); 2.0718 (1.0); 2.0651 (0.9); 2.0546 (0.5); 1.5859 (0.4); 1.2548 (0.8); 1.0426 (0.5); 1.0329 (2.5); 1.0295 (2.7); 1.0161 (2.7); 1.0126 (2.7); 1.0033 (0.8); 0.9930 (0.5); 0.9826 (0.4); 0.8088 (0.3); 0.7919 (1.7); 0.7817 (2.6); 0.7788 (2.8); 0.7768 (2.9); 0.7666 (1.9); 0.7535 (0.5); 0.7480 (0.6); 0.7386 (0.4); −0.0002 (15.6)

TABLE 2-continued

I-057: $^1$H-NMR(300.2 MHz, CDCl3):
δ = 7.9592 (5.2); 7.2995 (12.8); 7.1388 (0.7); 7.1124 (1.8); 7.0860 (1.4); 7.0315 (2.9); 7.0051 (3.6); 6.9819 (0.6); 6.9767 (0.6); 6.8597 (1.0); 6.8412 (3.7); 6.8170 (0.8); 6.8129 (0.7); 6.5738 (1.4); 6.5481 (1.2); 6.2798 (1.7); 5.3386 (8.0); 4.2659 (1.2); 4.2411 (1.4); 3.8811 (0.7); 3.8576 (2.0); 3.8245 (1.6); 3.8041 (0.8); 3.0342 (0.7); 3.0188 (0.8); 2.9889 (1.2); 2.9733 (1.2); 2.7860 (1.0); 2.7655 (0.7); 2.7553 (1.0); 2.7406 (0.9); 2.7099 (0.7); 2.6679 (16.0); 2.3524 (0.8); 2.3123 (12.8); 2.1571 (0.5); 2.1456 (0.6); 2.1286 (1.1); 2.1117 (0.7); 2.1011 (0.7); 2.0842 (0.5); 1.7700 (0.6); 1.7585 (0.6); 1.7419 (1.2); 1.7254 (0.7); 1.7138 (0.6); 1.6965 (0.3); 1.6000 (12.3); 1.2947 (0.4); 1.0883 (0.7); 1.0738 (1.5); 1.0686 (2.0); 1.0610 (1.5); 1.0558 (1.4); 1.0460 (1.7); 1.0402 (2.0); 1.0271 (1.0); 0.9081 (2.7); 0.8848 (2.5); 0.8803 (2.5); 0.8571 (0.4); 0.8361 (1.0); 0.8206 (2.2); 0.8137 (2.2); 0.8045 (2.4); 0.7878 (0.9); 0.5893 (0.4); 0.5735 (1.3); 0.5523 (1.6); 0.5442 (1.5); 0.5273 (1.3); 0.5148 (0.3); 0.1080 (1.2); 0.0385 (16.6)
I-058: $^1$H-NMR(300.2 MHz, CDCl3):
δ = 7.2993 (16.7); 7.1281 (2.1); 7.1179 (1.4); 7.1148 (1.5); 7.1030 (2.7); 7.0558 (1.4); 7.0301 (2.1); 7.0149 (2.0); 6.9399 (1.1); 6.9148 (0.7); 6.8558 (0.5); 6.8453 (0.5); 6.8343 (1.0); 6.8227 (0.8); 6.8134 (0.4); 6.8018 (0.4); 4.7922 (1.2); 4.2187 (0.9); 4.1935 (1.0); 3.9560 (0.5); 3.9469 (0.5); 3.9281 (1.6); 3.9104 (0.6); 3.8946 (1.1); 3.8764 (0.6); 3.8730 (0.4); 3.0399 (0.4); 3.0230 (0.4); 2.9935 (0.9); 2.9765 (0.8); 2.8977 (0.7); 2.8683 (0.7); 2.8514 (0.5); 2.8227 (0.4); 2.5587 (12.9); 2.3218 (9.9); 2.3084 (9.4); 2.1237 (0.4); 2.1119 (0.5); 2.0950 (0.8); 2.0784 (0.5); 2.0667 (0.5); 1.5883 (16.0); 1.2927 (0.5); 1.0784 (0.4); 1.0635 (1.3); 1.0573 (1.6); 1.0427 (0.7); 1.0351 (1.5); 1.0288 (1.6); 1.0144 (0.6); 0.8218 (0.6); 0.8077 (1.7); 0.8019 (1.8); 0.7907 (1.6); 0.7846 (1.8); 0.7694 (0.6); 0.1079 (4.9); 0.0494 (0.6); 0.0385 (21.6); 0.0279 (1.1)
I-059: $^1$H-NMR(499.9 MHz, CDCl3):
δ = 8.1139 (8.8); 7.5958 (0.6); 7.5933 (0.6); 7.5813 (5.2); 7.5667 (2.1); 7.5510 (0.6); 7.3129 (2.5); 7.2580 (3.0); 7.2422 (1.0); 7.2381 (1.4); 7.2282 (1.1); 7.2240 (1.6); 7.2196 (0.7); 6.9438 (2.6); 6.9285 (2.8); 6.8774 (2.9); 6.6591 (1.6); 6.6441 (1.4); 6.0812 (1.8); 4.2843 (1.3); 4.2779 (1.3); 4.2627 (1.4); 4.2562 (1.4); 3.8805 (0.6); 3.8767 (0.6); 3.8730 (0.8); 3.8672 (0.7); 3.8641 (0.7); 3.8605 (0.8); 3.8567 (0.6); 3.8534 (0.6); 3.8510 (0.6); 3.8091 (2.2); 3.7964 (1.4); 3.7875 (1.9); 3.7748 (1.4); 3.0035 (1.1); 2.9942 (1.1); 2.9760 (1.3); 2.9668 (1.3); 2.6950 (1.4); 2.6748 (1.5); 2.6676 (1.3); 2.6474 (1.2); 2.2563 (16.0); 2.1411 (14.7); 1.5971 (3.6); 1.1369 (0.7); 1.1247 (0.7); −0.0002 (2.5)
I-060: $^1$H-NMR(300.2 MHz, CDCl3):
δ = 8.7742 (4.7); 8.6566 (3.0); 8.6400 (3.1); 8.6154 (6.9); 7.6617 (5.0); 7.6488 (5.2); 7.6447 (4.6); 7.6170 (0.5); 7.4264 (2.4); 7.3760 (1.0); 7.3675 (1.2); 7.3589 (1.5); 7.3523 (1.4); 7.3462 (1.0); 7.3383 (0.8); 7.2986 (12.9); 7.0239 (2.2); 6.9984 (2.6); 6.9324 (2.7); 6.7212 (1.5); 6.6967 (1.3); 6.1765 (1.9); 4.3741 (1.1); 4.3646 (1.2); 4.3388 (1.3); 4.3290 (1.2); 3.9732 (0.6); 3.9590 (0.8); 3.9408 (0.8); 3.9239 (0.7); 3.8933 (2.0); 3.8720 (1.0); 3.8580 (1.6); 3.8366 (1.1); 3.0877 (0.9); 3.0728 (0.9); 3.0417 (1.2); 3.0274 (1.1); 2.7800 (1.2); 2.7470 (1.2); 2.7349 (1.1); 2.7014 (0.9); 2.3610 (0.7); 2.3430 (0.8); 2.3183 (13.3); 2.2498 (0.4); 2.1945 (12.5); 1.6136 (16.0); 1.2928 (0.6); 0.1072 (1.3); 0.0370 (14.8); 0.0263 (1.1)
I-061: $^1$H-NMR(499.9 MHz, CDCl3):
δ = 7.8861 (4.6); 7.4878 (0.5); 7.4724 (1.5); 7.4572 (2.9); 7.4393 (0.4); 7.3795 (1.8); 7.3362 (0.9); 7.3323 (1.3); 7.3283 (0.8); 7.3177 (0.9); 7.2118 (3.5); 7.2079 (1.5); 7.1943 (4.5); 7.1895 (10.0); 6.8319 (3.9); 6.8279 (1.4); 6.8183 (1.5); 6.8145 (3.3); 6.8086 (0.4); 6.0588 (1.4); 5.2277 (3.8); 4.6454 (0.7); 4.6432 (0.7); 4.6374 (0.8); 4.6348 (0.8); 4.6308 (0.8); 4.6225 (0.7); 4.2570 (0.9); 4.2488 (0.9); 4.2348 (1.0); 4.2266 (0.9); 3.7263 (16.0); 3.6518 (1.3); 3.6366 (1.3); 3.6296 (1.2); 3.6145 (1.2); 2.6223 (14.3); 1.9722 (0.5); 1.4836 (4.0); 1.1873 (0.5); −0.0002 (15.1); −0.0645 (1.0); −0.0706 (10.6); −0.0771 (0.4)
I-062: $^1$H-NMR(499.9 MHz, CDCl3):
δ = 9.3730 (0.4); 8.2205 (0.6); 8.0631 (0.4); 7.6952 (0.4); 7.6815 (0.5); 7.6686 (0.4); 7.6548 (0.4); 7.6357 (0.4); 7.6204 (0.4); 7.6019 (0.4); 7.5868 (0.4); 7.5711 (0.4); 7.5568 (0.7); 7.5430 (0.8); 7.5219 (0.6); 7.5101 (0.5); 7.4949 (0.5); 7.4807 (0.5); 7.4668 (0.6); 7.4483 (0.4); 7.4412 (0.4); 7.4335 (0.4); 7.4255 (0.4); 7.3922 (0.5); 7.3780 (0.7); 7.3596 (0.8); 7.3416 (1.0); 7.3267 (0.9); 7.2940 (2.0); 7.2796 (2.5); 7.2601 (19.7); 7.2362 (1.8); 7.2204 (2.3); 7.2051 (1.5); 7.1856 (0.8); 7.1807 (0.8); 7.1701 (1.0); 7.1537 (3.6); 7.1421 (1.6); 7.1255 (1.2); 7.1020 (0.7); 7.0824 (0.4); 7.0446 (2.2); 7.0346 (3.4); 7.0284 (4.8); 6.7240 (0.8); 6.6794 (1.6); 6.6628 (1.4); 6.2983 (2.5); 6.2925 (2.6); 5.6003 (0.6); 5.5858 (1.1); 5.5712 (0.6); 4.6604 (0.3); 4.6449 (0.8); 4.6303 (0.8); 4.6153 (0.4); 4.5481 (1.0); 4.5408 (1.0); 3.7037 (0.4); 3.6803 (16.0); 3.3172 (0.7); 3.2609 (0.6); 3.2161 (0.5); 3.0668 (1.0); 3.0547 (1.0); 3.0441 (1.3); 2.9324 (1.0); 2.8568 (0.8); 2.5180 (1.1); 2.4929 (1.1); 2.4795 (0.9); 2.4619 (0.4); 2.4000 (4.1); 1.9994 (14.5); 1.2982 (0.4); 1.2839 (0.7); 1.2563 (3.5); 0.8936 (0.4); 0.8801 (0.8); 0.8664 (0.5); 0.0062 (0.8); −0.0002 (21.7); −0.0066 (1.2)
I-063: $^1$H-NMR(499.9 MHz, CDCl3):
δ = 8.6578 (5.4); 7.5859 (3.4); 7.5845 (3.1); 7.5789 (1.7); 7.5758 (2.2); 7.3339 (1.8); 7.2798 (0.7); 7.2746 (0.9); 7.2718 (0.6); 7.2683 (1.1); 7.2642 (1.0); 7.2601 (2.9); 6.9650 (1.8); 6.9497 (2.0); 6.8854 (2.1); 6.6821 (1.1); 6.6672 (1.0); 6.0109 (1.4); 5.2949 (4.2); 4.2979 (0.9); 4.2913 (1.0); 4.2763 (1.0); 4.2697 (1.0); 3.9235 (16.0); 3.9051 (0.6); 3.9009 (0.6); 3.8971 (0.7); 3.8914 (0.6); 3.8848 (0.7); 3.8811 (0.5); 3.8776 (0.5); 3.8353 (1.4); 3.8226 (1.0); 3.8137 (1.2); 3.8010 (0.9); 3.0129 (0.7); 3.0037 (0.8); 2.9855 (0.9); 2.9763 (0.9); 2.7226 (1.0); 2.7025 (1.0); 2.6953 (0.9); 2.6751 (0.8); 2.3336 (15.4); 2.2675 (10.8); 2.1527 (10.1); 1.5897 (0.5); −0.0002 (2.8)
I-064: $^1$H-NMR(499.9 MHz, CDCl3):
δ = 8.6875 (5.6); 7.5797 (3.1); 7.5721 (1.5); 7.5693 (2.4); 7.3360 (1.5); 7.2841 (0.7); 7.2792 (0.7); 7.2736 (1.0); 7.2697 (0.9); 7.2660 (0.7); 7.2596 (3.9); 6.9694 (1.6); 6.9542 (1.8); 6.8870 (1.8); 6.6856 (1.0); 6.6706 (0.8); 5.9863 (1.2); 4.2861 (0.8); 4.2800 (0.8); 4.2647 (0.9); 4.2585 (0.9); 4.0366 (16.0); 3.8992 (0.4); 3.8953 (0.4); 3.8902 (0.6); 3.8857 (0.5); 3.8827 (0.4); 3.8793 (0.5); 3.8755 (0.4); 3.8725 (0.4); 3.8695 (0.4); 3.8424 (1.4); 3.8299 (0.8); 3.8209 (1.2); 3.8085 (0.8); 3.0061 (0.7); 2.9969 (0.7); 2.9788 (0.8); 2.9694 (0.8); 2.7318 (0.9); 2.7119 (0.9); 2.7044 (0.8); 2.6845 (0.7); 2.3291 (15.0); 2.2680 (9.8); 2.1537 (9.0); 2.0419 (0.5); 2.0017 (0.9); 1.5664 (1.0); −0.0002 (4.4)
I-065: $^1$H-NMR(400.1 MHz, $d_6$-DMSO):
δ = 7.7607 (0.8); 7.7412 (2.5); 7.7216 (2.5); 7.7035 (3.2); 7.6840 (1.4); 7.6253 (3.6); 7.6014 (2.2); 7.5814 (1.6); 7.4082 (2.4); 7.4028 (2.5); 7.0822 (2.0); 7.0632 (2.3); 6.9530 (3.7); 6.8487 (1.5); 6.8304 (1.4); 3.8004 (7.4); 3.3444 (21.3); 2.8242 (3.1); 2.8095 (3.0); 2.5137 (4.1); 2.5098 (5.3); 2.5058 (4.0); 2.2356 (14.4); 2.2138 (16.0); 2.0841 (1.5)
I-066: $^1$H-NMR(300.2 MHz, CDCl3):
δ = 8.1875 (7.1); 7.6297 (4.7); 7.6125 (3.7); 7.3652 (2.6); 7.3143 (1.0); 7.2983 (13.3); 7.2769 (0.7); 7.0047 (2.5); 6.9792 (3.0); 6.9213 (3.0); 6.7137 (1.6); 6.6886 (1.4); 6.1361 (1.6); 5.3368 (9.5); 5.1204 (0.8); 5.1003 (1.0); 5.0823 (0.9); 4.3441 (1.1); 4.3341 (1.3); 4.3089 (1.4); 4.2989 (1.4); 3.9464 (0.5); 3.9291 (0.7); 3.9127

(0.8); 3.8965 (0.6); 3.8890 (0.6); 3.8737 (2.3); 3.8526 (1.0); 3.8387 (1.8); 3.8177 (1.1); 3.4839 (1.0); 3.4751 (1.3); 3.4595 (1.1); 3.0622 (1.0); 3.0476 (1.0); 3.0169 (1.4); 3.0016 (1.3); 2.7648 (1.2); 2.7322 (1.2); 2.7198 (1.0); 2.6866 (0.9); 2.3035 (16.0); 2.1871 (14.3); 2.0823 (0.8); 1.6094 (10.8); 1.6044 (8.6); 1.5866 (6.3); 1.5822 (6.9); 1.3028 (0.4); 1.2964 (0.7); 1.2797 (0.6); 0.0478 (0.4); 0.0371 (15.0); 0.0263 (0.6)

I-067: $^1$H-NMR(300.2 MHz, CDCl3):
δ = 8.3181 (6.0); 7.6233 (4.5); 7.6065 (3.3); 7.5784 (0.3); 7.3678 (2.4); 7.3120 (1.0); 7.2988 (8.6); 7.2861 (1.1); 7.2741 (0.6); 7.0082 (2.3); 6.9827 (2.8); 6.9230 (2.9); 6.7174 (1.3); 6.6922 (1.1); 6.1085 (1.9); 5.9760 (0.7); 5.9705 (0.7); 5.9543 (0.8); 5.9489 (0.7); 5.8177 (0.7); 5.8124 (0.7); 5.7961 (0.7); 5.7905 (0.7); 4.3479 (1.1); 4.3378 (1.2); 4.3130 (1.4); 4.3029 (1.3); 3.9505 (0.5); 3.9351 (0.7); 3.9288 (0.7); 3.9239 (0.7); 3.9177 (0.8); 3.9075 (0.6); 3.9014 (0.7); 3.8941 (0.6); 3.8816 (2.2); 3.8606 (0.9); 3.8468 (1.6); 3.8257 (1.0); 3.0646 (0.9); 3.0499 (1.0); 3.0191 (1.3); 3.0040 (1.2); 2.7731 (0.8); 2.7670 (0.9); 2.7404 (0.8); 2.7343 (0.9); 2.7287 (0.8); 2.7218 (0.8); 2.6952 (0.6); 2.6889 (0.7); 2.3062 (16.0); 2.1889 (14.8); 1.8262 (2.6); 1.8148 (3.1); 1.8044 (2.7); 1.7930 (3.1); 1.7451 (2.7); 1.7337 (3.2); 1.7233 (2.7); 1.7120 (3.0); 1.6043 (2.4); 1.3030 (1.1); 0.9422 (0.4); 0.9204 (1.1); 0.8972 (0.4); 0.1091 (0.4); 0.0384 (9.3); 0.0276 (0.4)

I-068: $^1$H-NMR(300.2 MHz, CDCl3):
δ = 7.9029 (8.4); 7.5863 (4.4); 7.5690 (4.7); 7.3267 (2.5); 7.2985 (11.1); 7.2792 (1.0); 7.2707 (1.0); 7.2626 (1.6); 7.2564 (1.3); 7.2491 (0.9); 7.2409 (0.7); 6.9986 (2.5); 6.9731 (2.9); 6.9166 (3.0); 6.7121 (1.6); 6.6866 (1.4); 6.1474 (1.9); 4.3254 (1.1); 4.3158 (1.3); 4.2907 (1.4); 4.2806 (1.4); 4.2141 (0.6); 3.9315 (0.6); 3.9194 (0.8); 3.9096 (0.7); 3.8986 (0.8); 3.8914 (0.6); 3.8825 (0.7); 3.8749 (0.6); 3.8613 (2.5); 3.8403 (1.0); 3.8264 (1.9); 3.8053 (1.2); 3.0466 (1.0); 3.0320 (1.0); 3.0012 (1.4); 2.9860 (1.3); 2.7576 (1.4); 2.7251 (1.4); 2.7123 (1.2); 2.6793 (1.0); 2.2974 (16.0); 2.1858 (15.1); 2.1659 (0.9); 2.1568 (1.8); 2.1455 (0.7); 2.1397 (0.9); 2.1302 (1.0); 2.1128 (0.6); 1.6075 (3.2); 1.2927 (0.4); 1.1820 (0.4); 1.1597 (1.7); 1.1513 (3.9); 1.1451 (3.4); 1.1346 (5.3); 1.1286 (5.4); 1.1211 (1.9); 1.1088 (2.1); 1.1021 (3.1); 1.0932 (1.7); 1.0724 (0.4); 0.7120 (0.4); 0.7038 (0.6); 0.6948 (0.5); 0.6822 (0.6); 0.6737 (0.9); 0.6650 (0.6); 0.6519 (0.4); 0.6453 (0.4); 0.6200 (0.3); 0.6108 (0.6); 0.6007 (0.5); 0.5912 (0.7); 0.5835 (0.4); 0.5182 (0.4); 0.5061 (0.4); 0.0483 (0.5); 0.0376 (13.4); 0.0268 (0.6); −0.1248 (0.4)

I-069: $^1$H-NMR(300.2 MHz, CDCl3):
δ = 8.2219 (1.7); 7.6115 (1.1); 7.6089 (1.1); 7.6028 (0.5); 7.5982 (0.5); 7.5898 (0.6); 7.3508 (0.6); 7.2988 (2.8); 6.9956 (0.6); 6.9702 (0.7); 6.9213 (0.7); 6.7079 (0.4); 6.0933 (0.5); 4.2941 (0.3); 4.2841 (0.3); 3.8595 (0.5); 3.8246 (0.4); 2.2962 (3.6); 2.1896 (3.3); 1.6004 (2.6); 0.3194 (0.5); 0.3125 (0.8); 0.3008 (16.0); 0.2895 (0.8); 0.0379 (3.3)

I-070: $^1$H-NMR(499.9 MHz, CDCl3):
δ = 8.1126 (16.0); 7.5854 (1.0); 7.5708 (10.5); 7.5561 (4.7); 7.5405 (1.5); 7.5325 (0.4); 7.2596 (10.0); 7.2541 (6.1); 7.2374 (2.6); 7.2335 (3.2); 7.2235 (2.6); 7.2193 (3.4); 7.2153 (1.9); 7.2024 (0.4); 7.1703 (1.5); 7.1560 (5.0); 7.1499 (9.7); 7.1402 (17.4); 7.1342 (10.4); 7.1267 (6.0); 6.0810 (3.7); 4.2867 (2.6); 4.2799 (2.9); 4.2649 (3.0); 4.2582 (3.2); 3.9225 (0.4); 3.9099 (1.2); 3.9059 (1.3); 3.9022 (1.7); 3.8992 (1.6); 3.8962 (1.6); 3.8899 (1.9); 3.8863 (1.5); 3.8824 (1.4); 3.8698 (0.7); 3.8137 (4.1); 3.8011 (3.2); 3.7919 (3.8); 3.7793 (3.0); 3.0428 (2.6); 3.0333 (2.7); 3.0158 (3.1); 3.0064 (3.1); 2.7014 (3.3); 2.6814 (3.3); 2.6744 (3.1); 2.6544 (2.8); 2.1659 (7.3); 1.5873 (0.8); 0.0062 (0.4); −0.0002 (9.4); −0.0065 (0.7)

I-071: $^1$H-NMR(300.2 MHz, CDCl3):
δ = 7.6492 (8.8); 7.4138 (1.0); 7.3877 (2.7); 7.3712 (1.9); 7.3457 (2.3); 7.3199 (1.0); 7.2989 (4.7); 7.1656 (1.7); 7.1397 (1.6); 7.1254 (4.0); 7.0988 (3.6); 7.0341 (4.4); 7.0170 (1.7); 4.3139 (1.9); 4.2769 (2.3); 4.1709 (0.7); 4.1471 (0.7); 4.0378 (0.7); 4.0150 (1.3); 3.9878 (0.7); 3.9066 (1.5); 3.8989 (1.5); 3.8695 (1.4); 3.8619 (1.3); 3.2617 (9.0); 3.0687 (2.2); 3.0572 (2.0); 3.0402 (2.8); 3.0116 (0.4); 2.3339 (15.3); 2.2980 (0.4); 2.2414 (16.0); 2.0818 (3.7); 1.7418 (0.4); 1.3197 (1.0); 1.2957 (2.7); 1.2722 (0.9); 0.0379 (4.3)

I-072: $^1$H-NMR(300.2 MHz, CDCl3):
δ = 7.5830 (1.1); 7.5616 (3.2); 7.5398 (0.4); 7.4678 (1.5); 7.4343 (0.7); 7.4255 (1.1); 7.4183 (0.6); 7.4112 (0.4); 7.4035 (0.6); 7.3967 (0.4); 7.2990 (4.8); 7.0362 (2.8); 7.0109 (2.2); 6.9696 (1.2); 6.9443 (0.6); 5.3365 (0.9); 4.9700 (1.1); 4.7061 (0.4); 4.6931 (0.5); 4.6772 (0.4); 4.6697 (0.8); 4.6555 (1.5); 4.6411 (0.8); 4.6183 (0.7); 4.6032 (1.4); 4.5885 (0.8); 4.5821 (0.4); 4.5687 (0.4); 4.5652 (0.5); 4.5522 (0.3); 4.1810 (0.4); 4.1720 (0.8); 4.1465 (1.0); 4.1376 (0.6); 3.9367 (0.5); 3.9277 (0.5); 3.9183 (0.6); 3.9090 (0.8); 3.9015 (1.4); 3.8674 (1.0); 3.8495 (0.6); 3.8008 (2.1); 3.7866 (3.1); 3.7715 (1.8); 3.4187 (16.0); 3.0154 (0.4); 2.9970 (0.4); 2.9696 (0.9); 2.9509 (0.8); 2.8856 (0.7); 2.8570 (0.7); 2.8391 (0.5); 2.8111 (0.4); 2.3497 (0.5); 2.3172 (12.2); 2.0405 (9.2); 1.6172 (1.0); 0.0384 (5.0)

I-073: $^1$H-NMR(300.2 MHz, CDCl3):
δ = 8.4004 (0.4); 8.3143 (5.2); 7.7190 (0.5); 7.6709 (0.5); 7.6603 (4.7); 7.6576 (4.7); 7.6409 (3.1); 7.6136 (0.4); 7.3830 (2.7); 7.3483 (0.3); 7.3358 (1.2); 7.3273 (1.4); 7.3170 (1.7); 7.3101 (1.6); 7.2991 (10.8); 7.0081 (2.5); 6.9826 (3.0); 6.9222 (3.0); 6.6987 (1.6); 6.6735 (1.4); 6.2869 (2.1); 4.3887 (1.1); 4.3789 (1.2); 4.3536 (1.4); 4.3439 (1.4); 3.9680 (0.5); 3.9510 (0.7); 3.9347 (0.8); 3.9185 (0.7); 3.9113 (0.6); 3.8954 (2.3); 3.8741 (1.0); 3.8604 (1.8); 3.8390 (1.1); 3.0893 (1.0); 3.0747 (1.0); 3.0439 (1.4); 3.0290 (1.2); 2.7679 (1.4); 2.7350 (1.3); 2.7227 (1.2); 2.6892 (1.0); 2.3320 (0.8); 2.3135 (16.0); 2.2506 (0.6); 2.1783 (15.0); 1.7670 (0.5); 1.2922 (1.5); 0.0374 (10.2); 0.0266 (0.5)

I-074: $^1$H-NMR(499.9 MHz, $d_6$-DMSO):
δ = 8.3436 (2.3); 7.8313 (6.3); 7.7605 (2.6); 7.7368 (2.3); 7.7305 (2.2); 7.7216 (2.1); 7.6751 (2.8); 7.6596 (1.7); 6.9652 (2.4); 6.7853 (2.3); 5.0047 (1.3); 4.1443 (1.0); 4.1364 (1.1); 4.1225 (1.2); 4.1146 (1.1); 3.5631 (1.2); 3.5513 (1.2); 3.5413 (1.2); 3.5295 (1.1); 3.3168 (36.0); 2.6156 (16.0); 2.5116 (5.9); 2.5083 (12.5); 2.5047 (17.4); 2.5012 (13.2); 2.4978 (6.8); 2.1474 (1.4); 2.1378 (12.0); 2.0675 (1.1); 1.9924 (0.8); 1.8396 (11.8); 1.1789 (0.4)

I-075: $^1$H-NMR(300.2 MHz, CDCl3):
δ = 7.9550 (5.2); 7.2987 (14.4); 7.1410 (0.6); 7.1136 (3.4); 7.0876 (3.4); 7.0603 (3.4); 7.0551 (2.9); 7.0424 (1.1); 7.0371 (1.4); 7.0157 (0.6); 7.0099 (0.6); 6.8645 (0.8); 6.8584 (0.7); 6.8380 (1.2); 6.8166 (0.6); 6.8112 (0.6); 6.6263 (1.3); 6.6203 (1.3); 6.6002 (1.2); 6.5943 (1.2); 6.2336 (1.2); 5.3369 (9.3); 4.2320 (0.9); 4.2212 (1.0); 4.1959 (1.1); 4.1851 (1.2); 4.0257 (0.4); 4.0161 (0.5); 3.9963 (0.6); 3.9868 (0.6); 3.9778 (0.4); 3.9692 (0.3); 3.9173 (1.5); 3.8994 (1.0); 3.8813 (1.2); 3.8635 (0.9); 3.1906 (0.8); 3.1743 (0.8); 3.1460 (1.1); 3.1295 (1.1); 2.9936 (0.6); 2.9215 (1.6); 2.8912 (1.1); 2.8767 (0.9); 2.8464 (0.8); 2.7107 (0.5); 2.6723 (16.0); 2.1517 (0.4); 2.1406 (0.5); 2.1234 (1.0); 2.1061 (0.6); 2.0951 (0.6); 2.0784 (0.3); 1.7846 (0.6); 1.7735 (0.6); 1.7569 (1.1); 1.7401 (0.7); 1.7289 (0.6); 1.7124 (0.4); 1.6119 (1.3); 1.2967 (0.4); 1.0878 (0.7); 1.0748 (1.3); 1.0677 (1.8); 1.0598 (1.2); 1.0547 (1.2); 1.0460 (1.5); 1.0395 (1.8); 1.0264 (1.0); 0.9577 (2.2); 0.9517 (2.5); 0.9295 (2.4); 0.9237 (2.4); 0.8987 (0.4); 0.8328 (0.8); 0.8258 (0.9); 0.8167 (1.8); 0.8094 (1.8); 0.8018 (2.0); 0.7942 (1.4); 0.7838 (0.7); 0.6283 (0.3); 0.6231 (0.4); 0.6118 (0.3); 0.6062 (0.3); 0.6010 (0.4); 0.5918 (1.0); 0.5888

TABLE 2-continued (1.0); 0.5752 (1.0); 0.5712 (1.1); 0.5644 (0.9); 0.5580 (1.2); 0.5473 (0.8); 0.5414 (1.1); 0.5334 (0.4); 0.5166 (0.3); 0.1075 (2.0); 0.0484 (0.5); 0.0377 (16.4); 0.0267 (0.7)
I-076: $^{1}$H-NMR(300.2 MHz, CDCl3):
δ = 7.4211 (2.5); 7.4141 (2.6); 7.2989 (14.2); 7.2019 (2.0); 7.1745 (2.8); 7.1640 (0.4); 7.1461 (2.4); 7.1400 (1.7); 7.1369 (1.8); 7.1332 (1.6); 7.1208 (3.3); 7.0604 (1.7); 7.0534 (1.7); 7.0331 (1.1); 7.0261 (1.2); 6.8688 (0.6); 6.8595 (0.6); 6.8465 (1.2); 6.8348 (0.8); 6.8277 (0.5); 6.8143 (0.5); 5.3381 (0.4); 4.8325 (1.0); 4.8241 (1.0); 4.1418 (0.4); 4.1330 (0.9); 4.1064 (1.1); 4.1000 (1.4); 4.0924 (0.9); 4.0759 (0.8); 4.0655 (0.8); 4.0468 (1.9); 4.0140 (0.8); 4.0031 (0.4); 3.2014 (0.4); 3.1833 (0.4); 3.1561 (1.2); 3.1388 (1.2); 3.1158 (1.1); 3.0879 (1.0); 3.0700 (0.4); 3.0434 (0.4); 2.5696 (16.0); 2.1117 (0.4); 2.1008 (0.5); 2.0828 (1.3); 2.0663 (0.6); 2.0555 (0.5); 1.5887 (7.7); 1.2970 (0.6); 1.0865 (0.4); 1.0813 (0.4); 1.0716 (1.4); 1.0634 (1.6); 1.0533 (0.8); 1.0483 (0.7); 1.0428 (1.4); 1.0354 (1.7); 1.0258 (0.5); 1.0203 (0.5); 0.8248 (0.5); 0.8185 (0.5); 0.8086 (2.2); 0.8020 (2.1); 0.7916 (2.2); 0.7854 (2.0); 0.7743 (0.4); 0.7687 (0.4); 0.1073 (4.8); 0.0485 (0.6); 0.0377 (18.4); 0.0268 (0.7)
I-077: $^{1}$H-NMR(400.1 MHz, $d_6$-DMSO):
δ = 10.9075 (2.2); 8.1383 (6.9); 7.9621 (2.6); 7.3552 (1.5); 7.3357 (3.0); 7.3160 (1.9); 7.2458 (2.4); 7.2270 (2.8); 7.0556 (1.9); 7.0517 (2.1); 7.0293 (2.7); 7.0242 (2.8); 7.0014 (10.7); 6.9806 (1.9); 5.0954 (1.2); 5.0818 (1.3); 5.0642 (1.4); 5.0507 (1.2); 3.3154 (3.8); 2.8997 (16.0); 2.7410 (14.5); 2.6392 (1.1); 2.6255 (1.2); 2.5980 (1.7); 2.5844 (1.6); 2.5135 (13.0); 2.5095 (16.6); 2.4033 (1.6); 2.3720 (1.8); 2.3622 (1.5); 2.3306 (1.6); 2.3120 (15.5); 2.2578 (14.4); 2.2206 (0.4); 1.9992 (0.4); 1.9862 (0.8); 1.9775 (1.0); 1.9656 (1.7); 1.9530 (1.0); 1.9448 (0.9); 1.9322 (0.5); 1.0042 (1.0); 0.9932 (2.9); 0.9879 (3.2); 0.9724 (3.0); 0.9672 (3.0); 0.9569 (1.2); 0.7039 (1.2); 0.6930 (3.5); 0.6888 (3.5); 0.6809 (3.3); 0.6765 (3.6); 0.6650 (1.0)
I-078: $^{1}$H-NMR(499.9 MHz, CDCl3):
δ = 9.1273 (1.6); 8.6675 (0.5); 8.2413 (8.7); 8.0140 (1.6); 7.3345 (0.4); 7.3271 (1.8); 7.3187 (0.4); 7.3113 (3.6); 7.2954 (2.2); 7.2592 (12.4); 7.0889 (2.4); 7.0735 (3.2); 7.0472 (0.3); 7.0429 (0.3); 7.0222 (4.1); 7.0040 (2.0); 7.0012 (2.2); 6.9991 (2.0); 6.9831 (1.4); 6.9558 (1.5); 6.9541 (1.6); 6.9510 (1.7); 6.9493 (1.6); 6.9396 (1.4); 6.9379 (1.4); 6.9348 (1.6); 6.9331 (1.4); 6.8813 (2.2); 6.8774 (2.9); 6.8733 (1.9); 4.0911 (0.4); 4.0795 (0.7); 4.0749 (0.6); 4.0684 (0.9); 4.0635 (0.8); 4.0571 (0.8); 4.0523 (0.8); 4.0457 (0.5); 4.0411 (0.7); 4.0295 (0.4); 3.2083 (1.2); 3.1961 (1.2); 3.1807 (1.4); 3.1686 (1.3); 2.9531 (14.4); 2.8806 (12.2); 2.8801 (12.4); 2.8608 (1.5); 2.8495 (1.4); 2.8332 (1.2); 2.5865 (1.5); 2.5755 (1.6); 2.5531 (2.0); 2.5421 (1.9); 2.3698 (2.6); 2.3571 (16.0); 2.3476 (2.4); 2.3364 (1.8); 2.3140 (2.4); 2.3064 (14.3); 2.2360 (0.9); 2.1111 (0.8); 2.0026 (0.5); 1.9395 (0.5); 1.9294 (0.9); 1.9228 (0.9); 1.9196 (0.6); 1.9127 (1.6); 1.9058 (0.6); 1.9026 (0.9); 1.8959 (0.8); 1.8858 (0.5); 1.5905 (0.6); 1.0039 (1.3); 0.9944 (2.8); 0.9908 (3.0); 0.9872 (1.6); 0.9816 (1.7); 0.9776 (2.9); 0.9740 (2.7); 0.9648 (1.3); 0.7282 (1.6); 0.7187 (3.7); 0.7154 (3.2); 0.7089 (2.9); 0.7056 (3.6); 0.6958 (1.1); 0.0063 (0.8); −0.0002 (15.6); −0.0069 (0.5)
I-079: $^{1}$H-NMR(300.1 MHz, $d_6$-DMSO):
δ = 7.7389 (0.7); 7.7172 (8.1); 7.6852 (2.8); 7.6763 (3.1); 7.6587 (2.5); 7.6327 (1.1); 7.5939 (1.8); 7.5678 (1.1); 7.5424 (3.1); 7.5357 (3.3); 7.4345 (2.4); 7.4068 (3.1); 7.2348 (2.0); 7.2277 (1.9); 7.2073 (1.6); 7.2002 (1.5); 6.8128 (2.0); 6.8026 (1.9); 4.2243 (0.4); 4.2057 (0.7); 4.1831 (1.0); 4.1641 (1.3); 4.1413 (1.2); 4.1289 (0.8); 4.1130 (0.8); 4.0010 (0.5); 3.9780 (1.2); 3.9567 (0.8); 3.9367 (0.9); 3.9133 (0.4); 3.3255 (1.4); 3.1423 (0.8); 3.1192 (0.8); 3.0961 (1.1); 3.0734 (1.0); 2.8798 (1.1); 2.8554 (1.1); 2.8339 (0.8); 2.8093 (0.8); 2.5810 (16.0); 2.5092 (5.3); 2.5034 (6.9); 2.4976 (4.9); 2.0613 (0.6); 2.0384 (1.0); 2.0124 (1.2); 1.9890 (1.1); −0.0005 (5.2)
I-080: $^{1}$H-NMR(400.1 MHz, CDCl3):
δ = 8.0017 (0.6); 7.9803 (0.6); 7.9065 (5.3); 7.6479 (0.7); 7.5681 (0.5); 7.5473 (2.6); 7.5320 (7.5); 7.5257 (6.6); 7.5092 (4.1); 7.5041 (5.5); 7.4565 (1.2); 7.4351 (3.8); 7.3813 (1.8); 7.3755 (2.2); 7.3560 (6.6); 7.3395 (3.3); 7.3346 (4.2); 7.2669 (2.4); 7.2612 (5.3); 7.2508 (0.8); 6.7548 (2.8); 5.6001 (0.5); 3.8279 (0.6); 3.8124 (2.1); 3.7967 (2.2); 3.7863 (0.7); 3.7812 (0.8); 3.2369 (1.2); 2.7506 (0.4); 2.6986 (16.0); 2.6095 (2.1); 1.6808 (0.4); 1.6203 (1.8); 1.6030 (2.1); 1.4230 (1.7); 1.3909 (0.5); 1.3735 (0.5); 1.3320 (0.9); 1.2571 (8.3); 1.1584 (8.1); 1.1427 (8.4); 1.0319 (0.5); 1.0155 (0.5); 0.9945 (0.4); 0.9782 (0.4); 0.8950 (1.0); 0.8801 (1.7); 0.8700 (1.3); 0.8629 (1.3); 0.0715 (0.5); 0.0057 (2.7); −0.0002 (6.1)
I-081: $^{1}$H-NMR(499.9 MHz, CDCl3):
δ = 8.0074 (5.1); 7.5465 (0.3); 7.5308 (1.4); 7.5168 (4.0); 7.5029 (0.3); 7.4219 (1.8); 7.3604 (0.7); 7.3558 (1.3); 7.3515 (0.8); 7.3479 (0.5); 7.3460 (0.6); 7.3409 (1.1); 7.3351 (3.6); 7.3313 (1.2); 7.3219 (1.5); 7.3181 (4.7); 7.3132 (0.6); 7.2614 (4.1); 7.2306 (0.7); 7.2261 (4.4); 7.2224 (1.3); 7.2128 (1.2); 7.2092 (3.2); 7.2043 (0.4); 6.5340 (0.9); 6.5254 (0.9); 4.5924 (1.1); 4.5863 (1.3); 4.5836 (1.3); 4.5774 (1.1); 4.1824 (1.0); 4.1765 (1.0); 4.1695 (1.0); 4.1635 (1.0); 2.6861 (16.0); 1.9977 (0.5); 1.5905 (0.3); 1.0315 (7.0); 1.0186 (6.9); −0.0002 (4.9)
I-082: $^{1}$H-NMR(300.2 MHz, CDCl3):
δ = 8.6780 (3.4); 8.6717 (3.5); 8.3307 (0.3); 8.3202 (3.4); 8.3122 (3.5); 8.1643 (8.6); 7.6383 (2.3); 7.6308 (3.6); 7.6240 (2.3); 7.2991 (5.3); 6.9977 (2.4); 6.9721 (3.0); 6.9485 (2.9); 6.7777 (1.6); 6.7523 (1.2); 5.9734 (1.8); 4.3550 (1.1); 4.3453 (1.3); 4.3197 (1.4); 4.3098 (1.4); 3.9450 (0.5); 3.9390 (0.5); 3.9297 (0.7); 3.9234 (0.7); 3.9118 (0.8); 3.9051 (0.6); 3.9008 (0.6); 3.8952 (0.6); 3.8894 (0.5); 3.8798 (0.4); 3.8608 (2.4); 3.8396 (1.2); 3.8254 (1.9); 3.8042 (1.3); 3.0706 (1.0); 3.0555 (1.0); 3.0251 (1.3); 3.0096 (1.3); 2.7437 (1.5); 2.7102 (1.4); 2.6982 (1.2); 2.6643 (1.1); 2.4286 (0.4); 2.3063 (16.0); 2.2424 (14.7); 2.0427 (4.5); 1.6422 (0.9); 0.0361 (6.4)
I-083: $^{1}$H-NMR(499.9 MHz, CDCl3):
δ = 8.2832 (2.8); 8.2780 (2.8); 8.1440 (7.0); 7.7726 (3.3); 7.7673 (3.1); 7.2602 (12.4); 6.9574 (2.6); 6.9422 (2.9); 6.9081 (3.4); 6.7340 (1.9); 6.7191 (1.6); 5.8274 (2.2); 4.3260 (1.4); 4.3195 (1.4); 4.3043 (1.5); 4.2978 (1.5); 3.9177 (0.7); 3.9097 (1.0); 3.8978 (1.0); 3.8936 (0.8); 3.8900 (0.7); 3.8265 (1.9); 3.8137 (1.5); 3.8047 (1.7); 3.7920 (1.3); 3.0301 (1.2); 3.0210 (1.2); 3.0026 (1.4); 2.9934 (1.3); 2.6971 (1.5); 2.6764 (1.5); 2.6696 (1.4); 2.6489 (1.2); 2.3270 (0.3); 2.3149 (0.3); 2.3035 (0.6); 2.2742 (16.0); 2.1789 (15.2); 1.5479 (12.8); 1.2734 (0.6); 1.2608 (0.7); −0.0002 (15.1)
I-084: $^{1}$H-NMR(300.2 MHz, CDCl3):
δ = 7.5701 (2.5); 7.5638 (2.6); 7.2989 (11.2); 7.2116 (1.0); 7.2052 (0.9); 7.1845 (1.9); 7.1781 (2.0); 7.1451 (2.7); 7.1356 (4.8); 7.1199 (3.2); 7.1086 (1.7); 6.8693 (0.6); 6.8595 (0.6); 6.8473 (1.1); 6.8359 (0.9); 6.8269 (0.5); 6.8150 (0.5); 4.8462 (1.1); 4.8382 (1.1); 4.1687 (0.4); 4.1448 (0.5); 4.1366 (0.4); 4.1283 (0.9); 4.1219 (0.4); 4.1004 (1.3); 4.0959 (1.4); 4.0879 (0.9); 4.0778 (0.8); 4.0713 (0.7); 4.0608 (0.9); 4.0439 (1.9); 4.0126 (0.8); 4.0011 (0.4); 3.1868 (0.4); 3.1689 (0.4); 3.1411 (1.2); 3.1243 (1.2); 3.1026 (1.0); 3.0746 (1.0); 3.0571 (0.4); 3.0301 (0.4); 2.5670 (16.0); 2.1168 (0.4); 2.1058 (0.5); 2.0885 (1.0); 2.0816 (2.8); 2.0713 (0.6); 2.0605 (0.5); 1.5965 (10.9); 1.3201 (0.5); 1.2963 (1.1); 1.2725 (0.4); 1.0906 (0.3); 1.0820 (0.4); 1.0744 (1.3); 1.0658

TABLE 2-continued (1.7); 1.0456 (1.4); 1.0382 (1.8); 1.0313 (0.6); 1.0225 (0.4); 0.9969 (0.3); 0.9726 (0.5); 0.8277 (0.5); 0.8188 (0.4); 0.8108 (2.1); 0.8038 (1.7); 0.7943 (2.0); 0.7873 (1.8); 0.7790 (0.4); 0.7706 (0.4); 0.1071 (3.8); 0.0482 (0.4); 0.0373 (11.6); 0.0264 (0.4)
I-085: $^{1}$H-NMR(300.2 MHz, CDCl3):
δ = 7.2989 (13.4); 7.1569 (0.4); 7.1359 (1.8); 7.1291 (4.2); 7.1121 (4.1); 7.1025 (4.9); 7.0859 (0.5); 6.8599 (0.6); 6.8513 (0.7); 6.8374 (1.2); 6.8242 (2.2); 6.8190 (1.9); 6.8059 (0.7); 6.7986 (1.2); 6.7926 (1.2); 4.8268 (1.2); 4.8173 (1.2); 4.1651 (0.8); 4.1548 (1.0); 4.1466 (0.5); 4.1289 (1.2); 4.1188 (1.5); 4.0785 (0.4); 4.0633 (0.6); 4.0486 (0.7); 4.0379 (0.6); 4.0201 (0.4); 3.9935 (1.4); 3.9792 (0.8); 3.9575 (0.9); 3.9432 (0.7); 3.1701 (0.6); 3.1519 (0.6); 3.1249 (1.3); 3.1066 (1.2); 3.0459 (1.2); 3.0180 (1.2); 3.0009 (0.7); 2.9728 (0.6); 2.5597 (16.0); 2.1279 (0.5); 2.1167 (0.5); 2.0996 (1.0); 2.0827 (3.0); 2.0715 (0.6); 1.8776 (0.5); 1.8662 (0.6); 1.8495 (1.1); 1.8328 (0.6); 1.8216 (0.6); 1.5941 (13.3); 1.3208 (0.5); 1.2970 (1.1); 1.2731 (0.4); 1.0781 (0.4); 1.0625 (1.8); 1.0558 (2.0); 1.0344 (2.1); 1.0273 (2.0); 1.0211 (2.1); 1.0145 (2.5); 0.9993 (1.2); 0.9927 (2.0); 0.9864 (1.8); 0.9720 (1.2); 0.8231 (0.8); 0.8090 (1.9); 0.8052 (2.0); 0.7918 (1.9); 0.7874 (1.8); 0.7708 (0.6); 0.7079 (0.9); 0.6924 (2.3); 0.6868 (2.0); 0.6762 (1.9); 0.6704 (2.4); 0.6543 (0.7); 0.1073 (1.6); 0.0486 (0.4); 0.0376 (14.2); 0.0265 (0.5)
I-086: $^{1}$H-NMR(300.2 MHz, CDCl3):
δ = 8.1343 (5.8); 7.3665 (1.2); 7.3402 (2.5); 7.3138 (1.6); 7.2990 (16.2); 7.0495 (1.5); 7.0237 (1.2); 6.9870 (1.8); 6.9616 (2.2); 6.9259 (2.2); 6.8496 (1.0); 6.8442 (1.2); 6.8224 (0.8); 6.8173 (1.1); 6.7829 (1.7); 6.7768 (2.2); 6.7702 (1.3); 6.6910 (1.2); 6.6680 (1.0); 6.2783 (1.4); 4.2975 (0.7); 4.2887 (1.0); 4.2634 (1.1); 4.2545 (0.9); 4.1962 (0.3); 4.1723 (1.0); 4.1485 (1.0); 4.1247 (0.4); 3.8854 (0.5); 3.8807 (0.5); 3.8705 (0.5); 3.8644 (0.6); 3.8568 (0.5); 3.8427 (2.1); 3.8228 (0.5); 3.8088 (1.4); 3.7879 (0.8); 3.0419 (0.7); 3.0268 (0.6); 2.9968 (1.0); 2.9810 (1.0); 2.7490 (0.9); 2.7176 (0.9); 2.7111 (0.6); 2.7035 (0.9); 2.6721 (0.8); 2.3334 (0.4); 2.3164 (0.5); 2.2986 (11.7); 2.2185 (10.9); 2.0843 (4.6); 1.9800 (0.5); 1.9690 (0.6); 1.9522 (1.1); 1.9355 (0.6); 1.9243 (0.6); 1.9076 (0.3); 1.5911 (16.0); 1.3221 (1.2); 1.2983 (2.3); 1.2745 (1.1); 1.0762 (0.7); 1.0609 (1.8); 1.0543 (2.0); 1.0395 (1.0); 1.0326 (2.0); 1.0262 (1.8); 1.0117 (0.9); 0.7767 (0.8); 0.7613 (2.3); 0.7556 (2.1); 0.7452 (2.0); 0.7393 (2.4); 0.7234 (0.8); 0.0494 (0.6); 0.0385 (19.1); 0.0278 (0.9)
I-087: $^{1}$H-NMR(300.2 MHz, CDCl3):
δ = 7.9885 (5.2); 7.5896 (1.3); 7.5673 (4.1); 7.5456 (0.4); 7.4894 (1.9); 7.4509 (0.8); 7.4423 (1.4); 7.4349 (0.8); 7.4201 (0.8); 7.4127 (0.4); 7.2990 (8.7); 7.2289 (2.1); 7.1343 (1.1); 7.1289 (1.0); 7.1070 (1.2); 7.1020 (1.2); 6.8063 (2.5); 6.7790 (2.1); 6.1439 (1.5); 4.7393 (0.6); 4.7250 (0.8); 4.7181 (0.8); 4.7142 (0.7); 4.7033 (0.7); 4.6331 (2.1); 4.6042 (4.0); 4.5747 (2.4); 4.3707 (0.9); 4.3590 (0.8); 4.3339 (1.0); 4.3219 (0.9); 4.1698 (0.5); 4.1460 (0.5); 4.1226 (0.3); 4.1011 (0.4); 3.7539 (1.4); 3.7284 (1.4); 3.7170 (1.3); 3.6916 (1.2); 3.2304 (0.3); 3.2073 (0.7); 3.1787 (1.2); 3.1683 (0.7); 3.1494 (0.7); 3.1386 (1.2); 3.1099 (0.6); 3.0867 (0.3); 2.7304 (16.0); 2.0821 (3.4); 1.6084 (2.3); 1.3202 (0.7); 1.2963 (1.5); 1.2725 (0.6); 0.9726 (0.6); 0.1075 (4.1); 0.0483 (0.4); 0.0373 (10.6); 0.0267 (0.4)
I-088: $^{1}$H-NMR(400.1 MHz, CDCl3):
δ = 8.7679 (3.6); 8.7592 (3.8); 7.6044 (0.5); 7.5847 (2.2); 7.5690 (6.7); 7.4657 (4.0); 7.4341 (2.1); 7.4293 (2.1); 7.4169 (1.7); 7.3367 (4.8); 7.3255 (5.0); 7.2639 (4.3); 7.2599 (4.5); 6.9715 (4.5); 6.8823 (1.8); 6.8631 (2.9); 6.8025 (3.4); 6.7835 (2.2); 5.2996 (0.5); 5.2958 (0.5); 4.6223 (3.1); 3.8036 (1.5); 3.7763 (2.0); 3.6596 (1.3); 3.6528 (1.3); 3.5978 (1.9); 3.5870 (1.4); 3.5704 (1.5); 3.5598 (1.2); 2.7710 (1.0); 2.7589 (1.1); 2.7363 (1.6); 2.7239 (1.6); 2.6000 (1.5); 2.5767 (1.5); 2.5666 (1.2); 2.5424 (1.1); 2.2787 (15.7); 2.1913 (16.0); 2.0922 (0.4); 1.6137 (0.8); 1.2585 (0.5); 0.0038 (4.2); −0.0002 (4.4)
I-089: $^{1}$H-NMR(300.2 MHz, CDCl3):
δ = 8.2317 (8.4); 7.2989 (10.4); 7.1428 (0.8); 7.1390 (0.8); 7.1162 (1.9); 7.1127 (2.0); 7.0896 (1.4); 7.0863 (1.6); 7.0318 (4.7); 7.0068 (4.3); 6.9938 (2.1); 6.9820 (1.0); 6.9761 (1.1); 6.9714 (2.2); 6.9345 (2.0); 6.9117 (3.0); 6.8689 (1.0); 6.8634 (1.0); 6.8422 (1.8); 6.8207 (0.9); 6.8154 (0.8); 6.7119 (1.6); 6.6870 (1.3); 6.2528 (4.9); 6.1934 (2.8); 5.6604 (3.2); 5.6232 (3.1); 5.3373 (0.8); 4.3082 (1.0); 4.2994 (1.4); 4.2740 (1.5); 4.2651 (1.2); 3.9212 (0.7); 3.9151 (0.8); 3.9049 (0.7); 3.8994 (0.8); 3.8931 (0.7); 3.8772 (2.9); 3.8574 (0.7); 3.8433 (2.0); 3.8227 (1.1); 3.0533 (0.9); 3.0380 (0.9); 3.0087 (1.4); 2.9921 (1.3); 2.8035 (1.2); 2.7729 (1.2); 2.7584 (1.1); 2.7276 (1.0); 2.3161 (16.0); 2.1821 (15.1); 2.1512 (0.7); 2.1401 (0.8); 2.1229 (1.4); 2.1055 (0.9); 2.0946 (0.8); 2.0775 (0.4); 1.6227 (0.9); 1.0957 (0.9); 1.0822 (1.9); 1.0758 (2.4); 1.0710 (1.5); 1.0677 (1.5); 1.0628 (1.5); 1.0537 (2.0); 1.0475 (2.3); 1.0345 (1.2); 0.8379 (1.2); 0.8309 (1.2); 0.8219 (2.6); 0.8147 (2.4); 0.8062 (2.7); 0.7991 (1.7); 0.7888 (0.9); 0.0492 (0.4); 0.0384 (13.1); 0.0275 (0.5)
I-090: $^{1}$H-NMR(499.9 MHz, CDCl3):
δ = 7.9242 (5.2); 7.5668 (0.5); 7.5513 (1.5); 7.5358 (2.5); 7.5319 (2.2); 7.5161 (0.5); 7.4530 (1.8); 7.4096 (0.8); 7.4060 (1.2); 7.4020 (0.8); 7.3910 (0.9); 7.2613 (6.0); 6.5759 (2.5); 5.9837 (1.4); 4.7968 (0.7); 4.7942 (0.7); 4.7883 (0.8); 4.7856 (0.8); 4.7809 (0.8); 4.7781 (0.8); 4.7722 (0.7); 4.7696 (0.7); 4.2757 (0.8); 4.2743 (0.9); 4.2673 (0.8); 4.2657 (0.9); 4.2537 (0.9); 4.2521 (1.0); 4.2451 (0.9); 4.2436 (0.9); 3.7076 (1.4); 3.6915 (1.4); 3.6855 (1.4); 3.6694 (1.3); 2.6872 (16.0); 2.3844 (11.4); 2.2880 (9.2); 2.0425 (1.3); 1.5864 (0.8); 1.2724 (0.4); 1.2581 (0.7); 1.2438 (0.3); −0.0002 (6.3)
I-091: $^{1}$H-NMR(499.9 MHz, CDCl3):
δ = 7.9085 (5.6); 7.5517 (0.6); 7.5361 (1.7); 7.5210 (3.1); 7.5021 (0.6); 7.4658 (1.9); 7.4195 (0.8); 7.4158 (1.3); 7.4117 (0.8); 7.4044 (0.6); 7.4009 (0.9); 7.3973 (0.6); 7.2655 (1.2); 6.8568 (2.2); 6.8499 (2.3); 6.6336 (1.5); 6.6314 (1.6); 6.6291 (1.2); 6.6267 (1.5); 6.6245 (1.5); 6.3102 (1.3); 5.2913 (3.7); 4.9634 (0.6); 4.9601 (0.7); 4.9555 (0.7); 4.9507 (0.9); 4.9461 (0.7); 4.9415 (0.7); 4.9382 (0.6); 4.3320 (1.0); 4.3254 (0.9); 4.3239 (1.0); 4.3111 (0.9); 4.3099 (1.1); 4.3033 (0.9); 4.3019 (1.0); 3.8426 (1.5); 3.8284 (1.5); 3.8205 (1.4); 3.8063 (1.4); 2.6695 (2.2); 2.6640 (16.0); 2.4647 (1.7); 2.4334 (8.8); 2.4316 (10.3); 2.4155 (0.4); 2.4135 (0.4); 2.0313 (0.5); −0.0002 (1.1)
I-092: $^{1}$H-NMR(499.9 MHz, CDCl3):
δ = 8.3438 (1.5); 8.3410 (1.7); 8.3345 (1.6); 8.3317 (1.7); 7.9737 (5.2); 7.9564 (1.6); 7.9536 (1.7); 7.9406 (1.6); 7.9378 (1.7); 7.4972 (3.0); 7.4869 (3.9); 7.3556 (2.0); 7.3143 (0.8); 7.3093 (0.8); 7.3052 (1.1); 7.3014 (1.0); 7.2962 (0.8); 7.2913 (0.6); 7.2654 (3.9); 7.2306 (4.6); 6.9768 (1.5); 6.9674 (1.6); 6.9610 (1.6); 6.9516 (1.5); 6.2094 (1.7); 5.0486 (0.7); 5.0458 (0.7); 5.0406 (0.8); 5.0375 (0.9); 5.0338 (0.9); 5.0306 (0.8); 5.0254 (0.8); 5.0225 (0.8); 4.3966 (1.0); 4.3885 (1.0); 4.3745 (1.1); 4.3664 (1.0); 4.1387 (1.1); 4.1244 (3.3); 4.1101 (3.4); 4.0959 (1.2); 4.0372 (1.4); 4.0219 (1.4); 4.0151 (1.3); 3.9998 (1.2); 3.8770 (0.3); 3.8474 (16.0); 2.7143 (0.5); 2.6950 (15.6); 2.6682 (0.3); 2.0403 (13.9); 1.6847 (1.3); 1.2707 (3.7); 1.2564 (7.3); 1.2421 (3.6); −0.0002 (3.6)
I-093: $^{1}$H-NMR(300.2 MHz, CDCl3):
δ = 7.9640 (5.3); 7.6306 (0.3); 7.6047 (1.3); 7.5814 (4.1); 7.5583 (0.4); 7.5255 (1.9); 7.4632 (0.8); 7.4553 (1.4); 7.4481 (0.8); 7.4423 (0.5); 7.4394 (0.5); 7.4325 (0.8); 7.4254 (0.5); 7.2989 (2.2); 6.9466 (0.4); 6.9313

TABLE 2-continued (3.7); 6.9072 (3.7); 6.8921 (0.4); 6.3688 (1.0); 6.3588 (1.1); 4.0732 (0.9); 4.0620 (1.0); 4.0365 (1.4); 4.0252 (1.5); 3.9118 (1.2); 3.8980 (1.4); 3.8749 (0.8); 3.8612 (0.9); 3.6071 (0.4); 3.5922 (0.6); 3.5790 (0.8); 3.5657 (0.6); 3.5509 (0.4); 2.8386 (0.8); 2.8123 (1.4); 2.7853 (0.7); 2.6957 (16.0); 2.0252 (0.6); 2.0017 (0.7); 1.9746 (0.6); 1.9409 (0.3); 1.9232 (0.4); 1.9141 (0.7); 1.8964 (0.8); 1.8880 (0.4); 1.8690 (0.6); 1.8508 (0.3); 1.6872 (1.2); 1.2885 (0.5); 0.1067 (1.1); 0.0327 (2.2)
I-094: $^{1}$H-NMR(300.2 MHz, CDCl3):
δ = 7.9769 (5.0); 7.5949 (3.5); 7.5777 (2.7); 7.3439 (1.7); 7.3415 (1.7); 7.2983 (10.5); 7.2791 (0.7); 7.2715 (0.8); 7.2606 (1.0); 7.2543 (0.9); 7.2490 (0.6); 7.2408 (0.5); 7.0949 (2.4); 7.0684 (3.8); 6.9821 (3.3); 6.9559 (2.1); 6.1624 (1.2); 4.3289 (0.8); 4.3176 (0.9); 4.2933 (1.0); 4.2819 (1.0); 3.9204 (0.4); 3.9088 (0.5); 3.9045 (0.5); 3.8983 (0.5); 3.8932 (0.5); 3.8872 (0.6); 3.8810 (0.4); 3.8761 (0.4); 3.8711 (0.4); 3.8299 (1.7); 3.8082 (0.9); 3.7944 (1.4); 3.7726 (0.9); 3.0386 (0.7); 3.0236 (0.7); 2.9939 (0.9); 2.9789 (0.8); 2.7145 (0.3); 2.7045 (1.2); 2.6770 (16.0); 2.6599 (1.0); 2.6269 (0.8); 2.2320 (10.4); 2.0445 (0.7); 1.6121 (0.4); 1.2935 (0.4); 0.0483 (0.4); 0.0375 (12.4); 0.0282 (0.4); 0.0266 (0.4)
I-095: $^{1}$H-NMR(499.9 MHz, CDCl3):
δ = 7.9642 (5.3); 7.7837 (0.6); 7.7707 (0.6); 7.7654 (1.2); 7.7525 (1.2); 7.7473 (0.7); 7.7343 (0.6); 7.5635 (0.4); 7.5480 (1.4); 7.5321 (3.5); 7.5191 (0.5); 7.5162 (0.5); 7.4751 (2.0); 7.4380 (0.4); 7.4196 (0.9); 7.4157 (1.5); 7.4117 (0.9); 7.4012 (1.0); 7.2632 (3.2); 7.1944 (1.9); 6.9462 (0.5); 6.9415 (0.6); 6.9299 (0.8); 6.9278 (1.0); 6.9134 (0.5); 6.9088 (0.6); 6.8344 (0.7); 6.8294 (0.7); 6.8173 (0.7); 6.8100 (1.0); 6.8047 (0.7); 6.7927 (0.7); 6.7876 (0.7); 5.2975 (1.5); 3.5148 (3.4); 2.6879 (16.0); 2.6071 (1.3); 2.0381 (0.5); 1.6754 (2.2); 1.6156 (2.1); 1.3315 (11.1); 1.2691 (0.3); 1.2546 (0.8); 1.2479 (6.0); 1.2424 (6.3); 0.0725 (0.6); −0.0002 (3.6)
I-096: $^{1}$H-NMR(499.9 MHz, CDCl3):
δ = 8.0252 (5.0); 7.9715 (1.2); 7.7436 (0.4); 7.5661 (0.4); 7.5534 (0.4); 7.5458 (0.6); 7.5380 (1.7); 7.5243 (4.5); 7.4259 (2.6); 7.4222 (2.7); 7.4059 (2.3); 7.3889 (2.9); 7.3798 (2.8); 7.3756 (3.3); 7.3682 (0.9); 7.3623 (1.0); 7.3575 (1.7); 7.3537 (1.6); 7.3439 (1.1); 7.3374 (1.2); 7.2619 (7.7); 7.2577 (2.2); 7.2494 (0.7); 7.2448 (1.7); 7.2404 (1.4); 7.2327 (0.4); 7.2286 (0.4); 6.5471 (1.1); 6.5374 (1.2); 6.1503 (0.4); 5.2979 (2.6); 5.2719 (1.2); 5.2659 (1.4); 5.2620 (1.4); 5.2560 (1.3); 4.9665 (0.3); 4.9603 (0.3); 4.9557 (0.3); 4.1244 (0.7); 4.1101 (0.7); 3.9345 (0.6); 3.9279 (1.1); 3.9215 (0.7); 3.9158 (0.8); 3.9092 (1.1); 3.9026 (0.7); 3.4398 (0.9); 2.6840 (16.0); 2.6409 (0.4); 2.0405 (3.6); 2.0012 (0.4); 1.6225 (0.4); 1.6166 (0.3); 1.6074 (0.5); 1.5862 (1.7); 1.5786 (1.5); 1.5710 (1.0); 1.5635 (0.9); 1.5561 (0.8); 1.5496 (0.8); 1.5422 (0.7); 1.5347 (0.6); 1.5275 (0.6); 1.2710 (1.1); 1.2566 (2.7); 1.2424 (1.0); 1.1931 (0.4); 1.1783 (0.6); 1.1742 (0.5); 1.1642 (0.6); 1.1596 (0.6); 1.1495 (0.5); 1.1456 (0.6); 1.1355 (0.3); 1.1308 (0.4); 1.0793 (0.9); 1.0611 (3.9); 1.0463 (6.5); 1.0316 (2.6); 0.9793 (0.4); 0.9594 (0.4); 0.9446 (0.6); 0.9346 (0.4); 0.9299 (0.4); 0.0710 (3.4); −0.0002 (5.8)
I-097: $^{1}$H-NMR(499.9 MHz, CDCl3):
δ = 8.7031 (2.8); 8.7014 (2.9); 8.4501 (2.3); 8.4453 (2.5); 8.1332 (8.2); 7.6000 (2.4); 7.2619 (4.0); 6.9540 (2.5); 6.9388 (2.9); 6.8914 (4.5); 6.7801 (3.1); 6.7059 (1.6); 6.6909 (1.5); 6.6689 (1.6); 5.9697 (2.0); 4.3061 (1.3); 4.2996 (1.4); 4.2844 (1.4); 4.2779 (1.5); 3.9034 (0.6); 3.8996 (0.6); 3.8955 (0.8); 3.8899 (0.7); 3.8834 (0.9); 3.8796 (0.7); 3.8760 (0.6); 3.8737 (0.6); 3.8634 (0.4); 3.8230 (2.0); 3.8104 (1.4); 3.8013 (1.8); 3.7887 (1.4); 3.0207 (1.1); 3.0113 (1.1); 2.9932 (1.3); 2.9838 (1.3); 2.7030 (1.4); 2.6827 (1.4); 2.6756 (1.3); 2.6552 (1.2); 2.3239 (0.3); 2.2999 (0.4); 2.2670 (16.0); 2.1593 (14.9); 2.0014 (1.5); 1.6105 (2.1); −0.0002 (4.5)
I-098: $^{1}$H-NMR(300.2 MHz, CDCl3):
δ = 8.4063 (8.2); 7.3548 (1.6); 7.3285 (3.5); 7.2989 (13.9); 7.0134 (3.5); 6.9876 (3.8); 6.9345 (2.9); 6.8785 (1.3); 6.8758 (1.4); 6.8706 (1.7); 6.8680 (1.7); 6.8517 (1.1); 6.8490 (1.2); 6.8439 (1.6); 6.8412 (1.5); 6.8076 (2.3); 6.8013 (3.1); 6.7947 (1.8); 6.7207 (1.6); 6.6960 (1.3); 6.2671 (2.0); 5.5662 (3.6); 5.5585 (3.7); 5.3375 (15.9); 4.4268 (3.1); 4.4191 (3.2); 4.2866 (0.8); 4.2778 (1.4); 4.2528 (1.6); 4.2447 (1.1); 4.0329 (1.5); 4.0096 (4.7); 3.9863 (4.7); 3.9631 (1.5); 3.8984 (0.6); 3.8927 (0.8); 3.8841 (0.7); 3.8771 (0.9); 3.8642 (2.4); 3.8448 (0.6); 3.8309 (2.0); 3.8104 (1.1); 3.0389 (0.8); 3.0239 (0.8); 2.9940 (1.4); 2.9779 (1.3); 2.7803 (1.1); 2.7492 (1.1); 2.7349 (1.1); 2.7109 (0.5); 2.7038 (0.9); 2.6669 (0.3); 2.3352 (0.4); 2.3060 (16.0); 2.2580 (0.4); 2.2298 (14.9); 1.9888 (0.4); 1.9720 (0.7); 1.9608 (0.8); 1.9441 (1.5); 1.9274 (0.9); 1.9161 (0.9); 1.8993 (0.5); 1.6006 (13.8); 1.4882 (5.2); 1.4650 (10.9); 1.4417 (5.1); 1.4090 (0.4); 1.3848 (0.3); 1.3610 (0.6); 1.3335 (0.4); 1.3071 (0.6); 1.2980 (0.5); 1.0584 (1.0); 1.0431 (2.5); 1.0364 (2.8); 1.0309 (1.5); 1.0217 (1.5); 1.0148 (2.8); 1.0082 (2.5); 0.9938 (1.3); 0.9855 (0.7); 0.9611 (1.3); 0.9427 (0.4); 0.9367 (0.7); 0.9203 (0.5); 0.7723 (1.3); 0.7571 (3.2); 0.7511 (2.9); 0.7408 (2.7); 0.7348 (3.4); 0.7188 (1.0); 0.1085 (0.5); 0.0494 (0.4); 0.0384 (15.6); 0.0274 (0.6)
I-099: $^{1}$H-NMR(499.9 MHz, CDCl3):
δ = 7.9843 (2.1); 7.9094 (3.3); 7.5519 (1.0); 7.5365 (1.7); 7.5329 (1.5); 7.5171 (0.4); 7.4655 (1.2); 7.4058 (0.5); 7.4023 (0.8); 7.3985 (0.5); 7.3873 (0.6); 7.2708 (1.8); 6.8574 (1.3); 6.8499 (1.7); 6.8024 (2.3); 6.7948 (1.8); 6.5050 (0.8); 4.9677 (0.4); 4.9614 (0.6); 4.9559 (0.8); 4.9505 (0.6); 4.9441 (0.4); 4.2840 (0.7); 4.2766 (0.7); 4.2618 (0.8); 4.2545 (0.7); 3.9547 (0.9); 3.9432 (0.9); 3.9326 (0.8); 3.9210 (0.8); 2.9450 (16.0); 2.8643 (14.1); 2.6741 (10.1); 1.7417 (1.6); −0.0002 (2.3)
I-100: $^{1}$H-NMR(499.9 MHz, CDCl3):
δ = 8.0006 (2.0); 7.9130 (3.1); 7.5652 (0.3); 7.5497 (0.9); 7.5339 (1.3); 7.5286 (1.2); 7.5129 (0.3); 7.4751 (1.1); 7.4264 (0.5); 7.4230 (0.7); 7.4193 (0.5); 7.4079 (0.5); 7.2735 (1.7); 6.3133 (0.8); 6.2066 (1.3); 6.2003 (1.3); 5.9351 (0.9); 5.9333 (1.0); 5.9315 (0.8); 5.9290 (0.9); 5.9272 (0.8); 4.8087 (0.4); 4.8046 (0.4); 4.8009 (0.4); 4.7959 (0.6); 4.7908 (0.4); 4.7871 (0.4); 4.7830 (0.3); 4.3383 (0.6); 4.3302 (0.6); 4.3164 (0.7); 4.3085 (0.6); 3.9721 (0.9); 3.9581 (0.9); 3.9502 (0.8); 3.9362 (0.8); 2.9506 (16.0); 2.8734 (13.8); 2.7409 (0.4); 2.6721 (9.7); 2.2084 (6.3); −0.0002 (2.2)
I-101: $^{1}$H-NMR(300.2 MHz, CDCl3):
δ = 8.0518 (2.0); 7.9603 (1.7); 7.5885 (0.6); 7.5655 (1.5); 7.5432 (0.4); 7.4724 (0.7); 7.4506 (0.4); 7.4416 (0.5); 7.4338 (0.3); 7.4200 (0.3); 7.2985 (13.4); 5.9276 (0.4); 5.8869 (0.9); 4.2664 (0.3); 4.2520 (0.3); 3.7468 (0.5); 3.7197 (0.4); 3.7103 (0.4); 3.6829 (0.4); 2.9931 (16.0); 2.9195 (14.4); 2.7836 (0.6); 2.7352 (0.5); 2.7184 (5.4); 2.6870 (0.4); 2.6780 (0.5); 2.6686 (0.5); 2.5486 (0.4); 2.5413 (0.3); 2.5078 (0.7); 2.4517 (0.3); 2.3490 (0.6); 2.3111 (0.6); 2.2906 (4.1); 2.2100 (3.4); 2.1955 (0.7); 2.1118 (1.0); 2.0652 (1.1); 1.8253 (0.9); 1.6586 (1.2); 1.2893 (0.8); 0.0353 (15.3)
I-102: $^{1}$H-NMR(499.9 MHz, CDCl3):
δ = 8.0114 (2.1); 7.9275 (3.6); 7.5675 (0.4); 7.5520 (1.1); 7.5363 (1.8); 7.5321 (1.6); 7.5164 (0.4); 7.4734 (1.5); 7.4334 (0.6); 7.4299 (0.9); 7.4262 (0.6); 7.4149 (0.7); 7.2639 (6.2); 6.2298 (0.9); 6.0954 (2.6); 4.7636 (0.4); 4.7598 (0.5); 4.7558 (0.5); 4.7507 (0.7); 4.7458 (0.5); 4.7417 (0.5); 4.7378 (0.4); 4.3296 (0.7); 4.3215

TABLE 2-continued (0.7); 4.3077 (0.8); 4.2997 (0.8); 3.9367 (1.0); 3.9224 (1.0); 3.9148 (1.0); 3.9006 (0.9); 2.9545 (16.0); 2.8805 (14.2); 2.6762 (11.3); 2.1101 (7.1); 1.8848 (7.1); 1.6447 (1.0); −0.0002 (6.1); −0.0065 (0.4)
I-103: $^{1}$H-NMR(499.9 MHz, CDCl3):
δ = 7.9928 (2.2); 7.9231 (0.6); 7.9055 (2.8); 7.5731 (0.4); 7.5576 (1.1); 7.5416 (1.4); 7.5353 (1.6); 7.5196 (0.4); 7.4683 (1.3); 7.3982 (0.8); 7.3829 (0.6); 7.2670 (2.8); 6.7808 (2.7); 6.1278 (0.8); 4.8065 (0.4); 4.8032 (0.5); 4.7984 (0.5); 4.7947 (0.5); 4.7926 (0.6); 4.7887 (0.5); 4.7838 (0.4); 4.7805 (0.4); 4.2503 (0.6); 4.2418 (0.6); 4.2281 (0.7); 4.2197 (0.6); 3.7546 (0.8); 3.7399 (0.8); 3.7323 (0.7); 3.7177 (0.7); 2.9485 (16.0); 2.8703 (14.4); 2.6847 (9.1); 2.6795 (2.2); 2.3849 (8.9); 2.3416 (1.0); 2.3131 (0.6); 2.3113 (0.6); 2.1183 (0.8); 1.6763 (1.3); −0.0002 (3.5)
I-104: $^{1}$H-NMR(499.9 MHz, CDCl3):
δ = 8.0138 (2.1); 7.9777 (2.7); 7.5406 (1.3); 7.5236 (1.4); 7.5044 (1.1); 7.4988 (1.0); 7.4941 (2.0); 7.4926 (2.0); 7.3464 (1.1); 7.3267 (0.5); 7.3191 (0.8); 7.3146 (2.0); 7.3110 (1.7); 7.3039 (0.3); 7.2612 (9.2); 7.0707 (2.5); 7.0061 (0.9); 7.0026 (0.8); 6.9891 (0.8); 6.9856 (0.8); 6.1904 (0.9); 5.0544 (0.4); 5.0518 (0.4); 5.0462 (0.4); 5.0434 (0.4); 5.0391 (0.4); 5.0363 (0.4); 5.0307 (0.4); 4.4016 (0.5); 4.3939 (0.5); 4.3795 (0.6); 4.3718 (0.5); 4.0100 (0.7); 3.9944 (0.7); 3.9880 (0.7); 3.9724 (0.6); 3.7086 (8.5); 2.9538 (16.0); 2.8809 (14.3); 2.6967 (8.2); 2.0046 (0.4); 1.5842 (0.9); −0.0002 (11.7); −0.0067 (0.4)
I-105: $^{1}$H-NMR(499.9 MHz, CDCl3):
δ = 7.9551 (2.2); 7.8911 (3.9); 7.8852 (0.4); 7.5504 (0.3); 7.5349 (1.1); 7.5192 (1.8); 7.5143 (1.6); 7.4988 (0.5); 7.4653 (1.5); 7.4106 (0.6); 7.4074 (0.9); 7.4036 (0.6); 7.3923 (0.7); 7.2983 (1.2); 7.2963 (1.2); 7.2882 (1.3); 7.2861 (1.3); 7.2821 (1.1); 7.0850 (1.2); 7.0783 (1.4); 7.0052 (1.3); 6.9981 (1.2); 6.9951 (1.3); 6.9880 (1.1); 6.5474 (1.0); 5.0768 (0.4); 5.0728 (0.5); 5.0692 (0.6); 5.0644 (0.8); 5.0597 (0.6); 5.0560 (0.6); 5.0521 (0.5); 4.3399 (0.7); 4.3325 (0.7); 4.3180 (0.8); 4.3104 (0.8); 3.9075 (1.1); 3.8941 (1.1); 3.8854 (1.0); 3.8721 (1.0); 2.9336 (16.0); 2.8490 (14.1); 2.6633 (11.8); 1.9319 (0.6); −0.0002 (0.9)
I-106: $^{1}$H-NMR(499.9 MHz, CDCl3):
δ = 7.9425 (2.5); 7.9175 (2.8); 7.8837 (1.0); 7.8690 (1.0); 7.8194 (0.9); 7.8048 (0.9); 7.5284 (0.3); 7.5125 (1.1); 7.4992 (2.4); 7.4462 (2.4); 7.4203 (1.3); 7.3888 (0.4); 7.3766 (1.0); 7.3747 (0.9); 7.3668 (0.7); 7.3617 (1.8); 7.3593 (1.7); 7.3483 (0.8); 7.3441 (1.2); 7.3295 (0.4); 7.3276 (0.4); 7.2753 (0.8); 6.6147 (0.9); 5.2321 (0.4); 5.2251 (0.5); 5.2203 (0.6); 5.2155 (0.4); 5.2086 (0.4); 4.4403 (0.6); 4.4327 (0.6); 4.4182 (0.6); 4.4106 (0.6); 4.0454 (0.7); 4.0319 (0.7); 4.0232 (0.7); 4.0098 (0.6); 2.9171 (16.0); 2.8365 (14.6); 2.6734 (8.2); 2.6673 (1.0); 1.8968 (0.7); −0.0002 (0.9)
I-107: $^{1}$H-NMR(499.9 MHz, CDCl3):
δ = 7.9528 (2.2); 7.8657 (3.8); 7.5613 (0.4); 7.5458 (1.2); 7.5302 (1.5); 7.5240 (1.5); 7.5083 (0.4); 7.4729 (1.4); 7.4129 (0.6); 7.4096 (0.9); 7.4059 (0.6); 7.3943 (0.7); 7.2837 (0.9); 6.7581 (3.0); 6.5827 (0.9); 4.9035 (0.5); 4.8971 (0.6); 4.8917 (0.9); 4.8863 (0.6); 4.8797 (0.4); 4.2536 (0.8); 4.2460 (0.8); 4.2314 (0.9); 4.2240 (0.8); 3.9114 (1.0); 3.8995 (1.0); 3.8892 (0.9); 3.8774 (0.9); 2.9344 (16.0); 2.8463 (14.0); 2.6601 (11.3); 2.1094 (11.4); 1.9315 (0.6); −0.0002 (1.0)
I-108: $^{1}$H-NMR(300.2 MHz, CDCl3):
δ = 7.5460 (0.6); 7.5190 (2.1); 7.5101 (1.8); 7.5055 (2.0); 7.4999 (5.2); 7.4967 (4.9); 7.4846 (0.4); 7.4803 (0.4); 7.4611 (0.4); 7.3585 (8.3); 7.2987 (7.9); 7.2754 (2.5); 7.2277 (1.0); 7.2172 (1.6); 7.2101 (1.3); 7.1970 (1.1); 7.1896 (0.7); 6.9996 (2.4); 6.9741 (2.9); 6.9321 (2.9); 6.7551 (1.6); 6.7302 (1.4); 6.1424 (2.0); 5.3361 (1.4); 4.2728 (1.0); 4.2629 (1.3); 4.2378 (1.4); 4.2286 (1.3); 3.9024 (0.5); 3.8861 (0.7); 3.8754 (0.7); 3.8698 (0.8); 3.8629 (0.6); 3.8537 (0.7); 3.8380 (2.6); 3.8171 (0.9); 3.8033 (1.8); 3.7824 (1.2); 3.5514 (2.7); 3.5292 (7.3); 3.5073 (2.9); 3.0120 (0.9); 2.9973 (0.9); 2.9667 (1.4); 2.9512 (1.2); 2.7551 (1.4); 2.7236 (1.3); 2.7099 (1.1); 2.6777 (1.0); 2.3167 (0.3); 2.2903 (16.0); 2.2125 (14.5); 2.1097 (0.5); 2.0959 (0.4); 2.0757 (3.0); 2.0634 (3.2); 2.0536 (8.1); 2.0435 (3.3); 2.0313 (2.9); 2.0110 (0.4); 1.2923 (0.8); 0.0372 (8.8); 0.0262 (0.4)
I-109: $^{1}$H-NMR(300.2 MHz, CDCl3):
δ = 8.2328 (8.0); 7.3549 (1.6); 7.3286 (3.4); 7.2986 (15.5); 7.0324 (2.0); 7.0240 (2.2); 7.0076 (2.9); 6.9959 (3.7); 6.9823 (3.3); 6.9734 (2.5); 6.9363 (4.7); 6.8715 (1.4); 6.8688 (1.5); 6.8637 (1.8); 6.8611 (1.7); 6.8448 (1.2); 6.8419 (1.2); 6.8370 (1.7); 6.8342 (1.6); 6.8058 (2.4); 6.7996 (3.1); 6.7929 (1.8); 6.7139 (1.6); 6.6893 (1.4); 6.3269 (1.8); 6.2412 (3.1); 6.1822 (2.7); 5.6520 (3.0); 5.6146 (2.8); 5.3374 (5.3); 4.2908 (0.9); 4.2824 (1.4); 4.2566 (1.5); 4.2479 (1.2); 4.1719 (0.5); 4.1481 (0.5); 3.8977 (0.7); 3.8916 (0.8); 3.8824 (0.8); 3.8765 (0.9); 3.8693 (0.8); 3.8569 (2.6); 3.8374 (0.8); 3.8234 (2.0); 3.8026 (1.2); 3.0411 (0.9); 3.0263 (0.9); 2.9965 (1.4); 2.9803 (1.3); 2.7721 (1.2); 2.7411 (1.2); 2.7268 (1.2); 2.6957 (1.0); 2.6796 (1.0); 2.4362 (0.4); 2.3052 (16.0); 2.2278 (15.0); 2.0841 (2.3); 1.9912 (0.4); 1.9745 (0.8); 1.9633 (0.9); 1.9466 (1.6); 1.9299 (1.0); 1.9187 (1.0); 1.9018 (0.6); 1.6416 (0.6); 1.3216 (0.6); 1.2978 (1.1); 1.2741 (0.5); 1.0609 (1.0); 1.0458 (2.5); 1.0391 (2.9); 1.0243 (1.6); 1.0175 (2.9); 1.0108 (2.6); 0.9965 (1.4); 0.9739 (0.4); 0.7742 (1.3); 0.7592 (3.2); 0.7530 (3.0); 0.7428 (2.9); 0.7370 (3.4); 0.7209 (1.2); 0.0491 (0.4); 0.0382 (18.8); 0.0274 (0.9)
I-110: $^{1}$H-NMR(300.2 MHz, CDCl3):
δ = 7.9707 (7.8); 7.2989 (14.6); 7.1322 (0.8); 7.1284 (0.8); 7.1055 (2.0); 7.1019 (2.0); 7.0789 (1.4); 7.0757 (1.6); 7.0300 (2.8); 7.0202 (1.7); 7.0038 (3.6); 6.9754 (0.9); 6.9698 (0.8); 6.9100 (2.9); 6.8525 (1.0); 6.8473 (1.0); 6.8262 (1.7); 6.8044 (0.9); 6.7994 (0.8); 6.7105 (1.6); 6.6864 (1.4); 6.2729 (1.9); 4.2946 (1.0); 4.2859 (1.4); 4.2601 (1.5); 4.2513 (1.3); 4.1712 (0.4); 4.1474 (0.4); 3.9054 (0.8); 3.8898 (0.8); 3.8744 (0.9); 3.8652 (2.8); 3.8447 (0.8); 3.8309 (1.9); 3.8102 (1.2); 3.0455 (0.9); 3.0300 (1.0); 3.0135 (1.8); 3.0011 (1.6); 2.9881 (5.9); 2.9628 (5.4); 2.9375 (1.8); 2.7975 (1.3); 2.7671 (1.2); 2.7524 (1.1); 2.7216 (1.0); 2.3126 (16.0); 2.1812 (15.0); 2.1495 (0.8); 2.1382 (0.8); 2.1213 (1.4); 2.1038 (0.9); 2.0933 (0.8); 2.0845 (2.2); 2.0764 (0.4); 1.6160 (1.6); 1.3936 (6.1); 1.3684 (12.8); 1.3430 (5.9); 1.3213 (0.7); 1.2974 (1.6); 1.2910 (1.5); 1.2737 (0.7); 1.0909 (1.0); 1.0777 (1.9); 1.0710 (2.5); 1.0662 (1.6); 1.0627 (1.5); 1.0581 (1.5); 1.0488 (2.0); 1.0427 (2.3); 1.0299 (1.2); 0.8858 (0.3); 0.8682 (0.3); 0.8326 (1.2); 0.8262 (1.2); 0.8170 (2.6); 0.8096 (2.4); 0.8013 (2.7); 0.7941 (1.7); 0.7841 (0.9); 0.1074 (7.4); 0.0478 (0.6); 0.0370 (17.2); 0.0261 (0.7)
I-111: $^{1}$H-NMR(300.2 MHz, CDCl3):
δ = 7.9690 (7.4); 7.3430 (1.6); 7.3167 (3.5); 7.2989 (15.7); 7.2907 (2.4); 7.0046 (4.3); 6.9792 (4.6); 6.9317 (3.1); 6.8589 (1.5); 6.8537 (1.7); 6.8321 (1.2); 6.8270 (1.7); 6.7986 (2.4); 6.7926 (3.1); 6.7859 (1.8); 6.7142 (1.7); 6.6902 (1.4); 6.3377 (1.8); 4.2747 (1.0); 4.2663 (1.4); 4.2407 (1.5); 4.2320 (1.2); 4.1952 (0.5); 4.1713 (1.4); 4.1475 (1.4); 4.1238 (0.6); 3.8807 (0.8); 3.8646 (0.9); 3.8581 (0.8); 3.8437 (2.8); 3.8238 (0.8); 3.8100 (2.0); 3.7892 (1.2); 3.0316 (1.0); 3.0105 (1.9); 2.9851 (6.1); 2.9708 (1.6); 2.9596 (5.2); 2.9343 (1.8); 2.7647 (1.2); 2.7340 (1.3); 2.7193 (1.2); 2.6885 (1.0); 2.6788 (1.1); 2.4322 (0.4); 2.3373 (0.4); 2.3260 (0.6); 2.3013 (16.0); 2.2281 (14.9); 2.1814 (0.4); 2.0846 (6.9); 1.9851 (0.4); 1.9682 (0.8); 1.9569 (0.9); 1.9403 (1.6); 1.9235 (1.0); 1.9122 (0.9); 1.8957 (0.5); 1.6343 (2.0); 1.3890 (5.7); 1.3637 (11.9); 1.3383 (5.4); 1.3215 (1.8); 1.2977

TABLE 2-continued (3.5); 1.2738 (1.7); 1.0545 (1.0); 1.0393 (2.6); 1.0327 (2.9); 1.0179 (1.6); 1.0110 (2.9); 1.0046 (2.6); 0.9901 (1.4); 0.9731 (0.5); 0.9675 (0.4); 0.7704 (1.4); 0.7553 (3.3); 0.7492 (3.0); 0.7390 (2.9); 0.7331 (3.4); 0.7171 (1.1); 0.1072 (0.6); 0.0480 (0.6); 0.0372 (18.4); 0.0263 (0.9)
I-112: $^{1}$H-NMR(300.2 MHz, CDCl3):
δ = 8.4109 (8.4); 7.2988 (15.2); 7.1415 (0.8); 7.1377 (0.8); 7.1149 (1.9); 7.1113 (2.0); 7.0883 (1.4); 7.0850 (1.6); 7.0367 (3.3); 7.0102 (4.6); 6.9877 (0.9); 6.9821 (0.8); 6.9140 (2.9); 6.8618 (1.0); 6.8563 (1.1); 6.8353 (1.7); 6.8136 (0.9); 6.8085 (0.8); 6.7188 (1.6); 6.6936 (1.3); 6.1933 (1.9); 5.5710 (3.6); 5.5631 (3.7); 4.4338 (3.2); 4.4259 (3.2); 4.3053 (0.8); 4.2963 (1.4); 4.2710 (1.6); 4.2628 (1.1); 4.0330 (1.5); 4.0097 (4.7); 3.9863 (4.7); 3.9632 (1.5); 3.9330 (0.5); 3.9155 (0.8); 3.8995 (0.8); 3.8855 (2.5); 3.8659 (0.6); 3.8518 (2.0); 3.8313 (1.1); 3.0509 (0.8); 3.0346 (0.8); 3.0058 (1.4); 2.9892 (1.3); 2.8108 (1.1); 2.7798 (1.1); 2.7654 (1.1); 2.7346 (0.9); 2.3397 (0.4); 2.3162 (16.0); 2.2957 (0.6); 2.1850 (14.9); 2.1665 (0.5); 2.1486 (0.7); 2.1376 (0.8); 2.1202 (1.4); 2.1033 (0.9); 2.0919 (0.8); 2.0844 (0.4); 2.0748 (0.4); 1.5989 (14.1); 1.4881 (5.2); 1.4649 (11.1); 1.4416 (5.1); 1.4096 (0.5); 1.3838 (0.4); 1.3608 (0.7); 1.3336 (0.5); 1.3075 (0.4); 1.0933 (0.9); 1.0799 (1.8); 1.0733 (2.4); 1.0688 (1.5); 1.0653 (1.4); 1.0603 (1.5); 1.0513 (2.0); 1.0450 (2.3); 1.0319 (1.2); 0.9850 (0.9); 0.9609 (1.6); 0.9366 (0.7); 0.8337 (1.2); 0.8267 (1.1); 0.8176 (2.5); 0.8103 (2.3); 0.8022 (2.6); 0.7949 (1.6); 0.7845 (0.9); 0.1082 (0.5); 0.0489 (0.5); 0.0381 (18.6); 0.0271 (0.7)
I-113: $^{1}$H-NMR(499.9 MHz, CDCl3):
δ = 8.0980 (8.5); 7.4563 (1.0); 7.4535 (1.0); 7.4405 (1.8); 7.4273 (1.0); 7.4246 (0.9); 7.2591 (8.8); 7.1851 (1.1); 7.1834 (1.1); 7.1690 (2.2); 7.1675 (2.2); 7.1531 (1.2); 7.1515 (1.2); 7.0769 (1.2); 7.0739 (1.2); 7.0601 (1.7); 7.0466 (0.9); 7.0435 (0.8); 6.9590 (2.7); 6.9438 (2.9); 6.8505 (3.1); 6.8326 (1.6); 6.8196 (1.6); 6.7972 (1.5); 6.6448 (1.7); 6.6298 (1.4); 6.1193 (1.9); 5.8860 (2.7); 5.8848 (2.7); 5.8506 (2.5); 5.8493 (2.4); 5.4687 (2.7); 5.4678 (2.6); 5.4463 (2.5); 5.4452 (2.5); 4.2751 (1.4); 4.2690 (1.4); 4.2537 (1.5); 4.2474 (1.4); 3.8901 (0.3); 3.8778 (0.7); 3.8735 (0.8); 3.8701 (0.9); 3.8674 (0.9); 3.8639 (0.8); 3.8603 (0.9); 3.8576 (0.9); 3.8543 (0.8); 3.8512 (0.7); 3.8480 (0.7); 3.8442 (0.5); 3.8378 (0.4); 3.8136 (2.3); 3.8011 (1.5); 3.7921 (1.9); 3.7795 (1.4); 2.9984 (1.2); 2.9885 (1.2); 2.9711 (1.4); 2.9612 (1.3); 2.7187 (1.5); 2.6991 (1.5); 2.6915 (1.3); 2.6718 (1.2); 2.2619 (16.0); 2.1331 (0.5); 2.1129 (15.0); 1.5587 (3.1); 0.0061 (0.6); −0.0002 (8.5); −0.0067 (0.4)
I-114: $^{1}$H-NMR(499.9 MHz, CDCl3):
δ = 7.9145 (5.4); 7.5379 (0.8); 7.5223 (4.5); 7.5096 (6.6); 7.4865 (3.0); 7.3952 (3.2); 7.3860 (1.8); 7.3799 (3.0); 7.2938 (1.2); 7.2925 (1.2); 7.2781 (2.1); 7.2633 (1.5); 7.2609 (1.5); 7.2582 (1.6); 7.2371 (1.7); 7.2221 (2.3); 7.2075 (1.0); 6.7082 (4.5); 6.5376 (2.0); 6.5349 (2.0); 4.9913 (0.9); 4.9847 (1.5); 4.9800 (1.6); 4.9752 (1.5); 4.9685 (0.8); 4.3520 (1.3); 4.3446 (1.3); 4.3299 (1.7); 4.3225 (1.6); 4.2144 (1.7); 4.2033 (1.6); 4.1923 (1.3); 4.1813 (1.2); 2.7219 (0.3); 2.6557 (16.0); 1.9701 (1.7); 1.6965 (0.4); −0.0002 (1.0)
I-115: $^{1}$H-NMR(499.9 MHz, CDCl3):
δ = 7.9253 (5.4); 7.5498 (0.5); 7.5344 (1.6); 7.5191 (3.0); 7.5157 (2.4); 7.4999 (0.6); 7.4683 (2.0); 7.4111 (1.0); 7.4074 (1.4); 7.4035 (0.9); 7.3926 (1.0); 7.2649 (1.0); 7.1959 (2.4); 7.1857 (2.4); 6.8454 (2.7); 6.8353 (2.5); 6.3374 (1.5); 5.1064 (0.8); 5.1039 (0.9); 5.0983 (0.9); 5.0956 (0.9); 5.0913 (0.9); 5.0886 (0.9); 5.0831 (0.8); 5.0806 (0.7); 4.3492 (1.0); 4.3475 (1.0); 4.3411 (1.0); 4.3393 (0.9); 4.3271 (1.0); 4.3254 (1.0); 4.3190 (1.0); 4.3173 (0.9); 3.7962 (1.5); 3.7809 (1.6); 3.7741 (1.4); 3.7588 (1.4); 2.6671 (16.0); 2.2617 (15.2); 1.9859 (1.2); 1.7375 (0.6); −0.0002 (0.9)
I-116: $^{1}$H-NMR(499.9 MHz, CDCl3):
δ = 7.9413 (5.1); 7.5600 (0.5); 7.5445 (1.7); 7.5290 (3.4); 7.5112 (0.6); 7.4652 (2.4); 7.4106 (1.4); 7.3959 (1.1); 7.2614 (3.3); 6.8922 (3.2); 6.8609 (2.7); 6.3099 (1.6); 5.0027 (0.7); 4.9999 (0.8); 4.9950 (0.8); 4.9905 (1.1); 4.9860 (0.8); 4.9811 (0.8); 4.9783 (0.7); 4.3637 (1.1); 4.3559 (1.1); 4.3417 (1.2); 4.3338 (1.2); 3.8607 (1.4); 3.8466 (1.4); 3.8387 (1.4); 3.8245 (1.3); 2.6793 (16.0); 2.4379 (0.3); 2.2698 (0.8); 2.2071 (11.7); 1.6064 (1.7); −0.0002 (3.2)
I-117: $^{1}$H-NMR(300.2 MHz, CDCl3):
δ = 8.2689 (15.3); 8.0219 (1.4); 7.6190 (1.0); 7.6081 (9.3); 7.6048 (9.8); 7.5973 (4.2); 7.5927 (4.5); 7.5869 (5.3); 7.5560 (1.1); 7.5376 (1.2); 7.5140 (0.5); 7.4890 (0.8); 7.4378 (0.6); 7.3955 (0.4); 7.3889 (0.6); 7.3814 (0.6); 7.3551 (2.8); 7.2989 (6.2); 7.2631 (1.7); 7.0214 (2.2); 6.9969 (2.4); 6.9049 (3.3); 6.7155 (1.1); 3.7959 (1.2); 3.7818 (1.6); 3.7658 (2.4); 3.7508 (2.8); 3.7358 (2.5); 3.7212 (1.6); 3.7052 (0.9); 3.6402 (1.0); 3.6014 (1.0); 2.9536 (1.0); 2.7554 (0.6); 2.3015 (16.0); 2.1892 (10.8); 2.1026 (1.3); 2.0920 (1.3); 2.0814 (1.8); 2.0615 (1.4); 2.0521 (1.4); 2.0361 (10.1); 1.7319 (1.1); 1.7028 (1.0); 1.2969 (0.8); 0.1139 (0.5); 0.0403 (5.2)
I-118: $^{1}$H-NMR(300.2 MHz, CDCl3):
δ = 8.2465 (12.0); 7.3503 (2.8); 7.3241 (6.0); 7.2984 (5.1); 7.0304 (5.6); 7.0048 (5.2); 6.9720 (0.4); 6.9245 (3.6); 6.8518 (2.0); 6.8249 (1.9); 6.7923 (3.6); 6.7306 (1.1); 3.7671 (1.0); 3.7374 (2.0); 3.7217 (2.3); 3.7075 (2.2); 3.6774 (0.9); 3.5985 (0.8); 3.5709 (0.9); 2.9204 (1.1); 2.8540 (0.4); 2.7985 (0.5); 2.3506 (0.8); 2.3128 (16.0); 2.2367 (14.2); 2.0653 (1.0); 2.0528 (1.0); 2.0227 (1.3); 2.0103 (1.2); 1.9922 (1.1); 1.9750 (1.5); 1.9637 (1.6); 1.9471 (2.9); 1.9303 (1.7); 1.9192 (1.7); 1.9023 (0.9); 1.7057 (1.0); 1.6915 (0.9); 1.6765 (0.9); 1.3075 (0.4); 1.0646 (1.6); 1.0491 (4.5); 1.0427 (5.1); 1.0279 (2.8); 1.0210 (5.1); 1.0145 (4.7); 1.0001 (2.3); 0.9772 (0.4); 0.7760 (2.2); 0.7608 (5.9); 0.7548 (5.4); 0.7445 (5.3); 0.7386 (6.0); 0.7226 (1.9); 0.0507 (1.7)
I-119: $^{1}$H-NMR(499.9 MHz, CDCl3):
δ = 7.9139 (5.2); 7.2598 (4.9); 7.0773 (2.2); 7.0621 (3.3); 7.0467 (2.3); 6.9816 (4.2); 6.9680 (4.8); 6.9432 (1.6); 6.8707 (4.7); 6.8076 (2.1); 6.7940 (2.8); 6.7808 (1.4); 6.6682 (2.9); 6.6538 (2.3); 6.2125 (3.3); 5.2968 (0.6); 4.2334 (2.3); 4.2138 (2.2); 3.8583 (2.3); 3.8125 (2.4); 3.8000 (1.9); 3.7917 (2.0); 3.7794 (1.3); 2.9869 (2.0); 2.9778 (2.0); 2.9601 (2.2); 2.9514 (1.9); 2.9011 (0.4); 2.7465 (2.4); 2.7271 (2.6); 2.7005 (2.0); 2.6267 (16.0); 2.4974 (0.4); 2.4801 (0.4); 2.4652 (0.4); 2.3939 (0.6); 2.2711 (15.8); 2.1440 (15.4); 2.0762 (2.1); 1.5793 (6.6); 1.0243 (4.5); 0.7720 (5.0); −0.0002 (5.5)
I-120: $^{1}$H-NMR(300.2 MHz, CDCl3):
δ = 8.7215 (5.8); 7.2989 (7.9); 7.1815 (0.5); 7.1775 (0.5); 7.1548 (1.2); 7.1509 (1.3); 7.1282 (0.8); 7.1245 (0.9); 7.0419 (0.8); 7.0363 (1.0); 7.0279 (1.7); 7.0180 (1.0); 7.0131 (1.3); 7.0024 (2.0); 6.9914 (0.7); 6.9860 (0.6); 6.9143 (1.9); 6.8816 (1.1); 6.8597 (0.6); 6.8549 (0.5); 6.7148 (1.0); 6.6909 (0.9); 6.0572 (1.2); 4.3216 (0.6); 4.3131 (0.9); 4.2871 (1.0); 4.2790 (0.7); 3.9234 (0.4); 3.9177 (0.5); 3.9087 (0.4); 3.9022 (0.5); 3.8940 (0.5); 3.8854 (1.6); 3.8655 (0.4); 3.8515 (1.3); 3.8310 (0.7); 3.0612 (0.5); 3.0460 (0.5); 3.0166 (1.0); 3.0002 (0.8); 2.8624 (0.4); 2.8047 (16.0); 2.7678 (0.8); 2.7538 (0.8); 2.7226 (0.6); 2.3409 (0.3); 2.3148 (10.1); 2.1830 (9.5); 2.1605 (0.6); 2.1434 (0.9); 2.1262 (0.5); 2.1152 (0.5); 1.6014 (6.7); 1.3039 (1.4); 1.2977 (1.3); 1.1228 (0.6); 1.1095 (1.2); 1.1027 (1.6); 1.0981 (1.0); 1.0949 (1.0); 1.0894 (1.0); 1.0806 (1.3); 1.0744 (1.5); 1.0611

TABLE 2-continued (0.8); 0.9412 (0.5); 0.9195 (1.5); 0.8961 (0.6); 0.8572 (0.8); 0.8499 (0.7); 0.8408 (1.6); 0.8337 (1.4); 0.8258 (1.6); 0.8188 (1.1); 0.8078 (0.5); 0.1079 (0.4); 0.0375 (9.3); 0.0266 (0.4)
I-121: $^{1}$H-NMR(300.2 MHz, CDCl3):
δ = 8.7079 (3.7); 7.4030 (0.7); 7.3767 (1.5); 7.3503 (0.9); 7.2988 (3.9); 7.0732 (0.8); 7.0471 (0.7); 7.0047 (1.1); 6.9792 (1.2); 6.9296 (1.2); 6.9079 (0.6); 6.9050 (0.6); 6.9000 (0.7); 6.8972 (0.7); 6.8811 (0.5); 6.8782 (0.5); 6.8731 (0.7); 6.8704 (0.6); 6.8277 (0.9); 6.8214 (1.3); 6.8147 (0.8); 6.7020 (0.7); 6.6784 (0.6); 6.1351 (0.8); 4.3083 (0.4); 4.3000 (0.6); 4.2739 (0.7); 4.2657 (0.5); 4.1931 (1.1); 4.1692 (3.5); 4.1454 (3.5); 4.1217 (1.2); 3.8985 (0.3); 3.8831 (0.4); 3.8753 (0.4); 3.8655 (1.1); 3.8317 (0.8); 3.8110 (0.5); 3.0534 (0.4); 3.0385 (0.4); 3.0084 (0.6); 2.9926 (0.6); 2.7924 (10.3); 2.7727 (0.6); 2.7410 (0.5); 2.7267 (0.5); 2.6956 (0.4); 2.3054 (6.7); 2.2193 (6.3); 2.0815 (16.0); 1.9849 (0.4); 1.9682 (0.6); 1.9515 (0.4); 1.9402 (0.4); 1.6240 (3.3); 1.3194 (4.3); 1.2956 (8.7); 1.2718 (4.1); 1.0868 (0.4); 1.0715 (1.1); 1.0648 (1.2); 1.0593 (0.7); 1.0499 (0.6); 1.0431 (1.2); 1.0367 (1.1); 1.0221 (0.5); 0.9179 (0.4); 0.7915 (0.5); 0.7763 (1.4); 0.7701 (1.2); 0.7599 (1.2); 0.7541 (1.4); 0.7379 (0.4); 0.0360 (4.4)
I-122: $^{1}$H-NMR(300.2 MHz, CDCl3):
δ = 8.1520 (6.4); 7.2987 (14.0); 7.1576 (0.8); 7.1536 (0.8); 7.1306 (1.9); 7.1272 (2.1); 7.1007 (1.5); 7.0291 (3.2); 7.0225 (1.7); 7.0040 (4.2); 6.9769 (0.9); 6.9719 (0.9); 6.9118 (3.0); 6.8820 (1.1); 6.8770 (1.1); 6.8553 (1.8); 6.8338 (0.9); 6.8286 (0.9); 6.7128 (1.6); 6.6875 (1.4); 6.2374 (1.5); 5.1212 (0.4); 5.0988 (1.3); 5.0767 (1.3); 5.0553 (0.5); 4.3102 (1.0); 4.3011 (1.3); 4.2758 (1.5); 4.2667 (1.3); 4.1711 (0.6); 4.1474 (0.6); 3.9149 (0.8); 3.8985 (0.8); 3.8731 (2.6); 3.8530 (0.8); 3.8389 (1.8); 3.8182 (1.1); 3.6124 (0.5); 3.0556 (0.9); 3.0400 (0.9); 3.0108 (1.4); 2.9941 (1.3); 2.7974 (1.1); 2.7672 (1.1); 2.7528 (1.0); 2.7215 (0.9); 2.3463 (0.5); 2.3150 (16.0); 2.1803 (14.0); 2.1630 (1.0); 2.1511 (0.9); 2.1343 (1.4); 2.1173 (0.9); 2.1061 (0.9); 2.0833 (3.1); 1.6582 (0.6); 1.6354 (0.6); 1.6067 (6.8); 1.6009 (5.8); 1.5847 (6.7); 1.5790 (5.6); 1.3209 (0.8); 1.2971 (1.6); 1.2733 (0.7); 1.1074 (0.9); 1.0938 (1.8); 1.0874 (2.4); 1.0822 (1.5); 1.0796 (1.5); 1.0745 (1.5); 1.0654 (2.0); 1.0592 (2.4); 1.0461 (1.3); 1.0204 (0.4); 0.8452 (1.1); 0.8384 (1.1); 0.8294 (2.5); 0.8222 (2.4); 0.8135 (2.7); 0.8066 (1.7); 0.7962 (1.0); 0.1080 (1.3); 0.0484 (0.6); 0.0376 (17.8); 0.0268 (0.7)
I-123: $^{1}$H-NMR(300.2 MHz, CDCl3):
δ = 8.1333 (16.0); 7.3876 (3.0); 7.3612 (6.8); 7.3553 (7.2); 7.3482 (7.0); 7.3349 (3.9); 7.2989 (18.2); 7.1396 (5.4); 7.1225 (0.8); 7.1123 (6.8); 7.0614 (3.5); 7.0354 (3.0); 6.9187 (4.2); 6.9116 (4.2); 6.8915 (3.4); 6.8844 (3.4); 6.8745 (2.4); 6.8716 (2.6); 6.8665 (3.0); 6.8637 (3.0); 6.8477 (1.9); 6.8448 (2.1); 6.8397 (2.9); 6.8368 (2.8); 6.8103 (4.0); 6.8041 (5.2); 6.7972 (3.1); 6.2560 (2.7); 6.2497 (2.7); 5.3375 (1.7); 4.1952 (2.2); 4.1852 (2.6); 4.1595 (3.0); 4.1495 (3.3); 4.0404 (0.4); 4.0300 (0.6); 4.0242 (0.9); 4.0136 (1.4); 3.9970 (1.5); 3.9843 (1.7); 3.9749 (1.1); 3.9675 (1.1); 3.9581 (0.8); 3.9462 (4.0); 3.9303 (2.1); 3.9106 (2.8); 3.8945 (2.0); 3.1891 (2.0); 3.1726 (2.0); 3.1443 (3.1); 3.1274 (2.8); 2.9761 (3.0); 2.9463 (2.8); 2.9312 (2.1); 2.9012 (2.0); 2.6931 (0.8); 2.0054 (0.6); 1.9886 (1.3); 1.9775 (1.4); 1.9721 (1.0); 1.9607 (2.8); 1.9440 (1.6); 1.9327 (1.6); 1.9159 (0.8); 1.6015 (9.7); 1.3665 (0.4); 1.3439 (0.9); 1.3036 (5.6); 1.0802 (1.8); 1.0649 (4.4); 1.0583 (5.0); 1.0527 (2.8); 1.0434 (2.8); 1.0365 (5.0); 1.0302 (4.5); 1.0154 (2.4); 0.9931 (0.4); 0.9651 (0.4); 0.9410 (2.0); 0.9192 (6.5); 0.8959 (2.4); 0.7815 (2.3); 0.7662 (5.8); 0.7601 (5.1); 0.7498 (5.0); 0.7442 (6.0); 0.7279 (1.9); 0.1076 (0.8); 0.0483 (0.7); 0.0374 (23.1); 0.0265 (0.9)
I-124: $^{1}$H-NMR(300.2 MHz, CDCl3):
δ = 8.2941 (5.2); 7.2988 (12.0); 7.1462 (0.9); 7.1198 (2.0); 7.0933 (1.5); 7.0334 (2.8); 7.0245 (1.5); 7.0179 (1.1); 7.0078 (3.7); 6.9800 (0.7); 6.9739 (0.9); 6.9137 (3.1); 6.8768 (1.0); 6.8719 (1.0); 6.8504 (1.8); 6.8285 (0.9); 6.7192 (1.4); 6.6936 (1.2); 6.2021 (1.7); 5.9711 (0.6); 5.9664 (0.8); 5.9493 (0.7); 5.9448 (0.8); 5.8129 (0.7); 5.8082 (0.8); 5.7911 (0.7); 5.7865 (0.8); 4.3115 (1.0); 4.3028 (1.4); 4.2774 (1.5); 4.2686 (1.2); 3.9238 (0.7); 3.9182 (0.8); 3.9030 (0.8); 3.8957 (0.8); 3.8815 (2.8); 3.8619 (0.7); 3.8478 (1.9); 3.8273 (1.1); 3.0557 (0.8); 3.0409 (0.8); 3.0115 (1.3); 2.9950 (1.2); 2.8049 (1.0); 2.7774 (0.9); 2.7636 (0.8); 2.7324 (0.7); 2.7272 (0.6); 2.3405 (0.5); 2.3172 (16.0); 2.1830 (14.9); 2.1570 (0.8); 2.1453 (0.8); 2.1288 (1.4); 2.1117 (0.9); 2.1006 (0.8); 2.0832 (0.4); 1.8271 (2.9); 1.8169 (2.6); 1.8054 (3.1); 1.7952 (2.6); 1.7460 (3.0); 1.7358 (2.7); 1.7243 (3.0); 1.7141 (2.5); 1.5931 (6.1); 1.3463 (0.4); 1.3062 (2.2); 1.1031 (0.9); 1.0886 (1.9); 1.0831 (2.5); 1.0783 (1.6); 1.0700 (1.6); 1.0611 (2.1); 1.0548 (2.4); 1.0418 (1.3); 0.9431 (0.8); 0.9213 (2.2); 0.8978 (0.9); 0.8414 (1.2); 0.8255 (2.7); 0.8185 (2.5); 0.8101 (2.8); 0.8030 (1.8); 0.7926 (1.0); 0.1093 (0.9); 0.0499 (0.6); 0.0392 (14.8); 0.0284 (0.7)
I-125: $^{1}$H-NMR(300.2 MHz, CDCl3):
δ = 8.2886 (5.6); 8.2800 (1.7); 7.3647 (1.2); 7.3384 (2.7); 7.3299 (1.0); 7.3099 (2.5); 7.3003 (7.9); 7.2983 (8.8); 7.2901 (2.9); 7.0332 (2.2); 7.0088 (4.3); 6.9835 (3.1); 6.9323 (3.4); 6.8694 (1.9); 6.8427 (1.7); 6.8031 (3.3); 6.7164 (1.7); 6.6914 (1.5); 6.2739 (2.4); 5.9688 (0.8); 5.9473 (0.8); 5.9256 (0.4); 5.8103 (0.8); 5.7888 (0.8); 5.7684 (0.3); 4.2968 (1.2); 4.2882 (1.7); 4.2632 (1.8); 4.2541 (1.6); 3.8966 (1.1); 3.8815 (1.3); 3.8620 (3.0); 3.8426 (1.1); 3.8283 (1.9); 3.8195 (0.8); 3.8080 (1.1); 3.0440 (0.9); 3.0316 (1.0); 3.0006 (1.4); 2.9856 (1.4); 2.7746 (1.1); 2.7437 (1.2); 2.7317 (1.2); 2.6984 (0.9); 2.3381 (0.6); 2.3073 (16.0); 2.2262 (14.8); 2.1841 (0.4); 1.9979 (0.4); 1.9805 (0.8); 1.9700 (1.0); 1.9629 (0.9); 1.9529 (1.6); 1.9430 (1.1); 1.9358 (1.2); 1.9255 (1.1); 1.9079 (0.6); 1.8204 (2.8); 1.8107 (3.4); 1.7989 (3.2); 1.7899 (3.3); 1.7806 (1.2); 1.7393 (2.8); 1.7296 (3.4); 1.7178 (3.2); 1.7088 (3.2); 1.6995 (1.2); 1.5957 (7.5); 1.5873 (2.7); 1.3627 (0.4); 1.3021 (2.0); 1.0677 (0.9); 1.0527 (2.9); 1.0454 (3.3); 1.0311 (2.4); 1.0246 (3.3); 1.0176 (3.1); 1.0049 (1.5); 0.9878 (0.6); 0.9705 (0.5); 0.9623 (0.7); 0.9374 (0.9); 0.9214 (1.6); 0.9132 (0.8); 0.8986 (0.7); 0.7784 (1.2); 0.7632 (3.6); 0.7579 (3.7); 0.7484 (3.8); 0.7414 (4.0); 0.7262 (1.3); 0.1092 (0.6); 0.0466 (2.1); 0.0410 (9.5); 0.0391 (10.9); 0.0309 (3.7)
I-126: $^{1}$H-NMR(499.9 MHz, CDCl3):
δ = 7.9136 (5.3); 7.5848 (0.5); 7.5690 (1.7); 7.5563 (4.2); 7.5455 (0.4); 7.5435 (0.4); 7.4563 (2.0); 7.3848 (0.8); 7.3796 (1.4); 7.3753 (1.0); 7.3711 (0.6); 7.3665 (1.0); 7.3621 (0.6); 7.2593 (1.7); 7.1176 (1.9); 7.1023 (2.1); 6.9442 (2.3); 6.8860 (1.3); 6.8708 (1.1); 6.6620 (1.1); 6.6538 (1.1); 4.9467 (0.8); 4.9424 (1.6); 4.9380 (1.5); 4.9336 (1.6); 4.9293 (0.8); 4.7514 (1.7); 4.7277 (2.4); 4.6307 (2.5); 4.6070 (1.7); 4.2059 (1.1); 4.2022 (1.1); 4.1831 (1.2); 4.1794 (1.2); 3.7888 (1.5); 3.7844 (1.6); 3.7660 (1.4); 3.7616 (1.3); 2.6508 (16.0); 2.3075 (0.4); 2.2783 (12.1); 2.2558 (11.3); 1.9877 (0.7); −0.0002 (1.7)
I-127: $^{1}$H-NMR(499.9 MHz, CDCl3):
δ = 9.1297 (0.3); 8.1906 (16.0); 7.3232 (8.1); 7.3189 (8.1); 7.3097 (7.2); 7.2939 (4.1); 7.2604 (19.5); 7.1093 (6.1); 7.0930 (7.1); 6.9944 (3.7); 6.9829 (4.4); 6.9791 (3.9); 6.9612 (3.7); 6.9477 (3.9); 6.9256 (3.7); 6.8781 (4.1); 6.8739 (4.2); 6.8618 (3.6); 6.8576 (3.7); 6.8441 (2.8); 6.8407 (3.3); 6.8395 (3.2); 6.8294 (2.5); 6.8280 (2.6); 6.8247 (3.2); 6.8234 (3.0); 6.7913 (4.2); 6.7876 (6.0); 6.7836 (3.9); 6.2600 (3.1); 6.2560 (3.2); 6.2016 (6.3); 6.1660 (5.8); 5.6193 (6.3); 5.5971 (6.1); 4.1503 (2.6); 4.1439 (3.1); 4.1283 (3.9); 4.1221 (3.6); 4.1135 (1.0); 4.0992 (0.4); 3.9922 (0.4); 3.9856 (0.7); 3.9822 (1.0); 3.9758 (1.7); 3.9662 (1.8); 3.9582 (2.0); 3.9520 (1.3); 3.9481 (1.2); 3.9418 (0.7); 3.9087 (3.7); 3.8990 (2.8); 3.8869 (3.2); 3.8772 (2.6); 3.1437 (2.4); 3.1335

TABLE 2-continued (2.5); 3.1167 (3.1); 3.1064 (3.1); 2.9380 (3.0); 2.9199 (3.0); 2.9110 (2.6); 2.8928 (2.4); 2.0433 (3.4); 1.9451 (0.7); 1.9349 (1.5); 1.9282 (1.7); 1.9252 (1.2); 1.9181 (3.1); 1.9111 (1.3); 1.9081 (1.8); 1.9014 (1.8); 1.8912 (0.9); 1.5724 (3.2); 1.2727 (0.9); 1.2584 (1.8); 1.2441 (0.9); 1.0129 (2.0); 1.0036 (5.0); 1.0000 (5.6); 0.9963 (3.2); 0.9910 (3.1); 0.9868 (5.5); 0.9832 (5.4); 0.9743 (2.6); 0.9608 (0.4); 0.8817 (0.3); 0.7311 (2.4); 0.7218 (6.3); 0.7186 (5.7); 0.7120 (5.7); 0.7088 (6.8); 0.6992 (2.3); 0.0063 (0.7); −0.0002 (22.9); −0.0066 (1.5)
I-128: $^{1}$H-NMR(300.2 MHz, CDCl3):
δ = 8.6747 (2.1); 8.6171 (1.6); 8.6089 (1.7); 7.7456 (1.7); 7.2991 (10.6); 7.0350 (3.5); 7.0097 (2.7); 6.9725 (1.6); 6.9676 (1.7); 6.9395 (0.7); 6.7883 (2.3); 6.6029 (1.1); 4.8018 (1.4); 4.2199 (1.2); 4.1939 (1.4); 4.1759 (0.5); 4.0996 (0.6); 3.9909 (0.3); 3.9623 (2.0); 3.9457 (0.6); 3.9351 (1.6); 3.9183 (0.6); 3.0505 (0.5); 3.0340 (0.6); 3.0044 (1.0); 2.9875 (0.9); 2.9215 (0.9); 2.8928 (0.9); 2.8762 (0.5); 2.8462 (0.5); 2.5663 (16.0); 2.5332 (0.5); 2.3702 (0.5); 2.3591 (0.6); 2.3234 (13.9); 2.3194 (13.8); 1.6045 (5.9); 0.1074 (0.6); 0.0483 (0.4); 0.0375 (12.9); 0.0268 (0.6)
I-129: $^{1}$H-NMR(300.2 MHz, CDCl3):
δ = 7.9701 (4.1); 7.3609 (2.5); 7.3535 (2.1); 7.3366 (1.9); 7.3103 (1.2); 7.2984 (6.5); 7.1470 (1.6); 7.1197 (2.0); 7.0199 (1.0); 6.9940 (0.9); 6.9145 (1.3); 6.9073 (1.3); 6.8872 (1.1); 6.8802 (1.7); 6.8725 (1.0); 6.8696 (0.9); 6.8538 (0.6); 6.8506 (0.6); 6.8458 (0.9); 6.8429 (0.8); 6.8234 (1.2); 6.8174 (1.6); 6.8104 (0.8); 6.3166 (0.8); 6.3096 (0.8); 4.1841 (0.6); 4.1739 (0.8); 4.1483 (0.9); 4.1382 (1.0); 4.0086 (0.4); 3.9916 (0.5); 3.9793 (0.5); 3.9626 (0.3); 3.9420 (1.2); 3.9260 (0.6); 3.9063 (0.8); 3.8904 (0.6); 3.1874 (0.6); 3.1708 (0.6); 3.1426 (0.9); 3.1257 (0.8); 3.0214 (0.9); 2.9960 (2.8); 2.9773 (1.1); 2.9707 (3.0); 2.9460 (1.5); 2.9329 (0.7); 2.9030 (0.6); 2.0428 (16.0); 1.9768 (0.4); 1.9660 (0.5); 1.9494 (0.8); 1.9325 (0.5); 1.9213 (0.5); 1.3963 (3.3); 1.3710 (7.0); 1.3456 (3.2); 1.2909 (0.4); 1.0579 (0.6); 1.0429 (1.4); 1.0359 (1.6); 1.0301 (0.8); 1.0211 (0.9); 1.0145 (1.5); 1.0079 (1.4); 0.9932 (0.8); 0.7742 (0.7); 0.7591 (1.8); 0.7533 (1.5); 0.7426 (1.5); 0.7371 (1.8); 0.7207 (0.6); 0.1060 (0.6); 0.0357 (7.8)
I-130: $^{1}$H-NMR(499.9 MHz, CDCl3):
δ = 7.9135 (5.2); 7.2597 (3.9); 7.0779 (1.0); 7.0622 (2.2); 7.0465 (1.5); 6.9825 (2.6); 6.9675 (3.2); 6.9584 (2.2); 6.9438 (1.1); 6.8703 (3.3); 6.8074 (1.2); 6.7938 (1.9); 6.7801 (1.1); 6.6686 (1.9); 6.6537 (1.7); 6.2127 (2.3); 4.2361 (1.3); 4.2300 (1.4); 4.2148 (1.5); 4.2087 (1.5); 3.8584 (1.1); 3.8510 (1.2); 3.8126 (1.9); 3.8003 (1.2); 3.7913 (1.6); 3.7790 (1.2); 2.9876 (1.1); 2.9776 (1.2); 2.9604 (1.4); 2.9503 (1.4); 2.7468 (1.4); 2.7279 (1.5); 2.7198 (1.3); 2.7007 (1.2); 2.6263 (16.0); 2.2710 (14.1); 2.1441 (13.7); 2.1031 (0.6); 2.0925 (0.9); 2.0858 (1.0); 2.0758 (1.5); 2.0659 (1.0); 2.0592 (0.9); 2.0487 (0.5); 1.5911 (4.8); 1.0239 (2.6); 1.0176 (2.4); 1.0097 (2.5); 1.0071 (2.5); 0.7824 (1.8); 0.7715 (2.9); 0.7681 (3.0); −0.0002 (4.5)
I-131: $^{1}$H-NMR(300.2 MHz, CDCl3):
δ = 7.9635 (5.2); 7.6147 (2.1); 7.6093 (1.5); 7.6003 (3.3); 7.5973 (3.8); 7.4300 (1.8); 7.3869 (0.8); 7.3740 (2.9); 7.3672 (1.1); 7.3570 (0.8); 7.3486 (2.7); 7.2987 (2.4); 7.0316 (1.9); 6.8036 (1.0); 6.8009 (1.0); 6.7775 (0.9); 6.7749 (0.9); 6.5811 (1.3); 4.9614 (0.7); 4.9544 (0.7); 4.9486 (0.9); 4.9410 (1.4); 4.9334 (0.9); 4.9276 (0.8); 4.9206 (0.7); 4.4547 (1.0); 4.4422 (1.0); 4.4173 (1.2); 4.4047 (1.1); 3.9154 (1.4); 3.8943 (1.3); 3.8778 (1.2); 3.8568 (1.2); 2.6863 (16.0); 2.4418 (11.7); 2.2473 (11.2); 1.6627 (1.4); 1.3028 (0.5); 0.9177 (0.5); 0.0362 (2.5)
I-132: $^{1}$H-NMR(300.2 MHz, CDCl3):
δ = 7.9377 (5.2); 7.6040 (2.6); 7.5866 (3.7); 7.3405 (1.8); 7.2988 (10.9); 7.2658 (0.8); 7.2570 (0.8); 7.2513 (1.2); 7.2448 (1.2); 7.2332 (6.9); 7.2271 (7.3); 7.0920 (1.7); 7.0860 (2.9); 7.0800 (1.4); 5.9166 (1.2); 5.3367 (1.8); 4.2371 (0.8); 4.2250 (0.8); 4.1998 (1.1); 4.1899 (1.1); 4.1701 (1.3); 4.1463 (1.3); 4.1230 (0.9); 4.1014 (1.1); 4.0791 (0.6); 3.9664 (1.1); 3.9465 (1.5); 3.9296 (0.7); 3.9097 (1.4); 3.8695 (0.8); 3.8617 (1.0); 3.8580 (1.0); 3.8500 (1.2); 3.8423 (0.7); 3.8300 (0.5); 2.6726 (16.0); 2.0817 (9.3); 2.0433 (1.3); 1.9121 (0.3); 1.8875 (0.3); 1.6706 (0.4); 1.6470 (0.5); 1.6340 (1.2); 1.6074 (2.6); 1.4561 (0.4); 1.4322 (11.7); 1.4202 (10.8); 1.3812 (0.7); 1.3565 (0.4); 1.3198 (1.9); 1.2960 (4.2); 1.2722 (1.7); 1.2222 (0.4); 1.1985 (0.4); 0.9966 (0.9); 0.9801 (0.4); 0.9722 (1.8); 0.9578 (0.3); 0.9478 (0.8); 0.9172 (0.4); 0.1134 (0.8); 0.1066 (4.1); 0.0476 (0.4); 0.0367 (12.4); 0.0259 (0.6)
I-133: $^{1}$H-NMR(300.2 MHz, CDCl3):
δ = 7.9636 (5.1); 7.6466 (0.3); 7.6208 (1.4); 7.5987 (4.1); 7.5771 (0.4); 7.5151 (1.9); 7.4524 (0.8); 7.4438 (1.3); 7.4365 (0.8); 7.4289 (0.5); 7.4222 (0.8); 7.4142 (0.5); 7.2986 (13.7); 7.2668 (3.2); 7.2605 (1.2); 7.2452 (1.4); 7.2388 (4.6); 7.1113 (4.0); 7.0833 (2.8); 6.1074 (1.1); 6.0984 (1.1); 5.3374 (1.4); 4.1705 (0.5); 4.1467 (0.5); 4.1244 (1.2); 4.1135 (1.1); 4.1017 (0.4); 4.0883 (1.3); 4.0771 (1.4); 3.8777 (1.2); 3.8613 (1.4); 3.8411 (0.9); 3.8245 (1.1); 3.6814 (0.5); 3.6701 (0.7); 3.6589 (0.6); 3.6543 (0.7); 3.6427 (0.5); 2.7870 (0.8); 2.7623 (1.6); 2.7406 (1.8); 2.7040 (16.0); 2.0826 (3.3); 2.0183 (1.1); 1.9930 (2.3); 1.9692 (2.4); 1.9437 (0.9); 1.5976 (5.2); 1.3205 (0.7); 1.2967 (1.6); 1.2730 (0.6); 0.9728 (0.5); 0.1071 (4.2); 0.0481 (0.6); 0.0373 (17.0); 0.0264 (0.8)
I-134: $^{1}$H-NMR(300.2 MHz, CDCl3):
δ = 8.0243 (5.4); 7.6547 (2.9); 7.6476 (3.2); 7.6166 (1.5); 7.5945 (4.4); 7.5726 (0.4); 7.5272 (2.2); 7.5187 (2.6); 7.4903 (3.8); 7.4651 (0.9); 7.4566 (1.5); 7.4491 (1.0); 7.4306 (2.7); 7.4236 (2.2); 7.4024 (1.2); 7.3952 (1.1); 7.2987 (11.2); 6.7359 (2.3); 5.3373 (2.5); 3.5815 (1.0); 3.5581 (1.1); 3.5528 (1.2); 3.5295 (1.1); 3.5063 (0.4); 3.2517 (1.1); 3.2283 (1.2); 3.2231 (1.1); 3.1997 (1.0); 2.7482 (16.0); 1.5974 (1.0); 1.4621 (11.8); 1.2899 (5.8); 1.2662 (8.2); 1.2429 (3.9); 1.0820 (12.2); 0.9173 (0.4); 0.1073 (1.4); 0.0477 (0.6); 0.0371 (12.4)
I-135: $^{1}$H-NMR(300.2 MHz, CDCl3):
δ = 8.0279 (0.4); 7.9920 (5.2); 7.5683 (0.7); 7.5504 (3.7); 7.5424 (1.5); 7.5291 (1.8); 7.5029 (0.5); 7.4374 (1.8); 7.3626 (0.8); 7.3555 (1.0); 7.3401 (0.8); 7.3328 (1.1); 7.3243 (0.5); 7.2987 (7.4); 7.2884 (0.5); 7.2584 (0.5); 7.2004 (0.4); 7.1889 (4.0); 7.1815 (1.3); 7.1663 (1.4); 7.1588 (4.5); 7.1474 (0.4); 6.9329 (0.4); 6.9028 (0.4); 6.8448 (1.9); 6.7539 (0.5); 6.7425 (4.5); 6.7350 (1.4); 6.7198 (1.2); 6.7124 (3.9); 6.7009 (0.4); 5.3361 (1.0); 4.5252 (0.5); 4.3210 (1.8); 4.2824 (2.2); 4.1508 (1.7); 4.1180 (3.3); 4.0589 (3.2); 4.0261 (1.7); 3.9603 (2.8); 3.9217 (2.4); 3.8713 (0.7); 3.8644 (0.5); 3.8479 (0.8); 3.8410 (1.5); 3.8243 (0.4); 3.8175 (1.8); 3.7932 (1.8); 3.7695 (1.5); 3.7628 (0.8); 3.7461 (0.5); 3.7392 (0.7); 2.7273 (16.0); 1.2923 (1.5); 1.2614 (4.3); 1.2381 (8.6); 1.2147 (4.0); 0.0371 (7.8); 0.0263 (0.3)
I-136: $^{1}$H-NMR(300.2 MHz, CDCl3):
δ = 8.7028 (5.8); 7.4227 (1.1); 7.3963 (2.3); 7.3699 (1.5); 7.3589 (2.4); 7.3518 (2.5); 7.2985 (7.1); 7.1665 (2.0); 7.1392 (2.5); 7.0872 (1.2); 7.0612 (1.1); 6.9322 (1.9); 6.9256 (2.2); 6.9190 (1.2); 6.9050 (1.6); 6.8983 (1.8); 6.8922 (1.0); 6.8575 (1.5); 6.8513 (1.9); 6.8444 (1.1); 6.0984 (1.0); 6.0913 (1.0); 4.2064 (0.8); 4.1965 (1.0); 4.1706 (1.2); 4.1611 (1.2); 4.0327 (0.5); 4.0162 (0.6); 4.0037 (0.6); 3.9944 (0.4); 3.9870 (0.4); 3.9723 (1.5); 3.9567 (0.7); 3.9366 (1.0); 3.9210 (0.7); 3.2038 (0.7); 3.1872 (0.7); 3.1590 (1.1); 3.1420 (1.0); 3.0096 (1.1); 2.9802 (1.0); 2.9649 (0.8); 2.9350 (0.7); 2.8021 (16.0); 2.0810 (0.5); 2.0064 (0.5); 1.9951 (0.5); 1.9784 (1.0); 1.9617 (0.6); 1.9504 (0.6); 1.5990 (7.1); 1.3436 (0.4); 1.3194 (0.7); 1.3038 (2.3); 1.2962 (2.1); 1.2721

TABLE 2-continued (0.3); 1.0901 (0.7); 1.0749 (1.6); 1.0681 (1.9); 1.0625 (1.0); 1.0531 (1.0); 1.0464 (1.8); 1.0400 (1.7); 1.0252 (0.9); 0.9597 (0.4); 0.9404 (0.8); 0.9187 (2.6); 0.8954 (1.0); 0.7970 (0.8); 0.7816 (2.2); 0.7756 (1.8); 0.7651 (1.8); 0.7595 (2.2); 0.7432 (0.7); 0.1194 (0.4); 0.1073 (10.1); 0.0952 (0.4); 0.0367 (8.3); 0.0259 (0.3)
I-137: $^1$H-NMR(300.2 MHz, CDCl3):
δ = 8.1464 (11.5); 7.3954 (2.6); 7.3691 (6.0); 7.3618 (6.8); 7.3547 (6.7); 7.3428 (3.6); 7.2983 (30.0); 7.1553 (4.8); 7.1281 (6.1); 7.0543 (3.2); 7.0281 (2.8); 6.9471 (0.4); 6.9209 (2.9); 6.9164 (2.8); 6.8958 (4.2); 6.8901 (4.6); 6.8719 (1.9); 6.8688 (1.9); 6.8638 (2.7); 6.8342 (3.8); 6.8282 (5.0); 6.8214 (2.8); 6.2853 (2.5); 5.1330 (0.4); 5.1110 (1.4); 5.0896 (1.8); 5.0726 (1.5); 5.0516 (0.5); 4.2034 (1.9); 4.1936 (2.5); 4.1682 (2.8); 4.1577 (2.9); 4.1467 (1.0); 4.1233 (0.5); 4.1017 (0.4); 4.0509 (0.4); 4.0345 (0.8); 4.0241 (1.4); 4.0077 (1.4); 3.9953 (1.5); 3.9866 (1.0); 3.9784 (1.0); 3.9687 (0.7); 3.9557 (3.3); 3.9396 (1.9); 3.9200 (2.4); 3.9040 (1.7); 3.6352 (1.9); 3.6271 (2.4); 3.6190 (2.1); 3.6107 (2.1); 3.1997 (1.8); 3.1830 (1.8); 3.1548 (2.8); 3.1380 (2.6); 2.9898 (2.5); 2.9601 (2.3); 2.9453 (1.8); 2.9151 (1.6); 2.0824 (4.4); 2.0104 (0.6); 1.9936 (1.2); 1.9825 (1.3); 1.9658 (2.5); 1.9490 (1.5); 1.9377 (1.5); 1.9209 (0.8); 1.6697 (0.4); 1.6478 (0.4); 1.6082 (12.6); 1.6040 (16.0); 1.5865 (10.1); 1.5820 (11.1); 1.3203 (1.1); 1.3143 (0.4); 1.2964 (2.4); 1.2726 (1.0); 1.0757 (1.6); 1.0606 (4.1); 1.0538 (4.7); 1.0388 (2.6); 1.0323 (4.6); 1.0258 (4.3); 1.0110 (2.2); 0.9972 (0.7); 0.9726 (0.7); 0.9604 (0.6); 0.9542 (0.4); 0.9481 (0.4); 0.9295 (0.5); 0.7866 (2.0); 0.7714 (5.3); 0.7658 (4.7); 0.7550 (4.5); 0.7495 (5.7); 0.7331 (1.8); 0.1071 (9.4); 0.0477 (1.2); 0.0369 (38.3); 0.0260 (1.5)
I-138: $^1$H-NMR(300.2 MHz, CDCl3):
δ = 7.9565 (5.2); 7.2987 (12.7); 7.1347 (2.4); 7.1194 (0.9); 7.1109 (2.0); 7.0923 (1.9); 7.0850 (2.6); 7.0696 (1.2); 7.0666 (1.2); 7.0198 (1.0); 7.0141 (1.1); 6.9910 (1.4); 6.9693 (0.7); 6.9638 (0.7); 6.9493 (1.5); 6.9238 (1.1); 6.8494 (0.8); 6.8441 (0.8); 6.8233 (1.3); 6.8013 (0.7); 6.7964 (0.6); 6.6059 (1.0); 6.5696 (1.1); 6.5473 (1.2); 6.5109 (1.2); 6.2725 (1.5); 5.6538 (2.0); 5.5952 (1.8); 5.3378 (6.2); 5.2142 (2.0); 5.1778 (1.9); 4.2677 (1.1); 4.2426 (1.3); 4.2340 (0.9); 4.1716 (0.7); 4.1478 (0.7); 3.9336 (0.4); 3.9229 (0.6); 3.9163 (0.7); 3.8862 (2.0); 3.8676 (0.5); 3.8523 (1.4); 3.8325 (0.8); 3.0678 (0.7); 3.0521 (0.6); 3.0227 (1.2); 3.0063 (1.1); 2.8494 (0.9); 2.8182 (0.9); 2.8036 (0.9); 2.7731 (0.7); 2.6697 (16.0); 2.3483 (12.2); 2.1241 (0.5); 2.1128 (0.6); 2.0959 (1.1); 2.0838 (3.6); 2.0680 (0.6); 2.0458 (0.5); 1.5979 (2.8); 1.3213 (1.0); 1.2975 (1.9); 1.2738 (0.8); 1.0724 (0.8); 1.0595 (1.5); 1.0527 (1.9); 1.0444 (1.3); 1.0401 (1.3); 1.0305 (1.5); 1.0244 (1.8); 1.0118 (0.9); 0.8171 (0.9); 0.8117 (1.0); 0.8024 (2.1); 0.7951 (2.0); 0.7864 (2.1); 0.7794 (1.2); 0.7695 (0.7); 0.1074 (3.7); 0.0377 (16.6); 0.0270 (0.8)
I-139: $^1$H-NMR(499.9 MHz, CDCl3):
δ = 7.9215 (5.3); 7.5367 (3.3); 7.5264 (2.9); 7.4475 (1.8); 7.3641 (0.7); 7.3591 (0.8); 7.3535 (1.0); 7.3496 (1.0); 7.3460 (0.6); 7.3409 (0.5); 7.2611 (3.8); 7.2042 (0.4); 7.1972 (4.2); 7.1928 (1.4); 7.1837 (1.3); 7.1792 (4.6); 7.1723 (0.5); 6.7660 (0.4); 6.7591 (4.5); 6.7546 (1.4); 6.7455 (1.3); 6.7410 (4.2); 6.7342 (0.4); 6.5356 (1.1); 5.2961 (1.6); 4.1452 (0.7); 4.1350 (1.3); 4.1312 (1.1); 4.1190 (1.9); 4.1160 (1.8); 4.1125 (1.9); 4.1062 (1.2); 4.0997 (1.0); 4.0925 (0.9); 4.0836 (1.8); 4.0641 (0.9); 4.0588 (0.5); 4.0408 (0.9); 4.0253 (1.1); 4.0117 (0.5); 2.6635 (16.0); −0.0002 (4.8)
I-140: $^1$H-NMR(300.2 MHz, CDCl3):
δ = 8.6825 (1.2); 8.6768 (1.3); 8.6195 (0.9); 8.6144 (1.0); 8.6036 (1.0); 8.5983 (1.0); 7.9766 (3.7); 7.7337 (0.6); 7.7280 (0.8); 7.7204 (0.6); 7.7074 (0.7); 7.7017 (0.8); 7.6997 (0.8); 7.6941 (0.7); 7.3785 (0.8); 7.3760 (0.7); 7.3623 (0.8); 7.3600 (0.8); 7.3521 (0.7); 7.3496 (0.7); 7.3300 (1.5); 7.3242 (1.5); 7.2987 (15.8); 7.2809 (1.3); 7.2549 (1.6); 7.1225 (0.9); 7.1164 (0.8); 7.0967 (0.6); 7.0905 (0.6); 7.0159 (1.4); 7.0086 (1.0); 6.9959 (2.4); 6.9878 (0.9); 6.9804 (1.0); 6.7599 (0.4); 6.7471 (0.5); 6.7388 (0.6); 6.7295 (0.7); 6.7134 (0.4); 6.7061 (0.4); 6.3273 (1.0); 4.3124 (0.4); 4.3038 (0.7); 4.2787 (0.8); 4.2701 (0.5); 4.1943 (0.7); 4.1705 (2.1); 4.1467 (2.1); 4.1234 (1.5); 4.1017 (1.8); 4.0793 (0.9); 3.9767 (0.4); 3.9689 (0.4); 3.9604 (0.4); 3.9468 (1.2); 3.9291 (0.3); 3.9131 (0.9); 3.8943 (0.5); 3.1385 (0.4); 3.1229 (0.4); 3.0931 (0.7); 3.0774 (0.7); 2.9348 (0.6); 2.9029 (0.5); 2.8897 (0.5); 2.8580 (0.4); 2.6726 (11.0); 2.4426 (7.6); 2.0963 (0.6); 2.0829 (16.0); 2.0451 (0.9); 2.0231 (0.3); 2.0119 (0.4); 1.9950 (0.6); 1.9779 (0.4); 1.9669 (0.4); 1.6943 (0.3); 1.6703 (0.8); 1.6615 (0.6); 1.6484 (1.2); 1.6391 (1.0); 1.6269 (0.9); 1.6221 (1.1); 1.5997 (0.6); 1.4562 (0.4); 1.4304 (0.6); 1.4051 (0.6); 1.3809 (0.4); 1.3202 (2.8); 1.2964 (5.6); 1.2726 (2.6); 0.9966 (1.5); 0.9801 (1.4); 0.9720 (3.4); 0.9637 (0.8); 0.9579 (1.2); 0.9537 (1.5); 0.9479 (1.9); 0.9411 (0.7); 0.9357 (0.6); 0.9308 (0.7); 0.9260 (1.0); 0.7187 (0.4); 0.7082 (0.9); 0.7034 (1.3); 0.6975 (1.1); 0.6914 (1.3); 0.6862 (1.2); 0.6807 (1.2); 0.1061 (5.1); 0.0472 (0.6); 0.0364 (18.0); 0.0255 (0.6)
I-141: $^1$H-NMR(300.2 MHz, CDCl3):
δ = 8.2914 (11.6); 7.3869 (3.0); 7.3613 (12.0); 7.3561 (7.7); 7.3343 (3.9); 7.2987 (34.0); 7.1575 (6.4); 7.1303 (7.9); 7.0473 (3.8); 7.0214 (3.4); 6.9474 (0.4); 6.9305 (3.0); 6.9233 (3.0); 6.9172 (2.7); 6.9100 (2.7); 6.9032 (2.8); 6.8958 (5.0); 6.8898 (4.8); 6.8843 (3.6); 6.8684 (2.4); 6.8606 (3.3); 6.8340 (4.8); 6.8279 (6.2); 6.8210 (3.5); 6.2510 (3.2); 6.0024 (0.6); 5.9802 (1.7); 5.9584 (1.7); 5.9366 (0.6); 5.8433 (0.6); 5.8218 (1.8); 5.7999 (1.8); 5.7784 (0.6); 4.2048 (2.5); 4.1948 (3.0); 4.1691 (3.6); 4.1592 (3.8); 4.0541 (0.4); 4.0377 (1.1); 4.0270 (1.7); 4.0106 (1.8); 3.9979 (2.0); 3.9884 (1.3); 3.9813 (1.4); 3.9634 (4.0); 3.9474 (2.0); 3.9278 (2.7); 3.9117 (1.8); 3.2005 (1.8); 3.1842 (1.8); 3.1556 (2.8); 3.1389 (2.6); 2.9965 (2.0); 2.9913 (2.2); 2.9669 (1.9); 2.9618 (2.1); 2.9521 (1.5); 2.9465 (1.6); 2.9217 (1.3); 2.9167 (1.5); 2.8045 (0.8); 2.0065 (0.7); 1.9893 (1.5); 1.9781 (1.7); 1.9613 (3.2); 1.9445 (1.8); 1.9333 (1.8); 1.9166 (0.9); 1.8271 (5.9); 1.8196 (7.0); 1.8053 (6.1); 1.7978 (7.0); 1.7459 (6.2); 1.7385 (7.3); 1.7242 (6.0); 1.7167 (6.8); 1.5968 (16.0); 1.3676 (0.4); 1.3430 (0.9); 1.3039 (5.5); 1.0727 (2.2); 1.0575 (5.2); 1.0508 (6.1); 1.0359 (3.4); 1.0291 (5.8); 1.0227 (5.3); 1.0080 (2.8); 0.9855 (0.6); 0.9595 (0.7); 0.9408 (2.1); 0.9192 (6.4); 0.8960 (2.4); 0.8164 (0.4); 0.7834 (2.7); 0.7681 (6.8); 0.7622 (6.1); 0.7517 (5.8); 0.7460 (7.0); 0.7298 (2.1); 0.1072 (2.1); 0.0480 (1.4); 0.0372 (41.6); 0.0263 (1.7)
I-142: $^1$H-NMR(300.2 MHz, CDCl3):
δ = 7.9508 (1.0); 7.9441 (4.6); 7.2985 (6.3); 7.2411 (2.0); 7.1475 (0.7); 7.1442 (0.7); 7.1208 (1.6); 7.1167 (1.9); 7.0882 (3.3); 7.0613 (1.7); 7.0570 (1.8); 7.0411 (1.1); 7.0355 (1.6); 7.0169 (1.1); 7.0123 (1.3); 6.9906 (0.6); 6.9851 (0.6); 6.8657 (0.6); 6.8603 (0.7); 6.8390 (1.2); 6.8173 (0.6); 6.8123 (0.6); 6.2313 (1.2); 5.3347 (1.8); 4.2339 (0.6); 4.2263 (1.1); 4.2013 (1.1); 4.1929 (0.9); 4.1690 (1.1); 4.1452 (1.0); 4.1225 (1.9); 4.1004 (3.3); 4.0780 (1.7); 3.9383 (0.4); 3.9293 (0.5); 3.9198 (0.6); 3.8994 (1.7); 3.8832 (1.0); 3.8736 (0.4); 3.8660 (1.3); 3.8481 (0.8); 3.0627 (0.6); 3.0465 (0.6); 3.0339 (4.6); 3.0179 (1.2); 3.0012 (1.0); 2.8923 (0.8); 2.8617 (0.9); 2.8470 (0.6); 2.8164 (0.6); 2.6723 (14.1); 2.3492 (1.8); 2.3385 (0.9); 2.3238 (10.3); 2.1563 (0.6); 2.1410 (0.5); 2.1294 (0.6); 2.1212 (0.7); 2.1124 (1.0); 2.0948 (1.3); 2.0815 (16.0); 2.0413 (0.6); 1.6936 (0.4); 1.6691 (1.0); 1.6603 (0.4); 1.6470 (1.3); 1.6382 (0.7); 1.6207 (1.1); 1.5982 (0.5); 1.4794 (0.3); 1.4641 (0.4); 1.4549 (0.8); 1.4455 (0.4); 1.4289 (1.1); 1.4036 (1.2); 1.3798 (0.8); 1.3694 (0.4); 1.3558 (0.5); 1.3396 (0.4); 1.3186 (1.7); 1.2947 (4.3); 1.2710 (1.5); 1.2635 (0.4); 1.2397 (0.4); 1.0796 (0.6); 1.0770 (0.6); 1.0655 (1.7); 1.0586 (2.0); 1.0481 (1.1); 1.0445 (1.0); 1.0366 (1.8); 1.0303 (1.9); 1.0164 (0.8); 1.0095 (0.5); 0.9953 (2.8); 0.9789 (1.0); 0.9709 (5.4); 0.9566 (0.8); 0.9465 (2.2); 0.9156 (0.5); 0.8909 (0.5); 0.8678 (0.5); 0.8306 (0.9); 0.8244

TABLE 2-continued (1.0); 0.8151 (1.9); 0.8078 (2.0); 0.7988 (2.0); 0.7912 (1.3); 0.7822 (0.7); 0.1127 (1.0); 0.1062 (2.8); 0.0355 (7.4); 0.0246 (0.3)
I-143: $^{1}$H-NMR(300.2 MHz, CDCl3):
δ = 8.0094 (5.3); 7.5950 (1.5); 7.5749 (4.2); 7.5723 (3.6); 7.5592 (0.4); 7.5547 (0.4); 7.4835 (2.0); 7.4536 (0.4); 7.4279 (21.0); 7.4067 (1.0); 7.3988 (0.7); 7.2984 (2.4); 6.3373 (1.6); 6.0795 (1.0); 6.0748 (1.3); 5.9068 (0.9); 5.9021 (1.3); 5.8973 (0.9); 5.3335 (2.5); 4.7576 (1.2); 4.7526 (1.2); 4.6921 (1.2); 4.6870 (1.2); 2.7327 (16.0); 2.0729 (0.6); 1.2919 (0.7); 0.1096 (1.1); 0.0362 (3.0)
I-144: $^{1}$H-NMR(499.9 MHz, CDCl3):
δ = 7.9500 (5.0); 7.5200 (6.9); 7.4341 (4.4); 7.3359 (2.8); 7.2584 (4.2); 6.9615 (0.4); 6.9468 (0.5); 6.9150 (2.7); 6.8972 (6.3); 6.6860 (3.0); 6.6707 (2.7); 6.6113 (0.6); 6.5725 (3.3); 5.2952 (1.8); 4.1339 (6.8); 4.1179 (7.2); 4.0341 (1.7); 4.0153 (2.9); 2.7247 (0.4); 2.6630 (16.0); 2.2822 (1.4); 2.2344 (14.6); 2.1731 (0.8); 2.0322 (14.5); 1.6016 (0.4); 1.2559 (0.6); −0.0002 (4.9)
I-145: $^{1}$H-NMR(499.9 MHz, CDCl3):
δ = 7.5306 (0.6); 7.5151 (1.6); 7.4996 (1.8); 7.4919 (2.0); 7.4762 (0.7); 7.4076 (2.0); 7.3601 (1.2); 7.3447 (1.0); 7.2592 (4.1); 6.9892 (2.6); 6.9854 (2.4); 6.9750 (2.4); 6.9003 (1.3); 6.8849 (1.0); 4.7171 (1.4); 4.1491 (0.6); 4.1435 (1.1); 4.1281 (1.3); 4.1228 (0.9); 3.9091 (0.4); 3.9032 (0.6); 3.8979 (0.6); 3.8920 (0.7); 3.8858 (0.9); 3.8812 (1.8); 3.8606 (1.3); 3.8503 (0.8); 2.9734 (0.5); 2.9631 (0.6); 2.9459 (1.0); 2.9353 (1.0); 2.8527 (0.8); 2.8349 (0.9); 2.8250 (0.8); 2.8072 (0.7); 2.5795 (14.3); 2.5470 (0.3); 2.3914 (14.2); 2.2747 (16.0); 2.2196 (0.4); 2.2012 (0.4); 1.5881 (0.4); 0.0710 (3.5); −0.0002 (4.8); −0.0066 (0.4)
I-146: $^{1}$H-NMR(499.9 MHz, CDCl3):
δ = 7.5302 (0.5); 7.5147 (1.4); 7.4991 (1.6); 7.4916 (1.9); 7.4760 (0.6); 7.4079 (1.8); 7.3599 (1.1); 7.3446 (0.9); 7.2591 (2.8); 6.9888 (2.4); 6.9853 (2.3); 6.9748 (2.1); 6.9001 (1.2); 6.8847 (0.9); 4.7263 (1.4); 4.1475 (0.6); 4.1421 (1.0); 4.1266 (1.2); 4.1214 (0.8); 3.9082 (0.4); 3.9022 (0.6); 3.8970 (0.6); 3.8912 (0.7); 3.8805 (1.7); 3.8601 (1.1); 3.8498 (0.7); 2.9728 (0.5); 2.9626 (0.5); 2.9453 (1.0); 2.9348 (0.9); 2.8531 (0.8); 2.8352 (0.8); 2.8253 (0.7); 2.8077 (0.6); 2.5787 (12.1); 2.3909 (12.0); 2.2748 (16.0); 1.5934 (1.1); −0.0002 (3.3)
I-147: $^{1}$H-NMR(300.2 MHz, CDCl3):
δ = 8.1266 (16.0); 7.3610 (6.9); 7.3540 (7.4); 7.2986 (28.3); 7.1781 (6.5); 7.1505 (9.8); 7.1224 (2.9); 7.1187 (3.2); 7.0710 (2.4); 7.0653 (2.9); 7.0470 (2.7); 7.0425 (3.5); 7.0205 (1.6); 7.0150 (1.6); 6.9503 (4.3); 6.9432 (4.2); 6.9231 (3.4); 6.9160 (3.4); 6.9038 (2.1); 6.8984 (2.0); 6.8770 (3.3); 6.8553 (1.7); 6.8499 (1.6); 6.1439 (3.0); 5.3379 (0.6); 4.2090 (2.4); 4.1989 (2.9); 4.1732 (3.4); 4.1632 (3.8); 4.0718 (0.4); 4.0555 (1.0); 4.0451 (1.6); 4.0293 (1.8); 4.0154 (1.8); 4.0068 (1.2); 3.9990 (1.2); 3.9893 (0.8); 3.9789 (4.3); 3.9634 (2.4); 3.9432 (3.0); 3.9276 (2.2); 3.2102 (2.2); 3.1937 (2.2); 3.1654 (3.4); 3.1487 (3.2); 3.0043 (3.3); 2.9744 (3.2); 2.9595 (2.4); 2.9291 (2.2); 2.1590 (0.6); 2.1417 (1.2); 2.1306 (1.4); 2.1136 (2.5); 2.0962 (1.5); 2.0845 (1.7); 2.0677 (0.7); 1.5879 (12.6); 1.2976 (0.8); 1.1100 (1.2); 1.1069 (1.2); 1.0953 (4.1); 1.0891 (4.8); 1.0785 (2.8); 1.0746 (2.2); 1.0670 (4.4); 1.0608 (4.5); 1.0499 (1.7); 1.0469 (1.6); 0.9194 (0.6); 0.8969 (0.5); 0.8420 (2.5); 0.8355 (2.3); 0.8267 (5.1); 0.8192 (5.0); 0.8101 (5.8); 0.8028 (3.3); 0.7932 (1.9); 0.7711 (0.4); 0.0485 (1.2); 0.0375 (35.8); 0.0271 (1.5)
I-148: $^{1}$H-NMR(300.2 MHz, CDCl3):
δ = 8.6134 (4.6); 8.5969 (3.1); 8.5803 (2.8); 8.3197 (7.6); 8.2906 (0.3); 7.6531 (4.4); 7.6361 (4.6); 7.4188 (2.7); 7.3985 (3.0); 7.3817 (3.0); 7.3716 (1.2); 7.3631 (1.2); 7.3546 (1.6); 7.3486 (1.3); 7.3411 (1.0); 7.3329 (0.8); 7.2983 (6.2); 7.0579 (0.4); 7.0214 (2.4); 6.9959 (2.8); 6.9299 (3.1); 6.7168 (1.7); 6.6923 (1.4); 6.2299 (2.2); 4.3686 (1.2); 4.3583 (1.3); 4.3333 (1.4); 4.3228 (1.5); 4.2424 (0.5); 4.1686 (1.0); 4.1448 (1.0); 4.1213 (0.5); 3.9694 (0.6); 3.9551 (0.8); 3.9368 (0.8); 3.9253 (0.7); 3.9208 (0.7); 3.8874 (2.1); 3.8661 (1.1); 3.8521 (1.7); 3.8307 (1.1); 3.0843 (1.0); 3.0696 (1.0); 3.0388 (1.3); 3.0238 (1.2); 2.7768 (1.4); 2.7436 (1.4); 2.7315 (1.2); 2.6979 (1.0); 2.4409 (16.0); 2.3600 (0.8); 2.3378 (1.0); 2.3159 (15.2); 2.1936 (14.2); 2.1050 (0.9); 2.0807 (5.0); 1.6993 (0.5); 1.3186 (1.1); 1.2948 (2.3); 1.2710 (1.1); 0.9711 (0.4); 0.1075 (0.4); 0.0358 (6.8)
I-149: $^{1}$H-NMR(300.2 MHz, CDCl3):
δ = 8.7500 (6.2); 8.4871 (4.3); 8.4181 (2.7); 8.4018 (2.8); 7.8519 (2.5); 7.8357 (2.4); 7.6405 (3.2); 7.6232 (3.4); 7.4022 (1.8); 7.3547 (0.7); 7.3459 (0.7); 7.3379 (1.1); 7.3319 (0.9); 7.3243 (0.7); 7.3162 (0.5); 7.2983 (5.5); 7.0230 (1.8); 6.9975 (2.1); 6.9320 (2.1); 6.7300 (1.2); 6.7051 (1.0); 6.1511 (1.5); 4.3642 (0.8); 4.3539 (0.9); 4.3291 (1.0); 4.3187 (1.0); 4.1687 (0.6); 4.1448 (0.6); 4.0491 (16.0); 3.9724 (0.4); 3.9600 (0.5); 3.9392 (0.6); 3.9254 (1.1); 3.9084 (0.3); 3.8959 (1.6); 3.8746 (0.8); 3.8607 (1.3); 3.8395 (0.8); 3.0783 (0.7); 3.0637 (0.7); 3.0330 (1.0); 3.0178 (0.9); 2.7866 (1.0); 2.7538 (1.0); 2.7412 (0.8); 2.7081 (0.7); 2.3399 (0.4); 2.3152 (11.2); 2.1984 (10.4); 2.0808 (3.1); 1.6921 (0.4); 1.3187 (0.7); 1.2949 (1.5); 1.2710 (0.7); 0.1076 (0.4); 0.0360 (6.1)
I-150: $^{1}$H-NMR(300.2 MHz, CDCl3):
δ = 8.7825 (4.1); 8.7771 (2.6); 8.7676 (2.7); 8.7623 (4.2); 7.4856 (4.4); 7.4802 (2.8); 7.4708 (2.8); 7.4654 (4.3); 7.2985 (11.6); 7.1942 (0.4); 7.1874 (0.5); 7.1671 (1.4); 7.1604 (1.3); 7.1503 (3.5); 7.1390 (1.4); 7.1282 (2.1); 7.1007 (0.7); 7.0879 (1.7); 7.0623 (2.4); 7.0250 (2.3); 6.9585 (1.4); 6.9323 (1.0); 6.8642 (0.8); 6.8577 (0.8); 6.8409 (1.1); 6.8322 (1.1); 6.8215 (0.6); 6.8104 (0.6); 4.8753 (1.6); 4.2537 (0.6); 4.2452 (1.4); 4.2196 (1.3); 4.2110 (0.8); 4.1939 (0.4); 4.1701 (1.0); 4.1463 (1.0); 4.1226 (0.4); 3.9990 (0.4); 3.9889 (0.6); 3.9799 (0.6); 3.9702 (0.8); 3.9544 (1.8); 3.9209 (1.2); 3.9028 (0.7); 3.0597 (0.5); 3.0428 (0.5); 3.0137 (1.1); 2.9960 (1.0); 2.9256 (0.9); 2.8959 (0.9); 2.8793 (0.6); 2.8503 (0.6); 2.5007 (16.0); 2.3340 (11.8); 2.3151 (11.2); 2.1464 (0.6); 2.1356 (0.6); 2.1185 (1.0); 2.1012 (0.7); 2.0822 (4.6); 1.6283 (2.1); 1.3203 (1.2); 1.2965 (2.4); 1.2727 (1.2); 1.0862 (0.6); 1.0714 (1.8); 1.0644 (2.1); 1.0500 (1.0); 1.0427 (1.9); 1.0361 (2.0); 1.0221 (0.7); 0.8338 (0.8); 0.8191 (2.3); 0.8139 (2.3); 0.8019 (2.2); 0.7963 (2.2); 0.7805 (0.6); 0.1073 (0.9); 0.0479 (0.7); 0.0372 (14.0); 0.0263 (0.6)
I-151: $^{1}$H-NMR(499.9 MHz, CDCl3):
δ = 8.1189 (16.0); 7.6061 (9.8); 7.5959 (8.2); 7.5791 (0.9); 7.3657 (5.3); 7.2964 (7.3); 7.2923 (7.7); 7.2809 (0.7); 7.2726 (2.2); 7.2671 (2.9); 7.2605 (19.7); 7.2497 (2.3); 7.1243 (6.1); 7.1079 (7.4); 6.9526 (4.3); 6.9484 (4.5); 6.9363 (3.7); 6.9321 (3.8); 6.0300 (3.4); 4.1553 (2.8); 4.1491 (3.3); 4.1335 (3.6); 4.1272 (3.9); 4.0208 (0.4); 4.0142 (0.9); 4.0106 (1.1); 4.0042 (1.9); 3.9943 (2.0); 3.9869 (2.1); 3.9808 (1.4); 3.9765 (1.3); 3.9703 (0.7); 3.9265 (3.9); 3.9169 (3.1); 3.9046 (3.3); 3.8951 (2.8); 3.1355 (2.4); 3.1250 (2.5); 3.1084 (3.5); 3.0978 (3.4); 2.9774 (3.4); 2.9593 (3.4); 2.9503 (2.7); 2.9321 (2.5); 2.6072 (0.4); 1.5517 (6.0); 1.2553 (0.8); 0.0060 (0.9); −0.0002 (19.7); −0.0064 (1.5)
I-152: $^{1}$H-NMR(499.9 MHz, CDCl3):
δ = 8.1188 (16.0); 7.6063 (9.7); 7.5986 (4.9); 7.5960 (7.2); 7.5788 (0.5); 7.3667 (4.9); 7.2965 (7.4); 7.2923 (7.2); 7.2725 (2.6); 7.2670 (3.4); 7.2606 (19.6); 7.2496 (1.5); 7.1243 (5.9); 7.1079 (6.8); 6.9527 (4.4); 6.9485 (4.3); 6.9364 (3.6); 6.9322 (3.4); 6.0339 (3.2); 4.1552 (2.9); 4.1489 (3.1); 4.1334 (3.5); 4.1271 (3.4); 4.0207 (0.6); 4.0143 (1.0); 4.0107 (1.3); 4.0042 (1.9); 3.9944 (1.9); 3.9868 (1.9); 3.9825 (1.1); 3.9806 (1.1); 3.9765

TABLE 2-continued (1.0); 3.9701 (0.5); 3.9265 (3.8); 3.9169 (3.0); 3.9045 (3.1); 3.8950 (2.4); 3.4879 (0.6); 3.1355 (2.4); 3.1249 (2.4); 3.1083 (3.3); 3.0978 (3.0); 2.9775 (3.3); 2.9593 (3.3); 2.9504 (2.5); 2.9322 (2.3); 2.6073 (0.7); 1.5530 (5.2); 1.2553 (0.6); 0.0062 (1.6); −0.0002 (19.8); −0.0067 (0.8)
I-153: $^1$H-NMR(300.2 MHz, CDCl3):
δ = 8.1653 (3.3); 8.1409 (3.5); 7.2983 (38.6); 7.2320 (0.6); 7.2158 (0.9); 7.2059 (1.1); 7.1892 (1.2); 7.1786 (1.5); 7.1553 (1.7); 7.1296 (1.0); 7.1048 (0.7); 7.0998 (0.5); 7.0784 (0.3); 7.0140 (1.2); 6.9839 (1.4); 6.9217 (1.1); 6.8903 (1.1); 6.7110 (0.6); 6.6867 (1.0); 6.6651 (0.6); 6.1834 (0.7); 6.1180 (0.7); 4.3248 (0.4); 4.3151 (0.8); 4.3045 (0.6); 4.2908 (0.6); 4.2800 (1.0); 4.2697 (0.5); 3.9084 (0.6); 3.8933 (0.6); 3.8697 (1.7); 3.8469 (0.4); 3.8368 (1.0); 3.8163 (0.5); 3.0525 (0.5); 3.0142 (0.6); 3.0078 (0.7); 2.9995 (0.6); 2.9917 (0.6); 2.9070 (0.6); 2.8940 (0.5); 2.8819 (0.4); 2.8666 (0.6); 2.7792 (0.6); 2.7544 (0.6); 2.7404 (0.6); 2.7094 (0.4); 2.7016 (0.5); 2.3385 (0.4); 2.3086 (10.6); 2.1787 (5.6); 2.1461 (5.6); 2.0392 (0.3); 2.0220 (0.4); 2.0127 (0.4); 2.0000 (0.6); 1.9825 (0.6); 1.9731 (0.8); 1.9557 (0.8); 1.9432 (0.4); 1.9339 (0.4); 1.9168 (0.4); 1.7648 (0.4); 1.7572 (0.4); 1.7518 (0.5); 1.7444 (0.6); 1.7377 (0.4); 1.7296 (0.4); 1.7235 (0.5); 1.7159 (0.5); 1.7026 (0.4); 1.5781 (16.0); 1.2983 (0.9); 0.9416 (0.3); 0.9202 (1.0); 0.8969 (0.4); 0.0487 (1.8); 0.0379 (50.8); 0.0270 (1.9)
I-154: $^1$H-NMR(300.2 MHz, CDCl3):
δ = 8.0367 (4.6); 7.5989 (1.5); 7.5797 (3.8); 7.4870 (1.9); 7.4537 (0.8); 7.4427 (1.4); 7.4319 (3.0); 7.4032 (2.8); 7.2983 (10.6); 6.9827 (3.7); 6.9535 (3.2); 6.5887 (1.0); 4.9199 (0.9); 4.8869 (0.9); 3.9353 (0.5); 3.8517 (16.0); 2.7829 (0.8); 2.7547 (14.0); 2.6993 (0.4); 1.3221 (0.5); 1.2933 (1.1); 0.8898 (0.4); 0.8730 (0.4); 0.1076 (2.6); 0.0480 (0.6); 0.0375 (12.9); 0.0266 (0.6)
I-155: $^1$H-NMR(300.2 MHz, CDCl3):
δ = 7.9810 (2.8); 7.9566 (2.8); 7.2986 (19.6); 7.2114 (0.7); 7.1942 (0.6); 7.1862 (2.0); 7.1788 (1.0); 7.1669 (1.3); 7.1586 (0.8); 7.1499 (0.6); 7.1377 (1.6); 7.1293 (0.9); 7.1192 (1.3); 7.1148 (1.3); 7.1066 (0.6); 7.0901 (0.5); 7.0237 (1.2); 6.9982 (1.4); 6.9244 (1.1); 6.8946 (1.1); 6.7220 (0.6); 6.6985 (1.0); 6.6775 (0.5); 6.2293 (0.7); 6.1603 (0.7); 4.2987 (0.5); 4.2905 (0.9); 4.2828 (0.6); 4.2640 (0.6); 4.2558 (1.0); 4.2479 (0.6); 3.9088 (0.5); 3.8935 (0.6); 3.8674 (1.8); 3.8469 (0.5); 3.8346 (1.1); 3.8142 (0.6); 3.0483 (0.4); 3.0408 (0.5); 3.0337 (0.4); 3.0264 (0.4); 3.0042 (0.6); 2.9969 (0.7); 2.9879 (0.6); 2.9803 (0.6); 2.9011 (0.6); 2.8896 (0.4); 2.8740 (0.4); 2.8611 (0.6); 2.7966 (0.7); 2.7708 (0.7); 2.7660 (0.6); 2.7566 (0.6); 2.7515 (0.6); 2.7261 (0.6); 2.7203 (0.5); 2.6709 (16.0); 2.3101 (11.2); 2.1872 (5.6); 2.1560 (5.6); 2.0840 (0.8); 2.0196 (0.3); 2.0022 (0.4); 1.9929 (0.4); 1.9798 (0.7); 1.9758 (0.6); 1.9627 (0.7); 1.9533 (0.8); 1.9362 (0.8); 1.9233 (0.4); 1.9139 (0.4); 1.8967 (0.4); 1.7537 (0.4); 1.7471 (0.4); 1.7403 (0.5); 1.7337 (0.5); 1.7260 (0.4); 1.7193 (0.4); 1.7115 (0.5); 1.7052 (0.5); 1.6986 (0.4); 1.6919 (0.4); 1.5911 (8.7); 1.3217 (0.4); 1.2979 (0.9); 0.9202 (0.6); 0.0488 (0.9); 0.0380 (25.2); 0.0289 (0.7); 0.0272 (0.9)
I-156: $^1$H-NMR(499.9 MHz, CDCl3):
δ = 8.0662 (16.0); 7.6775 (0.3); 7.5574 (0.9); 7.5470 (10.9); 7.5344 (4.9); 7.5187 (1.1); 7.2627 (5.6); 7.2584 (8.8); 7.2297 (2.1); 7.2253 (2.8); 7.2167 (2.6); 7.2122 (3.2); 7.2070 (1.6); 7.2004 (0.3); 7.1965 (0.3); 7.1591 (2.8); 7.1543 (3.8); 7.1472 (5.9); 7.1399 (7.1); 7.1316 (1.7); 7.1226 (2.7); 7.1158 (15.4); 7.1106 (11.3); 7.1070 (5.8); 7.1030 (6.6); 5.8108 (3.9); 3.9784 (0.4); 3.9747 (0.5); 3.9662 (1.2); 3.9568 (1.7); 3.9523 (1.5); 3.9475 (1.8); 3.9383 (1.3); 3.9299 (0.6); 3.9261 (0.5); 3.3707 (2.7); 3.3632 (2.8); 3.3492 (3.1); 3.3417 (3.0); 3.0213 (2.5); 3.0117 (2.6); 2.9946 (3.0); 2.9849 (2.9); 2.9726 (3.5); 2.9599 (3.4); 2.9510 (3.2); 2.9383 (3.1); 2.7010 (3.1); 2.6816 (3.1); 2.6743 (2.9); 2.6549 (2.8); 2.1657 (0.9); 1.9962 (1.6); −0.0002 (6.1); −0.0064 (0.4)
I-157: $^1$H-NMR(300.2 MHz, CDCl3):
δ = 7.5877 (1.1); 7.5682 (2.8); 7.5649 (2.5); 7.4429 (1.4); 7.4139 (0.6); 7.4039 (0.9); 7.3966 (0.7); 7.3832 (0.6); 7.3764 (0.4); 7.2986 (13.5); 7.0347 (2.6); 7.0092 (1.9); 6.9550 (1.1); 6.9288 (0.6); 4.6804 (1.0); 4.2132 (0.8); 4.1872 (0.9); 4.1697 (0.3); 3.9684 (0.5); 3.9452 (1.3); 3.9147 (1.0); 3.8981 (0.4); 3.0411 (0.4); 3.0247 (0.4); 2.9952 (0.7); 2.9789 (0.7); 2.9067 (0.7); 2.8770 (0.6); 2.8608 (0.4); 2.8301 (0.3); 2.5760 (11.7); 2.5600 (0.9); 2.3191 (16.0); 1.5850 (11.2); 1.3042 (0.8); 1.2975 (0.8); 0.9200 (0.8); 0.8963 (0.3); 0.1074 (0.4); 0.0487 (0.8); 0.0379 (15.9); 0.0271 (0.7)
I-158: $^1$H-NMR(300.2 MHz, CDCl3):
δ = 8.9079 (6.3); 8.9070 (6.2); 8.8864 (0.6); 8.5297 (9.5); 8.5072 (0.8); 8.4290 (6.5); 8.4278 (6.5); 8.2951 (0.6); 7.6427 (5.0); 7.6394 (4.6); 7.6308 (2.4); 7.6254 (3.4); 7.5965 (0.4); 7.3836 (2.6); 7.3378 (1.1); 7.3289 (1.2); 7.3243 (0.9); 7.3192 (1.7); 7.3127 (1.4); 7.3064 (1.2); 7.2987 (14.4); 7.1089 (0.4); 7.0586 (0.7); 7.0153 (2.6); 6.9898 (3.0); 6.9244 (3.0); 6.7060 (1.6); 6.6817 (1.4); 6.2183 (2.1); 4.3836 (1.0); 4.3747 (1.3); 4.3487 (1.4); 4.3395 (1.4); 4.1709 (0.7); 4.1471 (0.7); 3.9700 (0.6); 3.9484 (0.8); 3.9440 (0.7); 3.9371 (0.9); 3.9269 (0.7); 3.9208 (0.8); 3.9030 (2.6); 3.8819 (1.0); 3.8683 (2.0); 3.8469 (1.3); 3.8362 (0.4); 3.0858 (1.0); 3.0718 (1.0); 3.0406 (1.4); 3.0254 (1.3); 2.7771 (1.4); 2.7446 (1.4); 2.7319 (1.2); 2.6988 (1.1); 2.3618 (1.6); 2.3512 (1.0); 2.3387 (2.2); 2.3155 (16.0); 2.2758 (0.4); 2.1828 (14.8); 2.0829 (3.6); 1.6485 (1.3); 1.3206 (1.0); 1.2968 (2.0); 1.2730 (0.9); 0.1082 (0.5); 0.0482 (0.6); 0.0374 (16.4); 0.0265 (0.6)
I-159: $^1$H-NMR(300.2 MHz, CDCl3):
δ = 8.4940 (8.2); 7.7014 (0.5); 7.6819 (5.2); 7.6590 (2.2); 7.6326 (0.7); 7.3703 (2.6); 7.3145 (1.2); 7.3069 (1.7); 7.2987 (7.7); 7.2924 (1.5); 7.2848 (1.7); 7.2774 (0.8); 6.9847 (2.5); 6.9593 (2.9); 6.9157 (3.0); 6.6783 (1.7); 6.6536 (1.4); 6.1265 (2.0); 4.3831 (1.2); 4.3737 (1.3); 4.3477 (1.4); 4.3383 (1.4); 3.9448 (0.6); 3.9293 (0.8); 3.9234 (0.8); 3.9116 (0.8); 3.9007 (0.6); 3.8953 (0.7); 3.8888 (0.6); 3.8805 (0.5); 3.8694 (2.4); 3.8479 (1.1); 3.8342 (1.9); 3.8127 (1.2); 3.0851 (1.0); 3.0706 (1.0); 3.0397 (1.4); 3.0247 (1.3); 2.7366 (1.5); 2.7033 (1.4); 2.6913 (1.2); 2.6575 (1.1); 2.3027 (16.0); 2.1679 (14.8); 1.5940 (1.8); 0.1091 (0.5); 0.0491 (0.4); 0.0385 (8.5); 0.0277 (0.4)
I-160: $^1$H-NMR(499.9 MHz, CDCl3):
δ = 7.9338 (4.8); 7.5181 (0.8); 7.5024 (2.0); 7.4865 (1.3); 7.4227 (1.6); 7.4073 (1.2); 7.2604 (3.1); 7.2056 (2.2); 7.1446 (1.2); 7.1423 (1.2); 7.1284 (1.1); 7.1261 (1.1); 6.9589 (2.1); 6.9436 (2.4); 6.8862 (2.5); 6.7753 (1.2); 6.6850 (1.4); 6.6694 (1.3); 6.6626 (2.7); 6.5497 (1.3); 6.1586 (1.6); 4.2517 (1.1); 4.2452 (1.2); 4.2302 (1.2); 4.2237 (1.2); 3.8719 (0.5); 3.8679 (0.5); 3.8622 (0.7); 3.8584 (0.6); 3.8521 (0.7); 3.8487 (0.6); 3.8451 (0.5); 3.8427 (0.5); 3.8041 (1.7); 3.7915 (1.1); 3.7825 (1.5); 3.7699 (1.1); 2.9866 (0.9); 2.9771 (1.0); 2.9592 (1.1); 2.9498 (1.2); 2.7112 (1.2); 2.6915 (1.2); 2.6839 (1.1); 2.6641 (1.0); 2.6575 (0.3); 2.6324 (16.0); 2.2577 (13.2); 2.1642 (12.4); 1.9988 (8.9); 1.6185 (0.4); −0.0002 (3.0)
I-161: $^1$H-NMR(499.9 MHz, CDCl3):
δ = 9.7273 (0.4); 7.9335 (5.0); 7.5179 (0.8); 7.5022 (1.9); 7.4863 (1.3); 7.4227 (1.7); 7.4073 (1.2); 7.2606 (3.3); 7.2053 (2.2); 7.1441 (1.2); 7.1420 (1.2); 7.1279 (1.1); 7.1257 (1.1); 6.9587 (2.1); 6.9435 (2.4); 6.8862 (2.6); 6.7753 (1.2); 6.6850 (1.4); 6.6693 (1.4); 6.6625 (2.6); 6.5497 (1.2); 6.1582 (1.6); 4.2517 (1.1); 4.2452 (1.2); 4.2302 (1.2); 4.2236 (1.2); 3.8718 (0.5); 3.8623 (0.7); 3.8585 (0.7); 3.8521 (0.7); 3.8451 (0.6); 3.842
9

TABLE 2-continued (0.6); 3.8039 (1.6); 3.7913 (1.1); 3.7823 (1.4); 3.7697 (1.1); 2.9866 (0.9); 2.9771 (0.9); 2.9592 (1.1); 2.9498 (1.2); 2.7111 (1.2); 2.6914 (1.2); 2.6838 (1.1); 2.6639 (1.1); 2.6568 (0.8); 2.6321 (16.0); 2.3083 (0.6); 2.2577 (12.8); 2.1642 (12.1); 1.9990 (10.8); −0.0002 (3.3)
I-162: $^{1}$H-NMR(499.9 MHz, CDCl3):
δ = 8.1157 (16.0); 7.6279 (0.5); 7.6114 (8.6); 7.6012 (10.4); 7.5857 (0.3); 7.4499 (7.6); 7.4462 (7.8); 7.3769 (5.4); 7.2770 (0.6); 7.2690 (2.4); 7.2607 (20.0); 7.2513 (2.2); 7.2464 (1.6); 7.1025 (2.6); 7.0988 (2.5); 7.0862 (5.8); 7.0825 (5.9); 7.0603 (9.2); 7.0440 (4.0); 6.0336 (3.3); 4.1497 (2.9); 4.1434 (3.1); 4.1278 (3.5); 4.1216 (3.6); 4.0169 (0.5); 4.0069 (1.2); 4.0003 (1.8); 3.9907 (2.0); 3.9831 (1.9); 3.9770 (1.2); 3.9729 (1.0); 3.9666 (0.5); 3.9268 (3.8); 3.9173 (2.9); 3.9049 (3.1); 3.8955 (2.5); 3.7962 (0.4); 3.1210 (2.4); 3.1105 (2.4); 3.0939 (3.4); 3.0833 (3.2); 2.9674 (3.4); 2.9493 (3.4); 2.9403 (2.5); 2.9221 (2.4); 2.6088 (0.6); 2.3990 (0.4); 2.0028 (13.4); 1.5537 (2.3); 1.2554 (1.2); 0.8456 (0.4); −0.0002 (18.8); −0.0067 (0.7)
I-163: $^{1}$H-NMR(499.9 MHz, CDCl3):
δ = 8.1153 (16.0); 7.6280 (0.4); 7.6114 (8.6); 7.6011 (11.0); 7.5855 (0.4); 7.4498 (8.0); 7.4460 (8.5); 7.3767 (5.7); 7.2773 (0.5); 7.2694 (2.0); 7.2607 (21.2); 7.2517 (2.5); 7.2466 (1.8); 7.1025 (2.7); 7.0987 (2.6); 7.0862 (6.0); 7.0825 (6.2); 7.0720 (0.3); 7.0604 (9.6); 7.0441 (4.3); 6.0313 (3.2); 4.1495 (2.7); 4.1433 (3.2); 4.1276 (3.4); 4.1214 (3.7); 4.0169 (0.5); 4.0070 (1.1); 4.0005 (1.8); 3.9910 (1.9); 3.9834 (1.9); 3.9732 (1.1); 3.9669 (0.5); 3.9270 (3.7); 3.9176 (2.9); 3.9051 (3.0); 3.8957 (2.5); 3.1210 (2.5); 3.1104 (2.5); 3.0938 (3.5); 3.0833 (3.4); 2.9676 (3.4); 2.9495 (3.4); 2.9405 (2.6); 2.9223 (2.4); 2.6113 (0.6); 2.0026 (14.9); 1.5559 (1.7); 1.4318 (0.5); 1.2842 (0.4); 1.2554 (1.6); 1.2420 (0.3); 1.2147 (2.0); 1.2025 (1.9); 0.8586 (0.5); 0.8456 (0.7); 0.0772 (0.4); 0.0700 (9.6); 0.0628 (0.5); 0.0062 (0.7); −0.0002 (20.6); −0.0067 (1.0)
I-164: $^{1}$H-NMR(499.9 MHz, CDCl3):
δ = 8.1190 (8.7); 7.6120 (2.8); 7.6088 (2.2); 7.6032 (4.6); 7.6017 (5.2); 7.3536 (2.5); 7.2606 (8.1); 7.2117 (3.7); 7.2039 (1.6); 7.2001 (1.6); 7.1969 (0.9); 7.1939 (1.2); 7.1887 (0.9); 7.0098 (1.1); 7.0060 (1.1); 6.9936 (1.9); 6.9898 (2.0); 6.9514 (3.7); 6.9352 (2.2); 6.0439 (1.7); 4.2125 (0.8); 4.2077 (1.6); 4.1923 (1.6); 4.1874 (1.0); 3.8828 (0.5); 3.8773 (0.7); 3.8722 (0.7); 3.8670 (0.8); 3.8581 (2.3); 3.8487 (1.2); 3.8375 (2.0); 3.8265 (1.1); 2.9836 (0.9); 2.9790 (0.6); 2.9740 (0.9); 2.9562 (1.4); 2.9517 (0.6); 2.9464 (1.4); 2.7712 (1.1); 2.7624 (0.3); 2.7523 (1.1); 2.7436 (1.1); 2.7248 (1.0); 2.2805 (16.0); 2.0022 (11.9); 1.5574 (1.0); 1.2555 (0.3); −0.0002 (8.9); −0.0067 (0.5)
I-165: $^{1}$H-NMR(499.9 MHz, CDCl3):
δ = 8.1193 (8.3); 7.6296 (0.3); 7.6122 (3.2); 7.6089 (2.5); 7.6036 (4.6); 7.6019 (5.0); 7.3545 (2.5); 7.2606 (8.3); 7.2151 (3.3); 7.2118 (3.8); 7.2039 (1.5); 7.2000 (1.5); 7.1968 (0.8); 7.1938 (1.1); 7.1886 (0.8); 7.0097 (1.2); 7.0058 (1.1); 6.9935 (2.0); 6.9897 (1.9); 6.9514 (3.7); 6.9352 (2.1); 6.0440 (1.7); 4.2129 (0.9); 4.2081 (1.5); 4.1926 (1.6); 4.1880 (1.0); 3.8879 (0.3); 3.8828 (0.6); 3.8774 (0.8); 3.8722 (0.8); 3.8670 (1.0); 3.8583 (2.4); 3.8489 (1.1); 3.8376 (1.9); 3.8266 (1.0); 2.9837 (1.0); 2.9793 (0.6); 2.9741 (0.9); 2.9563 (1.5); 2.9465 (1.3); 2.7711 (1.1); 2.7618 (0.4); 2.7521 (1.2); 2.7435 (1.0); 2.7247 (0.9); 2.2806 (16.0); 2.0024 (11.8); 1.5566 (1.2); 1.2555 (0.5); 0.0062 (0.7); −0.0002 (9.1); −0.0068 (0.3)
I-166: $^{1}$H-NMR(499.9 MHz, CDCl3):
δ = 7.9800 (4.0); 7.6528 (1.6); 7.6368 (1.6); 7.5021 (0.3); 7.4846 (1.9); 7.4746 (3.6); 7.3536 (1.9); 7.3302 (1.7); 7.3207 (1.3); 7.3150 (2.6); 7.2592 (6.5); 7.2414 (1.4); 7.2252 (0.7); 7.0794 (3.8); 7.0548 (1.0); 7.0405 (1.5); 7.0248 (0.8); 6.1856 (1.4); 5.2969 (3.7); 5.0872 (0.7); 5.0789 (0.8); 5.0712 (0.8); 5.0628 (0.7); 4.4304 (0.9); 4.4219 (0.8); 4.4083 (1.0); 4.3999 (0.9); 4.0363 (1.1); 4.0199 (1.1); 4.0143 (1.1); 3.9980 (1.0); 3.7432 (12.5); 2.6938 (12.0); 2.0019 (16.0); 1.5663 (1.8); −0.0002 (6.4)
I-167: $^{1}$H-NMR(499.9 MHz, CDCl3):
δ = 7.9811 (5.0); 7.6528 (1.7); 7.6368 (1.8); 7.5022 (0.4); 7.4863 (2.0); 7.4841 (2.0); 7.4808 (1.8); 7.4760 (3.5); 7.4742 (3.7); 7.3531 (1.9); 7.3315 (1.8); 7.3200 (1.4); 7.3152 (2.9); 7.3099 (1.0); 7.3045 (0.5); 7.2584 (9.2); 7.2435 (1.3); 7.2417 (1.6); 7.2271 (0.8); 7.2254 (0.7); 7.0793 (4.4); 7.0566 (1.0); 7.0551 (1.1); 7.0409 (1.7); 7.0266 (0.8); 7.0251 (0.8); 6.1856 (1.5); 5.2966 (5.4); 5.0893 (0.8); 5.0870 (0.8); 5.0810 (0.8); 5.0785 (0.8); 5.0732 (0.8); 5.0708 (0.8); 5.0647 (0.7); 5.0625 (0.7); 4.4320 (0.9); 4.4308 (0.9); 4.4238 (0.9); 4.4224 (0.9); 4.4101 (1.0); 4.4088 (1.0); 4.4017 (0.9); 4.0362 (1.4); 4.0199 (1.4); 4.0142 (1.3); 3.9979 (1.2); 3.7434 (16.0); 2.6940 (15.3); 1.5617 (1.5); 0.0061 (0.7); −0.0002 (9.3); −0.0066 (0.4)
I-168: $^{1}$H-NMR(499.9 MHz, CDCl3):
δ = 8.2557 (2.7); 8.2516 (3.0); 7.9074 (5.3); 7.7310 (3.1); 7.7269 (3.2); 7.5203 (0.5); 7.5111 (2.2); 7.5067 (2.2); 7.4897 (1.9); 7.4749 (2.1); 7.4700 (1.9); 7.4649 (2.0); 7.4504 (0.9); 7.2318 (1.4); 7.1902 (31.8); 5.2290 (11.7); 5.0100 (0.6); 5.0025 (0.9); 4.9964 (0.8); 4.9940 (0.9); 4.9864 (0.9); 4.9803 (0.7); 4.7926 (1.2); 4.7848 (1.2); 4.7717 (1.3); 4.7638 (1.2); 4.0730 (0.4); 4.0587 (1.2); 4.0444 (1.2); 4.0301 (0.4); 3.2432 (1.3); 3.2268 (1.4); 3.2223 (1.5); 3.2059 (1.3); 2.6335 (16.0); 2.2104 (0.3); 1.9741 (5.4); 1.9358 (4.1); 1.4856 (2.6); 1.2233 (0.4); 1.2142 (0.4); 1.2032 (1.8); 1.1889 (4.1); 1.1845 (2.9); 1.1747 (1.9); 1.1627 (0.4); 1.0994 (0.4); 1.0959 (0.4); 1.0867 (0.5); 1.0832 (0.5); 1.0629 (0.3); 0.8101 (0.5); 0.1164 (0.4); −0.0002 (89.6); −0.0638 (1.1); −0.0703 (34.5); −0.0765 (2.9); −0.1196 (0.6)
I-169: $^{1}$H-NMR(300.2 MHz, CDCl3):
δ = 7.9111 (1.1); 7.9004 (1.1); 7.6445 (0.4); 7.6184 (1.5); 7.5972 (4.4); 7.5809 (0.8); 7.4673 (2.4); 7.4407 (1.0); 7.4320 (1.5); 7.4247 (1.0); 7.4112 (1.0); 7.4033 (0.6); 7.2983 (9.1); 7.0593 (1.8); 7.0332 (5.3); 6.9629 (1.7); 6.9360 (1.0); 5.3359 (1.0); 4.6975 (1.5); 4.2290 (0.4); 4.2125 (1.2); 4.1865 (1.4); 4.1700 (0.6); 3.9993 (0.8); 3.9840 (2.1); 3.9561 (1.8); 3.4764 (0.4); 3.0485 (0.4); 3.0324 (0.5); 3.0028 (1.2); 2.9866 (1.2); 2.9551 (1.2); 2.9383 (1.1); 2.9264 (2.1); 2.9140 (1.5); 2.9024 (1.1); 2.8834 (16.0); 2.8174 (1.7); 2.5233 (0.6); 2.3283 (14.0); 2.3172 (13.6); 1.7869 (0.3); 1.6704 (0.6); 1.2915 (0.4); 0.9114 (0.6); 0.8877 (2.5); 0.8695 (2.5); 0.8641 (2.0); 0.8465 (0.8); 0.6380 (0.8); 0.6239 (1.9); 0.6207 (2.1); 0.6143 (2.1); 0.6077 (2.0); 0.6034 (1.9); 0.5847 (0.6); 0.1071 (0.6); 0.0474 (0.4); 0.0366 (9.9); 0.0259 (0.4)
I-170: $^{1}$H-NMR(300.2 MHz, CDCl3):
δ = 8.2165 (16.0); 8.0518 (0.3); 7.3659 (6.9); 7.3589 (7.1); 7.2985 (23.7); 7.1937 (5.7); 7.1664 (8.3); 7.1391 (3.9); 7.1104 (3.7); 7.0889 (2.6); 7.0825 (3.3); 7.0653 (2.8); 7.0600 (3.4); 7.0406 (3.9); 7.0329 (1.7); 7.0040 (3.5); 6.9816 (3.9); 6.9453 (7.6); 6.9388 (4.7); 6.9186 (3.5); 6.9115 (3.4); 6.8823 (1.9); 6.8762 (1.9); 6.8561 (3.0); 6.8341 (1.7); 6.8287 (1.6); 6.2618 (6.3); 6.2023 (7.7); 5.6757 (6.2); 5.6384 (5.8); 4.2157 (2.3); 4.2056 (2.9); 4.1940 (0.5); 4.1800 (3.2); 4.1701 (4.2); 4.1464 (0.7); 4.0792 (0.4); 4.0630 (1.0); 4.0526 (1.6); 4.0367 (1.8); 4.0231 (1.8); 4.0137 (1.1); 4.0066 (1.2); 3.9883 (4.1); 3.9730 (2.2); 3.9528 (2.9); 3.9372 (2.0); 3.2175 (2.1); 3.2010 (2.1); 3.1728 (3.2); 3.1560 (3.0); 3.0166 (3.1); 2.9927 (3.3); 2.9870 (3.2); 2.9719 (2.2); 2.9417 (2.1); 2.9206 (2.4); 2.1596 (0.6); 2.1422 (1.2); 2.1311 (1.3); 2.1140 (2.4); 2.0968 (1.5); 2.0824 (3.7); 2.0686 (0.8); 1.6048 (10.8); 1.3674 (0.4); 1.3437 (0.9); 1.3200 (2.2); 1.3034 (5.6); 1.2965 (6.0); 1.2726 (1.2); 1.0968 (1.1); 1.0932 (1.2); 1.0823 (4.1); 1.0755 (4.9); 1.0650 (2.8); 1.0610 (2.2); 1.0536 (4.4); 1.0473 (4.5); 1.0366 (1.7); 1.0330 (1.6); 1.0156 (0.3); 0.9405 (2.0); 0.9187 (6.2); 0.8955 (2.4); 0.8721 (0.3); 0.8570 (0.4); 0.8351

TABLE 2-continued (2.4); 0.8287 (2.4); 0.8199 (4.9); 0.8123 (4.9); 0.8033 (5.6); 0.7960 (3.4); 0.7864 (2.0); 0.7653 (0.4); 0.1069 (1.6); 0.0476 (0.9); 0.0367 (27.9); 0.0259 (1.2)
I-171: $^1$H-NMR(300.2 MHz, CDCl3):
δ = 8.7047 (5.9); 7.3638 (2.4); 7.3568 (2.4); 7.2983 (9.5); 7.2052 (0.6); 7.1955 (2.0); 7.1784 (1.4); 7.1743 (1.4); 7.1683 (2.5); 7.1516 (1.0); 7.1485 (1.0); 7.0983 (0.8); 7.0925 (0.9); 7.0744 (0.9); 7.0695 (1.1); 7.0477 (0.5); 7.0423 (0.5); 6.9592 (1.4); 6.9521 (1.4); 6.9320 (1.2); 6.9246 (1.6); 6.9181 (0.7); 6.8965 (1.1); 6.8750 (0.5); 6.8697 (0.5); 5.9875 (1.0); 5.9804 (1.0); 4.2173 (0.7); 4.2075 (0.9); 4.1817 (1.1); 4.1721 (1.2); 4.0697 (0.3); 4.0587 (0.5); 4.0428 (0.6); 4.0294 (0.6); 4.0217 (0.4); 4.0132 (0.4); 4.0029 (1.5); 3.9877 (0.7); 3.9671 (0.9); 3.9520 (0.7); 3.2195 (0.7); 3.2032 (0.7); 3.1749 (1.1); 3.1580 (1.0); 3.0299 (1.0); 3.0005 (1.0); 2.9853 (0.7); 2.9553 (0.7); 2.8133 (16.0); 2.1621 (0.4); 2.1508 (0.4); 2.1338 (0.8); 2.1164 (0.5); 2.1055 (0.4); 1.5939 (8.3); 1.3033 (1.1); 1.1217 (0.4); 1.1183 (0.4); 1.1070 (1.4); 1.1001 (1.6); 1.0896 (0.9); 1.0854 (0.7); 1.0783 (1.5); 1.0719 (1.5); 1.0607 (0.5); 1.0574 (0.5); 0.9398 (0.4); 0.9183 (1.3); 0.8951 (0.5); 0.8541 (0.8); 0.8467 (0.8); 0.8381 (1.6); 0.8314 (1.5); 0.8219 (1.8); 0.8151 (1.1); 0.8046 (0.6); 0.1064 (0.8); 0.0470 (0.3); 0.0362 (11.2); 0.0270 (0.4); 0.0254 (0.5)
I-172: $^1$H-NMR(300.2 MHz, CDCl3):
δ = 7.9751 (0.4); 7.9587 (9.7); 7.3650 (5.0); 7.3580 (5.0); 7.2986 (22.6); 7.1915 (4.0); 7.1642 (5.0); 7.1556 (1.5); 7.1283 (3.0); 7.1004 (2.8); 7.0838 (2.1); 7.0773 (2.4); 7.0602 (2.1); 7.0550 (2.4); 7.0336 (1.2); 7.0278 (1.0); 6.9428 (3.0); 6.9357 (2.8); 6.9155 (2.5); 6.9085 (2.4); 6.8686 (1.4); 6.8620 (1.4); 6.8445 (2.3); 6.8202 (1.3); 6.8151 (1.2); 6.2138 (2.1); 4.2037 (1.7); 4.1938 (2.2); 4.1690 (2.7); 4.1580 (2.6); 4.1468 (1.2); 4.1234 (0.5); 4.0699 (0.4); 4.0534 (0.8); 4.0426 (1.2); 4.0271 (1.4); 4.0135 (1.4); 4.0067 (1.0); 3.9972 (1.0); 3.9877 (0.7); 3.9760 (2.9); 3.9605 (1.7); 3.9402 (2.1); 3.9247 (1.5); 3.2112 (1.5); 3.1945 (1.5); 3.1663 (2.3); 3.1496 (2.2); 3.0271 (2.3); 3.0095 (2.9); 3.0018 (7.1); 2.9766 (7.9); 2.9656 (2.1); 2.9512 (2.6); 2.9350 (1.6); 2.9219 (0.5); 2.1568 (0.4); 2.1403 (1.0); 2.1293 (1.1); 2.1122 (1.9); 2.0950 (1.3); 2.0828 (5.9); 2.0667 (0.6); 1.6148 (2.5); 1.4036 (7.7); 1.3783 (16.0); 1.3529 (7.3); 1.3203 (1.3); 1.2965 (2.6); 1.2727 (1.2); 1.2154 (0.4); 1.1480 (0.4); 1.0921 (1.0); 1.0880 (1.0); 1.0773 (3.2); 1.0709 (3.7); 1.0605 (2.2); 1.0562 (1.9); 1.0488 (3.4); 1.0427 (3.4); 1.0322 (1.4); 1.0282 (1.3); 0.9962 (0.4); 0.9723 (0.5); 0.8534 (0.4); 0.8310 (1.9); 0.8247 (2.0); 0.8160 (3.7); 0.8083 (3.8); 0.7993 (4.2); 0.7919 (2.6); 0.7826 (1.5); 0.7618 (0.4); 0.1065 (2.1); 0.0474 (1.0); 0.0367 (23.3); 0.0258 (1.2)
I-173: $^1$H-NMR(499.9 MHz, CDCl3):
δ = 8.0750 (10.2); 7.5797 (0.4); 7.5743 (0.7); 7.5721 (0.7); 7.5616 (5.6); 7.5567 (1.8); 7.5488 (2.2); 7.5330 (0.5); 7.3157 (2.5); 7.2584 (10.3); 7.2355 (1.0); 7.2313 (1.4); 7.2266 (0.7); 7.2244 (0.7); 7.2221 (1.3); 7.2178 (1.7); 7.2126 (0.7); 6.9483 (2.7); 6.9331 (2.8); 6.8612 (2.8); 6.6324 (1.6); 6.6172 (1.4); 5.7973 (1.9); 5.3681 (1.4); 5.2968 (2.2); 3.9547 (0.3); 3.9459 (0.7); 3.9418 (0.7); 3.9381 (0.8); 3.9320 (0.7); 3.9263 (0.8); 3.9224 (0.6); 3.9183 (0.6); 3.3820 (1.2); 3.3747 (1.2); 3.3606 (1.3); 3.3533 (1.2); 2.9929 (1.3); 2.9855 (2.2); 2.9730 (1.7); 2.9647 (2.5); 2.9563 (1.4); 2.9516 (1.5); 2.6989 (1.5); 2.6792 (1.5); 2.6717 (1.3); 2.6520 (1.2); 2.2512 (16.0); 2.1429 (14.8); 1.5545 (3.0); 0.0063 (0.7); −0.0002 (12.8); −0.0069 (0.4)
I-174: $^1$H-NMR(300.2 MHz, CDCl3):
δ = 7.2988 (1.7); 7.2858 (0.4); 7.2716 (0.7); 7.2672 (0.7); 7.2586 (0.7); 7.2522 (0.8); 7.2430 (0.6); 7.2361 (0.6); 7.2293 (0.6); 7.2239 (0.7); 7.2126 (0.7); 7.1962 (1.0); 7.1862 (1.0); 7.1695 (0.5); 7.1593 (0.5); 7.1255 (0.8); 7.1030 (1.1); 7.0796 (0.5); 7.0528 (0.8); 7.0416 (0.9); 7.0162 (3.6); 6.9458 (1.5); 6.9201 (0.9); 5.3334 (2.0); 4.9457 (0.8); 4.9061 (0.8); 4.2042 (0.5); 4.1782 (0.7); 4.1695 (0.6); 4.1588 (0.6); 4.1327 (0.7); 3.9242 (1.4); 3.9023 (1.3); 3.8966 (1.3); 3.8787 (0.4); 3.8700 (0.6); 3.8517 (0.3); 3.0245 (0.5); 3.0073 (0.5); 2.9790 (1.0); 2.9614 (0.9); 2.9093 (0.6); 2.8818 (1.1); 2.8650 (1.0); 2.8523 (1.0); 2.8363 (1.0); 2.8254 (0.7); 2.8080 (0.5); 2.5437 (7.4); 2.5354 (7.6); 2.3073 (16.0); 1.9572 (0.6); 1.9401 (0.5); 1.9343 (0.5); 1.9173 (0.6); 1.7314 (0.4); 1.7185 (0.6); 1.7070 (0.6); 1.6904 (0.6); 1.6786 (0.6); 1.6662 (0.5); 1.6511 (0.4); 0.0413 (1.7)
I-175: $^1$H-NMR(499.9 MHz, CDCl3):
δ = 8.1195 (16.0); 7.6182 (0.4); 7.6034 (1.7); 7.5876 (5.7); 7.5816 (5.2); 7.5658 (4.7); 7.5502 (2.0); 7.5190 (0.4); 7.4077 (6.5); 7.3915 (9.2); 7.3626 (0.4); 7.3384 (5.3); 7.3098 (8.6); 7.2936 (6.3); 7.2606 (13.4); 7.1951 (2.8); 7.1799 (2.9); 7.1768 (2.0); 6.0747 (3.3); 4.2144 (2.4); 4.2084 (2.9); 4.1930 (3.1); 4.1871 (3.1); 3.9386 (0.4); 3.9324 (0.6); 3.9279 (1.1); 3.9222 (1.5); 3.9172 (1.5); 3.9125 (1.6); 3.9090 (1.6); 3.9036 (1.6); 3.8982 (1.3); 3.8934 (1.4); 3.8849 (4.5); 3.8742 (2.0); 3.8635 (3.5); 3.8528 (2.4); 3.0894 (2.0); 3.0797 (2.0); 3.0625 (2.5); 3.0526 (2.4); 2.8706 (2.7); 2.8519 (2.6); 2.8438 (2.3); 2.8248 (2.1); 1.5603 (13.3); 0.0063 (0.5); −0.0002 (14.7); −0.0066 (0.7)
I-176: $^1$H-NMR(300.2 MHz, CDCl3):
δ = 7.5785 (1.0); 7.5541 (2.1); 7.5236 (0.3); 7.4362 (1.4); 7.4208 (0.8); 7.4141 (1.0); 7.4074 (0.5); 7.3900 (0.6); 7.2987 (7.1); 7.0418 (1.2); 7.0276 (1.7); 7.0168 (2.0); 6.9547 (1.1); 6.9293 (0.6); 4.6790 (1.0); 4.2087 (0.8); 4.1829 (1.0); 3.9618 (0.5); 3.9391 (1.3); 3.9086 (1.0); 3.8914 (0.4); 3.0338 (0.4); 3.0180 (0.4); 2.9879 (0.8); 2.9716 (0.7); 2.9056 (0.7); 2.8756 (0.6); 2.8601 (0.4); 2.8296 (0.4); 2.6636 (12.4); 2.4262 (12.0); 2.3187 (16.0); 1.5962 (0.3); 0.1200 (0.6); 0.1082 (10.9); 0.0959 (0.6); 0.0489 (0.5); 0.0381 (9.0); 0.0274 (0.4)
I-177: $^1$H-NMR(300.2 MHz, CDCl3):
δ = 8.1047 (3.8); 7.6302 (0.7); 7.6045 (9.5); 7.5800 (4.1); 7.5496 (0.9); 7.5306 (2.7); 7.4646 (5.7); 7.4454 (1.3); 7.2986 (19.1); 7.0484 (3.1); 7.0039 (0.7); 6.9679 (5.2); 6.9417 (0.7); 5.8345 (2.0); 4.1620 (0.4); 4.1422 (1.4); 4.1174 (1.7); 4.0972 (0.6); 3.8625 (0.9); 3.8432 (2.6); 3.8278 (1.6); 3.8197 (2.4); 3.8008 (0.8); 2.9570 (0.7); 2.9388 (0.7); 2.9110 (1.3); 2.8926 (1.2); 2.8047 (1.2); 2.7784 (1.2); 2.7586 (0.7); 2.7326 (0.7); 2.3389 (15.0); 2.3200 (16.0); 2.2962 (0.7); 2.1853 (14.1); 1.5955 (6.9); 1.3715 (0.3); 1.3224 (0.5); 1.2931 (1.8); 1.2605 (0.4); 0.8940 (0.5); 0.8779 (0.4); 0.8692 (0.5); 0.1078 (1.8); 0.0380 (17.5); 0.0273 (0.9)
I-178: $^1$H-NMR(300.2 MHz, CDCl3):
δ = 7.5813 (1.0); 7.5568 (2.0); 7.5525 (1.8); 7.4325 (1.4); 7.4168 (0.7); 7.4104 (1.0); 7.4035 (0.5); 7.3943 (0.4); 7.3859 (0.6); 7.2986 (11.4); 7.0383 (1.2); 7.0276 (1.6); 7.0138 (1.9); 6.9541 (1.0); 6.9284 (0.6); 6.0502 (0.5); 6.0168 (0.8); 5.9938 (0.8); 5.9603 (0.6); 5.3793 (0.4); 5.3749 (1.1); 5.3703 (1.1); 5.3183 (0.9); 5.3138 (0.9); 5.3095 (0.4); 5.1848 (1.0); 5.1804 (1.0); 5.1514 (0.9); 5.1471 (0.9); 4.6572 (1.0); 4.2069 (0.8); 4.1811 (0.9); 3.9819 (2.4); 3.9787 (1.8); 3.9591 (2.6); 3.9556 (1.9); 3.9377 (1.2); 3.9140 (0.4); 3.9070 (1.0); 3.8901 (0.4); 3.0315 (0.4); 3.0153 (0.4); 2.9852 (0.7); 2.9692 (0.7); 2.9026 (0.6); 2.8726 (0.6); 2.8573 (0.4); 2.8263 (0.3); 2.4189 (12.6); 2.3181 (16.0); 1.5980 (1.2); 0.1075 (0.9); 0.0487 (0.4); 0.0378 (13.0); 0.0270 (0.5)
I-179: $^1$H-NMR(499.9 MHz, CDCl3):
δ = 8.0923 (8.6); 7.6036 (0.4); 7.5877 (2.2); 7.5825 (1.9); 7.5797 (2.0); 7.5762 (5.3); 7.5744 (5.4); 7.5007 (2.6); 7.4372 (0.9); 7.4310 (1.5); 7.4266 (1.5); 7.4189 (1.2); 7.4141 (0.8); 7.2588 (5.5); 7.2181 (2.8); 7.2023 (3.1); 6.9924 (2.8); 6.9089 (1.5); 6.9076 (1.5); 6.8933 (1.4); 6.8920 (1.4); 6.7314 (1.7); 4.1307 (1.3); 4.1238 (1.5); 4.1086 (1.7); 4.1017 (1.7); 3.8850 (1.6); 3.8743 (1.8); 3.8629 (1.4); 3.8521 (1.6); 3.6649 (0.5); 3.6594 (0.7); 3.6572 (0.7); 3.6503 (0.9); 3.6412 (0.8); 3.6358 (0.6); 3.1578 (1.5); 3.1485 (1.6); 3.1306 (1.8); 3.1212

TABLE 2-continued (1.8); 2.8608 (1.7); 2.8420 (1.7); 2.8335 (1.6); 2.8148 (1.4); 2.3860 (0.4); 2.2862 (16.0); 2.2623 (15.6); 0.0710 (0.4); −0.0002 (6.1); −0.0066 (0.4)
I-180: $^1$H-NMR(499.9 MHz, CDCl3):
δ = 7.7251 (1.0); 7.6237 (0.5); 7.6081 (2.0); 7.5940 (4.9); 7.5800 (0.5); 7.4353 (2.6); 7.4001 (1.0); 7.3961 (1.6); 7.3822 (1.2); 7.3682 (0.5); 7.3523 (0.4); 7.2596 (9.2); 7.0813 (0.6); 7.0035 (2.4); 6.9950 (3.3); 6.9891 (3.2); 6.9209 (1.9); 6.9055 (1.4); 5.2980 (1.7); 4.6981 (2.0); 4.1913 (1.4); 4.1847 (0.6); 4.1755 (1.6); 4.1657 (0.6); 4.1550 (0.5); 4.1429 (0.4); 3.9415 (2.5); 3.9235 (1.8); 3.9136 (0.7); 3.4298 (16.0); 3.0029 (0.8); 2.9934 (0.8); 2.9751 (1.2); 2.9655 (1.1); 2.8886 (1.1); 2.8707 (1.1); 2.8613 (0.8); 2.8427 (0.7); 2.8020 (15.4); 2.4847 (1.4); 2.3464 (2.0); 2.2881 (14.9); 2.2812 (13.5); 2.1644 (0.8); 2.0397 (0.7); 1.5484 (2.2); 1.2568 (0.6); −0.0002 (10.3)
I-181: $^1$H-NMR(499.9 MHz, CDCl3):
δ = 8.1255 (7.3); 7.5722 (0.6); 7.5643 (3.7); 7.5625 (4.3); 7.5570 (1.6); 7.5503 (1.8); 7.5345 (0.4); 7.3179 (2.1); 7.2585 (8.0); 7.2422 (0.9); 7.2379 (1.1); 7.2329 (0.6); 7.2292 (1.1); 7.2248 (1.2); 7.2193 (0.6); 6.9353 (2.1); 6.9200 (2.3); 6.8670 (2.3); 6.6343 (1.3); 6.6193 (1.1); 5.8391 (0.9); 3.9805 (0.6); 3.9720 (0.6); 3.1553 (0.8); 3.1479 (0.8); 3.1335 (0.9); 3.1263 (0.8); 2.9821 (1.1); 2.9725 (1.1); 2.9548 (1.4); 2.9380 (16.0); 2.6823 (1.2); 2.6627 (1.2); 2.6551 (1.1); 2.6356 (1.0); 2.6195 (1.4); 2.6065 (1.4); 2.5976 (1.3); 2.5847 (1.2); 2.2760 (0.5); 2.2452 (12.8); 2.1515 (11.7); 0.0699 (0.6); 0.0062 (0.5); −0.0002 (8.6)
I-182: $^1$H-NMR(499.9 MHz, CDCl3):
δ = 8.1228 (9.3); 7.5650 (0.8); 7.5572 (4.5); 7.5555 (5.6); 7.5503 (2.0); 7.5431 (2.3); 7.5273 (0.5); 7.3565 (0.4); 7.3124 (2.7); 7.2582 (12.1); 7.2329 (1.1); 7.2288 (1.5); 7.2239 (0.8); 7.2199 (1.4); 7.2156 (1.6); 7.2101 (0.8); 6.9374 (2.7); 6.9221 (2.8); 6.8645 (3.0); 6.6315 (1.6); 6.6166 (1.4); 5.7947 (0.8); 3.9664 (0.7); 3.1671 (0.8); 3.1491 (1.8); 3.1349 (3.0); 3.1206 (2.8); 3.1065 (1.0); 2.9815 (1.0); 2.9719 (1.0); 2.9543 (1.2); 2.9448 (1.1); 2.6713 (1.4); 2.6589 (1.8); 2.6518 (1.7); 2.6456 (2.5); 2.6373 (1.7); 2.6244 (2.5); 2.2914 (0.7); 2.2456 (16.0); 2.2122 (0.7); 2.1496 (14.7); 1.3100 (3.3); 1.2958 (6.4); 1.2816 (3.1); 1.2712 (0.4); 1.0585 (0.4); 0.0062 (1.0); −0.0002 (14.5); −0.0068 (0.6)
I-183: $^1$H-NMR(300.2 MHz, CDCl3):
δ = 8.1668 (16.0); 7.6526 (0.8); 7.6388 (8.2); 7.6357 (9.3); 7.6154 (4.3); 7.5891 (1.1); 7.3838 (4.5); 7.2983 (33.3); 7.2874 (2.4); 7.2797 (2.8); 7.2646 (3.1); 7.2543 (9.2); 7.2256 (10.0); 7.0435 (6.7); 7.0171 (5.3); 6.1203 (3.3); 5.3377 (5.5); 4.2605 (2.8); 4.2348 (3.2); 4.2274 (1.6); 4.2167 (0.8); 3.9614 (0.3); 3.9432 (0.9); 3.9331 (1.3); 3.9253 (1.5); 3.9103 (4.3); 3.9024 (3.9); 3.8764 (3.8); 3.8579 (1.8); 3.0841 (1.7); 3.0697 (1.6); 3.0390 (2.7); 3.0237 (2.5); 2.8493 (2.2); 2.8332 (0.7); 2.8182 (2.2); 2.8044 (1.8); 2.7731 (1.6); 1.5856 (12.7); 1.3466 (0.5); 1.2925 (1.1); 0.9180 (0.3); 0.1069 (5.2); 0.0478 (1.5); 0.0371 (44.2); 0.0262 (1.9); −0.0297 (0.4)
I-184: $^1$H-NMR(400.2 MHz, $d_6$-DMSO):
δ = 10.1012 (5.6); 8.2715 (16.0); 7.8018 (5.5); 7.7810 (14.2); 7.7760 (8.8); 7.7625 (3.8); 7.7422 (4.5); 7.7307 (5.9); 7.7234 (5.3); 7.7038 (2.2); 7.6876 (3.6); 7.6686 (2.1); 7.4753 (3.7); 7.4700 (3.6); 7.4542 (3.3); 7.4488 (3.3); 5.5264 (1.7); 5.5161 (1.9); 5.4964 (2.0); 5.4854 (1.8); 3.8482 (1.8); 3.8377 (2.0); 3.8142 (2.4); 3.8038 (2.2); 3.5946 (2.4); 3.5636 (3.1); 3.5303 (2.0); 3.3414 (13.7); 2.6716 (0.4); 2.5069 (50.8); 2.5025 (68.1); 2.4980 (50.1); 2.3336 (0.4); 2.3293 (0.4); 0.0080 (0.4); 0.0001 (8.2)
I-185: $^1$H-NMR(300.1 MHz, $d_6$-DMSO):
δ = 11.0094 (5.2); 8.2358 (16.0); 8.1566 (0.6); 7.8011 (5.9); 7.7774 (1.1); 7.7518 (3.4); 7.7263 (5.7); 7.7094 (5.9); 7.6891 (5.8); 7.6643 (2.1); 7.5211 (6.5); 7.4927 (12.4); 7.4339 (14.4); 7.4055 (7.4); 5.0679 (2.0); 5.0498 (2.3); 5.0250 (2.5); 5.0069 (2.1); 3.3270 (1.5); 2.7891 (1.9); 2.7707 (2.1); 2.7343 (3.2); 2.7160 (2.8); 2.5516 (3.1); 2.5079 (33.8); 2.5022 (41.1); 2.4966 (30.5); 2.4538 (2.2); 2.0755 (3.5); −0.0005 (5.8)
I-186: $^1$H-NMR(400.2 MHz, $d_6$-DMSO):
δ = 8.1261 (10.9); 7.9532 (1.6); 7.6102 (1.0); 7.6062 (1.1); 7.5936 (1.2); 7.5896 (2.2); 7.5860 (1.4); 7.5738 (1.2); 7.5694 (1.2); 7.4468 (0.9); 7.4427 (1.0); 7.4297 (3.0); 7.4259 (3.7); 7.4221 (3.5); 7.4092 (1.8); 7.4048 (1.4); 7.3784 (1.8); 7.3753 (1.7); 7.3581 (2.2); 7.3548 (2.3); 7.3377 (0.8); 7.3342 (0.8); 7.0562 (2.7); 7.0371 (3.2); 6.9243 (3.3); 6.8250 (1.8); 6.8060 (1.5); 3.7625 (6.4); 3.7520 (1.2); 3.7434 (1.2); 3.7342 (1.0); 3.7250 (0.8); 3.7163 (0.5); 3.3321 (34.6); 2.8915 (11.2); 2.8527 (0.4); 2.8348 (0.4); 2.8180 (1.6); 2.8045 (2.7); 2.7883 (1.9); 2.7711 (0.4); 2.7323 (9.5); 2.5258 (0.7); 2.5209 (1.1); 2.5123 (13.2); 2.5079 (26.0); 2.5033 (33.7); 2.4988 (24.5); 2.4943 (11.9); 2.2407 (16.0); 2.1887 (14.6); −0.0002 (6.2)
I-187: $^1$H-NMR(300.2 MHz, CDCl3):
δ = 7.5821 (1.0); 7.5574 (2.0); 7.5527 (1.8); 7.5273 (0.3); 7.4362 (1.4); 7.4156 (0.7); 7.4087 (1.0); 7.4023 (0.5); 7.3896 (0.5); 7.3838 (0.6); 7.2983 (6.6); 7.0382 (1.3); 7.0267 (1.7); 7.0134 (1.9); 6.9532 (1.0); 6.9270 (0.6); 4.6657 (1.0); 4.2026 (0.8); 4.1768 (0.9); 3.9376 (1.3); 3.9084 (1.0); 3.8915 (0.4); 3.7231 (1.1); 3.7024 (3.0); 3.6838 (2.0); 3.5541 (2.0); 3.5348 (2.8); 3.5161 (1.0); 3.3973 (15.2); 3.0300 (0.4); 3.0142 (0.4); 2.9838 (0.7); 2.9678 (0.6); 2.9051 (0.6); 2.8755 (0.6); 2.8598 (0.4); 2.4285 (12.0); 2.3174 (16.0); 1.6183 (0.5); 0.1075 (0.6); 0.0373 (6.7)
I-188: $^1$H-NMR(300.2 MHz, CDCl3):
δ = 8.1487 (16.0); 8.0661 (1.0); 7.9641 (0.4); 7.6337 (14.9); 7.6204 (9.3); 7.5880 (1.9); 7.5348 (0.8); 7.5091 (0.6); 7.4441 (0.7); 7.3817 (8.9); 7.3435 (1.1); 7.2985 (9.3); 7.2789 (6.0); 7.2668 (5.7); 7.2598 (5.6); 7.2139 (12.5); 7.1860 (14.4); 7.1564 (1.8); 7.1269 (1.4); 7.1048 (1.4); 7.0827 (1.2); 7.0536 (0.7); 7.0325 (0.7); 7.0046 (0.8); 6.9449 (13.7); 6.9173 (11.0); 6.8539 (0.4); 6.7847 (0.4); 6.6385 (4.1); 6.5391 (0.6); 6.3933 (8.1); 6.2928 (0.4); 6.1479 (6.0); 6.1301 (7.0); 5.3349 (0.6); 4.2616 (4.6); 4.2357 (5.3); 4.1693 (0.4); 4.0366 (0.4); 4.0094 (0.5); 3.8795 (8.6); 3.8464 (5.2); 3.8273 (3.0); 3.7955 (0.8); 3.7618 (0.4); 3.0621 (3.1); 3.0478 (3.1); 3.0176 (4.7); 3.0019 (4.2); 2.9611 (0.4); 2.9155 (0.6); 2.8958 (0.8); 2.8711 (0.5); 2.8051 (3.7); 2.7739 (3.8); 2.7603 (3.5); 2.7291 (2.8); 1.6319 (6.7); 1.2900 (0.7); 0.1080 (1.8); 0.0354 (8.2)
I-189: $^1$H-NMR(300.2 MHz, CDCl3):
δ = 8.2358 (6.4); 7.4223 (0.7); 7.4143 (0.7); 7.3974 (1.2); 7.3897 (1.0); 7.3743 (1.0); 7.3681 (1.0); 7.2986 (10.7); 7.2206 (0.7); 7.2163 (0.5); 7.1932 (1.8); 7.1889 (1.6); 7.1658 (3.1); 7.1578 (1.5); 7.1447 (1.2); 7.1385 (1.5); 7.1173 (0.6); 7.1111 (0.5); 7.0280 (1.6); 7.0214 (2.1); 6.9953 (2.6); 6.9689 (1.6); 6.9321 (1.6); 6.9102 (2.3); 6.7312 (1.3); 6.7061 (1.0); 6.2635 (2.8); 6.2044 (2.4); 6.0891 (1.5); 5.6836 (2.7); 5.6467 (2.5); 4.3355 (0.9); 4.3258 (1.1); 4.3010 (1.1); 4.2909 (1.1); 4.1946 (1.2); 4.1708 (3.5); 4.1470 (3.5); 4.1232 (1.2); 3.9478 (0.4); 3.9309 (0.6); 3.9256 (0.6); 3.9199 (0.6); 3.9149 (0.7); 3.8989 (0.6); 3.8915 (0.6); 3.8812 (2.1); 3.8604 (0.7); 3.8463 (1.5); 3.8255 (1.0); 3.0598 (0.8); 3.0443 (0.8); 3.0148 (1.1); 2.9985 (1.0); 2.7882 (1.2); 2.7567 (1.1); 2.7432 (0.9); 2.7110 (0.8); 2.3124 (12.7); 2.1859 (11.9); 2.0831 (16.0); 1.6073 (6.4); 1.3205 (4.3); 1.2967 (8.9); 1.2729 (4.1); 0.9190 (0.7); 0.0475 (0.4); 0.0368 (13.3); 0.0259 (0.5)
I-190: $^1$H-NMR(499.9 MHz, CDCl3):
δ = 7.8522 (5.3); 7.2856 (0.7); 7.2820 (0.8); 7.2696 (1.5); 7.2664 (1.0); 7.2565 (0.9); 7.2534 (0.9); 7.1890 (5.2); 7.0843 (0.7); 7.0818 (0.7); 7.0678 (1.6); 7.0654 (1.7); 7.0495 (1.4); 7.0372 (1.1); 7.0337 (1.2); 7.0240

TABLE 2-continued (1.1); 7.0210 (1.5); 7.0077 (0.6); 7.0047 (0.6); 6.9004 (2.1); 6.8851 (2.4); 6.7973 (2.7); 6.6168 (1.4); 6.6017 (1.3); 5.9699 (1.7); 4.1921 (1.1); 4.1856 (1.2); 4.1706 (1.2); 4.1640 (1.3); 3.8143 (0.5); 3.8042 (0.8); 3.8007 (0.7); 3.7948 (0.8); 3.7849 (0.6); 3.7748 (0.3); 3.7462 (1.6); 3.7337 (1.1); 3.7246 (1.4); 3.7121 (1.1); 2.9231 (0.9); 2.9132 (1.0); 2.8958 (1.2); 2.8858 (1.1); 2.6614 (1.2); 2.6419 (1.2); 2.6343 (1.1); 2.6146 (0.9); 2.5625 (16.0); 2.5522 (0.7); 2.2313 (0.4); 2.1965 (13.2); 2.0772 (12.4); 1.9725 (1.7); 1.1870 (0.8); 0.8644 (0.4); −0.0002 (6.5); −0.0712 (6.2)

I-192: $^{1}$H-NMR(300.2 MHz, CDCl3):
δ = 7.9700 (5.3); 7.2984 (10.0); 7.1265 (1.0); 7.1020 (2.4); 7.0711 (3.3); 7.0433 (3.3); 6.9991 (4.1); 6.8461 (1.2); 6.8231 (2.0); 6.8010 (1.2); 6.7718 (2.1); 6.7466 (1.8); 6.3163 (2.5); 5.3375 (0.5); 4.2789 (1.6); 4.2538 (1.7); 4.1710 (0.7); 4.1474 (0.6); 4.1243 (0.7); 4.1019 (1.0); 4.0797 (0.6); 3.8670 (2.9); 3.8345 (1.8); 3.8147 (0.9); 3.0478 (1.0); 3.0342 (1.0); 3.0035 (1.6); 2.9892 (1.4); 2.8809 (0.4); 2.8538 (0.9); 2.8271 (1.5); 2.7924 (1.9); 2.7602 (1.4); 2.7454 (1.3); 2.7149 (1.2); 2.6672 (16.0); 2.3330 (14.1); 2.1703 (0.6); 2.1520 (0.9); 2.1421 (1.1); 2.1255 (1.7); 2.1089 (1.4); 2.0972 (1.8); 2.0843 (5.8); 2.0467 (0.6); 1.9563 (1.9); 1.7832 (2.3); 1.7718 (2.0); 1.7617 (2.0); 1.7426 (1.7); 1.7277 (1.7); 1.7006 (2.2); 1.6854 (2.3); 1.6731 (2.6); 1.6612 (2.4); 1.6462 (2.8); 1.6231 (3.1); 1.4530 (1.7); 1.4312 (1.9); 1.4058 (1.5); 1.3817 (1.0); 1.3571 (0.6); 1.3210 (1.1); 1.2972 (2.0); 1.2733 (0.9); 1.0860 (1.2); 1.0662 (2.8); 1.0440 (2.6); 1.0381 (2.6); 1.0251 (1.5); 0.9970 (1.2); 0.9725 (1.8); 0.9480 (0.9); 0.9168 (0.4); 0.8813 (0.4); 0.8630 (0.4); 0.8108 (3.4); 0.7966 (3.3); 0.7784 (1.2); 0.1666 (0.7); 0.1346 (0.5); 0.1067 (2.7); 0.0367 (12.4)

I-193: $^{1}$H-NMR(300.2 MHz, CDCl3):
δ = 7.9644 (5.4); 7.2987 (2.7); 7.1288 (0.6); 7.1025 (1.7); 7.0806 (2.9); 7.0559 (2.5); 7.0283 (1.0); 7.0227 (1.2); 6.9999 (1.5); 6.9778 (0.7); 6.9724 (0.8); 6.9547 (2.6); 6.8572 (0.8); 6.8520 (0.8); 6.8310 (1.5); 6.8092 (0.8); 6.8042 (0.7); 6.7573 (1.4); 6.7317 (1.2); 6.3076 (1.8); 4.2720 (1.2); 4.2469 (1.4); 4.2397 (0.8); 4.1697 (0.4); 4.1460 (0.4); 4.1232 (0.4); 4.1013 (0.5); 3.8964 (0.6); 3.8902 (0.7); 3.8654 (2.0); 3.8323 (1.5); 3.8120 (0.8); 3.4151 (0.6); 3.3836 (0.7); 3.3569 (0.7); 3.0500 (0.7); 3.0350 (0.7); 3.0050 (1.2); 2.9895 (1.1); 2.7991 (0.9); 2.7681 (0.9); 2.7539 (0.9); 2.7232 (0.8); 2.6653 (16.0); 2.3352 (12.8); 2.3128 (0.6); 2.3068 (0.6); 2.3011 (0.5); 2.2876 (0.8); 2.2777 (1.5); 2.2678 (1.3); 2.2521 (1.5); 2.2418 (1.0); 2.2342 (0.6); 2.2281 (0.7); 2.2194 (0.4); 2.1710 (0.3); 2.1531 (0.6); 2.1420 (0.7); 2.1249 (1.2); 2.1078 (0.8); 2.0965 (0.9); 2.0831 (3.5); 2.0579 (0.6); 2.0519 (0.7); 2.0378 (0.7); 2.0307 (1.4); 2.0207 (1.6); 2.0086 (1.9); 2.0025 (2.4); 1.9921 (1.8); 1.9860 (1.4); 1.9635 (0.6); 1.9595 (0.6); 1.9500 (0.5); 1.8559 (0.4); 1.8338 (0.8); 1.8265 (0.9); 1.8173 (0.7); 1.8078 (0.6); 1.7991 (0.4); 1.3201 (0.5); 1.2962 (1.0); 1.2725 (0.4); 1.0892 (0.8); 1.0751 (1.8); 1.0686 (2.0); 1.0550 (1.4); 1.0468 (1.9); 1.0403 (1.9); 1.0268 (1.0); 0.9968 (0.5); 0.9723 (0.9); 0.9478 (0.4); 0.8330 (1.0); 0.8155 (2.4); 0.8019 (2.3); 0.7820 (0.7); 0.1808 (0.4); 0.1757 (0.4); 0.1696 (0.4); 0.1095 (0.3); 0.0373 (3.0)

I-194: $^{1}$H-NMR(300.1 MHz, $d_6$-DMSO):
δ = 11.1329 (3.6); 8.2414 (16.0); 7.8090 (5.9); 7.7810 (1.0); 7.7555 (3.2); 7.7300 (5.4); 7.7122 (5.9); 7.6950 (5.4); 7.6717 (7.8); 7.6628 (9.3); 7.6556 (8.7); 7.6439 (7.6); 7.4971 (4.6); 7.4902 (4.2); 7.4690 (3.4); 7.4621 (3.2); 5.2573 (2.2); 5.2397 (2.5); 5.2122 (2.7); 5.1946 (2.2); 3.3274 (2.6); 2.7605 (1.8); 2.7426 (2.1); 2.7304 (0.4); 2.7234 (0.3); 2.7055 (2.9); 2.6878 (2.6); 2.5317 (3.7); 2.5097 (21.9); 2.5040 (28.0); 2.4983 (20.0); 2.4772 (2.6); 2.4317 (2.1); 2.0772 (5.8); −0.0001 (4.3)

I-195: $^{1}$H-NMR(400.2 MHz, $d_6$-DMSO):
δ = 10.0195 (2.3); 8.2622 (16.0); 7.7817 (1.1); 7.7626 (3.3); 7.7421 (3.8); 7.7200 (10.7); 7.7042 (2.4); 7.6810 (3.8); 7.6575 (9.8); 7.6361 (10.2); 7.4643 (10.8); 7.4431 (8.9); 5.2581 (2.0); 5.2477 (2.2); 5.2269 (2.3); 5.2163 (2.1); 4.0946 (0.6); 3.7996 (2.0); 3.7889 (2.2); 3.7658 (2.7); 3.7552 (2.4); 3.5227 (2.2); 3.4901 (3.4); 3.4574 (1.8); 3.3292 (14.2); 3.1609 (0.3); 2.8905 (1.6); 2.7309 (1.4); 2.6708 (0.4); 2.6670 (0.4); 2.5106 (24.6); 2.5064 (49.0); 2.5020 (65.0); 2.4975 (47.2); 2.4934 (23.2); 2.4441 (0.4); 2.3331 (0.4); 2.3286 (0.4); 2.3240 (0.3); 2.0762 (3.1); 0.0081 (0.3); 0.0000 (8.0)

I-196: $^{1}$H-NMR(499.9 MHz, CDCl3):
δ = 8.1061 (6.7); 7.2601 (6.1); 7.1886 (3.4); 7.1855 (4.3); 7.1563 (3.3); 6.9955 (2.6); 6.9802 (3.0); 6.9608 (3.2); 6.7899 (1.8); 6.7750 (1.6); 5.9616 (2.0); 4.2837 (1.3); 4.2770 (1.5); 4.2620 (1.5); 4.2553 (1.6); 3.9031 (0.6); 3.8990 (0.7); 3.8949 (0.9); 3.8906 (0.8); 3.8832 (1.0); 3.8795 (0.8); 3.8752 (0.8); 3.8633 (0.4); 3.8174 (1.9); 3.8049 (1.5); 3.7957 (1.8); 3.7832 (1.4); 3.0129 (1.1); 3.0037 (1.2); 2.9853 (1.4); 2.9761 (1.4); 2.7178 (1.5); 2.6975 (1.5); 2.6903 (1.4); 2.6699 (1.2); 2.2848 (16.0); 2.2322 (15.1); 2.1687 (0.9); 1.5633 (5.0); 0.0059 (0.4); −0.0002 (7.1)

I-197: $^{1}$H-NMR(499.9 MHz, CDCl3):
δ = 8.6129 (2.8); 8.5973 (2.7); 8.5222 (0.8); 8.4418 (0.7); 8.3317 (2.8); 8.3157 (2.8); 8.1354 (6.6); 7.9525 (0.7); 7.2620 (4.7); 6.9665 (2.7); 6.9513 (3.0); 6.9397 (0.5); 6.8818 (3.6); 6.7244 (2.0); 6.7093 (1.7); 5.8554 (2.2); 4.3135 (1.4); 4.3070 (1.5); 4.2918 (1.6); 4.2853 (1.5); 3.9004 (1.0); 3.8948 (1.0); 3.8890 (1.0); 3.8813 (0.8); 3.8300 (2.0); 3.8174 (1.5); 3.8083 (1.8); 3.7957 (1.3); 3.0382 (0.3); 3.0256 (1.3); 3.0160 (1.2); 2.9982 (1.6); 2.9886 (1.4); 2.7155 (1.5); 2.6953 (1.6); 2.6883 (1.4); 2.6680 (1.2); 2.3885 (0.6); 2.2738 (16.0); 2.2587 (0.9); 2.2436 (1.8); 2.1538 (15.4); 2.1422 (2.3); 2.0042 (6.7); 1.5956 (5.1); −0.0002 (5.7)

I-198: $^{1}$H-NMR(499.9 MHz, CDCl3):
δ = 8.3713 (3.3); 8.3687 (3.6); 8.1234 (3.2); 8.1185 (3.4); 8.1094 (6.3); 7.2615 (5.8); 7.0288 (1.9); 7.0247 (3.2); 7.0211 (2.2); 6.9419 (2.6); 6.9266 (2.9); 6.8872 (3.4); 6.6802 (1.8); 6.6651 (1.6); 6.0662 (2.2); 4.2829 (1.3); 4.2764 (1.4); 4.2613 (1.5); 4.2548 (1.5); 3.8778 (0.6); 3.8686 (0.9); 3.8584 (0.9); 3.8489 (0.7); 3.8086 (1.9); 3.7959 (1.3); 3.7870 (1.7); 3.7743 (1.2); 3.0064 (1.1); 2.9969 (1.2); 2.9790 (1.4); 2.9695 (1.3); 2.6971 (1.4); 2.6772 (1.4); 2.6698 (1.3); 2.6498 (1.2); 2.2634 (16.0); 2.1781 (15.3); 2.0038 (4.3); 1.9860 (0.4); 1.9759 (0.8); 1.9689 (0.9); 1.9591 (1.5); 1.9493 (1.0); 1.9424 (0.8); 1.9322 (0.4); 1.6075 (0.8); 1.1130 (0.8); 1.1013 (2.8); 1.0872 (2.6); 1.0845 (2.7); 1.0751 (0.8); 0.7733 (1.0); 0.7632 (3.2); 0.7526 (3.1); 0.7422 (0.9); −0.0002 (6.7)

I-199: $^{1}$H-NMR(400.2 MHz, $d_6$-DMSO):
δ = 8.0368 (10.5); 7.9520 (1.4); 7.5037 (0.4); 7.4984 (2.5); 7.4933 (1.0); 7.4795 (4.4); 7.4777 (4.2); 7.4632 (1.4); 7.4586 (3.7); 7.4528 (0.6); 7.4314 (2.0); 7.4243 (2.0); 7.3185 (1.7); 7.3161 (1.1); 7.3000 (2.8); 7.2840 (0.7); 7.2815 (1.2); 7.2790 (0.7); 7.2519 (4.1); 7.2491 (5.0); 7.2441 (1.3); 7.2302 (4.2); 7.2281 (3.5); 7.2216 (0.4); 7.0504 (2.7); 7.0312 (3.2); 6.9337 (3.2); 6.8020 (1.7); 6.7830 (1.5); 3.7570 (0.6); 3.7389 (1.6); 3.7292 (4.6); 3.7217 (3.3); 3.7100 (1.3); 3.7009 (1.7); 3.6821 (0.4); 3.3374 (62.1); 2.8904 (10.0); 2.8113 (0.4); 2.7942 (1.7); 2.7844 (2.2); 2.7796 (2.1); 2.7679 (1.9); 2.7504 (0.3); 2.7322 (8.6); 2.7314 (8.2); 2.5248 (0.7); 2.5199 (1.0); 2.5113 (13.1); 2.5069 (25.9); 2.5023 (33.6); 2.4977 (24.4); 2.4933 (11.9); 2.2340 (16.0); 2.1914 (14.7); −0.0002 (7.4)

I-200: $^{1}$H-NMR(400.2 MHz, $d_6$-DMSO):
δ = 8.0264 (10.8); 7.9518 (1.2); 7.4085 (2.1); 7.4010 (2.0); 7.3687 (1.5); 7.3493 (3.2); 7.3300 (1.9); 7.1216 (2.1); 7.1027 (1.8); 7.0468 (4.7); 7.0445 (4.3); 7.0405 (4.8); 7.0289 (3.4); 7.0199 (1.7); 6.9388 (3.2); 6.8064

TABLE 2-continued (1.7); 6.7874 (1.5); 3.7542 (0.6); 3.7361 (1.6); 3.7260 (4.4); 3.7178 (3.2); 3.7058 (1.2); 3.6969 (1.8); 3.6783 (0.4); 3.3317 (40.4); 2.8901 (9.1); 2.7874 (1.9); 2.7811 (2.2); 2.7722 (2.0); 2.7639 (2.0); 2.7312 (7.8); 2.5244 (0.7); 2.5196 (1.0); 2.5109 (12.6); 2.5065 (25.4); 2.5019 (33.5); 2.4973 (24.5); 2.4928 (12.1); 2.3452 (15.8); 2.3289 (0.4); 2.2333 (16.0); 2.1965 (14.6); −0.0002 (6.0)
I-201: $^{1}$H-NMR(400.2 MHz, $d_6$-DMSO):
δ = 8.0473 (10.7); 7.9521 (2.0); 7.5156 (1.4); 7.4960 (3.6); 7.4762 (3.0); 7.4320 (1.7); 7.4290 (3.0); 7.4260 (2.2); 7.4130 (1.1); 7.4097 (2.0); 7.4068 (1.3); 7.3845 (2.8); 7.3790 (5.2); 7.3757 (4.2); 7.3702 (2.3); 7.3388 (1.8); 7.3362 (1.9); 7.3330 (1.6); 7.3303 (1.4); 7.3186 (1.4); 7.3159 (1.4); 7.3127 (1.4); 7.3100 (1.2); 7.0405 (2.8); 7.0213 (3.3); 6.9225 (3.3); 6.7801 (1.7); 6.7622 (1.5); 4.3067 (8.3); 3.7743 (0.4); 3.7558 (2.1); 3.7467 (4.4); 3.7315 (1.0); 3.7224 (1.4); 3.7167 (1.2); 3.7042 (0.8); 3.6954 (0.5); 3.3311 (34.2); 2.8906 (14.9); 2.7890 (3.5); 2.7722 (3.5); 2.7315 (12.4); 2.5248 (0.7); 2.5199 (1.0); 2.5114 (14.0); 2.5069 (28.3); 2.5024 (37.2); 2.4978 (27.3); 2.4933 (13.5); 2.2285 (16.0); 2.1921 (14.8); −0.0002 (8.1)
I-202: $^{1}$H-NMR(400.2 MHz, $d_6$-DMSO):
δ = 10.0480 (10.1); 8.0739 (11.2); 7.9525 (2.0); 7.8987 (1.3); 7.8957 (2.2); 7.8926 (1.5); 7.8799 (1.8); 7.8767 (2.9); 7.8737 (1.9); 7.7946 (0.4); 7.7893 (2.5); 7.7836 (3.1); 7.7800 (2.6); 7.7526 (2.0); 7.7327 (3.6); 7.7135 (2.2); 7.6308 (1.8); 7.6282 (2.0); 7.6247 (1.8); 7.6221 (1.8); 7.6105 (1.4); 7.6079 (1.4); 7.6044 (1.4); 7.6018 (1.2); 7.4569 (2.1); 7.4489 (2.1); 7.0457 (2.8); 7.0265 (3.2); 6.9114 (3.2); 6.7744 (1.7); 6.7554 (1.5); 3.7486 (6.2); 3.7310 (1.2); 3.7222 (1.1); 3.7126 (0.8); 3.7038 (0.5); 3.3315 (31.6); 2.8910 (14.7); 2.7923 (2.5); 2.7804 (2.1); 2.7753 (2.3); 2.7326 (12.1); 2.7315 (12.4); 2.5252 (0.8); 2.5206 (1.1); 2.5118 (14.1); 2.5073 (28.7); 2.5027 (37.8); 2.4981 (27.6); 2.4936 (13.5); 2.2683 (0.4); 2.2273 (16.0); 2.1696 (14.7); −0.0002 (8.6)
I-203: $^{1}$H-NMR(400.2 MHz, $d_6$-DMSO):
δ = 8.0265 (9.6); 7.9520 (0.8); 7.4125 (2.0); 7.4052 (2.0); 7.3939 (1.9); 7.3743 (3.6); 7.3548 (2.3); 7.1564 (2.1); 7.1372 (1.8); 7.0756 (3.2); 7.0524 (4.0); 7.0330 (4.5); 6.9366 (3.2); 6.7952 (1.7); 6.7765 (1.5); 3.7550 (0.6); 3.7369 (1.6); 3.7271 (4.5); 3.7192 (3.2); 3.7066 (1.2); 3.6980 (1.7); 3.6792 (0.4); 3.3299 (26.4); 2.8901 (5.5); 2.7824 (2.3); 2.7723 (2.1); 2.7650 (2.0); 2.7313 (4.8); 2.6775 (1.4); 2.6587 (4.2); 2.6397 (4.3); 2.6207 (1.5); 2.5243 (0.6); 2.5195 (1.0); 2.5108 (12.2); 2.5064 (24.5); 2.5018 (32.2); 2.4973 (23.7); 2.4928 (11.7); 2.2335 (16.0); 2.1907 (14.7); 1.2369 (0.4); 1.2211 (6.6); 1.2022 (13.9); 1.1832 (6.3); −0.0002 (5.3)
I-204: $^{1}$H-NMR(400.2 MHz, $d_6$-DMSO):
δ = 8.0331 (6.6); 7.9520 (0.8); 7.4001 (1.2); 7.3915 (2.3); 7.3710 (2.5); 7.3505 (1.4); 7.0489 (1.6); 7.0297 (1.9); 6.9333 (1.8); 6.8935 (0.8); 6.8917 (1.0); 6.8875 (1.1); 6.8857 (1.2); 6.8728 (0.8); 6.8711 (0.8); 6.8667 (1.1); 6.8649 (1.1); 6.8418 (1.3); 6.8363 (2.6); 6.8306 (1.5); 6.8213 (1.3); 6.8194 (1.4); 6.8159 (0.9); 6.8139 (0.9); 6.8015 (1.6); 6.7997 (1.4); 6.7958 (1.1); 6.7938 (1.1); 6.7890 (0.9); 3.7654 (16.0); 3.7419 (1.0); 3.7302 (1.6); 3.7171 (1.8); 3.7100 (0.9); 3.6966 (0.9); 3.6908 (0.6); 3.3311 (21.3); 2.8903 (5.6); 2.7866 (1.1); 2.7804 (1.3); 2.7715 (1.1); 2.7638 (1.2); 2.7322 (4.7); 2.7310 (4.8); 2.5244 (0.4); 2.5197 (0.6); 2.5111 (7.1); 2.5066 (14.4); 2.5020 (19.0); 2.4974 (14.0); 2.4929 (6.8); 2.2330 (9.3); 2.1933 (8.5); −0.0002 (4.4)
I-205: $^{1}$H-NMR(400.2 MHz, $d_6$-DMSO):
δ = 8.0824 (9.6); 7.9525 (1.5); 7.4187 (2.1); 7.4107 (2.0); 7.2695 (0.5); 7.2649 (0.6); 7.2527 (1.2); 7.2467 (1.5); 7.2389 (1.0); 7.2303 (1.5); 7.2154 (1.8); 7.2103 (1.3); 7.2010 (5.9); 7.1932 (1.2); 7.1845 (2.4); 7.1641 (0.6); 7.0566 (2.7); 7.0374 (3.2); 6.9327 (3.2); 6.8270 (1.7); 6.8094 (1.5); 3.7812 (0.4); 3.7628 (2.0); 3.7536 (4.3); 3.7383 (1.0); 3.7290 (1.4); 3.7232 (1.2); 3.7108 (0.8); 3.7021 (0.5); 3.3305 (28.1); 2.8906 (10.9); 2.8474 (0.3); 2.8297 (0.4); 2.8124 (1.7); 2.7995 (2.5); 2.7834 (1.8); 2.7662 (0.4); 2.7498 (0.3); 2.7319 (9.3); 2.5248 (0.6); 2.5199 (1.0); 2.5114 (12.4); 2.5070 (24.8); 2.5025 (32.6); 2.4979 (23.9); 2.4935 (11.8); 2.3001 (9.3); 2.2961 (9.4); 2.2416 (16.0); 2.1921 (14.6); −0.0002 (5.8)
I-206: $^{1}$H-NMR(400.2 MHz, $d_6$-DMSO):
δ = 8.0006 (7.9); 7.9492 (4.5); 7.9478 (4.4); 7.5006 (4.2); 7.4990 (4.1); 7.4429 (1.3); 7.4348 (1.3); 7.0869 (1.6); 7.0678 (2.0); 6.9731 (2.0); 6.8823 (1.1); 6.8637 (0.9); 4.5285 (0.4); 4.5118 (1.1); 4.4952 (1.5); 4.4786 (1.1); 4.4619 (0.4); 3.7362 (3.5); 3.7231 (0.6); 3.7136 (0.8); 3.7077 (0.6); 3.7043 (0.6); 3.6964 (0.5); 3.3280 (34.5); 2.8907 (3.6); 2.8391 (0.3); 2.8214 (0.9); 2.8049 (1.0); 2.7984 (1.1); 2.7805 (1.0); 2.7321 (3.0); 2.7308 (3.0); 2.5244 (0.7); 2.5196 (1.1); 2.5109 (13.7); 2.5064 (27.6); 2.5019 (36.0); 2.4973 (26.3); 2.4928 (12.8); 2.2561 (10.0); 2.2176 (9.1); 1.4407 (16.0); 1.4240 (15.8); −0.0002 (7.4)
I-207: $^{1}$H-NMR(400.2 MHz, $d_6$-DMSO):
δ = 8.1276 (10.9); 7.9532 (1.4); 7.4903 (0.4); 7.4864 (0.5); 7.4688 (1.1); 7.4651 (1.1); 7.4602 (0.8); 7.4499 (2.7); 7.4477 (2.7); 7.4428 (2.8); 7.4257 (0.6); 7.4218 (0.6); 7.3744 (0.5); 7.3696 (0.5); 7.3596 (0.5); 7.3535 (1.1); 7.3486 (1.1); 7.3386 (1.0); 7.3343 (1.2); 7.3275 (0.6); 7.3174 (0.6); 7.3138 (0.6); 7.2930 (0.8); 7.2890 (1.3); 7.2856 (0.9); 7.2726 (1.5); 7.2686 (1.3); 7.2518 (0.8); 7.0621 (2.7); 7.0429 (3.2); 6.9302 (3.2); 6.8394 (1.7); 6.8204 (1.5); 3.7606 (6.4); 3.7425 (1.2); 3.7337 (1.0); 3.7240 (0.7); 3.7153 (0.5); 3.3319 (32.7); 2.8914 (10.8); 2.8554 (0.4); 2.8376 (0.5); 2.8207 (1.5); 2.8045 (3.1); 2.7874 (1.8); 2.7698 (0.4); 2.7536 (0.4); 2.7331 (8.6); 2.7322 (9.0); 2.5257 (0.7); 2.5210 (1.1); 2.5122 (12.6); 2.5078 (25.3); 2.5032 (33.1); 2.4986 (24.2); 2.4941 (11.8); 2.2429 (16.0); 2.1931 (14.6); −0.0002 (6.6)
I-208: $^{1}$H-NMR(400.2 MHz, $d_6$-DMSO):
δ = 11.2170 (2.0); 8.3156 (0.3); 7.9940 (10.5); 7.9519 (0.4); 7.4546 (3.5); 7.4481 (2.4); 7.4404 (2.3); 7.4329 (3.9); 7.4220 (3.6); 7.4151 (2.3); 7.3697 (3.6); 7.3641 (3.7); 7.0650 (2.8); 7.0458 (3.2); 6.9717 (2.4); 6.9660 (2.3); 6.9500 (2.3); 6.9441 (2.5); 6.9346 (3.3); 6.8085 (1.7); 6.7896 (1.5); 6.4575 (1.9); 6.4523 (2.8); 6.4472 (1.9); 3.7882 (0.3); 3.7768 (1.0); 3.7584 (1.7); 3.7468 (1.8); 3.7335 (1.6); 3.7253 (2.9); 3.7107 (1.2); 3.7046 (1.7); 3.3360 (50.2); 2.8891 (3.1); 2.8419 (0.3); 2.8253 (0.4); 2.8077 (1.6); 2.7936 (2.6); 2.7782 (1.7); 2.7609 (0.4); 2.7316 (2.6); 2.7307 (2.6); 2.5242 (0.8); 2.5195 (1.2); 2.5108 (14.7); 2.5064 (29.2); 2.5018 (38.1); 2.4972 (27.8); 2.4927 (13.6); 2.2397 (16.0); 2.1770 (14.6); −0.0002 (7.5)
I-209: $^{1}$H-NMR(400.2 MHz, $d_6$-DMSO):
δ = 8.0448 (10.4); 7.9522 (1.6); 7.3686 (2.0); 7.3613 (2.0); 7.2510 (1.1); 7.2321 (2.9); 7.2129 (2.4); 7.1842 (2.9); 7.1667 (1.5); 7.0486 (2.8); 7.0294 (3.2); 7.0069 (2.6); 6.9875 (2.2); 6.9326 (3.2); 6.8133 (1.7); 6.7943 (1.5); 3.7669 (0.8); 3.7490 (1.6); 3.7374 (4.0); 3.7278 (3.3); 3.7195 (1.4); 3.7077 (1.6); 3.7007 (1.0); 3.6916 (0.4); 3.3306 (31.7); 2.9548 (1.8); 2.9364 (3.5); 2.9178 (1.9); 2.8904 (12.2); 2.8148 (0.3); 2.7972 (1.6); 2.7885 (2.2); 2.7823 (2.0); 2.7720 (1.9); 2.7319 (10.0); 2.7314 (10.0); 2.5975 (1.1); 2.5881 (1.1); 2.5790 (2.2); 2.5698 (2.1); 2.5603 (1.2); 2.5517 (1.2); 2.5287 (0.4); 2.5247 (0.8); 2.5198 (1.1); 2.5111 (13.0); 2.5067 (26.1); 2.5021 (34.3); 2.4975 (25.0); 2.4930 (12.3); 2.2342 (16.0); 2.1938 (14.6); 2.0208 (0.6); 2.0024 (2.2); 1.9839 (3.1); 1.9652 (2.0); 1.9462 (0.5); −0.0002 (6.9)
I-210: $^{1}$H-NMR(400.2 MHz, $d_6$-DMSO):
δ = 8.0074 (10.5); 7.9519 (1.7); 7.3966 (2.1); 7.3890 (2.1); 7.2947 (2.5); 7.2744 (2.8); 7.0710 (2.9); 7.0662 (3.1); 7.0481 (2.7); 7.0290 (3.2); 6.9804 (2.0); 6.9747 (1.8); 6.9601 (1.8); 6.9545 (1.7); 6.9401 (3.3); 6.8091 (1.7); 6.7907 (1.5); 3.7603 (0.8); 3.7421 (1.7); 3.7305 (3.1); 3.7196 (3.0); 3.7040 (1.2); 3.6971 (1.7); 3.6859

TABLE 2-continued (0.8); 3.6770 (0.4); 3.3299 (34.2); 2.9003 (3.1); 2.8902 (14.4); 2.8827 (5.8); 2.8639 (3.1); 2.7874 (2.1); 2.7820 (2.2); 2.7719 (2.2); 2.7644 (2.0); 2.7475 (0.3); 2.7315 (10.5); 2.5242 (0.8); 2.5193 (1.2); 2.5108 (14.2); 2.5064 (27.9); 2.5018 (36.1); 2.4972 (26.3); 2.4928 (12.8); 2.2348 (16.0); 2.1965 (14.6); 2.1091 (0.7); 2.0906 (2.4); 2.0720 (3.4); 2.0538 (2.3); 2.0353 (0.6); −0.0002 (6.9)

I-211: $^1$H-NMR(400.2 MHz, $d_6$-DMSO):
δ = 8.2211 (2.9); 8.2148 (3.1); 8.0498 (10.1); 7.9522 (2.0); 7.5363 (2.7); 7.5303 (2.8); 7.4099 (2.0); 7.4021 (2.0); 7.0500 (2.7); 7.0308 (3.1); 6.9279 (3.1); 6.7980 (1.7); 6.7800 (1.4); 3.7805 (0.4); 3.7622 (1.9); 3.7526 (4.4); 3.7291 (1.3); 3.7235 (1.3); 3.7134 (0.8); 3.7044 (0.5); 3.3397 (13.4); 2.9659 (1.8); 2.9488 (4.9); 2.9307 (5.5); 2.9120 (2.4); 2.8910 (14.5); 2.8169 (0.3); 2.7951 (2.4); 2.7832 (2.1); 2.7776 (2.2); 2.7323 (12.1); 2.7314 (11.7); 2.5248 (0.8); 2.5201 (1.2); 2.5115 (14.0); 2.5070 (28.4); 2.5024 (37.4); 2.4978 (27.4); 2.4934 (13.5); 2.2620 (0.4); 2.2349 (16.0); 2.1900 (14.3); 2.1601 (2.4); 2.1411 (3.2); 2.1225 (2.2); 2.1035 (0.6); −0.0002 (7.3)

I-212: $^1$H-NMR(400.2 MHz, $d_6$-DMSO):
δ = 7.9916 (11.5); 7.3976 (2.1); 7.3898 (2.1); 7.1111 (2.8); 7.1050 (3.0); 7.0593 (2.7); 7.0401 (3.2); 6.9477 (4.5); 6.9328 (2.2); 6.9264 (2.1); 6.8286 (1.8); 6.8188 (5.0); 6.8128 (1.7); 6.7975 (3.6); 4.6007 (2.6); 4.5789 (5.6); 4.5571 (2.8); 3.7697 (0.7); 3.7515 (1.8); 3.7406 (3.5); 3.7310 (3.1); 3.7219 (1.0); 3.7113 (1.6); 3.7054 (1.5); 3.6939 (0.8); 3.6849 (0.5); 3.3317 (37.3); 3.2348 (1.9); 3.2132 (3.7); 3.1915 (1.8); 2.8903 (1.3); 2.7971 (2.0); 2.7908 (2.2); 2.7814 (2.1); 2.7735 (1.9); 2.7319 (1.1); 2.5243 (0.7); 2.5196 (1.0); 2.5109 (12.6); 2.5065 (25.4); 2.5019 (33.3); 2.4973 (24.3); 2.4928 (11.8); 2.2400 (16.0); 2.2038 (14.7); −0.0002 (6.8)

I-213: $^1$H-NMR(400.2 MHz, $d_6$-DMSO):
δ = 8.0603 (7.4); 7.9523 (1.2); 7.9360 (0.9); 7.9327 (1.3); 7.9297 (1.0); 7.9168 (1.1); 7.9132 (1.5); 7.9105 (1.1); 7.8173 (1.6); 7.8123 (2.2); 7.8077 (1.6); 7.6678 (1.2); 7.6479 (2.5); 7.6283 (1.5); 7.5541 (1.2); 7.5517 (1.3); 7.5482 (1.2); 7.5458 (1.2); 7.5339 (0.9); 7.5315 (0.9); 7.5279 (0.9); 7.5255 (0.8); 7.4515 (1.4); 7.4436 (1.3); 7.0477 (1.8); 7.0285 (2.0); 6.9130 (2.0); 6.7775 (1.1); 6.7589 (1.0); 3.7611 (1.2); 3.7517 (2.9); 3.7401 (0.8); 3.7272 (0.8); 3.7225 (0.9); 3.7122 (0.5); 3.3317 (27.3); 2.8908 (8.4); 2.7929 (1.7); 2.7791 (1.5); 2.7755 (1.5); 2.7324 (6.9); 2.7313 (7.1); 2.6060 (16.0); 2.5250 (0.6); 2.5201 (0.8); 2.5115 (9.5); 2.5070 (18.9); 2.5025 (24.6); 2.4978 (17.9); 2.4933 (8.7); 2.2283 (10.2); 2.1703 (9.4); −0.0002 (5.0)

I-214: $^1$H-NMR(400.2 MHz, $d_6$-DMSO):
δ = 8.0246 (11.2); 7.9522 (0.5); 7.4096 (2.1); 7.4020 (2.1); 7.3878 (1.4); 7.3687 (2.7); 7.3673 (2.8); 7.3482 (1.7); 7.1339 (2.3); 7.1145 (1.9); 7.0534 (8.3); 7.0339 (4.8); 6.9353 (3.2); 6.7911 (1.7); 6.7732 (1.5); 3.7551 (0.6); 3.7370 (1.7); 3.7274 (4.4); 3.7200 (3.3); 3.7063 (1.2); 3.6980 (1.6); 3.6876 (0.8); 3.6787 (0.5); 3.3301 (32.0); 2.8903 (3.9); 2.7822 (2.3); 2.7714 (2.1); 2.7648 (2.1); 2.7322 (3.4); 2.7312 (3.4); 2.6117 (2.4); 2.5933 (3.5); 2.5738 (2.6); 2.5245 (0.7); 2.5197 (1.0); 2.5110 (12.6); 2.5066 (25.5); 2.5020 (33.4); 2.4974 (24.4); 2.4929 (12.0); 2.2315 (16.0); 2.1900 (14.7); 1.6579 (0.4); 1.6394 (1.7); 1.6207 (2.9); 1.6017 (2.9); 1.5832 (1.7); 1.5649 (0.4); 0.9287 (6.3); 0.9105 (12.9); 0.8921 (5.7); −0.0002 (7.1)

I-215: $^1$H-NMR(400.2 MHz, $d_6$-DMSO):
δ = 8.0036 (3.9); 7.9519 (0.6); 7.3949 (0.8); 7.3877 (0.8); 7.2556 (0.7); 7.2352 (1.4); 7.2148 (0.9); 7.0527 (1.0); 7.0335 (1.2); 6.9399 (1.2); 6.8189 (0.6); 6.7998 (0.6); 6.6436 (0.6); 6.6377 (0.6); 6.6227 (0.5); 6.6173 (0.6); 6.5457 (0.8); 6.5400 (1.4); 6.5343 (0.8); 6.4784 (0.7); 6.4737 (0.6); 6.4587 (0.6); 6.4543 (0.6); 3.7603 (0.4); 3.7418 (0.6); 3.7302 (0.6); 3.7051 (1.1); 3.6920 (0.5); 3.6846 (0.6); 3.3289 (28.5); 2.9018 (16.0); 2.8905 (4.2); 2.7770 (0.9); 2.7660 (0.8); 2.7609 (0.8); 2.7312 (3.5); 2.5241 (0.5); 2.5193 (0.8); 2.5107 (9.8); 2.5063 (19.7); 2.5018 (25.8); 2.4972 (18.9); 2.4928 (9.4); 2.2351 (6.0); 2.1947 (5.5); −0.0002 (4.8)

I-216: $^1$H-NMR(400.2 MHz, $d_6$-DMSO):
δ = 8.0306 (11.3); 7.9521 (1.1); 7.3869 (2.2); 7.3794 (2.2); 7.3736 (2.4); 7.3532 (3.9); 7.3328 (2.2); 7.0455 (2.8); 7.0263 (3.2); 6.9329 (3.2); 6.8705 (1.6); 6.8665 (1.8); 6.8648 (1.8); 6.8500 (1.4); 6.8456 (1.9); 6.8441 (1.8); 6.8187 (2.0); 6.8133 (4.2); 6.8051 (4.3); 6.8032 (4.3); 6.8000 (3.0); 6.7848 (3.3); 6.7834 (3.4); 6.7798 (2.9); 4.0477 (1.6); 4.0303 (5.3); 4.0128 (5.4); 3.9954 (1.7); 3.7596 (0.9); 3.7416 (1.7); 3.7301 (2.6); 3.7254 (2.3); 3.7160 (3.2); 3.7078 (1.4); 3.6959 (1.7); 3.6888 (1.1); 3.6807 (0.4); 3.3307 (38.4); 2.8904 (8.2); 2.7797 (2.4); 2.7676 (2.2); 2.7628 (2.2); 2.7320 (6.9); 2.5245 (0.7); 2.5197 (1.1); 2.5110 (13.6); 2.5066 (27.4); 2.5021 (35.7); 2.4975 (26.0); 2.4930 (12.7); 2.2311 (16.0); 2.1930 (14.7); 1.3440 (5.9); 1.3266 (12.4); 1.3092 (5.7); −0.0002 (7.1)

I-217: $^1$H-NMR(400.2 MHz, $d_6$-DMSO):
δ = 8.0319 (11.6); 7.9519 (0.7); 7.4689 (1.8); 7.4493 (3.8); 7.4297 (4.0); 7.2481 (2.2); 7.2290 (1.9); 7.2092 (2.0); 7.2044 (3.1); 7.1715 (1.8); 7.1673 (1.4); 7.1515 (1.4); 7.1472 (1.3); 7.0501 (2.8); 7.0310 (3.2); 6.9354 (3.2); 6.8018 (1.7); 6.7844 (1.4); 4.4582 (11.5); 3.7587 (0.4); 3.7405 (2.0); 3.7310 (4.4); 3.7178 (1.1); 3.7073 (1.3); 3.7013 (1.2); 3.6904 (0.8); 3.6817 (0.5); 3.3313 (38.8); 3.3211 (34.2); 2.8902 (5.2); 2.7862 (2.4); 2.7741 (2.1); 2.7688 (2.2); 2.7321 (4.3); 2.7310 (4.2); 2.5244 (0.7); 2.5196 (1.1); 2.5110 (12.6); 2.5065 (25.7); 2.5019 (34.0); 2.4973 (24.8); 2.4927 (12.1); 2.2331 (16.0); 2.1917 (14.6); −0.0002 (7.2)

I-218: $^1$H-NMR(400.2 MHz, $d_6$-DMSO):
δ = 8.2138 (1.0); 8.2082 (2.0); 8.2054 (1.1); 8.2014 (2.3); 8.1983 (2.5); 8.1952 (4.1); 8.1933 (6.3); 8.1885 (6.6); 8.1787 (0.4); 8.0908 (12.9); 7.9527 (2.1); 7.8229 (0.5); 7.8200 (0.4); 7.8026 (3.4); 7.7965 (3.4); 7.7912 (4.1); 7.7877 (3.7); 7.7846 (6.3); 7.7755 (0.6); 7.4419 (2.0); 7.4338 (2.0); 7.0467 (2.8); 7.0275 (3.2); 6.8947 (3.2); 6.7646 (1.7); 6.7457 (1.5); 3.7702 (6.3); 3.7551 (1.2); 3.7465 (1.0); 3.7370 (0.7); 3.7284 (0.5); 3.3324 (44.2); 2.8915 (15.4); 2.8001 (3.0); 2.7835 (2.9); 2.7331 (12.8); 2.7318 (13.0); 2.5256 (0.8); 2.5209 (1.2); 2.5122 (14.0); 2.5077 (28.2); 2.5031 (37.0); 2.4984 (26.8); 2.4939 (12.8); 2.2239 (16.0); 2.1581 (14.7); −0.0002 (8.4)

I-219: $^1$H-NMR(400.2 MHz, $d_6$-DMSO):
δ = 10.2376 (7.3); 8.1356 (10.4); 7.9526 (1.9); 7.8429 (0.8); 7.8389 (1.0); 7.8276 (1.0); 7.8237 (1.8); 7.8195 (1.2); 7.8085 (1.0); 7.8044 (1.0); 7.7818 (0.8); 7.7778 (0.9); 7.7620 (1.7); 7.7585 (1.6); 7.7429 (1.1); 7.7388 (0.9); 7.5267 (1.5); 7.5069 (2.6); 7.4870 (1.2); 7.4632 (2.0); 7.4551 (2.0); 7.0633 (2.7); 7.0441 (3.1); 6.9232 (3.2); 6.8321 (1.7); 6.8131 (1.4); 3.7680 (6.2); 3.7512 (1.2); 3.7421 (1.1); 3.7329 (0.8); 3.7241 (0.5); 3.3574 (0.3); 3.3328 (72.2); 2.8913 (13.7); 2.8607 (0.4); 2.8430 (0.5); 2.8260 (1.4); 2.8101 (3.0); 2.7933 (1.8); 2.7760 (0.4); 2.7592 (0.3); 2.7324 (11.4); 2.6717 (0.4); 2.5252 (1.2); 2.5205 (1.7); 2.5118 (20.4); 2.5073 (41.3); 2.5028 (54.4); 2.4982 (40.0); 2.4937 (19.7); 2.3297 (0.4); 2.2431 (16.0); 2.1804 (14.4); 1.2394 (0.6); −0.0002 (10.0)

I-220: $^1$H-NMR(400.2 MHz, $d_6$-DMSO):
δ = 8.0828 (11.1); 7.9528 (1.0); 7.4192 (2.0); 7.4110 (2.0); 7.2919 (0.5); 7.2840 (0.7); 7.2763 (1.2); 7.2678 (1.6); 7.2616 (0.9); 7.2523 (1.4); 7.2465 (0.9); 7.2322 (3.7); 7.2273 (3.6); 7.2231 (2.6); 7.2133 (2.9); 7.0584 (2.8); 7.0392 (3.2); 6.9299 (3.2); 6.8201 (1.7); 6.8018 (1.5); 3.7815 (0.4); 3.7535 (4.8); 3.7386 (1.0); 3.7282 (1.3); 3.7195 (1.0); 3.7111 (0.8); 3.7022 (0.5); 3.3326 (39.5); 2.8908 (7.5); 2.8479 (0.4); 2.8304 (0.4); 2.8132 (1.7); 2.8009 (2.4); 2.7845 (1.8); 2.7674 (0.4); 2.7506 (0.3); 2.7326 (6.2); 2.7317 (6.2); 2.7119 (1.1); 2.6930

TABLE 2-continued (3.3); 2.6742 (3.5); 2.6553 (1.2); 2.5252 (0.7); 2.5204 (1.0); 2.5118 (12.7); 2.5073 (25.7); 2.5027 (33.8); 2.4981 (24.7); 2.4936 (12.1); 2.2417 (16.0); 2.1871 (14.6); 1.2274 (6.1); 1.2086 (13.1); 1.1897 (5.8); −0.0002 (6.8)
I-221: $^1$H-NMR(400.2 MHz, $d_6$-DMSO):
δ = 8.0358 (12.4); 7.9518 (1.4); 7.4278 (2.0); 7.4078 (4.4); 7.3879 (4.7); 7.3812 (2.2); 7.2042 (1.6); 7.2022 (2.0); 7.2000 (2.1); 7.1980 (2.0); 7.1845 (1.4); 7.1824 (1.6); 7.1802 (1.9); 7.1782 (1.7); 7.1533 (2.7); 7.1483 (4.2); 7.1434 (2.4); 7.0447 (2.8); 7.0262 (4.8); 7.0084 (1.7); 7.0064 (1.7); 7.0028 (1.7); 7.0008 (1.6); 6.9315 (3.2); 6.7958 (1.7); 6.7783 (1.5); 3.7715 (0.8); 3.7532 (1.7); 3.7417 (2.9); 3.7296 (3.0); 3.7160 (1.2); 3.7081 (1.9); 3.6886 (0.5); 3.3309 (40.9); 2.8902 (10.6); 2.7854 (3.4); 2.7687 (3.1); 2.7319 (8.5); 2.7310 (8.8); 2.5243 (0.7); 2.5196 (1.2); 2.5109 (13.2); 2.5065 (26.5); 2.5019 (34.6); 2.4973 (25.4); 2.4928 (12.8); 2.4858 (28.2); 2.2310 (16.0); 2.1955 (14.7); −0.0002 (6.7)
I-222: $^1$H-NMR(400.2 MHz, $d_6$-DMSO):
δ = 8.0384 (12.8); 7.4652 (2.7); 7.4442 (3.0); 7.4433 (3.0); 7.3792 (4.2); 7.3731 (4.8); 7.3670 (2.4); 7.3588 (2.1); 7.1791 (2.3); 7.1731 (2.2); 7.1584 (2.1); 7.1524 (2.0); 7.0430 (2.7); 7.0238 (3.2); 6.9261 (3.2); 6.7913 (1.7); 6.7726 (1.5); 3.7755 (0.5); 3.7574 (1.8); 3.7484 (4.2); 3.7428 (3.7); 3.7335 (1.1); 3.7223 (1.4); 3.7164 (1.3); 3.7057 (0.8); 3.6968 (0.5); 3.3295 (28.9); 2.8906 (1.4); 2.7879 (3.4); 2.7710 (3.2); 2.7324 (1.2); 2.7313 (1.2); 2.5248 (0.8); 2.5201 (1.0); 2.5113 (12.5); 2.5068 (25.4); 2.5022 (33.4); 2.4976 (24.6); 2.4931 (12.1); 2.3677 (16.0); 2.2301 (15.8); 2.1921 (14.5); −0.0002 (7.4)
I-223: $^1$H-NMR(400.2 MHz, $d_6$-DMSO):
δ = 8.0803 (10.0); 8.0432 (3.0); 8.0208 (3.3); 8.0060 (1.8); 7.9873 (1.9); 7.9841 (1.8); 7.9529 (2.1); 7.9269 (1.8); 7.9080 (2.0); 7.7449 (3.2); 7.7392 (3.4); 7.5925 (0.6); 7.5889 (0.8); 7.5753 (2.0); 7.5717 (1.8); 7.5574 (3.0); 7.5537 (3.0); 7.5393 (1.8); 7.5357 (1.9); 7.5221 (0.8); 7.5185 (0.6); 7.4777 (2.1); 7.4718 (2.1); 7.4493 (2.4); 7.4434 (2.3); 7.4271 (2.2); 7.4211 (2.2); 7.0478 (2.8); 7.0286 (3.2); 6.9102 (3.3); 6.7676 (1.8); 6.7499 (1.6); 3.7658 (1.0); 3.7472 (1.8); 3.7356 (3.4); 3.7306 (3.1); 3.7218 (2.8); 3.7019 (1.4); 3.3353 (43.9); 2.8900 (14.6); 2.8358 (0.4); 2.8191 (0.4); 2.8017 (1.2); 2.7838 (2.5); 2.7676 (1.6); 2.7502 (0.4); 2.7323 (12.6); 2.5250 (0.8); 2.5117 (13.2); 2.5073 (26.5); 2.5028 (34.9); 2.4982 (25.9); 2.4939 (13.0); 2.2270 (16.0); 2.1406 (14.8); 0.9123 (0.4); −0.0002 (6.4)
I-224: $^1$H-NMR(400.2 MHz, $d_6$-DMSO):
δ = 8.8912 (4.7); 8.8845 (4.8); 8.2638 (3.2); 8.2574 (3.2); 8.1237 (12.4); 8.0984 (2.4); 8.0280 (1.9); 8.0092 (2.1); 8.0071 (2.1); 7.8224 (1.2); 7.8188 (1.3); 7.8051 (1.7); 7.8014 (2.4); 7.7977 (1.2); 7.7840 (1.5); 7.7804 (1.4); 7.7069 (1.5); 7.7041 (1.5); 7.6867 (2.4); 7.6840 (1.6); 7.6693 (1.1); 7.6665 (1.0); 7.4969 (2.0); 7.4903 (1.9); 7.0545 (2.7); 7.0353 (3.1); 6.8868 (3.1); 6.7458 (1.6); 6.7288 (1.5); 3.7921 (0.5); 3.7661 (6.2); 3.7421 (0.9); 3.3314 (265.9); 3.2973 (0.3); 2.8909 (1.7); 2.8520 (0.3); 2.8346 (0.4); 2.8183 (1.1); 2.8015 (2.4); 2.7860 (1.6); 2.7311 (1.4); 2.6802 (0.4); 2.6759 (0.7); 2.6713 (1.0); 2.6668 (0.8); 2.6623 (0.4); 2.5249 (3.1); 2.5201 (4.6); 2.5114 (59.7); 2.5070 (121.3); 2.5024 (159.8); 2.4978 (117.0); 2.4933 (57.5); 2.3381 (0.3); 2.3337 (0.7); 2.3292 (1.0); 2.3247 (0.7); 2.3201 (0.4); 2.2294 (16.0); 2.1116 (14.6); 1.2398 (1.1); 0.0080 (1.0); −0.0002 (33.0); −0.0085 (1.1)
I-225: $^1$H-NMR(400.2 MHz, $d_6$-DMSO):
δ = 8.0839 (12.1); 7.4439 (1.3); 7.4386 (2.0); 7.4335 (1.4); 7.4221 (1.3); 7.4171 (2.0); 7.4118 (1.3); 7.3355 (2.1); 7.3276 (2.1); 7.3131 (1.7); 7.3082 (3.3); 7.3056 (3.3); 7.3011 (1.9); 7.2798 (1.6); 7.2743 (2.2); 7.2689 (1.1); 7.2557 (1.5); 7.2503 (2.3); 7.2448 (1.1); 7.0395 (2.8); 7.0203 (3.2); 6.9201 (3.3); 6.7871 (1.8); 6.7686 (1.5); 3.7514 (6.3); 3.7373 (1.3); 3.7284 (1.2); 3.7187 (0.8); 3.7099 (0.5); 3.3317 (39.5); 2.8910 (1.2); 2.7876 (3.4); 2.7707 (3.3); 2.7327 (1.0); 2.7316 (1.0); 2.5251 (0.7); 2.5204 (1.0); 2.5116 (12.2); 2.5072 (24.6); 2.5026 (32.2); 2.4980 (23.7); 2.4935 (11.7); 2.2265 (16.0); 2.1943 (14.7); −0.0002 (6.8)
I-226: $^1$H-NMR(400.2 MHz, $d_6$-DMSO):
δ = 8.0558 (9.3); 7.9520 (1.7); 7.5986 (1.9); 7.5915 (2.1); 7.5827 (2.1); 7.5754 (3.7); 7.5524 (3.9); 7.5298 (2.1); 7.3616 (2.3); 7.3531 (3.4); 7.3458 (1.8); 7.3433 (1.9); 7.3358 (1.3); 7.3304 (1.2); 7.3207 (1.3); 7.3132 (1.0); 7.0465 (2.7); 7.0273 (3.2); 6.9189 (3.5); 6.7885 (1.9); 6.7693 (1.6); 3.7600 (6.3); 3.7488 (1.3); 3.7385 (1.3); 3.7306 (1.2); 3.7217 (0.8); 3.7130 (0.5); 3.3339 (44.9); 2.8911 (10.6); 2.7958 (3.7); 2.7789 (3.6); 2.7318 (9.7); 2.5073 (23.3); 2.5029 (30.8); 2.4984 (23.5); 2.2299 (16.0); 2.1910 (14.8); −0.0002 (4.1)
I-227: $^1$H-NMR(400.2 MHz, $d_6$-DMSO):
δ = 8.1186 (9.4); 7.9532 (1.6); 7.9091 (0.7); 7.8901 (0.8); 7.8829 (1.3); 7.8642 (1.3); 7.8567 (0.8); 7.8380 (0.6); 7.6990 (0.7); 7.6796 (1.2); 7.6720 (0.8); 7.6605 (0.8); 7.6529 (1.2); 7.6337 (0.6); 7.3903 (2.0); 7.3824 (2.0); 7.0617 (2.6); 7.0426 (3.2); 6.9212 (3.2); 6.8429 (1.7); 6.8234 (1.5); 3.7696 (6.4); 3.7569 (1.3); 3.7477 (1.2); 3.7382 (0.8); 3.7292 (0.6); 3.3311 (25.3); 2.8917 (11.0); 2.8566 (0.4); 2.8383 (0.5); 2.8218 (1.4); 2.8065 (2.8); 2.7903 (1.8); 2.7725 (0.4); 2.7328 (9.4); 2.5256 (0.7); 2.5121 (12.8); 2.5077 (25.2); 2.5032 (32.6); 2.4986 (23.9); 2.4943 (11.8); 2.2696 (0.6); 2.2381 (16.0); 2.1938 (14.2); −0.0002 (6.2)
I-228: $^1$H-NMR(400.2 MHz, $d_6$-DMSO):
δ = 8.0248 (10.7); 7.9519 (1.2); 7.4088 (3.6); 7.4035 (2.2); 7.3890 (3.9); 7.3694 (2.5); 7.1710 (2.1); 7.1518 (1.8); 7.0952 (1.9); 7.0908 (3.3); 7.0519 (4.5); 7.0326 (4.7); 6.9344 (3.2); 6.7839 (1.7); 6.7665 (1.5); 3.7626 (0.7); 3.7445 (1.7); 3.7337 (3.9); 3.7246 (3.1); 3.7091 (1.2); 3.7017 (1.6); 3.6905 (0.8); 3.6818 (0.5); 3.5848 (1.0); 3.5625 (1.5); 3.5406 (1.0); 3.5188 (0.3); 3.3332 (51.8); 2.8903 (9.4); 2.7852 (2.8); 2.7694 (2.4); 2.7313 (7.8); 2.5246 (0.8); 2.5199 (1.1); 2.5112 (13.4); 2.5067 (27.2); 2.5021 (36.0); 2.4975 (26.4); 2.4930 (13.0); 2.3429 (0.7); 2.3363 (0.9); 2.3295 (0.7); 2.3225 (1.4); 2.3155 (2.4); 2.3087 (1.4); 2.3016 (1.2); 2.2947 (2.4); 2.2884 (1.8); 2.2803 (0.7); 2.2742 (1.1); 2.2690 (1.0); 2.2332 (16.0); 2.1878 (14.7); 2.1503 (0.4); 2.1474 (0.4); 2.1437 (0.4); 2.1248 (1.4); 2.1187 (1.0); 2.1011 (2.2); 2.0957 (1.8); 2.0794 (1.5); 2.0727 (1.7); 2.0569 (0.5); 2.0529 (0.5); 2.0506 (0.6); 2.0326 (0.5); 2.0141 (0.9); 2.0087 (0.7); 1.9941 (0.5); 1.9893 (1.4); 1.9819 (0.4); 1.9726 (0.3); 1.9644 (1.3); 1.9458 (0.5); 1.9401 (0.6); 1.8499 (0.4); 1.8444 (0.6); 1.8242 (1.1); 1.8224 (1.1); 1.8178 (0.8); 1.8062 (0.5); 1.8027 (0.8); 1.7991 (0.8); 1.7962 (0.9); −0.0002 (7.1)
I-229: $^1$H-NMR(400.2 MHz, $d_6$-DMSO):
δ = 8.0397 (10.3); 7.9519 (1.4); 7.4946 (1.7); 7.4750 (3.7); 7.4552 (2.6); 7.4273 (2.1); 7.4199 (2.0); 7.3456 (2.2); 7.3261 (1.7); 7.2979 (2.2); 7.2930 (3.4); 7.2887 (2.1); 7.1581 (1.7); 7.1542 (1.6); 7.1524 (1.5); 7.1399 (1.4); 7.1379 (1.5); 7.1341 (1.5); 7.0508 (2.7); 7.0316 (3.2); 6.9303 (3.2); 6.7818 (1.7); 6.7642 (1.5); 4.9745 (2.6); 4.9727 (2.7); 4.9598 (3.1); 4.9578 (3.2); 4.9538 (3.2); 4.9518 (3.1); 4.9390 (3.1); 4.9371 (3.1); 4.6345 (3.9); 4.6186 (6.2); 4.6030 (4.0); 4.3343 (0.5); 4.3139 (1.0); 4.2965 (1.7); 4.2792 (0.9); 4.2764 (0.9); 4.2588 (0.3); 3.7609 (0.6); 3.7428 (1.6); 3.7331 (4.4); 3.7255 (3.2); 3.7117 (1.2); 3.7035 (1.6); 3.6931 (0.8); 3.6842 (0.4); 3.3333 (95.9); 2.8905 (11.0); 2.7836 (2.4); 2.7713 (2.2); 2.7660 (2.1); 2.7311 (9.2); 2.6710 (0.4); 2.5246 (1.1); 2.5198 (1.6); 2.5111 (21.4); 2.5067 (43.3); 2.5021 (56.9); 2.4975 (41.7); 2.4930 (20.6); 2.3290 (0.4); 2.2314 (16.0); 2.1819 (14.7); 1.2391 (0.4); −0.0002 (10.0); −0.0085 (0.4)
I-230: $^1$H-NMR(400.2 MHz, $d_6$-DMSO):

TABLE 2-continued

δ = 8.0576 (9.9); 7.9730 (3.8); 7.9516 (6.1); 7.8960 (3.5); 7.8907 (3.5); 7.7958 (4.7); 7.7822 (5.2); 7.5166 (3.5); 7.5029 (3.2); 7.4408 (2.2); 7.4341 (2.1); 7.3079 (2.7); 7.3024 (2.6); 7.2863 (2.6); 7.2809 (2.5); 7.0488 (2.8); 7.0296 (3.2); 6.9165 (3.3); 6.7702 (1.8); 6.7513 (1.6); 3.7739 (0.8); 3.7556 (1.6); 3.7436 (3.6); 3.7329 (3.0); 3.7209 (1.2); 3.7124 (1.5); 3.3369 (64.4); 2.8902 (15.9); 2.8162 (0.4); 2.7989 (1.5); 2.7891 (2.6); 2.7734 (2.0); 2.7547 (0.3); 2.7315 (13.5); 2.5250 (0.9); 2.5115 (15.4); 2.5072 (30.2); 2.5027 (39.0); 2.4981 (28.6); 2.4937 (14.2); 2.2289 (16.0); 2.1574 (14.9); 1.2383 (0.3); −0.0002 (6.6)
I-231: $^{1}$H-NMR(400.2 MHz, $d_6$-DMSO):
δ = 8.0570 (7.7); 7.9529 (1.2); 7.9202 (0.9); 7.9171 (1.5); 7.9138 (1.1); 7.9011 (1.1); 7.8976 (1.7); 7.8946 (1.2); 7.8545 (1.7); 7.8495 (2.3); 7.8451 (1.6); 7.6679 (1.2); 7.6479 (2.6); 7.6284 (1.6); 7.5797 (1.3); 7.5770 (1.4); 7.5737 (1.3); 7.5711 (1.2); 7.5594 (0.8); 7.5567 (0.8); 7.5533 (0.9); 7.5507 (0.8); 7.4513 (1.4); 7.4430 (1.4); 7.0453 (1.8); 7.0261 (2.1); 6.9084 (2.2); 6.7631 (1.2); 6.7451 (1.0); 3.8789 (16.0); 3.7624 (2.1); 3.7553 (4.1); 3.7409 (0.7); 3.7318 (0.8); 3.7230 (0.7); 3.7143 (0.5); 3.7056 (0.3); 3.3336 (34.6); 2.8913 (8.4); 2.7954 (2.2); 2.7786 (2.2); 2.7328 (7.2); 2.5256 (0.5); 2.5208 (0.7); 2.5120 (8.9); 2.5077 (17.9); 2.5031 (23.5); 2.4986 (17.4); 2.4942 (8.7); 2.2285 (10.6); 2.1677 (9.8); −0.0002 (4.3)
I-232: $^{1}$H-NMR(400.2 MHz, $d_6$-DMSO):
δ = 8.3163 (0.6); 8.0320 (6.3); 8.0284 (4.2); 7.9518 (2.0); 7.4209 (1.4); 7.4100 (1.8); 7.3898 (4.1); 7.3700 (3.2); 7.3503 (1.1); 7.1979 (1.2); 7.1788 (1.1); 7.1368 (1.8); 7.1323 (1.8); 7.0992 (1.3); 7.0934 (1.0); 7.0783 (1.7); 7.0760 (1.7); 7.0728 (1.6); 7.0515 (1.9); 7.0417 (1.6); 7.0318 (1.8); 7.0268 (2.3); 7.0229 (2.4); 7.0084 (0.8); 6.9929 (0.8); 6.9872 (1.4); 6.9824 (1.2); 6.9344 (3.4); 6.8003 (0.7); 6.7873 (1.7); 6.7716 (1.3); 5.0389 (0.4); 5.0319 (0.4); 5.0237 (0.7); 5.0166 (0.7); 5.0085 (0.4); 5.0014 (0.3); 4.9623 (0.4); 4.9566 (0.4); 4.8721 (0.3); 4.8651 (0.4); 4.8570 (0.7); 4.8498 (0.7); 4.8417 (0.4); 4.8345 (0.4); 4.8024 (0.4); 4.7968 (0.4); 3.7616 (0.4); 3.7574 (0.5); 3.7337 (2.5); 3.7260 (3.6); 3.7179 (2.6); 3.7042 (1.4); 3.6973 (1.5); 3.3294 (35.0); 2.8900 (14.9); 2.7830 (2.5); 2.7766 (2.3); 2.7671 (2.4); 2.7317 (12.3); 2.7309 (12.4); 2.5402 (0.3); 2.5352 (0.4); 2.5298 (0.4); 2.5242 (1.0); 2.5192 (1.4); 2.5106 (17.7); 2.5062 (35.0); 2.5016 (45.3); 2.4970 (33.0); 2.4925 (16.2); 2.4622 (0.3); 2.4572 (0.3); 2.2314 (16.0); 2.1930 (9.9); 2.1887 (11.5); 2.1636 (0.3); 1.5820 (0.4); 1.5536 (0.3); 1.5241 (0.3); 1.5211 (0.3); 1.3932 (0.6); 1.3863 (0.6); 1.3739 (0.4); 1.3669 (0.4); 1.3358 (0.6); 1.3288 (0.6); 1.3167 (0.4); 1.3099 (0.4); 1.2912 (0.4); 1.2763 (0.5); 1.2730 (0.4); 1.2656 (0.4); 1.2577 (0.8); 1.2508 (0.6); 1.2474 (0.5); 1.2424 (0.7); 1.2392 (0.8); 1.2322 (0.8); 1.2244 (0.4); 1.2170 (0.5); 1.2138 (0.4); 1.1987 (0.3); 1.1922 (0.6); 1.1747 (0.6); 1.1650 (0.6); 1.1474 (0.5); −0.0002 (9.7)
I-233: $^{1}$H-NMR(400.2 MHz, $d_6$-DMSO):
δ = 8.3161 (0.4); 8.0969 (11.6); 7.9525 (1.1); 7.8756 (4.0); 7.8540 (4.5); 7.4866 (4.2); 7.4655 (3.9); 7.4297 (2.0); 7.4220 (2.0); 7.0317 (2.7); 7.0125 (3.1); 6.9112 (3.1); 6.7618 (1.7); 6.7441 (1.5); 3.7307 (6.1); 3.7191 (1.3); 3.7096 (1.2); 3.7003 (0.8); 3.6914 (0.5); 3.3320 (81.7); 2.8911 (8.1); 2.7846 (1.6); 2.7776 (2.4); 2.7689 (1.8); 2.7609 (2.1); 2.7324 (6.8); 2.7315 (6.8); 2.6715 (0.4); 2.5250 (1.3); 2.5202 (2.0); 2.5116 (22.7); 2.5071 (45.8); 2.5026 (60.2); 2.4980 (44.2); 2.4935 (21.8); 2.3293 (0.4); 2.3250 (0.3); 2.2247 (16.0); 2.1713 (14.6); 1.2392 (0.5); 0.0080 (0.4); −0.0002 (11.4); −0.0085 (0.4)
I-234: $^{1}$H-NMR(400.2 MHz, $d_6$-DMSO):
δ = 8.0690 (9.7); 7.9524 (1.9); 7.7725 (4.4); 7.7505 (4.9); 7.6366 (4.5); 7.6299 (4.8); 7.3580 (2.2); 7.3501 (2.2); 7.3430 (3.0); 7.3362 (2.6); 7.3210 (2.4); 7.3142 (2.4); 7.0391 (2.7); 7.0199 (3.2); 6.9149 (3.4); 6.7831 (1.8); 6.7639 (1.6); 3.7545 (6.3); 3.7377 (1.3); 3.7287 (1.2); 3.7191 (0.8); 3.7105 (0.5); 3.3374 (68.8); 2.8915 (12.7); 2.7897 (3.4); 2.7728 (3.3); 2.7323 (11.0); 2.5256 (0.7); 2.5120 (13.3); 2.5077 (26.4); 2.5032 (34.4); 2.4987 (25.6); 2.4944 (12.9); 2.2272 (16.0); 2.1876 (14.8); −0.0002 (5.1)
I-235: $^{1}$H-NMR(400.2 MHz, $d_6$-DMSO):
δ = 8.0608 (1.2); 8.0552 (9.9); 7.9523 (2.3); 7.7732 (0.6); 7.7515 (0.6); 7.7138 (0.4); 7.6910 (3.0); 7.6876 (4.2); 7.6692 (4.6); 7.6320 (1.4); 7.6287 (1.1); 7.6124 (2.9); 7.6094 (2.1); 7.5897 (2.5); 7.5701 (3.6); 7.5577 (2.4); 7.5520 (4.2); 7.5031 (2.3); 7.4988 (1.0); 7.4849 (5.0); 7.4653 (3.1); 7.4158 (3.9); 7.4080 (2.4); 7.3975 (2.8); 7.3927 (0.8); 7.3865 (0.4); 7.3794 (0.9); 7.3477 (0.6); 7.3261 (0.6); 7.2718 (1.4); 7.2693 (1.7); 7.2664 (1.6); 7.2635 (1.5); 7.2522 (1.3); 7.2497 (1.4); 7.2468 (1.5); 7.2440 (1.3); 7.0458 (2.8); 7.0267 (3.0); 6.9375 (0.3); 6.8976 (3.2); 6.7336 (1.7); 6.7144 (1.5); 3.7970 (0.3); 3.7865 (0.8); 3.7681 (1.7); 3.7569 (2.3); 3.7515 (2.0); 3.7422 (3.1); 3.7278 (1.3); 3.7202 (2.0); 3.7012 (0.5); 3.3337 (46.3); 2.8900 (16.0); 2.7918 (3.5); 2.7750 (3.2); 2.7313 (14.1); 2.5247 (0.9); 2.5111 (15.0); 2.5069 (30.0); 2.5024 (39.7); 2.4979 (29.8); 2.4936 (15.2); 2.2434 (1.6); 2.2220 (15.3); 2.1853 (1.4); 2.1201 (14.2); −0.0002 (7.4)
I-236: $^{1}$H-NMR(400.2 MHz, $d_6$-DMSO):
δ = 8.3152 (0.4); 8.0538 (11.2); 7.9521 (1.5); 7.5401 (1.8); 7.5373 (5.1); 7.5334 (6.0); 7.5304 (2.5); 7.5181 (2.4); 7.5155 (2.7); 7.5139 (2.3); 7.5110 (1.7); 7.4743 (1.9); 7.4729 (1.7); 7.4542 (3.2); 7.4514 (1.6); 7.4363 (0.9); 7.4333 (1.5); 7.3710 (2.1); 7.3628 (2.0); 7.3173 (1.9); 7.3132 (2.8); 7.3090 (1.8); 7.2970 (1.5); 7.2944 (1.5); 7.2915 (1.6); 7.2889 (1.4); 7.0399 (2.8); 7.0207 (3.2); 6.9248 (3.2); 6.7787 (1.7); 6.7611 (1.5); 3.7772 (0.4); 3.7493 (5.0); 3.7346 (1.0); 3.7261 (1.4); 3.7158 (1.0); 3.7073 (0.8); 3.6987 (0.5); 3.3375 (69.0); 2.8909 (11.2); 2.7887 (3.6); 2.7718 (3.5); 2.7326 (9.0); 2.7316 (9.3); 2.5254 (0.6); 2.5206 (1.0); 2.5119 (12.4); 2.5074 (25.0); 2.5029 (32.7); 2.4982 (23.8); 2.4937 (11.6); 2.2293 (16.0); 2.1955 (14.7); −0.0002 (3.9)
I-237: $^{1}$H-NMR(400.2 MHz, $d_6$-DMSO):
δ = 8.0687 (10.4); 7.9527 (0.6); 7.6426 (1.7); 7.6217 (3.5); 7.6015 (1.9); 7.3943 (2.1); 7.3865 (2.1); 7.3517 (3.6); 7.3497 (3.5); 7.3445 (4.0); 7.3402 (2.2); 7.3242 (3.2); 7.3191 (2.1); 7.0472 (2.8); 7.0280 (3.2); 6.9155 (3.2); 6.7625 (1.7); 6.7445 (1.5); 3.7793 (0.4); 3.7510 (4.7); 3.7319 (1.2); 3.7276 (1.2); 3.7232 (1.3); 3.7131 (0.8); 3.7045 (0.5); 3.3382 (75.7); 2.8913 (4.7); 2.7901 (3.3); 2.7733 (3.1); 2.7325 (3.9); 2.5256 (0.8); 2.5208 (1.2); 2.5122 (13.8); 2.5078 (27.3); 2.5032 (35.5); 2.4986 (25.7); 2.4942 (12.4); 2.2249 (16.0); 2.1765 (14.7); −0.0002 (5.9)
I-238: $^{1}$H-NMR(400.2 MHz, $d_6$-DMSO):
δ = 8.0634 (11.4); 7.9524 (0.7); 7.5080 (3.0); 7.4869 (4.4); 7.4854 (4.4); 7.4122 (2.5); 7.4033 (9.5); 7.3974 (2.6); 7.3862 (1.9); 7.3804 (5.8); 7.3716 (0.5); 7.0417 (2.8); 7.0225 (3.2); 6.9137 (3.2); 6.7530 (1.7); 6.7341 (1.5); 3.7527 (3.1); 3.7450 (5.9); 3.7290 (1.0); 3.7193 (1.2); 3.7107 (1.1); 3.7019 (0.8); 3.6932 (0.5); 3.3350 (60.0); 2.8909 (5.5); 2.7918 (3.1); 2.7748 (2.9); 2.7328 (4.3); 2.7317 (4.7); 2.5253 (0.6); 2.5206 (0.9); 2.5118 (12.8); 2.5073 (26.5); 2.5028 (35.3); 2.4982 (26.2); 2.4936 (13.1); 2.2298 (16.0); 2.1735 (14.7); 1.2394 (0.3); −0.0002 (6.9)
I-239: $^{1}$H-NMR(400.2 MHz, $d_6$-DMSO):
δ = 8.1218 (10.8); 7.9530 (1.6); 7.7160 (1.1); 7.7121 (1.3); 7.7005 (1.2); 7.6961 (2.0); 7.6919 (1.4); 7.6802 (1.3); 7.6764 (1.3); 7.4717 (1.0); 7.4679 (1.1); 7.4507 (2.2); 7.4475 (1.6); 7.4333 (1.6); 7.4294 (1.6); 7.4215 (2.1); 7.4132 (2.1); 7.3203 (1.5); 7.3167 (1.5); 7.2998 (2.4); 7.2962 (2.4); 7.2793 (1.1); 7.2757 (1.0); 7.0535 (2.7); 7.0343 (3.2); 6.9228 (3.2); 6.8198 (1.7); 6.8007 (1.5); 4.2232 (0.3); 3.7688 (3.2); 3.7620 (6.3); 3.7499 (1.2); 3.7415 (1.2); 3.7321 (1.1); 3.7234 (0.8); 3.7144 (0.5); 3.3363 (64.6); 2.8916 (11.3); 2.8506 (0.4); 2.8327

TABLE 2-continued (0.4); 2.8159 (1.6); 2.8043 (2.4); 2.7878 (1.9); 2.7705 (0.4); 2.7333 (9.2); 2.7323 (9.6); 2.5261 (0.6); 2.5213 (1.0); 2.5126 (13.8); 2.5081 (27.7); 2.5036 (36.2); 2.4990 (26.6); 2.4945 (13.1); 2.2399 (16.0); 2.1882 (14.6); 1.2385 (0.4); 0.9132 (0.6); −0.0002 (5.9)

I-240: $^1$H-NMR(400.2 MHz, $d_6$-DMSO):

δ = 8.0671 (12.0); 7.9525 (0.9); 7.6758 (8.3); 7.6692 (2.9); 7.6597 (4.3); 7.6497 (0.4); 7.6394 (0.9); 7.5521 (0.4); 7.5475 (1.6); 7.5410 (2.5); 7.5333 (1.6); 7.5317 (1.4); 7.5265 (1.3); 7.5243 (1.4); 7.5185 (1.1); 7.4203 (2.1); 7.4122 (2.1); 7.0521 (2.8); 7.0329 (3.2); 6.9157 (3.3); 6.7652 (1.7); 6.7461 (1.5); 3.7559 (5.4); 3.7447 (1.2); 3.7342 (1.3); 3.7278 (1.2); 3.7176 (0.8); 3.7087 (0.5); 3.3336 (54.1); 2.8911 (6.2); 2.7941 (3.2); 2.7774 (3.0); 2.7329 (5.2); 2.7317 (5.2); 2.5253 (0.7); 2.5206 (1.1); 2.5118 (13.6); 2.5074 (27.4); 2.5028 (35.9); 2.4982 (26.3); 2.4937 (12.9); 2.2258 (16.0); 2.1762 (14.7); −0.0002 (7.2)

I-241: $^1$H-NMR(400.2 MHz, $d_6$-DMSO):

δ = 8.3142 (0.5); 8.0412 (9.8); 7.9520 (1.8); 7.6963 (1.1); 7.6921 (2.3); 7.6868 (1.6); 7.6705 (5.4); 7.3636 (2.1); 7.3552 (2.1); 7.3205 (0.8); 7.3151 (0.6); 7.3045 (2.8); 7.3000 (6.9); 7.2949 (2.6); 7.2825 (2.9); 7.2621 (0.8); 7.0384 (2.8); 7.0192 (3.2); 6.9300 (3.2); 6.7815 (1.7); 6.7634 (1.5); 3.7777 (0.4); 3.7490 (4.2); 3.7263 (1.0); 3.7202 (1.4); 3.7115 (1.1); 3.7032 (0.8); 3.6943 (0.5); 3.3662 (0.4); 3.3397 (87.8); 3.3178 (0.5); 2.8911 (13.0); 2.7859 (3.7); 2.7689 (3.6); 2.7321 (11.0); 2.5253 (0.8); 2.5206 (1.1); 2.5119 (14.0); 2.5075 (27.9); 2.5030 (36.5); 2.4984 (26.7); 2.4940 (13.1); 2.2301 (16.0); 2.2044 (14.7); 0.9128 (0.3); −0.0002 (3.3)

I-242: $^1$H-NMR(400.2 MHz, $d_6$-DMSO):

δ = 8.7889 (2.6); 8.7848 (2.7); 8.0704 (9.8); 8.0439 (0.4); 7.9539 (2.1); 7.8755 (1.3); 7.8717 (1.8); 7.8537 (6.1); 7.8509 (6.0); 7.6893 (1.5); 7.6681 (3.0); 7.6481 (1.5); 7.4533 (2.1); 7.4453 (2.1); 7.3335 (1.9); 7.3293 (1.8); 7.3148 (1.4); 7.3111 (2.0); 7.3073 (1.4); 7.3023 (0.4); 7.0926 (3.5); 7.0862 (3.4); 7.0469 (2.8); 7.0278 (3.2); 6.8975 (3.3); 6.7597 (1.8); 6.7397 (1.6); 3.7935 (0.6); 3.7752 (1.9); 3.7659 (3.9); 3.7577 (3.2); 3.7448 (0.9); 3.7359 (1.6); 3.7255 (1.1); 3.7169 (0.8); 3.7081 (0.5); 3.3361 (56.7); 2.8923 (15.0); 2.7942 (3.6); 2.7774 (3.5); 2.7335 (12.8); 2.5268 (1.0); 2.5219 (1.3); 2.5133 (16.1); 2.5089 (31.8); 2.5044 (41.2); 2.4998 (29.9); 2.4954 (14.6); 2.2257 (16.0); 2.2056 (0.7); 2.1225 (14.8); 1.2384 (0.4); 0.9137 (0.4); −0.0002 (6.7)

I-243: $^1$H-NMR(300.2 MHz, CDCl3):

δ = 8.1687 (5.4); 7.9487 (1.2); 7.9226 (1.5); 7.9205 (1.4); 7.7716 (0.4); 7.7289 (1.7); 7.7253 (1.6); 7.7183 (2.3); 7.7118 (1.5); 7.7032 (2.5); 7.6768 (1.3); 7.3811 (1.2); 7.3786 (1.1); 7.3733 (1.1); 7.3538 (1.0); 7.3461 (1.0); 7.2985 (7.2); 7.0645 (0.4); 6.9873 (1.8); 6.9619 (2.2); 6.9320 (2.2); 6.7494 (1.2); 6.7243 (1.0); 6.0714 (1.5); 4.3139 (0.8); 4.3043 (1.0); 4.2791 (1.1); 4.2696 (1.0); 3.9113 (0.6); 3.9024 (0.6); 3.8952 (0.6); 3.8885 (0.6); 3.8796 (0.6); 3.8657 (1.9); 3.8455 (0.6); 3.8310 (1.3); 3.8105 (0.8); 3.1418 (15.4); 3.1202 (0.4); 3.0554 (0.7); 3.0401 (0.7); 3.0103 (1.0); 2.9941 (1.0); 2.7618 (1.0); 2.7305 (0.9); 2.7165 (0.8); 2.6846 (0.8); 2.3505 (0.9); 2.3360 (1.0); 2.3035 (11.6); 2.1975 (10.9); 2.0444 (16.0); 1.6222 (3.0); 1.2899 (1.7); 0.0366 (5.4); 0.0348 (7.5)

I-244: $^1$H-NMR(300.2 MHz, CDCl3):

δ = 8.1453 (8.4); 7.2987 (4.6); 7.0274 (2.5); 7.0019 (3.0); 6.9271 (2.9); 6.7491 (1.6); 6.7238 (1.3); 6.1505 (1.9); 4.2900 (1.0); 4.2809 (1.4); 4.2555 (1.5); 4.2463 (1.3); 3.9247 (0.5); 3.9126 (0.6); 3.9066 (0.8); 3.8959 (0.8); 3.8898 (0.8); 3.8841 (0.7); 3.8751 (0.8); 3.8654 (2.8); 3.8458 (0.8); 3.8308 (1.9); 3.8109 (1.2); 3.0433 (0.9); 3.0277 (0.9); 2.9984 (1.4); 2.9816 (1.3); 2.7965 (1.3); 2.7657 (1.3); 2.7512 (1.2); 2.7200 (1.0); 2.3476 (12.9); 2.3460 (12.7); 2.3078 (16.0); 2.2337 (14.9); 2.2087 (0.5); 2.0448 (0.4); 1.6518 (1.2); 0.0365 (5.6)

I-245: $^1$H-NMR(499.9 MHz, CDCl3):

δ = 7.9043 (5.1); 7.3247 (3.0); 7.3206 (2.8); 7.2614 (12.0); 7.1435 (2.4); 7.1272 (2.7); 7.1043 (0.7); 7.0885 (1.8); 7.0726 (1.2); 7.0325 (1.0); 7.0295 (1.0); 7.0161 (1.4); 7.0022 (0.7); 6.9994 (0.6); 6.8967 (1.7); 6.8925 (1.6); 6.8804 (1.5); 6.8762 (1.4); 6.8254 (0.9); 6.8230 (0.9); 6.8099 (1.5); 6.7965 (0.8); 6.1556 (1.4); 4.1483 (1.1); 4.1420 (1.2); 4.1265 (1.4); 4.1201 (1.4); 4.0004 (0.5); 3.9942 (0.8); 3.9852 (0.8); 3.9767 (0.8); 3.9670 (0.4); 3.9247 (1.5); 3.9154 (1.1); 3.9029 (1.2); 3.8935 (1.0); 3.4877 (14.0); 3.4371 (0.8); 3.1551 (1.0); 3.1450 (1.0); 3.1281 (1.3); 3.1180 (1.2); 2.9585 (1.3); 2.9402 (1.3); 2.9315 (1.0); 2.9132 (0.9); 2.6681 (0.6); 2.6423 (16.0); 2.0867 (0.6); 2.0800 (0.7); 2.0699 (1.2); 2.0596 (0.7); 2.0530 (0.6); 2.0055 (5.0); 1.5712 (1.1); 1.2427 (0.3); 1.0396 (0.5); 1.0304 (2.1); 1.0269 (2.2); 1.0240 (1.8); 1.0134 (2.2); 1.0099 (2.1); 1.0009 (0.6); 0.7834 (1.5); 0.7808 (1.3); 0.7771 (1.4); 0.7734 (2.2); 0.7701 (2.2); 0.7680 (2.2); 0.7579 (1.3); −0.0002 (14.6)

I-246: $^1$H-NMR(499.9 MHz, CDCl3):

δ = 7.9040 (4.8); 7.4760 (2.6); 7.4726 (2.7); 7.2609 (11.5); 7.1091 (0.8); 7.0929 (1.8); 7.0835 (1.7); 7.0772 (1.4); 7.0673 (3.4); 7.0424 (1.9); 7.0391 (2.0); 7.0269 (1.7); 7.0231 (1.2); 7.0138 (1.5); 6.9998 (0.6); 6.8255 (0.9); 6.8122 (1.4); 6.7985 (0.7); 6.1529 (1.4); 4.1455 (1.0); 4.1392 (1.2); 4.1237 (1.3); 4.1174 (1.4); 3.9967 (0.4); 3.9900 (0.7); 3.9812 (0.8); 3.9727 (0.8); 3.9253 (1.4); 3.9159 (1.1); 3.9034 (1.2); 3.8941 (0.9); 3.4856 (0.5); 3.4375 (0.4); 3.1423 (1.0); 3.1322 (1.0); 3.1153 (1.2); 3.1052 (1.2); 2.9460 (1.2); 2.9277 (1.2); 2.9192 (1.0); 2.9008 (0.9); 2.6680 (1.0); 2.6418 (14.6); 2.0943 (0.6); 2.0875 (0.6); 2.0775 (1.1); 2.0674 (0.7); 2.0606 (0.6); 2.0052 (16.0); 1.5580 (10.7); 1.0338 (1.8); 1.0304 (2.0); 1.0169 (2.0); 1.0135 (2.0); 1.0044 (0.6); 0.7884 (1.3); 0.7781 (2.1); 0.7736 (2.2); 0.7635 (1.4); −0.0002 (14.0)

I-247: $^1$H-NMR(499.9 MHz, CDCl3):

δ = 7.9036 (3.8); 7.4760 (2.2); 7.4725 (2.1); 7.2612 (7.6); 7.1099 (0.6); 7.0933 (1.4); 7.0838 (1.4); 7.0777 (1.0); 7.0675 (2.6); 7.0426 (1.7); 7.0390 (1.6); 7.0268 (1.4); 7.0228 (0.9); 7.0138 (1.1); 6.9997 (0.5); 6.8255 (0.7); 6.8124 (1.1); 6.7989 (0.6); 6.1559 (1.1); 4.1452 (0.8); 4.1389 (0.9); 4.1234 (1.0); 4.1171 (1.0); 3.9965 (0.4); 3.9900 (0.6); 3.9811 (0.6); 3.9726 (0.6); 3.9253 (1.1); 3.9160 (0.8); 3.9034 (0.9); 3.8942 (0.7); 3.1423 (0.8); 3.1322 (0.8); 3.1153 (1.0); 3.1052 (0.9); 2.9463 (0.9); 2.9279 (0.9); 2.9194 (0.8); 2.9010 (0.7); 2.6660 (1.1); 2.6415 (11.4); 2.0945 (0.5); 2.0878 (0.5); 2.0776 (0.9); 2.0675 (0.6); 2.0608 (0.5); 2.0050 (16.0); 1.5636 (5.5); 1.0339 (1.5); 1.0305 (1.6); 1.0170 (1.6); 1.0135 (1.6); 1.0044 (0.4); 0.7885 (1.1); 0.7786 (1.8); 0.7755 (1.8); 0.7736 (1.8); 0.7638 (1.0); −0.0002 (9.4)

I-248: $^1$H-NMR(300.2 MHz, CDCl3):

δ = 7.9692 (5.4); 7.2990 (7.5); 7.1670 (2.0); 7.1402 (3.8); 7.1202 (0.7); 7.1099 (0.3); 7.0970 (1.6); 7.0937 (1.6); 7.0704 (1.1); 7.0674 (1.2); 7.0193 (0.9); 7.0135 (1.1); 6.9953 (1.1); 6.9904 (1.3); 6.9687 (0.6); 6.9632 (0.6); 6.9381 (1.3); 6.9323 (1.2); 6.9123 (1.0); 6.9068 (1.0); 6.8563 (0.8); 6.8507 (0.7); 6.8298 (1.3); 6.8080 (0.7); 6.8029 (0.6); 6.2922 (1.5); 5.3361 (4.3); 5.0228 (1.5); 5.0169 (1.5); 5.0030 (1.8); 4.9959 (2.6); 4.9890 (1.7); 4.9751 (1.8); 4.9692 (1.7); 4.6478 (1.5); 4.6308 (2.0); 4.6257 (2.3); 4.6088 (2.4); 4.5889 (1.5); 4.2779 (0.6); 4.2699 (1.1); 4.2447 (1.2); 4.2368 (0.7); 4.1932 (0.7); 4.1694 (2.1); 4.1456 (2.1); 4.1219 (0.8); 4.0971 (0.3); 4.0737 (0.7); 4.0695 (0.7); 4.0463 (1.1); 4.0232 (0.6); 4.0190 (0.6); 3.9960 (0.4); 3.9345 (0.5); 3.9233 (0.6); 3.9174 (0.6); 3.8945 (1.8); 3.8607 (1.6); 3.8413 (0.9); 3.0768 (0.6); 3.0613 (0.6); 3.0318 (1.1); 3.0158 (1.1); 2.8565 (0.8); 2.8415 (1.0); 2.8253 (0.8); 2.8111 (0.7); 2.7801 (0.6); 2.6683 (16.0); 2.3741 (11.8); 2.1360 (0.5); 2.1250 (0.6); 2.1080 (1.0); 2.0820 (9.9); 2.0627 (0.4); 1.3195 (2.6); 1.2957 (5.2); 1.2719 (2.4); 1.0979 (0.7); 1.0836 (1.6); 1.0769 (1.9); 1.0701 (1.1); 1.0630 (1.2); 1.0550 (1.7); 1.0485 (1.8); 1.0348 (1.0); 0.8358

TABLE 2-continued (0.9); 0.8218 (2.0); 0.8179 (2.0); 0.8091 (1.3); 0.8047 (2.0); 0.8007 (1.9); 0.7839 (0.8); 0.1063 (2.4); 0.0359 (9.0); 0.0251 (0.4)
I-249: $^{1}$H-NMR(300.2 MHz, CDCl3):
δ = 7.9706 (5.1); 7.2989 (7.3); 7.2037 (0.4); 7.1955 (0.5); 7.1887 (0.5); 7.1642 (0.7); 7.1512 (0.5); 7.1352 (1.1); 7.1078 (4.3); 7.0817 (3.9); 7.0597 (0.5); 7.0332 (1.3); 7.0289 (1.3); 7.0052 (4.0); 6.9834 (0.7); 6.9788 (0.7); 6.8551 (0.9); 6.8315 (1.4); 6.8065 (0.9); 6.7876 (1.7); 6.7615 (1.3); 6.2972 (1.8); 5.3356 (2.2); 4.2640 (1.3); 4.2388 (1.4); 4.1687 (0.6); 4.1453 (0.5); 4.1225 (0.4); 4.1137 (0.4); 4.1005 (0.4); 4.0806 (1.0); 4.0681 (0.9); 4.0540 (2.0); 4.0401 (2.0); 4.0264 (2.2); 4.0095 (1.4); 3.9979 (1.2); 3.9761 (0.4); 3.9494 (1.1); 3.9427 (1.0); 3.9228 (1.8); 3.9163 (1.8); 3.8912 (2.2); 3.8793 (2.4); 3.8730 (2.4); 3.8469 (1.9); 3.8275 (1.0); 3.7598 (0.4); 3.7472 (0.4); 3.7217 (0.4); 3.6010 (0.8); 3.5747 (1.3); 3.5660 (0.8); 3.5476 (0.8); 3.5392 (1.3); 3.5121 (0.8); 3.2613 (0.6); 3.2527 (0.6); 3.2348 (0.8); 3.2265 (0.9); 3.2086 (0.6); 3.2004 (0.6); 3.0544 (0.9); 3.0397 (0.8); 3.0095 (1.4); 2.9941 (1.3); 2.8392 (1.2); 2.8232 (1.0); 2.8053 (0.5); 2.7919 (1.3); 2.7782 (0.8); 2.7522 (1.8); 2.7344 (0.6); 2.7105 (0.3); 2.6970 (0.6); 2.6852 (1.0); 2.6668 (16.0); 2.6393 (0.4); 2.3911 (0.5); 2.3615 (2.3); 2.3452 (13.5); 2.3176 (1.3); 2.3056 (0.8); 2.2889 (0.8); 2.2791 (0.9); 2.2639 (0.9); 2.2537 (0.7); 2.2379 (0.7); 2.2287 (0.4); 2.2136 (0.4); 2.1674 (0.4); 2.1498 (0.6); 2.1378 (0.8); 2.1222 (1.2); 2.1057 (1.0); 2.0938 (1.0); 2.0821 (2.4); 2.0415 (0.4); 1.9072 (0.8); 1.8797 (1.1); 1.8663 (0.7); 1.8524 (0.8); 1.8388 (0.9); 1.8114 (0.7); 1.3196 (0.5); 1.2956 (1.2); 1.2719 (0.4); 1.0961 (0.7); 1.0817 (1.7); 1.0753 (2.0); 1.0613 (1.5); 1.0535 (2.1); 1.0468 (2.5); 1.0335 (1.5); 1.0170 (0.8); 1.0102 (0.8); 0.9964 (0.6); 0.9717 (0.4); 0.8335 (0.8); 0.8184 (2.3); 0.8015 (2.4); 0.7973 (2.4); 0.7548 (0.4); 0.1751 (0.8); 0.1611 (0.8); 0.1359 (0.4); 0.1070 (2.6); 0.0470 (0.3); 0.0363 (9.0)
I-250: $^{1}$H-NMR(499.9 MHz, CDCl3):
δ = 7.9038 (4.0); 7.3244 (2.3); 7.3203 (2.2); 7.2611 (8.6); 7.1433 (1.8); 7.1270 (2.0); 7.1027 (0.6); 7.0869 (1.4); 7.0711 (1.0); 7.0321 (0.7); 7.0291 (0.8); 7.0153 (1.1); 7.0017 (0.5); 6.9990 (0.5); 6.8966 (1.3); 6.8926 (1.2); 6.8804 (1.1); 6.8763 (1.0); 6.8225 (0.8); 6.8094 (1.2); 6.7960 (0.6); 6.1544 (1.2); 4.1478 (0.9); 4.1415 (0.9); 4.1260 (1.1); 4.1196 (1.1); 4.0000 (0.4); 3.9936 (0.6); 3.9846 (0.7); 3.9761 (0.6); 3.9698 (0.4); 3.9665 (0.4); 3.9240 (1.2); 3.9146 (0.9); 3.9021 (1.0); 3.8928 (0.7); 3.1546 (0.8); 3.1446 (0.8); 3.1277 (1.0); 3.1176 (1.0); 2.9581 (1.0); 2.9397 (1.0); 2.9311 (0.8); 2.9128 (0.7); 2.6671 (1.0); 2.6415 (12.2); 2.0863 (0.5); 2.0795 (0.6); 2.0695 (0.9); 2.0593 (0.6); 2.0526 (0.5); 2.0050 (16.0); 1.5617 (4.4); 1.0392 (0.4); 1.0301 (1.6); 1.0267 (1.6); 1.0237 (1.4); 1.0132 (1.8); 1.0098 (1.6); 1.0073 (1.3); 1.0007 (0.4); 0.7831 (1.2); 0.7807 (1.1); 0.7730 (1.9); 0.7702 (1.9); 0.7677 (1.9); 0.7577 (1.1); −0.0002 (10.4)
I-251: $^{1}$H-NMR(300.2 MHz, CDCl3):
δ = 7.5985 (0.4); 7.5723 (1.4); 7.5483 (2.6); 7.5221 (0.4); 7.4533 (2.1); 7.4300 (0.9); 7.4231 (1.3); 7.4076 (0.6); 7.3992 (0.8); 7.2988 (13.4); 7.0495 (1.5); 7.0253 (3.4); 6.9558 (1.4); 6.9312 (0.9); 5.3375 (0.5); 4.8697 (1.2); 4.6754 (1.3); 4.2116 (0.9); 4.1856 (1.1); 3.9738 (0.6); 3.9440 (1.7); 3.9129 (1.4); 3.9081 (1.8); 3.8964 (0.7); 3.8852 (3.7); 3.8629 (2.0); 3.6653 (0.4); 3.6570 (0.4); 3.6492 (0.6); 3.5716 (0.6); 3.5635 (0.4); 3.5563 (0.4); 3.5422 (0.3); 3.4180 (1.8); 3.4080 (0.6); 3.3912 (3.6); 3.3719 (14.5); 3.3555 (0.4); 3.3211 (0.3); 3.2013 (1.7); 3.1789 (3.4); 3.1563 (1.6); 3.0378 (0.5); 3.0220 (0.5); 2.9919 (1.0); 2.9762 (0.9); 2.9139 (0.9); 2.8842 (0.8); 2.8678 (0.5); 2.8379 (0.4); 2.6049 (1.1); 2.6004 (1.2); 2.5933 (2.4); 2.5723 (0.4); 2.5326 (0.7); 2.4878 (11.2); 2.3210 (16.0); 2.2881 (0.6); 2.2705 (0.4); 2.2557 (0.4); 2.0445 (0.6); 1.6878 (0.5); 1.6675 (0.5); 1.2918 (0.5); 0.2209 (0.5); 0.2068 (0.5); 0.1930 (0.8); 0.1848 (1.0); 0.1775 (1.0); 0.1634 (1.1); 0.1072 (0.4); 0.0481 (0.4); 0.0373 (11.1); 0.0264 (0.6)
I-252: $^{1}$H-NMR(300.2 MHz, CDCl3):
δ = 7.9788 (6.3); 7.4090 (0.8); 7.4004 (0.9); 7.3850 (1.4); 7.3765 (1.2); 7.3612 (1.1); 7.3549 (1.2); 7.2989 (12.1); 7.2101 (0.8); 7.1826 (2.1); 7.1789 (2.0); 7.1557 (3.0); 7.1381 (1.6); 7.1318 (1.9); 7.1108 (0.8); 7.1045 (0.7); 7.0361 (0.4); 7.0187 (2.5); 6.9932 (3.0); 6.9478 (0.4); 6.9077 (3.0); 6.7283 (1.6); 6.7046 (1.3); 6.0997 (1.8); 4.3227 (1.0); 4.3128 (1.2); 4.2877 (1.4); 4.2779 (1.3); 4.1942 (1.1); 4.1704 (3.4); 4.1466 (3.4); 4.1228 (1.3); 4.1014 (0.4); 3.9218 (0.9); 3.9058 (0.9); 3.8998 (0.8); 3.8900 (0.8); 3.8814 (0.8); 3.8694 (2.4); 3.8486 (1.1); 3.8346 (1.8); 3.8136 (1.2); 3.0519 (0.9); 3.0366 (1.0); 3.0183 (1.6); 3.0071 (1.5); 2.9928 (5.4); 2.9677 (4.6); 2.9423 (1.7); 2.7823 (1.4); 2.7507 (1.4); 2.7374 (1.2); 2.7051 (1.0); 2.3338 (0.8); 2.3088 (15.1); 2.2420 (0.8); 2.2168 (0.5); 2.1848 (14.2); 2.1182 (0.3); 2.0840 (16.0); 1.6703 (0.5); 1.6486 (0.5); 1.6213 (0.3); 1.3943 (4.9); 1.3691 (10.1); 1.3437 (4.8); 1.3207 (4.0); 1.2969 (8.0); 1.2731 (4.0); 0.9721 (0.5); 0.0472 (0.3); 0.0364 (14.5); 0.0257 (0.8)
I-253: $^{1}$H-NMR(300.2 MHz, CDCl3):
δ = 9.0325 (0.6); 9.0159 (0.6); 8.1695 (7.8); 8.1306 (0.6); 8.1141 (0.6); 7.6278 (5.3); 7.6105 (4.3); 7.5822 (0.3); 7.3626 (2.8); 7.3148 (1.3); 7.2988 (14.4); 7.2911 (1.6); 7.2768 (0.7); 7.0043 (2.6); 6.9787 (3.0); 6.9208 (3.2); 6.7060 (1.8); 6.6806 (1.5); 6.1911 (2.0); 5.1198 (2.9); 5.0996 (4.4); 5.0916 (3.4); 5.0713 (4.7); 5.0238 (2.4); 5.0154 (2.4); 5.0017 (3.4); 4.9936 (3.3); 4.9809 (1.8); 4.9726 (1.7); 4.6289 (0.5); 4.6063 (1.1); 4.6010 (1.0); 4.5835 (0.7); 4.5783 (1.8); 4.5556 (0.8); 4.5501 (0.8); 4.5275 (0.3); 4.3517 (1.1); 4.3423 (1.4); 4.3168 (1.4); 4.3069 (1.5); 3.9470 (0.6); 3.9311 (0.8); 3.9140 (0.9); 3.9034 (0.7); 3.8977 (0.7); 3.8734 (2.5); 3.8522 (1.1); 3.8384 (1.9); 3.8171 (1.2); 3.0667 (1.0); 3.0523 (1.0); 3.0214 (1.4); 3.0064 (1.3); 2.7607 (1.6); 2.7279 (1.5); 2.7153 (1.3); 2.6821 (1.2); 2.3047 (16.0); 2.1844 (15.0); 1.6327 (1.8); 1.2913 (0.6); 1.2565 (1.9); 1.2361 (1.9); 0.0471 (0.5); 0.0363 (12.9); 0.0254 (0.5)
I-254: $^{1}$H-NMR(300.2 MHz, CDCl3):
δ = 8.0397 (4.6); 7.5998 (2.7); 7.5824 (2.4); 7.3536 (1.4); 7.2989 (12.3); 7.2798 (0.9); 7.2733 (0.8); 7.2670 (0.5); 7.2588 (0.4); 7.0023 (1.5); 6.9768 (1.7); 6.9206 (1.7); 6.7170 (0.9); 6.6913 (0.8); 6.1224 (1.1); 4.3288 (0.6); 4.3196 (0.8); 4.2943 (0.8); 4.2843 (0.8); 3.9211 (0.4); 3.9029 (0.5); 3.8867 (0.4); 3.8803 (0.4); 3.8715 (0.4); 3.8631 (1.5); 3.8417 (0.8); 3.8346 (1.8); 3.8283 (1.4); 3.8132 (4.2); 3.7919 (2.1); 3.4322 (0.3); 3.3682 (16.0); 3.2259 (2.0); 3.2046 (3.9); 3.1832 (1.7); 3.0504 (0.6); 3.0357 (0.6); 3.0051 (0.8); 2.9897 (0.8); 2.7572 (0.8); 2.7247 (0.8); 2.7119 (0.7); 2.6789 (0.6); 2.2995 (9.4); 2.1898 (8.7); 1.6101 (4.1); 1.2916 (0.4); 0.0476 (0.4); 0.0368 (12.2); 0.0260 (0.5)
I-255: $^{1}$H-NMR(300.2 MHz, CDCl3):
δ = 8.0465 (8.3); 7.6130 (4.5); 7.5961 (3.9); 7.3514 (2.6); 7.2987 (23.2); 7.2882 (1.6); 7.2853 (1.5); 7.2671 (0.7); 7.0004 (2.4); 6.9749 (2.8); 6.9184 (2.9); 6.7065 (1.6); 6.6823 (1.3); 6.1588 (2.0); 4.3427 (1.2); 4.3328 (1.3); 4.3073 (1.5); 4.2976 (1.4); 4.2616 (1.6); 4.2363 (2.3); 4.2332 (2.3); 4.2080 (2.1); 4.1365 (0.6); 4.1176 (0.7); 4.1084 (1.4); 4.0905 (1.5); 4.0811 (1.0); 4.0626 (0.9); 4.0185 (1.2); 3.9941 (2.5); 3.9694 (1.7); 3.9661 (1.8); 3.9537 (1.5); 3.9487 (1.6); 3.9412 (1.5); 3.9301 (2.2); 3.9252 (2.9); 3.9202 (1.8); 3.9016 (1.8); 3.8967 (1.8); 3.8677 (2.5); 3.8467 (1.1); 3.8328 (2.0); 3.8115 (1.3); 3.8031 (0.6); 3.7787 (1.4); 3.7507 (1.5); 3.7264 (1.2); 3.7021 (0.4); 3.0588 (1.0); 3.0446 (1.0); 3.0138 (1.4); 2.9987 (1.3); 2.7572 (1.2); 2.7239 (1.2); 2.7122

TABLE 2-continued (1.0); 2.6785 (0.9); 2.4983 (0.4); 2.4805 (0.4); 2.4715 (0.5); 2.4563 (0.9); 2.4390 (0.7); 2.4295 (1.0); 2.4127 (0.8); 2.4034 (0.6); 2.3862 (0.6); 2.3454 (0.7); 2.3190 (1.8); 2.3013 (16.0); 2.2776 (1.1); 2.2533 (0.9); 2.2293 (0.4); 2.1831 (14.7); 1.6145 (4.4); 1.2913 (0.9); 1.2574 (0.3); 0.0471 (1.0); 0.0363 (20.6); 0.0253 (0.9)
I-256: $^{1}$H-NMR(300.2 MHz, CDCl3):
δ = 8.0537 (6.4); 7.6303 (4.7); 7.6132 (4.1); 7.5857 (0.6); 7.4773 (0.5); 7.3582 (2.8); 7.2987 (13.1); 7.2846 (1.9); 7.2712 (1.1); 7.0018 (2.6); 6.9763 (3.0); 6.9481 (0.4); 6.9166 (3.2); 6.7033 (1.8); 6.6787 (1.5); 6.1610 (2.2); 4.3441 (1.1); 4.3349 (1.3); 4.3094 (1.4); 4.2996 (1.5); 3.9182 (0.9); 3.9071 (1.0); 3.8904 (0.8); 3.8653 (2.3); 3.8440 (1.2); 3.8302 (1.8); 3.8089 (1.2); 3.3168 (2.2); 3.2922 (5.1); 3.2678 (3.2); 3.0619 (1.1); 3.0478 (1.2); 3.0170 (1.5); 3.0019 (1.6); 2.9892 (3.6); 2.9648 (5.4); 2.9401 (2.4); 2.7542 (1.4); 2.7214 (1.4); 2.7090 (1.3); 2.6755 (1.1); 2.3430 (1.1); 2.3296 (1.0); 2.3026 (16.0); 2.2459 (0.7); 2.1794 (14.2); 2.0906 (0.4); 1.9021 (0.4); 1.8946 (0.4); 1.8823 (0.4); 1.6454 (1.4); 1.5037 (0.4); 1.4813 (0.5); 1.4733 (0.5); 1.4629 (0.6); 1.4258 (0.5); 1.2907 (0.6); 1.2583 (0.4); 0.2277 (1.2); 0.2010 (1.2); 0.1948 (1.1); 0.1698 (0.7); 0.1402 (0.4); 0.0362 (9.4)
I-257: $^{1}$H-NMR(499.9 MHz, CDCl3):
δ = 7.8888 (6.4); 7.5502 (5.4); 7.5403 (3.9); 7.5235 (0.5); 7.3135 (3.1); 7.2604 (8.7); 7.2494 (1.4); 7.2444 (1.5); 7.2381 (1.6); 7.2347 (1.5); 7.2269 (0.9); 6.9573 (2.7); 6.9421 (2.9); 6.8797 (3.4); 6.6718 (2.0); 6.6567 (1.7); 6.1097 (2.3); 4.2785 (1.5); 4.2718 (1.5); 4.2569 (1.6); 4.2503 (1.5); 3.8842 (0.8); 3.8765 (1.1); 3.8651 (1.1); 3.8573 (0.9); 3.8129 (2.0); 3.8001 (1.4); 3.7913 (1.7); 3.7786 (1.3); 3.0032 (5.8); 2.9968 (2.3); 2.9879 (7.2); 2.9691 (1.6); 2.9599 (1.5); 2.7526 (0.7); 2.7369 (1.4); 2.7213 (1.9); 2.7059 (2.8); 2.6863 (1.7); 2.6789 (1.5); 2.6588 (1.2); 2.3126 (0.4); 2.3040 (0.5); 2.2584 (16.0); 2.2326 (0.4); 2.1511 (15.4); 2.0891 (0.8); 2.0743 (1.7); 2.0667 (1.9); 2.0575 (2.0); 2.0528 (1.9); 2.0470 (1.5); 2.0430 (1.6); 2.0322 (0.8); 2.0277 (0.8); 1.9137 (0.3); 1.8921 (0.7); 1.8731 (1.6); 1.8659 (1.5); 1.8589 (2.5); 1.8566 (2.5); 1.8494 (1.5); 1.8407 (2.5); 1.8293 (1.2); 1.7903 (1.0); 1.7874 (1.0); 1.7710 (1.9); 1.7516 (2.2); 1.7340 (1.5); 1.7177 (0.5); 1.5735 (4.6); 1.3333 (0.4); 1.2840 (0.7); 1.2554 (3.3); 1.2178 (0.5); 0.8934 (0.4); 0.8804 (0.5); 0.8662 (0.5); 0.8582 (0.8); 0.8455 (1.0); −0.0002 (9.0)
I-258: $^{1}$H-NMR(300.2 MHz, CDCl3):
δ = 8.1576 (9.5); 7.6702 (1.0); 7.6645 (1.1); 7.6519 (1.1); 7.6451 (1.9); 7.6386 (1.4); 7.6262 (1.2); 7.6203 (1.3); 7.5680 (0.4); 7.5158 (0.9); 7.5100 (0.9); 7.4918 (1.1); 7.4880 (2.0); 7.4826 (1.5); 7.4646 (1.7); 7.4586 (1.4); 7.4133 (1.9); 7.4097 (1.8); 7.3858 (2.1); 7.3836 (2.2); 7.3600 (1.0); 7.3561 (1.0); 7.2988 (9.8); 7.0064 (2.5); 6.9810 (3.0); 6.9174 (2.9); 6.7366 (1.6); 6.7105 (1.3); 5.9193 (1.9); 4.3410 (1.2); 4.3320 (1.4); 4.3057 (1.5); 4.2966 (1.5); 3.9502 (0.6); 3.9432 (0.7); 3.9374 (0.8); 3.9332 (0.8); 3.9271 (0.8); 3.9216 (0.8); 3.9167 (0.9); 3.9006 (0.7); 3.8932 (0.7); 3.8793 (2.6); 3.8588 (1.1); 3.8442 (2.0); 3.8236 (1.3); 3.0662 (1.1); 3.0506 (1.0); 3.0209 (1.4); 3.0048 (1.3); 2.7760 (1.5); 2.7439 (1.4); 2.7307 (1.2); 2.6981 (1.1); 2.3646 (0.6); 2.3412 (0.7); 2.3088 (16.0); 2.2090 (2.6); 2.1925 (15.0); 2.0454 (4.6); 1.6023 (7.3); 0.0477 (0.5); 0.0369 (12.3); 0.0260 (0.6)
I-259: $^{1}$H-NMR(499.9 MHz, CDCl3):
δ = 7.9086 (5.4); 7.3117 (2.9); 7.2648 (1.2); 7.0812 (0.7); 7.0671 (3.9); 7.0517 (3.6); 7.0158 (0.9); 7.0127 (1.1); 6.9989 (1.5); 6.9856 (0.6); 6.9826 (0.6); 6.8065 (0.8); 6.8038 (0.8); 6.7909 (1.5); 6.7777 (0.8); 6.7751 (0.7); 6.7318 (1.5); 6.7165 (1.4); 6.1799 (1.6); 4.1825 (1.1); 4.1758 (1.2); 4.1606 (1.3); 4.1540 (1.4); 4.0174 (0.5); 4.0110 (0.7); 4.0052 (0.7); 4.0023 (0.8); 3.9997 (0.8); 3.9940 (0.8); 3.9880 (0.6); 3.9839 (0.4); 3.8817 (1.4); 3.8711 (1.2); 3.8598 (1.2); 3.8492 (1.1); 3.1430 (0.9); 3.1328 (1.0); 3.1161 (1.2); 3.1059 (1.1); 2.9028 (1.2); 2.8843 (1.2); 2.8759 (1.0); 2.8574 (0.9); 2.6296 (16.0); 2.1631 (12.3); 2.0869 (0.6); 2.0802 (0.7); 2.0700 (1.1); 2.0598 (0.7); 2.0531 (0.6); 1.9962 (0.6); 1.6990 (1.2); 1.0292 (1.0); 1.0252 (1.6); 1.0224 (2.0); 1.0172 (1.6); 1.0147 (1.5); 1.0087 (1.7); 1.0054 (2.0); 1.0013 (1.2); 0.7772 (1.2); 0.7738 (1.2); 0.7683 (1.9); 0.7650 (2.0); 0.7624 (2.2); 0.7547 (1.2); 0.7519 (1.3); −0.0002 (1.7)
I-260: $^{1}$H-NMR(300.2 MHz, CDCl3):
δ = 8.1222 (16.0); 7.4002 (6.2); 7.3933 (6.4); 7.2990 (9.6); 7.2957 (4.2); 7.2896 (5.5); 7.2862 (4.7); 7.2684 (9.9); 7.2625 (6.5); 7.2054 (4.3); 7.1782 (7.4); 7.1121 (4.8); 7.1051 (4.6); 7.0849 (2.7); 7.0779 (2.6); 5.9521 (2.5); 5.9445 (2.5); 4.1739 (2.1); 4.1639 (2.6); 4.1379 (3.0); 4.1280 (3.6); 4.0768 (0.4); 4.0616 (0.8); 4.0482 (1.4); 4.0435 (1.1); 4.0373 (1.4); 4.0329 (1.7); 4.0221 (1.7); 4.0127 (1.0); 4.0040 (1.0); 3.9940 (0.6); 3.9732 (3.8); 3.9582 (2.3); 3.9374 (2.5); 3.9223 (1.9); 3.1891 (1.7); 3.1709 (1.7); 3.1439 (3.2); 3.1256 (3.0); 3.0485 (3.2); 3.0194 (3.1); 3.0034 (1.8); 2.9741 (1.8); 2.2035 (2.1); 1.6101 (3.9); 0.9966 (0.3); 0.1070 (0.5); 0.0469 (0.4); 0.0360 (10.9); 0.0252 (0.4)
I-261: $^{1}$H-NMR(300.2 MHz, CDCl3):
δ = 8.1225 (16.0); 7.5511 (6.7); 7.5447 (6.8); 7.3106 (4.6); 7.3051 (6.4); 7.2988 (12.4); 7.2617 (4.3); 7.2558 (12.0); 7.2501 (8.0); 7.2347 (5.0); 7.2282 (4.6); 7.1396 (7.4); 7.1124 (4.8); 5.9485 (2.9); 5.9416 (2.9); 4.1726 (2.2); 4.1627 (2.7); 4.1367 (3.2); 4.1269 (3.7); 4.0750 (0.5); 4.0598 (1.0); 4.0462 (1.6); 4.0418 (1.4); 4.0350 (1.6); 4.0310 (1.9); 4.0203 (1.8); 4.0117 (1.2); 4.0023 (1.2); 3.9921 (0.8); 3.9753 (4.0); 3.9604 (2.4); 3.9395 (2.7); 3.9245 (2.0); 3.1765 (1.8); 3.1586 (1.8); 3.1315 (3.4); 3.1133 (3.1); 3.0375 (3.4); 3.0085 (3.2); 2.9925 (1.9); 2.9632 (1.8); 2.2045 (6.1); 2.0417 (3.8); 1.6129 (1.9); 0.1065 (0.6); 0.0465 (0.8); 0.0359 (13.5); 0.0250 (0.6)
I-262: $^{1}$H-NMR(300.2 MHz, CDCl3):
δ = 8.1526 (0.5); 8.1431 (8.7); 7.5304 (0.5); 7.5257 (0.7); 7.5238 (0.7); 7.5199 (0.6); 7.5011 (1.5); 7.4830 (0.7); 7.4783 (1.0); 7.4731 (0.7); 7.2988 (3.9); 7.2668 (2.2); 7.2406 (1.8); 7.2274 (1.0); 7.2248 (1.1); 7.2209 (1.2); 7.2011 (1.4); 7.1992 (1.4); 7.1745 (0.6); 7.0107 (2.5); 6.9852 (2.9); 6.9105 (3.0); 6.7154 (1.6); 6.6906 (1.4); 6.1589 (2.0); 4.3121 (1.0); 4.3037 (1.4); 4.2777 (1.5); 4.2692 (1.2); 3.9222 (0.5); 3.9052 (0.8); 3.8951 (0.7); 3.8895 (0.8); 3.8824 (0.7); 3.8664 (2.9); 3.8464 (0.7); 3.8321 (1.9); 3.8116 (1.1); 3.0533 (0.9); 3.0383 (0.9); 3.0086 (1.4); 2.9924 (1.3); 2.7778 (1.2); 2.7466 (1.2); 2.7326 (1.1); 2.7010 (1.0); 2.3086 (16.0); 2.1616 (15.0); 2.0412 (1.9); 1.6467 (1.4); 1.5431 (0.6); 1.5171 (2.1); 1.4968 (0.8); 1.4802 (0.6); 1.4538 (2.1); 1.4335 (0.8); 1.2289 (0.6); 1.2221 (0.5); 1.2052 (2.2); 1.1989 (2.4); 1.1754 (2.6); 1.1688 (1.9); 1.1523 (0.4); 1.1457 (0.4); 0.0383 (3.8)
I-263: $^{1}$H-NMR(300.2 MHz, CDCl3):
δ = 7.4738 (0.3); 7.4483 (0.5); 7.4269 (0.4); 7.3453 (0.6); 7.3217 (0.5); 7.3191 (0.4); 7.2987 (17.9); 7.2791 (0.7); 7.2528 (0.7); 7.0508 (0.8); 7.0246 (2.1); 6.9477 (0.8); 6.9225 (0.4); 4.7748 (0.7); 4.2165 (0.6); 4.1909 (0.7); 3.9375 (0.9); 3.9238 (0.4); 3.9071 (0.7); 2.9959 (0.5); 2.9788 (0.5); 2.9038 (0.5); 2.8746 (0.4); 2.5591 (9.3); 2.3245 (6.2); 2.3065 (5.8); 2.0460 (16.0); 1.5902 (7.6); 1.4943 (0.8); 1.4312 (0.8); 1.4090 (0.3); 1.1862 (0.8); 1.1792 (0.9); 1.1565 (0.9); 0.0483 (0.8); 0.0375 (21.6); 0.0266 (0.7)
I-264: $^{1}$H-NMR(300.2 MHz, CDCl3):
δ = 8.1623 (1.6); 7.6310 (0.9); 7.6277 (1.0); 7.6229 (0.5); 7.6098 (0.6); 7.5867 (1.1); 7.5616 (3.1); 7.5563 (1.7); 7.5374 (0.4); 7.5093 (1.7); 7.4814 (0.8); 7.4740 (1.2); 7.4668 (0.6); 7.4593 (0.5); 7.4567 (0.5); 7.4509

TABLE 2-continued (0.7); 7.4436 (0.4); 7.3508 (0.4); 7.2988 (6.7); 7.0805 (1.2); 7.0549 (2.3); 7.0410 (1.9); 7.0011 (1.3); 6.9755 (0.7); 6.9631 (0.6); 6.9180 (0.5); 5.6422 (1.1); 4.1494 (0.9); 4.1235 (1.0); 3.9395 (0.4); 3.9314 (0.6); 3.9081 (1.7); 3.8938 (0.7); 3.8854 (0.6); 3.8765 (1.3); 3.8592 (0.9); 3.8249 (0.4); 3.8040 (0.3); 3.7236 (0.9); 3.7188 (0.9); 3.7034 (2.0); 3.6852 (1.0); 3.6790 (1.0); 3.1836 (0.8); 3.1624 (1.4); 3.1510 (1.6); 3.1433 (0.9); 3.1318 (0.8); 3.1035 (0.4); 3.0884 (16.0); 2.9193 (1.0); 2.8990 (1.8); 2.8721 (0.9); 2.3372 (10.2); 2.3197 (9.5); 2.2971 (3.0); 2.1801 (2.6); 1.4843 (0.6); 1.4720 (0.7); 1.2926 (0.5); 0.1087 (0.4); 0.0380 (6.9)

I-265: $^{1}$H-NMR(499.9 MHz, CDCl3):
δ = 7.5506 (0.5); 7.5351 (1.7); 7.5196 (4.4); 7.5047 (0.6); 7.4170 (2.6); 7.3727 (1.6); 7.3584 (1.2); 7.2591 (3.2); 6.9995 (3.0); 6.9852 (1.8); 6.9698 (2.8); 6.9247 (1.9); 6.9095 (1.2); 4.6809 (1.9); 4.1229 (1.0); 4.1171 (1.2); 4.1013 (1.3); 4.0954 (1.3); 3.9300 (0.8); 3.9201 (0.9); 3.9134 (0.9); 3.9081 (0.7); 3.9027 (0.6); 3.8927 (1.7); 3.8830 (0.8); 3.8709 (1.2); 3.8612 (0.9); 3.5416 (0.8); 3.5232 (1.2); 3.5052 (0.8); 2.9721 (0.7); 2.9616 (0.8); 2.9444 (1.3); 2.9337 (1.2); 2.8718 (1.3); 2.8539 (1.2); 2.8443 (0.8); 2.8261 (0.8); 2.2822 (15.0); 2.2782 (16.0); 2.2594 (0.4); 2.1659 (0.6); 2.1486 (1.1); 2.1391 (1.2); 2.1314 (1.2); 2.0996 (0.4); 1.9969 (0.6); 1.9659 (2.4); 1.9581 (2.2); 1.9410 (1.6); 1.7424 (1.4); 1.7353 (1.5); 1.5712 (2.3); 1.2562 (0.4); −0.0002 (3.7)

I-266: $^{1}$H-NMR(300.2 MHz, CDCl3):
δ = 7.5347 (1.2); 7.5107 (3.3); 7.4871 (0.3); 7.4209 (1.6); 7.3758 (0.7); 7.3682 (1.2); 7.3610 (0.6); 7.3544 (0.4); 7.3516 (0.5); 7.3455 (0.7); 7.3381 (0.4); 7.2989 (4.3); 7.0283 (1.8); 7.0111 (0.9); 6.9855 (2.5); 6.9612 (1.4); 6.9354 (0.5); 5.9718 (0.7); 5.9573 (0.4); 5.0851 (1.1); 5.0801 (1.2); 4.1354 (0.6); 4.1239 (0.7); 4.0987 (0.8); 4.0872 (0.8); 3.9200 (0.3); 3.9111 (0.4); 3.9004 (0.5); 3.8920 (0.6); 3.8818 (0.5); 3.8726 (0.4); 3.8061 (1.0); 3.7868 (0.7); 3.7696 (0.9); 3.7503 (0.8); 3.7288 (16.0); 3.6910 (0.8); 3.6739 (0.9); 3.6555 (0.8); 3.6371 (0.7); 3.6146 (0.4); 2.9907 (0.5); 2.9706 (0.5); 2.9445 (0.8); 2.9244 (0.8); 2.8125 (0.8); 2.7847 (0.8); 2.7665 (0.6); 2.7385 (0.5); 2.5322 (1.5); 2.5095 (3.2); 2.4868 (1.8); 2.3163 (9.2); 2.2988 (9.8); 2.1019 (0.5); 2.0793 (1.6); 2.0567 (2.2); 2.0341 (1.4); 2.0112 (0.3); 1.6466 (0.6); 0.0374 (4.8)

I-267: $^{1}$H-NMR(300.2 MHz, CDCl3):
δ = 7.5571 (0.5); 7.5311 (2.0); 7.5074 (5.6); 7.4842 (0.6); 7.4414 (2.8); 7.3855 (1.1); 7.3780 (1.9); 7.3709 (1.1); 7.3643 (0.7); 7.3552 (1.2); 7.2989 (9.1); 7.0345 (3.2); 7.0089 (1.2); 6.9833 (4.5); 6.9690 (2.8); 6.9409 (0.7); 6.0630 (0.8); 6.0451 (1.5); 6.0263 (0.8); 5.2446 (2.0); 4.1009 (0.9); 4.0907 (1.1); 4.0652 (1.2); 4.0549 (1.3); 3.8906 (0.7); 3.8806 (0.8); 3.8718 (0.9); 3.8643 (0.9); 3.8438 (0.6); 3.8306 (1.9); 3.8129 (0.8); 3.7947 (1.3); 3.7770 (0.9); 3.5758 (0.5); 3.5568 (0.5); 3.5314 (1.8); 3.5123 (2.0); 3.5051 (1.8); 3.4852 (1.4); 3.4604 (0.4); 3.4411 (0.4); 2.9973 (0.8); 2.9773 (0.8); 2.9519 (1.4); 2.9309 (1.3); 2.8350 (1.3); 2.8090 (1.3); 2.7892 (0.8); 2.7627 (0.8); 2.5402 (1.2); 2.3208 (15.1); 2.2944 (16.0); 1.6456 (2.7); 1.3312 (15.6); 1.3194 (15.9); 1.2921 (1.0); 1.2648 (0.3); 1.2587 (0.4); 0.1079 (0.7); 0.0375 (10.6); 0.0267 (0.5)

I-268: $^{1}$H-NMR(300.2 MHz, CDCl3):
δ = 8.0565 (2.3); 8.0535 (2.4); 8.0477 (2.5); 8.0448 (2.2); 7.6358 (2.5); 7.6320 (2.5); 7.6269 (2.2); 7.6188 (5.2); 7.6154 (5.7); 7.6009 (0.4); 7.4929 (2.7); 7.4722 (0.4); 7.4650 (0.4); 7.4584 (1.2); 7.4454 (1.6); 7.4385 (1.5); 7.4283 (1.1); 7.4198 (0.7); 7.2988 (13.8); 7.0904 (0.4); 7.0679 (0.4); 7.0350 (2.3); 7.0095 (6.4); 6.9330 (2.0); 6.9074 (1.1); 6.8841 (3.2); 6.8753 (3.2); 6.8595 (0.4); 6.8504 (0.3); 5.0046 (1.8); 4.9954 (1.8); 3.9002 (1.1); 3.8895 (1.4); 3.8643 (1.3); 3.8537 (2.1); 3.8236 (0.8); 3.8132 (0.8); 3.8050 (0.8); 3.7957 (0.8); 3.7861 (0.6); 3.7757 (0.5); 3.7289 (0.5); 3.7022 (1.8); 3.6863 (1.4); 3.6664 (1.3); 3.6506 (1.0); 2.9169 (0.5); 2.8970 (0.6); 2.8705 (1.8); 2.8462 (2.4); 2.8166 (1.7); 2.7992 (0.5); 2.7706 (0.5); 2.3586 (1.7); 2.3415 (1.6); 2.3119 (15.1); 2.2947 (16.0); 2.0813 (0.7); 1.6469 (0.6); 1.2929 (0.8); 0.1088 (1.4); 0.0491 (0.5); 0.0458 (0.4); 0.0383 (16.6); 0.0290 (0.6); 0.0274 (0.7)

I-269: $^{1}$H-NMR(300.2 MHz, CDCl3):
δ = 7.5276 (0.5); 7.5007 (2.3); 7.4805 (6.0); 7.4613 (0.6); 7.4224 (3.0); 7.3812 (0.4); 7.3651 (1.3); 7.3553 (1.7); 7.3476 (1.4); 7.3342 (1.2); 7.3268 (0.7); 7.2984 (18.0); 7.0145 (3.7); 6.9918 (1.4); 6.9662 (4.6); 6.9495 (3.0); 6.9236 (0.8); 6.0218 (0.8); 6.0053 (1.6); 5.9887 (0.8); 5.3805 (1.7); 4.1931 (0.8); 4.1693 (2.5); 4.1455 (2.5); 4.1218 (1.0); 4.1006 (0.4); 4.0844 (1.0); 4.0730 (1.1); 4.0479 (1.2); 4.0368 (1.2); 3.8627 (1.0); 3.7884 (1.6); 3.7699 (1.1); 3.7516 (1.3); 3.7329 (1.1); 3.7014 (0.7); 3.6796 (1.2); 3.6622 (1.4); 3.6419 (1.4); 3.6232 (1.1); 3.6010 (0.7); 3.5803 (0.4); 3.0141 (0.4); 3.0010 (0.4); 2.9523 (1.3); 2.9322 (1.4); 2.9069 (2.0); 2.8858 (2.0); 2.8132 (2.5); 2.7866 (2.6); 2.7672 (2.1); 2.7406 (1.9); 2.5335 (2.3); 2.5121 (3.9); 2.4900 (2.5); 2.3738 (0.4); 2.3080 (16.0); 2.2717 (16.0); 2.1158 (1.3); 2.0829 (11.9); 2.0523 (2.0); 2.0307 (2.6); 2.0089 (1.6); 1.9868 (0.5); 1.4680 (1.6); 1.3195 (3.1); 1.2957 (6.3); 1.2719 (3.1); 1.2571 (1.0); 0.1057 (9.4); 0.0934 (0.4); 0.0462 (1.0); 0.0354 (22.9); 0.0261 (0.7); 0.0246 (0.8)

I-270: $^{1}$H-NMR(300.2 MHz, CDCl3):
δ = 8.1526 (10.5); 7.6416 (0.6); 7.6284 (5.6); 7.6253 (6.4); 7.6162 (2.4); 7.6052 (2.9); 7.5788 (0.7); 7.3624 (3.2); 7.3441 (1.1); 7.3126 (19.1); 7.2990 (7.2); 7.2822 (1.0); 7.2529 (1.3); 7.2457 (1.8); 7.2369 (0.9); 7.2312 (1.6); 7.2239 (1.8); 7.2149 (0.9); 6.7125 (2.2); 6.5247 (4.3); 6.3369 (2.1); 6.1198 (2.2); 5.3355 (5.7); 4.2806 (1.4); 4.2715 (1.8); 4.2458 (2.0); 4.2365 (1.8); 4.1909 (0.9); 4.1671 (2.8); 4.1433 (2.8); 4.1200 (1.4); 4.0987 (1.2); 4.0764 (0.6); 3.9684 (0.7); 3.9594 (0.8); 3.9517 (0.9); 3.9430 (0.9); 3.9363 (1.0); 3.9276 (1.0); 3.9189 (1.0); 3.9083 (3.4); 3.8900 (1.1); 3.8735 (2.4); 3.8547 (1.4); 3.1250 (1.0); 3.1100 (1.0); 3.0806 (1.5); 3.0646 (1.4); 2.8740 (1.6); 2.8431 (1.6); 2.8295 (1.4); 2.7980 (1.2); 2.0928 (0.4); 2.0796 (16.0); 2.0392 (1.8); 1.6690 (0.5); 1.6467 (0.7); 1.6376 (0.7); 1.6205 (1.2); 1.5988 (0.5); 1.4288 (0.4); 1.4041 (0.4); 1.3184 (3.5); 1.2945 (7.7); 1.2708 (3.3); 0.9957 (1.0); 0.9790 (0.4); 0.9712 (2.0); 0.9469 (0.8); 0.1074 (2.0); 0.0361 (8.0); 0.0252 (0.3)

I-271: $^{1}$H-NMR(300.2 MHz, CDCl3):
δ = 8.1283 (9.7); 7.4820 (1.8); 7.4545 (3.9); 7.4270 (2.3); 7.2991 (1.4); 7.1318 (1.5); 7.1294 (1.3); 7.1262 (1.5); 7.1246 (1.5); 7.1042 (1.2); 7.1016 (1.1); 7.0988 (1.3); 6.9948 (2.5); 6.9693 (3.0); 6.9439 (1.6); 6.9413 (2.0); 6.9338 (4.4); 6.9168 (1.3); 6.9142 (1.4); 6.9093 (1.7); 6.9067 (1.7); 6.8745 (2.0); 6.8671 (3.2); 6.8600 (1.5); 6.8252 (2.2); 6.7383 (1.6); 6.7130 (1.3); 6.5809 (4.6); 6.3365 (2.3); 6.1467 (1.9); 5.3310 (0.5); 4.3019 (1.1); 4.2919 (1.3); 4.2668 (1.5); 4.2576 (1.4); 3.9149 (0.5); 3.9085 (0.6); 3.9031 (0.7); 3.8987 (0.7); 3.8927 (0.7); 3.8878 (0.7); 3.8822 (0.8); 3.8758 (0.6); 3.8731 (0.6); 3.8662 (0.7); 3.8582 (0.7); 3.8466 (2.5); 3.8260 (1.0); 3.8118 (1.9); 3.7910 (1.2); 3.0447 (1.0); 3.0295 (1.0); 2.9994 (1.4); 2.9836 (1.3); 2.7524 (1.4); 2.7206 (1.4); 2.7072 (1.2); 2.6748 (1.1); 2.2965 (16.0); 2.2161 (14.9); 1.6829 (4.2); 0.0412 (1.7)

I-272: $^{1}$H-NMR(300.2 MHz, CDCl3):
δ = 8.1079 (9.0); 7.2991 (0.8); 7.1374 (3.4); 7.1091 (4.0); 7.0066 (2.5); 6.9811 (3.1); 6.9411 (3.0); 6.8138 (2.9); 6.8069 (4.8); 6.7971 (3.6); 6.7891 (1.6); 6.7686 (3.3); 6.7608 (3.4); 6.7377 (1.4); 6.1056 (2.2); 4.3091 (1.2); 4.2990 (1.3); 4.2738 (1.5); 4.2637 (1.4); 3.9259 (0.5); 3.9192 (0.6); 3.9097 (0.8); 3.9035 (0.7); 3.8930 (0.8); 3.8872 (0.6); 3.8767 (0.6); 3.8698 (0.5); 3.8610 (0.4); 3.8438 (2.3); 3.8230 (1.2); 3.8084 (1.8); 3.7876 (1.2); 3.0525 (1.0); 3.0368 (1.0); 3.0071 (1.4); 2.9910 (1.3); 2.7532 (1.5); 2.7207 (1.4); 2.7078 (1.2); 2.6749 (1.1); 2.3035 (16.0); 2.2287 (15.0); 2.1965 (0.9); 2.0299 (2.6); 0.0402 (0.8)

TABLE 2-continued

I-273: $^1$H-NMR(300.2 MHz, CDCl3):
δ = 7.9511 (5.2); 7.6284 (2.2); 7.4035 (1.4); 7.3774 (2.0); 7.2987 (8.3); 7.2179 (1.4); 7.1914 (1.0); 7.1348 (0.6); 7.1079 (1.6); 7.0812 (1.4); 7.0528 (1.0); 7.0467 (1.1); 7.0290 (1.1); 7.0239 (1.2); 7.0024 (0.6); 6.9967 (0.5); 6.8555 (0.7); 6.8496 (0.7); 6.8290 (1.2); 6.8074 (0.7); 6.8019 (0.6); 6.2083 (1.2); 6.2012 (1.2); 5.3366 (9.0); 4.1933 (0.8); 4.1838 (1.1); 4.1580 (1.4); 4.1489 (1.4); 4.0865 (0.4); 4.0753 (0.6); 4.0599 (0.7); 4.0461 (0.6); 4.0266 (1.9); 4.0131 (0.7); 3.9916 (1.0); 3.9777 (0.7); 3.3038 (0.6); 3.2888 (0.6); 3.2599 (1.1); 3.2440 (1.0); 3.1217 (1.0); 3.0920 (1.0); 3.0776 (0.8); 3.0474 (0.7); 2.6832 (16.0); 2.6373 (0.6); 2.1128 (0.5); 2.1014 (0.6); 2.0835 (1.2); 2.0671 (0.6); 2.0562 (0.5); 1.6032 (9.0); 1.2964 (0.5); 1.0803 (0.4); 1.0660 (1.6); 1.0591 (1.9); 1.0485 (1.0); 1.0444 (0.9); 1.0374 (1.7); 1.0309 (1.8); 1.0196 (0.7); 0.8115 (0.9); 0.7957 (2.0); 0.7889 (1.8); 0.7795 (2.1); 0.7725 (1.3); 0.7620 (0.8); 0.1074 (2.9); 0.0480 (0.4); 0.0372 (11.6); 0.0264 (0.5)
I-274: $^1$H-NMR(499.9 MHz, CDCl3):
δ = 8.1159 (5.7); 7.5661 (1.2); 7.5528 (4.0); 7.5377 (2.4); 7.5286 (1.6); 7.5125 (2.1); 7.4969 (0.9); 7.2596 (19.4); 7.2071 (6.5); 7.1994 (4.9); 7.0789 (0.8); 7.0710 (1.4); 7.0627 (2.6); 7.0556 (2.1); 7.0468 (1.9); 6.8197 (4.3); 6.1876 (1.8); 5.2984 (4.6); 4.3560 (1.1); 4.3490 (1.2); 4.3342 (1.2); 4.3273 (1.3); 4.0189 (0.5); 4.0110 (0.7); 4.0055 (0.7); 3.9990 (0.8); 3.9914 (0.6); 3.8370 (1.4); 3.8240 (1.2); 3.8152 (1.4); 3.8022 (1.2); 3.4563 (16.0); 3.1722 (0.9); 3.1628 (1.0); 3.1436 (1.2); 3.1343 (1.2); 2.8727 (1.2); 2.8527 (1.2); 2.8442 (1.1); 2.8242 (1.0); 2.0050 (0.3); 1.7880 (0.7); 1.6424 (0.3); 1.6022 (0.4); 1.5920 (0.4); 1.5778 (0.4); 1.5651 (0.4); 1.5424 (0.5); 1.5250 (0.3); 1.4218 (0.3); 1.3208 (0.3); 1.3078 (0.4); 1.2838 (0.5); 1.2546 (3.5); 1.2317 (0.6); 1.2159 (0.5); 0.8802 (0.5); 0.8579 (1.1); 0.8451 (1.5); −0.0002 (24.2)
I-275: $^1$H-NMR(300.2 MHz, CDCl3):
δ = 8.1152 (6.1); 7.2988 (2.8); 7.1320 (1.6); 7.1064 (2.0); 7.0016 (1.7); 6.9761 (2.0); 6.9334 (2.0); 6.8585 (1.2); 6.8514 (1.5); 6.8322 (1.0); 6.8252 (1.3); 6.7823 (2.1); 6.7757 (1.9); 6.7340 (1.1); 6.7087 (0.9); 6.2953 (1.3); 4.2905 (0.7); 4.2822 (0.9); 4.2569 (1.0); 4.2475 (0.8); 3.8998 (0.3); 3.8887 (0.4); 3.8828 (0.5); 3.8727 (0.5); 3.8675 (0.5); 3.8607 (0.5); 3.8438 (1.9); 3.8235 (0.5); 3.8095 (1.3); 3.7887 (0.8); 3.2373 (16.0); 3.0421 (0.6); 3.0266 (0.6); 2.9973 (1.0); 2.9808 (0.9); 2.7581 (0.8); 2.7272 (0.8); 2.7127 (0.8); 2.6816 (0.7); 2.3019 (10.8); 2.2288 (10.0); 1.6484 (0.5); 0.0401 (2.9)
I-276: $^1$H-NMR(300.2 MHz, CDCl3):
δ = 8.1422 (10.2); 7.2988 (2.9); 7.2744 (1.3); 7.2714 (1.3); 7.2681 (1.2); 7.2530 (3.1); 7.2292 (2.1); 7.2245 (2.2); 7.2011 (0.7); 7.1966 (1.0); 7.1093 (1.4); 7.1030 (1.4); 7.0875 (1.4); 7.0825 (1.2); 7.0783 (1.6); 7.0635 (1.0); 7.0544 (0.9); 7.0087 (2.5); 6.9832 (3.0); 6.9093 (2.8); 6.8612 (1.9); 6.7297 (1.6); 6.7045 (1.3); 6.6187 (3.9); 6.3762 (2.0); 6.0757 (1.9); 4.3131 (1.1); 4.3040 (1.4); 4.2782 (1.4); 4.2692 (1.4); 3.9279 (0.5); 3.9207 (0.6); 3.9158 (0.7); 3.9107 (0.8); 3.9041 (0.7); 3.8999 (0.7); 3.8948 (0.8); 3.8883 (0.6); 3.8789 (0.8); 3.8651 (2.8); 3.8448 (0.9); 3.8304 (2.0); 3.8099 (1.2); 3.0530 (1.0); 3.0375 (1.0); 3.0080 (1.4); 2.9916 (1.3); 2.7770 (1.4); 2.7457 (1.3); 2.7320 (1.2); 2.7001 (1.1); 2.3039 (16.0); 2.1724 (15.0); 1.6681 (0.8); 0.0389 (2.3)
I-277: $^1$H-NMR(300.2 MHz, CDCl3):
δ = 8.0748 (0.4); 8.0680 (0.5); 7.8830 (4.3); 7.8780 (4.2); 7.5795 (4.6); 7.5625 (4.2); 7.5346 (0.5); 7.5111 (0.4); 7.3519 (0.4); 7.3180 (2.6); 7.2987 (37.3); 7.2865 (0.7); 7.2703 (1.0); 7.2629 (1.0); 7.2541 (1.4); 7.2473 (1.1); 7.2401 (0.9); 7.2321 (0.8); 7.0338 (0.4); 6.9962 (2.3); 6.9708 (2.7); 6.9153 (2.9); 6.7144 (1.6); 6.6886 (1.3); 6.1638 (0.3); 6.1296 (1.9); 4.3200 (1.0); 4.3097 (1.2); 4.2854 (1.3); 4.2755 (1.2); 3.9493 (0.3); 3.9080 (0.9); 3.8952 (0.9); 3.8800 (0.8); 3.8580 (2.0); 3.8365 (1.0); 3.8234 (1.4); 3.8024 (1.0); 3.3985 (0.6); 3.3901 (0.4); 3.1339 (0.5); 3.0424 (1.0); 3.0281 (0.9); 2.9973 (1.3); 2.9819 (1.2); 2.7557 (1.3); 2.7243 (1.3); 2.7113 (1.1); 2.6775 (1.0); 2.3576 (0.4); 2.3285 (1.3); 2.2957 (16.0); 2.1859 (14.4); 1.9616 (0.5); 1.9437 (1.0); 1.9295 (1.0); 1.9155 (1.1); 1.9007 (0.6); 1.6002 (9.7); 1.5465 (1.6); 1.5320 (1.5); 1.5171 (1.4); 1.4969 (1.3); 1.4810 (0.8); 1.4591 (0.5); 1.4210 (0.3); 1.3242 (1.0); 1.3169 (1.1); 1.2938 (4.0); 1.2794 (1.5); 1.2720 (1.3); 1.2629 (1.0); 1.2557 (0.9); 1.1671 (0.3); 0.9797 (0.4); 0.9663 (1.1); 0.9522 (1.6); 0.9478 (1.5); 0.9365 (1.9); 0.9187 (2.0); 0.8980 (1.1); 0.8718 (0.4); 0.4991 (0.6); 0.4847 (1.4); 0.4696 (1.6); 0.4553 (1.8); 0.4423 (1.4); 0.4278 (0.8); 0.4088 (0.4); 0.3980 (0.4); 0.2215 (0.5); 0.1939 (1.9); 0.1833 (2.2); 0.1074 (0.9); 0.0487 (1.2); 0.0379 (45.2); 0.0287 (2.3); 0.0271 (2.4); −0.0022 (0.4); −0.0301 (0.3)
I-278: $^1$H-NMR(499.9 MHz, CDCl3):
δ = 7.5541 (0.5); 7.5384 (1.4); 7.5255 (3.4); 7.5230 (3.5); 7.5110 (0.5); 7.3864 (2.0); 7.3488 (1.3); 7.3446 (1.3); 7.3404 (0.9); 7.3348 (1.0); 7.3308 (1.0); 7.2600 (11.3); 7.0032 (2.4); 6.9998 (2.3); 6.9883 (2.9); 6.9222 (0.9); 6.9059 (0.6); 6.8957 (0.9); 6.8801 (0.6); 4.7032 (1.0); 4.6853 (0.9); 4.2035 (0.5); 4.1972 (0.6); 4.1818 (0.6); 4.1752 (0.7); 4.1602 (0.7); 4.1447 (0.7); 3.9342 (0.4); 3.9281 (0.5); 3.9226 (0.6); 3.9051 (1.5); 3.8978 (0.9); 3.8889 (1.2); 3.8798 (1.2); 3.8685 (0.6); 3.8578 (0.7); 3.8466 (0.5); 3.8041 (0.7); 3.7816 (0.7); 3.7710 (0.6); 3.7483 (0.6); 3.0127 (0.4); 3.0027 (0.5); 2.9917 (0.6); 2.9847 (0.7); 2.9809 (0.8); 2.9752 (0.6); 2.9641 (0.6); 2.9528 (0.6); 2.8642 (0.6); 2.8475 (0.6); 2.8367 (0.4); 2.8184 (0.8); 2.8002 (0.6); 2.7900 (0.5); 2.7723 (0.4); 2.3743 (0.4); 2.3691 (0.4); 2.3251 (0.9); 2.2820 (16.0); 2.2760 (8.2); 1.8252 (0.4); 1.8132 (0.7); 1.8102 (0.7); 1.8079 (0.7); 1.7974 (1.1); 1.7867 (0.7); 1.7846 (0.7); 1.7813 (0.8); 1.7693 (0.5); 1.5708 (2.0); 1.4769 (0.4); 1.4656 (0.6); 1.4579 (0.7); 1.4476 (0.9); 1.4391 (0.9); 1.4288 (0.7); 1.4212 (0.6); 1.4098 (0.3); 1.2840 (0.4); 1.2568 (1.7); 1.1690 (0.4); 1.1604 (0.7); 1.1522 (0.9); 1.1437 (1.0); 1.1351 (0.9); 1.1269 (0.6); 1.1181 (0.4); 1.0818 (0.5); 1.0705 (0.7); 1.0640 (0.5); 1.0588 (0.6); 1.0526 (0.6); 1.0410 (0.5); 1.0282 (0.4); 1.0169 (0.7); 1.0104 (0.5); 1.0052 (0.6); 0.9992 (0.6); 0.9874 (0.5); 0.9486 (0.6); 0.9378 (1.0); 0.9269 (1.0); 0.9201 (1.0); 0.9092 (0.9); 0.8983 (0.5); 0.8942 (0.4); 0.8802 (0.5); 0.8665 (0.4); 0.5735 (0.4); 0.5640 (0.6); 0.5553 (0.8); 0.5459 (1.0); 0.5376 (0.8); 0.5293 (0.6); 0.5199 (0.4); 0.4486 (0.4); 0.4460 (0.4); 0.4374 (0.6); 0.4348 (0.6); 0.4292 (0.8); 0.4209 (0.9); 0.4104 (0.7); 0.4026 (0.5); 0.2718 (0.4); 0.2656 (0.5); 0.2609 (0.6); 0.2577 (0.7); 0.2530 (0.8); 0.2469 (0.8); 0.2425 (0.8); 0.2385 (0.7); 0.2341 (0.7); 0.2280 (0.4); 0.2233 (0.4); 0.2037 (0.5); 0.1947 (1.0); 0.1846 (1.0); 0.1758 (0.8); 0.1658 (0.5); 0.0060 (0.8); −0.0002 (11.6); −0.0066 (0.6)
I-279: $^1$H-NMR(300.2 MHz, CDCl3):
δ = 8.4114 (0.5); 7.6165 (0.4); 7.5901 (1.5); 7.5688 (4.0); 7.5485 (0.5); 7.4643 (2.0); 7.4352 (0.9); 7.4264 (1.3); 7.4187 (0.8); 7.4053 (0.9); 7.2993 (16.0); 7.0382 (2.5); 7.0080 (2.8); 6.9720 (1.7); 6.9469 (0.8); 6.1375 (0.6); 6.1197 (0.5); 6.1025 (0.7); 6.0806 (0.8); 6.0628 (0.6); 6.0456 (0.8); 6.0271 (0.4); 5.5680 (1.3); 5.5636 (1.3); 5.5109 (1.1); 5.5064 (1.1); 5.4135 (1.4); 5.4100 (1.4); 5.3787 (1.2); 5.3751 (1.2); 5.3378 (1.2); 5.0691 (0.5); 5.0505 (0.5); 5.0287 (1.2); 5.0104 (1.1); 4.9858 (1.2); 4.9674 (1.1); 4.9454 (0.4); 4.9269 (0.4); 4.8564 (1.4); 4.2052 (0.9); 4.1948 (1.0); 4.1693 (1.2); 4.1592 (1.1); 3.9841 (0.3); 3.9753 (0.4); 3.9650 (0.7); 3.9553 (0.6); 3.9462 (0.8); 3.9364 (0.7); 3.9278 (0.6); 3.9081 (1.8); 3.8902 (0.7); 3.8723 (1.2); 3.8543 (0.8); 3.7191 (0.4); 3.6962 (0.5); 3.6747 (0.4); 3.1490 (0.3); 3.1244 (0.8); 3.0995 (0.8); 3.0757 (0.4); 3.0327 (0.8); 3.0141 (0.8); 2.9869 (1.3); 2.9682 (1.2); 2.8845 (1.4); 2.8557 (1.3); 2.8384 (0.9); 2.8093 (0.9); 2.7587 (0.4); 2.7508 (0.4); 2.7401 (0.4); 2.7078 (0.4); 2.6696 (0.4); 2.6378 (0.4); 2.6153 (0.4); 2.5271 (0.4); 2.5004 (0.4); 2.4102 (0.6); 2.3845 (0.6); 2.3591 (0.9); 2.3197 (16.0); 2.2518 (0.4); 2.1343 (0.5); 1.6191 (0.4); 1.5988 (0.4); 1.5734 (0.4); 1.5040 (1.1); 1.4795 (1.9); 1.4543 (6.5); 1.4322 (5.8); 1.3662 (0.5); 1.2915 (1.9); 1.2550 (0.5); 0.9587

TABLE 2-continued (0.4); 0.9411 (0.4); 0.8988 (1.2); 0.8776 (1.3); 0.1073 (0.8); 0.0569 (0.3); 0.0480 (0.8); 0.0374 (14.5); 0.0268 (0.7)
I-280: $^{1}$H-NMR(400.1 MHz, CDCl3):
δ = 8.0072 (2.2); 7.5345 (0.6); 7.5155 (1.8); 7.4906 (3.7); 7.4715 (0.7); 7.3897 (2.4); 7.3418 (1.6); 7.3242 (1.1); 7.2621 (19.2); 7.0038 (3.6); 6.9710 (0.6); 6.9520 (2.0); 6.9351 (3.5); 6.9076 (0.5); 6.0694 (0.5); 6.0242 (0.7); 6.0124 (0.6); 5.3007 (1.0); 5.2271 (0.6); 5.2152 (0.7); 5.2044 (0.7); 5.1924 (0.6); 5.0549 (1.0); 5.0485 (0.5); 5.0429 (1.1); 5.0369 (1.0); 5.0306 (0.5); 5.0248 (0.9); 4.9629 (0.9); 4.9110 (0.7); 4.8802 (0.8); 4.3992 (0.8); 4.3904 (1.1); 4.3820 (0.9); 4.3730 (1.0); 4.3621 (0.6); 4.2208 (0.8); 4.2044 (0.8); 4.1993 (0.9); 4.1830 (0.7); 4.1487 (0.4); 4.1401 (0.4); 4.1214 (0.9); 4.1123 (1.0); 4.1013 (0.5); 4.0930 (0.9); 4.0847 (0.7); 4.0741 (0.5); 4.0654 (0.5); 4.0012 (0.7); 3.9802 (1.3); 3.9592 (1.0); 3.9353 (0.7); 3.9247 (0.7); 3.9130 (0.5); 3.9024 (0.6); 3.8679 (1.8); 3.8612 (1.4); 3.8564 (1.4); 3.8463 (1.2); 3.8353 (0.9); 3.7757 (0.7); 3.7580 (1.1); 3.7424 (1.3); 3.7274 (1.4); 3.7149 (1.8); 3.6831 (0.6); 3.6693 (0.9); 3.6551 (0.5); 3.6463 (0.5); 3.6304 (0.5); 3.6245 (0.5); 3.6089 (0.8); 3.5933 (0.6); 3.5874 (0.7); 3.5718 (0.7); 3.5496 (0.5); 2.9552 (16.0); 2.9246 (1.1); 2.9110 (1.1); 2.8800 (13.8); 2.7663 (0.5); 2.7466 (1.0); 2.7262 (0.8); 2.7129 (0.9); 2.7054 (0.6); 2.6914 (0.5); 2.6830 (0.4); 2.2858 (13.3); 2.2651 (13.0); 1.5821 (7.6); 1.4676 (4.2); 1.4632 (4.4); 1.4557 (4.5); 1.4512 (4.2); 1.3878 (3.8); 1.3760 (3.8); 0.0077 (1.3); −0.0002 (23.6)
I-281: $^{1}$H-NMR(400.1 MHz, CDCl3):
δ = 8.0124 (2.1); 7.6080 (1.2); 7.5930 (2.9); 7.5494 (0.4); 7.5386 (1.1); 7.5253 (2.0); 7.5233 (2.1); 7.4413 (1.5); 7.3952 (1.3); 7.3803 (1.0); 7.3748 (0.8); 7.3643 (0.7); 7.3417 (0.5); 7.3326 (0.6); 7.3276 (0.6); 7.3189 (0.5); 7.3129 (0.4); 7.2620 (17.5); 7.0874 (0.9); 7.0682 (1.3); 7.0095 (1.3); 6.9984 (0.4); 6.9757 (0.9); 6.9499 (1.5); 6.9304 (1.5); 6.8866 (1.6); 6.7357 (0.9); 6.7172 (0.8); 5.3006 (1.1); 5.1570 (0.8); 5.1031 (0.9); 5.0952 (1.0); 4.1073 (0.8); 4.0993 (0.8); 4.0931 (0.9); 4.0763 (1.3); 4.0710 (1.5); 4.0621 (0.7); 4.0542 (0.9); 4.0396 (0.5); 3.9280 (2.1); 3.9189 (2.9); 3.8393 (0.5); 3.8291 (0.8); 3.8204 (1.0); 3.8128 (1.0); 3.8029 (0.8); 3.7951 (0.8); 3.7768 (0.9); 3.7614 (1.2); 3.7585 (1.1); 3.7393 (1.0); 3.7203 (0.4); 3.6625 (0.6); 3.6479 (0.6); 3.6351 (0.6); 3.6206 (0.5); 2.9556 (15.6); 2.9288 (0.5); 2.9111 (0.6); 2.8934 (1.1); 2.8815 (16.0); 2.8646 (1.7); 2.7892 (0.6); 2.7703 (0.6); 2.7549 (0.4); 2.7358 (0.4); 2.6467 (0.4); 2.6282 (0.6); 2.6098 (0.5); 2.5980 (0.4); 2.5795 (0.4); 2.5739 (0.6); 2.5643 (0.5); 2.5553 (1.1); 2.5418 (0.8); 2.5372 (0.9); 2.5320 (0.7); 2.5219 (0.7); 2.5099 (1.0); 2.4990 (0.4); 2.4892 (0.8); 2.4794 (0.4); 2.4669 (0.4); 2.3710 (0.4); 2.3581 (0.8); 2.3393 (1.3); 2.3199 (2.2); 2.3027 (7.2); 2.2865 (6.3); 2.2602 (0.5); 2.2267 (11.5); 1.6067 (2.1); 1.2217 (0.5); 0.0078 (1.1); −0.0002 (21.7); −0.0083 (1.1)
I-282: $^{1}$H-NMR(400.1 MHz, CDCl3):
δ = 8.0094 (1.5); 7.5258 (0.5); 7.5065 (1.4); 7.4866 (2.4); 7.4813 (2.2); 7.4618 (0.5); 7.3865 (2.0); 7.3322 (1.2); 7.3133 (0.9); 7.2622 (12.1); 7.0255 (2.5); 6.9696 (0.3); 6.9510 (5.6); 5.3007 (0.7); 4.8266 (1.1); 4.7961 (1.7); 4.7736 (16.0); 4.7026 (1.2); 4.6790 (0.8); 4.1407 (0.4); 4.1303 (0.4); 4.1227 (0.4); 3.9172 (0.6); 3.9088 (0.7); 3.9021 (0.7); 3.7101 (0.4); 2.9762 (0.8); 2.9557 (11.4); 2.9416 (1.0); 2.9272 (0.9); 2.8811 (9.8); 2.7482 (0.4); 2.7250 (0.5); 2.7147 (0.4); 2.2997 (11.6); 2.2820 (11.5); 1.5851 (5.6); 0.0078 (0.8); −0.0002 (15.1)
I-283: $^{1}$H-NMR(400.1 MHz, CDCl3):
δ = 8.1232 (1.2); 8.0006 (2.1); 7.5894 (0.8); 7.5732 (0.5); 7.5614 (1.0); 7.5467 (2.4); 7.5445 (2.2); 7.5236 (0.3); 7.5041 (0.9); 7.4890 (2.1); 7.4276 (1.2); 7.4009 (0.5); 7.3931 (0.7); 7.3876 (0.6); 7.3777 (0.6); 7.3111 (1.5); 7.2620 (16.2); 7.2471 (0.8); 7.2364 (0.6); 7.0550 (1.0); 7.0358 (1.4); 6.9985 (1.4); 6.9555 (1.6); 6.9346 (1.3); 6.9270 (1.2); 6.9066 (0.6); 6.8800 (0.4); 6.8520 (0.7); 6.8342 (0.5); 5.3007 (0.8); 5.1839 (0.5); 4.7495 (0.8); 4.1962 (0.5); 4.1868 (0.6); 4.1728 (0.8); 4.1602 (0.7); 4.1537 (0.8); 3.9663 (0.5); 3.9546 (1.0); 3.9443 (0.4); 3.9330 (1.0); 3.9047 (0.4); 3.8969 (0.4); 3.8907 (0.4); 3.8812 (0.4); 3.7800 (0.7); 3.7638 (0.5); 3.7527 (0.6); 3.7365 (0.4); 3.0069 (0.4); 2.9940 (0.4); 2.9717 (1.0); 2.9542 (16.0); 2.9363 (0.8); 2.9279 (0.8); 2.9142 (1.1); 2.9013 (0.4); 2.8770 (13.9); 2.7302 (0.5); 2.7067 (0.6); 2.6967 (0.6); 2.6722 (0.6); 2.2979 (6.8); 2.2860 (6.5); 2.2752 (1.0); 2.2597 (2.8); 2.2498 (10.8); 2.1422 (2.0); 2.0614 (0.4); 1.5827 (4.2); 1.5471 (6.1); 0.9551 (0.8); 0.9477 (1.1); 0.8098 (0.4); 0.7959 (1.6); 0.0078 (0.9); −0.0002 (19.5); −0.0083 (1.0)
I-284: $^{1}$H-NMR(400.1 MHz, CDCl3):
δ = 8.0097 (1.1); 7.5235 (0.7); 7.5042 (2.1); 7.4848 (3.7); 7.4801 (3.2); 7.4601 (0.7); 7.3881 (2.8); 7.3414 (1.8); 7.3225 (1.3); 7.2616 (16.3); 7.0013 (3.3); 6.9804 (1.8); 6.9612 (3.6); 6.9295 (2.2); 6.9105 (1.0); 5.8225 (0.8); 5.3006 (0.5); 4.9025 (1.8); 4.1189 (0.9); 4.1106 (1.0); 4.0913 (1.1); 4.0829 (1.1); 3.9015 (0.6); 3.8949 (0.8); 3.8873 (1.0); 3.8805 (1.0); 3.8725 (0.9); 3.8655 (0.6); 3.7940 (1.4); 3.7797 (1.0); 3.7663 (1.2); 3.7521 (1.0); 3.7308 (0.5); 3.7165 (0.8); 3.6999 (1.0); 3.6865 (0.9); 3.6698 (0.4); 3.6372 (0.7); 3.6235 (0.8); 3.6077 (0.6); 3.5925 (0.4); 2.9756 (1.0); 2.9556 (8.4); 2.9409 (1.4); 2.9265 (1.3); 2.8812 (7.1); 2.7826 (1.3); 2.7608 (1.3); 2.7481 (1.0); 2.7263 (0.9); 2.3219 (0.5); 2.3057 (0.6); 2.2844 (15.4); 2.2709 (16.0); 1.6508 (0.3); 1.6328 (0.9); 1.6157 (2.1); 1.6054 (2.2); 1.5989 (2.4); 1.5882 (2.9); 1.5747 (10.3); 0.7386 (0.6); 0.7210 (1.0); 0.7134 (0.6); 0.7017 (0.7); 0.6893 (0.4); 0.5817 (1.1); 0.5678 (3.1); 0.5567 (1.6); 0.5506 (2.8); 0.5369 (0.9); 0.1837 (1.0); 0.1709 (3.6); 0.1584 (3.4); 0.1467 (0.9); 0.0078 (1.0); −0.0002 (20.2); −0.0084 (1.0)
I-285: $^{1}$H-NMR(400.1 MHz, CDCl3):
δ = 8.1252 (0.6); 8.0065 (2.0); 7.5895 (0.5); 7.5619 (0.6); 7.5472 (1.3); 7.5449 (1.3); 7.5319 (0.6); 7.5128 (1.4); 7.4946 (2.8); 7.4911 (2.6); 7.4865 (2.4); 7.4803 (3.3); 7.4272 (0.7); 7.3996 (0.4); 7.3927 (0.7); 7.3796 (1.8); 7.3473 (1.7); 7.3363 (0.9); 7.3315 (1.1); 7.3264 (0.9); 7.3130 (1.1); 7.3077 (1.1); 7.3009 (1.1); 7.2958 (0.8); 7.2838 (0.9); 7.2617 (24.3); 7.0536 (0.6); 7.0344 (0.8); 6.9910 (3.2); 6.9739 (1.3); 6.9538 (2.5); 6.9332 (2.2); 6.9077 (2.0); 6.8868 (0.8); 5.9738 (0.5); 5.9624 (0.5); 5.9476 (0.6); 5.9362 (0.6); 5.9306 (0.7); 5.9193 (0.9); 5.9045 (0.8); 5.8932 (0.9); 5.8760 (0.5); 5.8646 (0.5); 5.8499 (0.5); 5.8383 (0.5); 5.8330 (0.6); 5.8214 (0.6); 5.8068 (0.5); 5.7953 (0.6); 5.6980 (0.4); 5.6798 (0.4); 5.3006 (1.0); 5.2009 (1.0); 5.1981 (1.0); 5.1691 (1.2); 5.1576 (1.0); 5.1550 (1.0); 5.1452 (1.0); 5.1430 (1.0); 5.0845 (1.0); 5.0391 (0.9); 4.9914 (1.1); 4.9655 (1.9); 4.8942 (0.4); 4.8875 (0.4); 4.8771 (0.4); 4.8602 (0.4); 4.8459 (0.5); 4.8293 (0.5); 4.8120 (0.4); 4.7684 (1.0); 4.7249 (0.4); 4.1851 (0.8); 4.1757 (1.0); 4.1568 (1.1); 4.1498 (0.9); 4.0916 (0.6); 4.0837 (0.7); 4.0646 (0.8); 4.0564 (0.8); 3.9555 (0.6); 3.9329 (0.6); 3.8993 (0.4); 3.8851 (0.6); 3.8779 (0.7); 3.8717 (0.7); 3.8639 (0.7); 3.8576 (0.6); 3.8501 (0.5); 3.8431 (0.5); 3.8257 (1.4); 3.8126 (1.0); 3.7986 (1.1); 3.7851 (0.7); 3.7697 (1.2); 3.7536 (0.7); 3.7424 (0.9); 3.7263 (0.6); 3.1205 (2.1); 3.0703 (0.4); 2.9688 (1.1); 2.9552 (16.0); 2.9346 (1.4); 2.9267 (0.9); 2.9196 (1.0); 2.9049 (0.9); 2.8910 (1.0); 2.8796 (13.5); 2.7791 (0.9); 2.7574 (0.9); 2.7441 (0.7); 2.7209 (1.1); 2.6974 (0.8); 2.6854 (0.6); 2.6628 (0.6); 2.2969 (4.0); 2.2856 (6.5); 2.2766 (12.6); 2.2665 (11.3); 2.2564 (9.3); 2.1422 (1.1); 1.7467 (0.4); 1.7320 (0.4); 1.5776 (10.8); 1.4124 (5.0); 1.4041 (5.4); 1.3959 (5.3); 1.3876 (5.1); 0.0078 (1.4); −0.0002 (29.6); −0.0083 (1.7)
I-286: $^{1}$H-NMR(400.1 MHz, CDCl3):
δ = 8.0097 (2.2); 7.5435 (0.4); 7.5232 (1.7); 7.5078 (4.1); 7.3441 (2.1); 7.2953 (0.9); 7.2886 (1.4); 7.2830 (1.1); 7.2715 (1.4); 7.2620 (17.2); 6.9892 (2.4); 6.9663 (1.5); 6.9472 (2.4); 6.8900 (1.5); 6.8710 (1.0); 6.7660 (0.4); 5.3008 (0.8); 5.1414 (1.3); 5.0232 (0.7); 5.0068 (1.6); 5.0008 (1.0); 4.9888 (1.6); 4.9836 (2.2); 4.9688

TABLE 2-continued (1.8); 4.9597 (1.0); 4.9468 (0.6); 4.9298 (0.4); 4.6307 (1.0); 4.6184 (1.4); 4.6139 (1.3); 4.6019 (1.4); 4.5874 (1.5); 4.5729 (0.8); 4.2104 (0.8); 4.2010 (0.9); 4.1827 (1.0); 4.1733 (1.0); 3.9340 (0.7); 3.9253 (0.7); 3.7631 (1.2); 3.7467 (1.0); 3.7353 (1.1); 3.7192 (0.9); 3.0035 (0.8); 2.9902 (0.8); 2.9686 (1.2); 2.9563 (16.0); 2.8814 (13.8); 2.7456 (0.9); 2.7225 (1.0); 2.7109 (0.8); 2.6876 (0.7); 2.3161 (0.5); 2.2800 (11.6); 2.2645 (11.8); 2.2353 (0.4); 2.1792 (0.4); 1.6049 (1.1); −0.0002 (21.2)

I-287: $^1$H-NMR(400.1 MHz, CDCl3):
δ = 8.0052 (1.6); 7.5403 (0.6); 7.5207 (2.2); 7.5029 (5.4); 7.4859 (0.5); 7.3696 (2.8); 7.3259 (1.1); 7.3204 (1.8); 7.3152 (1.2); 7.3032 (1.4); 7.2616 (16.6); 6.9939 (3.1); 6.9618 (1.8); 6.9427 (3.6); 6.9111 (2.2); 6.8921 (1.0); 6.0560 (0.9); 5.3005 (0.4); 5.0332 (1.9); 4.1530 (1.2); 4.1439 (1.3); 4.1253 (1.4); 4.1164 (1.4); 3.9262 (0.4); 3.9100 (0.9); 3.9049 (1.0); 3.8906 (1.7); 3.8747 (2.8); 3.8586 (3.3); 3.8424 (2.2); 3.8259 (0.8); 3.8071 (0.4); 3.7768 (1.6); 3.7617 (1.3); 3.7490 (1.4); 3.7339 (1.1); 3.0698 (0.3); 2.9761 (1.1); 2.9548 (12.2); 2.9415 (1.5); 2.9272 (1.3); 2.8790 (10.6); 2.7579 (1.4); 2.7357 (1.3); 2.7233 (1.1); 2.7010 (1.0); 2.6058 (0.4); 2.5893 (0.7); 2.5797 (1.1); 2.5732 (0.6); 2.5630 (2.0); 2.5536 (1.3); 2.5465 (1.2); 2.5368 (2.0); 2.5269 (0.6); 2.5201 (1.0); 2.5107 (0.7); 2.3170 (0.6); 2.3066 (0.8); 2.2745 (15.2); 2.2647 (16.0); 1.5748 (7.7); 0.0077 (1.1); −0.0002 (20.6); −0.0082 (1.0)

I-288: $^1$H-NMR(400.1 MHz, CDCl3):
δ = 8.0122 (2.0); 7.5373 (0.5); 7.5183 (1.6); 7.4993 (3.4); 7.4915 (3.2); 7.4867 (3.5); 7.3734 (1.8); 7.3472 (1.7); 7.3247 (1.6); 7.3058 (1.3); 7.2996 (1.3); 7.2823 (0.8); 7.2759 (0.7); 7.2618 (22.4); 6.9842 (3.1); 6.9694 (1.5); 6.9498 (2.3); 6.9397 (1.2); 6.9186 (0.6); 6.9038 (1.6); 6.8866 (1.6); 6.8679 (0.6); 6.1756 (0.4); 6.1116 (0.4); 5.3006 (0.9); 5.0572 (0.8); 4.9332 (1.0); 4.8651 (0.3); 4.1883 (0.5); 4.1800 (0.6); 4.1612 (0.8); 4.1495 (1.1); 4.1391 (0.8); 4.1202 (1.0); 4.1117 (0.8); 3.8690 (1.0); 3.8622 (1.1); 3.8546 (1.0); 3.8482 (1.0); 3.7745 (0.8); 3.7600 (1.3); 3.7472 (1.3); 3.7325 (1.4); 3.7172 (0.7); 3.1815 (0.4); 3.1732 (0.5); 3.1641 (0.7); 3.1549 (0.5); 3.1463 (0.4); 2.9730 (0.7); 2.9562 (16.0); 2.9396 (1.9); 2.9249 (2.0); 2.9211 (2.0); 2.9069 (1.5); 2.8822 (13.6); 2.7442 (1.0); 2.7240 (1.1); 2.7126 (1.0); 2.7019 (0.7); 2.6896 (0.8); 2.3255 (0.3); 2.3054 (0.7); 2.2742 (11.3); 2.2681 (12.0); 2.2568 (14.4); 1.5762 (13.5); 1.1762 (0.5); 1.1657 (0.7); 1.1522 (0.7); 1.1427 (0.6); 1.0119 (0.4); 1.0009 (0.5); 0.9912 (0.6); 0.9797 (0.8); 0.9668 (0.7); 0.9587 (0.8); 0.9483 (0.8); 0.9380 (0.6); 0.9281 (0.4); 0.6861 (0.6); 0.6765 (0.9); 0.6624 (0.8); 0.6528 (1.3); 0.6365 (1.3); 0.6197 (0.8); 0.6029 (0.8); 0.5917 (0.7); 0.5865 (0.7); 0.5783 (0.8); 0.5697 (1.5); 0.5546 (1.1); 0.5430 (0.6); 0.5331 (0.5); 0.5207 (0.5); 0.5076 (0.8); 0.4988 (1.0); 0.4878 (1.1); 0.4770 (1.0); 0.4652 (0.9); 0.4544 (0.8); 0.4455 (0.4); 0.4054 (0.4); 0.3878 (0.9); 0.3815 (0.9); 0.3767 (1.0); 0.3674 (1.0); 0.3565 (0.6); 0.2583 (0.5); 0.2488 (0.7); 0.2437 (0.7); 0.2324 (0.6); 0.2215 (0.5); 0.2099 (0.4); 0.1989 (0.4); 0.1889 (0.4); 0.1789 (0.5); 0.1655 (0.5); 0.1548 (0.8); 0.1419 (1.1); 0.1308 (1.2); 0.1179 (1.1); 0.1073 (0.7); 0.0941 (0.4); 0.0828 (0.4); 0.0704 (0.7); 0.0544 (0.9); 0.0428 (0.9); 0.0306 (0.7); 0.0175 (0.6); −0.0002 (27.9)

I-289: $^1$H-NMR(400.1 MHz, CDCl3):
δ = 8.0078 (1.1); 7.5305 (0.5); 7.5113 (1.4); 7.4921 (2.5); 7.4682 (0.5); 7.3925 (1.8); 7.3445 (1.1); 7.3259 (0.8); 7.2620 (10.8); 7.0016 (2.1); 6.9688 (1.0); 6.9496 (2.5); 6.9289 (1.5); 6.9082 (0.6); 6.2002 (0.7); 5.3007 (0.5); 4.9305 (1.2); 4.1389 (0.7); 4.1299 (0.7); 4.1113 (0.8); 4.1021 (0.8); 3.9096 (0.4); 3.9027 (0.5); 3.8947 (0.6); 3.8877 (0.6); 3.8805 (0.5); 3.8728 (0.4); 3.8151 (0.4); 3.7981 (0.5); 3.7795 (1.4); 3.7647 (1.1); 3.7516 (1.0); 3.7364 (0.7); 3.6957 (0.6); 3.6808 (0.6); 3.6634 (0.4); 3.6477 (0.3); 2.9686 (0.8); 2.9553 (8.8); 2.9342 (0.9); 2.9198 (0.8); 2.8802 (7.2); 2.8380 (1.0); 2.8315 (1.1); 2.8227 (1.8); 2.8161 (1.6); 2.8076 (1.1); 2.7997 (0.9); 2.7696 (0.9); 2.7476 (0.8); 2.7349 (0.6); 2.7129 (0.6); 2.3189 (0.4); 2.3048 (0.5); 2.2838 (9.7); 2.2679 (10.1); 2.1226 (16.0); 2.0998 (0.4); 1.5783 (7.4); 0.0077 (0.7); −0.0002 (13.4); −0.0084 (0.7)

I-290: $^1$H-NMR(300.2 MHz, CDCl3):
δ = 7.9513 (5.2); 7.2991 (11.6); 7.1523 (2.4); 7.1384 (0.6); 7.1127 (3.4); 7.0870 (3.3); 7.0620 (1.0); 7.0556 (1.2); 7.0381 (1.1); 7.0333 (1.3); 7.0117 (0.6); 7.0060 (0.5); 6.8578 (0.8); 6.8520 (0.7); 6.8319 (1.2); 6.8098 (0.6); 6.8048 (0.6); 6.7423 (1.3); 6.7190 (1.2); 6.2145 (1.3); 4.2405 (1.0); 4.2294 (1.1); 4.2044 (1.2); 4.1933 (1.3); 4.0527 (0.4); 4.0416 (0.6); 4.0330 (0.6); 4.0227 (0.7); 4.0138 (0.7); 4.0040 (0.5); 3.9959 (0.4); 3.9184 (1.5); 3.9005 (1.1); 3.8823 (1.2); 3.8643 (1.0); 3.1979 (0.8); 3.1808 (0.8); 3.1532 (1.2); 3.1363 (1.1); 2.9372 (1.2); 2.9068 (1.2); 2.8927 (0.9); 2.8621 (0.8); 2.6724 (16.0); 2.2087 (11.9); 2.1399 (0.5); 2.1285 (0.6); 2.1114 (1.0); 2.0943 (0.6); 2.0829 (0.6); 2.0663 (0.3); 2.0443 (5.3); 1.6057 (3.5); 1.2933 (0.8); 1.0884 (0.7); 1.0747 (1.5); 1.0684 (1.9); 1.0557 (1.2); 1.0465 (1.6); 1.0401 (1.8); 1.0272 (0.9); 0.8828 (0.3); 0.8650 (0.3); 0.8294 (0.9); 0.8223 (0.9); 0.8133 (2.0); 0.8061 (1.9); 0.7975 (2.1); 0.7905 (1.3); 0.7803 (0.7); 0.1076 (2.6); 0.0486 (0.6); 0.0379 (15.8); 0.0271 (0.7)

I-291: $^1$H-NMR(300.2 MHz, CDCl3):
δ = 7.9364 (0.9); 7.9278 (1.7); 7.9193 (0.9); 7.6253 (0.9); 7.6030 (2.4); 7.5108 (1.2); 7.4744 (0.5); 7.4647 (0.8); 7.4575 (0.5); 7.4431 (0.5); 7.2986 (21.0); 7.0352 (0.9); 7.0108 (2.4); 6.9479 (0.9); 6.9216 (0.5); 6.5852 (1.0); 6.5763 (1.0); 6.5715 (1.0); 6.5628 (0.9); 5.3376 (0.4); 5.0231 (0.6); 5.0077 (0.6); 4.9872 (0.3); 4.9345 (0.8); 4.0731 (0.5); 4.0523 (0.6); 4.0277 (0.3); 3.9776 (0.5); 3.9532 (1.0); 3.9429 (0.7); 3.9334 (0.6); 3.9264 (0.6); 3.9088 (0.8); 3.7656 (0.8); 3.7287 (0.7); 3.6926 (0.4); 2.8701 (0.7); 2.8503 (0.6); 2.8210 (0.5); 2.7929 (0.5); 2.3683 (0.4); 2.3564 (0.4); 2.3426 (0.6); 2.3185 (6.9); 2.3013 (7.3); 2.1150 (0.5); 2.1000 (0.9); 2.0825 (1.4); 2.0601 (0.8); 2.0446 (0.4); 1.5959 (16.0); 1.2936 (0.8); 0.0489 (0.9); 0.0473 (0.7); 0.0382 (24.5); 0.0290 (0.8); 0.0273 (0.9)

I-292: $^1$H-NMR(300.2 MHz, CDCl3):
δ = 7.5739 (3.6); 7.4593 (2.3); 7.4167 (1.3); 7.3005 (5.7); 7.0488 (3.4); 7.0271 (2.0); 6.9816 (1.8); 6.9551 (0.9); 4.7633 (1.9); 4.2308 (1.0); 4.1957 (1.3); 3.9545 (1.0); 3.9150 (1.3); 3.8766 (0.8); 3.0376 (0.6); 2.9959 (1.0); 2.8877 (0.9); 2.8572 (0.9); 2.8168 (0.5); 2.7403 (8.4); 2.3267 (16.0); 1.5876 (6.1); 1.3000 (0.6); 0.0403 (7.9)

I-293: $^1$H-NMR(499.9 MHz, CDCl3):
δ = 8.1090 (0.4); 7.9834 (4.3); 7.6876 (4.4); 7.5809 (1.0); 7.5643 (3.3); 7.5573 (5.4); 7.5360 (2.2); 7.5251 (2.4); 7.5091 (4.1); 7.4906 (1.4); 7.4700 (3.9); 7.4583 (4.1); 7.4166 (0.9); 7.4019 (2.2); 7.3871 (1.4); 7.2583 (3.4); 6.9870 (3.9); 6.9726 (2.9); 6.9566 (3.7); 6.9419 (2.9); 6.9268 (1.2); 6.8918 (0.6); 6.8775 (0.7); 5.3935 (2.0); 5.0670 (0.6); 3.8947 (1.8); 3.8789 (2.1); 3.8230 (6.0); 3.8085 (16.0); 3.7850 (15.4); 3.7509 (0.9); 3.7440 (0.8); 3.7319 (1.5); 3.7215 (2.1); 3.7010 (2.5); 3.6869 (1.4); 2.8512 (1.0); 2.8376 (1.1); 2.8331 (1.1); 2.8233 (1.5); 2.8112 (1.2); 2.7978 (0.6); 2.7805 (0.6); 2.7696 (0.4); 2.7526 (1.4); 2.7382 (1.3); 2.7250 (0.8); 2.7108 (0.6); 2.3172 (1.0); 2.2847 (13.5); 2.2750 (6.1); 2.2576 (16.0); 2.1415 (1.1); 1.7036 (0.3); 1.2561 (0.5); 0.0722 (0.9); −0.0002 (4.0)

I-294: $^1$H-NMR(300.2 MHz, CDCl3):
δ = 8.9328 (4.5); 7.9802 (4.3); 7.6442 (0.8); 7.5916 (7.1); 7.5234 (4.4); 7.4754 (3.2); 7.2998 (8.4); 7.1556 (0.3); 7.0126 (4.9); 6.9316 (9.8); 4.8526 (3.6); 3.9255 (1.9); 3.8947 (2.5); 3.7330 (4.4); 3.7022 (1.9); 2.8647 (1.1); 2.8202 (2.2); 2.7551 (1.7); 2.7271 (1.7); 2.6848 (0.8); 2.3159 (15.8); 2.2728 (16.0); 2.0441 (1.0); 1.6119

TABLE 2-continued (8.3); 0.1096 (1.1); 0.0400 (11.3)
I-295: $^{1}$H-NMR(300.2 MHz, CDCl3):
δ = 7.9357 (5.2); 7.3546 (2.6); 7.3480 (2.6); 7.2987 (16.4); 7.2130 (2.2); 7.1858 (3.2); 7.1470 (0.6); 7.1206 (1.6); 7.0940 (1.4); 7.0920 (1.4); 7.0801 (1.8); 7.0734 (1.7); 7.0653 (1.1); 7.0589 (1.3); 7.0529 (1.3); 7.0456 (1.4); 7.0416 (1.3); 7.0378 (1.3); 7.0147 (0.6); 7.0089 (0.5); 6.8594 (0.8); 6.8539 (0.8); 6.8328 (1.3); 6.8108 (0.6); 6.8061 (0.6); 6.2520 (1.2); 5.3375 (1.7); 4.2123 (0.4); 4.1949 (2.0); 4.1707 (3.8); 4.1471 (2.7); 4.1233 (0.9); 3.9275 (1.0); 3.9116 (1.9); 3.8979 (0.7); 3.8858 (1.8); 3.8699 (0.6); 3.0176 (0.6); 3.0024 (0.7); 2.9730 (1.0); 2.9564 (1.0); 2.8715 (1.1); 2.8435 (1.0); 2.8272 (0.7); 2.7969 (0.6); 2.6782 (16.0); 2.1311 (0.5); 2.1200 (0.6); 2.1031 (1.0); 2.0830 (12.0); 2.0573 (0.4); 1.6042 (5.8); 1.3205 (3.2); 1.2967 (6.4); 1.2729 (3.0); 1.0830 (0.4); 1.0725 (1.8); 1.0654 (1.9); 1.0549 (1.0); 1.0504 (0.8); 1.0439 (1.8); 1.0370 (1.8); 1.0265 (0.7); 1.0225 (0.7); 0.8231 (1.0); 0.8076 (2.0); 0.8009 (1.9); 0.7911 (2.2); 0.7841 (1.4); 0.7736 (0.8); 0.1065 (5.0); 0.0476 (0.7); 0.0368 (23.6); 0.0276 (0.8); 0.0259 (0.9)
I-296: $^{1}$H-NMR(300.2 MHz, CDCl3):
δ = 8.1563 (13.7); 8.0581 (8.1); 8.0292 (8.6); 7.6479 (0.8); 7.6279 (8.3); 7.6037 (3.6); 7.5776 (1.0); 7.4148 (8.2); 7.3860 (7.3); 7.3507 (4.1); 7.2984 (22.8); 7.2685 (1.8); 7.2616 (2.3); 7.2453 (1.7); 7.2383 (2.5); 7.2311 (1.2); 6.1043 (2.6); 5.3369 (13.6); 4.2139 (1.2); 4.2054 (2.6); 4.1792 (3.0); 4.1711 (1.9); 4.1012 (0.5); 4.0352 (0.3); 4.0177 (0.8); 4.0091 (1.2); 4.0006 (1.2); 3.9814 (4.1); 3.9622 (1.4); 3.9471 (2.9); 3.9316 (1.5); 3.1946 (1.2); 3.1772 (1.2); 3.1495 (2.6); 3.1319 (2.4); 3.0356 (2.1); 3.0232 (0.6); 3.0057 (2.1); 2.9907 (1.4); 2.9608 (1.4); 2.0816 (2.0); 2.0423 (0.7); 1.5903 (16.0); 1.3198 (0.4); 1.2960 (0.8); 0.9971 (0.4); 0.9727 (0.7); 0.1069 (4.0); 0.0478 (1.2); 0.0371 (27.6); 0.0263 (1.0)
I-297: $^{1}$H-NMR(300.2 MHz, CDCl3):
δ = 8.1645 (7.0); 7.6614 (0.4); 7.6433 (4.4); 7.6217 (1.9); 7.5954 (0.5); 7.4913 (3.2); 7.4645 (4.1); 7.3898 (2.1); 7.2987 (13.7); 7.2920 (5.2); 7.2806 (1.5); 7.2646 (4.3); 7.2572 (1.8); 7.2491 (0.6); 6.1210 (1.5); 5.3374 (1.1); 4.2434 (1.3); 4.2176 (1.4); 4.2095 (0.8); 3.9682 (0.4); 3.9590 (0.6); 3.9512 (0.6); 3.9317 (2.0); 3.8990 (1.6); 3.8814 (0.8); 3.1077 (0.7); 3.0918 (0.7); 3.0628 (1.3); 3.0468 (1.2); 2.9039 (1.0); 2.8731 (1.0); 2.8592 (0.8); 2.8284 (0.7); 1.5842 (16.0); 0.1078 (1.9); 0.0489 (0.7); 0.0381 (16.4); 0.0289 (0.4); 0.0272 (0.5)
I-298: $^{1}$H-NMR(300.2 MHz, CDCl3):
δ = 7.9606 (5.3); 7.4108 (0.7); 7.3969 (0.8); 7.3918 (1.1); 7.3796 (1.4); 7.3662 (1.0); 7.3567 (1.0); 7.2986 (8.2); 7.2219 (0.5); 7.2090 (0.4); 7.1949 (4.6); 7.1810 (2.4); 7.1794 (2.4); 7.1760 (2.1); 7.1711 (2.6); 7.1517 (0.4); 7.1030 (2.3); 7.0769 (2.6); 7.0430 (2.6); 7.0372 (2.6); 6.6897 (1.4); 6.6839 (1.4); 6.6635 (1.2); 6.6578 (1.2); 6.0532 (1.3); 4.2478 (0.9); 4.2369 (1.1); 4.2118 (1.2); 4.2006 (1.3); 4.0454 (0.4); 4.0355 (0.6); 4.0198 (0.6); 4.0149 (0.6); 4.0056 (0.6); 3.9964 (0.5); 3.9887 (0.4); 3.9221 (1.5); 3.9041 (1.1); 3.8860 (1.2); 3.8680 (0.9); 3.1863 (0.9); 3.1700 (0.9); 3.1415 (1.2); 3.1251 (1.2); 2.9248 (1.2); 2.8938 (1.2); 2.8799 (0.9); 2.8490 (0.9); 2.7434 (0.4); 2.6795 (16.0); 1.7928 (0.6); 1.7818 (0.6); 1.7651 (1.1); 1.7482 (0.6); 1.7372 (0.7); 1.7201 (0.3); 1.6034 (4.8); 0.9932 (0.4); 0.9765 (1.7); 0.9703 (2.1); 0.9668 (1.6); 0.9481 (1.9); 0.9423 (1.9); 0.9259 (0.5); 0.6030 (1.0); 0.5989 (1.0); 0.5936 (1.1); 0.5885 (1.7); 0.5822 (1.9); 0.5769 (1.7); 0.5659 (1.1); 0.5598 (0.9); 0.0484 (0.4); 0.0377 (10.8); 0.0285 (0.4); 0.0268 (0.4)
I-299: $^{1}$H-NMR(300.2 MHz, CDCl3):
δ = 7.9665 (4.0); 7.4121 (0.5); 7.4043 (0.6); 7.3869 (1.0); 7.3794 (0.7); 7.3641 (0.8); 7.3579 (0.7); 7.2986 (19.5); 7.2144 (0.5); 7.2099 (0.4); 7.1869 (1.3); 7.1825 (1.2); 7.1576 (2.1); 7.1499 (1.1); 7.1364 (1.0); 7.1303 (1.1); 7.1089 (0.4); 7.1028 (0.4); 7.0197 (1.5); 6.9937 (1.6); 6.8312 (1.7); 6.6202 (0.9); 6.6141 (0.9); 6.5939 (0.8); 6.0979 (1.1); 4.2992 (0.6); 4.2911 (0.8); 4.2660 (0.9); 4.2567 (0.7); 4.1728 (0.4); 4.1489 (0.4); 3.9000 (0.5); 3.8840 (0.5); 3.8764 (0.5); 3.8639 (1.5); 3.8439 (0.4); 3.8303 (1.1); 3.8096 (0.6); 3.0387 (0.6); 3.0236 (0.5); 2.9938 (0.8); 2.9778 (0.8); 2.7776 (0.7); 2.7460 (0.8); 2.7320 (0.7); 2.7002 (0.6); 2.6755 (12.4); 2.3519 (0.5); 2.3107 (9.2); 2.0830 (2.2); 1.7686 (0.4); 1.7575 (0.4); 1.7409 (0.8); 1.7236 (0.5); 1.7126 (0.5); 1.5803 (16.0); 1.3217 (0.5); 1.2979 (1.2); 1.2741 (0.5); 0.9428 (0.4); 0.9367 (0.4); 0.9277 (1.3); 0.9213 (1.6); 0.9064 (0.6); 0.8994 (1.4); 0.8933 (1.4); 0.8784 (0.4); 0.5831 (0.7); 0.5736 (0.8); 0.5683 (1.5); 0.5605 (1.5); 0.5520 (1.7); 0.5447 (0.9); 0.5357 (0.6); 0.0496 (1.0); 0.0389 (27.7); 0.0297 (0.9); 0.0281 (1.1)
I-300: $^{1}$H-NMR(300.2 MHz, CDCl3):
δ = 7.9619 (5.3); 7.4224 (0.6); 7.4162 (0.7); 7.4008 (0.8); 7.3956 (1.4); 7.3898 (1.0); 7.3738 (1.0); 7.3681 (0.9); 7.2989 (12.5); 7.2554 (1.9); 7.2500 (2.1); 7.2383 (0.9); 7.2331 (0.8); 7.2109 (1.6); 7.2059 (1.6); 7.1836 (1.1); 7.1792 (1.2); 7.1581 (1.2); 7.1520 (1.3); 7.1361 (1.1); 7.1306 (1.5); 7.1246 (0.6); 7.1088 (0.7); 7.1030 (0.6); 7.0943 (0.8); 7.0880 (0.8); 7.0673 (1.5); 7.0609 (1.5); 7.0220 (2.9); 6.9950 (1.3); 6.0635 (1.2); 5.3373 (1.8); 4.2396 (1.1); 4.2141 (1.2); 4.1955 (0.4); 3.9344 (0.4); 3.9248 (0.6); 3.9168 (0.8); 3.9088 (1.4); 3.9032 (1.7); 3.8951 (1.0); 3.8868 (0.6); 3.8764 (1.7); 3.8582 (0.7); 3.0260 (0.7); 3.0103 (0.7); 2.9806 (1.0); 2.9644 (1.0); 2.8541 (1.0); 2.8239 (0.9); 2.8091 (0.7); 2.7778 (0.6); 2.7021 (0.6); 2.6834 (16.0); 2.3519 (0.6); 2.3299 (11.7); 2.0825 (0.6); 1.5902 (5.6); 1.2974 (0.4); 0.0495 (0.6); 0.0385 (17.2); 0.0278 (0.7)
I-301: $^{1}$H-NMR(300.2 MHz, CDCl3):
δ = 7.9548 (4.4); 7.2989 (10.6); 7.1469 (2.1); 7.1186 (2.5); 7.0873 (2.2); 7.0780 (1.2); 7.0630 (0.9); 7.0570 (1.0); 7.0362 (0.4); 7.0299 (0.3); 6.9005 (2.2); 6.8918 (2.3); 6.8600 (0.6); 6.8522 (0.6); 6.8371 (1.0); 6.8311 (0.8); 6.8127 (0.5); 6.8065 (0.5); 6.5032 (1.3); 6.4945 (1.2); 6.4751 (1.2); 6.4664 (1.1); 6.2321 (1.0); 4.2297 (0.8); 4.2187 (0.8); 4.1937 (1.0); 4.1827 (1.0); 4.0275 (0.3); 4.0171 (0.5); 4.0074 (0.5); 3.9977 (0.5); 3.9890 (0.5); 3.9794 (0.4); 3.9183 (1.2); 3.9005 (0.9); 3.8823 (1.0); 3.8645 (0.8); 3.6949 (16.0); 3.1682 (0.7); 3.1512 (0.7); 3.1230 (1.0); 3.1060 (0.9); 2.9230 (1.0); 2.8930 (1.0); 2.8778 (0.7); 2.8477 (0.7); 2.6747 (13.6); 2.1345 (0.4); 2.1237 (0.4); 2.1068 (0.8); 2.0893 (0.5); 2.0829 (0.9); 1.5976 (7.9); 1.3442 (0.4); 1.3208 (0.8); 1.3051 (2.3); 1.2975 (2.1); 1.2734 (0.3); 1.0793 (0.5); 1.0658 (1.3); 1.0586 (1.6); 1.0549 (1.0); 1.0510 (0.8); 1.0453 (0.9); 1.0369 (1.4); 1.0304 (1.4); 1.0170 (0.7); 0.9418 (0.8); 0.9200 (2.6); 0.8968 (1.0); 0.8212 (0.8); 0.8126 (0.8); 0.8075 (1.5); 0.8040 (1.6); 0.7994 (1.4); 0.7903 (1.6); 0.7873 (1.5); 0.7823 (1.2); 0.7704 (0.6); 0.1076 (5.3); 0.0486 (0.6); 0.0379 (15.2); 0.0269 (0.6)
I-302: $^{1}$H-NMR(300.2 MHz, CDCl3):
δ = 7.9580 (5.1); 7.4077 (0.7); 7.3956 (0.8); 7.3867 (1.3); 7.3751 (1.5); 7.3644 (0.9); 7.3534 (1.0); 7.2989 (12.0); 7.2202 (0.4); 7.2113 (0.4); 7.1954 (3.8); 7.1832 (2.1); 7.1742 (1.9); 7.1709 (3.1); 7.1497 (2.3); 7.1469 (2.3); 7.1356 (0.5); 7.1052 (2.1); 7.0796 (2.4); 6.7903 (1.1); 6.7647 (0.9); 6.0392 (1.0); 4.2576 (0.8); 4.2467 (1.0); 4.2215 (1.1); 4.2104 (1.2); 4.1950 (0.5); 4.1711 (1.3); 4.1473 (1.4); 4.1236 (0.5); 4.0681 (0.4); 4.0584 (0.5); 4.0498 (0.5); 4.0428 (0.5); 4.0372 (0.5); 4.0285 (0.5); 4.0196 (0.4); 3.9240 (1.4); 3.9059 (1.1); 3.8879 (1.2); 3.8697 (1.0); 3.1951 (0.7); 3.1786 (0.7); 3.1505 (1.0); 3.1336 (1.0); 2.9379 (1.2); 2.9070 (1.1); 2.8930 (0.9); 2.8621 (0.8); 2.6796 (16.0); 2.6684 (0.8); 2.5492 (1.7); 2.3907 (1.2); 2.2241 (10.3); 2.0826 (6.4); 1.6144 (4.4); 1.4694 (2.0); 1.3204 (1.7); 1.2967 (3.5); 1.2729 (1.6); 0.1072 (3.6); 0.0480 (0.5); 0.0462 (0.3); 0.0446 (0.4); 0.0372 (15.8); 0.0294 (0.4); 0.0278 (0.4); 0.0263 (0.6)

TABLE 2-continued

I-303: $^1$H-NMR(300.2 MHz, CDCl3):
δ = 7.9489 (4.9); 7.4000 (0.6); 7.3924 (0.7); 7.3746 (1.2); 7.3672 (0.9); 7.3518 (0.9); 7.3458 (0.8); 7.2988 (9.5); 7.2015 (0.7); 7.1970 (0.5); 7.1741 (1.6); 7.1696 (1.4); 7.1441 (2.2); 7.1354 (1.3); 7.1217 (1.1); 7.1156 (1.4); 7.0942 (0.6); 7.0882 (0.4); 6.9785 (2.4); 6.9464 (0.4); 6.9131 (4.3); 6.8861 (0.4); 6.0956 (1.3); 4.3239 (0.8); 4.3125 (0.9); 4.2878 (1.0); 4.2765 (1.1); 3.9428 (0.4); 3.9266 (0.6); 3.9208 (0.5); 3.9107 (0.6); 3.8991 (0.4); 3.8948 (0.4); 3.8309 (1.6); 3.8091 (1.0); 3.7950 (1.3); 3.7733 (0.9); 3.0175 (0.7); 3.0009 (0.7); 2.9725 (1.0); 2.9563 (0.9); 2.6893 (1.2); 2.6685 (15.3); 2.6577 (1.8); 2.6446 (1.0); 2.6121 (0.8); 2.1437 (11.4); 2.1273 (11.4); 1.6113 (16.0); 1.3042 (1.3); 0.9412 (0.4); 0.9193 (1.4); 0.8963 (0.5); 0.1071 (0.6); 0.0480 (0.4); 0.0372 (12.3); 0.0280 (0.4); 0.0263 (0.5)
I-304: $^1$H-NMR(300.1 MHz, $d_6$-DMSO):
δ = 8.1840 (16.0); 8.1689 (3.0); 7.7574 (4.4); 7.7351 (2.8); 7.7093 (3.6); 7.6889 (3.7); 7.6640 (3.4); 7.6589 (3.6); 7.6328 (1.6); 7.6014 (6.5); 7.5944 (7.0); 7.5205 (4.1); 7.4925 (6.2); 7.3910 (3.8); 7.3840 (3.6); 7.3630 (2.5); 7.3560 (2.5); 4.8376 (1.3); 4.8240 (1.6); 4.8134 (1.6); 4.7983 (1.3); 3.4683 (0.6); 3.4543 (0.8); 3.4383 (0.8); 3.4231 (1.5); 3.4098 (1.2); 3.3939 (1.4); 3.3799 (1.3); 3.3176 (1.0); 3.2839 (1.4); 3.2673 (2.2); 3.2497 (1.3); 3.2403 (1.0); 3.2221 (1.3); 3.2037 (0.7); 2.7339 (0.5); 2.7277 (0.6); 2.7216 (0.4); 2.5135 (41.2); 2.5075 (81.7); 2.5015 (109.2); 2.4956 (75.8); 2.4898 (35.2); 2.2776 (0.5); 2.2715 (0.7); 2.2650 (0.5); 2.1469 (0.9); 2.1308 (1.0); 2.1169 (0.8); 2.1023 (1.1); 2.0872 (1.0); 1.5063 (0.6); 1.4897 (0.9); 1.4753 (0.7); 1.4624 (0.8); 1.4483 (0.6); 0.0108 (0.9); −0.0002 (24.7); −0.0112 (0.8)
I-305: $^1$H-NMR(300.2 MHz, CDCl3):
δ = 7.9502 (5.3); 7.5550 (0.7); 7.5288 (1.8); 7.5026 (1.4); 7.4525 (1.6); 7.4269 (0.9); 7.2983 (0.9); 7.2431 (1.9); 7.2420 (1.9); 7.1687 (1.0); 7.1655 (1.2); 7.1617 (1.0); 7.1421 (0.9); 7.1387 (1.0); 7.1349 (0.9); 6.9671 (2.7); 6.9048 (6.6); 6.9021 (6.4); 6.8746 (1.2); 6.6867 (2.4); 6.4989 (1.2); 6.2326 (1.6); 4.2939 (0.9); 4.2825 (1.0); 4.2581 (1.1); 4.2466 (1.1); 3.9168 (0.4); 3.9044 (0.6); 3.9006 (0.6); 3.8945 (0.6); 3.8885 (0.6); 3.8844 (0.6); 3.8727 (0.5); 3.8684 (0.4); 3.8058 (1.6); 3.7840 (1.0); 3.7700 (1.4); 3.7482 (1.0); 2.9972 (0.8); 2.9813 (0.8); 2.9524 (1.0); 2.9363 (1.0); 2.6693 (1.6); 2.6564 (16.0); 2.6377 (1.3); 2.6250 (1.0); 2.5926 (1.0); 2.1976 (0.6); 2.1477 (12.1); 2.1083 (12.2); 0.0364 (1.1)
I-306: $^1$H-NMR(300.2 MHz, CDCl3):
δ = 7.9665 (5.4); 7.5785 (0.7); 7.5524 (1.7); 7.5260 (1.3); 7.4733 (1.6); 7.4476 (0.9); 7.2991 (2.0); 7.2695 (1.9); 7.1881 (1.1); 7.1843 (1.0); 7.1646 (0.8); 7.1613 (1.0); 7.1575 (0.9); 7.0038 (2.0); 6.9778 (2.3); 6.8966 (1.2); 6.8359 (2.2); 6.8318 (2.3); 6.7087 (2.4); 6.6111 (1.3); 6.6054 (1.2); 6.5852 (1.1); 6.5796 (1.1); 6.5209 (1.2); 6.2074 (1.5); 4.2824 (0.8); 4.2733 (1.0); 4.2480 (1.1); 4.2392 (1.0); 3.9022 (0.4); 3.8909 (0.5); 3.8860 (0.6); 3.8805 (0.5); 3.8764 (0.6); 3.8702 (0.6); 3.8618 (0.5); 3.8464 (2.1); 3.8261 (0.6); 3.8121 (1.4); 3.7914 (0.8); 3.0270 (0.8); 3.0126 (0.7); 2.9820 (1.1); 2.9666 (1.1); 2.7564 (1.0); 2.7249 (1.0); 2.7109 (1.0); 2.6695 (16.0); 2.2956 (12.3); 2.0361 (4.9); 1.8012 (0.4); 1.7843 (0.7); 1.7731 (0.7); 1.7563 (1.2); 1.7447 (0.5); 1.7395 (0.8); 1.7284 (0.7); 1.7114 (0.4); 0.9571 (0.4); 0.9405 (2.0); 0.9341 (2.2); 0.9175 (1.0); 0.9123 (2.1); 0.9058 (2.0); 0.8899 (0.5); 0.5917 (0.8); 0.5848 (1.2); 0.5749 (1.6); 0.5681 (2.2); 0.5617 (1.7); 0.5514 (1.3); 0.5449 (0.9); 0.0371 (2.6)
I-307: $^1$H-NMR(300.2 MHz, CDCl3):
δ = 8.1461 (16.0); 8.0469 (8.1); 8.0395 (7.9); 7.8515 (1.8); 7.6487 (12.2); 7.6322 (15.1); 7.5876 (6.0); 7.5794 (5.5); 7.5600 (6.2); 7.5519 (5.9); 7.5216 (1.4); 7.4683 (9.9); 7.4500 (7.0); 7.4113 (4.1); 7.3974 (5.2); 7.3919 (4.7); 7.3821 (3.8); 7.2988 (13.2); 7.2496 (0.4); 7.2321 (0.4); 7.1681 (7.9); 7.1407 (6.8); 5.3362 (0.7); 4.3141 (3.8); 4.3029 (4.3); 4.2780 (4.4); 4.2667 (4.9); 4.1729 (3.1); 4.1664 (3.3); 4.1601 (3.4); 3.9018 (4.9); 3.8818 (4.4); 3.8653 (4.3); 3.8457 (3.6); 3.0635 (14.2); 3.0418 (10.3); 2.9887 (0.7); 2.6570 (0.7); 2.3408 (0.3); 2.1482 (0.4); 2.0817 (0.5); 1.6317 (3.1); 1.2908 (3.5); 0.9162 (0.5); 0.8926 (0.4); 0.1066 (5.1); 0.0357 (15.8)
I-308: $^1$H-NMR(499.9 MHz, CDCl3):
δ = 8.0500 (16.0); 8.0146 (1.1); 7.4739 (0.5); 7.4474 (3.7); 7.4334 (6.2); 7.4204 (4.4); 7.3921 (1.1); 7.3812 (0.9); 7.3666 (0.8); 7.3061 (12.1); 7.2705 (2.8); 7.2364 (3.5); 7.2208 (6.8); 7.2066 (6.0); 7.1920 (7.3); 7.1764 (8.3); 7.1603 (3.8); 7.1359 (8.5); 7.1197 (9.8); 7.0533 (0.7); 7.0284 (0.7); 7.0093 (0.7); 6.9756 (7.2); 6.9593 (6.1); 6.9125 (0.5); 6.0321 (7.2); 4.1085 (4.3); 4.1038 (4.8); 4.0867 (5.4); 4.0819 (5.7); 3.9862 (4.0); 3.9790 (4.5); 3.9719 (4.3); 3.9129 (5.7); 3.9039 (4.8); 3.8910 (4.8); 3.8821 (4.0); 3.4250 (0.4); 3.3750 (15.2); 3.3306 (0.8); 3.1269 (3.7); 3.1163 (3.9); 3.0998 (5.1); 3.0891 (4.9); 3.0623 (0.9); 3.0487 (0.9); 3.0235 (0.5); 2.9675 (4.8); 2.9496 (5.0); 2.9406 (4.1); 2.9226 (3.6); 1.9907 (4.5); −0.0002 (1.7)
I-309: $^1$H-NMR(499.9 MHz, $d_6$-DMSO):
δ = 7.7226 (7.6); 7.3443 (2.5); 7.3381 (2.6); 7.2808 (3.8); 7.2204 (3.7); 7.1631 (0.4); 7.1473 (4.6); 7.1365 (4.2); 7.1206 (0.8); 7.0632 (3.9); 6.9126 (0.9); 6.9005 (1.5); 6.8939 (1.6); 6.8856 (1.1); 6.8806 (0.9); 5.7547 (0.4); 3.8020 (2.7); 3.7925 (1.5); 3.7849 (3.3); 3.7797 (2.0); 3.7219 (1.4); 3.7118 (1.8); 3.6984 (1.4); 3.6889 (0.8); 3.3456 (65.7); 2.8019 (4.0); 2.7887 (4.0); 2.5729 (19.2); 2.5084 (1.9); 2.5051 (2.5); 2.5018 (2.0); 2.1733 (16.0); 2.0870 (0.4); 2.0766 (0.8); 2.0700 (0.9); 2.0599 (1.6); 2.0497 (1.0); 2.0433 (1.0); 2.0328 (0.5); 1.0323 (0.9); 1.0239 (2.8); 1.0196 (3.0); 1.0117 (1.8); 1.0071 (2.9); 1.0028 (3.0); 0.9951 (1.3); 0.7839 (1.1); 0.7756 (3.0); 0.7723 (3.4); 0.7656 (3.4); 0.7620 (3.3); 0.7534 (1.2)
I-310: $^1$H-NMR(300.2 MHz, CDCl3):
δ = 8.1605 (9.8); 7.6440 (0.4); 7.6300 (4.8); 7.6126 (4.8); 7.3922 (2.6); 7.3425 (1.1); 7.3343 (1.1); 7.3257 (1.7); 7.3193 (1.4); 7.3123 (1.1); 7.2989 (13.0); 6.7089 (5.3); 6.2273 (2.0); 4.3514 (1.2); 4.3421 (1.4); 4.3159 (1.5); 4.3062 (1.5); 3.9054 (0.6); 3.8994 (0.6); 3.8933 (0.8); 3.8898 (0.8); 3.8782 (0.7); 3.8719 (0.9); 3.8657 (0.6); 3.8558 (0.6); 3.8145 (2.6); 3.7926 (1.4); 3.7789 (2.0); 3.7571 (1.4); 2.9493 (1.0); 2.9342 (1.0); 2.9020 (1.5); 2.8876 (1.4); 2.7077 (1.7); 2.6744 (1.6); 2.6607 (1.2); 2.6272 (1.2); 2.2636 (16.0); 2.0705 (16.0); 2.0459 (1.1); 1.6052 (2.2); 1.2919 (1.6); 1.2686 (0.3); 1.2437 (0.4); 0.9172 (0.3); 0.8931 (0.3); 0.1072 (5.6); 0.0480 (0.5); 0.0372 (15.5); 0.0263 (0.6)
I-311: $^1$H-NMR(300.2 MHz, CDCl3):
δ = 7.9678 (6.9); 7.6456 (0.5); 7.6203 (1.5); 7.5964 (4.4); 7.5730 (1.1); 7.5483 (3.6); 7.5120 (1.4); 7.4881 (1.4); 7.4814 (1.8); 7.4737 (1.0); 7.4448 (1.7); 7.3255 (1.3); 7.2986 (16.8); 7.2774 (3.1); 7.2417 (2.2); 7.2254 (0.8); 7.2180 (1.8); 7.1928 (0.7); 7.1753 (2.5); 7.1630 (3.4); 7.1539 (3.6); 7.1411 (0.6); 7.0967 (2.8); 7.0922 (3.4); 7.0687 (2.7); 7.0106 (1.7); 6.9987 (1.8); 6.9864 (1.4); 6.9788 (1.2); 6.2992 (1.2); 6.1797 (1.6); 5.3375 (6.1); 4.3859 (0.8); 4.3718 (1.0); 4.3646 (1.1); 4.3506 (1.7); 4.3350 (1.1); 4.3283 (1.3); 4.3157 (1.2); 3.8838 (1.3); 3.8614 (1.5); 3.8467 (1.6); 3.8246 (1.5); 3.8197 (1.3); 3.8064 (0.9); 3.7827 (0.9); 3.2524 (0.4); 3.2403 (0.5); 3.2320 (0.7); 3.2233 (0.8); 3.2169 (0.8); 3.2107 (0.8); 3.2032 (1.0); 3.1949 (0.8); 3.1888 (0.8); 3.1821 (0.8); 3.1722 (0.6); 3.1665 (0.6); 3.1594 (0.6); 3.1439 (0.4); 2.7134 (16.0); 2.6948 (12.0); 2.0413 (0.4); 2.0250 (0.8); 2.0112 (1.2); 1.9957 (1.4); 1.9890 (1.2); 1.9740 (1.1); 1.9494 (0.6); 1.6069 (15.5); 1.3811 (0.4); 1.3550 (0.8); 1.3429 (1.0); 1.3343 (1.0); 1.3194 (1.1); 1.3136 (1.1); 1.3044 (1.2); 1.2912 (1.6); 1.2733 (0.9); 1.2579

TABLE 2-continued (0.7); 1.2460 (0.5); 1.2275 (0.4); 1.1667 (0.5); 1.1484 (1.2); 1.1391 (0.6); 1.1302 (1.0); 1.1181 (3.1); 1.0938 (3.7); 1.0830 (1.5); 1.0709 (2.8); 1.0532 (1.1); 1.0352 (0.4); 0.1073 (5.4); 0.0373 (19.3)
I-312: $^{1}$H-NMR(499.9 MHz, CDCl3):
δ = 8.0976 (8.0); 7.5320 (0.9); 7.5280 (1.1); 7.5200 (1.0); 7.5168 (1.3); 7.5129 (1.9); 7.5076 (1.1); 7.5006 (1.1); 7.2591 (2.3); 7.1452 (0.4); 7.1411 (0.6); 7.1289 (1.9); 7.1247 (1.8); 7.1197 (5.4); 7.1127 (2.0); 7.1057 (2.6); 7.0888 (0.8); 6.9547 (2.6); 6.9394 (3.0); 6.8670 (3.2); 6.6759 (1.7); 6.6608 (1.6); 6.0109 (2.1); 5.2946 (2.3); 4.2771 (1.3); 4.2706 (1.4); 4.2556 (1.5); 4.2491 (1.6); 3.8791 (0.6); 3.8750 (0.7); 3.8690 (0.9); 3.8655 (0.8); 3.8592 (0.9); 3.8559 (0.8); 3.8528 (0.7); 3.8495 (0.8); 3.8394 (0.4); 3.8130 (2.1); 3.8005 (1.4); 3.7914 (1.9); 3.7789 (1.4); 3.0015 (1.1); 2.9917 (1.2); 2.9742 (1.4); 2.9643 (1.4); 2.7125 (1.5); 2.6927 (1.5); 2.6852 (1.4); 2.6654 (1.3); 2.2639 (16.0); 2.1413 (15.2); 1.5976 (1.5); −0.0002 (2.1)
I-314: $^{1}$H-NMR(300.2 MHz, CDCl3):
δ = 7.6449 (0.4); 7.3843 (0.4); 7.3651 (0.7); 7.3292 (20.9); 7.3164 (16.8); 7.3106 (18.7); 7.2988 (76.8); 7.2836 (0.8); 7.2440 (0.6); 7.2323 (0.4); 7.2103 (0.4); 7.1809 (0.4); 7.1491 (10.3); 7.1447 (9.8); 7.1208 (7.4); 7.1165 (7.2); 6.9477 (0.4); 5.3371 (0.7); 3.7565 (1.4); 3.7361 (2.6); 3.7155 (1.3); 3.7000 (11.0); 3.6872 (11.9); 3.6647 (14.7); 3.6520 (15.6); 3.6280 (2.2); 3.6063 (1.1); 3.4614 (13.0); 3.4384 (16.0); 3.4261 (10.0); 3.4032 (12.6); 3.2783 (3.3); 3.2653 (3.6); 3.2596 (4.7); 3.2510 (5.5); 3.2469 (5.3); 3.2377 (6.9); 3.2325 (5.7); 3.2282 (5.0); 3.2238 (4.7); 3.2196 (5.4); 3.2096 (4.0); 3.1967 (3.3); 3.1585 (0.3); 2.9942 (10.0); 2.9755 (8.7); 2.9490 (14.1); 2.9304 (12.6); 2.8250 (0.3); 2.7615 (14.2); 2.7343 (12.9); 2.7164 (10.1); 2.6891 (8.9); 2.6244 (0.4); 2.3395 (0.3); 2.3172 (0.3); 2.2785 (0.3); 2.2381 (0.4); 2.0560 (0.6); 2.0391 (0.6); 1.9759 (0.7); 1.9495 (1.0); 1.9298 (1.2); 1.9008 (1.2); 1.8807 (1.1); 1.8269 (1.1); 1.8050 (1.3); 1.7866 (1.8); 1.7578 (1.9); 1.7483 (2.0); 1.7285 (2.8); 1.7171 (2.4); 1.7093 (2.3); 1.5696 (3.5); 1.3838 (1.4); 1.3224 (1.2); 1.2932 (1.8); 1.2571 (0.8); 1.2271 (0.8); 1.0531 (0.4); 1.0099 (0.5); 0.9171 (0.4); 0.8904 (0.4); 0.2034 (0.6); 0.1925 (20.0); 0.1817 (0.8); 0.1651 (1.6); 0.1063 (5.6); 0.0473 (2.6); 0.0442 (1.7); 0.0366 (84.4); 0.0273 (3.2); 0.0257 (3.6); 0.0024 (0.4); −0.0299 (0.5); −0.1621 (0.4)
I-315: $^{1}$H-NMR(300.2 MHz, CDCl3):
δ = 7.9471 (5.3); 7.2988 (8.3); 7.2705 (2.2); 7.1365 (0.6); 7.1015 (2.2); 7.0754 (2.5); 7.0524 (1.0); 7.0463 (1.1); 7.0285 (1.1); 7.0238 (1.3); 7.0021 (0.6); 6.9964 (0.5); 6.8548 (0.9); 6.8479 (1.8); 6.8284 (1.4); 6.8228 (1.5); 6.8079 (0.8); 6.8021 (0.6); 6.2214 (1.4); 5.3375 (0.5); 4.2693 (0.9); 4.2580 (1.0); 4.2331 (1.1); 4.2218 (1.2); 4.0819 (0.4); 4.0711 (0.6); 4.0640 (0.6); 4.0517 (0.6); 4.0446 (0.6); 4.0344 (0.5); 3.8907 (1.4); 3.8712 (1.2); 3.8545 (1.2); 3.8350 (1.0); 3.2652 (5.4); 3.2514 (0.9); 3.2346 (0.8); 3.2072 (1.1); 3.1906 (1.0); 2.9531 (1.1); 2.9226 (1.1); 2.9092 (0.9); 2.8788 (0.9); 2.6677 (16.0); 2.2034 (11.3); 2.1406 (0.5); 2.1294 (0.6); 2.1124 (1.0); 2.0953 (0.6); 2.0843 (0.6); 1.6122 (5.9); 1.0880 (0.7); 1.0748 (1.5); 1.0680 (1.8); 1.0599 (1.0); 1.0553 (1.1); 1.0462 (1.6); 1.0398 (1.7); 1.0269 (0.8); 0.8298 (0.9); 0.8226 (0.9); 0.8135 (1.9); 0.8067 (1.7); 0.7980 (2.0); 0.7908 (1.2); 0.7806 (0.6); 0.1187 (0.6); 0.1067 (15.2); 0.0944 (0.6); 0.0473 (0.5); 0.0367 (11.7); 0.0258 (0.5)
I-316: $^{1}$H-NMR(300.2 MHz, CDCl3):
δ = 7.9734 (5.2); 7.5974 (0.4); 7.5796 (0.9); 7.5676 (0.8); 7.5535 (0.5); 7.5494 (0.5); 7.5457 (0.5); 7.3494 (3.7); 7.3315 (2.3); 7.3252 (1.8); 7.2988 (2.9); 7.0973 (1.1); 7.0163 (1.7); 6.9908 (2.0); 6.9146 (2.6); 6.9036 (2.1); 6.7321 (1.2); 6.7172 (1.1); 6.6917 (1.0); 6.1098 (1.3); 4.3139 (0.8); 4.3044 (0.9); 4.2792 (1.0); 4.2694 (1.0); 3.9352 (0.4); 3.9283 (0.4); 3.9230 (0.5); 3.9183 (0.5); 3.9124 (0.5); 3.9074 (0.5); 3.9020 (0.6); 3.8960 (0.4); 3.8862 (0.5); 3.8783 (0.5); 3.8685 (1.8); 3.8479 (0.7); 3.8336 (1.4); 3.8129 (0.9); 3.0490 (0.7); 3.0335 (0.7); 3.0040 (1.0); 2.9879 (0.9); 2.7831 (1.1); 2.7518 (1.0); 2.7384 (1.3); 2.7061 (0.8); 2.6721 (16.0); 2.3053 (11.2); 2.2878 (0.4); 2.1571 (10.5); 0.0372 (3.8)
I-317: $^{1}$H-NMR(300.2 MHz, CDCl3):
δ = 7.9610 (4.9); 7.5909 (0.4); 7.5753 (0.8); 7.5624 (0.7); 7.5464 (0.5); 7.5427 (0.5); 7.3690 (0.4); 7.3415 (2.7); 7.3237 (2.5); 7.3184 (1.9); 7.3109 (1.1); 7.2986 (3.0); 7.0888 (1.0); 6.9818 (2.1); 6.9434 (0.6); 6.9175 (1.9); 6.9120 (2.1); 6.9060 (3.0); 6.9007 (3.0); 6.8748 (0.7); 6.7237 (1.1); 6.1214 (1.2); 4.3159 (0.8); 4.3063 (0.9); 4.2802 (0.9); 4.2703 (1.0); 3.9378 (0.4); 3.9314 (0.4); 3.9261 (0.5); 3.9213 (0.5); 3.9155 (0.5); 3.9099 (0.5); 3.9054 (0.5); 3.9000 (0.4); 3.8942 (0.4); 3.8890 (0.4); 3.8349 (1.6); 3.8133 (0.9); 3.7991 (1.3); 3.7776 (0.9); 3.0137 (0.7); 2.9975 (0.7); 2.9689 (0.9); 2.9526 (0.8); 2.6994 (1.1); 2.6679 (16.0); 2.6553 (1.3); 2.6225 (0.8); 2.1207 (10.7); 2.1135 (11.0); 0.0372 (3.7)
I-318: $^{1}$H-NMR(300.2 MHz, CDCl3):
δ = 7.9778 (4.9); 7.6071 (0.7); 7.5825 (2.3); 7.5599 (5.6); 7.5205 (3.1); 7.4593 (2.0); 7.4369 (1.3); 7.2993 (4.8); 6.9232 (3.7); 6.9049 (1.7); 6.8772 (4.4); 6.8596 (3.2); 6.8320 (1.0); 6.8271 (0.9); 6.1626 (2.5); 4.7046 (1.2); 4.6832 (1.4); 4.6695 (1.2); 4.3650 (1.6); 4.3520 (1.6); 4.3285 (1.9); 4.3156 (1.9); 4.2709 (16.0); 4.1919 (0.8); 4.1683 (1.8); 4.1445 (1.8); 4.1204 (0.7); 3.7407 (1.5); 3.7155 (1.6); 3.7038 (1.5); 3.6787 (1.3); 2.7262 (15.1); 2.0810 (6.7); 1.6349 (1.9); 1.3191 (2.5); 1.2951 (5.4); 1.2716 (2.3); 0.9166 (0.4); 0.1071 (2.8); 0.0363 (5.8)
I-319: $^{1}$H-NMR(499.9 MHz, CDCl3):
δ = 8.2201 (0.7); 8.1037 (16.0); 8.1028 (15.8); 7.8124 (0.7); 7.4671 (0.5); 7.4574 (2.7); 7.4530 (2.8); 7.4417 (6.0); 7.4375 (5.9); 7.4260 (3.9); 7.4218 (3.6); 7.4096 (0.8); 7.3918 (0.8); 7.3751 (0.4); 7.3649 (0.5); 7.3485 (0.4); 7.3152 (6.9); 7.3103 (9.7); 7.3053 (6.4); 7.2801 (4.1); 7.2606 (42.6); 7.2295 (0.5); 7.2257 (0.6); 7.2031 (0.5); 7.1867 (0.5); 7.1826 (0.4); 7.1739 (0.5); 7.1623 (0.4); 7.1435 (0.4); 7.1278 (0.4); 7.1073 (8.9); 7.0909 (10.3); 7.0488 (0.4); 7.0093 (2.5); 7.0048 (3.1); 6.9990 (3.0); 6.9947 (4.6); 6.9899 (3.3); 6.9735 (10.0); 6.9252 (3.3); 6.9211 (3.2); 6.9088 (3.0); 6.9044 (3.4); 6.9012 (3.9); 6.8970 (3.4); 6.8847 (3.0); 6.8807 (2.8); 6.1420 (5.4); 5.7650 (0.5); 5.0348 (0.6); 4.1525 (2.6); 4.1468 (4.5); 4.1412 (2.8); 4.1307 (3.3); 4.1250 (5.4); 4.1194 (3.2); 3.9801 (3.0); 3.9719 (3.4); 3.9650 (3.1); 3.9108 (7.1); 3.9068 (9.4); 3.9023 (9.8); 3.8986 (9.1); 3.8898 (4.0); 3.8860 (3.7); 3.8801 (2.9); 3.8764 (2.7); 3.3633 (0.3); 3.1808 (3.7); 3.1779 (3.9); 3.1699 (7.3); 3.1618 (4.6); 3.1590 (4.2); 3.1364 (3.4); 3.1264 (3.4); 3.1093 (4.4); 3.0992 (4.3); 2.9481 (2.6); 2.9380 (2.9); 2.9299 (2.8); 2.9202 (4.2); 2.9109 (2.3); 2.9028 (2.1); 2.8926 (2.0); 2.7911 (3.6); 2.7859 (6.6); 2.7805 (6.8); 2.7750 (6.4); 2.7698 (3.6); 1.5551 (24.7); 1.2551 (1.3); 0.8818 (0.3); 0.0695 (0.5); −0.0002 (52.8)
I-320: $^{1}$H-NMR(300.2 MHz, CDCl3):
δ = 7.5913 (1.2); 7.5685 (3.5); 7.5462 (0.4); 7.4871 (1.8); 7.4617 (0.8); 7.4538 (1.2); 7.4465 (0.7); 7.4413 (0.5); 7.4381 (0.5); 7.4319 (0.7); 7.2991 (5.5); 7.0809 (1.3); 7.0553 (2.2); 7.0311 (2.0); 6.9805 (1.2); 6.9557 (0.7); 5.2802 (1.2); 4.1627 (0.9); 4.1371 (1.1); 4.1205 (0.4); 3.9665 (0.7); 3.9504 (1.5); 3.9365 (0.6); 3.9226 (1.5); 3.9007 (0.5); 3.6408 (0.9); 3.6252 (1.7); 3.6198 (1.4); 3.6112 (1.3); 3.6046 (1.7); 3.5907 (1.2); 3.4632 (0.4); 3.4488 (0.4); 3.4416 (0.3); 3.4268 (0.3); 3.4169 (0.9); 3.4019 (1.0); 3.3955 (0.9); 3.3806 (0.7); 3.3565 (0.8); 3.3395 (0.9); 3.3360 (1.0); 3.3192 (0.7); 3.3103 (0.4); 3.2939 (0.4); 3.2891 (0.4); 3.1594 (16.0); 3.1408 (0.4); 2.9716 (1.2); 2.9537 (1.9); 2.9272 (0.9); 2.3703 (0.4); 2.3364 (9.9); 2.3183 (9.3); 1.6290 (1.4); 0.1080 (1.3); 0.0376 (5.9)

TABLE 2-continued

I-321: $^1$H-NMR(300.2 MHz, CDCl3):
δ = 8.1345 (10.4); 7.5040 (0.9); 7.4924 (1.0); 7.4836 (1.9); 7.4724 (2.0); 7.4633 (1.0); 7.4520 (1.2); 7.2989 (3.0); 7.2393 (0.4); 7.2335 (0.4); 7.2169 (4.7); 7.2122 (2.7); 7.2059 (2.4); 7.2030 (2.6); 7.1960 (2.4); 7.1916 (4.4); 7.1755 (0.4); 7.1689 (0.3); 7.0008 (2.5); 6.9753 (3.0); 6.9004 (2.8); 6.7174 (1.5); 6.6920 (1.3); 6.0870 (1.8); 4.3209 (1.1); 4.3119 (1.3); 4.2856 (1.4); 4.2768 (1.4); 3.9253 (0.5); 3.9185 (0.6); 3.9133 (0.7); 3.9083 (0.8); 3.9023 (0.7); 3.8975 (0.7); 3.8921 (0.8); 3.8862 (0.6); 3.8829 (0.6); 3.8762 (0.7); 3.8677 (0.7); 3.8582 (2.6); 3.8376 (1.0); 3.8234 (2.0); 3.8026 (1.3); 3.4046 (5.8); 3.0518 (1.0); 3.0362 (1.0); 3.0068 (1.4); 2.9904 (1.3); 2.7657 (1.4); 2.7341 (1.4); 2.7207 (1.2); 2.6885 (1.1); 2.3518 (0.5); 2.3328 (0.5); 2.3014 (16.0); 2.2059 (0.4); 2.1794 (15.0); 2.0394 (7.0); 1.6666 (0.5); 0.0378 (4.0)
I-322: $^1$H-NMR(499.9 MHz, CDCl3):
δ = 7.9095 (5.3); 7.2604 (13.4); 7.2106 (2.7); 7.1075 (0.7); 7.0916 (1.8); 7.0756 (1.1); 7.0050 (0.6); 7.0016 (0.5); 6.9856 (3.1); 6.9774 (4.6); 6.9607 (1.6); 6.8269 (0.8); 6.8136 (1.5); 6.8002 (0.8); 6.7979 (0.8); 6.1901 (1.6); 4.1964 (0.4); 4.1854 (1.3); 4.1703 (1.4); 4.1592 (0.5); 3.8680 (0.4); 3.8505 (2.2); 3.8454 (1.2); 3.8355 (2.3); 3.8247 (0.9); 2.9680 (0.8); 2.9588 (0.9); 2.9407 (1.1); 2.9312 (1.1); 2.8005 (1.0); 2.7828 (1.0); 2.7737 (0.9); 2.7636 (0.4); 2.7550 (0.7); 2.6367 (16.0); 2.2866 (13.1); 2.0995 (0.5); 2.0928 (0.6); 2.0826 (1.1); 2.0724 (0.7); 2.0657 (0.7); 2.0552 (0.4); 1.5588 (7.4); 1.2552 (0.5); 1.0432 (0.3); 1.0333 (1.9); 1.0298 (2.1); 1.0275 (1.9); 1.0164 (2.1); 1.0128 (2.2); 1.0035 (0.6); 0.7925 (1.3); 0.7905 (1.2); 0.7869 (1.2); 0.7824 (2.0); 0.7793 (2.1); 0.7771 (2.3); 0.7669 (1.5); 0.7542 (0.3); 0.7485 (0.4); 0.0061 (0.6); −0.0002 (15.6)
I-323: $^1$H-NMR(499.9 MHz, CDCl3):
δ = 7.9094 (5.3); 7.2606 (11.9); 7.2110 (2.8); 7.1079 (0.8); 7.0920 (1.8); 7.0761 (1.2); 7.0049 (0.6); 7.0020 (0.5); 6.9874 (3.2); 6.9775 (4.8); 6.9608 (1.6); 6.8273 (0.8); 6.8138 (1.5); 6.8002 (0.8); 6.1910 (1.7); 4.1962 (0.4); 4.1854 (1.4); 4.1703 (1.5); 4.1593 (0.5); 3.8678 (0.4); 3.8509 (2.3); 3.8356 (2.3); 3.8248 (0.8); 2.9681 (0.9); 2.9589 (0.9); 2.9407 (1.1); 2.9313 (1.1); 2.8006 (1.0); 2.7830 (1.0); 2.7739 (0.8); 2.7639 (0.4); 2.7552 (0.7); 2.6367 (16.0); 2.2866 (13.5); 2.0995 (0.6); 2.0928 (0.7); 2.0827 (1.1); 2.0725 (0.7); 2.0659 (0.7); 2.0554 (0.3); 1.5632 (8.4); 1.3191 (0.4); 1.2557 (0.5); 1.0432 (0.4); 1.0334 (2.0); 1.0298 (2.2); 1.0165 (2.2); 1.0129 (2.2); 1.0036 (0.6); 0.9362 (0.3); 0.9213 (0.6); 0.9062 (0.4); 0.8958 (0.5); 0.7925 (1.4); 0.7869 (1.2); 0.7823 (2.1); 0.7792 (2.2); 0.7773 (2.3); 0.7670 (1.5); −0.0002 (13.2)
I-324: $^1$H-NMR(300.2 MHz, CDCl3):
δ = 7.9749 (5.2); 7.6011 (0.4); 7.5834 (1.0); 7.5715 (0.8); 7.5572 (0.5); 7.5530 (0.5); 7.3822 (0.3); 7.3555 (3.7); 7.3377 (2.3); 7.3315 (1.8); 7.3100 (0.3); 7.2987 (3.2); 7.1090 (1.1); 7.0202 (1.9); 6.9943 (2.2); 6.9263 (2.3); 6.8172 (2.0); 6.8128 (2.1); 6.7437 (1.2); 6.6082 (1.2); 6.6025 (1.1); 6.5823 (1.0); 6.5767 (1.0); 6.1224 (1.4); 4.2980 (0.7); 4.2898 (1.0); 4.2639 (1.1); 4.2552 (0.8); 3.9196 (0.4); 3.9079 (0.5); 3.9031 (0.5); 3.8970 (0.5); 3.8932 (0.5); 3.8872 (0.6); 3.8792 (0.6); 3.8674 (1.9); 3.8479 (0.5); 3.8336 (1.4); 3.8132 (0.8); 3.0378 (0.7); 3.0229 (0.7); 2.9929 (1.1); 2.9770 (1.0); 2.7795 (0.9); 2.7477 (0.9); 2.7340 (0.9); 2.7024 (0.8); 2.6734 (16.0); 2.3052 (11.6); 2.0410 (0.6); 1.7615 (0.3); 1.7446 (0.6); 1.7334 (0.6); 1.7166 (1.1); 1.7050 (0.5); 1.6998 (0.7); 1.6886 (0.6); 1.6717 (0.3); 0.9363 (0.4); 0.9202 (1.7); 0.9142 (2.0); 0.9101 (1.5); 0.8922 (1.8); 0.8861 (1.7); 0.8825 (1.3); 0.8708 (0.4); 0.5583 (1.4); 0.5541 (1.0); 0.5486 (1.0); 0.5417 (1.9); 0.5365 (1.7); 0.5322 (1.8); 0.5264 (1.0); 0.5189 (1.0); 0.5162 (1.1); 0.0374 (4.1)
I-325: $^1$H-NMR(300.2 MHz, CDCl3):
δ = 7.9534 (5.3); 7.4775 (0.6); 7.4716 (0.6); 7.4511 (1.2); 7.4294 (0.7); 7.4240 (0.7); 7.2988 (2.7); 7.2175 (0.6); 7.2144 (0.6); 7.1906 (1.5); 7.1881 (1.5); 7.1620 (1.1); 7.1362 (0.9); 7.1301 (1.0); 7.1122 (1.0); 7.1072 (1.1); 7.0857 (0.5); 7.0801 (0.5); 7.0163 (1.8); 6.9908 (2.0); 6.9133 (1.0); 6.8900 (2.0); 6.8761 (1.1); 6.8542 (1.1); 6.8168 (1.1); 6.6975 (1.1); 6.6726 (0.9); 6.2088 (1.3); 5.9215 (1.8); 5.9187 (1.9); 5.8624 (1.6); 5.8596 (1.6); 5.4888 (1.8); 5.4861 (1.8); 5.4515 (1.7); 5.4488 (1.7); 4.2993 (0.8); 4.2900 (0.9); 4.2645 (1.0); 4.2552 (1.0); 3.9259 (0.4); 3.9188 (0.4); 3.9142 (0.5); 3.9087 (0.6); 3.9027 (0.5); 3.8979 (0.5); 3.8927 (0.6); 3.8771 (0.5); 3.8687 (0.5); 3.8598 (1.9); 3.8391 (0.7); 3.8250 (1.4); 3.8043 (0.9); 3.0393 (0.7); 3.0236 (0.7); 2.9943 (1.0); 2.9778 (0.9); 2.7861 (1.0); 2.7550 (1.0); 2.7411 (0.8); 2.7093 (0.8); 2.6631 (16.0); 2.3013 (11.2); 2.1600 (10.6); 2.0408 (1.3); 1.6708 (1.2); 0.1094 (0.3); 0.0377 (3.3)
I-326: $^1$H-NMR(300.2 MHz, CDCl3):
δ = 7.9465 (5.2); 7.2987 (1.6); 7.1681 (0.4); 7.1480 (1.0); 7.1434 (0.9); 7.1290 (2.8); 7.1223 (1.0); 7.1044 (2.4); 7.0786 (1.0); 7.0559 (0.8); 7.0499 (0.8); 7.0318 (1.1); 7.0212 (2.3); 7.0094 (0.6); 6.9950 (2.2); 6.9030 (2.2); 6.7018 (1.2); 6.6765 (1.0); 6.2424 (1.4); 4.2789 (0.8); 4.2701 (1.0); 4.2448 (1.1); 4.2355 (1.0); 3.9154 (0.4); 3.9039 (0.5); 3.8976 (0.6); 3.8871 (0.6); 3.8833 (0.6); 3.8807 (0.6); 3.8767 (0.5); 3.8668 (0.6); 3.8569 (2.1); 3.8367 (0.6); 3.8225 (1.4); 3.8020 (0.8); 3.0347 (0.7); 3.0189 (0.7); 2.9899 (1.1); 2.9731 (1.0); 2.7940 (1.0); 2.7636 (1.0); 2.7489 (0.8); 2.7181 (0.8); 2.6587 (16.0); 2.3480 (6.9); 2.3409 (7.2); 2.3038 (11.8); 2.1839 (11.0); 2.0366 (2.2); 0.0379 (2.2)
I-327: $^1$H-NMR(300.2 MHz, CDCl3):
δ = 7.9563 (5.4); 7.3531 (1.2); 7.3269 (2.6); 7.2986 (10.7); 7.0739 (2.4); 7.0472 (5.4); 7.0162 (1.5); 6.9902 (1.3); 6.8816 (1.0); 6.8787 (1.0); 6.8737 (1.4); 6.8473 (1.5); 6.8444 (1.4); 6.8366 (2.0); 6.8310 (2.4); 6.6090 (1.5); 6.6033 (1.4); 6.5828 (1.3); 6.5770 (1.3); 6.3105 (1.4); 4.2165 (0.9); 4.2056 (1.1); 4.1805 (1.2); 4.1701 (1.6); 4.1472 (0.4); 3.9978 (0.4); 3.9880 (0.6); 3.9677 (0.6); 3.9588 (0.6); 3.9496 (0.5); 3.9419 (0.4); 3.8890 (1.5); 3.8708 (1.0); 3.8530 (1.2); 3.8348 (0.9); 3.1667 (0.9); 3.1504 (0.9); 3.1220 (1.2); 3.1056 (1.1); 2.8944 (1.2); 2.8641 (1.2); 2.8496 (0.9); 2.8192 (0.9); 2.6690 (16.0); 2.0833 (1.9); 1.9740 (0.6); 1.9626 (0.6); 1.9460 (1.2); 1.9291 (0.7); 1.9180 (0.7); 1.9011 (0.4); 1.8061 (0.6); 1.7948 (0.7); 1.7782 (1.2); 1.7615 (0.8); 1.7502 (0.7); 1.7335 (0.4); 1.6431 (0.4); 1.3207 (0.5); 1.2969 (1.1); 1.2730 (0.5); 1.0537 (0.6); 1.0391 (2.0); 1.0321 (2.1); 1.0177 (1.2); 1.0107 (2.1); 1.0038 (2.0); 0.9898 (1.1); 0.9814 (2.3); 0.9746 (2.7); 0.9532 (2.4); 0.9466 (2.4); 0.9280 (0.4); 0.7765 (1.0); 0.7619 (2.4); 0.7453 (2.2); 0.7406 (2.2); 0.7241 (0.8); 0.6161 (1.3); 0.6082 (0.9); 0.5988 (2.0); 0.5915 (2.1); 0.5818 (0.9); 0.5747 (1.4); 0.1069 (7.4); 0.0476 (0.5); 0.0368 (13.8); 0.0276 (0.6); 0.0260 (0.6)
I-328: $^1$H-NMR(300.2 MHz, CDCl3):
δ = 7.9519 (5.3); 7.3518 (0.8); 7.3475 (0.5); 7.3233 (1.5); 7.2989 (13.9); 7.1268 (0.4); 7.0119 (1.6); 7.0029 (2.1); 6.9861 (1.5); 6.9769 (2.2); 6.8546 (2.8); 6.8475 (1.9); 6.8233 (4.2); 6.8196 (3.7); 6.5801 (1.1); 6.5743 (1.1); 6.5543 (1.0); 6.5484 (1.0); 6.3248 (1.4); 4.2535 (0.5); 4.2464 (1.1); 4.2214 (1.1); 3.8621 (0.5); 3.8561 (0.6); 3.8471 (0.6); 3.8337 (1.7); 3.8003 (1.5); 3.7799 (0.7); 3.0194 (0.6); 3.0039 (0.6); 2.9739 (1.0); 2.9585 (0.9); 2.7538 (0.8); 2.7232 (0.9); 2.7084 (0.8); 2.6659 (16.0); 2.3399 (0.7); 2.3000 (11.4); 2.0842 (0.5); 1.9752 (0.5); 1.9641 (0.6); 1.9474 (1.1); 1.9304 (0.7); 1.9192 (0.6); 1.9026 (0.3); 1.8072 (0.5); 1.7960 (0.6); 1.7792 (1.0); 1.7621 (0.6); 1.7511 (0.6); 1.6046 (12.9); 1.3448 (0.3); 1.3213 (0.6); 1.3047 (2.2); 1.2984 (2.0); 1.0520 (0.7); 1.0368 (1.9); 1.0300 (2.1); 1.0244 (1.1); 1.0153 (1.1); 1.0084 (2.1); 1.0018 (1.9); 0.9874 (1.0); 0.9605 (0.5); 0.9431 (2.5); 0.9369 (2.8); 0.9200 (3.4); 0.9157 (2.6); 0.9087 (2.2); 0.8968 (1.1); 0.7780 (0.9); 0.7629

TABLE 2-continued (2.2); 0.7566 (2.1); 0.7464 (2.1); 0.7406 (2.4); 0.7246 (0.8); 0.6104 (1.1); 0.6026 (0.9); 0.5972 (1.5); 0.5907 (2.1); 0.5854 (1.4); 0.5736 (1.2); 0.5677 (0.8); 0.1077 (0.9); 0.0491 (0.5); 0.0381 (17.5); 0.0272 (0.7)
I-329: $^{1}$H-NMR(300.2 MHz, CDCl3):
δ = 7.9663 (5.2); 7.3698 (0.8); 7.3429 (2.0); 7.3180 (1.3); 7.3080 (0.5); 7.2989 (12.6); 7.2676 (2.2); 7.0406 (0.7); 7.0342 (0.6); 7.0146 (2.4); 7.0072 (2.1); 6.9945 (1.9); 6.9873 (3.9); 6.9600 (1.2); 6.8367 (0.9); 6.8317 (1.3); 6.8289 (1.3); 6.8057 (3.4); 6.8031 (3.5); 6.3226 (1.3); 4.2259 (0.3); 4.2074 (1.2); 4.1948 (0.6); 4.1822 (1.3); 4.1710 (1.5); 4.1472 (1.4); 4.1234 (0.4); 3.8801 (0.8); 3.8650 (1.8); 3.8501 (0.7); 3.8406 (1.9); 3.8226 (0.6); 3.1222 (0.3); 3.0080 (0.8); 2.9926 (0.7); 2.9584 (1.1); 2.9462 (0.9); 2.8119 (0.9); 2.7833 (0.9); 2.7676 (0.7); 2.7425 (0.8); 2.7375 (0.8); 2.7001 (0.4); 2.6788 (16.0); 2.3392 (0.5); 2.3101 (12.2); 2.2301 (0.4); 2.2062 (0.4); 2.0831 (5.9); 1.9857 (0.6); 1.9746 (0.6); 1.9577 (1.2); 1.9408 (0.8); 1.9299 (0.7); 1.9127 (0.4); 1.7536 (0.6); 1.3208 (1.7); 1.2969 (3.5); 1.2732 (1.7); 1.0633 (0.7); 1.0480 (1.9); 1.0412 (2.2); 1.0263 (1.2); 1.0196 (2.1); 1.0131 (1.9); 0.9984 (1.1); 0.7800 (0.9); 0.7646 (2.4); 0.7588 (2.2); 0.7484 (2.1); 0.7425 (2.6); 0.7262 (0.9); 0.1069 (1.2); 0.0479 (0.5); 0.0371 (16.6); 0.0262 (0.7)
I-330: $^{1}$H-NMR(300.2 MHz, CDCl3):
δ = 7.9422 (5.1); 7.3307 (1.1); 7.2985 (8.6); 7.2785 (1.4); 6.9987 (1.5); 6.9675 (3.0); 6.9127 (6.3); 6.9097 (6.0); 6.8317 (1.0); 6.8286 (1.0); 6.8237 (1.4); 6.8209 (1.1); 6.8052 (0.6); 6.7974 (1.6); 6.7939 (1.7); 6.7898 (2.0); 6.7841 (2.3); 6.7780 (1.0); 6.3312 (1.4); 5.3371 (3.1); 4.2797 (0.9); 4.2684 (1.0); 4.2440 (1.0); 4.2326 (1.1); 3.8992 (0.4); 3.8827 (0.6); 3.8671 (0.6); 3.8509 (0.4); 3.8013 (1.7); 3.7795 (1.0); 3.7657 (1.4); 3.7439 (1.0); 2.9825 (0.8); 2.9663 (0.8); 2.9378 (1.0); 2.9213 (1.0); 2.6824 (1.2); 2.6593 (16.0); 2.6377 (1.0); 2.6062 (0.9); 2.1764 (11.8); 2.1164 (11.9); 1.9592 (0.6); 1.9479 (0.6); 1.9313 (1.1); 1.9144 (0.7); 1.9032 (0.8); 1.8864 (0.3); 1.6225 (3.6); 1.2972 (0.4); 1.0497 (0.7); 1.0351 (1.9); 1.0280 (2.1); 1.0219 (1.0); 1.0135 (1.0); 1.0066 (2.0); 1.0000 (1.9); 0.9856 (0.9); 0.7610 (0.9); 0.7463 (2.4); 0.7415 (2.0); 0.7295 (2.0); 0.7246 (2.3); 0.7081 (0.7); 0.0483 (0.4); 0.0375 (11.6); 0.0284 (0.4); 0.0267 (0.4)
I-331: $^{1}$H-NMR(300.2 MHz, CDCl3):
δ = 7.9512 (4.1); 7.5078 (1.7); 7.3604 (1.2); 7.3341 (1.4); 7.2987 (13.0); 7.1394 (0.4); 7.1354 (0.4); 7.1126 (1.2); 7.0869 (1.5); 7.0674 (0.9); 7.0552 (0.8); 7.0489 (0.9); 7.0313 (0.8); 7.0260 (0.9); 7.0045 (0.4); 6.9988 (0.4); 6.8570 (0.6); 6.8508 (0.6); 6.8301 (0.9); 6.8088 (0.5); 6.8030 (0.4); 6.6654 (0.8); 6.4780 (1.7); 6.2907 (0.8); 6.2041 (0.8); 4.2067 (0.7); 4.1964 (0.9); 4.1709 (1.1); 4.1606 (1.1); 4.0772 (0.5); 4.0619 (0.5); 4.0478 (0.5); 4.0020 (1.2); 3.9870 (0.7); 3.9661 (0.8); 3.9510 (0.6); 3.2872 (0.5); 3.2710 (0.5); 3.2431 (0.7); 3.2263 (0.7); 3.0858 (0.8); 3.0556 (0.8); 3.0415 (0.6); 3.0112 (0.5); 2.6810 (12.4); 2.5382 (0.4); 2.1233 (0.4); 2.1119 (0.4); 2.0951 (0.7); 2.0833 (0.8); 2.0778 (0.5); 2.0667 (0.4); 1.6021 (16.0); 1.2968 (0.5); 1.0876 (0.4); 1.0734 (1.2); 1.0667 (1.4); 1.0561 (0.8); 1.0522 (0.7); 1.0448 (1.3); 1.0385 (1.3); 1.0270 (0.5); 1.0242 (0.5); 0.8201 (0.7); 0.8131 (0.7); 0.8044 (1.4); 0.7971 (1.4); 0.7881 (1.6); 0.7810 (1.0); 0.7708 (0.6); 0.1065 (4.3); 0.0474 (0.6); 0.0367 (17.1); 0.0258 (0.7)
I-332: $^{1}$H-NMR(300.2 MHz, CDCl3):
δ = 7.9550 (5.2); 7.2987 (12.4); 7.2597 (2.3); 7.2318 (2.6); 7.1624 (2.2); 7.1543 (2.2); 7.1213 (1.5); 7.0930 (1.5); 7.0773 (1.1); 7.0706 (1.3); 7.0539 (1.1); 7.0483 (1.3); 7.0271 (0.6); 7.0212 (0.5); 6.8631 (0.7); 6.8564 (0.7); 6.8390 (1.1); 6.8150 (0.7); 6.8091 (0.6); 6.7384 (1.2); 6.7303 (1.1); 6.7107 (1.0); 6.7025 (1.0); 6.5663 (1.6); 6.3222 (3.1); 6.2061 (1.1); 6.0783 (1.6); 4.2068 (0.8); 4.1966 (1.1); 4.1710 (1.8); 4.1615 (1.3); 4.1470 (0.6); 4.0496 (0.4); 4.0389 (0.6); 4.0234 (0.6); 4.0090 (0.6); 3.9997 (0.4); 3.9931 (0.5); 3.9797 (1.6); 3.9643 (0.8); 3.9443 (1.1); 3.9286 (0.8); 3.2239 (0.8); 3.2082 (0.8); 3.1793 (1.2); 3.1630 (1.1); 3.0126 (1.2); 2.9828 (1.1); 2.9679 (0.8); 2.9375 (0.8); 2.6802 (16.0); 2.5653 (0.6); 2.1299 (0.4); 2.1187 (0.5); 2.1016 (1.0); 2.0831 (3.1); 2.0736 (0.6); 1.6050 (6.4); 1.3437 (0.7); 1.3205 (1.7); 1.3032 (3.8); 1.2968 (4.5); 1.2729 (1.0); 1.0908 (0.5); 1.0769 (1.6); 1.0699 (1.8); 1.0568 (0.9); 1.0482 (1.8); 1.0417 (1.7); 1.0283 (0.8); 0.9405 (1.3); 0.9187 (4.4); 0.8955 (1.6); 0.8256 (0.9); 0.8085 (1.9); 0.8038 (1.6); 0.7946 (1.9); 0.7918 (1.9); 0.7866 (1.4); 0.7748 (0.8); 0.1066 (4.5); 0.0474 (0.6); 0.0367 (17.6); 0.0257 (0.7)
I-333: $^{1}$H-NMR(300.2 MHz, CDCl3):
δ = 7.9621 (5.3); 7.5684 (0.6); 7.5423 (1.6); 7.5160 (1.2); 7.4585 (1.5); 7.4329 (0.9); 7.2991 (1.3); 7.2627 (1.9); 7.2293 (1.0); 7.2260 (1.2); 7.2223 (1.1); 7.2187 (0.8); 7.2027 (0.9); 7.1993 (1.0); 7.1954 (0.9); 7.1919 (0.7); 7.1344 (2.2); 7.1320 (2.3); 7.0793 (2.1); 7.0537 (2.4); 6.8868 (1.1); 6.7649 (1.3); 6.7618 (1.3); 6.7393 (1.1); 6.7362 (1.1); 6.6990 (2.3); 6.5112 (1.2); 6.1963 (1.3); 5.3271 (5.4); 4.2354 (0.9); 4.2245 (1.0); 4.1993 (1.1); 4.1885 (1.2); 4.0357 (0.4); 4.0264 (0.5); 4.0185 (0.5); 4.0112 (0.6); 4.0048 (0.6); 3.9963 (0.6); 3.9874 (0.5); 3.9795 (0.4); 3.8981 (1.5); 3.8797 (1.1); 3.8620 (1.2); 3.8436 (1.0); 3.1666 (0.8); 3.1503 (0.8); 3.1217 (1.1); 3.1055 (1.0); 2.9205 (1.2); 2.8894 (1.1); 2.8758 (1.0); 2.8445 (0.8); 2.6641 (16.0); 2.2075 (11.0); 1.7663 (0.9); 0.0325 (1.4)
I-334: $^{1}$H-NMR(300.2 MHz, CDCl3):
δ = 7.9519 (5.2); 7.2988 (13.0); 7.2702 (2.7); 7.2584 (1.7); 7.2530 (1.7); 7.1430 (0.5); 7.1397 (0.5); 7.1160 (1.5); 7.0879 (1.5); 7.0735 (1.0); 7.0667 (1.2); 7.0500 (1.1); 7.0445 (1.2); 7.0232 (0.6); 7.0173 (0.5); 6.8570 (0.8); 6.8501 (1.4); 6.8415 (1.1); 6.8344 (1.5); 6.8218 (1.0); 6.8183 (1.0); 6.8101 (1.2); 6.2116 (1.1); 5.3376 (3.4); 4.1907 (0.7); 4.1814 (1.1); 4.1557 (1.3); 4.1464 (1.2); 4.0549 (0.4); 4.0439 (0.6); 4.0287 (0.7); 4.0151 (0.7); 3.9978 (1.8); 3.9833 (0.6); 3.9625 (1.0); 3.9479 (0.7); 3.2400 (0.7); 3.2245 (0.7); 3.1956 (1.2); 3.1792 (1.1); 3.0479 (1.0); 3.0184 (1.0); 3.0030 (0.8); 2.9734 (0.7); 2.6824 (16.0); 2.1260 (0.5); 2.1147 (0.5); 2.0975 (0.9); 2.0808 (0.6); 2.0694 (0.5); 1.6072 (9.5); 1.0835 (0.5); 1.0709 (1.6); 1.0641 (1.8); 1.0517 (0.9); 1.0423 (1.7); 1.0358 (1.7); 1.0231 (0.7); 0.8184 (1.0); 0.8013 (2.0); 0.7965 (1.6); 0.7874 (1.8); 0.7846 (1.8); 0.7795 (1.4); 0.7675 (0.7); 0.1066 (3.8); 0.0474 (0.6); 0.0366 (15.6); 0.0257 (0.6)
I-335: $^{1}$H-NMR(300.2 MHz, CDCl3):
δ = 7.9551 (4.9); 7.2986 (14.6); 7.1298 (0.5); 7.1263 (0.5); 7.1030 (1.4); 7.1001 (1.3); 7.0767 (1.0); 7.0736 (1.0); 7.0329 (1.9); 7.0218 (0.9); 7.0159 (1.1); 7.0076 (2.2); 6.9929 (1.2); 6.9711 (0.6); 6.9657 (0.5); 6.8537 (0.7); 6.8484 (0.7); 6.8270 (1.2); 6.8056 (0.6); 6.8007 (0.5); 6.7277 (2.1); 6.6924 (1.2); 6.6675 (1.0); 6.2726 (1.3); 5.3378 (12.4); 4.3082 (0.8); 4.2966 (0.9); 4.2722 (0.9); 4.2608 (1.0); 4.1713 (0.4); 4.1475 (0.4); 4.0277 (0.5); 4.0146 (0.6); 4.0078 (0.5); 3.9959 (0.4); 3.8839 (1.4); 3.8631 (1.0); 3.8478 (1.1); 3.8270 (0.9); 3.2672 (0.7); 3.2499 (0.7); 3.2221 (0.9); 3.2047 (0.9); 2.9493 (1.0); 2.9177 (1.0); 2.9038 (0.8); 2.8726 (0.7); 2.6668 (14.7); 2.1789 (10.4); 2.1388 (0.4); 2.1283 (0.5); 2.1109 (1.0); 2.0935 (0.6); 2.0837 (2.3); 2.0461 (0.5); 1.9572 (0.5); 1.9468 (0.5); 1.9408 (0.3); 1.9292 (0.9); 1.9115(0.5); 1.9011 (0.5); 1.6037 (16.0); 1.3210 (0.7); 1.2971 (1.4); 1.2734 (0.6); 1.0862 (0.6); 1.0731 (1.4); 1.0660 (1.7); 1.0614 (1.0); 1.0582 (1.0); 1.0530 (1.0); 1.0442 (1.4); 1.0378 (1.6); 1.0246 (0.8); 1.0046 (0.3); 0.9894 (0.5); 0.9750 (1.2); 0.9604 (1.4); 0.9545 (1.1); 0.9461 (1.3); 0.9323 (1.2); 0.9167 (0.7); 0.9014 (0.4); 0.8301 (0.8); 0.8133 (1.7); 0.8077 (1.5); 0.7985 (1.8); 0.7911 (1.2); 0.7802 (0.6); 0.6935 (0.6); 0.6826 (1.2); 0.6648 (2.1); 0.6550 (1.0); 0.6471 (1.0); 0.6378 (0.6); 0.1067 (4.2); 0.0478 (0.7); 0.0462 (0.5); 0.0370 (19.2); 0.0294 (0.6); 0.0278 (0.6); 0.0262 (0.7)

TABLE 2-continued

I-336: $^1$H-NMR(499.9 MHz, CDCl3):
δ = 7.9211 (5.3); 7.3693 (1.0); 7.3561 (2.0); 7.3537 (1.9); 7.3403 (1.7); 7.2620 (6.0); 7.2120 (3.5); 7.1871 (1.3); 7.1844 (1.4); 7.1678 (2.4); 7.1515 (1.8); 7.1066 (1.3); 7.0931 (2.1); 7.0773 (1.4); 7.0433 (1.5); 7.0271 (2.6); 6.9794 (3.1); 6.9632 (2.5); 6.0258 (2.4); 5.2989 (0.4); 4.1931 (1.7); 4.1775 (2.0); 3.8593 (3.1); 3.8428 (2.9); 3.8322 (1.9); 3.4869 (7.2); 2.9726 (0.9); 2.9632 (1.2); 2.9552 (1.4); 2.9456 (1.8); 2.9357 (1.9); 2.8816 (0.8); 2.8029 (1.0); 2.7931 (0.7); 2.7842 (1.4); 2.7756 (1.4); 2.7570 (1.2); 2.6442 (16.0); 2.2905 (14.1); 1.5839 (5.6); −0.0002 (7.4)
I-337: $^1$H-NMR(499.9 MHz, CDCl3):
δ = 8.0116 (0.5); 7.9208 (5.2); 7.3719 (0.7); 7.3689 (0.8); 7.3558 (1.6); 7.3527 (1.1); 7.3425 (0.9); 7.3396 (1.0); 7.2619 (6.3); 7.2121 (2.6); 7.1867 (0.8); 7.1837 (0.8); 7.1702 (1.6); 7.1672 (1.8); 7.1538 (1.0); 7.1509 (1.1); 7.1095 (1.0); 7.1065 (1.1); 7.0960 (1.1); 7.0932 (1.6); 7.0797 (0.7); 7.0767 (0.7); 7.0467 (1.0); 7.0433 (1.0); 7.0305 (1.6); 7.0271 (1.7); 6.9794 (2.9); 6.9632 (1.8); 6.0277 (1.6); 4.1927 (1.3); 4.1772 (1.4); 3.8840 (0.4); 3.8785 (0.6); 3.8733 (0.7); 3.8620 (2.1); 3.8426 (1.7); 3.8318 (0.9); 3.4866 (1.9); 2.9726 (0.8); 2.9630 (0.9); 2.9547 (3.7); 2.9455 (1.4); 2.9355 (1.2); 2.8812 (3.2); 2.8031 (1.0); 2.7934 (0.4); 2.7845 (1.0); 2.7758 (0.9); 2.7571 (0.8); 2.6439 (16.0); 2.2905 (12.9); 1.5854 (6.9); −0.0002 (8.0)
I-338: $^1$H-NMR(499.9 MHz, CDCl3):
δ = 7.9181 (5.2); 7.3573 (0.7); 7.3502 (0.8); 7.3446 (1.3); 7.3377 (1.4); 7.3315 (0.8); 7.3248 (0.8); 7.2614 (5.6); 7.1672 (0.5); 7.1620 (0.6); 7.1523 (3.8); 7.1450 (2.5); 7.1381 (3.2); 7.1280 (0.4); 7.1234 (0.4); 7.1092 (2.6); 7.0620 (2.2); 7.0466 (2.4); 6.7473 (1.4); 6.7329 (1.2); 5.9996 (1.4); 4.2072 (1.1); 4.2005 (1.2); 4.1853 (1.2); 4.1787 (1.2); 4.0190 (0.6); 4.0129 (0.7); 4.0077 (0.7); 4.0041 (0.7); 4.0009 (0.7); 3.9955 (0.7); 3.9896 (0.5); 3.9852 (0.4); 3.8755 (1.5); 3.8645 (1.3); 3.8536 (1.3); 3.8427 (1.1); 3.4865 (0.3); 3.1426 (1.0); 3.1325 (1.0); 3.1157 (1.2); 3.1056 (1.0); 2.8876 (1.2); 2.8689 (1.2); 2.8607 (1.0); 2.8420 (0.9); 2.6413 (16.0); 2.1865 (11.8); 1.5792 (4.8); 0.0061 (0.6); −0.0002 (7.2)
I-339: $^1$H-NMR(499.9 MHz, CDCl3):
δ = 7.9180 (5.2); 7.3574 (0.6); 7.3503 (0.7); 7.3447 (1.3); 7.3379 (1.4); 7.3316 (0.8); 7.3250 (0.9); 7.2616 (5.6); 7.1523 (3.6); 7.1451 (2.5); 7.1383 (3.4); 7.1284 (0.5); 7.1238 (0.4); 7.1091 (3.0); 7.0620 (2.3); 7.0466 (2.6); 6.7475 (1.6); 6.7323 (1.5); 5.9992 (1.6); 4.2071 (1.1); 4.2005 (1.2); 4.1853 (1.3); 4.1786 (1.4); 4.0189 (0.5); 4.0127 (0.7); 4.0073 (0.8); 4.0009 (0.8); 3.9956 (0.8); 3.9897 (0.6); 3.8756 (1.4); 3.8647 (1.3); 3.8537 (1.3); 3.8428 (1.2); 3.1426 (1.0); 3.1325 (1.0); 3.1157 (1.2); 3.1056 (1.2); 2.9550 (1.8); 2.8876 (1.3); 2.8824 (1.9); 2.8691 (1.3); 2.8609 (1.1); 2.8422 (1.0); 2.6414 (16.0); 2.1865 (12.7); 1.5834 (4.2); −0.0002 (6.8)
I-340: $^1$H-NMR(499.9 MHz, CDCl3):
δ = 7.6087 (16.0); 7.5194 (4.3); 7.5035 (7.6); 7.4877 (4.6); 7.4666 (1.1); 7.4573 (7.9); 7.4532 (8.0); 7.4417 (0.7); 7.4294 (5.7); 7.4130 (6.6); 7.3656 (0.4); 7.2775 (5.8); 7.2734 (5.8); 7.2603 (48.1); 6.9052 (7.5); 6.8898 (7.0); 6.6143 (5.3); 6.5980 (5.0); 5.2992 (14.3); 4.4164 (1.7); 4.4019 (2.9); 4.3870 (1.6); 4.3079 (4.0); 4.3056 (4.1); 4.2859 (4.4); 4.2837 (4.4); 3.9983 (3.5); 3.9944 (3.6); 3.9765 (3.1); 3.9725 (2.9); 3.3313 (2.2); 3.3177 (2.2); 3.3036 (3.0); 3.2900 (2.8); 3.1815 (3.5); 3.1654 (3.4); 3.1537 (2.5); 3.1376 (2.3); 1.7006 (0.4); 1.5621 (3.7); 1.4796 (0.5); 1.2544 (1.7); 0.1164 (0.4); 0.0691 (2.5); 0.0059 (3.3); −0.0002 (48.0); −0.0064 (2.3)
I-341: $^1$H-NMR(300.2 MHz, CDCl3):
δ = 8.1297 (16.0); 7.4699 (2.1); 7.4440 (6.0); 7.4181 (5.1); 7.3933 (5.2); 7.3673 (2.2); 7.3413 (6.7); 7.3343 (6.9); 7.2988 (6.5); 7.1470 (5.9); 7.1404 (4.2); 7.1338 (5.4); 7.1276 (4.2); 7.1198 (7.4); 6.9887 (2.4); 6.9844 (2.7); 6.9811 (2.6); 6.9770 (2.2); 6.9629 (2.2); 6.9585 (2.4); 6.9550 (2.4); 6.9508 (2.1); 6.9423 (4.5); 6.9352 (4.3); 6.9151 (3.4); 6.9080 (3.3); 6.7956 (2.5); 6.7594 (2.8); 6.7371 (3.0); 6.7009 (3.0); 6.2353 (2.9); 6.2284 (2.9); 5.8228 (6.0); 5.7644 (5.3); 5.3864 (5.8); 5.3500 (5.5); 4.1904 (2.3); 4.1802 (2.7); 4.1545 (3.1); 4.1443 (3.4); 4.0496 (0.4); 4.0389 (0.7); 4.0330 (1.0); 4.0225 (1.6); 4.0162 (1.2); 4.0059 (1.6); 3.9934 (1.7); 3.9835 (1.1); 3.9763 (1.1); 3.9665 (0.6); 3.9464 (4.0); 3.9304 (2.4); 3.9105 (2.8); 3.8945 (2.1); 3.1832 (2.0); 3.1661 (2.0); 3.1382 (3.2); 3.1210 (3.0); 2.9885 (3.2); 2.9586 (3.0); 2.9436 (2.2); 2.9134 (2.0); 2.0373 (3.0); 0.0366 (7.8)
I-342: $^1$H-NMR(300.2 MHz, CDCl3):
δ = 7.6222 (1.3); 7.6026 (7.2); 7.5822 (4.1); 7.5102 (1.9); 7.4729 (0.7); 7.4633 (1.1); 7.4558 (0.8); 7.4423 (0.7); 7.4353 (0.4); 7.2989 (14.4); 7.0479 (1.4); 7.0219 (3.9); 6.9452 (1.2); 6.9185 (0.7); 4.9396 (1.1); 4.9305 (1.2); 3.9820 (0.7); 3.9725 (0.9); 3.9475 (1.1); 3.9375 (1.1); 3.8707 (16.0); 3.8532 (1.1); 3.8329 (1.2); 3.8177 (0.5); 3.8102 (0.6); 3.7996 (0.6); 3.7913 (0.5); 3.7734 (1.6); 3.7575 (0.6); 3.7384 (0.9); 3.7221 (0.6); 2.9365 (0.4); 2.9182 (0.4); 2.8911 (1.1); 2.8720 (1.0); 2.8510 (1.0); 2.8228 (1.0); 2.8059 (0.4); 2.7768 (0.4); 2.3184 (10.4); 2.3083 (10.4); 1.6113 (7.9); 1.2982 (0.8); 1.2923 (0.9); 0.1073 (2.2); 0.0481 (0.6); 0.0375 (15.7); 0.0266 (0.6)
I-343: $^1$H-NMR(300.2 MHz, CDCl3):
δ = 7.5808 (1.1); 7.5613 (2.9); 7.5583 (2.6); 7.4230 (1.4); 7.3975 (0.6); 7.3872 (0.8); 7.3798 (0.6); 7.3667 (0.6); 7.3594 (0.4); 7.2990 (3.6); 7.0397 (1.2); 7.0264 (1.7); 7.0148 (1.9); 6.9393 (1.0); 6.9137 (0.6); 4.8214 (1.0); 4.2075 (0.8); 4.1817 (0.9); 3.9625 (0.4); 3.9422 (1.4); 3.9260 (0.4); 3.9142 (1.1); 3.8970 (0.4); 3.0469 (0.4); 3.0300 (0.4); 3.0006 (0.7); 2.9834 (0.6); 2.9027 (0.6); 2.8746 (0.6); 2.8571 (0.4); 2.8279 (0.3); 2.3142 (16.0); 2.0709 (0.4); 2.0617 (0.4); 2.0421 (0.9); 2.0223 (0.5); 2.0132 (0.5); 1.6259 (0.8); 1.2927 (0.4); 1.2821 (0.4); 1.2642 (1.4); 1.2602 (1.4); 1.2529 (1.0); 1.2443 (0.7); 1.2354 (1.0); 1.2313 (1.2); 1.2244 (0.8); 1.2155 (0.4); 1.0466 (0.8); 1.0392 (0.7); 1.0361 (0.8); 1.0317 (0.9); 1.0260 (1.2); 1.0201 (1.2); 1.0057 (0.6); 1.0017 (0.7); 0.1088 (0.5); 0.0379 (3.9)
I-344: $^1$H-NMR(300.2 MHz, CDCl3):
δ = 7.9635 (5.2); 7.5882 (0.5); 7.5627 (0.8); 7.5496 (0.5); 7.5399 (0.5); 7.4082 (0.3); 7.3875 (1.0); 7.3856 (1.0); 7.3814 (0.8); 7.3656 (3.1); 7.3588 (0.9); 7.3421 (1.4); 7.3142 (0.4); 7.2986 (2.2); 7.1401 (2.1); 7.1377 (2.1); 7.1032 (2.1); 7.0935 (1.2); 7.0776 (2.4); 6.9109 (2.2); 6.7749 (1.2); 6.7720 (1.2); 6.7493 (1.0); 6.7463 (1.0); 6.7283 (1.1); 6.0664 (1.2); 4.2522 (0.9); 4.2414 (1.0); 4.2161 (1.1); 4.2052 (1.2); 4.0622 (0.4); 4.0524 (0.5); 4.0435 (0.5); 4.0369 (0.5); 4.0315 (0.6); 4.0227 (0.6); 4.0131 (0.4); 3.9230 (1.4); 3.9049 (1.1); 3.8868 (1.2); 3.8687 (0.9); 3.1924 (0.8); 3.1758 (0.8); 3.1476 (1.1); 3.1310 (1.0); 2.9369 (1.1); 2.9060 (1.1); 2.8921 (0.9); 2.8612 (0.8); 2.6743 (16.0); 2.2035 (0.5); 2.1894 (10.8); 2.0383 (0.4); 0.0341 (2.9)
I-345: $^1$H-NMR(300.2 MHz, CDCl3):
δ = 10.3610 (4.4); 9.9815 (0.4); 7.9845 (5.2); 7.8765 (0.7); 7.8705 (0.7); 7.8565 (0.7); 7.8504 (1.4); 7.8446 (0.8); 7.8308 (0.8); 7.8247 (0.7); 7.7702 (0.4); 7.5012 (0.6); 7.4953 (0.6); 7.4746 (1.2); 7.4695 (1.1); 7.4504 (1.0); 7.4442 (0.9); 7.3962 (1.2); 7.3699 (1.6); 7.3435 (0.6); 7.2987 (4.6); 7.0310 (1.8); 7.0056 (2.1); 6.8927 (2.0); 6.7094 (1.1); 6.6850 (1.0); 6.0840 (1.3); 4.3229 (0.8); 4.3127 (1.0); 4.2875 (1.0); 4.2775 (1.1); 3.9565 (0.4); 3.9487 (0.4); 3.9388 (0.5); 3.9328 (0.5); 3.9276 (0.5); 3.9227 (0.6); 3.9172 (0.5); 3.9069 (0.5); 3.8988

TABLE 2-continued

| |
|---|
| (0.4); 3.8913 (0.4); 3.8827 (1.8); 3.8622 (0.8); 3.8476 (1.4); 3.8270 (0.9); 3.0569 (0.7); 3.0407 (0.7); 3.0117 (1.0); 2.9951 (1.0); 2.8022 (1.1); 2.7706 (1.0); 2.7570 (0.8); 2.7331 (1.2); 2.7250 (0.8); 2.6806 (16.0); 2.3094 (11.6); 2.2605 (0.9); 2.1483 (10.8); 2.0439 (3.1); 0.0355 (6.4) |
| I-346: $^{1}$H-NMR(300.2 MHz, CDCl3): |
| δ = 7.9573 (5.1); 7.3432 (1.2); 7.3170 (2.6); 7.2988 (8.8); 7.2908 (1.7); 7.1491 (2.1); 7.0760 (2.0); 7.0504 (2.3); 7.0118 (1.4); 6.9859 (1.2); 6.8761 (0.9); 6.8731 (1.0); 6.8682 (1.2); 6.8652 (1.1); 6.8493 (0.8); 6.8462 (0.8); 6.8414 (1.1); 6.8383 (1.0); 6.8018 (1.6); 6.7956 (2.1); 6.7887 (1.2); 6.7342 (1.2); 6.7310 (1.2); 6.7086 (1.0); 6.7054 (1.0); 6.3037 (1.1); 4.2237 (0.9); 4.2129 (1.0); 4.1877 (1.1); 4.1768 (1.2); 4.0210 (0.4); 4.0104 (0.5); 4.0025 (0.5); 3.9908 (0.6); 3.9820 (0.6); 3.9728 (0.4); 3.8919 (1.4); 3.8735 (1.0); 3.8559 (1.2); 3.8375 (0.9); 3.1723 (0.8); 3.1556 (0.8); 3.1275 (1.0); 3.1108 (1.0); 2.9090 (1.1); 2.8787 (1.1); 2.8643 (0.8); 2.8338 (0.8); 2.6689 (16.0); 2.2369 (10.5); 2.0835 (0.8); 1.9668 (0.5); 1.9557 (0.6); 1.9389 (1.1); 1.9222 (0.6); 1.9110 (0.6); 1.6146 (3.4); 1.3208 (0.6); 1.3035 (1.6); 1.2972 (1.7); 1.2733 (0.3); 1.0554 (0.6); 1.0409 (1.7); 1.0340 (2.0); 1.0277 (0.9); 1.0195 (0.9); 1.0123 (1.9); 1.0059 (1.7); 0.9918 (0.8); 0.9406 (0.7); 0.9191 (1.8); 0.8959 (0.7); 0.7671 (1.0); 0.7528 (2.0); 0.7499 (1.9); 0.7454 (1.8); 0.7395 (1.2); 0.7361 (2.0); 0.7317 (1.9); 0.7287 (1.7); 0.7150 (0.8); 0.1071 (0.4); 0.0480 (0.4); 0.0371 (12.1); 0.0262 (0.5) |
| I-347: $^{1}$H-NMR(499.9 MHz, CDCl3): |
| δ = 8.1955 (0.3); 8.1353 (11.6); 8.1319 (12.5); 8.0891 (1.0); 8.0855 (1.0); 7.8055 (0.4); 7.7711 (0.4); 7.7591 (0.4); 7.7464 (0.5); 7.7271 (0.5); 7.6582 (0.7); 7.5742 (16.0); 7.5017 (10.4); 7.4703 (1.4); 7.4205 (6.6); 7.4089 (5.7); 7.3503 (6.6); 7.3378 (26.2); 7.3229 (14.5); 7.3092 (7.6); 7.2961 (6.7); 7.2925 (6.5); 7.2822 (6.0); 7.2633 (19.1); 7.2596 (19.8); 7.2296 (1.6); 7.1952 (1.0); 7.1842 (1.0); 7.1408 (1.3); 7.1257 (1.1); 7.0886 (0.4); 7.0481 (0.4); 7.0293 (0.4); 7.0052 (0.3); 6.9853 (0.3); 6.9670 (0.4); 6.9329 (0.3); 6.8675 (0.3); 6.8335 (0.3); 6.7718 (0.3); 6.7173 (6.0); 6.6855 (6.6); 6.1720 (3.7); 6.1568 (4.0); 6.1404 (3.6); 6.1252 (3.7); 6.0942 (7.3); 5.9845 (0.5); 4.3792 (4.4); 4.2813 (3.9); 4.2612 (4.4); 4.0964 (0.4); 4.0725 (0.4); 3.8190 (3.9); 3.8058 (4.1); 3.8002 (4.0); 3.7971 (4.0); 3.7844 (3.5); 3.6330 (0.3); 2.7611 (0.4); 2.7453 (0.4); 2.1688 (0.3); 1.9937 (0.3); 1.9805 (0.6); 1.9665 (0.6); 1.9496 (0.3); 1.5768 (2.4); 1.3662 (0.4); 1.3325 (0.4); 1.2552 (1.2); 0.0701 (2.3); 0.0036 (19.3); −0.0002 (21.7) |
| I-348: $^{1}$H-NMR(300.2 MHz, CDCl3): |
| δ = 7.9593 (5.2); 7.4751 (0.7); 7.4681 (0.8); 7.4547 (0.8); 7.4506 (0.9); 7.4439 (1.4); 7.4337 (0.8); 7.4233 (0.8); 7.2987 (8.1); 7.2526 (0.4); 7.2456 (0.5); 7.2251 (1.4); 7.2183 (1.2); 7.2060 (4.1); 7.1965 (1.3); 7.1835 (1.8); 7.1546 (0.6); 7.0155 (1.8); 6.9901 (2.1); 6.9038 (2.0); 6.7288 (1.1); 6.7030 (0.9); 6.1207 (1.3); 4.3083 (0.8); 4.2987 (0.9); 4.2728 (1.0); 4.2636 (1.0); 3.9301 (0.4); 3.9229 (0.4); 3.9178 (0.5); 3.9125 (0.6); 3.9068 (0.5); 3.9021 (0.5); 3.8967 (0.6); 3.8809 (0.5); 3.8723 (0.5); 3.8612 (1.8); 3.8405 (0.7); 3.8263 (1.4); 3.8056 (0.9); 3.3798 (4.0); 3.0440 (0.7); 3.0283 (0.7); 2.9991 (1.0); 2.9827 (1.0); 2.7831 (1.1); 2.7517 (1.0); 2.7378 (0.9); 2.7315 (0.7); 2.7062 (0.8); 2.6689 (16.0); 2.3057 (11.4); 2.2881 (1.1); 2.1877 (10.7); 2.1559 (0.5); 2.0452 (2.4); 0.0480 (0.4); 0.0372 (11.0); 0.0264 (0.5) |

The compounds as shown in table 3, 5, 7, 9, 11, 13, 15, 17, 19, 21, 23, 25, 27, 29, 31, 33, 35, 37, 39, 41 and 43 below were prepared in analogy with the examples provided above or following methods described herein. $^{1}$H-NMR data of these compounds is respectively shown in tables 4, 6, 8, 10, 12, 14, 16, 18, 20, 22, 24, 26, 28, 30, 32, 34, 36, 38 40, 42 and 44.

TABLE 3

Compounds according to formula (1)

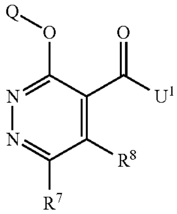

(1)

| Ex No | $R^7$ | $R^8$ | Q | $U^1$ | LogP |
|---|---|---|---|---|---|
| 1-01 | Cl | H | 3-(difluoromethyl)phenyl | hydroxy | 1.45[a] |
| 1-02 | Cl | methyl | 3-cyclopropyl-2-fluorophenyl | hydroxy | 1.84[a] |
| 1-03 | methyl | H | 3-(trifluoromethyl)phenyl | methoxy(methyl)amino | 2.33[a] |
| 1-04 | Cl | methyl | 3-(trifluoromethyl)phenyl | hydroxy | 1.70[a] |
| 1-05 | Cl | cyclo-propyl-amino | 3-(trifluoromethyl)phenyl | hydroxy | 2.20[a] |
| 1-06 | Cl | H | 3-cyclopropylphenyl | hydroxy | 1.87[a] |
| 1-07 | Cl | H | 3-(trifluoromethyl)phenyl | methoxy(methyl)amino | 2.90[a] |
| 1-08 | Cl | H | 3-(difluoromethyl)-2-fluorophenyl | isopropyloxy | 3.68[a] |

TABLE 3-continued

Compounds according to formula (1)

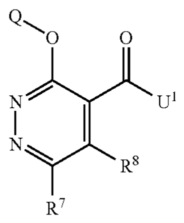

(1)

| Ex No | $R^7$ | $R^8$ | Q | $U^1$ | LogP |
|---|---|---|---|---|---|
| 1-09 | Cl | cyclo-propyl-amino | 3-(trifluoromethyl)phenyl | methoxy | 3.35[a] |
| 1-10 | Cl | H | 3-cyclopropyl-2-fluorophenyl | hydroxy | 2.01[a] |
| 1-11 | ethyl | H | 3-(trifluoromethyl)phenyl | hydroxy | 1.82[a] |
| 1-12 | ethyl | H | 3-(trifluoromethyl)phenyl | isopropyloxy | 3.96[a] |
| 1-13 | acetyl | H | 3-(trifluoromethyl)phenyl | hydroxy | 2.01[a] |
| 1-14 | methyl | H | 3-(trifluoromethyl)phenyl | methoxy | 2.77[a] |
| 1-15 | vinyl | H | 3-(trifluoromethyl)phenyl | isopropyloxy | 4.01[a] |
| 1-16 | methyl | H | 3-cyclopropylphenyl | hydroxy | 1.46[a] |
| 1-17 | methyl | H | 2-fluoro-3-(trifluoromethyl)phenyl | methoxy | 2.90[a] |
| 1-18 | Cl | H | 2-fluoro-3-(trifluoromethyl)phenyl | hydroxy | 1.98[a] |
| 1-19 | Cl | H | 2-fluoro-3-(trifluoromethyl)phenyl | methoxy | 3.35[a] |
| 1-20 | Cl | I | 3-(trifluoromethyl)phenyl | methoxy | 3.25[a] |
| 1-21 | Cl | H | 3-cyclopropyl-2-fluorophenyl | isopropyloxy | 4.30[a] |
| 1-22 | Cl | H | 3-cyclopropylphenyl | isopropyloxy | 4.15[a] |
| 1-23 | Cl | H | 3-(difluoromethyl)-2-fluorophenyl | hydroxy | 1.63[a] |
| 1-24 | Cl | methyl | 3-cyclopropyl-2-fluorophenyl | isopropyloxy | 4.51[a] |
| 1-25 | I | H | 3-(trifluoromethyl)phenyl | isopropyloxy | 4.25[a] |
| 1-26 | methyl | H | 2-fluoro-3-(trifluoromethyl)phenyl | hydroxy | 1.75[a] |
| 1-27 | methyl | methyl | 3-(trifluoromethyl)phenyl | hydroxy | 1.52[a] |
| 1-28 | 1-ethoxyethen-1-yl | H | 3-(trifluoromethyl)phenyl | isopropyloxy | 4.90[a] |
| 1-29 | acetyl | H | 3-(trifluoromethyl)phenyl | isopropyloxy | 3.99[a] |
| 1-30 | methyl | H | 3-cyclopropyl-2-fluorophenyl | hydroxy | 1.70[a] |
| 1-31 | methyl | methyl | 3-(trifluoromethyl)phenyl | methoxy | 2.98[a] |
| 1-32 | Cl | H | 3-(trifluoromethyl)phenyl | isopropyloxy | 4.06[a] |
| 1-33 | Cl | methyl | 3-(trifluoromethyl)phenyl | methoxy | 3.55[a] |
| 1-34 | Cl | H | 6-chloro-5-(trifluoromethyl)pyridin-3-yl | hydroxy | 1.14[b] |
| 1-35 | Cl | H | 6-chloro-5-(trifluoromethyl)pyridin-3-yl | ethoxy | 3.74[b] |
| 1-36 | Cl | H | 5-bromopyridin-3-yl | hydroxy | 0.94[a]; 0.53[b] |
| 1-37 | Cl | H | 3-(1-fluorocyclopropyl)phenyl | hydroxy | 1.82[a] |
| 1-38 | Cl | H | 3-(1-fluorocyclopropyl)phenyl | isopropyloxy | 3.99[a] |
| 1-39 | Cl | H | 2-fluoro-3-[rac-2,2-difluorocyclopropyl]phenyl | hydroxy | 1.95[a] |
| 1-40 | Cl | H | 2-fluoro-3-[rac-2,2-difluorocyclopropyl]phenyl | isopropyloxy | 3.96[a] |
| 1-41 | Cl | methyl | 2-fluoro-3-[rac-2,2-difluorocyclopropyl]phenyl | hydroxy | 1.82[a] |
| 1-42 | Cl | methyl | 2-fluoro-3-[rac-2,2-difluorocyclopropyl]phenyl | isopropyloxy | 4.23[a] |
| 1-43 | Cl | H | 2-fluoro-3-(1-fluorocyclopropyl)phenyl | hydroxy | 1.99[a] |
| 1-44 | Cl | H | 2-fluoro-3-(1-fluorocyclopropyl)phenyl | isopropyloxy | 4.62[a] |

TABLE 3-continued

Compounds according to formula (1)

(1)

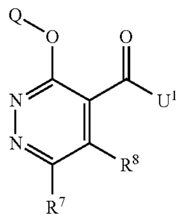

| Ex No | $R^7$ | $R^8$ | Q | $U^1$ | LogP |
|---|---|---|---|---|---|
| 1-45 | Cl | methyl | 2-fluoro-3-(1-fluorocyclopropyl)phenyl | isopropyloxy | 4.33[a] |
| 1-46 | methyl | H | 3-(difluoromethyl)-2-fluorophenyl | hydroxy | 1.43[a] |

TABLE 4

1-01: $^1$H-NMR(400.1 MHz, $d_6$-DMSO):
δ = 8.2400 (16.0); 7.6498 (2.3); 7.6302 (5.4); 7.6106 (3.8); 7.5151 (4.9); 7.4824 (7.4); 7.4627 (4.5); 7.4423 (3.4); 7.2113 (3.0); 7.0721 (6.5); 6.9329 (3.2); 2.5098 (2.1)
1-02: $^1$H-NMR(499.9 MHz, $d_6$-DMSO):
δ = 7.2008 (0.5); 7.1974 (0.6); 7.1845 (1.3); 7.1815 (1.2); 7.1714 (1.3); 7.1667 (1.4); 7.1639 (2.1); 7.1483 (1.9); 7.1323 (0.7); 6.9341 (0.8); 6.9309 (0.8); 6.9188 (1.1); 6.9163 (1.2); 6.9061 (0.6); 6.9020 (0.5); 2.5135 (0.4); 2.5099 (0.5); 2.5063 (0.4); 2.3968 (16.0); 2.3846 (0.4); 2.0707 (0.6); 2.0641 (0.6); 2.0539 (1.1); 2.0436 (0.7); 2.0371 (0.6); 1.0253 (0.9); 1.0166 (2.2); 1.0122 (2.3); 1.0086 (1.3); 1.0039 (1.3); 0.9997 (2.2); 0.9953 (2.2); 0.9871 (0.9); 0.7823 (1.0); 0.7739 (2.4); 0.7720 (2.1); 0.7698 (2.5); 0.7637 (2.4); 0.7596 (2.5); 0.7507 (0.8)
1-03: $^1$H-NMR(300.2 MHz, CDCl3):
δ = 7.5607 (0.9); 7.5349 (2.7); 7.5100 (2.2); 7.4700 (0.9); 7.4634 (1.4); 7.4561 (0.7); 7.4478 (0.5); 7.4453 (0.5); 7.4390 (0.7); 7.4323 (0.5); 7.4022 (1.8); 7.2986 (8.6); 5.3359 (5.0); 3.7789 (0.8); 3.6362 (3.8); 3.4357 (4.8); 3.2797 (1.0); 2.7276 (16.0); 1.6155 (15.9); 1.2931 (0.5); 0.9180 (0.4); 0.1060 (4.2); 0.0360 (5.0)
1-04: $^1$H-NMR(300.2 MHz, $d_6$-DMSO):
δ = 7.7747 (2.4); 7.7475 (8.1); 7.7204 (13.3); 7.7120 (13.1); 7.6924 (16.0); 7.6526 (0.5); 7.6169 (7.8); 7.5910 (5.1); 3.6770 (0.3); 3.6257 (0.3); 3.6165 (0.3); 3.5687 (0.4); 3.5321 (0.4); 3.4984 (0.4); 3.4631 (0.4); 3.4373 (0.4); 3.4027 (0.4); 3.3673 (0.4); 3.2814 (0.3); 3.2318 (0.3); 2.6507 (0.6); 2.5397 (13.4); 2.5340 (16.5); 2.4347 (75.8); 2.2151 (0.4); 2.1066 (1.0); 1.3861 (0.4); 1.2634 (1.1); 1.2122 (0.8); 0.0288 (8.6)
1-05: $^1$H-NMR(300.2 MHz, CDCl3):
δ = 7.6445 (0.5); 7.5698 (2.7); 7.5445 (7.8); 7.5195 (16.0); 7.5093 (9.8); 7.4764 (11.2); 7.4396 (5.2); 7.4332 (8.1); 7.4263 (4.2); 7.4086 (5.5); 7.3826 (0.6); 7.3637 (0.7); 7.3254 (0.6); 7.3137 (0.6); 7.2986 (53.8); 7.2646 (0.4); 6.2623 (0.4); 6.1844 (3.5); 6.0638 (0.7); 6.0086 (0.3); 4.1995 (0.8); 4.1756 (2.3); 4.1519 (2.3); 4.1283 (0.8); 3.9955 (1.5); 3.7885 (5.4); 2.9593 (1.0); 2.9468 (2.0); 2.9363 (3.0); 2.9243 (4.0); 2.9173 (4.2); 2.9054 (2.9); 2.8954 (2.1); 2.8833 (1.1); 2.1754 (0.6); 2.0898 (11.2); 1.3210 (2.9); 1.2972 (5.9); 1.2734 (2.9); 1.2573 (0.8); 1.0060 (0.5); 0.9871 (0.6); 0.9703 (0.5); 0.9336 (2.4); 0.9096 (10.1); 0.8908 (10.0); 0.8686 (4.7); 0.8384 (1.8); 0.8233 (1.3); 0.8183 (1.3); 0.7839 (4.0); 0.7680 (10.0); 0.7601 (11.9); 0.7312 (2.6); 0.0482 (1.6); 0.0450 (0.8); 0.0374 (52.7); 0.0282 (1.7); 0.0265 (2.1)
1-06: $^1$H-NMR(300.2 MHz, $d_6$-DMSO):
δ = 8.2130 (16.0); 7.3593 (2.5); 7.3332 (5.6); 7.3070 (3.4); 7.0221 (3.3); 7.0179 (3.1); 7.0083 (2.7); 7.0051 (2.6); 7.0002 (5.0); 6.9971 (5.0); 6.9819 (1.8); 6.9786 (1.8); 6.9739 (3.5); 6.9708 (2.8); 6.9607 (4.6); 6.9548 (5.0); 6.9484 (2.6); 5.7756 (1.8); 2.5344 (1.4); 2.5284 (3.0); 2.5223 (4.1); 2.5162 (3.0); 2.5103 (1.4); 2.0139 (0.6); 2.0090 (0.4); 1.9970 (1.2); 1.9859 (1.4); 1.9807 (1.0); 1.9693 (2.6); 1.9578 (1.0); 1.9524 (1.5); 1.9414 (1.4); 1.9245 (0.7); 1.0128 (1.6); 0.9983 (4.4); 0.9908 (4.9); 0.9852 (2.4); 0.9772 (2.6); 0.9702 (4.7); 0.9628 (4.5); 0.9494 (2.0); 0.7347 (2.0); 0.7209 (5.0); 0.7178 (4.2); 0.7139 (5.2); 0.7044 (4.8); 0.6974 (5.3); 0.6822 (1.6); 0.0194 (4.1)
1-07: $^1$H-NMR(499.9 MHz, CDCl3):
δ = 7.5660 (0.9); 7.5561 (3.4); 7.5510 (2.4); 7.5352 (2.5); 7.5283 (2.4); 7.5127 (0.7); 7.4844 (2.5); 7.4365 (1.2); 7.4331 (1.7); 7.4293 (1.1); 7.4207 (0.9); 7.4177 (1.2); 7.4143 (0.8); 7.3066 (0.4); 4.0134 (0.5); 4.0012 (1.2); 3.9889 (1.6); 3.9767 (1.2); 3.9644 (0.5); 3.6270 (7.7); 3.3918 (8.4); 1.9661 (0.7); 1.1838 (15.7); 1.1790 (0.7); 1.1715 (16.0); −0.0002 (0.4)
1-08: $^1$H-NMR(300.2 MHz, CDCl3):
δ = 7.9376 (5.4); 7.6355 (0.5); 7.5766 (0.4); 7.5552 (0.8); 7.5345 (0.5); 7.5325 (0.5); 7.5089 (0.4); 7.5061 (0.4); 7.4818 (0.9); 7.4792 (0.8); 7.4575 (0.6); 7.4549 (0.6); 7.3709 (0.8); 7.3437 (1.2); 7.3177 (0.4); 7.2984 (2.8); 7.1103 (0.9); 6.9278 (1.8); 6.7452 (0.9); 5.4078 (0.4); 5.3870 (1.0); 5.3661 (1.3); 5.3452 (1.0); 5.3244 (0.4); 1.6170 (0.8); 1.4798 (1.5); 1.4609 (16.0); 1.4400 (15.1); 1.4256 (0.5); 1.4046 (0.4); 1.2465 (0.4); 0.0361 (2.9)
1-09: $^1$H-NMR(300.2 MHz, CDCl3):
δ = 7.5541 (0.4); 7.5433 (0.9); 7.5165 (2.2); 7.5102 (1.3); 7.4902 (1.5); 7.4883 (1.4); 7.4831 (1.6); 7.4402 (0.7); 7.4327 (1.2); 7.4255 (0.6); 7.4169 (0.4); 7.4144 (0.4); 7.4090 (0.6); 7.4018 (0.3); 7.2985 (2.8); 5.6931 (0.8); 4.0184 (1.9); 4.0071 (0.4); 3.9923 (16.0); 2.7929 (0.4); 2.7891 (0.4); 2.7825 (0.4); 2.7771 (0.6); 2.7705 (0.7); 2.7651 (0.5); 2.7585 (0.4); 2.7550 (0.4); 2.7483 (0.4); 2.0802 (0.7); 1.6331 (0.7); 1.2941 (0.4); 0.8795 (1.4); 0.8742 (0.9); 0.8618 (1.4); 0.8570 (1.2); 0.8517 (0.9); 0.8395 (0.7); 0.8107 (0.4); 0.7720 (0.7); 0.7589 (1.5); 0.7490 (1.5); 0.7455 (1.5); 0.7325 (0.8); 0.7197 (0.3); 0.0350 (2.4)

TABLE 4-continued 1-10: $^1$H-NMR(499.9 MHz, $d_6$-DMSO):
δ = 8.2502 (16.0); 8.0080 (1.2); 7.2221 (0.5); 7.2063 (1.3); 7.2027 (1.4); 7.1899 (3.5); 7.1868 (3.2); 7.1767 (7.8); 7.1620 (5.1); 7.1458 (1.7); 6.9476 (2.0); 6.9442 (2.1); 6.9334 (2.8); 6.9290 (3.0); 6.9209 (1.5); 6.9154 (1.3); 2.5087 (2.8); 2.5051 (3.7); 2.5016 (2.6); 2.0890 (0.9); 2.0788 (1.6); 2.0720 (1.8); 2.0620 (2.9); 2.0519 (1.7); 2.0452 (1.5); 2.0348 (0.7); 1.9900 (0.6); 1.1759 (0.4); 1.0341 (2.4); 1.0255 (5.8); 1.0211 (5.8); 1.0175 (3.2); 1.0127 (3.3); 1.0086 (5.4); 1.0042 (5.4); 0.9960 (2.0); 0.8237 (0.4); 0.8130 (0.5); 0.7937 (2.7); 0.7854 (6.6); 0.7813 (6.5); 0.7753 (6.2); 0.7712 (6.0); 0.7622 (1.8)
1-11: $^1$H-NMR(300.2 MHz, $d_6$-DMSO):
δ = 8.0139 (9.2); 7.7429 (0.8); 7.7169 (2.4); 7.6915 (2.4); 7.6678 (3.0); 7.6430 (4.7); 7.5644 (2.0); 7.5380 (1.5); 3.0021 (1.8); 2.9768 (5.6); 2.9515 (5.7); 2.9263 (1.9); 2.5341 (2.3); 2.5281 (4.7); 2.5221 (6.5); 2.5161 (4.7); 2.5102 (2.2); 2.0085 (0.5); 1.9290 (0.4); 1.3136 (7.2); 1.2884 (16.0); 1.2631 (6.9); 0.0182 (7.1); −0.0419 (1.3)
1-12: $^1$H-NMR(300.2 MHz, CDCl3):
δ = 7.7672 (4.6); 7.5697 (1.0); 7.5431 (1.7); 7.5290 (2.2); 7.5215 (1.8); 7.4764 (0.8); 7.4707 (1.1); 7.4641 (0.7); 7.4453 (0.7); 7.2990 (5.2); 5.3887 (0.4); 5.3679 (1.0); 5.3470 (1.3); 5.3261 (1.0); 5.3053 (0.4); 3.1003 (1.0); 3.0749 (3.3); 3.0496 (3.4); 3.0243 (1.2); 1.6181 (9.2); 1.4489 (4.2); 1.4341 (16.0); 1.4236 (8.8); 1.4132 (15.9); 1.3982 (3.9); 0.1066 (1.2); 0.0359 (4.9)
1-13: $^1$H-NMR(300.2 MHz, CDCl3):
δ = 8.9312 (0.5); 8.7218 (5.7); 7.6865 (0.4); 7.6605 (1.5); 7.6368 (4.5); 7.6136 (0.6); 7.5818 (2.3); 7.5362 (1.0); 7.5285 (1.6); 7.5213 (0.9); 7.5058 (1.0); 7.2986 (8.3); 7.1162 (0.3); 4.1844 (0.7); 4.1606 (0.8); 3.8821 (0.4); 2.8702 (16.0); 2.6686 (1.2); 2.1970 (2.5); 2.1014 (3.4); 1.9497 (0.5); 1.6815 (0.4); 1.4679 (0.4); 1.4314 (0.3); 1.4067 (0.5); 1.3816 (0.5); 1.3593 (0.8); 1.3319 (0.6); 1.3261 (1.1); 1.3023 (2.0); 1.2902 (0.4); 1.2784 (1.0); 0.9825 (1.0); 0.9582 (1.8); 0.9340 (0.8); 0.1065 (0.7); 0.0352 (8.0); 0.0243 (0.4)
1-14: $^1$H-NMR(400.1 MHz, $d_6$-DMSO):
δ = 8.0394 (5.5); 7.7256 (0.6); 7.7063 (1.9); 7.6866 (1.6); 7.6542 (2.3); 7.6331 (3.8); 7.5609 (1.6); 7.5403 (1.4); 3.9145 (16.0); 3.3269 (11.0); 2.6442 (15.2); 2.5097 (1.8)
1-15: $^1$H-NMR(300.2 MHz, CDCl3):
δ = 8.0165 (5.2); 7.5853 (1.0); 7.5593 (2.0); 7.5527 (1.6); 7.5470 (1.9); 7.5370 (1.8); 7.4918 (0.7); 7.4850 (1.1); 7.4782 (0.6); 7.4654 (0.4); 7.4598 (0.6); 7.2985 (4.6); 7.1094 (1.0); 7.0725 (1.2); 7.0501 (1.2); 7.0133 (1.2); 6.2880 (2.3); 6.2288 (2.0); 5.7406 (2.3); 5.7037 (2.1); 5.4053 (0.4); 5.3845 (1.0); 5.3636 (1.4); 5.3427 (1.0); 5.3219 (0.4); 1.6133 (1.8); 1.4481 (16.0); 1.4272 (15.8); 0.0363 (4.3)
1-16: $^1$H-NMR(400.1 MHz, $d_6$-DMSO):
δ = 7.8912 (5.7); 7.3097 (1.3); 7.2902 (2.8); 7.2706 (1.7); 6.9569 (2.0); 6.9376 (1.9); 6.9046 (1.9); 6.8752 (3.4); 2.6079 (16.0); 2.5101 (2.7); 1.9793 (0.3); 1.9665 (0.7); 1.9580 (0.9); 1.9458 (1.4); 1.9335 (1.0); 1.9250 (0.9); 1.9123 (0.4); 0.9823 (0.8); 0.9712 (2.4); 0.9660 (2.8); 0.9504 (2.7); 0.9453 (2.8); 0.9351 (1.2); 0.7049 (1.0); 0.6935 (3.0); 0.6899 (3.2); 0.6818 (3.0); 0.6774 (3.3); 0.6659 (1.0)
1-17: $^1$H-NMR(300.2 MHz, CDCl3):
δ = 7.8520 (4.3); 7.5819 (0.6); 7.5583 (1.4); 7.5372 (1.4); 7.5170 (0.7); 7.3531 (0.7); 7.3263 (1.1); 7.2986 (2.2); 4.0423 (16.0); 2.7528 (14.2); 1.2898 (0.5); 0.0335 (1.6)
1-18: $^1$H-NMR(300.2 MHz, $d_6$-DMSO):
δ = 8.2409 (16.0); 8.1115 (0.6); 7.9405 (1.1); 7.8747 (1.8); 7.8503 (3.7); 7.8227 (2.3); 7.8127 (2.0); 7.7868 (3.6); 7.7656 (2.3); 7.5853 (2.5); 7.5587 (4.1); 7.5321 (1.8); 4.1145 (0.5); 4.0839 (0.4); 4.0726 (1.0); 4.0489 (1.0); 3.5064 (0.4); 3.3515 (0.6); 3.3099 (0.5); 3.0723 (1.7); 3.0521 (0.7); 3.0411 (0.5); 3.0096 (0.3); 2.9228 (1.8); 2.8928 (0.7); 2.8579 (0.4); 2.7637 (1.5); 2.5463 (9.6); 2.5404 (20.1); 2.5343 (27.5); 2.5283 (19.6); 2.5224 (9.0); 2.0211 (3.9); 1.3872 (0.8); 1.2914 (0.5); 1.2660 (1.1); 1.2300 (1.3); 1.2062 (2.6); 1.2012 (1.1); 1.1825 (1.2); 0.1641 (0.4); 0.1162 (0.4); 0.0419 (0.5); 0.0310 (14.4); 0.0201 (0.6)
1-19: $^1$H-NMR(499.9 MHz, CDCl3):
δ = 7.9753 (5.2); 7.6683 (0.6); 7.5512 (0.8); 7.5390 (1.8); 7.5259 (2.2); 7.5122 (1.1); 7.3323 (1.0); 7.3162 (1.8); 7.3001 (0.8); 7.2636 (1.5); 7.0994 (0.4); 4.0289 (16.0); 3.1503 (0.4); 2.9572 (1.4); 2.9112 (0.4); 2.8836 (1.2); −0.0002 (1.2)
1-20: $^1$H-NMR(499.9 MHz, CDCl3):
δ = 7.5717 (0.3); 7.5706 (0.3); 7.5562 (1.2); 7.5436 (3.3); 7.4786 (1.5); 7.4294 (0.6); 7.4239 (1.1); 7.4197 (0.8); 7.4157 (0.5); 7.4107 (0.7); 7.4065 (0.4); 7.2606 (2.2); 4.1428 (0.3); 4.0748 (1.1); 4.0582 (16.0); 3.9978 (0.3); 1.5556 (2.7); −0.0002 (2.2)
1-21: $^1$H-NMR(300.2 MHz, CDCl3):
δ = 7.8995 (5.5); 7.5887 (0.6); 7.2987 (3.4); 7.1384 (0.3); 7.1201 (1.3); 7.1163 (1.4); 7.1109 (2.2); 7.0931 (3.4); 7.0661 (0.3); 6.8539 (0.6); 6.8451 (0.7); 6.8314 (1.0); 6.8215 (0.8); 6.8166 (1.1); 6.8003 (0.4); 5.4035 (0.4); 5.3827 (1.0); 5.3618 (1.4); 5.3409 (1.0); 5.3201 (0.4); 2.1478 (0.4); 2.1369 (0.5); 2.1304 (0.4); 2.1196 (0.9); 2.1087 (0.4); 2.1021 (0.6); 2.0914 (0.5); 1.6022 (2.8); 1.4751 (1.8); 1.4579 (16.0); 1.4371 (15.5); 1.0643 (0.7); 1.0492 (1.6); 1.0423 (1.7); 1.0362 (0.9); 1.0329 (0.7); 1.0275 (1.2); 1.0206 (1.8); 1.0138 (1.6); 0.9993 (0.9); 0.8139 (0.8); 0.7990 (1.9); 0.7929 (1.8); 0.7818 (1.8); 0.7764 (1.9); 0.7645 (0.6); 0.7597 (0.9); 0.7476 (0.4); 0.7418 (0.4); 0.0381 (3.4)
1-22: $^1$H-NMR(300.2 MHz, CDCl3):
δ = 7.8527 (4.8); 7.8448 (0.7); 7.4713 (1.5); 7.3465 (0.9); 7.3329 (0.6); 7.3203 (1.7); 7.3065 (0.4); 7.2983 (1.8); 7.2940 (1.3); 7.0217 (1.2); 7.0137 (1.9); 7.0082 (1.4); 6.9977 (1.0); 6.9945 (1.0); 6.9866 (1.6); 6.9832 (1.3); 6.9467 (1.3); 6.9404 (1.7); 6.9331 (1.1); 6.9253 (0.5); 5.3803 (0.4); 5.3706 (0.3); 5.3595 (1.0); 5.3497 (0.4); 5.3387 (1.3); 5.3309 (0.7); 5.3178 (1.0); 5.2970 (0.4); 1.9690 (0.5); 1.9576 (0.5); 1.9410 (0.9); 1.9242 (0.5); 1.9131 (0.5); 1.6409 (2.4); 1.4629 (2.6); 1.4591 (4.6); 1.4361 (16.0); 1.4151 (14.5); 1.4033 (0.6); 1.3822 (0.4); 1.0347 (0.9); 1.0296 (0.6); 1.0194 (1.5); 1.0125 (1.7); 1.0096 (1.3); 0.9978 (1.0); 0.9910 (1.6); 0.9847 (1.4); 0.9697 (0.8); 0.7664 (0.9); 0.7513 (2.3); 0.7453 (2.0); 0.7348 (1.8); 0.7290 (2.4); 0.7126 (0.7); 0.0368 (1.6)
1-23: $^1$H-NMR(300.2 MHz, $d_6$-DMSO):
δ = 8.3083 (0.5); 8.3008 (16.0); 8.2931 (0.5); 8.0538 (0.7); 7.7123 (1.1); 7.6854 (2.4); 7.6603 (1.4); 7.6429 (1.1); 7.6185 (2.3); 7.5975 (1.6); 7.4964 (2.2); 7.4816 (2.6); 7.4699 (3.2); 7.4433 (1.2); 7.3016 (5.2); 7.1217 (2.6); 4.1088 (2.0); 2.5343 (1.6); 2.5284 (3.4); 2.5223 (4.6); 2.5162 (3.4); 2.5104 (1.6); 2.0075 (1.0); 1.1924 (0.6); 0.0159 (4.0)
1-24: $^1$H-NMR(300.2 MHz, CDCl3):
δ = 7.2986 (6.2); 7.1237 (0.4); 7.1045 (1.4); 7.0965 (2.2); 7.0911 (2.7); 7.0769 (1.8); 7.0728 (2.5); 7.0454 (0.5); 6.8423 (0.3); 6.8363 (0.7); 6.8284 (0.8); 6.8208 (0.5); 6.8141 (1.1); 6.8033 (0.8); 6.7976 (0.8); 6.7828 (0.5); 5.8161 (0.4); 5.4585 (0.4); 5.4377 (1.0); 5.4168 (1.4); 5.3959 (1.1); 5.3751 (0.4); 2.6527 (8.2); 2.4601 (15.6); 2.4508 (2.3); 2.1444 (0.5); 2.1331 (0.6); 2.1162 (1.0); 2.0996 (0.7); 2.0878 (0.6); 2.0711 (0.3); 1.6184 (0.6); 1.4808 (1.7); 1.4701 (0.6); 1.4552 (16.0); 1.4343 (15.6); 1.4130 (0.5); 1.3921 (0.4); 1.2935 (0.4); 1.0594 (0.8);

TABLE 4-continued 1.0441 (1.9); 1.0373 (2.0); 1.0312 (1.4); 1.0226 (1.5); 1.0155 (2.0); 1.0091 (1.8); 0.9945 (1.1); 0.8051 (1.0); 0.7901 (2.2); 0.7840 (2.1); 0.7732 (2.0); 0.7670 (2.3); 0.7574 (0.7); 0.7509 (0.8); 0.7410 (0.5); 0.1079 (1.1); 0.0374 (5.2)
1-25: $^1$H-NMR(499.9 MHz, CDCl3):
δ = 8.1443 (5.2); 7.5649 (0.5); 7.5494 (1.7); 7.5338 (2.0); 7.5254 (2.4); 7.5099 (0.9); 7.4936 (2.5); 7.4298 (1.5); 7.4146 (1.2); 7.2672 (0.5); 5.3302 (0.5); 5.3177 (1.2); 5.3052 (1.6); 5.2927 (1.2); 5.2802 (0.5); 1.6345 (0.4); 1.4002 (15.4); 1.3876 (16.0); −0.0002 (0.5)
1-26: $^1$H-NMR(499.9 MHz, $d_6$-DMSO):
δ = 8.0179 (6.6); 7.7953 (0.7); 7.7804 (1.4); 7.7656 (0.8); 7.7208 (0.7); 7.7069 (1.2); 7.6936 (0.8); 7.5189 (1.0); 7.5027 (1.6); 7.4865 (0.7); 2.6214 (16.0); 2.5058 (0.4); 1.3515 (0.9)
1-27: $^1$H-NMR(400.2 MHz, $d_6$-DMSO):
δ = 7.7089 (0.7); 7.6892 (2.0); 7.6694 (1.7); 7.6395 (2.0); 7.6200 (1.1); 7.5614 (2.6); 7.5153 (1.4); 7.4954 (1.1); 2.5592 (16.4); 2.5156 (2.0); 2.5112 (4.2); 2.5069 (5.7); 2.5024 (4.1); 2.4983 (2.0); 2.3154 (0.5); 2.3022 (16.0); 0.0008 (4.3)
1-28: $^1$H-NMR(300.2 MHz, CDCl3):
δ = 8.2043 (5.1); 7.5859 (1.0); 7.5595 (2.0); 7.5517 (1.6); 7.5471 (1.5); 7.5332 (2.0); 7.4915 (0.8); 7.4854 (1.1); 7.4788 (0.6); 7.4604 (0.6); 7.2986 (5.3); 5.6409 (2.3); 5.6325 (2.4); 5.4040 (0.4); 5.3831 (1.0); 5.3623 (1.4); 5.3414 (1.0); 5.3205 (0.4); 4.5051 (2.0); 4.4967 (2.0); 4.0863 (0.9); 4.0630 (3.0); 4.0397 (3.1); 4.0164 (1.0); 1.5943 (5.2); 1.5232 (3.4); 1.5000 (7.1); 1.4767 (3.4); 1.4479 (16.0); 1.4270 (15.8); 1.4090 (0.3); 1.3594 (0.3); 0.9838 (0.4); 0.9596 (0.8); 0.9353 (0.3); 0.1073 (0.3); 0.0366 (5.2)
1-29: $^1$H-NMR(300.2 MHz, CDCl3):
δ = 8.5419 (5.5); 7.6428 (1.0); 7.6180 (2.9); 7.6128 (1.5); 7.5942 (0.4); 7.5693 (1.4); 7.5279 (0.7); 7.5201 (1.2); 7.5129 (0.6); 7.5057 (0.4); 7.5029 (0.4); 7.4971 (0.6); 7.4897 (0.4); 7.2985 (4.3); 5.4235 (0.4); 5.4026 (1.0); 5.3817 (1.4); 5.3609 (1.0); 5.3400 (0.4); 2.8544 (16.0); 1.6014 (4.4); 1.4677 (15.6); 1.4468 (15.8); 1.4331 (0.4); 1.4255 (0.6); 1.4068 (0.3); 1.3583 (0.5); 1.3309 (0.4); 0.9821 (0.6); 0.9579 (1.2); 0.9336 (0.5); 0.1058 (0.5); 0.0345 (4.0)
1-30: $^1$H-NMR(499.9 MHz, $d_6$-DMSO):
δ = 7.9572 (6.3); 7.1617 (0.3); 7.1570 (0.4); 7.1478 (3.0); 7.1410 (1.9); 7.1387 (1.9); 7.1330 (2.8); 6.9088 (0.7); 6.9020 (0.7); 6.8961 (1.2); 6.8896 (1.1); 6.8827 (0.6); 6.8765 (0.5); 2.7404 (0.9); 2.6089 (16.0); 2.5168 (0.3); 2.5134 (0.6); 2.5098 (0.8); 2.5062 (0.6); 2.0661 (0.6); 2.0596 (0.7); 2.0494 (1.2); 2.0424 (0.5); 2.0391 (0.7); 2.0326 (0.6); 1.0221 (0.9); 1.0134 (2.3); 1.0091 (2.4); 1.0053 (1.3); 1.0007 (1.4); 0.9965 (2.2); 0.9922 (2.3); 0.9840 (0.9); 0.7812 (1.0); 0.7729 (2.5); 0.7706 (2.3); 0.7689 (2.6); 0.7627 (2.5); 0.7587 (2.5); 0.7498 (0.8)
1-31: $^1$H-NMR(400.1 MHz, CDCl3):
δ = 7.5310 (0.4); 7.5109 (1.2); 7.4911 (1.8); 7.4829 (1.9); 7.4692 (2.3); 7.4189 (1.2); 7.3997 (0.7); 7.2594 (7.0); 3.9970 (16.0); 2.6349 (13.6); 2.3177 (13.5); 1.5482 (6.2); −0.0002 (6.0)
1-32: $^1$H-NMR(300.2 MHz, CDCl3):
δ = 7.9240 (16.0); 7.6334 (0.9); 7.6078 (3.4); 7.5830 (11.0); 7.5582 (1.3); 7.5351 (5.3); 7.5109 (0.6); 7.4887 (2.3); 7.4814 (3.8); 7.4742 (2.2); 7.4641 (1.5); 7.4581 (2.4); 7.3042 (16.9); 5.4053 (1.2); 5.3845 (3.1); 5.3636 (4.1); 5.3428 (3.1); 5.3220 (1.3); 3.2115 (0.5); 3.0865 (0.6); 1.6662 (0.7); 1.6272 (3.0); 1.4829 (4.0); 1.4561 (47.2); 1.4352 (46.6); 1.4148 (1.2); 1.4098 (1.0); 1.3939 (1.0); 1.3890 (0.9); 1.2961 (1.1); 1.2429 (0.4); 1.2215 (0.3); 0.1139 (0.4); 0.0523 (0.6); 0.0415 (15.6); 0.0307 (0.6)
1-33: $^1$H-NMR(499.9 MHz, CDCl3):
δ = 7.5580 (0.4); 7.5425 (1.5); 7.5268 (3.1); 7.5088 (0.6); 7.4751 (2.1); 7.4226 (1.3); 7.4079 (1.0); 7.2602 (3.1); 4.0240 (16.0); 2.4323 (15.4); 1.5511 (4.0); −0.0002 (3.2)
1-34: $^1$H-NMR(300.2 MHz, CDCl3):
δ = 8.6515 (4.6); 8.6433 (4.4); 8.1431 (16.0); 8.0830 (0.7); 8.0735 (0.9); 8.0629 (5.2); 8.0538 (5.0); 8.0328 (1.6); 7.8430 (1.9); 7.2989 (30.5); 5.6864 (0.3); 5.6319 (0.3); 5.6114 (0.3); 4.2139 (0.5); 4.1900 (1.7); 4.1662 (1.7); 4.1424 (0.6); 2.2125 (0.5); 2.1079 (8.1); 1.3303 (2.2); 1.3065 (4.4); 1.2932 (0.5); 1.2827 (2.2); 0.1072 (4.5); 0.0480 (1.1); 0.0371 (32.3); 0.0263 (1.2)
1-35: $^1$H-NMR(300.2 MHz, CDCl3):
δ = 8.5958 (2.6); 8.5877 (2.5); 8.0485 (0.4); 8.0394 (0.5); 8.0248 (3.6); 8.0199 (11.4); 7.8867 (0.8); 7.6915 (1.2); 7.2987 (16.5); 5.3377 (0.8); 4.5648 (2.2); 4.5550 (1.1); 4.5410 (7.0); 4.5310 (1.5); 4.5172 (7.1); 4.5070 (1.0); 4.4935 (2.3); 1.5921 (15.2); 1.5188 (0.9); 1.5025 (7.9); 1.4950 (2.2); 1.4787 (16.0); 1.4714 (1.5); 1.4549 (7.6); 1.2911 (0.4); 0.1061 (0.7); 0.0470 (0.6); 0.0361 (16.8); 0.0252 (0.6)
1-36: $^1$H-NMR(300.2 MHz, $d_6$-DMSO):
δ = 8.7017 (1.3); 8.6952 (1.5); 8.6861 (6.0); 8.6850 (5.6); 8.6797 (6.3); 8.6674 (1.4); 8.6596 (1.4); 8.6268 (5.9); 8.6189 (6.2); 8.3059 (16.0); 8.2818 (0.9); 8.2749 (1.4); 8.2674 (0.8); 8.2297 (4.5); 8.2230 (6.4); 8.2154 (4.1); 8.1457 (0.4); 8.0647 (0.3); 8.0472 (3.3); 5.7778 (0.4); 4.0597 (0.5); 4.0360 (0.4); 3.1873 (0.4); 2.5611 (14.4); 2.5339 (3.5); 2.5279 (7.4); 2.5218 (10.0); 2.5158 (7.2); 2.5099 (3.3); 2.0085 (1.8); 1.9286 (1.0); 1.2173 (0.5); 1.1936 (1.0); 1.1698 (0.5); 0.0294 (0.5); 0.0186 (13.5); 0.0093 (0.4); 0.0076 (0.5)
1-37: $^1$H-NMR(300.2 MHz, $d_6$-DMSO):
δ = 8.2172 (16.0); 7.8172 (1.1); 7.5335 (0.4); 7.5209 (2.7); 7.5083 (1.1); 7.4950 (5.9); 7.4813 (1.3); 7.4687 (4.0); 7.4323 (0.4); 7.2414 (0.8); 7.2065 (8.3); 7.1989 (5.9); 7.1802 (5.2); 7.1726 (5.8); 7.1660 (6.8); 7.1604 (6.4); 5.7866 (0.5); 5.5279 (0.3); 5.4410 (0.6); 5.2844 (0.6); 4.0613 (0.8); 4.0377 (0.8); 4.0142 (0.4); 3.6447 (0.3); 3.3505 (11.6); 3.2182 (0.8); 3.1169 (0.4); 2.7483 (0.5); 2.5853 (0.4); 2.5346 (21.8); 2.5287 (46.6); 2.5227 (64.6); 2.5167 (46.8); 2.5108 (21.7); 2.2933 (0.4); 2.0100 (3.1); 1.9297 (5.9); 1.7140 (0.4); 1.5738 (1.3); 1.5537 (4.9); 1.5468 (4.9); 1.5277 (1.9); 1.5086 (1.4); 1.4880 (4.7); 1.4816 (5.0); 1.4631 (2.0); 1.3997 (0.4); 1.2828 (0.4); 1.2537 (2.2); 1.2318 (5.2); 1.2236 (6.3); 1.2011 (6.3); 1.1951 (6.3); 1.1713 (2.0); 0.2153 (0.4); 0.0318 (2.5); 0.0208 (76.8); 0.0098 (2.6)
1-38: $^1$H-NMR(300.2 MHz, CDCl3):
δ = 7.8774 (4.8); 7.8763 (4.8); 7.5175 (0.7); 7.4681 (0.7); 7.4420 (1.6); 7.4164 (0.9); 7.2999 (5.3); 7.2987 (5.2); 7.1733 (4.2); 7.1458 (2.4); 7.1188 (1.3); 5.3926 (0.4); 5.3715 (1.0); 5.3635 (0.4); 5.3507 (1.3); 5.3300 (1.2); 5.3091 (0.4); 1.5965 (4.9); 1.5767 (1.5); 1.5715 (1.5); 1.5498 (0.6); 1.5350 (0.6); 1.5130 (1.6); 1.5078 (1.6); 1.4867 (0.7); 1.4693 (2.5); 1.4462 (16.0); 1.4250 (14.6); 1.4046 (0.4); 1.1657 (0.6); 1.1437 (1.7); 1.1387 (2.1); 1.1150 (2.0); 1.1095 (1.8); 1.0871 (0.5); 0.0391 (7.1); 0.0378 (6.9)
1-39: $^1$H-NMR(300.2 MHz, $d_6$-DMSO):
δ = 8.2768 (16.0); 7.4354 (1.2); 7.4196 (2.2); 7.4107 (1.5); 7.4026 (2.9); 7.3861 (1.8); 7.3781 (1.9); 7.3314 (1.5); 7.3053 (8.5); 7.2868 (6.3); 7.2596 (0.6); 7.2507 (0.4); 3.1586 (0.9); 3.1303 (1.2); 3.1189 (1.7); 3.0879 (1.7); 3.0500 (1.0); 2.5338 (2.8); 2.5279 (5.7); 2.5219 (7.5); 2.5158 (5.4); 2.5100 (2.6); 2.1738 (0.4); 2.1459

TABLE 4-continued (1.0); 2.1356 (0.7); 2.1246 (1.3); 2.1079 (2.6); 2.0856 (2.4); 2.0732 (2.9); 2.0612 (1.6); 2.0469 (2.2); 2.0323 (1.4); 2.0196 (0.5); 1.9291 (12.3); 0.0183 (5.8)

1-40: $^1$H-NMR(300.2 MHz, CDCl3):

δ = 7.9179 (6.4); 7.6094 (0.4); 7.2986 (12.0); 7.2758 (0.9); 7.2703 (0.8); 7.2528 (0.8); 7.2468 (0.8); 7.2235 (0.9); 7.1975 (1.4); 7.1945 (1.4); 7.1706 (0.7); 7.1679 (0.8); 7.1405 (0.6); 7.1375 (0.6); 7.1348 (0.6); 7.1165 (0.8); 7.1141 (0.7); 5.4071 (0.4); 5.3862 (1.1); 5.3653 (1.4); 5.3445 (1.1); 5.3236 (0.4); 2.9082 (0.3); 2.8949 (0.6); 2.8677 (0.6); 2.8544 (0.3); 2.8268 (0.3); 1.9830 (0.3); 1.9734 (0.4); 1.9603 (0.6); 1.9564 (0.5); 1.9434 (0.6); 1.9339 (0.7); 1.9207 (0.4); 1.9168 (0.7); 1.8944 (0.4); 1.8772 (0.3); 1.7473 (0.3); 1.7342 (0.4); 1.7204 (0.6); 1.7069 (0.8); 1.6927 (0.6); 1.6785 (0.7); 1.6652 (0.6); 1.6511 (0.4); 1.5844 (7.9); 1.4782 (1.3); 1.4618 (16.0); 1.4409 (15.7); 0.0481 (0.4); 0.0433 (0.4); 0.0374 (14.2); 0.0297 (0.4); 0.0280 (0.4); 0.0265 (0.5)

1-41: $^1$H-NMR(300.2 MHz, $d_6$-DMSO):

δ = 8.2790 (2.3); 7.4340 (0.6); 7.4198 (2.0); 7.4024 (3.7); 7.3950 (2.2); 7.3866 (4.6); 7.3720 (2.9); 7.3623 (3.1); 7.3269 (1.8); 7.3015 (16.0); 7.2845 (9.6); 7.2771 (8.0); 7.2585 (1.1); 3.6128 (0.3); 3.5872 (0.4); 3.3811 (0.8); 3.3129 (0.7); 3.2895 (0.7); 3.1978 (0.4); 3.1540 (1.7); 3.1237 (2.2); 3.1138 (3.0); 3.0836 (3.1); 3.0453 (1.9); 2.9110 (2.3); 2.7518 (2.1); 2.7092 (1.2); 2.5340 (13.1); 2.5280 (28.4); 2.5219 (39.3); 2.5158 (28.3); 2.5100 (13.3); 2.4263 (55.4); 2.4070 (3.8); 2.3600 (0.4); 2.2074 (0.4); 2.1720 (0.7); 2.1441 (1.7); 2.1347 (1.0); 2.1229 (2.1); 2.1062 (4.3); 2.0840 (4.2); 2.0712 (5.1); 2.0587 (2.6); 2.0447 (3.8); 2.0300 (2.4); 2.0159 (0.8); 2.0093 (1.0); 2.0035 (0.5); 1.9289 (1.1); 0.0307 (1.7); 0.0290 (0.9); 0.0275 (1.2); 0.0199 (53.0); 0.0122 (1.8); 0.0107 (1.8); 0.0090 (1.9)

1-42: $^1$H-NMR(300.2 MHz, CDCl3):

δ = 7.9172 (0.6); 7.2981 (5.1); 7.2842 (0.6); 7.2625 (1.2); 7.2397 (0.9); 7.2341 (1.0); 7.2004 (1.0); 7.1740 (1.8); 7.1470 (1.0); 7.1173 (1.0); 7.0966 (1.1); 7.0713 (0.4); 5.4608 (0.4); 5.4399 (1.1); 5.4190 (1.4); 5.3981 (1.1); 5.3773 (0.4); 2.9312 (0.4); 2.9033 (0.5); 2.8906 (0.8); 2.8629 (0.9); 2.8501 (0.5); 2.8224 (0.5); 2.4670 (16.0); 2.4551 (1.6); 2.2082 (8.2); 1.9938 (0.3); 1.9766 (0.4); 1.9673 (0.4); 1.9540 (0.7); 1.9371 (0.7); 1.9278 (0.7); 1.9110 (0.8); 1.8974 (0.4); 1.8882 (0.4); 1.8710 (0.4); 1.7393 (0.4); 1.7261 (0.4); 1.7122 (0.6); 1.6988 (0.9); 1.6847 (0.7); 1.6707 (0.9); 1.6571 (0.7); 1.6434 (0.4); 1.6300 (0.3); 1.6007 (4.9); 1.4817 (1.2); 1.4683 (1.5); 1.4570 (14.6); 1.4361 (14.0); 1.2956 (0.5); 0.9183 (0.4); 0.0361 (3.6)

1-43: $^1$H-NMR(300.2 MHz, $d_6$-DMSO):

δ = 8.2836 (1.4); 8.2772 (16.0); 8.0256 (0.8); 7.5855 (0.4); 7.5487 (1.7); 7.5442 (1.5); 7.5229 (3.8); 7.5103 (3.4); 7.5049 (3.4); 7.4983 (2.9); 7.4936 (2.4); 7.4892 (2.2); 7.4835 (2.2); 7.3768 (2.8); 7.3503 (3.9); 7.3238 (1.6); 4.0603 (0.6); 4.0366 (0.6); 3.3605 (1.2); 3.2371 (0.6); 2.5342 (7.1); 2.5283 (15.8); 2.5223 (22.2); 2.5162 (16.4); 2.5104 (7.8); 2.0093 (2.6); 1.9292 (7.7); 1.5028 (1.0); 1.4759 (3.9); 1.4545 (1.6); 1.4402 (1.2); 1.4132 (4.0); 1.3921 (1.8); 1.2548 (0.4); 1.2247 (1.6); 1.2181 (1.1); 1.2027 (4.2); 1.1948 (5.8); 1.1732 (5.1); 1.1443 (1.2); 0.0302 (0.7); 0.0194 (25.5); 0.0085 (1.1)

1-44: $^1$H-NMR(300.2 MHz, CDCl3):

δ = 7.9261 (0.4); 7.9166 (5.3); 7.6145 (0.4); 7.4855 (0.3); 7.4803 (0.5); 7.4756 (0.4); 7.4594 (0.9); 7.4543 (1.0); 7.4502 (0.6); 7.4386 (0.5); 7.4333 (0.6); 7.4286 (0.5); 7.3637 (0.4); 7.3600 (0.4); 7.3388 (1.0); 7.3366 (0.9); 7.3154 (0.8); 7.3128 (0.7); 7.3095 (0.7); 7.2990 (4.7); 7.2686 (1.1); 7.2422 (1.3); 7.2156 (0.5); 7.0516 (1.2); 7.0471 (0.8); 7.0317 (0.7); 7.0277 (0.4); 5.4051 (0.4); 5.3843 (1.0); 5.3634 (1.4); 5.3425 (1.0); 5.3217 (0.4); 5.2848 (0.6); 5.2686 (0.6); 1.6046 (3.3); 1.5156 (0.5); 1.4927 (1.6); 1.4894 (1.6); 1.4769 (1.7); 1.4597 (16.0); 1.4388 (15.7); 1.4037 (0.7); 1.3039 (1.0); 1.2341 (0.6); 1.2131 (1.4); 1.2057 (1.6); 1.1833 (1.7); 1.1758 (1.3); 1.1636 (0.5); 1.1557 (0.8); 1.1340 (0.5); 1.1287 (0.4); 0.9410 (0.3); 0.9194 (1.1); 0.8961 (0.4); 0.0375 (6.0)

1-45: $^1$H-NMR(300.2 MHz, CDCl3):

δ = 7.4720 (0.4); 7.4670 (0.6); 7.4621 (0.4); 7.4457 (0.9); 7.4409 (1.0); 7.4252 (0.5); 7.4199 (0.6); 7.4152 (0.5); 7.3599 (0.3); 7.3545 (0.4); 7.3508 (0.4); 7.3296 (0.9); 7.3275 (0.9); 7.2991 (13.2); 7.2490 (0.9); 7.2224 (1.2); 7.1957 (0.5); 7.0557 (1.4); 7.0506 (1.0); 7.0353 (0.7); 7.0309 (0.4); 5.4608 (0.4); 5.4399 (1.0); 5.4191 (1.3); 5.3982 (1.0); 5.3773 (0.4); 5.2403 (0.8); 5.2239 (0.8); 2.4655 (15.5); 2.4545 (1.8); 1.5914 (11.8); 1.5121 (0.4); 1.4898 (1.6); 1.4817 (2.4); 1.4570 (16.0); 1.4361 (15.8); 1.4231 (1.7); 1.4001 (0.6); 1.3042 (1.3); 1.2301 (0.6); 1.2093 (1.4); 1.2019 (1.6); 1.1796 (1.6); 1.1717 (1.4); 1.1587 (0.6); 1.1516 (0.5); 1.1363 (0.6); 0.9417 (0.5); 0.9200 (1.4); 0.8966 (0.6); 0.0489 (0.5); 0.0380 (16.4); 0.0270 (0.6)

1-46: $^1$H-NMR(300.2 MHz, $d_6$-DMSO):

δ = 14.2022 (0.6); 8.7327 (0.4); 8.0182 (16.0); 7.6607 (1.6); 7.6333 (3.2); 7.6098 (3.3); 7.5871 (3.0); 7.5663 (2.2); 7.4954 (0.4); 7.4753 (3.5); 7.4691 (3.9); 7.4488 (4.2); 7.4232 (1.6); 7.2887 (6.9); 7.1086 (3.4); 4.1060 (0.6); 4.0607 (0.8); 4.0369 (0.7); 3.5879 (2.3); 3.3496 (11.3); 2.7485 (0.3); 2.6346 (42.2); 2.5682 (0.4); 2.5340 (17.1); 2.5280 (36.5); 2.5220 (50.3); 2.5159 (36.1); 2.5100 (16.8); 2.4556 (0.5); 2.0093 (3.1); 1.2181 (0.9); 1.1944 (1.8); 1.1706 (0.9); 0.0308 (1.3); 0.0199 (43.9); 0.0089 (1.6); −0.0465 (0.4)

TABLE 5
Compounds according to formula (2)
(2)
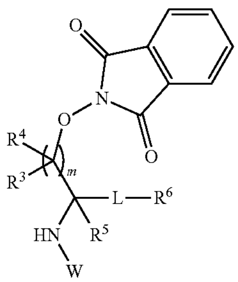
table 5, "#" denotes the point of attachment to the L—$R^6$ group.
| Ex No | 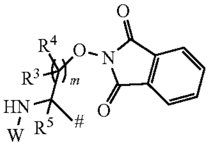 | L—$R^6$ | LogP | Salt |
|---|---|---|---|---|
| 2-01 | 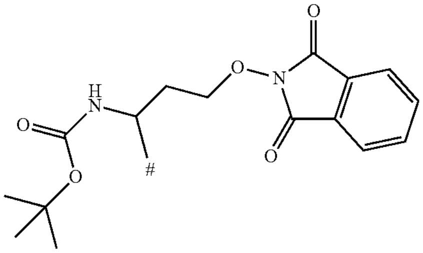 [SMILES: CC(CCON1C(=O)c2ccccc2C1=O)NC(=O)OC(C)(C)C] | 3-methylphenyl | 3.71[a] | |
| 2-02 | 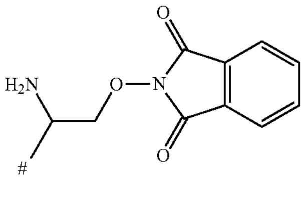 [SMILES: CC(N)CON1C(=O)c2ccccc2C1=O] | (2,4-dimethylphenyl)methyl | 1.60[a] | TFA |
| 2-03 | 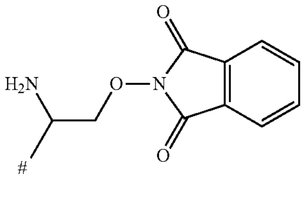 [SMILES: CC(N)CON1C(=O)c2ccccc2C1=O] | (2-chloro-4-cyclopropylphenyl)methyl | 1.60[a] | TFA |
| 2-04 | 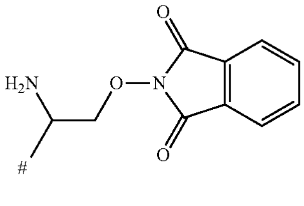 [SMILES: CC(N)CON1C(=O)c2ccccc2C1=O] | (4-cyclopropyl-2-methylphenyl)methyl | 1.56[a] | TFA |
| 2-05 | 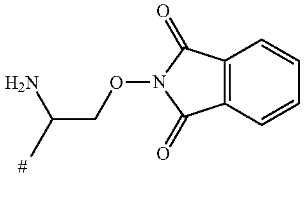 | (2,4-dichlorophenyl)methyl | 1.54[a] | TFA |

TABLE 5-continued
Compounds according to formula (2)
(2)
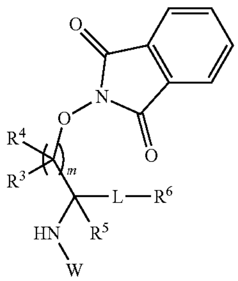
table 5, "#" denotes the point of attachment to the L—$R^6$ group.
| Ex No | 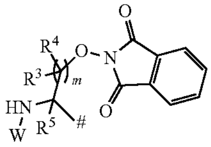 | L—$R^6$ | LogP | Salt |
|---|---|---|---|---|
| 2-06 | 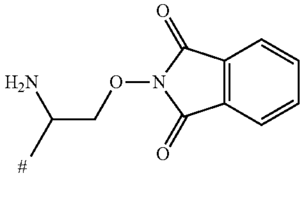 [SMILES: CC(N)CON1C(=O)c2ccccc2C1=O] | (2-chloro-4-isopropylphenyl)methyl | 1.59[a] | TFA |
| 2-07 | 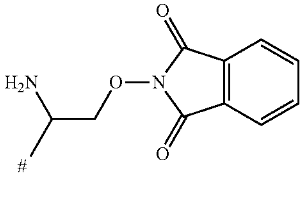 [SMILES: CC(N)CON1C(=O)c2ccccc2C1=O] | (4-isopropyl-2-methylphenyl)methyl | 1.55[a] | TFA |
| 2-08 | 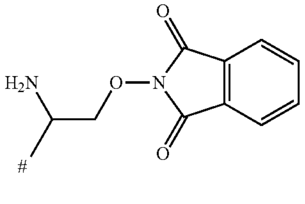 [SMILES: CC(N)CON1C(=O)c2ccccc2C1=O] | (3,4-dimethylphenyl)methyl | 1.32[a] | TFA |
| 2-09 | 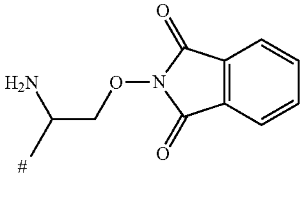 [SMILES: CC(N)CON1C(=O)c2ccccc2C1=O] | (4-bromo-2-chlorophenyl)methyl | 1.54[a] | TFA |
| 2-10 | 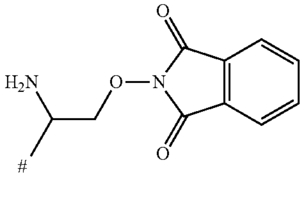 | (4-bromo-2-methylphenyl)methyl | 1.52[a] | TFA |

TABLE 5-continued
Compounds according to formula (2)
(2)
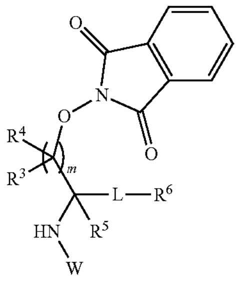
table 5, "#" denotes the point of attachment to the L—$R^6$ group.
| Ex No | 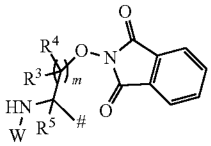 | L—$R^6$ | LogP | Salt |
|---|---|---|---|---|
| 2-11 | 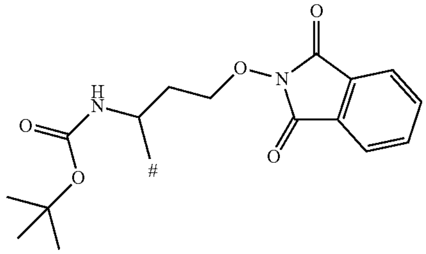 [SMILES: CC(CCON1C(=O)c2ccccc2C1=O)NC(=O)OC(C)(C)C] | (2,4-dichlorophenyl)methyl | 4.41[a] | |
| 2-12 | 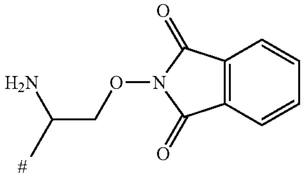 [SMILES: CC(N)CON1C(=O)c2ccccc2C1=O] | (2,4-dimethylphenoxy)methyl | 1.70[a] | TFA |
| 2-13 | 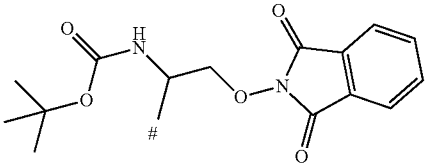 [SMILES: CC(CON1C(=O)c2ccccc2C1=O)NC(=O)OC(C)(C)C] | (2,4-dimethylphenoxy)methyl | 4.51[a] | |
| 2-14 | 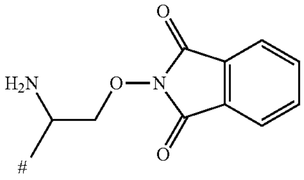 | (4-chlorophenoxy)methyl | 1.53[a] | TFA |
| 2-15 | 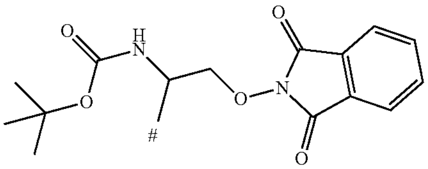 | (4-chlorophenoxy)methyl | 4.20[a] | |

TABLE 5-continued
Compounds according to formula (2)
(2)
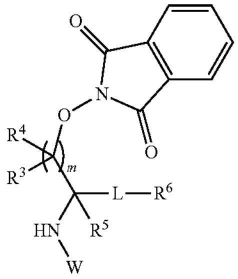
table 5, "#" denotes the point of attachment to the L—$R^6$ group.
| Ex No | 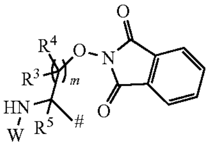 | L—$R^6$ | LogP | Salt |
|---|---|---|---|---|
| 2-16 | 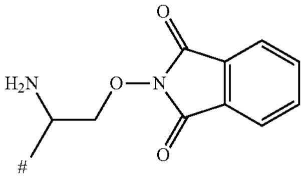 [SMILES: CC(N)CON1C(=O)c2ccccc2C1=O] | [(2,4-dimethylphenyl)thio]methyl | 1.79[a] | TFA |
| 2-17 | 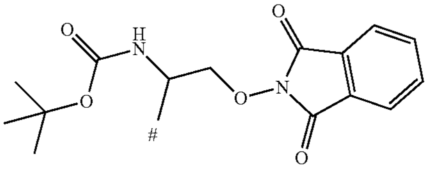 [SMILES: CC(CON1C(=O)c2ccccc2C1=O)NC(=O)OC(C)(C)C] | [(2,4-dimethylphenyl)thio]methyl | 4.74[a] | |
| 2-18 | 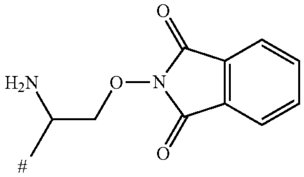 [SMILES: CC(N)CON1C(=O)c2ccccc2C1=O] | (5-chloropyridin-2-yl)methyl | 1.23[a] | TFA |
| 2-19 | 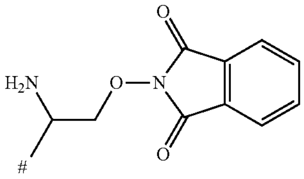 [SMILES: CC(N)CON1C(=O)c2ccccc2C1=O] | (4,5-dimethyl-3-thienyl)methyl | 1.64[a] | TFA |
| 2-20 | 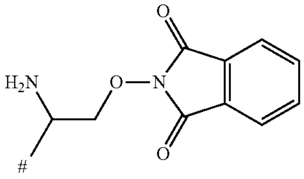 | (2-chloro-4-methylphenyl)methyl | 1.61[a] | TFA |

TABLE 5-continued
Compounds according to formula (2)
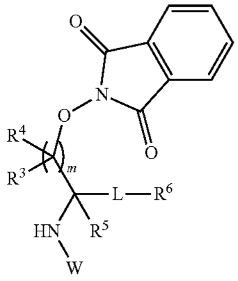
(2)
table 5, "#" denotes the point of attachment to the L—$R^6$ group.
| Ex No | 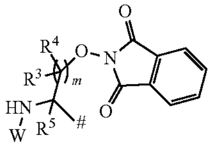 | L—$R^6$ | LogP | Salt |
|---|---|---|---|---|
| 2-21 | 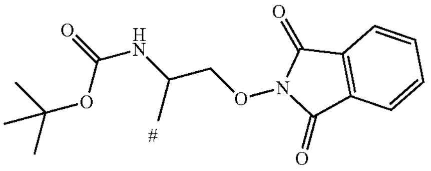 [SMILES: CC(CON1C(=O)c2ccccc2C1=O)NC(=O)OC(C)(C)C] | (2-chloro-4-methylphenyl)methyl | 4.51[a] | |
TABLE 6
2-01: $^1$H-NMR(400.2 MHz, $d_6$-DMSO):
δ = 7.8588 (11.8); 7.8355 (0.4); 7.4419 (0.8); 7.4196 (0.8); 7.2178 (0.7); 7.2089 (0.4); 7.1988 (1.9); 7.1804 (1.4); 7.1339 (2.1); 7.1076 (0.8); 7.0372 (1.3); 7.0195 (1.1); 4.7012 (0.5); 4.6852 (0.6); 4.6034 (0.4); 4.1784 (0.5); 4.1695 (0.5); 4.1521 (0.7); 4.1363 (0.3); 4.0846 (0.4); 4.0684 (0.7); 4.0529 (0.5); 4.0431 (0.5); 3.3205 (109.8); 2.6736 (0.3); 2.6694 (0.4); 2.5089 (28.2); 2.5046 (56.6); 2.5001 (75.0); 2.4957 (53.0); 2.4913 (24.6); 2.3317 (0.3); 2.3271 (0.4); 2.3220 (0.3); 2.2878 (11.1); 2.0501 (1.2); 2.0312 (0.4); 2.0151 (0.8); 1.9955 (1.1); 1.9788 (0.9); 1.9636 (0.4); 1.3501 (16.0); 1.2356 (0.6); 1.2103 (0.7); −0.0014 (6.8)
2-02: $^1$H-NMR(499.9 MHz, $d_6$-DMSO):
δ = 8.3331 (4.3); 7.8923 (16.0); 7.1867 (2.1); 7.1714 (2.5); 6.9966 (3.3); 6.9726 (2.0); 6.9574 (1.8); 4.2888 (0.8); 4.2756 (1.0); 4.2668 (1.5); 4.2540 (1.5); 4.2169 (1.6); 4.2106 (1.8); 4.1952 (1.1); 4.1888 (1.0); 3.7123 (1.1); 3.7064 (1.1); 3.7009 (1.1); 3.3434 (3.2); 2.9949 (0.4); 2.9828 (0.6); 2.9669 (1.6); 2.9529 (2.4); 2.9328 (1.6); 2.9049 (0.6); 2.5088 (3.2); 2.2745 (12.3); 2.2293 (12.2)
2-03: $^1$H-NMR(400.2 MHz, $d_6$-DMSO):
δ = 8.3411 (2.0); 7.8880 (16.0); 7.3658 (2.0); 7.3459 (2.4); 7.1652 (2.8); 7.1612 (2.9); 7.0376 (1.5); 7.0335 (1.5); 7.0178 (1.4); 7.0136 (1.3); 4.2982 (0.4); 4.2822 (0.5); 4.2703 (1.4); 4.2534 (2.0); 4.2407 (1.6); 4.2224 (0.6); 4.2129 (0.4); 3.7788 (0.7); 3.3905 (0.5); 3.3731 (0.4); 3.0783 (2.6); 3.0598 (2.2); 2.5045 (18.0); 2.5002 (23.4); 2.4960 (17.8); 1.9344 (0.6); 1.9259 (0.7); 1.9135 (1.1); 1.9011 (0.7); 1.8927 (0.6); 1.8801 (0.3); 1.1071 (0.3); 1.0895 (0.7); 1.0720 (0.3); 0.9822 (0.6); 0.9711 (2.0); 0.9659 (2.2); 0.9553 (1.3); 0.9503 (2.1); 0.9450 (2.1); 0.9349 (0.9); 0.6997 (0.8); 0.6889 (2.4); 0.6843 (2.4); 0.6768 (2.3); 0.6721 (2.4); 0.6607 (0.8); −0.0017 (2.7)
2-04: $^1$H-NMR(400.2 MHz, $d_6$-DMSO):
δ = 8.2662 (1.8); 7.9096 (0.5); 7.8877 (16.0); 7.8654 (0.5); 7.1680 (2.1); 7.1485 (2.3); 6.8848 (2.7); 6.8630 (1.6); 6.8434 (1.4); 4.2706 (0.6); 4.2541 (0.7); 4.2431 (1.4); 4.2270 (1.5); 4.2123 (1.5); 4.2033 (1.6); 4.1851 (0.7); 4.1760 (0.6); 3.6896 (0.7); 3.4075 (0.4); 3.3904 (0.8); 3.3729 (1.0); 3.3554 (0.8); 2.9473 (0.3); 2.9281 (2.4); 2.9128 (1.6); 2.9061 (1.6); 2.5044 (32.8); 2.5000 (43.1); 2.4956 (31.6); 2.3269 (0.3); 2.3139 (0.8); 2.2604 (11.3); 1.8500 (0.6); 1.8416 (0.7); 1.8292 (1.2); 1.8167 (0.8); 1.8083 (0.7); 1.7952 (0.4); 1.1069 (0.4); 1.0894 (0.7); 1.0720 (0.3); 0.9254 (0.8); 0.9148 (2.2); 0.9094 (2.4); 0.9045 (1.2); 0.8994 (1.3); 0.8938 (2.3); 0.8885 (2.3); 0.8786 (0.9); 0.6309 (0.9); 0.6208 (2.4); 0.6159 (2.5); 0.6083 (2.5); 0.6034 (2.4); 0.5926 (0.9); 0.0064 (0.4); −0.0015 (7.0); −0.0099 (0.4)
2-05: $^1$H-NMR(400.2 MHz, $d_6$-DMSO):
δ = 8.3427 (3.2); 7.9146 (0.5); 7.8924 (16.0); 7.6434 (3.4); 7.6385 (3.8); 7.5409 (2.2); 7.5202 (3.4); 7.4546 (2.3); 7.4496 (2.3); 7.4340 (1.6); 7.4290 (1.6); 4.2841 (3.5); 4.2717 (4.2); 3.8317 (0.8); 3.8200 (1.2); 3.8061 (0.9); 3.3429 (0.6); 3.1333 (2.4); 3.1288 (2.4); 3.1145 (2.6); 2.5004 (16.3); −0.0018 (4.8)
2-06: $^1$H-NMR(400.2 MHz, $d_6$-DMSO):
δ = 8.3621 (1.7); 7.9167 (0.5); 7.9031 (1.8); 7.8934 (13.0); 7.8713 (0.4); 7.8692 (0.4); 7.4399 (2.2); 7.4201 (2.7); 7.3358 (2.9); 7.3317 (3.1); 7.2431 (0.4); 7.2352 (1.7); 7.2310 (1.6); 7.2154 (1.4); 7.2112 (1.3); 4.2830 (1.3); 4.2687 (2.6); 4.2592 (1.8); 4.2414 (0.6); 4.2315 (0.4); 3.8155 (0.6); 3.8062 (0.7); 3.3927 (0.8); 3.3752 (0.8); 3.1039 (2.4); 3.0857 (2.2); 2.9229 (0.4); 2.9057 (0.9); 2.8884 (1.3); 2.8712 (1.0); 2.8540 (0.4); 2.5255 (0.5); 2.5120 (9.0); 2.5076 (18.2); 2.5031 (24.5); 2.4986 (17.4); 2.4942 (8.1); 1.1938 (16.0); 1.1766 (15.6); 1.1551 (0.3); 1.1094 (0.7); 1.0919 (1.4); 1.0744 (0.7); 0.8789 (0.4); 0.0007 (1.9)

TABLE 6-continued 2-07: $^{1}$H-NMR(400.2 MHz, $d_6$-DMSO):
δ = 8.3080 (1.3); 7.9160 (0.5); 7.9132 (0.4); 7.9026 (1.6); 7.8938 (11.0); 7.8920 (11.1); 7.8832 (1.6); 7.8699 (0.4); 7.2333 (1.9); 7.2139 (2.3); 7.0596 (2.7); 7.0435 (1.6); 7.0241 (1.3); 4.2877 (0.3); 4.2611 (0.9); 4.2450 (1.0); 4.2321 (1.4); 4.2231 (1.5); 4.2050 (0.6); 4.1959 (0.5); 3.7189 (0.6); 3.3924 (0.6); 3.3749 (0.6); 3.3575 (0.4); 2.9529 (1.8); 2.9342 (1.6); 2.8492 (0.4); 2.8322 (0.9); 2.8149 (1.2); 2.7977 (0.9); 2.7805 (0.4); 2.5112 (11.1); 2.5069 (22.4); 2.5024 (29.8); 2.4979 (21.4); 2.4935 (10.1); 2.3158 (0.4); 2.2934 (11.6); 1.1805 (16.0); 1.1632 (15.6); 1.1091 (0.5); 1.0916 (0.9); 1.0741 (0.4); 0.0006 (2.8)
2-08: $^{1}$H-NMR(400.2 MHz, $d_6$-DMSO):
δ = 8.2269 (1.6); 7.9157 (0.5); 7.9020 (1.9); 7.8923 (16.0); 7.8702 (0.5); 7.1019 (2.0); 7.0847 (5.1); 7.0377 (2.3); 7.0187 (1.3); 5.7587 (0.4); 4.2409 (0.5); 4.2244 (3.6); 4.2137 (2.9); 3.7359 (0.8); 3.7220 (1.0); 3.7096 (0.7); 3.3344 (0.6); 2.9028 (2.6); 2.8853 (2.6); 2.5113 (13.6); 2.5069 (28.1); 2.5024 (38.0); 2.4979 (27.2); 2.4935 (12.8); 2.1946 (15.6); 2.1763 (14.8); 1.1067 (0.9); 0.0007 (3.4)
2-09: $^{1}$H-NMR(400.2 MHz, $d_6$-DMSO):
δ = 8.3668 (3.1); 7.9176 (0.5); 7.8953 (16.0); 7.8726 (0.4); 7.7539 (4.1); 7.7489 (4.3); 7.5803 (1.7); 7.5752 (1.6); 7.5597 (2.5); 7.5547 (2.4); 7.4744 (3.7); 7.4537 (2.5); 4.2906 (2.7); 4.2881 (2.6); 4.2765 (3.8); 4.2592 (0.4); 3.8354 (0.7); 3.8228 (1.0); 3.8088 (0.6); 3.1559 (0.3); 3.1269 (2.0); 3.1205 (2.0); 3.1075 (2.0); 3.1031 (2.0); 2.5126 (6.5); 2.5083 (13.2); 2.5038 (17.8); 2.4994 (12.7); 2.4950 (6.0); 0.0007 (1.2)
2-10: $^{1}$H-NMR(400.2 MHz, $d_6$-DMSO):
δ = 8.3381 (3.4); 7.9140 (0.6); 7.8920 (16.0); 7.8688 (0.6); 7.4251 (2.9); 7.4209 (3.3); 7.3677 (1.4); 7.3630 (1.2); 7.3474 (2.1); 7.3425 (2.0); 7.2808 (3.5); 7.2603 (2.2); 7.1732 (0.4); 4.2842 (0.5); 4.2692 (0.6); 4.2565 (2.0); 4.2429 (3.4); 4.2345 (2.4); 4.2169 (0.7); 4.2067 (0.4); 3.7575 (0.8); 3.7467 (1.0); 3.7332 (0.8); 2.9774 (2.5); 2.9581 (2.9); 2.5060 (6.1); 2.5017 (7.9); 2.4975 (5.8); 2.3132 (15.1); −0.0020 (3.4)
2-11: $^{1}$H-NMR(300.1 MHz, $d_6$-DMSO):
δ = 7.8598 (15.3); 7.5312 (1.4); 7.5249 (1.4); 7.3677 (0.5); 7.3616 (0.4); 7.3400 (1.3); 7.3336 (1.2); 7.3171 (1.6); 7.2894 (0.6); 6.8031 (0.6); 6.7729 (0.6); 4.1931 (0.7); 4.1715 (1.2); 4.1471 (0.6); 3.9005 (0.4); 3.8715 (0.3); 3.3414 (4.6); 2.9636 (0.4); 2.9468 (0.5); 2.9186 (0.6); 2.9025 (0.6); 2.7338 (0.6); 2.7276 (0.6); 2.7037 (0.4); 2.6910 (0.3); 2.5134 (25.8); 2.5074 (51.6); 2.5014 (69.3); 2.4954 (47.3); 2.4895 (21.4); 2.2712 (0.4); 1.9037 (0.5); 1.8769 (0.5); 1.8284 (0.3); 1.2494 (16.0); 1.1197 (1.9); 0.0105 (0.4); −0.0004 (11.5); −0.0115 (0.4)
2-12: $^{1}$H-NMR(300.2 MHz, CDCl3):
δ = 7.8522 (0.6); 7.8435 (2.0); 7.8314 (2.3); 7.8278 (2.2); 7.8228 (2.8); 7.8143 (5.7); 7.8030 (3.0); 7.7915 (5.7); 7.7830 (2.6); 7.7738 (2.3); 7.7623 (1.9); 7.3225 (1.3); 7.3170 (0.6); 7.2986 (12.1); 7.2821 (1.1); 7.2740 (3.7); 7.2266 (5.1); 7.2025 (3.0); 7.1728 (0.5); 6.9253 (4.9); 6.9026 (1.8); 6.7442 (2.2); 6.7146 (1.7); 4.7935 (0.5); 4.7654 (0.7); 4.7532 (1.2); 4.7260 (1.2); 4.6923 (1.3); 4.6814 (1.4); 4.6527 (0.7); 4.6413 (0.6); 4.3871 (0.5); 4.3697 (0.6); 4.3529 (1.4); 4.3350 (1.6); 4.3274 (1.6); 4.3096 (1.4); 4.2926 (0.5); 4.2752 (0.5); 4.0616 (0.9); 4.0472 (0.8); 2.3964 (16.0); 2.2962 (1.1); 2.2448 (14.4); 2.2252 (0.7); 2.1836 (14.4); 1.4798 (0.9); 1.4742 (0.8); 1.4532 (0.6); 0.0522 (0.4); 0.0413 (11.8); 0.0307 (0.5)
2-13: $^{1}$H-NMR(300.2 MHz, CDCl3):
δ = 7.8812 (1.0); 7.8707 (1.1); 7.8640 (1.0); 7.8617 (0.9); 7.8526 (1.8); 7.8140 (0.3); 7.8010 (1.8); 7.7915 (1.0); 7.7893 (0.9); 7.7826 (1.1); 7.7721 (1.0); 7.2984 (4.6); 6.9715 (1.0); 6.8385 (1.0); 6.8091 (0.7); 5.3378 (4.5); 4.5030 (0.4); 4.4884 (0.4); 4.4521 (0.6); 4.4315 (0.9); 4.4206 (0.5); 4.3968 (0.6); 4.3910 (0.5); 4.1961 (0.5); 4.1788 (0.4); 4.1652 (0.4); 4.1480 (0.3); 2.3504 (0.4); 2.2861 (4.8); 2.2345 (5.0); 1.6061 (2.8); 1.4776 (16.0); 1.4520 (0.4); 0.0378 (6.0)
2-14: $^{1}$H-NMR(300.2 MHz, CDCl3):
δ = 8.5726 (0.6); 7.8154 (1.6); 7.8082 (1.3); 7.7999 (3.1); 7.7917 (5.8); 7.7858 (16.0); 7.7776 (15.6); 7.7633 (3.1); 7.7551 (1.2); 7.7479 (1.6); 7.7397 (0.5); 7.3197 (1.1); 7.3142 (0.6); 7.3107 (0.5); 7.2983 (6.6); 7.2793 (1.0); 7.2715 (3.0); 7.2246 (4.2); 7.2040 (10.0); 7.1974 (5.2); 7.1813 (3.2); 7.1742 (10.3); 7.1631 (1.3); 6.8614 (1.1); 6.8502 (9.3); 6.8432 (3.1); 6.8272 (2.7); 6.8202 (7.9); 6.8089 (0.9); 4.7388 (0.9); 4.7115 (1.2); 4.6990 (2.0); 4.6722 (2.2); 4.6450 (2.2); 4.6321 (2.5); 4.6055 (1.2); 4.5925 (1.0); 4.3808 (0.6); 4.3632 (0.9); 4.3462 (2.6); 4.3308 (4.4); 4.3153 (2.9); 4.2983 (0.8); 4.2810 (0.7); 4.0622 (1.2); 4.0486 (1.5); 4.0358 (1.4); 4.0225 (1.0); 2.3937 (12.7); 1.2928 (0.8); 1.2720 (0.8); 0.0406 (5.9)
2-15: $^{1}$H-NMR(300.2 MHz, CDCl3):
δ = 7.8812 (0.8); 7.8706 (0.9); 7.8641 (0.7); 7.8615 (0.8); 7.8524 (1.6); 7.8068 (1.6); 7.7975 (0.8); 7.7950 (0.8); 7.7885 (1.0); 7.7779 (0.9); 7.2986 (2.2); 7.2803 (1.6); 7.2729 (0.5); 7.2577 (0.5); 7.2502 (1.9); 6.9369 (1.9); 6.9294 (0.6); 6.9143 (0.5); 6.9068 (1.6); 4.4878 (0.3); 4.4732 (0.4); 4.4138 (0.3); 4.4044 (0.4); 4.3833 (0.6); 4.3490 (0.4); 4.1977 (0.6); 4.1793 (0.4); 4.1667 (0.5); 4.1484 (0.3); 1.6261 (1.1); 1.4799 (16.0); 1.2924 (0.4); 0.0361 (2.8)
2-16: $^{1}$H-NMR(300.2 MHz, CDCl3):
δ = 7.8646 (0.6); 7.8551 (0.6); 7.8515 (0.8); 7.8491 (0.7); 7.8431 (1.0); 7.8352 (2.3); 7.8295 (1.2); 7.8227 (1.2); 7.8178 (2.3); 7.8094 (1.0); 7.8035 (0.8); 7.8009 (0.8); 7.7975 (0.6); 7.7879 (0.7); 7.2986 (2.5); 7.2748 (1.2); 6.9980 (1.1); 6.9180 (0.6); 6.8916 (0.5); 4.6936 (0.4); 4.6637 (0.6); 4.6535 (0.6); 4.6026 (0.5); 4.5750 (0.6); 3.7770 (0.3); 3.7694 (16.0); 3.7604 (0.4); 3.4399 (0.4); 3.3922 (0.5); 3.3717 (0.4); 3.1601 (0.5); 3.1326 (0.4); 3.1125 (0.4); 3.0850 (0.3); 2.3843 (5.9); 2.2377 (5.6); 2.2202 (0.9); 0.0376 (2.4)
2-17: $^{1}$H-NMR(300.2 MHz, CDCl3):
δ = 7.8888 (1.1); 7.8783 (1.2); 7.8716 (1.1); 7.8693 (1.0); 7.8602 (2.0); 7.8468 (0.4); 7.8241 (0.3); 7.8218 (0.3); 7.8088 (2.0); 7.7993 (1.1); 7.7971 (1.0); 7.7905 (1.2); 7.7799 (1.1); 7.4011 (0.5); 7.3750 (0.6); 7.2982 (3.1); 7.0174 (1.1); 6.9823 (0.5); 4.5948 (0.6); 4.5808 (0.6); 4.5605 (0.7); 4.5466 (0.7); 4.3163 (0.4); 4.3009 (0.4); 4.2822 (0.3); 4.2667 (0.4); 3.2991 (0.6); 3.2742 (0.6); 2.4199 (5.8); 2.2971 (5.6); 1.6199 (2.0); 1.4724 (0.4); 1.4503 (16.0); 1.3035 (1.3); 0.9406 (0.5); 0.9188 (1.5); 0.8957 (0.5); 0.0368 (3.9)
2-19: $^{1}$H-NMR(499.9 MHz, $d_6$-DMSO):
δ = 8.8714 (0.4); 8.2981 (3.5); 7.9160 (0.6); 7.8967 (14.7); 7.8812 (1.2); 7.8789 (1.2); 7.1212 (5.9); 4.2957 (0.4); 4.2810 (4.5); 4.2736 (3.5); 4.2696 (3.4); 4.2471 (0.5); 3.7070 (0.3); 3.6960 (0.9); 3.6858 (1.1); 3.6782 (1.2); 3.6692 (0.9); 3.6585 (0.4); 3.3929 (0.3); 3.3548 (156.6); 2.9562 (0.8); 2.9382 (0.9); 2.9272 (1.6); 2.9093 (1.6); 2.8698 (1.5); 2.8581 (1.7); 2.8409 (1.0); 2.8291 (0.9); 2.5091 (4.1); 2.5061 (5.5); 2.5028 (4.4); 2.2780 (16.0); 2.0370 (15.8); 1.1904 (1.9); 1.1780 (2.0)
2-20: $^{1}$H-NMR(300.2 MHz, $d_6$-DMSO):
δ = 8.3905 (1.6); 7.9068 (16.0); 7.8779 (0.3); 7.4117 (1.8); 7.3858 (2.2); 7.3075 (2.2); 7.1760 (1.2); 7.1728 (1.2); 7.1502 (1.0); 7.1470 (1.0); 5.7761 (0.6); 4.3304 (0.3); 4.3091 (0.4); 4.2933 (1.1); 4.2707 (2.0); 4.2563 (1.4); 4.2320 (0.4); 4.2195 (0.3); 3.8116 (0.5); 3.1178 (2.0); 3.0959 (1.3); 3.0901 (1.3); 2.5342 (1.5); 2.5283 (3.0); 2.5222 (4.1); 2.5162 (3.0); 2.5102 (1.5); 2.2951 (8.9); 1.5526 (4.8); 1.3275 (0.4); 1.1290 (1.1); 0.0169 (3.1)

TABLE 6-continued
| |
|---|
| 2-21: $^1$H-NMR(300.2 MHz, CDCl3):<br>δ = 7.9005 (2.2); 7.8901 (2.5); 7.8833 (2.3); 7.8813 (2.1); 7.8720 (3.8); 7.8585 (0.6); 7.8560 (0.5); 7.8271 (0.6); 7.8245 (0.6); 7.8114 (3.8); 7.8019 (2.4); 7.7931 (2.5); 7.7826 (2.2); 7.3523 (1.4); 7.3265 (1.8); 7.2984 (7.6); 7.2157 (2.3); 7.0894 (1.3); 7.0637 (1.1); 5.3343 (0.4); 4.3680 (0.4); 4.3533 (1.1); 4.3345 (1.5); 4.3215 (0.8); 4.2467 (0.6); 4.2344 (1.1); 4.2115 (1.2); 4.1978 (1.0); 4.1838 (0.6); 4.1707 (0.4); 3.2056 (1.6); 3.1823 (1.5); 2.3394 (10.9); 1.6190 (13.4); 1.3998 (16.0); 0.1059 (0.8); 0.0465 (0.4); 0.0358 (9.5) |
TABLE 7
Compounds according to formula (3)
(3)
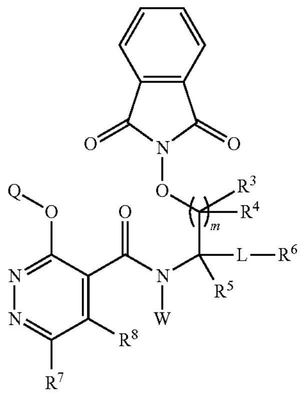
In table 7, "#" denotes the point of attachment to the L—$R^6$ group and "*" denotes the point of attachment to the pyridazin-4-yl group
| Ex-No | $R^7$ | $R^8$ | Q | 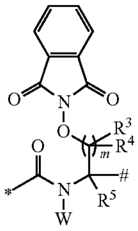 W | L—$R^6$ | LogP |
|---|---|---|---|---|---|---|
| 3-02 | Cl | H | 3-(trifluoro-methyl)phenyl | 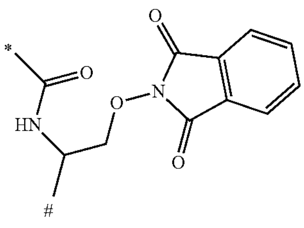 | (4-chloro-phenyl)methyl | 4.51[a]; 4.35[b] |
| 3-03 | $CH_3$ | H | 3-(trifluoro-methyl)phenyl | 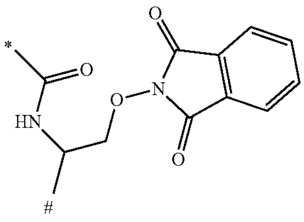 | 2,4-dichlorophenyl | 4.27[a]; 4.24[b] |

TABLE 7-continued
Compounds according to formula (3)
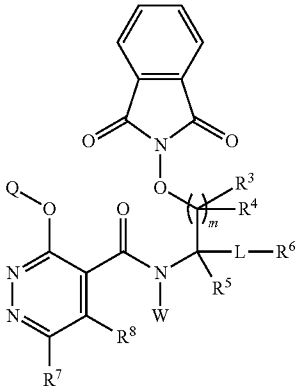
(3)
In table 7, "#" denotes the point of attachment to the L—$R^6$ group and "*" denotes the point of attachment to the pyridazin-4-yl group
| Ex-No | $R^7$ | $R^8$ | Q | 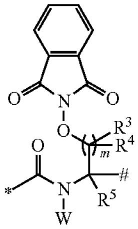 | L—$R^6$ | LogP |
|---|---|---|---|---|---|---|
| 3-04 | Cl | H | 3-(trifluoro-methyl)phenyl | 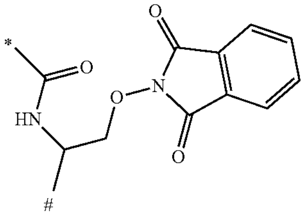 | 2,4-dichlorophenyl | 4.72[a]; 4.63[b] |
| 3-05 | Cl | $CH_3$ | 3-(trifluoro-methyl)phenyl | 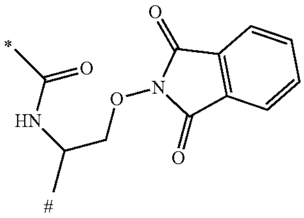 | (2,4-dimethyl-phenyl)methyl | 4.65[a] |
| 3-06 | I | H | 3-(trifluoro-methyl)phenyl | 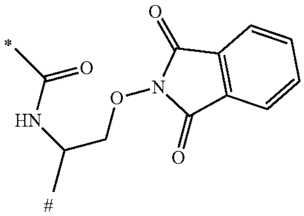 | (2,4-dimethyl-phenyl)methyl | 5.03[a] |

TABLE 7-continued

Compounds according to formula (3)

(3)

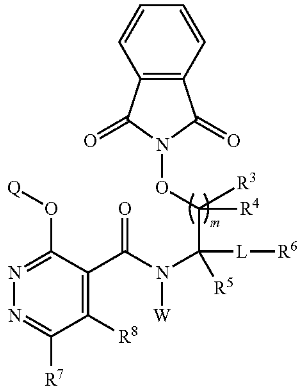

In table 7, "#" denotes the point of attachment to the L—$R^6$ group and "*" denotes the point of attachment to the pyridazin-4-yl group

| Ex-No | $R^7$ | $R^8$ | Q | 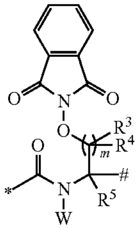 | L—$R^6$ | LogP |
|---|---|---|---|---|---|---|
| 3-07 | $CH_3$ | $CH_3$ | 3-(trifluoro-methyl)phenyl | 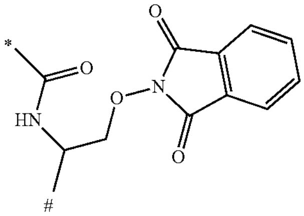 | (2,4-dimethyl-phenyl)methyl | 3.99[a] |
| 3-08 | $CH_3$ | H | 3-cyclopropyl-phenyl | 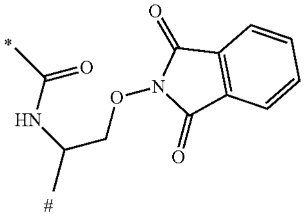 | (2,4-dimethyl-phenyl)methyl | 4.59[a] |
| 3-09 | $CH_3$ | H | 3-cyclopropyl-2-fluorophenyl | 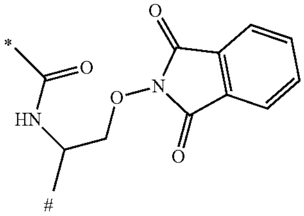 | (2,4-dimethyl-phenyl)methyl | 4.61[a] |

TABLE 7-continued

Compounds according to formula (3)

(3)

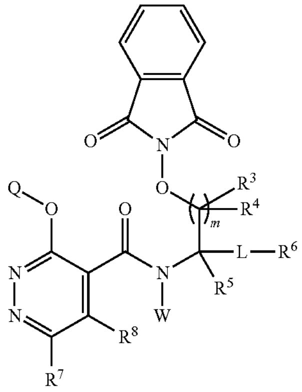

In table 7, "#" denotes the point of attachment to the L—$R^6$ group and "*" denotes the point of attachment to the pyridazin-4-yl group

| Ex-No | $R^7$ | $R^8$ | Q | 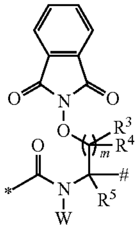 | L—$R^6$ | LogP |
|---|---|---|---|---|---|---|
| 3-10 | Cl | H | 3-(trifluoro-methyl)phenyl | 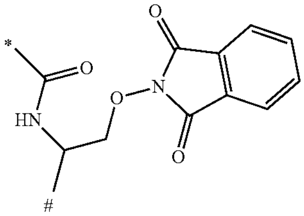 | (3,4-dimethyl-phenyl)methyl | 4.92[a] |
| 3-11 | Cl | H | 3-(trifluoro-methyl)phenyl | 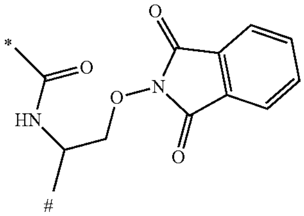 | (4-bromo-2-chloro-phenyl)methyl | 5.16[a] |
| 3-12 | Cl | H | 3-(trifluoro-methyl)phenyl | 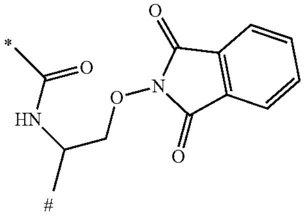 | (4-bromo-2-methyl-phenyl)methyl | 5.08[a] |

TABLE 7-continued

Compounds according to formula (3)

(3)

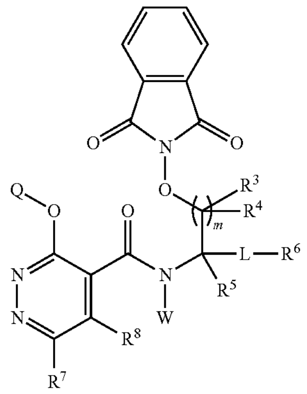

In table 7, "#" denotes the point of attachment to the L—$R^6$ group and "*" denotes the point of attachment to the pyridazin-4-yl group

| Ex-No | $R^7$ | $R^8$ | Q | 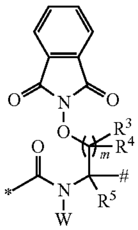 | L—$R^6$ | LogP |
|---|---|---|---|---|---|---|
| 3-13 | Cl | H | 3-(difluoro-methyl)-2-fluorophenyl | 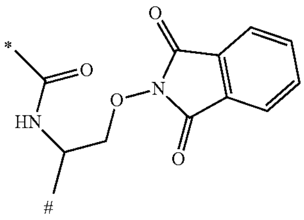 | (2,4-dimethyl-phenyl)methyl | 4.56[a] |
| 3-14 | $CH_3$ | H | 3-cyclopropyl-2-fluorophenyl | 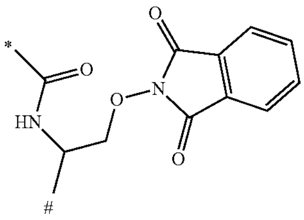 | (4-bromo-2-chloro-phenyl)methyl | 4.86[a] |
| 3-15 | $CH_3$ | H | 3-cyclopropyl-2-fluorophenyl | 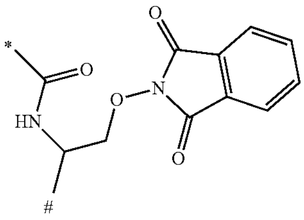 | (3,4-dimethyl-phenyl)methyl | 4.64[a] |

TABLE 7-continued

Compounds according to formula (3)

(3)

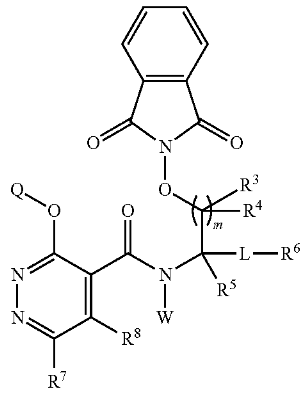

In table 7, "#" denotes the point of attachment to the L—$R^6$ group and "*" denotes the point of attachment to the pyridazin-4-yl group

| Ex-No | $R^7$ | $R^8$ | Q | 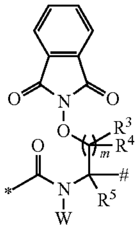 | L—$R^6$ | LogP |
|---|---|---|---|---|---|---|
| 3-16 | Cl | H | 3-(trifluoro-methyl)phenyl | 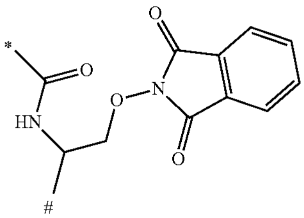 | (2,4-dimethyl-phenyl)methyl | 5.00[a] |
| 3-17 | Cl | H | 3-(trifluoro-methyl)phenyl | 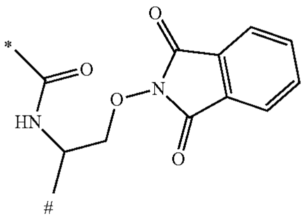 | (4-cyclopropyl-2-methyl-phenyl)methyl | 5.14[a] |
| 3-18 | Cl | H | 3-(trifluoro-methyl)phenyl | 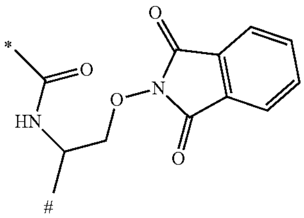 | (2-chloro-4-cyclo-propyl-phenyl)methyl | 5.17[a] |

TABLE 7-continued

Compounds according to formula (3)

(3)

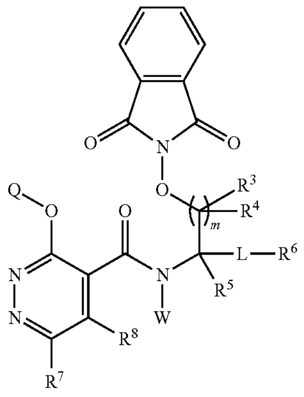

In table 7, "#" denotes the point of attachment to the L—$R^6$ group and "*" denotes the point of attachment to the pyridazin-4-yl group

| Ex-No | $R^7$ | $R^8$ | Q | 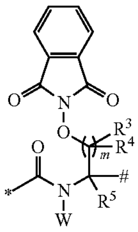 | L—$R^6$ | LogP |
|---|---|---|---|---|---|---|
| 3-19 | Cl | H | 3-(trifluoro-methyl)phenyl | 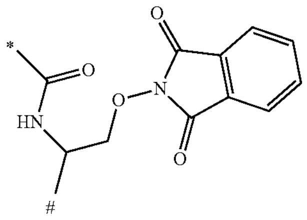 | (2-chloro-4-isopropyl-phenyl)methyl | 5.48[a] |
| 3-20 | $CH_3$ | H | 3-(difluoro-methyl)phenyl | 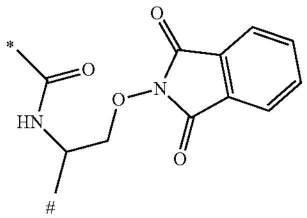 | (2,4-dimethyl-phenyl)methyl | 4.04[a] |
| 3-21 | Cl | H | 3-(trifluoro-methyl)phenyl | 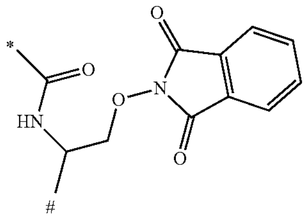 | (4-isopropyl-2-methyl-phenyl)methyl | 5.48[a] |

TABLE 7-continued

Compounds according to formula (3)

(3)

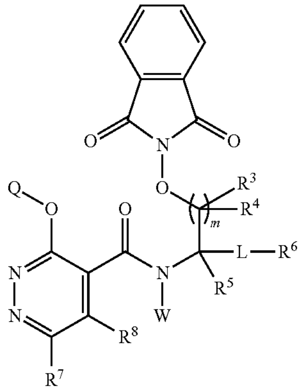

In table 7, "#" denotes the point of attachment to the L—$R^6$ group and "*" denotes the point of attachment to the pyridazin-4-yl group

| Ex-No | $R^7$ | $R^8$ | Q | 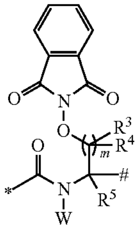 | L—$R^6$ | LogP |
|---|---|---|---|---|---|---|
| 3-22 | Cl | H | 3-(trifluoro-methyl)phenyl | 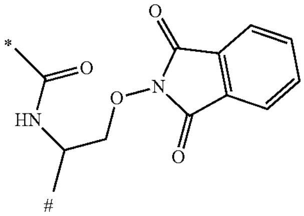 | (2,4-dichloro-phenyl)methyl | 5.03[a] |
| 3-23 | Cl | H | 5-bromopyridin-3-yl | 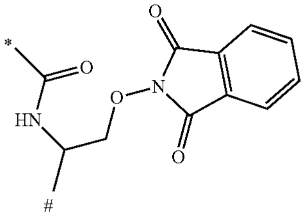 | (2,4-dimethyl-phenyl)methyl | 4.19 & 4.34[a] |
| 3-24 | Cl | H | 6-chloro-5-(trifluoromethyl) pyridin-3-yl | 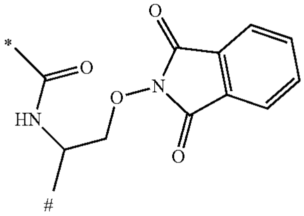 | (2,4-dimethyl-phenyl)methyl | 5.01[a] |

TABLE 7-continued

Compounds according to formula (3)

(3)

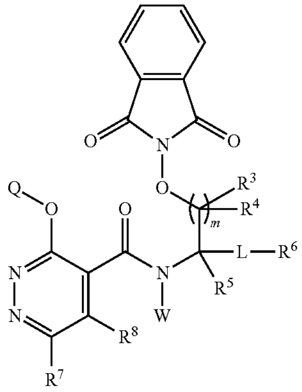

In table 7, "#" denotes the point of attachment to the L—$R^6$ group and "*" denotes the point of attachment to the pyridazin-4-yl group

| Ex-No | $R^7$ | $R^8$ | Q | 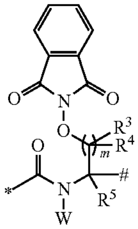 | L—$R^6$ | LogP |
|---|---|---|---|---|---|---|
| 3-25 | Cl | $CH_3$ | 3-cyclopropyl-2-fluorophenyl | 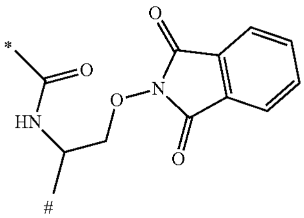 | (4-bromo-2-chloro-phenyl)methyl | 5.03[a] |
| 3-26 | Cl | $CH_3$ | 3-cyclopropyl-2-fluorophenyl | 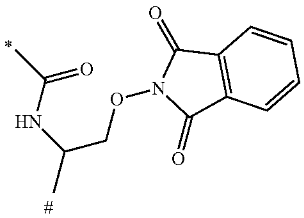 | (2-chloro-4-cyclo-propyl-phenyl)methyl | 5.05[a] |
| 3-27 | Cl | H | 3-cyclopropyl-phenyl | 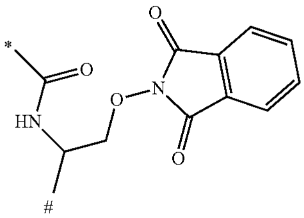 | (2,4-dimethyl-phenyl)methyl | 5.11[a] |

TABLE 7-continued

Compounds according to formula (3)

(3)

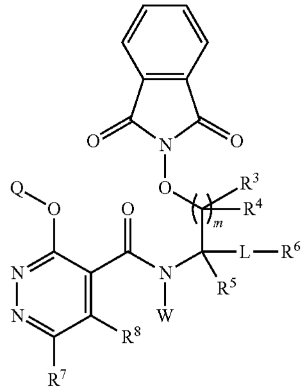

In table 7, "#" denotes the point of attachment to the L—$R^6$ group and "*" denotes the point of attachment to the pyridazin-4-yl group

| Ex-No | $R^7$ | $R^8$ | Q | 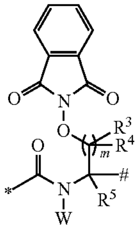 | L—$R^6$ | LogP |
|---|---|---|---|---|---|---|
| 3-28 | Cl | H | 3-(1-fluoro-cyclo-propyl)phenyl | 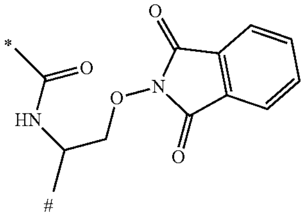 | (2,4-dimethyl-phenyl)methyl | 4.92[a] |
| 3-29 | $CH_3$ | H | 3-cyclopropyl-2-fluorophenyl | 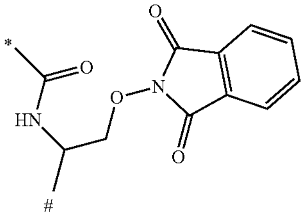 | (2-chloro-4-cyclo-propyl-phenyl)methyl | 4.90[a] |
| 3-30 | Cl | $CH_3$ | 3-cyclopropyl-2-fluorophenyl | 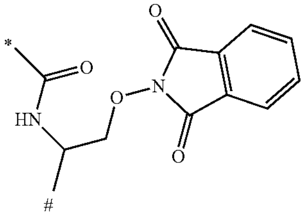 | (2,4-dichloro-phenyl)methyl | 4.90[a] |

TABLE 7-continued

Compounds according to formula (3)

(3)

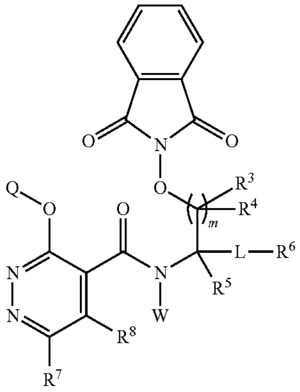

In table 7, "#" denotes the point of attachment to the L—$R^6$ group and "*" denotes the point of attachment to the pyridazin-4-yl group

| Ex-No | $R^7$ | $R^8$ | Q | 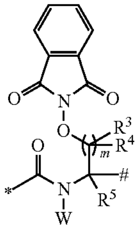 | L—$R^6$ | LogP |
|---|---|---|---|---|---|---|
| 3-31 | Cl | H | 3-cyclopropylphenyl | 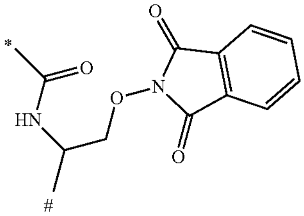 | (2,4-dichlorophenyl)methyl | 5.27[a] |
| 3-32 | Cl | H | 2-fluoro-3-[rac-2,2-difluorocyclopropyl]phenyl | 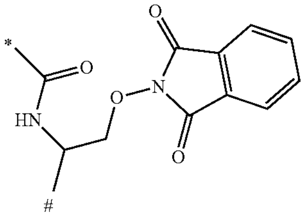 | (2,4-dimethylphenyl)methyl | 4.85[a] |
| 3-33 | $CH_3$ | H | 3-(trifluoromethyl)phenyl | 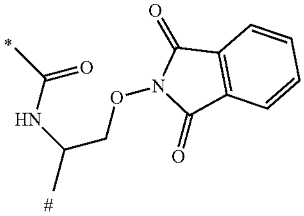 | (2,4-dimethylphenoxy)methyl | 4.56[a] |

TABLE 7-continued

Compounds according to formula (3)

(3)

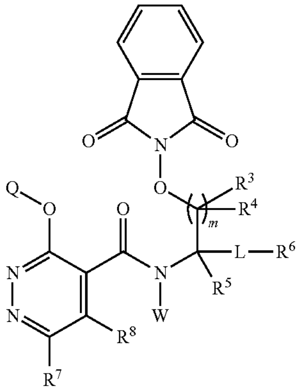

In table 7, "#" denotes the point of attachment to the L—$R^6$ group and "*" denotes the point of attachment to the pyridazin-4-yl group

| Ex-No | $R^7$ | $R^8$ | Q | 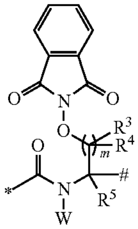 | L—$R^6$ | LogP |
|---|---|---|---|---|---|---|
| 3-34 | $CH_3$ | H | 3-(trifluoro-methyl)phenyl | 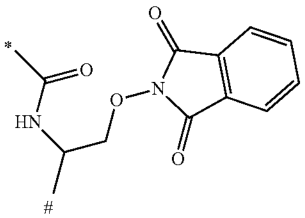 | (4-chloro-phenoxy)methyl | 4.37[a] |
| 3-35 | Cl | H | 3-(trifluoro-methyl)phenyl | 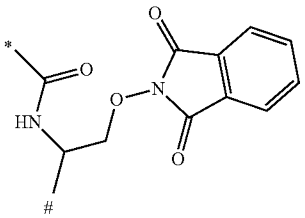 | [(2,4-dimethyl-phenyl)thio]methyl | 5.28[a] |
| 3-36 | Cl | $CH_3$ | 2-fluoro-3-[rac-2,2-difluoro-cyclo-propyl]phenyl | 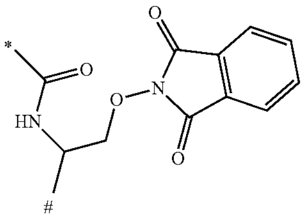 | (2,4-dimethyl-phenyl)methyl | 4.59[a] |

TABLE 7-continued

Compounds according to formula (3)

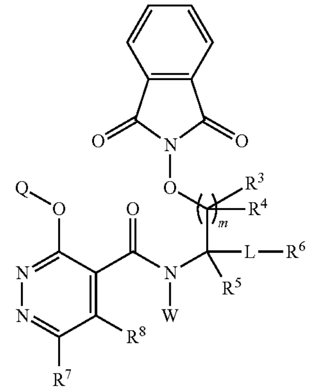

(3)

In table 7, "#" denotes the point of attachment to the L—$R^6$ group and "*" denotes the point of attachment to the pyridazin-4-yl group

| Ex-No | $R^7$ | $R^8$ | Q | 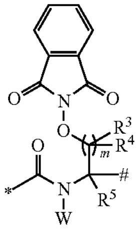 | L—$R^6$ | LogP |
|---|---|---|---|---|---|---|
| 3-37 | $CH_3$ | H | 2-fluoro-3-(trifluoro-methyl)phenyl | 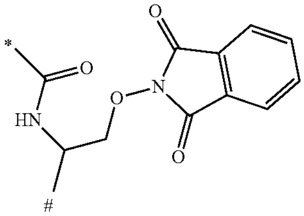 | (2,4-dichloro-phenyl)methyl | 4.64[a] |
| 3-38 | $CH_3$ | H | 2-fluoro-3-(trifluoro-methyl)phenyl | 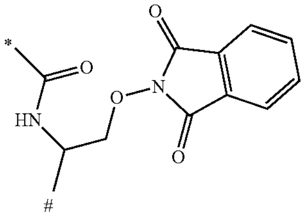 | (2,4-dimethyl-phenyl)methyl | 4.54[a] |
| 3-39 | $CH_3$ | H | 3-(difluoro-methyl)phenyl | 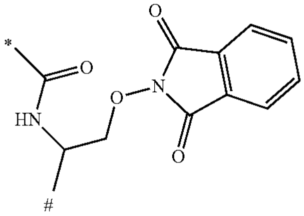 | (2,4-dichloro-phenyl)methyl | 4.18[a] |

TABLE 7-continued

Compounds according to formula (3)

(3)

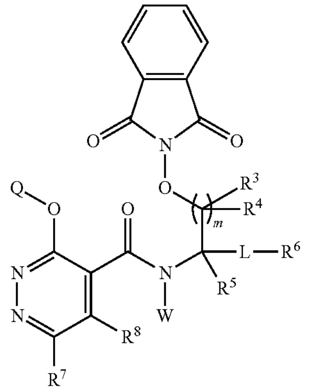

In table 7, "#" denotes the point of attachment to the L—$R^6$ group and "*" denotes the point of attachment to the pyridazin-4-yl group

| Ex-No | $R^7$ | $R^8$ | Q | 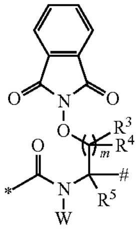 | L—$R^6$ | LogP |
|---|---|---|---|---|---|---|
| 3-40 | Cl | H | 2-fluoro-3-(1-fluorocyclo-propyl)phenyl | 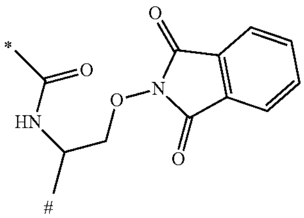 | (2,4-dimethyl-phenyl)methyl | 4.97[a] |
| 3-41 | Cl | $CH_3$ | 2-fluoro-3-(1-fluorocyclo-propyl)phenyl | 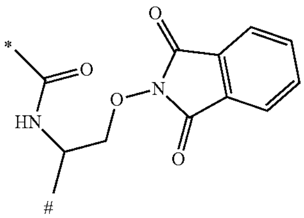 | (2,4-dimethyl-phenyl)methyl | 4.62[a] |
| 3-42 | $CH_3$ | H | 3-chloro-2-fluorophenyl | 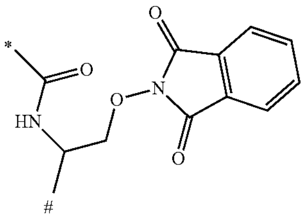 | (2-chloro-4-cyclo-propyl-phenyl)methyl | 4.70[a] |

TABLE 7-continued

Compounds according to formula (3)

(3)

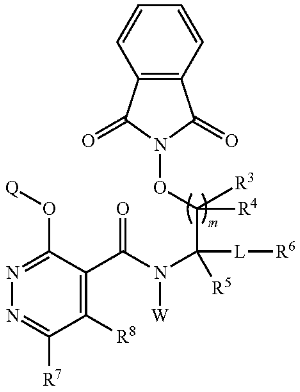

In table 7, "#" denotes the point of attachment to the L—$R^6$ group and "*" denotes the point of attachment to the pyridazin-4-yl group

| Ex-No | $R^7$ | $R^8$ | Q | 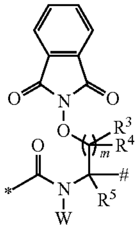 | L—$R^6$ | LogP |
|---|---|---|---|---|---|---|
| 3-43 | $CH_3$ | H | 3-chloro-2-fluorophenyl | 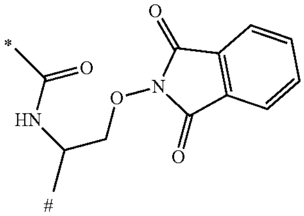 | (4-cyclopropyl-2-methyl-phenyl)methyl | 4.74[a] |
| 3-44 | $CH_3$ | H | 3-chloro-2-fluorophenyl | 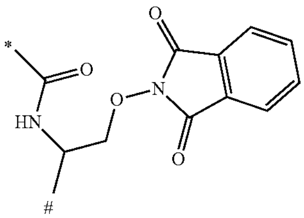 | (4-bromo-2-methyl-phenyl)methyl | 4.62[a] |
| 3-45 | $CH_3$ | H | 3-chloro-2-fluorophenyl | 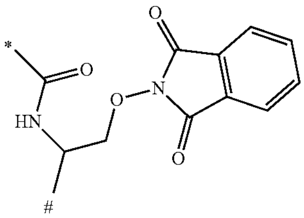 | (3,4-dimethyl-phenyl)methyl | 442[a] |

TABLE 7-continued

Compounds according to formula (3)

(3)

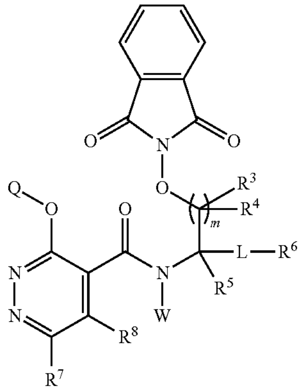

In table 7, "#" denotes the point of attachment to the L—$R^6$ group and "*" denotes the point of attachment to the pyridazin-4-yl group

| Ex-No | $R^7$ | $R^8$ | Q | 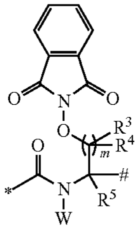 | L—$R^6$ | LogP |
|---|---|---|---|---|---|---|
| 3-46 | $CH_3$ | H | 3-(difluoro-methyl)-2-fluorophenyl | 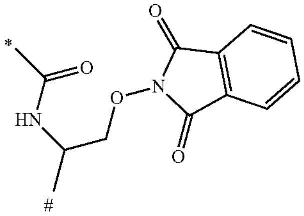 | (4-cyclopropyl-2-methyl-phenyl)methyl | 4.55[a] |
| 3-47 | $CH_3$ | H | 3-(difluor-omethyl)phenyl | 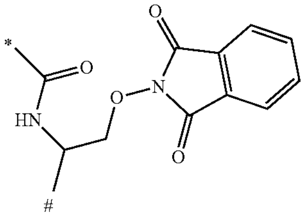 | (3,4-dimethyl-phenyl)methyl | 4.12[a] |
| 3-48 | $CH_3$ | H | 3-(difluoro-methyl)phenyl | 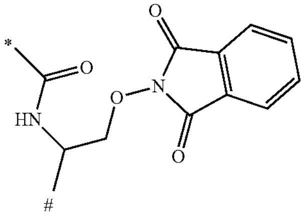 | (4-cyclopropyl-2-methyl-phenyl)methyl | 4.37[a] |

TABLE 7-continued

Compounds according to formula (3)

(3)

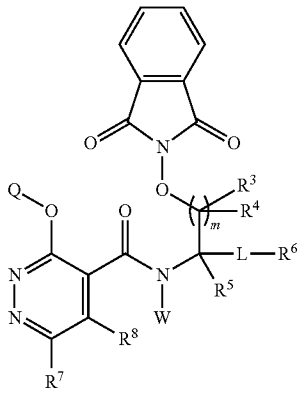

In table 7, "#" denotes the point of attachment to the L—$R^6$ group and "*" denotes the point of attachment to the pyridazin-4-yl group

| Ex-No | $R^7$ | $R^8$ | Q | 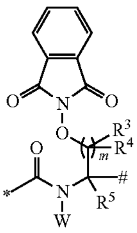 | L—$R^6$ | LogP |
|---|---|---|---|---|---|---|
| 3-49 | $CH_3$ | H | 3-(difluoro-methyl)-2-fluorophenyl | 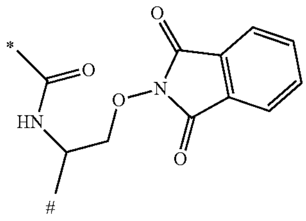 | (3,4-dimethyl-phenyl)methyl | 4.30[a] |
| 3-50 | $CH_3$ | H | 3-cyclopropyl-2-fluorophenyl | 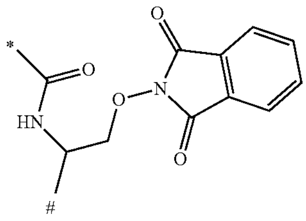 | (4-bromo-2-methyl-phenyl)methyl | 4.82[a] |
| 3-51 | Cl | H | 3-(trifluoro-methyl)phenyl | 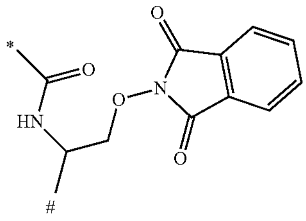 | (5-chloropyridin-2-yl)methyl | 4.06 & 4.15[a] |

TABLE 7-continued

| Compounds according to formula (3) | | | | | | |
|---|---|---|---|---|---|---|
| (3) 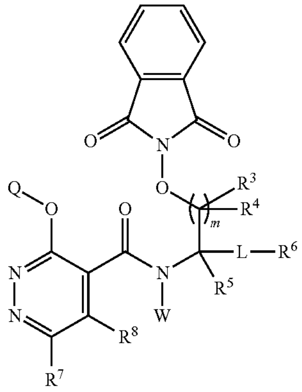 | | | | | | |
| In table 7, "#" denotes the point of attachment to the L—$R^6$ group and "*" denotes the point of attachment to the pyridazin-4-yl group | | | | | | |
| Ex-No | $R^7$ | $R^8$ | Q | 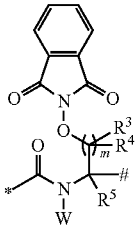 | L—$R^6$ | LogP |
| 3-52 | Cl | H | 3-(trifluoro-methyl)phenyl | 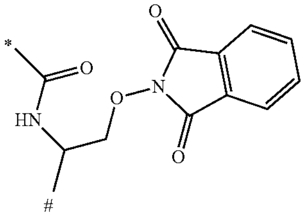 | (4,5-dimethyl-3-thienyl)methyl | 4.88[a] |
| 3-53 | $CH_3$ | H | 3-cyclopropyl-phenyl | 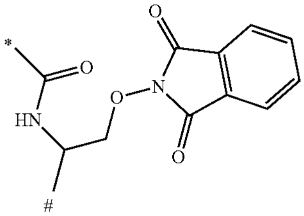 | (3,4-dimethyl-phenyl)methyl | 4.70[a] |
| 3-54 | $CH_3$ | H | 3-cyclopropyl-phenyl | 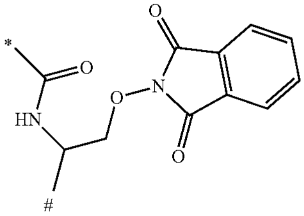 | (4-bromo-2-methyl-phenyl)methyl | 4.89[a] |

TABLE 7-continued

Compounds according to formula (3)

(3)

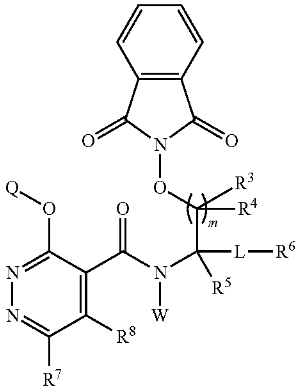

In table 7, "#" denotes the point of attachment to the L—$R^6$ group and "*" denotes the point of attachment to the pyridazin-4-yl group

| Ex-No | $R^7$ | $R^8$ | Q | 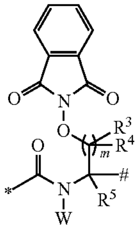 | L—$R^6$ | LogP |
|---|---|---|---|---|---|---|
| 3-55 | $CH_3$ | H | 3-cyclopropyl-phenyl | 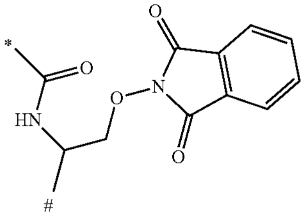 | (4-cyclopropyl-2-methyl-phenyl)methyl | 4.93[a] |
| 3-56 | $CH_3$ | H | 3-(difluoro-methyl)-2-fluorophenyl | 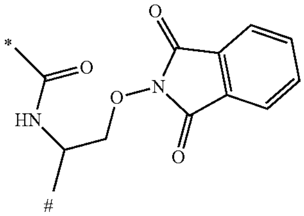 | (2-chloro-4-methyl-phenyl)methyl | 4.21[a] |
| 3-57 | Cl | H | 3-cyclopropyl-2-fluorophenyl | 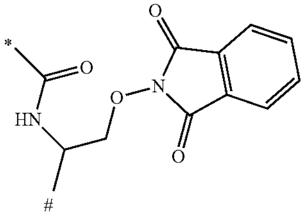 | (2,4-dimethyl-phenyl)methyl | 5.08[a] |

TABLE 7-continued
Compounds according to formula (3)
(3)
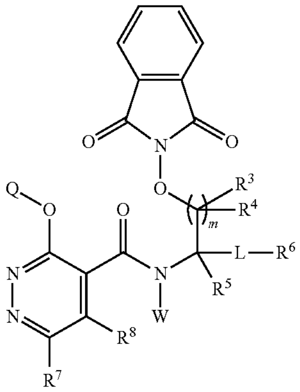
In table 7, "#" denotes the point of attachment to the L—$R^6$ group and "*" denotes the point of attachment to the pyridazin-4-yl group
| Ex-No | $R^7$ | $R^8$ | Q | 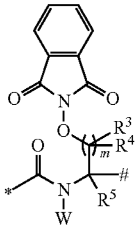 W | L—$R^6$ | LogP |
|---|---|---|---|---|---|---|
| 3-58 | $CH_3$ | H | 3-(difluoro-methyl)-2-fluorophenyl | 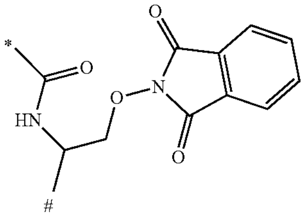 | (2,4-dimethyl-phenyl)methyl | 4.32[a] |
TABLE 8
3-01: $^1$H-NMR(400.2 MHz, $d_6$-DMSO):
δ = 9.2013 (1.7); 9.1803 (1.8); 7.8708 (0.7); 7.8670 (0.7); 7.8585 (1.5); 7.8488 (9.6); 7.8452 (9.6); 7.8356 (1.4); 7.8225 (7.4); 7.6798 (0.7); 7.6600 (2.0); 7.6410 (3.5); 7.5973 (2.0); 7.5781 (1.3); 7.5656 (1.5); 7.5462 (1.0); 7.2508 (3.2); 7.2272 (2.0); 7.2060 (1.6); 7.1876 (2.4); 7.1689 (1.0); 7.0456 (1.6); 7.0272 (1.3); 5.3251 (0.4); 5.3114 (0.5); 5.3030 (0.9); 5.2898 (0.8); 5.2812 (0.6); 5.2675 (0.4); 4.3016 (0.3); 4.2851 (0.7); 4.2755 (0.7); 4.2676 (0.6); 4.2593 (1.0); 4.2421 (0.5); 4.1981 (0.5); 4.1838 (1.1); 4.1690 (0.8); 4.1579 (0.7); 4.1428 (0.3); 3.3314 (29.1); 2.6054 (16.0); 2.5118 (9.4); 2.5076 (19.0); 2.5032 (25.5); 2.4987 (18.3); 2.4945 (8.7); 2.2157 (0.3); 2.1967 (0.7); 2.1778 (13.3); 2.1500 (1.0); 2.1357 (0.6); 2.1269 (0.8); 2.1124 (0.5); 2.0773 (5.6); 0.0091 (0.8); 0.0010 (20.0); −0.0072 (0.8)
3-02: $^1$H-NMR(400.0 MHz, $d_6$-DMSO):
δ = 8.9386 (2.3); 8.9181 (2.4); 7.9829 (11.3); 7.9103 (0.7); 7.8974 (2.2); 7.8882 (16.0); 7.8857 (15.5); 7.8636 (0.8); 7.8267 (0.4); 7.7634 (0.9); 7.7437 (2.8); 7.7241 (2.8); 7.7078 (3.4); 7.6885 (1.4); 7.6363 (3.9); 7.5592 (2.2); 7.5390 (1.7); 7.3224 (5.6); 7.3015 (6.7); 7.0934 (7.4); 7.0725 (6.2); 6.5891 (0.8); 4.4548 (0.8); 4.4431 (1.0); 4.4342 (1.0); 4.4215 (0.9); 4.4110 (0.6); 4.3400 (1.1); 4.3255 (1.0); 4.3146 (2.4); 4.3009 (1.8); 4.2808 (2.2); 4.2667 (2.0); 4.2555 (1.2); 4.2416 (0.9); 4.0558 (0.7); 4.0380 (2.2); 4.0201 (2.2); 4.0023 (0.8); 3.3237 (121.9); 3.2013 (1.2); 3.1903 (1.3); 3.1660 (1.5); 3.1555 (1.4); 2.8923 (1.4); 2.8681 (1.4); 2.8583 (1.3); 2.8339 (1.1); 2.6707 (1.0); 2.6664 (0.7); 2.5063 (135.6); 2.5019 (175.8); 2.4975 (126.0); 2.3333 (0.8); 2.3287 (1.0); 2.3245 (0.7); 2.0572 (0.6); 2.0367 (0.5); 1.9888 (9.5); 1.3975 (8.3); 1.2410 (0.8); 1.2348 (0.8); 1.2248 (0.5); 1.2123 (0.5); 1.1927 (2.8); 1.1749 (5.4); 1.1570 (2.6); 0.1462 (0.6); 0.0079 (6.0); −0.0003 (140.6); −0.0085 (5.6); −0.1499 (0.6)
3-03: $^1$H-NMR(400.2 MHz, $d_6$-DMSO):
δ = 9.6166 (1.0); 9.5974 (1.0); 8.3148 (1.3); 7.8731 (16.0); 7.8040 (4.2); 7.7169 (0.4); 7.6979 (1.0); 7.6775 (0.9); 7.6601 (2.4); 7.6548 (2.5); 7.6383 (2.8); 7.6301 (1.8); 7.6220 (0.7); 7.6088 (1.9); 7.5768 (0.9); 7.5582 (0.6); 7.3653 (1.1); 7.3601 (1.1); 7.3443 (1.0); 7.3390 (1.0); 5.7550 (2.5); 5.7371 (0.8); 4.4326 (2.0); 4.4167 (1.9); 4.0379 (0.4); 4.0201 (0.4); 3.3194 (193.5); 2.6794 (1.2); 2.6749 (2.4); 2.6704 (3.2); 2.6659 (2.3); 2.6613

TABLE 8-continued (1.2); 2.6538 (0.4); 2.6330 (9.9); 2.5238 (11.2); 2.5190 (17.7); 2.5105 (183.5); 2.5060 (360.1); 2.5014 (470.6); 2.4968 (346.0); 2.4924 (170.3); 2.3373 (1.0); 2.3328 (2.2); 2.3283 (3.0); 2.3237 (2.1); 2.3193 (1.0); 1.9885 (1.8); 1.1927 (0.5); 1.1749 (1.0); 1.1583 (1.0); −0.0002 (4.2)
3-04: $^1$H-NMR(400.2 MHz, $d_6$-DMSO):
δ = 9.7249 (0.7); 9.7057 (0.7); 8.1326 (3.5); 7.8726 (12.5); 7.7269 (0.8); 7.7083 (1.5); 7.6806 (0.9); 7.6675 (1.7); 7.6622 (2.0); 7.6500 (1.4); 7.6289 (1.6); 7.4007 (0.8); 7.3954 (0.8); 7.3796 (0.7); 7.3742 (0.7); 5.7426 (0.5); 5.7309 (0.4); 4.4549 (0.9); 4.4481 (0.9); 4.4435 (0.8); 4.4283 (0.7); 3.3216 (34.1); 2.6709 (0.4); 2.5244 (1.3); 2.5196 (2.1); 2.5109 (25.0); 2.5065 (49.9); 2.5019 (65.8); 2.4974 (48.8); 2.4929 (24.4); 2.3780 (0.3); 2.3288 (0.4); 1.9886 (0.4); 1.3978 (16.0); 0.1460 (0.5); 0.0079 (4.4); −0.0002 (106.0); −0.0085 (4.1); −0.1495 (0.5)
3-05: $^1$H-NMR(300.2 MHz, $d_6$-DMSO):
δ = 9.1301 (0.8); 9.1012 (0.9); 7.8984 (10.4); 7.7347 (0.9); 7.7088 (1.2); 7.6978 (1.3); 7.6715 (0.4); 7.5699 (1.3); 7.5259 (0.8); 7.5000 (0.6); 7.1130 (1.1); 7.0873 (1.2); 6.8433 (1.3); 6.5679 (0.7); 6.5445 (0.6); 4.5774 (0.3); 4.5625 (0.4); 4.3261 (1.6); 4.3094 (1.2); 3.3512 (16.0); 3.1072 (0.3); 3.0927 (0.4); 3.0589 (0.5); 3.0450 (0.4); 2.8591 (0.4); 2.8254 (0.4); 2.8107 (0.4); 2.5341 (1.4); 2.5282 (3.0); 2.5221 (4.0); 2.5161 (2.9); 2.5101 (1.4); 2.2850 (13.3); 2.0769 (5.5); 0.0193 (3.0)
3-06: $^1$H-NMR(300.2 MHz, CDCl3):
δ = 8.5193 (1.1); 8.0509 (2.1); 7.8044 (1.6); 7.7976 (1.6); 7.6930 (0.5); 7.6078 (0.9); 7.2987 (3.0); 7.2523 (0.4); 7.2269 (0.5); 7.0071 (0.5); 6.9614 (0.4); 5.3343 (0.4); 3.2164 (0.4); 2.9925 (16.0); 2.9173 (14.6); 2.8370 (4.8); 2.6222 (1.1); 2.4428 (2.4); 2.3666 (0.4); 2.2982 (2.3); 2.2361 (0.3); 1.5414 (0.3); 1.5164 (0.7); 1.4914 (0.8); 0.0327 (3.6)
3-07: $^1$H-NMR(300.2 MHz, CDCl3):
δ = 8.0489 (2.0); 7.8577 (0.6); 7.8491 (0.5); 7.8433 (1.0); 7.8354 (1.3); 7.8276 (3.8); 7.8167 (3.8); 7.8085 (1.1); 7.8007 (1.0); 7.7944 (0.5); 7.7861 (0.7); 7.6118 (0.6); 7.5848 (0.7); 7.5096 (1.4); 7.4824 (0.8); 7.4580 (1.9); 7.4337 (0.3); 7.4146 (0.6); 7.4070 (0.9); 7.4003 (0.4); 7.3830 (0.4); 7.2985 (8.8); 7.2674 (1.1); 7.2418 (1.3); 7.0242 (1.4); 6.9911 (0.8); 6.9654 (0.7); 4.6662 (0.3); 4.6445 (0.3); 4.6062 (0.9); 4.5956 (0.5); 4.5728 (0.8); 4.5622 (0.6); 4.1676 (0.6); 4.1582 (0.7); 4.1343 (0.6); 4.1249 (0.6); 3.7640 (0.4); 3.7422 (0.5); 3.7201 (0.4); 3.3161 (0.4); 3.2935 (0.4); 3.2700 (0.6); 3.2469 (0.7); 3.2166 (0.8); 3.1920 (0.7); 3.1365 (0.6); 3.1076 (0.6); 3.0907 (0.4); 3.0612 (0.4); 2.9940 (15.4); 2.9172 (13.9); 2.8368 (16.0); 2.6547 (8.3); 2.6132 (2.0); 2.4645 (6.6); 2.3675 (0.7); 2.2977 (11.9); 2.2374 (0.6); 1.6962 (1.0); 1.5315 (0.9); 1.5068 (1.9); 1.4828 (4.4); 1.4618 (3.7); 0.0334 (9.4)
3-08: $^1$H-NMR(300.2 MHz, CDCl3):
δ = 8.5184 (0.9); 8.4920 (1.0); 8.0672 (5.3); 7.8441 (1.7); 7.8339 (1.8); 7.8276 (1.7); 7.8236 (2.0); 7.8153 (4.1); 7.8009 (1.9); 7.7871 (4.1); 7.7781 (1.9); 7.7741 (1.6); 7.7692 (1.8); 7.7577 (1.7); 7.3651 (1.2); 7.3381 (2.7); 7.3112 (1.8); 7.2985 (10.5); 7.2613 (1.8); 7.2358 (2.1); 7.0980 (0.9); 7.0945 (1.2); 7.0906 (1.2); 7.0872 (1.2); 7.0711 (0.8); 7.0678 (0.9); 7.0634 (1.1); 7.0603 (1.0); 7.0321 (1.9); 7.0273 (2.5); 7.0200 (2.5); 7.0122 (2.2); 7.0072 (1.7); 6.9955 (2.2); 6.9355 (1.2); 6.9095 (1.0); 5.3370 (2.7); 4.6830 (0.4); 4.6704 (0.7); 4.6580 (0.6); 4.6447 (0.7); 4.6327 (0.4); 4.4702 (0.9); 4.4585 (0.8); 4.4382 (1.4); 4.4267 (1.2); 4.3362 (1.3); 4.3236 (1.3); 4.3043 (0.9); 4.2917 (0.8); 3.2161 (2.9); 3.1907 (2.6); 2.9952 (0.9); 2.9231 (0.8); 2.8411 (16.0); 2.7139 (15.1); 2.4400 (10.8); 2.2968 (10.2); 1.9694 (0.6); 1.9581 (0.6); 1.9415 (1.1); 1.9248 (0.6); 1.9135 (0.6); 1.6312 (10.6); 1.0180 (0.4); 1.0001 (1.7); 0.9931 (2.3); 0.9717 (1.7); 0.9652 (2.3); 0.9481 (0.5); 0.7797 (0.7); 0.7697 (1.4); 0.7624 (1.7); 0.7543 (2.1); 0.7470 (1.5); 0.7387 (1.2); 0.7273 (0.4); 0.1073 (0.5); 0.0475 (0.5); 0.0367 (11.2); 0.0258 (0.4)
3-09: $^1$H-NMR(300.2 MHz, CDCl3):
δ = 8.3935 (0.9); 8.3674 (0.9); 8.0770 (5.2); 7.8323 (1.5); 7.8203 (1.4); 7.8161 (1.4); 7.8115 (1.9); 7.8031 (4.1); 7.7909 (2.2); 7.7791 (4.1); 7.7704 (1.8); 7.7658 (1.5); 7.7615 (1.6); 7.7496 (1.6); 7.2986 (16.3); 7.2715 (1.8); 7.2556 (0.7); 7.2460 (2.1); 7.2284 (1.2); 7.2234 (1.0); 7.2053 (0.9); 7.1997 (0.9); 7.1458 (0.9); 7.1423 (0.8); 7.1193 (1.3); 7.1158 (1.4); 7.0927 (0.6); 7.0892 (0.6); 6.9800 (2.0); 6.9301 (1.1); 6.9049 (0.9); 6.8626 (0.7); 6.8576 (0.7); 6.8360 (1.2); 6.8144 (0.6); 6.8096 (0.5); 5.3380 (1.3); 4.7022 (0.4); 4.6897 (0.7); 4.6769 (0.6); 4.6641 (0.7); 4.6515 (0.4); 4.4842 (0.8); 4.4721 (0.8); 4.4517 (1.4); 4.4397 (1.2); 4.3551 (1.3); 4.3417 (1.2); 4.3227 (0.9); 4.3093 (0.8); 3.2482 (2.8); 3.2231 (2.7); 2.8414 (4.1); 2.7194 (14.8); 2.4454 (10.3); 2.2797 (9.7); 2.1626 (0.4); 2.1518 (0.5); 2.1346 (0.9); 2.1171 (0.5); 2.1064 (0.5); 1.6071 (16.0); 1.0688 (0.4); 1.0567 (1.6); 1.0496 (1.8); 1.0386 (0.8); 1.0349 (0.8); 1.0281 (1.7); 1.0213 (1.6); 1.0093 (0.5); 0.8250 (0.9); 0.8113 (1.6); 0.8077 (1.9); 0.8034 (1.6); 0.7942 (1.7); 0.7912 (1.6); 0.7862 (1.3); 0.7740 (0.6); 0.0477 (0.6); 0.0369 (17.7); 0.0259 (0.7)
3-10: $^1$H-NMR(300.2 MHz, CDCl3):
δ = 8.3459 (0.6); 8.3201 (0.6); 8.2535 (4.6); 7.8416 (0.7); 7.8331 (0.6); 7.8270 (1.2); 7.8192 (1.4); 7.8112 (4.6); 7.8007 (4.6); 7.7928 (1.3); 7.7849 (1.2); 7.7787 (0.5); 7.7703 (0.7); 7.6720 (1.3); 7.6426 (1.0); 7.6226 (3.0); 7.6197 (2.5); 7.5451 (0.6); 7.5339 (0.8); 7.5269 (0.7); 7.5134 (0.6); 7.2986 (12.7); 7.1382 (1.6); 7.0922 (0.5); 7.0866 (0.4); 7.0668 (1.2); 7.0616 (1.2); 7.0375 (1.9); 7.0120 (0.7); 4.6552 (0.5); 4.6439 (0.4); 4.6320 (0.4); 4.4499 (0.6); 4.4363 (0.6); 4.4170 (1.1); 4.4035 (0.9); 4.3337 (1.0); 4.3212 (1.0); 4.3009 (0.6); 4.2883 (0.6); 4.1961 (0.4); 4.1722 (1.2); 4.1484 (1.2); 4.1247 (0.4); 3.1786 (1.0); 3.1563 (1.8); 3.1301 (0.9); 2.2265 (16.0); 2.0835 (5.2); 1.5879 (9.2); 1.3216 (1.6); 1.2979 (3.3); 1.2740 (1.4); 0.9204 (0.7); 0.1083 (3.2); 0.0491 (0.5); 0.0384 (15.9); 0.0275 (0.6)
3-11: $^1$H-NMR(300.2 MHz, CDCl3):
δ = 8.4360 (0.7); 8.4091 (0.7); 8.2289 (5.4); 8.2202 (0.5); 7.8510 (0.6); 7.8442 (0.5); 7.8358 (1.2); 7.8277 (2.0); 7.8215 (5.9); 7.8130 (5.7); 7.8070 (2.2); 7.7987 (1.2); 7.7906 (0.4); 7.7837 (0.6); 7.7127 (1.4); 7.6795 (0.4); 7.6542 (1.0); 7.6315 (3.4); 7.6136 (0.4); 7.5532 (0.8); 7.5404 (2.5); 7.5382 (2.6); 7.5232 (0.8); 7.5157 (0.5); 7.3707 (5.5); 7.3657 (3.0); 7.2987 (20.3); 4.8371 (0.4); 4.8240 (0.6); 4.8113 (0.5); 4.7986 (0.6); 4.7868 (0.4); 4.5119 (0.8); 4.4996 (0.8); 4.4786 (1.1); 4.4663 (1.0); 4.3421 (1.0); 4.3306 (1.1); 4.3088 (0.8); 4.2973 (0.8); 4.1720 (0.6); 4.1482 (0.7); 3.4516 (0.6); 3.4246 (0.6); 3.4053 (1.0); 3.3787 (1.0); 3.3038 (1.0); 3.2791 (1.0); 3.2578 (0.6); 3.2332 (0.6); 2.6132 (0.4); 2.5489 (0.4); 2.0833 (2.9); 1.5843 (16.0); 1.3214 (1.0); 1.2977 (2.1); 1.2739 (0.8); 0.9201 (0.7); 0.1078 (1.1); 0.0488 (0.9); 0.0381 (25.5); 0.0272 (0.8)
3-12: $^1$H-NMR(300.2 MHz, CDCl3):
δ = 8.5824 (0.7); 8.5563 (0.8); 8.2650 (5.2); 7.8456 (0.6); 7.8398 (0.4); 7.8297 (1.0); 7.8163 (6.2); 7.8106 (6.4); 7.7973 (1.1); 7.7806 (0.5); 7.7395 (1.5); 7.6447 (1.2); 7.6215 (3.6); 7.6005 (0.4); 7.5604 (0.9); 7.5517 (1.4); 7.5444 (0.8); 7.5293 (0.8); 7.3595 (2.1); 7.2986 (26.4); 4.6233 (0.5); 4.6048 (0.5); 4.5966 (0.5); 4.4896 (0.9); 4.4791 (0.8); 4.4573 (1.1); 4.4470 (1.1); 4.2482 (1.0); 4.2381 (1.0); 4.2164 (0.8); 4.2059 (0.8); 4.1722 (0.5); 4.1484 (0.5); 3.2868 (0.5); 3.2647 (0.5); 3.2407 (1.0); 3.2189 (1.0); 3.1810 (1.1); 3.1506 (1.1); 3.1352 (0.5); 3.1043 (0.5); 2.5095 (0.5); 2.4966 (1.5); 2.4845 (10.0); 2.0836 (2.1); 1.5811 (16.0); 1.3216 (0.7); 1.2978 (1.6);

TABLE 8-continued 1.2741 (0.6); 0.9202 (0.5); 0.1079 (0.9); 0.0489 (1.0); 0.0382 (30.9); 0.0272 (1.2)
3-13: $^1$H-NMR(300.2 MHz, $d_6$-DMSO):
δ = 7.9942 (1.7); 7.8900 (3.4); 7.8241 (1.3); 7.3116 (0.5); 7.1359 (0.4); 7.1108 (0.4); 6.8937 (0.5); 4.3518 (0.6); 4.3332 (0.5); 3.3406 (16.0); 2.5340 (0.8); 2.5280 (1.7); 2.5219 (2.4); 2.5158 (1.7); 2.5098 (0.8); 2.3102 (2.1); 2.2774 (0.6); 2.1694 (0.6); 2.1089 (2.0); 0.0201 (2.1)
3-14: $^1$H-NMR(300.2 MHz, CDCl3):
δ = 8.2952 (0.8); 8.2683 (0.8); 8.0574 (0.3); 8.0321 (4.6); 7.8452 (1.4); 7.8334 (1.4); 7.8290 (1.3); 7.8246 (1.8); 7.8158 (3.8); 7.8037 (2.0); 7.7914 (3.6); 7.7830 (1.7); 7.7784 (1.4); 7.7740 (1.4); 7.7622 (1.4); 7.5135 (2.2); 7.5071 (2.4); 7.3991 (1.4); 7.3718 (2.8); 7.3254 (1.8); 7.3189 (1.7); 7.2990 (17.5); 7.2573 (0.5); 7.2517 (0.5); 7.2301 (1.1); 7.2251 (0.9); 7.2073 (0.9); 7.2014 (0.8); 7.1604 (0.8); 7.1572 (0.8); 7.1340 (1.2); 7.1306 (1.3); 7.1073 (0.6); 7.1040 (0.6); 6.8765 (0.6); 6.8716 (0.6); 6.8500 (1.0); 6.8287 (0.5); 6.8237 (0.5); 5.3373 (1.2); 4.8609 (0.4); 4.8473 (0.6); 4.8347 (0.5); 4.8216 (0.6); 4.8093 (0.4); 4.5003 (0.6); 4.4874 (0.6); 4.4667 (1.3); 4.4541 (1.2); 4.4158 (1.3); 4.4017 (1.3); 4.3822 (0.7); 4.3682 (0.6); 3.3929 (2.7); 3.3677 (2.4); 2.9941 (2.9); 2.9213 (2.5); 2.8413 (12.6); 2.7158 (13.2); 2.7062 (1.4); 2.6599 (0.4); 2.1703 (0.4); 2.1600 (0.4); 2.1427 (0.8); 2.1259 (0.5); 2.1146 (0.4); 1.6004 (16.0); 1.0821 (0.6); 1.0678 (1.3); 1.0607 (1.6); 1.0541 (1.0); 1.0466 (1.0); 1.0391 (1.5); 1.0323 (1.5); 1.0184 (0.8); 0.8339 (0.8); 0.8198 (1.6); 0.8158 (1.7); 0.8127 (1.6); 0.8025 (1.6); 0.7981 (1.7); 0.7813 (0.6); 0.0486 (0.7); 0.0378 (22.2); 0.0268 (0.8)
3-15: $^1$H-NMR(300.2 MHz, CDCl3):
δ = 8.2283 (0.6); 8.2029 (0.6); 8.0706 (3.3); 8.0561 (0.7); 7.8436 (1.1); 7.8329 (1.2); 7.8269 (1.1); 7.8235 (1.3); 7.8146 (2.5); 7.8015 (0.6); 7.7940 (0.6); 7.7812 (2.5); 7.7722 (1.3); 7.7688 (1.2); 7.7631 (1.3); 7.7521 (1.3); 7.2986 (7.3); 7.2175 (0.3); 7.2119 (0.4); 7.1904 (0.8); 7.1851 (0.7); 7.1681 (0.8); 7.1616 (0.9); 7.1495 (1.6); 7.1146 (1.0); 7.1057 (0.7); 7.0871 (0.6); 7.0800 (0.9); 6.9841 (1.3); 6.9585 (1.0); 6.8660 (0.5); 6.8612 (0.5); 6.8392 (0.8); 6.8189 (0.4); 6.8131 (0.3); 5.3360 (1.4); 4.7020 (0.4); 4.6881 (0.3); 4.6781 (0.4); 4.4263 (0.4); 4.4124 (0.4); 4.3932 (1.1); 4.3794 (1.0); 4.3630 (1.1); 4.3467 (1.0); 4.3298 (0.4); 4.3135 (0.4); 3.2064 (1.5); 3.1830 (1.5); 2.9932 (5.3); 2.9216 (4.5); 2.9204 (4.4); 2.8405 (16.0); 2.7453 (0.7); 2.7189 (9.4); 2.1968 (9.4); 2.1739 (0.7); 2.1525 (0.7); 2.1291 (0.7); 2.1121 (0.4); 2.1006 (0.3); 2.0820 (0.6); 1.6299 (5.6); 1.2962 (0.4); 1.0600 (1.1); 1.0530 (1.2); 1.0425 (0.7); 1.0383 (0.6); 1.0314 (1.1); 1.0248 (1.1); 1.0140 (0.4); 1.0104 (0.4); 0.8251 (0.6); 0.8090 (1.2); 0.8028 (1.1); 0.7930 (1.3); 0.7860 (0.8); 0.7756 (0.4); 0.1072 (2.2); 0.0476 (0.4); 0.0369 (8.9)
3-16: $^1$H-NMR(300.2 MHz, CDCl3):
δ = 8.5044 (1.3); 8.4786 (1.3); 8.2554 (10.1); 7.8397 (1.0); 7.8320 (0.8); 7.8243 (2.0); 7.8160 (3.4); 7.8101 (10.9); 7.8014 (10.2); 7.7948 (3.0); 7.7866 (2.1); 7.7787 (0.7); 7.7718 (1.0); 7.7066 (2.7); 7.6685 (0.4); 7.6430 (1.8); 7.6206 (6.2); 7.6039 (0.6); 7.5861 (0.3); 7.5687 (1.3); 7.5593 (1.9); 7.5522 (1.3); 7.5449 (0.6); 7.5376 (1.0); 7.5299 (0.6); 7.2982 (12.4); 7.2596 (2.6); 7.2341 (3.0); 7.0138 (3.1); 6.9688 (1.7); 6.9432 (1.4); 4.6767 (0.4); 4.6481 (0.8); 4.6381 (0.7); 4.6256 (0.8); 4.5991 (0.4); 4.5149 (1.5); 4.5033 (1.3); 4.4825 (2.0); 4.4711 (1.7); 4.2888 (1.7); 4.2779 (1.7); 4.2565 (1.4); 4.2456 (1.3); 3.2916 (0.7); 3.2692 (0.7); 3.2458 (1.6); 3.2232 (1.5); 3.1837 (1.6); 3.1546 (1.6); 3.1376 (0.8); 3.1086 (0.7); 2.4490 (16.0); 2.3037 (15.1); 2.0451 (5.9); 1.6237 (1.1); 0.0481 (0.4); 0.0373 (12.0); 0.0264 (0.4)
3-17: $^1$H-NMR(300.2 MHz, CDCl3):
δ = 8.5172 (1.5); 8.4917 (1.4); 8.2586 (9.3); 8.0646 (0.6); 8.0551 (0.8); 7.8696 (0.4); 7.8382 (1.2); 7.8310 (0.9); 7.8227 (2.2); 7.8144 (3.9); 7.8086 (11.0); 7.8007 (10.7); 7.7867 (2.2); 7.7781 (1.3); 7.7711 (1.1); 7.7196 (2.8); 7.7050 (0.6); 7.6959 (0.5); 7.6857 (0.6); 7.6669 (0.4); 7.6409 (1.8); 7.6185 (6.6); 7.5974 (0.7); 7.5827 (0.4); 7.5646 (1.6); 7.5558 (2.4); 7.5488 (1.6); 7.5415 (0.9); 7.5334 (1.2); 7.5259 (1.0); 7.5201 (0.8); 7.2987 (21.4); 7.2652 (2.8); 7.2392 (3.2); 7.1880 (0.3); 6.9717 (0.4); 6.9096 (3.4); 6.8589 (1.9); 6.8527 (1.9); 6.8329 (1.7); 6.8273 (1.4); 4.6575 (0.4); 4.6279 (0.8); 4.6183 (0.7); 4.6079 (0.8); 4.5797 (0.4); 4.5057 (1.6); 4.4942 (1.4); 4.4734 (2.0); 4.4621 (1.7); 4.4249 (0.4); 4.2767 (1.8); 4.2659 (1.7); 4.2445 (1.5); 4.2337 (1.2); 3.7987 (0.3); 3.7766 (0.9); 3.7543 (1.2); 3.7321 (1.0); 3.7098 (0.4); 3.2814 (0.8); 3.2596 (0.9); 3.2355 (1.7); 3.2213 (1.0); 3.2133 (1.8); 3.1969 (1.8); 3.1717 (3.4); 3.1415 (1.8); 3.1248 (1.0); 3.0951 (0.8); 2.9954 (6.3); 2.9213 (5.5); 2.8406 (5.3); 2.6207 (9.5); 2.4963 (1.1); 2.4786 (0.7); 2.4518 (16.0); 2.4081 (0.4); 2.3767 (0.4); 2.3647 (2.0); 2.0977 (0.3); 1.8906 (0.8); 1.8740 (1.2); 1.8628 (1.3); 1.8461 (2.0); 1.8291 (1.4); 1.8180 (1.2); 1.8011 (0.8); 1.7872 (0.5); 1.7693 (0.4); 1.5298 (2.1); 1.5051 (4.7); 1.4802 (5.1); 0.9920 (1.1); 0.9772 (2.9); 0.9705 (3.2); 0.9564 (1.8); 0.9489 (3.2); 0.9423 (2.9); 0.9285 (1.4); 0.9107 (0.5); 0.9041 (0.5); 0.8822 (0.4); 0.8765 (0.4); 0.7041 (1.4); 0.6896 (3.3); 0.6837 (3.1); 0.6730 (3.1); 0.6676 (3.2); 0.6517 (1.2); 0.6304 (0.4); 0.6126 (0.4); 0.1075 (1.0); 0.0478 (0.8); 0.0370 (26.6); 0.0261 (1.1)
3-18: $^1$H-NMR(300.2 MHz, CDCl3):
δ = 8.5153 (0.4); 8.3645 (2.0); 8.3380 (2.0); 8.2481 (0.5); 8.2221 (12.5); 8.1835 (0.4); 8.0544 (1.2); 8.0320 (0.6); 7.8893 (0.3); 7.8796 (0.4); 7.8705 (0.6); 7.8413 (2.0); 7.8338 (1.7); 7.8265 (3.8); 7.8183 (5.4); 7.8117 (16.0); 7.8023 (15.4); 7.7958 (4.8); 7.7874 (3.6); 7.7725 (1.8); 7.7630 (0.6); 7.7458 (0.3); 7.7219 (0.7); 7.7113 (0.5); 7.6912 (4.0); 7.6497 (2.9); 7.6280 (9.2); 7.6119 (1.1); 7.5795 (1.0); 7.5622 (2.2); 7.5527 (3.2); 7.5456 (2.3); 7.5305 (1.9); 7.5233 (1.5); 7.5082 (1.0); 7.4973 (0.7); 7.4755 (0.5); 7.4458 (0.4); 7.4342 (0.4); 7.3721 (0.4); 7.3634 (0.4); 7.3538 (0.4); 7.3448 (0.6); 7.3314 (4.6); 7.3046 (6.2); 7.2988 (33.3); 7.2393 (0.5); 7.2295 (0.7); 7.2179 (0.5); 7.2109 (0.6); 7.1984 (0.6); 7.0501 (5.4); 7.0443 (5.6); 7.0276 (0.9); 6.9972 (0.5); 6.9092 (2.9); 6.9033 (2.8); 6.8830 (2.6); 6.8772 (2.5); 4.8343 (0.6); 4.8215 (0.9); 4.8097 (1.4); 4.7972 (1.3); 4.7844 (1.5); 4.7712 (1.0); 4.7589 (0.6); 4.7470 (0.4); 4.5040 (1.9); 4.4907 (1.8); 4.4708 (3.0); 4.4575 (2.7); 4.4039 (0.5); 4.3756 (2.7); 4.3637 (2.8); 4.3423 (1.9); 4.3305 (1.8); 3.7984 (0.6); 3.7764 (1.7); 3.7541 (2.3); 3.7318 (1.8); 3.7096 (0.8); 3.4247 (1.4); 3.3983 (1.3); 3.3785 (2.5); 3.3520 (2.7); 3.3253 (0.3); 3.2891 (2.4); 3.2652 (2.5); 3.2428 (1.5); 3.2174 (2.0); 3.1917 (3.2); 3.1669 (3.3); 3.1421 (1.2); 2.9949 (9.6); 2.9666 (0.6); 2.9204 (8.4); 2.8396 (8.7); 2.6407 (9.4); 2.0914 (0.3); 2.0646 (0.3); 2.0425 (0.5); 1.9762 (0.5); 1.9418 (0.5); 1.9280 (0.5); 1.9139 (0.6); 1.8976 (0.6); 1.8809 (1.0); 1.8645 (1.5); 1.8534 (1.6); 1.8364 (2.6); 1.8197 (1.7); 1.8088 (1.6); 1.7919 (1.1); 1.7652 (0.4); 1.5233 (3.6); 1.4985 (8.6); 1.4737 (10.0); 1.3849 (0.4); 1.2901 (0.5); 1.0269 (1.5); 1.0112 (4.0); 1.0049 (4.5); 0.9899 (2.4); 0.9831 (4.5); 0.9768 (4.3); 0.9621 (2.1); 0.9545 (0.9); 0.9470 (0.8); 0.9322 (0.5); 0.9254 (0.5); 0.9175 (0.5); 0.7240 (0.4); 0.6990 (1.9); 0.6835 (5.0); 0.6781 (4.5); 0.6672 (4.4); 0.6616 (5.2); 0.6455 (1.9); 0.6253 (0.8); 0.6178 (0.6); 0.1064 (1.5); 0.0470 (0.9); 0.0361 (40.4); 0.0254 (2.2)
3-19: $^1$H-NMR(300.2 MHz, CDCl3):
δ = 8.3834 (1.0); 8.3572 (1.0); 8.2244 (6.6); 8.2184 (1.0); 8.0533 (0.7); 8.0347 (0.4); 7.8415 (1.0); 7.8338 (0.8); 7.8267 (2.0); 7.8186 (2.8); 7.8118 (8.5); 7.8023 (8.3); 7.7958 (2.7); 7.7874 (2.0); 7.7725 (1.0); 7.7187 (0.4); 7.7010 (2.1); 7.6742 (0.5); 7.6484 (1.4); 7.6268 (4.9); 7.6117 (0.7); 7.5862 (0.5); 7.5803 (0.5); 7.5682 (1.3); 7.5593 (1.8); 7.5522 (1.2); 7.5458 (0.8); 7.5372 (1.0); 7.4990 (0.5); 7.3813 (2.2); 7.3551 (2.7); 7.2988 (14.5); 7.2731 (0.4); 7.2231 (2.6); 7.2176 (3.0); 7.1983 (0.5); 7.1925 (0.4); 7.1720 (0.4); 7.1631 (0.4); 7.0740 (1.5);

TABLE 8-continued 7.0684 (1.4); 7.0479 (1.3); 7.0421 (1.2); 4.8313 (0.5); 4.8191 (0.8); 4.8063 (0.7); 4.7937 (0.7); 4.7806 (0.5); 4.5133 (1.0); 4.4996 (0.9); 4.4798 (1.5); 4.4662 (1.4); 4.4027 (0.4); 4.3904 (1.4); 4.3786 (1.5); 4.3571 (0.9); 4.3453 (0.9); 3.7957 (0.4); 3.7734 (0.9); 3.7511 (1.2); 3.7289 (0.9); 3.7067 (0.4); 3.4394 (0.8); 3.4129 (0.8); 3.3932 (1.3); 3.3668 (1.3); 3.3043 (1.3); 3.2800 (1.3); 3.2581 (0.8); 3.2337 (0.7); 3.2126 (0.6); 3.1879 (1.7); 3.1631 (1.7); 3.1383 (0.6); 2.9943 (5.7); 2.9193 (5.0); 2.8861 (0.9); 2.8632 (1.2); 2.8394 (6.1); 2.8170 (0.5); 2.6203 (5.5); 1.5190 (1.9); 1.4943 (4.2); 1.4697 (5.3); 1.4517 (4.0); 1.2950 (0.9); 1.2796 (0.7); 1.2721 (1.0); 1.2459 (16.0); 1.2228 (15.7); 1.2064 (1.5); 1.2000 (1.2); 1.1897 (1.0); 1.1832 (1.0); 1.1769 (0.9); 0.9453 (0.4); 0.1066 (0.7); 0.0467 (0.6); 0.0359 (17.5); 0.0250 (0.6)

3-20: $^{1}$H-NMR(300.2 MHz, CDCl3):

δ = 8.4697 (0.7); 8.4436 (0.7); 7.9844 (5.3); 7.7663 (1.0); 7.7580 (0.8); 7.7517 (1.8); 7.7439 (2.2); 7.7359 (7.2); 7.7257 (7.0); 7.7180 (2.0); 7.7100 (1.8); 7.7038 (0.8); 7.6954 (1.0); 7.5276 (0.6); 7.5015 (1.8); 7.4751 (1.4); 7.4450 (2.0); 7.3938 (1.6); 7.3695 (2.1); 7.3469 (0.9); 7.3432 (0.8); 7.2979 (3.9); 7.1631 (1.9); 7.1376 (2.2); 6.9112 (2.3); 6.8547 (1.3); 6.8273 (2.2); 6.6395 (2.4); 6.4518 (1.2); 5.2682 (1.3); 4.5955 (0.4); 4.5852 (0.6); 4.5716 (0.6); 4.5593 (0.6); 4.5462 (0.4); 4.4073 (1.0); 4.3950 (0.9); 4.3752 (1.4); 4.3629 (1.3); 4.2464 (1.3); 4.2346 (1.3); 4.2144 (1.0); 4.2026 (0.9); 3.5649 (4.7); 3.3193 (0.7); 3.1593 (0.3); 3.1370 (1.5); 3.1183 (1.8); 3.1149 (1.8); 3.0922 (1.4); 3.0732 (0.3); 2.7622 (1.1); 2.6423 (16.0); 2.3490 (11.7); 2.2027 (11.1); 2.0010 (0.9); 1.2133 (0.5); −0.0536 (3.9)

3-21: $^{1}$H-NMR(300.2 MHz, CDCl3):

δ = 8.5383 (1.0); 8.5126 (1.2); 8.2637 (6.8); 8.0688 (0.4); 8.0535 (0.8); 7.8386 (0.8); 7.8321 (0.7); 7.8237 (1.6); 7.8157 (2.6); 7.8095 (8.0); 7.8012 (7.9); 7.7871 (1.7); 7.7802 (1.0); 7.7718 (0.9); 7.7630 (0.4); 7.7298 (2.1); 7.7134 (0.6); 7.7035 (0.4); 7.6953 (0.5); 7.6850 (0.4); 7.6403 (1.4); 7.6178 (4.7); 7.5955 (0.5); 7.5909 (0.5); 7.5723 (1.0); 7.5635 (1.8); 7.5564 (1.2); 7.5412 (1.0); 7.5050 (0.4); 7.3062 (2.1); 7.2988 (12.5); 7.2806 (2.4); 7.0620 (2.5); 7.0464 (0.4); 7.0309 (1.5); 7.0247 (1.4); 7.0050 (1.2); 6.9989 (1.2); 4.6443 (0.6); 4.6339 (0.5); 4.6263 (0.6); 4.6185 (0.6); 4.5212 (1.2); 4.5094 (1.0); 4.4889 (1.5); 4.4772 (1.2); 4.2919 (1.2); 4.2812 (1.2); 4.2596 (1.0); 4.2491 (0.9); 3.7971 (0.3); 3.7748 (0.8); 3.7525 (1.2); 3.7303 (0.9); 3.7080 (0.4); 3.2940 (0.6); 3.2722 (0.6); 3.2479 (1.2); 3.2264 (1.2); 3.2152 (0.7); 3.1902 (1.8); 3.1807 (1.4); 3.1655 (1.8); 3.1509 (1.3); 3.1409 (0.8); 3.1355 (0.7); 3.1048 (0.6); 2.9949 (6.2); 2.9197 (5.3); 2.8876 (1.2); 2.8646 (1.4); 2.8400 (6.3); 2.8190 (0.5); 2.6042 (7.6); 2.4936 (1.1); 2.4803 (11.5); 2.4626 (0.6); 2.4357 (0.4); 2.3897 (1.5); 1.5205 (1.9); 1.4958 (4.2); 1.4712 (5.2); 1.4532 (3.7); 1.2988 (0.8); 1.2859 (0.7); 1.2757 (1.3); 1.2620 (16.0); 1.2390 (15.6); 1.2178 (0.9); 1.2052 (1.2); 1.1983 (1.2); 1.1822 (1.1); 1.1753 (1.1); 0.1075 (0.6); 0.0474 (0.5); 0.0366 (14.6); 0.0257 (0.6)

3-22: $^{1}$H-NMR(300.2 MHz, CDCl3):

δ = 8.4361 (0.7); 8.4090 (0.7); 8.2269 (4.4); 7.8510 (0.5); 7.8437 (0.4); 7.8358 (1.1); 7.8276 (1.8); 7.8214 (5.4); 7.8128 (5.3); 7.7983 (1.1); 7.7905 (0.4); 7.7832 (0.5); 7.7082 (1.4); 7.6522 (1.0); 7.6301 (3.2); 7.5558 (0.6); 7.5470 (1.1); 7.5399 (0.7); 7.5244 (0.7); 7.4510 (1.6); 7.4235 (2.0); 7.3909 (1.9); 7.3839 (2.1); 7.2990 (8.4); 7.2317 (1.3); 7.2246 (1.2); 7.2043 (1.0); 7.1972 (0.9); 4.8258 (0.5); 4.8132 (0.5); 4.8002 (0.6); 4.7875 (0.3); 4.5140 (0.7); 4.5016 (0.7); 4.4807 (1.0); 4.4684 (0.9); 4.3435 (1.0); 4.3321 (1.0); 4.3104 (0.7); 4.2989 (0.7); 3.4610 (0.5); 3.4343 (0.5); 3.4151 (0.9); 3.3885 (0.9); 3.3165 (0.9); 3.2920 (0.9); 3.2705 (0.5); 3.2460 (0.5); 1.6008 (16.0); 1.2972 (0.9); 0.9194 (0.7); 0.1080 (2.2); 0.0376 (6.8)

3-23: $^{1}$H-NMR(300.2 MHz, CDCl3):

δ = 10.3413 (0.5); 8.7359 (0.5); 8.7298 (0.5); 8.7114 (0.5); 8.7038 (0.5); 8.6767 (3.8); 8.6706 (3.9); 8.6511 (3.8); 8.6433 (3.9); 8.4418 (1.3); 8.4155 (1.3); 8.2757 (0.9); 8.2584 (10.0); 7.9782 (3.0); 7.9711 (4.2); 7.9640 (2.6); 7.8533 (1.5); 7.8446 (1.1); 7.8390 (2.3); 7.8312 (2.9); 7.8228 (8.5); 7.8111 (8.6); 7.8029 (2.9); 7.7951 (2.7); 7.7896 (1.6); 7.7809 (2.5); 7.7694 (0.7); 7.7570 (1.0); 7.7484 (0.5); 7.7391 (0.4); 7.7282 (0.4); 7.2989 (23.3); 7.2605 (2.6); 7.2351 (3.1); 7.0281 (3.1); 6.9991 (1.8); 6.9679 (1.5); 6.9404 (0.6); 6.8727 (0.3); 5.3379 (4.1); 4.6678 (0.3); 4.6383 (0.8); 4.6269 (0.8); 4.6120 (0.8); 4.5897 (0.6); 4.5368 (1.6); 4.5254 (1.3); 4.5042 (1.9); 4.4928 (1.6); 4.2507 (1.7); 4.2403 (1.8); 4.2181 (1.4); 4.2077 (1.3); 3.2966 (0.8); 3.2751 (0.8); 3.2511 (1.7); 3.2290 (1.7); 3.1708 (1.6); 3.1409 (1.5); 3.1251 (0.8); 3.0949 (0.8); 2.4561 (16.0); 2.3220 (15.1); 2.2705 (2.4); 2.2573 (2.8); 1.6017 (12.0); 0.0485 (1.0); 0.0378 (30.5); 0.0268 (1.1)

3-24: $^{1}$H-NMR(300.2 MHz, CDCl3):

δ = 8.6979 (1.3); 8.6890 (1.3); 8.4932 (0.6); 8.4672 (0.6); 8.2986 (4.6); 8.2361 (0.6); 8.2166 (0.5); 8.2090 (1.6); 8.1998 (1.6); 7.8517 (0.4); 7.8464 (0.4); 7.8136 (16.0); 7.7975 (0.5); 7.7936 (0.4); 7.7796 (0.3); 7.2988 (12.2); 7.2799 (1.3); 7.2546 (1.5); 7.0399 (2.0); 7.0234 (1.0); 6.9976 (0.7); 5.3381 (1.6); 4.6400 (0.3); 4.6294 (0.4); 4.6128 (0.4); 4.6032 (0.4); 4.5526 (0.8); 4.5414 (0.6); 4.5205 (0.9); 4.5093 (0.7); 4.1878 (0.8); 4.1781 (0.8); 4.1559 (0.7); 4.1461 (0.6); 3.3000 (0.4); 3.2795 (0.4); 3.2542 (0.7); 3.2339 (0.7); 3.1476 (0.8); 3.1160 (0.7); 3.1016 (0.4); 3.0704 (0.4); 2.4713 (8.5); 2.4597 (1.1); 2.3247 (8.2); 1.6005 (1.8); 1.3154 (0.5); 1.2945 (0.6); 0.0487 (0.5); 0.0378 (15.3); 0.0269 (0.5)

3-25: $^{1}$H-NMR(300.2 MHz, CDCl3):

δ = 7.8863 (1.7); 7.8756 (2.0); 7.8698 (1.8); 7.8660 (2.2); 7.8573 (4.5); 7.8425 (1.8); 7.8281 (4.4); 7.8191 (2.2); 7.8158 (1.9); 7.8100 (2.0); 7.7989 (1.8); 7.4866 (2.8); 7.4801 (3.0); 7.3678 (2.1); 7.3403 (4.1); 7.3100 (1.5); 7.2989 (18.0); 7.2463 (1.9); 7.2398 (1.8); 7.2190 (1.3); 7.2125 (1.2); 7.0709 (3.0); 7.0588 (1.8); 7.0557 (1.9); 7.0511 (1.9); 7.0460 (3.1); 7.0242 (0.4); 6.8095 (0.7); 6.7968 (0.6); 6.7884 (1.1); 6.7773 (1.2); 6.7660 (0.6); 6.7555 (0.6); 5.3380 (1.8); 4.8528 (0.5); 4.8445 (0.6); 4.8250 (0.6); 4.6138 (1.1); 4.6002 (1.0); 4.5789 (1.4); 4.5656 (1.2); 4.3315 (1.3); 4.3200 (1.3); 4.2968 (1.1); 4.2853 (1.0); 3.4323 (0.7); 3.4025 (0.7); 3.3853 (1.2); 3.3557 (1.2); 3.2941 (1.2); 3.2729 (1.2); 3.2474 (0.7); 3.2264 (0.6); 2.8395 (1.1); 2.4032 (16.0); 2.3576 (1.1); 2.0614 (0.5); 2.0505 (0.6); 2.0332 (1.1); 2.0161 (0.6); 2.0050 (0.6); 1.6025 (15.2); 1.2916 (0.4); 1.0292 (0.7); 1.0150 (1.6); 1.0077 (1.9); 0.9935 (1.2); 0.9863 (1.7); 0.9793 (1.9); 0.9653 (0.9); 0.7820 (0.9); 0.7674 (2.1); 0.7625 (2.2); 0.7503 (2.1); 0.7448 (2.4); 0.7289 (0.8); 0.1073 (7.5); 0.0482 (0.8); 0.0375 (22.5); 0.0266 (0.9)

3-26: $^{1}$H-NMR(300.2 MHz, $d_6$-DMSO):

δ = 7.9029 (1.6); 7.1243 (0.4); 7.1184 (0.5); 3.3492 (16.0); 2.5345 (0.8); 2.5287 (1.7); 2.5227 (2.4); 2.5167 (1.7); 2.5109 (0.8); 2.2965 (1.6); 0.0206 (1.6)

3-27: $^{1}$H-NMR(300.2 MHz, CDCl3):

δ = 8.4821 (0.4); 8.4555 (0.4); 8.2039 (2.9); 8.0482 (1.8); 7.8413 (0.7); 7.8316 (0.6); 7.8280 (0.8); 7.8257 (0.8); 7.8201 (1.0); 7.8117 (2.3); 7.8051 (1.1); 7.7992 (1.3); 7.7927 (2.2); 7.7845 (1.1); 7.7791 (0.8); 7.7759 (0.8); 7.7721 (0.9); 7.7629 (1.0); 7.7533 (0.4); 7.3814 (0.5); 7.3554 (1.1); 7.3292 (0.7); 7.2988 (3.2); 7.2373 (0.8); 7.2118 (1.0); 7.0975 (0.5); 7.0926 (0.5); 7.0897 (0.6); 7.0695 (0.7); 7.0632 (1.1); 7.0384 (0.7); 7.0229 (0.9); 7.0164 (1.1); 7.0102 (0.6); 6.9931 (1.1); 6.9646 (0.3); 6.9334 (0.6); 6.9091 (0.6); 4.6506 (0.4); 4.6237 (0.4); 4.4819 (0.4); 4.4702 (0.4); 4.4496 (0.6); 4.4379 (0.6); 4.3193 (0.6); 4.3075 (0.6); 4.2871 (0.5); 4.2753 (0.4); 3.2222 (0.4); 3.2058 (1.0); 3.1988 (1.1); 3.1820 (1.0); 3.1723 (1.0); 2.9944 (14.4); 2.9134 (16.0); 2.8347 (11.5); 2.4264 (5.0); 2.3482 (1.2); 2.3261 (0.4); 2.2939 (4.7); 2.2345 (1.1); 1.9470 (0.5); 1.5072 (1.0); 1.4820 (4.7);

TABLE 8-continued 1.4584 (3.9); 1.4479 (3.3); 1.4257 (3.0); 1.0156 (0.7); 1.0083 (1.1); 0.9870 (0.8); 0.9808 (1.1); 0.7684 (0.7); 0.7601 (0.6); 0.7519 (1.1); 0.7462 (0.6); 0.7425 (0.6); 0.7360 (0.6); 0.0317 (3.6)
3-28: $^{1}$H-NMR(300.2 MHz, CDCl3):
δ = 8.4990 (0.5); 8.4731 (0.5); 8.2278 (3.6); 7.8700 (0.4); 7.8442 (0.8); 7.8319 (1.0); 7.8230 (1.2); 7.8148 (2.8); 7.8079 (1.3); 7.8031 (1.2); 7.7960 (2.7); 7.7877 (1.1); 7.7822 (0.8); 7.7792 (0.9); 7.7665 (0.8); 7.5092 (0.4); 7.4830 (1.1); 7.4567 (1.2); 7.2989 (16.2); 7.2561 (1.0); 7.2490 (1.6); 7.2237 (1.7); 7.1938 (1.0); 7.1660 (0.8); 7.0652 (0.4); 7.0057 (1.3); 6.9536 (0.7); 6.9277 (0.6); 4.6582 (0.4); 4.6322 (0.4); 4.4994 (0.6); 4.4877 (0.5); 4.4669 (0.8); 4.4554 (0.7); 4.3172 (0.7); 4.3057 (0.7); 4.2850 (0.6); 4.2734 (0.5); 4.1726 (0.4); 4.1488 (0.4); 3.2266 (0.8); 3.2038 (1.4); 3.1764 (0.8); 2.4747 (1.0); 2.4394 (6.4); 2.3484 (0.9); 2.3013 (6.0); 2.0840 (1.8); 1.5876 (16.0); 1.5705 (0.9); 1.5638 (1.0); 1.5440 (0.4); 1.5266 (0.4); 1.5073 (0.8); 1.5001 (1.0); 1.4801 (0.4); 1.3221 (0.6); 1.2983 (1.5); 1.2745 (0.5); 1.1723 (0.5); 1.1674 (1.0); 1.1602 (1.0); 1.1432 (0.6); 1.1378 (1.2); 1.1302 (0.9); 0.9207 (0.8); 0.0495 (0.7); 0.0387 (19.3); 0.0277 (0.7)
3-29: $^{1}$H-NMR(300.2 MHz, CDCl3):
δ = 8.2631 (1.1); 8.2369 (1.1); 8.0329 (5.4); 7.8263 (1.7); 7.8151 (2.0); 7.8100 (1.9); 7.8060 (2.2); 7.7970 (4.5); 7.7834 (2.3); 7.7698 (4.5); 7.7613 (2.1); 7.7575 (2.0); 7.7518 (2.0); 7.7409 (1.7); 7.3521 (2.3); 7.3258 (2.6); 7.2992 (2.2); 7.2505 (0.6); 7.2453 (0.7); 7.2231 (1.4); 7.2006 (1.0); 7.1951 (1.0); 7.1454 (1.1); 7.1187 (1.8); 7.0919 (0.9); 7.0364 (2.6); 7.0307 (2.8); 6.8586 (2.2); 6.8524 (1.7); 6.8378 (1.7); 6.8326 (2.1); 6.8262 (1.5); 6.8174 (0.8); 6.8122 (0.7); 5.3275 (0.9); 4.8378 (0.5); 4.8247 (0.8); 4.8118 (0.7); 4.7991 (0.8); 4.7858 (0.5); 4.4842 (0.5); 4.4706 (0.5); 4.4509 (1.8); 4.4340 (2.5); 4.4190 (1.8); 4.3997 (0.6); 4.3855 (0.5); 3.3667 (3.3); 3.3421 (3.2); 2.8345 (6.3); 2.6990 (16.0); 2.6037 (0.4); 2.1628 (0.5); 2.1518 (0.6); 2.1347 (1.0); 2.1237 (0.5); 2.1174 (0.6); 2.1067 (0.6); 2.0755 (0.5); 1.8449 (0.6); 1.8335 (0.6); 1.8170 (1.2); 1.8003 (0.7); 1.7891 (0.7); 1.7718 (0.4); 1.7563 (4.3); 1.2901 (0.4); 1.0714 (0.6); 1.0560 (2.0); 1.0496 (2.1); 1.0354 (1.3); 1.0278 (2.1); 1.0212 (2.1); 1.0074 (1.0); 0.9964 (0.9); 0.9804 (2.1); 0.9742 (2.2); 0.9589 (1.2); 0.9524 (2.2); 0.9461 (2.0); 0.9315 (1.0); 0.8273 (0.9); 0.8089 (2.4); 0.7958 (2.2); 0.7906 (2.4); 0.7743 (0.8); 0.6810 (0.9); 0.6651 (2.6); 0.6599 (2.3); 0.6492 (2.2); 0.6432 (2.7); 0.6272 (0.8); 0.0330 (1.0)
3-30: $^{1}$H-NMR(300.2 MHz, CDCl3):
δ = 7.8866 (0.9); 7.8755 (0.9); 7.8701 (0.8); 7.8663 (1.0); 7.8575 (2.1); 7.8425 (0.7); 7.8277 (2.1); 7.8189 (1.0); 7.8152 (0.9); 7.8098 (0.9); 7.7985 (0.9); 7.4293 (1.1); 7.4017 (1.4); 7.3361 (1.7); 7.3289 (1.6); 7.3121 (0.6); 7.2988 (11.9); 7.1049 (0.8); 7.0978 (0.8); 7.0775 (0.8); 7.0688 (1.8); 7.0577 (0.9); 7.0547 (0.8); 7.0433 (1.6); 6.8091 (0.3); 6.7877 (0.6); 6.7765 (0.5); 4.6153 (0.5); 4.6019 (0.5); 4.5807 (0.7); 4.5674 (0.6); 4.3340 (0.6); 4.3224 (0.6); 4.2994 (0.5); 4.2878 (0.5); 3.4448 (0.3); 3.3979 (0.6); 3.3686 (0.6); 3.3091 (0.6); 3.2879 (0.6); 3.2621 (0.3); 2.4047 (8.1); 2.0826 (0.8); 2.0313 (0.5); 1.5965 (16.0); 1.3209 (0.4); 1.2972 (0.8); 1.0284 (0.4); 1.0143 (0.8); 1.0069 (0.9); 0.9927 (0.5); 0.9855 (0.8); 0.9785 (0.9); 0.9645 (0.4); 0.9199 (0.5); 0.7805 (0.4); 0.7659 (1.0); 0.7598 (1.0); 0.7488 (0.9); 0.7429 (1.0); 0.7273 (0.4); 0.1075 (0.7); 0.0488 (0.4); 0.0379 (13.7); 0.0270 (0.5)
3-31: $^{1}$H-NMR(300.2 MHz, CDCl3):
δ = 8.3987 (0.7); 8.3709 (0.7); 8.1721 (3.4); 8.0509 (2.0); 7.8531 (0.8); 7.8435 (0.7); 7.8402 (0.9); 7.8374 (1.0); 7.8318 (1.3); 7.8235 (2.6); 7.8170 (1.4); 7.8116 (1.3); 7.8051 (2.6); 7.7970 (1.1); 7.7913 (0.9); 7.7884 (0.9); 7.7755 (0.8); 7.4219 (1.3); 7.4110 (0.4); 7.3947 (2.1); 7.3831 (0.4); 7.3710 (2.1); 7.3649 (2.0); 7.3426 (0.8); 7.2988 (5.7); 7.1704 (1.0); 7.1633 (0.9); 7.1431 (0.8); 7.1360 (0.7); 7.0860 (0.8); 7.0786 (1.4); 7.0586 (0.6); 7.0507 (1.3); 7.0106 (1.0); 7.0042 (1.3); 6.9977 (0.7); 4.8128 (0.3); 4.8010 (0.3); 4.7890 (0.4); 4.4865 (0.4); 4.4743 (0.5); 4.4531 (0.8); 4.4410 (0.7); 4.3817 (0.8); 4.3691 (0.8); 4.3485 (0.5); 4.3359 (0.4); 3.7742 (0.4); 3.7605 (0.4); 3.7520 (0.6); 3.7384 (0.6); 3.7300 (0.5); 3.7162 (0.4); 3.3757 (0.8); 3.3465 (1.2); 3.3215 (0.7); 3.2256 (0.8); 3.2113 (0.8); 3.2010 (0.8); 3.1865 (0.8); 3.1763 (0.3); 2.9972 (16.0); 2.9679 (1.3); 2.9160 (13.5); 2.8344 (13.6); 2.0459 (0.4); 1.9732 (0.3); 1.9564 (0.6); 1.9396 (0.4); 1.9286 (0.3); 1.5261 (1.7); 1.4985 (7.0); 1.4759 (7.3); 1.4637 (6.3); 1.4415 (6.0); 1.0278 (0.9); 1.0207 (1.2); 0.9992 (0.9); 0.9930 (1.2); 0.9757 (0.3); 0.7739 (0.8); 0.7676 (1.0); 0.7598 (1.0); 0.7575 (1.0); 0.7508 (0.9); 0.7437 (0.7); 0.1032 (0.4); 0.0322 (6.1)
3-32: $^{1}$H-NMR(300.2 MHz, CDCl3):
δ = 8.3902 (0.3); 8.3776 (0.4); 8.2485 (2.0); 8.2445 (1.9); 7.8314 (0.3); 7.8249 (0.4); 7.8170 (0.6); 7.8093 (0.9); 7.8021 (2.0); 7.7950 (2.1); 7.7903 (2.1); 7.7857 (2.0); 7.7703 (0.6); 7.7595 (0.3); 7.3966 (0.3); 7.3148 (0.3); 7.3103 (0.6); 7.2983 (47.4); 7.2862 (0.5); 7.2716 (0.6); 7.2609 (0.9); 7.2466 (0.6); 7.2339 (1.3); 7.2055 (0.6); 7.1788 (0.4); 7.1580 (0.5); 6.9986 (1.0); 6.9475 (0.6); 6.9274 (0.4); 4.5010 (0.4); 4.4783 (0.4); 4.4678 (0.5); 4.4585 (0.3); 4.3120 (0.6); 4.3003 (0.4); 4.2795 (0.4); 3.2424 (0.4); 3.2248 (0.9); 3.1982 (0.5); 2.8969 (0.3); 2.4529 (2.9); 2.4436 (2.9); 2.2904 (3.9); 1.9406 (0.4); 1.7484 (0.4); 1.7340 (0.3); 1.7208 (0.4); 1.7062 (0.3); 1.5764 (16.0); 0.0486 (2.1); 0.0470 (1.3); 0.0378 (65.6); 0.0301 (2.3); 0.0286 (2.2); 0.0270 (2.6); 0.0199 (0.5); 0.0169 (0.4)
3-33: $^{1}$H-NMR(300.2 MHz, CDCl3):
δ = 8.5695 (0.9); 8.5428 (0.9); 8.1512 (5.4); 7.8535 (1.6); 7.8437 (1.4); 7.8412 (1.7); 7.8373 (1.7); 7.8325 (2.2); 7.8239 (4.4); 7.8142 (2.1); 7.8123 (2.0); 7.8026 (4.3); 7.7939 (1.9); 7.7891 (1.6); 7.7852 (1.6); 7.7829 (1.3); 7.7730 (1.7); 7.6511 (1.7); 7.6487 (1.8); 7.5778 (2.8); 7.5602 (3.9); 7.5149 (0.3); 7.5031 (0.9); 7.4951 (0.9); 7.4864 (1.0); 7.4805 (1.0); 7.4726 (0.5); 7.4640 (0.4); 7.2987 (14.7); 6.9608 (0.8); 6.9335 (1.2); 6.9084 (1.9); 6.8146 (2.2); 6.7873 (1.6); 4.9746 (0.4); 4.9615 (0.5); 4.9564 (0.6); 4.9450 (0.6); 4.9350 (0.5); 4.9294 (0.5); 4.9171 (0.4); 4.6717 (0.7); 4.6535 (0.7); 4.6372 (1.6); 4.6191 (1.4); 4.5929 (1.5); 4.5742 (1.5); 4.5586 (0.8); 4.5397 (0.7); 4.5071 (0.9); 4.4947 (0.9); 4.4748 (1.2); 4.4625 (1.1); 4.3257 (1.2); 4.3079 (1.1); 4.2932 (0.9); 4.2756 (0.8); 2.7625 (16.0); 2.3243 (0.7); 2.2625 (10.2); 2.2419 (0.8); 2.0839 (1.1); 2.0382 (10.5); 2.0223 (0.9); 1.6177 (0.5); 1.2977 (0.6); 0.1083 (0.7); 0.0488 (0.7); 0.0380 (18.0); 0.0289 (0.5); 0.0271 (0.7)
3-34: $^{1}$H-NMR(499.9 MHz, CDCl3):
δ = 8.5428 (1.0); 8.5272 (1.0); 8.0976 (5.5); 7.8042 (1.8); 7.7977 (2.1); 7.7941 (1.8); 7.7923 (2.2); 7.7867 (4.2); 7.7784 (0.9); 7.7727 (0.9); 7.7647 (4.1); 7.7594 (2.0); 7.7577 (1.9); 7.7538 (2.1); 7.7475 (1.9); 7.6265 (1.9); 7.5520 (1.9); 7.5489 (1.5); 7.5434 (3.7); 7.5418 (4.3); 7.4779 (0.8); 7.4730 (0.8); 7.4702 (1.0); 7.4664 (1.1); 7.4600 (0.7); 7.4548 (0.5); 7.2610 (6.7); 7.1930 (0.4); 7.1860 (4.1); 7.1817 (1.4); 7.1724 (1.3); 7.1680 (4.7); 7.1612 (0.5); 6.8142 (0.4); 6.8073 (4.5); 6.8029 (1.5); 6.7937 (1.3); 6.7893 (4.2); 6.7824 (0.4); 5.2976 (12.8); 4.8559 (0.4); 4.8477 (0.5); 4.8446 (0.6); 4.8377 (0.6); 4.8329 (0.6); 4.8297 (0.6); 4.8216 (0.4); 4.6262 (1.1); 4.6160 (1.0); 4.6054 (1.4); 4.5952 (1.3); 4.5027 (1.1); 4.4948 (1.2); 4.4910 (1.5); 4.4833 (1.5); 4.4796 (1.7); 4.4758 (1.4); 4.4701 (1.2); 4.4588 (1.0); 4.2768 (1.2); 4.2651 (1.2); 4.2575 (1.1); 4.2459 (1.0); 4.1279 (0.5); 4.1136 (0.5); 2.7296 (16.0); 2.0432 (2.2); 1.5759 (3.8); 1.2726 (0.6); 1.2583 (1.2); 1.2440 (0.6); −0.0002 (8.6); −0.0067 (0.4)
3-35: $^{1}$H-NMR(300.2 MHz, CDCl3):
δ = 8.5282 (1.4); 8.5031 (1.4); 8.2283 (9.2); 7.8325 (0.5); 7.8299 (0.5); 7.8120 (1.7); 7.8004 (13.8); 7.7984 (13.2); 7.7868 (1.6); 7.7687 (0.5); 7.6989 (2.7); 7.6205 (1.6); 7.6000 (6.2); 7.5858 (0.7); 7.5782 (0.8); 7.5716

TABLE 8-continued (0.5); 7.5619 (1.4); 7.5511 (1.6); 7.5443 (1.3); 7.5305 (0.9); 7.5230 (0.6); 7.4021 (2.7); 7.3760 (3.1); 7.2983 (3.6); 6.9851 (3.1); 6.9668 (1.8); 6.9404 (1.4); 4.7335 (1.3); 4.7178 (1.5); 4.6995 (1.5); 4.6838 (1.9); 4.5878 (0.6); 4.5756 (0.8); 4.5637 (0.8); 4.5540 (0.8); 4.5434 (0.6); 4.4162 (1.7); 4.4036 (1.6); 4.3822 (1.5); 4.3697 (1.3); 3.5093 (1.0); 3.4891 (1.0); 3.4626 (1.9); 3.4426 (1.7); 3.3731 (1.8); 3.3489 (1.8); 3.3264 (1.0); 3.3022 (1.0); 2.3679 (16.0); 2.2643 (15.3); 2.0399 (4.0); 0.0372 (4.3)
3-36: $^{1}$H-NMR(300.2 MHz, CDCl3):
δ = 8.2432 (0.3); 7.8764 (1.4); 7.8694 (1.7); 7.8655 (1.9); 7.8598 (2.3); 7.8562 (2.4); 7.8480 (4.3); 7.8406 (3.9); 7.8340 (2.4); 7.8286 (2.3); 7.8211 (4.0); 7.8165 (4.4); 7.8081 (2.7); 7.8030 (3.0); 7.7920 (2.0); 7.7872 (1.8); 7.7735 (0.6); 7.7002 (0.4); 7.6352 (0.8); 7.6082 (0.8); 7.5411 (0.8); 7.5138 (0.9); 7.2986 (26.5); 7.2825 (0.4); 7.2708 (0.6); 7.2574 (2.4); 7.2490 (2.0); 7.2317 (3.1); 7.2245 (2.2); 7.2135 (1.3); 7.2067 (0.9); 7.1492 (1.2); 7.1228 (2.5); 7.0961 (1.5); 7.0625 (1.2); 7.0402 (1.5); 7.0130 (2.3); 6.9953 (1.8); 6.9755 (1.3); 6.9494 (2.0); 6.9247 (0.8); 4.7062 (0.5); 4.6947 (0.7); 4.6794 (0.8); 4.6671 (0.9); 4.6547 (0.8); 4.6423 (0.6); 4.6287 (1.2); 4.6183 (0.8); 4.6081 (1.0); 4.5957 (1.6); 4.5842 (0.9); 4.5742 (1.0); 4.5632 (0.8); 4.2118 (0.9); 4.2015 (1.0); 4.1921 (0.9); 4.1807 (1.2); 4.1679 (0.9); 4.1575 (1.0); 4.1478 (0.8); 3.3161 (0.5); 3.3021 (0.6); 3.2937 (0.6); 3.2702 (1.0); 3.2557 (1.0); 3.2474 (1.0); 3.2328 (0.8); 3.1625 (1.4); 3.1346 (1.4); 3.1172 (0.8); 3.0879 (0.7); 2.8309 (0.5); 2.8038 (0.6); 2.7912 (1.0); 2.7633 (1.0); 2.7510 (0.6); 2.7229 (0.6); 2.6022 (4.0); 2.5343 (3.7); 2.4856 (1.3); 2.4605 (9.3); 2.4514 (9.3); 2.4195 (11.8); 2.4046 (12.6); 2.3737 (1.4); 2.3543 (1.2); 2.3160 (1.3); 2.2880 (9.0); 2.2646 (7.7); 2.2397 (1.4); 2.0834 (0.7); 1.9456 (0.4); 1.9282 (0.4); 1.9191 (0.5); 1.9018 (0.9); 1.8886 (0.6); 1.8849 (0.6); 1.8789 (0.8); 1.8752 (0.7); 1.8619 (0.9); 1.8491 (0.3); 1.8449 (0.3); 1.8398 (0.4); 1.8189 (0.4); 1.6966 (0.4); 1.6855 (0.5); 1.6692 (0.7); 1.6569 (1.1); 1.6440 (0.7); 1.6298 (1.0); 1.6144 (0.9); 1.6008 (16.0); 1.2975 (0.6); 0.0489 (1.1); 0.0379 (33.4); 0.0271 (1.2)
3-37: $^{1}$H-NMR(300.2 MHz, CDCl3):
δ = 8.3020 (0.4); 8.2763 (0.4); 8.0712 (2.2); 8.0521 (1.0); 7.8195 (0.6); 7.8114 (0.8); 7.8047 (2.9); 7.7954 (2.9); 7.7891 (0.9); 7.7807 (0.6); 7.7656 (0.3); 7.6933 (0.5); 7.5960 (0.4); 7.4730 (0.9); 7.4455 (1.1); 7.4034 (0.4); 7.3777 (1.5); 7.3709 (1.4); 7.2989 (16.2); 7.2324 (0.7); 7.2255 (0.6); 7.2052 (0.5); 7.1980 (0.5); 4.5166 (0.4); 4.5040 (0.4); 4.4833 (0.6); 4.4707 (0.5); 4.3607 (0.5); 4.3480 (0.5); 4.3279 (0.4); 4.3150 (0.4); 3.4103 (0.6); 3.3830 (0.6); 3.3698 (0.5); 3.3460 (0.6); 2.9942 (8.6); 2.9204 (7.4); 2.8400 (1.0); 2.7548 (0.8); 2.7398 (6.2); 1.6330 (16.0); 1.5291 (0.4); 0.1059 (1.9); 0.0470 (0.6); 0.0362 (19.9); 0.0253 (0.8)
3-38: $^{1}$H-NMR(300.2 MHz, CDCl3):
δ = 8.3877 (0.9); 8.3621 (0.9); 8.1146 (5.5); 7.8174 (0.6); 7.8107 (0.5); 7.8020 (1.3); 7.7940 (2.4); 7.7880 (7.4); 7.7802 (7.3); 7.7745 (2.3); 7.7662 (1.3); 7.7576 (0.4); 7.7504 (0.6); 7.7189 (0.6); 7.6955 (1.2); 7.6726 (0.7); 7.6687 (0.7); 7.6099 (0.6); 7.5876 (1.1); 7.5662 (0.7); 7.3902 (0.8); 7.3638 (1.3); 7.3358 (0.6); 7.2985 (11.9); 7.2876 (2.0); 7.2618 (2.1); 6.9997 (2.2); 6.9661 (1.2); 6.9403 (1.0); 5.3372 (0.7); 4.6667 (0.6); 4.6560 (0.5); 4.6453 (0.6); 4.5108 (1.1); 4.4988 (0.9); 4.4785 (1.4); 4.4667 (1.2); 4.3054 (1.2); 4.2936 (1.2); 4.2733 (1.0); 4.2614 (0.9); 3.3085 (0.4); 3.2865 (0.4); 3.2625 (1.2); 3.2404 (1.2); 3.2220 (1.3); 3.1934 (1.2); 3.1759 (0.5); 3.1473 (0.4); 2.7440 (16.0); 2.4622 (11.3); 2.2860 (10.7); 1.5950 (5.1); 0.1086 (0.4); 0.0492 (0.5); 0.0383 (15.0); 0.0275 (0.6)
3-39: $^{1}$H-NMR(300.2 MHz, CDCl3):
δ = 8.4206 (0.9); 8.3936 (0.9); 8.0605 (5.6); 7.8468 (1.4); 7.8373 (1.2); 7.8339 (1.6); 7.8312 (1.6); 7.8255 (2.1); 7.8171 (4.7); 7.8112 (2.2); 7.8052 (2.0); 7.7990 (4.8); 7.7908 (1.9); 7.7851 (1.8); 7.7823 (1.7); 7.7789 (1.3); 7.7693 (1.5); 7.6107 (0.6); 7.5846 (1.6); 7.5581 (1.4); 7.5378 (1.8); 7.4785 (1.5); 7.4546 (4.1); 7.4273 (3.5); 7.3741 (2.8); 7.3671 (3.1); 7.2988 (15.5); 7.2021 (1.7); 7.1950 (1.7); 7.1748 (1.5); 7.1676 (1.4); 7.1028 (0.4); 7.0964 (0.4); 6.9043 (1.1); 6.7163 (2.3); 6.5285 (1.2); 4.8523 (0.4); 4.8402 (0.7); 4.8280 (0.6); 4.8154 (0.7); 4.8030 (0.4); 4.4895 (0.9); 4.4771 (0.8); 4.4564 (1.5); 4.4441 (1.4); 4.3807 (1.5); 4.3684 (1.5); 4.3478 (0.9); 4.3353 (0.8); 3.4499 (0.5); 3.4229 (0.5); 3.4038 (1.3); 3.3769 (1.3); 3.3518 (1.3); 3.3280 (1.3); 3.3054 (0.6); 3.2819 (0.6); 2.9943 (2.4); 2.9201 (2.1); 2.9045 (2.6); 2.8402 (1.0); 2.7612 (0.6); 2.7273 (16.0); 1.6548 (1.1); 1.5569 (0.4); 1.5318 (0.6); 1.5257 (0.6); 1.5034 (0.6); 1.4832 (0.5); 1.4620 (0.5); 1.2939 (0.4); 0.1071 (7.5); 0.0478 (0.5); 0.0370 (16.3); 0.0260 (0.6)
3-40: $^{1}$H-NMR(300.2 MHz, CDCl3):
δ = 8.4025 (0.4); 8.3760 (0.4); 8.2476 (2.3); 7.8302 (0.4); 7.8158 (0.7); 7.8077 (0.8); 7.7997 (2.4); 7.7881 (2.4); 7.7721 (0.7); 7.7576 (0.4); 7.5055 (0.5); 7.4846 (0.5); 7.4621 (0.5); 7.4387 (0.3); 7.2989 (17.8); 7.2795 (0.8); 7.2651 (0.9); 7.2532 (0.4); 7.2397 (0.9); 7.0007 (1.0); 6.9570 (0.5); 6.9338 (0.4); 4.5057 (0.4); 4.4939 (0.3); 4.4731 (0.6); 4.4613 (0.5); 4.3141 (0.5); 4.3022 (0.5); 4.2815 (0.4); 4.2700 (0.4); 3.2451 (0.6); 3.2219 (1.0); 3.1942 (0.5); 2.6019 (0.4); 2.5345 (0.4); 2.4820 (0.4); 2.4498 (4.5); 2.3560 (0.3); 2.2901 (4.3); 2.0846 (0.6); 1.5856 (16.0); 1.5034 (0.6); 1.4401 (0.6); 1.3218 (0.4); 1.2983 (1.1); 1.2309 (0.7); 1.2244 (0.8); 1.2005 (0.8); 0.9201 (0.9); 0.8969 (0.4); 0.0487 (0.8); 0.0379 (22.9); 0.0272 (0.9)
3-41: $^{1}$H-NMR(300.2 MHz, CDCl3):
δ = 7.4279 (0.4); 7.2985 (15.1); 7.2761 (0.4); 7.2733 (0.4); 7.2573 (0.6); 7.2318 (0.6); 7.1077 (0.6); 7.0821 (0.8); 6.9754 (0.7); 6.8899 (0.4); 6.8646 (0.6); 5.5893 (1.9); 4.1713 (0.6); 4.1475 (0.6); 3.8339 (0.6); 3.8232 (0.5); 3.7556 (0.5); 3.7376 (0.5); 2.9808 (1.2); 2.9557 (1.1); 2.8403 (2.7); 2.4018 (4.1); 2.3884 (6.0); 2.2488 (3.7); 2.0837 (2.6); 1.5893 (16.0); 1.4921 (0.5); 1.4293 (0.5); 1.3213 (0.9); 1.2975 (2.1); 1.2737 (0.7); 1.1826 (0.6); 1.1753 (0.6); 1.1531 (0.6); 0.9197 (1.0); 0.8967 (0.4); 0.0482 (0.6); 0.0466 (0.4); 0.0374 (18.6); 0.0297 (0.6); 0.0282 (0.6); 0.0265 (0.7)
3-42: $^{1}$H-NMR(300.2 MHz, CDCl3):
δ = 8.1996 (0.9); 8.1732 (0.9); 8.0545 (5.3); 7.8339 (1.4); 7.8243 (1.3); 7.8212 (1.6); 7.8180 (1.5); 7.8126 (2.2); 7.8047 (4.6); 7.7975 (2.1); 7.7923 (2.2); 7.7859 (4.6); 7.7773 (2.0); 7.7719 (1.6); 7.7687 (1.6); 7.7654 (1.3); 7.7560 (1.4); 7.4184 (0.6); 7.4129 (1.3); 7.4098 (1.2); 7.4041 (0.7); 7.3970 (0.7); 7.3916 (1.6); 7.3870 (2.4); 7.3814 (2.1); 7.3760 (0.7); 7.3709 (0.7); 7.3654 (1.7); 7.3590 (1.6); 7.3489 (2.2); 7.3226 (2.4); 7.2987 (8.6); 7.2334 (1.3); 7.2278 (1.2); 7.2052 (1.3); 7.2012 (1.4); 7.1788 (0.7); 7.1731 (0.7); 7.0371 (2.4); 7.0311 (2.6); 6.8929 (1.4); 6.8870 (1.3); 6.8666 (1.2); 6.8607 (1.2); 4.8357 (0.4); 4.8225 (0.6); 4.8110 (0.6); 4.7985 (0.7); 4.7852 (0.4); 4.5047 (0.8); 4.4912 (0.8); 4.4711 (1.5); 4.4577 (1.3); 4.4092 (1.4); 4.3959 (1.4); 4.3756 (0.9); 4.3622 (0.7); 4.1700 (0.9); 4.1462 (1.0); 4.1225 (0.3); 3.4251 (0.4); 3.3983 (0.4); 3.3789 (1.4); 3.3532 (2.4); 3.3312 (1.4); 3.3080 (0.4); 2.8399 (3.0); 2.7545 (0.8); 2.7171 (16.0); 2.7018 (0.6); 2.0816 (4.3); 1.8570 (0.5); 1.8458 (0.6); 1.8403 (0.4); 1.8291 (1.0); 1.8175 (0.4); 1.8121 (0.6); 1.8011 (0.6); 1.6253 (15.5); 1.3194 (1.6); 1.2957 (3.8); 1.2718 (1.3); 1.0143 (0.7); 0.9990 (1.8); 0.9924 (2.0); 0.9866 (1.1); 0.9774 (1.1); 0.9706 (2.1); 0.9643 (1.9); 0.9495 (1.0); 0.9400 (0.9); 0.9266 (0.6); 0.9181 (2.4); 0.8949 (0.8); 0.6961 (0.9); 0.6808 (2.3); 0.6750 (2.0); 0.6643 (2.0); 0.6587 (2.4); 0.6425 (0.8); 0.1072 (0.5); 0.0470 (0.4); 0.0363 (10.2); 0.0254 (0.4)
3-43: $^{1}$H-NMR(300.2 MHz, CDCl3):
δ = 8.3440 (0.5); 8.3184 (0.5); 8.0901 (3.2); 8.0546 (1.8); 7.8260 (0.7); 7.8168 (0.6); 7.8121 (1.0); 7.8040 (1.2); 7.7965 (3.1); 7.7822 (3.1); 7.7740 (1.1); 7.7669 (0.9); 7.7611 (0.5); 7.7520 (0.7); 7.4064 (1.2); 7.3849 (1.2);

TABLE 8-continued 7.3826 (1.2); 7.3791 (1.8); 7.3573 (1.7); 7.2986 (8.7); 7.2724 (1.1); 7.2463 (1.3); 7.2223 (0.7); 7.2167 (0.6); 7.1969 (0.6); 7.1922 (0.8); 7.1675 (0.5); 7.1619 (0.4); 6.8919 (1.3); 6.8347 (0.7); 6.8293 (0.6); 6.8088 (0.6); 6.8035 (0.6); 4.6554 (0.4); 4.6441 (0.3); 4.6307 (0.3); 4.4946 (0.6); 4.4826 (0.5); 4.4621 (0.8); 4.4502 (0.7); 4.3183 (0.7); 4.3062 (0.7); 4.2860 (0.6); 4.2737 (0.5); 3.2420 (0.8); 3.2205 (1.4); 3.1939 (0.8); 2.9933 (16.0); 2.9209 (14.0); 2.8397 (11.7); 2.7319 (9.3); 2.7156 (0.3); 2.4989 (0.4); 2.4511 (6.5); 2.0812 (0.5); 1.8479 (0.3); 1.8309 (0.6); 1.8140 (0.4); 1.8030 (0.4); 1.6331 (14.3); 1.2955 (0.4); 0.9772 (0.4); 0.9625 (1.1); 0.9555 (1.2); 0.9493 (0.6); 0.9415 (0.6); 0.9341 (1.2); 0.9275 (1.1); 0.9136 (0.5); 0.6936 (0.5); 0.6791 (1.3); 0.6734 (1.2); 0.6625 (1.2); 0.6570 (1.3); 0.6411 (0.4); 0.0469 (0.4); 0.0360 (12.0); 0.0250 (0.4)

3-44: $^{1}$H-NMR(300.2 MHz, CDCl3):

δ = 8.3984 (0.6); 8.3720 (0.6); 8.0900 (4.0); 7.8342 (0.7); 7.8257 (0.6); 7.8196 (1.3); 7.8117 (1.6); 7.8036 (5.0); 7.7935 (4.9); 7.7856 (1.7); 7.7777 (1.4); 7.7714 (0.6); 7.7630 (0.8); 7.4105 (1.4); 7.3897 (1.4); 7.3875 (1.6); 7.3838 (2.1); 7.3618 (2.0); 7.3390 (1.6); 7.3152 (0.4); 7.3080 (0.4); 7.3064 (0.4); 7.2989 (11.5); 7.2905 (4.9); 7.2313 (0.9); 7.2256 (0.9); 7.2061 (0.7); 7.2001 (1.0); 7.1967 (0.8); 7.1766 (0.6); 7.1708 (0.7); 4.6610 (0.5); 4.6494 (0.4); 4.6346 (0.4); 4.4844 (0.7); 4.4734 (0.7); 4.4520 (1.0); 4.4409 (0.8); 4.2953 (0.9); 4.2836 (0.9); 4.2629 (0.7); 4.2512 (0.6); 3.2448 (1.2); 3.2323 (1.2); 3.2214 (1.1); 3.2044 (1.0); 2.8413 (2.1); 2.7609 (0.4); 2.7445 (11.5); 2.7351 (1.4); 2.7245 (0.4); 2.5002 (0.8); 2.4818 (8.2); 2.4616 (0.3); 2.0827 (0.5); 1.6016 (16.0); 1.2971 (0.4); 0.0484 (0.5); 0.0452 (0.3); 0.0377 (14.5); 0.0283 (0.4); 0.0268 (0.5)

3-45: $^{1}$H-NMR(300.2 MHz, CDCl3):

δ = 8.1718 (0.6); 8.1464 (0.6); 8.0882 (3.6); 7.8403 (1.0); 7.8283 (1.0); 7.8242 (1.0); 7.8195 (1.3); 7.8110 (2.9); 7.7992 (1.5); 7.7874 (2.8); 7.7789 (1.2); 7.7744 (1.0); 7.7700 (1.1); 7.7581 (1.0); 7.4148 (0.4); 7.4094 (0.5); 7.3935 (0.5); 7.3879 (1.0); 7.3824 (0.8); 7.3772 (0.6); 7.3715 (0.5); 7.3667 (0.6); 7.3611 (0.7); 7.3550 (0.6); 7.3494 (1.1); 7.3440 (0.6); 7.3273 (0.8); 7.3217 (0.5); 7.2990 (6.6); 7.2262 (0.8); 7.2206 (0.7); 7.1988 (1.0); 7.1933 (1.0); 7.1716 (0.4); 7.1659 (0.5); 7.1479 (1.5); 7.1020 (0.6); 7.0764 (1.0); 7.0710 (0.9); 7.0080 (1.5); 6.9830 (0.9); 4.6879 (0.5); 4.6751 (0.4); 4.6630 (0.5); 4.4454 (0.5); 4.4318 (0.5); 4.4123 (1.0); 4.3988 (0.9); 4.3533 (1.0); 4.3384 (1.0); 4.3202 (0.6); 4.3054 (0.5); 3.1994 (1.8); 3.1754 (1.5); 2.7329 (10.4); 2.7168 (0.4); 2.2121 (16.0); 2.0835 (0.4); 1.6181 (11.5); 1.3208 (0.5); 1.3038 (1.5); 1.2974 (1.5); 0.9410 (0.5); 0.9192 (1.7); 0.8959 (0.6); 0.1077 (0.4); 0.0373 (8.7)

3-46: $^{1}$H-NMR(300.2 MHz, CDCl3):

δ = 8.4217 (0.5); 8.3963 (0.4); 8.1160 (2.7); 7.8021 (0.6); 7.7941 (1.2); 7.7882 (3.5); 7.7797 (3.4); 7.7737 (1.1); 7.7656 (0.6); 7.7504 (0.4); 7.6006 (0.8); 7.5750 (0.8); 7.5548 (0.3); 7.3845 (0.5); 7.3579 (0.7); 7.2989 (14.0); 7.2675 (1.0); 7.1349 (0.5); 6.9521 (1.0); 6.8968 (1.0); 6.8501 (0.6); 6.8237 (0.5); 6.8185 (0.5); 6.7695 (0.5); 4.4934 (0.5); 4.4816 (0.4); 4.4614 (0.6); 4.4494 (0.5); 4.2989 (0.6); 4.2870 (0.6); 4.2670 (0.4); 4.2551 (0.4); 3.2496 (0.6); 3.2275 (0.6); 3.2119 (0.6); 3.1832 (0.6); 2.7408 (7.6); 2.5080 (0.4); 2.4631 (5.1); 1.8327 (0.5); 1.5932 (16.0); 0.9662 (0.9); 0.9593 (1.0); 0.9454 (0.5); 0.9378 (1.0); 0.9310 (0.9); 0.9174 (0.4); 0.6953 (0.4); 0.6812 (1.0); 0.6778 (0.9); 0.6644 (0.9); 0.6596 (0.9); 0.1071 (0.4); 0.0483 (0.7); 0.0375 (19.7); 0.0267 (0.7)

3-47: $^{1}$H-NMR(300.2 MHz, CDCl3):

δ = 8.3569 (0.7); 8.3313 (0.7); 8.0976 (4.0); 7.8406 (1.2); 7.8305 (1.1); 7.8287 (1.2); 7.8244 (1.2); 7.8199 (1.5); 7.8117 (3.2); 7.7990 (1.7); 7.7870 (3.1); 7.7781 (1.4); 7.7737 (1.2); 7.7693 (1.3); 7.7574 (1.2); 7.6002 (0.4); 7.5739 (1.2); 7.5476 (1.0); 7.5147 (1.4); 7.4731 (1.1); 7.4445 (1.3); 7.4141 (0.6); 7.4103 (0.6); 7.2990 (4.3); 7.1499 (1.7); 7.1002 (0.6); 7.0744 (1.1); 7.0698 (1.1); 7.0207 (1.7); 6.9952 (0.9); 6.8974 (0.8); 6.7095 (1.7); 6.5216 (0.8); 5.3360 (16.0); 4.6740 (0.5); 4.6619 (0.4); 4.6498 (0.5); 4.6368 (0.3); 4.4272 (0.5); 4.4138 (0.5); 4.3946 (1.2); 4.3812 (1.1); 4.3524 (1.2); 4.3385 (1.1); 4.3198 (0.6); 4.3059 (0.5); 4.1708 (0.4); 4.1471 (0.4); 3.1812 (1.6); 3.1608 (1.2); 3.1546 (1.3); 2.7333 (11.5); 2.2146 (9.3); 2.0826 (1.7); 1.6356 (7.2); 1.3205 (0.5); 1.2967 (1.0); 1.2729 (0.5); 0.0375 (5.8)

3-48: $^{1}$H-NMR(300.2 MHz, CDCl3):

δ = 8.5232 (0.9); 8.4975 (0.9); 8.1022 (5.3); 7.8355 (1.3); 7.8259 (1.2); 7.8227 (1.5); 7.8197 (1.5); 7.8142 (2.0); 7.8064 (4.3); 7.7993 (2.0); 7.7939 (1.9); 7.7876 (4.4); 7.7790 (1.8); 7.7735 (1.5); 7.7704 (1.5); 7.7673 (1.1); 7.7577 (1.3); 7.5992 (0.6); 7.5689 (1.3); 7.5561 (1.9); 7.5493 (2.1); 7.5472 (2.2); 7.4691 (2.6); 7.4667 (2.5); 7.4418 (1.6); 7.2989 (10.4); 7.2774 (1.8); 7.2513 (2.0); 6.9021 (2.3); 6.8439 (1.2); 6.8386 (1.0); 6.8182 (1.0); 6.8129 (1.0); 6.7087 (2.2); 6.5206 (1.1); 5.3373 (1.5); 4.6481 (0.6); 4.6373 (0.5); 4.6249 (0.5); 4.4803 (0.9); 4.4687 (0.8); 4.4483 (1.3); 4.4367 (1.1); 4.3161 (1.2); 4.3045 (1.1); 4.2841 (0.9); 4.2726 (0.8); 3.2799 (0.4); 3.2574 (0.4); 3.2337 (1.2); 3.2114 (1.2); 3.1978 (1.2); 3.1691 (1.1); 3.1515 (0.4); 3.1231 (0.4); 2.7343 (15.2); 2.4981 (0.6); 2.4534 (10.6); 2.0837 (0.6); 1.8705 (0.5); 1.8593 (0.5); 1.8426 (1.0); 1.8258 (0.6); 1.8146 (0.6); 1.6088 (16.0); 1.2976 (0.5); 0.9845 (0.6); 0.9699 (1.8); 0.9630 (2.0); 0.9487 (1.0); 0.9415 (1.9); 0.9349 (1.8); 0.9207 (0.9); 0.7009 (0.8); 0.6863 (2.1); 0.6836 (1.9); 0.6807 (2.0); 0.6696 (1.9); 0.6643 (2.1); 0.6482 (0.6); 0.0487 (0.5); 0.0471 (0.4); 0.0454 (0.4); 0.0380 (14.6); 0.0287 (0.4); 0.0271 (0.5)

3-49: $^{1}$H-NMR(300.2 MHz, CDCl3):

δ = 8.2403 (1.0); 8.2145 (1.0); 8.1071 (5.4); 7.8289 (1.2); 7.8196 (1.0); 7.8139 (1.6); 7.8073 (2.1); 7.7989 (5.1); 7.7836 (5.0); 7.7756 (1.9); 7.7675 (1.6); 7.7632 (1.0); 7.7538 (1.3); 7.5978 (1.0); 7.5727 (1.7); 7.5562 (0.9); 7.5452 (0.9); 7.3883 (1.0); 7.3619 (1.5); 7.3344 (0.6); 7.2989 (6.9); 7.1594 (2.3); 7.1254 (1.2); 7.1120 (1.0); 7.0867 (1.6); 7.0174 (2.3); 6.9920 (1.3); 6.9428 (2.3); 6.7602 (1.1); 5.3370 (0.4); 4.6950 (0.4); 4.6816 (0.7); 4.6695 (0.6); 4.6579 (0.7); 4.6444 (0.4); 4.4392 (0.8); 4.4256 (0.8); 4.4064 (1.6); 4.3929 (1.4); 4.3396 (1.5); 4.3253 (1.4); 4.3069 (0.9); 4.2926 (0.8); 3.1997 (1.6); 3.1902 (1.8); 3.1776 (1.6); 3.1650 (1.5); 2.7392 (15.6); 2.2113 (16.0); 2.0835 (0.4); 1.6221 (3.5); 0.0482 (0.3); 0.0374 (8.8); 0.0266 (0.4)

3-50: $^{1}$H-NMR(300.2 MHz, CDCl3):

δ = 8.4207 (1.0); 8.3941 (1.0); 8.0769 (0.6); 8.0691 (5.6); 7.8370 (1.5); 7.8272 (1.3); 7.8245 (1.5); 7.8210 (1.5); 7.8159 (2.1); 7.8077 (4.6); 7.7993 (1.9); 7.7955 (1.9); 7.7874 (4.6); 7.7789 (2.1); 7.7736 (1.6); 7.7702 (1.6); 7.7577 (1.5); 7.3195 (2.2); 7.2986 (18.0); 7.2698 (3.8); 7.2603 (2.9); 7.2550 (2.4); 7.2336 (1.7); 7.2113 (1.0); 7.2056 (0.9); 7.1531 (1.1); 7.1496 (1.0); 7.1266 (1.5); 7.1231 (1.7); 7.0998 (0.7); 7.0964 (0.7); 6.8690 (0.7); 6.8641 (0.8); 6.8421 (1.3); 6.8208 (0.6); 6.8159 (0.6); 4.6933 (0.4); 4.6812 (0.7); 4.6682 (0.6); 4.6548 (0.7); 4.6428 (0.5); 4.4692 (0.9); 4.4578 (0.9); 4.4368 (1.4); 4.4255 (1.3); 4.3388 (1.4); 4.3257 (1.4); 4.3063 (1.0); 4.2932 (0.8); 4.1718 (0.5); 4.1480 (0.5); 3.2454 (2.7); 3.2199 (2.8); 2.8416 (0.3); 2.7296 (16.0); 2.4928 (1.0); 2.4667 (11.8); 2.1654 (0.5); 2.1547 (0.5); 2.1371 (1.0); 2.1200 (0.6); 2.1088 (0.5); 2.0831 (2.2); 1.5947 (13.3); 1.3211 (0.7); 1.2973 (1.6); 1.2735 (0.6); 1.0706 (0.5); 1.0576 (1.8); 1.0508 (2.0); 1.0364 (0.9); 1.0291 (1.9); 1.0224 (1.8); 1.0095 (0.7); 0.9199 (0.6); 0.8255 (0.9); 0.8118 (1.9); 0.8080 (2.2); 0.8041 (1.8); 0.7945 (2.0); 0.7911 (1.9); 0.7867 (1.6); 0.7739 (0.7); 0.0485 (0.7); 0.0378 (22.2); 0.0269 (0.8)

3-51: $^{1}$H-NMR(300.2 MHz, CDCl3):

δ = 10.6536 (0.5); 10.6346 (0.4); 9.0611 (2.0); 9.0354 (2.0); 8.4177 (0.7); 8.4096 (0.7); 8.3715 (2.0); 8.3640 (2.0); 8.2929 (2.4); 8.2486 (12.5); 8.0699 (4.6); 8.0628 (4.7); 8.0014 (2.4); 7.8667 (1.2); 7.8563 (3.7); 7.8468 (3.3); 7.8398 (4.5); 7.8352 (4.9); 7.8268 (10.1); 7.8197 (5.4); 7.8144 (5.0); 7.8080 (10.4); 7.7993 (5.4); 7.7939

TABLE 8-continued (5.3); 7.7910 (5.5); 7.7781 (4.0); 7.7573 (3.0); 7.7417 (8.2); 7.7344 (7.8); 7.7206 (1.6); 7.7119 (0.9); 7.7040 (1.2); 7.6674 (8.9); 7.6567 (16.0); 7.6407 (5.2); 7.6214 (4.2); 7.6130 (4.0); 7.6001 (1.0); 7.5914 (1.4); 7.5617 (2.8); 7.5516 (3.8); 7.5434 (3.9); 7.5325 (2.5); 7.5247 (3.1); 7.5163 (2.2); 7.4797 (0.6); 7.4728 (0.7); 7.4477 (0.4); 7.3714 (4.9); 7.3438 (4.0); 7.2992 (34.0); 7.2679 (0.9); 7.2406 (0.8); 7.1310 (2.2); 7.1036 (1.9); 5.3608 (0.3); 5.3374 (11.3); 5.3134 (0.7); 5.2960 (0.7); 5.2794 (0.4); 4.9627 (0.9); 4.9432 (1.5); 4.9202 (1.6); 4.9011 (1.0); 4.7985 (1.6); 4.7762 (0.9); 4.5436 (0.7); 4.5100 (2.9); 4.4943 (2.2); 4.4764 (3.1); 4.4603 (2.8); 4.4214 (1.2); 4.4080 (1.3); 4.3819 (0.7); 4.3680 (0.6); 4.2895 (2.8); 4.2696 (2.8); 4.2556 (2.2); 4.2357 (2.0); 4.1711 (0.5); 4.1474 (0.4); 3.7877 (0.7); 3.7551 (0.8); 3.7401 (0.9); 3.7076 (0.9); 3.5798 (0.5); 3.5445 (1.6); 3.5229 (1.9); 3.4949 (2.8); 3.4745 (2.8); 3.4086 (2.6); 3.3898 (2.7); 3.3601 (1.4); 3.3408 (1.4); 3.3267 (1.2); 3.3067 (1.1); 3.2784 (0.9); 3.2591 (0.8); 2.1179 (0.4); 2.0835 (2.4); 1.9363 (3.8); 1.7465 (0.5); 1.3204 (1.1); 1.2966 (2.0); 1.2729 (0.8); 0.9182 (0.5); 0.1068 (7.9); 0.0364 (41.2); 0.0256 (2.0)

3-52: $^1$H-NMR(300.2 MHz, CDCl3):
δ = 8.4948 (0.4); 8.4696 (0.4); 8.2870 (3.1); 7.8291 (0.7); 7.8209 (1.0); 7.8146 (3.2); 7.8053 (3.0); 7.7985 (0.8); 7.7903 (0.6); 7.7147 (0.8); 7.6335 (0.5); 7.6105 (1.8); 7.5686 (0.4); 7.5592 (0.6); 7.5522 (0.4); 7.2989 (6.6); 7.0175 (1.6); 5.3378 (0.3); 4.5166 (0.5); 4.5047 (0.4); 4.4848 (0.6); 4.4729 (0.5); 4.3087 (0.5); 4.2977 (0.5); 4.2769 (0.4); 4.2660 (0.4); 3.1513 (1.0); 3.1301 (0.7); 3.1227 (0.7); 2.3596 (4.4); 2.2062 (4.3); 1.6049 (16.0); 1.3160 (1.9); 1.2951 (2.0); 0.1072 (0.9); 0.0371 (8.1)

3-53: $^1$H-NMR(300.2 MHz, CDCl3):
δ = 8.3637 (0.8); 8.3378 (0.8); 8.0640 (4.8); 7.8507 (1.6); 7.8401 (1.8); 7.8340 (1.5); 7.8307 (1.8); 7.8218 (3.6); 7.8087 (0.8); 7.8003 (0.9); 7.7874 (3.6); 7.7784 (1.7); 7.7752 (1.6); 7.7693 (1.8); 7.7584 (1.7); 7.3647 (0.9); 7.3384 (2.0); 7.3123 (1.4); 7.2989 (8.6); 7.1431 (1.9); 7.0942 (0.8); 7.0635 (1.9); 7.0558 (1.2); 7.0526 (1.3); 7.0364 (1.5); 7.0326 (2.0); 7.0292 (1.9); 6.9994 (3.7); 6.9934 (2.2); 6.9745 (1.2); 4.6768 (0.6); 4.6637 (0.5); 4.6521 (0.6); 4.6380 (0.4); 4.4149 (0.6); 4.4015 (0.5); 4.3822 (1.5); 4.3689 (1.3); 4.3513 (1.4); 4.3361 (1.4); 4.3187 (0.6); 4.3035 (0.5); 3.1788 (2.3); 3.1549 (2.3); 2.8416 (2.2); 2.7147 (13.8); 2.2216 (8.9); 2.2040 (9.2); 1.9726 (0.5); 1.9613 (0.5); 1.9560 (0.4); 1.9446 (1.0); 1.9279 (0.6); 1.9165 (0.5); 1.6262 (16.0); 1.0265 (0.4); 1.0181 (0.4); 1.0102 (1.6); 1.0030 (2.0); 0.9869 (0.7); 0.9817 (1.7); 0.9750 (1.8); 0.9677 (0.5); 0.9591 (0.5); 0.7804 (0.6); 0.7763 (0.5); 0.7684 (1.2); 0.7638 (1.8); 0.7572 (1.6); 0.7513 (1.3); 0.7473 (1.6); 0.7405 (1.3); 0.7324 (0.4); 0.7285 (0.4); 0.0483 (0.4); 0.0375 (12.1); 0.0265 (0.4)

3-54: $^1$H-NMR(300.2 MHz, CDCl3):
δ = 8.5469 (1.0); 8.5205 (1.0); 8.0676 (1.0); 8.0602 (5.7); 7.8510 (1.7); 7.8409 (1.6); 7.8391 (1.7); 7.8347 (1.8); 7.8303 (2.3); 7.8220 (4.4); 7.8092 (2.4); 7.7969 (4.4); 7.7882 (2.3); 7.7836 (1.8); 7.7792 (2.0); 7.7674 (1.8); 7.7607 (0.4); 7.3709 (1.2); 7.3607 (0.5); 7.3546 (0.4); 7.3438 (3.0); 7.3348 (2.6); 7.3170 (1.9); 7.3094 (0.5); 7.2988 (12.5); 7.2866 (0.6); 7.2595 (4.4); 7.2496 (2.3); 7.2278 (0.3); 7.2223 (0.3); 7.0924 (1.0); 7.0887 (1.2); 7.0849 (1.2); 7.0814 (1.4); 7.0655 (1.0); 7.0622 (1.0); 7.0577 (1.3); 7.0544 (1.2); 7.0294 (3.2); 7.0224 (2.7); 7.0149 (1.9); 7.0093 (1.7); 4.6832 (0.3); 4.6684 (0.4); 4.6567 (0.8); 4.6446 (0.6); 4.6305 (0.8); 4.6184 (0.4); 4.4502 (1.0); 4.4394 (0.9); 4.4182 (1.4); 4.4075 (1.3); 4.3190 (1.4); 4.3067 (1.4); 4.2870 (1.0); 4.2748 (0.9); 3.2324 (0.4); 3.2132 (3.2); 3.1874 (3.1); 2.8411 (0.7); 2.7410 (1.1); 2.7233 (16.0); 2.4856 (1.2); 2.4598 (11.8); 2.2927 (0.8); 2.0835 (0.7); 1.9736 (0.6); 1.9623 (0.6); 1.9454 (1.2); 1.9289 (0.7); 1.9175 (0.6); 1.9006 (0.3); 1.6163 (14.1); 1.3208 (0.4); 1.2971 (1.2); 1.0204 (0.4); 1.0023 (1.8); 0.9995 (1.7); 0.9949 (2.7); 0.9735 (1.9); 0.9671 (2.6); 0.9493 (0.5); 0.9410 (0.4); 0.9305 (0.4); 0.9189 (1.1); 0.8956 (0.4); 0.7806 (0.9); 0.7721 (1.7); 0.7664 (1.4); 0.7628 (1.7); 0.7554 (2.8); 0.7497 (1.5); 0.7455 (1.5); 0.7388 (1.3); 0.7319 (0.6); 0.0478 (0.6); 0.0370 (16.8); 0.0277 (0.5); 0.0261 (0.6)

3-55: $^1$H-NMR(300.2 MHz, CDCl3):
δ = 8.5228 (1.1); 8.4966 (1.0); 8.0672 (5.6); 7.8426 (1.7); 7.8325 (1.8); 7.8310 (1.8); 7.8261 (1.7); 7.8221 (2.1); 7.8139 (4.3); 7.7996 (2.0); 7.7861 (4.4); 7.7769 (2.1); 7.7729 (1.8); 7.7681 (2.0); 7.7565 (1.8); 7.3648 (1.0); 7.3385 (2.1); 7.3109 (1.4); 7.2987 (10.3); 7.2639 (2.0); 7.2378 (2.2); 7.0978 (1.0); 7.0924 (1.4); 7.0866 (1.3); 7.0706 (0.8); 7.0675 (0.9); 7.0629 (1.2); 7.0600 (1.1); 7.0339 (4.0); 7.0296 (4.0); 7.0063 (1.4); 6.8969 (2.3); 6.8129 (1.2); 6.8075 (1.2); 6.7868 (1.1); 6.7815 (1.1); 4.6642 (0.4); 4.6520 (0.7); 4.6391 (0.6); 4.6262 (0.7); 4.6144 (0.5); 4.4616 (0.9); 4.4498 (0.9); 4.4297 (1.4); 4.4181 (1.3); 4.3314 (1.4); 4.3190 (1.3); 4.2995 (1.0); 4.2871 (0.8); 3.2070 (3.0); 3.1814 (2.5); 2.8416 (7.2); 2.7155 (16.0); 2.4865 (0.7); 2.4415 (11.5); 1.9708 (0.6); 1.9596 (0.6); 1.9428 (1.2); 1.9260 (0.7); 1.9150 (0.6); 1.8979 (0.4); 1.8677 (0.5); 1.8564 (0.6); 1.8397 (1.1); 1.8229 (0.6); 1.8118 (0.6); 1.7950 (0.3); 1.6244 (10.6); 1.3036 (0.9); 1.0163 (0.4); 0.9985 (1.9); 0.9916 (2.5); 0.9789 (1.0); 0.9638 (4.3); 0.9576 (2.6); 0.9431 (1.5); 0.9360 (2.3); 0.9292 (2.2); 0.9193 (1.4); 0.9154 (1.2); 0.8963 (0.5); 0.7815 (0.7); 0.7716 (1.5); 0.7644 (1.8); 0.7562 (2.3); 0.7489 (1.7); 0.7408 (1.3); 0.7295 (0.5); 0.6984 (0.9); 0.6837 (2.4); 0.6783 (2.2); 0.6671 (2.1); 0.6617 (2.4); 0.6455 (0.7); 0.0482 (0.5); 0.0374 (14.2); 0.0283 (0.5); 0.0266 (0.5)

3-56: $^1$H-NMR(300.2 MHz, CDCl3):
δ = 8.0711 (1.7); 7.8298 (0.3); 7.8156 (0.5); 7.8077 (0.6); 7.7993 (1.8); 7.7872 (1.8); 7.7790 (0.6); 7.7710 (0.5); 7.7569 (0.4); 7.6027 (0.5); 7.5814 (0.4); 7.3644 (0.8); 7.3382 (0.8); 7.2990 (8.4); 7.1563 (0.7); 7.1325 (0.3); 7.0032 (0.4); 6.9773 (0.4); 6.9497 (0.7); 6.7672 (0.4); 4.4789 (0.5); 4.4657 (0.4); 4.4002 (0.5); 4.3871 (0.5); 3.3939 (0.4); 3.3669 (0.5); 3.3582 (0.5); 3.3345 (0.4); 2.7221 (4.9); 2.2891 (3.4); 2.0839 (0.8); 1.5977 (16.0); 1.3212 (0.4); 1.2975 (1.0); 0.9193 (0.7); 0.1068 (0.9); 0.0479 (0.4); 0.0372 (9.9); 0.0263 (0.3)

3-57: $^1$H-NMR(300.2 MHz, CDCl3):
δ = 8.3646 (1.0); 8.3387 (1.0); 8.2237 (7.2); 7.8349 (1.5); 7.8253 (1.3); 7.8219 (1.7); 7.8191 (1.5); 7.8135 (2.2); 7.8060 (4.8); 7.7992 (2.1); 7.7934 (2.1); 7.7876 (4.8); 7.7789 (1.9); 7.7733 (1.8); 7.7702 (1.5); 7.7670 (1.1); 7.7575 (1.4); 7.5206 (0.4); 7.2983 (23.6); 7.2640 (0.8); 7.2582 (0.9); 7.2513 (2.0); 7.2367 (1.5); 7.2311 (1.5); 7.2260 (2.3); 7.2141 (1.1); 7.2084 (0.9); 7.1632 (1.0); 7.1367 (1.5); 7.1334 (1.5); 7.1103 (0.8); 7.1068 (0.8); 6.9868 (2.2); 6.9327 (1.2); 6.9066 (1.1); 6.8915 (0.8); 6.8697 (1.3); 6.8488 (0.7); 5.3375 (16.0); 4.6831 (0.4); 4.6712 (0.8); 4.6584 (0.7); 4.6455 (0.8); 4.6330 (0.5); 4.4989 (1.0); 4.4868 (0.8); 4.4660 (1.5); 4.4540 (1.2); 4.3459 (1.4); 4.3333 (1.3); 4.3131 (1.0); 4.3006 (0.9); 4.1721 (0.7); 4.1485 (0.5); 3.2379 (2.8); 3.2123 (2.2); 2.6030 (1.6); 2.5349 (1.4); 2.4806 (0.6); 2.4386 (11.3); 2.3741 (0.7); 2.3526 (0.5); 2.2848 (10.7); 2.2403 (0.6); 2.1671 (0.5); 2.1559 (0.5); 2.1388 (1.0); 2.1219 (0.6); 2.1102 (0.5); 2.0925 (0.4); 2.0833 (2.5); 1.5871 (15.9); 1.3214 (0.9); 1.2976 (2.1); 1.2738 (0.7); 1.0900 (0.4); 1.0864 (0.4); 1.0749 (1.8); 1.0678 (2.0); 1.0573 (1.0); 1.0523 (0.8); 1.0462 (1.9); 1.0396 (1.9); 1.0282 (0.6); 1.0245 (0.6); 0.9203 (0.8); 0.8352 (0.9); 0.8180 (2.0); 0.8135 (1.8); 0.8042 (1.9); 0.7964 (1.5); 0.7843 (0.7); 0.1079 (2.9); 0.0490 (0.9); 0.0473 (0.6); 0.0382 (23.5); 0.0305 (0.8); 0.0290 (0.8); 0.0273 (0.9)

3-58: $^1$H-NMR(300.2 MHz, CDCl3):
δ = 8.4089 (1.0); 8.3832 (1.0); 8.1117 (5.6); 7.8165 (0.8); 7.8090 (0.6); 7.8016 (1.6); 7.7935 (2.4); 7.7870 (7.7); 7.7777 (7.5); 7.7713 (2.3); 7.7630 (1.6); 7.7556 (0.6); 7.7481 (0.9); 7.6273 (0.6); 7.6017 (1.7); 7.5756 (1.7); 7.5542 (0.7); 7.3861 (1.0); 7.3593 (1.5); 7.3327 (0.6); 7.2990 (2.8); 7.2878 (1.9); 7.2623 (2.2); 7.1323 (1.1);

TABLE 8-continued

| |
|---|
| 6.9952 (2.3); 6.9499 (2.9); 6.9332 (1.1); 6.7669 (1.1); 5.3337 (6.3); 4.6801 (0.4); 4.6678 (0.6); 4.6563 (0.6); 4.6453 (0.6); 4.6317 (0.4); 4.5022 (1.0); 4.4903 (1.0); 4.4700 (1.4); 4.4582 (1.2); 4.3107 (1.2); 4.2987 (1.3); 4.2785 (1.0); 4.2666 (0.9); 3.3047 (0.4); 3.2822 (0.4); 3.2586 (1.3); 3.2361 (1.3); 3.2247 (1.4); 3.1961 (1.2); 3.1785 (0.4); 3.1500 (0.4); 2.7365 (16.0); 2.4601 (11.4); 2.2850 (10.8); 1.6740 (2.9); 0.0374 (3.8) |

TABLE 9

Compounds according to formula (4)

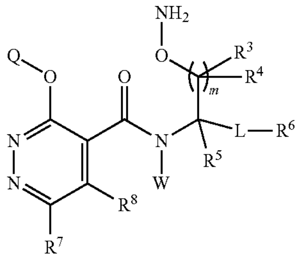
(4)

In table 9, "#" denotes the point of attachment to the L—$R^6$ group and "*" denotes the point of attachment to the pyridazin-4-yl group.

| Ex No | $R^7$ | $R^8$ | Q | 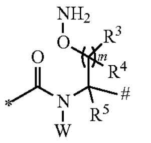 | L—$R^6$ | LogP |
|---|---|---|---|---|---|---|
| 4-01 | $CH_3$ | H | 3-(trifluoro-methyl)phenyl | 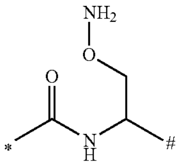 | 2,4-dichlorophenyl | 3.29[a]; 3.36[b] |
| 4-02 | Cl | H | 3-(trifluoro-methyl)phenyl | 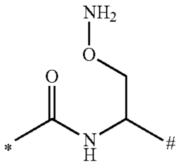 | 2,4-dichlorophenyl | 3.76[a]; 3.82[b] |
| 4-03 | Cl | H | 3-cyclopropyl-2-fluorophenyl | 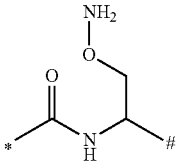 | (2,4-dimethyl-phenyl)methyl | 3.46[a] |
| 4-04 | Cl | H | 3-(difluoromethyl)-2-fluorophenyl | 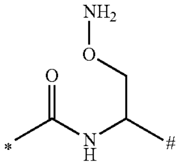 | (2,4-dimethyl-phenyl)methyl | 3.02[a] |
| 4-05 | $CH_3$ | H | 3-cyclopropyl-2-fluorophenyl | 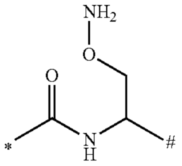 | (4-bromo-2-chloro-phenyl)methyl | 3.17[a] |

TABLE 9-continued

Compounds according to formula (4)

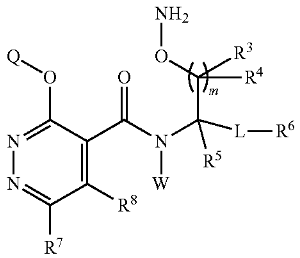

(4)

In table 9, "#" denotes the point of attachment to the L—$R^6$ group and "*" denotes the point of attachment to the pyridazin-4-yl group.

| Ex No | $R^7$ | $R^8$ | Q | 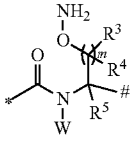 | L—$R^6$ | LogP |
|---|---|---|---|---|---|---|
| 4-06 | Cl | $CH_3$ | 3-(trifluoro-methyl)phenyl | 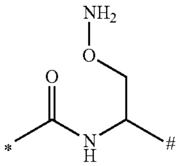 | (2,4-dimethyl-phenyl)methyl | 3.06[a] |
| 4-07 | $CH_3$ | H | 3-cyclopropylphenyl | 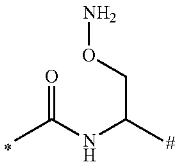 | (2,4-dimethyl-phenyl)methyl | 2.69[a] |
| 4-08 | I | H | 3-(trifluor-omethyl)phenyl | 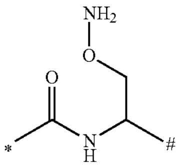 | (2,4-dimethyl-phenyl)methyl | 3.37[a] |
| 4-09 | $CH_3$ | H | 3-cyclopropyl-2-fluorophenyl | 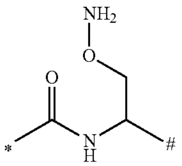 | (2,4-dimethyl-phenyl)methyl | 2.90[a] |
| 4-10 | Cl | H | 3-(trifluoro-methyl)phenyl | 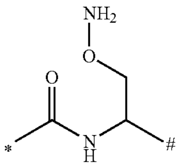 | (3,4-dimethyl-phenyl)methyl | 3.25[a] |
| 4-11 | Cl | H | 3-(trifluoro-methyl)phenyl | 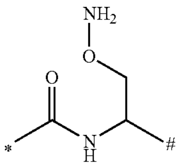 | (2,4-dichloro-phenyl)methyl | 3.51[a] |

TABLE 9-continued

Compounds according to formula (4)

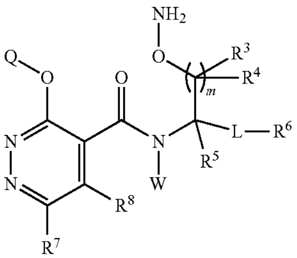
(4)

In table 9, "#" denotes the point of attachment to the L—$R^6$ group and "*" denotes the point of attachment to the pyridazin-4-yl group.

| Ex No | $R^7$ | $R^8$ | Q | 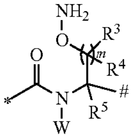 | L—$R^6$ | LogP |
|---|---|---|---|---|---|---|
| 4-12 | Cl | H | 3-(trifluoro-methyl)phenyl | 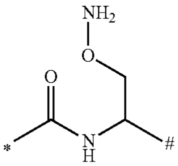 | (4-cyclopropyl-2-methyl-phenyl)methyl | 3.59[a] |
| 4-13 | Cl | H | 3-(trifluoro-methyl)phenyl | 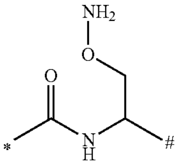 | (2-chloro-4-cyclopropyl-phenyl)methyl | 3.68[a] |
| 4-14 | Cl | H | 3-(trifluoro-methyl)phenyl | 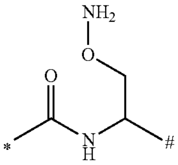 | (2-chloro-4-isopropyl-phenyl)methyl | 4.01[a] |
| 4-15 | Cl | H | 3-(trifluoro-methyl)phenyl | 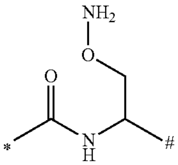 | (4-isopropyl-2-methyl-phenyl)methyl | 3.94[a] |
| 4-16 | $CH_3$ | H | 3-cyclopropyl-2-fluorophenyl | 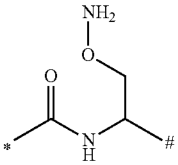 | (3,4-dimethyl-phenyl)methyl | 2.78[a] |
| 4-17 | Cl | H | 3-(trifluoro-methyl)phenyl | 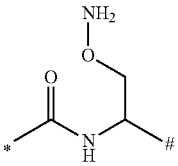 | (2,4-dimethyl-phenyl)methyl | 3.37[a] |

TABLE 9-continued

Compounds according to formula (4)

(4)

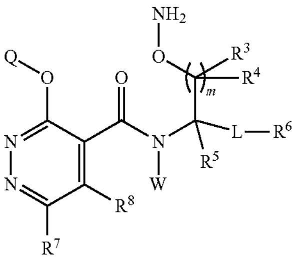

In table 9, "#" denotes the point of attachment to the L—$R^6$ group and "*" denotes the point of attachment to the pyridazin-4-yl group.

| Ex No | $R^7$ | $R^8$ | Q | 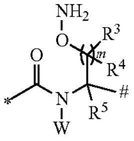 | L—$R^6$ | LogP |
|---|---|---|---|---|---|---|
| 4-18 | Cl | H | 3-(trifluoro-methyl)phenyl | 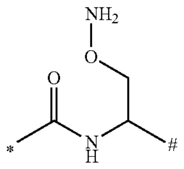 | (4-chlorophenyl)methyl | 3.18[a]; 3.42[b] |
| 4-19 | $CH_3$ | $CH_3$ | 3-(trifluoro-methyl)phenyl | 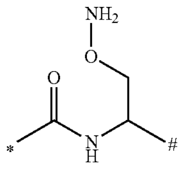 | (2,4-dimethyl-phenyl)methyl | 2.51[a] |
| 4-20 | $CH_3$ | H | 3-(difluoro-methyl)phenyl | 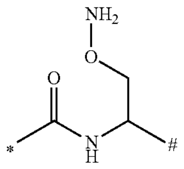 | (2,4-dimethyl-phenyl)methyl | 2.40[a] |
| 4-21 | Cl | H | 3-(trifluoro-methyl)phenyl | 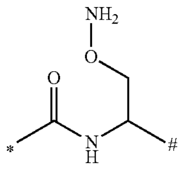 | (4-bromo-2-chloro-phenyl)methyl | 3.63[a] |
| 4-22 | Cl | H | 3-(trifluoro-methyl)phenyl | 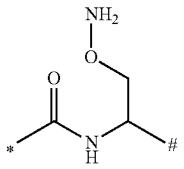 | (4-bromo-2-methyl-phenyl)methyl | 3.55[a] |
| 4-23 | Cl | H | 5-bromopyridin-3-yl | 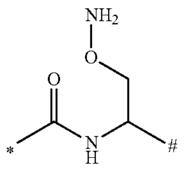 | (2,4-dimethyl-phenyl)methyl | 2.50[a] |

TABLE 9-continued

Compounds according to formula (4)

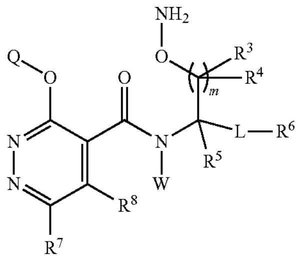

(4)

In table 9, "#" denotes the point of attachment to the L—$R^6$ group and "*" denotes the point of attachment to the pyridazin-4-yl group.

| Ex No | $R^7$ | $R^8$ | Q | 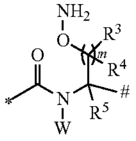 | L—$R^6$ | LogP |
|---|---|---|---|---|---|---|
| 4-24 | Cl | H | 6-chloro-5-(trifluoro-methyl)pyridin-3-yl | 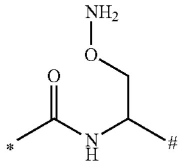 | (2,4-dimethyl-phenyl)methyl | 3.37[a] |
| 4-25 | Cl | $CH_3$ | 3-cyclopropyl-2-fluorophenyl | 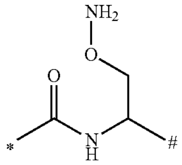 | (4-bromo-2-chlorophenyl)methyl | 3.41[a] |
| 4-26 | Cl | $CH_3$ | 3-cyclopropyl-2-fluorophenyl | 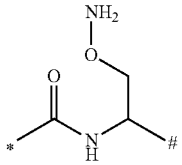 | (2-chloro-4-cyclo-propylphenyl)methyl | 3.46[a] |
| 4-27 | Cl | H | 3-cyclopropylphenyl | 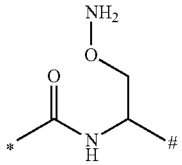 | (2,4-dimethyl-phenyl)methyl | 3.39[a] |
| 4-28 | Cl | H | 3-(1-fluoro-cyclopropyl)phenyl | 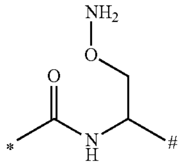 | (2,4-dimethyl-phenyl)methyl | 3.27[a] |
| 4-29 | $CH_3$ | H | 3-cyclopropyl-2-fluorophenyl | 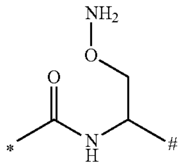 | (2-chloro-4-cyclopropyl-phenyl)methyl | 3.21[a] |

TABLE 9-continued

Compounds according to formula (4)

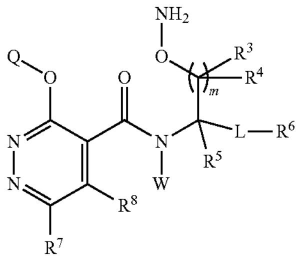

(4)

In table 9, "#" denotes the point of attachment to the L—$R^6$ group and "*" denotes the point of attachment to the pyridazin-4-yl group.

| Ex No | $R^7$ | $R^8$ | Q | 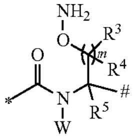 | L—$R^6$ | LogP |
|---|---|---|---|---|---|---|
| 4-30 | Cl | $CH_3$ | 3-cyclopropyl-2-fluorophenyl | 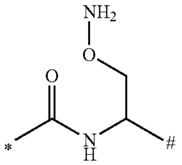 | (2,4-dichloro-phenyl)methyl | 3.33[a] |
| 4-31 | Cl | H | 3-cyclopropylphenyl | 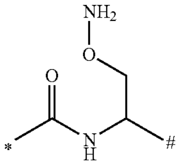 | (2,4-dichloro-phenyl)methyl | 3.68[a] |
| 4-32 | Cl | H | 2-fluoro-3-[rac-2,2-difluoro-cyclopropyl]phenyl | 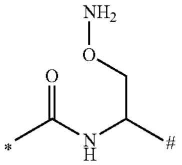 | (2,4-dimethyl-phenyl)methyl | 3.23[a] |
| 4-33 | $CH_3$ | H | 3-(trifluoro-methyl)phenyl | 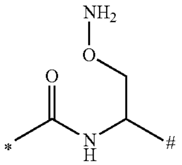 | (2,4-dimethyl-phenoxy)methyl | 3.13[a] |
| 4-34 | $CH_3$ | H | 3-(trifluoro-methyl)phenyl | 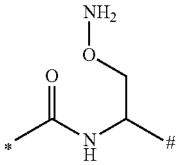 | (4-chlorophenoxy)methyl | 2.88[a] |
| 4-35 | Cl | H | 3-(trifluoro-methyl)phenyl | 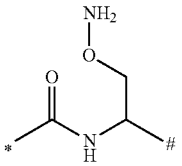 | [(2,4-dimethyl-phenyl)thio]methyl | 4.76[a] |

TABLE 9-continued

Compounds according to formula (4)

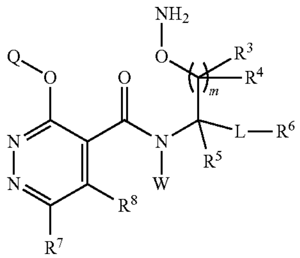

(4)

In table 9, "#" denotes the point of attachment to the L—$R^6$ group and "*" denotes the point of attachment to the pyridazin-4-yl group.

| Ex No | $R^7$ | $R^8$ | Q | 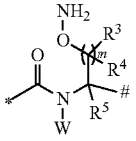 | L—$R^6$ | LogP |
|---|---|---|---|---|---|---|
| 4-36 | Cl | $CH_3$ | 2-fluoro-3-[rac-2,2-difluoro-cyclopropyl]phenyl | 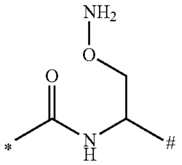 | (2,4-dimethyl-phenyl)methyl | 3.03[a] |
| 4-37 | $CH_3$ | H | 2-fluoro-3-(trifluoro-methyl)phenyl | 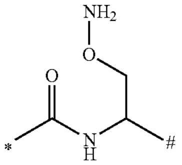 | (2,4-dimethyl-phenyl)methyl | 2.88[a] |
| 4-38 | $CH_3$ | H | 2-fluoro-3-(trifluoro-methyl)phenyl | 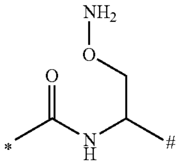 | (2,4-dichloro-phenyl)methyl | 3.04[a] |
| 4-39 | $CH_3$ | H | 3-(difluoro-methyl)phenyl | 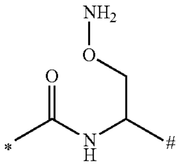 | (2,4-dichloro-phenyl)methyl | 2.61[a] |
| 4-40 | Cl | H | 2-fluoro-3-(1-fluoro-cyclopropyl)phenyl | 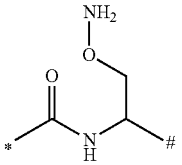 | (2,4-dimethyl-phenyl)methyl | 3.28[a] |
| 4-41 | Cl | $CH_3$ | 2-fluoro-3-(1-fluoro-cyclopropyl)phenyl | 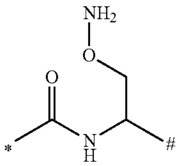 | (2,4-dimethylphenyl)methyl | 3.01 [a] |

TABLE 9-continued

Compounds according to formula (4)

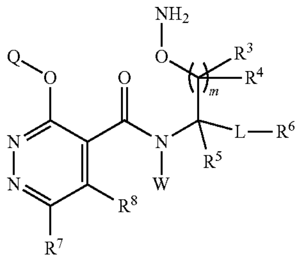

(4)

In table 9, "#" denotes the point of attachment to the L—$R^6$ group and "*" denotes the point of attachment to the pyridazin-4-yl group.

| Ex No | $R^7$ | $R^8$ | Q | 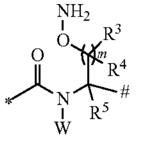 | L—$R^6$ | LogP |
|---|---|---|---|---|---|---|
| 4-42 | $CH_3$ | H | 3-chloro-2-fluorophenyl | 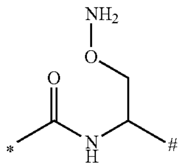 | (2-chloro-4-cyclo-propylphenyl)methyl | 3.01[a] |
| 4-43 | $CH_3$ | H | 3-chloro-2-fluorophenyl | 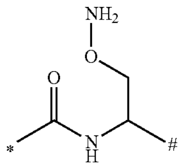 | (4-cyclopropyl-2-methylphenyl)methyl | 2.91[a] |
| 4-44 | $CH_3$ | H | 3-chloro-2-fluorophenyl | 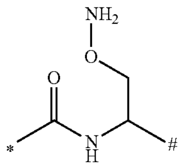 | (4-bromo-2-methyl-phenyl)methyl | 2.86[a] |
| 4-45 | $CH_3$ | H | 3-chloro-2-fluorophenyl | 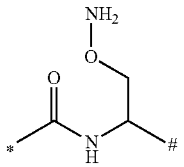 | (3,4-dimethyl-phenyl)methyl | 2.65[a] |
| 4-46 | $CH_3$ | H | 3-(difluoromethyl)-2-fluorophenyl | 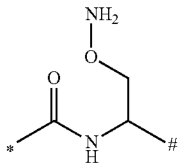 | (4-cyclopropyl-2-methylphenyl)methyl | 2.83[a] |
| 4-47 | $CH_3$ | H | 3-(difluoro-methyl)phenyl | 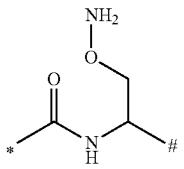 | (3,4-dimethyl-phenyl)methyl | 2.44[a] |

TABLE 9-continued

Compounds according to formula (4)

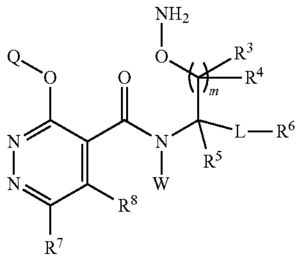

(4)

In table 9, "#" denotes the point of attachment to the L—$R^6$ group and "*" denotes the point of attachment to the pyridazin-4-yl group.

| Ex No | $R^7$ | $R^8$ | Q | 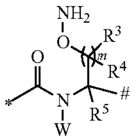 | L—$R^6$ | LogP |
|---|---|---|---|---|---|---|
| 4-48 | $CH_3$ | H | 3-(difluoro-methyl)phenyl | 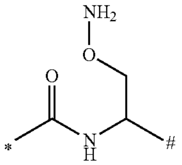 | (4-cyclopropyl-2-methylphenyl)methyl | 2.73[a] |
| 4-49 | $CH_3$ | H | 3-(difluoromethyl)-2-fluorophenyl | 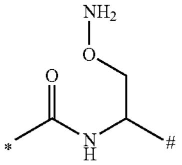 | (2,4-dimethyl-phenyl)methyl | 2.59[a] |
| 4-50 | $CH_3$ | H | 3-(difluoromethyl)-2-fluorophenyl | 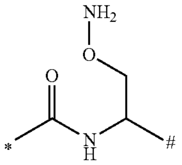 | (3,4-dimethyl-phenyl)methyl | 2.51[a] |
| 4-51 | $CH_3$ | H | 3-cyclopropyl-2-fluorophenyl | 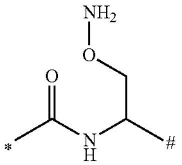 | (4-bromo-2-methyl-phenyl)methyl | 3.08[a] |
| 4-52 | Cl | H | 3-(trifluoro-methyl)phenyl | 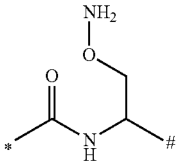 | (5-chloropyridin-2-yl)methyl | 2.50[a] |
| 4-53 | Cl | H | 3-(trifluoro-methyl)phenyl | 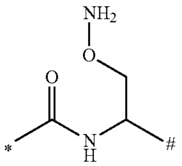 | (4,5-dimethyl-3-thienyl)methyl | 3.24[a] |

TABLE 9-continued

Compounds according to formula (4)

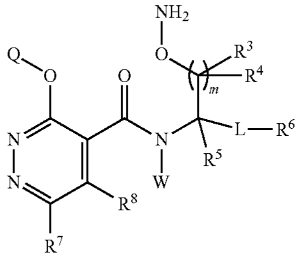

(4)

In table 9, "#" denotes the point of attachment to the L—$R^6$ group and "*" denotes the point of attachment to the pyridazin-4-yl group.

| Ex No | $R^7$ | $R^8$ | Q | 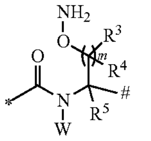 | L—$R^6$ | LogP |
|---|---|---|---|---|---|---|
| 4-54 | $CH_3$ | H | 3-cyclopropylphenyl | 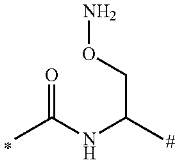 | (3,4-dimethyl-phenyl)methyl | 2.83[a] |
| 4-55 | $CH_3$ | H | 3-cyclopropylphenyl | 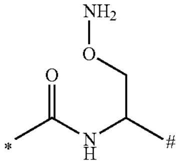 | (4-bromo-2-methyl -phenyl)methyl | 3.10[a] |
| 4-56 | $CH_3$ | H | 3-cyclopropylphenyl | 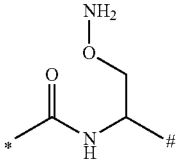 | (2-chloro-4-cyclopropyl-phenyl)methyl | 3.25[a] |
| 4-57 | $CH_3$ | H | 3-(difluoromethyl)-2-fluorophenyl | 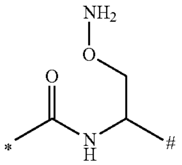 | (2-chloro-4-methyl-phenyl)methyl | 2.67[a] |

TABLE 10

4-01: $^1$H-NMR(400.2 MHz, $d_6$-DMSO):
δ = 9.4264 (1.4); 9.4079 (1.4); 7.8269 (5.7); 7.7301 (0.7); 7.7105 (1.9); 7.6908 (1.6); 7.6581 (3.5); 7.6362 (1.1); 7.6128 (4.2); 7.6074 (4.2); 7.5899 (1.5); 7.5714 (1.0); 7.5396 (2.2); 7.5185 (2.6); 7.3288 (1.8); 7.3235 (1.8); 7.3078 (1.5); 7.3025 (1.5); 5.6745 (0.5); 5.6565 (1.2); 5.6435 (1.0); 5.6382 (0.8); 5.6253 (0.5); 3.7626 (0.4); 3.7466 (2.1); 3.7428 (2.1); 3.7352 (1.8); 3.7239 (1.5); 3.6958 (0.3); 3.4354 (0.3); 3.3975 (0.4); 3.3754 (0.4); 3.3686 (0.5); 3.3433 (0.5); 3.3158 (0.4); 2.6756 (0.4); 2.6709 (0.5); 2.6663 (0.4); 2.6181 (16.0); 2.5242 (1.4); 2.5194 (2.2); 2.5107 (29.1); 2.5064 (57.5); 2.5018 (75.0); 2.4973 (55.0); 2.4930 (27.3); 2.3330 (0.3); 2.3287 (0.5); 2.3242 (0.4); 2.0737 (0.4); 0.1461 (0.4); 0.1230 (0.4); 0.0080 (2.6); −0.0002 (82.1); −0.0085 (3.1); −0.1495 (0.4)
4-02: $^1$H-NMR(400.2 MHz, $d_6$-DMSO):
δ = 9.5104 (2.8); 9.4918 (2.8); 8.3144 (0.7); 8.1803 (16.0); 7.7577 (1.1); 7.7380 (3.4); 7.7234 (4.6); 7.7195 (6.1); 7.6939 (3.8); 7.6749 (1.7); 7.6429 (2.6); 7.6173 (7.8); 7.6120 (7.2); 7.5398 (4.9); 7.5187 (6.0); 7.3351 (3.5); 7.3298 (3.4); 7.3141 (2.9); 7.3087 (2.9); 5.7543 (5.1); 5.6710 (0.9); 5.6592 (1.1); 5.6523 (2.1); 5.6403 (1.9); 5.6337 (1.3); 5.6215 (0.9); 3.7807 (0.9); 3.7686 (1.2); 3.7524 (3.5); 3.7393 (4.9); 3.7187 (3.1); 3.7099 (1.1); 3.6907 (1.1); 3.3237 (59.5); 2.6797 (0.7); 2.6753 (1.5); 2.6707 (2.1); 2.6662 (1.5); 2.6617 (0.7); 2.6176

TABLE 10-continued (0.5); 2.5242 (6.6); 2.5194 (10.0); 2.5108 (126.0); 2.5063 (250.8); 2.5018 (328.0); 2.4972 (239.8); 2.4928 (118.0); 2.3377 (0.8); 2.3331 (1.6); 2.3286 (2.1); 2.3241 (1.6); 2.3198 (0.7); 2.0735 (1.3); 0.1461 (1.7); 0.0184 (0.5); 0.0080 (13.0); −0.0002 (382.0); −0.0085 (14.4); −0.1494 (1.7)

4-03: $^1$H-NMR(300.2 MHz, CDCl3):

δ = 8.4942 (1.0); 8.4682 (1.0); 8.2884 (8.9); 7.2986 (24.3); 7.1809 (0.6); 7.1539 (2.0); 7.1281 (4.0); 7.1238 (2.5); 7.1104 (1.5); 7.1041 (1.9); 7.0849 (2.8); 7.0598 (3.1); 6.9700 (2.9); 6.9075 (1.0); 6.8859 (3.0); 6.8789 (1.6); 6.8608 (2.0); 5.5759 (5.8); 5.3377 (10.9); 4.6628 (0.5); 4.6524 (0.6); 4.6452 (0.7); 4.6349 (0.8); 4.6255 (0.7); 4.6189 (0.6); 4.6075 (0.6); 3.8733 (1.2); 3.8622 (1.2); 3.8352 (2.4); 3.8241 (2.2); 3.7703 (2.2); 3.7520 (2.1); 3.7321 (1.2); 3.7139 (1.1); 3.0017 (4.7); 2.9773 (4.6); 2.6036 (0.5); 2.5355 (0.4); 2.4075 (16.0); 2.3743 (0.4); 2.2727 (14.8); 2.2402 (0.4); 2.1933 (0.4); 2.1756 (0.6); 2.1650 (0.7); 2.1475 (1.3); 2.1304 (0.8); 2.1190 (0.7); 2.1023 (0.4); 2.0836 (0.8); 1.5892 (13.4); 1.3218 (0.4); 1.2977 (0.9); 1.1173 (1.0); 1.1024 (2.4); 1.0954 (2.7); 1.0807 (1.6); 1.0738 (2.6); 1.0671 (2.5); 1.0525 (1.2); 0.8495 (1.3); 0.8344 (3.0); 0.8285 (2.9); 0.8174 (2.7); 0.8121 (3.1); 0.7956 (1.0); 0.1080 (4.1); 0.0493 (0.9); 0.0385 (23.5); 0.0276 (0.9)

4-04: $^1$H-NMR(300.2 MHz, CDCl3):

δ = 8.3531 (0.8); 8.3266 (0.9); 8.3029 (9.1); 8.2979 (1.4); 7.6447 (0.8); 7.6209 (1.3); 7.6017 (0.8); 7.4923 (0.6); 7.4684 (1.3); 7.4480 (1.0); 7.4415 (0.8); 7.4208 (1.9); 7.3936 (2.0); 7.3667 (0.7); 7.2987 (15.0); 7.1293 (1.5); 7.0969 (0.3); 7.0763 (2.1); 7.0507 (2.7); 6.9910 (0.5); 6.9656 (2.5); 6.9472 (3.1); 6.8896 (1.5); 6.8637 (1.1); 6.7649 (1.5); 5.5723 (2.6); 5.3374 (16.0); 4.6678 (0.5); 4.6569 (0.5); 4.6500 (0.6); 4.6403 (0.7); 4.6303 (0.6); 4.6233 (0.6); 4.6124 (0.5); 4.1731 (0.4); 4.1678 (0.3); 3.8756 (1.0); 3.8646 (1.1); 3.8373 (2.2); 3.8263 (2.0); 3.7736 (2.0); 3.7555 (2.0); 3.7353 (1.0); 3.7172 (1.0); 3.0308 (0.5); 3.0077 (4.3); 2.9834 (4.1); 2.4224 (2.0); 2.4021 (14.3); 2.2882 (2.0); 2.2628 (13.1); 2.0092 (0.4); 1.7645 (2.2); 1.6738 (1.5); 1.5973 (4.0); 1.2976 (0.5); 0.9950 (0.4); 0.9916 (0.6); 0.9694 (1.0); 0.9667 (1.3); 0.9416 (0.6); 0.1087 (1.3); 0.0496 (0.6); 0.0387 (16.6); 0.0279 (0.5)

4-05: $^1$H-NMR(300.2 MHz, CDCl3):

δ = 8.3293 (0.7); 8.3029 (0.7); 8.0813 (3.9); 8.0578 (0.4); 7.9229 (0.4); 7.9124 (0.4); 7.9050 (0.4); 7.8949 (0.5); 7.7956 (0.6); 7.7854 (0.4); 7.7782 (0.4); 7.5138 (2.0); 7.5075 (2.0); 7.2993 (27.9); 7.2652 (1.5); 7.2593 (1.5); 7.2107 (2.5); 7.1835 (1.3); 7.1500 (2.7); 7.1328 (2.0); 7.1256 (2.2); 6.8830 (0.5); 6.8625 (0.8); 6.8513 (0.9); 6.8393 (0.5); 6.8296 (0.4); 5.6053 (2.6); 5.3384 (9.3); 4.8221 (0.5); 4.8139 (0.5); 4.7902 (0.3); 4.1798 (0.6); 3.9277 (0.7); 3.9160 (0.7); 3.8904 (1.2); 3.8782 (1.1); 3.8037 (1.2); 3.7848 (1.1); 3.7659 (0.7); 3.7471 (0.7); 3.1483 (0.3); 3.1240 (1.5); 3.1126 (1.5); 3.1019 (1.4); 3.0864 (1.3); 2.9947 (2.6); 2.9225 (2.4); 2.8422 (13.2); 2.7308 (11.6); 2.1745 (0.4); 2.1637 (0.5); 2.1461 (0.8); 2.1297 (0.5); 2.1184 (0.5); 1.5902 (16.0); 1.1037 (0.5); 1.0877 (1.4); 1.0818 (1.6); 1.0667 (0.9); 1.0593 (1.5); 1.0531 (1.6); 1.0389 (0.7); 0.8430 (0.6); 0.8220 (1.9); 0.8109 (1.7); 0.8049 (2.0); 0.7888 (0.6); 0.1076 (0.4); 0.0384 (33.0)

4-06: $^1$H-NMR(300.2 MHz, CDCl3):

δ = 7.5743 (1.6); 7.5543 (4.2); 7.5518 (3.7); 7.4635 (2.0); 7.4208 (0.8); 7.4106 (1.2); 7.4032 (1.0); 7.3903 (0.8); 7.3822 (0.4); 7.2991 (5.8); 7.1002 (1.8); 7.0746 (2.2); 6.9869 (2.2); 6.8936 (1.3); 6.8681 (1.0); 6.7547 (0.9); 6.7260 (1.0); 5.5895 (1.4); 5.3373 (0.5); 4.7540 (0.4); 4.7436 (0.4); 4.7352 (0.5); 4.7252 (0.6); 4.7152 (0.5); 4.7066 (0.4); 4.6994 (0.4); 3.8770 (0.9); 3.8660 (0.9); 3.8389 (1.6); 3.8281 (1.4); 3.7527 (1.4); 3.7334 (1.4); 3.7147 (0.8); 3.6954 (0.8); 2.9608 (2.8); 2.9359 (2.5); 2.3908 (12.0); 2.3557 (16.0); 2.2590 (11.0); 1.6273 (1.7); 1.2959 (0.4); 0.9197 (0.3); 0.0380 (5.9)

4-07: $^1$H-NMR(300.2 MHz, CDCl3):

δ = 8.5484 (0.8); 8.5220 (0.8); 8.1316 (5.3); 7.3789 (1.2); 7.3527 (2.6); 7.3264 (1.6); 7.2985 (8.9); 7.0784 (1.8); 7.0528 (2.3); 7.0303 (1.5); 7.0042 (1.4); 6.9990 (1.3); 6.9972 (1.4); 6.9938 (1.2); 6.9887 (1.5); 6.9856 (1.5); 6.9726 (2.4); 6.9621 (1.4); 6.9326 (1.8); 6.9265 (2.2); 6.9197 (1.2); 6.8903 (1.2); 6.8640 (0.9); 5.5661 (3.3); 5.3373 (4.8); 4.6634 (0.4); 4.6523 (0.4); 4.6455 (0.5); 4.6356 (0.6); 4.6260 (0.5); 4.6188 (0.4); 4.6081 (0.4); 3.8555 (0.8); 3.8440 (0.8); 3.8179 (1.7); 3.8065 (1.5); 3.7563 (1.6); 3.7378 (1.5); 3.7187 (0.8); 3.7002 (0.8); 2.9746 (3.4); 2.9502 (3.3); 2.8414 (1.0); 2.7284 (16.0); 2.4032 (11.7); 2.2843 (10.8); 1.9859 (0.6); 1.9745 (0.6); 1.9578 (1.1); 1.9411 (0.6); 1.9300 (0.6); 1.6272 (4.9); 1.0670 (0.7); 1.0521 (1.9); 1.0451 (2.1); 1.0304 (1.1); 1.0237 (2.0); 1.0169 (1.8); 1.0025 (0.9); 0.7874 (0.9); 0.7723 (2.4); 0.7662 (2.0); 0.7558 (2.0); 0.7504 (2.4); 0.7340 (0.7); 0.0480 (0.4); 0.0372 (9.5); 0.0264 (0.3)

4-08: $^1$H-NMR(300.2 MHz, CDCl3):

δ = 8.5851 (2.9); 8.3666 (0.4); 8.3414 (0.4); 8.0516 (1.9); 7.6494 (1.5); 7.6325 (2.0); 7.4774 (1.1); 7.4438 (0.5); 7.4354 (0.5); 7.4294 (0.6); 7.4230 (0.6); 7.4138 (0.5); 7.4064 (0.3); 7.2991 (5.9); 7.0597 (0.9); 7.0341 (1.2); 6.9704 (1.4); 6.8836 (0.7); 6.8586 (0.6); 5.5622 (0.6); 5.3360 (3.0); 4.6248 (0.4); 3.8703 (0.4); 3.8593 (0.5); 3.8320 (0.8); 3.8211 (0.8); 3.7676 (0.8); 3.7496 (0.8); 3.7294 (0.5); 3.7114 (0.4); 2.9928 (16.0); 2.9685 (2.0); 2.9189 (12.9); 2.8535 (0.6); 2.8398 (12.6); 2.5989 (0.9); 2.5341 (0.8); 2.4302 (0.4); 2.3931 (6.0); 2.3705 (1.0); 2.3247 (0.6); 2.3156 (0.7); 2.2994 (0.5); 2.2723 (5.7); 2.2366 (0.8); 1.2893 (0.4); 0.1063 (0.6); 0.0355 (7.4); 0.0250 (0.6)

4-09: $^1$H-NMR(300.2 MHz, CDCl3):

δ = 8.4893 (0.7); 8.4622 (0.7); 8.1340 (5.3); 7.2986 (10.2); 7.1365 (3.4); 7.1187 (2.5); 7.1142 (2.0); 7.1083 (1.7); 7.0964 (1.8); 7.0708 (2.1); 6.9661 (2.0); 6.8878 (1.2); 6.8740 (0.8); 6.8578 (1.7); 6.8429 (1.1); 6.8290 (0.6); 6.8202 (0.5); 5.5930 (4.3); 5.3376 (6.4); 4.6797 (0.4); 4.6686 (0.4); 4.6615 (0.5); 4.6519 (0.5); 4.6418 (0.4); 4.6346 (0.4); 4.6237 (0.4); 3.8724 (0.8); 3.8609 (0.8); 3.8347 (1.6); 3.8232 (1.5); 3.7705 (1.5); 3.7517 (1.5); 3.7328 (0.8); 3.7140 (0.8); 2.9963 (3.2); 2.9720 (3.1); 2.8413 (0.4); 2.7316 (16.0); 2.4111 (11.1); 2.2693 (10.3); 2.1737 (0.5); 2.1624 (0.5); 2.1454 (1.0); 2.1281 (0.5); 2.1172 (0.5); 1.6214 (7.0); 1.0988 (0.7); 1.0841 (1.7); 1.0770 (1.9); 1.0708 (1.0); 1.0624 (1.1); 1.0555 (1.8); 1.0487 (1.7); 1.0342 (0.8); 0.8393 (0.9); 0.8244 (2.0); 0.8217 (1.9); 0.8184 (2.0); 0.8074 (1.8); 0.8020 (2.1); 0.7856 (0.7); 0.1072 (1.5); 0.0479 (0.4); 0.0371 (10.7); 0.0262 (0.4)

4-10: $^1$H-NMR(300.2 MHz, CDCl3):

δ = 8.3120 (8.0); 8.1748 (0.9); 8.1483 (0.9); 8.1096 (0.4); 7.6560 (4.2); 7.6387 (4.1); 7.5841 (0.4); 7.4593 (2.3); 7.4293 (0.4); 7.4171 (1.0); 7.4088 (1.0); 7.3996 (1.4); 7.3929 (1.2); 7.3867 (0.9); 7.3784 (0.6); 7.2986 (15.0); 7.0095 (3.2); 6.9479 (7.9); 6.9448 (7.9); 5.5944 (2.4); 5.3373 (5.2); 4.7284 (0.5); 4.7159 (0.6); 4.7062 (0.7); 4.6940 (0.7); 4.6894 (0.7); 4.6799 (0.6); 4.6677 (0.5); 3.8849 (1.2); 3.8729 (1.2); 3.8467 (2.2); 3.8347 (2.0); 3.7582 (2.0); 3.7375 (1.9); 3.7200 (1.2); 3.6993 (1.1); 2.9561 (2.7); 2.9511 (2.7); 2.9306 (3.1); 2.2886 (0.7); 2.2781 (0.8); 2.1918 (16.0); 2.1817 (15.7); 1.6069 (2.1); 1.2931 (0.4); 0.1082 (1.2); 0.0490 (0.6); 0.0383 (19.0); 0.0273 (0.7)

4-11: $^1$H-NMR(300.2 MHz, CDCl3):

δ = 8.3034 (1.9); 8.2671 (16.0); 8.0569 (0.6); 7.8932 (0.3); 7.7950 (0.4); 7.6958 (0.5); 7.6681 (5.2); 7.6627 (3.8); 7.6507 (9.6); 7.5985 (0.6); 7.5021 (4.5); 7.4706 (1.0); 7.4569 (2.0); 7.4431 (2.7); 7.4369 (2.7); 7.4270 (2.1); 7.4186 (1.4); 7.3549 (6.5); 7.3479 (6.8); 7.2986 (39.9); 7.2800 (4.8); 7.2643 (0.8); 7.2525 (8.0); 7.2318

TABLE 10-continued (0.4); 7.1838 (5.0); 7.1768 (4.6); 7.1563 (2.8); 7.1494 (2.6); 5.5747 (10.3); 5.3375 (4.8); 4.8424 (0.3); 4.8153 (1.0); 4.8006 (1.2); 4.7900 (1.5); 4.7635 (1.1); 4.7468 (0.5); 4.7347 (0.4); 4.3179 (0.5); 3.9240 (2.3); 3.9127 (2.4); 3.9000 (0.4); 3.8857 (4.3); 3.8745 (3.9); 3.7995 (3.9); 3.7815 (3.9); 3.7611 (2.4); 3.7432 (2.2); 3.2068 (1.0); 3.1809 (1.0); 3.1603 (4.4); 3.1359 (6.7); 3.1144 (4.2); 3.0912 (1.0); 3.0678 (0.8); 1.5910 (12.7); 1.2941 (0.9); 0.1073 (2.1); 0.0485 (1.7); 0.0377 (51.4); 0.0267 (1.8)

4-12: $^1$H-NMR(300.2 MHz, CDCl3):
δ = 8.4370 (1.1); 8.4102 (1.0); 8.3174 (8.6); 8.1076 (0.4); 7.6916 (0.3); 7.6629 (3.5); 7.6456 (5.4); 7.5911 (0.4); 7.5393 (0.4); 7.5044 (2.6); 7.4686 (0.6); 7.4555 (1.3); 7.4475 (1.1); 7.4410 (1.7); 7.4346 (1.5); 7.4254 (1.1); 7.4171 (0.8); 7.2986 (19.3); 7.1630 (0.4); 7.1519 (0.4); 7.1072 (0.6); 7.0807 (0.5); 7.0655 (2.5); 7.0395 (3.0); 6.8983 (0.5); 6.8726 (3.3); 6.7781 (1.7); 6.7725 (1.6); 6.7520 (1.4); 6.7465 (1.3); 5.5561 (0.5); 5.3378 (12.9); 4.6404 (0.6); 4.6227 (0.7); 4.6138 (0.8); 4.6047 (0.7); 4.5892 (0.6); 4.2910 (0.3); 3.8671 (1.1); 3.8563 (1.1); 3.8451 (0.3); 3.8288 (2.2); 3.8180 (2.0); 3.7649 (2.3); 3.7472 (2.1); 3.7264 (1.3); 3.7089 (1.1); 3.0508 (0.3); 3.0174 (0.4); 2.9948 (4.7); 2.9690 (3.2); 2.9227 (0.6); 2.8608 (0.8); 2.8530 (1.0); 2.8425 (5.2); 2.7206 (0.5); 2.6503 (2.0); 2.5976 (0.8); 2.5321 (0.8); 2.4973 (0.6); 2.4844 (0.6); 2.4606 (0.5); 2.4465 (1.0); 2.4387 (0.9); 2.4010 (16.0); 2.3710 (0.6); 2.3203 (1.3); 2.0073 (0.4); 1.8635 (0.6); 1.8469 (1.0); 1.8358 (1.0); 1.8191 (1.6); 1.8023 (1.0); 1.7911 (1.0); 1.7742 (0.5); 1.3947 (0.5); 1.3734 (0.5); 1.2921 (0.8); 0.9795 (1.3); 0.9648 (3.0); 0.9581 (3.4); 0.9439 (1.8); 0.9366 (3.2); 0.9299 (3.0); 0.9161 (1.4); 0.7074 (0.5); 0.6943 (0.7); 0.6880 (0.7); 0.6742 (1.6); 0.6597 (3.2); 0.6544 (2.9); 0.6431 (2.9); 0.6377 (3.1); 0.6219 (1.0); 0.1081 (2.7); 0.0485 (0.7); 0.0379 (24.0); 0.0270 (1.0)

4-13: $^1$H-NMR(300.2 MHz, CDCl3):
δ = 8.3099 (0.4); 8.2680 (16.0); 8.1493 (2.0); 8.1212 (2.0); 8.0665 (0.7); 8.0229 (0.4); 7.8920 (0.4); 7.8079 (0.5); 7.7950 (0.6); 7.7795 (0.5); 7.7666 (0.3); 7.7239 (0.4); 7.7075 (0.6); 7.6898 (0.8); 7.6633 (7.2); 7.6458 (10.6); 7.6213 (0.4); 7.6091 (0.4); 7.5934 (0.6); 7.5833 (0.6); 7.5539 (0.7); 7.5422 (0.5); 7.4987 (4.9); 7.4689 (1.4); 7.4556 (2.4); 7.4458 (2.9); 7.4409 (3.5); 7.4343 (2.9); 7.4252 (2.4); 7.4171 (1.8); 7.3855 (0.5); 7.3574 (0.3); 7.2987 (31.6); 7.2496 (0.5); 7.2242 (0.5); 7.1890 (1.0); 7.1779 (6.1); 7.1515 (6.6); 7.1038 (0.7); 7.0909 (0.4); 7.0836 (0.4); 7.0653 (0.6); 7.0387 (0.6); 7.0150 (6.9); 7.0092 (6.9); 6.9476 (0.5); 6.9239 (0.5); 6.8969 (0.4); 6.8608 (3.9); 6.8549 (3.6); 6.8345 (3.3); 6.8286 (3.0); 5.6459 (0.4); 5.6374 (0.4); 5.5899 (0.4); 5.5433 (0.4); 5.5253 (0.4); 5.3373 (2.6); 4.8645 (0.4); 4.8525 (0.5); 4.8405 (1.0); 4.8286 (1.2); 4.8207 (1.4); 4.8094 (1.5); 4.7930 (1.3); 4.7810 (1.1); 4.7682 (0.6); 4.7566 (0.5); 4.3030 (0.6); 4.1825 (0.4); 4.1639 (0.4); 3.9301 (2.6); 3.9182 (2.6); 3.9087 (0.6); 3.8922 (4.4); 3.8805 (4.0); 3.8165 (0.4); 3.7884 (3.9); 3.7686 (3.9); 3.7505 (2.6); 3.7307 (2.5); 3.7018 (0.4); 3.1801 (0.5); 3.1540 (0.7); 3.1125 (7.9); 3.0882 (8.8); 3.0668 (0.7); 3.0438 (0.4); 3.0197 (0.3); 2.9948 (0.3); 2.8409 (4.2); 2.7308 (0.3); 2.6474 (0.7); 2.6029 (1.6); 2.5410 (1.6); 2.5226 (0.6); 2.5002 (0.6); 1.8814 (0.4); 1.8592 (1.0); 1.8425 (1.6); 1.8311 (1.9); 1.8143 (3.1); 1.7975 (1.9); 1.7865 (1.8); 1.7695 (0.9); 1.7490 (0.6); 1.7160 (0.5); 1.4777 (0.5); 1.4528 (1.1); 1.4360 (2.4); 1.4139 (2.4); 1.2912 (0.8); 1.0175 (2.2); 1.0021 (5.5); 0.9957 (6.3); 0.9807 (3.6); 0.9739 (6.0); 0.9677 (5.6); 0.9528 (2.8); 0.9344 (0.6); 0.9225 (0.5); 0.9025 (0.4); 0.7254 (0.7); 0.7083 (0.9); 0.6753 (2.8); 0.6599 (6.6); 0.6545 (5.7); 0.6434 (5.9); 0.6381 (6.8); 0.6219 (2.3); 0.1074 (3.3); 0.0477 (1.1); 0.0370 (40.0); 0.0261 (1.8)

4-14: $^1$H-NMR(300.2 MHz, CDCl3):
δ = 8.2695 (5.8); 8.2625 (0.9); 8.1828 (0.8); 8.1548 (0.8); 7.6916 (0.4); 7.6631 (3.0); 7.6457 (4.2); 7.5532 (0.5); 7.5434 (0.4); 7.5142 (2.0); 7.4767 (0.4); 7.4648 (1.0); 7.4566 (1.0); 7.4500 (1.3); 7.4434 (1.2); 7.4345 (1.0); 7.4128 (0.4); 7.2989 (12.8); 7.2709 (0.4); 7.2285 (2.2); 7.2151 (0.5); 7.2021 (2.9); 7.1897 (2.8); 7.1842 (2.8); 7.0880 (0.4); 7.0270 (1.5); 7.0213 (1.4); 7.0008 (1.2); 6.9950 (1.1); 4.8509 (0.4); 4.8210 (0.6); 4.8040 (0.5); 4.7921 (0.4); 3.9394 (1.0); 3.9276 (1.0); 3.9016 (1.7); 3.8899 (1.6); 3.7964 (1.5); 3.7767 (1.4); 3.7585 (1.0); 3.7388 (1.0); 3.1540 (0.4); 3.1281 (2.5); 3.1056 (2.8); 3.0816 (0.4); 2.9943 (0.4); 2.8876 (0.4); 2.8645 (1.0); 2.8411 (4.0); 2.8185 (1.0); 2.7956 (0.5); 2.6492 (0.4); 2.6027 (0.8); 2.5422 (0.8); 1.4561 (0.5); 1.4389 (1.4); 1.4165 (1.4); 1.2823 (0.8); 1.2748 (0.7); 1.2586 (1.3); 1.2522 (0.8); 1.2427 (0.9); 1.2292 (16.0); 1.2062 (16.0); 1.1802 (0.8); 0.9339 (0.4); 0.1075 (1.1); 0.0371 (15.8); 0.0262 (0.9)

4-15: $^1$H-NMR(300.2 MHz, CDCl3):
δ = 8.4712 (0.8); 8.4447 (0.8); 8.3224 (5.9); 7.6768 (0.3); 7.6632 (2.7); 7.6459 (3.9); 7.5189 (2.0); 7.4824 (0.5); 7.4673 (0.9); 7.4586 (0.8); 7.4525 (1.3); 7.4462 (1.1); 7.4368 (0.8); 7.4285 (0.7); 7.2988 (10.0); 7.1102 (1.8); 7.0843 (2.5); 7.0590 (0.4); 7.0294 (2.6); 6.9486 (1.4); 6.9434 (1.2); 6.9229 (1.0); 6.9176 (0.9); 5.3376 (1.4); 4.6526 (0.4); 4.6419 (0.5); 4.6355 (0.5); 4.6258 (0.6); 4.6141 (0.5); 4.6022 (0.5); 3.8770 (0.8); 3.8662 (0.8); 3.8387 (1.7); 3.8280 (1.5); 3.7791 (1.6); 3.7616 (1.5); 3.7407 (0.9); 3.7233 (0.8); 3.0131 (2.0); 3.0075 (2.2); 2.9911 (1.9); 2.9809 (1.8); 2.8848 (0.6); 2.8617 (1.4); 2.8420 (3.2); 2.8158 (1.1); 2.7931 (0.5); 2.7293 (0.4); 2.6419 (0.4); 2.5964 (0.7); 2.5343 (0.7); 2.4973 (0.5); 2.4886 (0.5); 2.4618 (0.6); 2.4321 (11.9); 2.3959 (0.8); 2.3282 (0.5); 1.4441 (0.7); 1.4222 (0.7); 1.2840 (1.1); 1.2753 (1.0); 1.2597 (2.0); 1.2419 (16.0); 1.2188 (15.5); 1.2028 (0.9); 1.1862 (0.6); 1.1793 (0.6); 0.1089 (1.1); 0.0383 (12.4); 0.0274 (0.6)

4-16: $^1$H-NMR(300.2 MHz, CDCl3):
δ = 8.2731 (0.7); 8.2461 (0.7); 8.1328 (5.3); 7.2989 (11.8); 7.1537 (0.5); 7.1257 (1.7); 7.1141 (1.4); 7.1035 (4.1); 7.0926 (1.2); 7.0858 (1.4); 7.0658 (0.5); 7.0589 (0.4); 7.0230 (2.3); 7.0025 (0.8); 6.9766 (1.9); 6.9717 (1.7); 6.9543 (2.7); 6.9290 (0.8); 6.8727 (0.7); 6.8618 (0.7); 6.8510 (1.2); 6.8429 (1.0); 6.8254 (0.6); 6.8188 (0.6); 5.6229 (1.2); 5.3372 (2.5); 4.7436 (0.4); 4.7309 (0.5); 4.7218 (0.6); 4.7161 (0.5); 4.7091 (0.5); 4.7034 (0.5); 4.6943 (0.5); 4.6814 (0.4); 3.8777 (0.9); 3.8651 (0.9); 3.8399 (1.6); 3.8274 (1.5); 3.7492 (1.5); 3.7277 (1.4); 3.7115 (0.9); 3.6900 (0.8); 2.9940 (0.5); 2.9450 (3.2); 2.9223 (3.5); 2.8419 (9.9); 2.7348 (16.0); 2.2637 (0.4); 2.2083 (0.7); 2.1883 (10.9); 2.1765 (11.2); 2.1540 (0.7); 2.1368 (1.0); 2.1193 (0.6); 2.1087 (0.6); 1.7825 (0.6); 1.7429 (0.6); 1.6276 (0.4); 1.2936 (0.3); 1.0957 (0.7); 1.0813 (1.6); 1.0744 (1.9); 1.0679 (1.1); 1.0603 (1.2); 1.0526 (1.8); 1.0460 (1.8); 1.0321 (0.9); 0.8360 (0.9); 0.8217 (2.0); 0.8178 (2.0); 0.8046 (2.0); 0.8001 (2.0); 0.7835 (0.7); 0.1081 (2.6); 0.0492 (0.5); 0.0384 (14.4); 0.0275 (0.6)

4-17: $^1$H-NMR(300.2 MHz, CDCl3):
δ = 8.4081 (1.0); 8.3812 (1.0); 8.3154 (9.0); 7.6623 (3.6); 7.6447 (5.2); 7.4867 (2.6); 7.4710 (0.4); 7.4574 (1.1); 7.4490 (0.9); 7.4426 (1.6); 7.4360 (1.2); 7.4272 (1.0); 7.4190 (0.6); 7.2983 (9.0); 7.0656 (2.4); 7.0401 (3.1); 6.9740 (2.9); 6.8883 (1.6); 6.8622 (1.2); 5.3371 (3.3); 4.6641 (0.6); 4.6534 (0.7); 4.6468 (0.8); 4.6371 (0.9); 4.6272 (0.7); 4.6208 (0.7); 4.6101 (0.6); 3.8790 (1.1); 3.8680 (1.2); 3.8407 (2.3); 3.8298 (2.1); 3.7752 (2.1); 3.7574 (2.1); 3.7369 (1.1); 3.7191 (1.1); 3.0029 (4.7); 2.9784 (4.6); 2.4252 (0.6); 2.3972 (16.0); 2.2980 (0.7); 2.2754 (14.8); 1.7687 (0.8); 1.6801 (0.7); 1.2936 (0.4); 0.0380 (8.2)

4-18: $^1$H-NMR(400.2 MHz, $d_6$-DMSO):
δ = 8.6892 (3.3); 8.6678 (3.4); 8.0001 (16.0); 7.7646 (1.4); 7.7451 (4.1); 7.7255 (4.1); 7.7092 (4.9); 7.6895 (1.9); 7.6467 (5.6); 7.5657 (3.1); 7.5458 (2.5); 7.2498 (8.2); 7.2289 (10.6); 7.0991 (11.6); 7.0782 (8.9); 6.1717 (2.2); 5.7565 (8.3); 4.4375 (0.8); 4.4253 (1.1); 4.4151 (1.6); 4.4033 (1.6); 4.3937 (1.2); 4.3815 (0.8); 3.6291 (0.4); 3.6012 (7.2); 3.5860 (7.1); 3.5586 (0.3); 3.3272 (85.1); 2.9543 (1.7); 2.9424 (1.9); 2.9196 (2.4); 2.9079

TABLE 10-continued (2.2); 2.7369 (2.3); 2.7143 (2.4); 2.7025 (1.9); 2.6796 (2.2); 2.6712 (1.5); 2.6667 (1.0); 2.5243 (6.3); 2.5107 (83.4); 2.5066 (162.9); 2.5022 (211.7); 2.4977 (157.3); 2.3334 (1.0); 2.3289 (1.4); 2.3245 (1.0); 2.0746 (5.0); 0.1461 (0.5); 0.0079 (4.9); −0.0002 (123.5); −0.1496 (0.6)
4-19: $^1$H-NMR(300.2 MHz, CDCl3):
δ = 8.0332 (0.6); 7.5717 (0.4); 7.5459 (1.5); 7.5210 (3.9); 7.4956 (0.5); 7.4616 (2.2); 7.4198 (0.9); 7.4127 (1.5); 7.4057 (0.8); 7.3891 (0.9); 7.2988 (8.6); 7.1126 (1.9); 7.0870 (2.4); 6.9864 (2.4); 6.8986 (1.3); 6.8726 (1.1); 6.6832 (1.0); 6.6545 (1.0); 5.5815 (3.8); 5.3369 (1.1); 4.7528 (0.4); 4.7424 (0.5); 4.7341 (0.5); 4.7239 (0.7); 4.7137 (0.5); 4.7053 (0.5); 4.6958 (0.4); 3.8683 (0.9); 3.8572 (1.0); 3.8307 (1.7); 3.8197 (1.5); 3.7449 (1.5); 3.7256 (1.5); 3.7072 (0.9); 3.6881 (0.9); 2.9878 (5.0); 2.9601 (3.5); 2.9352 (3.4); 2.9113 (4.5); 2.6225 (15.1); 2.4649 (0.3); 2.4169 (0.4); 2.3932 (12.5); 2.3341 (0.4); 2.2726 (16.0); 2.2640 (12.5); 1.6449 (1.8); 0.0471 (0.4); 0.0363 (9.4); 0.0271 (0.3); 0.0255 (0.4)
4-20: $^1$H-NMR(300.2 MHz, CDCl3):
δ = 8.4595 (0.7); 8.4329 (0.7); 8.1585 (5.2); 7.6163 (0.6); 7.5901 (1.6); 7.5641 (1.2); 7.4915 (1.4); 7.4659 (0.9); 7.3861 (1.8); 7.3698 (1.1); 7.3666 (1.2); 7.3432 (0.8); 7.3399 (0.9); 7.3361 (0.7); 7.2984 (10.5); 7.0769 (1.6); 7.0513 (2.1); 6.9720 (2.0); 6.9148 (1.1); 6.8908 (1.2); 6.8650 (0.9); 6.7270 (2.2); 6.5392 (1.1); 5.5669 (5.1); 5.3372 (0.5); 4.6689 (0.4); 4.6583 (0.4); 4.6516 (0.5); 4.6417 (0.6); 4.6314 (0.4); 4.6259 (0.4); 4.6144 (0.4); 4.1711 (0.6); 4.1473 (0.6); 3.8679 (0.8); 3.8566 (0.8); 3.8302 (1.6); 3.8190 (1.5); 3.7684 (1.5); 3.7504 (1.5); 3.7307 (0.8); 3.7127 (0.8); 2.9934 (3.3); 2.9690 (3.0); 2.8410 (2.3); 2.7424 (16.0); 2.4022 (11.2); 2.2764 (10.3); 2.0835 (2.6); 1.6153 (10.0); 1.3208 (0.7); 1.2971 (1.5); 1.2732 (0.7); 0.0479 (0.4); 0.0371 (10.9); 0.0262 (0.4)
4-21: $^1$H-NMR(300.2 MHz, CDCl3):
δ = 8.3034 (1.9); 8.2740 (2.1); 8.2654 (16.0); 8.0558 (0.6); 7.7849 (0.3); 7.6968 (0.5); 7.6706 (4.5); 7.6623 (3.9); 7.6538 (8.8); 7.6508 (9.8); 7.5951 (0.6); 7.5866 (0.9); 7.5047 (10.8); 7.4984 (9.2); 7.4882 (1.2); 7.4743 (0.8); 7.4670 (1.0); 7.4533 (2.0); 7.4401 (2.7); 7.4335 (2.8); 7.4233 (2.1); 7.4146 (1.4); 7.3920 (0.4); 7.3849 (0.4); 7.3644 (0.4); 7.3315 (3.2); 7.3250 (3.1); 7.3040 (6.1); 7.2984 (31.9); 7.2753 (0.4); 7.2149 (7.8); 7.1875 (5.5); 7.1696 (0.4); 7.1567 (0.5); 5.5738 (6.6); 5.3366 (7.0); 4.8391 (0.4); 4.8280 (0.5); 4.8127 (1.0); 4.7985 (1.2); 4.7867 (1.5); 4.7769 (1.1); 4.7605 (1.0); 4.7446 (0.5); 4.7338 (0.4); 4.3157 (0.3); 3.9345 (0.4); 3.9210 (2.3); 3.9097 (2.6); 3.8969 (0.6); 3.8827 (4.3); 3.8715 (3.9); 3.8174 (0.4); 3.7966 (4.0); 3.7786 (4.0); 3.7582 (2.4); 3.7402 (2.2); 3.1939 (1.0); 3.1786 (0.6); 3.1676 (1.2); 3.1476 (4.3); 3.1224 (7.7); 3.1000 (4.2); 3.0769 (1.0); 3.0539 (0.9); 2.8451 (0.8); 2.6575 (0.4); 2.6119 (1.0); 2.5504 (0.8); 1.6958 (0.3); 1.6138 (6.2); 1.2931 (1.2); 0.1189 (0.4); 0.1070 (11.8); 0.0947 (0.4); 0.0477 (0.9); 0.0369 (27.1); 0.0259 (1.0)
4-22: $^1$H-NMR(300.2 MHz, CDCl3):
δ = 8.6098 (1.1); 8.5848 (1.0); 8.3157 (7.9); 8.1002 (0.3); 7.6698 (2.3); 7.6647 (2.3); 7.6600 (2.3); 7.6522 (5.1); 7.6493 (5.4); 7.5979 (0.3); 7.5096 (2.6); 7.4825 (0.5); 7.4723 (0.5); 7.4575 (1.1); 7.4453 (1.5); 7.4385 (1.5); 7.4275 (1.3); 7.4188 (0.8); 7.3212 (3.1); 7.2987 (18.0); 7.2380 (1.4); 7.2324 (1.3); 7.2110 (1.9); 7.2047 (1.8); 7.1888 (0.3); 7.1625 (0.4); 7.0793 (3.5); 7.0522 (2.6); 5.5291 (5.3); 5.3371 (6.8); 4.5874 (0.6); 4.5768 (0.7); 4.5602 (0.8); 4.5505 (0.7); 4.5394 (0.6); 3.8568 (1.0); 3.8468 (1.2); 3.8338 (0.4); 3.8178 (2.2); 3.8079 (2.0); 3.7649 (0.3); 3.7487 (2.2); 3.7328 (2.1); 3.7099 (1.2); 3.6939 (1.1); 3.0645 (0.5); 3.0435 (0.7); 3.0189 (2.2); 2.9959 (3.6); 2.9664 (2.0); 2.9494 (0.6); 2.9206 (0.6); 2.4656 (0.6); 2.4346 (16.0); 2.4106 (0.4); 1.6023 (9.4); 1.2930 (0.7); 0.1074 (2.0); 0.0482 (0.6); 0.0375 (18.1)
4-23: $^1$H-NMR(300.2 MHz, CDCl3):
δ = 8.7061 (3.1); 8.7000 (3.3); 8.5022 (3.0); 8.4943 (3.1); 8.3147 (7.1); 8.2932 (0.9); 8.2672 (1.0); 7.9204 (0.4); 7.9100 (0.4); 7.9021 (0.4); 7.8921 (0.6); 7.8128 (2.0); 7.8059 (3.2); 7.7985 (2.2); 7.7850 (0.6); 7.7774 (0.6); 7.7669 (0.6); 7.2989 (13.7); 7.0695 (2.0); 7.0440 (2.8); 6.9835 (2.7); 6.9132 (1.5); 6.8869 (1.1); 5.5729 (0.9); 5.3376 (16.0); 4.6530 (0.5); 4.6431 (0.6); 4.6369 (0.6); 4.6270 (0.8); 4.6179 (0.5); 4.6114 (0.6); 4.6013 (0.6); 3.8776 (0.9); 3.8669 (1.0); 3.8391 (2.0); 3.8284 (1.9); 3.7778 (1.8); 3.7604 (1.8); 3.7394 (1.0); 3.7220 (0.9); 3.0090 (4.1); 2.9845 (3.9); 2.4009 (13.8); 2.3299 (0.4); 2.3185 (0.8); 2.2940 (13.4); 2.2715 (0.9); 2.2568 (0.8); 1.6331 (0.3); 0.0480 (0.6); 0.0372 (17.0); 0.0263 (0.7)
4-24: $^1$H-NMR(300.2 MHz, CDCl3):
δ = 8.5386 (0.4); 8.5271 (2.5); 8.5179 (2.5); 8.3170 (8.8); 8.2250 (1.2); 8.2127 (0.9); 8.1620 (0.9); 8.1354 (1.0); 7.9786 (3.0); 7.9694 (2.9); 7.9453 (0.4); 7.9353 (0.4); 7.9220 (0.3); 7.9118 (0.4); 7.8935 (0.5); 7.7965 (0.5); 7.7864 (0.3); 7.7783 (0.3); 7.7680 (0.3); 7.2990 (24.4); 7.1074 (0.4); 7.0909 (0.4); 7.0689 (2.2); 7.0434 (3.1); 7.0116 (0.6); 6.9805 (3.0); 6.9481 (0.4); 6.9109 (1.6); 6.8859 (1.2); 5.5826 (2.1); 5.3383 (10.8); 4.6635 (0.6); 4.6528 (0.7); 4.6466 (0.8); 4.6370 (0.9); 4.6270 (0.7); 4.6221 (0.7); 4.6107 (0.7); 3.8861 (1.0); 3.8754 (1.1); 3.8476 (2.3); 3.8370 (2.2); 3.8172 (0.4); 3.8045 (0.4); 3.7861 (2.2); 3.7686 (2.1); 3.7474 (1.4); 3.7301 (1.2); 3.0142 (4.5); 2.9896 (4.2); 2.9438 (0.5); 2.9207 (0.7); 2.4432 (0.4); 2.4011 (16.0); 2.3329 (0.7); 2.3103 (2.2); 2.2831 (14.0); 1.6055 (1.7); 1.3149 (0.8); 1.2940 (1.2); 0.1075 (0.4); 0.0484 (1.0); 0.0377 (29.5); 0.0268 (1.0)
4-25: $^1$H-NMR(300.2 MHz, CDCl3):
δ = 7.9196 (0.5); 7.9093 (0.5); 7.9016 (0.5); 7.8912 (0.8); 7.7948 (0.8); 7.7847 (0.6); 7.7767 (0.6); 7.7664 (0.5); 7.4570 (2.4); 7.4532 (2.4); 7.2988 (13.3); 7.2539 (0.4); 7.2258 (6.3); 7.2200 (3.2); 7.1925 (0.3); 7.1405 (0.7); 7.1147 (1.5); 7.0866 (1.4); 7.0690 (0.4); 7.0593 (1.0); 7.0530 (1.1); 7.0302 (1.2); 7.0085 (0.5); 7.0029 (0.5); 6.8549 (0.7); 6.8488 (0.8); 6.8281 (1.2); 6.8014 (1.5); 6.7719 (0.9); 5.6181 (4.4); 5.3376 (0.8); 4.8889 (0.3); 4.8788 (0.4); 4.8683 (0.5); 4.8582 (0.6); 4.8492 (0.6); 4.8395 (0.5); 4.8287 (0.4); 4.1784 (0.7); 3.9303 (0.9); 3.9190 (0.9); 3.8920 (1.6); 3.8808 (1.6); 3.7994 (1.4); 3.7799 (1.4); 3.7613 (0.9); 3.7418 (0.9); 3.1451 (0.4); 3.1167 (0.4); 3.0976 (1.8); 3.0834 (1.8); 3.0693 (2.1); 3.0617 (2.0); 2.8357 (0.8); 2.3794 (16.0); 2.3239 (1.1); 2.1326 (0.5); 2.1214 (0.5); 2.1044 (1.0); 2.0875 (0.6); 2.0766 (0.6); 1.5989 (5.9); 1.2920 (0.4); 1.0795 (0.6); 1.0656 (1.6); 1.0582 (1.9); 1.0443 (1.0); 1.0370 (1.7); 1.0298 (2.0); 1.0162 (0.8); 0.8242 (0.7); 0.8097 (2.1); 0.8043 (2.4); 0.7929 (2.1); 0.7868 (2.4); 0.7715 (0.7); 0.1071 (1.8); 0.0479 (0.6); 0.0372 (17.8); 0.0263 (0.7)
4-26: $^1$H-NMR(300.2 MHz, CDCl3):
δ = 7.9193 (0.5); 7.9089 (0.6); 7.9015 (0.5); 7.8909 (0.8); 7.7944 (0.8); 7.7844 (0.6); 7.7762 (0.6); 7.7659 (0.6); 7.2987 (12.3); 7.2294 (2.2); 7.2030 (2.5); 7.1225 (0.6); 7.0958 (1.7); 7.0689 (2.4); 7.0580 (1.5); 7.0423 (1.1); 7.0368 (1.4); 7.0215 (2.7); 7.0156 (3.2); 6.8431 (0.7); 6.8354 (0.8); 6.8144 (2.6); 6.7949 (0.8); 6.7884 (1.9); 6.7822 (1.3); 6.6886 (1.0); 6.6592 (1.0); 5.6212 (3.9); 4.8800 (0.3); 4.8690 (0.4); 4.8597 (0.4); 4.8491 (0.6); 4.8299 (0.4); 4.1775 (0.8); 3.9284 (0.9); 3.9168 (1.0); 3.8906 (1.6); 3.8791 (1.5); 3.7845 (1.4); 3.7640 (1.4); 3.7466 (0.9); 3.7263 (0.9); 3.0768 (2.1); 3.0724 (2.2); 3.0499 (3.3); 2.3638 (0.3); 2.3372 (16.0); 2.3249 (1.2); 2.1361 (0.5); 2.1256 (0.6); 2.1082 (1.0); 2.0911 (0.6); 2.0803 (0.6); 2.0439 (1.0); 1.8122 (0.4); 1.8014 (0.6); 1.7904 (0.6); 1.7734 (1.1); 1.7568 (0.6); 1.7455 (0.6); 1.6028 (5.1); 1.2914 (0.4); 1.0765 (0.6); 1.0617 (1.8); 1.0547 (2.1); 1.0405 (1.1); 1.0331 (2.0); 1.0264 (2.1); 1.0123 (0.9); 0.9830 (0.5); 0.9684 (1.6); 0.9624 (2.0); 0.9518 (1.0); 0.9403 (1.8); 0.9345 (1.8); 0.9235 (0.6); 0.9203 (0.7); 0.8168 (0.8); 0.8020 (2.2); 0.7968 (2.4); 0.7851 (2.2); 0.7795 (2.5); 0.7636 (0.8); 0.6314 (0.9); 0.6255 (0.9); 0.6162 (2.1); 0.6090 (1.8); 0.5999 (2.2); 0.5928 (1.1); 0.5837 (0.7); 0.1071 (6.3); 0.0481 (0.5); 0.0373 (16.0); 0.0264 (0.7)

TABLE 10-continued 4-27: $^1$H-NMR(300.2 MHz, CDCl3):
δ = 8.5619 (1.0); 8.5346 (1.0); 8.2838 (8.1); 7.7928 (0.6); 7.7836 (0.5); 7.7744 (0.7); 7.7657 (0.3); 7.7025 (0.5); 7.6923 (0.4); 7.6843 (0.4); 7.6740 (0.3); 7.3996 (1.6); 7.3733 (3.5); 7.3469 (2.1); 7.2988 (6.2); 7.0700 (3.2); 7.0449 (3.8); 7.0160 (0.4); 6.9932 (1.8); 6.9843 (3.4); 6.9767 (3.7); 6.9611 (2.0); 6.9587 (1.9); 6.9248 (2.3); 6.9187 (3.1); 6.9121 (1.9); 6.8917 (1.8); 6.8664 (1.4); 4.6466 (0.6); 4.6360 (0.6); 4.6293 (0.7); 4.6192 (0.9); 4.6097 (0.7); 4.6031 (0.7); 4.5922 (0.6); 4.1949 (0.6); 4.1711 (1.7); 4.1473 (1.6); 4.1233 (0.6); 3.8587 (1.1); 3.8477 (1.2); 3.8207 (2.2); 3.8097 (2.2); 3.7581 (2.2); 3.7401 (2.1); 3.7202 (1.2); 3.7022 (1.1); 2.9941 (1.4); 2.9830 (4.7); 2.9585 (4.6); 2.9196 (1.2); 2.8414 (6.7); 2.7765 (0.7); 2.7476 (0.5); 2.5799 (4.9); 2.4403 (0.4); 2.4167 (0.4); 2.4004 (16.0); 2.3736 (2.3); 2.3263 (0.7); 2.3142 (1.4); 2.3081 (1.3); 2.2866 (15.0); 2.2395 (1.7); 2.0831 (6.8); 2.0120 (0.4); 2.0035 (0.6); 1.9950 (0.8); 1.9838 (0.8); 1.9670 (1.6); 1.9504 (0.9); 1.9391 (0.9); 1.9223 (0.5); 1.5055 (0.5); 1.4812 (1.7); 1.4591 (1.5); 1.3211 (1.8); 1.2973 (3.7); 1.2735 (1.8); 1.0862 (0.9); 1.0709 (2.4); 1.0643 (2.7); 1.0496 (1.4); 1.0427 (2.7); 1.0363 (2.6); 1.0216 (1.3); 0.7921 (1.1); 0.7767 (3.1); 0.7710 (2.9); 0.7605 (2.7); 0.7548 (3.4); 0.7387 (1.1); 0.1102 (0.5); 0.0385 (7.4)
4-28: $^1$H-NMR(300.2 MHz, CDCl3):
δ = 8.2998 (1.3); 7.4893 (0.4); 7.2986 (8.8); 7.2093 (0.4); 7.2028 (0.4); 7.1543 (0.4); 7.1462 (0.5); 7.1265 (0.3); 7.1187 (0.5); 7.0742 (0.4); 7.0487 (0.5); 6.9802 (0.5); 5.5613 (1.1); 3.8287 (0.4); 3.8178 (0.3); 3.7662 (0.4); 3.7485 (0.3); 2.9941 (0.7); 2.9695 (0.7); 2.4038 (2.5); 2.2835 (2.2); 1.6232 (0.4); 1.6179 (0.5); 1.6126 (0.4); 1.5880 (16.0); 1.5590 (0.4); 1.5544 (0.4); 1.2979 (0.5); 1.1756 (0.4); 1.1698 (0.4); 1.1460 (0.4); 1.1411 (0.3); 0.9201 (0.4); 0.0488 (0.6); 0.0380 (10.3); 0.0270 (0.4)
4-29: $^1$H-NMR(300.2 MHz, CDCl3):
δ = 8.2419 (0.7); 8.2122 (0.8); 8.0974 (5.3); 8.0861 (0.4); 7.8929 (0.4); 7.7941 (0.4); 7.7760 (0.3); 7.2989 (13.3); 7.1923 (2.2); 7.1661 (2.6); 7.1436 (3.1); 7.1315 (1.8); 7.1281 (1.8); 7.1243 (2.1); 7.1188 (2.7); 7.1013 (0.4); 7.0417 (2.4); 7.0357 (2.6); 6.8800 (0.7); 6.8672 (0.6); 6.8591 (1.1); 6.8478 (1.2); 6.8356 (0.6); 6.8269 (1.9); 6.8213 (1.5); 6.8009 (1.3); 6.7949 (1.2); 5.6215 (1.3); 5.3370 (4.1); 4.8519 (0.4); 4.8295 (0.5); 4.8247 (0.5); 4.8173 (0.5); 4.8031 (0.4); 4.7917 (0.4); 3.9274 (0.9); 3.9151 (1.0); 3.8899 (1.6); 3.8775 (1.4); 3.7826 (1.4); 3.7619 (1.4); 3.7450 (1.0); 3.7244 (0.9); 3.1532 (0.3); 3.1079 (1.8); 3.0969 (1.8); 3.0858 (1.8); 3.0715 (1.6); 2.8410 (4.4); 2.7235 (16.0); 2.5966 (0.4); 2.1746 (0.5); 2.1637 (0.5); 2.1463 (1.0); 2.1290 (0.6); 2.1182 (0.6); 1.8443 (0.6); 1.8332 (0.6); 1.8164 (1.1); 1.7996 (0.6); 1.7887 (0.6); 1.7716 (0.3); 1.6153 (1.6); 1.0977 (0.6); 1.0825 (1.8); 1.0758 (2.0); 1.0611 (1.1); 1.0540 (2.0); 1.0474 (2.0); 1.0329 (1.0); 0.9983 (0.7); 0.9833 (1.9); 0.9768 (2.0); 0.9623 (0.9); 0.9551 (2.0); 0.9486 (1.8); 0.9344 (0.8); 0.8414 (0.9); 0.8264 (2.1); 0.8205 (2.2); 0.8096 (2.0); 0.8036 (2.4); 0.7875 (0.8); 0.6747 (0.9); 0.6597 (2.1); 0.6535 (1.8); 0.6433 (2.0); 0.6381 (2.1); 0.6220 (0.8); 0.1077 (0.7); 0.0486 (0.5); 0.0377 (16.6); 0.0267 (0.6)
4-30: $^1$H-NMR(300.2 MHz, CDCl3):
δ = 7.3096 (5.0); 7.2989 (16.5); 7.2825 (2.6); 7.1373 (0.5); 7.1340 (0.5); 7.1103 (1.4); 7.0917 (1.8); 7.0845 (2.6); 7.0642 (1.5); 7.0574 (1.8); 7.0530 (1.3); 7.0353 (1.0); 7.0299 (1.2); 7.0085 (0.5); 7.0028 (0.4); 6.8553 (0.7); 6.8489 (0.7); 6.8287 (1.1); 6.8067 (0.7); 6.8012 (0.7); 6.7892 (0.8); 6.7592 (0.8); 5.6176 (3.0); 5.3374 (12.2); 4.8777 (0.4); 4.8697 (0.4); 4.8602 (0.5); 4.8501 (0.5); 4.8402 (0.4); 4.8286 (0.4); 4.1028 (0.4); 3.9329 (0.9); 3.9216 (0.9); 3.8948 (1.5); 3.8835 (1.4); 3.8026 (1.4); 3.7831 (1.4); 3.7646 (0.9); 3.7451 (0.8); 3.1123 (1.7); 3.0995 (1.6); 3.0842 (1.9); 3.0775 (1.9); 2.3821 (16.0); 2.2885 (0.4); 2.1316 (0.4); 2.1204 (0.5); 2.1034 (0.9); 2.0822 (0.7); 2.0751 (0.5); 1.5982 (6.8); 1.2964 (0.6); 1.2918 (0.6); 1.0792 (0.6); 1.0654 (1.5); 1.0579 (1.8); 1.0438 (1.0); 1.0367 (1.5); 1.0296 (1.7); 1.0156 (0.8); 0.8232 (0.7); 0.8089 (1.9); 0.8028 (2.1); 0.7918 (1.9); 0.7856 (2.1); 0.7704 (0.7); 0.1074 (7.8); 0.0488 (0.6); 0.0379 (18.2); 0.0270 (0.7)
4-31: $^1$H-NMR(300.2 MHz, CDCl3):
δ = 8.4207 (0.4); 8.3917 (0.4); 8.2335 (3.6); 7.4023 (0.8); 7.3760 (1.6); 7.3621 (1.8); 7.3551 (1.8); 7.3499 (1.1); 7.2986 (4.6); 7.2540 (1.2); 7.2264 (1.8); 7.1469 (1.2); 7.1399 (1.1); 7.1195 (0.7); 7.1125 (0.6); 7.0670 (0.9); 7.0409 (0.7); 6.9860 (0.6); 6.9833 (0.6); 6.9781 (0.8); 6.9593 (0.5); 6.9565 (0.5); 6.9513 (0.7); 6.9487 (0.6); 6.9156 (1.0); 6.9096 (1.3); 6.9030 (0.7); 4.7806 (0.4); 4.1917 (1.2); 4.1678 (3.5); 4.1440 (3.6); 4.1203 (1.2); 3.9080 (0.5); 3.8964 (0.6); 3.8699 (0.9); 3.8584 (0.9); 3.7813 (0.9); 3.7626 (1.0); 3.7429 (0.7); 3.7244 (0.5); 3.1204 (2.2); 3.0960 (2.1); 2.9933 (1.2); 2.9180 (1.0); 2.8382 (6.0); 2.7013 (1.4); 2.0802 (16.0); 1.9951 (0.4); 1.9839 (0.4); 1.9722 (0.5); 1.9673 (0.8); 1.9503 (0.5); 1.9392 (0.5); 1.7230 (0.6); 1.7108 (0.6); 1.5112 (0.7); 1.4863 (0.8); 1.4791 (0.6); 1.3178 (4.1); 1.2940 (8.4); 1.2701 (4.1); 1.0869 (0.4); 1.0716 (1.0); 1.0649 (1.2); 1.0500 (0.7); 1.0433 (1.2); 1.0369 (1.2); 1.0220 (0.6); 0.7904 (0.5); 0.7750 (1.4); 0.7693 (1.2); 0.7588 (1.2); 0.7530 (1.6); 0.7367 (0.5); 0.1050 (0.8); 0.0342 (4.5)
4-32: $^1$H-NMR(300.2 MHz, CDCl3):
δ = 8.5021 (0.6); 8.4782 (0.7); 8.4594 (0.6); 8.2996 (8.4); 7.2986 (26.2); 7.2793 (1.0); 7.2719 (2.0); 7.2658 (3.1); 7.2600 (2.0); 7.2515 (1.6); 7.2470 (3.1); 7.2421 (2.7); 7.2206 (0.7); 7.2153 (0.6); 7.1960 (1.0); 7.1802 (1.0); 7.1659 (0.9); 7.1506 (0.4); 7.0859 (1.5); 7.0608 (1.9); 6.9723 (2.0); 6.8936 (1.5); 6.8690 (1.2); 5.5708 (3.8); 5.5626 (3.6); 4.6565 (0.4); 4.6463 (0.6); 4.6290 (0.7); 4.6207 (0.7); 4.6123 (0.6); 4.6051 (0.6); 4.1959 (1.2); 4.1721 (3.6); 4.1482 (3.5); 4.1244 (1.2); 3.8721 (0.9); 3.8615 (1.0); 3.8339 (2.0); 3.8231 (1.8); 3.7708 (1.6); 3.7534 (1.5); 3.7314 (0.8); 3.7132 (0.7); 3.0096 (4.0); 2.9856 (3.4); 2.9618 (0.4); 2.9203 (0.7); 2.8903 (0.7); 2.8509 (0.4); 2.4095 (10.9); 2.2747 (7.4); 2.2666 (7.6); 2.0839 (16.0); 2.0469 (0.5); 2.0295 (0.5); 2.0200 (0.6); 2.0074 (0.9); 2.0028 (0.7); 1.9901 (0.8); 1.9807 (1.0); 1.9681 (0.6); 1.9633 (1.0); 1.9507 (0.5); 1.9415 (0.5); 1.9241 (0.5); 1.7924 (0.3); 1.7752 (0.3); 1.7613 (0.6); 1.7485 (0.8); 1.7375 (0.6); 1.7341 (0.6); 1.7229 (0.8); 1.7103 (0.6); 1.7063 (0.6); 1.5885 (8.1); 1.3676 (0.4); 1.3453 (0.8); 1.3217 (5.6); 1.2980 (12.7); 1.2741 (4.6); 0.9420 (1.9); 0.9202 (6.1); 0.8971 (2.2); 0.0489 (1.3); 0.0381 (35.2); 0.0272 (1.5)
4-33: $^1$H-NMR(300.2 MHz, CDCl3):
δ = 8.5286 (0.7); 8.5005 (0.7); 8.2051 (5.0); 7.9219 (0.4); 7.9115 (0.4); 7.9037 (0.4); 7.8935 (0.5); 7.7953 (0.5); 7.7853 (0.4); 7.7772 (0.4); 7.7669 (0.4); 7.5796 (3.1); 7.5762 (3.6); 7.5670 (1.5); 7.5562 (1.9); 7.5298 (0.5); 7.4890 (1.8); 7.4218 (0.8); 7.4144 (1.0); 7.3996 (0.9); 7.3924 (1.0); 7.3835 (0.5); 7.2985 (15.9); 6.9612 (0.9); 6.9339 (1.1); 6.8975 (1.8); 6.7512 (2.2); 6.7237 (1.7); 5.6826 (3.0); 5.3377 (8.4); 4.9848 (0.3); 4.9715 (0.6); 4.9587 (0.6); 4.9464 (0.6); 4.9342 (0.5); 4.9197 (0.4); 4.2084 (3.1); 4.1955 (3.7); 4.1060 (0.8); 4.0822 (0.8); 4.0678 (1.7); 4.0440 (1.6); 4.0116 (1.6); 3.9964 (1.6); 3.9734 (0.8); 3.9582 (0.7); 2.7713 (16.0); 2.3256 (0.7); 2.2648 (10.3); 2.2413 (0.4); 2.1848 (0.4); 1.9744 (10.4); 1.6013 (2.6); 0.1075 (0.8); 0.0486 (0.8); 0.0378 (19.7); 0.0268 (0.7)
4-34: $^1$H-NMR(300.2 MHz, CDCl3):
δ = 8.6187 (0.7); 8.5920 (0.7); 8.1920 (5.3); 7.9206 (0.3); 7.9103 (0.4); 7.8922 (0.5); 7.7945 (0.5); 7.7848 (0.3); 7.7763 (0.4); 7.7660 (0.4); 7.6089 (3.3); 7.6055 (3.0); 7.5969 (1.5); 7.5920 (2.2); 7.5888 (2.1); 7.5203 (1.7); 7.4600 (0.8); 7.4504 (0.8); 7.4460 (0.5); 7.4403 (1.0); 7.4337 (0.8); 7.4293 (0.6); 7.4211 (0.4); 7.2985 (12.5); 7.2341 (0.4); 7.2226 (4.1); 7.2152 (1.3); 7.2000 (1.4); 7.1925 (4.6); 7.1812 (0.4); 6.7972 (0.5); 6.7857 (4.7); 6.7782 (1.4); 6.7631 (1.3); 6.7556 (4.0); 6.7441 (0.4); 5.6493 (3.9); 5.3370 (4.7); 4.8959 (0.4); 4.8903 (0.5);

TABLE 10-continued 4.8837 (0.5); 4.8789 (0.5); 4.8691 (0.5); 4.8626 (0.5); 4.8578 (0.4); 4.2576 (0.6); 4.2468 (0.7); 4.2262 (1.8); 4.2155 (1.6); 4.1973 (1.8); 4.1796 (2.0); 4.1659 (0.7); 4.1480 (0.7); 4.0809 (0.8); 4.0590 (0.7); 4.0424 (1.7); 4.0206 (1.6); 3.9863 (1.6); 3.9711 (1.7); 3.9479 (0.8); 3.9327 (0.7); 2.7754 (16.0); 1.6059 (2.7); 0.1068 (0.6); 0.0476 (0.6); 0.0368 (15.6); 0.0259 (0.5)
4-35: $^1$H-NMR(300.2 MHz, CDCl3):
δ = 8.6003 (0.9); 8.5741 (0.9); 8.3001 (8.1); 7.6370 (3.8); 7.6197 (4.9); 7.5115 (2.4); 7.4735 (1.0); 7.4652 (0.9); 7.4579 (1.4); 7.4516 (1.2); 7.4430 (0.8); 7.4348 (0.6); 7.3728 (2.2); 7.3471 (2.5); 7.2991 (8.9); 6.9878 (5.4); 6.9615 (1.4); 5.5215 (3.5); 5.3380 (12.9); 4.6777 (0.4); 4.6665 (0.5); 4.6542 (0.7); 4.6408 (0.7); 4.6342 (0.7); 4.6274 (0.5); 4.6163 (0.4); 4.0228 (1.3); 4.0038 (1.2); 3.9842 (2.0); 3.9653 (1.9); 3.8697 (2.0); 3.8573 (1.9); 3.8311 (1.3); 3.8188 (1.2); 3.3324 (0.8); 3.3156 (0.8); 3.2865 (2.2); 3.2697 (2.1); 3.2431 (2.3); 3.2199 (2.3); 3.1972 (1.0); 3.1740 (0.8); 2.4148 (0.5); 2.3205 (16.0); 2.2827 (15.2); 1.6218 (0.5); 0.1081 (0.8); 0.0486 (0.4); 0.0377 (10.5); 0.0269 (0.4)
4-36: $^1$H-NMR(300.2 MHz, CDCl3):
δ = 7.2983 (3.2); 7.2436 (0.4); 7.2238 (0.9); 7.2170 (0.9); 7.2036 (2.7); 7.2000 (2.1); 7.1941 (2.4); 7.1793 (2.9); 7.1761 (2.7); 7.1522 (0.8); 7.1222 (1.2); 7.1022 (2.3); 7.0889 (2.0); 7.0770 (1.9); 7.0633 (1.5); 7.0413 (0.8); 7.0131 (0.7); 6.9793 (1.6); 6.9559 (2.0); 6.9286 (0.7); 6.8896 (0.9); 6.8630 (0.8); 6.8475 (0.8); 6.8206 (0.6); 5.5829 (1.2); 4.7230 (0.5); 4.7118 (0.6); 4.7053 (0.7); 4.6948 (0.7); 4.6871 (0.6); 4.6766 (0.6); 4.1846 (0.5); 4.1608 (1.7); 4.1369 (1.7); 4.1132 (0.6); 3.8525 (0.6); 3.8453 (0.7); 3.8420 (0.8); 3.8352 (0.6); 3.8145 (1.1); 3.8075 (1.4); 3.7974 (1.1); 3.7377 (0.9); 3.7258 (1.0); 3.7196 (1.1); 3.7064 (0.9); 3.6999 (0.7); 3.6879 (0.6); 3.6816 (0.6); 3.6685 (0.5); 2.9586 (2.2); 2.9468 (2.3); 2.9336 (2.3); 2.9221 (2.1); 2.8998 (0.4); 2.8810 (0.4); 2.8694 (0.8); 2.8597 (0.6); 2.8396 (0.6); 2.8299 (0.8); 2.8186 (0.4); 2.8001 (0.4); 2.7910 (0.3); 2.4134 (1.0); 2.3959 (7.9); 2.3816 (16.0); 2.3425 (10.1); 2.3296 (1.1); 2.2935 (0.6); 2.2831 (0.6); 2.2588 (6.9); 2.2246 (6.5); 2.0752 (7.7); 1.9970 (0.4); 1.9798 (0.4); 1.9703 (0.5); 1.9572 (0.9); 1.9537 (0.7); 1.9403 (0.8); 1.9308 (0.9); 1.9138 (1.0); 1.9009 (0.5); 1.8915 (0.5); 1.8742 (0.4); 1.7434 (0.6); 1.7298 (0.8); 1.7162 (1.1); 1.7022 (1.1); 1.6882 (1.0); 1.6745 (1.0); 1.6608 (0.7); 1.6473 (0.4); 1.3166 (2.2); 1.2928 (4.4); 1.2690 (2.1); 0.0382 (3.3)
4-37: $^1$H-NMR(300.2 MHz, CDCl3):
δ = 8.2876 (0.6); 8.2607 (0.6); 8.1486 (5.1); 7.6268 (0.6); 7.6044 (1.5); 7.5780 (1.6); 7.5535 (0.7); 7.4033 (0.8); 7.3759 (1.2); 7.3496 (0.5); 7.2985 (4.2); 7.0874 (1.6); 7.0618 (2.0); 6.9601 (1.9); 6.8875 (1.1); 6.8621 (0.8); 5.5849 (1.6); 5.3350 (12.2); 4.6868 (0.3); 4.6755 (0.4); 4.6685 (0.4); 4.6589 (0.5); 4.6492 (0.4); 4.6424 (0.4); 4.6311 (0.4); 4.1708 (0.6); 4.1470 (0.6); 3.8762 (0.7); 3.8647 (0.8); 3.8385 (1.6); 3.8271 (1.4); 3.7780 (1.4); 3.7595 (1.4); 3.7402 (0.7); 3.7218 (0.7); 3.0075 (3.2); 2.9833 (3.0); 2.7472 (16.0); 2.4296 (0.8); 2.4052 (10.6); 2.2830 (0.7); 2.2552 (9.7); 2.0817 (2.8); 1.7931 (1.0); 1.7119 (1.0); 1.3202 (0.7); 1.2964 (1.5); 1.2726 (0.7); 0.0379 (5.2)
4-38: $^1$H-NMR(300.2 MHz, $d_6$-DMSO):
δ = 8.7017 (1.5); 8.6718 (1.5); 7.8368 (1.3); 7.7887 (0.7); 7.7665 (1.9); 7.7400 (2.2); 7.7098 (7.4); 7.5775 (1.1); 7.5505 (1.6); 7.5231 (0.7); 7.4864 (3.3); 7.4792 (3.5); 7.3898 (2.5); 7.3622 (3.1); 7.1153 (1.8); 7.1081 (1.8); 7.0878 (1.5); 7.0806 (1.5); 6.1721 (1.7); 5.7775 (14.2); 4.6318 (0.5); 4.6126 (0.6); 4.6007 (0.6); 4.5819 (0.5); 3.7275 (0.3); 3.7071 (0.4); 3.6918 (1.9); 3.6819 (2.0); 3.6715 (2.0); 3.6621 (1.9); 3.6465 (0.4); 3.6269 (0.3); 3.3477 (16.0); 3.1251 (0.8); 3.1110 (0.8); 3.0785 (1.1); 3.0646 (1.0); 2.8723 (1.0); 2.8378 (1.0); 2.8254 (0.8); 2.7915 (0.7); 2.7580 (0.5); 2.7369 (0.5); 2.7103 (0.8); 2.6054 (15.8); 2.5479 (0.6); 2.5348 (3.7); 2.5287 (8.0); 2.5227 (10.9); 2.5166 (7.9); 2.5107 (3.8); 2.4635 (2.1); 2.3667 (1.8); 0.0206 (8.2)
4-39: $^1$H-NMR(300.2 MHz, CDCl3):
δ = 8.3324 (0.7); 8.3049 (0.7); 8.1039 (5.2); 7.6217 (0.6); 7.5960 (1.6); 7.5695 (1.2); 7.4957 (1.4); 7.4699 (0.9); 7.3878 (1.8); 7.3639 (1.3); 7.3600 (1.2); 7.3527 (3.0); 7.3456 (3.0); 7.3374 (1.1); 7.2988 (11.9); 7.2668 (1.9); 7.2394 (3.0); 7.1571 (1.9); 7.1500 (1.8); 7.1296 (1.2); 7.1226 (1.1); 6.9191 (1.1); 6.7312 (2.2); 6.5435 (1.1); 5.5799 (2.6); 5.3368 (3.7); 4.8289 (0.4); 4.8178 (0.4); 4.8112 (0.5); 4.8000 (0.6); 4.7895 (0.5); 4.7832 (0.4); 4.7718 (0.4); 3.9172 (0.9); 3.9055 (0.9); 3.8795 (1.6); 3.8678 (1.6); 3.7948 (1.5); 3.7764 (1.5); 3.7570 (0.9); 3.7387 (0.9); 3.1338 (3.3); 3.1093 (3.5); 2.8453 (0.6); 2.8403 (0.6); 2.8350 (0.3); 2.7397 (16.0); 2.6125 (1.5); 2.5495 (1.4); 2.5157 (0.4); 1.6176 (1.8); 0.1069 (1.4); 0.0479 (0.4); 0.0370 (13.9); 0.0262 (0.6)
4-40: $^1$H-NMR(300.2 MHz, CDCl3):
δ = 8.4530 (0.6); 8.4252 (0.6); 8.2973 (5.7); 7.5343 (0.5); 7.5289 (0.4); 7.5193 (0.9); 7.5104 (1.0); 7.5046 (0.8); 7.4916 (0.6); 7.4868 (0.6); 7.4825 (0.5); 7.3646 (0.4); 7.3412 (1.0); 7.3220 (1.2); 7.3154 (2.6); 7.2989 (17.2); 7.2638 (0.5); 7.0842 (1.5); 7.0586 (2.0); 6.9716 (1.9); 6.8960 (1.1); 6.8709 (0.8); 5.6073 (0.4); 5.5762 (5.0); 4.6576 (0.4); 4.6469 (0.4); 4.6404 (0.5); 4.6310 (0.6); 4.6212 (0.5); 4.6145 (0.5); 4.6042 (0.4); 4.1722 (0.9); 4.1484 (0.9); 3.8721 (0.7); 3.8612 (0.8); 3.8340 (1.6); 3.8230 (1.5); 3.7709 (1.5); 3.7530 (1.5); 3.7328 (0.8); 3.7147 (0.7); 3.0064 (3.1); 2.9822 (2.9); 2.4415 (0.9); 2.4075 (10.4); 2.3358 (0.8); 2.2694 (9.7); 2.0843 (3.9); 1.5935 (16.0); 1.5570 (0.4); 1.5308 (1.4); 1.5080 (0.6); 1.4945 (0.5); 1.4714 (1.2); 1.4674 (1.3); 1.4452 (0.6); 1.3450 (0.4); 1.3219 (1.5); 1.2982 (3.6); 1.2744 (1.2); 1.2454 (0.6); 1.2234 (1.5); 1.2164 (1.6); 1.1938 (1.7); 1.1868 (1.3); 1.1668 (0.4); 0.9421 (0.7); 0.9203 (2.1); 0.8970 (0.8); 0.0491 (0.7); 0.0382 (21.3); 0.0273 (0.9)
4-41: $^1$H-NMR(300.2 MHz, CDCl3):
δ = 7.8732 (1.6); 7.8631 (1.6); 7.8615 (1.5); 7.8569 (1.5); 7.8526 (2.0); 7.8441 (4.0); 7.8311 (2.2); 7.8184 (4.0); 7.8096 (1.8); 7.8054 (1.5); 7.8007 (1.6); 7.7890 (1.6); 7.5862 (1.0); 7.5588 (1.0); 7.4160 (0.4); 7.4110 (0.6); 7.4061 (0.4); 7.3897 (1.0); 7.3849 (1.0); 7.3686 (0.5); 7.3641 (0.7); 7.3590 (0.5); 7.3304 (0.5); 7.3255 (0.4); 7.2988 (15.8); 7.2835 (0.7); 7.2802 (0.8); 7.2504 (1.7); 7.2249 (1.9); 7.1945 (1.0); 7.1679 (1.3); 7.1416 (0.5); 7.0038 (1.9); 6.9642 (1.1); 6.9388 (0.9); 4.6866 (0.6); 4.6756 (0.5); 4.6623 (0.6); 4.6512 (0.4); 4.6163 (1.2); 4.6052 (0.8); 4.5824 (1.2); 4.5713 (1.0); 4.2033 (1.0); 4.1934 (1.1); 4.1699 (1.0); 4.1596 (0.9); 3.3053 (0.5); 3.2821 (0.5); 3.2589 (0.9); 3.2352 (0.9); 3.1605 (0.9); 3.1323 (0.9); 3.1142 (0.6); 3.0859 (0.5); 2.9939 (0.3); 2.8404 (6.7); 2.4840 (0.5); 2.4542 (10.0); 2.4112 (15.0); 2.3531 (0.4); 2.3131 (0.6); 2.2740 (9.4); 2.0836 (0.5); 1.6095 (16.0); 1.4447 (0.4); 1.4224 (1.2); 1.4187 (1.3); 1.3963 (0.6); 1.3818 (0.4); 1.3595 (1.2); 1.3554 (1.3); 1.3333 (0.6); 1.2975 (0.6); 1.1599 (0.5); 1.1380 (1.4); 1.1308 (1.6); 1.1083 (1.6); 1.1009 (1.2); 1.0814 (0.4); 0.9197 (0.5); 0.0486 (0.6); 0.0378 (18.9); 0.0268 (0.8)
4-42: $^1$H-NMR(300.2 MHz, CDCl3):
δ = 8.1022 (5.4); 8.0922 (1.3); 8.0640 (0.8); 7.8915 (0.3); 7.7933 (0.3); 7.4291 (0.7); 7.4231 (0.8); 7.4076 (0.8); 7.4022 (1.4); 7.3966 (1.1); 7.3821 (0.8); 7.3751 (0.9); 7.2989 (8.7); 7.2812 (0.5); 7.2745 (1.6); 7.2685 (1.0); 7.2539 (1.4); 7.2469 (1.1); 7.2353 (1.7); 7.2317 (1.5); 7.2095 (1.4); 7.2047 (1.6); 7.1856 (2.4); 7.1773 (0.9); 7.1595 (2.6); 7.0244 (2.4); 7.0186 (2.6); 6.8480 (1.4); 6.8421 (1.4); 6.8217 (1.2); 6.8159 (1.2); 5.6152 (0.6); 5.3363 (0.4); 4.8492 (0.4); 4.8370 (0.4); 4.8279 (0.5); 4.8158 (0.5); 4.8006 (0.4); 4.7885 (0.4); 3.9276 (0.9); 3.9152 (1.0); 3.8900 (1.6); 3.8777 (1.4); 3.7879 (1.4); 3.7683 (1.7); 3.7503 (0.9); 3.7299 (0.9); 3.1079 (3.5); 3.0837 (2.9); 2.8403 (2.4); 2.7314 (16.0); 1.8440 (0.6); 1.8326 (0.6); 1.8161 (1.2); 1.7996 (0.7); 1.7882 (0.7); 1.7713 (0.4); 1.6558 (0.5); 1.2920 (0.4); 1.0066 (0.7); 0.9913 (1.9); 0.9847 (2.1); 0.9697 (1.1); 0.9630 (2.0);

TABLE 10-continued 0.9567 (1.9); 0.9419 (0.9); 0.6788 (0.9); 0.6635 (2.4); 0.6581 (2.1); 0.6470 (2.0); 0.6415 (2.5); 0.6253 (0.8); 0.1074 (1.8); 0.0478 (0.3); 0.0370 (11.4); 0.0262 (0.5)
4-43: $^{1}$H-NMR(300.2 MHz, CDCl3):
δ = 8.3602 (0.6); 8.3335 (0.6); 8.1421 (5.1); 7.4271 (0.7); 7.4209 (0.8); 7.4056 (0.7); 7.4005 (1.1); 7.3980 (1.0); 7.3945 (1.0); 7.3807 (0.8); 7.3730 (0.9); 7.2988 (8.8); 7.2906 (0.6); 7.2840 (0.6); 7.2703 (0.4); 7.2628 (1.6); 7.2566 (1.0); 7.2429 (1.4); 7.2350 (1.3); 7.2312 (1.8); 7.2281 (1.5); 7.2061 (1.2); 7.2014 (1.4); 7.1787 (0.4); 7.1739 (0.5); 7.0840 (1.7); 7.0579 (2.0); 6.8671 (1.9); 6.7738 (1.1); 6.7680 (1.0); 6.7478 (0.9); 6.7417 (0.8); 5.5789 (1.3); 4.6600 (0.4); 4.6490 (0.4); 4.6420 (0.4); 4.6337 (0.5); 4.6077 (0.3); 4.1713 (0.5); 4.1474 (0.5); 3.8635 (0.7); 3.8521 (0.8); 3.8256 (1.5); 3.8143 (1.4); 3.7618 (1.4); 3.7434 (1.4); 3.7240 (0.8); 3.7056 (0.7); 2.9935 (2.6); 2.9718 (1.8); 2.9667 (1.8); 2.8411 (1.0); 2.7429 (16.0); 2.7301 (0.7); 2.4580 (0.6); 2.4374 (0.4); 2.4081 (10.7); 2.0833 (2.4); 1.8413 (0.5); 1.8301 (0.5); 1.8132 (1.0); 1.7964 (0.6); 1.7854 (0.6); 1.6250 (0.8); 1.3209 (0.6); 1.2971 (1.3); 1.2733 (0.6); 0.9681 (0.7); 0.9537 (1.8); 0.9467 (2.0); 0.9402 (1.0); 0.9325 (1.1); 0.9252 (1.9); 0.9186 (1.7); 0.9045 (0.9); 0.6718 (0.9); 0.6574 (2.1); 0.6547 (1.8); 0.6511 (1.8); 0.6406 (1.9); 0.6354 (2.0); 0.6193 (0.7); 0.1079 (0.7); 0.0482 (0.3); 0.0375 (11.6); 0.0298 (0.4); 0.0282 (0.3); 0.0266 (0.4)
4-44: $^{1}$H-NMR(300.2 MHz, CDCl3):
δ = 8.4905 (0.7); 8.4635 (0.7); 8.1392 (0.7); 8.1295 (5.1); 7.4299 (0.7); 7.4237 (0.8); 7.4082 (0.8); 7.4032 (1.2); 7.4006 (1.2); 7.3974 (1.1); 7.3833 (0.8); 7.3756 (0.9); 7.3140 (2.0); 7.3082 (2.4); 7.2989 (11.8); 7.2725 (1.7); 7.2664 (1.1); 7.2526 (1.6); 7.2447 (1.4); 7.2402 (2.0); 7.2370 (1.9); 7.2262 (1.0); 7.2151 (1.4); 7.2102 (2.0); 7.2063 (1.8); 7.1989 (1.4); 7.1878 (0.6); 7.1830 (0.8); 7.1509 (0.4); 7.0898 (2.6); 7.0627 (1.8); 5.5643 (1.4); 4.6248 (0.4); 4.6137 (0.5); 4.6079 (0.5); 4.5974 (0.6); 4.5864 (0.5); 4.5751 (0.4); 4.1706 (0.6); 4.1468 (0.6); 3.8593 (0.8); 3.8486 (0.8); 3.8209 (1.6); 3.8103 (1.5); 3.7530 (1.5); 3.7360 (1.5); 3.7145 (0.8); 3.6975 (0.8); 3.0487 (0.4); 3.0280 (0.3); 3.0048 (1.7); 2.9942 (1.8); 2.9827 (1.7); 2.9673 (1.7); 2.8404 (0.6); 2.7494 (16.0); 2.7023 (0.4); 2.4578 (1.4); 2.4371 (11.6); 2.4009 (0.4); 2.0828 (2.4); 1.6224 (0.7); 1.3204 (0.8); 1.2965 (1.5); 1.2727 (0.7); 0.1072 (1.8); 0.0476 (0.5); 0.0460 (0.3); 0.0444 (0.4); 0.0368 (15.1); 0.0276 (0.5); 0.0259 (0.5)
4-45: $^{1}$H-NMR(300.2 MHz, CDCl3):
δ = 8.1411 (5.4); 8.1244 (0.8); 8.0974 (0.7); 7.4247 (0.7); 7.4176 (0.8); 7.4031 (0.8); 7.3990 (1.0); 7.3922 (1.6); 7.3813 (0.8); 7.3705 (0.9); 7.2988 (10.9); 7.2644 (0.4); 7.2574 (0.5); 7.2369 (1.6); 7.2299 (1.3); 7.2193 (4.2); 7.2097 (1.3); 7.1968 (1.4); 7.1933 (1.4); 7.1658 (0.5); 7.0152 (2.4); 6.9906 (0.6); 6.9646 (2.3); 6.9593 (2.4); 6.9520 (3.4); 6.9261 (0.6); 5.6229 (0.4); 4.7434 (0.4); 4.7308 (0.5); 4.7217 (0.6); 4.7160 (0.6); 4.7091 (0.6); 4.7036 (0.6); 4.6944 (0.5); 4.6819 (0.4); 4.1707 (0.8); 4.1469 (0.8); 4.1233 (0.3); 3.8816 (0.9); 3.8692 (0.9); 3.8437 (1.6); 3.8313 (1.5); 3.7556 (1.5); 3.7343 (1.4); 3.7178 (0.9); 3.6964 (0.9); 2.9484 (3.0); 2.9259 (3.2); 2.7434 (16.0); 2.1864 (12.1); 2.1795 (12.5); 2.0834 (4.0); 1.6494 (1.0); 1.3206 (1.0); 1.2968 (2.0); 1.2729 (1.0); 0.1068 (2.0); 0.0474 (0.5); 0.0366 (13.4); 0.0258 (0.7)
4-46: $^{1}$H-NMR(300.2 MHz, CDCl3):
δ = 8.3531 (0.7); 8.3271 (0.7); 8.1514 (5.2); 7.6115 (0.5); 7.5891 (1.0); 7.5688 (0.6); 7.5004 (0.4); 7.4738 (1.0); 7.4710 (1.0); 7.4499 (0.7); 7.4001 (1.1); 7.3726 (1.4); 7.3459 (0.5); 7.2986 (15.7); 7.1288 (1.1); 7.0852 (1.8); 7.0591 (2.0); 6.9464 (2.1); 6.8622 (2.0); 6.7713 (1.2); 6.7644 (2.0); 6.7457 (1.0); 6.7395 (0.9); 5.5759 (3.2); 5.3378 (10.7); 4.6672 (0.4); 4.6556 (0.5); 4.6479 (0.5); 4.6398 (0.6); 4.6140 (0.4); 3.8659 (0.8); 3.8545 (0.8); 3.8280 (1.6); 3.8167 (1.4); 3.7634 (1.5); 3.7449 (1.4); 3.7255 (0.8); 3.7071 (0.7); 2.9953 (2.6); 2.9742 (1.8); 2.9682 (1.8); 2.7447 (16.0); 2.4533 (0.7); 2.4060 (10.8); 2.3844 (0.3); 1.8342 (0.5); 1.8231 (0.5); 1.8064 (1.0); 1.7893 (0.6); 1.7783 (0.6); 1.6031 (8.1); 0.9668 (0.7); 0.9523 (1.8); 0.9454 (2.0); 0.9390 (1.0); 0.9312 (1.1); 0.9239 (1.9); 0.9173 (1.8); 0.9033 (0.9); 0.6652 (0.9); 0.6507 (2.1); 0.6480 (1.8); 0.6445 (1.9); 0.6339 (2.0); 0.6288 (2.1); 0.6126 (0.7); 0.1071 (0.5); 0.0482 (0.7); 0.0374 (21.3); 0.0265 (0.9)
4-47: $^{1}$H-NMR(300.2 MHz, CDCl3):
δ = 8.2539 (0.8); 8.2264 (0.8); 8.1553 (5.3); 7.6054 (0.6); 7.5792 (1.7); 7.5530 (1.3); 7.4885 (1.6); 7.4628 (0.9); 7.3589 (1.9); 7.3268 (1.1); 7.3238 (1.2); 7.3199 (1.0); 7.2987 (5.0); 7.0150 (2.6); 6.9528 (6.2); 6.9062 (1.1); 6.7184 (2.3); 6.5306 (1.2); 5.6022 (3.1); 5.3353 (4.2); 4.7319 (0.4); 4.7193 (0.5); 4.7103 (0.6); 4.7047 (0.5); 4.6976 (0.6); 4.6922 (0.6); 4.6831 (0.5); 4.6708 (0.4); 3.8731 (0.9); 3.8608 (0.9); 3.8354 (1.6); 3.8231 (1.5); 3.7479 (1.5); 3.7270 (1.5); 3.7101 (0.9); 3.6892 (0.9); 2.9442 (3.1); 2.9215 (3.2); 2.7437 (16.0); 2.1949 (11.9); 2.1791 (12.0); 1.6631 (1.4); 0.0371 (5.4)
4-48: $^{1}$H-NMR(300.2 MHz, CDCl3):
δ = 8.4737 (0.7); 8.4469 (0.7); 8.1580 (5.3); 7.6170 (0.6); 7.5907 (1.6); 7.5647 (1.2); 7.4925 (1.4); 7.4667 (0.9); 7.3951 (1.7); 7.3691 (1.0); 7.3658 (1.1); 7.3621 (0.9); 7.3425 (0.8); 7.3390 (0.8); 7.3351 (0.7); 7.3315 (0.6); 7.2987 (8.0); 7.0753 (1.8); 7.0494 (2.1); 6.9163 (1.1); 6.8760 (1.9); 6.8715 (2.0); 6.7773 (1.2); 6.7716 (1.1); 6.7514 (1.0); 6.7454 (0.9); 6.7285 (2.2); 6.5407 (1.1); 5.5584 (4.0); 5.3368 (10.1); 4.6500 (0.4); 4.6390 (0.4); 4.6326 (0.5); 4.6233 (0.5); 4.6119 (0.4); 4.5981 (0.4); 3.8579 (0.7); 3.8467 (0.8); 3.8203 (1.6); 3.8090 (1.4); 3.7587 (1.5); 3.7407 (1.4); 3.7209 (0.8); 3.7030 (0.7); 2.9848 (2.3); 2.9639 (1.8); 2.9572 (1.8); 2.7440 (16.0); 2.4501 (0.6); 2.4037 (11.0); 1.8501 (0.5); 1.8388 (0.5); 1.8221 (1.0); 1.8052 (0.6); 1.7941 (0.6); 1.6237 (4.3); 0.9737 (0.7); 0.9593 (1.8); 0.9523 (2.0); 0.9457 (0.9); 0.9384 (1.0); 0.9309 (1.9); 0.9243 (1.7); 0.9104 (0.8); 0.6761 (0.9); 0.6619 (2.0); 0.6586 (1.8); 0.6451 (1.9); 0.6402 (1.9); 0.6241 (0.7); 0.0482 (0.4); 0.0375 (10.8); 0.0266 (0.4)
4-49: $^{1}$H-NMR(300.2 MHz, CDCl3):
δ = 8.3383 (0.8); 8.3119 (0.8); 8.1497 (5.3); 7.8904 (0.4); 7.7933 (0.4); 7.6111 (0.5); 7.5877 (1.0); 7.5659 (0.6); 7.4958 (0.5); 7.4715 (1.1); 7.4691 (1.0); 7.4477 (0.8); 7.3979 (1.2); 7.3709 (1.4); 7.3442 (0.5); 7.2986 (4.4); 7.1259 (1.1); 7.0857 (1.8); 7.0601 (2.2); 6.9600 (2.1); 6.9434 (2.3); 6.8850 (1.2); 6.8597 (1.0); 6.7609 (1.1); 5.5870 (3.0); 5.3357 (10.2); 4.6853 (0.4); 4.6739 (0.5); 4.6668 (0.5); 4.6573 (0.6); 4.6473 (0.5); 4.6405 (0.5); 4.6293 (0.4); 4.1836 (0.4); 3.8744 (0.8); 3.8630 (0.8); 3.8366 (1.7); 3.8253 (1.5); 3.7729 (1.5); 3.7544 (1.5); 3.7351 (0.8); 3.7165 (0.8); 3.0026 (3.4); 2.9784 (3.3); 2.7409 (16.0); 2.4043 (11.5); 2.3840 (0.4); 2.2581 (10.7); 1.6489 (1.6); 0.0367 (6.0)
4-50: $^{1}$H-NMR(300.2 MHz, CDCl3):
δ = 8.1521 (4.0); 8.1305 (0.6); 8.1029 (0.5); 7.6110 (0.4); 7.5885 (0.7); 7.5696 (0.4); 7.4669 (0.3); 7.4402 (0.8); 7.4196 (0.6); 7.3918 (1.0); 7.3649 (1.1); 7.3378 (0.4); 7.2989 (11.6); 7.1178 (0.8); 7.0173 (1.7); 6.9915 (0.5); 6.9653 (1.5); 6.9603 (1.5); 6.9477 (2.3); 6.9354 (1.8); 6.9221 (0.6); 6.7529 (0.8); 5.6231 (1.8); 5.3383 (5.3); 4.7373 (0.4); 4.7279 (0.4); 4.7220 (0.4); 4.7154 (0.4); 4.7096 (0.4); 4.7006 (0.4); 3.8820 (0.7); 3.8696 (0.7); 3.8441 (1.2); 3.8317 (1.1); 3.7533 (1.1); 3.7318 (1.1); 3.7153 (0.7); 3.6940 (0.6); 2.9518 (2.4); 2.9295 (2.4); 2.7460 (12.1); 2.1747 (16.0); 1.6073 (7.8); 0.0480 (0.6); 0.0372 (15.6); 0.0263 (0.7)
4-51: $^{1}$H-NMR(300.2 MHz, CDCl3):
δ = 8.5932 (0.9); 8.5672 (0.9); 8.1311 (0.7); 8.1206 (5.2); 7.2990 (18.0); 7.2211 (1.2); 7.2149 (1.0); 7.1940 (1.6); 7.1879 (1.5); 7.1711 (0.5); 7.1441 (3.7); 7.1259 (3.2); 7.0923 (3.1); 7.0650 (1.9); 6.8781 (0.8); 6.8618 (1.2); 6.8564 (1.0); 6.8470 (1.2); 6.8332 (0.8); 6.8243 (0.6); 5.6126 (0.3); 5.5706 (5.4); 5.3381 (0.5); 4.6377

TABLE 10-continued (0.5); 4.6118 (0.7); 4.5977 (0.6); 4.5863 (0.5); 3.8636 (0.8); 3.8525 (0.9); 3.8254 (1.7); 3.8144 (1.6); 3.7556 (1.6); 3.7381 (1.6); 3.7175 (0.9); 3.6999 (0.8); 3.0398 (0.4); 3.0174 (0.4); 2.9928 (3.1); 2.9707 (2.3); 2.9658 (2.4); 2.8414 (1.1); 2.7395 (16.0); 2.6943 (0.8); 2.4596 (1.8); 2.4342 (12.6); 2.1741 (0.6); 2.1627 (0.6); 2.1458 (1.1); 2.1285 (0.7); 2.1171 (0.6); 2.1001 (0.3); 1.5988 (13.5); 1.2917 (0.6); 1.1017 (0.6); 1.0863 (1.9); 1.0797 (2.2); 1.0652 (1.2); 1.0580 (2.0); 1.0515 (2.2); 1.0372 (1.0); 0.8398 (0.9); 0.8197 (2.6); 0.8080 (2.3); 0.8023 (2.7); 0.7861 (0.9); 0.1072 (5.3); 0.0481 (0.8); 0.0375 (22.2)

4-52: $^{1}$H-NMR(300.2 MHz, CDCl3):

δ = 9.2470 (1.9); 9.2200 (1.9); 8.3241 (16.0); 8.3046 (2.5); 8.1121 (0.6); 8.1045 (0.6); 8.0472 (0.5); 8.0382 (0.5); 7.9332 (5.7); 7.9254 (5.9); 7.7161 (0.5); 7.6893 (7.5); 7.6720 (12.5); 7.6131 (0.8); 7.6042 (1.2); 7.5972 (4.2); 7.5888 (4.1); 7.5692 (7.6); 7.5612 (9.9); 7.5290 (1.0); 7.5154 (2.6); 7.5072 (2.7); 7.5016 (3.6); 7.4955 (3.1); 7.4861 (2.3); 7.4774 (1.6); 7.3917 (0.4); 7.3722 (0.5); 7.2991 (26.8); 7.2209 (0.9); 7.1909 (6.8); 7.1632 (5.4); 6.6003 (0.6); 6.5817 (0.5); 5.6810 (1.0); 5.3374 (5.6); 5.0383 (0.4); 5.0192 (1.3); 5.0104 (0.7); 5.0003 (2.2); 4.9918 (1.6); 4.9817 (1.7); 4.9728 (2.1); 4.9632 (0.7); 4.9543 (1.4); 4.9354 (0.4); 4.8914 (0.4); 4.8693 (0.4); 4.2712 (0.5); 4.2559 (0.5); 4.2130 (0.6); 4.1948 (1.4); 4.1702 (2.7); 4.1583 (0.4); 4.1464 (2.7); 4.1228 (1.2); 4.1014 (0.7); 4.0907 (0.4); 4.0788 (0.4); 4.0733 (0.4); 3.7480 (12.6); 3.7282 (11.7); 3.2718 (1.6); 3.2544 (1.6); 3.2219 (4.8); 3.2047 (4.5); 3.1648 (4.2); 3.1466 (4.2); 3.1152 (1.7); 3.0971 (1.7); 2.0826 (13.7); 2.0451 (0.8); 1.7621 (3.5); 1.7585 (2.8); 1.7437 (3.5); 1.7388 (2.6); 1.6708 (1.4); 1.6490 (1.4); 1.4517 (0.3); 1.4294 (0.4); 1.4035 (0.4); 1.3201 (3.5); 1.2963 (7.0); 1.2725 (3.2); 0.9964 (0.6); 0.9719 (1.0); 0.9467 (0.6); 0.9213 (0.5); 0.9036 (0.4); 0.1186 (0.4); 0.1064 (11.0); 0.0471 (1.5); 0.0363 (36.8); 0.0256 (1.8)

4-53: $^{1}$H-NMR(300.2 MHz, CDCl3):

δ = 8.3852 (1.1); 8.3591 (1.1); 8.3338 (10.3); 7.6531 (3.5); 7.6480 (2.4); 7.6389 (5.0); 7.6358 (5.8); 7.4946 (2.7); 7.4725 (0.4); 7.4591 (1.2); 7.4500 (1.1); 7.4447 (1.7); 7.4385 (1.4); 7.4292 (1.1); 7.4204 (0.7); 7.2988 (15.4); 6.7705 (5.4); 5.5580 (4.5); 5.0161 (0.4); 4.6575 (0.6); 4.6463 (0.6); 4.6393 (0.8); 4.6287 (0.9); 4.6200 (0.7); 4.6128 (0.7); 4.6021 (0.6); 3.8835 (1.1); 3.8723 (1.2); 3.8452 (2.7); 3.8340 (2.5); 3.7953 (2.5); 3.7770 (2.4); 3.7570 (1.2); 3.7387 (1.1); 2.9333 (4.5); 2.9096 (4.8); 2.3255 (16.0); 2.1521 (16.0); 1.6024 (4.5); 1.3157 (5.4); 1.2948 (5.5); 0.1075 (1.8); 0.0483 (0.9); 0.0375 (21.8); 0.0265 (0.8)

4-54: $^{1}$H-NMR(300.2 MHz, CDCl3):

δ = 8.3508 (0.8); 8.3239 (0.8); 8.1300 (5.3); 7.3696 (1.2); 7.3434 (2.6); 7.3171 (1.6); 7.2986 (8.8); 7.0266 (1.8); 7.0133 (2.9); 6.9861 (0.4); 6.9545 (7.4); 6.9351 (1.0); 6.9274 (1.6); 6.9055 (1.9); 6.8998 (2.4); 5.6023 (0.9); 4.7241 (0.4); 4.7116 (0.5); 4.7028 (0.6); 4.6973 (0.6); 4.6900 (0.6); 4.6753 (0.5); 4.6629 (0.4); 4.1944 (0.8); 4.1706 (2.3); 4.1468 (2.3); 4.1231 (0.8); 3.8609 (0.9); 3.8484 (0.9); 3.8232 (1.6); 3.8108 (1.5); 3.7321 (1.5); 3.7108 (1.5); 3.6944 (0.9); 3.6732 (0.9); 2.9262 (2.8); 2.9034 (3.0); 2.8407 (1.1); 2.7305 (16.0); 2.2065 (12.1); 2.1829 (12.3); 2.0831 (10.3); 1.9962 (0.3); 1.9796 (0.6); 1.9682 (0.7); 1.9516 (1.2); 1.9350 (0.7); 1.9237 (0.7); 1.9068 (0.3); 1.6501 (2.0); 1.3204 (2.8); 1.2966 (5.6); 1.2728 (2.7); 1.0628 (0.7); 1.0481 (1.9); 1.0411 (2.2); 1.0265 (1.2); 1.0197 (2.0); 1.0132 (1.9); 0.9987 (0.9); 0.7797 (0.9); 0.7649 (2.5); 0.7602 (2.1); 0.7482 (2.2); 0.7433 (2.4); 0.7268 (0.8); 0.1069 (2.2); 0.0473 (0.4); 0.0365 (11.5); 0.0256 (0.5)

4-55: $^{1}$H-NMR(300.2 MHz, CDCl3):

δ = 8.6557 (0.8); 8.6299 (0.8); 8.1587 (0.4); 8.1283 (0.7); 8.1206 (5.2); 7.3836 (1.1); 7.3574 (2.6); 7.3310 (1.7); 7.3176 (2.1); 7.3115 (2.4); 7.2993 (15.6); 7.2149 (1.0); 7.2082 (0.9); 7.1878 (1.4); 7.1809 (1.4); 7.0692 (2.7); 7.0420 (2.2); 7.0290 (1.7); 7.0030 (1.5); 6.9893 (1.2); 6.9866 (1.2); 6.9815 (1.5); 6.9788 (1.4); 6.9600 (1.0); 6.9549 (1.4); 6.9521 (1.3); 6.9337 (2.1); 6.9276 (2.6); 5.5388 (1.0); 4.6156 (0.4); 4.5986 (0.5); 4.5886 (0.6); 4.5749 (0.5); 4.5631 (0.4); 4.1948 (0.6); 4.1709 (1.7); 4.1471 (1.8); 4.1233 (0.6); 3.8431 (0.8); 3.8322 (0.8); 3.8052 (1.6); 3.7942 (1.5); 3.7390 (1.5); 3.7219 (1.5); 3.7009 (0.8); 3.6839 (0.8); 3.0187 (0.3); 2.9962 (0.4); 2.9738 (2.1); 2.9692 (2.2); 2.9510 (1.9); 2.9423 (1.9); 2.8411 (0.4); 2.7572 (1.6); 2.7365 (16.0); 2.4499 (1.0); 2.4247 (11.8); 2.3849 (0.4); 2.3250 (1.0); 2.0836 (7.6); 2.0046 (0.3); 1.9876 (0.6); 1.9766 (0.7); 1.9599 (1.3); 1.9431 (0.8); 1.9320 (0.8); 1.9148 (0.4); 1.6548 (0.9); 1.5550 (0.3); 1.3209 (2.1); 1.2971 (4.2); 1.2733 (2.1); 1.0708 (0.7); 1.0545 (1.8); 1.0490 (2.2); 1.0342 (1.3); 1.0270 (2.2); 1.0206 (2.1); 1.0064 (1.1); 0.7875 (1.0); 0.7724 (2.6); 0.7660 (2.4); 0.7560 (2.5); 0.7497 (2.7); 0.7341 (1.1); 0.1069 (4.1); 0.0478 (0.6); 0.0369 (19.1); 0.0261 (1.0)

4-56: $^{1}$H-NMR(300.2 MHz, CDCl3):

δ = 8.3067 (0.9); 8.2790 (0.8); 8.0914 (5.2); 8.0822 (0.4); 7.3771 (1.2); 7.3509 (2.7); 7.3246 (1.7); 7.2986 (3.9); 7.1651 (2.3); 7.1388 (2.6); 7.0338 (4.0); 7.0285 (3.9); 7.0058 (1.4); 6.9897 (1.2); 6.9867 (1.1); 6.9818 (1.4); 6.9630 (1.0); 6.9598 (1.0); 6.9552 (1.4); 6.9329 (1.9); 6.9270 (2.4); 6.9203 (1.3); 6.8143 (1.5); 6.8085 (1.4); 6.7881 (1.3); 6.7822 (1.2); 5.6043 (0.5); 4.8376 (0.4); 4.8249 (0.4); 4.8164 (0.5); 4.8042 (0.5); 4.7889 (0.4); 4.7767 (0.4); 4.1917 (0.5); 4.1679 (1.5); 4.1441 (1.5); 4.1204 (0.5); 3.9070 (0.9); 3.8945 (1.0); 3.8695 (1.6); 3.8572 (1.4); 3.7608 (1.4); 3.7402 (1.4); 3.7234 (0.9); 3.7028 (0.9); 3.0840 (2.0); 3.0769 (2.0); 3.0618 (1.8); 3.0516 (1.8); 2.8379 (4.4); 2.7471 (0.4); 2.7163 (16.0); 2.0803 (6.7); 2.0031 (0.3); 1.9864 (0.6); 1.9750 (0.7); 1.9584 (1.3); 1.9417 (0.8); 1.9304 (0.8); 1.9136 (0.4); 1.8631 (0.4); 1.8460 (0.6); 1.8347 (0.7); 1.8181 (1.2); 1.8014 (0.7); 1.7902 (0.7); 1.7733 (0.4); 1.3178 (1.8); 1.2940 (3.7); 1.2702 (1.8); 1.0640 (0.8); 1.0489 (2.1); 1.0419 (2.3); 1.0363 (1.2); 1.0270 (1.4); 1.0205 (2.3); 1.0139 (2.2); 1.0043 (1.0); 0.9992 (1.3); 0.9895 (2.1); 0.9827 (2.3); 0.9680 (1.1); 0.9610 (2.1); 0.9547 (2.0); 0.9402 (0.9); 0.7893 (0.9); 0.7742 (2.6); 0.7690 (2.3); 0.7576 (2.2); 0.7522 (2.8); 0.7356 (0.8); 0.6778 (0.9); 0.6629 (2.4); 0.6583 (2.0); 0.6462 (2.1); 0.6414 (2.4); 0.6250 (0.8); 0.1068 (1.1); 0.0349 (5.2)

4-57: $^{1}$H-NMR(300.2 MHz, CDCl3):

δ = 8.1097 (5.4); 8.0920 (0.8); 8.0642 (0.8); 7.9214 (0.4); 7.9111 (0.4); 7.8930 (0.5); 7.7952 (0.5); 7.7856 (0.3); 7.7771 (0.4); 7.7667 (0.4); 7.6141 (0.5); 7.5905 (1.0); 7.5690 (0.6); 7.5121 (0.5); 7.4876 (1.1); 7.4635 (0.8); 7.4029 (1.2); 7.3759 (1.5); 7.3490 (0.5); 7.2985 (10.6); 7.1962 (2.1); 7.1703 (2.5); 7.1327 (2.4); 6.9433 (2.9); 6.9252 (1.1); 6.7603 (1.1); 5.6266 (3.3); 5.3373 (13.4); 4.8692 (0.4); 4.8568 (0.4); 4.8484 (0.5); 4.8355 (0.5); 4.8211 (0.4); 4.8091 (0.4); 4.1807 (0.4); 3.9366 (1.0); 3.9243 (1.0); 3.8990 (1.6); 3.8868 (1.5); 3.7989 (1.5); 3.7785 (1.5); 3.7612 (1.0); 3.7410 (0.9); 3.1193 (3.2); 3.0943 (2.3); 2.7300 (16.0); 2.2696 (11.4); 1.6096 (4.4); 0.0471 (0.5); 0.0455 (0.4); 0.0363 (14.4); 0.0287 (0.5); 0.0271 (0.5); 0.0255 (0.5)

TABLE 11

Compounds according to formula (6)

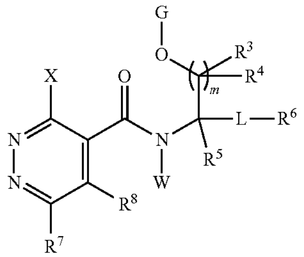

(6)

In table 11, "#" denotes the point of attachment to the L—$R^6$ group and "*" denotes the point of attachment to the pyridazin-4-yl group.

| Ex No | $R^7$ | $R^8$ | X | 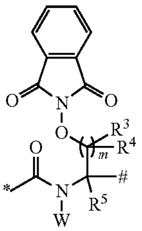 | 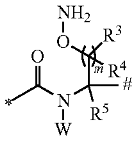 | L—$R^6$ | LogP |
|---|---|---|---|---|---|---|---|
| 6-01 | Cl | H | Cl | 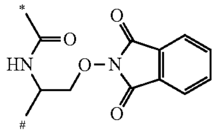 | — | (2,4-dimethyl-phenyl)methyl | 3.72[a] |
| 6-02 | Cl | H | Cl | — | 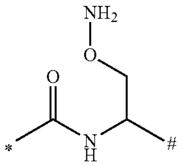 | (2,4-dimethyl-phenyl)methyl | 1.93[a] |
| 6-03 | Cl | $CH_3$ | Cl | — | 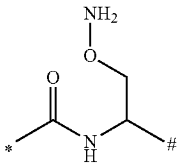 | (2,4-dimethyl-phenyl)methyl | 1.96[a] |
| 6-04 | Cl | $CH_3$ | Cl | 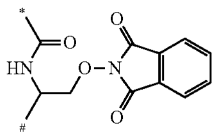 | — | (2,4-dimethyl-phenyl)methyl | 3.79[a] |
| 6-05 | $CH_3$ | H | Cl | 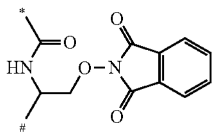 | — | (2,4-dimethyl-phenyl)methyl | 3.17[a] |
| 6-06 | $CH_3$ | H | Cl | — | 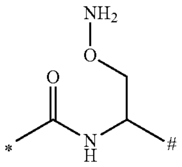 | (2,4-dimethyl-phenyl)methyl | 1.53[a] |

TABLE 11-continued
Compounds according to formula (6)
(6)
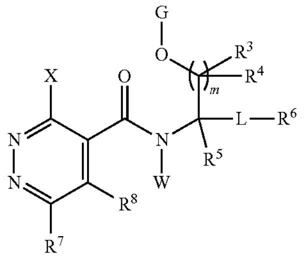
In table 11, "#" denotes the point of attachment to the L—$R^6$ group and "*" denotes the point of attachment to the pyridazin-4-yl group.
| Ex No | $R^7$ | $R^8$ | X | 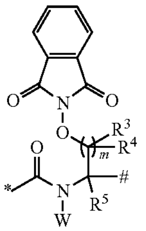 | 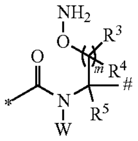 | L—$R^6$ | LogP |
|---|---|---|---|---|---|---|---|
| 6-07 | Cl | H | Cl | — | 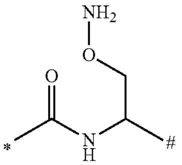 | (2,4-dichloro-phenyl)methyl | 2.30[a] |
| 6-08 | Cl | H | Cl | — | 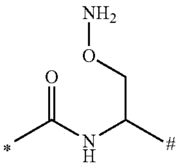 | (4-bromo-2-chloro-phenyl)methyl | 2.40[a] |
TABLE 12
6-01: 1H-NMR(300.2 MHz, CDCl3):
δ = 8.2099 (0.5); 7.8978 (2.5); 7.8864 (2.8); 7.8813 (2.6); 7.8775 (3.2); 7.8684 (5.9); 7.8540 (2.8); 7.8391 (6.0); 7.8304 (3.4); 7.8267 (3.4); 7.8211 (3.9); 7.8102 (3.2); 7.7920 (1.7); 7.7731 (0.8); 7.7607 (9.1); 7.2991 (10.6); 7.2605 (2.1); 7.2355 (2.6); 7.0697 (6.2); 7.0444 (1.6); 4.6013 (1.4); 4.5909 (2.2); 4.5587 (2.6); 4.5329 (0.6); 4.5213 (0.4); 4.1646 (1.7); 4.1405 (1.5); 4.1325 (1.0); 3.2737 (0.7); 3.2525 (0.7); 3.2282 (1.5); 3.2072 (1.4); 3.1614 (1.6); 3.1314 (1.5); 3.1159 (0.8); 3.0850 (0.7); 2.8360 (3.4); 2.5356 (0.4); 2.4648 (16.0); 2.4377 (0.5); 2.3529 (14.9); 2.3192 (1.1); 1.6452 (13.9); 1.2914 (0.3); 0.1072 (1.2); 0.0473 (0.5); 0.0365 (10.6); 0.0258 (0.6)
6-02: 1H-NMR(300.2 MHz, CDCl3):
δ = 7.7365 (6.3); 7.4863 (0.9); 7.4609 (0.9); 7.2997 (10.2); 7.1523 (0.4); 7.1169 (2.2); 7.0916 (3.4); 7.0689 (0.6); 7.0430 (3.6); 7.0044 (2.4); 6.9780 (1.5); 5.6118 (0.9); 4.5915 (0.6); 4.5801 (0.7); 4.5755 (0.7); 4.5652 (0.9); 4.5520 (0.7); 4.5409 (0.6); 3.8608 (0.9); 3.8510 (1.0); 3.8223 (2.2); 3.8125 (2.1); 3.7881 (0.4); 3.7795 (0.4); 3.7678 (2.1); 3.7514 (2.2); 3.7293 (1.1); 3.7130 (1.0); 3.0153 (3.4); 2.9950 (2.4); 2.9864 (2.6); 2.9704 (0.6); 2.9408 (0.5); 2.4268 (15.5); 2.3947 (0.8); 2.3688 (0.4); 2.3344 (16.0); 2.3055 (0.8); 2.0827 (0.4); 2.0538 (0.5); 2.0463 (0.4); 1.6254 (2.2); 1.2920 (1.1); 0.1076 (0.9); 0.0474 (0.4); 0.0378 (12.2)
6-03: 1H-NMR(300.2 MHz, CDCl3):
δ = 7.2991 (3.5); 7.2693 (0.9); 7.0968 (1.7); 7.0713 (2.5); 7.0177 (2.3); 6.9780 (1.4); 6.9525 (1.0); 5.6453 (2.4); 5.3355 (5.7); 4.7585 (0.4); 4.7478 (0.4); 4.7288 (0.6); 4.7102 (0.4); 4.7031 (0.4); 4.0194 (1.2); 3.8879 (0.8); 3.8762 (0.8); 3.8505 (1.6); 3.8388 (1.5); 3.7887 (1.5); 3.7683 (1.5); 3.7512 (0.8); 3.7308 (0.8); 3.0130 (0.4); 2.9888 (0.4); 2.9662 (1.4); 2.9415 (1.5); 2.9341 (1.6); 2.9071 (1.3); 2.8869 (0.4); 2.8602 (0.4); 2.4098 (0.4); 2.3906 (12.0); 2.3676 (0.5); 2.3225 (11.7); 2.2559 (16.0); 2.1947 (1.2); 2.1032 (0.4); 1.3059 (0.8); 1.2851 (0.9); 0.0367 (3.1)
6-05: 1H-NMR(300.2 MHz, d6-DMSO):
δ = 9.0523 (0.8); 9.0241 (0.8); 7.9728 (1.8); 7.9147 (0.6); 7.9025 (5.0); 7.8991 (5.2); 7.8867 (0.8); 7.5732 (3.0); 7.1726 (1.0); 7.1471 (1.2); 7.0074 (1.4); 6.9831 (0.8); 6.9572 (0.6); 4.4854 (0.4); 4.4659 (0.4); 4.2938 (1.8); 4.2756 (1.5); 3.3515 (16.0); 3.1042 (0.3); 3.0841 (0.4); 3.0568 (0.5); 3.0365 (0.4); 2.9109 (13.2); 2.8742 (0.5); 2.8456 (0.5); 2.8268 (0.4); 2.7984 (0.3); 2.7516 (11.0); 2.7092 (1.6); 2.6716 (7.8); 2.5284 (2.1); 2.5224 (2.9); 2.5166 (2.1); 2.3343 (6.0); 2.2611 (5.6); 0.0199 (2.5)

TABLE 12-continued 6-06: 1H-NMR(300.2 MHz, CDCl3):
δ = 7.6200 (4.8); 7.4446 (0.6); 7.4168 (0.6); 7.2987 (7.6); 7.1318 (1.6); 7.1062 (2.3); 7.0390 (2.2); 7.0006 (1.4); 6.9752 (1.0); 5.6037 (2.5); 5.3375 (1.5); 4.5950 (0.4); 4.5844 (0.5); 4.5733 (0.5); 4.5677 (0.6); 4.5566 (0.6); 4.5457 (0.4); 3.8533 (0.8); 3.8431 (0.8); 3.8151 (1.7); 3.8050 (1.6); 3.7606 (1.6); 3.7441 (1.6); 3.7225 (0.8); 3.7061 (0.8); 3.0473 (0.3); 3.0238 (1.6); 3.0046 (2.3); 2.9777 (1.5); 2.9608 (0.3); 2.9320 (0.4); 2.7799 (16.0); 2.4318 (12.0); 2.4025 (0.4); 2.3307 (11.0); 1.6229 (0.7); 0.1067 (0.8); 0.0474 (0.4); 0.0368 (10.0); 0.0261 (0.4)
6-07: 1H-NMR(400.2 MHz, d6-DMSO):
δ = 8.8676 (2.8); 8.8455 (3.0); 8.8348 (0.6); 8.8315 (0.5); 8.8133 (0.4); 8.7923 (0.3); 8.2245 (0.8); 8.0032 (16.0); 7.5994 (6.4); 7.4597 (0.4); 7.4542 (0.4); 7.4454 (0.4); 7.4218 (0.7); 7.4174 (0.4); 7.3972 (15.4); 7.3784 (0.6); 6.2059 (3.3); 4.5405 (0.7); 4.5280 (1.0); 4.5174 (1.4); 4.5049 (1.4); 4.4945 (1.0); 4.4820 (0.7); 3.6675 (1.2); 3.6519 (1.3); 3.6408 (3.5); 3.6252 (3.9); 3.6204 (3.8); 3.6058 (3.4); 3.5936 (1.4); 3.5792 (1.1); 3.3400 (0.6); 3.0866 (1.8); 3.0744 (1.9); 3.0513 (2.4); 3.0391 (2.2); 2.8077 (2.2); 2.7838 (2.2); 2.7724 (1.8); 2.7485 (1.7); 2.5148 (4.0); 2.5105 (7.8); 2.5061 (10.1); 2.5016 (7.2); 2.4974 (3.4); 0.0001 (1.3)
6-08: 1H-NMR(300.1 MHz, d6-DMSO):
δ = 8.8488 (2.4); 8.8194 (2.4); 7.9916 (16.0); 7.7106 (6.1); 7.7038 (6.5); 7.5395 (2.9); 7.5328 (2.6); 7.5121 (3.7); 7.5054 (3.5); 7.3382 (5.6); 7.3107 (4.4); 6.1450 (10.9); 4.5456 (0.6); 4.5285 (0.8); 4.5144 (1.2); 4.4983 (1.2); 4.4844 (0.8); 4.4675 (0.6); 3.6722 (0.8); 3.6514 (0.9); 3.6366 (3.3); 3.6183 (4.6); 3.6005 (3.1); 3.5844 (0.9); 3.5650 (0.7); 3.3187 (6.9); 3.0769 (1.4); 3.0605 (1.4); 3.0299 (2.0); 3.0136 (1.8); 2.8016 (1.8); 2.7699 (1.8); 2.7545 (1.4); 2.7228 (1.3); 2.5143 (2.4); 2.5084 (4.7); 2.5024 (6.1); 2.4964 (4.2); 2.4906 (1.9); 2.0753 (0.4); −0.0004 (7.0)

TABLE 13

Compounds according to formula (7)

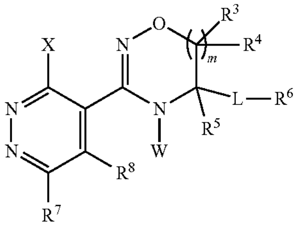

(7)

In table 13, "#" denotes the point of attachment to the L—$R^6$ group and "*" denotes the point of attachment to the pyridazin-4-yl group.

| Ex No | $R^7$ | $R^8$ | X | 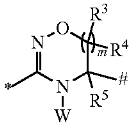 | L—$R^6$ | LogP |
|---|---|---|---|---|---|---|
| 7-01 (*) | Cl | H | Cl | 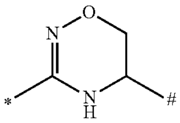 | (2,4-dimethylphenyl)methyl | 2.98[a] |
| 7-02 | Cl | $CH_3$ | Cl | 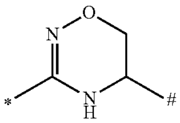 | (2,4-dimethylphenyl)methyl | 3.00[a] |
| 7-03 (*) | $CH_3$ | H | Cl | 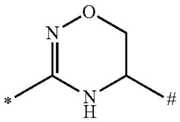 | (2,4-dimethylphenyl)methyl | 2.45[a] |
| 7-04 (*) | $CH_3$ | H | Cl | 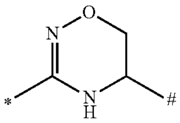 | (2,4-dimethylphenyl)methyl | 2.44[a] |

TABLE 13-continued

Compounds according to formula (7)

(7)

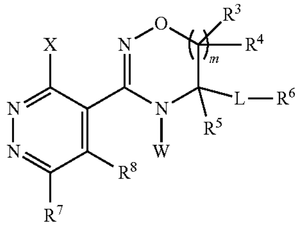

In table 13, "#" denotes the point of attachment to the L—$R^6$ group and "*" denotes the point of attachment to the pyridazin-4-yl group.

| Ex No | $R^7$ | $R^8$ | X | 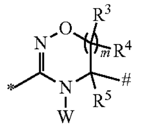 | L—$R^6$ | LogP |
|---|---|---|---|---|---|---|
| 7-05 (*) | Cl | H | Cl | 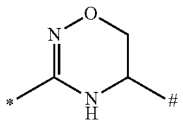 | (2,4-dichlorophenyl)methyl | 3.17[a] |
| 7-06 (*) | Cl | H | Cl | 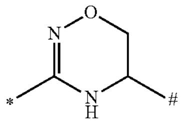 | (4-bromo-2-chloro-phenyl)methyl | 3.28[a] |
| 7-07 (*) | Cl | H | Cl | 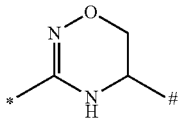 | (2,4-dichlorophenyl)methyl | 3.19[a] |
| 7-08 (*) | Cl | H | Cl | 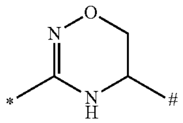 | (2,4-dichlorophenyl)methyl | 3.19[a] |
| 7-09 (*) | Cl | H | Cl | 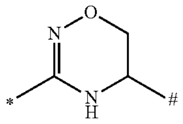 | (4-bromo-2-chloro-phenyl)methyl | 3.31[a] |
| 7-10 (*) | Cl | H | Cl | 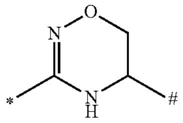 | (4-bromo-2-chloro-phenyl)methyl | 3.31[a] |
| 7-11 (*) | Cl | H | Cl | 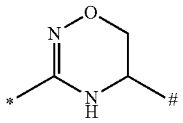 | (2,4-dimethylphenyl)methyl | 3.04[a] |

TABLE 13-continued

Compounds according to formula (7)

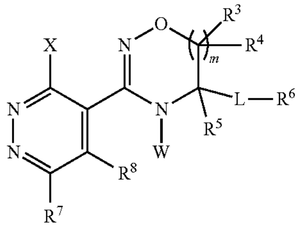

(7)

In table 13, "#" denotes the point of attachment to the L—$R^6$ group and "*" denotes the point of attachment to the pyridazin-4-yl group.

| Ex No | $R^7$ | $R^8$ | X | 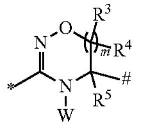 W | L—$R^6$ | LogP |
|---|---|---|---|---|---|---|
| 7-12 (*) | Cl | H | Cl | 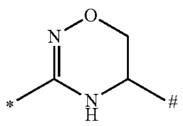 | (2,4-dimethylphenyl)methyl | 3.04[a] |

(*) Ex 7-07 and 7-08 are the 2 enantiomers of Ex 7-05
Ex 7-07: Optical rotation: +61.9° (c = 2.23, CDCl3, 20° C.); concentration c is expressed in g/100 mL.
Ex 7-08: Optical rotation: −59.6° (c = 2.45, CDCl3, 20° C.); concentration c is expressed in g/100 mL.
(*) Ex 7-09 and 7-10 are the 2 enantiomers of Ex 7-06
Ex 7-09: Optical rotation: +62.4° (c = 2.28, CDCl3, 20° C.); concentration c is expressed in g/100 mL.
Ex 7-10: Optical rotation: −59.6° (c = 2.35, CDCl3, 20° C.); concentration c is expressed in g/100 mL.
(*) Ex 7-11 and 7-12 are the 2 enantiomers of Ex 7-01
Ex 7-11: Optical rotation: −90.1° (c = 2.18, CDCl3, 20° C.); concentration c is expressed in g/100 mL.
Ex 7-12: Optical rotation: +93.2° (c = 1.83, CDCl3, 20° C.); concentration c is expressed in g/100 mL.
(*) Ex 7-03 is Single Stereoisomer; Ex 7-04 is racemate

TABLE 14

7-01: 1H-NMR(300.2 MHz, CDCl3):
δ = 7.7686 (8.3); 7.7444 (0.7); 7.2987 (6.5); 7.1869 (0.4); 7.1608 (0.4); 7.0830 (1.5); 7.0568 (6.5); 7.0283 (2.4); 7.0021 (1.0); 5.1557 (1.6); 4.1917 (1.0); 4.1832 (1.6); 4.1652 (0.6); 4.1570 (1.8); 4.1479 (1.4); 4.1423 (0.8); 3.9419 (0.5); 3.9324 (0.8); 3.9231 (0.9); 3.9135 (1.0); 3.9046 (1.1); 3.8897 (2.5); 3.8722 (0.7); 3.8552 (1.8); 3.8368 (1.0); 3.0482 (0.8); 3.0295 (0.8); 3.0205 (0.4); 3.0028 (1.6); 2.9833 (1.5); 2.8882 (1.3); 2.8600 (1.3); 2.8421 (1.0); 2.8139 (0.9); 2.4274 (1.3); 2.3479 (16.0); 2.3293 (15.0); 2.0792 (2.4); 1.6221 (1.2); 1.3191 (0.6); 1.2952 (1.2); 1.2714 (0.5); 0.1071 (0.7); 0.0368 (7.6)
7-02: 1H-NMR(300.2 MHz, CDCl3):
δ = 7.2986 (9.5); 7.1704 (0.3); 7.0662 (1.2); 7.0399 (3.6); 7.0011 (1.4); 6.9745 (0.6); 4.9509 (1.0); 4.1927 (0.6); 4.1828 (1.0); 4.1569 (1.1); 4.1477 (0.8); 4.1012 (0.4); 3.9669 (0.5); 3.9573 (0.6); 3.9477 (0.6); 3.9392 (0.8); 3.9287 (1.5); 3.9121 (0.4); 3.8937 (1.0); 3.8762 (0.6); 3.0600 (0.5); 3.0402 (0.5); 3.0143 (1.2); 2.9944 (1.1); 2.9229 (0.8); 2.8952 (0.8); 2.8767 (0.6); 2.8489 (0.5); 2.5357 (16.0); 2.4138 (0.8); 2.4101 (1.5); 2.3656 (1.4); 2.3469 (11.4); 2.3118 (10.0); 2.2791 (2.2); 2.2677 (1.1); 2.2591 (2.3); 1.9072 (1.4); 1.9006 (1.6); 1.8791 (2.0); 1.8171 (0.4); 1.7937 (2.0); 1.6050 (2.4); 1.3137 (1.4); 1.2926 (3.0); 0.1068 (0.5); 0.0478 (0.4); 0.0370 (11.4); 0.0260 (0.4)
7-03: 1H-NMR(300.2 MHz, CDCl3):
δ = 7.5488 (5.1); 7.3040 (0.6); 7.3003 (1.3); 7.2983 (1.5); 7.2941 (0.9); 7.0889 (1.6); 7.0636 (2.9); 7.0365 (3.4); 7.0110 (2.3); 6.9853 (1.2); 5.3719 (1.2); 4.1347 (1.4); 4.1085 (1.6); 4.1002 (1.3); 3.9197 (0.7); 3.9105 (0.8); 3.8798 (2.2); 3.8457 (1.4); 3.8279 (1.0); 3.0325 (0.6); 3.0129 (0.6); 2.9871 (1.4); 2.9667 (1.3); 2.9172 (1.1); 2.8905 (1.1); 2.8718 (0.8); 2.8443 (0.6); 2.7086 (16.0); 2.6614 (1.8); 2.3748 (0.6); 2.3421 (13.1); 2.3191 (12.8); 2.2094 (2.6); 1.3369 (0.4); 1.3029 (1.6); 1.2821 (6.9); 0.9134 (0.3); 0.8900 (0.3); 0.0387 (0.5); 0.0351 (1.2); 0.0332 (1.4); 0.0291 (0.8)
7-04: 1H-NMR(300.2 MHz, CDCl3):
δ = 7.6408 (1.0); 7.5715 (4.8); 7.2988 (6.8); 7.1867 (0.7); 7.1604 (0.8); 7.1440 (0.4); 7.1183 (0.5); 7.0967 (1.2); 7.0712 (2.7); 7.0566 (2.2); 7.0314 (1.6); 7.0041 (1.0); 6.5721 (0.6); 6.5458 (0.6); 5.3372 (0.8); 5.0665 (1.1); 4.2669 (0.3); 4.1969 (0.4); 4.1886 (0.8); 4.1800 (1.2); 4.1540 (1.2); 4.1443 (1.2); 3.9390 (0.4); 3.9297 (0.6); 3.9202 (0.6); 3.9107 (0.7); 3.9016 (0.8); 3.8848 (2.0); 3.8669 (0.6); 3.8503 (1.3); 3.8316 (0.8); 3.0495 (0.6); 3.0311 (0.6); 3.0178 (0.4); 3.0039 (1.2); 2.9849 (1.2); 2.8930 (1.0); 2.8651 (0.9); 2.8470 (0.7); 2.8190 (0.7); 2.7773 (3.6); 2.7436 (16.0); 2.4360 (2.5); 2.3510 (11.6); 2.3315 (13.0); 2.0812 (0.9); 1.6260 (2.6); 1.2958 (0.5); 0.1069 (1.8); 0.0368 (9.1); 0.0260 (0.3)
7-05: 1H-NMR(300.1 MHz, d6-DMSO):
δ = 8.2197 (16.0); 7.6184 (6.6); 7.6119 (7.2); 7.5499 (3.6); 7.5392 (3.7); 7.4737 (3.0); 7.4462 (8.5); 7.4229 (6.0); 7.4162 (5.5); 7.3954 (2.2); 7.3887 (2.2); 5.7586 (1.1); 3.8657 (3.5); 3.8339 (5.2); 3.8233 (3.3); 3.8069 (3.5); 3.7936 (3.4); 3.7680 (1.6); 3.7551 (0.8); 3.4504 (0.3); 3.4426 (0.3); 3.0545 (0.7); 3.0309 (0.7); 3.0099

TABLE 14-continued (3.4); 2.9929 (4.5); 2.9860 (4.2); 2.9733 (3.6); 2.9491 (0.7); 2.9271 (0.5); 2.5127 (5.5); 2.5070 (6.9); 2.5014 (5.0); 1.9933 (0.8); 1.2849 (0.5); 1.2299 (0.5); 1.1782 (0.5); 0.9138 (0.5); 0.8885 (0.3); 0.8776 (0.6); 0.8621 (0.5); 0.8544 (0.6); 0.8323 (0.4); −0.0004 (0.9)

7-06: 1H-NMR(300.1 MHz, d6-DMSO):

δ = 8.2155 (16.0); 7.7341 (7.2); 7.7275 (7.7); 7.5506 (3.7); 7.5436 (4.5); 7.5372 (4.2); 7.5236 (7.6); 7.5168 (5.3); 7.4449 (0.3); 7.4157 (0.4); 7.3984 (6.8); 7.3709 (4.8); 3.8599 (3.8); 3.8492 (2.5); 3.8298 (5.2); 3.8195 (3.2); 3.8003 (3.4); 3.7868 (3.4); 3.7610 (1.7); 3.7479 (0.8); 3.3219 (11.9); 3.0330 (0.6); 3.0099 (0.7); 2.9888 (3.5); 2.9737 (4.4); 2.9646 (4.0); 2.9539 (3.7); 2.9298 (0.7); 2.9071 (0.4); 2.5086 (8.0); 2.5028 (10.3); 2.4971 (7.5); −0.0005 (5.0)

7-07: 1H-NMR(499.9 MHz, CDCl3):

δ = 7.7140 (16.0); 7.4065 (7.6); 7.4032 (7.7); 7.2656 (5.4); 7.2307 (1.6); 7.2271 (1.3); 7.2143 (8.0); 7.2106 (9.0); 7.2056 (11.5); 7.1892 (2.1); 5.4993 (3.4); 5.3006 (2.8); 4.0313 (0.4); 4.0240 (1.1); 4.0171 (1.8); 4.0099 (2.6); 4.0029 (2.8); 3.9958 (2.1); 3.9887 (1.7); 3.9841 (3.1); 3.9784 (1.7); 3.9618 (5.6); 3.9557 (4.4); 3.9353 (4.4); 3.9277 (3.9); 3.9130 (1.9); 3.9054 (1.6); 3.7266 (1.2); 3.7126 (3.6); 3.6986 (3.6); 3.6845 (1.2); 3.0865 (11.0); 3.0723 (10.4); 1.6189 (0.7); 1.2466 (4.2); 1.2325 (8.2); 1.2185 (4.1); −0.0002 (7.5)

7-08: 1H-NMR(499.9 MHz, CDCl3):

δ = 7.7124 (16.0); 7.4052 (6.8); 7.4019 (7.1); 7.2660 (5.6); 7.2295 (1.4); 7.2259 (1.1); 7.2131 (7.5); 7.2094 (8.7); 7.2050 (11.2); 7.1886 (1.8); 5.5207 (3.3); 5.5152 (3.1); 5.3006 (2.8); 4.0308 (0.4); 4.0235 (1.0); 4.0166 (1.7); 4.0093 (2.4); 4.0024 (2.6); 3.9952 (2.0); 3.9883 (1.4); 3.9820 (2.9); 3.9762 (1.4); 3.9598 (5.4); 3.9536 (4.2); 3.9347 (4.4); 3.9270 (3.7); 3.9123 (1.8); 3.9047 (1.5); 3.7258 (1.3); 3.7118 (4.0); 3.6978 (4.0); 3.6837 (1.4); 3.0860 (10.7); 3.0718 (10.3); 1.6191 (0.5); 1.2542 (0.5); 1.2460 (4.6); 1.2320 (8.9); 1.2179 (4.4); −0.0002 (6.9); −0.0066 (0.4)

7-09: 1H-NMR(499.9 MHz, CDCl3):

δ = 7.7134 (16.0); 7.5543 (7.9); 7.5505 (7.7); 7.3725 (4.0); 7.3686 (3.6); 7.3562 (4.6); 7.3524 (4.2); 7.2649 (5.7); 7.1463 (7.1); 7.1300 (6.1); 5.4857 (3.4); 5.3005 (0.5); 4.0322 (0.4); 4.0250 (1.1); 4.0180 (1.8); 4.0108 (2.6); 4.0038 (2.7); 3.9967 (2.1); 3.9898 (1.5); 3.9836 (3.0); 3.9778 (1.5); 3.9613 (5.6); 3.9553 (4.3); 3.9370 (4.6); 3.9293 (3.9); 3.9146 (1.8); 3.9069 (1.6); 3.4736 (3.7); 3.0745 (10.6); 3.0603 (10.0); 2.9415 (0.4); 2.8305 (0.3); 1.6217 (0.8); 1.2548 (0.4); 1.2471 (0.5); 1.2330 (0.8); 1.2190 (0.4); −0.0002 (7.5)

7-10: 1H-NMR(499.9 MHz, CDCl3):

δ = 7.7114 (16.0); 7.5523 (7.6); 7.5485 (8.2); 7.3704 (3.8); 7.3666 (3.8); 7.3541 (4.4); 7.3503 (4.4); 7.2651 (5.4); 7.1454 (7.0); 7.1291 (6.1); 5.5112 (3.8); 5.5053 (3.6); 4.0314 (0.4); 4.0242 (1.1); 4.0172 (1.9); 4.0100 (2.7); 4.0031 (2.8); 3.9959 (2.1); 3.9891 (1.4); 3.9811 (2.8); 3.9750 (1.5); 3.9584 (5.7); 3.9524 (4.5); 3.9358 (4.8); 3.9282 (4.0); 3.9134 (1.8); 3.9058 (1.5); 3.4723 (4.3); 3.0738 (10.8); 3.0596 (10.4); 1.6192 (1.5); 1.2547 (0.5); 1.2464 (0.4); 1.2323 (0.6); −0.0002 (7.1)

7-11: 1H-NMR(499.9 MHz, CDCl3):

δ = 7.7119 (8.6); 7.2611 (2.8); 7.0321 (2.0); 7.0168 (3.4); 7.0016 (3.3); 6.9848 (0.4); 6.9697 (2.2); 6.9560 (1.4); 5.2907 (1.8); 4.1155 (1.3); 4.1093 (1.5); 4.0938 (1.6); 4.0877 (1.8); 3.8916 (0.3); 3.8859 (0.6); 3.8806 (0.9); 3.8748 (1.0); 3.8691 (1.1); 3.8635 (1.0); 3.8582 (0.8); 3.8521 (0.7); 3.8467 (0.5); 3.8397 (2.3); 3.8289 (1.2); 3.8180 (1.8); 3.8072 (1.3); 2.9820 (1.0); 2.9700 (1.0); 2.9545 (1.5); 2.9422 (1.5); 2.8545 (1.5); 2.8379 (1.5); 2.8270 (1.1); 2.8101 (1.0); 2.3045 (16.0); 2.2828 (15.3); 1.6297 (0.9); 1.3879 (3.7); −0.0002 (3.7)

7-12: 1H-NMR(499.9 MHz, CDCl3):

δ = 7.7147 (8.0); 7.2607 (2.9); 7.0332 (2.2); 7.0179 (3.5); 7.0045 (3.1); 6.9744 (2.0); 6.9590 (1.2); 5.2531 (1.7); 4.1214 (1.4); 4.1152 (1.5); 4.0997 (1.6); 4.0935 (1.6); 3.8992 (0.3); 3.8930 (0.5); 3.8874 (0.7); 3.8820 (1.0); 3.8761 (1.1); 3.8705 (1.1); 3.8648 (1.1); 3.8594 (0.8); 3.8534 (0.7); 3.8479 (0.6); 3.8402 (2.2); 3.8293 (1.2); 3.8185 (1.7); 3.8076 (1.2); 2.9847 (1.1); 2.9727 (1.0); 2.9572 (1.5); 2.9449 (1.4); 2.8515 (1.6); 2.8347 (1.5); 2.8240 (1.1); 2.8069 (1.0); 2.3058 (16.0); 2.2846 (14.6); 1.5927 (1.7); −0.0002 (3.8)

TABLE 43

Compounds according to formula (8)

(8)

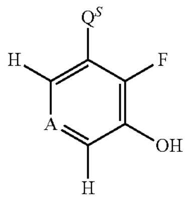

| Ex No | A | $Q^S$ | LogP |
|---|---|---|---|
| 8-01 | CH | vinyl | 1.96[a] |
| 8-02 | CH | ethynyl | 1.72[a] |
| 8-03 | CH | cyclopropyl | 2.12[a] |

TABLE 43-continued

Compounds according to formula (8)

(8)

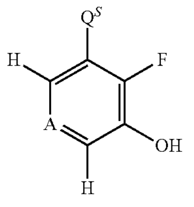

| Ex No | A | $Q^S$ | LogP |
|---|---|---|---|
| 8-04 | CH | rac-2,2-difluorocyclopropyl | |
| 8-05 | CH | 1-fluorocyclopropyl | |

TABLE 44

8-01: $^1$H-NMR(300.2 MHz, CDCl3):

δ = 7.2988 (8.3); 7.0822 (1.8); 7.0748 (2.4); 7.0563 (7.2); 7.0491 (7.3); 7.0406 (18.4); 7.0294 (8.8); 7.0183 (16.0); 7.0042 (0.7); 6.9921 (5.6); 6.9704 (6.4); 6.9630 (5.7); 6.9437 (7.8); 6.9375 (3.4); 6.9324 (4.6); 6.9257 (7.2); 6.9223 (4.7); 6.9109 (3.1); 6.8885 (6.8); 6.8667 (7.3); 6.8294 (7.6); 5.8978 (11.2); 5.8944 (11.6); 5.8387 (10.0); 5.8353 (10.3); 5.4557 (11.1); 5.4523 (11.2); 5.4184 (10.5); 5.4150 (10.7); 5.3378 (12.9); 5.2491 (9.5);

TABLE 44-continued 4.1831 (0.6); 4.1593 (0.6); 2.0946 (2.9); 1.6957 (8.4); 1.3266 (1.2); 1.3201 (1.8); 1.3029 (3.6); 1.2968 (3.9); 1.2790 (1.0); 1.2733 (1.4); 1.2639 (0.5); 0.9451 (0.6); 0.9234 (1.7); 0.9002 (0.7); 0.3136 (0.6); 0.3114 (0.6); 0.1135 (0.5); 0.0418 (9.8); 0.0309 (0.3)

8-02: $^{1}$H-NMR(300.2 MHz, $d_6$-DMSO):

δ = 10.1455 (8.9); 7.0552 (1.1); 7.0470 (1.7); 7.0289 (5.0); 7.0205 (9.8); 7.0119 (10.7); 6.9960 (16.0); 6.9699 (3.5); 6.9607 (5.1); 6.9527 (4.7); 6.9417 (4.7); 6.9369 (2.7); 6.9275 (4.1); 6.9101 (2.0); 5.7739 (1.2); 4.4408 (14.4); 3.3664 (6.0); 2.5345 (1.2); 2.5285 (2.7); 2.5225 (3.8); 2.5164 (2.8); 2.5105 (1.3); 1.2949 (0.5); 1.2576 (3.4); 1.0987 (1.2); 1.0754 (2.3); 1.0521 (1.1); 0.8946 (0.9); 0.8730 (3.1); 0.8497 (1.1); 0.0148 (5.1)

8-03: $^{1}$H-NMR(300.1 MHz, $d_6$-DMSO):

δ = 9.6264 (16.0); 6.8628 (2.1); 6.8591 (2.1); 6.8364 (5.2); 6.8326 (5.3); 6.8101 (3.6); 6.8066 (3.8); 6.7434 (3.5); 6.7378 (3.8); 6.7159 (5.1); 6.7104 (5.3); 6.6887 (2.4); 6.6832 (2.3); 6.3737 (2.6); 6.3684 (2.6); 6.3475 (4.7); 6.3262 (2.4); 6.3211 (2.2); 5.7578 (0.4); 4.0415 (0.8); 4.0178 (0.9); 3.3382 (6.7); 2.5154 (2.8); 2.5095 (5.4); 2.5036 (7.2); 2.4976 (4.9); 2.4918 (2.2); 2.0462 (0.7); 2.0289 (1.6); 2.0180 (1.8); 2.0009 (3.3); 1.9896 (5.1); 1.9730 (1.8); 1.9556 (0.9); 1.1988 (1.0); 1.1751 (2.1); 1.1513 (1.0); 0.9636 (2.7); 0.9495 (7.4); 0.9420 (7.8); 0.9356 (3.5); 0.9287 (4.0); 0.9210 (7.8); 0.9136 (7.1); 0.9005 (3.3); 0.8787 (0.4); 0.7131 (0.3); 0.6811 (3.5); 0.6678 (8.1); 0.6606 (8.4); 0.6506 (7.8); 0.6434 (8.0); 0.6289 (2.6); −0.0004 (5.8)

8-04: $^{1}$H-NMR(300.2 MHz, CDCl3):

δ = 7.2988 (0.5); 7.0418 (0.4); 7.0149 (1.2); 6.9891 (2.4); 6.9810 (1.1); 6.9623 (0.9); 6.9569 (0.9); 6.9354 (0.3); 6.7340 (0.4); 6.7264 (0.4); 6.7100 (0.8); 6.6868 (0.4); 6.6841 (0.4); 5.4977 (1.0); 5.3330 (0.8); 2.8803 (0.3); 2.8674 (0.6); 2.8398 (0.6); 2.8264 (0.4); 2.7988 (0.3); 2.0439 (16.0); 1.9405 (0.4); 1.9265 (0.6); 1.9103 (0.5); 1.9009 (0.6); 1.8842 (0.6); 1.8612 (0.4); 1.8442 (0.4); 1.7154 (0.3); 1.7014 (0.5); 1.6880 (0.7); 1.6738 (0.5); 1.6597 (0.7); 1.6462 (0.6); 0.0359 (0.7)

8-05: $^{1}$H-NMR(300.2 MHz, CDCl3):

δ = 7.2989 (22.6); 7.1680 (0.4); 7.1558 (0.6); 7.1500 (0.9); 7.1325 (1.2); 7.1213 (0.4); 7.1047 (1.8); 7.0896 (1.0); 7.0770 (4.3); 7.0605 (33.6); 7.0549 (23.8); 7.0432 (11.9); 7.0398 (16.0); 7.0347 (9.4); 7.0256 (4.5); 7.0210 (3.8); 7.0125 (2.1); 7.0074 (1.9); 7.0039 (1.9); 5.1920 (11.4); 3.6842 (0.4); 3.3468 (0.4); 2.1527 (0.4); 2.1394 (0.3); 2.1195 (0.3); 2.1161 (0.3); 2.0859 (0.3); 2.0500 (0.4); 1.6703 (0.4); 1.6596 (0.6); 1.6394 (7.8); 1.5230 (3.1); 1.5003 (9.4); 1.4973 (10.4); 1.4743 (4.2); 1.4603 (3.2); 1.4377 (9.4); 1.4345 (10.3); 1.4116 (4.9); 1.3500 (0.5); 1.2497 (0.7); 1.2391 (0.5); 1.2200 (0.8); 1.1889 (4.2); 1.1732 (5.5); 1.1681 (11.0); 1.1612 (12.7); 1.1386 (13.2); 1.1327 (9.8); 1.1110 (3.1); 0.0502 (0.9); 0.0394 (29.9); 0.0285 (1.1)

TABLE 15

Compounds according to formula (9)

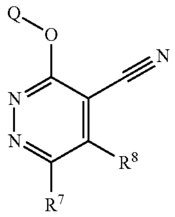

(9)

| Ex No | $R^7$ | $R^8$ | Q | LogP |
|---|---|---|---|---|
| 9-01 | Cl | H | 3-cyclopropylphenyl | 3.37[a] |
| 9-02 | $CH_3$ | H | 3-(trifluoromethyl)phenyl | 2.84[a] |
| 9-03 | Cl | H | 3-(trifluoromethyl)phenyl | 3.25[a] |
| 9-04 | Cl | H | 3-cyclopropyl-2-fluorophenyl | 3.54[a] |
| 9-05 | Cl | H | 3-bromo-2-fluorophenyl | 3.28[a] |

TABLE 15-continued

Compounds according to formula (9)

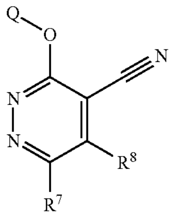

(9)

| Ex No | $R^7$ | $R^8$ | Q | LogP |
|---|---|---|---|---|
| 9-06 | Cl | H | 3-chloro-2-fluorophenyl | 3.23[a] |
| 9-07 | Cl | H | 3-chlorophenyl | 3.14[a] |
| 9-08 | Cl | H | 3-methoxyphenyl | 2.75[a] |
| 9-09 | Cl | H | 3-(difluoromethyl)-2-fluorophenyl | 3.00[a] |

TABLE 16

9-01: $^{1}$H-NMR(300.2 MHz, $d_6$-DMSO):

δ = 8.8636 (0.4); 8.7495 (0.4); 8.7364 (8.6); 8.4333 (0.4); 7.4065 (1.6); 7.3804 (3.7); 7.3543 (2.6); 7.1249 (2.0); 7.1174 (2.3); 7.0975 (4.0); 7.0683 (5.1); 7.0618 (3.7); 3.3454 (16.0); 2.5285 (3.7); 2.5226 (5.0); 2.5167 (3.6); 2.0302 (0.4); 2.0131 (1.0); 2.0022 (1.1); 1.9856 (1.9); 1.9689 (1.1); 1.9578 (1.1); 1.9411 (0.5); 1.0323 (1.2); 1.0176 (3.3); 1.0102 (3.7); 0.9965 (1.9); 0.9897 (3.5); 0.9824 (3.3); 0.9689 (1.4); 0.7438 (1.4); 0.7298 (3.8); 0.7230 (4.0); 0.7135 (3.7); 0.7066 (4.1); 0.6913 (1.1); 0.0207 (3.9)

9-02: $^{1}$H-NMR(499.9 MHz, $d_6$-DMSO):

δ = 8.3226 (5.8); 7.8030 (2.1); 7.7645 (0.5); 7.7488 (1.7); 7.7330 (1.7); 7.7108 (1.8); 7.6949 (1.0); 7.6900 (1.4); 7.6870 (1.4); 7.6711 (0.8); 3.3405 (9.8); 2.6232 (16.0); 2.5124 (1.0); 2.5089 (2.1); 2.5053 (2.9); 2.5018 (2.2); 2.4984 (1.1)

9-03: $^{1}$H-NMR(499.9 MHz, CDCl3):

δ = 7.8051 (16.0); 7.7925 (0.5); 7.6282 (0.7); 7.6123 (4.7); 7.6047 (4.6); 7.6008 (11.6); 7.5994 (11.9); 7.5751 (0.4); 7.5593 (5.7); 7.5460 (0.6); 7.5055 (0.5); 7.5014 (0.5); 7.4962 (2.1); 7.4897 (3.3); 7.4855 (3.2); 7.4780 (2.6); 7.4732 (1.7); 7.2595 (5.8); 4.1272 (0.3); 4.1129 (0.3); 2.0409 (1.4); 1.5504 (11.9); 1.2892 (0.4); 1.2712 (0.9); 1.2659 (1.2); 1.2572 (1.3); 1.2429 (0.6); 0.8953 (0.7); 0.8817 (1.8); 0.8675 (0.9); −0.0002 (4.6)

9-04: $^{1}$H-NMR(300.2 MHz, CDCl3):

δ = 7.8211 (16.0); 7.5866 (0.7); 7.2986 (19.8); 7.1715 (0.7); 7.1570 (0.5); 7.1443 (8.9); 7.1296 (5.4); 7.1264 (6.9); 7.1215 (4.7); 7.1169 (4.3); 7.0990 (1.1); 7.0899 (0.4); 6.9111 (1.7); 6.8941 (2.4); 6.8893 (2.0); 6.8796 (2.8); 6.8664 (1.6); 6.8573 (1.4); 2.1713 (0.6); 2.1541 (1.2); 2.1429 (1.3); 2.1257 (2.4); 2.1083 (1.4); 2.0975

TABLE 16-continued (1.3); 2.0802 (0.7); 1.5885 (9.5); 1.2911 (1.0); 1.0918 (1.8); 1.0765 (4.7); 1.0697 (5.0); 1.0637 (2.5); 1.0547 (2.7); 1.0478 (4.9); 1.0414 (4.4); 1.0265 (2.2); 1.0049 (0.3); 0.8975 (0.4); 0.8794 (0.6); 0.8615 (0.4); 0.8294 (2.4); 0.8143 (5.5); 0.8082 (5.2); 0.7973 (4.8); 0.7919 (5.8); 0.7752 (1.7); 0.1071 (6.8); 0.0482 (1.0); 0.0465 (0.6); 0.0374 (26.7); 0.0280 (1.0); 0.0265 (1.2)
9-05: $^1$H-NMR(300.2 MHz, CDCl3):
δ = 7.8483 (16.0); 7.6320 (0.6); 7.6035 (1.9); 7.5983 (2.1); 7.5835 (2.1); 7.5776 (3.4); 7.5712 (2.4); 7.5564 (2.3); 7.5510 (2.4); 7.3553 (1.7); 7.3501 (1.8); 7.3330 (1.9); 7.3279 (4.2); 7.3227 (2.6); 7.3054 (3.4); 7.2987 (23.6); 7.2069 (2.8); 7.2015 (2.7); 7.1796 (4.2); 7.1742 (4.2); 7.1523 (1.7); 7.1469 (1.8); 5.3383 (0.4); 2.0467 (0.6); 1.5894 (7.8); 1.3214 (0.3); 1.2924 (1.1); 0.8972 (0.6); 0.8770 (0.7); 0.1066 (0.6); 0.0479 (0.5); 0.0371 (30.2); 0.0263 (1.8)
9-06: $^1$H-NMR(300.2 MHz, CDCl3):
δ = 7.8612 (0.3); 7.8506 (16.0); 7.6349 (0.8); 7.4606 (1.7); 7.4545 (1.8); 7.4390 (1.9); 7.4336 (3.1); 7.4279 (2.5); 7.4136 (2.1); 7.4064 (2.4); 7.3149 (1.3); 7.3088 (1.6); 7.2987 (18.4); 7.2874 (4.3); 7.2812 (2.7); 7.2672 (3.6); 7.2600 (2.8); 7.2509 (4.1); 7.2471 (3.6); 7.2253 (3.7); 7.2202 (3.8); 7.1978 (1.2); 7.1928 (1.3); 5.3383 (0.4); 1.5935 (2.8); 1.3708 (0.4); 1.2919 (2.4); 1.2543 (0.4); 0.9173 (0.4); 0.8981 (0.9); 0.8773 (1.1); 0.1068 (1.2); 0.0479 (0.5); 0.0370 (24.2); 0.0263 (1.2)
9-07: $^1$H-NMR(300.2 MHz, CDCl3):
δ = 7.8274 (16.0); 7.5440 (0.3); 7.4731 (2.2); 7.4652 (0.6); 7.4521 (0.8); 7.4445 (5.0); 7.4222 (1.7); 7.4173 (4.1); 7.3734 (2.1); 7.3673 (4.1); 7.3636 (4.1); 7.3525 (3.4); 7.3451 (8.3); 7.3399 (8.1); 7.2990 (12.4); 7.2359 (2.8); 7.2323 (3.0); 7.2283 (2.8); 7.2247 (2.6); 7.2091 (2.2); 7.2028 (2.7); 7.1976 (2.0); 1.5900 (5.7); 1.2927 (0.5); 0.0485 (0.5); 0.0376 (16.9); 0.0267 (0.7)
9-08: $^1$H-NMR(300.2 MHz, CDCl3):
δ = 7.8019 (5.3); 7.4234 (1.0); 7.3960 (2.2); 7.3687 (1.3); 7.2987 (4.8); 6.9231 (0.8); 6.9207 (0.9); 6.9152 (1.0); 6.9128 (1.0); 6.8956 (1.5); 6.8929 (1.5); 6.8880 (2.0); 6.8854 (1.7); 6.8689 (0.6); 6.8661 (0.7); 6.8615 (1.2); 6.8587 (0.9); 6.8445 (1.6); 6.8370 (2.1); 6.8294 (0.9); 3.8603 (16.0); 1.5917 (2.5); 0.0375 (6.6)
9-09: $^1$H-NMR(300.2 MHz, CDCl3):
δ = 7.8680 (0.3); 7.8574 (16.0); 7.6502 (2.0); 7.6241 (2.3); 7.6015 (1.5); 7.5329 (1.0); 7.5302 (1.0); 7.5086 (2.4); 7.5059 (2.4); 7.4846 (1.8); 7.4819 (1.7); 7.4791 (1.5); 7.4205 (2.2); 7.3927 (3.0); 7.3653 (1.3); 7.2988 (20.2); 7.1180 (2.6); 6.9358 (5.1); 6.7537 (2.6); 1.5905 (3.2); 1.2925 (1.2); 0.8974 (0.6); 0.8773 (0.8); 0.1070 (0.5); 0.0481 (0.6); 0.0373 (28.1); 0.0264 (1.5)

TABLE 17

Compounds according to formula (10)

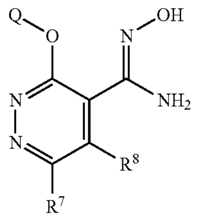

(10)

| Ex No | $R^7$ | $R^8$ | Q | LogP |
|---|---|---|---|---|
| 10-01 | Cl | H | 3-(trifluoromethyl)phenyl | 2.18[a] |
| 10-02 | $CH_3$ | H | 3-(trifluoromethyl)phenyl | 1.69[a] |
| 10-03 | Cl | H | 3-methoxyphenyl | 1.59[a] |
| 10-04 | Cl | H | 3-chlorophenyl | 2.00[a] |
| 10-05 | Cl | H | 3-bromo-2-fluorophenyl | 2.21[a] |
| 10-06 | Cl | H | 3-chloro-2-fluorophenyl | 2.12[a] |

TABLE 17-continued

Compounds according to formula (10)

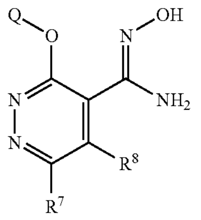

(10)

| Ex No | $R^7$ | $R^8$ | Q | LogP |
|---|---|---|---|---|
| 10-07 | Cl | H | 3-cyclopropyl-2-fluorophenyl | 2.34[a] |
| 10-08 | Cl | H | 3-cyclopropylphenyl | 2.19[a] |
| 10-09 | Cl | H | 3-(difluoromethyl)-2-fluorophenyl | 1.91[a] |
| 10-01 | Cl | H | 3-(trifluoromethyl)phenyl | 2.18[a] |

TABLE 18

10-01: 1H-NMR(300.2 MHz, d6-DMSO):
δ = 10.2733 (5.4); 8.0186 (5.3); 7.7748 (1.5); 7.7413 (1.1); 7.7155 (1.4); 7.6965 (1.5); 7.6706 (0.6); 7.6530 (1.1); 7.6271 (0.6); 6.1846 (2.2); 3.3428 (16.0); 2.5343 (1.0); 2.5284 (2.0); 2.5223 (2.7); 2.5163 (2.0); 2.5104 (0.9); 1.2674 (0.7); 0.8788 (0.7); 0.0204 (1.5)
10-02: 1H-NMR(499.9 MHz, CDCl3):
δ = 7.7682 (5.0); 7.7215 (0.9); 7.5696 (0.5); 7.5541 (1.5); 7.5386 (1.9); 7.5317 (1.9); 7.5161 (0.6); 7.4900 (1.8); 7.4271 (0.9); 7.4239 (1.2); 7.4203 (0.8); 7.4085 (0.9); 7.2612 (3.8); 5.5062 (1.6); 2.7415 (0.6); 2.6724 (16.0); 2.0465 (1.1); 1.6500 (0.5); 1.2593 (0.6); −0.0002 (3.9)
10-03: 1H-NMR(300.2 MHz, CDCl3):
δ = 7.9700 (5.3); 7.8904 (0.6); 7.4004 (1.2); 7.3734 (2.3); 7.3460 (1.4); 7.2992 (2.0); 6.8900 (1.1); 6.8826 (1.2); 6.8616 (1.0); 6.8562 (1.1); 6.8382 (1.2); 6.8326 (1.4); 6.8020 (2.6); 6.7936 (2.5); 6.7865 (1.0); 5.6142 (2.0); 5.3362 (1.5); 3.8566 (1.5); 3.8453 (16.0); 1.7378 (0.5); 0.1086 (0.7); 0.0373 (2.5)
10-07: 1H-NMR(300.2 MHz, CDCl3):
δ = 8.3416 (0.4); 7.9757 (16.0); 7.5480 (1.0); 7.4814 (0.3); 7.2990 (10.6); 7.1786 (0.6); 7.1711 (1.0); 7.1641 (0.4); 7.1518 (3.6); 7.1438 (6.0); 7.1384 (7.2); 7.1242 (4.2); 7.1199 (6.7); 7.0926 (1.3); 6.8834 (1.8); 6.8758 (1.8); 6.8602 (2.8); 6.8510 (1.8); 6.8444 (2.0); 6.8294 (1.3); 5.6089 (3.9); 5.3373 (1.6); 2.1656 (0.6); 2.1482 (1.2); 2.1372 (1.3); 2.1200 (2.4); 2.1027 (1.4); 2.0918 (1.3); 2.0743 (0.7); 1.6747 (1.7); 1.5523 (0.5); 1.2925

TABLE 18-continued

| |
|---|
| (1.0); 1.0807 (1.8); 1.0653 (4.5); 1.0585 (5.0); 1.0528 (2.7); 1.0438 (2.7); 1.0367 (4.9); 1.0302 (4.5); 1.0155 (2.2); 0.8718 (0.4); 0.8219 (2.3); 0.8068 (5.4); 0.8007 (5.4); 0.7899 (4.8); 0.7841 (5.8); 0.7677 (1.7); 0.1078 (4.1); 0.0481 (0.4); 0.0371 (12.8); 0.0262 (0.5) |
| 10-08: 1H-NMR(300.2 MHz, d6-DMSO): |
| δ = 10.2338 (5.4); 7.9672 (5.9); 7.3559 (0.9); 7.3298 (1.8); 7.3038 (1.2); 7.0338 (1.6); 7.0267 (2.7); 7.0066 (1.4); 7.0000 (3.0); 6.9839 (1.8); 6.9778 (2.0); 6.9717 (1.0); 6.1422 (2.4); 4.0838 (1.2); 4.0601 (3.5); 4.0364 (3.6); 4.0127 (1.2); 3.3534 (16.0); 2.5338 (1.6); 2.5279 (3.2); 2.5218 (4.3); 2.5158 (3.1); 2.5099 (1.5); 2.0092 (15.8); 1.9907 (0.6); 1.9792 (0.6); 1.9627 (1.0); 1.9458 (0.6); 1.9348 (0.5); 1.2177 (4.3); 1.1940 (8.6); 1.1703 (4.2); 1.0158 (0.6); 1.0013 (1.7); 0.9938 (1.8); 0.9883 (1.0); 0.9803 (1.1); 0.9733 (1.8); 0.9659 (1.6); 0.9526 (0.7); 0.9040 (0.3); 0.7246 (0.8); 0.7109 (1.9); 0.7039 (1.9); 0.6943 (1.8); 0.6874 (1.9); 0.6724 (0.6); 0.0195 (3.6) |
| 10-09: 1H-NMR(300.2 MHz, CDCl3): |
| δ = 8.3615 (0.4); 7.9923 (16.0); 7.6200 (2.6); 7.6096 (2.6); 7.5837 (3.0); 7.5607 (2.0); 7.5368 (1.9); 7.5113 (3.2); 7.4869 (2.0); 7.3976 (2.8); 7.3704 (3.8); 7.3432 (1.5); 7.2989 (8.7); 7.1114 (3.0); 6.9290 (6.1); 6.7467 (3.0); 5.5443 (4.3); 5.3371 (2.9); 1.6823 (2.5); 1.2920 (0.5); 0.1076 (0.9); 0.0473 (0.3); 0.0366 (10.8); 0.0258 (0.5) |

TABLE 19

Compounds according to formula (12)

(12)

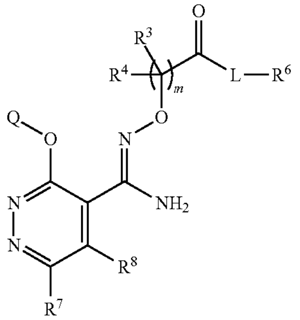

In table 19, "#" denotes the point of attachment to the L—$R^6$ group and "*" denotes the point of attachment to the pyridazin-4-yl group.

| Ex No | $R^7$ | $R^8$ | Q | 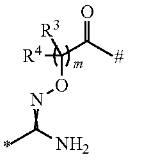 | L—$R^6$ | LogP |
|---|---|---|---|---|---|---|
| 12-01 | $CH_3$ | H | 3-(trifluoro-methyl)phenyl | 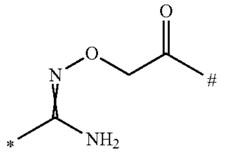 | 4-methoxyphenyl | 3.00[a] |
| 12-02 | $CH_3$ | H | 3-(trifluoro-methyl)phenyl | 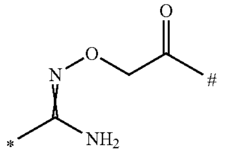 | phenyl | 3.04[a] |
| 12-03 | $CH_3$ | H | 3-(trifluoro-methyl)phenyl | 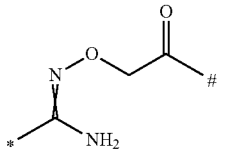 | 4-chlorophenyl | 3.42[a] |

TABLE 19-continued

Compounds according to formula (12)

(12)

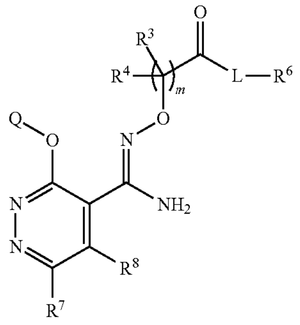

In table 19, "#" denotes the point of attachment to the L—$R^6$ group and "*" denotes the point of attachment to the pyridazin-4-yl group.

| Ex No | $R^7$ | $R^8$ | Q | 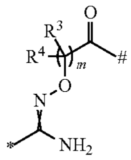 | L—$R^6$ | LogP |
|---|---|---|---|---|---|---|
| 12-04 | $CH_3$ | H | 3-(trifluoro-methyl)phenyl | 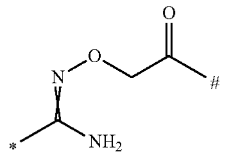 | 3,4-dimethylphenyl | 3.60[a] |
| 12-05 | $CH_3$ | H | 3-(trifluoro-methyl)phenyl | 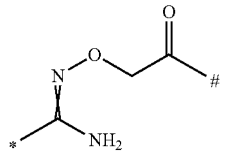 | 1-methyl-1H-indol-3-yl | 3.00[a] |
| 12-06 | $CH_3$ | H | 3-(trifluoro-methyl)phenyl | 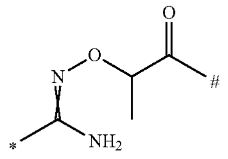 | 4-chlorophenyl | 3.35 & 3.79[a] |
| 12-07 | $CH_3$ | H | 3-(trifluoro-methyl)phenyl | 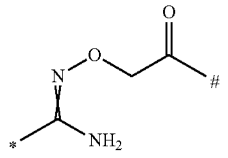 | 2,3-dihydro-1-benzofuran-5-yl | 3.00[a] |
| 12-08 | $CH_3$ | H | 3-(trifluoro-methyl)phenyl | 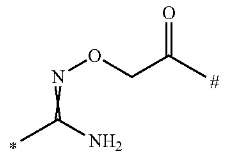 | 2-(4-chloro-2,6-difluorophenyl)ethyl | 3.42 & 4.03[a] |

TABLE 19-continued

Compounds according to formula (12)

(12)

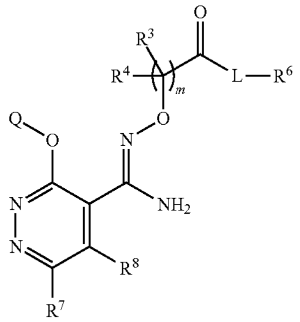

In table 19, "#" denotes the point of attachment to the L—$R^6$ group and "*" denotes the point of attachment to the pyridazin-4-yl group.

| Ex No | $R^7$ | $R^8$ | Q | 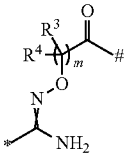 | L—$R^6$ | LogP |
|---|---|---|---|---|---|---|
| 12-09 | $CH_3$ | H | 3-(trifluoro-methyl)phenyl | 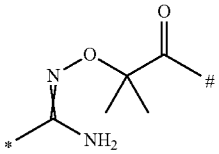 | 2,4-difluorophenyl | 3.88[a] |
| 12-10 | $CH_3$ | H | 3-(trifluoro-methyl)phenyl | 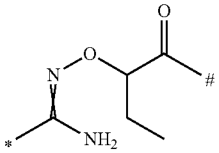 | 2,4-dichlorophenyl | 4.06 & 4.49[a] |
| 12-11 | $CH_3$ | H | 3-(trifluoro-methyl)phenyl | 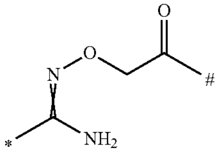 | 2-(4-chlorophenyl)ethyl | 3.19[a] |
| 12-12 | $CH_3$ | H | 3-(trifluoro-methyl)phenyl | 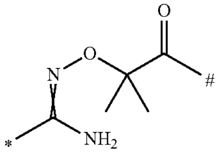 | 3,4-dichlorophenyl | 4.59[a] |
| 12-13 | $CH_3$ | H | 3-(trifluoro-methyl)phenyl | 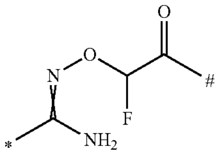 | 4-chlorophenyl | 3.19[a] |

TABLE 19-continued

Compounds according to formula (12)

(12)

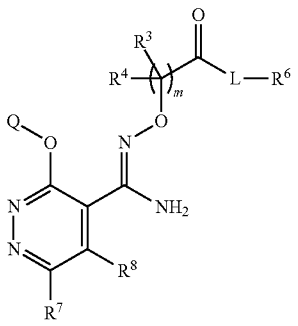

In table 19, "#" denotes the point of attachment to the L—$R^6$ group and "*" denotes the point of attachment to the pyridazin-4-yl group.

| Ex No | $R^7$ | $R^8$ | Q | 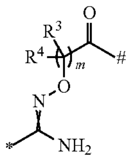 | L—$R^6$ | LogP |
|---|---|---|---|---|---|---|
| 12-14 | $CH_3$ | H | 3-(trifluoro-methyl)phenyl | 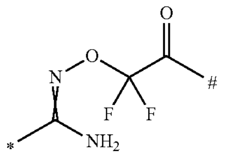 | 4-methoxyphenyl | 3.13[a] |
| 12-15 | $CH_3$ | H | 3-(trifluoro-methyl)phenyl | 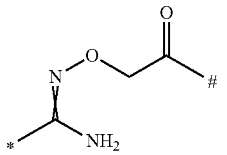 | 2-phenylcyclopropyl | 3.57[a] |
| 12-16 | $CH_3$ | H | 3-(trifluoro-methyl)phenyl | 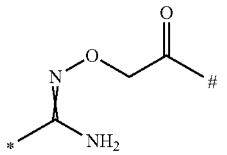 | 2,3-dihydro-1,4-benzo-dioxin-6-yl | 3.07[a] |

TABLE 20

12-02: $^1$H-NMR(300.2 MHz, CDCl3):
δ = 8.1719 (0.8); 8.0856 (0.3); 8.0280 (2.6); 8.0044 (3.2); 7.9996 (2.5); 7.9595 (0.4); 7.9386 (0.4); 7.9154 (0.4); 7.8590 (0.5); 7.8431 (0.5); 7.8347 (0.6); 7.8300 (0.5); 7.8114 (5.0); 7.7793 (0.6); 7.7553 (0.6); 7.7513 (0.6); 7.7031 (1.0); 7.6761 (1.3); 7.6591 (0.9); 7.6518 (2.0); 7.6447 (1.1); 7.6316 (1.4); 7.6269 (1.9); 7.6222 (1.7); 7.6095 (1.1); 7.5971 (2.3); 7.5871 (1.4); 7.5711 (4.7); 7.5655 (4.3); 7.5381 (4.1); 7.5203 (2.8); 7.5143 (2.7); 7.4913 (1.3); 7.4823 (1.3); 7.4697 (2.1); 7.4612 (2.2); 7.4542 (1.7); 7.4381 (1.6); 7.4087 (0.5); 7.3699 (0.6); 7.3434 (0.7); 7.3182 (0.5); 7.2987 (25.4); 5.8101 (0.6); 5.7328 (1.7); 5.4210 (10.8); 5.3829 (0.4); 5.3375 (7.1); 3.9859 (0.3); 2.7983 (0.5); 2.7516 (0.8); 2.7265 (1.9); 2.7090 (0.5); 2.6908 (2.5); 2.6728 (16.0); 1.6253 (0.5); 1.2932 (0.8); 0.1083 (0.7); 0.0492 (1.0); 0.0384 (27.6); 0.0277 (1.1)
12-03: $^1$H-NMR(300.2 MHz, CDCl3):
δ = 7.9778 (4.0); 7.9714 (1.4); 7.9552 (1.6); 7.9490 (4.4); 7.9410 (0.7); 7.7872 (5.1); 7.6443 (0.3); 7.6225 (0.6); 7.5959 (1.6); 7.5722 (4.1); 7.5476 (0.8); 7.5251 (6.0); 7.5187 (3.4); 7.5025 (1.8); 7.4964 (4.1); 7.4620 (1.1); 7.4540 (1.7); 7.4467 (1.0); 7.4372 (0.9); 7.4315 (1.2); 7.4142 (0.4); 7.2984 (16.0); 5.7581 (0.3); 5.7160 (1.9); 5.3565 (11.0); 5.3370 (8.4); 2.7744 (0.4); 2.7492 (0.6); 2.7019 (0.7); 2.6727 (16.0); 2.0823 (0.3); 1.6105 (1.4); 1.2963 (0.8); 0.9198 (0.4); 0.0483 (0.8); 0.0377 (16.4); 0.0267 (0.6)
12-04: $^1$H-NMR(300.2 MHz, CDCl3):
δ = 7.8196 (3.4); 7.7834 (1.8); 7.7570 (1.0); 7.7309 (1.0); 7.5940 (1.0); 7.5691 (2.9); 7.5439 (0.5); 7.5239 (1.5); 7.4670 (0.7); 7.4594 (1.0); 7.4526 (0.6); 7.4362 (0.7); 7.2984 (4.8); 7.2663 (1.3); 5.7438 (1.6); 5.3956 (6.8); 4.1939 (0.4); 4.1701 (1.1); 4.1464 (1.1); 4.1227 (0.4); 2.6685 (10.4); 2.3923 (0.5); 2.3680 (16.0); 2.3455 (1.0);

TABLE 20-continued 2.2569 (0.4); 2.1591 (0.4); 2.0821 (5.0); 1.6509 (1.4); 1.3196 (1.3); 1.2958 (2.7); 1.2720 (1.2); 0.1075 (1.6); 0.0377 (5.4); 0.0365 (5.8)
12-05: $^1$H-NMR(499.9 MHz, CDCl3):
δ = 8.4050 (1.0); 8.4035 (1.1); 8.3969 (0.7); 8.3915 (1.1); 8.3869 (1.0); 8.0076 (0.5); 7.9742 (0.6); 7.8914 (4.7); 7.7961 (5.1); 7.6517 (0.6); 7.5515 (0.4); 7.5361 (1.4); 7.5211 (2.9); 7.5035 (0.5); 7.4816 (2.0); 7.4719 (0.5); 7.4701 (0.5); 7.4087 (0.8); 7.4047 (1.3); 7.4005 (0.8); 7.3901 (0.9); 7.3862 (0.6); 7.3762 (0.3); 7.3748 (0.3); 7.3693 (0.6); 7.3642 (0.8); 7.3594 (2.0); 7.3561 (3.1); 7.3512 (1.1); 7.3473 (2.4); 7.3431 (2.8); 7.3348 (1.6); 7.3281 (2.1); 7.3231 (1.1); 7.3194 (0.3); 7.3153 (0.6); 7.3105 (0.7); 7.2839 (0.4); 7.2594 (5.6); 7.0776 (0.5); 5.7284 (2.1); 5.1739 (10.2); 3.8656 (0.5); 3.8514 (16.0); 3.7950 (0.6); 3.7721 (1.3); 3.7371 (2.0); 3.3521 (0.7); 3.3351 (0.4); 2.9475 (3.9); 2.8759 (3.4); 2.7301 (0.4); 2.6900 (1.9); 2.6113 (15.7); 2.0415 (1.0); 1.6621 (2.3); 1.2568 (0.5); −0.0002 (5.6)
12-06: $^1$H-NMR(300.2 MHz, CDCl3):
δ = 8.1894 (0.4); 8.0615 (1.4); 8.0491 (2.3); 8.0333 (1.8); 8.0201 (4.2); 8.0036 (1.6); 7.9914 (2.2); 7.9779 (0.7); 7.9589 (3.5); 7.9383 (0.8); 7.9286 (1.3); 7.9002 (0.4); 7.6900 (2.5); 7.6454 (0.5); 7.6171 (1.0); 7.5725 (6.2); 7.5444 (5.2); 7.5250 (2.6); 7.5170 (3.3); 7.5083 (3.1); 7.5015 (4.4); 7.4958 (4.3); 7.4888 (3.7); 7.4787 (3.8); 7.4728 (4.0); 7.4561 (1.8); 7.4427 (1.4); 7.4231 (1.9); 7.4157 (2.2); 7.4019 (5.2); 7.3730 (3.4); 7.3324 (0.5); 7.2996 (27.1); 7.2505 (0.6); 7.2261 (0.5); 7.1571 (0.6); 7.0382 (0.4); 6.9101 (0.6); 6.7943 (1.2); 5.6440 (1.2); 5.5646 (0.4); 5.5417 (1.1); 5.5187 (1.2); 5.4961 (0.6); 5.4794 (0.6); 5.4572 (0.6); 5.3381 (0.4); 5.2734 (0.7); 5.2511 (0.8); 5.2286 (0.9); 5.2064 (0.7); 4.2017 (0.4); 4.1934 (0.8); 4.1796 (0.5); 4.1697 (2.1); 4.1460 (2.1); 4.1220 (0.8); 3.8602 (1.1); 3.8392 (1.1); 3.8176 (0.3); 3.7251 (0.4); 3.3231 (0.5); 3.3077 (0.4); 3.2934 (1.2); 3.2839 (1.0); 3.2698 (1.6); 3.2566 (1.7); 3.2439 (1.5); 3.2334 (2.3); 3.2097 (0.5); 3.0283 (0.9); 3.0042 (0.9); 2.8353 (5.0); 2.8015 (5.5); 2.7751 (1.8); 2.7433 (12.9); 2.6817 (0.5); 2.6513 (8.0); 2.6119 (0.9); 2.0822 (9.7); 2.0452 (0.4); 1.9517 (2.8); 1.9297 (2.7); 1.7936 (3.0); 1.7786 (2.8); 1.7716 (3.6); 1.7557 (2.5); 1.7279 (0.4); 1.7025 (0.4); 1.6650 (4.0); 1.6419 (4.2); 1.6157 (16.0); 1.5688 (0.5); 1.5500 (0.3); 1.4934 (1.0); 1.4625 (10.9); 1.4374 (1.0); 1.4142 (0.9); 1.3202 (2.6); 1.2964 (5.3); 1.2850 (1.4); 1.2726 (2.7); 1.2595 (3.6); 1.2352 (5.1); 1.2114 (6.4); 1.1905 (4.3); 1.1138 (0.4); 1.0836 (1.8); 1.0618 (1.7); 0.1071 (1.3); 0.0479 (1.4); 0.0371 (34.0)
12-07: $^1$H-NMR(300.2 MHz, CDCl3):
δ = 8.6214 (0.3); 8.1868 (0.4); 7.9076 (1.7); 7.8686 (1.0); 7.8630 (0.9); 7.8407 (1.2); 7.8239 (3.3); 7.6164 (0.8); 7.5932 (1.4); 7.5857 (1.0); 7.5682 (2.5); 7.5432 (0.7); 7.5217 (1.3); 7.4933 (0.4); 7.4658 (0.7); 7.4584 (1.1); 7.4519 (0.7); 7.4347 (0.7); 7.2987 (14.2); 6.8835 (2.1); 6.8556 (2.0); 6.3723 (0.3); 5.7407 (1.2); 5.3717 (0.8); 5.3555 (5.9); 5.3366 (16.0); 5.2948 (0.9); 4.7521 (1.2); 4.7431 (1.8); 4.7232 (2.3); 4.7139 (3.4); 4.6935 (1.6); 4.6846 (2.1); 4.6740 (2.9); 4.6620 (0.5); 3.3341 (1.5); 3.3051 (2.9); 3.2755 (1.9); 3.2617 (0.8); 3.2377 (0.5); 3.2225 (0.4); 2.9866 (0.9); 2.8389 (0.8); 2.8049 (0.9); 2.7902 (0.8); 2.7740 (1.4); 2.7568 (0.3); 2.7423 (0.4); 2.7129 (0.4); 2.6926 (0.6); 2.6691 (9.1); 2.0822 (0.9); 1.6578 (2.5); 1.4680 (1.6); 1.4658 (1.6); 1.2957 (0.6); 1.2635 (0.4); 1.2397 (0.7); 1.2160 (0.3); 0.1062 (5.2); 0.0470 (0.7); 0.0361 (18.0); 0.0254 (0.8)
12-09: $^1$H-NMR(499.9 MHz, CDCl3):
δ = 7.6446 (0.3); 7.6283 (0.7); 7.6148 (0.6); 7.6122 (0.6); 7.5986 (0.4); 7.5453 (0.9); 7.5299 (1.9); 7.5126 (0.3); 7.4418 (3.0); 7.4222 (1.3); 7.3556 (0.8); 7.3520 (0.5); 7.3409 (0.6); 7.2607 (4.0); 6.8640 (0.4); 6.8520 (0.6); 6.8474 (0.7); 6.8322 (0.7); 6.8147 (0.5); 6.8118 (0.7); 6.8077 (0.5); 6.7944 (0.4); 6.7897 (0.4); 5.4371 (1.5); 2.6997 (0.4); 2.6145 (9.2); 1.6786 (16.0); 1.5624 (3.6); 1.2548 (0.6); 0.0701 (0.9); −0.0002 (4.5)
12-10: $^1$H-NMR(300.2 MHz, CDCl3):
δ = 8.0836 (0.9); 8.0419 (0.5); 8.0131 (0.5); 7.7172 (2.2); 7.6770 (0.4); 7.6492 (0.6); 7.6349 (0.4); 7.6139 (0.8); 7.5921 (0.8); 7.5679 (2.0); 7.5496 (1.3); 7.5439 (1.3); 7.5281 (1.3); 7.5160 (1.1); 7.5005 (2.6); 7.4960 (2.0); 7.4894 (2.3); 7.4816 (2.8); 7.4745 (1.9); 7.4580 (0.9); 7.4506 (1.1); 7.4419 (1.1); 7.4320 (0.9); 7.4246 (0.5); 7.4079 (1.0); 7.3982 (0.9); 7.3918 (1.2); 7.3865 (1.1); 7.3806 (1.1); 7.3637 (1.1); 7.3544 (0.6); 7.3412 (1.1); 7.3347 (1.0); 7.3134 (0.8); 7.3066 (1.0); 7.2988 (18.8); 7.2731 (0.4); 7.1033 (0.4); 5.5598 (1.0); 5.3376 (16.0); 5.2373 (0.5); 5.2216 (0.5); 5.2102 (0.6); 5.1942 (0.5); 5.0645 (0.3); 5.0584 (0.4); 5.0381 (0.4); 3.2934 (0.6); 3.2793 (0.4); 3.2694 (0.6); 3.2559 (0.7); 3.2317 (0.5); 3.0234 (0.7); 2.9993 (0.7); 2.8402 (2.3); 2.8149 (1.2); 2.8063 (2.7); 2.7763 (1.3); 2.7429 (0.4); 2.7265 (2.9); 2.6994 (0.7); 2.6836 (6.8); 2.1479 (0.5); 2.1233 (0.6); 2.1069 (0.4); 2.0995 (0.6); 2.0839 (0.5); 2.0755 (0.6); 2.0595 (0.6); 2.0376 (0.6); 2.0271 (0.4); 2.0134 (0.7); 2.0060 (0.5); 1.9882 (0.6); 1.9822 (0.4); 1.9649 (0.4); 1.6705 (0.3); 1.4633 (4.5); 1.3466 (0.3); 1.3383 (0.4); 1.3043 (0.5); 1.2847 (1.2); 1.2732 (1.2); 1.2606 (1.6); 1.2495 (2.1); 1.2364 (0.9); 1.2254 (1.1); 1.1973 (0.7); 1.1796 (1.1); 1.1616 (2.4); 1.1554 (2.5); 1.1371 (4.8); 1.1271 (1.7); 1.1125 (2.2); 1.1025 (0.8); 1.0399 (0.8); 1.0152 (1.4); 0.9905 (0.7); 0.1066 (3.4); 0.0476 (0.6); 0.0369 (22.3); 0.0261 (1.1)
12-11: $^1$H-NMR(400.1 MHz, $d_6$-DMSO):
δ = 7.9907 (3.5); 7.7237 (3.5); 7.7109 (6.1); 7.6847 (2.3); 7.6651 (2.2); 7.6298 (2.7); 7.6089 (3.3); 7.5865 (1.3); 7.2503 (4.3); 7.2299 (5.7); 7.1867 (0.4); 7.1769 (0.4); 7.1065 (5.3); 7.0860 (3.9); 5.9670 (5.1); 3.7999 (2.0); 3.7727 (2.6); 3.6163 (2.8); 3.5884 (2.2); 3.4305 (0.4); 3.3130 (289.4); 2.6897 (2.0); 2.6749 (2.4); 2.6016 (16.0); 2.5009 (57.6); 2.3256 (0.4); 2.0835 (0.4); 1.9868 (0.4); 1.8835 (2.1); 1.8677 (2.0); 1.8512 (1.1); −0.0002 (14.4)
12-15: $^1$H-NMR(300.2 MHz, CDCl3):
δ = 7.6709 (5.0); 7.6227 (0.3); 7.5970 (1.3); 7.5740 (3.9); 7.5515 (0.4); 7.4943 (1.8); 7.4442 (0.7); 7.4356 (1.3); 7.4283 (0.8); 7.4231 (0.5); 7.4197 (0.5); 7.4137 (0.8); 7.4059 (0.5); 7.2987 (15.0); 7.2780 (0.6); 7.2718 (0.8); 7.2661 (0.4); 7.2495 (2.5); 7.2442 (1.3); 7.2254 (3.0); 7.2162 (1.1); 7.2102 (1.7); 7.2048 (1.1); 7.1965 (0.5); 7.1878 (1.3); 7.1630 (0.4); 7.1237 (2.4); 7.1180 (2.9); 7.0959 (2.1); 5.6457 (2.0); 5.3379 (9.7); 4.8253 (6.6); 4.8221 (6.4); 2.6511 (16.0); 2.6277 (0.6); 2.6190 (0.6); 2.6103 (0.6); 2.6058 (0.7); 2.5978 (0.7); 2.5890 (0.5); 2.5756 (0.6); 2.5478 (0.7); 2.5341 (0.7); 2.5297 (1.0); 2.5209 (0.9); 2.5164 (0.7); 2.5074 (0.8); 2.5029 (0.9); 2.4894 (0.6); 2.0837 (0.7); 1.8899 (0.7); 1.8759 (0.9); 1.8719 (0.8); 1.8594 (1.2); 1.8460 (0.8); 1.8419 (0.8); 1.8281 (0.6); 1.6017 (10.5); 1.5040 (0.7); 1.4902 (0.8); 1.4818 (0.8); 1.4771 (0.9); 1.4680 (0.8); 1.4635 (0.8); 1.4550 (0.8); 1.4413 (0.6); 1.3215 (0.3); 1.2974 (0.7); 0.1074 (4.3); 0.0484 (0.7); 0.0377 (20.6); 0.0283 (0.6); 0.0268 (0.7)

TABLE 20-continued
| |
|---|
| 12-16: $^1$H-NMR(300.2 MHz, CDCl3):<br>δ = 7.9519 (0.5); 7.8240 (3.6); 7.6362 (0.7); 7.6207 (0.9); 7.5962 (1.4); 7.5694 (7.8); 7.5433 (2.0); 7.5361 (1.6); 7.5234 (1.8); 7.4812 (0.4); 7.4670 (0.9); 7.4591 (1.3); 7.4521 (0.8); 7.4361 (1.0); 7.2985 (18.9); 6.9890 (1.6); 6.9629 (1.5); 6.9433 (0.4); 5.7332 (1.8); 5.7051 (1.1); 5.3385 (11.1); 4.3764 (2.2); 4.3634 (3.0); 4.3589 (3.6); 4.3412 (3.6); 4.3352 (2.7); 4.3293 (2.0); 4.3231 (2.2); 4.3147 (2.8); 4.3024 (1.4); 4.1709 (0.4); 4.1472 (0.4); 2.7775 (0.9); 2.7564 (0.4); 2.7461 (0.5); 2.7149 (0.9); 2.7036 (0.5); 2.6725 (12.7); 2.0836 (1.6); 1.6030 (16.0); 1.3208 (0.7); 1.2969 (1.3); 1.2730 (0.4); 0.1064 (2.4); 0.0367 (26.3) |
TABLE 21
Compounds according to formula (13)
(13)
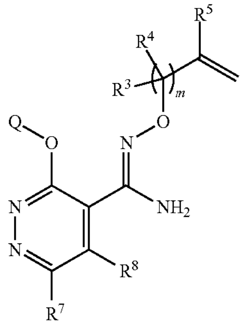
In table 21, "*" denotes the point of attachment to the pyridazin-4-yl group.
| Ex No | $R^7$ | $R^8$ | Q | 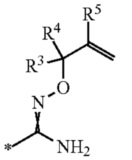 | LogP |
|---|---|---|---|---|---|
| 13-01 | $CH_3$ | H | 3-(trifluoromethyl)phenyl | 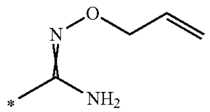 | 2.88[a] |
TABLE 22
| |
|---|
| 13-01: $^1$H-NMR(400.2 MHz, $d_6$-DMSO):<br>δ = 8.3350 (1.3); 7.8120 (0.4); 7.7348 (0.4); 7.7165 (0.8); 7.6962 (3.5); 7.6853 (6.8); 7.6760 (1.8); 7.6415 (1.8); 7.6220 (1.0); 7.5837 (1.2); 7.5640 (0.9); 6.4004 (3.2); 6.0510 (0.4); 6.0374 (0.8); 6.0243 (0.7); 6.0111 (1.0); 6.0078 (0.6); 5.9975 (0.5); 5.9941 (1.1); 5.9809 (0.8); 5.9678 (1.0); 5.9542 (0.5); 5.3533 (0.5); 5.3492 (1.5); 5.3445 (1.6); 5.3404 (0.6); 5.3100 (0.5); 5.3058 (1.3); 5.3012 (1.4); 5.2970 (0.6); 5.1856 (0.6); 5.1823 (1.4); 5.1776 (1.4); 5.1743 (0.7); 5.1593 (0.6); 5.1560 (1.3); 5.1513 (1.3); 5.1481 (0.6); 4.4739 (2.0); 4.4703 (3.5); 4.4668 (2.2); 4.4603 (2.2); 4.4567 (3.5); 4.4531 (2.1); 3.3302 (10.7); 2.6206 (3.5); 2.5747 (16.0); 2.5115 (5.5); 2.5071 (11.6); 2.5026 (16.1); 2.4981 (11.8); 2.4937 (5.8); 0.0089 (0.4); 0.0007 (11.1); −0.0076 (0.4) |

TABLE 23

Compounds according to formula (14)

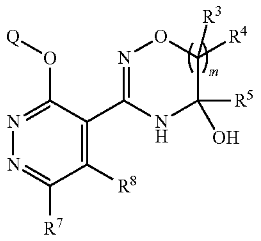

(14)

In table 23, "*" denotes the point of attachment to the pyridazin-4-yl group.

| Ex No | $R^7$ | $R^8$ | Q | 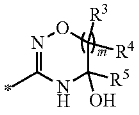 | LogP |
|---|---|---|---|---|---|
| 14-01 | methyl | H | 3-(trifluoromethyl) phenyl | 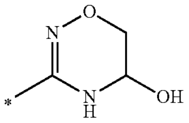 | 1.59[a] |

TABLE 24

| |
|---|
| 14-01: $^1$H-NMR(499.9 MHz, $d_6$-DMSO): δ = 8.1864 (2.7); 7.9128 (5.7); 7.9095 (3.8); 7.8930 (1.0); 7.8730 (5.1); 7.8246 (2.8); 7.8095 (1.7); 7.7633 (2.3); 7.7480 (1.8); 6.2754 (2.8); 6.2720 (2.2); 6.2626 (2.8); 5.1829 (2.1); 5.1780 (2.1); 4.2128 (0.8); 4.2093 (0.5); 4.2062 (0.4); 4.1986 (0.8); 4.1954 (0.5); 3.9584 (1.6); 3.9542 (1.7); 3.9361 (2.1); 3.9320 (2.2); 3.7960 (2.1); 3.7921 (2.3); 3.7736 (1.7); 3.7697 (1.8); 3.5161 (0.4); 3.4921 (53.5); 3.4569 (0.3); 2.7970 (0.4); 2.7638 (16.0); 2.7608 (11.2); 2.6771 (15.2); 2.6741 (13.4); 2.1696 (1.2); 2.1644 (3.1); 2.1613 (2.0); 1.3705 (0.3); 1.3652 (0.8); 1.3620 (0.7); 1.3581 (0.7); 1.3563 (0.6); 1.3510 (1.6); 1.3478 (1.1); 1.3446 (0.7); 1.3367 (0.8); 1.3336 (0.6) |

TABLE 25

Compound according to formula (16)

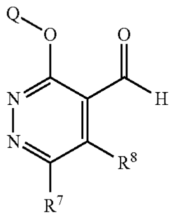

(16)

| Ex No | $R^7$ | $R^8$ | Q | LogP |
|---|---|---|---|---|
| 16-01 | Cl | H | 3-(trifluoromethyl)phenyl | 2.04[a] |

TABLE 26

| |
|---|
| 16-01: $^1$H-NMR(300.2 MHz, CDCl3): δ = 10.5580 (16.0); 7.9322 (15.8); 7.8206 (0.6); 7.7859 (1.8); 7.7263 (2.4); 7.6892 (0.8); 7.6636 (3.5); 7.6416 (11.1); 7.6200 (1.4); 7.5996 (5.4); 7.5701 (2.2); 7.5529 (4.4); 7.5427 (4.8); 7.5360 (3.8); 7.5203 (2.8); 7.4913 (0.4); 7.4602 (1.2); 7.4305 (0.4); 7.4165 (0.6); 7.4013 (0.8); 7.3954 (0.8); 7.3774 (1.1); 7.3040 (22.8); 7.2888 (0.5); 7.2787 (0.3); 6.4615 (0.8); 6.4242 (1.0); 3.7775 (0.6); 3.7541 (0.6); 1.6618 (3.9); 1.5797 (0.3); 1.3863 (0.4); 1.3636 (0.9); 1.3401 (1.2); 1.2976 (7.5); 1.2856 (2.9); 1.2620 (1.5); 0.9215 (1.0); 0.8985 (0.8); 0.8740 (0.5); 0.1126 (4.4); 0.0526 (0.7); 0.0419 (18.2); 0.0310 (0.8) |

TABLE 27

Compound according to formula (17)

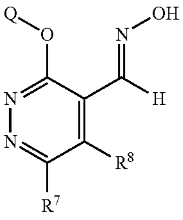

(17)

| Ex No | $R^7$ | $R^8$ | Q | LogP |
|---|---|---|---|---|
| 17-01 | Cl | H | 3-(trifluoromethyl)phenyl | 2.88[a] |

TABLE 28
17-01: $^1$H-NMR(300.2 MHz, CDCl3):
δ = 8.5770 (3.1); 8.4318 (16.0); 8.0705 (0.4); 7.9391 (16.0); 7.9021 (2.4); 7.8912 (0.5); 7.8754 (0.7); 7.7791 (0.4); 7.6673 (0.6); 7.6366 (1.1); 7.6109 (4.2); 7.5868 (13.7); 7.5641 (3.1); 7.5324 (7.4); 7.5070 (1.8); 7.4856 (3.2); 7.4783 (5.4); 7.4711 (3.4); 7.4617 (2.6); 7.4557 (3.6); 7.3980 (0.5); 7.3719 (0.5); 7.2982 (33.3); 7.2317 (0.5); 7.2023 (0.4); 7.1131 (0.5); 7.0160 (0.5); 6.1094 (0.5); 5.4728 (0.4); 3.8536 (0.5); 3.8439 (1.4); 3.6757 (1.7); 3.5771 (0.3); 3.5687 (0.5); 3.5030 (1.6); 3.4970 (1.8); 3.4515 (2.1); 3.4123 (3.1); 3.3468 (0.4); 3.3327 (1.0); 3.0167 (2.4); 2.9451 (2.1); 2.8681 (0.4); 2.8019 (2.5); 2.7821 (0.4); 2.7550 (1.3); 2.6951 (0.5); 2.6692 (1.5); 2.4815 (0.3); 2.4560 (0.9); 2.4305 (1.0); 2.4048 (0.4); 2.3068 (1.1); 2.2814 (2.6); 2.2696 (0.6); 2.2564 (2.7); 2.2443 (0.7); 2.2316 (1.0); 2.1491 (6.0); 2.0501 (2.4); 1.9364 (11.8); 1.9237 (1.4); 1.9168 (4.1); 1.4698 (4.0); 1.3681 (0.6); 1.3445 (1.1); 1.3210 (0.8); 1.2929 (1.4); 1.2259 (0.4); 1.2004 (0.5); 1.1633 (3.5); 1.1562 (1.4); 1.1482 (0.9); 1.1384 (7.0); 1.1307 (2.7); 1.1233 (1.5); 1.1133 (3.3); 1.1051 (1.4); 1.0983 (0.8); 0.9168 (0.3); 0.1078 (11.8); 0.0956 (0.5); 0.0481 (1.0); 0.0373 (36.4); 0.0264 (1.6)
TABLE 31
Compounds according to formula (19)
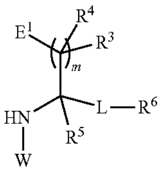
(19)
In table 31, "#" denotes the point of attachment to the L—$R^6$ group.
| Ex No | 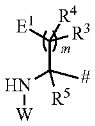 | L—$R^6$ | Log P | Salt |
|---|---|---|---|---|
| 19-01 | 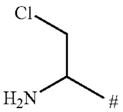 | (2,4-dimethylphenyl)methyl | 1.13[a] | HCl |
| 19-02 | 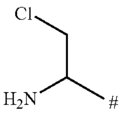 | [4-(trifluoromethyl)phenyl]methyl | 1.27[a] | HCl |
| 19-03 | 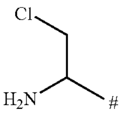 | [4-(difluoromethoxy)phenyl]methyl | 3.40[a] | HCl |
| 19-04 | 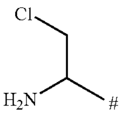 | [4-(trifluoromethoxy)phenyl]methyl | 1.38[a] | HCl |
| 19-05 | 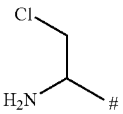 | (2,4-dimethylphenyl)methyl | 1.16[a] | HCl |
| 19-06 | 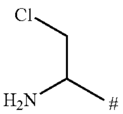 | (2,4-dimethylphenyl)methyl | 1.28[a] | HCl |

TABLE 31-continued

Compounds according to formula (19)

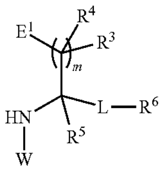

(19)

In table 31, "#" denotes the point of attachment to the L—$R^6$ group.

| Ex No | 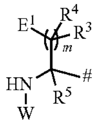 | L—$R^6$ | Log P | Salt |
|---|---|---|---|---|
| 19-07 | 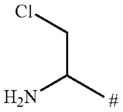 | [(2,4-dimethylphenyl)thio]methyl | 1.42[a] | HCl |
| 19-08 | 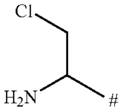 | [4-(difluoromethyl)phenyl]methyl | 0.83[a] | HCl |
| 19-09 | 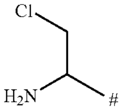 | (2-bromo-4-methylphenyl)methyl | 1.23[a] | HCl |
| 19-10 | 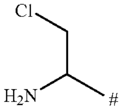 | [2-chloro-4-(trifluoromethyl)phenyl]methyl | 1.43[a] | HCl |
| 19-11 | 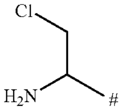 | (2-chloro-4-methylphenyl)methyl | 1.09[a] | HCl |
| 19-12 | 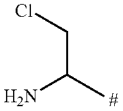 | (3,4-dichlorophenyl)methyl | 1.34[a] | HCl |
| 19-13 | 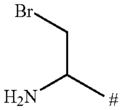 | (1-methyl-1H-indol-3-yl)methyl | 1.23[a] | TFA |
| 19-14 | 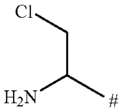 | (4-nitrophenyl)methyl | 0.63[a] | HCl |
| 19-15 | 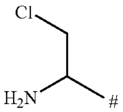 | (4-methylsulfanylphenyl)methyl | 1.14[a] | HCl |

TABLE 31-continued

Compounds according to formula (19)

(19)

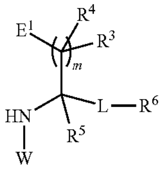

In table 31, "#" denotes the point of attachment to the L—$R^6$ group.

| Ex No | 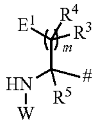 | L—$R^6$ | Log P | Salt |
|---|---|---|---|---|
| 19-16 | 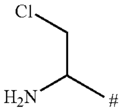 | (2-chloro-4-methoxyphenyl)methyl | 1.09[a] | HCl |
| 19-17 | 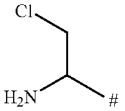 | [2-chloro-4-(difluoromethyl)phenyl]methyl | 1.18[a] | HCl |
| 19-18 | 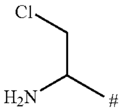 | [2-chloro-4-(difluoromethoxy)phenyl]methyl | 1.30[a] | HCl |
| 19-19 | 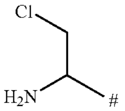 | [2-chloro-4-(trifluoromethoxy)phenyl]methyl | 1.55[a] | HCl |
| 19-20 | 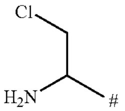 | (3-bromo-5-methylphenyl)methyl | 1.51[a] | HCl |
| 19-21 | 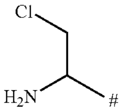 | (2-bromo-4-methylphenyl)methyl | 1.27[a] | HCl |
| 19-22 | 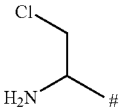 | (2-cyclopropyl-4-methylphenyl)methyl | 1.48[a] | HCl |

TABLE 32

19-01: $^1$H-NMR(300.2 MHz, CDCl3):
δ = 7.6438 (0.5); 7.3661 (0.6); 7.3167 (0.5); 7.2990 (107.3); 7.2639 (0.4); 7.2354 (0.5); 7.1375 (1.2); 7.1101 (1.9); 7.0359 (2.6); 7.0282 (2.3); 7.0171 (1.6); 6.9904 (1.0); 6.9484 (0.8); 4.5372 (0.5); 4.5099 (0.4); 4.2226 (0.4); 4.2061 (0.5); 4.0962 (0.4); 3.8770 (0.7); 3.8498 (0.8); 3.8306 (0.6); 3.8113 (0.5); 3.7436 (16.0); 3.7105 (1.5); 3.6820 (1.5); 3.2699 (0.5); 3.2302 (0.7); 3.1379 (0.5); 3.1032 (0.6); 3.0910 (0.7); 3.0610 (0.4); 2.9134 (0.4); 2.8926 (0.7); 2.8630 (0.4); 2.3783 (9.4); 2.3379 (3.1); 2.3211 (13.5); 2.0640 (0.3); 1.7885 (0.7); 1.7676 (0.8); 1.7013 (2.1); 1.6039 (3.8); 1.3928 (1.2); 1.3716 (2.1); 1.3493 (1.3); 1.3233 (0.6); 1.2923 (1.1); 1.2598 (2.2); 1.2395 (1.4); 0.2335 (0.6); 0.1071 (9.8); 0.0771 (0.4); 0.0551 (0.5); 0.0487 (3.2); 0.0380 (131.2); 0.0275 (5.8); −0.0108 (0.4); −0.0221 (0.5); −0.0306 (0.5); −0.1608 (0.5)

TABLE 32-continued 19-02: $^1$H-NMR(300.2 MHz, $d_6$-DMSO):
δ = 8.3651 (10.2); 7.7615 (11.8); 7.7346 (15.2); 7.6880 (0.5); 7.6309 (0.3); 7.5701 (14.4); 7.5433 (11.2); 7.4918 (0.4); 3.9314 (3.6); 3.9201 (4.8); 3.8822 (7.9); 3.8626 (3.6); 3.8481 (3.5); 3.8425 (3.2); 3.8288 (2.2); 3.8158 (1.3); 3.7302 (0.5); 3.7034 (4.7); 3.6892 (5.3); 3.6641 (4.6); 3.6508 (3.1); 3.5861 (1.0); 3.3564 (16.0); 3.1792 (2.1); 3.1588 (2.2); 3.1330 (4.3); 3.1133 (4.1); 3.0771 (5.0); 3.0508 (4.8); 3.0312 (2.1); 3.0052 (1.9); 2.5337 (7.6); 2.5279 (14.8); 2.5219 (19.4); 2.5160 (14.2); 2.5102 (7.0); 1.2534 (0.4); 0.0278 (0.8); 0.0173 (15.6); 0.0063 (0.8)
19-03: $^1$H-NMR(300.2 MHz, $d_6$-DMSO):
δ = 8.3448 (1.4); 7.5005 (1.1); 7.3804 (2.3); 7.3521 (3.0); 7.2536 (2.4); 7.2001 (3.1); 7.1720 (2.3); 7.1498 (0.3); 7.0067 (1.2); 3.9042 (0.6); 3.8943 (0.8); 3.8644 (0.8); 3.8543 (0.9); 3.7826 (0.6); 3.7708 (0.6); 3.6638 (0.9); 3.6490 (0.8); 3.6240 (0.8); 3.6093 (0.8); 3.5861 (16.0); 3.3614 (2.8); 3.0797 (0.5); 3.0610 (0.4); 3.0340 (0.8); 3.0149 (0.8); 2.9573 (0.8); 2.9295 (0.8); 2.9114 (0.5); 2.8834 (0.4); 2.5279 (2.7); 2.5221 (3.4); 2.5163 (2.6); 0.0177 (1.7)
19-04: $^1$H-NMR(300.2 MHz, $d_6$-DMSO):
δ = 8.1127 (3.4); 7.4631 (7.7); 7.4341 (16.0); 7.3819 (11.7); 7.3550 (6.2); 3.9068 (2.5); 3.8956 (3.1); 3.8675 (3.4); 3.8564 (4.2); 3.8119 (0.8); 3.7869 (2.2); 3.7746 (2.4); 3.7522 (1.7); 3.7406 (1.0); 3.7270 (0.4); 3.7142 (0.3); 3.6848 (4.2); 3.6698 (3.4); 3.6453 (3.2); 3.6305 (2.6); 3.5861 (0.6); 3.3562 (3.6); 3.0893 (1.4); 3.0686 (1.5); 3.0431 (3.8); 3.0225 (3.6); 2.9992 (4.1); 2.9730 (3.8); 2.9532 (1.7); 2.9268 (1.5); 2.5338 (5.0); 2.5278 (10.6); 2.5218 (14.5); 2.5157 (10.6); 2.5099 (5.0); 0.0280 (0.4); 0.0172 (11.6); 0.0062 (0.5)
19-05: $^1$H-NMR(300.2 MHz, CDCl3):
δ = 8.9346 (1.8); 7.2989 (17.2); 7.1470 (2.1); 7.1216 (3.0); 7.0363 (3.7); 7.0169 (2.2); 6.9911 (1.5); 3.9223 (0.9); 3.8910 (1.2); 3.8479 (0.4); 3.8296 (0.8); 3.8103 (1.0); 3.7631 (1.9); 3.7436 (7.7); 3.7263 (1.1); 3.7103 (0.7); 3.7050 (0.7); 3.6845 (0.5); 3.4173 (0.7); 3.3824 (0.9); 3.3726 (0.9); 3.1976 (0.7); 3.1618 (0.8); 3.1544 (0.8); 3.1198 (0.5); 2.3904 (14.8); 2.3184 (16.0); 1.7116 (3.4); 1.4012 (0.4); 1.3776 (0.7); 1.3539 (0.4); 0.0489 (0.8); 0.0380 (21.8); 0.0270 (0.8)
19-06: $^1$H-NMR(300.2 MHz, CDCl3):
δ = 8.9132 (1.8); 7.2991 (19.2); 7.1628 (0.4); 7.1461 (2.2); 7.1206 (3.1); 7.0718 (1.1); 7.0458 (2.9); 7.0329 (5.5); 7.0083 (2.9); 6.9838 (1.8); 5.2500 (0.5); 5.2354 (0.5); 5.2238 (0.5); 5.2099 (0.5); 3.9307 (1.2); 3.8997 (1.4); 3.8285 (0.6); 3.8111 (1.0); 3.7951 (1.1); 3.7645 (2.4); 3.7470 (1.6); 3.7325 (1.5); 3.7280 (1.4); 3.7099 (2.4); 3.6956 (1.9); 3.6757 (0.4); 3.6486 (1.7); 3.6250 (1.6); 3.6115 (0.9); 3.5881 (0.8); 3.4217 (0.8); 3.3895 (1.1); 3.3756 (1.0); 3.1983 (0.9); 3.1620 (0.9); 3.1508 (1.6); 3.1290 (0.9); 3.1187 (0.7); 3.1045 (1.1); 3.0833 (1.0); 2.9046 (1.1); 2.8779 (1.0); 2.8587 (0.7); 2.8322 (0.7); 2.3885 (15.7); 2.3747 (10.8); 2.3277 (12.3); 2.3178 (16.0); 1.6923 (3.7); 1.6375 (0.4); 1.6139 (0.6); 1.4807 (0.4); 1.4709 (0.4); 1.4213 (0.4); 1.4130 (0.4); 1.2944 (1.2); 0.9418 (0.4); 0.9205 (1.0); 0.8965 (0.4); 0.0488 (0.9); 0.0385 (23.9); 0.0277 (1.0)
19-07: $^1$H-NMR(300.2 MHz, $d_6$-DMSO):
δ = 8.6579 (0.8); 7.4235 (0.6); 7.3971 (0.7); 7.1170 (0.7); 7.0699 (0.4); 7.0435 (0.3); 4.0532 (1.1); 4.0402 (1.1); 3.5863 (16.0); 3.3664 (2.3); 3.2852 (0.4); 3.2666 (0.3); 3.1844 (0.4); 3.1563 (0.3); 2.5335 (0.4); 2.5279 (0.7); 2.5219 (0.9); 2.5159 (0.7); 2.3484 (3.4); 2.2743 (3.3); 0.0182 (0.5)
19-08: $^1$H-NMR(300.2 MHz, CDCl3):
δ = 8.8682 (0.5); 7.5387 (0.6); 7.5121 (1.0); 7.4409 (1.1); 7.4143 (0.7); 7.2988 (1.6); 6.6564 (0.7); 6.4687 (0.3); 3.9633 (0.3); 3.9282 (0.5); 3.7411 (16.0); 0.1055 (0.4); 0.0356 (2.3)
19-09: $^1$H-NMR(300.2 MHz, CDCl3):
δ = 8.9628 (1.0); 7.4374 (1.8); 7.3198 (1.3); 7.2993 (6.0); 7.2946 (2.1); 7.1333 (1.0); 7.1104 (0.8); 4.0085 (0.4); 3.9705 (0.7); 3.9301 (0.8); 3.9194 (0.6); 3.7796 (0.7); 3.7622 (0.8); 3.7563 (0.5); 3.7548 (0.5); 3.7534 (0.5); 3.7518 (0.5); 3.7427 (16.0); 3.7307 (0.3); 3.7219 (0.5); 3.5169 (0.4); 3.4989 (0.4); 3.4709 (0.6); 3.4532 (0.5); 3.3356 (0.6); 3.3039 (0.6); 3.2899 (0.4); 3.2582 (0.4); 2.3388 (7.4); 1.7299 (1.1); 0.1070 (2.0); 0.0483 (0.3); 0.0375 (8.3)
19-10: $^1$H-NMR(300.2 MHz, CDCl3):
δ = 9.0001 (0.7); 7.7214 (1.0); 7.6215 (0.3); 7.5948 (1.0); 7.5742 (0.8); 7.2987 (3.6); 4.0018 (0.4); 3.9605 (0.5); 3.9499 (0.4); 3.7420 (16.0); 3.7314 (0.5); 3.7298 (0.5); 3.7285 (0.5); 3.7032 (0.3); 3.5700 (0.4); 3.4327 (0.4); 3.4011 (0.4); 1.7790 (0.4); 0.1060 (0.5); 0.0363 (5.2)
19-11: $^1$H-NMR(300.2 MHz, CDCl3):
δ = 7.3110 (3.0); 7.2987 (10.0); 7.2853 (3.6); 7.2445 (3.7); 7.0862 (2.0); 7.0833 (2.0); 7.0605 (1.7); 3.9922 (0.7); 3.9792 (1.0); 3.9628 (1.0); 3.9489 (2.1); 3.9398 (1.6); 3.9083 (1.9); 3.8973 (1.3); 3.7592 (1.4); 3.7416 (11.2); 3.7191 (1.2); 3.7016 (0.9); 3.4903 (0.7); 3.4720 (0.8); 3.4444 (1.4); 3.4266 (1.2); 3.3066 (1.2); 3.2747 (1.2); 3.2603 (1.0); 3.2297 (0.8); 2.3404 (16.0); 0.1069 (3.3); 0.0479 (0.6); 0.0372 (13.0); 0.0262 (0.4)
19-12: $^1$H-NMR(300.2 MHz, $d_6$-DMSO):
δ = 8.5130 (0.6); 7.6534 (0.8); 7.6379 (0.9); 7.6311 (1.1); 7.6263 (1.1); 7.3496 (0.5); 7.3431 (0.4); 7.3221 (0.4); 7.3155 (0.4); 3.9050 (0.4); 3.7472 (0.4); 3.7322 (0.3); 3.5870 (16.0); 3.3605 (5.8); 3.0564 (0.4); 3.0350 (0.3); 3.0075 (0.4); 2.9826 (0.4); 2.5287 (1.0); 2.5228 (1.4); 2.5169 (1.0); 0.0181 (0.4)
19-14: $^1$H-NMR(400.1 MHz, $d_6$-DMSO):
δ = 8.4809 (9.4); 8.2759 (0.4); 8.2398 (14.0); 8.2189 (16.0); 8.1999 (2.1); 8.1799 (0.4); 8.1574 (0.4); 8.0897 (0.9); 7.6671 (0.4); 7.6147 (14.1); 7.5938 (14.2); 7.5753 (1.9); 3.9090 (7.4); 3.8842 (8.2); 3.7360 (0.4); 3.6985 (3.5); 3.6855 (4.6); 3.6661 (4.0); 3.6537 (2.5); 3.6069 (0.5); 3.5675 (2.6); 3.5449 (1.8); 3.4262 (1587.9); 3.2834 (0.9); 3.2378 (0.6); 3.1997 (2.4); 3.1844 (2.5); 3.1651 (4.6); 3.1501 (4.4); 3.1134 (4.6); 3.0943 (4.5); 3.0793 (2.5); 3.0597 (2.2); 3.0314 (1.1); 3.0196 (1.3); 3.0028 (0.8); 2.5083 (24.0)
19-15: $^1$H-NMR(400.1 MHz, $d_6$-DMSO):
δ = 8.3662 (3.7); 7.9724 (1.6); 7.2680 (2.1); 7.2613 (1.7); 7.2463 (16.0); 7.2415 (14.2); 7.2250 (10.7); 7.2009 (0.6); 5.3558 (0.3); 3.8614 (1.5); 3.8536 (1.8); 3.8311 (1.9); 3.8235 (2.2); 3.7599 (1.2); 3.7139 (0.5); 3.7010 (0.7); 3.6805 (0.7); 3.6669 (0.6); 3.6512 (0.4); 3.6343 (2.3); 3.6231 (2.1); 3.6040 (2.1); 3.5929 (1.9); 3.5686 (3.9); 3.4925 (6.0); 3.4244 (1340.4); 3.3430 (1.6); 3.3241 (0.8); 3.3053 (0.9); 3.2854 (0.9); 3.0030 (1.2); 2.9884 (1.2); 2.9685 (2.0); 2.9538 (1.9); 2.8951 (2.0); 2.8732 (2.3); 2.8601 (1.6); 2.8385 (2.1); 2.8240 (1.1); 2.7994 (1.2); 2.7776 (1.1); 2.7661 (0.6); 2.7437 (0.5); 2.5084 (16.9); 2.4640 (29.0); 2.4587 (17.0); 2.4306 (0.5); 2.4211 (0.4); 1.3543 (0.5)
19-16: $^1$H-NMR(400.1 MHz, $d_6$-DMSO):
δ = 8.4813 (2.3); 7.3558 (2.2); 7.3344 (2.4); 7.0779 (2.6); 7.0715 (2.8); 7.0486 (0.3); 6.9553 (1.6); 6.9489 (1.4); 6.9339 (1.5); 6.9276 (1.3); 3.8732 (0.9); 3.8650 (1.0); 3.8430 (1.2); 3.8349 (1.3); 3.8198 (0.6); 3.8103 (0.3); 3.7882 (1.4); 3.7705 (16.0); 3.7404 (0.8); 3.6795 (1.3); 3.6686 (1.1); 3.6494 (1.0); 3.6384 (0.8); 3.5679 (10.9); 3.5503 (0.4); 3.4269 (400.8); 3.3447 (0.4); 3.0942 (0.4); 3.0790 (0.5); 3.0594 (1.5); 3.0444 (2.7); 3.0234 (1.4); 3.0097 (0.4); 2.9882 (0.4); 2.5123 (3.8); 2.5085 (4.8)

TABLE 32-continued

| |
|---|
| 19-17: $^1$H-NMR(300.2 MHz, $d_6$-DMSO):<br>δ = 8.5982 (2.8); 8.1942 (0.8); 7.7276 (4.0); 7.7096 (1.9); 7.6521 (1.7); 7.6256 (4.4); 7.6125 (2.5); 7.5992 (3.4); 7.5748 (2.3); 7.5531 (0.7); 7.2650 (1.6); 7.2572 (0.9); 7.0800 (3.6); 7.0716 (1.8); 6.8952 (1.8); 6.8868 (0.9); 5.4431 (0.7); 3.9516 (1.1); 3.9400 (1.6); 3.9018 (2.8); 3.8796 (1.4); 3.7671 (1.6); 3.7540 (1.8); 3.7281 (1.5); 3.7159 (0.9); 3.5866 (1.1); 3.5320 (0.6); 3.4608 (0.8); 3.4468 (0.9); 3.4238 (1.0); 3.3584 (16.0); 3.2148 (3.5); 3.1905 (2.7); 3.1428 (0.3); 3.0988 (1.6); 3.0763 (1.3); 2.5279 (9.2); 2.5222 (11.5); 2.5166 (8.7); 2.3155 (0.3); 0.0183 (5.6) |
| 19-18: $^1$H-NMR(300.2 MHz, CDCl3):<br>δ = 8.9078 (1.1); 7.4704 (1.9); 7.4422 (2.2); 7.2986 (5.6); 7.2480 (2.3); 7.2401 (2.4); 7.0924 (1.2); 7.0846 (1.1); 7.0645 (1.1); 7.0568 (1.0); 6.7833 (1.4); 6.5401 (3.0); 6.2969 (1.5); 4.0135 (0.6); 3.9952 (1.5); 3.9581 (1.1); 3.9480 (0.8); 3.7594 (0.8); 3.7550 (0.7); 3.7534 (0.7); 3.7414 (16.0); 3.7308 (0.4); 3.7293 (0.4); 3.7278 (0.4); 3.7191 (0.8); 3.7028 (0.5); 3.5210 (0.5); 3.5032 (0.5); 3.4748 (0.8); 3.4570 (0.7); 3.3437 (0.7); 3.3123 (0.7); 3.2977 (0.6); 3.2661 (0.4); 1.8785 (0.7); 0.1055 (0.8); 0.0356 (7.0) |
| 19-19: $^1$H-NMR(300.2 MHz, CDCl3):<br>δ = 7.5131 (0.5); 7.4848 (0.6); 7.3376 (0.6); 7.3329 (0.6); 7.2989 (2.1); 4.0040 (0.4); 3.7415 (16.0); 1.8525 (0.3); 0.0355 (2.6) |
| 19-20: $^1$H-NMR(300.2 MHz, $d_6$-DMSO):<br>δ = 8.5216 (6.7); 7.3467 (11.2); 7.3411 (9.7); 7.1413 (8.8); 3.9265 (2.8); 3.9155 (3.6); 3.8868 (3.4); 3.8762 (5.2); 3.8237 (2.1); 3.7030 (4.5); 3.6880 (4.0); 3.6634 (3.6); 3.6487 (2.8); 3.5874 (0.6); 3.4075 (16.0); 3.0693 (2.0); 3.0494 (2.0); 3.0233 (3.6); 3.0036 (3.4); 2.9316 (3.9); 2.9044 (3.8); 2.8854 (2.3); 2.8585 (2.0); 2.5349 (4.7); 2.5290 (9.6); 2.5230 (12.9); 2.5169 (9.3); 2.5110 (4.4); 2.3826 (0.3); 2.3165 (40.5); 0.0298 (0.4); 0.0190 (8.5); 0.0080 (0.3) |
| 19-21: $^1$H-NMR(300.2 MHz, $d_6$-DMSO):<br>δ = 8.6186 (1.2); 7.5130 (1.6); 7.5105 (1.6); 7.3597 (1.2); 7.3338 (1.7); 7.2347 (1.0); 7.2315 (0.9); 7.2088 (0.7); 7.2057 (0.6); 3.9187 (0.5); 3.9074 (0.6); 3.8792 (0.6); 3.8681 (0.9); 3.8089 (0.4); 3.7192 (0.8); 3.7047 (0.7); 3.6797 (0.6); 3.6655 (0.5); 3.5866 (2.4); 3.3809 (16.0); 3.1318 (0.9); 3.1154 (1.3); 3.0882 (0.8); 2.5350 (0.8); 2.5290 (1.6); 2.5230 (2.1); 2.5169 (1.5); 2.5110 (0.7); 2.3116 (6.9); 0.0179 (1.5) |
| 19-22: $^1$H-NMR(300.2 MHz, $d_6$-DMSO):<br>δ = 8.5284 (3.2); 7.1867 (2.2); 7.1255 (2.7); 7.1000 (3.9); 6.9895 (2.2); 6.9639 (1.6); 6.8054 (3.6); 3.8936 (1.1); 3.8837 (1.4); 3.8539 (1.4); 3.8442 (1.9); 3.8256 (0.5); 3.8117 (0.8); 3.7951 (1.1); 3.7813 (1.0); 3.7683 (0.8); 3.6825 (1.8); 3.6685 (1.5); 3.6427 (1.4); 3.6291 (1.1); 3.3544 (8.5); 3.2607 (0.8); 3.2444 (0.8); 3.2148 (1.4); 3.1981 (1.2); 3.0841 (1.4); 3.0522 (1.4); 3.0382 (1.0); 3.0063 (1.0); 2.5340 (3.1); 2.5281 (6.2); 2.5221 (8.2); 2.5161 (6.0); 2.5103 (2.8); 2.3061 (1.4); 2.2555 (16.0); 2.0957 (0.3); 2.0784 (0.8); 2.0685 (0.9); 2.0611 (0.7); 2.0506 (1.5); 2.0412 (0.8); 2.0329 (0.9); 2.0230 (0.8); 2.0051 (0.4); 0.9907 (0.7); 0.9754 (2.8); 0.9690 (3.2); 0.9591 (1.6); 0.9550 (1.5); 0.9475 (2.8); 0.9412 (3.1); 0.9276 (0.9); 0.6964 (1.0); 0.6829 (3.0); 0.6768 (3.4); 0.6655 (3.4); 0.6600 (2.8); 0.6463 (0.9); 0.0188 (6.3) |

TABLE 29

Compounds according to formula (20)

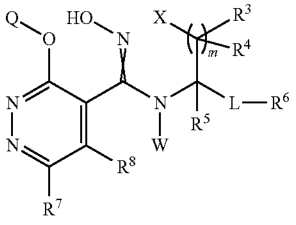

(20)

In table 29, "#" denotes the point of attachment to the L—$R^6$ group and "*" denotes the point of attachment to the pyridazin-4-yl group.

| Ex No | $R^7$ | $R^8$ | Q | 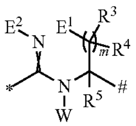 | L—$R^6$ | Log P |
|---|---|---|---|---|---|---|
| 20-01 | Cl | H | 3-(trifluoro-methyl)phenyl | 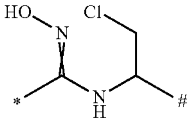 | (2,4-dimethyl-phenyl)methyl | 4.34[a] |
| 20-02 | Cl | H | 3-(trifluoro-methyl)phenyl | 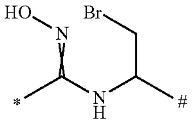 | (2,4-dimethyl-phenyl)methyl | 4.49[a] |

TABLE 29-continued

Compounds according to formula (20)

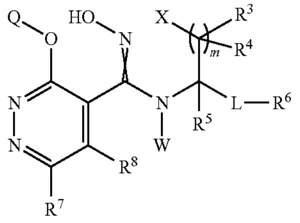

(20)

In table 29, "#" denotes the point of attachment to the L—$R^6$ group and "*" denotes the point of attachment to the pyridazin-4-yl group.

| Ex No | $R^7$ | $R^8$ | Q | 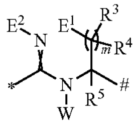 | L—$R^6$ | Log P |
|---|---|---|---|---|---|---|
| 20-03 | Cl | H | 3-(trifluoro-methyl)phenyl | 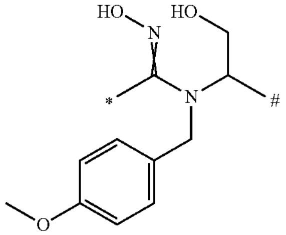 | (4-chlorophenyl)methyl | 4.15[a] |
| 20-04 | $CH_3$ | H | 3-cyclopropyl-2-fluorophenyl | 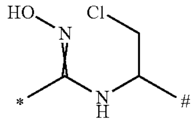 | (2,4-dimethyl-phenyl)methyl | 3.94[a] |
| 20-05 | Cl | H | 3-(trifluoro-methyl)phenyl | 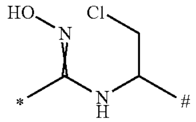 | [4-(trifluoro-methyl)phenyl]methyl | 4.32[a] |
| 20-06 | Cl | H | 3-(trifluoro-methyl)phenyl | 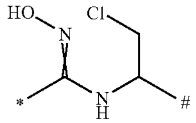 | [4-(difluoro-methoxy)phenyl]methyl | 3.91[a] |
| 20-07 | Cl | H | 3-(trifluoro-methyl)phenyl | 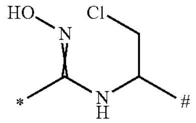 | [4-(trifluoro-methoxy)phenyl]methyl | 4.37[a] |
| 20-08 | Cl | H | 3-(trifluoro-methyl)phenyl | 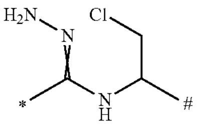 | (2,4-dimethylphenyl)methyl | 2.77[a] |
| 20-09 | $CH_3$ | H | 3-cyclopropyl-2-fluorophenyl | 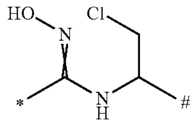 | (2,4-dimethylphenyl)methyl | 3.98[a] |

TABLE 29-continued

Compounds according to formula (20)

(20)

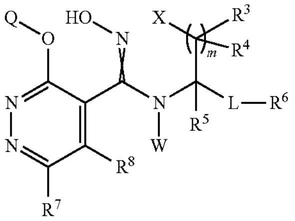

In table 29, "#" denotes the point of attachment to the L—$R^6$ group and "*" denotes the point of attachment to the pyridazin-4-yl group.

| Ex No | $R^7$ | $R^8$ | Q | 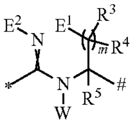 | L—$R^6$ | Log P |
|---|---|---|---|---|---|---|
| 20-10 | $CH_3$ | H | 3-cyclopropyl-2-fluorophenyl | 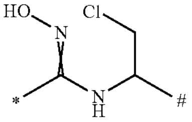 | (2-bromo-4-methyl-phenyl)methyl | 4.12[a] |
| 20-11 | $CH_3$ | H | 3-cyclopropyl-2-fluorophenyl | 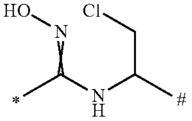 | (3,4-dichloro-phenyl)methyl | 4.15[a] |
| 20-12 | Cl | H | 3-(trifluoro-methyl)phenyl | 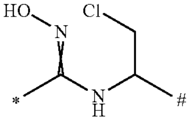 | [4-(difluoro-methyl)phenyl]methyl | 3.87[a] |
| 20-13 | $CH_3$ | H | 3-cyclopropyl-2-fluorophenyl | 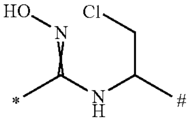 | [2-chloro-4-(trifluoro-methyl)phenyl]methyl | 4.30[a] |
| 20-14 | $CH_3$ | H | 3-cyclopropyl-2-fluorophenyl | 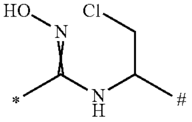 | (2-chloro-4-methyl-phenyl)methyl | 4.05[a] |
| 20-15 | Cl | H | 3-(trifluoro-methyl)phenyl | 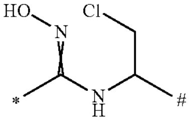 | (4-nitrophenyl)methyl | 3.71[a] |
| 20-16 | Cl | H | 3-(trifluoro-methyl)phenyl | 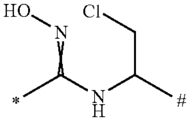 | [4-(trifluoromethyl-thio)phenyl]methyl | 4.67[a] |
| 20-17 | $CH_3$ | H | 3-chloro-2-fluorophenyl | 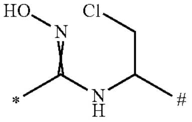 | (2-chloro-4-methyl-phenyl)methyl | 3.88[a] |

TABLE 29-continued

Compounds according to formula (20)

(20)

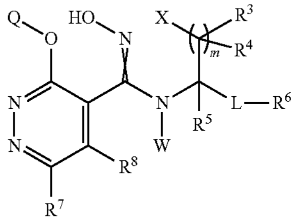

In table 29, "#" denotes the point of attachment to the L—$R^6$ group and "*" denotes the point of attachment to the pyridazin-4-yl group.

| Ex No | $R^7$ | $R^8$ | Q | 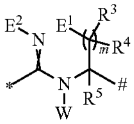 | L—$R^6$ | Log P |
|---|---|---|---|---|---|---|
| 20-18 | $CH_3$ | H | 3-cyclopropyl-2-fluorophenyl | 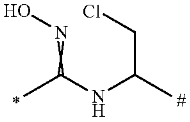 | (2-chloro-4-methoxy-phenyl)methyl | 3.81[a] |
| 20-19 | $CH_3$ | H | 3-(difluoro-methyl)phenyl | 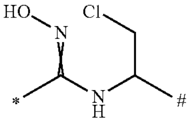 | (2-chloro-4-methyl-phenyl)methyl | 3.49[a] |
| 20-20 | $CH_3$ | H | 3-cyclopropyl-2-fluorophenyl | 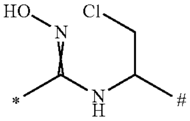 | [2-chloro-4-(difluoro-methyl)phenyl]methyl | 3.86[a] |
| 20-21 | $CH_3$ | H | 3-cyclopropyl-2-fluorophenyl | 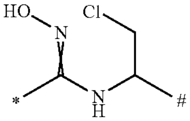 | [2-chloro-4-(difluoro-methoxy)phenyl]methyl | 4.02[a] |
| 20-22 | $CH_3$ | H | 3-cyclopropyl-2-fluorophenyl | 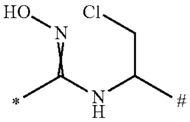 | [2-chloro-4-(trifluoro-methoxy)phenyl]methyl] | 4.51[a] |
| 20-23 | $CH_3$ | H | 3-cyclopropyl-2-fluorophenyl | 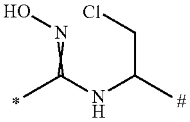 | (2-bromo-4-methyl-phenyl)methyl | 4.12[a] |
| 20-24 | $CH_3$ | H | 3-cyclopropyl-2-fluorophenyl | 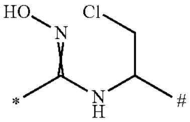 | (3-bromo-5-methyl-phenyl)methyl | 4.32[a] |
| 20-25 | Cl | H | 3-cyclopropyl-phenyl | 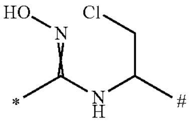 | (2,4-dimethylphenyl)methyl | 4.51[a] |

TABLE 29-continued

Compounds according to formula (20)

(20)

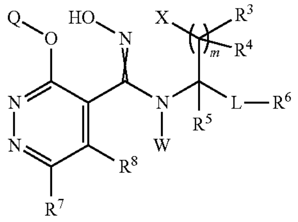

In table 29, "#" denotes the point of attachment to the L—$R^6$ group and "*" denotes the point of attachment to the pyridazin-4-yl group.

| Ex No | $R^7$ | $R^8$ | Q | 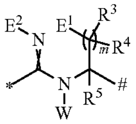 | L—$R^6$ | Log P |
|---|---|---|---|---|---|---|
| 20-26 | Cl | H | 3-cyclopropyl-2-fluorophenyl | 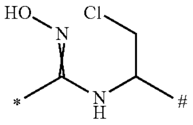 | (2,4-dimethylphenyl)methyl | 4.62[a] |
| 20-27 | Cl | H | 3-(difluoro-methyl)phenyl | 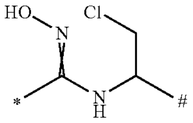 | (2,4-dimethylphenyl)methyl | 4.05[a] |
| 20-28 | Cl | H | 3-bromophenyl | 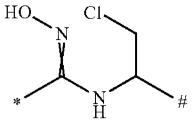 | (2,4-dimethylphenyl)methyl | 4.40[a] |
| 20-29 | Cl | H | 3-chlorophenyl | 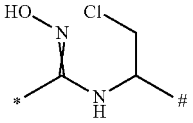 | (2,4-dimethylphenyl)methyl | 4.33[a] |
| 20-30 | $CH_3$ | H | 2-fluoro-3-(trifluoro-methyl)phenyl | 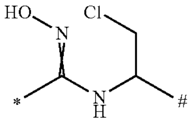 | (2,4-dimethylphenyl)methyl | 4.01[a] |
| 20-31 | Cl | H | 3-(difluoro-methyl)phenyl | 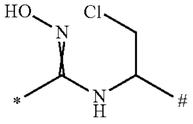 | (2-bromo-4-methyl-phenyl)methyl | 4.15[a] |
| 20-32 | Cl | H | 3-cyclopropyl-2-fluorophenyl | 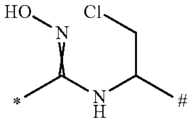 | (4-bromo-2-methyl-phenyl)methyl | 4.74[a] |
| 20-33 | $CH_3$ | H | 3-cyclopropyl-2-fluorophenyl | 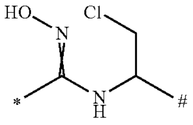 | (4-bromo-2-methyl-phenyl)methyl | 4.19[a] |

TABLE 29-continued

Compounds according to formula (20)

(20)

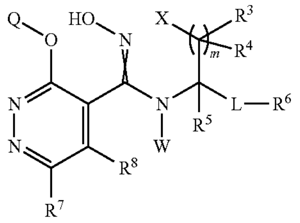

In table 29, "#" denotes the point of attachment to the L—$R^6$ group and "*" denotes the point of attachment to the pyridazin-4-yl group.

| Ex No | $R^7$ | $R^8$ | Q | 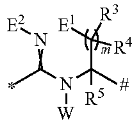 | L—$R^6$ | Log P |
|---|---|---|---|---|---|---|
| 20-34 | Cl | H | 3-cyclopropyl-phenyl | 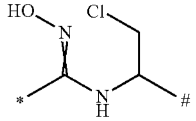 | (2-bromo-4-methyl-phenyl)methyl | 4.62[a] |
| 20-35 | Cl | H | 3-cyclopropyl-2-fluorophenyl | 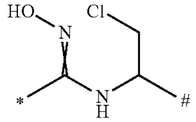 | (2-bromo-4-methyl-phenyl)methyl | 4.74[a] |
| 20-36 | $CH_3$ | H | 3-cyclopropyl-2-fluorophenyl | 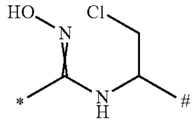 | (2-cyclopropyl-4-methylphenyl)methyl | 4.24[a] |

TABLE 30

20-01: $^1$H-NMR(300.2 MHz, CDCl3):
δ = 7.6137 (0.6); 7.5864 (2.6); 7.5738 (2.3); 7.5673 (5.6); 7.5651 (5.6); 7.5531 (0.7); 7.5184 (0.3); 7.4835 (0.5); 7.4473 (2.9); 7.4262 (0.4); 7.4022 (0.5); 7.3866 (1.1); 7.3761 (1.5); 7.3690 (1.4); 7.3563 (1.2); 7.3485 (0.8); 7.2992 (8.7); 7.0071 (1.7); 6.9893 (4.8); 6.9670 (0.5); 6.9438 (3.7); 6.9272 (0.6); 6.9165 (1.7); 6.2302 (3.6); 5.6560 (1.5); 5.6183 (1.5); 5.3382 (1.4); 3.8359 (0.5); 3.8223 (0.6); 3.7993 (2.5); 3.7851 (4.4); 3.7660 (2.5); 3.7479 (0.6); 3.7296 (0.7); 3.4491 (0.7); 3.4331 (0.7); 3.4164 (0.5); 3.3963 (0.3); 3.0941 (1.1); 3.0840 (1.1); 3.0481 (1.5); 3.0378 (1.4); 2.9975 (0.4); 2.9271 (0.4); 2.7997 (1.4); 2.7655 (1.3); 2.7537 (1.2); 2.7194 (1.0); 2.4069 (15.5); 2.3735 (0.4); 2.3469 (1.4); 2.3261 (0.4); 2.2946 (0.4); 2.1032 (1.2); 2.0749 (16.0); 1.6890 (0.4); 1.2937 (0.9); 0.1096 (0.7); 0.0393 (8.8); 0.0286 (0.4)
20-03: $^1$H-NMR(499.9 MHz, $d_6$-DMSO):
δ = 10.9854 (5.4); 9.5820 (0.5); 8.1369 (0.4); 7.7406 (0.4); 7.7193 (0.5); 7.7035 (0.5); 7.6942 (0.5); 7.6775 (0.4); 7.6611 (0.4); 7.6379 (0.8); 7.6224 (1.7); 7.6065 (3.2); 7.5932 (0.5); 7.5902 (0.6); 7.4155 (0.3); 7.3802 (3.2); 7.3765 (1.6); 7.3633 (5.8); 7.3424 (0.6); 7.3169 (4.3); 7.3000 (2.6); 7.2776 (0.3); 7.2687 (0.4); 7.2648 (0.4); 7.2518 (0.4); 7.2475 (0.4); 7.2395 (0.6); 7.2305 (0.4); 7.2227 (0.6); 7.2175 (0.5); 7.2051 (0.6); 7.1891 (0.5); 7.1743 (1.0); 7.1707 (1.5); 7.1668 (1.1); 7.1560 (1.3); 7.1521 (1.2); 7.1350 (0.5); 7.1024 (2.0); 7.0643 (0.5); 7.0592 (0.4); 7.0444 (2.9); 7.0271 (3.1); 6.9195 (0.3); 6.9021 (0.4); 6.7815 (3.9); 6.7641 (3.5); 6.7542 (0.5); 5.7593 (0.9); 4.9835 (1.0); 4.9737 (1.9); 4.9637 (0.9); 4.4109 (1.0); 4.3790 (1.2); 4.2791 (0.4); 4.2650 (0.7); 4.2509 (0.4); 4.1803 (1.4); 4.1484 (1.1); 4.1040 (0.5); 4.0926 (0.7); 4.0802 (0.5); 3.7895 (0.4); 3.7594 (0.5); 3.7493 (1.0); 3.7413 (0.8); 3.7301 (1.4); 3.7191 (1.9); 3.7147 (1.0); 3.7071 (1.0); 3.7040 (0.9); 3.7009 (0.9); 3.6946 (1.3); 3.6777 (0.8); 3.6691 (0.9); 3.6588 (16.0); 3.6286 (1.0); 3.5016 (0.6); 3.4918 (1.0); 3.4815 (0.8); 3.4696 (0.8); 3.4599 (0.5); 3.3220 (43.6); 3.1838 (0.6); 3.1709 (0.7); 3.1569 (0.8); 3.1441 (0.7); 2.9661 (0.8); 2.9497 (0.9); 2.9392 (0.7); 2.9229 (0.6); 2.5141 (3.2); 2.5105 (6.2); 2.5069 (8.2); 2.5033 (5.8); 2.4997 (2.7); 2.4288 (0.6); 2.4122 (0.4); 1.2961 (0.5); 1.2826 (1.0); 1.2710 (1.1); 1.2676 (1.2); 1.2502 (2.9); 0.8769 (1.9); 0.8633 (5.2); 0.8490 (2.2)
20-04: $^1$H-NMR(300.2 MHz, CDCl3):
δ = 7.2990 (28.0); 7.0996 (0.5); 7.0732 (1.3); 7.0455 (1.3); 7.0293 (1.0); 7.0225 (1.1); 7.0000 (1.2); 6.9804 (5.0); 6.9776 (5.5); 6.9156 (1.9); 6.8123 (0.6); 6.8062 (0.6); 6.7886 (1.0); 6.7646 (0.5); 6.7586 (0.4); 6.1773 (1.4); 5.8058 (0.8); 5.7684 (0.8); 4.6349 (0.4); 4.5797 (0.5); 4.1723 (0.4); 4.1484 (0.4); 3.9148 (0.3); 3.8991 (0.4); 3.8775 (1.0); 3.8625 (1.2); 3.8413 (1.1); 3.8314 (1.3); 3.8048 (0.4); 3.7956 (0.4); 3.6822 (0.5); 3.6709 (0.4); 3.6615 (0.4); 2.9929 (0.4); 2.9805 (0.5); 2.9467 (1.0); 2.9342 (0.9); 2.8823 (1.0); 2.8491 (0.9); 2.8360 (0.5); 2.8028 (0.4); 2.5246 (0.7); 2.4914 (11.8); 2.3842 (9.2); 2.3623 (0.7); 2.3501 (0.4); 2.1329 (0.5); 2.1218 (0.6); 2.1055 (0.9); 2.0847 (2.2); 2.0468 (3.1); 2.0279 (5.3); 2.0149 (9.4); 1.8953 (16.0); 1.3213 (0.4); 1.2975

TABLE 30-continued (0.9); 1.2736 (0.4); 1.0638 (0.6); 1.0484 (1.5); 1.0416 (1.6); 1.0270 (1.0); 1.0197 (1.6); 1.0132 (1.6); 0.9988 (0.8); 0.8072 (0.7); 0.7921 (1.8); 0.7864 (1.8); 0.7755 (1.6); 0.7695 (1.9); 0.7536 (0.6); 0.0482 (0.7); 0.0372 (35.8); 0.0263 (1.8)
20-06: $^1$H-NMR(300.2 MHz, CDCl3):
δ = 7.5997 (1.6); 7.5885 (1.6); 7.5809 (3.7); 7.5659 (0.7); 7.5125 (0.4); 7.4571 (1.8); 7.4101 (0.4); 7.3961 (0.8); 7.3848 (1.1); 7.3775 (1.0); 7.3655 (1.0); 7.3574 (0.6); 7.2984 (16.1); 7.1490 (0.8); 7.1183 (9.4); 7.0957 (0.5); 7.0846 (0.6); 7.0679 (0.6); 6.9863 (0.4); 6.9476 (0.3); 6.8246 (1.2); 6.7247 (1.8); 6.5794 (2.4); 6.3344 (1.2); 5.6259 (1.0); 5.5886 (1.1); 5.3379 (0.6); 4.1953 (1.2); 4.1715 (3.5); 4.1477 (3.6); 4.1240 (1.3); 3.7442 (0.8); 3.7368 (0.4); 3.7140 (1.8); 3.7071 (2.0); 3.6998 (2.0); 3.6899 (1.9); 3.4969 (0.3); 3.4814 (0.4); 3.4660 (0.5); 3.4438 (0.5); 3.4295 (0.4); 3.4130 (0.3); 3.0725 (0.7); 3.0579 (0.7); 3.0268 (1.2); 3.0124 (1.1); 2.8982 (1.1); 2.8687 (1.0); 2.8525 (0.7); 2.8229 (0.6); 2.0845 (16.0); 1.6278 (0.8); 1.3208 (4.3); 1.2970 (8.5); 1.2732 (4.0); 0.1062 (4.5); 0.0472 (0.6); 0.0363 (17.7); 0.0256 (0.7)
20-07: $^1$H-NMR(300.2 MHz, CDCl3):
δ = 7.6445 (0.5); 7.6275 (1.0); 7.6012 (7.0); 7.5960 (6.2); 7.5911 (6.1); 7.5834 (15.9); 7.5802 (16.0); 7.5657 (1.7); 7.5159 (0.8); 7.4607 (7.4); 7.4305 (0.4); 7.4137 (1.2); 7.3989 (3.2); 7.3869 (4.6); 7.3801 (4.2); 7.3690 (3.4); 7.3608 (2.3); 7.3210 (0.8); 7.2984 (52.3); 7.2151 (7.2); 7.1918 (17.9); 7.1763 (25.5); 7.1550 (3.0); 7.1466 (5.3); 6.9474 (0.3); 6.7551 (8.7); 5.6253 (4.5); 5.5877 (4.8); 4.1967 (0.8); 4.1729 (2.4); 4.1491 (2.5); 4.1253 (0.9); 3.7456 (0.9); 3.7311 (1.4); 3.7085 (7.9); 3.7012 (8.9); 3.6941 (8.9); 3.6841 (8.8); 3.6643 (1.1); 3.6471 (1.5); 3.6277 (0.4); 3.6172 (0.3); 3.5319 (0.6); 3.5165 (1.3); 3.5014 (1.8); 3.4862 (2.1); 3.4794 (1.8); 3.4709 (2.0); 3.4654 (1.9); 3.4494 (1.8); 3.4338 (1.3); 3.4194 (0.5); 3.0973 (3.1); 3.0821 (3.1); 3.0515 (5.0); 3.0364 (4.6); 2.9236 (4.7); 2.8944 (4.3); 2.8777 (3.1); 2.8487 (2.7); 2.0852 (11.4); 1.6150 (4.0); 1.3218 (3.4); 1.2980 (6.7); 1.2741 (3.0); 0.9180 (0.4); 0.1196 (0.4); 0.1075 (12.3); 0.0954 (0.6); 0.0485 (2.4); 0.0377 (70.0); 0.0267 (2.7)
20-09: $^1$H-NMR(300.2 MHz, CDCl3):
δ = 7.2986 (10.3); 7.1030 (0.6); 7.0759 (1.7); 7.0486 (1.8); 7.0364 (1.2); 7.0295 (1.4); 7.0127 (1.2); 7.0071 (1.4); 6.9858 (0.9); 6.9700 (6.6); 6.9464 (0.4); 6.9130 (2.5); 6.8158 (0.8); 6.8092 (0.8); 6.7922 (1.2); 6.7675 (0.7); 6.7621 (0.6); 6.1817 (2.0); 5.7998 (1.1); 5.7626 (1.2); 5.3377 (2.4); 3.9131 (0.5); 3.8984 (0.6); 3.8768 (1.4); 3.8620 (1.6); 3.8395 (1.4); 3.8298 (1.6); 3.8030 (0.6); 3.7933 (0.6); 3.7218 (0.3); 3.6876 (0.6); 3.6755 (0.6); 3.6659 (0.4); 3.6542 (0.4); 2.9858 (0.6); 2.9736 (0.6); 2.9399 (1.3); 2.9278 (1.2); 2.8756 (1.2); 2.8427 (1.1); 2.8298 (0.7); 2.7968 (0.6); 2.4971 (16.0); 2.3837 (11.9); 2.1362 (0.5); 2.1247 (0.6); 2.1079 (1.0); 2.0853 (1.4); 2.0801 (0.7); 2.0622 (0.4); 2.0083 (11.8); 1.3221 (0.5); 1.2983 (1.1); 1.2745 (0.4); 1.0656 (0.8); 1.0504 (1.9); 1.0436 (2.2); 1.0376 (1.2); 1.0290 (1.2); 1.0218 (2.1); 1.0151 (2.0); 1.0008 (1.0); 0.9204 (0.7); 0.8097 (1.0); 0.7949 (2.4); 0.7924 (2.2); 0.7887 (2.4); 0.7778 (2.2); 0.7722 (2.5); 0.7559 (0.8); 0.1081 (2.5); 0.0492 (0.6); 0.0384 (13.8); 0.0275 (0.6)
20-10: $^1$H-NMR(300.2 MHz, CDCl3):
δ = 7.2990 (19.4); 7.1801 (1.1); 7.1543 (3.8); 7.1373 (2.2); 7.1106 (0.7); 7.0974 (0.6); 7.0707 (1.7); 7.0437 (2.0); 7.0364 (1.3); 7.0290 (1.4); 7.0129 (1.2); 7.0074 (1.3); 6.9862 (0.6); 6.9804 (0.5); 6.8524 (0.4); 6.8092 (0.9); 6.8021 (0.9); 6.7860 (1.4); 6.7611 (0.7); 6.7552 (0.6); 6.3131 (2.6); 5.8564 (1.0); 5.8193 (1.0); 5.3386 (7.0); 3.9895 (0.3); 3.9667 (0.9); 3.9567 (1.6); 3.9401 (0.8); 3.9283 (1.8); 3.9166 (1.2); 3.8196 (1.4); 3.7922 (1.0); 3.1019 (0.6); 3.0886 (0.6); 3.0567 (1.3); 3.0435 (1.2); 2.9815 (1.0); 2.9497 (1.0); 2.9364 (0.6); 2.9042 (0.5); 2.5377 (16.0); 2.3979 (11.7); 2.1410 (0.5); 2.1298 (0.6); 2.1132 (1.0); 2.0959 (0.6); 2.0848 (0.6); 1.6159 (1.2); 1.2923 (0.4); 1.0623 (0.7); 1.0470 (2.0); 1.0403 (2.2); 1.0257 (1.2); 1.0185 (2.1); 1.0119 (2.0); 0.9975 (0.9); 0.8060 (1.0); 0.7912 (2.4); 0.7852 (2.3); 0.7742 (2.2); 0.7688 (2.4); 0.7524 (0.7); 0.1073 (6.5); 0.0487 (1.1); 0.0379 (24.0); 0.0271 (1.2)
20-11: $^1$H-NMR(300.2 MHz, CDCl3):
δ = 7.6035 (0.6); 7.4458 (0.7); 7.4278 (2.0); 7.4208 (3.0); 7.4034 (2.4); 7.3940 (1.0); 7.3789 (3.9); 7.3518 (3.7); 7.2985 (19.8); 7.2200 (2.9); 7.2134 (3.0); 7.1980 (0.5); 7.1689 (0.4); 7.1470 (0.6); 7.1223 (0.9); 7.1149 (1.0); 7.0872 (2.0); 7.0593 (1.7); 7.0348 (1.2); 7.0284 (1.5); 7.0053 (1.8); 6.9919 (1.8); 6.9850 (2.2); 6.9646 (1.5); 6.9578 (1.4); 6.9211 (1.2); 6.8482 (0.4); 6.8340 (0.9); 6.8277 (1.0); 6.8092 (1.4); 6.7858 (0.8); 6.7807 (0.7); 6.6546 (1.5); 5.7742 (0.7); 5.7382 (0.8); 4.6344 (6.3); 3.8233 (0.4); 3.8083 (0.6); 3.7869 (1.1); 3.7710 (1.4); 3.7459 (1.4); 3.7363 (1.9); 3.7073 (1.4); 3.6780 (1.0); 3.6679 (0.7); 3.6548 (0.6); 2.9519 (0.6); 2.9215 (3.6); 2.8996 (2.6); 2.7552 (0.6); 2.5983 (16.0); 2.3497 (0.4); 2.2796 (0.4); 2.1375 (0.7); 2.1268 (0.8); 2.1097 (1.2); 2.0919 (0.8); 2.0815 (0.8); 2.0644 (0.4); 1.7108 (0.8); 1.2937 (0.6); 1.0723 (1.1); 1.0568 (2.4); 1.0500 (2.6); 1.0356 (1.5); 1.0284 (2.4); 1.0219 (2.3); 1.0074 (1.0); 0.8293 (0.4); 0.8158 (1.5); 0.8006 (2.9); 0.7959 (3.0); 0.7842 (2.4); 0.7786 (2.9); 0.7619 (1.0); 0.1073 (2.7); 0.0484 (0.6); 0.0376 (21.7); 0.0268 (1.0)
20-12: $^1$H-NMR(300.2 MHz, CDCl3):
δ = 8.3093 (0.9); 7.6816 (0.5); 7.6643 (0.5); 7.5937 (0.8); 7.5847 (0.7); 7.5761 (1.6); 7.5734 (1.6); 7.5379 (0.4); 7.5109 (1.1); 7.4844 (1.4); 7.4514 (1.2); 7.4285 (1.0); 7.4012 (0.7); 7.3938 (0.9); 7.3856 (0.7); 7.3735 (0.9); 7.3669 (0.8); 7.3560 (0.5); 7.3474 (0.4); 7.2987 (4.0); 7.2418 (1.3); 7.2155 (1.0); 6.8947 (0.4); 6.7069 (0.9); 6.6275 (0.4); 6.5592 (0.7); 6.5192 (0.4); 5.6695 (0.4); 5.6321 (0.4); 4.6345 (1.1); 3.7463 (16.0); 3.7371 (0.6); 3.7326 (0.9); 3.7213 (1.1); 3.7045 (1.0); 3.6929 (0.3); 3.1207 (0.5); 3.0897 (0.5); 3.0759 (0.5); 2.9477 (0.4); 2.9172 (0.4); 2.0862 (0.6); 0.1077 (0.6); 0.0372 (5.6)
20-13: $^1$H-NMR(300.2 MHz, CDCl3):
δ = 7.5433 (2.7); 7.5349 (1.4); 7.5067 (1.7); 7.4396 (2.2); 7.4132 (1.3); 7.2988 (15.3); 7.1016 (0.7); 7.0780 (1.8); 7.0492 (1.6); 7.0211 (1.1); 7.0150 (1.3); 6.9971 (1.2); 6.9920 (1.4); 6.9706 (0.7); 6.9650 (0.6); 6.8218 (0.8); 6.8162 (0.8); 6.7956 (1.3); 6.7737 (0.7); 6.7685 (0.6); 6.4365 (2.0); 5.8781 (1.1); 5.8413 (1.1); 5.3378 (4.7); 4.0144 (0.3); 3.9961 (0.5); 3.9821 (0.6); 3.9505 (1.2); 3.9138 (1.5); 3.9005 (1.1); 3.8136 (1.2); 3.8050 (1.4); 3.7773 (0.9); 3.7682 (0.7); 3.2292 (0.6); 3.2147 (0.6); 3.1842 (1.2); 3.1698 (1.1); 3.0953 (1.1); 3.0642 (1.0); 3.0504 (0.7); 3.0194 (0.6); 2.5406 (16.0); 2.1338 (0.5); 2.1238 (0.6); 2.1058 (1.0); 2.0845 (0.8); 2.0775 (0.6); 1.6213 (1.5); 1.3047 (0.6); 1.2977 (0.7); 1.0686 (0.7); 1.0534 (1.9); 1.0466 (2.2); 1.0320 (1.2); 1.0248 (2.1); 1.0182 (2.0); 1.0038 (1.0); 0.9199 (0.4); 0.8094 (0.9); 0.7945 (2.3); 0.7919 (2.2); 0.7885 (2.3); 0.7775 (2.2); 0.7719 (2.5); 0.7557 (0.8); 0.1075 (1.9); 0.0488 (0.7); 0.0379 (21.3); 0.0270 (1.0)
20-14: $^1$H-NMR(300.2 MHz, CDCl3):
δ = 7.2990 (16.3); 7.1616 (1.7); 7.1361 (3.0); 7.0973 (3.2); 7.0816 (2.0); 7.0698 (2.0); 7.0555 (1.2); 7.0426 (2.0); 7.0336 (1.2); 7.0265 (1.4); 7.0101 (1.2); 7.0046 (1.4); 6.9834 (0.6); 6.9775 (0.6); 6.8100 (0.8); 6.8029 (0.8); 6.7865 (1.3); 6.7621 (0.7); 6.7564 (0.6); 6.3830 (2.4); 5.8550 (0.9); 5.8179 (0.9); 4.1959 (0.4); 4.1722 (1.1); 4.1484 (1.1); 4.1248 (0.4); 3.9303 (1.2); 3.8988 (1.8); 3.8600 (0.4); 3.7998 (1.4); 3.7727 (1.0); 3.1118 (0.6); 3.0983 (0.6); 3.0662 (1.0); 3.0527 (0.9); 2.9676 (1.0); 2.9376 (0.9); 2.9229 (0.6); 2.8918 (0.5); 2.5405 (16.0); 2.3929 (11.4); 2.3381 (0.4); 2.1375 (0.5); 2.1265 (0.6); 2.1089 (1.0); 2.0841 (5.8); 2.0634 (0.4); 1.6411 (1.0); 1.3213 (1.5); 1.2975 (2.9); 1.2737 (1.3); 1.0598 (0.7); 1.0445 (1.9); 1.0377 (2.0); 1.0232 (1.2); 1.0159

TABLE 30-continued (2.0); 1.0092 (1.9); 0.9951 (1.0); 0.9732 (0.4); 0.8042 (0.9); 0.7892 (2.2); 0.7833 (2.2); 0.7723 (2.1); 0.7665 (2.5); 0.7503 (0.8); 0.1071 (4.8); 0.0486 (0.6); 0.0376 (20.4); 0.0266 (0.9)

20-15: $^{1}$H-NMR(300.2 MHz, CDCl3):

δ = 8.3004 (1.5); 8.2075 (15.1); 8.1785 (16.0); 8.1419 (0.4); 7.6878 (0.7); 7.6706 (1.0); 7.6446 (0.6); 7.6223 (0.9); 7.5945 (10.8); 7.5771 (15.7); 7.5518 (1.2); 7.5391 (1.4); 7.5241 (0.7); 7.5026 (1.5); 7.4794 (1.8); 7.4290 (10.0); 7.4020 (4.0); 7.3834 (3.1); 7.3699 (4.5); 7.3558 (7.6); 7.3469 (17.9); 7.3327 (3.8); 7.3179 (14.8); 7.2989 (56.2); 7.2734 (0.8); 7.2312 (0.7); 7.1957 (0.5); 7.1205 (0.3); 6.8042 (8.5); 5.6595 (4.5); 5.6224 (4.8); 5.3382 (11.5); 4.6350 (9.2); 4.1727 (0.8); 4.1488 (1.1); 4.1257 (0.8); 4.1040 (1.0); 4.0815 (0.5); 3.8156 (0.3); 3.7756 (0.4); 3.7524 (1.0); 3.7375 (1.3); 3.7150 (8.0); 3.7087 (8.6); 3.7004 (9.3); 3.6916 (9.2); 3.6544 (1.5); 3.6212 (0.8); 3.6068 (1.5); 3.5923 (2.0); 3.5772 (2.3); 3.5635 (2.1); 3.5558 (2.0); 3.5404 (1.8); 3.5250 (1.4); 3.2529 (0.4); 3.2292 (0.4); 3.2232 (0.5); 3.2033 (2.8); 3.1883 (2.8); 3.1577 (4.9); 3.1434 (4.6); 3.1189 (0.4); 3.0493 (4.6); 3.0201 (4.2); 3.0044 (2.9); 2.9751 (2.5); 2.3936 (1.1); 2.0855 (7.2); 2.0729 (0.5); 2.0461 (0.4); 1.9397 (1.4); 1.7942 (0.4); 1.7851 (0.5); 1.6711 (2.1); 1.6480 (2.5); 1.6234 (2.3); 1.5582 (1.1); 1.5049 (0.5); 1.4837 (0.5); 1.4559 (0.5); 1.4337 (0.6); 1.4067 (0.6); 1.3810 (0.5); 1.3449 (0.6); 1.3217 (1.7); 1.2978 (3.0); 1.2834 (1.3); 1.2741 (1.3); 1.2600 (0.5); 1.0113 (0.4); 0.9982 (1.0); 0.9731 (1.7); 0.9587 (0.3); 0.9482 (0.7); 0.9175 (0.4); 0.1192 (0.8); 0.1072 (22.3); 0.0481 (2.1); 0.0373 (71.4); 0.0281 (2.8); 0.0264 (3.2); −0.0286 (0.4)

20-16: $^{1}$H-NMR(300.2 MHz, CDCl3):

δ = 8.3054 (3.9); 8.0981 (0.6); 8.0728 (0.6); 7.6857 (2.4); 7.6685 (3.0); 7.6494 (11.3); 7.6227 (13.0); 7.6036 (8.0); 7.5940 (6.5); 7.5832 (16.0); 7.5556 (1.8); 7.5073 (1.0); 7.4944 (0.6); 7.4579 (8.1); 7.4222 (2.7); 7.4036 (2.9); 7.3961 (3.5); 7.3840 (5.3); 7.3770 (5.6); 7.3721 (5.4); 7.3452 (2.9); 7.2987 (52.2); 7.2196 (14.2); 7.1925 (12.5); 7.1496 (0.9); 7.1242 (2.0); 7.0409 (0.5); 7.0189 (0.4); 6.9480 (0.5); 6.7538 (0.6); 6.7061 (7.6); 5.6396 (4.2); 5.6023 (4.3); 4.7827 (0.4); 4.7719 (0.5); 4.7602 (0.4); 4.6354 (4.6); 4.1042 (0.4); 4.0277 (0.7); 3.9809 (1.0); 3.8507 (0.6); 3.8367 (0.6); 3.8118 (0.9); 3.7985 (1.0); 3.7579 (0.9); 3.7442 (1.2); 3.7213 (6.8); 3.7123 (8.5); 3.7077 (8.6); 3.6953 (8.2); 3.6760 (1.1); 3.6577 (1.7); 3.6283 (0.4); 3.5633 (0.6); 3.5462 (1.2); 3.5320 (1.7); 3.5169 (2.0); 3.5017 (1.8); 3.4791 (1.6); 3.4635 (1.1); 3.4482 (0.4); 3.2155 (0.4); 3.1934 (0.4); 3.1695 (1.1); 3.1471 (1.4); 3.1329 (2.9); 3.1175 (2.8); 3.0875 (4.3); 3.0728 (4.0); 2.9981 (0.3); 2.9532 (4.0); 2.9237 (3.7); 2.9078 (2.7); 2.8786 (2.4); 2.3501 (1.6); 2.2807 (1.4); 2.0857 (1.9); 1.9222 (1.9); 1.8047 (0.3); 1.6265 (2.7); 1.4311 (0.4); 1.4095 (0.4); 1.3220 (0.6); 1.2954 (1.1); 0.9984 (0.6); 0.9733 (0.8); 0.9182 (0.3); 0.1076 (6.6); 0.0486 (3.1); 0.0378 (70.6); 0.0271 (3.3); −0.0286 (0.5); −0.1601 (0.4)

20-17: $^{1}$H-NMR(300.2 MHz, CDCl3):

δ = 7.3617 (0.8); 7.3537 (0.9); 7.3399 (0.9); 7.3372 (1.0); 7.3289 (1.2); 7.3254 (1.1); 7.3224 (0.9); 7.3073 (1.1); 7.2990 (7.0); 7.1882 (0.5); 7.1688 (1.8); 7.1599 (3.2); 7.1561 (3.8); 7.1507 (2.1); 7.1417 (1.8); 7.1369 (2.2); 7.1248 (3.1); 7.1079 (0.6); 7.0938 (2.7); 7.0749 (1.9); 7.0493 (0.9); 6.4302 (2.4); 5.8519 (0.9); 5.8159 (0.9); 3.8940 (0.5); 3.8826 (1.3); 3.8720 (0.5); 3.8500 (1.7); 3.8286 (0.5); 3.8192 (0.4); 3.8058 (0.4); 3.7855 (0.9); 3.7770 (1.3); 3.7507 (0.9); 3.1014 (0.6); 3.0874 (0.6); 3.0558 (1.0); 3.0422 (1.0); 2.9513 (1.0); 2.9217 (0.9); 2.9060 (0.6); 2.8765 (0.5); 2.5552 (16.0); 2.5397 (0.7); 2.3867 (11.2); 2.0442 (10.8); 1.6646 (0.5); 0.1074 (0.4); 0.0482 (0.4); 0.0375 (9.2); 0.0265 (0.3)

20-18: $^{1}$H-NMR(300.2 MHz, CDCl3):

δ = 7.2986 (14.2); 7.1672 (1.8); 7.1400 (2.0); 7.0970 (0.5); 7.0704 (1.5); 7.0439 (1.7); 7.0356 (1.0); 7.0283 (1.2); 7.0120 (1.0); 7.0066 (1.1); 6.9855 (0.5); 6.9793 (0.5); 6.9294 (0.8); 6.8313 (1.5); 6.8232 (4.0); 6.8120 (1.2); 6.8053 (0.8); 6.7934 (1.8); 6.7848 (1.8); 6.7644 (0.6); 6.7589 (0.5); 6.5156 (2.4); 5.8450 (0.8); 5.8086 (0.9); 4.1964 (0.4); 4.1726 (1.3); 4.1488 (1.3); 4.1250 (0.5); 3.9415 (0.6); 3.9292 (1.2); 3.9179 (0.5); 3.8957 (1.5); 3.8738 (0.7); 3.8506 (16.0); 3.8054 (0.8); 3.7970 (1.2); 3.7699 (0.9); 3.0815 (0.5); 3.0674 (0.6); 3.0352 (1.0); 3.0217 (0.9); 2.9422 (0.9); 2.9119 (0.9); 2.8959 (0.5); 2.8665 (0.5); 2.5530 (13.4); 2.1390 (0.4); 2.1274 (0.5); 2.1106 (0.9); 2.0837 (6.4); 1.6128 (3.3); 1.3213 (1.7); 1.2975 (3.5); 1.2737 (1.6); 1.0606 (0.6); 1.0455 (1.7); 1.0386 (1.8); 1.0239 (1.0); 1.0170 (1.8); 1.0104 (1.7); 0.9958 (0.8); 0.8055 (0.8); 0.7906 (2.1); 0.7855 (2.0); 0.7736 (1.8); 0.7684 (2.1); 0.7517 (0.6); 0.1075 (5.2); 0.0488 (0.8); 0.0472 (0.6); 0.0381 (20.2); 0.0304 (0.5); 0.0288 (0.6); 0.0272 (0.7)

20-19: $^{1}$H-NMR(300.2 MHz, CDCl3):

δ = 7.5404 (0.8); 7.5144 (2.0); 7.4882 (1.5); 7.4589 (0.6); 7.4436 (0.4); 7.4346 (0.5); 7.4288 (0.7); 7.4119 (2.2); 7.3859 (1.4); 7.3656 (0.7); 7.3404 (2.6); 7.3126 (1.8); 7.2990 (7.0); 7.2862 (1.4); 7.1705 (0.5); 7.1454 (2.2); 7.1201 (3.8); 7.0862 (3.4); 7.0725 (2.6); 7.0465 (1.4); 6.9468 (0.8); 6.8599 (1.3); 6.6884 (0.4); 6.6719 (2.7); 6.5230 (2.4); 6.4841 (1.4); 5.8071 (1.1); 5.7721 (1.1); 4.6322 (1.4); 4.1945 (1.0); 4.1707 (2.9); 4.1469 (3.0); 4.1231 (1.0); 3.8049 (0.3); 3.7676 (1.6); 3.7595 (1.0); 3.7412 (2.7); 3.7274 (2.0); 3.7141 (1.8); 3.6986 (1.8); 3.6747 (1.1); 3.1486 (0.9); 3.1342 (1.0); 3.1037 (1.7); 3.0889 (1.2); 2.8982 (0.9); 2.8688 (0.9); 2.8529 (0.8); 2.8236 (0.7); 2.7361 (0.5); 2.5703 (16.0); 2.3711 (13.0); 2.3441 (2.0); 2.3201 (0.5); 2.3105 (0.6); 2.2927 (0.6); 2.2778 (0.5); 2.0831 (13.4); 1.9213 (1.4); 1.6009 (0.6); 1.5761 (1.3); 1.5514 (1.1); 1.5048 (0.6); 1.4819 (0.7); 1.3192 (3.6); 1.2954 (7.2); 1.2715 (3.6); 0.0466 (0.3); 0.0359 (8.3); 0.0250 (0.4)

20-20: $^{1}$H-NMR(300.2 MHz, CDCl3):

δ = 8.0677 (0.4); 7.6320 (0.4); 7.6238 (0.4); 7.6164 (0.4); 7.6062 (0.6); 7.6003 (0.5); 7.4443 (3.4); 7.4323 (1.9); 7.4217 (1.8); 7.4021 (1.9); 7.3906 (7.2); 7.3560 (0.4); 7.2990 (18.0); 7.2314 (0.4); 7.1992 (0.5); 7.1885 (0.4); 7.1697 (0.5); 7.1616 (0.4); 7.1449 (0.6); 7.1238 (1.0); 7.1035 (0.9); 7.0765 (2.0); 7.0482 (1.8); 7.0252 (1.2); 7.0188 (1.4); 7.0013 (1.3); 6.9961 (1.4); 6.9746 (0.6); 6.9689 (0.6); 6.9324 (0.3); 6.8461 (1.3); 6.8176 (0.9); 6.8117 (0.9); 6.7921 (1.3); 6.7694 (0.7); 6.7645 (0.7); 6.7538 (1.1); 6.6591 (2.6); 6.4720 (1.3); 6.4095 (2.2); 5.8703 (1.2); 5.8331 (1.2); 5.3382 (0.5); 4.6353 (3.0); 4.0264 (0.4); 4.0107 (0.3); 3.9800 (1.0); 3.9541 (1.4); 3.9435 (1.1); 3.9298 (0.7); 3.9175 (1.8); 3.9047 (1.2); 3.8182 (1.1); 3.8102 (1.4); 3.7824 (1.0); 3.7728 (0.7); 3.2082 (0.7); 3.1949 (0.7); 3.1634 (1.2); 3.1494 (1.1); 3.0677 (1.1); 3.0365 (1.0); 3.0234 (0.7); 2.9917 (0.6); 2.7335 (1.1); 2.5440 (16.0); 2.5205 (0.3); 2.3499 (0.8); 2.2802 (0.7); 2.1364 (0.6); 2.1261 (0.7); 2.1083 (1.2); 2.0911 (0.8); 2.0848 (1.2); 2.0627 (0.4); 1.6256 (2.1); 1.3217 (0.4); 1.2979 (0.8); 1.0672 (0.9); 1.0522 (2.2); 1.0454 (2.4); 1.0308 (1.4); 1.0236 (2.2); 1.0170 (2.2); 1.0027 (1.0); 0.8087 (1.1); 0.7938 (2.7); 0.7879 (2.6); 0.7769 (2.5); 0.7712 (2.7); 0.7548 (0.8); 0.1075 (3.9); 0.0486 (0.9); 0.0378 (23.8); 0.0269 (1.0)

20-21: $^{1}$H-NMR(300.2 MHz, CDCl3):

δ = 8.0778 (0.3); 7.6061 (0.3); 7.4558 (0.5); 7.4468 (0.5); 7.4381 (0.8); 7.4322 (1.0); 7.4220 (1.1); 7.4021 (0.8); 7.3775 (0.5); 7.3209 (0.4); 7.2986 (22.3); 7.2882 (2.8); 7.2602 (2.9); 7.1991 (0.3); 7.1698 (0.5); 7.1466 (0.4); 7.1238 (0.9); 7.0966 (2.4); 7.0883 (3.1); 7.0765 (2.0); 7.0609 (2.0); 7.0510 (2.5); 7.0301 (2.0); 7.0236 (2.2); 7.0059 (1.3); 7.0007 (1.4); 6.9793 (0.7); 6.9737 (0.6); 6.9477 (0.3); 6.9403 (0.6); 6.8172 (0.9); 6.8107 (0.9); 6.8011 (1.8); 6.7932 (1.4); 6.7689 (0.7); 6.7635 (0.7); 6.7536 (0.8); 6.5585 (4.4); 6.5438 (0.4); 6.3155 (1.5); 5.8490 (1.1); 5.8125 (1.2); 5.3381 (0.6); 4.6352 (2.2); 3.9800 (0.5); 3.9368 (1.4); 3.9301 (1.4); 3.9026 (1.8); 3.7900 (1.4); 3.7622 (1.1); 3.7520 (0.6); 3.1428 (0.6); 3.1288 (0.6); 3.0980 (1.3); 3.0837 (1.2); 3.0069 (1.0); 2.9764 (1.0); 2.9611 (0.7); 2.9308 (0.6); 2.7365 (1.0); 2.5711 (16.0); 2.3499 (0.6); 2.2804 (0.5); 2.1524

TABLE 30-continued (0.3); 2.1347 (0.6); 2.1240 (0.7); 2.1070 (1.2); 2.0846 (1.2); 2.0788 (0.7); 2.0627 (0.5); 1.9023 (1.6); 1.6174 (0.7); 1.3214 (0.4); 1.2976 (0.8); 1.0655 (1.0); 1.0503 (2.2); 1.0434 (2.4); 1.0289 (1.3); 1.0217 (2.2); 1.0152 (2.1); 1.0007 (0.9); 0.8076 (1.2); 0.7928 (2.6); 0.7870 (2.5); 0.7761 (2.4); 0.7702 (2.6); 0.7537 (0.8); 0.1069 (0.9); 0.0482 (1.1); 0.0374 (31.8); 0.0265 (1.3)

20-22: $^1$H-NMR(300.2 MHz, CDCl3):

δ = 8.0730 (0.3); 7.6323 (0.4); 7.6060 (0.5); 7.6003 (0.4); 7.4561 (0.7); 7.4476 (0.6); 7.4383 (1.0); 7.4325 (1.5); 7.4221 (1.6); 7.4029 (1.2); 7.3954 (0.4); 7.3847 (0.6); 7.3779 (0.7); 7.3696 (0.6); 7.3551 (0.4); 7.3373 (2.6); 7.3093 (3.7); 7.2990 (26.0); 7.2322 (0.4); 7.1991 (0.6); 7.1800 (2.2); 7.1533 (1.6); 7.1242 (1.8); 7.1072 (0.8); 7.0800 (1.7); 7.0516 (1.7); 7.0323 (1.2); 7.0258 (1.4); 7.0086 (1.2); 7.0031 (1.4); 6.9818 (0.7); 6.9760 (0.6); 6.9445 (0.4); 6.8200 (0.9); 6.8140 (0.9); 6.7943 (1.3); 6.7720 (0.7); 6.7663 (0.7); 6.7538 (1.0); 6.5678 (2.4); 5.8514 (1.1); 5.8149 (1.1); 5.3386 (4.0); 4.6356 (3.5); 4.0265 (0.4); 3.9809 (0.7); 3.9658 (0.5); 3.9421 (1.4); 3.9237 (0.7); 3.9060 (1.9); 3.8929 (1.1); 3.7864 (1.4); 3.7587 (1.0); 3.7505 (0.6); 3.1658 (0.6); 3.1514 (0.6); 3.1210 (1.2); 3.1057 (1.2); 3.0345 (1.1); 3.0054 (1.0); 2.9902 (0.7); 2.9595 (0.6); 2.7373 (1.0); 2.5693 (16.0); 2.3504 (0.8); 2.2804 (0.7); 2.1309 (0.6); 2.1199 (0.6); 2.1029 (1.1); 2.0850 (1.6); 2.0750 (0.7); 2.0575 (0.4); 1.9025 (0.6); 1.6107 (1.7); 1.3219 (0.5); 1.2981 (1.0); 1.2919 (0.8); 1.2743 (0.4); 1.0654 (0.9); 1.0503 (2.0); 1.0434 (2.2); 1.0374 (1.4); 1.0289 (1.3); 1.0215 (2.1); 1.0149 (2.1); 1.0005 (1.0); 0.8073 (1.1); 0.7924 (2.5); 0.7863 (2.5); 0.7754 (2.3); 0.7697 (2.6); 0.7535 (0.8); 0.1074 (5.8); 0.0488 (1.1); 0.0379 (36.1); 0.0271 (1.7)

20-23: $^1$H-NMR(300.2 MHz, CDCl3):

δ = 7.7077 (0.4); 7.2989 (5.5); 7.2913 (2.6); 7.1648 (1.0); 7.1391 (4.0); 7.1256 (2.2); 7.1221 (2.1); 7.0964 (1.0); 7.0703 (1.6); 7.0433 (2.7); 7.0336 (1.4); 7.0184 (1.1); 7.0125 (1.3); 6.9917 (0.5); 6.9854 (0.4); 6.8098 (0.7); 6.8021 (0.7); 6.7869 (1.2); 6.7809 (1.0); 6.7621 (0.6); 6.7563 (0.6); 6.3328 (2.6); 5.8637 (0.9); 5.8270 (1.0); 4.1729 (0.8); 4.1491 (0.8); 3.9643 (0.4); 3.9493 (1.2); 3.9428 (1.3); 3.9150 (1.7); 3.9031 (1.0); 3.8084 (1.3); 3.7809 (0.9); 3.7711 (0.4); 3.0956 (0.5); 3.0824 (0.5); 3.0503 (1.1); 3.0368 (1.0); 2.9662 (0.9); 2.9349 (0.9); 2.9207 (0.6); 2.8899 (0.5); 2.5416 (16.0); 2.3912 (11.5); 2.1415 (0.5); 2.1304 (0.5); 2.1133 (1.0); 2.0960 (0.6); 2.0845 (4.1); 1.3449 (0.5); 1.3211 (1.7); 1.3049 (3.0); 1.2974 (4.2); 1.2736 (1.2); 1.0609 (0.7); 1.0458 (1.8); 1.0390 (2.0); 1.0330 (1.1); 1.0245 (1.1); 1.0172 (1.9); 1.0105 (1.9); 0.9963 (0.9); 0.9419 (1.1); 0.9200 (3.6); 0.8968 (1.3); 0.8060 (0.9); 0.7913 (2.2); 0.7884 (2.0); 0.7853 (2.1); 0.7743 (2.0); 0.7688 (2.3); 0.7525 (0.7); 0.0381 (6.8)

20-24: $^1$H-NMR(300.2 MHz, $d_6$-DMSO):

δ = 10.3120 (11.4); 9.2399 (0.5); 7.3633 (0.5); 7.3163 (3.6); 7.1855 (1.0); 7.1595 (2.8); 7.1331 (2.6); 7.1130 (4.0); 7.0943 (1.5); 7.0886 (1.7); 7.0649 (2.0); 7.0432 (1.0); 7.0378 (0.9); 6.9400 (5.2); 6.9131 (2.1); 6.8907 (1.2); 6.8858 (1.0); 6.5325 (0.9); 6.3513 (2.4); 6.3147 (2.5); 5.7781 (0.5); 4.0847 (0.4); 4.0610 (1.2); 4.0373 (1.2); 4.0136 (0.4); 3.7837 (0.6); 3.7661 (0.9); 3.7477 (2.0); 3.7293 (2.5); 3.7026 (2.0); 3.6878 (0.7); 3.6664 (0.7); 3.4157 (0.7); 3.3964 (0.8); 3.3807 (0.9); 3.3508 (11.7); 2.9358 (1.0); 2.9238 (1.1); 2.8919 (1.6); 2.8803 (1.4); 2.7623 (1.3); 2.7296 (1.2); 2.7190 (1.0); 2.6861 (0.8); 2.5858 (1.1); 2.5345 (3.0); 2.5284 (6.3); 2.5223 (8.7); 2.5163 (6.4); 2.5102 (3.2); 2.4900 (21.2); 2.2376 (16.0); 2.1048 (0.4); 2.0867 (0.8); 2.0756 (1.0); 2.0591 (1.7); 2.0419 (1.0); 2.0312 (1.0); 2.0094 (5.4); 1.3010 (0.5); 1.2657 (3.1); 1.2184 (1.5); 1.1946 (2.9); 1.1709 (1.4); 1.0763 (0.3); 1.0584 (1.1); 1.0437 (3.0); 1.0364 (3.4); 1.0307 (1.9); 1.0229 (1.9); 1.0155 (3.1); 1.0083 (3.2); 0.9951 (1.3); 0.8996 (0.9); 0.8777 (3.1); 0.8545 (1.1); 0.8121 (1.4); 0.7986 (3.5); 0.7923 (3.8); 0.7819 (3.5); 0.7753 (3.6); 0.7600 (1.1); 0.0196 (7.3)

20-28: $^1$H-NMR(400.1 MHz, CDCl3):

δ = 8.2581 (2.5); 8.0622 (0.5); 8.0424 (0.4); 7.5078 (0.7); 7.4881 (0.9); 7.4061 (2.7); 7.4008 (2.2); 7.3901 (3.3); 7.3704 (1.5); 7.3502 (0.8); 7.3052 (4.7); 7.2829 (3.7); 7.2610 (29.0); 7.2015 (1.2); 7.1829 (1.3); 7.1595 (1.0); 7.1321 (0.6); 7.1114 (0.7); 7.0872 (3.2); 7.0678 (1.8); 7.0464 (1.0); 7.0273 (1.2); 6.9970 (0.5); 6.9682 (3.0); 6.9523 (6.8); 6.9070 (3.1); 6.8865 (2.3); 6.8695 (0.7); 6.1766 (2.7); 5.6167 (1.5); 5.5889 (1.6); 5.3009 (0.6); 4.6747 (0.3); 4.6550 (0.4); 4.6453 (0.4); 4.5983 (0.6); 3.9882 (0.8); 3.9432 (1.0); 3.8272 (0.5); 3.8174 (0.5); 3.7989 (1.2); 3.7901 (1.3); 3.7732 (2.2); 3.7639 (2.6); 3.7572 (2.5); 3.7433 (2.2); 3.7302 (0.7); 3.7160 (0.8); 3.7084 (0.9); 3.7020 (0.9); 3.6803 (0.6); 3.6736 (0.6); 3.3927 (1.0); 3.0303 (2.6); 3.0031 (1.8); 2.9950 (1.6); 2.7660 (1.5); 2.7394 (1.5); 2.7317 (1.3); 2.7053 (1.1); 2.4274 (0.4); 2.3712 (16.0); 2.3603 (6.9); 2.3360 (0.8); 2.3124 (2.3); 2.2722 (5.9); 2.2426 (2.0); 2.1901 (0.5); 2.1746 (0.7); 2.1195 (0.4); 2.0894 (0.8); 2.0332 (15.8); 1.9824 (0.6); 1.9601 (0.5); 1.8693 (4.5); 1.7859 (0.5); 1.7227 (0.4); 1.6717 (0.4); 1.6392 (0.5); 1.6015 (0.6); 1.5817 (0.6); 1.5630 (0.6); 1.5438 (0.8); 1.4837 (0.5); 1.4734 (0.5); 1.4219 (0.6); 1.3594 (0.5); 1.2541 (5.6); 1.2253 (1.2); 1.1344 (0.4); 1.1204 (0.4); 1.1039 (0.4); 0.9961 (0.3); 0.9827 (0.3); 0.9624 (0.3); 0.8960 (0.7); 0.8796 (1.2); 0.8583 (1.9); 0.8424 (1.9); −0.0002 (30.0)

20-31: $^1$H-NMR(400.1 MHz, CDCl3):

δ = 8.2278 (0.5); 7.5356 (1.2); 7.5161 (2.6); 7.4958 (1.8); 7.4163 (2.6); 7.3973 (2.1); 7.3691 (0.4); 7.3433 (0.5); 7.3209 (3.6); 7.2984 (4.9); 7.2879 (2.8); 7.2612 (21.0); 7.2002 (0.8); 7.1840 (1.0); 7.1690 (0.8); 7.1593 (1.3); 7.1326 (1.4); 7.1098 (8.7); 7.0868 (2.4); 6.7955 (1.4); 6.6549 (3.0); 6.5141 (1.5); 6.3458 (3.2); 5.7365 (1.6); 5.7088 (1.6); 3.9887 (1.3); 3.9431 (1.5); 3.8428 (0.5); 3.8339 (0.6); 3.8020 (1.5); 3.7750 (3.6); 3.7651 (4.4); 3.7556 (2.4); 3.7378 (0.7); 3.7287 (0.6); 3.1223 (1.3); 3.1147 (1.3); 3.0887 (1.7); 3.0805 (1.5); 2.8566 (1.3); 2.8329 (1.3); 2.8229 (1.2); 2.7978 (1.0); 2.3839 (16.0); 2.3119 (2.7); 2.2627 (1.4); 2.2424 (2.6); 1.8833 (0.9); 1.8412 (0.4); 1.8032 (0.4); 1.7564 (0.5); 1.6947 (0.5); 1.6731 (0.5); 1.6402 (0.5); 1.6022 (0.6); 1.5794 (0.6); 1.5430 (0.6); 1.4857 (0.4); 1.4287 (0.4); 1.2536 (2.9); 1.2082 (0.6); 0.8792 (0.5); 0.8575 (1.1); 0.8418 (1.3); −0.0002 (21.1)

20-33: $^1$H-NMR(400.1 MHz, CDCl3):

δ = 8.0736 (0.7); 7.5690 (0.3); 7.4113 (0.5); 7.4001 (0.7); 7.3846 (0.6); 7.3664 (0.5); 7.2876 (0.9); 7.2612 (25.2); 7.2394 (2.2); 7.2031 (3.7); 7.1715 (0.8); 7.1591 (1.1); 7.1310 (1.0); 7.1123 (1.2); 7.0859 (2.1); 7.0646 (1.7); 7.0441 (2.6); 7.0232 (1.7); 7.0006 (0.7); 6.9887 (1.1); 6.9775 (1.7); 6.9693 (1.1); 6.9606 (1.9); 6.9422 (1.2); 6.9256 (2.9); 6.9055 (2.4); 6.8699 (0.8); 6.8164 (0.4); 6.7995 (0.5); 6.7790 (1.3); 6.7590 (1.8); 6.7422 (1.2); 6.7160 (0.5); 6.2610 (1.8); 5.7603 (1.5); 5.7326 (1.6); 5.7091 (0.4); 5.3006 (0.9); 4.7249 (0.6); 4.7064 (0.6); 4.5975 (0.9); 3.9885 (1.0); 3.9430 (1.2); 3.8730 (0.6); 3.8613 (0.7); 3.8450 (1.6); 3.8341 (1.7); 3.8082 (1.8); 3.8026 (2.0); 3.7752 (1.2); 3.7554 (0.4); 3.7297 (0.4); 3.6936 (0.6); 3.6763 (1.1); 3.6683 (1.2); 3.6486 (0.9); 3.0374 (0.5); 3.0180 (0.6); 2.9813 (0.3); 2.9305 (0.9); 2.9219 (1.0); 2.8959 (1.7); 2.8874 (1.6); 2.8457 (1.7); 2.8204 (1.7); 2.8112 (1.1); 2.7857 (0.9); 2.7435 (0.4); 2.7114 (1.9); 2.5436 (16.0); 2.5248 (0.7); 2.3936 (1.8); 2.3793 (0.5); 2.3518 (0.4); 2.3320 (0.4); 2.3122 (2.3); 2.2425 (2.1); 2.1918 (0.4); 2.1741 (0.4); 2.1643 (0.4); 2.1419 (0.4); 2.0991 (0.8); 2.0808 (1.4); 2.0669 (1.8); 2.0539 (1.3); 2.0458 (1.3); 2.0321 (0.9); 2.0067 (16.0); 1.8750 (1.5); 1.8197 (0.4); 1.7885 (0.4); 1.7212 (0.4); 1.6471 (0.5); 1.6016 (0.6); 1.5628 (0.6); 1.5412 (0.7); 1.4234 (0.5); 1.3571 (0.6); 1.2536 (6.2); 1.2245 (1.2); 1.1355 (0.4); 1.1226 (0.4); 1.1062 (0.4); 1.0929 (0.4); 1.0542 (0.5); 1.0384 (1.0); 1.0262 (2.0); 1.0144 (3.2); 1.0097 (3.5); 0.9934 (3.0); 0.9889 (2.9); 0.9776

TABLE 30-continued (1.4); 0.9620 (0.6); 0.9405 (0.4); 0.8796 (1.4); 0.8588 (1.9); 0.8424 (1.9); 0.7930 (0.9); 0.7688 (2.0); 0.7570 (4.1); 0.7457 (3.3); 0.7415 (3.4); 0.7292 (1.1); −0.0002 (24.8)

20-34: $^1$H-NMR(400.1 MHz, CDCl3):

δ = 8.2040 (1.4); 7.3983 (0.4); 7.3869 (0.4); 7.3744 (0.5); 7.3645 (0.4); 7.3545 (0.8); 7.3350 (1.4); 7.2978 (6.0); 7.2777 (4.2); 7.2611 (26.4); 7.2008 (0.6); 7.1838 (0.8); 7.1692 (0.6); 7.1594 (1.0); 7.1316 (1.6); 7.1047 (6.5); 7.0858 (2.1); 7.0514 (0.6); 7.0332 (0.5); 7.0039 (0.7); 6.9712 (2.6); 6.9518 (2.3); 6.9178 (2.4); 6.9132 (2.3); 6.8928 (1.7); 6.8293 (3.4); 6.3072 (3.5); 5.7293 (1.6); 5.7016 (1.6); 5.3016 (0.5); 3.9889 (0.9); 3.9436 (1.0); 3.8655 (0.6); 3.8557 (0.8); 3.8477 (0.7); 3.8136 (1.6); 3.8041 (1.0); 3.7868 (3.1); 3.7754 (2.7); 3.7619 (2.2); 3.7429 (0.8); 3.7348 (0.6); 3.7140 (0.5); 3.7062 (0.4); 3.6848 (0.3); 3.6782 (0.3); 3.1747 (0.4); 3.1541 (0.4); 3.1391 (0.5); 3.1213 (1.6); 3.1136 (1.3); 3.0870 (1.7); 3.0794 (1.5); 2.8537 (1.2); 2.8289 (1.3); 2.8203 (1.2); 2.7949 (1.0); 2.3886 (16.0); 2.3124 (1.8); 2.2683 (3.3); 2.2429 (1.7); 1.9643 (0.4); 1.9445 (0.5); 1.9327 (0.5); 1.9216 (0.8); 1.9090 (1.1); 1.9002 (1.3); 1.8881 (2.0); 1.8754 (1.6); 1.8673 (1.3); 1.8535 (0.8); 1.8311 (0.4); 1.7960 (0.4); 1.7858 (0.5); 1.7636 (0.6); 1.6399 (1.0); 1.6098 (1.0); 1.6010 (1.1); 1.5459 (0.9); 1.4236 (0.5); 1.2541 (3.2); 1.0460 (0.4); 1.0297 (0.8); 1.0085 (0.9); 0.9812 (3.1); 0.9767 (3.2); 0.9601 (3.1); 0.9559 (3.0); 0.9191 (0.3); 0.8800 (0.6); 0.8574 (1.2); 0.8423 (1.3); 0.7614 (0.3); 0.7491 (0.9); 0.7330 (0.9); 0.7217 (0.6); 0.6923 (3.2); 0.6869 (3.2); 0.6808 (3.2); 0.6688 (1.2); −0.0002 (27.5)

20-35: $^1$H-NMR(400.1 MHz, CDCl3):

δ = 8.2043 (1.0); 7.3992 (0.3); 7.3851 (0.4); 7.3660 (0.3); 7.3364 (0.9); 7.3187 (4.4); 7.2607 (24.7); 7.2018 (0.8); 7.1889 (1.1); 7.1696 (0.9); 7.1590 (1.3); 7.1511 (1.2); 7.1357 (1.6); 7.1304 (1.7); 7.1079 (10.0); 7.0865 (2.2); 7.0714 (1.4); 7.0515 (2.5); 7.0313 (1.8); 6.9963 (0.5); 6.9807 (1.5); 6.9642 (2.2); 6.9461 (1.2); 6.8675 (0.5); 6.8605 (0.4); 6.7970 (1.3); 6.7784 (2.0); 6.7611 (1.1); 6.2293 (3.4); 5.8048 (1.4); 5.7767 (1.4); 5.3005 (0.4); 4.5971 (0.4); 3.9886 (1.1); 3.9425 (1.7); 3.9246 (2.2); 3.9031 (2.9); 3.8951 (1.8); 3.8737 (0.4); 3.8631 (0.4); 3.8336 (2.0); 3.8130 (1.3); 3.7155 (0.3); 3.1812 (0.4); 3.1653 (0.5); 3.1490 (0.4); 3.0603 (1.0); 3.0546 (1.0); 3.0269 (1.8); 3.0194 (1.6); 2.9325 (1.4); 2.9068 (1.3); 2.8975 (1.0); 2.8861 (0.4); 2.8737 (0.9); 2.3926 (16.0); 2.3525 (0.3); 2.3221 (0.8); 2.3122 (2.4); 2.2912 (0.6); 2.2637 (2.8); 2.2425 (2.3); 2.1917 (0.8); 2.1614 (0.5); 2.1413 (0.5); 2.1321 (0.4); 2.1191 (0.8); 2.1042 (1.1); 2.0968 (1.2); 2.0839 (1.8); 2.0716 (1.2); 2.0626 (1.1); 2.0491 (0.7); 1.9982 (0.4); 1.9501 (0.4); 1.9261 (0.4); 1.9106 (0.5); 1.8335 (0.6); 1.7658 (0.8); 1.7482 (0.9); 1.6657 (1.4); 1.6324 (1.6); 1.6016 (1.6); 1.5854 (1.6); 1.5680 (1.6); 1.5437 (1.5); 1.5249 (1.4); 1.4225 (1.1); 1.2536 (12.6); 1.2232 (2.8); 1.2063 (2.2); 1.1688 (1.2); 1.1338 (1.0); 1.0944 (0.9); 1.0750 (1.0); 1.0585 (1.3); 1.0388 (2.0); 1.0277 (3.7); 1.0233 (3.8); 1.0067 (3.7); 1.0023 (3.6); 0.9919 (1.9); 0.9719 (1.2); 0.9513 (1.2); 0.8800 (4.0); 0.8579 (4.2); 0.8430 (3.6); 0.8164 (2.0); 0.8047 (2.1); 0.7915 (1.9); 0.7745 (2.4); 0.7612 (4.3); 0.7505 (4.0); 0.7354 (1.6); −0.0002 (26.6)

20-36: $^1$H-NMR(300.2 MHz, CDCl3):

δ = 7.4556 (0.5); 7.4468 (0.7); 7.4381 (0.8); 7.4291 (1.9); 7.4219 (2.8); 7.4025 (2.2); 7.3953 (0.7); 7.3844 (1.1); 7.3777 (1.2); 7.3697 (0.6); 7.3548 (0.6); 7.3077 (0.7); 7.2987 (21.2); 7.2321 (0.4); 7.2216 (0.3); 7.1998 (0.4); 7.1887 (0.4); 7.1641 (0.3); 7.1513 (0.4); 7.1381 (0.5); 7.1245 (1.4); 7.0981 (1.6); 7.0700 (2.3); 7.0455 (2.9); 7.0293 (1.9); 7.0218 (5.4); 7.0058 (3.5); 7.0011 (3.7); 6.9792 (1.3); 6.9739 (1.1); 6.8543 (1.4); 6.8319 (0.4); 6.8150 (1.0); 6.8087 (1.0); 6.7914 (1.5); 6.7671 (0.9); 6.7618 (0.7); 6.7537 (0.6); 6.6909 (0.4); 6.6549 (2.4); 6.1202 (1.9); 5.8019 (1.1); 5.7652 (1.3); 5.3379 (0.8); 4.6354 (6.9); 4.1727 (0.3); 4.1489 (0.4); 3.9811 (0.4); 3.9328 (0.4); 3.9167 (0.5); 3.8963 (1.5); 3.8807 (2.1); 3.8718 (1.8); 3.8619 (2.2); 3.8415 (0.7); 3.8258 (1.1); 3.7843 (0.8); 3.7631 (0.6); 3.7520 (0.6); 3.2837 (0.9); 3.2731 (0.9); 3.2378 (1.2); 3.2278 (1.0); 2.9408 (1.0); 2.9074 (1.1); 2.8952 (0.9); 2.8617 (0.7); 2.7391 (0.9); 2.5206 (0.9); 2.4958 (1.0); 2.4605 (16.0); 2.4064 (0.8); 2.3808 (12.1); 2.3633 (2.2); 2.3502 (0.9); 2.2814 (1.2); 2.1384 (0.4); 2.1212 (0.7); 2.1101 (0.8); 2.0922 (1.3); 2.0851 (2.1); 2.0755 (0.9); 2.0643 (0.7); 2.0472 (0.4); 1.6583 (0.9); 1.6369 (0.8); 1.6126 (0.9); 1.5946 (1.0); 1.5845 (1.0); 1.5669 (1.4); 1.5492 (0.9); 1.5396 (0.8); 1.5220 (0.5); 1.3218 (0.6); 1.2980 (1.2); 1.2742 (0.5); 1.0592 (1.3); 1.0446 (2.5); 1.0376 (2.8); 1.0232 (1.6); 1.0160 (2.5); 1.0094 (2.2); 0.9952 (1.1); 0.8477 (0.4); 0.8303 (0.9); 0.8169 (1.0); 0.8066 (2.0); 0.8003 (1.9); 0.7889 (4.0); 0.7749 (3.4); 0.7707 (3.4); 0.7615 (1.5); 0.7533 (1.4); 0.7463 (1.1); 0.7323 (1.0); 0.7154 (0.7); 0.7070 (0.7); 0.6555 (0.5); 0.6377 (0.9); 0.6236 (1.0); 0.6118 (0.7); 0.6059 (1.0); 0.5945 (0.8); 0.5781 (0.3); 0.1076 (6.1); 0.0487 (1.0); 0.0379 (25.9); 0.0271 (1.0); 0.0126 (0.4); −0.0050 (0.7); −0.0156 (0.9); −0.0330 (0.9); −0.0479 (0.6)

TABLE 33

Compounds according to formula (21)

(21)

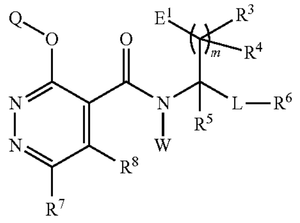

In table 33, "#" denotes the point of attachment to the L—$R^6$ group and "*" denotes the point of attachment to the pyridazin-4-yl group.

| Ex No | $R^7$ | $R^8$ | Q | 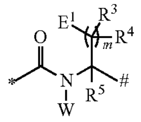 | L—$R^6$ | LogP |
|---|---|---|---|---|---|---|
| 21-01 | Cl | H | 3-(trifluoro-methyl)phenyl | 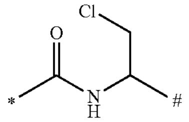 | (2,4-dimethyl-phenyl)methyl | 5.00[a] |
| 21-02 | $CH_3$ | H | 3-cyclopropyl-2-fluorophenyl | 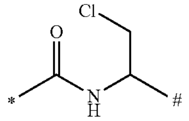 | (2,4-dimethyl-phenyl)methyl | 4.69[a] |
| 21-03 | Cl | H | 3-(trifluoro-methyl)phenyl | 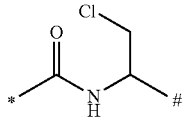 | benzyl | 4.33[a] |
| 21-04 | Cl | H | 3-(trifluoro-methyl)phenyl | 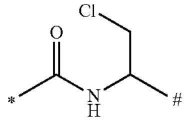 | [4-(trifluoro-methyl)phenyl]methyl | 4.62[a] |
| 21-05 | Cl | H | 3-(trifluoro-methyl)phenyl | 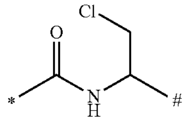 | [4-(difluoro-methoxy)phenyl]methyl | 4.30[a] |
| 21-06 | Cl | H | 3-(trifluoro-methyl)phenyl | 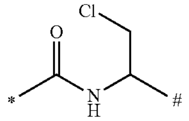 | [4-(trifluoro-methoxy)phenyl]methyl | 4.78[a] |
| 21-07 | $CH_3$ | H | 3-cyclopropyl-2-fluorophenyl | 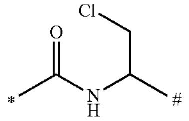 | (2,4-dimethyl-phenyl)methyl | 4.74[a] |
| 21-08 | $CH_3$ | H | 3-cyclopropyl-2-fluorophenyl | 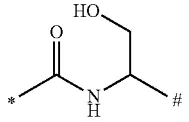 | (2-bromo-4-methyl-phenyl)methyl | 3.37[a] |

TABLE 33-continued

Compounds according to formula (21)

(21)

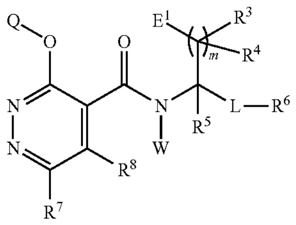

In table 33, "#" denotes the point of attachment to the L—$R^6$ group and "*" denotes the point of attachment to the pyridazin-4-yl group.

| Ex No | $R^7$ | $R^8$ | Q | 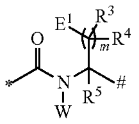 | L—$R^6$ | LogP |
|---|---|---|---|---|---|---|
| 21-09 | $CH_3$ | H | 3-cyclopropyl-2-fluorophenyl | 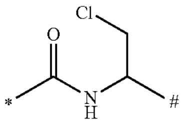 | (3,4-dichloro-phenyl)methyl | 4.66[a] |
| 21-10 | Cl | H | 3-(trifluoro-methyl)phenyl | 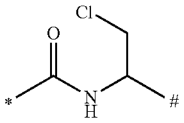 | [4 -(difluoro-methyl)phenyl]methyl | 4.19[a] |
| 21-11 | $CH_3$ | H | 3-cyclopropyl-2-fluorophenyl | 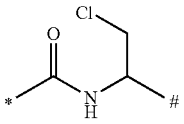 | [2-chloro-4-(trifluoro-methyl)phenyl]methyl | 4.81[a] |
| 21-12 | $CH_3$ | H | 3-cyclopropyl-2-fluorophenyl | 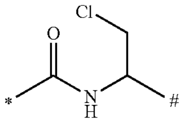 | (2-chloro-4-methyl-phenyl)methyl | 4.62[a] |
| 21-13 | Cl | H | 3-(trifluoro-methyl)phenyl | 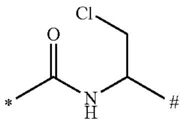 | (4-nitrophenyl)methyl | 3.98[a] |
| 21-14 | Cl | H | 3-(trifluoro-methyl)phenyl | 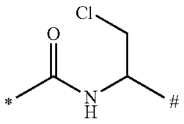 | [4-(trifluoromethyl-thio)phenyl]methyl | 5.08[a] |
| 21-15 | $CH_3$ | H | 3-chloro-2-fluorophenyl | 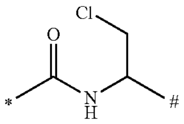 | (2-chloro-4-methyl-phenyl)methyl | 4.51[a] |
| 21-16 | $CH_3$ | H | 3-cyclopropyl-2-fluorophenyl | 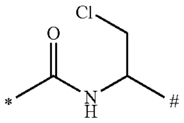 | (2-chloro-4-methoxy-phenyl)methyl | 4.36[a] |

TABLE 33-continued

Compounds according to formula (21)

(21)

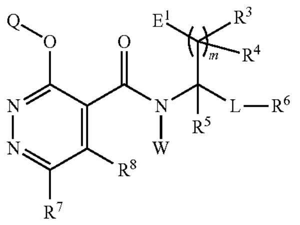

In table 33, "#" denotes the point of attachment to the L—$R^6$ group and "*" denotes the point of attachment to the pyridazin-4-yl group.

| Ex No | $R^7$ | $R^8$ | Q | 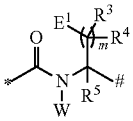 | L—$R^6$ | LogP |
|---|---|---|---|---|---|---|
| 21-17 | $CH_3$ | H | 3-(difluoromethyl) phenyl | 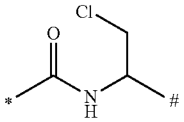 | (2-chloro-4-methylphenyl)methyl | 4.13[a] |
| 21-18 | Cl | H | 3-(difluoromethyl)-2-fluorophenyl | 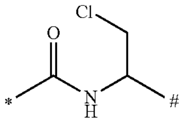 | (2-chloro-4-methylphenyl)methyl | 4.66[a] |
| 21-19 | $CH_3$ | H | 3-cyclopropyl-2-fluorophenyl | 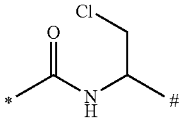 | [2-chloro-4-(difluoromethyl)phenyl] methyl | 4.40[a] |
| 21-20 | $CH_3$ | H | 3-cyclopropyl-2-fluorophenyl | 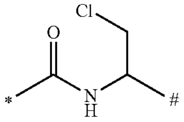 | [2-chloro-4-(difluoromethoxy)phenyl] methyl | 4.47[a] |
| 21-21 | $CH_3$ | H | 3-cyclopropyl-2-fluorophenyl | 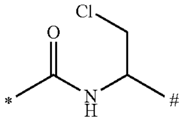 | [2-chloro-4-(trifluoromethoxy)phenyl] methyl | 5.08[a] |
| 21-22 | $CH_3$ | H | 3-cyclopropyl-2-fluorophenyl | 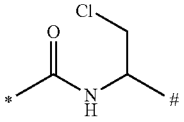 | (3-bromo-5-methylphenyl)methyl | 4.84[a] |
| 21-23 | $CH_3$ | H | 3-cyclopropyl-2-fluorophenyl | 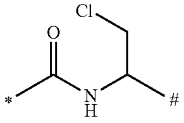 | (2-bromo-4-methylphenyl)methyl | 4.84[a] |
| 21-24 | $CH_3$ | H | 3-cyclopropyl-2-fluorophenyl | 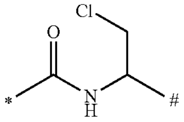 | (4-bromo-2-methylphenyl)methyl | 4.85[a] |

TABLE 33-continued

Compounds according to formula (21)

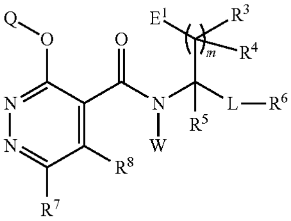

(21)

In table 33, "#" denotes the point of attachment to the L—$R^6$ group and "*" denotes the point of attachment to the pyridazin-4-yl group.

| Ex No | $R^7$ | $R^8$ | Q | 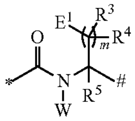 | L—$R^6$ | LogP |
|---|---|---|---|---|---|---|
| 21-25 | Cl | H | 3-cyclopropylphenyl | 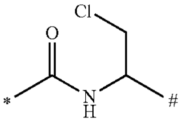 | (2,4-dimethylphenyl)methyl | 5.19[a] |
| 21-26 | Cl | H | 3-cyclopropyl-2-fluorophenyl | 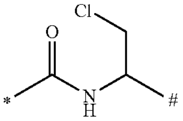 | (2,4-dimethylphenyl)methyl | 5.23[a] |
| 21-27 | Cl | H | 3-(difluoromethyl)phenyl | 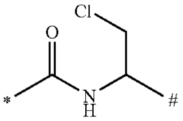 | (2,4-dimethylphenyl)methyl | 4.53[a] |
| 21-28 | Cl | H | 3-bromophenyl | 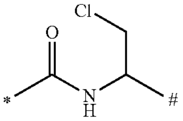 | (2,4-dimethylphenyl)methyl | 5.00[a] |
| 21-29 | Cl | H | 3-chlorophenyl | 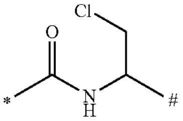 | (2,4-dimethylphenyl)methyl | 4.90[a] |
| 21-30 | Cl | H | 3-(difluoromethyl)phenyl | 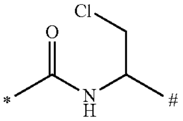 | (2-bromo-4-methylphenyl)methyl | 4.62[a] |
| 21-31 | $CH_3$ | H | 2-fluoro-3-(trifluoromethyl)phenyl | 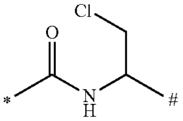 | (2,4-dimethylphenyl)methyl | 4.56[a] |
| 21-32 | Cl | H | 3-cyclopropyl-2-fluorophenyl | 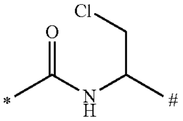 | (4-bromo-2-methylphenyl)methyl | 5.32[a] |

TABLE 33-continued

Compounds according to formula (21)

(21)

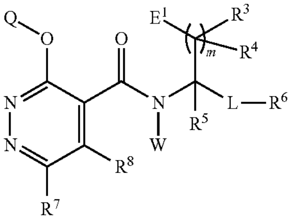

In table 33, "#" denotes the point of attachment to the L—$R^6$ group and "*" denotes the point of attachment to the pyridazin-4-yl group.

| Ex No | $R^7$ | $R^8$ | Q | 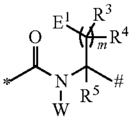 | L—$R^6$ | LogP |
|---|---|---|---|---|---|---|
| 21-33 | Cl | H | 3-cyclopropylphenyl | 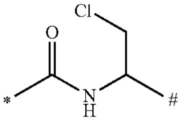 | (2-bromo-4-methylphenyl)methyl | 5.28[a] |
| 21-34 | Cl | H | 3-cyclopropyl-2-fluorophenyl | 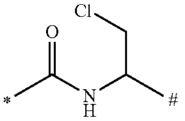 | (2-bromo-4-methylphenyl)methyl | 5.31[a] |
| 21-35 | $CH_3$ | H | 3-cyclopropyl-2-fluorophenyl | 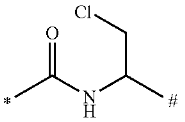 | (2-cyclopropyl-4-methylphenyl)methyl | 5.08[a] |

TABLE 34

21-01: $^1$H-NMR(499.9 MHz, CDCl3):
δ = 8.2680 (8.8); 8.0465 (1.1); 8.0311 (1.0); 7.6522 (0.5); 7.6349 (3.2); 7.6313 (2.4); 7.6260 (4.8); 7.6244 (5.2); 7.6185 (0.4); 7.6158 (0.4); 7.5084 (2.6); 7.4628 (0.4); 7.4544 (1.1); 7.4493 (1.2); 7.4463 (1.5); 7.4425 (1.5); 7.4365 (1.1); 7.4313 (0.7); 7.2577 (5.2); 7.0422 (2.6); 7.0269 (3.0); 6.9595 (3.0); 6.8715 (1.8); 6.8562 (1.4); 5.2958 (1.1); 4.6896 (0.4); 4.6817 (0.7); 4.6756 (1.0); 4.6678 (1.0); 4.6599 (0.9); 4.6536 (0.6); 3.8303 (1.4); 3.8223 (1.4); 3.8076 (2.0); 3.7996 (1.8); 3.7126 (2.2); 3.7071 (2.1); 3.6900 (1.5); 3.6844 (1.4); 3.0690 (0.5); 3.0551 (0.7); 3.0411 (2.3); 3.0305 (2.9); 3.0146 (2.1); 3.0030 (0.4); 2.9866 (0.4); 2.3588 (16.0); 2.2554 (14.7); 1.5535 (4.3); 0.0059 (0.5); −0.0002 (5.9)
21-02: $^1$H-NMR(300.2 MHz, CDCl3):
δ = 8.2238 (0.8); 8.1980 (0.8); 8.1207 (5.3); 7.2986 (7.3); 7.1850 (0.4); 7.1663 (1.9); 7.1643 (1.9); 7.1581 (2.8); 7.1405 (4.0); 7.1192 (1.9); 7.0937 (2.3); 6.9889 (2.3); 6.9151 (1.3); 6.8871 (1.7); 6.8729 (1.2); 6.8586 (0.9); 6.8416 (0.5); 4.7282 (0.5); 4.7154 (0.6); 4.7032 (0.7); 4.6915 (0.6); 4.6783 (0.5); 3.8621 (0.8); 3.8480 (0.9); 3.8246 (1.6); 3.8106 (1.5); 3.7412 (1.6); 3.7312 (1.6); 3.7037 (0.9); 3.6937 (0.9); 3.0852 (3.4); 3.0604 (3.4); 2.7425 (16.0); 2.4135 (12.0); 2.2895 (11.2); 2.1836 (0.5); 2.1724 (0.6); 2.1555 (1.0); 2.1382 (0.6); 2.1272 (0.6); 2.0456 (1.4); 1.6084 (6.1); 1.1004 (0.7); 1.0854 (1.8); 1.0785 (2.0); 1.0639 (1.1); 1.0568 (1.9); 1.0502 (1.8); 1.0357 (0.8); 0.8491 (0.9); 0.8341 (2.2); 0.8287 (2.1); 0.8172 (1.9); 0.8119 (2.3); 0.7953 (0.7); 0.0382 (9.0); 0.0273 (0.4)
21-03: $^1$H-NMR(499.9 MHz, CDCl3):
δ = 8.2630 (16.0); 7.9631 (1.8); 7.9477 (1.8); 7.6317 (8.3); 7.6214 (9.6); 7.6058 (0.5); 7.4670 (4.9); 7.4382 (0.4); 7.4302 (1.8); 7.4253 (2.0); 7.4206 (2.9); 7.4169 (2.6); 7.4121 (2.0); 7.4071 (1.5); 7.3996 (0.4); 7.2586 (11.5); 7.2368 (5.8); 7.2315 (39.9); 7.2113 (1.6); 7.2049 (0.6); 7.2008 (0.4); 4.7304 (0.4); 4.7236 (0.5); 4.7216 (0.6); 4.7150 (1.3); 4.7082 (1.6); 4.6998 (1.7); 4.6927 (1.6); 4.6859 (1.4); 4.6793 (0.7); 4.6704 (0.4); 3.7932 (2.5); 3.7842 (2.5); 3.7706 (3.8); 3.7615 (3.8); 3.6839 (4.0); 3.6775 (4.2); 3.6612 (2.8); 3.6549 (2.8); 3.1202 (1.7); 3.1069 (1.8); 3.0926 (3.8); 3.0793 (3.8); 3.0509 (4.0); 3.0353 (4.0); 3.0234 (2.0); 3.0077 (1.9); 1.5508 (5.7); 0.0061 (0.5); −0.0002 (13.9); −0.0064 (0.9)
21-04: $^1$H-NMR(300.2 MHz, CDCl3):
δ = 8.3083 (16.0); 8.0825 (1.8); 8.0562 (1.8); 7.6838 (8.2); 7.6664 (8.1); 7.6445 (0.4); 7.6398 (0.5); 7.5770 (5.5); 7.5499 (11.8); 7.4807 (0.5); 7.4678 (1.9); 7.4596 (2.0); 7.4507 (2.8); 7.4438 (2.9); 7.4319 (8.4); 7.4053 (5.4); 7.2985 (34.4); 5.3383 (0.4); 4.8199 (0.5); 4.8026 (1.0); 4.7929 (1.4); 4.7797 (1.5); 4.7665 (1.4); 4.7559 (1.0); 4.7438 (0.6); 4.7300 (0.4); 3.8470 (2.1); 3.8331 (2.1); 3.8086 (3.6); 3.7947 (3.4); 3.6961

TABLE 34-continued (4.0); 3.6862 (4.0); 3.6578 (2.6); 3.6479 (2.5); 3.2495 (0.9); 3.2268 (1.0); 3.2038 (3.0); 3.1818 (3.0); 3.1682 (3.5); 3.1411 (3.2); 3.1224 (1.1); 3.0955 (1.0); 1.7032 (3.3); 1.2940 (0.7); 0.1072 (1.5); 0.0483 (1.6); 0.0374 (46.8); 0.0266 (2.0)
21-05: $^{1}$H-NMR(300.2 MHz, CDCl3):
δ = 8.3108 (6.7); 8.0600 (0.9); 8.0338 (0.9); 7.6840 (3.3); 7.6668 (4.5); 7.5469 (2.2); 7.4823 (0.9); 7.4736 (0.9); 7.4666 (1.2); 7.4601 (1.1); 7.4517 (0.8); 7.4435 (0.6); 7.2988 (21.6); 7.2701 (4.6); 7.0663 (4.1); 7.0382 (3.3); 6.7470 (1.6); 6.5015 (3.3); 6.2561 (1.6); 5.3387 (3.6); 4.7491 (0.5); 4.7376 (0.7); 4.7247 (0.7); 4.7127 (0.7); 4.7016 (0.5); 3.8376 (1.0); 3.8236 (1.0); 3.7993 (1.7); 3.7853 (1.7); 3.7062 (1.8); 3.6963 (1.9); 3.6682 (1.1); 3.6583 (1.0); 3.1664 (0.5); 3.1442 (0.5); 3.1202 (1.7); 3.0984 (1.7); 3.0854 (1.9); 3.0583 (1.7); 3.0389 (0.6); 3.0122 (0.6); 1.5895 (16.0); 1.2916 (0.5); 0.1068 (4.2); 0.0479 (0.8); 0.0371 (21.2); 0.0264 (0.9)
21-06: $^{1}$H-NMR(300.2 MHz, CDCl3):
δ = 8.3091 (13.7); 8.0732 (1.4); 8.0471 (1.4); 7.6826 (5.9); 7.6653 (7.0); 7.5473 (3.4); 7.4925 (0.3); 7.4808 (1.4); 7.4716 (1.5); 7.4640 (2.2); 7.4578 (2.0); 7.4538 (1.0); 7.4500 (1.3); 7.4418 (1.0); 7.3345 (5.8); 7.3056 (8.5); 7.2985 (21.2); 7.1617 (5.2); 7.1354 (3.8); 5.3378 (3.5); 4.7745 (0.4); 4.7612 (0.8); 4.7510 (1.1); 4.7472 (1.0); 4.7378 (1.1); 4.7290 (1.0); 4.7248 (1.1); 4.7154 (0.8); 4.7014 (0.4); 3.8424 (1.6); 3.8285 (1.6); 3.8042 (2.8); 3.7903 (2.6); 3.7061 (3.1); 3.6962 (3.2); 3.6679 (1.9); 3.6580 (1.8); 3.1868 (0.8); 3.1646 (0.8); 3.1405 (2.6); 3.1186 (2.7); 3.1066 (3.0); 3.0793 (2.7); 3.0605 (0.9); 3.0334 (0.9); 1.5924 (16.0); 0.1073 (3.7); 0.0478 (0.9); 0.0370 (22.2); 0.0261 (0.9)
21-07: $^{1}$H-NMR(300.2 MHz, CDCl3):
δ = 8.2229 (0.8); 8.1964 (0.8); 8.1204 (5.3); 7.2983 (12.0); 7.1847 (0.4); 7.1663 (1.9); 7.1639 (1.8); 7.1578 (2.8); 7.1402 (4.0); 7.1191 (1.8); 7.0936 (2.3); 6.9890 (2.2); 6.9149 (1.3); 6.8940 (1.2); 6.8873 (1.7); 6.8729 (1.2); 6.8585 (0.9); 6.8419 (0.5); 5.3377 (0.9); 4.7282 (0.5); 4.7168 (0.6); 4.7031 (0.7); 4.6913 (0.7); 4.6780 (0.5); 3.8619 (0.9); 3.8478 (0.9); 3.8243 (1.6); 3.8103 (1.5); 3.7409 (1.6); 3.7309 (1.6); 3.7033 (0.9); 3.6934 (0.9); 3.0852 (3.4); 3.0604 (3.4); 2.7424 (16.0); 2.4134 (11.8); 2.3384 (0.4); 2.2894 (11.0); 2.1834 (0.5); 2.1724 (0.6); 2.1551 (1.0); 2.1377 (0.6); 2.1268 (0.6); 1.6010 (2.0); 1.1001 (0.7); 1.0852 (1.8); 1.0782 (2.0); 1.0636 (1.1); 1.0566 (1.9); 1.0499 (1.8); 1.0354 (0.9); 0.8488 (0.9); 0.8340 (2.2); 0.8289 (2.1); 0.8169 (1.9); 0.8118 (2.3); 0.7951 (0.7); 0.1079 (0.8); 0.0488 (0.5); 0.0380 (15.4); 0.0272 (0.6)
21-08: $^{1}$H-NMR(300.2 MHz, CDCl3):
δ = 8.0957 (5.6); 8.0600 (0.8); 7.3333 (2.4); 7.2990 (10.0); 7.1910 (2.1); 7.1653 (2.7); 7.1409 (3.6); 7.1229 (2.8); 7.1185 (2.1); 7.1137 (1.8); 7.0955 (0.4); 6.9527 (1.4); 6.9293 (1.1); 6.8816 (0.7); 6.8651 (1.0); 6.8598 (0.9); 6.8505 (1.2); 6.8365 (0.6); 6.8278 (0.6); 5.3379 (0.4); 4.5903 (0.4); 4.5780 (0.6); 4.5674 (0.6); 4.5552 (0.6); 4.5434 (0.4); 3.9217 (0.4); 3.8907 (0.9); 3.8388 (0.8); 3.8243 (0.8); 3.8029 (0.4); 3.7863 (0.4); 3.2302 (0.5); 3.2086 (0.6); 3.1835 (1.4); 3.1620 (1.3); 3.1302 (1.4); 3.1021 (1.4); 3.0838 (0.6); 3.0556 (0.6); 2.7278 (16.0); 2.6123 (0.5); 2.2684 (11.6); 2.1674 (0.5); 2.1564 (0.6); 2.1392 (1.0); 2.1223 (0.6); 2.1109 (0.6); 1.6168 (0.5); 1.0980 (0.6); 1.0825 (1.9); 1.0760 (2.0); 1.0613 (1.1); 1.0541 (2.0); 1.0475 (1.9); 1.0332 (0.8); 0.8421 (0.9); 0.8271 (2.3); 0.8213 (2.3); 0.8103 (2.1); 0.8044 (2.4); 0.7883 (0.7); 0.1074 (2.7); 0.0484 (0.5); 0.0376 (14.2); 0.0269 (0.7)
21-09: $^{1}$H-NMR(300.2 MHz, $d_6$-DMSO):
δ = 7.6095 (1.1); 7.5577 (0.5); 7.5514 (0.5); 7.3941 (0.4); 7.3667 (0.7); 7.2957 (0.4); 7.2891 (0.3); 7.1466 (0.4); 5.7760 (1.7); 3.3407 (16.0); 2.6006 (2.7); 2.5349 (0.6); 2.5289 (1.3); 2.5229 (1.8); 2.5168 (1.3); 2.5109 (0.6); 1.0502 (0.3); 1.0428 (0.4); 1.0220 (0.4); 1.0148 (0.4); 0.8035 (0.4); 0.7970 (0.4); 0.7865 (0.4); 0.7798 (0.4); 0.0212 (1.0)
21-10: $^{1}$H-NMR(300.2 MHz, CDCl3):
δ = 8.3056 (16.0); 8.2808 (1.1); 8.0621 (1.9); 8.0357 (1.9); 7.6823 (7.9); 7.6651 (9.3); 7.6394 (0.4); 7.5777 (0.6); 7.5373 (4.7); 7.5046 (0.4); 7.4998 (0.4); 7.4825 (0.7); 7.4670 (2.6); 7.4589 (5.8); 7.4520 (4.9); 7.4454 (3.4); 7.4305 (10.4); 7.3944 (10.0); 7.3671 (4.2); 7.2987 (16.0); 6.8163 (2.7); 6.6283 (5.7); 6.4404 (2.8); 5.3374 (4.6); 4.8160 (0.3); 4.8027 (0.5); 4.7903 (1.0); 4.7793 (1.5); 4.7663 (1.6); 4.7530 (1.5); 4.7426 (1.1); 4.7302 (0.6); 4.7164 (0.4); 3.8430 (2.1); 3.8288 (2.1); 3.8047 (3.7); 3.7906 (3.5); 3.7040 (4.1); 3.6939 (4.0); 3.6658 (2.5); 3.6557 (2.4); 3.2275 (0.9); 3.2058 (0.9); 3.1822 (2.9); 3.1598 (3.0); 3.1483 (3.3); 3.1214 (3.0); 3.1025 (1.0); 3.0757 (0.9); 1.6025 (2.4); 1.2969 (0.5); 0.1081 (2.3); 0.0481 (0.7); 0.0466 (0.5); 0.0374 (22.2); 0.0282 (0.8); 0.0265 (0.9)
21-11: $^{1}$H-NMR(300.2 MHz, CDCl3):
δ = 8.1805 (0.7); 8.1530 (0.8); 8.0622 (5.2); 7.6909 (1.1); 7.6441 (2.1); 7.5427 (0.4); 7.5199 (1.0); 7.5157 (1.0); 7.4846 (1.3); 7.4747 (1.0); 7.4476 (2.6); 7.4299 (1.9); 7.4252 (1.8); 7.4024 (0.6); 7.3986 (0.6); 7.2991 (12.7); 7.1876 (0.4); 7.1693 (2.2); 7.1610 (2.1); 7.1571 (1.8); 7.1442 (3.8); 7.1189 (0.3); 6.8998 (0.7); 6.8913 (0.7); 6.8776 (1.2); 6.8649 (0.8); 6.8606 (0.6); 6.8458 (0.5); 5.3376 (0.6); 4.9651 (0.4); 4.9531 (0.6); 4.9396 (0.6); 4.9264 (0.6); 4.9156 (0.4); 3.9478 (1.0); 3.9337 (1.0); 3.9096 (1.5); 3.8956 (1.5); 3.7731 (1.5); 3.7626 (1.6); 3.7424 (0.4); 3.7352 (1.2); 3.7245 (1.2); 3.7158 (0.9); 3.6918 (1.0); 3.6717 (0.4); 3.5710 (0.5); 3.5523 (1.3); 3.5276 (1.4); 3.5175 (0.6); 3.5075 (0.4); 3.3189 (1.7); 3.3101 (1.7); 3.2924 (1.9); 3.2875 (1.9); 3.1620 (0.3); 3.1158 (0.6); 3.0970 (0.6); 3.0096 (0.5); 2.9860 (0.5); 2.9634 (0.4); 2.9420 (0.4); 2.7356 (16.0); 2.1965 (0.3); 2.1794 (0.6); 2.1682 (0.6); 2.1511 (1.1); 2.1339 (0.7); 2.1228 (0.7); 2.1059 (0.4); 1.1068 (0.7); 1.0925 (1.5); 1.0852 (1.9); 1.0788 (1.1); 1.0707 (1.1); 1.0638 (1.6); 1.0569 (1.8); 1.0425 (1.0); 0.8467 (0.9); 0.8321 (2.0); 0.8255 (2.0); 0.8149 (1.9); 0.8098 (2.1); 0.7934 (0.8); 0.1076 (3.3); 0.0483 (0.6); 0.0374 (18.2); 0.0266 (1.0)
21-12: $^{1}$H-NMR(300.2 MHz, CDCl3):
δ = 8.1231 (0.7); 8.0963 (0.8); 8.0838 (5.4); 7.2986 (13.3); 7.2337 (0.5); 7.2011 (2.1); 7.1860 (0.6); 7.1744 (4.1); 7.1679 (4.0); 7.1585 (2.8); 7.1405 (3.9); 7.1135 (0.4); 7.0685 (0.3); 6.9575 (1.2); 6.9540 (1.2); 6.9314 (1.0); 6.8963 (0.7); 6.8880 (0.7); 6.8734 (1.1); 6.8638 (0.7); 6.8588 (1.0); 6.8422 (0.5); 5.3370 (9.4); 4.8993 (0.4); 4.8865 (0.6); 4.8744 (0.7); 4.8621 (0.6); 4.8488 (0.5); 3.9338 (1.0); 3.9196 (1.0); 3.8961 (1.6); 3.8819 (1.5); 3.7581 (1.5); 3.7472 (1.6); 3.7204 (1.1); 3.7095 (1.0); 3.6604 (0.4); 3.6490 (0.4); 3.5378 (0.3); 3.5173 (0.5); 3.4820 (0.4); 3.2082 (2.0); 3.2031 (2.0); 3.1818 (2.3); 2.7298 (16.0); 2.3482 (2.6); 2.2960 (10.8); 2.1820 (0.5); 2.1707 (0.5); 2.1538 (1.0); 2.1365 (0.6); 2.1256 (0.5); 1.6208 (3.8); 1.2970 (0.4); 1.1013 (0.7); 1.0865 (1.7); 1.0794 (1.9); 1.0648 (1.0); 1.0578 (1.8); 1.0512 (1.7); 1.0366 (0.9); 0.8501 (0.9); 0.8352 (2.1); 0.8298 (1.9); 0.8183 (1.8); 0.8128 (2.2); 0.7964 (0.7); 0.1080 (4.5); 0.0490 (0.6); 0.0383 (18.9); 0.0306 (0.6); 0.0289 (0.6); 0.0274 (0.7)
21-13: $^{1}$H-NMR(300.2 MHz, CDCl3):
δ = 8.2968 (16.0); 8.2877 (0.9); 8.2095 (1.2); 8.2015 (8.6); 8.1952 (3.2); 8.1789 (3.2); 8.1724 (9.7); 8.1363 (1.8); 8.1098 (1.8); 7.6874 (7.1); 7.6700 (8.5); 7.6446 (0.6); 7.5522 (4.0); 7.5026 (8.7); 7.4866 (2.5); 7.4736 (9.2); 7.4647 (3.4); 7.4571 (1.7); 7.4486 (1.2); 7.2990 (23.7); 5.3380 (0.7); 4.8694 (0.3); 4.8572 (0.5);

TABLE 34-continued 4.8424 (0.9); 4.8329 (1.4); 4.8198 (1.5); 4.8065 (1.4); 4.7974 (0.9); 4.7930 (0.8); 4.7825 (0.6); 4.7704 (0.4); 3.8673 (2.1); 3.8542 (2.2); 3.8286 (3.2); 3.8157 (3.0); 3.6878 (3.6); 3.6782 (3.6); 3.6491 (2.4); 3.6395 (2.4); 3.2991 (0.9); 3.2764 (1.0); 3.2533 (3.2); 3.2307 (3.5); 3.2226 (3.9); 3.1954 (3.3); 3.1769 (1.0); 3.1494 (1.0); 2.0829 (1.2); 1.5943 (12.8); 1.3207 (0.5); 1.2969 (1.0); 1.2732 (0.3); 0.1193 (0.4); 0.1072 (9.1); 0.0951 (0.4); 0.0479 (1.2); 0.0371 (32.3); 0.0261 (1.3)

21-14: $^1$H-NMR(300.2 MHz, CDCl3):
δ = 8.3023 (12.6); 8.0931 (1.6); 8.0664 (1.6); 7.6855 (6.2); 7.6684 (7.1); 7.6442 (0.4); 7.6104 (5.7); 7.5836 (7.0); 7.5522 (3.7); 7.4808 (1.5); 7.4715 (1.5); 7.4637 (2.2); 7.4575 (1.9); 7.4501 (1.3); 7.4420 (1.0); 7.3720 (7.8); 7.3449 (6.1); 7.2987 (22.1); 5.3380 (2.8); 4.8075 (0.4); 4.7929 (0.8); 4.7832 (1.2); 4.7706 (1.2); 4.7573 (1.1); 4.7470 (0.8); 4.7342 (0.5); 3.8505 (1.6); 3.8369 (1.7); 3.8122 (2.8); 3.7987 (2.7); 3.7038 (3.0); 3.6940 (3.1); 3.6654 (1.9); 3.6556 (1.8); 3.2150 (0.8); 3.1934 (0.8); 3.1693 (2.8); 3.1472 (3.0); 3.1389 (3.3); 3.1117 (2.9); 3.0930 (0.9); 3.0658 (0.8); 1.5896 (16.0); 1.2936 (0.4); 0.1075 (2.0); 0.0483 (1.2); 0.0375 (30.2); 0.0283 (0.9); 0.0266 (1.1)

21-15: $^1$H-NMR(300.2 MHz, CDCl3):
δ = 8.0953 (5.2); 7.9718 (0.8); 7.9462 (0.8); 7.4471 (0.7); 7.4413 (0.7); 7.4256 (0.8); 7.4201 (1.4); 7.4147 (1.0); 7.3996 (0.8); 7.3931 (0.9); 7.3320 (0.6); 7.3262 (0.6); 7.3107 (0.7); 7.2987 (10.8); 7.2834 (1.3); 7.2770 (1.0); 7.2541 (1.5); 7.2498 (1.3); 7.2277 (1.5); 7.2227 (1.6); 7.1967 (2.6); 7.1710 (2.9); 7.1566 (2.5); 6.9724 (1.4); 6.9471 (1.2); 4.8983 (0.5); 4.8863 (0.7); 4.8737 (0.7); 4.8603 (0.7); 4.8487 (0.5); 3.9378 (1.0); 3.9236 (1.0); 3.9001 (1.6); 3.8859 (1.5); 3.7658 (1.6); 3.7552 (1.6); 3.7280 (1.1); 3.7174 (1.1); 3.2752 (0.5); 3.2486 (0.5); 3.2288 (1.5); 3.2023 (1.6); 3.1902 (1.6); 3.1672 (1.5); 3.1438 (0.5); 3.1208 (0.4); 2.7387 (16.0); 2.2996 (11.9); 2.0838 (0.4); 1.6009 (13.1); 1.3441 (0.4); 1.3034 (2.7); 1.2735 (0.3); 0.9409 (0.9); 0.9192 (2.7); 0.8960 (1.1); 0.0478 (0.5); 0.0371 (13.2); 0.0278 (0.6); 0.0263 (0.6)

21-16: $^1$H-NMR(300.2 MHz, CDCl3):
δ = 8.1355 (0.6); 8.1089 (0.6); 8.0898 (4.6); 7.2990 (8.4); 7.2282 (2.0); 7.1999 (2.4); 7.1747 (1.2); 7.1660 (1.7); 7.1609 (2.5); 7.1472 (1.4); 7.1419 (2.1); 7.1146 (0.4); 6.9122 (2.2); 6.9035 (2.4); 6.8948 (0.7); 6.8874 (0.7); 6.8715 (0.9); 6.8617 (0.7); 6.8547 (0.6); 6.8408 (0.5); 6.7208 (1.3); 6.7121 (1.2); 6.6926 (1.2); 6.6838 (1.1); 5.3375 (5.4); 4.8809 (0.4); 4.8680 (0.5); 4.8557 (0.6); 4.8431 (0.5); 4.8301 (0.4); 3.9287 (0.8); 3.9146 (0.8); 3.8910 (1.3); 3.8769 (1.2); 3.8064 (0.4); 3.7798 (16.0); 3.7660 (0.4); 3.7497 (1.3); 3.7389 (1.3); 3.7120 (0.9); 3.7011 (0.9); 3.1808 (1.6); 3.1717 (1.6); 3.1555 (1.6); 3.1480 (1.6); 2.7331 (13.7); 2.1800 (0.4); 2.1686 (0.4); 2.1517 (0.8); 2.1345 (0.5); 2.1234 (0.4); 2.0835 (0.6); 1.6051 (5.9); 1.2972 (0.5); 1.0976 (0.6); 1.0824 (1.5); 1.0755 (1.7); 1.0697 (0.9); 1.0608 (0.9); 1.0538 (1.6); 1.0470 (1.5); 1.0326 (0.8); 0.8468 (0.8); 0.8318 (1.8); 0.8256 (1.8); 0.8148 (1.6); 0.8090 (1.9); 0.7927 (0.6); 0.1075 (0.8); 0.0483 (0.4); 0.0374 (11.6); 0.0266 (0.4)

21-17: $^1$H-NMR(300.2 MHz, CDCl3):
δ = 8.1059 (5.6); 8.0924 (0.9); 7.6316 (0.6); 7.6055 (1.6); 7.5793 (1.2); 7.5095 (1.4); 7.4839 (0.9); 7.4176 (1.9); 7.3996 (1.2); 7.3964 (1.2); 7.3926 (1.0); 7.3730 (0.8); 7.3696 (0.9); 7.3657 (0.8); 7.2988 (2.4); 7.1805 (2.0); 7.1553 (4.4); 6.9634 (1.3); 6.9606 (1.3); 6.9375 (1.0); 6.9345 (1.0); 6.9222 (1.2); 6.7344 (2.2); 6.5466 (1.1); 5.3335 (10.6); 4.8996 (0.4); 4.8881 (0.6); 4.8751 (0.7); 4.8618 (0.6); 4.8506 (0.5); 3.9341 (1.0); 3.9201 (1.0); 3.8963 (1.5); 3.8824 (1.5); 3.7604 (1.6); 3.7499 (1.6); 3.7226 (1.1); 3.7121 (1.0); 3.2693 (0.5); 3.2429 (0.5); 3.2231 (1.4); 3.1968 (1.4); 3.1732 (1.4); 3.1501 (1.4); 3.1270 (0.6); 3.1039 (0.5); 2.7354 (16.0); 2.3400 (0.4); 2.3315 (0.3); 2.2929 (11.0); 0.0358 (3.2)

21-18: $^1$H-NMR(300.2 MHz, CDCl3):
δ = 8.2516 (8.2); 8.1521 (0.4); 7.9205 (1.1); 7.8941 (1.1); 7.6641 (0.8); 7.6406 (1.5); 7.6187 (0.9); 7.5383 (0.7); 7.5139 (1.6); 7.4901 (1.1); 7.4407 (1.7); 7.4138 (2.1); 7.3871 (0.8); 7.2986 (3.3); 7.1914 (2.8); 7.1650 (4.2); 7.1581 (3.6); 7.1401 (1.6); 6.9821 (2.0); 6.9576 (4.5); 6.7756 (1.5); 5.3354 (16.0); 4.9066 (0.3); 4.8934 (0.6); 4.8811 (0.9); 4.8686 (0.9); 4.8554 (0.9); 4.8442 (0.7); 4.8311 (0.4); 4.3608 (1.1); 3.9397 (1.3); 3.9257 (1.3); 3.9017 (2.1); 3.8878 (2.0); 3.7684 (2.1); 3.7579 (2.1); 3.7305 (1.5); 3.7200 (1.4); 3.2923 (0.9); 3.2653 (0.8); 3.2460 (1.9); 3.2190 (1.9); 3.1763 (1.8); 3.1537 (1.9); 3.1302 (0.9); 3.1074 (0.8); 2.3400 (0.8); 2.2951 (15.9); 1.6225 (3.9); 0.0366 (4.4)

21-19: $^1$H-NMR(300.2 MHz, CDCl3):
δ = 8.1689 (0.8); 8.1423 (0.8); 8.0647 (5.2); 7.5246 (2.0); 7.4359 (1.3); 7.4097 (2.0); 7.3124 (1.4); 7.2988 (10.6); 7.2882 (1.0); 7.1878 (0.4); 7.1692 (2.3); 7.1611 (2.2); 7.1571 (1.8); 7.1441 (3.8); 6.8988 (0.7); 6.8901 (0.7); 6.8764 (1.2); 6.8637 (0.8); 6.8593 (0.6); 6.8449 (0.5); 6.7775 (1.1); 6.5901 (2.2); 6.4028 (1.1); 5.3377 (1.2); 4.9565 (0.4); 4.9439 (0.6); 4.9310 (0.6); 4.9177 (0.6); 4.9061 (0.4); 3.9447 (1.0); 3.9306 (1.0); 3.9066 (1.5); 3.8926 (1.5); 3.7699 (1.5); 3.7593 (1.5); 3.7319 (1.1); 3.7213 (1.0); 3.2983 (1.6); 3.2910 (1.6); 3.2699 (2.0); 2.7492 (0.4); 2.7331 (16.0); 2.1817 (0.5); 2.1705 (0.5); 2.1534 (1.0); 2.1361 (0.6); 2.1252 (0.5); 2.0836 (1.1); 1.6023 (7.9); 1.3210 (0.4); 1.2972 (0.9); 1.1071 (0.7); 1.0926 (1.6); 1.0854 (2.0); 1.0791 (1.1); 1.0709 (1.1); 1.0639 (1.7); 1.0570 (1.8); 1.0427 (0.9); 0.9190 (0.3); 0.8490 (0.9); 0.8343 (2.1); 0.8314 (1.9); 0.8281 (2.0); 0.8172 (1.9); 0.8119 (2.1); 0.7955 (0.7); 0.1072 (3.8); 0.0479 (0.5); 0.0371 (14.4); 0.0262 (0.6)

21-20: $^1$H-NMR(300.2 MHz, CDCl3):
δ = 8.1518 (0.8); 8.1255 (0.8); 8.0749 (5.3); 7.3293 (2.3); 7.2991 (10.5); 7.1924 (0.5); 7.1745 (3.1); 7.1685 (3.9); 7.1462 (3.8); 7.1191 (0.4); 6.9571 (1.2); 6.9488 (1.2); 6.9291 (1.1); 6.9209 (1.0); 6.8980 (0.7); 6.8896 (0.8); 6.8754 (1.2); 6.8661 (0.7); 6.8608 (1.0); 6.8442 (0.5); 6.7258 (1.5); 6.4819 (3.2); 6.2380 (1.6); 5.3377 (1.5); 4.9136 (0.4); 4.9014 (0.6); 4.8887 (0.6); 4.8753 (0.6); 4.8636 (0.5); 3.9377 (1.0); 3.9236 (1.0); 3.8997 (1.5); 3.8858 (1.4); 3.7622 (1.5); 3.7515 (1.5); 3.7242 (1.0); 3.7136 (1.0); 3.2348 (2.0); 3.2273 (2.0); 3.2086 (2.2); 3.2042 (2.2); 2.7360 (16.0); 2.1792 (0.5); 2.1682 (0.6); 2.1510 (1.0); 2.1339 (0.6); 2.1230 (0.5); 1.6046 (6.7); 1.1052 (0.7); 1.0906 (1.6); 1.0835 (2.0); 1.0690 (1.1); 1.0619 (1.7); 1.0552 (1.8); 1.0408 (0.9); 0.8475 (1.0); 0.8327 (2.1); 0.8301 (2.0); 0.8264 (2.1); 0.8157 (1.9); 0.8101 (2.2); 0.7940 (0.7); 0.1073 (0.5); 0.0480 (0.4); 0.0372 (12.3); 0.0263 (0.5)

21-21: $^1$H-NMR(300.2 MHz, CDCl3):
δ = 8.1740 (0.8); 8.1470 (0.9); 8.0704 (5.3); 7.3689 (2.4); 7.3406 (2.8); 7.2988 (13.8); 7.2694 (1.8); 7.2646 (1.8); 7.1920 (0.4); 7.1733 (1.6); 7.1640 (2.7); 7.1461 (3.8); 7.1188 (0.4); 7.0539 (1.1); 7.0496 (1.0); 7.0259 (0.9); 6.8979 (0.7); 6.8896 (0.8); 6.8753 (1.2); 6.8659 (0.7); 6.8605 (1.1); 6.8438 (0.6); 5.3381 (1.0); 4.9282 (0.5); 4.9154 (0.7); 4.9029 (0.7); 4.8898 (0.7); 4.8774 (0.5); 3.9419 (1.0); 3.9279 (1.0); 3.9038 (1.5); 3.8900 (1.4); 3.7649 (1.5); 3.7544 (1.5); 3.7268 (1.0); 3.7164 (1.0); 3.2546 (2.0); 3.2473 (2.1); 3.2281 (2.3); 3.2242 (2.4); 2.7369 (16.0); 2.1796 (0.5); 2.1681 (0.6); 2.1514 (1.0); 2.1343 (0.6); 2.1233 (0.6); 2.0838 (0.6); 1.5965 (7.4); 1.3210 (0.4); 1.2974 (1.2); 1.1046 (0.7); 1.0899 (1.8); 1.0829 (2.0); 1.0683 (1.1); 1.0613 (1.8); 1.0546 (1.9); 1.0403 (0.9); 0.9410 (0.3); 0.9192 (0.9); 0.8964 (0.4); 0.8464 (0.9); 0.8315 (2.2); 0.8263 (2.2); 0.8146 (2.0); 0.8093 (2.3); 0.7931 (0.7); 0.0480 (0.7); 0.0371 (20.1); 0.0263 (0.8)

TABLE 34-continued 21-22: $^{1}$H-NMR(499.9 MHz, $d_6$-DMSO):
δ = 8.7876 (2.3); 8.7708 (2.2); 7.5690 (7.6); 7.2853 (3.7); 7.1907 (3.7); 7.1683 (1.0); 7.1521 (3.0); 7.1440 (2.0); 7.1382 (5.2); 7.1307 (1.7); 7.1272 (1.8); 7.1147 (0.7); 7.1110 (0.5); 7.0821 (3.9); 6.9136 (1.0); 6.9073 (1.1); 6.9005 (1.8); 6.8959 (1.5); 6.8851 (1.0); 6.8820 (0.8); 4.4489 (0.6); 4.4390 (0.8); 4.4314 (1.0); 4.4217 (1.0); 4.4128 (0.7); 4.4033 (0.5); 3.8470 (1.3); 3.8377 (1.4); 3.8248 (2.0); 3.8155 (1.7); 3.7506 (1.8); 3.7381 (1.9); 3.7283 (1.3); 3.7159 (1.2); 3.3402 (33.7); 2.9809 (1.1); 2.9715 (1.2); 2.9533 (1.5); 2.9441 (1.4); 2.8227 (1.5); 2.8037 (1.5); 2.7953 (1.2); 2.7763 (1.0); 2.5890 (19.3); 2.5076 (1.5); 2.5041 (1.9); 2.5008 (1.4); 2.1623 (16.0); 2.0781 (0.5); 2.0678 (0.9); 2.0612 (1.0); 2.0511 (1.6); 2.0409 (1.0); 2.0343 (0.9); 2.0239 (0.4); 1.0292 (1.3); 1.0206 (3.0); 1.0164 (3.2); 1.0083 (1.8); 1.0039 (2.9); 0.9996 (2.9); 0.9916 (1.1); 0.7815 (1.5); 0.7731 (3.4); 0.7697 (3.7); 0.7632 (3.3); 0.7593 (3.3); 0.7505 (1.0)
21-23: $^{1}$H-NMR(300.2 MHz, CDCl3):
δ = 8.1287 (0.8); 8.1011 (0.8); 8.0838 (5.4); 7.3700 (2.3); 7.2989 (5.4); 7.2003 (2.2); 7.1917 (0.6); 7.1739 (3.4); 7.1646 (2.7); 7.1595 (2.8); 7.1417 (2.9); 7.1146 (0.7); 6.9988 (1.3); 6.9959 (1.3); 6.9731 (1.0); 6.8947 (0.7); 6.8871 (0.8); 6.8718 (1.1); 6.8621 (0.7); 6.8565 (1.0); 6.8410 (0.5); 4.9293 (0.5); 4.9162 (0.7); 4.9038 (0.7); 4.8915 (0.7); 4.8784 (0.5); 3.9454 (1.0); 3.9314 (1.0); 3.9077 (1.6); 3.8937 (1.5); 3.7643 (1.5); 3.7536 (1.6); 3.7266 (1.1); 3.7158 (1.0); 3.2135 (3.6); 3.1888 (3.6); 2.7288 (16.0); 2.3570 (0.6); 2.3446 (1.0); 2.2942 (11.3); 2.1824 (0.5); 2.1713 (0.5); 2.1542 (1.0); 2.1370 (0.6); 2.1260 (0.6); 1.6160 (1.1); 1.4701 (0.6); 1.2942 (0.6); 1.1013 (0.7); 1.0863 (1.8); 1.0793 (2.0); 1.0648 (1.1); 1.0578 (1.9); 1.0510 (1.8); 1.0366 (0.9); 0.8494 (0.9); 0.8346 (2.2); 0.8293 (2.1); 0.8176 (1.9); 0.8122 (2.3); 0.7958 (0.7); 0.1099 (0.3); 0.0381 (7.4)
21-24: $^{1}$H-NMR(400.1 MHz, CDCl3):
δ = 8.1965 (1.1); 8.1766 (1.1); 8.0709 (5.6); 7.2898 (2.9); 7.2617 (11.1); 7.2001 (1.3); 7.1799 (1.7); 7.1760 (1.6); 7.1446 (0.4); 7.1302 (2.8); 7.1249 (3.0); 7.1122 (4.0); 7.0931 (0.4); 7.0663 (2.9); 7.0459 (2.1); 6.8556 (0.8); 6.8489 (0.9); 6.8391 (1.4); 6.8306 (1.2); 6.8155 (0.6); 4.6895 (0.6); 4.6806 (0.8); 4.6715 (0.9); 4.6615 (0.8); 4.6527 (0.6); 3.8142 (1.1); 3.8039 (1.0); 3.7858 (1.6); 3.7754 (1.5); 3.6765 (1.6); 3.6694 (1.6); 3.6481 (1.2); 3.6410 (1.1); 3.0370 (3.8); 3.0182 (4.0); 2.9581 (1.5); 2.8851 (1.4); 2.7112 (16.0); 2.6750 (0.4); 2.6417 (0.3); 2.3943 (13.6); 2.3557 (0.5); 2.3481 (0.4); 2.2663 (0.4); 2.1409 (0.6); 2.1323 (0.7); 2.1199 (1.2); 2.1069 (0.8); 2.0989 (0.7); 2.0855 (0.4); 1.5742 (2.8); 1.0576 (0.8); 1.0461 (2.2); 1.0414 (2.4); 1.0302 (1.4); 1.0249 (2.3); 1.0204 (2.3); 1.0095 (0.9); 0.8054 (1.0); 0.7933 (2.9); 0.7813 (2.6); 0.7778 (2.8); 0.7655 (0.8); −0.0002 (14.8)
21-25: $^{1}$H-NMR(400.1 MHz, CDCl3):
δ = 8.2421 (7.0); 8.2130 (1.3); 7.3753 (1.4); 7.3555 (3.1); 7.3357 (1.8); 7.2614 (12.0); 7.0504 (4.7); 7.0311 (5.0); 7.0144 (1.8); 7.0100 (1.9); 6.9944 (1.6); 6.9892 (1.7); 6.9646 (3.6); 6.9255 (3.4); 6.8781 (2.1); 6.8590 (1.6); 4.6679 (0.7); 4.6601 (1.0); 4.6505 (1.1); 4.6409 (1.0); 4.6320 (0.7); 4.6228 (0.4); 3.8142 (1.2); 3.8043 (1.2); 3.7858 (1.9); 3.7760 (1.8); 3.6960 (2.0); 3.6892 (2.0); 3.6676 (1.3); 3.6609 (1.3); 3.0220 (4.8); 3.0033 (4.5); 2.9580 (0.9); 2.8848 (0.8); 2.3626 (16.0); 2.2659 (15.2); 1.9768 (0.4); 1.9641 (0.8); 1.9557 (0.9); 1.9436 (1.6); 1.9312 (1.0); 1.9226 (0.9); 1.9102 (0.4); 1.5745 (20.6); 1.0443 (0.9); 1.0320 (2.8); 1.0279 (2.9); 1.0114 (2.9); 1.0073 (2.7); 0.9959 (1.0); 0.7609 (1.1); 0.7486 (3.6); 0.7332 (3.4); 0.7208 (0.9); −0.0002 (9.2)
21-26: $^{1}$H-NMR(400.1 MHz, CDCl3):
δ = 8.2401 (6.7); 8.1113 (1.3); 8.0920 (1.3); 7.2611 (7.1); 7.1552 (0.6); 7.1343 (3.0); 7.1195 (4.5); 7.1100 (1.9); 7.0950 (0.5); 7.0636 (2.5); 7.0445 (3.0); 6.9546 (3.5); 6.8829 (1.2); 6.8722 (3.2); 6.8596 (2.2); 4.6867 (0.4); 4.6771 (0.8); 4.6684 (1.0); 4.6588 (1.1); 4.6496 (1.0); 4.6403 (0.7); 4.6320 (0.4); 3.8215 (1.2); 3.8113 (1.2); 3.7932 (1.9); 3.7830 (1.8); 3.6999 (2.0); 3.6929 (2.0); 3.6716 (1.3); 3.6646 (1.2); 3.0421 (4.9); 3.0235 (4.8); 2.9579 (1.3); 2.8849 (1.3); 2.3683 (16.0); 2.2537 (15.2); 2.1541 (0.4); 2.1415 (0.8); 2.1329 (0.9); 2.1204 (1.5); 2.1079 (0.9); 2.0991 (0.8); 2.0864 (0.4); 1.5844 (10.4); 1.0729 (0.9); 1.0613 (2.7); 1.0567 (2.8); 1.0401 (2.8); 1.0357 (2.6); 1.0247 (1.0); 0.8147 (1.2); 0.8028 (3.5); 0.7903 (3.1); 0.7871 (3.3); 0.7748 (0.9); −0.0002 (5.4)
21-27: $^{1}$H-NMR(400.1 MHz, CDCl3):
δ = 8.2684 (6.6); 8.1165 (1.2); 8.0974 (1.2); 8.0164 (0.7); 7.6177 (1.0); 7.5983 (2.4); 7.5786 (1.7); 7.5088 (2.3); 7.4896 (1.5); 7.4046 (3.0); 7.3707 (1.8); 7.3495 (1.5); 7.2620 (12.0); 7.0473 (2.4); 7.0281 (3.0); 6.9631 (3.5); 6.8782 (2.0); 6.8530 (2.1); 6.7114 (2.9); 6.5708 (1.5); 4.6922 (0.4); 4.6823 (0.7); 4.6737 (1.0); 4.6646 (1.0); 4.6545 (1.0); 4.6464 (0.7); 4.6361 (0.4); 3.8304 (1.2); 3.8204 (1.2); 3.8020 (1.9); 3.7920 (1.8); 3.7106 (2.0); 3.7040 (2.0); 3.6824 (1.3); 3.6758 (1.2); 3.0538 (0.4); 3.0327 (3.1); 3.0196 (2.6); 3.0120 (2.5); 2.9758 (0.3); 2.9583 (4.2); 2.8845 (4.0); 2.3613 (16.0); 2.2595 (15.4); 1.5863 (11.1); −0.0002 (9.0)
21-28: $^{1}$H-NMR(400.1 MHz, CDCl3):
δ = 8.2539 (6.9); 8.0583 (1.2); 8.0391 (1.2); 7.5067 (1.6); 7.4865 (2.2); 7.4038 (2.4); 7.3991 (3.7); 7.3942 (2.5); 7.3901 (2.2); 7.3694 (3.4); 7.3492 (1.7); 7.2612 (5.9); 7.2017 (1.9); 7.1973 (1.8); 7.1813 (1.5); 7.1771 (1.4); 7.0454 (2.4); 7.0263 (3.0); 6.9676 (3.4); 6.8869 (2.0); 6.8678 (1.6); 4.6826 (0.4); 4.6731 (0.7); 4.6645 (1.0); 4.6549 (1.0); 4.6455 (1.0); 4.6366 (0.7); 4.6267 (0.4); 3.8266 (1.2); 3.8165 (1.2); 3.7982 (1.9); 3.7882 (1.8); 3.7086 (2.0); 3.7019 (2.0); 3.6803 (1.3); 3.6736 (1.2); 3.0306 (3.7); 3.0141 (2.8); 3.0095 (2.8); 2.9573 (1.5); 2.8833 (1.4); 2.3595 (16.0); 2.2715 (15.1); 1.5862 (9.1); −0.0002 (4.4)
21-29: $^{1}$H-NMR(400.1 MHz, CDCl3):
δ = 8.2563 (6.9); 8.0676 (1.2); 8.0485 (1.2); 8.0164 (0.6); 7.4493 (1.3); 7.4290 (3.3); 7.4088 (2.3); 7.3538 (2.3); 7.3328 (1.4); 7.2609 (7.1); 7.2515 (2.4); 7.2465 (3.7); 7.2416 (2.1); 7.1557 (1.8); 7.1519 (1.7); 7.1360 (1.6); 7.1315 (1.4); 7.0476 (2.4); 7.0284 (3.0); 6.9665 (3.4); 6.8863 (2.0); 6.8673 (1.6); 4.6842 (0.4); 4.6743 (0.7); 4.6664 (1.0); 4.6569 (1.0); 4.6473 (1.0); 4.6388 (0.7); 4.6285 (0.4); 3.8262 (1.2); 3.8161 (1.2); 3.7978 (1.9); 3.7879 (1.8); 3.7083 (2.1); 3.7016 (2.0); 3.6799 (1.3); 3.6733 (1.2); 3.0508 (0.4); 3.0329 (3.0); 3.0294 (3.1); 3.0162 (2.6); 3.0089 (2.5); 2.9737 (0.3); 2.9576 (3.4); 2.8841 (3.2); 2.3607 (16.0); 2.2697 (15.2); 1.5838 (2.6); −0.0002 (9.2)
21-30: $^{1}$H-NMR(400.1 MHz, CDCl3):
δ = 8.2241 (7.2); 8.0182 (3.0); 8.0014 (1.4); 7.6167 (1.0); 7.5969 (2.5); 7.5771 (1.7); 7.5067 (2.3); 7.4875 (1.6); 7.3966 (3.2); 7.3696 (1.9); 7.3496 (1.6); 7.3269 (3.9); 7.2623 (12.4); 7.1392 (2.8); 7.1199 (3.5); 6.9803 (2.2); 6.9619 (1.7); 6.8530 (1.5); 6.7123 (3.1); 6.5716 (1.5); 4.8934 (0.4); 4.8838 (0.7); 4.8745 (1.0); 4.8651 (1.0); 4.8558 (1.0); 4.8470 (0.7); 4.8368 (0.4); 3.9050 (1.4); 3.8948 (1.4); 3.8765 (1.9); 3.8664 (1.8); 3.7293 (1.9); 3.7219 (2.0); 3.7009 (1.5); 3.6935 (1.4); 3.2422 (1.0); 3.2218 (1.0); 3.2073 (1.9); 3.1871 (1.8); 3.1416 (1.8); 3.1246 (1.8); 3.1067 (1.0); 3.0899 (0.9); 2.9579 (12.3); 2.8844 (11.6); 2.2849 (0.7); 2.2625 (16.0); 1.5788 (5.7); −0.0002 (16.0)

TABLE 34-continued 21-31: $^1$H-NMR(400.1 MHz, CDCl3):
δ = 8.1057 (5.5); 7.9851 (1.0); 7.9661 (1.0); 7.6073 (0.8); 7.5867 (1.9); 7.5676 (1.8); 7.5473 (1.0); 7.3795 (1.0); 7.3597 (1.7); 7.3403 (0.7); 7.2614 (20.3); 7.0691 (2.0); 7.0499 (2.4); 6.9502 (2.9); 6.8736 (1.6); 6.8541 (1.3); 4.7029 (0.3); 4.6932 (0.6); 4.6834 (0.8); 4.6745 (0.9); 4.6646 (0.8); 4.6556 (0.6); 3.8291 (1.0); 3.8185 (1.0); 3.8009 (1.6); 3.7905 (1.5); 3.7094 (1.7); 3.7022 (1.7); 3.6811 (1.1); 3.6739 (1.0); 3.0500 (3.9); 3.0313 (3.3); 2.9584 (1.3); 2.8854 (1.2); 2.7219 (16.0); 2.3724 (13.4); 2.2405 (12.6); 1.5600 (8.2); −0.0002 (26.9)
21-32: $^1$H-NMR(400.1 MHz, CDCl3):
δ = 8.2363 (6.9); 8.1320 (1.2); 8.1122 (1.3); 7.2957 (3.3); 7.2614 (7.9); 7.2051 (1.5); 7.1849 (2.0); 7.1810 (1.8); 7.1625 (0.6); 7.1420 (2.6); 7.1354 (1.9); 7.1259 (4.6); 7.1149 (1.8); 7.0995 (0.5); 7.0945 (0.4); 7.0568 (3.2); 7.0366 (2.5); 6.8876 (0.9); 6.8780 (1.0); 6.8717 (1.5); 6.8652 (1.4); 6.8525 (0.9); 6.8477 (0.8); 4.6903 (0.4); 4.6808 (0.7); 4.6723 (1.0); 4.6626 (1.0); 4.6534 (1.0); 4.6444 (0.7); 4.6351 (0.4); 3.8172 (1.2); 3.8072 (1.2); 3.7888 (1.9); 3.7787 (1.8); 3.6748 (1.9); 3.6679 (1.9); 3.6463 (1.3); 3.6393 (1.3); 3.0370 (4.9); 3.0183 (4.8); 2.9577 (1.4); 2.8846 (1.3); 2.3896 (16.0); 2.1574 (0.3); 2.1440 (0.7); 2.1356 (0.8); 2.1230 (1.4); 2.1103 (0.9); 2.1020 (0.8); 2.0889 (0.4); 1.5655 (4.8); 1.0761 (0.9); 1.0643 (2.6); 1.0598 (2.7); 1.0433 (2.7); 1.0387 (2.6); 1.0277 (1.0); 0.8151 (1.1); 0.8029 (3.4); 0.7907 (3.0); 0.7873 (3.3); 0.7751 (0.9); −0.0002 (10.5)
21-33: $^1$H-NMR(400.1 MHz, CDCl3):
δ = 8.2021 (7.4); 8.1382 (1.2); 8.1182 (1.2); 8.0192 (1.8); 7.3742 (1.6); 7.3544 (3.4); 7.3348 (5.7); 7.2617 (33.1); 7.1329 (2.8); 7.1135 (3.5); 7.0510 (2.2); 7.0318 (2.0); 7.0076 (1.7); 7.0035 (1.8); 6.9884 (1.5); 6.9832 (1.7); 6.9655 (2.2); 6.9466 (1.8); 6.9186 (3.4); 4.8826 (0.4); 4.8717 (0.7); 4.8637 (1.0); 4.8544 (1.0); 4.8449 (1.0); 4.8350 (0.7); 4.8257 (0.4); 3.8942 (1.4); 3.8840 (1.4); 3.8659 (2.0); 3.8559 (1.8); 3.7141 (1.9); 3.7066 (2.0); 3.6857 (1.5); 3.6783 (1.5); 3.2087 (0.7); 3.1892 (0.7); 3.1742 (2.0); 3.1545 (2.0); 3.1397 (2.0); 3.1222 (2.1); 3.1048 (0.8); 3.0875 (0.6); 2.9587 (12.1); 2.8858 (11.4); 2.2935 (0.5); 2.2687 (16.0); 1.9776 (0.4); 1.9644 (0.8); 1.9561 (1.0); 1.9440 (1.6); 1.9312 (1.0); 1.9228 (0.9); 1.9104 (0.4); 1.5618 (20.4); 1.0463 (0.9); 1.0342 (2.8); 1.0295 (3.0); 1.0133 (3.0); 1.0089 (2.8); 0.9974 (1.1); 0.7615 (1.1); 0.7496 (3.7); 0.7376 (3.1); 0.7334 (3.6); 0.7214 (1.0); −0.0002 (42.6)
21-34: $^1$H-NMR(400.1 MHz, CDCl3):
δ = 8.2016 (7.2); 8.0188 (2.5); 8.0066 (1.4); 7.3355 (3.8); 7.2623 (9.6); 7.1500 (3.0); 7.1360 (5.2); 7.1307 (4.6); 7.1230 (4.4); 7.1023 (0.6); 6.9693 (2.1); 6.9498 (1.7); 6.8819 (0.9); 6.8693 (1.5); 6.8586 (1.6); 6.8483 (0.9); 6.8416 (0.8); 4.8910 (0.4); 4.8810 (0.7); 4.8722 (1.0); 4.8627 (1.0); 4.8531 (1.0); 4.8441 (0.7); 4.8342 (0.4); 3.9018 (1.4); 3.8916 (1.4); 3.8734 (1.9); 3.8632 (1.8); 3.7233 (1.9); 3.7156 (1.9); 3.6949 (1.5); 3.6871 (1.4); 3.2159 (0.5); 3.1957 (0.5); 3.1813 (2.3); 3.1625 (3.0); 3.1488 (2.3); 3.1314 (0.5); 3.1141 (0.4); 2.9580 (11.4); 2.8848 (10.7); 2.2636 (16.0); 2.1549 (0.3); 2.1412 (0.8); 2.1328 (0.9); 2.1202 (1.5); 2.1075 (1.0); 2.0994 (0.9); 2.0861 (0.4); 1.5849 (3.4); 1.0747 (0.9); 1.0631 (2.7); 1.0586 (2.8); 1.0419 (2.8); 1.0375 (2.7); 1.0264 (1.1); 0.8155 (1.1); 0.8033 (3.4); 0.7912 (3.1); 0.7876 (3.3); 0.7755 (0.9); −0.0002 (12.4)
21-35: $^1$H-NMR(300.2 MHz, CDCl3):
δ = 8.2404 (0.7); 8.2149 (0.7); 8.1141 (4.5); 7.2986 (8.0); 7.1821 (0.4); 7.1631 (1.9); 7.1555 (2.3); 7.1380 (3.4); 7.1247 (1.9); 7.1121 (0.4); 7.0993 (2.0); 6.8933 (1.6); 6.8865 (1.5); 6.8707 (1.6); 6.8621 (1.6); 6.8401 (0.5); 6.7705 (2.0); 5.3375 (0.7); 4.8836 (0.4); 4.8725 (0.5); 4.8593 (0.6); 4.8463 (0.5); 4.8345 (0.4); 3.8782 (0.7); 3.8642 (0.7); 3.8407 (1.3); 3.8267 (1.2); 3.7612 (1.4); 3.7513 (1.4); 3.7237 (0.8); 3.7138 (0.7); 3.2725 (1.4); 3.2623 (1.6); 3.2499 (1.4); 3.2358 (1.4); 2.7393 (13.4); 2.2968 (0.8); 2.2827 (9.4); 2.1821 (0.5); 2.1709 (0.5); 2.1537 (1.0); 2.1420 (0.8); 2.1353 (0.8); 2.1254 (0.8); 2.1141 (0.9); 2.0965 (0.5); 2.0862 (0.5); 1.6090 (16.0); 1.0992 (0.6); 1.0842 (1.6); 1.0772 (1.8); 1.0624 (1.6); 1.0549 (2.3); 1.0489 (2.7); 1.0340 (1.9); 1.0219 (1.2); 1.0159 (1.5); 1.0045 (0.7); 0.8480 (0.8); 0.8330 (2.0); 0.8279 (1.9); 0.8162 (1.8); 0.8107 (2.0); 0.7944 (0.6); 0.7238 (0.7); 0.7138 (1.5); 0.7076 (1.5); 0.6973 (1.6); 0.6904 (0.9); 0.1076 (2.3); 0.0483 (0.4); 0.0374 (9.5); 0.0266 (0.4)

TABLE 35

Compounds according to formula (22)

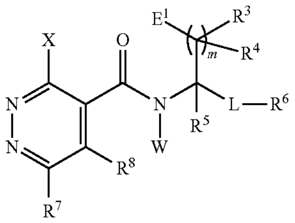

(22)

In table 35, "#" denotes the point of attachment to the L—$R^6$ group and "*" denotes the point of attachment to the pyridazin-4-yl group.

| Ex No | $R^7$ | $R^8$ | X | 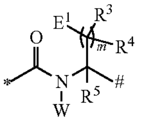 | L—$R^6$ | LogP |
|---|---|---|---|---|---|---|
| 22-01 | Cl | H | Cl | 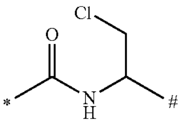 | (2,4-dimethylphenyl)methyl | 3.51[a] |
| 22-02 | $CH_3$ | H | Cl | 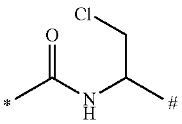 | (2,4-dimethylphenyl)methyl | 2.91[a] |
| 22-03 | Cl | H | Cl | 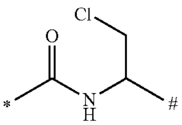 | (4-bromo-2-methylphenyl)methyl | 3.66[a] |
| 22-04 | $CH_3$ | H | Cl | 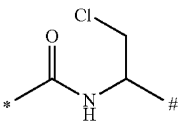 | (4-bromo-2-methylphenyl)methyl | 3.06[a] |
| 22-05 | Cl | H | Cl | 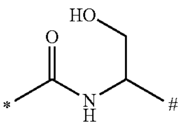 | (2,4-dichlorophenyl)methyl | 2.50[a] |
| 22-06 | $CH_3$ | H | Cl | 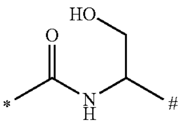 | (2,4-dichlorophenyl)methyl | 2.06[a] |

TABLE 35

22-01: $^1$H-NMR(400.1 MHz, CDCl3):
δ = 7.7580 (6.8); 7.2614 (12.3); 7.0994 (2.3); 7.0803 (3.1); 7.0260 (3.4); 6.9891 (2.1); 6.9694 (1.5); 6.8424 (1.0); 6.8226 (0.9); 4.6957 (0.4); 4.6842 (0.7); 4.6763 (1.1); 4.6670 (0.9); 4.6564 (1.1); 4.6476 (0.6); 4.6367 (0.4); 3.8240 (1.3); 3.8148 (1.3); 3.7952 (2.0); 3.7862 (1.8); 3.6895 (2.0); 3.6822 (2.0); 3.6607 (1.4); 3.6534 (1.3); 3.0370 (5.0); 3.0178 (4.7); 2.9557 (1.0); 2.8759 (1.0); 2.3856 (16.0); 2.3063 (15.0); 2.2812 (0.4); 1.5601 (11.3); −0.0002 (16.5)
22-02: $^1$H-NMR(400.1 MHz, CDCl3):
δ = 7.6311 (5.0); 7.2619 (7.1); 7.1157 (1.9); 7.0966 (2.4); 7.0214 (2.7); 6.9844 (1.6); 6.9654 (1.2); 6.9214 (0.8); 6.9012 (0.8); 4.6932 (0.3); 4.6814 (0.5); 4.6735 (0.8); 4.6640 (0.7); 4.6544 (0.8); 4.6465 (0.5); 3.8183 (1.0); 3.8091 (1.0); 3.7896 (1.6); 3.7805 (1.5); 3.6804 (1.6); 3.6731 (1.6); 3.6518 (1.1); 3.6444 (1.1); 3.0375 (3.8); 3.0183 (2.7); 2.7604 (16.0); 2.3922 (12.8); 2.3024 (12.0); 1.5770 (8.4); −0.0002 (9.5)

TABLE 35-continued 22-03: $^1$H-NMR(400.1 MHz, CDCl3):
δ = 8.1668 (0.9); 8.0091 (0.5); 7.8283 (6.5); 7.3646 (3.2); 7.3137 (1.8); 7.2936 (2.1); 7.2620 (27.6); 7.1017 (3.4); 7.0815 (2.7); 6.9418 (1.0); 6.9215 (1.0); 4.6923 (0.4); 4.6714 (1.0); 4.6623 (0.8); 4.6531 (1.0); 4.6338 (0.4); 3.8111 (1.3); 3.8026 (1.3); 3.7820 (1.9); 3.7735 (1.7); 3.6539 (2.0); 3.6468 (1.9); 3.6250 (1.6); 3.6178 (1.6); 3.0516 (0.4); 3.0312 (3.8); 3.0161 (2.6); 3.0091 (2.6); 2.9756 (0.4); 2.9577 (3.2); 2.8802 (2.9); 2.4143 (16.0); 2.3922 (2.2); 1.5604 (20.4); 1.2548 (0.6); −0.0002 (33.4)
22-04: $^1$H-NMR(400.1 MHz, CDCl3):
δ = 7.6381 (5.1); 7.3565 (2.6); 7.3041 (1.3); 7.2839 (1.6); 7.2797 (1.5); 7.2627 (7.8); 7.1096 (2.6); 7.0893 (2.1); 6.9978 (0.9); 6.9765 (0.8); 4.6988 (0.3); 4.6789 (0.8); 4.6698 (0.7); 4.6604 (0.8); 3.8127 (1.1); 3.8038 (1.1); 3.7838 (1.6); 3.7750 (1.4); 3.6539 (1.6); 3.6469 (1.6); 3.6250 (1.2); 3.6179 (1.1); 3.0328 (3.8); 3.0155 (2.5); 3.0121 (2.5); 2.9556 (0.6); 2.8763 (0.6); 2.7692 (16.0); 2.4174 (13.3); 1.5769 (6.0); −0.0002 (10.2)
22-05: $^1$H-NMR(400.1 MHz, CDCl3):
δ = 18.7908 (0.3); 16.3068 (0.3); 9.4412 (0.4); 8.0243 (0.3); 8.0119 (1.0); 7.7659 (16.0); 7.5199 (0.6); 7.4619 (0.4); 7.4202 (8.7); 7.4156 (8.3); 7.3272 (0.5); 7.3005 (5.3); 7.2798 (11.9); 7.2618 (113.7); 7.2453 (6.8); 7.2406 (5.9); 7.2247 (3.0); 7.2198 (2.6); 7.1244 (0.4); 6.9987 (0.9); 6.9608 (2.2); 6.9437 (2.2); 6.8868 (0.4); 4.5419 (0.8); 4.5325 (1.1); 4.5225 (1.6); 4.5136 (2.8); 4.5036 (2.4); 4.4936 (2.6); 4.4856 (1.7); 4.4744 (1.2); 4.4673 (0.6); 3.8436 (1.8); 3.8179 (3.5); 3.7669 (3.7); 3.7607 (3.6); 3.7400 (2.0); 3.7336 (1.7); 3.7117 (0.4); 3.5758 (0.4); 3.5509 (0.4); 3.5296 (0.4); 3.5157 (0.4); 3.2221 (0.3); 3.1851 (0.5); 3.1484 (8.7); 3.1295 (8.5); 3.0928 (0.4); 2.9586 (5.4); 2.9111 (0.4); 2.8814 (5.1); 1.9549 (0.7); 1.9279 (2.4); 1.7447 (0.4); 1.6874 (0.4); 1.6781 (0.4); 1.5566 (103.3); 1.4813 (0.4); 1.3480 (0.4); 1.2869 (0.4); 1.2564 (0.9); 1.2369 (0.4); 0.8855 (0.4); 0.8455 (0.4); 0.1459 (0.8); −0.0002 (147.4); −0.1491 (0.7); −3.4400 (0.4)
22-06: $^1$H-NMR(400.1 MHz, CDCl3):
δ = 7.5766 (5.2); 7.4137 (3.0); 7.4088 (2.9); 7.3099 (1.9); 7.2894 (3.3); 7.2619 (38.8); 7.2370 (2.1); 7.2322 (1.9); 7.2165 (1.1); 7.2116 (1.1); 6.9980 (0.4); 6.9818 (0.8); 6.9619 (0.8); 4.5338 (0.4); 4.5240 (0.6); 4.5143 (1.0); 4.5039 (0.8); 4.4945 (0.9); 4.4859 (0.6); 4.4746 (0.4); 3.8543 (0.6); 3.8283 (1.1); 3.7658 (1.1); 3.7338 (0.6); 3.1495 (4.1); 3.1305 (3.9); 2.9584 (1.6); 2.8825 (1.5); 2.7561 (16.0); 2.7243 (1.1); 2.1569 (0.8); 1.5602 (30.8); 1.2889 (0.5); 1.2726 (0.5); 1.1257 (0.4); 1.1093 (0.4); −0.0002 (50.5)

TABLE 37

Compounds according to formula (23)

(23)

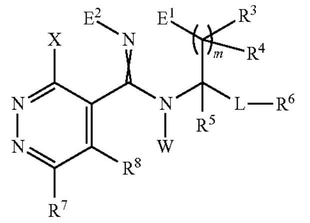

In table 37, "#" denotes the point of attachment to the L—R$^6$ group and "*" denotes the point of attachment to the pyridazin-4-yl group.

| Ex No | $R^7$ | $R^8$ | X | 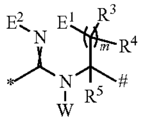 | L—$R^6$ | LogP |
|---|---|---|---|---|---|---|
| 23-01 | Cl | H | Cl | 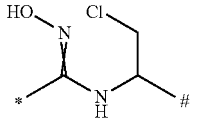 | (2,4-dimethylphenyl)methyl | 3.40[a] |
| 23-02 | Cl | H | Cl | 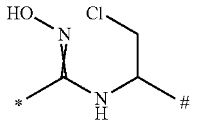 | (4-bromo-2-methylphenyl)methyl | 3.54[a] |
| 23-03 | $CH_3$ | H | Cl | 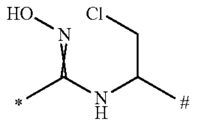 | (4-bromo-2-methylphenyl)methyl | 2.98[a] |

TABLE 37-continued

Compounds according to formula (23)

(23)

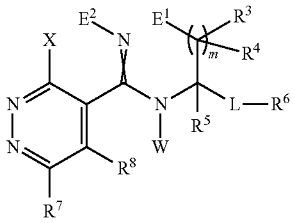

In table 37, "#" denotes the point of attachment to the L—$R^6$ group and "*" denotes the point of attachment to the pyridazin-4-yl group.

| Ex No | $R^7$ | $R^8$ | X | 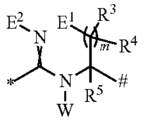 | L—$R^6$ | LogP |
|---|---|---|---|---|---|---|
| 23-04 | Cl | H | Cl | 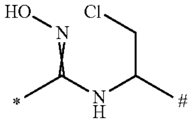 | (2,4-dichlorophenyl)methyl | 3.54[a] |
| 23-05 | $CH_3$ | H | Cl | 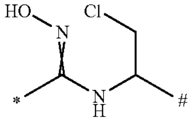 | (2,4-dichlorophenyl)methyl | 2.95[a] |

TABLE 38

23-05: $^1$H-NMR(400.1 MHz, CDCl3):
δ = 7.6204 (0.4); 7.4786 (0.3); 7.4252 (0.8); 7.3994 (0.6); 7.3891 (0.6); 7.3660 (0.5); 7.3395 (0.7); 7.3170 (1.1); 7.2981 (4.5); 7.2937 (5.0); 7.2618 (35.2); 7.2446 (3.6); 7.2282 (1.0); 7.1930 (4.7); 7.1726 (3.0); 7.1594 (1.6); 7.1347 (0.9); 7.1108 (0.9); 7.0865 (2.1); 7.0495 (0.4); 6.9975 (0.8); 6.4099 (1.0); 5.7768 (1.4); 5.7485 (1.4); 5.3015 (1.8); 4.8146 (0.9); 3.9885 (1.3); 3.9436 (1.4); 3.8619 (1.1); 3.8519 (1.1); 3.8327 (1.3); 3.8249 (1.4); 3.7953 (0.4); 3.7766 (0.3); 3.7351 (0.3); 3.7169 (0.4); 3.6961 (0.5); 3.6750 (1.6); 3.6682 (1.6); 3.6468 (1.3); 3.6399 (1.2); 3.4547 (1.2); 3.4257 (0.7); 3.4152 (0.4); 3.1434 (0.4); 3.1253 (0.4); 3.0425 (1.3); 3.0294 (1.3); 3.0075 (2.0); 2.9956 (1.7); 2.9346 (1.8); 2.9120 (1.6); 2.9008 (1.1); 2.8785 (0.9); 2.7647 (1.2); 2.7527 (0.4); 2.7387 (0.5); 2.7243 (0.8); 2.6389 (16.0); 2.3125 (2.6); 2.2921 (0.5); 2.2428 (2.5); 2.2073 (0.4); 2.1827 (0.4); 2.1544 (0.4); 2.1352 (0.4); 2.0808 (0.5); 1.9494 (0.4); 1.9100 (0.5); 1.8657 (0.6); 1.8472 (0.6); 1.8433 (0.6); 1.6803 (1.4); 1.6586 (1.5); 1.6427 (1.5); 1.5923 (1.6); 1.5746 (1.9); 1.5584 (2.0); 1.5424 (1.8); 1.4477 (1.0); 1.4293 (1.0); 1.3756 (0.8); 1.2541 (8.4); 1.2070 (1.5); 1.1365 (0.8); 1.1258 (0.8); 1.1101 (0.8); 1.0896 (0.6); 1.0386 (0.5); 1.0184 (0.5); 1.0044 (0.5); 0.9810 (0.5); 0.8797 (1.8); 0.8582 (2.9); 0.8425 (3.0); −0.0002 (37.0)

TABLE 39

Compounds according to formula (25)

(25)

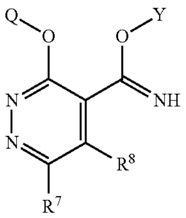

| Ex No | $R^7$ | $R^8$ | Q | Y | LogP |
|---|---|---|---|---|---|
| 25-01 | Cl | H | 3-cyclopropylphenyl | $CH_3$ | 3.08[a] |
| 25-02 | Cl | H | 3-(trifluoromethyl)phenyl | $CH_3$ | 3.00[a] |

TABLE 40

| |
|---|
| 25-02: $^{1}$H-NMR(300.2 MHz, CDCl3): |
| δ = 8.3217 (0.8); 8.2067 (0.3); 7.9791 (1.3); 7.9518 (5.6); 7.9445 (3.3); 7.8565 (0.4); 7.8352 (4.0); 7.8335 (4.2); 7.8211 (1.1); 7.7997 (0.6); 7.6983 (0.8); 7.6463 (0.8); 7.6264 (3.1); 7.6051 (6.6); 7.5701 (2.2); 7.5341 (4.0); 7.4973 (0.7); 7.4804 (1.8); 7.4711 (2.6); 7.4637 (2.5); 7.4507 (1.9); 7.3467 (1.2); 7.3206 (2.6); 7.2997 (4.1); 7.1607 (2.8); 7.1326 (4.4); 7.0469 (1.8); 7.0194 (1.6); 4.5171 (0.5); 4.4932 (0.4); 4.4743 (0.6); 4.4604 (0.4); 4.4508 (2.0); 4.4367 (0.5); 4.4271 (2.0); 4.4127 (0.7); 4.4036 (0.8); 4.3890 (1.7); 4.3653 (1.4); 4.3435 (1.0); 4.3167 (10.9); 4.3132 (9.9); 4.2989 (3.0); 4.2520 (3.8); 4.2483 (3.6); 4.2031 (0.3); 4.1751 (0.5); 4.0500 (3.8); 4.0223 (16.0); 4.0078 (1.7); 3.9919 (3.4); 3.9624 (10.8); 2.0707 (1.2); 1.5051 (1.8); 1.4812 (4.3); 1.4655 (1.7); 1.4570 (3.6); 1.4422 (3.2); 1.4333 (2.0); 1.4185 (1.8); 1.4101 (1.0); 1.2849 (0.4); 1.2739 (0.4); 0.0297 (3.2) |

TABLE 41

Compounds according to formula (30)

(30)

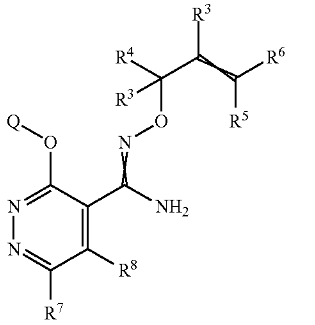

In table 41, "#" denotes the point of attachment to the $R^6$ group and "*" denotes the point of attachment to the pyridazin-4-yl group.

| Ex No | $R^7$ | $R^8$ | Q | 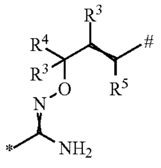 | $R^6$ | LogP |
|---|---|---|---|---|---|---|
| 30-01 | $CH_3$ | H | 3-(trifluoro-methyl)phenyl | 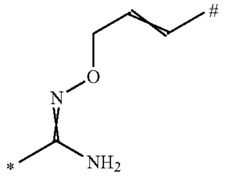 | 1-methyl-1H-indol-5-yl | 3.92[a] |

TABLE 42

| |
|---|
| 30-01: $^{1}$H-NMR(400.1 MHz, $d_6$-DMSO): |
| δ = 7.9615 (2.0); 7.7306 (6.3); 7.7206 (3.1); 7.6923 (2.0); 7.6727 (1.9); 7.6479 (2.4); 7.6283 (1.3); 7.5904 (1.7); 7.5736 (4.3); 7.4225 (0.4); 7.4047 (1.5); 7.3833 (2.8); 7.3375 (2.3); 7.3157 (4.2); 7.3081 (3.3); 6.7820 (1.5); 6.7422 (1.9); 6.4213 (3.9); 6.4019 (3.6); 6.3940 (3.2); 6.3874 (1.9); 6.3715 (0.8); 6.3636 (0.8); 6.3475 (1.2); 6.3319 (0.6); 4.6461 (3.1); 4.6307 (3.1); 3.7957 (1.3); 3.7839 (16.0); 3.7691 (1.4); 3.3382 (32.0); 2.8983 (11.7); 2.7392 (10.7); 2.5978 (1.3); 2.5873 (14.6); 2.5735 (1.6); 2.5143 (10.9); 2.5102 (14.5); 2.5061 (11.3) |

Biological Examples

Example: In Vivo Preventive Test on *Alternaria brassicae* (Leaf Spot on Radish or Cabbage)

Solvent: 5% by volume of Dimethyl sulfoxide
10% by volume of Acetone
Emulsifier: 1 μl of Tween® 80 per mg of active ingredient The active ingredients were made soluble and homogenized in a mixture of Dimethyl sulfoxide/Acetone// Tween®80 and then diluted in water to the desired concentration.

The young plants of radish or cabbage were treated by spraying the active ingredient prepared as described above. Control plants were treated only with an aqueous solution of Acetone/Dimethyl sulfoxide/Tween® 80.

After 24 hours, the plants were contaminated by spraying the leaves with an aqueous suspension of *Alternaria brassicae* spores. The contaminated radish or cabbage plants were incubated for 6 days at 20° C. and at 100% relative humidity.

The test was evaluated 6 days after the inoculation. 0% means an efficacy which corresponds to that of the control plants while an efficacy of 100% means that no disease was observed.

In this test the following compounds according to the invention showed efficacy between 70% and 79% at a concentration of 500 ppm of active ingredient: I-180; I-184

In this test the following compounds according to the invention showed efficacy between 80% and 89% at a concentration of 500 ppm of active ingredient: I-031; I-074; I-182; I-235

In this test the following compounds according to the invention showed efficacy between 90% and 100% at a concentration of 500 ppm of active ingredient: I-001; I-002; I-003; I-004; I-005; I-006; I-007; I-008; I-009; I-010; I-011; I-012; I-013; I-014; I-015; I-016; I-017; I-018; I-019; I-020; I-021; I-022; I-023; I-024; I-025; I-026; I-027; I-028; I-029; I-030; I-032; I-033; I-034; I-035; I-036; I-037; I-038; I-039; I-040; I-041; I-042; I-043; I-044; I-045; I-046; I-047; I-048; I-049; I-050; I-051; I-052; I-053; I-054; I-055; I-056; I-057; I-058; I-059; I-060; I-061; I-062; I-063; I-064; I-065; I-066; I-067; I-068; I-069; I-070; I-071; I-072; I-073; I-075; I-076; I-077; I-078; I-079; I-080; I-081; I-082; I-083; I-084; I-085; I-086; I-087; I-088; I-089; I-090; I-091; I-092; I-093; I-094; I-095; I-096; I-097; I-098; I-099; I-100; I-103; I-104; I-105; I-106; I-107; I-108; I-109; I-110; I-111; I-112; I-113; I-114; I-115; I-116; I-117; I-118; I-119; I-120; I-121; I-122; I-123; I-124; I-125; I-126; I-127; I-128; I-129; I-130; I-131; I-132; I-133; I-134; I-135; I-136; I-137; I-138; I-139; I-140; I-141; I-142; I-143; I-144; I-145; I-146; I-147; I-148; I-149; I-150; I-151; I-152; I-153; I-154; I-155; I-156; I-157; I-158; I-159; I-160; I-161; I-162; I-163; I-164; I-165; I-166; I-167; I-169; I-170; I-171; I-172; I-173; I-174; I-175; I-178; I-181; I-183; I-185; I-186; I-187; I-188; I-189; I-190; I-192; I-193; I-194; I-195; I-196; I-197; I-198; I-199; I-200; I-201; I-202; I-203; I-204; I-205; I-206; I-207; I-208; I-209; I-210; I-211; I-212; I-213; I-214; I-215; I-216; I-217; I-218; I-219; I-220; I-221; I-222; I-223; I-225; I-226; I-227; I-228; I-229; I-230; I-231; I-232; I-233; I-234; I-236; I-237; I-238; I-239; I-240; I-241; I-242; I-243; I-244; I-245; I-246; I-247; I-248; I-249; I-250; I-251; I-252; I-253; I-256; I-258; I-259; I-260; I-261; I-262; I-263; I-264; I-265; I-266; I-267; I-268; I-270; I-271; I-273; I-274; I-275; I-276; I-279; I-280; I-281; I-282; I-283; I-284; I-285; I-286; I-287; I-288; I-289; I-290; I-292; I-293; I-294; I-295; I-296; I-297; I-298; I-299; I-300; I-301; I-302; I-303; I-304; I-305; I-306; I-307; I-308; I-310; I-311; I-340

Example: In Vivo Preventive Test on *Botrytis cinerea* (Grey Mould)

Solvent: 5% by volume of Dimethyl sulfoxide
10% by volume of Acetone
Emulsifier: 1 µl of Tween® 80 per mg of active ingredient The active ingredients were made soluble and homogenized in a mixture of Dimethyl sulfoxide/Acetone//Tween®80 and then diluted in water to the desired concentration.

The young plants of gherkin or cabbage were treated by spraying the active ingredient prepared as described above. Control plants were treated only with an aqueous solution of Acetone/Dimethyl sulfoxide/Tween® 80.

After 24 hours, the plants were contaminated by spraying the leaves with an aqueous suspension of *Botrytis cinerea* spores. The contaminated gherkin plants were incubated for 4 to 5 days at 17° C. and at 90% relative humidity. The contaminated cabbage plants were incubated for 4 to 5 days at 20° C. and at 100% relative humidity.

The test was evaluated 4 to 5 days after the inoculation. 0% means an efficacy which corresponds to that of the control plants while an efficacy of 100% means that no disease was observed.

In this test the following compounds according to the invention showed efficacy between 70% and 79% at a concentration of 500 ppm of active ingredient: I-182; I-235

In this test the following compounds according to the invention showed efficacy between 80% and 89% at a concentration of 500 ppm of active ingredient: I-106; I-115; I-176; I-181

In this test the following compounds according to the invention showed efficacy between 90% and 100% at a concentration of 500 ppm of active ingredient: I-001; I-002; I-003; I-004; I-005; I-006; I-007; I-008; I-009; I-010; I-011; I-012; I-014; I-015; I-016; I-017; I-018; I-019; I-020; I-021; I-022; I-023; I-024; I-025; I-026; I-027; I-028; I-029; I-030; I-031; I-032; I-033; I-034; I-035; I-036; I-037; I-038; I-039; I-040; I-041; I-042; I-043; I-044; I-045; I-046; I-047; I-048; I-049; I-050; I-051; I-052; I-053; I-054; I-055; I-056; I-057; I-058; I-059; I-060; I-061; I-062; I-063; I-066; I-067; I-068; I-069; I-070; I-071; I-072; I-073; I-074; I-075; I-076; I-077; I-078; I-079; I-080; I-081; I-082; I-083; I-084; I-085; I-086; I-087; I-088; I-089; I-090; I-091; I-092; I-093; I-094; I-095; I-096; I-097; I-098; I-099; I-100; I-103; I-104; I-105; I-107; I-108; I-109; I-110; I-111; I-112; I-113; I-114; I-116; I-117; I-118; I-119; I-120; I-121; I-122; I-123; I-124; I-125; I-127; I-128; I-129; I-130; I-131; I-133; I-134; I-136; I-137; I-138; I-139; I-140; I-141; I-142; I-143; I-144; I-145; I-146; I-147; I-148; I-149; I-150; I-151; I-152; I-153; I-154; I-155; I-156; I-157; I-158; I-159; I-160; I-161; I-162; I-163; I-164; I-165; I-166; I-167; I-169; I-170; I-171; I-172; I-173; I-174; I-175; I-178; I-180; I-184; I-186; I-187; I-188; I-190; I-192; I-193; I-194; I-195; I-196; I-197; I-198; I-202; I-203; I-208; I-209; I-210; I-211; I-212; I-213; I-214; I-216; I-217; I-221; I-222; I-223; I-225; I-226; I-228; I-230; I-231; I-234; I-240; I-242; I-244; I-245; I-246; I-247; I-248; I-249; I-250; I-252; I-258; I-259; I-260; I-261; I-272; I-274; I-275; I-276; I-279; I-292; I-293; I-294; I-295; I-296; I-297; I-298; I-299; I-300; I-301; I-302; I-303; I-304; I-305; I-306; I-307; I-308; I-310; I-311

Example: In Vivo Preventive Test on *Pyrenophora teres* (Net Blotch on Barley)

Solvent: 5% by volume of Dimethyl sulfoxide
10% by volume of Acetone
Emulsifier: 1 µl of Tween® 80 per mg of active ingredient The active ingredients were made soluble and homogenized in a mixture of Dimethyl sulfoxide/Acetone//Tween®80 and then diluted in water to the desired concentration.

The young plants of barley were treated by spraying the active ingredient prepared as described above. Control plants were treated only with an aqueous solution of Acetone/Dimethyl sulfoxide/Tween®80.

After 24 hours, the plants were contaminated by spraying the leaves with an aqueous suspension of *Pyrenophora teres* spores. The contaminated barley plants were incubated for 48 hours at 20° C. and at 100% relative humidity and then for 8 days at 20° C. and at 70-80% relative humidity.

The test was evaluated 10 days after the inoculation. 0% means an efficacy which corresponds to that of the control plants while an efficacy of 100% means that no disease was observed.

In this test the following compounds according to the invention showed efficacy between 70% and 79% at a concentration of 500 ppm of active ingredient: I-011; I-060; I-065; I-066; I-095; I-125; I-134; I-140; I-141; I-157; I-159; I-160; I-162; I-166; I-209; I-214; I-215; I-216; I-231; I-238; I-267; I-292; I-297; I-311

In this test the following compounds according to the invention showed efficacy between 80% and 89% at a concentration of 500 ppm of active ingredient: I-008; I-010; I-015; I-040; I-051; I-058; I-072; I-076; I-077; I-078; I-079; I-082; I-085; I-092; I-109; I-110; I-122; I-136; I-145; I-146; I-153; I-155; I-176; I-188; I-196; I-213; I-223; I-225; I-228; I-234; I-235; I-263; I-268; I-272; I-289; I-293; I-294; I-340

In this test the following compounds according to the invention showed efficacy between 90% and 100% at a concentration of 500 ppm of active ingredient: I-001; I-002; I-003; I-004; I-005; I-006; I-009; I-012; I-014; I-016; I-017; I-018; I-019; I-020; I-021; I-022; I-023; I-024; I-025; I-026; I-027; I-028; I-030; I-032; I-035; I-036; I-038; I-042; I-045; I-047; I-048; I-050; I-052; I-053; I-054; I-055; I-056; I-057; I-059; I-070; I-075; I-084; I-086; I-087; I-088; I-089; I-090; I-091; I-094; I-097; I-111; I-123; I-124; I-127; I-129; I-130; I-137; I-138; I-142; I-143; I-147; I-152; I-154; I-161; I-163; I-165; I-170; I-171; I-172; I-173; I-174; I-186; I-189; I-190; I-197; I-199; I-200; I-201; I-203; I-204; I-205; I-206; I-207; I-208; I-210; I-211; I-212; I-217; I-218; I-219; I-220; I-221; I-222; I-226; I-227; I-229; I-230; I-232; I-233; I-236; I-237; I-239; I-240; I-241; I-242; I-243; I-245; I-246; I-247; I-248; I-249; I-250; I-251; I-252; I-253; I-256; I-258; I-259; I-260; I-261; I-262; I-264; I-265; I-266; I-270; I-271; I-273; I-280; I-281; I-283; I-284; I-285; I-286; I-287; I-288; I-290; I-295; I-296; I-298; I-299; I-300; I-301; I-302; I-303; I-305; I-306; I-307; I-308; I-310

Example: In Vivo Preventive Test on *Septoria tritici* (Leaf Spot on Wheat)

Solvent: 5% by volume of Dimethyl sulfoxide
10% by volume of Acetone
Emulsifier: 1 μl of Tween® 80 per mg of active ingredient The active ingredients were made soluble and homogenized in a mixture of Dimethyl sulfoxide/Acetone//Tween®80 and then diluted in water to the desired concentration.

The young plants of wheat were treated by spraying the active ingredient prepared as described above. Control plants were treated only with an aqueous solution of Acetone/Dimethyl sulfoxide/Tween®80.

After 24 hours, the plants were contaminated by spraying the leaves with an aqueous suspension of *Septoria tritici* spores. The contaminated wheat plants were incubated for 72 hours at 17° C. and at 100% relative humidity and then for 15 days at 20° C. and at 90% relative humidity.

The test was evaluated 19 days after the inoculation. 0% means an efficacy which corresponds to that of the control plants while an efficacy of 100% means that no disease was observed.

In this test the following compounds according to the invention showed efficacy between 70% and 79% at a concentration of 500 ppm of active ingredient: I-003; I-013; I-032; I-088; I-091; I-123; I-129; I-130; I-146; I-161; I-189; I-196; I-197; I-198; I-233; I-241; I-252; I-272; I-282; I-286; I-287

In this test the following compounds according to the invention showed efficacy between 80% and 89% at a concentration of 500 ppm of active ingredient: I-001; I-004; I-008; I-012; I-035; I-052; I-053; I-057; I-075; I-082; I-087; I-089; I-090; I-131; I-136; I-140; I-153; I-159; I-170; I-186; I-188; I-239; I-261; I-265; I-266; I-271; I-283; I-284; I-288; I-289; I-292; I-294; I-299; I-304

In this test the following compounds according to the invention showed efficacy between 90% and 100% at a concentration of 500 ppm of active ingredient: I-002; I-005; I-006; I-009; I-016; I-017; I-019; I-020; I-021; I-022; I-023; I-025; I-026; I-027; I-028; I-030; I-036; I-038; I-042; I-054; I-056; I-059; I-072; I-076; I-084; I-085; I-086; I-097; I-128; I-138; I-147; I-152; I-163; I-165; I-176; I-247; I-250; I-259; I-260; I-264; I-267; I-270; I-273; I-280; I-281; I-285; I-290; I-298; I-300; I-302

Example: In Vivo Preventive Test on *Sphaerotheca fuliginea* (Powdery Mildew on Cucurbits)

Solvent: 5% by volume of Dimethyl sulfoxide
10% by volume of Acetone
Emulsifier: 1 μl of Tween® 80 per mg of active ingredient The active ingredients were made soluble and homogenized in a mixture of Dimethyl sulfoxide/Acetone//Tween®80 and then diluted in water to the desired concentration.

The young plants of gherkin were treated by spraying the active ingredient prepared as described above. Control plants were treated only with an aqueous solution of Acetone/Dimethyl sulfoxide/Tween® 80.

After 24 hours, the plants were contaminated by spraying the leaves with an aqueous suspension of *Sphaerotheca fuliginea* spores. The contaminated gherkin plants were incubated for 8 days at 20° C. and at 70-80% relative humidity.

The test was evaluated 8 days after the inoculation. 0% means an efficacy which corresponds to that of the control plants while an efficacy of 100% means that no disease was observed.

In this test the following compounds according to the invention showed efficacy between 70% and 79% at a concentration of 500 ppm of active ingredient: I-144; I-206; I-217; I-221; I-242; I-243; I-280

In this test the following compounds according to the invention showed efficacy between 80% and 89% at a concentration of 500 ppm of active ingredient: I-040; I-078; I-107; I-119; I-120; I-150; I-151; I-167; I-230; I-286; I-340

In this test the following compounds according to the invention showed efficacy between 90% and 100% at a concentration of 500 ppm of active ingredient: I-001; I-002; I-003; I-004; I-005; I-006; I-008; I-009; I-010; I-011; I-012; I-013; I-014; I-016; I-017; I-018; I-019; I-020; I-021; I-022; I-023; I-024; I-025; I-026; I-027; I-028; I-030; I-032; I-033; I-034; I-035; I-036; I-037; I-038; I-039; I-041; I-042; I-043; I-044; I-045; I-047; I-048; I-049; I-050; I-051; I-052; I-053; I-054; I-055; I-056; I-057; I-058; I-059; I-060; I-062; I-063; I-064; I-066; I-067; I-068; I-069; I-070; I-072; I-074; I-075; I-076; I-079; I-082; I-084; I-085; I-087; I-088; I-089; I-090; I-091; I-092; I-094; I-097; I-098; I-099; I-103; I-106; I-109; I-110; I-111; I-112; I-113; I-115; I-121; I-122; I-123; I-124; I-125; I-127; I-128; I-129; I-130; I-131; I-132; I-133; I-136; I-137; I-138; I-139; I-141; I-142; I-143; I-145; I-146; I-147; I-148; I-149; I-152; I-153; I-154; I-155; I-157; I-159; I-160; I-161; I-162; I-163; I-164; I-165; I-166; I-169; I-170; I-171; I-172; I-173; I-174; I-176; I-180; I-181; I-183; I-186; I-187; I-188; I-189; I-190; I-192; I-193; I-194; I-196; I-197; I-198;

I-199; I-200; I-201; I-203; I-204; I-205; I-207; I-208; I-209; I-210; I-211; I-212; I-214; I-216; I-218; I-220; I-222; I-223; I-225; I-226; I-227; I-228; I-229; I-232; I-233; I-234; I-235; I-236; I-237; I-238; I-239; I-240; I-241; I-245; I-246; I-247; I-248; I-249; I-250; I-251; I-252; I-253; I-256; I-258; I-259; I-260; I-261; I-262; I-263; I-264; I-265; I-266; I-267; I-268; I-270; I-272; I-273; I-275; I-276; I-279; I-281; I-282; I-283; I-284; I-285; I-287; I-288; I-289; I-290; I-292; I-293; I-294; I-295; I-296; I-297; I-298; I-299; I-300; I-301; I-302; I-303; I-305; I-306; I-307; I-308; I-310

Example: In Vivo Preventive Test on *Colletotrichum lindemuthianum* (Leaf Spot on Bean)

Solvent: 5% by volume of Dimethyl sulfoxide
10% by volume of Acetone
Emulsifier: 1 µl of Tween® 80 per mg of active ingredient The active ingredients were made soluble and homogenized in a mixture of Dimethyl sulfoxide/Acetone//Tween®80 and then diluted in water to the desired concentration.

The young plants of bean were treated by spraying the active ingredient prepared as described above. Control plants were treated only with an aqueous solution of Acetone/Dimethyl sulfoxide/Tween® 80.

After 24 hours, the plants were contaminated by spraying the leaves with an aqueous suspension of *Colletotrichum lindemuthianum* spores. The contaminated bean plants were incubated for 24 hours at 20° C. and at 100% relative humidity and then for 6 days at 20° C. and at 90% relative humidity.

The test was evaluated 7 days after the inoculation. 0% means an efficacy which corresponds to that of the control plants while an efficacy of 100% means that no disease was observed.

In this test the following compounds according to the invention showed efficacy between 70% and 79% at a concentration of 500 ppm of active ingredient: I-080; I-100; I-132; I-148; I-151; I-183; I-288

In this test the following compounds according to the invention showed efficacy between 80% and 89% at a concentration of 500 ppm of active ingredient: I-011; I-051; I-079; I-096; I-098; I-113; I-158; I-160; I-169; I-194; I-208; I-210; I-213; I-219; I-222; I-228; I-233; I-293

In this test the following compounds according to the invention showed efficacy between 90% and 100% at a concentration of 500 ppm of active ingredient: I-001; I-002; I-003; I-004; I-005; I-006; I-008; I-009; I-010; I-012; I-013; I-014; I-015; I-016; I-017; I-018; I-019; I-020; I-021; I-022; I-023; I-024; I-025; I-026; I-027; I-028; I-030; I-031; I-032; I-033; I-034; I-035; I-036; I-037; I-038; I-039; I-040; I-042; I-043; I-044; I-045; I-047; I-048; I-049; I-050; I-052; I-053; I-054; I-055; I-056; I-057; I-058; I-059; I-061; I-062; I-065; I-066; I-067; I-068; I-069; I-070; I-072; I-075; I-076; I-077; I-078; I-082; I-083; I-084; I-085; I-086; I-087; I-088; I-089; I-090; I-091; I-092; I-093; I-094; I-095; I-097; I-099; I-103; I-104; I-105; I-106; I-107; I-109; I-110; I-111; I-112; I-114; I-115; I-116; I-117; I-118; I-119; I-120; I-121; I-122; I-123; I-124; I-125; I-126; I-127; I-128; I-129; I-130; I-133; I-134; I-135; I-136; I-137; I-138; I-139; I-140; I-141; I-142; I-143; I-145; I-146; I-147; I-149; I-150; I-152; I-153; I-154; I-155; I-157; I-159; I-161; I-162; I-163; I-165; I-166; I-167; I-170; I-171; I-172; I-173; I-174; I-176; I-186; I-188; I-189; I-190; I-192; I-193; I-196; I-197; I-198; I-199; I-200; I-201; I-202; I-203; I-204; I-205; I-206; I-207; I-211; I-212; I-214; I-215; I-216; I-217; I-218; I-220; I-221; I-225; I-226; I-229; I-231; I-232; I-236; I-237; I-238; I-239; I-240; I-241; I-242; I-243; I-245; I-246; I-247; I-248; I-249; I-250; I-251; I-252; I-253; I-256; I-258; I-259; I-260; I-261; I-262; I-263; I-264; I-266; I-267; I-270; I-271; I-272; I-273; I-276; I-280; I-281; I-282; I-283; I-285; I-286; I-289; I-290; I-292; I-294; I-295; I-296; I-298; I-299; I-300; I-301; I-302; I-303; I-305; I-306; I-307; I-308; I-310

Example: *Alternaria alternata* In Vitro Cell Test

Solvent: DMSO
Culture medium: 14.6 g anhydrous D-glucose (VWR), 7.1 g Mycological Peptone (Oxoid), 1.4 g granulated Yeast Extract (Merck), QSP 1 liter
Inoculum: spores suspension Fungicides were solubilized in DMSO and the solution used to prepare the required range of concentrations. The final concentration of DMSO used in the assay was ≤1%.

A spore suspension of *A. alternata* was prepared and diluted to the desired spore density.

Fungicides were evaluated for their ability to inhibit spore germination and mycelium growth in liquid culture assay. The compounds were added in the desired concentration to the culture medium with spores. After 5 days incubation, fungi-toxicity of compounds was determined by spectrometric measurement of mycelium growth. Inhibition of fungal growth was determined by comparing the absorbance values in wells containing the fungicides with the absorbance in control wells without fungicides.

In this test the following compounds according to the invention showed efficacy between 70% and 79% at a concentration of 20 ppm of active ingredient: I-091; I-126; I-132; I-134; I-180; I-191; I-214; I-224; I-340

In this test the following compounds according to the invention showed efficacy between 80% and 89% at a concentration of 20 ppm of active ingredient: I-081; I-169; I-184; I-194; I-244; I-282

In this test the following compounds according to the invention showed efficacy between 90% and 100% at a concentration of 20 ppm of active ingredient: I-001; I-002; I-003; I-004; I-005; I-006; I-007; I-008; I-009; I-010; I-011; I-012; I-013; I-014; I-015; I-016; I-017; I-018; I-019; I-020; I-021; I-022; I-023; I-024; I-025; I-026; I-027; I-028; I-030; I-031; I-032; I-033; I-034; I-035; I-036; I-037; I-038; I-039; I-040; I-041; I-042; I-043; I-044; I-045; I-046; I-047; I-048; I-049; I-050; I-051; I-052; I-053; I-054; I-055; I-056; I-057; I-058; I-059; I-060; I-061; I-063; I-064; I-065; I-066; I-067; I-068; I-069; I-070; I-071; I-072; I-073; I-074; I-075; I-076; I-077; I-078; I-079; I-080; I-082; I-084; I-085; I-086; I-087; I-088; I-089; I-090; I-092; I-093; I-094; I-097; I-098; I-099; I-100; I-101; I-102; I-103; I-104; I-105; I-106; I-107; I-108; I-109; I-110; I-111; I-112; I-113; I-114; I-115; I-116; I-117; I-118; I-119; I-120; I-121; I-122; I-123; I-124; I-125; I-127; I-128; I-129; I-130; I-133; I-135; I-136; I-137; I-138; I-139; I-140; I-141; I-142; I-143; I-144; I-145; I-146; I-147; I-148; I-149; I-150; I-151; I-152; I-153; I-154; I-155; I-156; I-157; I-158; I-159; I-160; I-161; I-162; I-163; I-164; I-165; I-166; I-167; I-168; I-170; I-171; I-172; I-173; I-174; I-175; I-176; I-177; I-179; I-181; I-182; I-183; I-185; I-186; I-187; I-188; I-189; I-190; I-192; I-193; I-195; I-196; I-197; I-198; I-199; I-200; I-201; I-202; I-203; I-204; I-205; I-207; I-208; I-210; I-211; I-212; I-213; I-216; I-217; I-218; I-219; I-220; I-221; I-222; I-223; I-225; I-226; I-227; I-229; I-230; I-232; I-233; I-234; I-236; I-237; I-239; I-240; I-241; I-242; I-243; I-245; I-246; I-247; I-248; I-249; I-250; I-251; I-252; I-253; I-254; I-255; I-256; I-257; I-258; I-259; I-260; I-261; I-262; I-263; I-264; I-265; I-266; I-267; I-268; I-269; I-270; I-271; I-272;

I-273; I-274; I-275; I-276; I-277; I-278; I-279; I-280; I-281; I-283; I-284; I-285; I-286; I-287; I-288; I-289; I-290; I-291; I-292; I-293; I-294; I-295; I-296; I-297; I-298; I-299; I-300; I-301; I-302; I-303; I-304; I-305; I-306; I-307; I-308; I-309; I-310; I-311; I-312; I-313; I-315; I-316; I-317; I-318; I-319

Example: *Colletotrichum lindemuthianum* In Vitro Cell Test

Solvent: DMSO

Culture medium: 14.6 g anhydrous D-glucose (VWR), 7.1 g Mycological Peptone (Oxoid), 1.4 g granulated Yeast Extract (Merck), QSP 1 liter Inoculum: spores suspension Fungicides were solubilized in DMSO and the solution used to prepare the required range of concentrations. The final concentration of DMSO used in the assay was ≤1%.

A spore suspension of *C. lindemuthianum* was prepared and diluted to the desired spore density.

Fungicides were evaluated for their ability to inhibit spores germination and mycelium growth in liquid culture assay. The compounds were added in the desired concentration to the culture medium with spores. After 6 days incubation, fungi-toxicity of compounds was determined by spectrometric measurement of mycelium growth. Inhibition of fungal growth was determined by comparing the absorbance values in wells containing the fungicides with the absorbance in control wells without fungicides.

In this test the following compounds according to the invention showed efficacy between 70% and 79% at a concentration of 20 ppm of active ingredient: I-083; I-132; I-185; I-234

In this test the following compounds according to the invention showed efficacy between 80% and 89% at a concentration of 20 ppm of active ingredient: I-126; I-134; I-180; I-194; I-206; I-227; I-235

In this test the following compounds according to the invention showed efficacy between 90% and 100% at a concentration of 20 ppm of active ingredient: I-001; I-002; I-003; I-004; I-005; I-006; I-007; I-008; I-009; I-010; I-011; I-012; I-013; I-014; I-015; I-016; I-017; I-018; I-019; I-020; I-021; I-022; I-023; I-024; I-025; I-026; I-027; I-028; I-029; I-030; I-031; I-032; I-033; I-034; I-035; I-036; I-037; I-038; I-039; I-040; I-041; I-042; I-043; I-044; I-045; I-046; I-047; I-048; I-049; I-050; I-051; I-052; I-053; I-054; I-055; I-056; I-057; I-058; I-059; I-060; I-061; I-063; I-064; I-065; I-066; I-067; I-068; I-069; I-070; I-071; I-072; I-073; I-074; I-075; I-076; I-077; I-078; I-079; I-080; I-081; I-082; I-084; I-085; I-086; I-087; I-088; I-089; I-090; I-091; I-092; I-093; I-094; I-097; I-098; I-099; I-100; I-101; I-102; I-103; I-104; I-105; I-106; I-107; I-108; I-109; I-110; I-111; I-112; I-113; I-114; I-115; I-116; I-117; I-118; I-119; I-120; I-121; I-122; I-123; I-124; I-125; I-127; I-128; I-129; I-130; I-133; I-135; I-136; I-137; I-138; I-139; I-140; I-141; I-142; I-143; I-144; I-145; I-146; I-147; I-148; I-149; I-150; I-151; I-152; I-153; I-154; I-155; I-156; I-157; I-158; I-159; I-160; I-161; I-162; I-163; I-164; I-165; I-166; I-167; I-168; I-169; I-170; I-171; I-172; I-173; I-174; I-175; I-176; I-177; I-179; I-181; I-182; I-183; I-186; I-187; I-188; I-189; I-190; I-191; I-192; I-193; I-195; I-196; I-197; I-198; I-199; I-200; I-201; I-202; I-203; I-204; I-205; I-207; I-208; I-210; I-211; I-212; I-213; I-214; I-216; I-217; I-218; I-219; I-220; I-221; I-222; I-223; I-224; I-225; I-226; I-228; I-229; I-230; I-231; I-232; I-233; I-236; I-237; I-238; I-239; I-240; I-241; I-242; I-243; I-244; I-245; I-246; I-247; I-248; I-249; I-250; I-251; I-252; I-253; I-254; I-255; I-256; I-257; I-258; I-259; I-260; I-261; I-262; I-263; I-264; I-265; I-266; I-267; I-268; I-269; I-270; I-271; I-272; I-273; I-274; I-275; I-276; I-277; I-278; I-279; I-280; I-281; I-282; I-283; I-284; I-285; I-286; I-287; I-288; I-289; I-290; I-291; I-292; I-293; I-294; I-295; I-296; I-297; I-298; I-299; I-300; I-301; I-302; I-303; I-304; I-305; I-306; I-307; I-308; I-309; I-310; I-311; I-312; I-313; I-315; I-316; I-317; I-318; I-319; I-347

Example: *Septoria tritici* In Vitro Cell Test

Solvent: DMSO

Culture medium: 14.6 g anhydrous D-glucose (VWR), 7.1 g Bacteriological Peptone (Oxoid), 1.4 g granulated Yeast Extract (Merck), QSP 1 liter Inoculum: spore suspension Fungicides were solubilized in DMSO and the solution used to prepare the required range of concentrations. The final concentration of DMSO used in the assay was ≤1%.

A spore suspension of *Septoria tritici* was prepared and diluted to the desired spore density.

Fungicides were evaluated for their ability to inhibit spore germination and mycelium growth in liquid culture assay. The compounds were added in the desired concentration to the culture medium with spores. After 7 days incubation, fungi-toxicity of compounds was determined by spectrometric measurement of mycelium growth. Inhibition of fungal growth was determined by comparing the absorbance values in wells containing the fungicides with the absorbance in control wells without fungicides.

In this test the following compounds according to the invention showed efficacy between 70% and 79% at a concentration of 20 ppm of active ingredient: I-005; I-024; I-066; I-104; I-123; I-132; I-142; I-146; I-148; I-198; I-248; I-249; I-291; I-343

In this test the following compounds according to the invention showed efficacy between 80% and 89% at a concentration of 20 ppm of active ingredient: I-008; I-018; I-020; I-026; I-048; I-067; I-070; I-072; I-086; I-089; I-097; I-109; I-110; I-111; I-112; I-113; I-124; I-127; I-128; I-138; I-140; I-143; I-152; I-157; I-174; I-175; I-188; I-190; I-193; I-196; I-197; I-199; I-200; I-201; I-207; I-225; I-233; I-241; I-247; I-250; I-252; I-255; I-256; I-278; I-279; I-283; I-284; I-285; I-286; I-288; I-289; I-290; I-294

In this test the following compounds according to the invention showed efficacy between 90% and 100% at a concentration of 20 ppm of active ingredient: I-001; I-003; I-004; I-007; I-009; I-011; I-013; I-016; I-017; I-019; I-021; I-022; I-023; I-025; I-027; I-028; I-030; I-032; I-035; I-036; I-038; I-043; I-045; I-050; I-052; I-053; I-054; I-055; I-059; I-075; I-076; I-082; I-084; I-085; I-130; I-147; I-153; I-155; I-159; I-161; I-163; I-165; I-166; I-170; I-172; I-186; I-189; I-195; I-205; I-218; I-226; I-236; I-239; I-259; I-260; I-261; I-273; I-275; I-280; I-281; I-298; I-299; I-300; I-301; I-302; I-303; I-305; I-306; I-307; I-308; I-320; I-323; I-342

The invention claimed is:

1. A compound of formula (I-302):

(I-302)

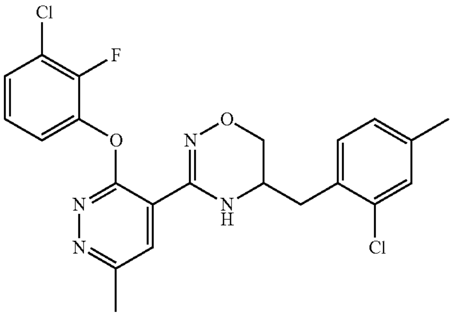

or a stereoisomer thereof, or a salt, an N-oxide, or a solvate of any of the foregoing.

2. A composition comprising at least one compound of claim 1, and at least one agriculturally suitable auxiliary.

3. A method for controlling phytopathogenic fungi comprising applying at least one compound of claim 1, to a plant, plant part, seed, fruit or soil in which the plant grows.

4. A method for controlling phytopathogenic fungi comprising applying a composition according to claim 2, to a plant, plant part, seed, fruit or soil in which the plant grows.

5. The compound of claim 1, wherein the compound is:

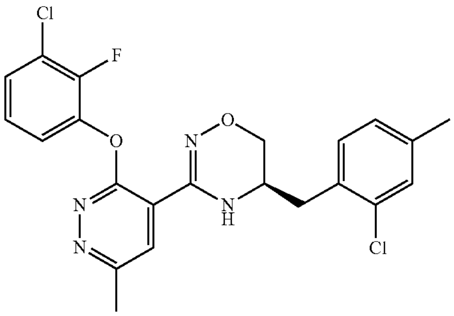 [SMILES: Cc1ccc(C[C@@H]2CON=C(c3cc(C)nnc3Oc3cccc(Cl)c3F)N2)c(Cl)c1]

or a salt, an N-oxide, or a solvate thereof.

6. A composition comprising the compound of claim 5, and at least one agriculturally suitable auxiliary.

7. A method for controlling phytopathogenic fungi comprising applying the compound of claim 5, to a plant, plant part, seed, fruit or soil in which the plant grows.

8. A method for controlling phytopathogenic fungi comprising applying a composition according to claim 6, to a plant, plant part, seed, fruit or soil in which the plant grows.

9. The compound of claim 1, wherein the compound is:

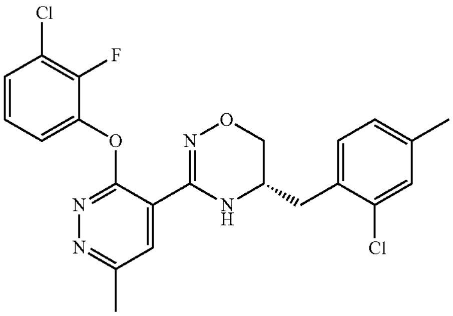 [SMILES: Cc1ccc(C[C@H]2CON=C(c3cc(C)nnc3Oc3cccc(Cl)c3F)N2)c(Cl)c1]

or a salt, an N-oxide, or a solvate thereof.

10. A composition comprising the compound of claim 9, and at least one agriculturally suitable auxiliary.

11. A method for controlling phytopathogenic fungi comprising applying the compound of claim 9, to a plant, plant part, seed, fruit or soil in which the plant grows.

12. A method for controlling phytopathogenic fungi comprising applying a composition according to claim 10, to a plant, plant part, seed, fruit or soil in which the plant grows.

* * * * *